US011541041B1

(12) United States Patent
Hadari et al.

(10) Patent No.: US 11,541,041 B1
(45) Date of Patent: Jan. 3, 2023

(54) COMPOUNDS THAT INTERACT WITH THE RAS SUPERFAMILY FOR THE TREATMENT OF CANCERS, INFLAMMATORY DISEASES, RASOPATHIES, AND FIBROTIC DISEASE

(71) Applicant: Shy Therapeutics LLC, Harrison, NY (US)

(72) Inventors: Yaron R. Hadari, Harrison, NY (US); Luca Carta, Scarsdale, NY (US); Michael Schmertzler, St. Petersburg, FL (US); Theresa M. Williams, Harleysville, PA (US); Charles H. Reynolds, Austin, TX (US); Rebecca Hutcheson, Stamford, CT (US)

(73) Assignee: SHY Therapeutics LLC, Harrison, NY (US)

( * ) Notice: Subject to any disclaimer, the term of this patent is extended or adjusted under 35 U.S.C. 154(b) by 72 days.

(21) Appl. No.: 17/373,450

(22) Filed: Jul. 12, 2021

Related U.S. Application Data

(60) Continuation of application No. 17/143,077, filed on Jan. 6, 2021, now Pat. No. 11,213,515, which is a division of application No. 16/847,467, filed on Apr. 13, 2020, now Pat. No. 11,026,930, which is a continuation of application No. 16/654,934, filed on Oct. 16, 2019, now Pat. No. 10,940,139, which is a continuation of application No. 16/013,872, filed on Jun. 20, 2018, now Pat. No. 10,588,894.

(60) Provisional application No. 62/523,114, filed on Jun. 21, 2017.

(51) Int. Cl.

| | |
|---|---|
| ***A61K 31/4365*** | (2006.01) |
| ***C12N 15/10*** | (2006.01) |
| ***A61P 35/00*** | (2006.01) |
| ***A61P 29/00*** | (2006.01) |
| ***C07K 14/435*** | (2006.01) |
| ***C07D 495/04*** | (2006.01) |
| ***A61K 31/505*** | (2006.01) |
| ***A61P 25/28*** | (2006.01) |

(52) U.S. Cl.
CPC ........ *A61K 31/4365* (2013.01); *A61K 31/505* (2013.01); *A61P 25/28* (2018.01); *A61P 29/00* (2018.01); *A61P 35/00* (2018.01); *C07D 495/04* (2013.01); *C07K 14/435* (2013.01); *C12N 15/1037* (2013.01); *C12N 15/1065* (2013.01)

(58) Field of Classification Search
CPC ... A61K 31/4365; A61K 31/505; A61P 25/28; A61P 29/00; A61P 35/00; C07D 495/04; C07K 14/435; C12N 15/1037; C12N 15/1065
USPC .......................................................... 435/6.13
See application file for complete search history.

(56) References Cited

U.S. PATENT DOCUMENTS

| | | | |
|---|---|---|---|
| 5,102,877 | A | 4/1992 | Murata et al. |
| 5,187,168 | A | 2/1993 | Primeau et al. |
| 5,654,307 | A | 8/1997 | Bridges et al. |
| 6,133,271 | A | 10/2000 | Pamukcu et al. |
| 6,492,383 | B1 | 12/2002 | Munchhof et al. |
| 7,173,040 | B2 | 2/2007 | Angibaud et al. |
| 8,022,076 | B2 | 9/2011 | Ford et al. |
| 8,153,639 | B2 | 4/2012 | Chuckowree et al. |
| 8,211,897 | B2 | 7/2012 | Holsinger |
| 8,314,112 | B2 | 11/2012 | Leblanc et al. |
| 8,691,829 | B2 | 4/2014 | Ulrich |
| 9,163,003 | B2 | 10/2015 | Chen et al. |
| 9,238,034 | B2 | 1/2016 | Tran et al. |
| 9,249,155 | B2 | 2/2016 | Ford et al. |
| 9,260,400 | B2 | 2/2016 | Leopoldo et al. |
| 9,260,462 | B2 | 2/2016 | Leopoldo et al. |
| 9,290,511 | B2 | 3/2016 | Madge et al. |
| 9,604,994 | B2 | 3/2017 | Dorsey et al. |
| 9,797,882 | B2 | 10/2017 | Tran et al. |
| 10,221,191 | B2 | 3/2019 | Hadari et al. |
| 10,463,649 | B2 | 11/2019 | Srivastava et al. |
| 10,588,894 | B2 | 3/2020 | Hadari et al. |
| 10,870,657 | B2 | 12/2020 | Hadari et al. |
| 10,933,054 | B2 | 3/2021 | Hadari et al. |
| 10,940,139 | B2 | 3/2021 | Hadari et al. |
| 11,000,515 | B2 | 5/2021 | Hadari et al. |
| 11,026,930 | B1 | 6/2021 | Hadari et al. |
| 2005/0176701 | A1 | 8/2005 | Borchardt et al. |
| 2006/0167029 | A1 | 7/2006 | Matasi et al. |
| 2007/0099877 | A1 | 5/2007 | Cai et al. |
| 2007/0287717 | A1 | 12/2007 | Fanning et al. |
| 2008/0161254 | A1 | 7/2008 | Green et al. |

(Continued)

FOREIGN PATENT DOCUMENTS

| | | | |
|---|---|---|---|
| CN | 101583616 | A | 11/2009 |
| CN | 104230952 | A | 12/2014 |

(Continued)

OTHER PUBLICATIONS

Ni et al. Drugging K-RasG12C through covalent inhibitors: Mission possible? Pharmacology & Therapeutics 202 (2019) 1-17. (Year: 2019).*

(Continued)

*Primary Examiner* — Yih-Horng Shiao

(74) *Attorney, Agent, or Firm* — Jones Day

(57) ABSTRACT

Provided herein are methods and compositions for treating cancers, inflammatory diseases, rasopathies, and fibrotic disease involving aberrant Ras superfamily signaling through the binding of compounds to the GTP binding domain of Ras superfamily proteins including, in certain cases, K-Ras and mutants thereof, and a novel method for assaying such compositions.

39 Claims, 18 Drawing Sheets

(56) References Cited

U.S. PATENT DOCUMENTS

| | | | |
|---|---|---|---|
| 2008/0161559 | A1 | 7/2008 | Penning et al. |
| 2008/0161578 | A1 | 7/2008 | Penning et al. |
| 2008/0269228 | A1 | 10/2008 | Moore et al. |
| 2009/0030196 | A1 | 1/2009 | Wang et al. |
| 2009/0163545 | A1 | 6/2009 | Goldfarb et al. |
| 2010/0069383 | A1 | 3/2010 | Anderson et al. |
| 2010/0093702 | A1 | 4/2010 | Barbay et al. |
| 2011/0144140 | A1 | 6/2011 | Eriksen et al. |
| 2012/0046290 | A1 | 2/2012 | Dumas et al. |
| 2013/0116267 | A1 | 5/2013 | Katsikis et al. |
| 2013/0317045 | A1 | 11/2013 | Hadd et al. |
| 2014/0072536 | A1 | 3/2014 | Burkin et al. |
| 2014/0228565 | A1 | 8/2014 | Choo et al. |
| 2014/0256717 | A1 | 9/2014 | Fernandez et al. |
| 2014/0256719 | A1 | 9/2014 | Finlay et al. |
| 2015/0175558 | A1 | 6/2015 | Stockwell et al. |
| 2015/0239900 | A1 | 8/2015 | Li et al. |
| 2015/0291590 | A1 | 10/2015 | Kandula |
| 2015/0315207 | A1 | 11/2015 | Morales et al. |
| 2017/0131278 | A1 | 5/2017 | Patricelli et al. |
| 2017/0158706 | A1 | 6/2017 | Dorsey |
| 2017/0174699 | A1 | 6/2017 | Hadari et al. |
| 2018/0118761 | A1 | 5/2018 | Sebti et al. |
| 2019/0022074 | A1 | 1/2019 | Hadari et al. |
| 2019/0218229 | A1 | 7/2019 | Hadari et al. |
| 2020/0054614 | A1 | 2/2020 | Hadari et al. |

FOREIGN PATENT DOCUMENTS

| | | | |
|---|---|---|---|
| CN | 107721982 | A | 8/2018 |
| DE | 1959402 | A1 | 6/1971 |
| DE | 1959403 | A1 | 6/1971 |
| DE | 2039662 | A1 | 2/1972 |
| DE | 2050814 | A1 | 4/1972 |
| DE | 2050815 | A1 | 4/1972 |
| DE | 2050816 | A1 | 4/1972 |
| DE | 295381 | A5 | 10/1991 |
| EP | 0 404 3 56 | A1 | 12/1990 |
| EP | 0 407 899 | A2 | 1/1991 |
| EP | 2 014 663 | A1 | 5/1991 |
| EP | 0 502 725 | A2 | 9/1992 |
| EP | 0 519 307 | A2 | 12/1992 |
| EP | 0 579 424 | A1 | 1/1994 |
| EP | 0 807 633 | A2 | 11/1997 |
| EP | 0 276 057 | A2 | 7/1998 |
| EP | 0 884 310 | A1 | 12/1998 |
| EP | 0 900 568 | A2 | 3/1999 |
| EP | 0 900 799 | A1 | 3/1999 |
| EP | 1 254 903 | A1 | 11/2002 |
| EP | 0 934 321 | B1 | 8/2003 |
| EP | 1 997 812 | A1 | 12/2008 |
| EP | 2 508 184 | A1 | 10/2012 |
| EP | 3 290 412 | A1 | 3/2018 |
| GB | 1057612 | | 2/1967 |
| JP | 56059778 | A | 5/1981 |
| JP | H04305630 | A | 10/1992 |
| JP | 2010-512337 | | 4/2010 |
| KR | 10-2018-0066985 | A | 6/2018 |
| WO | WO 92/20687 | A1 | 11/1992 |
| WO | WO 93/03040 | A1 | 2/1993 |
| WO | WO 94/08975 | A1 | 4/1994 |
| WO | WO 97/29110 | A1 | 8/1997 |
| WO | WO 97/46560 | A1 | 12/1997 |
| WO | WO 98/06722 | A1 | 2/1998 |
| WO | WO 98/23620 | A1 | 6/1998 |
| WO | WO 98/49899 | A1 | 11/1998 |
| WO | WO 99/14202 | A2 | 3/1999 |
| WO | WO 99/24440 | A1 | 5/1999 |
| WO | WO 99/40091 | A1 | 8/1999 |
| WO | WO 2000/059912 | | 10/2000 |
| WO | WO 2001/002409 | A1 | 1/2001 |
| WO | WO 2001/083456 | A1 | 11/2001 |
| WO | WO 2002/002549 | A1 | 1/2002 |
| WO | WO 2002/026745 | | 4/2002 |
| WO | WO 2002/055524 | A1 | 7/2002 |
| WO | WO 2003/033476 | A1 | 4/2003 |
| WO | WO 2003/035076 | A1 | 5/2003 |
| WO | WO 2003/035653 | | 5/2003 |
| WO | WO 2003/050064 | A2 | 6/2003 |
| WO | WO 2003/059913 | A1 | 7/2003 |
| WO | WO 2003/106435 | A1 | 12/2003 |
| WO | WO 2004/037176 | A2 | 5/2004 |
| WO | WO 2004/065392 | A1 | 8/2004 |
| WO | WO 2004/071460 | A2 | 8/2004 |
| WO | WO 2004/074270 | A2 | 9/2004 |
| WO | WO 2004/111058 | A1 | 12/2004 |
| WO | WO 2005/023782 | A1 | 3/2005 |
| WO | WO 2005/026126 | A1 | 3/2005 |
| WO | WO 2005/047292 | A1 | 5/2005 |
| WO | WO 2005/047293 | A1 | 5/2005 |
| WO | WO 2005/082887 | A1 | 9/2005 |
| WO | WO 2005/105760 | A1 | 11/2005 |
| WO | WO 2005/105780 | A2 | 11/2005 |
| WO | WO 2005/121147 | A1 | 12/2005 |
| WO | WO 2006/022955 | A2 | 3/2006 |
| WO | WO 2006/040966 | A1 | 4/2006 |
| WO | WO 2006/043145 | A1 | 4/2006 |
| WO | WO 2006/046040 | A1 | 5/2006 |
| WO | WO 2006/072831 | A1 | 7/2006 |
| WO | WO 2006/122200 | A1 | 11/2006 |
| WO | WO 2007/002701 | A2 | 1/2007 |
| WO | WO 2007/035010 | A2 | 3/2007 |
| WO | WO 2007/056214 | A2 | 5/2007 |
| WO | WO 2007/064883 | A2 | 6/2007 |
| WO | WO 2007/076085 | A2 | 7/2007 |
| WO | WO 2007/093365 | A2 | 8/2007 |
| WO | WO 2007/0102679 | A1 | 9/2007 |
| WO | WO 2007/127183 | A1 | 11/2007 |
| WO | WO 2007/132171 | A1 | 11/2007 |
| WO | WO 2007/139951 | A1 | 12/2007 |
| WO | WO 2008/012413 | A2 | 1/2008 |
| WO | WO 2008/016123 | A1 | 2/2008 |
| WO | WO 2008/020622 | A1 | 2/2008 |
| WO | WO 2008/024433 | A2 | 2/2008 |
| WO | WO 2008/024724 | A1 | 2/2008 |
| WO | WO 2008/028935 | A2 | 3/2008 |
| WO | WO 2008/063668 | A1 | 5/2008 |
| WO | WO 2008/064018 | A1 | 5/2008 |
| WO | WO 2008/066664 | A2 | 6/2008 |
| WO | WO 2008/092860 | A1 | 8/2008 |
| WO | WO 2008/092861 | A1 | 8/2008 |
| WO | WO 2008/092862 | A1 | 8/2008 |
| WO | WO 2008/094909 | A2 | 8/2008 |
| WO | WO 2008/131050 | A1 | 10/2008 |
| WO | WO 2008/134397 | A1 | 11/2008 |
| WO | WO 2009/026241 | A1 | 2/2009 |
| WO | WO 2009/027346 | A2 | 3/2009 |
| WO | WO 2009/064388 | | 5/2009 |
| WO | WO 2009/065472 | A1 | 5/2009 |
| WO | WO 2009/087225 | A2 | 7/2009 |
| WO | WO 2009/119880 | A1 | 10/2009 |
| WO | WO 2009/121036 | A2 | 10/2009 |
| WO | WO 2010/027236 | | 3/2010 |
| WO | WO 2010/037765 | A2 | 4/2010 |
| WO | WO 2010/045006 | | 4/2010 |
| WO | WO 2010/126960 | A1 | 11/2010 |
| WO | WO 2010/138828 | A2 | 12/2010 |
| WO | WO 2011/011550 | A1 | 1/2011 |
| WO | WO 2011/101429 | A1 | 2/2011 |
| WO | WO 2011/025774 | A1 | 3/2011 |
| WO | WO 2011/102399 | A1 | 8/2011 |
| WO | WO 2011/104183 | A1 | 9/2011 |
| WO | WO 2012/004900 | A1 | 1/2012 |
| WO | WO 2012/009452 | A1 | 1/2012 |
| WO | WO 2012/030894 | A1 | 3/2012 |
| WO | WO 2012/037204 | A1 | 3/2012 |
| WO | WO 2012/151567 | A1 | 11/2012 |
| WO | WO 2012/153796 | A1 | 11/2012 |
| WO | WO 2012/156756 | A2 | 11/2012 |
| WO | WO 2013/008217 | A1 | 1/2013 |
| WO | WO 2013/032591 | A1 | 3/2013 |
| WO | WO 2013/078126 | A1 | 5/2013 |
| WO | WO 2013/087578 | A1 | 6/2013 |
| WO | WO 2013/154878 | A1 | 10/2013 |

(56) References Cited

FOREIGN PATENT DOCUMENTS

| | | | |
|---|---|---|---|
| WO | WO 2014/040077 | A1 | 3/2014 |
| WO | WO 2014/045039 | A2 | 3/2014 |
| WO | WO 2014/124757 | A1 | 8/2014 |
| WO | WO 2014/138562 | A1 | 9/2014 |
| WO | WO 2014/143610 | A1 | 9/2014 |
| WO | WO 2014/169167 | A1 | 10/2014 |
| WO | WO 2015/025026 | A1 | 2/2015 |
| WO | WO 2015/042497 | A2 | 3/2015 |
| WO | WO 2015/043398 | A1 | 4/2015 |
| WO | WO 2015/050798 | A1 | 4/2015 |
| WO | WO 2015/054572 | A1 | 4/2015 |
| WO | WO 2015/148714 | A1 | 10/2015 |
| WO | WO 2015/160192 | A1 | 10/2015 |
| WO | WO 2015/169421 | A1 | 11/2015 |
| WO | WO 2015/183989 | A1 | 12/2015 |
| WO | WO 2016/044772 | A1 | 3/2016 |
| WO | WO 2016/049568 | A1 | 3/2016 |
| WO | WO 2016/068580 | A2 | 5/2016 |
| WO | WO 2016/142312 | A1 | 9/2016 |
| WO | WO 2016/161361 | A1 | 10/2016 |
| WO | WO 2016/164675 | A1 | 10/2016 |
| WO | WO 2016/172692 | A1 | 10/2016 |
| WO | WO 2016/183398 | A1 | 11/2016 |
| WO | WO 2016/201257 | A2 | 12/2016 |
| WO | WO 2017/015425 | A1 | 1/2017 |
| WO | WO 2017/015562 | A1 | 1/2017 |
| WO | WO 2017/031176 | A1 | 2/2017 |
| WO | WO 2017/034377 | A1 | 3/2017 |
| WO | WO 2017/040448 | A1 | 3/2017 |
| WO | WO 2017/058728 | A1 | 4/2017 |
| WO | WO 2017/058768 | A1 | 4/2017 |
| WO | WO 2017/058805 | A1 | 4/2017 |
| WO | WO 2017/058807 | A1 | 4/2017 |
| WO | WO 2017/058902 | A1 | 4/2017 |
| WO | WO 2017/059191 | A1 | 4/2017 |
| WO | WO 2017/070256 | A2 | 4/2017 |
| WO | WO 2017/087528 | A1 | 5/2017 |
| WO | WO 2017/112777 | A1 | 6/2017 |
| WO | WO 2017/0172565 | A1 | 10/2017 |
| WO | WO 2018/237084 | | 12/2018 |
| WO | WO 2019/018359 | A1 | 1/2019 |
| WO | WO 2019/105734 | A1 | 6/2019 |
| WO | WO 2019/129059 | A1 | 7/2019 |
| WO | WO 2019/180141 | A1 | 9/2019 |

OTHER PUBLICATIONS

Lu et al. Drugging Ras GTPase: a comprehensive mechanistic and signaling structural view. Chem. Soc. Rev., 2016, 45, 4929. DOI: 10.1039/c5cs00911a (Year: 2016).*

Andrews M. et al., "Cellular Mechanisms Underlying Complete Hematological Response of Chronic Myeloid Leukemia to BRAF and MEK1/2 Inhibition in a Patient with Concomitant Metastatic Melanoma." Clin Cancer Res. Dec. 1, 2015;21(23):5222-34.

Arlt A. & Schäfer H., Role of the immediate early response 3 (IER3) gene in cellular stress response, inflammation and tumorigenesis. Eur J Cell Biol. Jun.-Jul. 2011;90(6-7):545-52.

Arthur, J. et al., Mitogen-activated protein kinases in innate immunity. Nat. Rev. Immunol. 13, 679-692 (2013).

Bakir-Gungor, B. et al. Identification of possible pathogenic pathways in Behçet's disease using genome-wide association study data from two different populations. Eur. J. Hum. Genet. 23, 678-687 (2015).

Barili et al., 1985, "A facile one pot synthesis of 2,9-disubstiuted 8-azapurin-6-ones (3,5-disubstitued 7-hydroxy-3H-1,2,3-triazolo[4,5-d]pyrimidines)," J. Heterocyclic Chem., 22(6):1607-1609.

Bartold, P. M. & Narayanan, A. S. Molecular and cell biology of healthy and diseased periodontal tissues. Periodontol. 2000 40, 29-49 (2006).

Bhatia, M. & Moochhala, S. Role of inflammatory mediators in the pathophysiology of acute respiratory distress syndrome. J. Pathol. 202, 145-156 (2004).

Bogolubsky et al., "An old story in the parallel synthesis world: an approach to hydantoin libraries," *ACS Comb. Sci.*, 20(1):35-43 (2018).

Bogolubsky et al., "Dry HCl in parallel synthesis of fused pyrimidin-4-ones," *J. Comb. Chem.*, 10(6):858-862 (2008).

Bohm et al., "Über thieno-verbindungen 5. Mitteilung: basisch substituierte thieno[2,3-]pyrimidine," *Pharmazie*, Govi Verlag Pharmazeutischer Verlag GmbH, DE 41(1):23-25 (1986) with an English abstract.

Bonventre, J. V. & Zuk, A. Ischemic acute renal failure: An inflammatory disease? Kidney Int. 66, 480-485 (2004).

Bouskine A et al., "Estrogens promote human testicular germ cell cancer through a membrane-mediated activation of extracellular regulated kinase and protein kinase A." Endocrinology. Feb. 2008;149(2):565-73. Epub Nov. 26, 2007.

Briel et al., "Synthesis of thieno[3,3-d]- and -[3,4-d]pyrimidines by alternative ring closure reactions," *Pharmazie*, 47(8):577-579 (1992) with English abstract.

Briel, "Synthesis of thieno-heterocycles from substituted 5-(methylthio)thiophene-4-carbonitriles," *Pharmazie*, 53(4):227-231 (1998).

Buhler et al., 2014, "p38 MAPK inhibitors: a patent review (2012-2013)", Expert Opinion on Therapeutic Patents, 24(5): 535-554.

Burgess, J. K. et al. Dual ERK and phosphatidylinositol 3-kinase pathways control airway smooth muscle proliferation: Differences in asthma. J. Cell. Physiol. 216, 673-679 (2008).

Burotto et al., 2014, "The MAPK Pathway Across Different Malignancies: A New Perspective", Cancer: 3446-3456.

Caunt C.et al., "MEK1 and MEK2 inhibitors and cancer therapy: the long and winding road." Nat Rev Cancer. Oct. 2015;15(10):577-92.

Chang & Karin, Mammalian MAP kinase signalling cascades. Nature 410, 37-40 (2001).

Chapman and Miner, "Novel mitogen-activated protein kinase kinase inhibitors." Expert Opin Investig Drugs. Feb. 2011;20(2):209-20.

Choi et al., "In silico discovery of quinoxaline derivatives as novel LRP5/6-sclerostin interaction inhibitors," *Bioorg. Med. Chem. Lett.*, 28(6):1116-1121 (2018).

Choi, H. et al., Pathogenesis of Gout. Ann. Intern. Med. 143, 499-516 (2005).

Chu, A. J. Antagonism by bioactive polyphenols against inflammation: a systematic view. Inflamm. Allergy Drug Targets 13, 34-64 (2014).

Chung, "Pentafluorophenylhydrazine," *Encyclopedia Reagents Organic Synthesis*, e-EROS published online (2001) (5 pages).

Cichero et al., "Exhaustive 3D-QSAR analyses as a computational tool to explore the potency and selectivity profiles of thieno[3,2-d]pyrimidin-4(3H)-one derivatives as PDE7 inhibitors," *RSC Advances*, 6(66):61088-61108 (2016).

Colvin, R. B. & Smith, R. N. Antibody-mediated organ-allograft rejection. Nat. Rev. Immunol. 5, 807-817 (2005).

Crespo et al., "Design, synthesis, and biological activities of new thieno[3,2-d] pyrimidines as selective type 4 phosphodiesterase inhibitors," *J. Med. Chem.*, 41(21):4021-4035 (1998).

Croft M., et al., Clinical targeting of the TNF and TNFR superfamilies, Nat. Rev. Drug Discov. 12 (2013) 147-168.

Cuevas, B. et al., Role of mitogen-activated protein kinase kinase kinases in signal integration. Oncogene 26, 3159-3171 (2007).

Cummins A. et al., Persistent Localization of Activated Extracellular Signal-RegulatedKinases (ERK1/2) Is Epithelial Cell-Specific in an Inhalation Model of Asbestosis. Am. J. Pathol. 162, 713-720 (2003).

De Schutter et al., "Targeting Bacillosamine Biosynthesis in Bacterial Pathogens: Development of Inhibitors to a Bacterial Amino-Sugar Acetyltransferase from Campylobacter jejuni," *J. Med. Chem.*, 60(5):2099-2118 (2017).

Desai et al., "Thieno(3,2-d)pyrimidines. Part-I. Preparation and Antimicrobial Activity of 3-N-Substituted-thioureido-2-methyl-6-phenylthieno(3, 2-d)pyrimidin-4(3H)-ones," *J. Indian Chem. Soc.*, 74(2):160 (1997).

Desai et al., "Thieno[3,2-d]pyrimidines. Part II: Preparation and antimicrobial activity of 2-methyl-3-N-arylsulfonamido-6-

(56) References Cited

OTHER PUBLICATIONS phenylthieno[3,2-d]pyrimidin-4(3H)-ones," *J. Institution of Chemists (India)*, 67(5):136-137 (1995).
Desroches et al., "Discovery of new hit-molecules targeting Plasmodium falciparum through a global SAR study of the 4-substituted-2-trichloromethylquinazoline antiplasmodial scaffold," *Eur. J. Med. Chem.*, 125:68-86 (2017).
Dhillon et al., 2007, "MAP kinase signaling pathways in cancer", Oncogene, vol. 26: 3279-3290.
Doddareddy MR. et al., Targeting mitogen-activated protein kinase phosphatase-1 (MKP-1): structure-based design of MKP-1 inhibitors and upregulators. Curr Med Chem. 2012;19(2):163-73. Review.
Dumaitre et al., "Synthesis and cyclic GMP phosphodiesterase inhibitory activity of a series of 6-phenylpyrazolo[3,4-d]pyrimidones," *J. Med. Chem.*, 39(8):1635-1644 (1996).
Dumitru C.D., et al., TNF-alpha induction by LPS is regulated posttranscriptionally via a Tpl2/ERK-dependent pathway, Cell 103 (2000) 1071-1083.
Dupati et al., 2014, "Vemurafenib: Background, Patterns of Resistance, and Strategies to Combat Resistance in Melanoma", Med. Student Res. Journal, 3(Winter): 36-43.
Elneairy et al., "Bis-(cyanoacetamide)alkanes in heterocyclic synthesis: synthesis of bis-heteryl(carboxymido)alkanes and bis-(heteryl)alkanes of thiophene, pyrrole, thiazole and pyrimidinone series," *J. Sulfur Chem.*, 33(3):373-383 (2012).
Endo et al., "2-(Isopropylamino)thieno[3,2-d]pyrimidin-4(3H)-one derivatives as selective phosphodiesterase 7 inhibitors with potent in vivo efficacy," *Bioorg. Med. Chem. Lett.*, 25(9):1910-1914(2015).
Englert et al., "Fragment-based lead discovery: screening and optimizing fragments for thermolysin inhibition," *ChemMedChem*,5(6):930-940 (2010).
Fan W. et al., "Marsdenia tenacissima extract induces G0/G1 cell cycle arrest in human esophageal carcinoma cells by inhibiting mitogen-activated protein kinase (MAPK) signaling pathway." Chin J Nat Med. Jun. 2015;13(6):428-37.
Fortea, "4-Oxo-1,2,3,4-tetrahydrothienopyrimidine," *Afinidad*, 30(305):225-229 (1973) with English abstract.
Gaestel, M. et al. Targeting innate immunity protein kinase signalling in inflammation. Nat. Rev. Drug Discov. 8, 480-499 (2009).
Gantke T. et al., IκB kinase regulation of the TPL-2/ERK MAPK pathway. Immunol Rev. Mar. 2012;246(1):168-82.
Gascoigne et al., "Cancer cells display profound intra- and interline variation following prolonged exposure to antimitotic drugs," *Cancer Cell*, 14(2):111-122 (2008).
Gellibert et al., 2009, "Design of novel quinazoline derivatives and related analogues as potent and selective ALK5 inhibitors", Bioorganic & Medicinal Chemistry Letters, 19(8): 2277-2281.
Gillespie et al., "Antagonists of the human adenosine A2A receptor. Part 1: Discovery and synthesis of thieno[3,2-d]pyrimidine-4-methanone derivatives," *Bioorg. Med. Chem. Lett.*, 18(9):2916-2919 (2008).
Gillespie et al., "Antagonists of the human adenosine A2A receptor. Part 2: Design and synthesis of 4-arylthieno[3,2-d]pyrimidine derivatives," *Bioorg. Med. Chem. Lett.*, 18(9):2920-2923 (2008).
Girolomoni, G. & Pastore, S. The role of keratinocytes in the pathogenesis of atopic dermatitis. J. Am. Acad. Dermatol. 45, S25-S28 (2001).
Gronowitz et al., "On thiophene analogues of metaqualone-like compounds," *Acta Pharm. Suec.*, 5(6):563-578 (1968).
Guilding C. et al. ,"Restored plasticity in a mouse model of neurofibromatosis type 1 via inhibition of hyperactive ERK and CREB." Eur J Neurosci. Jan. 2007;25(1):99-105.
Gupta et al., "Identification of novel HIV-1 integrase inhibitors using shape-based screening, QSAR, and docking approach," *Chem. Biol. Drug Des.*, 79(5):835-849 (2012).
Haase & Hunzelmann, Activation of Epidermal Growth Factor Receptor/ERK Signaling Correlates with Suppressed Differentiation in Malignant Acanthosis Nigricans. J. Invest. Dermatol. 118, 891-893 (2002).
Hajjem et al., "Action Des Amines Et Des Hydrazines Sur Les Imidates Issus Du Methyl 3-Amino-2-Thiophene Carboxylate. Nouvelle Voie D'Acces Aux [3,2-d]4(3H)Thienopyrimidinones," *Bulletin des Societes Chimiques Belges*, 101(6):445-448 (1992).
Haswani et al., 2011, "Synthesis and antimicrobial activity of novel 2-(pyridine-2-yl)thieno[2,3-d]pyrimidin-4(3H)-ones," Turk. J. Chem., Jan. 1, 2011, 925-924.
Haswani et al., 2011, "Synthesis and antimicrobial activity of novel 2-(pyridine-2-yl)thieno[2,3-d]pyrimidin-4(3H)-ones", Turkish J. of Chemistry: 915-924.
Hayakawa et al., "Synthesis and biological evaluation of 4-morpholino-2-phenylquinazolines and related derivatives as novel PI3 kinase p110alpha inhibitors," *Bioorg. Med. Chem.*, 14(20):6847-6858 (2006).
Hilger et al., 2002, "The Ras-Raf-MEK-ERK Pathway in the Treatment of Cancer", Onkologie, 25: 511-518.
Holland et al., 1975, "Antiallergic activity of 8-azapurin-6-ones with heterocyclic 2-substituents", European Journal of Medicinal Chemistry, 10(5), 447-44.
Howlett M. et al., "Cytokine signalling via gp130 in gastric cancer." Biochim Biophys Acta. Nov. 2009;1793(11):1623-33.
Hrast et al., "Synthesis and structure-activity relationship study of novel quinazolinone-based inhibitors of MurA," *Bioorg. Med. Chem. Lett.*, 27(15):3529-3533 (2017).
Huang et al., 2010, "MAPK signaling in inflammation-associated cancer development," *Protein Cell*, 1(3):218-226.
Huang et al., 2013, "B-RAf and the inhibitors: from bench to bedside", J. of Hematol. & Oncology, 6: 30.
Hyman et al., 2015, "Vemurafenib in Multiple Nonmelanoma Cancers with BRAF V600 Mutations." N Engl J Med. 373(8):726-36.
Jeffrey, K. et al., Targeting dual-specificity phosphatases: manipulating MAP kinase signalling and immune responses. Nat. Rev. Drug Discov. 6, 391-403 (2007).
Ji, R. et al., MAP kinase and pain. Brain Res. Rev. 60, 135-148 (2009).
Ji, R.-R. & Suter, M. R. p38 MAPK, microglial signaling, and neuropathic pain. Mol. Pain 3, 33 (2007).
Johansen, C. et al. The mitogen-activated protein kinases p38 and ERK1/2 are increased in lesional psoriatic skin. Br. J. Dermatol. 152, 37-42 (2005).
Jokinen and Koivunen, "MEK and PI3K inhibition in solid tumors: rationale and evidence to date." Ther Adv Med Oncol. May 2015;7(3):170-80.
Kabir S., The role of interleukin-17 in the Helicobacter pylori induced infection and immunity. Helicobacter. Feb. 2011;16(1):1-8.
Kadmiel, M. & Cidlowski, J. A. Glucocorticoid receptor signaling in health and disease. Trends Pharmacol. Sci. 34, 518-530 (2013).
Kammoun et al., "Action des hydrazines perfluoroalkylees sur les iminoesters synthese des perfluoroalkyl-3-aminothienopyrimidinones et des perfluoroalkyl-1,2,4-triazin-6-ones," *J. Fluorine Chem.*, 105(1):83-86 (2000).
Kaul, M. et al., Pathways to neuronal injury and apoptosis in HIV-associated dementia. Nature 410, 988-994 (2001).
Kfoury A. et al., Dual function of MyD88 in inflammation and oncogenesis: implications for therapeutic intervention. Curr Opin Oncol. Jan. 2014;26(1):86-91.
Khan et al., 2013, "2,5-Disubstituted-1,3,4-oxadiazoles: thymidine phosphorylase inhibitors", Medicinal Chemistry Research, 22(12): 6022-6028.
Kim and Choi, Compromised MAPK signaling in human diseases: an update. Arch Toxicol. Jun. 2015;89(6):867-82.
Kim et al., "Serendipitous discovery of 2-((phenylsulfonyl)methyl)-thieno[3,2-d]pyrimidine derivatives as novel HIV-1 replication inhibitors," *Bioorg. Med. Chem. Lett.*, 24(23):5473-5477 (2014).
Kim, E. K. & Choi, E.-J. Pathological roles of MAPK signaling pathways in human diseases. Biochim. Biophys. Acta BBA—Mol. Basis Dis. 1802, 396-405 (2010).
King et al., 2013, "Dabrafenib: Preclinical Characterization, Increased Efficacy when Combined with Trametinib, while BRAF/MEK Tool Combination Reduced Skin Legions", PLOS ONE, 8(7): e67583.
Ko JK, Auyeung KK., Target-oriented mechanisms of novel herbal therapeutics in the chemotherapy of gastrointestinal cancer and inflammation. Curr Pharm Des. 2013;19(1):48-66. Review.

(56) References Cited

OTHER PUBLICATIONS

Kolata, G., "A Faster Way to Try Many Drugs on Many Cancers", The New York Times article dated Feb. 25, 2015 (5 pages); https://www.nytimes.com/2015/02/26/health/fast-track-attacks-on-cancer-accelerate-hopes.html accessed on Apr. 4, 2018.

Kontoyiannis D., et al., Genetic dissection of the cellular pathways and signaling mechanisms in modeled tumor necrosis factor-induced Crohn's-like inflammatory bowel disease, J. Exp. Med. 196 (2002) 1563-1574.

Kucherenko et al., "Positional isomers of thienopyrimidinones," *Chem. Heterocycl. Comp.*, 44(6):750-758 (2008).

Kumar et al., "Merging C—H Bond Functionalization with Amide Alcoholysis: En Route to 2-Aminopyridines," *ACS Catalysis*, 6(6):3531-3536 (2016).

Kumar et al., 2009, "An efficient synthesis and biological study of novel indolyl-1,3,4-oxadiazoles as potent anticancer agents", Bioorganic & Medicinal Chemistry Letters, 19(15): 4492-4494.

Kumar, S. et al., Intracellular signaling pathways as a target for the treatment of rheumatoid arthritis. Curr. Opin. Pharmacol. 1, 307-313 (2001).

Kurasawa et al., "2-Aminomethylthieno[3,2-d]pyrimidin-4(3H)-ones bearing 3-methylpyrazole hinge binding moiety: Highly potent, selective, and time-dependent inhibitors of Cdc7 kinase," *Bioorg. Med. Chem.*, 25(14):3658-3670 (2017).

Kyriakis, & Avruch, Mammalian Mito gen-Activated Protein Kinase Signal Transduction Pathways Activated by Stress and Inflammation. Physiol. Rev. 81, 807-869 (2001).

Kyrmizi I., et al., Tp12 kinase regulates FcgammaR signaling and immune thrombocytopenia in mice, J. Leukoc. Biol. 94 (2013) 751-757.

Labib et al., "Design, synthesis and biological evaluation of novel thiophene and theinopyrimidine derivatives as anticancer agents," *Med. Chem. Res.*, 25(11):2607-2618 (2016).

Lack et al., "Correction to Targeting the Binding Function 3 (BF3) Site of the Human Androgen Receptor through Virtual Screening," *J. Med. Chem.*,55(1):565 (2012).

Lack et al., "Targeting the binding function 3 (BF3) site of the human androgen receptor through virtual screening," *J. Med. Chem.*, 54(24):8563-8573 (2011).

Lawrenz M., et al., Genetic and pharmacological targeting of TPL-2 kinase ameliorates experimental colitis: a potential target for the treatment of Crohn's disease? Mucosal Immunol. 5 (2012) 129-139.

Lee et al., "A facile synthesis of 3-substituted 2-cyanoquinazolin-4(3H)-ones and 3-alkyl-2-cyanothieno[3,2-d]pyrimidin-4(3H)-ones via 1,2,3-dithiazoles," *J. Heterocyc. Chem.*, 35(3):659-668 (1998).

Leung, P. S. & Chan, Y. C. Role of oxidative stress in pancreatic inflammation. Antioxid. Redox Signal. 11, 135-165 (2009).

Li et al., 2011, "Induction of Cancer Cell Death by Isoflavone: The Role of Multiple Signaling Pathways", Nutrients, 3: 877-896.

Lindh et al., "Toward a benchmarking data set able to evaluate ligand- and structure-based virtual screening using public HTS data," *J. Chem. Inf. Model.*, 55(2):343-353 (2015).

Lingayya et al., "Palladium(ii)-catalyzed direct O-alkenylation of 2-arylquinazolinones with N-tosylhydrazones: an efficient route to O-alkenylquinazolines," *Chem. Commun. (Camb).*, 53(10):1672-1675 (2017).

Liu et al., "Design, synthesis and biological evaluation of novel thieno[3,2-d]pyrimidine derivatives containing diaryl urea moiety as potent antitumor agents," *Eur. J. Med. Chem.*, 85:215-227 (2014).

Liu et al., "Design, synthesis and biological evaluation of novel thieno[3,2-d]pyrimidine derivatives possessing diaryl semicarbazone scaffolds as potent antitumor agents," Eur. J. Med. Chem., 87:782-793 (2014).

Liu, Y., et al., MAPK phosphatases—regulating the immune response. Nat. Rev. Immunol. 7, 202-212 (2007).

Manzoor et al., 2012, "Mitogen-activated protein kinases in inflammation", J. Bacter. Virology, vol. 42(3): 189-195.

Mao H.et al., "Deregulated Signaling Pathways in Glioblastoma Multiforme: Molecular Mechanisms and Therapeutic Targets." Cancer Invest. Jan. 2012;30(1):48-56.

McCoull et al., "Identification of pyrazolo-pyrimidinones as GHS-R1a antagonists and inverse agonists for the treatment of obesity," *Med. Chem. Commun.*,4(2):456-462 (2013).

McLendon R, et al., "Comprehensive genomic characterization defines human glioblastoma genes and core pathways." Nature, 2008; 455(7216):1061-1068.

Memorial Sloan Kettering Press Release on Aug. 19, 2015 titled "Memorial Sloan Kettering Cancer Center Researchers Publish Landmark 'Basket Study'" (3 pages); https://www.mskcc.org/press-releases/memorial-sloan-kettering-center-researchers-publish-landmark-basket-study accessed on Apr. 4, 2018.

Memorial Sloan Kettering Press Release on Nov. 6, 2017 titled "FDA Announces First Approval of Targeted Therapy Based on Basket Study" (3 pages); https://www.mskcc.org/trending-topics/fda-announces-first-approval-targeted-therapy-based-basket-study accessed on Apr. 4, 2018.

Metz et al., "From determinants of RUNX1/ETO tetramerization to small-molecule protein-protein interaction inhibitors targeting acute myeloid leukemia," *J. Chem. Inf. Model.*,53(9):2197-2202 (2013).

Milligan, E. D. & Watkins, L. R. Pathological and protective roles of glia in chronic pain. Nat. Rev. Neurosci. 10, 23-36 (2009).

Mitra and Cote, "Molecular pathogenesis and diagnostics of bladder cancer." Annu Rev Pathol. 2009;4:251-85.

Mohan et al., "A facile synthesis and thio-Claisen rearrangement of 3-aryl-2-phenyl-5-prop-2-ynylsulfanyl-3H-pyrimidin-4-ones: regioselective transformation to thieno[3,2-d]pyrimidin-4-ones," *Tetrahedron*, 45(31):6075-6077 (2004).

Mohan et al., "Facile synthesis and regioselective thio-Claisen rearrangements of 5-prop-2-ynyl/enyl-sulfanyl pyrimidinones: transfoimation to thienopyrimidinones," *Tetrahedron*, 61(45):10774-10780 (2005).

Mohanta et al., "A short synthesis of quinazolinocarboline alkaloids rutaecarpine, hortiacine, euxylophoricine A and euxylophoricine D from methyl N-(4-chloro-5H-1,2,3-dithiazol-5-ylidene)anthranilates," *Tetrahedron Letters*, 43(22):3993-3996 (2002).

Mohanta et al., "New Synthetic Route to Tetracyclic Quinazolin-4(3H)-one Ring System," *Heterocycles*, 57(8):1471-1485 (2002).

Morel, J. & Berenbaum, F. Signal transduction pathways: new targets for treating rheumatoid arthritis. Joint Bone Spine 71, 503-510 (2004).

Mossman,B. et al., Oxidants and Signaling by Mitogen-Activated Protein Kinases in Lung Epithelium. Am. J. Respir. Cell Mol. Biol. 34, 666-669 (2006).

Murdoch et al., 1986, "Synthesis of [1,2,4]triazoloquinazolinones and imidazoquinazolinones", J. of Heterocyclic Chem., 23(3): 833-841.

Nara et al., "Thieno[2,3-d]pyrimidine-2-carboxamides bearing a carboxybenzene group at 5-position: highly potent, selective, and orally available MMP-13 inhibitors interacting with the S1" binding site," *Bioorg. Med. Chem.*, 22(19):5487-5505 (2014).

National Cancer Institute, "MEK: A Single Drug Target Shows Promise in Multiple Cancers" [https://www.cancer.gov/about-cancer/treatement/research/mek, accessed Nov. 27, 2017].

Neidlein et al., "Synthesis of 1,2,3,4-Tetrahydro-4-oxothieno[3,2-d]pyrimidine and Perhydropyrimidine Derivates from Alkyl Dicyanoacetates," *Helvetica Chimica Acta*, 74(3):579-584 (1991).

Nolan et al., "Identification of a novel selective serotonin reuptake inhibitor by coupling monoamine transporter-based virtual screening and rational molecular hybridization," *ACS Chem. Neurosci.*, 2(9):544-552 (2011).

Obata, K. & Noguchi, K. MAPK activation in nociceptive neurons and pain hypersensitivity. Life Sci. 74, 2643-2653 (2004).

O'Dowd et al., "Identification and Structure-Guided Development of Pyrimidinone Based USP7 Inhibitors," *ACS Med. Chem. Lett.*, 9(3):238-243 (2018).

Park et al., "Discovery of thienopyrimidine-based FLT3 inhibitors from the structural modification of known IKKβ inhibitors," *Bioorg. Med. Chem. Letts.*, 24:2655-2660 (2014).

Pearson and Regad, "Targeting cellular pathways in glioblastoma multifoime." Signal Transduction and Targeted Therapy. 2017; 2:e17040.

(56) References Cited

OTHER PUBLICATIONS

Pereda, J. et al. Effect of Simultaneous Inhibition of TNF-α Production and Xanthine Oxidase in Experimental Acute Pancreatitis. Ann. Surg. 240, 108-116 (2004).

Pereira et al., "Synthesis of novel 2,3-condensed thieno[2,3-d ]pyrimidin-4-ones via Appel's salt chemistry," *J. Sulfur Chem.*, 27(1):49-55 (2005).

Perspicace et al., "Design, synthesis and biological evaluation of new classes of thieno[3,2-d]pyrimidinone and thieno[1,2,3]triazine as inhibitor of vascular endothelial growth factor receptor-2 (VEGFR-2)," *Eur. J. Med. Chem.*, 63:765-781 (2013).

Perspicace et al., "Synthesis and biological evaluation of thieno[3,2-d]-pyrimidinones, thieno[3,2-d]pyrimidines and quinazolinones: conformationally restricted 17b-hydroxysteroid dehydrogenase type 2 (17b-HSD2) inhibitors," *Molecules*, 18(4):4487-4509 (2013).

Peti W, Page R., Molecular basis of MAP kinase regulation. Protein Sci. Dec. 2013;22(12):1698-710.

Plaskon et al., "A synthesis of 5-hetaryl-3-(2-hydroxybenzoyl)pyrroles," *Tetrahedron*, 64(25):5933-5943 (2008).

Principi M. et al., Fibrogenesis and fibrosis in inflammatory bowel diseases: Good and bad side of same coin? World J Gastrointest Pathophysiol. Nov. 15, 2013;4(4):100-7.

Puneet, P et al., . Chemokines in acute respiratory distress syndrome. Am. J. Physiol.-Lung Cell. Mol. Physiol. 288, L3-L15 (2005).

Qiu et al., "Potassium hydroxide-promoted transition-metal-free synthesis of 4(3H)-quinazolinones," *Monatsh. Chem.*, 146:1343-1347 (2015).

Rhee et al., "Synthesis and biological studies of catechol ether type derivatives as potential phosphodiesterase (PDE) IV inhibitors," *Arch. Pharm. Res.*, 22(2):202-207 (1999).

Ried et al., "New 4-hydroxythienopyrimidines," *Angewandte Chemie*, International Edition in English, 7(2):136 (1968).

Ried et al., "Reactions with imidic acid esters," *Justus Liebigs Annalen der Chemie*, 713:143-148 (1968) with English abstract.

Ried et al., "Thienopyrimidones," *Justus Liebigs Annalen der Chemie*, 716:219-221 (1968) with English abstract.

Ryabukhin et al., "Chlorotrimethylsilane-mediated synthesis of 2-ayl-1-chloro-1-heteroarylalkenes," *Synthesis*, 20:3163-3170 (2007).

Sanchez et al., Microwave-assisted synthesis of potent PDE7 inhibitors containing a thienopyrimidin-4-amine scaffold, *Org. Biomol. Chem.*, 12(24):4233-4242 (2014).

Santarpia et al., 2012, "Targeting the MAPK-RAS-RAF signaling pathway in cancer therapy", Expert Opin. Ther. Targets, vol. 16(1):103-119.

Sanz-Garcia C., et al., Sterile inflammation in acetaminophen-induced liver injury is mediated by Cot/tpl2, J. Biol. Chem. 288 (2013) 15342-15351.

Sarker et al., 2015, "First-in-human phase I study of pictilisib (GDC-0941), a potent pan-class I phosphatidylinositol-3-kinase (PI3K) inhibitor, in patients with advanced solid tumors." Clin Cancer Res. 21(1):77-86.

Sasaki K, et al., "The role of MAPK pathway in bone and soft tissue tumors." Anticancer Res. Feb. 2011;31(2):549-554.

Savino B. et al., "ERK-dependent downregulation of the atypical chemokine receptor D6 drives tumor aggressiveness in Kaposi sarcoma." Cancer Immunol Res. Jul. 2014;2(7):679-89.

Schuh, K. & Pahl, A. Inhibition of the MAP kinase ERK protects from lipopolysaccharide-induced lung injury. Biochem. Pharmacol. 77, 1827-1834 (2009).

Schultze, S. et al. PI3K/AKT, MAPK and AMPK signalling: protein kinases in glucose homeostasis. Expert Rev. Mol. Med. 14, e1 (2012).

Shishoo et al., "Synthesis of some tituted-6-phenyl-thieno(3,2-D)pyrimidin-4(3H)-ones and 7-phenyl-thieno[3,2-D]pyrimidin-4(3H)-ones," *Indian J. Chem. Sect. B: Organic Chemistry, including Medicinal Chemistry*, 33B(5):436-440 (1994).

Smith R. et al.,"Recent advances in the research and development of RAF kinase inhibitors." Curr Top Med Chem. 2006;6(11):1071-89. Review.

Snegaroff et al., "Direct metallation of thienopyrimidines using a mixed lithium-cadmium base and antitumor activity of functionalized derivatives," *Org. Biomol. Chem.*, 7(22):4782-4788 (2009).

Souza, R. F., Shewmake, K., Terada, L. S. & Spechler, S. J. Acid exposure activates the mitogen-activated protein kinase pathways in Barrett's esophagus. Gastroenterology 122, 299-307 (2002).

Sriskantharajah S., et al., Regulation of experimental autoimmune encephalomyelitis by TPL-2 kinase, J. Immunol. 192 (2014) 3518-3529.

Supuran et al., 2000, "Carbonic anhydrase inhibitors—Part 94. 1,3,4-Thiadiazole-2-sulfonamide derivatives as antitumor agents? ^#", European J. of Medicinal Chemistry, Editions Scientifique, 35(9): 867-874.

Supuran et al., 2001, "Carbonic Anhydrase Inhibitors: Sulfonamides as Antitumor Agents?", Bioorganic & Medicinal Chemistry, 9(3): 703-714.

Sutherlin et al., 2011, "Discovery of a potent, selective, and orally available class I phosphatidylinositol 3-kinase (PI3K)/mammalian target of rapamycin (mTOR) kinase inhibitor (GDC-0980) for the treatment of cancer." J Med Chem. 54(21):7579-87.

Svejda B. et al., "Limitations in small intestinal neuroendocrine tumor therapy by mTor kinase inhibition reflect growth factor-mediated PI3K feedback loop activation via ERK1/2 and AKT." Cancer. Sep. 15, 2011;117(18):4141-54.

Theoclitou et al., "Discovery of (+)-N-(3-aminopropyl)-N-[1-(5-benzyl-3-methyl-4-oxo-[1,2]thiazolo[5,4-d]pyrimidin-6-yl)-2-methylpropyl]-4-methylbenzamide (AZD4877), a kinesin spindle protein inhibitor and potential anticancer agent," *J. Med. Chem.*, 54(19):6734-6750 (2011).

Tominaga et al., "Synthesis and Reaction of 3, 4-Diaminothiophenes," *Yakugaku Zasshi*,99(11):1081-1090 (1979) with English abstract.

Toney et al., "Antibiotic sensitization using biphenyl tetrazoles as potent inhibitors of Bacteroides fragilis metallo-beta-lactamase," *Chem. Biol.*, 5(4):185-196 (1998).

Trujillo, 2011, "MEK inhibitors: a patent review 2008-2010", Expert Opinion on Therapeutic Patents, 21(7): 1045-1069.

Tsuboi et al., "Potent and selective inhibitors of glutathione S-transferase omega 1 that impair cancer drug resistance," *J. Am. Chem. Soc.*, 133(41):16605-16616 (2011).

Turkmen et al., 2005, "Carbonic anhydrase inhibitors. Novel sulfanilimide/acetazolamide derivatives obtained by the tail approach and their interaction with the cytosolic isozymes I and II, and the tumor-associated isozyme IX", Bioorganic & Medicinal Chemistry Letters, 15(2): 367-372.

Vairaktaris E. et al., "Diabetes and oral oncogenesis." Anticancer Res. Nov.-Dec. 2007;27(6B):4185-93. Review.

Vasan et al., "Inhibitors of the salicylate synthase (MbtI) from *Mycobacterium tuberculosis* discovered by high-throughput screening," *ChemMedChem*, 5(12):2079-2087 (2010).

Vigil et al., "Ras superfamily GEFs and GAPs: validated and tractable targets for cancer therapy?," *Nat. Rev. Cancer*, 10(12):842-857 (2010).

Vlaeminck-Guillem V. et al., "SRC: marker or actor in prostate cancer aggressiveness." Front Oncol. Aug. 18, 2014;4:222.

Vougioukalaki M., et al., Eliopoulos, Tpl2 kinase signal transduction in inflammation and cancer, Cancer Lett. 304 (2011) 80-89.

Vyas et al., "Pharmacophore and docking-based hierarchical virtual screening for the designing of aldose reductase inhibitors: synthesis and biological evaluation," *Med. Chem. Res.*, 25(4):609-626 (2016).

Wang et al., "Inhibition of tumor cell proliferation by thieno[2,3-d]pyrimidin-4(1H)-one-based analogs," *Bioorg. Med. Chem. Lett.*, 15(16):3763-3766 (2005).

Wang L, et al., "MicroRNA-302b suppresses cell proliferation by targeting EGFR in human hepatocellular carcinoma SMMC-7721 cells." BMC Cancer, 2013; 13:448.

Wei et al., "Anenvironment-friendly synthesis of 4(3H)-quinazolinones," *Toxicol. Environ. Chem.*, 97(1):2-10 (2015).

Westerlund, "The synthetic utility of heteroaromatic azido compounds. Part VII. Preparation of some 2- and 4-substituted thieno[3,2-d]pyrimidines," *J. Heterocyclic Chem.*, 17(8):1771-1775 (1980).

Wick, G. et al., Autoimmune and Inflammatory Mechanisms in Atherosclerosis. Annu. Rev. Immunol. 22, 361-403 (2004).

(56) References Cited

OTHER PUBLICATIONS

Williams, "Reverse fingerprinting, similarity searching by group fusion and fingerprint bit importance," *Mol. Divers.*, 10(3):311-332 (2006).
Williams, B., Granholm, A.-C. & Sambamurti, K. Age-dependent loss of NGF signaling in the rat basal forebrain is due to disrupted MAPK activation. Neurosci. Lett. 413, 110-114 (2007).
Wong, W. F. Inhibitors of the tyrosine kinase signaling cascade for asthma. Curr. Opin. Pharmacol. 5, 264-271 (2005).
Wu and Park, "MEK1/2 Inhibitors: Molecular Activity and Resistance Mechanisms." Semin Oncol. Dec. 2015;42(6):849-62.
Wu et al., "Cyclooxygenase-2 in tumorigenesis of gastrointestinal cancers: an update on the molecular mechanisms." Cancer Lett. Sep. 1, 2010;295(1):7-16.
Xia et al., 2010, "Synthesis and biological activity test of some new five membered heterocycles", Chinese J. of Chemistry, 28(12): 2433-2440.
Yamamoto R. et al., "B7-H1 expression is regulated by MEK/ERK signaling pathway in anaplastic large cell lymphoma and Hodgkin lymphoma." Cancer Sci. Nov. 2009;100(11):2093-100.
Yang et al., "Synthesis and biological evaluation of novel thieno[2,3-d]pyrimidine-based FLT3 inhibitors as anti-leukemic agents," *Eur. J. Med. Chem.*, 85:399-407 (2014).
Yin D, et al., "mi-R-34a functions as a tumor suppressor modulating EGFR in glioblastoma multiforme." Oncogene 2013; 32:1155-63.
Yurchenko and Sidorenko, "Hodgkin's lymphoma: the role of cell surface receptors in regulation of tumor cell fate." Exp Oncol. Dec. 2010;32(4):214-23. Review.
Zadorozhny et al., "Condensed isoquinolines 32. Synthesis of 4H-thieno-[3',2':5,6]-and-[2',3':5,6]pyrimido-[1,2-b]isoquinolines and 6,12-dihydro-5H-isoquino-[2,3-a]quinazoline-5,12-dione derivatives," *Chem. Heterocycl. Comp.*, 44(7):845-851 (2008).
Zadorozhny et al., "Synthesis of substituted 4-oxo-3,4-dihydro-thieno[3,4-d]pyrimidines and comparison of their properties with those of positionally isomeric thienopyrimidinones and benzo isosteres," *Chem. Heterocycl. Comp.*, 46(8):991-997 (2010).
Zaganjor et al., 2011, "Functions and modulation of MAP kinase pathways", Tocris Reviews, No. 35 (http:komabiotech.co.kr/pdf/mapk_signaling_review.pdf), 12 pages.
Zebisch A, et al., "Signaling through RAS-RAF-MEK-ERK: from basics to bedside." Curr Med Chem. 2007;14(5):601-23. Review.
Zenali M., et al., "Morphoproteomic confirmation of constitutively activated mTOR, ERK, and NF-kappaB pathways in Ewing family of tumors." Ann Clin Lab Sci. 2009 Spring;39(2):160-6. Review.
Zhang, H. Y. et al. Differences in activity and phosphorylation of MAPK enzymes in esophageal squamous cells of GERD patients with and without Barrett's esophagus. Am. J. Physiol.-Gastrointest. Liver Physiol. 295, G470-G478 (2008).
Zhao and Ramaswamy, "Mechanisms and therapeutic advances in the management of endocrine-resistant breast cancer." World J Clin Oncol. Aug. 10, 2014;5(3):248-62.
Zhou and Qi, "Larynx carcinoma regulates tumor-associated macrophages through PLGF signaling." Sci Rep. May 11, 2015;5:10071.
Zhu et al., "In-Water Synthesis of Quinazolinones from 1,1-Dichloro-2-nitroethene and Anthranilamides," *Synlett*, 27(14):2167-2170 (2016).
Pagare et al., "1,2,4-triazole—a versatile azole, proves and popular as an antifungal agent," Int. J. Chem. Concepts, 2(2):132-144 (2016).
Miyamoto, Antitumor activity of 5-substituted 2-acylamino-1,3,4-thiadiazoles against transplantable rodent tumors, Chem. Pharm. Bull., 33(11):5126-5129 (1985).
Iyer et al., "Synthesis of 1,3,4-oxadizoles as promising anticoagulant agents," RSC Adv., 6:24797-24807 (2016).
Al-Zaydi et al., "Microwave assisted reaction of condensed thiophenes with electron poor olefins," *J. Korean Chem. Soc.*, 47(6):591-596 (2003).
Dolly et al., "Phase I study of apitolisib (GDC-0980), dual phosphatidylinositol-3-kinase and mammalian target of rapamycin kinase inhibitor, in patients with advanced solid tumors," Clin. Cancer Res., 22(12):2874-2884 (2016). Abstract Only.
Muranen et al., "ERK and p38 MAPK activities determine sensitivity to P13K/mTOR inhibition via regulation of MYC and YAP," *Cancer Res.*, 76(24):7168-7180 (2016). Abstract Only.
Muranen et al., "ERK and p38 MAPK activities determine sensitivity to P13K/mTOR inhibition via regulation of MYC and YAP," Cancer Res., 76(24):7168-7180 (2016).
Anastassiadis et al., "A Highly Selective Dual Insulin Receptor (IR)/insulin-like Growth Factor 1 Receptor (IGF-1R) Inhibitor Derived From an Extracellular Signal-Regulated Kinase (ERK) Inhibitor," J. Biol. Chem., 28(29):26068-28077 (2013).
Arnst et al., "Discovery and characterization of small molecule Rac1 inhibitors," *Oncotarget*, 8(21):34586-34600 (2017).
Briel et al., "Selective nucleophilic replacement of the benzylsulfanyl group in 2,4-disulfanyl-substituted thieno[2,3-d ]pyrimidin-6-carboxylic acid derivatives by secondary amines," *J. Heterocylic Chem.*, 42(5):841-846 (2005).
Collin et al., "Discovery of Rogaratinib (BAY 1163877): A pan-FGFR Inhibitor," Chem. Med. Chem., 13(5):437-445 (2018).
Feuerstein et al., "Characterisation of the metal-ion-GDP complex at the active sites of transforming and nontransfoiming p21 proteins by observation of the $^{17}$ O-Mn superhyperfine coupling and by kinetic methods," *Eur. J. Biochem.*, 162:49-55 (1987).
Garg et al., "Identification of new insulin growth factor receptor-1 (IGF-1R) inhibitors via exploring ATPas kinase domain of IGF-1R through virtual screening," *Med. Chem. Res.*, 26:205-219 (2017).
Harikrishnan et al., "Heterobicyclic Inhibitors of Transforming Growth Factor Beta Receptor I (TGFβRI)," Bioorg. Med. Chem., 26(5):1026-1034 (2018).
John et al., "Kinetic and structural analysis of the Mg2+-binding site of the guanine nucleotide-binding protein $p21^{H\text{-}ras}$," *J. Bio. Chem.*, 268(2):923-929 (1993).
John et al., "Kinetics of interaction of nucleotides with nucleotide-free H-ras p21," *Biochem.*, 29:6058-6065 (1990).
Karnoub et al., "Ras oncogenes: split personalities," *Nat. Rev. Mol. Cell Biol.*, 9(7):517-531 (2008).
Kim et al., "Structural modifications at the 6-position of thieno[2,3-d]pyrimidines and their effects on potency at FLT3 for treatment of acute myeloid leukemia," *Eur. J. Med. Chem.*, 120:74-85 (2016).
Lorusso et al., "One step at a time—clinical evidence that KRAS is indeed druggable," *N. Engl. J. Med.*, doi: 10.1056/NEJMe202637, Epub Sep. 20, 2020.
Oh et al., "Synthetic strategy for increasing solubility of potential FLT3 inhibitor thieno [2,3-d]pyrimidine derivatives through structural modifications at the C2 and C6 positions," *Bioorg. Med. Chem. Lett.*, 27:496-500 (2017).
Ostrem et al., "Direct small-molecule inhibitors of KRAS: from structural insights to mechamsm-based design," *Nature Reviews Drug Discovery*, doi:10.1038/nrd.2016.139, pp. 1-25 (2016).
Pace et al., "Dihydroxypyrimidine-4-carboxamides as Novel Potent and Selective HIV Integrase Inhibitors," *J. Med. Chem.*, 50:2225-2239 (2007).
Papke et al., "Drugging RAS: know the enemy," *Science*, 355:1158-1163 (2017).
Sampognaro et al., "Proline Isosteres in a Series of 2,4-disubstituted pyrrolo[1,2-f][1,2,4]triazine Inhibitors of IGF-1R Kinase and IR Kinase," *Bioorg. Med. Chem. Lett.*, 20(17):5027-5030 (2010).
Sasikumar et al., "A-ring Modifications on the Triazafluorenone Core Structure and Their mGluR1 Antagonist Properties," Bioorg. Med. Chem. Lett., 20(8):2474-2477 (2010).
Shutes et al., "Specificity and mechanism of action of EHT 1864, a novel small molecule inhibitor of Rac family small GTPases," *J. Biol. Chem.*, 282(49):35666-35678 (2007).
Stephen et al., "Dragging Ras back in the ring," *Cancer Cell*, 25:272-281 (2014).
Bivona et al., "Analysis of Ras and Rap activation in living cells using fluorescent Ras binding domains," Methods 37:138-145 (2005).
Kopra et al., "A homogeneous quenching resonance energy transfer assay for the kinetic analysis of the GTPase nucleotide exchange reaction," Anal. Bioanal. Chem., 406:4147-4156 (2014).
Lenzen et al., "Kinetic analysis by fluorescence of the interaction between Ras and the catalytic domain of the guanine nucleotide exchange factor Cdc25," Biochem., 37:7420-7430 (1998).

(56) References Cited

OTHER PUBLICATIONS

Smith et al., "Activating K-Ras mutations outwith 'hotspot' codons in sporadic colorectal tumours—implications for personalised cancer medicine," *Br. J. Cancer*, 102:693-703 (2010).
Spangler et al., "Kinetic determination of the GTPase activity of Ras proteins by means of a luminescent terbium complex," Anal. Bioanal. Chem., 394:989-996 (2009).
Lu, et al., "Drugging Ras GTPase: a comprehensive mechanistic and signaling structural view," Chem. Soc. Rev., 45(18):4929-4592 (2016). DOI: 10.1039/c5cs00911a (Year: 2016).
Juszczak, Bioorg. & Med. Chem. Lett., 22:5466-5469 (2012).
Welsch M.E. et al. "Multivalent Small-Molecule Pan-RAS Inhibitors" 2017, Cell 168, 878-889, Feb. 23, 2017 a 2017 Elsevier Inc, http://dx.doi.org/10.1016/j.cell.2017.02.006.
Penultimate Official Action dated Oct. 5, 2021 in corresponding Japanese Application No. 2018-533689 (with English translation).
RN 1082254-06-5 Registry, Database Registry [Online], Retrieved from STN, Dec. 9, 2008, retrieved on Sep. 16, 2020.
RN 1082254-09-8 Registry, Database Registry [Online], Retrieved from STN, Dec. 9, 2008, retrieved on Sep. 16, 2020.
RN 1082254-12-3 Registry, Database Registry [Online], Retrieved from STN, Dec. 9, 2008, retrieved on Sep. 16, 2020.
RN 1082254-15-6 Registry, Database Registry [Online], Retrieved from STN, Dec. 9, 2008, retrieved on Sep. 16, 2020.
RN 1082436-68-7 Registry, Database Registry [Online], Retrieved from STN, Dec. 9, 2008, retrieved on Sep. 16, 2020.
RN 1082436-69-8 Registry, Database Registry [Online], Retrieved from STN, Dec. 9, 2008, retrieved on Sep. 16, 2020.
RN 1082436-71-2 Registry, Database Registry [Online], Retrieved from STN, Dec. 9, 2008, retrieved on Sep. 16, 2020.
RN 1082436-72-3 Registry, Database Registry [Online], Retrieved from STN, Dec. 9, 2008, retrieved on Sep. 16, 2020.
RN 1082436-73-4 Registry, Database Registry [Online], Retrieved from STN, Dec. 9, 2008, retrieved on Sep. 16, 2020.
RN 1082466-26-9 Registry, Database Registry [Online], Retrieved from STN, Dec. 9, 2008, retrieved on Sep. 16, 2020.
RN 1082466-31-6 Registry, Database Registry [Online], Retrieved from STN, Dec. 9, 2008, retrieved on Sep. 16, 2020.
RN 1082466-33-8 Registry, Database Registry [Online], Retrieved from STN, Dec. 9, 2008, retrieved on Sep. 16, 2020.
RN 1082466-37-2 Registry, Database Registry [Online], Retrieved from STN, Dec. 9, 2008, retrieved on Sep. 16, 2020.
RN 1082466-38-3 Registry, Database Registry [Online], Retrieved from STN, Dec. 9, 2008, retrieved on Sep. 16, 2020.
RN 1082530-53-7 Registry, Database Registry [Online], Retrieved from STN, Dec. 9, 2008, retrieved on Sep. 16, 2020.
RN 1082530-59-3 Registry, Database Registry [Online], Retrieved from STN, Dec. 9, 2008, retrieved on Sep. 16, 2020.
RN 1082530-61-7 Registry, Database Registry [Online], Retrieved from STN, Dec. 9, 2008, retrieved on Sep. 16, 2020.
RN 1159822-04-4 Registry, Database Registry [Online], Retrieved from STN, Jun. 24, 2009, retrieved on Sep. 16, 2020.
RN 1248137-85-0 Registry, Database Registry [Online], Retrieved from STN, Oct. 28, 2010, retrieved on Sep. 16, 2020.
RN 1248693-25-5 Registry, Database Registry [Online], Retrieved from STN, Oct. 29, 2010, retrieved on Sep. 16, 2020.
RN 1248913-17-8 Registry, Database Registry [Online], Retrieved from STN, Nov. 1, 2010, retrieved on Sep. 16, 2020.
RN 1248997-75-2 Registry, Database Registry [Online], Retrieved from STN, Oct. 31, 2010, retrieved on Sep. 16, 2020.
RN 1285166-39-3 Registry, Database Registry [Online], Retrieved from STN, Apr. 24, 2011, retrieved on Sep. 16, 2020.
RN 1484414-46-1 Registry, Database Registry [Online], Retrieved from STN, Dec. 1, 2013, retrieved on Sep. 16, 2020.
RN 1489808-81-2 Registry, Database Registry [Online], Retrieved from STN, Dec. 8, 2013, retrieved on Sep. 16, 2020.
RN 1517154-38-9 Registry, Database Registry [Online], Retrieved from STN, Jan. 12, 2014, retrieved on Sep. 16, 2020.

* cited by examiner

COMPOUNDS THAT INTERACT WITH THE RAS SUPERFAMILY FOR THE TREATMENT OF CANCERS, INFLAMMATORY DISEASES, RASOPATHIES, AND FIBROTIC DISEASE

This application is a continuation of U.S. application Ser. No. 17/143,077, filed Jan. 6, 2021, which is further a divisional of U.S. patent application Ser. No. 16/847,467, filed Apr. 13, 2020, now U.S. Pat. No. 11,026,930, which is a continuation of U.S. patent application Ser. No. 16/654,934, filed Oct. 16, 2019, now U.S. Pat. No. 10,940,139, which is a continuation of U.S. patent application Ser. No. 16/013,872, filed Jun. 20, 2018, now U.S. Pat. No. 10,588,894, which claims the benefit of U.S. Provisional Patent Application No. 62/523,114, filed Jun. 21, 2017, the entire contents of each of which are incorporated herein by reference.

1. FIELD

Provided herein are compositions and methods for treating cancers, inflammatory diseases, rasopathies, and fibrotic disease resulting from aberrant Ras signaling involving Ras, Rac, Rho, and Cdc42 members of the Ras superfamily of proteins through the binding of compounds to the GTP binding domain of these molecules.

2. BACKGROUND

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. (Roitt, I., Brostoff, J. and Kale, D., *Immunology,* 17.1-17.12 (3rd ed., Mosby, St. Louis, Mo., 1993))

Various stages of tumor development can be described generally as follows:

a) Tumor evolution commences when a cell within a normal population sustains a genetic mutation that expands its tendency to proliferate.

b) Such genetically altered cells and their offspring continue to appear normal, but they reproduce excessively and lead to a condition termed hyperplasia. The altered cells may also secrete signaling factors or other molecules that cause changes in their local cellular and extracellular environment, including without limitation, the response of the immune system to them. Such environmental effects may in turn affect the viability, proliferation, and further mutations of the altered cells. After some time (months or years) a very small fraction of these altered cells may sustain additional mutation with subsequent loss of control of cell growth and further potential effects on their environment.

c) The offspring of these cells not only proliferate excessively but also appear abnormal in shape and in orientation. The tissue is now said to exhibit a condition termed dysplasia. After some time, one or more additional mutations may further alter cell behavior and the effect of the cells on their environment.

d) The influenced and genetically altered cells turn still more abnormal in growth and appearance. If the tumor mass does not invade through any boundaries between tissues, it is termed an in situ tumor. This tumor may stay contained indefinitely, however, some cells may acquire still more mutations.

e) A malignant or invasive tumor results if the genetic changes allow the tumor mass to initiate invading underlying tissue and to cast off cells into the blood or lymph. The defector cells may install new tumors loci (metastases) throughout the body.

Metastases represent the end products of a multistep cell-biological process termed the invasion-metastasis cascade, which involves dissemination of cancer cells to anatomically distant organ sites and their subsequent adaptation to foreign tissue microenvironments. Each of these events is driven by the acquisition of genetic and/or epigenetic alterations within tumor cells and the co-option of non-neoplastic stromal cells, which together endow incipient metastatic cells with traits needed to generate macroscopic metastases. (Volastyan, S., et al., *Cell,* 2011, vol. 147, 275-292)

An enormous variety of cancers affect different tissues throughout the body, which are described in detail in the medical literature. Over 85% of human cancers are solid tumors, including carcinomas, sarcomas and lymphomas. Different types of solid tumors are named for the type of cells that form them. Examples include cancer of the lung, colon, rectum, pancreatic, prostate, breast, brain, and intestine. Other human tumors derive from cells involved in the formation of immune cells and other blood cells, including leukemias and myelomas.

The incidence of cancer continues to climb as the general population ages, as new cancers develop, and as susceptible populations grow. A tremendous demand therefore exists for new methods and compositions that can be used to treat subjects with cancer.

Methods of Treating Cancer

Current cancer therapy may involve surgery, chemotherapy, hormonal therapy, biological therapy, targeted therapy, immunotherapy and/or radiation treatment to eradicate neoplastic cells in a patient (see, e.g., Stockdale, 1998, *Medicine*, vol. 3, Rubenstein and Federman, eds., Chapter 12, Section IV; and Baudino T A "Targeted Cancer Therapy: The Next Generation of Cancer Treatment", Curr Drug Discov Technol. 2015; 12(1):3-20).

Such therapies may be used independently or in combinations. Choices of therapy will depend on the history and nature of the cancer, the condition of the patient, and, under the circumstances, the anticipated efficacy and adverse effects of the therapeutic agents and methods considered.

With respect to chemotherapy, there are a variety of chemotherapeutic agents and methods of delivery of such agents available for the treatment of different cancers. Most first generation chemotherapeutic agents were not tumor specific, have broad systemic effects, are toxic, and may cause significant and often dangerous side effects, including severe nausea, bone marrow depression, and immunosuppression.

Additionally, even with administration of combinations of chemotherapeutic agents, many tumor cells are or become resistant to chemotherapeutic agents. In fact, cells resistant to the particular chemotherapeutic agents used in a treatment protocol often prove to be resistant to other drugs, even if those agents act by different mechanism from those of the drugs used in the specific treatment. This phenomenon is referred to as multidrug resistance. Because of drug resistance, many cancers prove refractory to standard chemotherapeutic treatment protocols.

Thus, there exists a significant need for alternative compounds, compositions and methods for treating, preventing and managing cancer.

Further, whereas surgical resection and adjuvant therapy can cure well-confined primary tumors, metastatic disease is largely incurable because of its systemic nature and the resistance of disseminated tumor cells to existing therapeutic agents. This explains why greater than 90% of mortality from cancer is attributable to metastases, not the primary tumors from which these malignant lesions arise.

Pathobiology of Inflammatory Disease

Inflammation is a complex protective biological response of body tissues to harmful stimuli, such as pathogens, damaged cells, or irritants, involving immune cells, blood vessels, and molecular mediators. The function of inflammation is to eliminate the initial cause of cell injury, clear out necrotic cells and tissues damaged from the original insult and the inflammatory process, and to initiate tissue repair. (Ferrero-Miliani L, Nielsen O H, Andersen P S, Girardin S E; Nielsen; Andersen; Girardin (February 2007) *Clin. Exp. Immunol.* 147)

Inflammation is classified as either acute or chronic. Acute inflammation is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue.

Prolonged inflammation, known as chronic inflammation, is characterized by simultaneous destruction and healing of the tissue from the inflammatory process. It leads to a progressive shift in the type of cells present at the site of inflammation, such as mononuclear cells, and increases in systemic concentrations of cytokines such as TNF-α, IL-6, and CRP. (Petersen, A. M.; Pedersen, B. K. (2005). *J Appl Physiol.* 98 (4): 1154-1162)

Many proteins are involved in inflammation. Any of them are susceptible to genetic mutation which may impair or otherwise dysregulate their normal function and expression.

Methods of Treating Inflammatory Disease

Both small molecules and biologics are used to treat inflammatory diseases. Most treatments, however, are largely palliative.

A clear unmet medical need remains to find treatments that can mechanistically reduce chronic inflammatory diseases.

Pathobiology of Fibrotic Disease

Fibrosis, or the accumulation of extracellular matrix molecules that constitute scar tissue, is a common result of tissue injury. Pulmonary fibrosis, renal fibrosis, and hepatic cirrhosis are among the common fibrotic diseases which altogether represent a large unmet medical need. (Friedman S L, Sheppard D, Duffield J S, Violette S. Sci Transl Med January 9; 5(167)

Mechanisms of fibrogenesis include inflammatory as well as other pathways and generally involve reorganization of the actin cytoskeleton of affected cells, including epithelial cells, fibroblasts, endothelial cells, and macrophages.

Actin filament assembly and actomyosin contraction are directed by the Rho-associated coiled-coil forming protein kinase (ROCK) family of serine/threonine kinases (ROCK1 and ROCK2) and thus Rho is associated with fibrogenesis.

Tissue fibrosis is a leading cause of morbidity and mortality. 45% of deaths in the United States are attributable to fibrotic disorders. (Wynn T A. "Fibrotic Disease and the TH1/TH2 Paradigm." Nat Rev Immunol 2004 August: 4(8): 583-594.) Treatments are generally palliative.

Idiopathic pulmonary fibrosis (IPF) is characterized by progressive lung scarring, short median survival, and limited therapeutic options, creating great need for new pharmacologic therapies. It is thought to result from repetitive environmental injury to the lung epithelium.

Targeted Therapy of Cancer, Inflammatory, and Fibrotic Diseases

Targeted therapies are a cornerstone of what is also referred to as precision medicine, a form of medicine that uses information about a person's genes and proteins to prevent, diagnose, and treat disease. Such therapeutics are sometimes called "molecularly targeted drugs," "molecularly targeted therapies," or similar names. The process of discovering them is often referred to as "rational drug design."

A series of actions among molecules in a cell that leads to a certain end point or cell function is referred to as a molecular pathway.

Molecularly targeted drugs interact with a particular target molecule, or structurally related set of target molecules, in a pathway; thus modulating the endpoint effect of that pathway, such as a disease-related process; and, thus, yielding a therapeutic benefit.

Molecularly targeted drugs may be small molecules or biologics, usually antibodies. They may be useful alone or in combinations with other therapeutic agents and methods.

Because they target a particular molecule, or related set of molecules, and are usually designed to minimize their interactions with other molecules, targeted therapeutics may have fewer adverse side effects.

Targeted cancer drugs block the growth and spread of cancer by interacting with specific molecules or sets of structurally related molecules (altogether, "molecular targets") that are involved, broadly speaking, in the growth, progression, lack of suppression or elimination, or spread of cancer. Such molecular targets may include proteins or genes involved in one or more cellular functions including, for example and without limitation, signal transduction, gene expression modulation, apoptosis induction or suppression, angiogenesis inhibition, or immune system modulation.

In some cases, the development of targeted cancer therapeutics involves identifying genes or proteins that are present in cancer cells but not normal cells or that are more abundant or more highly stimulated in cancer cells, especially if they are known to be involved in cancer processes, and then discovering agents that will interact with those targets and be associated with a desired therapeutic effect.

Targeted cancer therapies generally differ from standard cancer chemotherapy in several ways:

a. Targeted therapies are deliberately chosen or designed to interact with their target(s), whereas many standard chemotherapies were identified because they were found in general to kill cells.

b. Targeted therapies are intended to act on specific molecular targets that are associated with cancer, whereas most standard chemotherapies act on all rapidly dividing normal and cancerous cells. They may, however, also have known and sometime unknown interactions with other molecules, so-called off-target effects.

c. Most targeted therapies are cytostatic (that is, they block tumor cell proliferation), whereas standard chemotherapy agents are usually cytotoxic (that is, they kill tumor cells). However, some targeted therapies such as Antibody Drug Conjugates are cytotoxic.

Targeted therapy monoclonal antibodies (mAbs) and targeted small molecules are being used as treatments for inflammatory diseases (Kotsovilis S, Andreakos E., *Methods Mol Biol.* 2014; 1060:37-59). They are used either as a monotherapy or in combination with other conventional therapeutic modalities, particularly if the disease under treatment is refractory to therapy using solely conventional techniques.

Some treatments for fibrotic disorders, such as idiopathic pulmonary fibrosis, hepatic fibrosis, and systemic sclerosis, target inflammatory pathways.

The Ras GTPase Family

The Ras superfamily of proteins are small GTPases with substantial amino acid sequence homology that act as signal transducers between cell surface receptors and several intracellular signaling cascades. These molecules are involved in the regulation of such essential cellular functions as cell survival, proliferation, motility, and cytoskeletal organization (see Karnoub et al., *Nat. Rev. Mol. Cell Biol.,* 9: 517-531 (2008)).

Research has defined a number of subfamilies of the Ras superfamily, based largely on amino acid sequence homologies. These subfamilies are often referred to in an abbreviated manner based on the most commonly studied member of the class.

The GTP binding domains of one subfamily of the Ras superfamily having substantial sequence homology is commonly referred to as the Ras family or Ras.

There are four isoforms of Ras proteins, expressed from three different genes: H-Ras (Harvey sarcoma viral oncogene), N-Ras (neuroblastoma oncogene), and the splice variants K-Ras4A and K-Ras4B (Kirsten sarcoma viral oncogene) (see Karnoub et al., supra).

The GTP binding domains of another subfamily of the Ras superfamily having substantial sequence homology, is commonly referred to as the Rho family and includes proteins and groups of proteins referred to as Rho, Rac and Cdc42.

Ras Function and Pathways

All Ras isoforms share sequence identity in all of the regions that are responsible for GDP/GTP binding, GTPase activity, and effector interactions, suggesting a functional redundancy. However, studies clearly demonstrate that each Ras isoform functions in a unique, different way from the other Ras proteins in normal physiological processes as well as in pathogenesis (Quinlan et al., *Future Oncol.,* 5: 105-116 (2009)).

Ras proteins cycle between ‘on’ and ‘off’ conformations that are conferred by the binding of GTP and GDP, respectively. Under physiological conditions, the transition between these two states is regulated by guanine nucleotide exchange factors (GEFs), which promote the activation of Ras proteins by stimulating the exchange of GDP for GTP exchange, and by GTPase-activating proteins (GAPs), which accelerate Ras-mediated GTP hydrolysis to GDP.

Several cell surface receptors activate Ras, such as Receptor Tyrosine Kinases (RTKs), growth factor receptors, cytokine receptors and integrins.

Once activated, Ras initiates signaling of the “MAPK pathway” (also referred to as the Ras-RAF-MEK-MAPK/ERK pathway) that affects cell growth, differentiation, proliferation, apoptosis and migration. It is also associated with other molecular pathways including phosphoinositide 3-kinases (PI3Ks), Rac1 GEF, and the Ral-guanine nucleotide dissociation stimulator (GDS).

The MAPK pathway operates through a sequence of interactions among kinases. Activated by Ras in the “on”, GTP bound, state, a MAPK kinase kinase (MAPK3), such as Raf, MLK, or TAK, phosphorylates and activates a MAPK kinase, such as MEK, which then phosphorylates and increases the activity of one or more MAPKs, such as ERK1/2. PI3K is part of the PI3K/AKT/mTOR pathway regulating intracellular signaling important for several cellular functions such as survival, anti-apoptotic and cell cycle.

Ras Dysfunction is Causally Associated with Important Diseases and Disease Processes Ras and its downstream pathways, including MAPK, have been studied extensively. They are causally associated with a range of diseases, including certain cancers, inflammatory disorders, Ras-associated autoimmune leukoproliferative disorder, and certain Rasopathies.

There is more than one distinct route to aberrant Ras activation including mutational activation of Ras itself, excessive activation of the wild-type protein through upstream signaling, and loss of a GAP function that is required to terminate activity of the protein.

One million deaths per year are attributed in the literature to mutations in K-Ras alone. (Frank McCormick. “K-Ras protein as a drug target.” *Journal of Molecular Medicine* (Berlin) 2016: 94: 253-258)

Ras is well documented in the literature as an oncogene. Ras oncogenes can initiate cancer in model organisms. Microinjection studies with antibodies that block Ras activity or block specific mutant alleles of Ras; ablation of K-Ras in mouse models of lung adenocarcinoma or pancreas cancer; and ablation of H-Ras all lead to tumor regression in mouse models.

About 30% (Prior I A, Lewis P D, Mattos C. *Cancer Res.* 2012 May 15; 72(10):2457-67) of human cancers have a mutated Ras protein with the most frequent mutations in residues G12, G13 and Q61. These oncogenic mutations result in impaired GTP hydrolysis and accumulation of Ras in the GTP-bound state leading to increased activation of Ras-dependent downstream effector pathways.

Table 1 summarizes recent data concerning the frequency of K-Ras and N-Ras mutations in an illustrative, but not exhaustive list, of human malignancies.

TABLE 1

| Mutation | Tumor Type | Frequency |
|---|---|---|
| K-Ras | Pancreas | 71% |
| K-Ras | Colon | 35% |
| K-Ras | Small intestine | 35% |
| K-Ras | Biliary tract | 28% |
| K-Ras | Endometrium | 22% |
| K-Ras | Lung | 20% |
| N-Ras | Skin (melanoma) | 20% |
| K-Ras | Cervix | 19% |
| K-Ras | Urinary tract | 16% |

Stephen AG, Esposito D, Bagni RK, McCormick F. *Cancer Cell.* 2014 Mar. 17; 25(3):272-81.

Ras mutants, and in some cases Ras over-activation, are associated in the literature with a wide range of significant cancer associated processes including: cell proliferation, DNA checkpoint integrity, replicative stress related clonal selection, suppression of apoptosis, metabolic reprogramming, autophagy, microenvironment remodeling, immune response evasion, and metastatic processes. The detailed mechanisms, interdependencies, and frequency of these effects across different tumor types and stages of cancer development remain to be elucidated comprehensively.

Proliferative effects associated in the literature with oncogenic Ras include transcriptional upregulation of growth factors; upregulation of growth factor receptor expression; upregulation of integrins that promote proliferation and downregulation of those associated with cellular quiescence; upregulation of transcription factors required for cell cycle entry; acceleration through cell cycle transitions; downregulation of anti-proliferative TGFβ signaling; and the suppression of cyclin-dependent kinase inhibitors.

MAPK signaling has been shown to enhance programmed death-ligand 1 (PD-L1) expression in KRas mutant lung cancer cells and thus Ras mutations are associated with the suppression of immune responses to cancer. (Sumimoto et al., *PLOS One* 2016 November 15; DOI:10.1371/journal-.pone.0166626) Anti-PD-1 and anti-PD-L1 monoclonal antibodies have demonstrated clinical activity against tumors including non-small cell lung cancers.

Ras is also implicated through the MAPK pathways as a cause of a range of pathological inflammatory conditions. In addition to ERK1/2, the MAPKs ERK5, c-Jun N-terminal kinases (JNKs) and p38 isoforms have been shown to be implicated in inflammatory response. (Huang, et al. 2010*, Protein Cell,* 1(3), 218-226)

Ras is causally associated with inflammatory diseases including the following: rheumatoid arthritis (Abreu J R, de Launay D, Sanders M E, Grabiec A M, Sande van de M G, Tak P P, Reedquist K A: The Ras guanine nucleotide exchange factor RasGRF1 promotes matrix metalloproteinase-3 production in rheumatoid arthritis synovial tissue. *Arthritis Res Ther.* 2009, 11: R121-10.1186/ar2785), which is the most common cause of disability (Hootman J M, Brault M W, Helmick C G, Theis K A, Armour B S. Prevalence and most common causes of disability among adults—United States 2005*, MMWR,* 2009, 58(16):421-6); atherosclerosis (Fonarow G (2003), *Cleve. Clin. J. Med.* 70: 431-434); inflammatory bowel disease (IBD), such as Crohn's disease (Ignacio C S, Sandvik A K, Bruland T, Andreu-Ballester J C, *J. Crohns Colitis,* 2017 Mar. 16. doi: 10); ulcerative colitis, spondyloarthropathies, idiopathic pulmonary fibrosis, juvenile arthritis, psoriasis, psoriatic arthritis, and others.

Ras has been causally associated with Ras-associated autoimmune leukoproliferative disorder, a nonmalignant clinical syndrome initially identified in a subset of putative autoimmune lymphoproliferative syndrome (ALPS) patients. (Katherin Calvo, et al. "JMML and RALD (Ras-associated autoimmune leukoproliferative disorder): common genetic etiology yet clinically distinct entities" *Blood,* 2015 Apr. 30; 125(18): 2753-2758)

Aberrant Ras signaling is causally implicated in the family of Rasopathies including neurofibromatosis type 1, Noonan's syndrome, and Costello syndrome.

Ras as a Therapeutic Molecular Target

Interference with Ras superfamily member signaling in cell based and animal models of the aforementioned diseases modulates disease processes.

Ras superfamily proteins, and particularly Ras and downstream pathway elements, have thus long been discussed as theoretical molecular targets for the development of targeted therapeutics. In theory, a molecule could serve as a therapeutic agent in diseases associated with aberrant Ras signaling if it could disrupt such Ras signaling.

In theory, it was recognized that a mechanism for downregulating aberrant Ras signaling could be to interfere with one or more steps in the Ras signaling process involving GTP binding in a manner that left the GTP in other than an "on" configuration. However, while this was a concept in theory, based on two widely accepted findings, it has also long been accepted by the scientific community that it would not be possible to achieve.

GTP and GDP had been found to bind to the GTP binding domain of Ras with single to double digit picomolar affinities.

The cellular concentration of GTP had been found to be substantially in excess of this range.

The widely accepted findings concerning the single to double digit picomolar range of affinities of GTP and GDP for the Ras GTP binding domain were determined by kinetic and filter binding measurements between Ras and radiolabeled GDP and GTP (Feuerstein J, Kalbitzer H R, John J, Goody R S, Wittinghofer A. *Eur. J. Biochem.,* 1987 Jan. 2, 162(1):49-55; and John J, Sohmen R, Feuerstein J, Linke R, Wittinghofer A, Goody R S. *Biochemistry,* 1990 Jun. 26, 29(25):6058-65).

Consistent with these findings, and often citing them, the GTP binding domain of Ras has widely been accepted and reported in preeminent journal editorials, reviews, and research papers to be "undruggable." (Papke B, Der C J., *Science,* 2017 Mar. 17, 355(6330):1158-1163; Stephen A G, Esposito D, Bagni R K, McCormick F, *Cancer Cell,* 2014 Mar. 17, 25(3):272-81; and Ostrem J M, Shokat K M, *Nat. Rev. Drug Discov.,* 2016 November, 15(11):771-785)

Accordingly, research concerning targeted Ras therapeutics has focused on domains of the Ras protein other than the GTP binding site. These include, for example, farnesyltransferase inhibitors (FTIs) that prevent Ras attachment to the inner side of the plasma membrane, and molecules that compete with the interaction of Ras with the exchange factor SOS or downstream effectors.

Thus, it has been thought that a molecule could not be developed to compete with GTP binding to the GTP binding domain of Ras. Compounds that do so, however, would fill a need in the field.

The Rho Family Function and Pathways

The Rho subfamily of the Ras superfamily currently includes approximately 22 proteins most of which scientists commonly divide into subgroups including those referred to as Cdc42, Rac, and Rho. (Boureux A, Vignal E, Faure S, Fort P (2007). "Evolution of the Rho family of ras-like GTPases in eukaryotes". Mol Biol Evol 24 (1): 203-16).

The three most commonly studied members of the Rho subfamily have been Cdc42, Rac1, and RhoA.

The Cdc42 group includes Cdc42, TC10, TCL, Chip, and Wrch-1.

The Rac group includes Rac1, Rac2, Rac3, and RhoG.

The RhoA group includes RhoA, RhoB, and RhoC.

Other Rho subfamily GTPases not included in the Cdc42. Rac, or Rho groups include RhoE/Rnd3, RhoH/TTF, Rif, RhoBTB1, RhoBTB2, Miro-1, Miro-2, RhoD, Rnd1, and Rnd2.

Like other Ras superfamily proteins, the Rho subfamily GTPases cycle between 'on' and 'off' conformations that are conferred by the binding of GTP and GDP, respectively. Under physiological conditions, the transition between these two states is regulated by guanine nucleotide exchange factors (GEFs), which promote the activation of Rho subfamily proteins by stimulating the release of GDP and the binding of GTP, and by GTPase-activating proteins (GAPs), which accelerate Rho subfamily member-mediated GTP hydrolysis to GDP. Guanine nucleotide dissociation inhibitors (GDIs) proteins form a large complex with the Rho protein, helping to prevent diffusion within the membrane and into the cytosol and thus acting as an anchor and allowing tight spatial control of Rho activation.

The Rho subfamily members are intracellular proteins that affect a large number of downstream pathways broadly involving cytoskeleton organization, cell polarity, migration, transcription and proliferation, and, more particularly, membrane and vesicular trafficking, cell cycling, microtubule stability, actin membrane linkages, actin polymerization, myosin phosphorylation, API dependent gene expression, cell adhesion, cell contractility, cell adhesion, and MTOC orientation. (Martin Schwartz. "Rho Signalling at a Glance." Journal of Cell Science. 2004: (117: pp. 5457-5458). and (Bustelo X R, Sauzeau V, Berenjeno I M (2007). "GTP-binding proteins of the Rho/Rac family: regulation, effectors and functions in vivo" BioEssays. 29 (4): 356-370).

Rho Family Dysfunction is Causally Associated with Important Diseases

Rho subfamily GTPases have been reported to contribute to most steps of cancer initiation and progression including the acquisition of unlimited proliferation potential, survival and evasion from apoptosis, angiogenesis, tissue invasion, motility, and the establishment of metastases. (Matteo Parri and Paolo Chiarugi. "Rac and Rho GTPases in Cancer Cell Motility Control." Cell Communication and Signalling. 2010(8:23))

High Rho subfamily protein levels are frequently associated with human tumors. High RhoA levels have been associated with human liver, skin, colon, ovarian, bladder, gastric, esophageal squamous cell, testicular, and breast cancer. High Rho B, C, or H levels have been associated with breast, squamous cell, pancreatic, breast, liver, ovarian, head and neck, prostate, non-small cell lung, and gastric cancers and melanoma metastase. High Rac1 levels have been associated with human testicular, gastric, breast, and squamous cell cancers. High Rac2 or Rac3 have been associated with breast colon, head and neck, and squamous cell cancers. (Matteo Parri and Paolo Chiarugi. "Rac and Rho GTPases in Cancer Cell Motility Control." Cell Communication and Signalling. 2010(8:23). Gain-of-function mutations such as P29S of Rac1 were detected in melanoma, breast, head and neck cancers (Alan J K, Lundquist E A. Mutationally activated Rho GTPases in cancer. Small GTPases. 2013 July-September; 4(3):159-63)

Unlike Ras proteins, which are frequently mutated in cancer (around 30%), Rho subfamily proteins themselves are generally not found to be mutated in cancer. Rather, aberrant activity of Rho subfamily proteins in cancer appears to occur by overexpression of these proteins or by aberrant regulation of molecules that control their activity, such as activation or overexpression of GEFs and inactivation or loss of GAPs or GDIs (Alan J K, Lundquist E A. Mutationally activated Rho GTPases in cancer. Small GTPases. 2013 July-September; 4(3):159-63).

Interactions between Rac and Rho proteins are believed to modulate certain forms of mesenchymal and amoeboid cell movement associated with cancer.

Rho subfamily associated kinases (ROCK1 and ROCK2) are implicated as mediators of multiple profibrotic processes including those associated with idiopathic pulmonary fibrosis. (Knipe R S, Tager E M, and Liao J K. "The Rho kinases: critical mediators of multiple profibrotic processes and rational targets for new therapies for pulmonary fibrosis." Pharmacol Rev. 2015 67(1):103-17.)

Rho Family Members as Therapeutic Molecular Targets

Given their roles in disease processes, Rho subfamily members have been identified as potential Therapeutic Molecular Targets.

Rho subfamily members have been identified as potential Therapeutic Molecular Targets in cancer.

Rho subfamily members have been identified as potential Therapeutic Molecular Targets in fibrotic disease.

3. SUMMARY

For the first time, the affinity of GTP for the GTP binding domain of K-Ras utilizing a Scintillation Proximity Assay (SPA) and MicroScale Thermophoresis (MST) has been measured and disclosed herein. These methods were not available when Wittinghofer and colleagues (referenced above) undertook their studies.

In SPA and MST studies, it was found and is disclosed herein that the affinity of GTP for the K-Ras GTP binding domain across wild type and mutant K-Ras is in the range of 100-465 nanomolar. This therefore led to the novel, unanticipated conclusion that compounds such as small molecules could be discovered that would bind to a Ras GTP binding domain and compete with the binding of GTP to Ras.

Provided herein is a novel cell-free assay for the identification of small molecules that bind to the GTP binding domain and compete with GTP binding to, for example, wild-type KRas, KRas G12D mutant, KRas G12C mutant, KRas Q61H mutant, KRas G12D/Q61H double mutant, KRas G12C/Q61H double mutant, Rac1 and RhoA proteins.

Utilizing this assay as a screening and analytical tool, over 1000 small molecules are provided that bind competitively with GTP to a Ras GTP binding domain, thereby confirming the significance of the novel and unanticipated binding affinity findings. Provided herein is a method of testing the affinity of a compound for a Ras GTP binding domain comprising the novel assay.

Utilizing this assay, it was also demonstrated that over 1000 small molecules provided herein also bind competitively with GTP to both Rac and Rho GTPase binding domains. Provided herein is a method of testing the affinity of a compound for Rac and Rho GTP binding domains comprising the novel assay.

It is also demonstrated herein in cell-based assays that certain of these molecules inhibit activation of the MAPK pathway and downregulate the proliferation of different human tumors.

It is further demonstrated herein in cell-based assays that certain of these molecules downregulate the excretion of inflammatory cytokines.

It is also demonstrated herein in cell-based assays that certain of these molecules inhibit activation of the MAPK pathway and downregulate the proliferation of different human tumors.

It is further demonstrated herein in cell-based assays that certain of these molecules downregulate the excretion of inflammatory cytokines.

It is also demonstrated herein in cell-based assays that certain of these molecules inhibit activation of the MAPK pathway and downregulate the proliferation of different human tumors.

It is further demonstrated herein in cell-based assays that certain of these molecules downregulate the excretion of inflammatory cytokines.

It has also been discovered and disclosed herein that certain amino acids in the Ras GTP binding domain enable the heretofore unanticipated competitive binding to that domain between compounds, such as small molecules, and GTP. They include the following amino acids: Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146, Lys147, and also Mg202 which is required for GTP binding. They also include the amino acid Gln61.

It has also been discovered and disclosed herein that certain amino acids in the Rac1 GTP binding domain enable the heretofore unanticipated competitive binding to that domain between compounds, such as small molecules, and GTP. They include the following amino acids: Gly12, Ala13, Gly15, Lys16, Thr17, Cys18, Leu19, Phe28, Ile33, Pro34, Val36, Ala59, Thr115, Lys116, Asp118, Leu119, Cys157, Ala159, and also Mg202 which is required for GTP binding.

It has also been discovered and disclosed herein that certain amino acids in the RhoA GTP binding domain enable the heretofore unanticipated competitive binding to that domain between compounds, such as small molecules, and GTP. They include the following amino acids: Gly14, Ala15, Cys16, Gly17, Lys18, Thr19, Cys20, Phe30, Pro31, Glu32, Tyr34, Val35, Pro36, Thr37, Asp59, Lys118, Asp120, Lys162, and also Mg202 which is required for GTP binding.

Therefore, provided herein is a method of inhibiting the function of Ras, comprising administering to a subject a compound which competitively binds to a Ras GTP binding domain. In one embodiment, the compound for use in the method has a binding affinity ($K_d$) to a Ras GTP binding domain of less than 10 μM. In one embodiment, the compound for use in the method has a binding affinity ($K_d$) to a Ras GTP binding domain of less than 1 μM. In one embodiment, the compound for use in the method has a binding affinity ($K_d$) to a Ras GTP binding domain of less than 500 nM. In one embodiment, the compound for use in the method has a binding affinity ($K_d$) to a Ras GTP binding domain of less than 465 nM. In one embodiment, the compound for use in the method has a binding affinity ($K_d$) to a Ras GTP binding domain of less than 270 nM. In one embodiment, the compound for use in the method has a binding affinity ($K_d$) to a Ras GTP binding domain of less than 200 nM. In one embodiment, the compound for use in the method has a binding affinity ($K_d$) to a Ras GTP binding domain of less than 150 nM. In one embodiment, the compound for use in the method has a binding affinity ($K_d$) to a Ras GTP binding domain of less than 100 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain with a binding affinity ($K_d$) of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain with a binding affinity ($K_d$) of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146 and Lys147 or Mg202 in a highly conserved Ras GTP binding domain with a binding affinity ($K_d$) of less than 10 μM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain with a binding affinity ($K_d$) of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain with a binding affinity ($K_d$) of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln 61, Lys117, Asp119, Leu120, Ser145, Ala146 and Lys147 or Mg202 in a highly conserved Ras GTP binding domain with a binding affinity ($K_d$) of less than 10 μM.

In an assay described herein, e.g., a cell-free assay, the compound for use in the method inhibits Ras and has an $IC_{50}$ value of less than 10 μM. In one embodiment, the compound for use in the method inhibits Ras and has an $IC_{50}$ value of less than 1 μM. In one embodiment, the compound for use in the method inhibits Ras and has an $IC_{50}$ value of less than 500 nM. In one embodiment, the compound for use in the method inhibits Ras and has an $IC_{50}$ value of less than 465 nM. In one embodiment, the compound for use in the method inhibits Ras and has an $IC_{50}$ value of less than 270 nM. In one embodiment, the compound for use in the method inhibits Ras and has an $IC_{50}$ value of less than 200 nM. In one embodiment, the compound for use in the method inhibits Ras and has an $IC_{50}$ value of less than 150 nM. In one embodiment, the compound for use in the method inhibits Ras and has an $IC_{50}$ value of less than 100 nM. In one embodiment, the compound for use in the method inhibits Ras with greater than 25% inhibition at 20 μM. In one embodiment, the compound for use in the method inhibits Ras with greater than 50% inhibition at 20 μM. In one embodiment, the compound for use in the method inhibits Ras with greater than 75% inhibition at 20 μM. In one embodiment, the compound for use in the method inhibits Ras with greater than 80% inhibition at 20 μM. In one embodiment, the compound for use in the method inhibits Ras with greater than 85% inhibition at 20 μM. In one embodiment, the compound for use in the method inhibits Ras with greater than 90% inhibition at 20 μM. In one embodiment, the compound for use in the method inhibits Ras with greater than 95% inhibition at 20 μM. In one embodiment, the compound for use in the method inhibits Ras with greater than 99% inhibition at 20 μM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146, Lys147 or Mg202 in a Ras GTP binding domain and inhibits Ras with a corresponding $IC_{50}$ value of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146, Lys147 or Mg202 in a Ras GTP binding domain and inhibits Ras with a corresponding $IC_{50}$ value of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146, Lys147 or Mg202 in a highly conserved Ras GTP binding domain and inhibits Ras with a corresponding $IC_{50}$ value of less than 10 μM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Lys117, Asp119, Leu120, Ser145, Ala146, Lys147 or Mg202 in a highly conserved Ras GTP binding domain and inhibits Ras with greater than 50% inhibition at 20 μM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain and inhibits Ras with a corresponding $IC_{50}$ value of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain and inhibits Ras with a corresponding $IC_{50}$ value of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a highly conserved Ras GTP binding domain and inhibits Ras with a corresponding $IC_{50}$ value of less than 10 μM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a highly conserved Ras GTP binding domain and inhibits Ras with greater than 50% inhibition at 20 μM.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In one embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

Also provided herein is a method of inhibiting the function of Rho, comprising administering to a subject a compound which competitively binds to a Rho GTP binding domain. In one embodiment, the compound for use in the method has a binding affinity ($K_d$) to a Rho GTP binding domain of less than 10 μM. In one embodiment, the compound for use in the method has a binding affinity ($K_d$) to a Rho GTP binding domain of less than 1 μM. In one embodiment, the compound for use in the method has a binding affinity ($K_d$) to a Rho GTP binding domain of less than 500 nM. In one embodiment, the compound for use in the method has a binding affinity ($K_d$) to a Rho GTP binding domain of less than 270 nM. In one embodiment, the compound for use in the method has a binding affinity ($K_d$) to a Rho GTP binding domain of less than 200 nM. In one embodiment, the compound for use in the method has a binding affinity ($K_d$) to a Rho GTP binding domain of less than 150 nM. In one embodiment, the compound for use in the method has a binding affinity ($K_d$) to a Rho GTP binding domain of less than 130 nM. In one embodiment, the compound for use in the method has a binding affinity ($K_d$) to a Rho GTP binding domain of less than 100 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain with a binding affinity ($K_d$) of less than 270 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain with a binding affinity ($K_d$) of less than 130 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain with a binding affinity ($K_d$) of less than 10 μM.

In an assay described herein, e.g., a cell-free assay, the compound for use in the method inhibits Rho and has an $IC_{50}$ value of less than 10 μM. In one embodiment, the compound for use in the method inhibits Rho and has an $IC_{50}$ value of less than 1 μM. In one embodiment, the compound for use in the method inhibits Rho and has an $IC_{50}$ value of less than 500 nM. In one embodiment, the compound for use in the method inhibits Rho and has an $IC_{50}$ value of less than 270 nM. In one embodiment, the compound for use in the method inhibits Rho and has an $IC_{50}$ value of less than 200 nM. In one embodiment, the compound for use in the method inhibits Rho and has an $IC_{50}$ value of less than 150 nM. In one embodiment, the compound for use in the method inhibits Rho and has an $IC_{50}$ value of less than 130 nM. In one embodiment, the compound for use in the method inhibits Rho and has an $IC_{50}$ value of less than 100 nM. In one embodiment, the compound for use in the method inhibits Rho with greater than 25% inhibition at 20 μM. In one embodiment, the compound for use in the method inhibits Rho with greater than 50% inhibition at 20 μM. In one embodiment, the compound for use in the method inhibits Rho with greater than 75% inhibition at 20 μM. In one embodiment, the compound for use in the method inhibits Rho with greater than 80% inhibition at 20 μM. In one embodiment, the compound for use in the method inhibits Rho with greater than 85% inhibition at 20 μM. In one embodiment, the compound for use in the method inhibits Rho with greater than 90% inhibition at 20 μM. In one embodiment, the compound for use in the method inhibits Rho with greater than 95% inhibition at 20 μM. In one embodiment, the compound for use in the method inhibits Rho with greater than 99% inhibition at 20 μM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain and inhibits Rho with a corresponding $IC_{50}$ value of less than 270 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain and inhibits Rho with a corresponding $IC_{50}$ value of less than 130 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain and inhibits Rho with a corresponding $IC_{50}$ value of less than 10 μM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain and inhibits Rho with greater than 50% inhibition at 20 μM.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

Also provided herein is a method of inhibiting the function of Rac, comprising administering to a subject a compound which competitively binds to a Rac GTP binding domain. In one embodiment, the compound for use in the method has a binding affinity ($K_d$) to a Rac GTP binding domain of less than 10 μM. In one embodiment, the compound for use in the method has a binding affinity ($K_d$) to a Rac GTP binding domain of less than 1 μM. In one embodiment, the compound for use in the method has a binding affinity ($K_d$) to a Rac GTP binding domain of less than 500 nM. In one embodiment, the compound for use in the method has a binding affinity ($K_d$) to a Rac GTP binding domain of less than 270 nM. In one embodiment, the compound for use in the method has a binding affinity ($K_d$) to a Rac GTP binding domain of less than 200 nM. In one embodiment, the compound for use in the method has a binding affinity ($K_d$) to a Rac GTP binding domain of less than 170 nM. In one embodiment, the compound for use in the method has a binding affinity ($K_d$) to a Rac GTP binding domain of less than 150 nM. In one embodiment, the compound for use in the method has a binding affinity ($K_d$) to a Rac GTP binding domain of less than 100 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain with a binding affinity ($K_d$) of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain with a binding affinity ($K_d$) of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain with a binding affinity ($K_d$) of less than 10 μM.

In an assay described herein, e.g., a cell-free assay, the compound for use in the method inhibits Rac and has an $IC_{50}$ value of less than 10 μM. In one embodiment, the compound for use in the method inhibits Rac and has an $IC_{50}$ value of less than 1 μM. In one embodiment, the compound for use in the method inhibits Rac and has an $IC_{50}$ value of less than 500 nM. In one embodiment, the compound for use in the method inhibits Rac and has an $IC_{50}$ value of less than 270 nM. In one embodiment, the compound for use in the method inhibits Rac and has an $IC_{50}$ value of less than 200 nM. In one embodiment, the compound for use in the method inhibits Rac and has an $IC_{50}$ value of less than 170 nM. In one embodiment, the compound for use in the method inhibits Rac and has an $IC_{50}$ value of less than 150 nM. In one embodiment, the compound for use in the method inhibits Rac and has an $IC_{50}$ value of less than 100 nM. In one embodiment, the compound for use in the method inhibits Rac with greater than 25% inhibition at 20 μM. In one embodiment, the compound for use in the method inhibits Rac with greater than 50% inhibition at 20 μM. In one embodiment, the compound for use in the method inhibits Rac with greater than 75% inhibition at 20 μM. In one embodiment, the compound for use in the method inhibits Rac with greater than 80% inhibition at 20 μM. In one embodiment, the compound for use in the method inhibits Rac with greater than 85% inhibition at 20 μM. In one embodiment, the compound for use in the method inhibits Rac with greater than 90% inhibition at 20 μM. In one embodiment, the compound for use in the method inhibits Rac with greater than 95% inhibition at 20 μM. In one embodiment, the compound for use in the method inhibits Rac with greater than 99% inhibition at 20 μM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Ras GTP binding domain and inhibits Rac with a corresponding $IC_{50}$ value of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding $IC_{50}$ value of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Ras GTP binding domain and inhibits Rac with a corresponding $IC_{50}$ value of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding $IC_{50}$ value of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rac with a corresponding $IC_{50}$ value of less than 10 μM. In one embodiment, the method of inhibiting the function of Rac, comprises administering to a subject a compound which binds to one or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rho with greater than 99% inhibition at 20 μM.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, provided herein is a method of treating or preventing cancer by administering a compound that inhibits the binding of GTP to the GTP binding domain of one or more members of the Ras superfamily. In one embodiment, provided herein is a method of treating or preventing inflammation by administering a compound that inhibits the binding of GTP to the GTP binding domain of one or more members of the Ras superfamily. In one embodiment, provided herein is a method of treating or preventing a rasopathy by administering a compound that inhibits the binding of GTP to the GTP binding domain of one or more members of the Ras superfamily. In one embodiment, provided herein is a method of treating or preventing fibrotic disease by administering a compound that inhibits the binding of GTP to the GTP binding domain of one or more members of the Ras superfamily. In one embodiment, provided herein is a method of treating or preventing cancer by administering a compound that inhibits the binding of GTP to a Ras GTP binding domain. In one embodiment, provided herein is a method of treating or preventing inflammation by administering a compound that inhibits the binding of GTP to a Ras GTP binding domain. In one embodiment, provided herein is a method of treating or preventing a rasopathy by administering a compound that inhibits the binding of GTP to a Ras GTP binding domain. In one embodiment, provided herein is a method of treating or preventing Ras-associated autoimmune leukoproliferative disorder by administering a compound that inhibits the binding of GTP to a Ras GTP binding domain. In one embodiment, provided herein is a method of treating or preventing fibrotic disease by administering a compound that inhibits the binding of GTP to a Ras GTP binding domain. In one embodiment, provided herein is a method of treating or preventing cancer by administering a compound that inhibits the binding of GTP to a Rho GTP binding domain. In one embodiment, provided herein is a method of treating or preventing inflammation by administering a compound that inhibits the binding of GTP to a Rho GTP binding domain. In one embodiment, provided herein is a method of treating or preventing a rasopathy by administering a compound that inhibits the binding of GTP to a Rho GTP binding domain. In one embodiment, provided herein is a method of treating or preventing fibrotic disease by administering a compound that inhibits the binding of GTP to a Rho GTP binding domain. In one embodiment, provided herein is a method of treating or preventing cancer by administering a compound that inhibits the binding of GTP to a Rac GTP binding domain. In one embodiment, provided herein is a method of treating or preventing inflammation by administering a compound that inhibits the binding of GTP to a Rac GTP binding domain. In one embodiment, provided herein is a method of treating or preventing a rasopathy by administering a compound that inhibits the binding of GTP to a Rac GTP binding domain. In one embodiment, provided herein is a method of treating or preventing fibrotic disease by administering a compound that inhibits the binding of GTP to a Rac GTP binding domain.

Provided herein are compounds which bind to a Ras GTP binding domain and compete with the binding of GTP to Ras. In one embodiment, the compounds also inhibit phosphorylation of MAPK, in particular MAPK1/2, cellular proliferation, secretion of IL-6 or TNF-α cytokines. The compounds provided herein are therefore useful in compositions and methods of treating cancer, inflammatory diseases, Ras-associated autoimmune leukoproliferative disorder and rasopathies.

Provided herein are compounds which bind to a Rac GTP binding domain and compete with the binding of GTP to Rac. In one embodiment, the compounds also inhibit the MAPK signaling pathway. In one embodiment, the compounds also inhibit the ROCK signaling pathway. The compounds provided herein are therefore useful in compositions and methods of treating cancer, inflammatory diseases and fibrotic disease.

Provided herein are compounds which bind to a Rho GTP binding domain and compete with the binding of GTP to Rho. In one embodiment, the compounds also inhibit the MAPK signaling pathway. In one embodiment, the compounds also inhibit the ROCK signaling pathway. The compounds provided herein are therefore useful in compositions and methods of treating cancer, inflammatory diseases and fibrotic disease.

In one embodiment, the compounds provided herein inhibit GTP binding to one or more members of the Ras superfamily. In one embodiment, the compounds provided herein inhibit GTP binding to Ras. In one embodiment, the compounds provided herein inhibit GTP binding to Rho. In one embodiment, the compounds provided herein inhibit GTP binding to Rac. In one embodiment, the compounds provided herein inhibit GTP binding to Ras and Rho. In one embodiment, the compounds provided herein inhibit GTP binding to Ras and Rac. In one embodiment, the compounds provided herein inhibit GTP binding to Rho and Rac. In one embodiment, the compounds provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl) pyrimidin-4(3H)-one, 2-(imidazol-4-yl)pyrimidin-4(1H)-one, 2-(imidazol-4-yl)pyrimidin-4-amine, 2-(imidazol-4-yl) pyrimidin-4(3H)-imine, or 2-(imidazol-4-yl)pyrimidin-4 (1H)-imine moiety.

4. BRIEF DESCRIPTION OF THE DRAWINGS

5. DETAILED DESCRIPTION

5.1. Definitions

Figure 1:
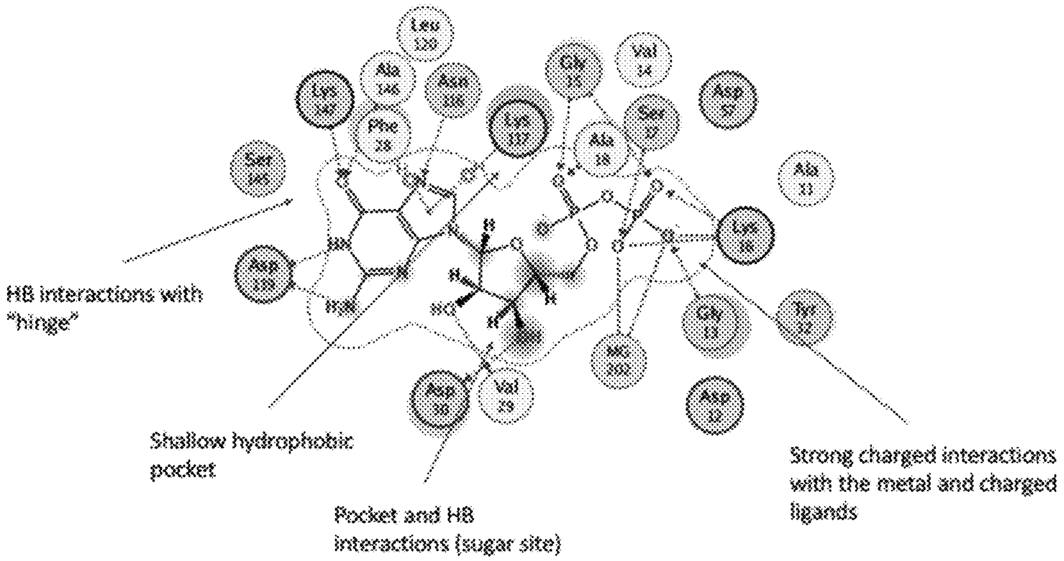
FIG. 1 depicts a crystal structure for GDP bound to the GTP binding site of KRas (PDB code: 4epr).

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro systems designed to test for such activities.

As used herein, pharmaceutically acceptable derivatives of a compound include, but are not limited to, salts, esters, enol ethers, enol esters, acetals, ketals, orthoesters, hemiacetals, hemiketals, acids, bases, clathrates, solvates or hydrates thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is alkyl, alkenyl, alkynyl, aryl, aralkyl and cycloalkyl. Pharmaceutically acceptable enol esters include, but are not limited to, derivatives of formula C═C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating cancer, inflammation or rasopathies.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a subject who has already suffered from the disease or disorder, and/or lengthening the time that a subject who has suffered from the disease or disorder remains in remission. The terms encompass modulating the threshold, development and/or duration of the disease or disorder, or changing the way that a subject responds to the disease or disorder.

As used herein, the $IC_{50}$ refers to an amount, concentration or dosage of a particular test compound that achieves a 50% inhibition of a maximal response in an assay that measures such response.

As used herein, the $K_d$ refers to the measured equilibrium dissociation constant between a compound (or ligand) and a protein (or binding domain of a protein).

As used herein, "Ras superfamily" means the protein superfamily of small guanosine triphosphatases (GTPases) which consists of the five main families Ras, Rho, Rab, Ran and Arf, or mutants thereof. Subfamilies of the five main families are also included, e.g., the Rac subfamily of the Rho main family.

As used herein, "Ras" or "Ras family" or "Ras subfamily" or "Ras group" means DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2, or mutants thereof.

As used herein, "Rho" or "Rho family" or "Rho subfamily" or "Rho group" means RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3; CDC42, or mutants thereof.

As used herein, "Rac" or "Rac family" or "Rac subfamily" or "Rac group" means RAC1; RAC2; RAC3; RHOG, or mutants thereof.

As used herein, "GTP binding site" or "GTP binding domain" both mean the region of a protein which binds GTP, and the surrounding region of said protein in which another compound may bind, wherein such binding blocks the ability of GTP to bind to said protein.

As used herein, "GDP binding site" or "GDP binding domain" both mean the region of a protein which binds GDP, and the surrounding region of said protein in which another compound may bind, wherein such binding blocks the ability of GDP to bind to said protein.

As used herein, "guanosine binding region" means a region of a protein which is part of the GDP binding domain or GTP binding domain, that mediates interaction with the guanosine portion of GDP or GTP.

As used herein, "metal region" means a region of a protein which is part of the GDP binding domain or GTP binding domain, that is proximal to a magnesium (Mg202) binding site.

As used herein, "alternative Tyr32 conformation" means the conformation of the GTP or GDP binding domain in the region of Tyr 32 in KRas crystal structure PDB code:3gft in comparison to the KRas crystal structure PDB code:4epr.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter enzymatic and biological activities of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as chiral reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included. For example, Formula VI includes, but is not limited to, the three tautomeric structures below when $R^5$=H.

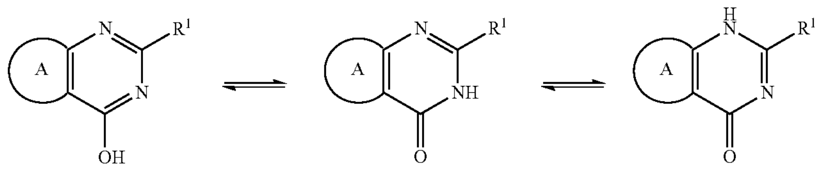

Formula VI
$R^5$ = H

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenyl and hexynyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight or branched aliphatic hydrocarbon group having, inserted in the hydrocarbon chain one or more oxygen, sulfur, including S(═O) and $S(═O)_2$ groups, or substituted or unsubstituted nitrogen atoms, including —NR— and —$N^+$RR— groups, where the nitrogen substituent(s) is(are) alkyl, aryl, aralkyl, heteroaryl, heteroaralkyl, $S(═O)_2$R' or COR', where R' is alkyl, aryl, aralkyl, heteroaryl, heteroaralkyl, OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond. In some embodiments, the cycloalkyl ring is unsaturated or partially saturated.

As used herein, "carbocyclic" refers to a mono- or multicyclic ring system, in which all of the atoms composing the ring are carbon atoms, such as benzene or cyclopropane. In some embodiments, the carbocyclic ring is unsaturated or partially saturated.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, in one embodiment selected from Q.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "heterocycloalkyl," "heterocyclyl" or "heterocyclic" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, amidino, sulfonyl or the nitrogen may be quaternized to form an ammonium group where the substituents are selected as above. In some embodiments, the heterocyclyl ring is saturated. In some embodiments, the heterocyclyl ring is unsaturated or partially saturated.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, in one embodiment selected from Q.

As used herein, "aralkyl" or "arylalkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO in which R is a haloalkyl group.

As used herein, "carboxy" refers to a divalent radical, —C(O)O—.

As used herein, "aminocarbonyl" refers to —$C(O)NH_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

As used herein, "cyclic structure" may be a cycloalkyl, carbocyclic, heterocyclic, aryl or heteroaryl group.

Where substitution is not specified (e.g., "aryl"), there may be one or more substituents present. For example, "aryl" may include a "substituted aryl" group. In some embodiments, each alkyl, alkenyl, alkynyl, cycloalkyl, cycloalkenyl, cycloalkynyl, aryl, aralkyl, heteroaryl, and heterocyclyl is optionally substituted with one or more substituents, in one embodiment one, two, three or four substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, —$OC(=NR^a)NR^bR^c$, —$OS(O)R^a$, $S(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, $NR^aC(=NR^d)NR^bR^c$, —$NR^as(O)R^d$, $NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(NR^e)NR^fR^g$, —$OC(O)R^e$, —$OC(O)OR^e$, —$OC(O)NR^fR^g$, —$OC(=NR^e)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^f$, —$NR^eC(O)NR^fR^g$, —$NR^eC(=NR^h)NR^fR^g$, —$NR^eS(O)R^h$, —$NR^eS(O)_2R^h$, —$NR^eS(O)NR^fR^g$, —$NR^eS(O)_2NR^fR^g$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl. In some embodiments, two Q substituents together with the atoms to which they are attached, may form a fused ring system.

As used herein, the abbreviations for any protective groups, amino acids and other compounds, are, unless indicated otherwise, in accord with their common usage, recognized abbreviations, the IUPAC-IUB Commission on Biochemical Nomenclature (see, (1972) Biochem. 11:942-944), or the IUPAC Nomenclature of Organic Chemistry (see, Favre H A and Powell W H, Nomenclature of Organic Chemistry: IUPAC Recommendations and Preferred Names 2013, Cambridge, UK: The Royal Society of Chemistry, 2013: Print ISBN 978-0-85404-182-4, PDF eISBN 978-1-84973-306-9, DOI 10.1039/9781849733069; Nomenclature of Organic Chemistry, Sections A, B, C, D, E, F, and H, Pergamon Press, Oxford, 1979. Copyright 1979 IUPAC; and A Guide to IUPAC Nomenclature of Organic Compounds (Recommendations 1993), 1993, Blackwell Scientific publications, Copyright 1993 IUPAC).

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. A therapeutically effective amount of a compound provided herein can be administered in one dose (i.e., a single dose administration) or divided and administered over time (i.e., continuous administration or multiple sub-dose administration). Single dose administration, continuous administration, or multiple sub-dose administration can be repeated, for example, to maintain the level of the compound in a biological molecule (e.g., a protein, enzyme, RNA, or DNA), cell, tissue, system, animal, or human.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 22nd ed.; Loyd et al., Eds.; The Pharmaceutical Press, 2012*; Handbook of Pharmaceutical Excipients,* 7th ed.; Rowe et al., Eds.; The Pharmaceutical Press, 2012*; Handbook of Pharmaceutical Additives,* 3rd ed.; Ash and Ash Eds.; Synapse Information Resources, Inc., 2007*; Pharmaceutical Preformulation and Formulation,* 2nd ed.; Gibson Ed.; CRC Press LLC, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "percent by weight" or "% by weight" refers to the weight of a specified component (e.g., an active compound or excipient) in a composition (e.g., a pharmaceutical composition) as a percentage of the total weight of the composition. Thus, the sum of the weight percentages of all the components in a composition is 100%.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$) fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$) iodine-125 ($^{125}$) iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12C}$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$) oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$) iodine-125 ($^{125}I$), iodine-129 ($^{129}I$), and iodine-131 ($^{131}I$). It will be understood that, in a compound as provided herein, any hydrogen can be $^2H$, for example, or any carbon can be $^{13}C$, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium. In some embodiments, a pharmaceutically acceptable deriviative of a compound is an isotopic variant.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable salt thereof; or a pharmaceutically acceptable solvate thereof" has the same meaning as the phrase "an isotopic variant of the compound referenced therein; or a pharmaceutically acceptable salt of the compound referenced therein; or a pharmaceutically acceptable salt of an isotopic variant of the compound referenced therein; or a pharmaceutically acceptable solvate of the compound referenced therein; or a pharmaceutically acceptable solvate of an isotopic variant of the compound referenced therein; or a pharmaceutically acceptable solvate of a pharmaceutically acceptable salt of the compound referenced therein; or a pharmaceutically acceptable solvate of a pharmaceutically acceptable salt of an isotopic variant of the compound referenced therein or its variant or its variant."

5.2. Ras GTP Binding Domain

Data Concerning the Affinity of GTP to the Ras GTP Binding Domain

For the first time, the affinity of GTP for the GTP binding domain of K-Ras utilizing a Scintillation Proximity Assay (SPA) and MicroScale Thermophoresis (MST) has been measured and disclosed herein. These methods were not available when Wittinghofer and colleagues undertook their studies.

In SPA and MST studies, it was found and is disclosed herein that the affinity of GTP for the K-Ras GTP binding domain across wild type and mutant K-Ras is in the range of 100-465 nanomolar (see results in Table 2). This therefore led to the novel, unanticipated conclusion that compounds such as small molecules could be discovered that would bind to a Ras GTP binding domain and compete with the binding of GTP to Ras. SPA and MST studies performed on the Rac-1 and Rho-A members of the Rho subfamily show that the affinity of GTP for the binding domain of these Rho subfamily members is in the range of 120-170 nanomolar (see results in Table 2).

TABLE 2

MST and SPA Results for GTP Affinity for K-Ras and Rho Subfamily Binding Domains

| Protein | MST | SPA |
|---|---|---|
| K-Ras (wild type) | 463 ± 2 nM | 243 ± 15 nM |
| K-Ras (G12D) | 244 ± 12 nM | 270 ± 15 nM |
| K-Ras (G12C) | 207 ± 46 nM | 258 ± 18 nM |
| K-Ras (Q61H) | 157 ± 21 nM | 118 ± 11 nM |
| K-Ras (Q61H/G12D) | 268 ± 108 nM | 135 ± 19 nM |
| K-Ras (Q61H/G12C) | 266 ± 57 nM | 104 ± 11 nM |
| Rac-1 | 166 ± 10 nM | 151 ± 14 nM |
| Rho-A | 130 ± 5 nM | 129 ± 12 nM |

See Khawaja et al., "Scintillation proximity assay in lead discovery", Expert Opin. Drug Discov., 2008 November; 3(11):1267-80 regarding SPA procedures. See the following references regarding MST technology: Wienken et al., Nature Communications (2010), Protein binding assays in biological liquids using MicroScale Thermophoresis; Jerabek-Willemsen et al., ASSAY and Drug Development Technologies (2011), Molecular interaction studies using MicroScale Thermophoresis; Lin et al., Cell (2012), Inhibition of basal FGF receptor signaling by dimeric Grb2; Seidel et al., Angewandte Chemie (2012), Label-Free MicroScale Thermophoresis discriminates sites and affinity of protein-ligand binding; Seidel et al., Methods (2012), MicroScale Thermophoresis quantifies biomolecular interactions under previously challenging conditions; Parker & Newstead, Nature (2014), Molecular basis of nitrate uptake by the plant nitrate transporter NRT1.1; and Jerabek-Willemsen et al., Journal of Molecular Structure (2014), MicroScale Thermophoresis: Interaction analysis and beyond.

The Discovery of Small Molecules that Bind to a Ras GTP Binding Domain in Competition with GTP Provided herein is an assay for the identification of small molecules that bind to a Ras GTP binding domain in competition with GTP.

The useful and novel approach for drug discovery described herein is to identify small molecule inhibitors that will compete and block interactions between GTP and GTP-binding proteins. By interacting with the GDP/GTP-binding site of GTP-binding proteins small molecules so identified may induce a GDP-bound or other inactive conformation of the GTP-binding proteins and thus block signal transduction pathways downstream of the GTP-binding protein.

The assay developed measures and quantifies the ability of tested small molecules in a cell-free system to compete with GTP or GDP binding. The assay can be used in low volumes or for High Throughput Screening (HTS) to screen a compound library and to support medicinal chemistry Structure Activity Relationship (SAR) efforts.

This is a competitive binding assay. It involves the immobilization of a protein on solid phase, interaction with a small molecule drug candidate, and then competitive binding with a labeled native GTP or GDP ligand.

In one embodiment, provided herein is a method of testing the ability of one or more compounds to bind to the GTP binding domain and to compete for GTP binding of one or more members of the Ras superfamily comprising:

a) expressing a Ras superfamily protein or mutant thereof as a tagged protein;

b) contacting the one or more compounds to the tagged protein, followed by incubating the combination;

c) adding labeled-GTP or labeled-GDP to each protein-compound combination, followed by incubating the resulting mixture; and d) measuring the amount of bound labeled-GTP or bound labeled-GDP.

In one embodiment, the method further comprises between step a) and step b): adding the tagged protein to one or more wells of a ligand coated single or multi-well plate and incubating the tagged protein.

In one embodiment of the method, one or more members of the Ras superfamily is Ras. In one embodiment of the method, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In one embodiment of the method, the Ras is HRAS, KRAS, NRAS, or a mutant thereof. In one embodiment of the method, the Ras is HRAS or a mutant thereof. In one embodiment of the method, the Ras is KRAS or a mutant thereof. In one embodiment of the method, the Ras is NRAS or a mutant thereof.

In one embodiment of the method, the Ras superfamily protein is KRas G12D mutant protein. In one embodiment of the method, the Ras superfamily protein is KRas G12C mutant protein. In one embodiment of the method, the Ras superfamily protein is KRas wild type protein. In one embodiment of the method, the Ras superfamily protein is KRas Q61H mutant protein. In one embodiment of the method, the Ras superfamily protein is KRas G12D/Q61H double mutant protein. In one embodiment of the method, the Ras superfamily protein is G12C/Q61H double mutant.

In one embodiment of the method, one or more members of the Ras superfamily is Rho. In one embodiment of the method, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3; CDC42, or a mutant thereof. In one embodiment of the method, the Ras superfamily protein is Rho-A protein.

In one embodiment of the method, one or more members of the Ras superfamily is Rac. In one embodiment of the method, the Rho is Rac or a mutant thereof. In one embodiment of the method, the Rac is RAC1; RAC2; RAC3; RHOG, or a mutant thereof. In one embodiment of the method, the Ras superfamily protein is Rac-1 protein.

In one embodiment of the method, the tagged protein is tagged with His. In one embodiment of the method, the ligand is nickel. In one embodiment of the method, the labeled-GTP is Cy3-GTP or Cy5-GTP. In one embodiment of the method, the buffer is Buffer-I which comprises 50 mM Tris (pH 7.5), 150 mM NaCl, 1 mM $MgCl_2$, and 1 mM DTT. In another embodiment of the method, the buffer is Buffer-I which comprises 50 mM Tris (pH 7.5), 1 mM $MgCl_2$, and 1 mM DTT.

The form of the assay involves the binding of His-tagged protein to nickel coated plates and a native form of GTP covalently labeled with Cy3 or Cy5 fluorescent probes.

In theory, the assay is suitable for use with any GTP or GDP binding protein. The Examples demonstrate that the assay can be utilized for Ras and Ras mutants, Rac-1 and Rho-A human proteins expressed and purified as recombinant proteins.

Different tag/ligand combinations can be used in the assay. The protein may be expressed as a fusion protein with a tag such as His, HA, Flag or GST; or, the protein can be labeled by a tag such as biotin via chemical reaction. The counter molecule (ligand or binder) interacting with the tag will bind or coat the solid phase. The solid phase could be a plate (96, 384 or 1536 wells plate) and column beads such as sepharose, agarose and cellulose. Binders could include nickel, antibodies, glutathione and streptavidin. Examples of tag:ligand combinations include His (polyhistidine, at least 6 histidines):nickel, GST (Glutathione-S-transferase):glutathione, HA (amino acids 98-106 of human influenza hemagglutinin):anti-HA antibodies, Fc (constant region of human IgG):protein A, FLAG (the peptide DYDDDDK):Antibodies (M1. M2, 4E11), Myc (the peptide EQKLISEED derived the myc protein): Anti-myc antibodies, and biotin: streptavidin (or avidin).

Heretofore, attempts to measure small molecule competitors for GTP protein interactions have relied on the ability of the tested small molecules to prevent binding of labeled GTP to the GTP-binding protein. A novel component of this assay is the use of the highly sensitive Cy3 or Cy5 probes. Similar probes which might be used include other high sensitivity fluorophores that can be detected at concentrations below 1 micromolar in solution, and radioactive labeling. The inventors are not aware of any publication suggesting the adaptation of the probes we have used, or similar probes, for use in a competitive binding assay.

The Identification of Amino Acids in the Ras GTP Binding Domain Enabling the Development and Function of Small Molecule Targeted Therapeutics As noted above, it has also been discovered that amino acids in the Ras GTP binding domain, including Ala11, Gly12, Val 14, Gly15, Lys 16, Ser17, Ala 18, Phe28, Val 29, Asp30, Glu31, Tyr32, Asp33, Pro34, Thr 35, Lys 36, Gly 60, Lys117, Asp119, Leu120, Ser145, Ala146 and Lys147 and Mg202, enable the heretofore unanticipated competitive binding to that domain between compounds, such as small molecules, and GTP. It has also been discovered that amino acids in the Ras GTP binding domain, including Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 and Mg202, enable the heretofore unanticipated competitive binding to that domain between compounds, such as small molecules, and GTP.

As described in Example 1, molecular modeling studies incorporating Ras superfamily protein structures from the RCSB PDB (www.rcsb.org) with either GDP, the GTP analog GNP (guanosine 5'[β,γ-imido]triphosphate trisodium salt hydrate), or small molecules disclosed herein, were used to determine the amino acids in the Ras superfamily domain in close proximity to the GDP, GTP or small molecules when bound to the Ras superfamily protein.

As noted above, it has also been discovered that amino acids in the Rac1 GTP binding domain, including Gly12, Ala13, Gly15, Lys16, Thr17, Cys18, Leu19, Phe28, Ile33, Pro34, Val36, Ala59, Thr115, Lys116, Asp118, Leu119, Cys157, Ala159, and Mg202, enable the heretofore unanticipated competitive binding to that domain between compounds, such as small molecules, and GTP.

As noted above, it has also been discovered that amino acids in the RhoA GTP binding domain, including Gly14, Ala15, Cys16, Gly17, Lys18, Thr19, Cys20, Phe30, Pro31, Glu32, Tyr34, Val35, Pro36, Thr37, Asp59, Lys118, Asp120, Lys162, and Mg202, enable the heretofore unanticipated competitive binding to that domain between compounds, such as small molecules, and GTP.

5.3. Methods of Treatment

5.3.1 Cancer

In one embodiment, provided herein is a method of treating or preventing cancer, which comprises administering to a subject a compound that inhibits the function of one or more members of the Ras superfamily by binding to the GTP binding domain or one or more members of the Ras superfamily. In one embodiment, provided herein is a method of treating or preventing cancer, which comprises administering to a subject a compound that inhibits the function of Ras by binding to a Ras GTP binding domain. In another embodiment, provided herein is a method of treating or preventing cancer, which comprises administering to a subject a compound that binds to a Ras GTP binding domain with an $IC_{50}$ of less than 10 μM and a $K_d$ of less than 10 μM. In another embodiment, provided herein is a method of treating or preventing cancer, which comprises administering to a subject a compound that binds to a Ras GTP binding domain with an $IC_{50}$ of less than 1 μM and a $K_d$ of less than 1 μM. In another embodiment, provided herein is a method of treating or preventing cancer, which comprises administering to a subject a compound that binds to a Ras GTP binding domain with an $IC_{50}$ of less than 500 nM and a $K_d$ of less than 500 nM. In another embodiment, provided herein is a method of treating or preventing cancer, which comprises administering to a subject a compound that binds to a Ras GTP binding domain with an $IC_{50}$ of less than 470 nM and a $K_d$ of less than 470 nM. In another embodiment, provided herein is a method of treating or preventing cancer, which comprises administering to a subject a compound that binds to a Ras GTP binding domain with an $IC_{50}$ of less than 270 nM and a $K_d$ of less than 270 nM. In another embodiment, provided herein is a method of treating or preventing cancer, which comprises administering to a subject a compound that binds to a Ras GTP binding domain with an $IC_{50}$ of less than 200 nM and a $K_d$ of less than 200 nM. In another embodiment, provided herein is a method of treating or preventing cancer, which comprises administering to a subject a compound that binds to a Ras GTP binding domain with an $IC_{50}$ of less than 150 nM and a $K_d$ of less than 150 nM. In another embodiment, provided herein is a method of treating or preventing cancer, which comprises administering to a subject a compound that binds to a Ras GTP binding domain with an $IC_{50}$ of less than 100 nM and a $K_d$ of less than 100 nM. In another embodiment, provided herein is a method of treating or preventing cancer, which comprises administering to a subject a compound that binds to a Ras GTP binding domain with greater than 25% inhibition at 20 μM. In another embodiment, provided herein is a method of treating or preventing cancer, which comprises administering to a subject a compound that binds to a Ras GTP binding domain with greater than 50% inhibition at 20 μM. In another embodiment, provided herein is a method of treating or preventing cancer, which comprises administering to a subject a compound that binds to a Ras GTP binding domain with greater than 75% inhibition at 20 μM. In another embodiment, provided herein is a method of treating or preventing cancer, which comprises administering to a subject a compound that binds to a Ras GTP binding domain with greater than 80% inhibition at 20 μM. In another embodiment, provided herein is a method of treating or preventing cancer, which comprises administering to a subject a compound that binds to a Ras GTP binding domain with greater than 85% inhibition at 20 μM. In another embodiment, provided herein is a method of treating or preventing cancer, which comprises administering to a subject a compound that binds to a Ras GTP binding domain with greater than 90% inhibition at 20 μM. In another embodiment, provided herein is a method of treating or preventing cancer, which comprises administering to a subject a compound that binds to a Ras GTP binding domain with greater than 95% inhibition at 20 μM. In another embodiment, provided herein is a method of treating or preventing cancer, which comprises administering to a subject a compound that binds to a Ras GTP binding domain with greater than 99% inhibition at 20 μM. In one embodiment, provided herein is a method of treating or preventing cancer, which comprises administering to a subject a compound that inhibits the function of Rho by binding to a Rho GTP binding domain. In another embodiment, provided herein is a method of treating or preventing cancer, which comprises administering to a subject a compound that binds to a Rho GTP binding domain with an $IC_{50}$ of less than 10 μM and a $K_d$ of less than 10 μM. In another embodiment, provided herein is a method of treating or preventing cancer, which comprises administering to a subject a compound that binds to a Rho GTP binding domain with an $IC_{50}$ of less than 1 μM and a $K_d$ of less than 1 μM. In another embodiment, provided herein is a method of treating or preventing cancer, which comprises administering to a subject a compound that binds to a Rho GTP binding domain with an $IC_{50}$ of less than 500 nM and a $K_d$ of less than 500 nM. In another embodiment, provided herein is a method of treating or preventing cancer, which comprises administering to a subject a compound that binds to a Rho GTP binding domain with an $IC_{50}$ of less than 270 nM and a $K_d$ of less than 270 nM. In another embodiment, provided herein is a method of treating or preventing cancer, which comprises administering to a subject a compound that binds to a Rho GTP binding domain with an $IC_{50}$ of less than 200 nM and a $K_d$ of less than 200 nM. In another embodiment, provided herein is a method of treating or preventing cancer, which comprises administering to a subject a compound that binds to a Rho GTP binding domain with an $IC_{50}$ of less than 150 nM and a $K_d$ of less than 150 nM. In another embodiment, provided herein is a method of treating or preventing cancer, which comprises administering to a subject a compound that binds to a Rho GTP binding domain with an $IC_{50}$ of less than 130 nM and a $K_d$ of less than 130 nM. In another embodiment, provided herein is a method of treating or preventing cancer, which comprises administering to a subject a compound that binds to a Rho GTP binding domain with an $IC_{50}$ of less than 100 nM and a $K_d$ of less than 100 nM. In another embodiment, provided herein is a method of treating or preventing cancer, which comprises administering to a subject a compound that binds to a Rho GTP binding domain with greater than 25% inhibition at 20 μM. In another embodiment, provided herein is a method of treating or preventing cancer, which comprises administering to a subject a compound that binds to a Rho GTP binding domain with greater than 50% inhibition at 20 μM. In another embodiment, provided herein is a method of treating or preventing cancer, which comprises administering to a subject a compound that binds to a Rho GTP binding domain with greater than 75% inhibition at 20 μM. In another embodiment, provided herein is a method of treating or preventing cancer, which comprises administering to a subject a compound that binds to a Rho GTP binding domain with greater than 80% inhibition at 20 μM. In another embodiment, provided herein is a method of treating or preventing cancer, which comprises administering to a subject a compound that binds to a Rho GTP binding domain with greater than 85% inhibition at 20 μM. In another embodiment, provided herein is a method of treating or preventing cancer, which comprises administering to a subject a compound that binds to a Rho GTP binding domain with greater than 90% inhibition at 20 μM. In another embodiment, provided herein is a method of treating or preventing cancer, which comprises administering to a subject a compound that binds to a Rho GTP binding domain with greater than 95% inhibition at 20 μM. In another embodiment, provided herein is a method of treating or preventing cancer, which comprises administering to a subject a compound that binds to a Rho GTP binding domain with greater than 99% inhibition at 20 μM. In one embodiment, provided herein is a method of treating or preventing cancer, which comprises administering to a subject a compound that inhibits the function of Rac by binding to a Rac GTP binding domain. In another embodiment, provided herein is a method of treating or preventing cancer, which comprises administering to a subject a compound that binds to a Rac GTP binding domain with an $IC_{50}$ of less than 10 μM and a $K_d$ of less than 10 μM. In another embodiment, provided herein is a method of treating or preventing cancer, which comprises administering to a subject a compound that binds to a Rac GTP binding domain with an $IC_{50}$ of less than 1 μM and a $K_d$ of less than 1 μM. In another embodiment, provided herein is a method of treating or preventing cancer, which comprises administering to a subject a compound that binds to a Rac GTP binding domain with an $IC_{50}$ of less than 500 nM and a $K_d$ of less than 500 nM. In another embodiment, provided herein is a method of treating or preventing cancer, which comprises administering to a subject a compound that binds to a Rac GTP binding domain with an $IC_{50}$ of less than 270 nM and a $K_d$ of less than 270 nM. In another embodiment, provided herein is a method of treating or preventing cancer, which comprises administering to a subject a compound that binds to a Rac GTP binding domain with an $IC_{50}$ of less than 200 nM and a $K_d$ of less than 200 nM. In another embodiment, provided herein is a method of treating or preventing cancer, which comprises administering to a subject a compound that binds to a Rac GTP binding domain with an $IC_{50}$ of less than 170 nM and a $K_d$ of less than 170 nM. In another embodiment, provided herein is a method of treating or preventing cancer, which comprises administering to a subject a compound that binds to a Rac GTP binding domain with an $IC_{50}$ of less than 150 nM and a $K_d$ of less than 150 nM. In another embodiment, provided herein is a method of treating or preventing cancer, which comprises administering to a subject a compound that binds to a Rac GTP binding domain with an $IC_{50}$ of less than 100 nM and a $K_d$ of less than 100 nM. In another embodiment, provided herein is a method of treating or preventing cancer, which comprises administering to a subject a compound that binds to a Rac GTP binding domain with greater than 25% inhibition at 20 μM. In another embodiment, provided herein is a method of treating or preventing cancer, which comprises administering to a subject a compound that binds to a Rac GTP binding domain with greater than 50% inhibition at 20 μM. In another embodiment, provided herein is a method of treating or preventing cancer, which comprises administering to a subject a compound that binds to a Rac GTP binding domain with greater than 75% inhibition at 20 μM. In another embodiment, provided herein is a method of treating or preventing cancer, which comprises administering to a subject a compound that binds to a Rac GTP binding domain with greater than 80% inhibition at 20 μM. In another embodiment, provided herein is a method of treating or preventing cancer, which comprises administering to a subject a compound that binds to a Rac GTP binding domain with greater than 85% inhibition at 20 μM. In another embodiment, provided herein is a method of treating or preventing cancer, which comprises administering to a subject a compound that binds to a Rac GTP binding domain with greater than 90% inhibition at 20 μM. In another embodiment, provided herein is a method of treating or preventing cancer, which comprises administering to a subject a compound that binds to a Rac GTP binding domain with greater than 95% inhibition at 20 μM. In another embodiment, provided herein is a method of treating or preventing cancer, which comprises administering to a subject a compound that binds to a Rac GTP binding domain with greater than 99% inhibition at 20 μM.

In another embodiment, provided herein is a method of treating or preventing cancer, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain.

In another embodiment, provided herein is a method of treating or preventing cancer, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing cancer, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing cancer, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rho GTP binding domain. In one embodiment, provided herein is a method of treating or preventing cancer, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac. In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole moiety, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl)pyrimidin-4(3H)-one, 2-(imidazol-4-yl)pyrimidin-4(1H)-one, 2-(imidazol-4-yl)pyrimidin-4-amine, 2-(imidazol-4-yl)pyrimidin-4(3H)-imine, or 2-(imidazol-4-yl)pyrimidin-4(1H)-imine moiety.

In one embodiment, provided herein is a method of treating or preventing cancer, which comprises administering to a subject a compound provided herein, or a derivative thereof.

In another embodiment, provided herein is method of managing cancer, which comprises administering to a subject a compound provided herein, or a derivative thereof.

Also provided herein are methods of treating subjects who have been previously treated for cancer but are non-responsive to standard therapies, as well as those who have not previously been treated. Also provided are methods of treating subjects regardless of subject's age, although some diseases or disorders are more common in certain age groups. Also provided are methods of treating subjects who have undergone surgery in an attempt to treat the disease or condition at issue, as well as those who have not. Because subjects with cancer have heterogeneous clinical manifestations and varying clinical outcomes, the treatment given to a subject may vary, depending on his/her prognosis. The skilled clinician will be able to readily determine without undue experimentation specific secondary agents, types of surgery, and types of non-drug based standard therapy that can be effectively used to treat an individual subject with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, pancreatic cancer, lung cancer, ovarian cancer, colon cancer, small intestine cancer, biliary tract cancer, endometrium cancer, skin cancer (melanoma), cervix cancer, urinary tract cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound provided herein or a derivative thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or a derivative thereof effective to treat, prevent or manage acute myeloid leukemia alone or in combination. In some embodiments, the methods comprise the step of administering to the subject a compound provided herein or a derivative thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or a derivative thereof effective to treat, prevent or manage acute lymphocytic leukemia alone or in combination with a second active agent. In some embodiments, the methods comprise the step of administering to the subject a compound provided herein or a derivative thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or a derivative thereof effective to treat, prevent or manage chronic myelogenous leukemia. In some embodiments, the methods comprise the step of administering to the subject a compound provided herein or a derivative thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or a derivative thereof effective to treat, prevent or manage chronic lymphocytic leukemia. In some embodiments, the methods comprise the step of administering to the subject a compound provided herein or a derivative thereof in combination with a second active agent in amounts effective to treat, prevent or manage chronic lymphocytic leukemia.

In certain embodiments, provided herein are methods of treating, preventing, and/or managing disease in subjects with impaired renal function. In certain embodiments, provided herein are method of treating, preventing, and/or managing cancer in subjects with impaired renal function. In certain embodiments, provided herein are methods of providing appropriate dose adjustments for subjects with impaired renal function due to, but not limited to, disease, aging, or other subject factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in subjects with impaired renal function or a symptom thereof, comprising administering a therapeutically effective amount of a compound provided herein, or a derivative thereof to a subject having relapsed/refractory multiple myeloma with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as $mg/m^2$/day. One of ordinary skill in the art would readily know how to convert doses from mg/kg/day to $mg/m^2$/day to given either the height or weight of a subject or both (see, www.fda.gov/cder/cancer/animalframe.htm). For example, a dose of 1 mg/kg/day for a 65 kg human is approximately equal to 38 $mg/m^2$/day.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the subject to be treated with one of the methods provided herein has not been treated with anticancer therapy prior to the administration of the compound provided herein, or a derivative thereof. In certain embodiments, the subject to be treated with one of the methods provided herein has been treated with anticancer therapy prior to the administration of the compound provided herein, or a derivative thereof. In certain embodiments, the subject to be treated with one of the methods provided herein has developed drug resistance to the anticancer therapy.

The methods provided herein encompass treating a patient regardless of subject's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancer described herein.

In one embodiment, provided herein is a method of treating, preventing, or managing cancer, comprising administering to a subject a compound provided herein, or a derivative thereof; in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the subject.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller subjects) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; the entireties of which are incorporated herein by reference.

Also provided for use in combination with a compound provided herein, or a derivative thereof, of are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with a compound provided herein, or a derivative thereof, include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The compounds provided herein or an enantiomer or a mixture of enantiomers thereof, or a pharmaceutically acceptable salt, solvate, hydrate, co-crystal, clathrate, or polymorph thereof can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of a compound provided herein, or a derivative thereof. However, like some large molecules, many are believed to be capable of providing a synergistic effect when administered with (e.g., before, after or simultaneously) a compound provided herein, or a derivative thereof. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, Ara-C, doxetaxol, pacilitaxel, vinblastine, IL-2, GM CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a compound provided herein, or a derivative thereof, may be modified or delayed during or shortly following administration of a compound provided herein, or a derivative thereof, as deemed appropriate by the practitioner of skill in the art. In certain embodiments, subjects being administered a compound provided herein, or a derivative thereof, alone or in combination with other therapies may receive supportive care including antiemetics, myeloid growth factors, and transfusions of platelets, when appropriate. In some embodiments, subjects being administered a compound provided herein, or a derivative thereof, may be administered a growth factor as a second active agent according to the judgment of the practitioner of skill in the art. In some embodiments, provided is administration of a compound provided herein, or a derivative thereof, in combination with erythropoietin or darbepoetin (Aranesp).

In certain embodiments, a compound provided herein, or a derivative thereof, is administered with gemcitabine and cisplatinum to subjects with locally advanced or metastatic transitional cell bladder cancer.

In certain embodiments, a compound provided herein, or a derivative thereof, is administered in combination with a second active ingredient as follows: temozolomide to pediatric subjects with relapsed or progressive brain tumors or recurrent neuroblastoma; celecoxib, etoposide and cyclophosphamide for relapsed or progressive CNS cancer; temodar to subjects with recurrent or progressive meningioma, malignant meningioma, hemangiopericytoma, multiple brain metastases, relapsed brain tumors, or newly diagnosed glioblastoma multiforms; irinotecan to subjects with recurrent glioblastoma; carboplatin to pediatric subjects with brain stem glioma; procarbazine to pediatric subjects with progressive malignant gliomas; cyclophosphamide to subjects with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, or a derivative thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to subjects with metastatic breast cancer.

In certain embodiments, a compound provided herein, or a derivative thereof, is administered with temozolomide to subjects with neuroendocrine tumors.

In certain embodiments, a compound provided herein, or a derivative thereof, is administered with gemcitabine to subjects with recurrent or metastatic head or neck cancer.

In certain embodiments, a compound provided herein, or a derivative thereof, is administered with gemcitabine to subjects with pancreatic cancer.

In certain embodiments, a compound provided herein, or a derivative thereof, is administered to subjects with colon cancer in combination with ARISA®, avastatin, taxol, and/or taxotere.

In certain embodiments, a compound provided herein, or a derivative thereof, is administered with capecitabine and/or PLX4032 (Plexxikon) to subjects with refractory colorectal cancer or subjects who fail first line therapy or have poor performance in colon or rectal adenocarcinoma.

In certain embodiments, a compound provided herein, or a derivative thereof, is administered in combination with fluorouracil, leucovorin, and irinotecan to subjects with Dukes C & D colorectal cancer or to subjects who have been previously treated for metastatic colorectal cancer.

In certain embodiments, a compound provided herein, or a derivative thereof, is administered to subjects with refractory colorectal cancer in combination with capecitabine, xeloda, and/or CPT-11.

In certain embodiments, a compound provided herein, or a derivative thereof, is administered with capecitabine and irinotecan to subjects with refractory colorectal cancer or to subjects with unresectable or metastatic colorectal carcinoma.

In certain embodiments, a compound provided herein, or a derivative thereof, is administered alone or in combination with interferon alpha or capecitabine to subjects with unresectable or metastatic hepatocellular carcinoma; or with cisplatin and thiotepa to subjects with primary or metastatic liver cancer.

In certain embodiments, a compound provided herein, or a derivative thereof, is administered in combination with pegylated interferon alpha to subjects with Kaposi's sarcoma.

In certain embodiments, a compound provided herein, or a derivative thereof, is administered in combination with fludarabine, carboplatin, and/or topotecan to subjects with refractory or relapsed or high-risk acute myeloid leukemia.

In certain embodiments, a compound provided herein, or a derivative thereof, is administered in combination with liposomal daunorubicin, topotecan and/or cytarabine to subjects with unfavorable karotype acute myeloblastic leukemia.

In certain embodiments, a compound provided herein, or a derivative thereof, is administered in combination with gemcitabine, abraxane, erlotinib, geftinib, and/or irinotecan to subjects with non-small cell lung cancer.

In certain embodiments, a compound provided herein, or a derivative thereof, is administered in combination with carboplatin and irinotecan to subjects with non-small cell lung cancer.

In certain embodiments, a compound provided herein, or a derivative thereof, is administered with doxetaxol to subjects with non-small cell lung cancer who have been previously treated with carbo/VP 16 and radiotherapy.

In certain embodiments, a compound provided herein, or a derivative thereof, is administered in combination with carboplatin and/or taxotere, or in combination with carboplatin, pacilitaxel and/or thoracic radiotherapy to subjects with non-small cell lung cancer.

In certain embodiments, a compound provided herein, or a derivative thereof, is administered in combination with taxotere to subjects with stage IIIB or IV non-small cell lung cancer.

In certain embodiments, a compound provided herein, or a derivative thereof, is administered in combination with oblimersen (Genasense®) to subjects with small cell lung cancer.

In certain embodiments, a compound provided herein, or a derivative thereof, is administered in combination with ABT-737 (Abbott Laboratories) and/or obatoclax (GX15-070) to subjects with lymphoma and other blood cancers.

In certain embodiments, a compound provided herein, or a derivative thereof, is administered alone or in combination with a second active ingredient such as vinblastine or fludarabine to subjects with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, or a derivative thereof, is administered in combination with taxotere, IL-2, IFN, GM-CSF, PLX4032 (Plexxikon) and/or dacarbazine to subjects with various types or stages of melanoma.

In certain embodiments, a compound provided herein, or a derivative thereof, is administered alone or in combination with vinorelbine to subjects with malignant mesothelioma, or stage IIIB non-small cell lung cancer with pleural implants or malignant pleural effusion mesothelioma syndrome.

In certain embodiments, a compound provided herein, or a derivative thereof, is administered to subjects with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, or a derivative thereof, is administered to subjects with relapsed or refractory multiple myeloma in combination with doxorubicin (Doxil®), vincristine and/or dexamethasone (Decadron®).

In certain embodiments, a compound provided herein, or a derivative thereof, is administered to subjects with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, or a derivative thereof, is administered to subjects with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, or a derivative thereof, is administered to subjects with various types or stages of renal cell cancer, in combination with capecitabine, IFN, tamoxifen, IL-2, GM-CSF, Celebrex®, or a combination thereof.

In certain embodiments, a compound provided herein, or a derivative thereof, is administered to subjects with various types or stages of gynecologic, uterus or soft tissue sarcoma cancer in combination with IFN, a COX-2 inhibitor such as Celebrex®, and/or sulindac.

In certain embodiments, a compound provided herein, or a derivative thereof, is administered to subjects with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, or a derivative thereof, is administered to subjects with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a subject, which comprises administering to the subject (e.g., a human) a compound provided herein, or a derivative thereof. Subjects that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, or a derivative thereof, alleviates or reduces adverse effects which are of such severity that it would otherwise limit the amount of anti-cancer drug.

In one embodiment, a compound provided herein, or a derivative thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a subject. In certain embodiments, a compound provided herein, or a derivative thereof, is administered in combination with specific agents such as heparin, aspirin, coumadin, or G CSF to avoid adverse effects that are associated with anti-cancer drugs such as but not limited to neutropenia or thrombocytopenia.

In one embodiment, a compound provided herein, or a derivative thereof, is administered to subjects with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound provided herein, or a derivative thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein, or a derivative thereof, and conventional therapy may provide a unique treatment regimen that is unexpectedly effective in certain subjects. Without being limited by theory, it is believed that the compound provided herein, or a derivative thereof, may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, or a derivative thereof, and other active ingredient can be administered to a subject prior to, during, or after the occurrence of the adverse effect associated with conventional therapy.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent disclosed herein, prior to, during, or after the use of conventional therapy.

In certain embodiments, a compound provided herein, or a derivative thereof, and doxetaxol are administered to subjects with non-small cell lung cancer who were previously treated with carbo/VP 16 and radiotherapy.

In certain embodiments, a compound provided herein, or a derivative thereof, is administered to subjects with various types or stages of cancer, in combination with an immune oncology drug or a combination of immune oncology drugs. In one embodiment, a compound provided herein, or a derivative thereof, is administered to subjects with various types or stages of cancer, in combination with Opdivo, Keytruda, Yervoy or a combination thereof.

6.3.2 Inflammation

As discussed herein, activation of MAPKs is a component of the inflammatory response. Thus, the compounds provided herein, which are MAPK inhibitors via inhibition of Ras and/or a Ras superfamily member, are useful in the treatment of inflammatory diseases.

In one embodiment, provided herein is a method of treating or preventing inflammatory disease, which comprises administering to a subject a compound that inhibits the function of one or more members of the Ras superfamily by binding to the GTP binding domain or one or more members of the Ras superfamily. In one embodiment, provided herein is a method of treating or preventing inflammatory disease, which comprises administering to a subject a compound that inhibits the function of Ras by binding to a Ras GTP binding domain. In another embodiment, provided herein is a method of treating or preventing inflammatory disease, which comprises administering to a subject a compound that binds to a Ras GTP binding domain with an $IC_{50}$ of less than 10 μM and a $K_d$ of less than 10 μM. In another embodiment, provided herein is a method of treating or preventing inflammatory disease, which comprises administering to a subject a compound that binds to a Ras GTP binding domain with an $IC_{50}$ of less than 1 μM and a $K_d$ of less than 1 μM. In another embodiment, provided herein is a method of treating or preventing inflammatory disease, which comprises administering to a subject a compound that binds to a Ras GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Ras GTP binding domain with an $IC_{50}$ of less than 470 nM and a $K_d$ of less than 470 nM. In another embodiment, provided herein is a method of treating or preventing inflammatory disease, which comprises administering to a subject a compound that binds to a Ras GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Ras GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Ras GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Ras GTP binding domain with an $IC_{50}$ of less than 100 nM and a $K_d$ of less than 100 nM. In another embodiment, provided herein is a method of treating or preventing inflammatory disease, which comprises administering to a subject a compound that binds to a Ras GTP binding domain with greater than 25% inhibition at 20 μM. In another embodiment, provided herein is a method of treating or preventing inflammatory disease, which comprises administering to a subject a compound that binds to a Ras GTP binding domain with greater than 50% inhibition at 20 μM. In another embodiment, provided herein is a method of treating or preventing inflammatory disease, which comprises administering to a subject a compound that binds to a Ras GTP binding domain with greater than 75% inhibition at 20 μM. In another embodiment, provided herein is a method of treating or preventing inflammatory disease, which comprises administering to a subject a compound that binds to a Ras GTP binding domain with greater than 80% inhibition at 20 μM. In another embodiment, provided herein is a method of treating or preventing inflammatory disease, which comprises administering to a subject a compound that binds to a Ras GTP binding domain with greater than 85% inhibition at 20 μM. In another embodiment, provided herein is a method of treating or preventing inflammatory disease, which comprises administering to a subject a compound that binds to a Ras GTP binding domain with greater than 90% inhibition at 20 μM. In another embodiment, provided herein is a method of treating or preventing inflammatory disease, which comprises administering to a subject a compound that binds to a Ras GTP binding domain with greater than 95% inhibition at 20 μM. In another embodiment, provided herein is a method of treating or preventing inflammatory disease, which comprises administering to a subject a compound that binds to a Ras GTP binding domain with greater than 99% inhibition at 20 μM. In one embodiment, provided herein is a method of treating or preventing inflammatory disease, which comprises administering to a subject a compound that inhibits the function of Rho by binding to a Rho GTP binding domain. In another embodiment, provided herein is a method of treating or preventing inflammatory disease, which comprises administering to a subject a compound that binds to a Rho GTP binding domain with an $IC_{50}$ of less than 10 μM and a $K_d$ of less than 10 μM. In another embodiment, provided herein is a method of treating or preventing inflammatory disease, which comprises administering to a subject a compound that binds to a Rho GTP binding domain with an $IC_{50}$ of less than 1 μM and a $K_d$ of less than 1 μM. In another embodiment, provided herein is a method of treating or preventing inflammatory disease, which comprises administering to a subject a compound that binds to a Rho GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Rho GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Rho GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Rho GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Rho GTP binding domain with an $IC_{50}$ of less than 130 nM and a $K_d$ of less than 130 nM. In another embodiment, provided herein is a method of treating or preventing inflammatory disease, which comprises administering to a subject a compound that binds to a Rho GTP binding domain with an $IC_{50}$ of less than 100 nM and a $K_d$ of less than 100 nM. In another embodiment, provided herein is a method of treating or preventing inflammatory disease, which comprises administering to a subject a compound that binds to a Rho GTP binding domain with greater than 25% inhibition at 20 μM. In another embodiment, provided herein is a method of treating or preventing inflammatory disease, which comprises administering to a subject a compound that binds to a Rho GTP binding domain with greater than 50% inhibition at 20 μM. In another embodiment, provided herein is a method of treating or preventing inflammatory disease, which comprises administering to a subject a compound that binds to a Rho GTP binding domain with greater than 75% inhibition at 20 μM. In another embodiment, provided herein is a method of treating or preventing inflammatory disease, which comprises administering to a subject a compound that binds to a Rho GTP binding domain with greater than 80% inhibition at 20 μM. In another embodiment, provided herein is a method of treating or preventing inflammatory disease, which comprises administering to a subject a compound that binds to a Rho GTP binding domain with greater than 85% inhibition at 20 μM. In another embodiment, provided herein is a method of treating or preventing inflammatory disease, which comprises administering to a subject a compound that binds to a Rho GTP binding domain with greater than 90% inhibition at 20 μM. In another embodiment, provided herein is a method of treating or preventing inflammatory disease, which comprises administering to a subject a compound that binds to a Rho GTP binding domain with greater than 95% inhibition at 20 μM. In another embodiment, provided herein is a method of treating or preventing inflammatory disease, which comprises administering to a subject a compound that binds to a Rho GTP binding domain with greater than 99% inhibition at 20 μM. In one embodiment, provided herein is a method of treating or preventing inflammatory disease, which comprises administering to a subject a compound that inhibits the function of Rac by binding to a Rac GTP binding domain. In another embodiment, provided herein is a method of treating or preventing inflammatory disease, which comprises administering to a subject a compound that binds to a Rac GTP binding domain with an $IC_{50}$ of less than 10 μM and a $K_d$ of less than 10 μM. In another embodiment, provided herein is a method of treating or preventing inflammatory disease, which comprises administering to a subject a compound that binds to a Rac GTP binding domain with an $IC_{50}$ of less than 1 μM and a $K_d$ of less than 1 μM. In another embodiment, provided herein is a method of treating or preventing inflammatory disease, which comprises administering to a subject a compound that binds to a Rac GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Rac GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Rac GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Rac GTP binding domain with an $IC_{50}$ of less than 170 nM and a $K_d$ of less than 170 nM. In another embodiment, provided herein is a method of treating or preventing inflammatory disease, which comprises administering to a subject a compound that binds to a Rac GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Rac GTP binding domain with an $IC_{50}$ of less than 100 nM and a $K_d$ of less than 100 nM. In another embodiment, provided herein is a method of treating or preventing inflammatory disease, which comprises administering to a subject a compound that binds to a Rac GTP binding domain with greater than 25% inhibition at 20 μM. In another embodiment, provided herein is a method of treating or preventing inflammatory disease, which comprises administering to a subject a compound that binds to a Rac GTP binding domain with greater than 50% inhibition at 20 μM. In another embodiment, provided herein is a method of treating or preventing inflammatory disease, which comprises administering to a subject a compound that binds to a Rac GTP binding domain with greater than 75% inhibition at 20 μM. In another embodiment, provided herein is a method of treating or preventing inflammatory disease, which comprises administering to a subject a compound that binds to a Rac GTP binding domain with greater than 80% inhibition at 20 μM. In another embodiment, provided herein is a method of treating or preventing inflammatory disease, which comprises administering to a subject a compound that binds to a Rac GTP binding domain with greater than 85% inhibition at 20 μM. In another embodiment, provided herein is a method of treating or preventing inflammatory disease, which comprises administering to a subject a compound that binds to a Rac GTP binding domain with greater than 90% inhibition at 20 μM. In another embodiment, provided herein is a method of treating or preventing inflammatory disease, which comprises administering to a subject a compound that binds to a Rac GTP binding domain with greater than 95% inhibition at 20 μM. In another embodiment, provided herein is a method of treating or preventing inflammatory disease, which comprises administering to a subject a compound that binds to a Rac GTP binding domain with greater than 99% inhibition at 20 μM.

In another embodiment, provided herein is a method of treating or preventing inflammatory disease, which comprises administering to a subject a compound that binds to one or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to two or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to three or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to four or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to five or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to six or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to seven or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eight or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to nine or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to ten or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eleven or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to all of Ala11, Gly12, Val14, Gly15, Lys16, Ser17, Ala 18, Phe28, Val 29, Asp30, Glu31, Tyr32, Asp33, Pro34, Thr35, Lys36, Gly 60, Lys117, Asp119, Leu120, Ser145, Ala146 and Lys147 or Mg202 in a Ras GTP binding domain.

In another embodiment, provided herein is a method of treating or preventing inflammatory disease, which comprises administering to a subject a compound that binds to one or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to two or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to three or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to four or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to five or more of Ala11, Gly12, Val14, Gly15, Lys16, Ser17, Ala 18, Phe28, Val 29, Asp30, Glu31, Tyr32, Asp33, Pro34, Thr35, Lys36, Gly 60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to six or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to seven or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eight or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to nine or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to ten or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eleven or more of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to all of Ala11, Gly12, Val14, Gly15, Lys16, Ser17, Ala 18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing inflammatory disease, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing inflammatory disease, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to twelve or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole moiety, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl)pyrimidin-4(3H)-one, 2-(imidazol-4-yl)pyrimidin-4(1H)-one, 2-(imidazol-4-yl)pyrimidin-4-amine, 2-(imidazol-4-yl)pyrimidin-4(3H)-imine, or 2-(imidazol-4-yl)pyrimidin-4(1H)-imine moiety.

In one embodiment, the inflammatory disease is inflammation-associated cancer development. As disclosed here, the compounds provided herein are useful in treatment of cancer. It is well recognized that the immune inflammatory state serves as a key mediator of the middle stages of tumor development. It is also well known that chronic inflammation can predispose an individual to cancer. Chronic inflammation is caused by a variety of factors, including bacterial, viral, and parasitic infections. The longer the inflammation persists, the higher the risk of associated carcinogenesis. Anti-inflammatory cancer therapy prevents premalignant cells from turning fully cancerous or impedes existing tumors from spreading to distant sites in the body. Thus, in one embodiment, the compounds provided herein are useful in treating inflammatory cancers. Such cancers, and the chronic inflammatory conditions that predispose susceptible cells to neoplastic transformation, include gastric adenocarcinoma (gastritis), mucosa-associated lymphoid tissue (MALT) lymphoma (gastritis), bladder, liver and rectal carcinomas (schistosomiasis), cholangiocarcinoma and colon carcinoma (cholangitis), gall bladder cancer (chronic cholecystitis), ovarian and cervical carcinoma (pelvic inflammatory disease, chronic cervicitis), skin carcinoma (osteomyelitis), colorectal carcinoma (inflammatory bowel disease), esophageal carcinoma (reflux esophagitis, Barrett's esophagus), bladder cancer (bladder inflammation (cystitis)), mesothelioma and lung carcinoma (asbestosis, silicosis), oral squamous cell carcinoma (gingivitis, lichen planus), pancreatic carcinoma (pancreatitis, protease mutation), vulvar squamous cell carcinoma (lichen sclerosis), salivary gland carcinoma (slaladenitis), lung carcinoma (bronchitis) and MALT lymphoma (Sjogren syndrome, Hashimoto's thyroiditis). Shacter, et al., 2002, *Oncology,* 16(2), 217-26.

In certain embodiments, the compounds provided herein are useful in treating inflammatory diseases in the airways, such as nonspecific bronchial hyper-reactivity, chronic bronchitis, cystic fibrosis, and acute respiratory distress syndrome (ARDS).

In certain embodiments, the compounds provided herein are useful in treating asthma and idiopathic lung fibrosis or idiopathic pulmonary fibrosis (IPF), pulmonary fibrosis, and interstitial lung disease. As known to one of skill in the art, the differentiation of fibroblasts into cell types called myofibroblasts occurs during wound healing, when the cells contribute to the deposition of extracellular matrix (ECM) in the transient process of wound repair. In chronic inflammatory diseases such as asthma, pathological tissue remodeling often occurs, and is mediated by the functions of increased numbers of myofibroblasts in the diseased tissue, see Hinz, B. et al. Am J Pathol. 2007; 170: 1807-1816. In certain embodiments, the compounds provided herein prevent or reduce TGF-β-induced myofibroblast differentiation, as measured by the expression of alpha smooth muscle actin (α-SMA), a hallmark of myofibroblast differentiation (Serini, G. and Gabbiani, G. 1999; Exp. Cell Res. 250: 273-283).

In certain embodiments, the compounds provided herein are useful in treating psoriasis, chronic plaque psoriasis, psoriatic arthritis, acanthosis, atopic dermatitis, various forms of eczema, contact dermatitis (includes allergic dermatitis), systemic sclerosis (scleroderma), wound healing, and drug eruption.

In one embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, eczema, Sjögren's syndrome, burns, dermatitis, neuroinflammation, allergy pain, autoimmune myositis, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, acute gout, pneumonitis, myocarditis, pericarditis, myositis, eczema, alopecia, vitiligo, bullous skin diseases, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs. endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, postsurgical syndromes, sarcoidosis, Herxheimer reactions, encephalitis, myelitis, SIRS associated with viral infections such as influenza, herpes zoster, herpes simplex, coronavirus or dry eye syndrome (or keratoconjunctivitis sicca (KCS)).

In certain embodiments, the compounds provided herein are useful in treating neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

In certain embodiments, the compounds provided herein are useful in treating Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury.

In one embodiment, the compounds provided herein are useful in treating Alzheimer's disease (AD), ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus, erythematous (SLE), nephritis, Parkinson's disease, ulcerative colitis.

When used for the treatment of inflammatory disease, the compounds provided herein may be administered in dosages, routes of administration and/or to achieve pK profiles as described herein for the treatment of cancer.

6.3.3 Rasopathies

As discussed herein, Ras signaling is causally implicated in rasopathies. Thus, the compounds provided herein, which inhibit the function of one or more members of the Ras superfamily, are useful in the treatment of rasopathies including neurofibromatosis type 1, Noonan's syndrome, and Costello syndrome.

In one embodiment, provided herein is a method of treating or preventing a rasopathy, which comprises administering to a subject a compound that inhibits the function of one or more members of the Ras superfamily by binding to the GTP binding domain or one or more members of the Ras superfamily. In one embodiment, provided herein is a method of treating or preventing a rasopathy, which comprises administering to a subject a compound that inhibits the function of Ras by binding to a Ras GTP binding domain. In another embodiment, provided herein is a method of treating or preventing a rasopathy, which comprises administering to a subject a compound that binds to a Ras GTP binding domain with an $IC_{50}$ of less than 10 μM and $K_d$ of less than 10 μM. In another embodiment, provided herein is a method of treating or preventing a rasopathy, which comprises administering to a subject a compound that binds to a Ras GTP binding domain with an $IC_{50}$ of less than 1 μM and a $K_d$ of less than 1 μM. In another embodiment, provided herein is a method of treating or preventing a rasopathy, which comprises administering to a subject a compound that binds to a Ras GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Ras GTP binding domain with an $IC_{50}$ of less than 470 nM and a $K_d$ of less than 470 nM. In another embodiment, provided herein is a method of treating or preventing a rasopathy, which comprises administering to a subject a compound that binds to a Ras GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Ras GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Ras GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Ras GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Ras GTP binding domain with greater than 25% inhibition at 20 μM. In another embodiment, provided herein is a method of treating or preventing a rasopathy, which comprises administering to a subject a compound that binds to a Ras GTP binding domain with greater than 50% inhibition at 20 μM. In another embodiment, provided herein is a method of treating or preventing a rasopathy, which comprises administering to a subject a compound that binds to a Ras GTP binding domain with greater than 75% inhibition at 20 μM. In another embodiment, provided herein is a method of treating or preventing a rasopathy, which comprises administering to a subject a compound that binds to a Ras GTP binding domain with greater than 80% inhibition at 20 μM. In another embodiment, provided herein is a method of treating or preventing a rasopathy, which comprises administering to a subject a compound that binds to a Ras GTP binding domain with greater than 85% inhibition at 20 μM. In another embodiment, provided herein is a method of treating or preventing a rasopathy, which comprises administering to a subject a compound that binds to a Ras GTP binding domain with greater than 90% inhibition at 20 μM. In another embodiment, provided herein is a method of treating or preventing a rasopathy, which comprises administering to a subject a compound that binds to a Ras GTP binding domain with greater than 95% inhibition at 20 μM. In another embodiment, provided herein is a method of treating or preventing a rasopathy, which comprises administering to a subject a compound that binds to a Ras GTP binding domain with greater than 99% inhibition at 20 μM. In one embodiment, provided herein is a method of treating or preventing a rasopathy, which comprises administering to a subject a compound that inhibits the function of Rho by binding to a Rho GTP binding domain. In another embodiment, provided herein is a method of treating or preventing a rasopathy, which comprises administering to a subject a compound that binds to a Rho GTP binding domain with an $IC_{50}$ of less than 10 μM and a $K_d$ of less than 10 μM. In another embodiment, provided herein is a method of treating or preventing a rasopathy, which comprises administering to a subject a compound that binds to a Rho GTP binding domain with an $IC_{50}$ of less than 1 μM and a $K_d$ of less than 1 μM. In another embodiment, provided herein is a method of treating or preventing a rasopathy, which comprises administering to a subject a compound that binds to a Rho GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Rho GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Rho GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Rho GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Rho GTP binding domain with an $IC_{50}$ of less than 130 nM and a $K_d$ of less than 130 nM. In another embodiment, provided herein is a method of treating or preventing a rasopathy, which comprises administering to a subject a compound that binds to a Rho GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Rho GTP binding domain with greater than 25% inhibition at 20 μM. In another embodiment, provided herein is a method of treating or preventing a rasopathy, which comprises administering to a subject a compound that binds to a Rho GTP binding domain with greater than 50% inhibition at 20 μM. In another embodiment, provided herein is a method of treating or preventing a rasopathy, which comprises administering to a subject a compound that binds to a Rho GTP binding domain with greater than 75% inhibition at 20 μM. In another embodiment, provided herein is a method of treating or preventing a rasopathy, which comprises administering to a subject a compound that binds to a Rho GTP binding domain with greater than 80% inhibition at 20 μM. In another embodiment, provided herein is a method of treating or preventing a rasopathy, which comprises administering to a subject a compound that binds to a Rho GTP binding domain with greater than 85% inhibition at 20 μM. In another embodiment, provided herein is a method of treating or preventing a rasopathy, which comprises administering to a subject a compound that binds to a Rho GTP binding domain with greater than 90% inhibition at 20 μM. In another embodiment, provided herein is a method of treating or preventing a rasopathy, which comprises administering to a subject a compound that binds to a Rho GTP binding domain with greater than 95% inhibition at 20 μM. In another embodiment, provided herein is a method of treating or preventing a rasopathy, which comprises administering to a subject a compound that binds to a Rho GTP binding domain with greater than 99% inhibition at 20 μM. In one embodiment, provided herein is a method of treating or preventing a rasopathy, which comprises administering to a subject a compound that inhibits the function of Rac by binding to a Rac GTP binding domain. In another embodiment, provided herein is a method of treating or preventing a rasopathy, which comprises administering to a subject a compound that binds to a Rac GTP binding domain with an $IC_{50}$ of less than 10 μM and a $K_d$ of less than 10 μM. In another embodiment, provided herein is a method of treating or preventing a rasopathy, which comprises administering to a subject a compound that binds to a Rac GTP binding domain with an $IC_{50}$ of less than 1 μM and a $K_d$ of less than 1 μM. In another embodiment, provided herein is a method of treating or preventing a rasopathy, which comprises administering to a subject a compound that binds to a Rac GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Rac GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Rac GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Rac GTP binding domain with an $IC_{50}$ of less than 170 nM and a $K_d$ of less than 170 nM. In another embodiment, provided herein is a method of treating or preventing a rasopathy, which comprises administering to a subject a compound that binds to a Rac GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Rac GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Rac GTP binding domain with greater than 25% inhibition at 20 μM. In another embodiment, provided herein is a method of treating or preventing a rasopathy, which comprises administering to a subject a compound that binds to a Rac GTP binding domain with greater than 50% inhibition at 20 μM. In another embodiment, provided herein is a method of treating or preventing a rasopathy, which comprises administering to a subject a compound that binds to a Rac GTP binding domain with greater than 75% inhibition at 20 μM. In another embodiment, provided herein is a method of treating or preventing a rasopathy, which comprises administering to a subject a compound that binds to a Rac GTP binding domain with greater than 80% inhibition at 20 μM. In another embodiment, provided herein is a method of treating or preventing a rasopathy, which comprises administering to a subject a compound that binds to a Rac GTP binding domain with greater than 85% inhibition at 20 μM. In another embodiment, provided herein is a method of treating or preventing a rasopathy, which comprises administering to a subject a compound that binds to a Rac GTP binding domain with greater than 90% inhibition at 20 μM. In another embodiment, provided herein is a method of treating or preventing a rasopathy, which comprises administering to a subject a compound that binds to a Rac GTP binding domain with greater than 95% inhibition at 20 μM. In another embodiment, provided herein is a method of treating or preventing a rasopathy, which comprises administering to a subject a compound that binds to a Rac GTP binding domain with greater than 99% inhibition at 20 μM.

In another embodiment, provided herein is a method of treating or preventing a rasopathy, which comprises administering to a subject a compound that binds to one or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to two or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to three or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to four or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to five or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to six or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to seven or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eight or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to nine or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to ten or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eleven or more of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to all of Ala11, Gly12, Val14, Gly15, Lys16, Ser17, Ala18, Phe28, Val 29, Asp30, Glu31, Tyr32, Asp33, Pro34, Thr35, Lys36, Gly60, Lys117, Asp119, Leu120, Ser145, Ala146 and Lys147 or Mg202 in a Ras GTP binding domain.

In another embodiment, provided herein is a method of treating or preventing a rasopathy, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to three or more of Ala 11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to four or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to five or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to six or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to seven or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eight or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to nine or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eleven or more of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to all of Ala11, Gly12, Val14, Gly15, Lys16, Ser17, Ala18, Phe28, Val 29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing a rasopathy, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing a rasopathy, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rho GTP binding domain. In one embodiment, provided herein is a method of treating or preventing a rasopathy, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole moiety, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl)pyrimidin-4(3H)-one, 2-(imidazol-4-yl)pyrimidin-4(1H)-one, 2-(imidazol-4-yl)pyrimidin-4-amine, 2-(imidazol-4-yl)pyrimidin-4(3H)-imine, or 2-(imidazol-4-yl)pyrimidin-4(1H)-imine moiety.

6.3.4 Ras-Associated Autoimmune Leukoproliferative Disorder

As discussed herein, Ras has been causally associated with Ras-associated autoimmune leukoproliferative disorder. Thus, the compounds provided herein, which inhibit the function of Ras, are useful in the treatment of Ras-associated autoimmune leukoproliferative disorder.

In one embodiment, provided herein is a method of treating or preventing Ras-associated autoimmune leukoproliferative disorder, which comprises administering to a subject a compound that inhibits the function of Ras by binding to a Ras GTP binding domain. In another embodiment, provided herein is a method of treating or preventing Ras-associated autoimmune leukoproliferative disorder, which comprises administering to a subject a compound that binds to a Ras GTP binding domain with an $IC_{50}$ of less than 10 μM and $K_d$ of less than 10 μM. In another embodiment, provided herein is a method of treating or preventing Ras-associated autoimmune leukoproliferative disorder, which comprises administering to a subject a compound that binds to a Ras GTP binding domain with an $IC_{50}$ of less than 1 μM and a $K_d$ of less than 1 μM. In another embodiment, provided herein is a method of treating or preventing Ras-associated autoimmune leukoproliferative disorder, which comprises administering to a subject a compound that binds to a Ras GTP binding domain with an $IC_{50}$ of less than 500 nM and a $K_d$ of less than 500 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 470 nM and a $K_d$ of less than 470 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 270 nM and a $K_d$ of less than 270 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 200 nM and a $K_d$ of less than 200 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 150 nM and a $K_d$ of less than 150 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 100 nM and a $K_d$ of less than 100 nM. In another embodiment, provided herein is a method of treating or preventing Ras-associated autoimmune leukoproliferative disorder, which comprises administering to a subject a compound that binds to a Ras GTP binding domain with greater than 25% inhibition at 20 μM. In another embodiment, provided herein is a method of treating or preventing Ras-associated autoimmune leukoproliferative disorder, which comprises administering to a subject a compound that binds to a Ras GTP binding domain with greater than 50% inhibition at 20 μM. In another embodiment, provided herein is a method of treating or preventing Ras-associated autoimmune leukoproliferative disorder, which comprises administering to a subject a compound that binds to a Ras GTP binding domain with greater than 75% inhibition at 20 μM. In another embodiment, provided herein is a method of treating or preventing Ras-associated autoimmune leukoproliferative disorder, which comprises administering to a subject a compound that binds to a Ras GTP binding domain with greater than 80% inhibition at 20 μM. In another embodiment, provided herein is a method of treating or preventing Ras-associated autoimmune leukoproliferative disorder, which comprises administering to a subject a compound that binds to a Ras GTP binding domain with greater than 85% inhibition at 20 μM. In another embodiment, provided herein is a method of treating or preventing Ras-associated autoimmune leukoproliferative disorder, which comprises administering to a subject a compound that binds to a Ras GTP binding domain with greater than 90% inhibition at 20 μM. In another embodiment, provided herein is a method of treating or preventing Ras-associated autoimmune leukoproliferative disorder, which comprises administering to a subject a compound that binds to a Ras GTP binding domain with greater than 95% inhibition at 20 μM. In another embodiment, provided herein is a method of treating or preventing Ras-associated autoimmune leukoproliferative disorder, which comprises administering to a subject a compound that binds to a Ras GTP binding domain with greater than 99% inhibition at 20 μM.

In another embodiment, provided herein is a method of treating or preventing Ras-associated autoimmune leukoproliferative disorder, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr 35, Lys 36, Gly60, Lys117, Asp119, Leu120, Ser145, Ala146 and Lys147 or Mg202 in a Ras GTP binding domain.

In another embodiment, provided herein is a method of treating or preventing Ras-associated autoimmune leukoproliferative disorder, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146 and Lys147 or Mg202 in a Ras GTP binding domain.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In one embodiment, the compound for use in the methods and compositions provided herein has a molecular weight less than 2000 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole moiety, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl)pyrimidin-4(3H)-one, 2-(imidazol-4-yl)pyrimidin-4(1H)-one, 2-(imidazol-4-yl)pyrimidin-4-amine, 2-(imidazol-4-yl)pyrimidin-4(3H)-imine, or 2-(imidazol-4-yl)pyrimidin-4(1H)-imine moiety.

6.3.5 Fibrotic Disease

As discussed herein, Ras superfamily members are potential targets in fibrotic disease treatment. In one embodiment, provided herein is a method of treating or preventing fibrotic disease, which comprises administering to a subject a compound that inhibits the function of one or more members of the Ras superfamily by binding to the GTP binding domain or one or more members of the Ras superfamily. In one embodiment, provided herein is a method of treating or preventing fibrotic disease, which comprises administering to a subject a compound that inhibits the function of Ras by binding to a Rho GTP binding domain. In another embodiment, provided herein is a method of treating or preventing fibrotic disease, which comprises administering to a subject a compound that binds to a Ras GTP binding domain with an $IC_{50}$ of less than 10 μM and $K_d$ of less than 10 μM. In another embodiment, provided herein is a method of treating or preventing fibrotic disease, which comprises administering to a subject a compound that binds to a Ras GTP binding domain with an $IC_{50}$ of less than 1 μM and a $K_d$ of less than 1 μM. In another embodiment, provided herein is a method of treating or preventing fibrotic disease, which comprises administering to a subject a compound that binds to a Ras GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Ras GTP binding domain with an $IC_{50}$ of less than 470 nM and a $K_d$ of less than 470 nM. In another embodiment, provided herein is a method of treating or preventing fibrotic disease, which comprises administering to a subject a compound that binds to a Ras GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Ras GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Ras GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Ras GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Ras GTP binding domain with greater than 25% inhibition at 20 μM. In another embodiment, provided herein is a method of treating or preventing fibrotic disease, which comprises administering to a subject a compound that binds to a Ras GTP binding domain with greater than 50% inhibition at 20 μM. In another embodiment, provided herein is a method of treating or preventing fibrotic disease, which comprises administering to a subject a compound that binds to a Ras GTP binding domain with greater than 75% inhibition at 20 μM. In another embodiment, provided herein is a method of treating or preventing fibrotic disease, which comprises administering to a subject a compound that binds to a Ras GTP binding domain with greater than 80% inhibition at 20 μM. In another embodiment, provided herein is a method of treating or preventing fibrotic disease, which comprises administering to a subject a compound that binds to a Ras GTP binding domain with greater than 85% inhibition at 20 μM. In another embodiment, provided herein is a method of treating or preventing fibrotic disease, which comprises administering to a subject a compound that binds to a Ras GTP binding domain with greater than 90% inhibition at 20 μM. In another embodiment, provided herein is a method of treating or preventing fibrotic disease, which comprises administering to a subject a compound that binds to a Ras GTP binding domain with greater than 95% inhibition at 20 μM. In another embodiment, provided herein is a method of treating or preventing fibrotic disease, which comprises administering to a subject a compound that binds to a Ras GTP binding domain with greater than 99% inhibition at 20 μM. In one embodiment, provided herein is a method of treating or preventing fibrotic disease, which comprises administering to a subject a compound that inhibits the function of Rho by binding to a Rho GTP binding domain.

In another embodiment, provided herein is a method of treating or preventing fibrotic disease, which comprises administering to a subject a compound that binds to a Rho GTP binding domain with an $IC_{50}$ of less than 10 μM and $K_d$ of less than 10 μM. In another embodiment, provided herein is a method of treating or preventing fibrotic disease, which comprises administering to a subject a compound that binds to a Rho GTP binding domain with an $IC_{50}$ of less than 1 μM and a $K_d$ of less than 1 μM. In another embodiment, provided herein is a method of treating or preventing fibrotic disease, which comprises administering to a subject a compound that binds to a Rho GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Rho GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Rho GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Rho GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Rho GTP binding domain with an $IC_{50}$ of less than 130 nM and a $K_d$ of less than 130 nM. In another embodiment, provided herein is a method of treating or preventing fibrotic disease, which comprises administering to a subject a compound that binds to a Rho GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Rho GTP binding domain with greater than 25% inhibition at 20 μM. In another embodiment, provided herein is a method of treating or preventing fibrotic disease, which comprises administering to a subject a compound that binds to a Rho GTP binding domain with greater than 50% inhibition at 20 μM. In another embodiment, provided herein is a method of treating or preventing fibrotic disease, which comprises administering to a subject a compound that binds to a Rho GTP binding domain with greater than 75% inhibition at 20 μM. In another embodiment, provided herein is a method of treating or preventing fibrotic disease, which comprises administering to a subject a compound that binds to a Rho GTP binding domain with greater than 80% inhibition at 20 μM. In another embodiment, provided herein is a method of treating or preventing fibrotic disease, which comprises administering to a subject a compound that binds to a Rho GTP binding domain with greater than 85% inhibition at 20 μM. In another embodiment, provided herein is a method of treating or preventing fibrotic disease, which comprises administering to a subject a compound that binds to a Rho GTP binding domain with greater than 90% inhibition at 20 μM. In another embodiment, provided herein is a method of treating or preventing fibrotic disease, which comprises administering to a subject a compound that binds to a Rho GTP binding domain with greater than 95% inhibition at 20 μM. In another embodiment, provided herein is a method of treating or preventing fibrotic disease, which comprises administering to a subject a compound that binds to a Rho GTP binding domain with greater than 99% inhibition at 20 μM. In one embodiment, provided herein is a method of treating or preventing fibrotic disease, which comprises administering to a subject a compound that inhibits the function of Rac by binding to a Rac GTP binding domain. In another embodiment, provided herein is a method of treating or preventing fibrotic disease, which comprises administering to a subject a compound that binds to a Rac GTP binding domain with an $IC_{50}$ of less than 10 μM and $K_d$ of less than 10 μM. In another embodiment, provided herein is a method of treating or preventing fibrotic disease, which comprises administering to a subject a compound that binds to a Rac GTP binding domain with an $IC_{50}$ of less than 1 μM and a $K_d$ of less than 1 μM. In another embodiment, provided herein is a method of treating or preventing fibrotic disease, which comprises administering to a subject a compound that binds to a Rac GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Rac GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Rac GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Rac GTP binding domain with an $IC_{50}$ of less than 170 nM and a $K_d$ of less than 170 nM. In another embodiment, provided herein is a method of treating or preventing fibrotic disease, which comprises administering to a subject a compound that binds to a Rac GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Rac GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Rac GTP binding domain with greater than 25% inhibition at 20 μM. In another embodiment, provided herein is a method of treating or preventing fibrotic disease, which comprises administering to a subject a compound that binds to a Rac GTP binding domain with greater than 50% inhibition at 20 μM. In another embodiment, provided herein is a method of treating or preventing fibrotic disease, which comprises administering to a subject a compound that binds to a Rac GTP binding domain with greater than 75% inhibition at 20 μM. In another embodiment, provided herein is a method of treating or preventing fibrotic disease, which comprises administering to a subject a compound that binds to a Rac GTP binding domain with greater than 80% inhibition at 20 μM. In another embodiment, provided herein is a method of treating or preventing fibrotic disease, which comprises administering to a subject a compound that binds to a Rac GTP binding domain with greater than 85% inhibition at 20 μM. In another embodiment, provided herein is a method of treating or preventing fibrotic disease, which comprises administering to a subject a compound that binds to a Rac GTP binding domain with greater than 90% inhibition at 20 μM. In another embodiment, provided herein is a method of treating or preventing fibrotic disease, which comprises administering to a subject a compound that binds to a Rac GTP binding domain with greater than 95% inhibition at 20 μM. In another embodiment, provided herein is a method of treating or preventing fibrotic disease, which comprises administering to a subject a compound that binds to a Rac GTP binding domain with greater than 99% inhibition at 20 μM.

In another embodiment, provided herein is a method of treating or preventing fibrotic disease, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-two or more of Alal 1, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr 35, Lys 36, Gly 60, Lys117, Asp119, Leu120, Ser145, Ala146, Lys147 or Mg202 in a Ras GTP binding domain.

In another embodiment, provided herein is a method of treating or preventing fibrotic disease, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Lys36, Gly60, Gln61, Lys117, Asp119, Leu120, Ser145, Ala146, Lys147 or Mg202 in a Ras GTP binding domain.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing fibrotic disease, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing fibrotic disease, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rho GTP binding domain. In one embodiment, provided herein is a method of treating or preventing fibrotic disease, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains an oxadiazole, thiadiazole or triazole moiety. In another embodiment, the compound for use in the methods and compositions provided herein contains a 1,2,4-oxadiazole, 1,2,4-thiadiazole, 1,2,4-triazole moiety, 2-acylaminothiazole, 2-(pyridine-2-yl)pyrimidine-4-amine, 2-(pyridine-2-yl)pyrimidine-4-ol, 2-(pyridine-2-yl)pyrimidine-4-(1H)-one, 2-(pyridin-2-yl)pyrimidin-4(3H)-one, 2-(pyridin-2-yl)pyrimidin-4(1H)-imine or 2-(pyridin-2-yl)pyrimidin-4(3H)-imine moiety. In another embodiment, the compound for use in the methods and compositions provided herein contains a 2-(pyridin-2-yl)pyrimidine-4-amine, 2-(pyridin-2-yl)pyrimidine-4-ol, 2-(pyridin-2-yl)pyrimidine-4-(1H)-one, 2-(imidazol-2-yl)pyrimidin-4-ol, 2-(imidazol-2-yl)pyrimidin-4(3H)-one, 2-(imidazol-2-yl)pyrimidin-4(1H)-one, 2-(imidazol-2-yl)pyrimidin-4-amine, 2-(imidazol-2-yl)pyrimidin-4(3H)-imine, 2-(imidazol-2-yl)pyrimidin-4(1H)-imine, 2-(imidazol-4-yl)pyrimidin-4-ol, 2-(imidazol-4-yl)pyrimidin-4(3H)-one, 2-(imidazol-4-yl)pyrimidin-4(1H)-one, 2-(imidazol-4-yl)pyrimidin-4-amine, 2-(imidazol-4-yl)pyrimidin-4(3H)-imine, or 2-(imidazol-4-yl)pyrimidin-4(1H)-imine moiety.

5.4. Compounds for Use in Compositions and Methods

Provided herein are compounds which bind to the GTP binding domain of one or more Ras superfamily members and compete with the binding of GTP to one or more Ras superfamily members.

Provided herein are compounds which bind to a Ras GTP binding domain and compete with the binding of GTP to Ras. In one embodiment, the compounds also inhibit phosphorylation of MAPK, in particular MAPK1/2, cellular proliferation, secretion of IL-6 or TNF-α cytokines. The compounds provided herein are therefore useful in compositions and methods of treating cancer, inflammatory diseases, Ras-associated autoimmune leukoproliferative disorder and rasopathies.

Provided herein are compounds which bind to a Rac GTP binding domain and compete with the binding of GTP to Rac. In one embodiment, the compounds also inhibit the MAPK signaling pathway. In one embodiment, the compounds also inhibit the ROCK signaling pathway. The compounds provided herein are therefore useful in compositions and methods of treating cancer, inflammatory diseases and fibrotic disease.

Provided herein are compounds which bind to a Rho GTP binding domain and compete with the binding of GTP to Rho. In one embodiment, the compounds also inhibit the MAPK signaling pathway. In one embodiment, the compounds also inhibit the ROCK signaling pathway. The compounds provided herein are therefore useful in compositions and methods of treating cancer, inflammatory diseases and fibrotic disease.

In one embodiment, the compounds provided herein inhibit GTP binding to one or more members of the Ras superfamily. In one embodiment, the compounds provided herein inhibit GTP binding to Ras. In one embodiment, the compounds provided herein inhibit GTP binding to Rho. In one embodiment, the compounds provided herein inhibit GTP binding to Rac. In one embodiment, the compounds provided herein inhibit GTP binding to Ras and Rho. In one embodiment, the compounds provided herein inhibit GTP binding to Ras and Rac. In one embodiment, the compounds provided herein inhibit GTP binding to Rho and Rac. In one embodiment, the compounds provided herein inhibit GTP binding to Ras, Rho and Rac.

In certain embodiments, the compounds for use in the compositions and methods provided herein are of Formula I:

Formula I

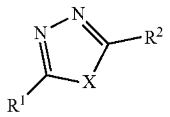

or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is O, S or $NR^5$.

In another embodiment, the compound of Formula I is a compound of Formula Ia:

Formula Ia

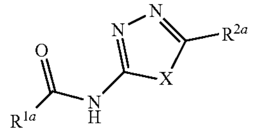

or pharmaceutically acceptable derivatives thereof, wherein $R^{1a}$ is selected from the group consisting of H, alkyl, alkenyl, alkynyl, aryl, cycloalkyl, heterocyclyl, heteroaryl, $OR^3$, and $NR^6R^7$;

wherein $R^{2a}$ is selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is O, S or $NR^5$.

In another embodiment, the compound of Formula I is a compound of Formula Ia or pharmaceutically acceptable derivatives thereof, wherein:

$R^{1a}$ is selected from the group consisting of H, phenyl, pyridinyl, or from one of the following:

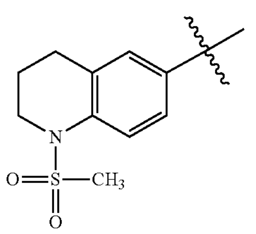
,
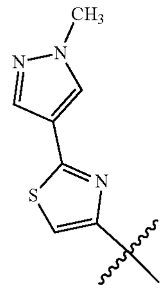
,
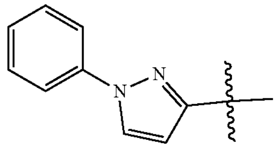
,
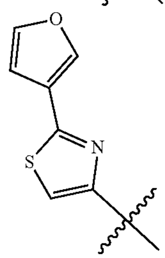
,

-continued
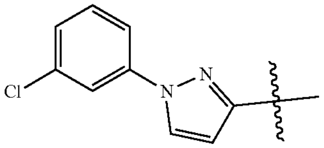
,
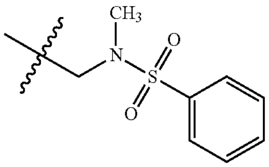
,
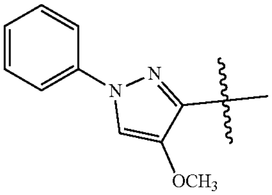
,
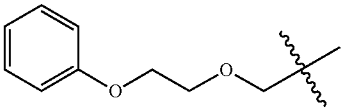
,
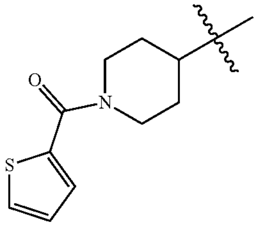
,
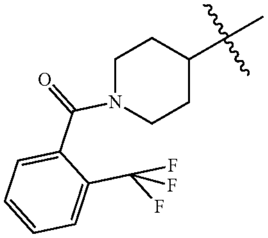
,
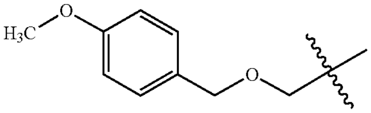
,
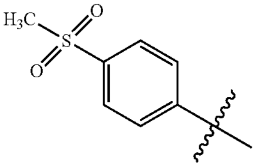
,
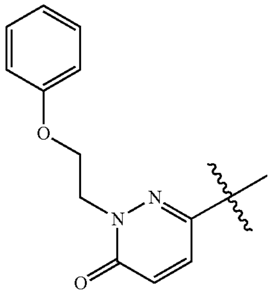
,
-continued
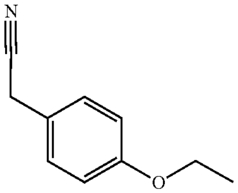
,
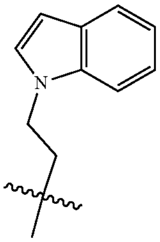
,
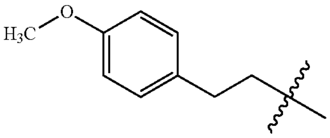
,
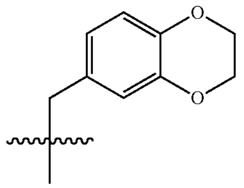
,
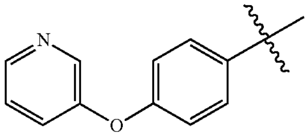
,
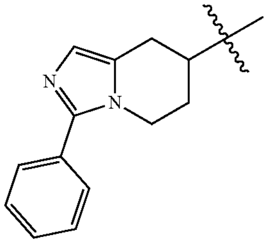
,
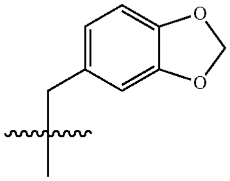
,
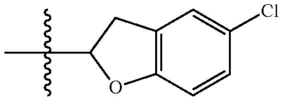
,
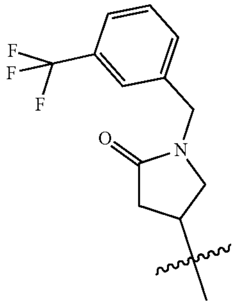
,
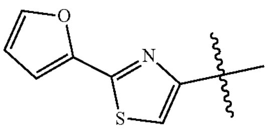
, -continued
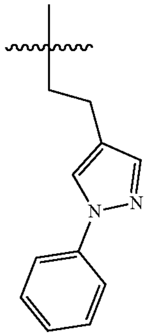
,
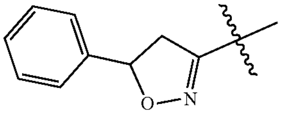
,
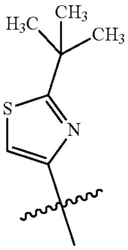
,
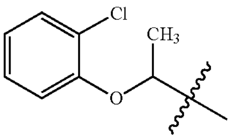
,
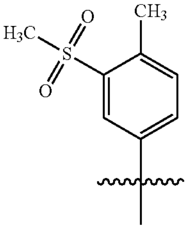
,
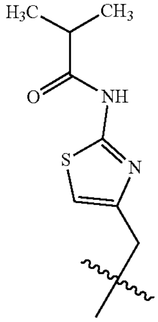
,
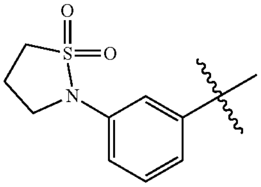
,
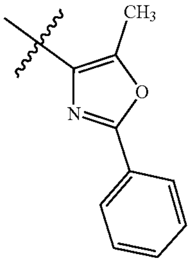
,
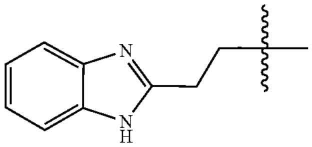
,
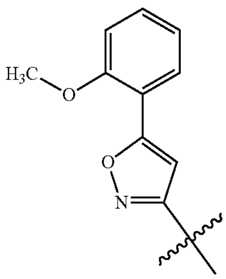
,
-continued
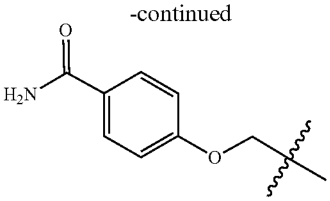
,
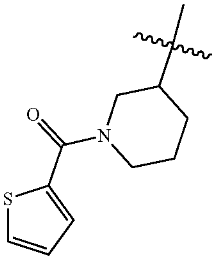
,
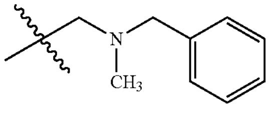
,
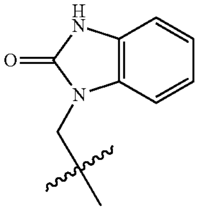
,
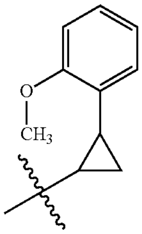
,
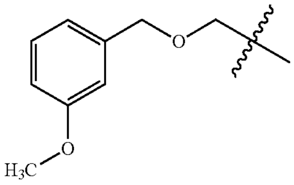
,
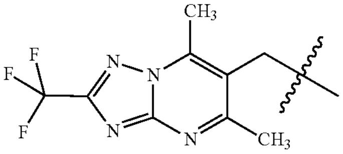
,
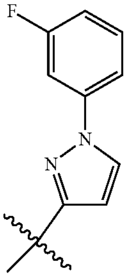
,
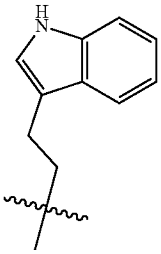
,
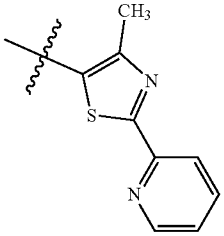
,
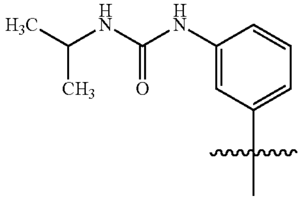
,
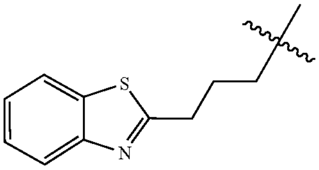
, -continued
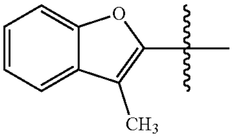
,
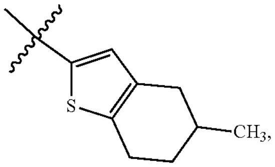
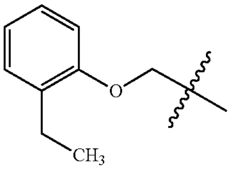
,
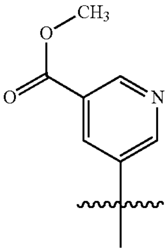
,
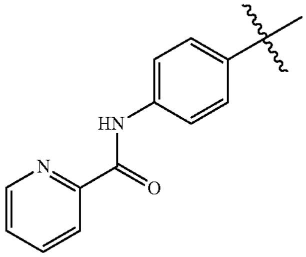
,
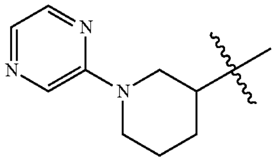
,
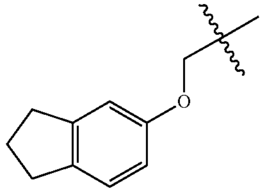
,
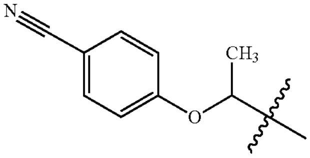
,
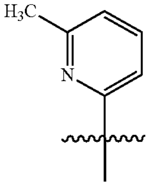
,
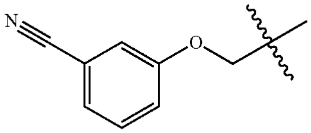
,
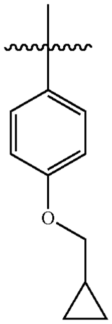
,
-continued
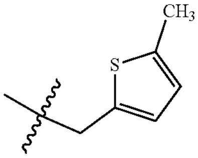
,
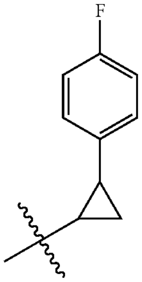
,
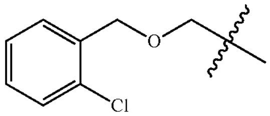
,
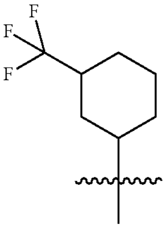
,
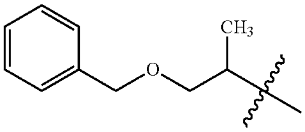
,
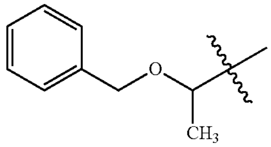
,
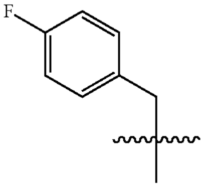
,
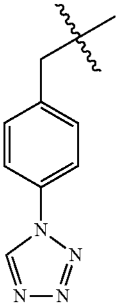
,
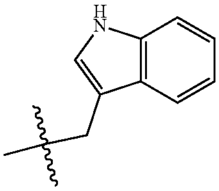
,
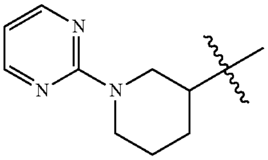
,
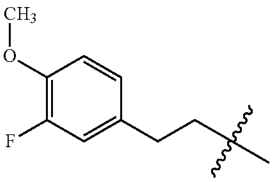
,
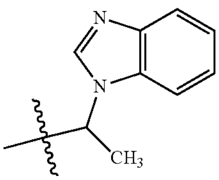
, -continued
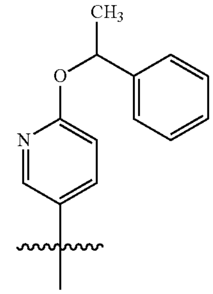
,
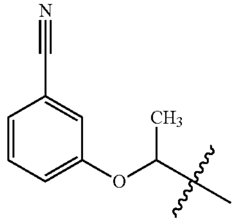
,
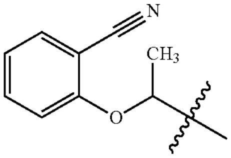
,
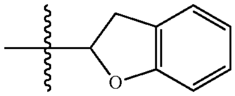
,
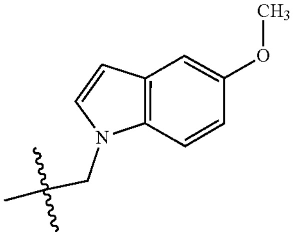
,
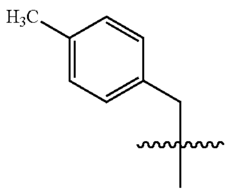
,
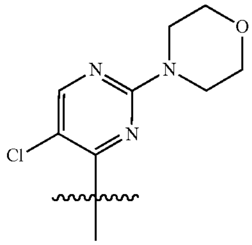
,
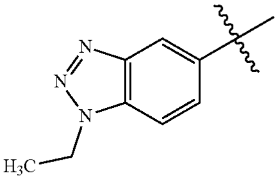
,
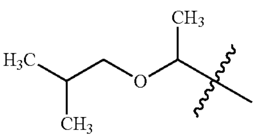
,
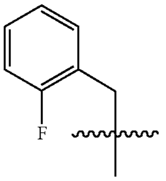
,
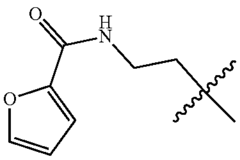
,
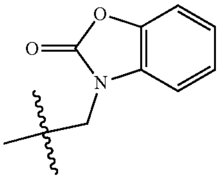
,
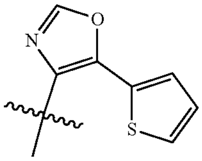
,
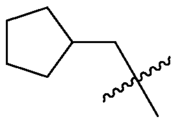
,
-continued
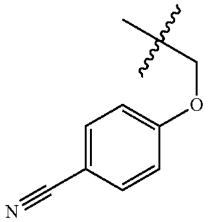
,
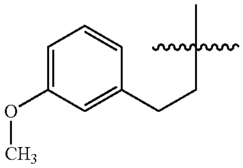
,
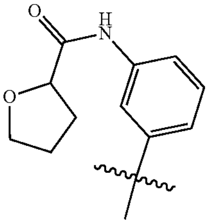
,
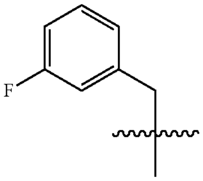
,
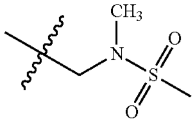
,
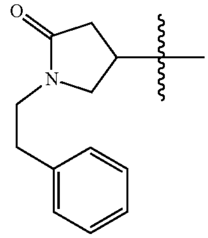
,
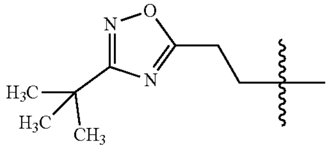
,
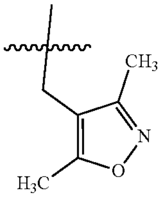
,
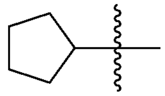
,
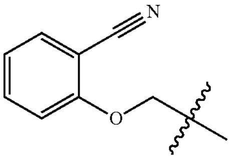
,
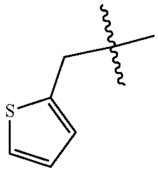
,
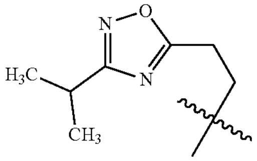
,
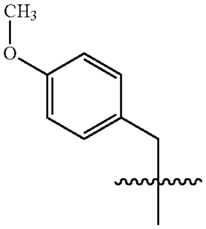
,
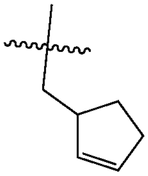
,
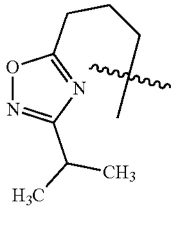
,
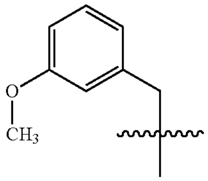
, -continued
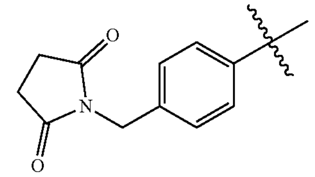,
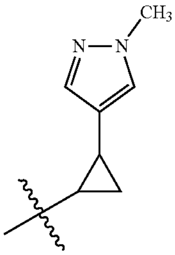, 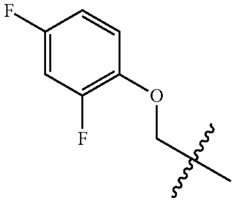,
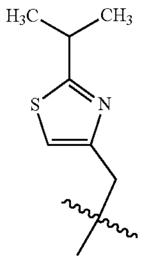, 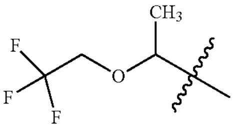,
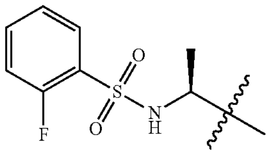, 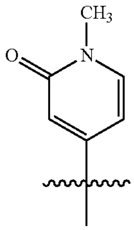,
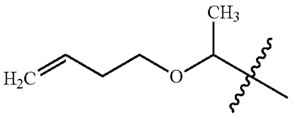, 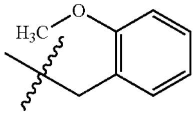,
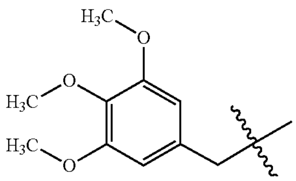,
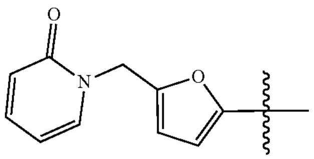,
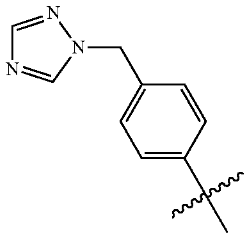,
-continued
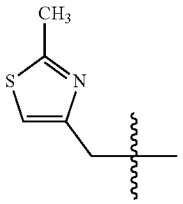, 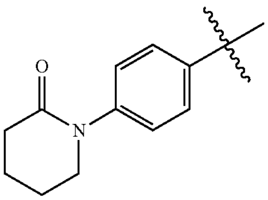,
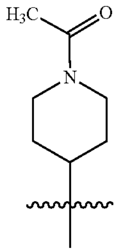, 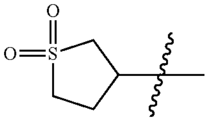,
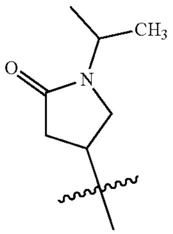, 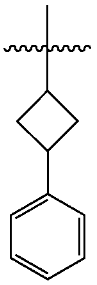, 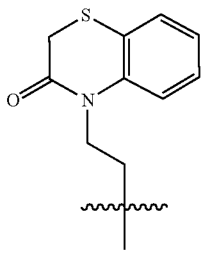,
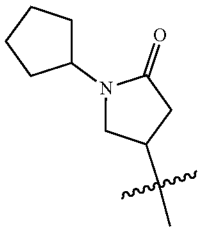, 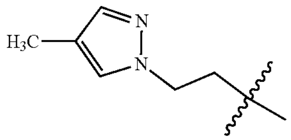,
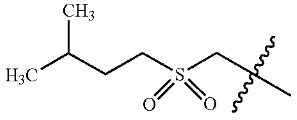 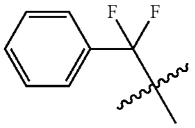,
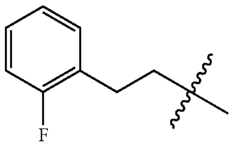, 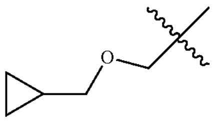,
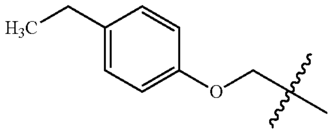,
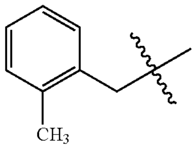, 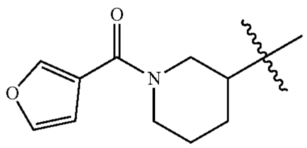, -continued
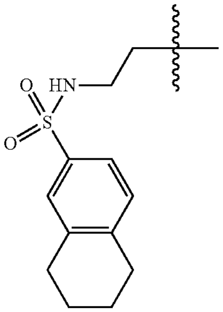,
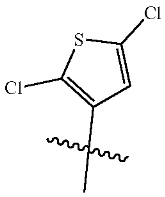,
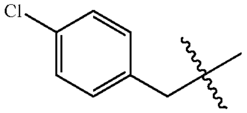,
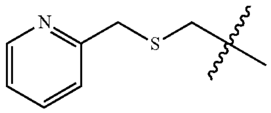,
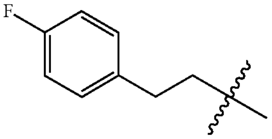,
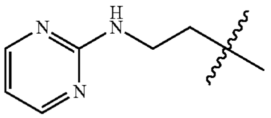,
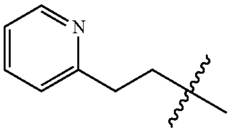,
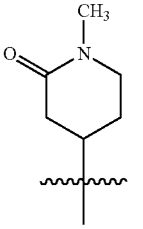,
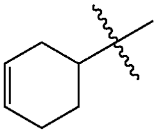,
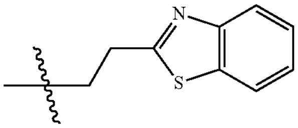,
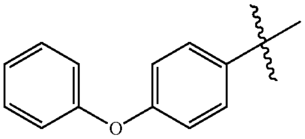,
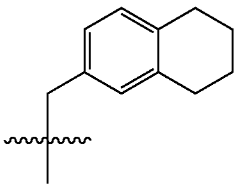,
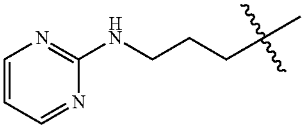,
-continued
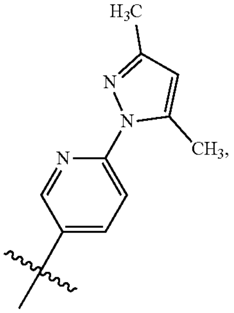,
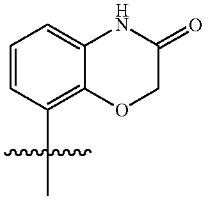,
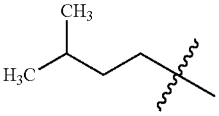,
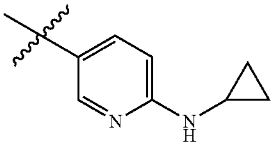,
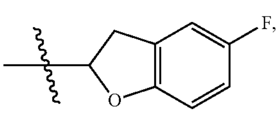,
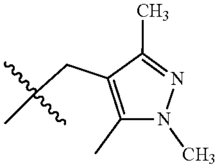,
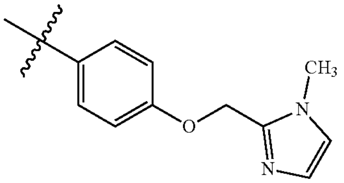,
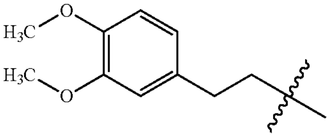,
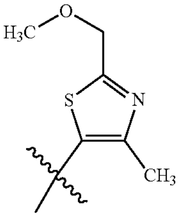,
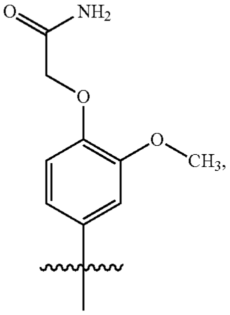,
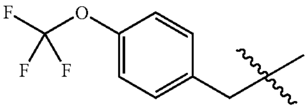,
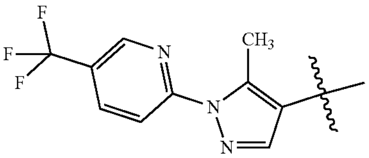, -continued
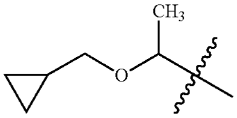,
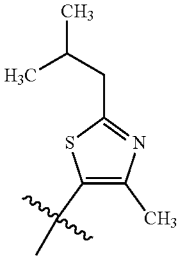,
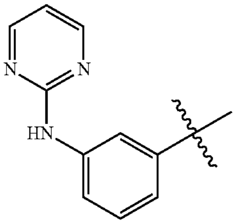,
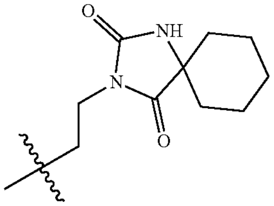,
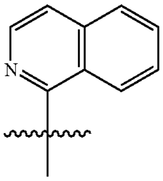,
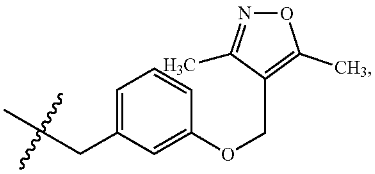
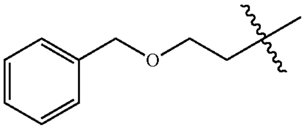,
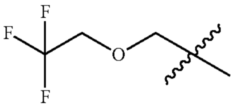,
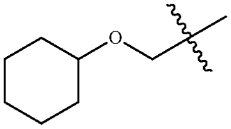,
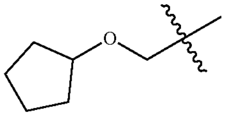,
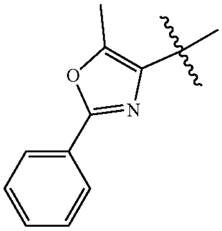,
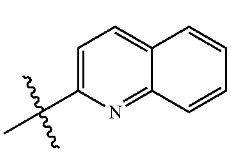,
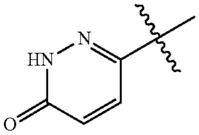,
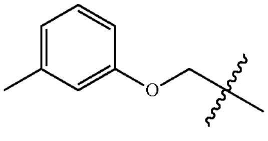,
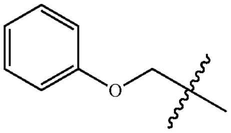,
-continued
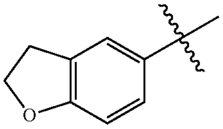,
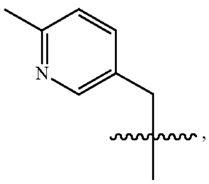,
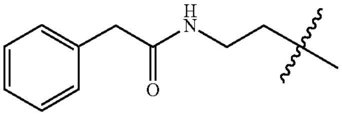,
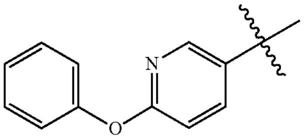,
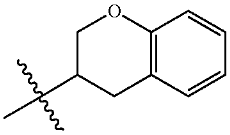,
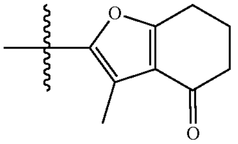,
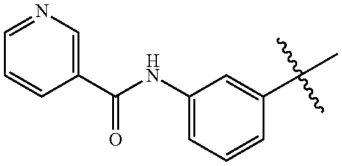, and
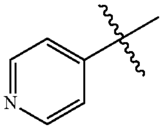;
$R^{2a}$ is aryl or heteroaryl; and X is NH or S.
In one embodiment, the compound of Formula Ia is:
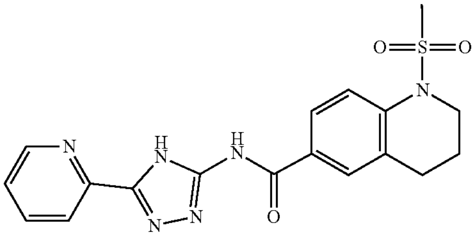
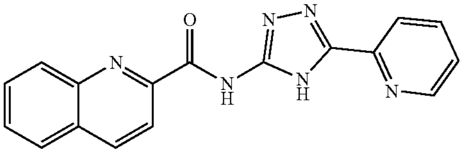
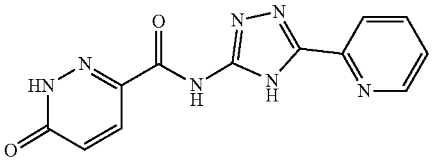

-continued
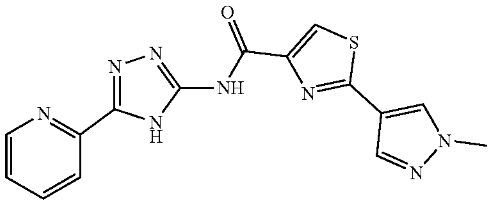
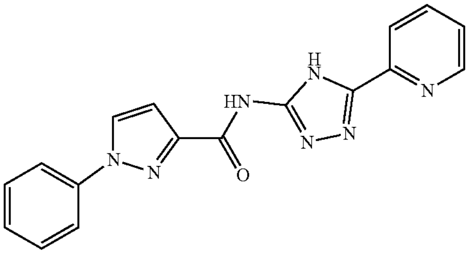
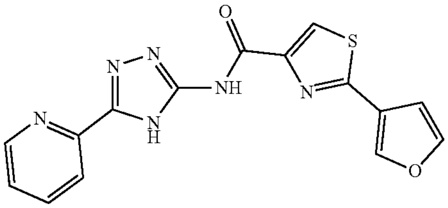
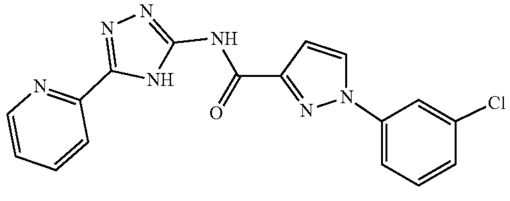
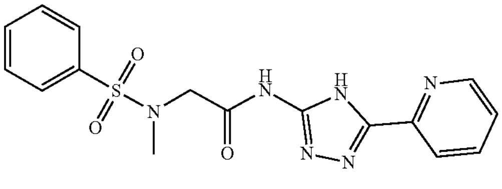
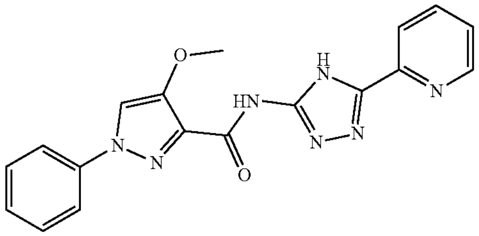
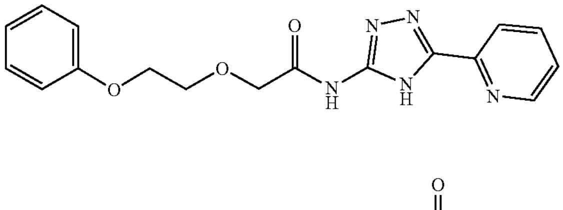
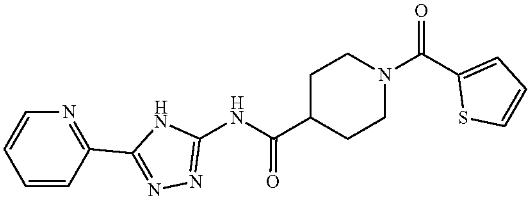
-continued
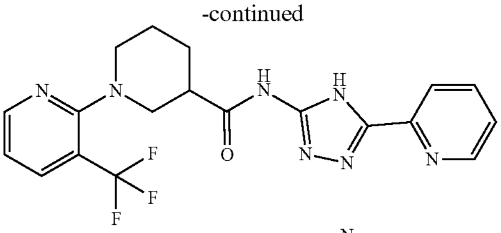
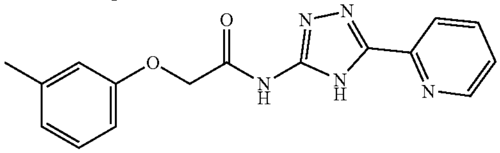
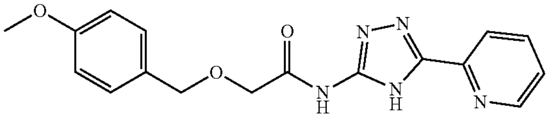
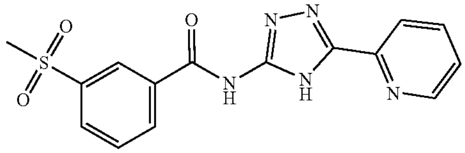
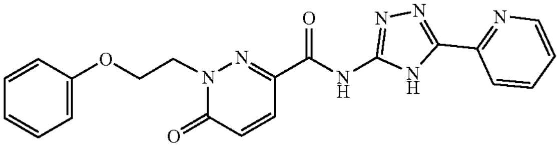
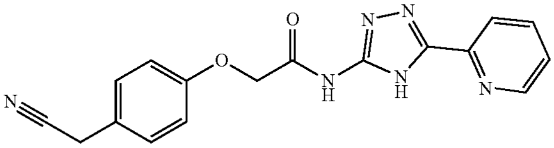
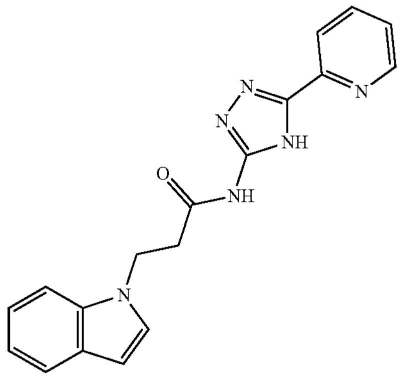
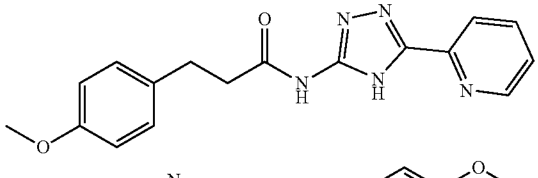
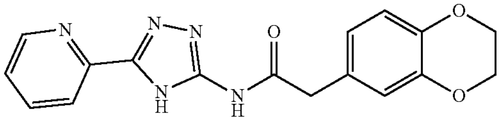
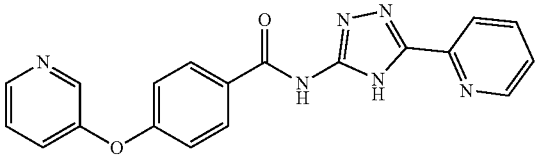

-continued
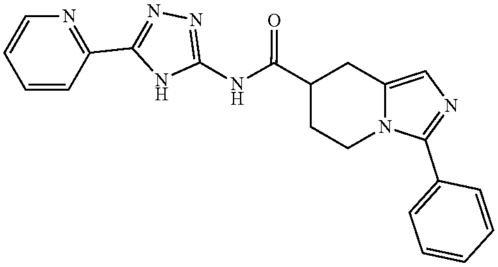
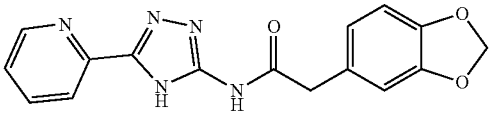
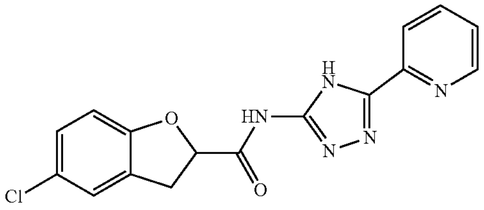
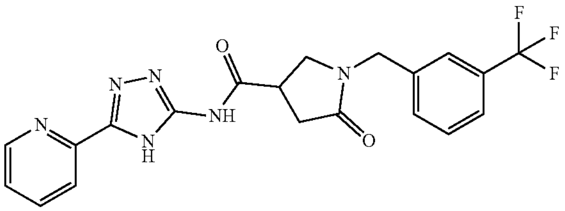
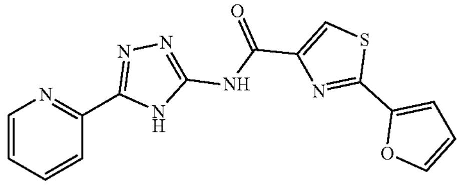
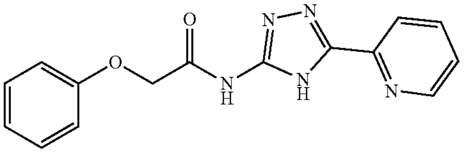
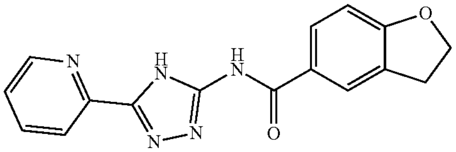
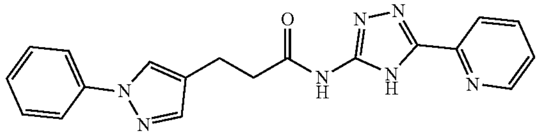
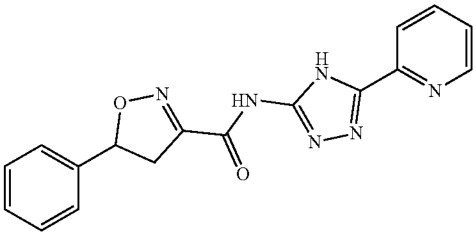
-continued
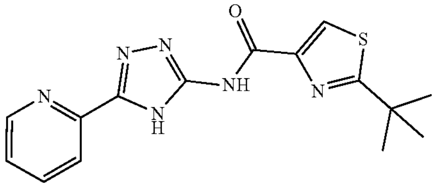
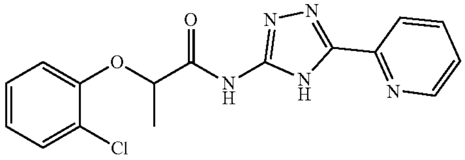
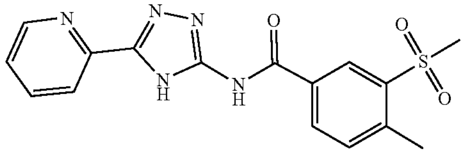
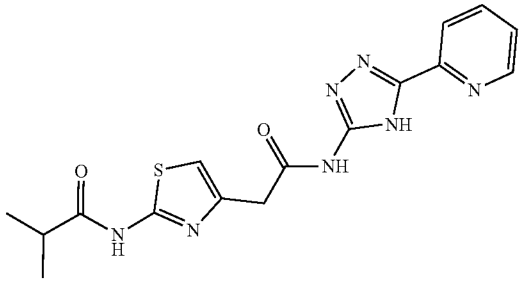
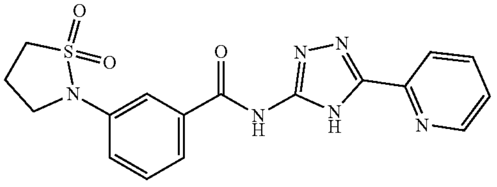
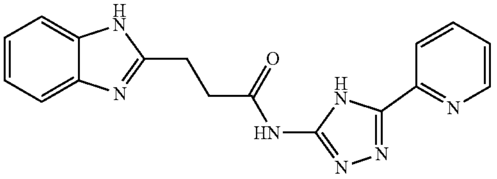
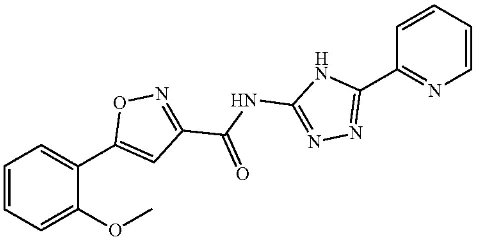
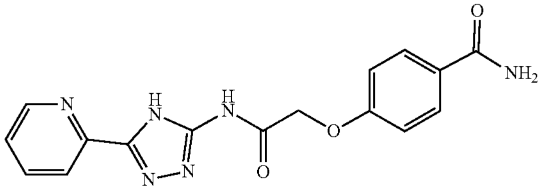
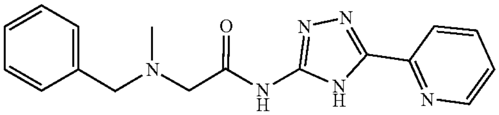

-continued
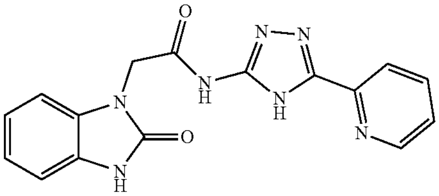
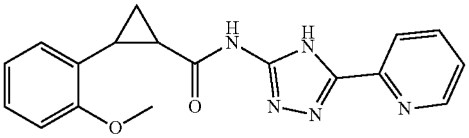
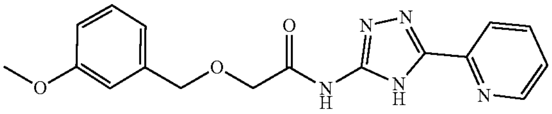
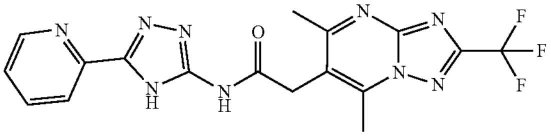
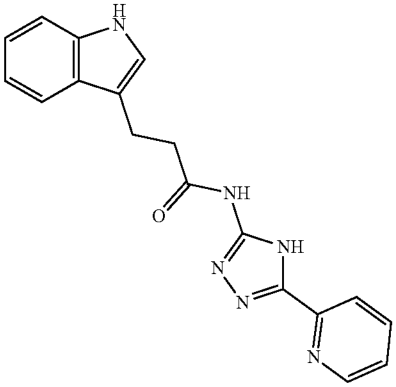
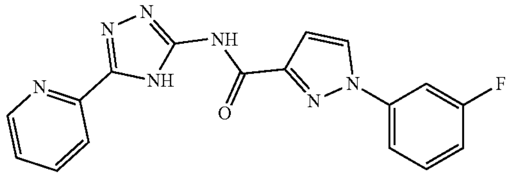
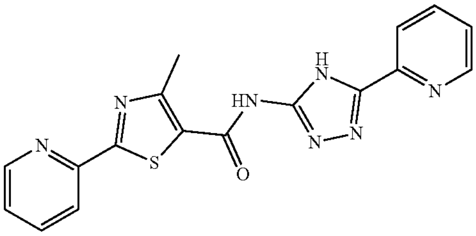
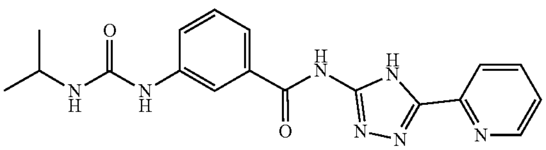
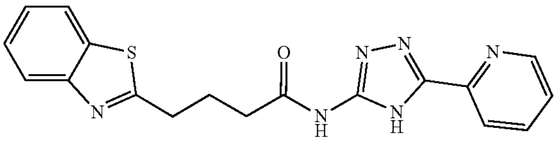
-continued
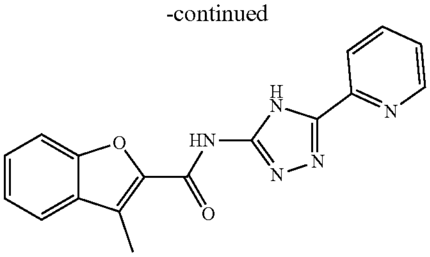
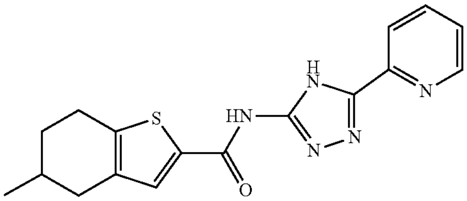
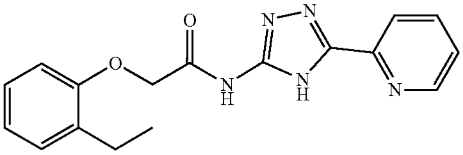
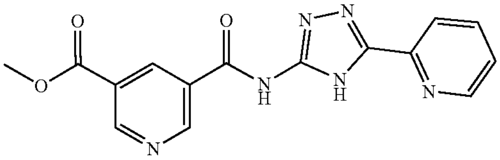
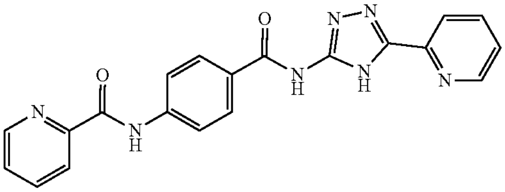
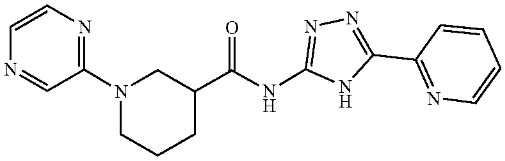
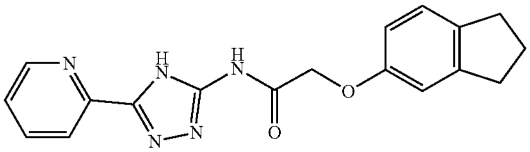
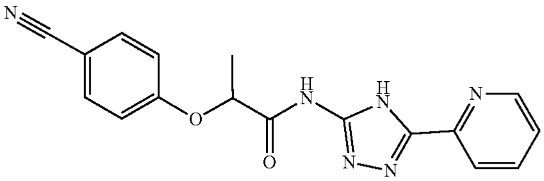
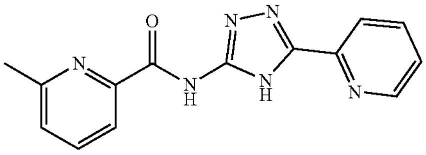
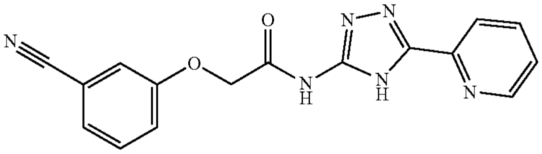

-continued
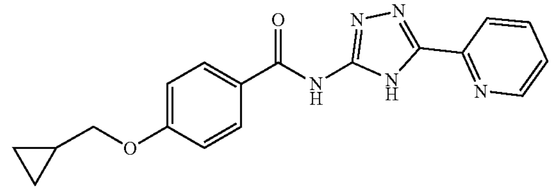
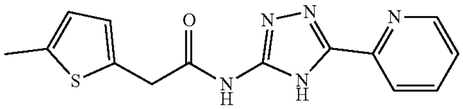
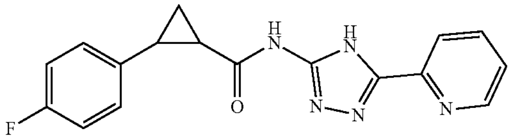
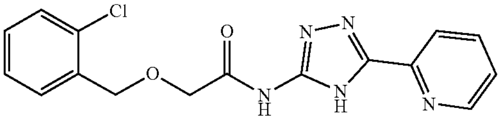
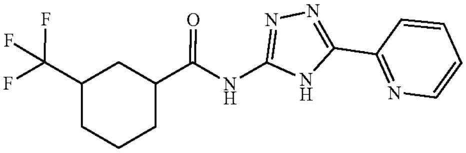
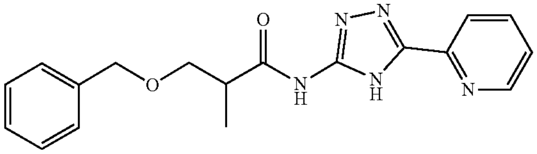
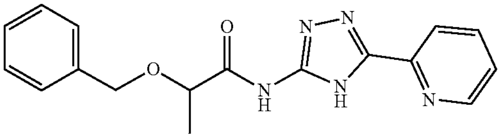
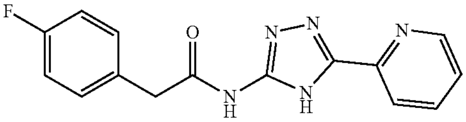
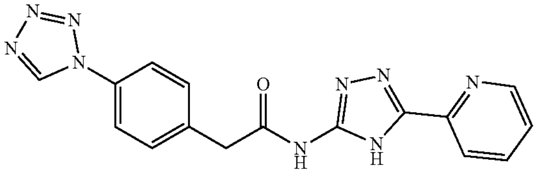
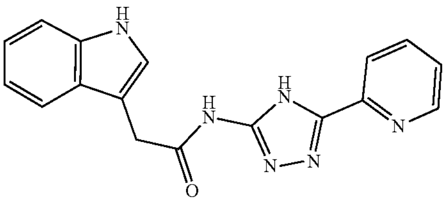
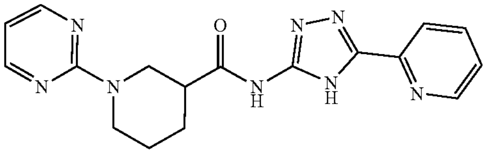
-continued
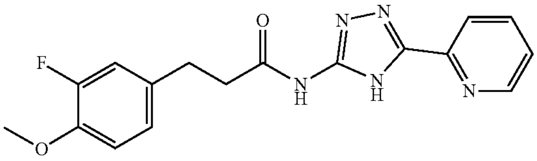
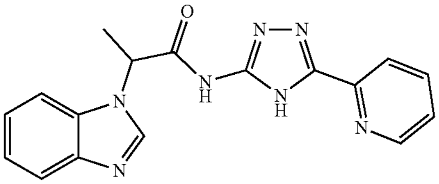
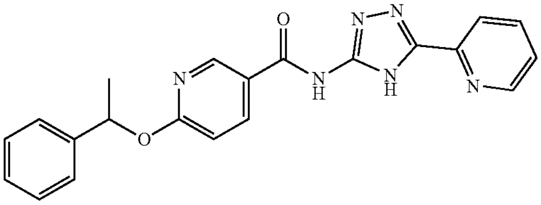
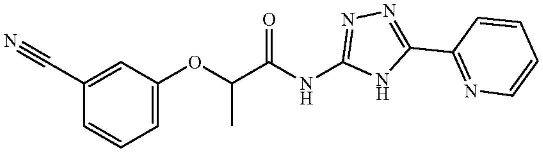
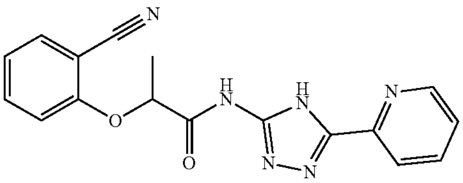
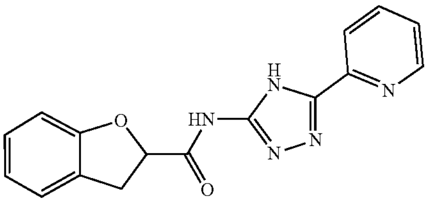
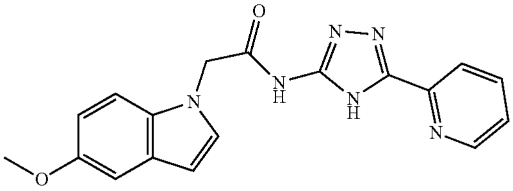
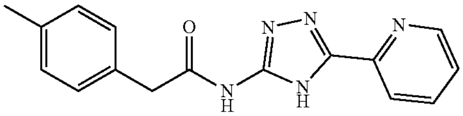
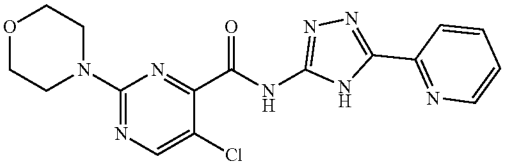

-continued
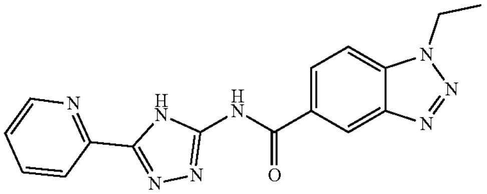
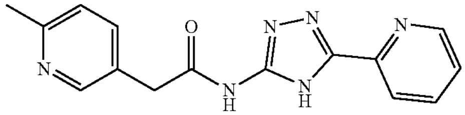
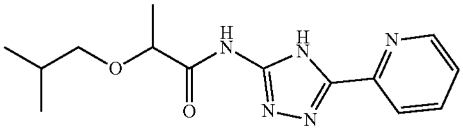
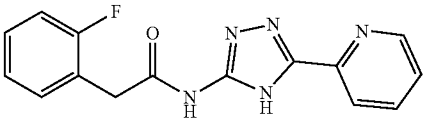
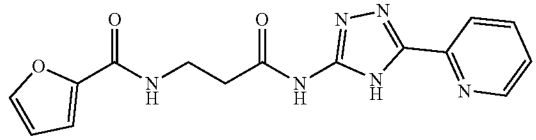
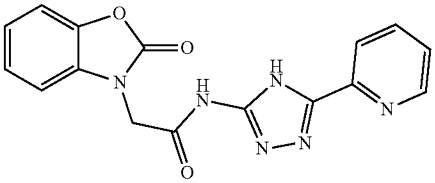
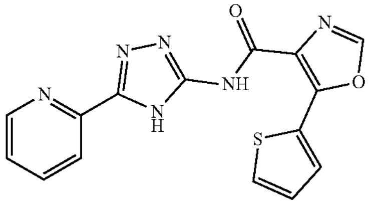
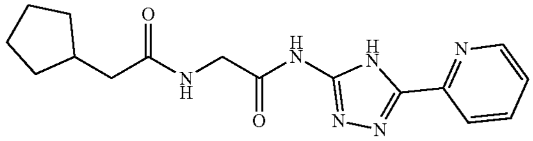
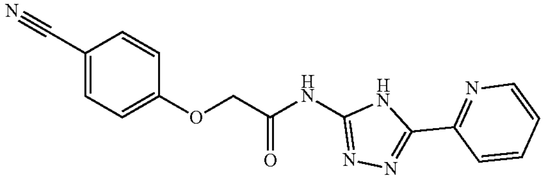
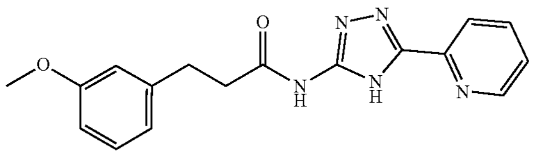
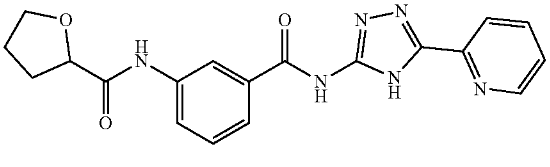
-continued
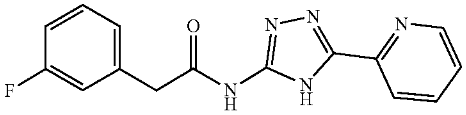
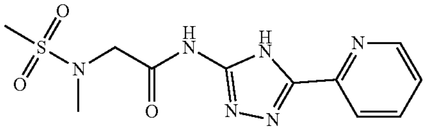
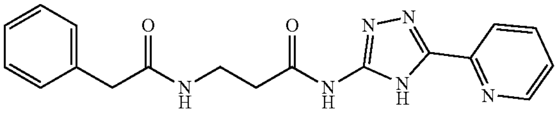
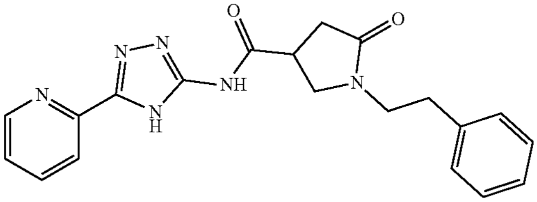
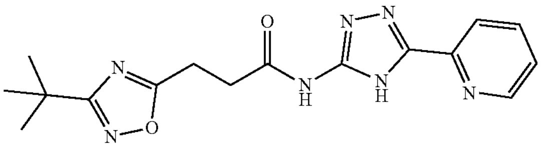
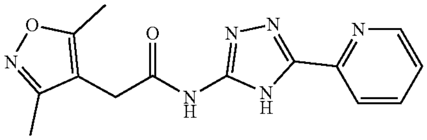
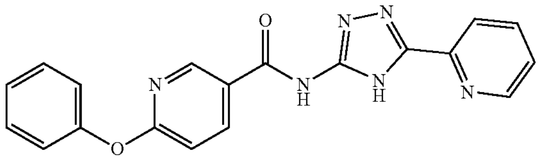
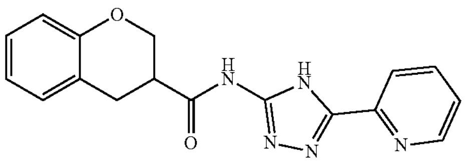
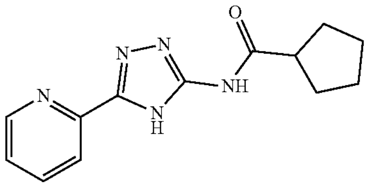
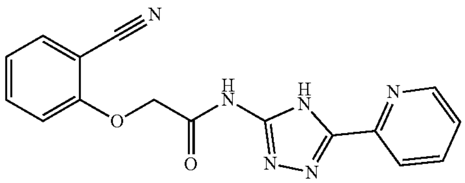
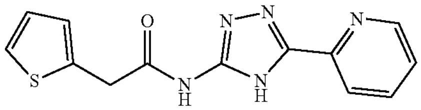

-continued
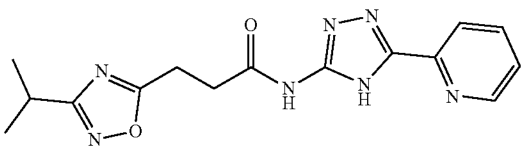
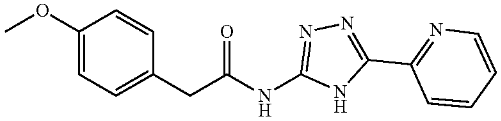
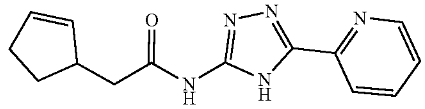
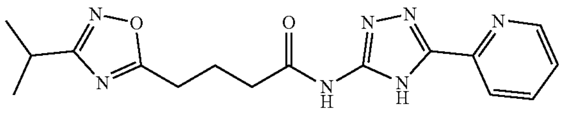
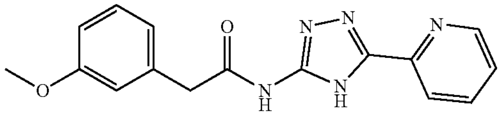
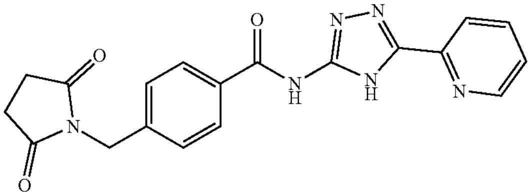
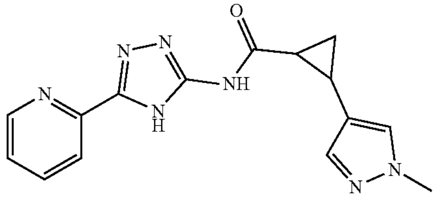
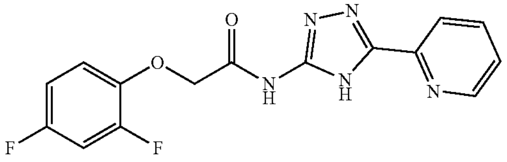
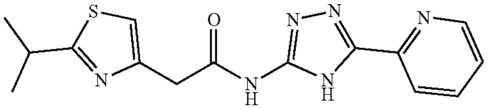
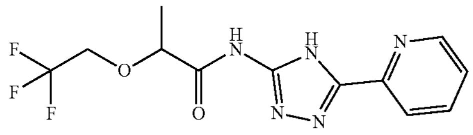
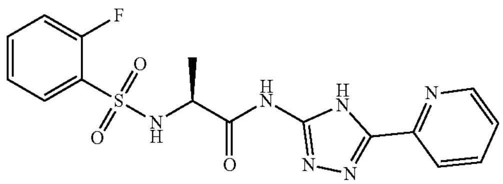
-continued
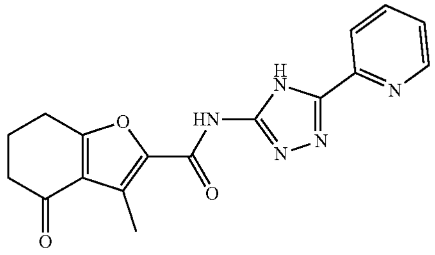
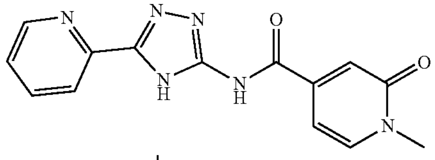
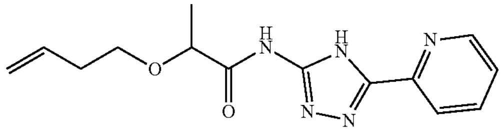
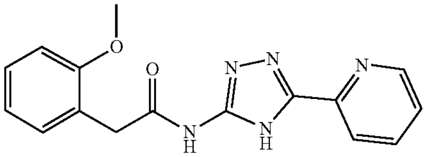
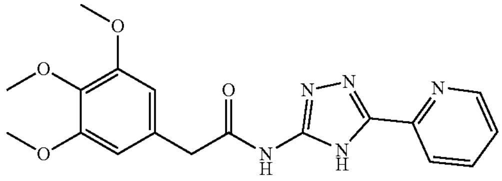
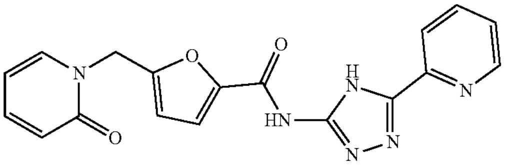
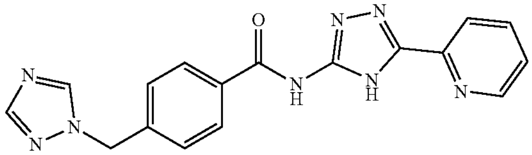
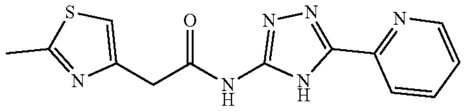
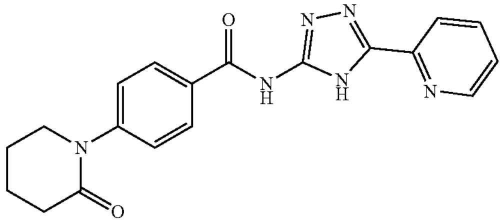
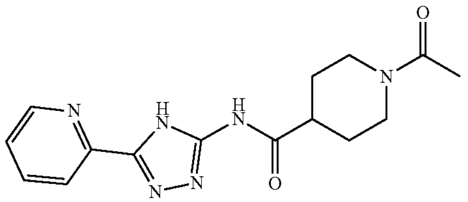

-continued
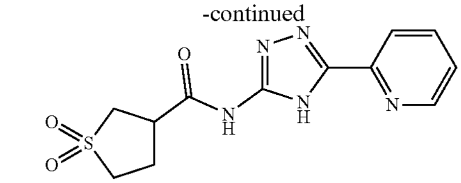
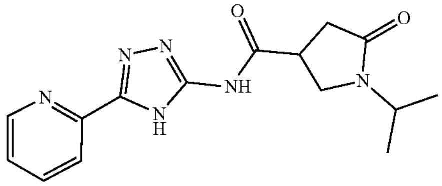
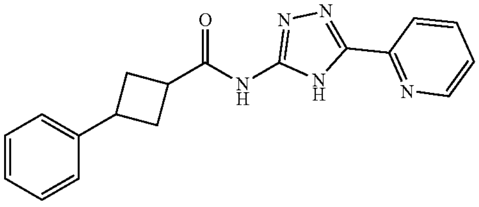
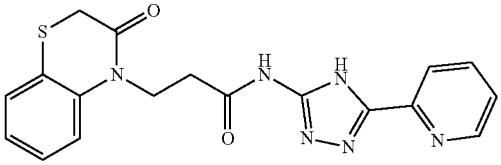
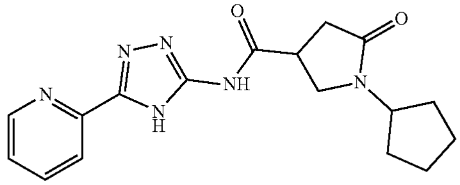
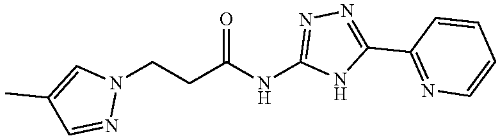
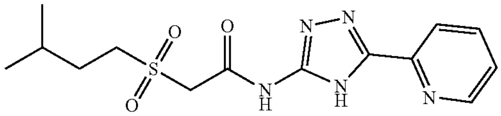
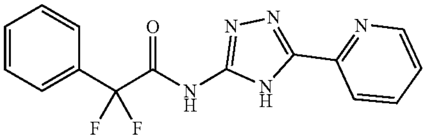
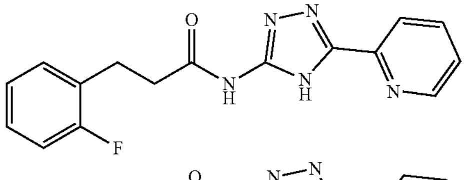
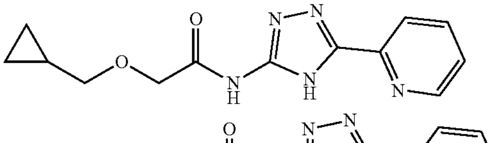
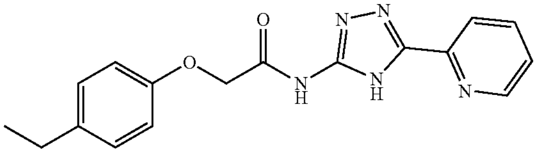
-continued
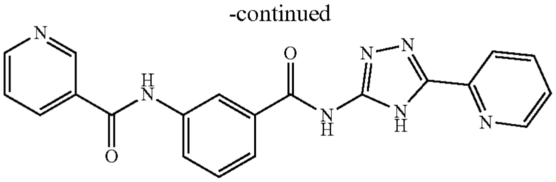
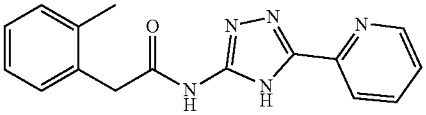
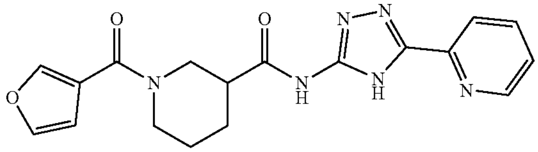
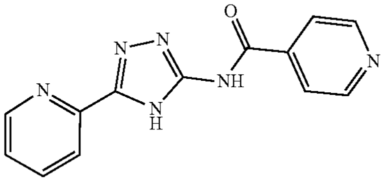
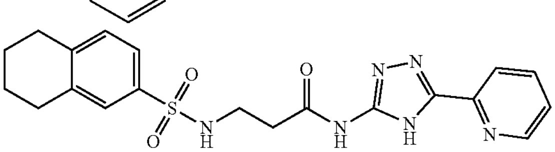
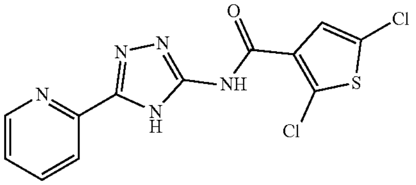
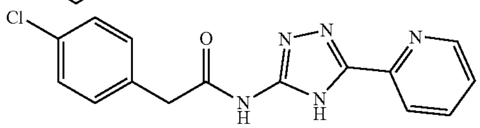
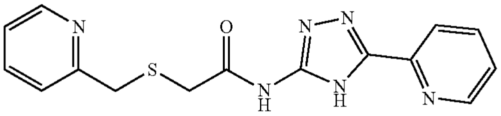
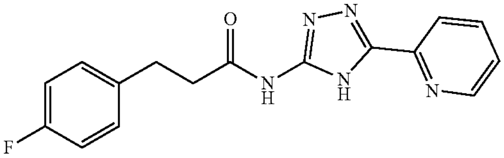
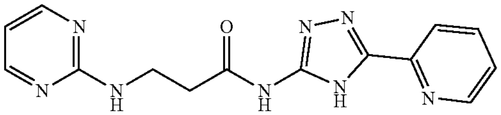
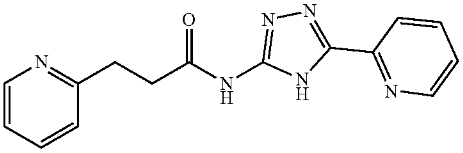
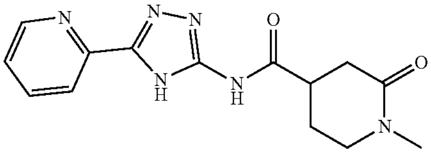

-continued
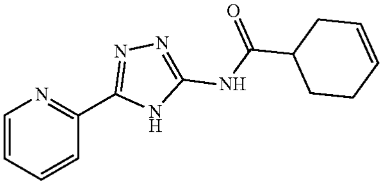
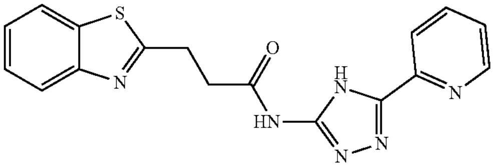
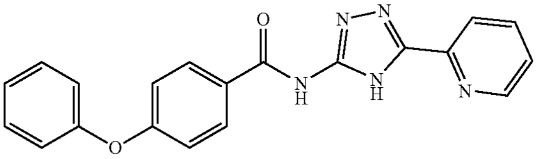
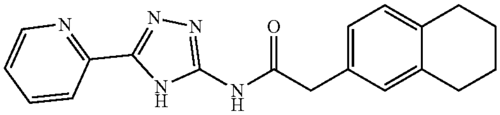
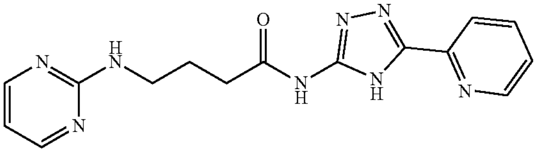
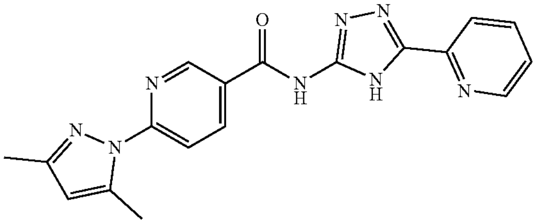
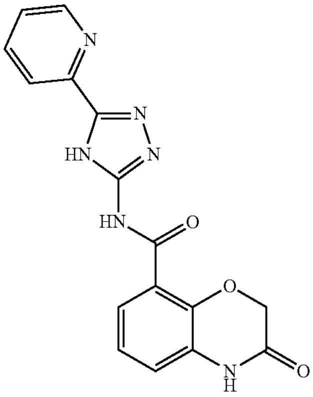
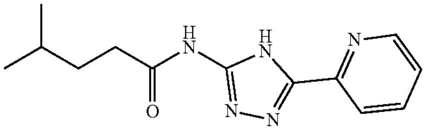
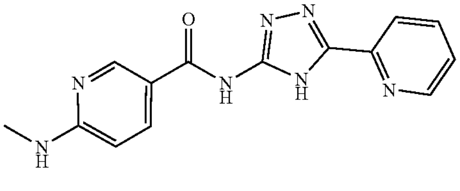
-continued
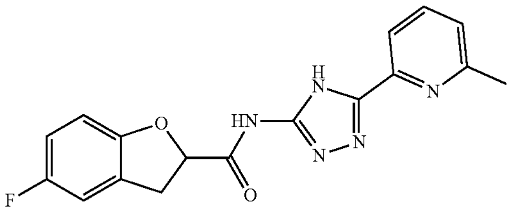
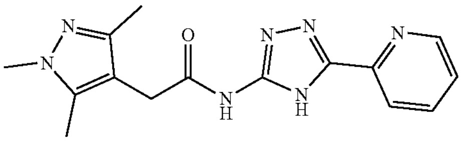
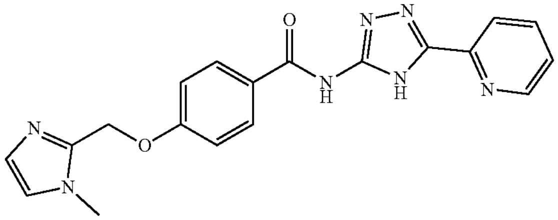
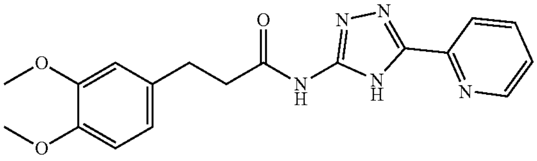
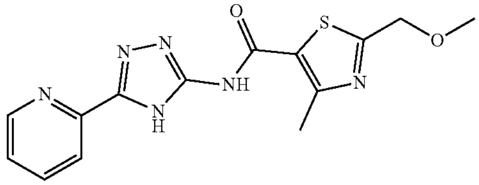
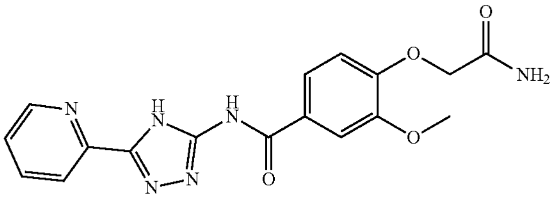
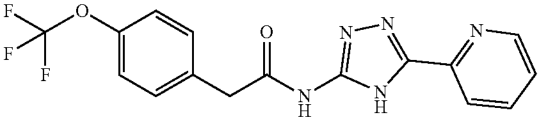
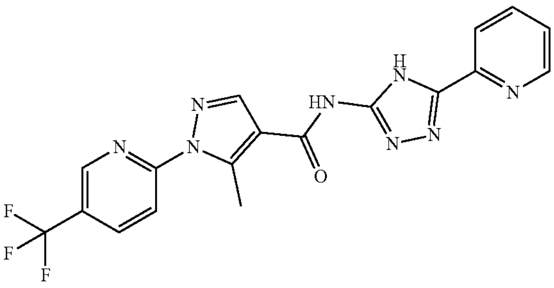
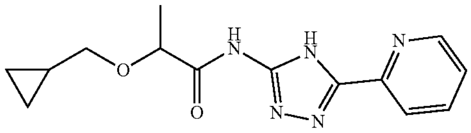

-continued

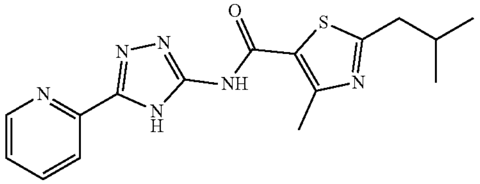

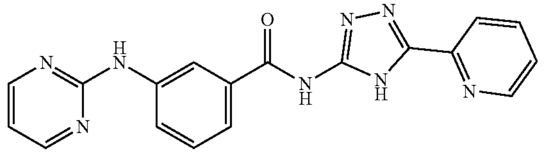

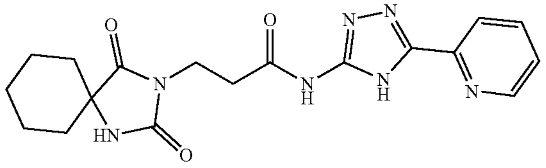

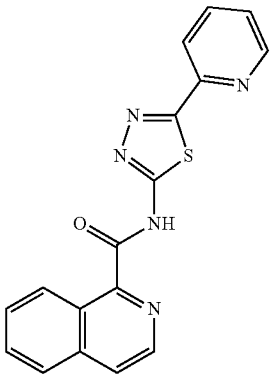

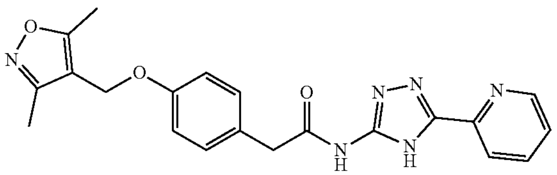

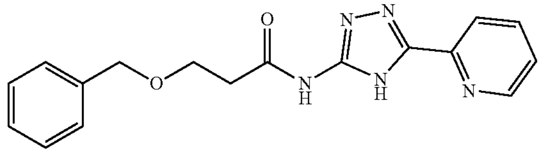

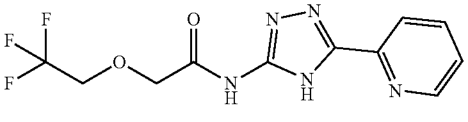

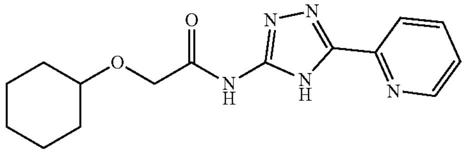

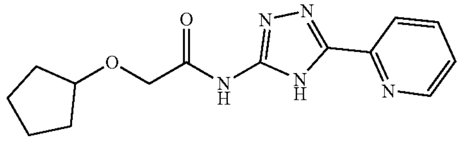

or

-continued

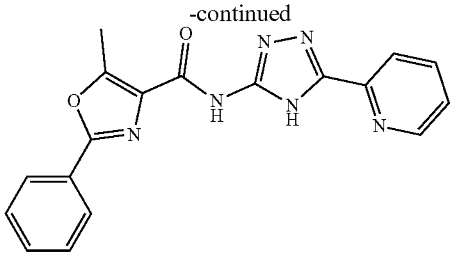

.

In another embodiment, the compound of Formula I is a compound of Formula Ia or pharmaceutically acceptable derivatives thereof, wherein:

$R^{1a}$ is:

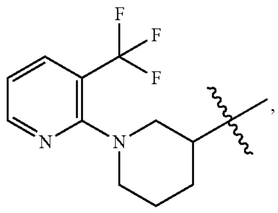 [SMILES: *C1CCCN(c2ncccc2C(F)(F)F)C1]

, $R^{2a}$ is heteroaryl; and X is NH or S.

In one embodiment, the compound of Formula Ia is:

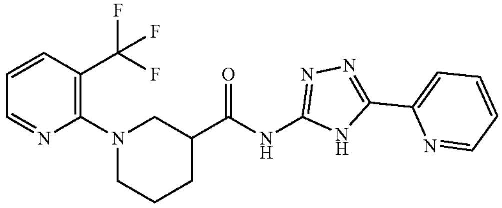 [SMILES: O=C(Nc1nnc(-c2ccccn2)[nH]1)C1CCCN(c2ncccc2C(F)(F)F)C1]

In another embodiment, the compound of Formula I is a compound of Formula Ib:

Formula Ib

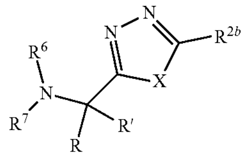

or pharmaceutically acceptable derivatives thereof, wherein $R^{2b}$ is selected from the group consisting of alkyl, aryl, cycloalkyl, heterocyclyl and heteroaryl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached;

p is 0-2; and

X is O or $NR^5$.

In another embodiment, the compound of Formula I is a compound of Formula Ib or pharmaceutically acceptable derivatives thereof, wherein:

$R^6$ and $R^7$ are independently selected from hydrogen, methyl, isopropyl, phenyl, cyclopropyl, adamantyl, or selected from one of the following:

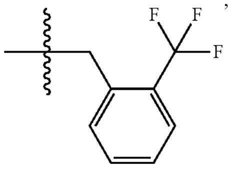

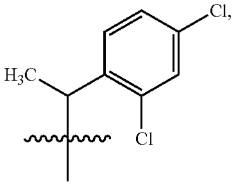

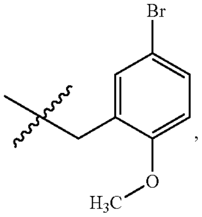

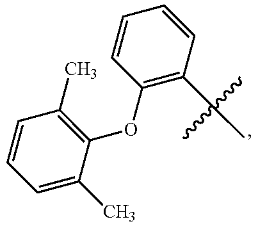

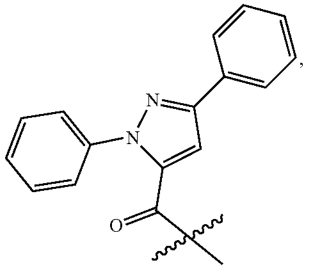

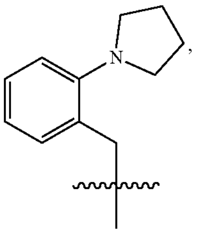

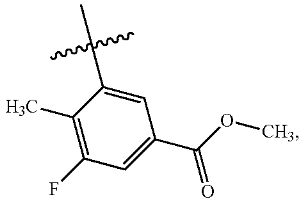

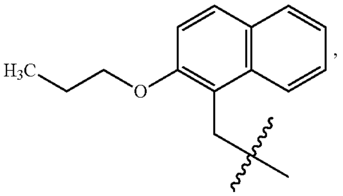

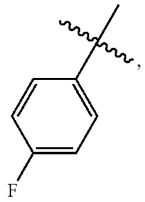

and

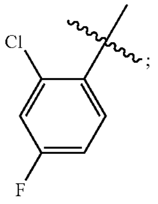

wherein phenyl is optionally substituted with one, two, or three substituents each selected from halogen, and $R^6$ and $R^7$ are combined to form a cyclic structure including the nitrogen atom to which they are both attached, wherein the cyclic structure is selected from one of the following:

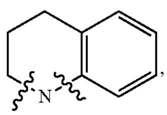

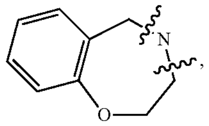

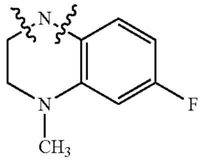

R and R' are independently selected from hydrogen and methyl; and

X is O or NH.

In one embodiment, the compound of Formula Ib is:

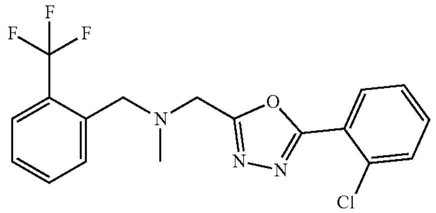

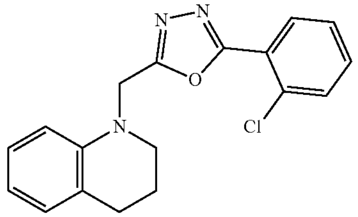

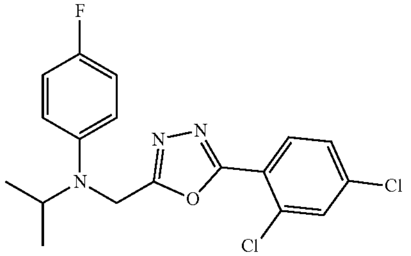

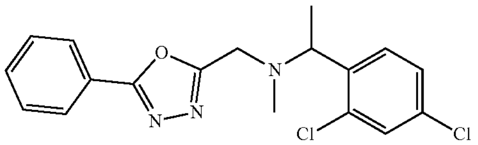

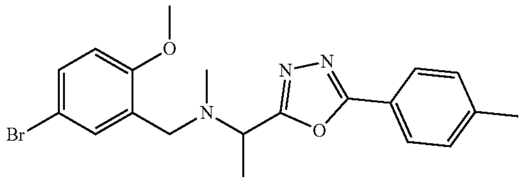

-continued

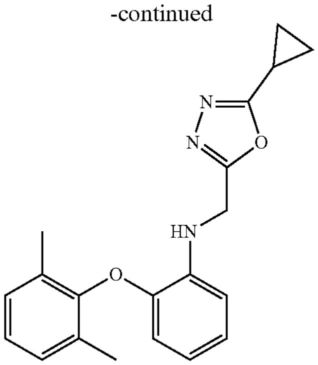

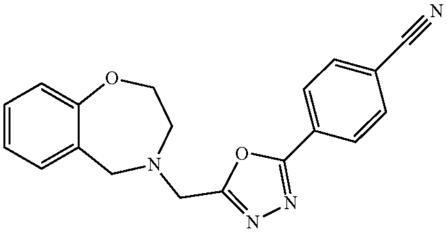

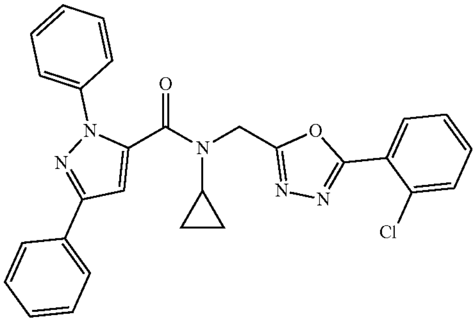

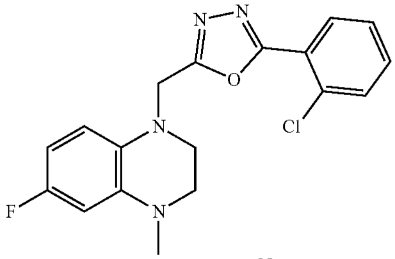

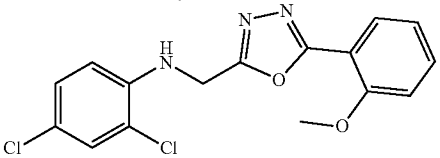

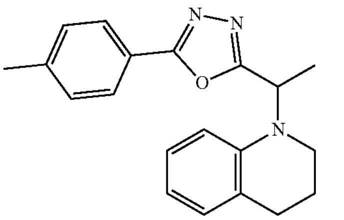

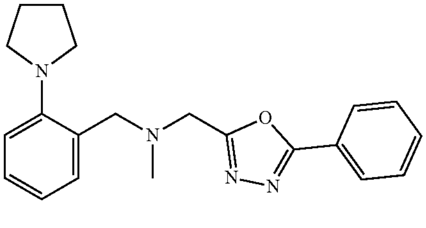

-continued

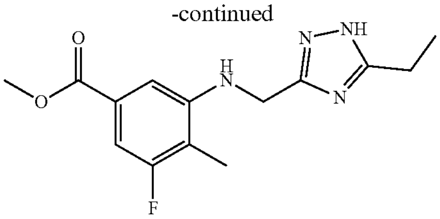

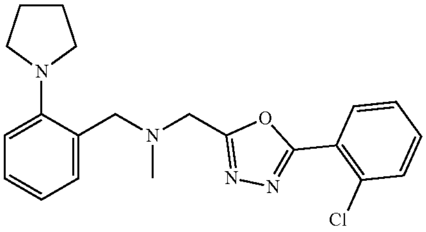

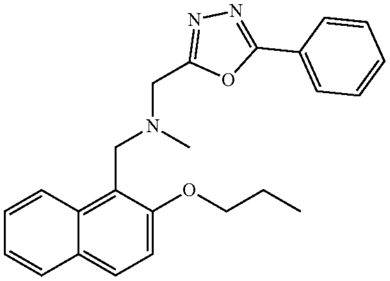

or

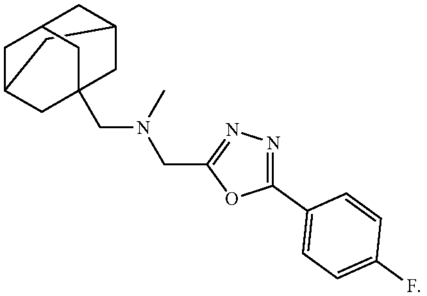

In another embodiment, the compound of Formula I is a compound of Formula Ic:

Formula Ic

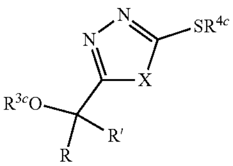

or pharmaceutically acceptable derivatives thereof, $R^{3c}$ is hydrogen, alkyl, alkenyl, alkynyl, aryl, heteroaryl, heterocyclyl, cycloalkyl, alkylcarbonyl, cycloalkylcarbonyl or arylcarbonyl;

$R^{4c}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached;

p is 0-2; and

X is O or $NR^5$.

In another embodiment, the compound of Formula Ic is a compound wherein:

$R^{3c}$ is phenyl or $R^{3c}$, R and R' are combined to form a cyclic structure, as shown below

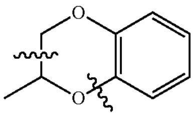

wherein phenyl is optionally substituted with one, two, or three substituents each selected from halogen, cyano, and methyl;

$R^{4c}$ is selected from one of the following;

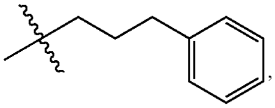,

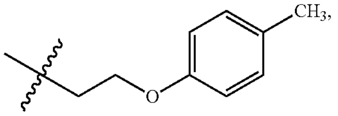

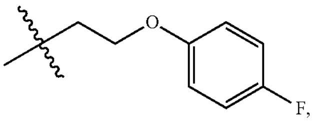

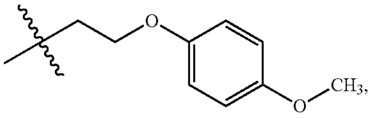

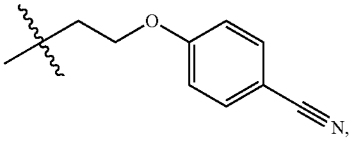

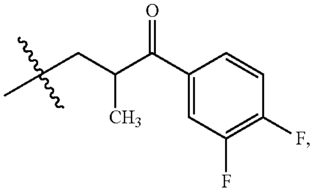

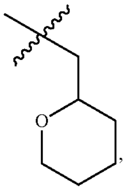,

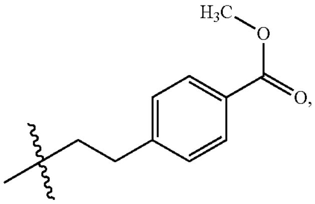

-continued

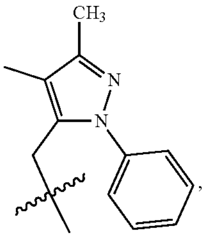,

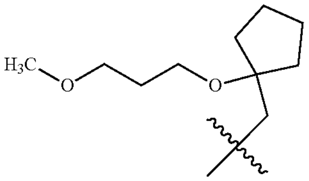

R and R' are independently selected from hydrogen and methyl, or R and R' are combined to form a cyclic structure including the carbon atom to which they are both attached; and X is O or N-phenyl.

In one embodiment, the compound of Formula Ic is:

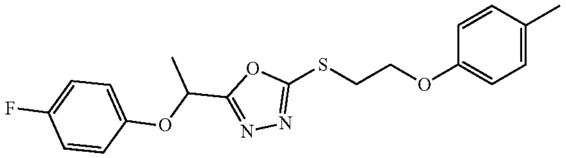

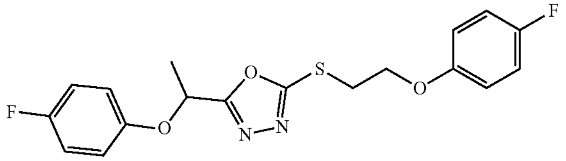

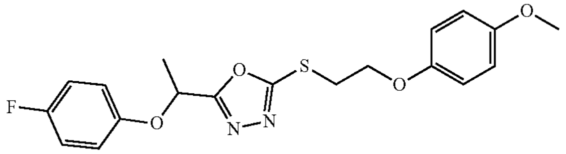

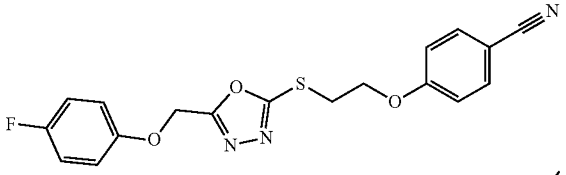

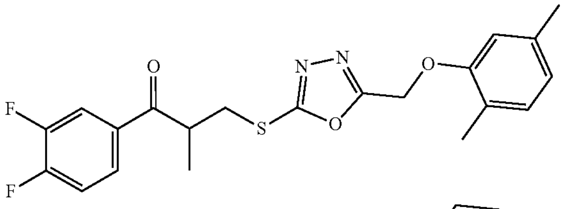

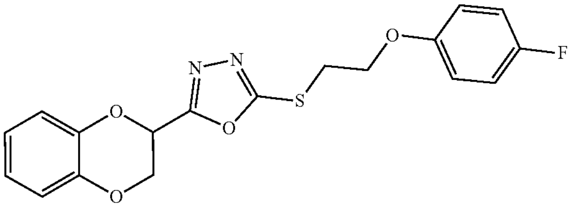

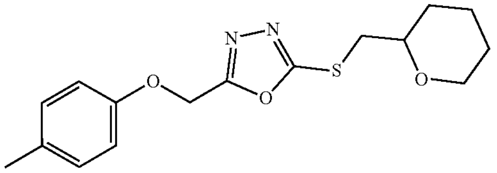

-continued

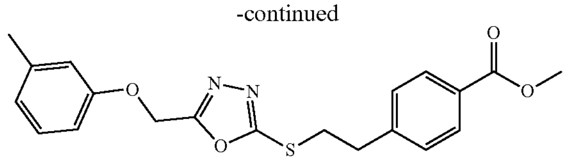

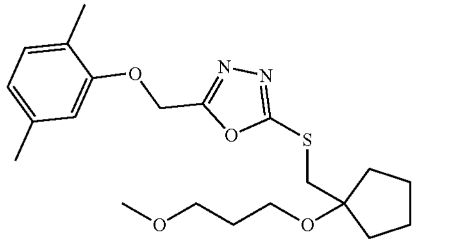

or

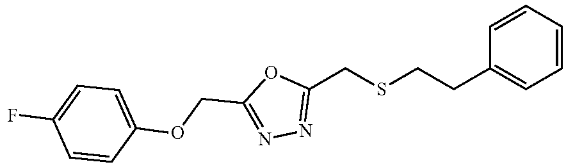

In another embodiment, the compound of Formula I is a compound of Formula Id:

Formula Id

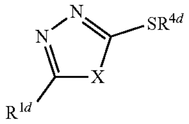

or pharmaceutically acceptable derivatives thereof, wherein $R^{1d}$ is selected from the group consisting of alkyl, aryl, cycloalkyl, heterocyclyl, heteroaryl and $SR^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{4d}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and X is O, S or $NR^5$.

In another embodiment, the compound of Formula I is a compound of Formula Id wherein:

$R^{1d}$ is selected from one of the following:

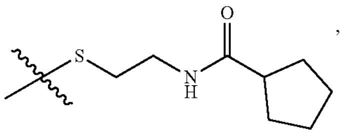

,

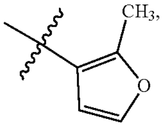

-continued

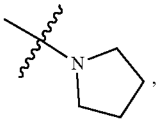

, or

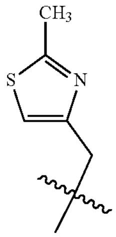

$R^{4d}$ is selected from one of the following:

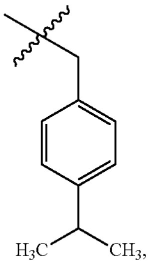

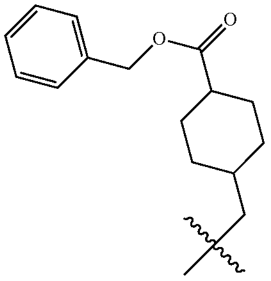

,

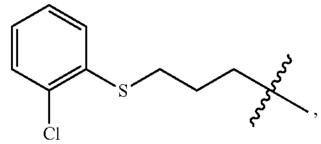

, or

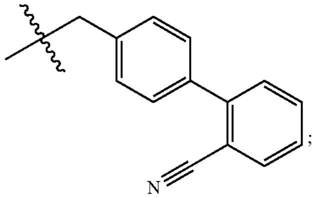

; and

X is O or S.

In one embodiment, the compound of Formula Id is:

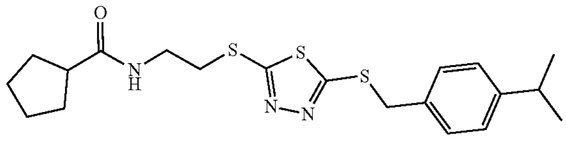

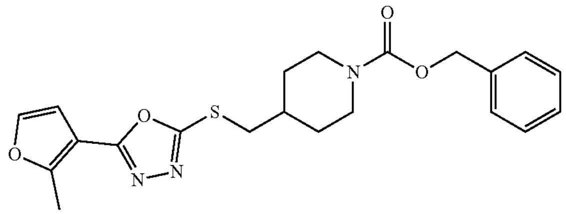

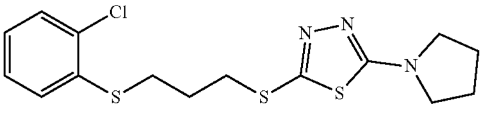

or

-continued

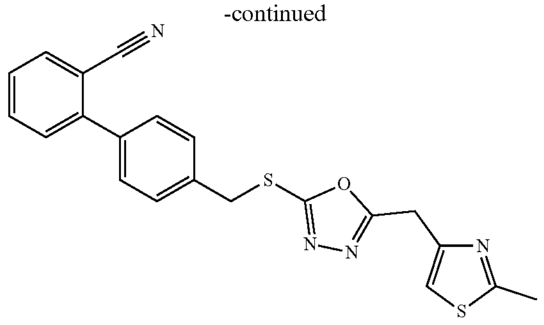

In another embodiment, the compound of Formula I is a compound of Formula Ie:

Formula Ie

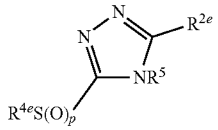

or pharmaceutically acceptable derivatives thereof, wherein:

$R^{2e}$ is selected from the group consisting of aryl, heteroaryl, arylalkyl or heteroarylalkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{4e}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula Ie, the compound of Formula Ie is a compound wherein:

$R^{2e}$ is selected from the group consisting of furyl, pyridinyl, phenyl, and naphthylmethyl, wherein phenyl is substituted with methyl;

$R^{4e}$ is selected from one of the following:

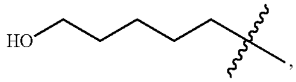

,

-continued

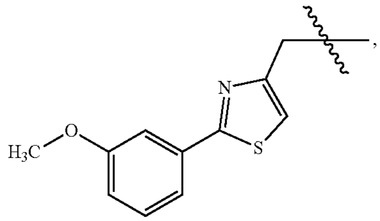

,

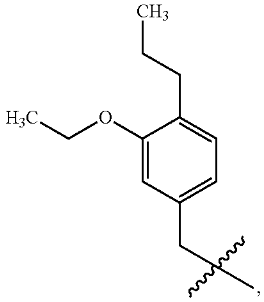

, or

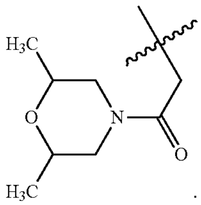

.

$R^5$ is hydrogen, propyl, cyclohexyl or phenyl; and p is 0-2.

In one embodiment, the compound of Formula Ie is:

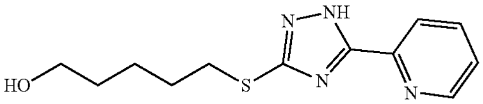

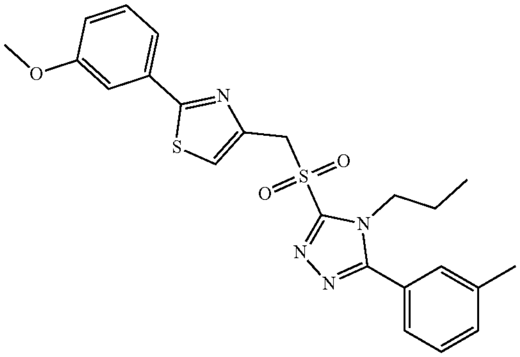

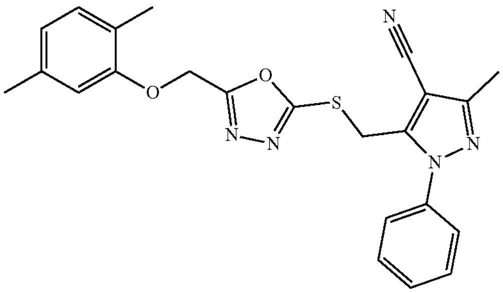

-continued

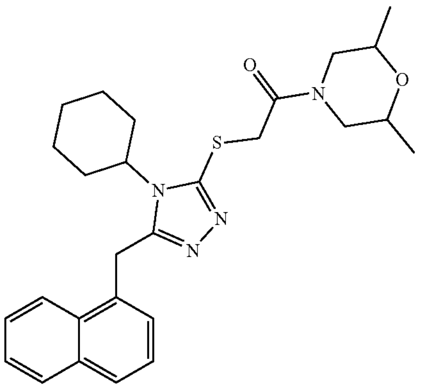

or

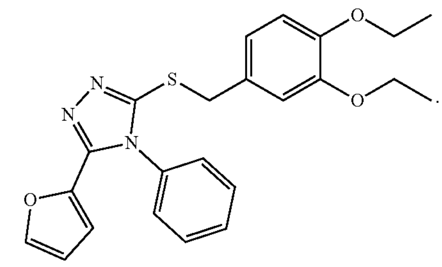

.

In one embodiment, the compound of Formula I is selected with the proviso that the compound is not

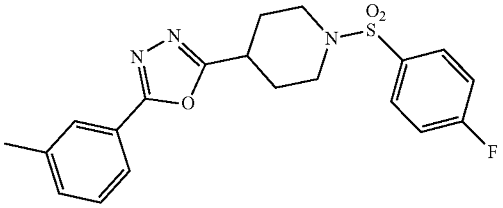

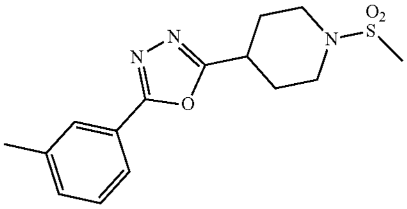

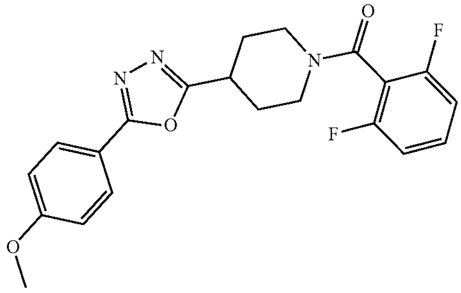

-continued

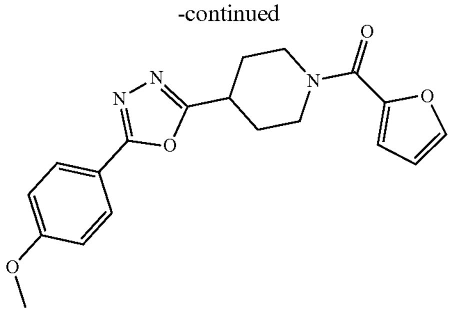

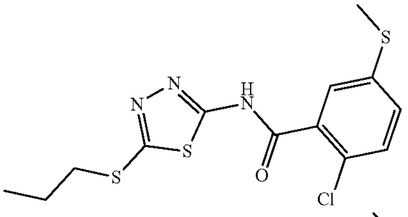

or

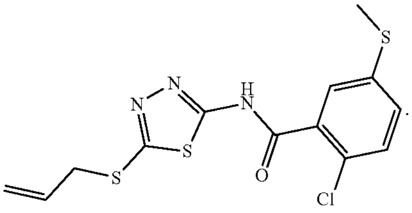

.

In one embodiment, the compound of Formula Ia is selected with the proviso that the compound is not

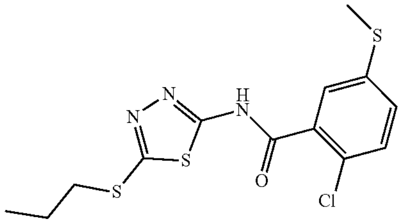

or

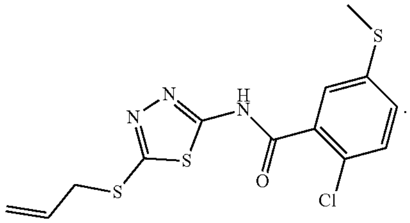

.

In one embodiment, the compound of Formula I is selected with the proviso that if X is NH and $R^1$ is phenyl, then $R^2$ is not pyridyl.

In certain embodiments, the compounds for use in the compositions and methods provided herein are of Formula II:

Formula II

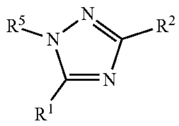

or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment, the compound of Formula II is a compound of Formula IIa:

Formula IIa

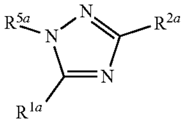

or pharmaceutically acceptable derivatives thereof, wherein $R^{1a}$ is heterocyclyl or $NR^6R^7$;

wherein $R^{2a}$ is H, aryl, or heteroaryl;

$R^{5a}$ is alkyl, alkylcarbonyl, cycloalkylcarbonyl or arylcarbonyl; and $R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula IIa, the compound of Formula II is a compound wherein:

$R^{1a}$ is amino, or as depicted below:

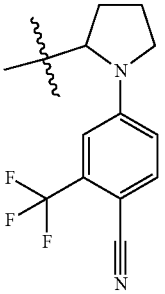

or

-continued

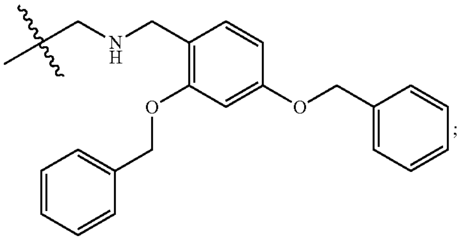

;

wherein $R^{2a}$ is H or pyridinyl;

$R^{5a}$ is isopropyl, or as depicted below:

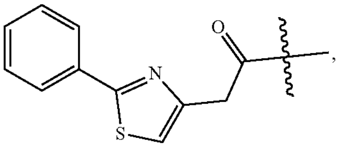

,

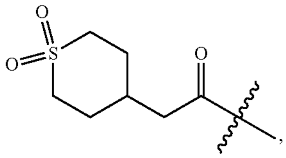

,

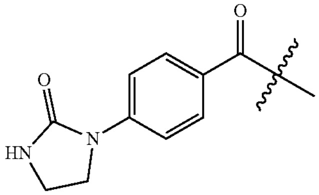

or

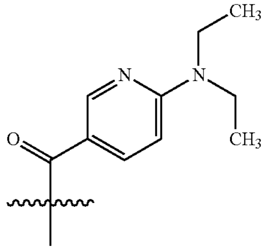

In one embodiment, the compound of Formula IIa is:

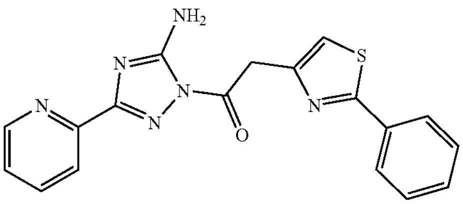

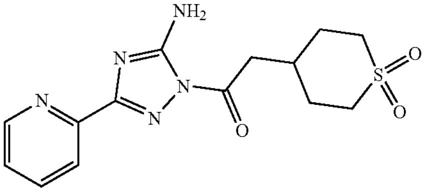

-continued

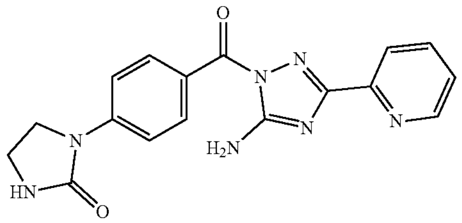

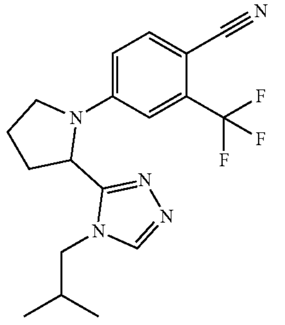

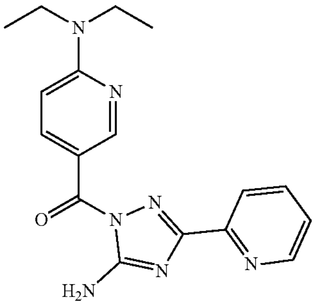

or

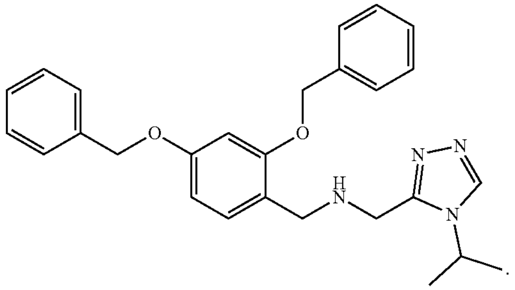

In certain embodiments, the compounds for use in the compositions and methods provided herein are of Formula III:

Formula III

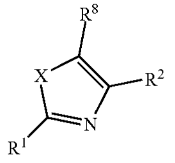

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is O or S; or X is NR, wherein R forms a non-aromatic ring with one of the carbon atoms adjacent to the nitrogen on the five-membered ring to which it is attached.

In another embodiment of Formula III, the compound of Formula III is a compound wherein $R^1$ is phenyl or as depicted below:

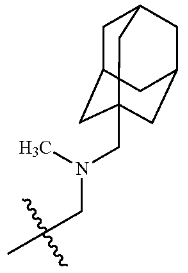 [SMILES: *CN(C)CC12CC3CC(CC(C3)C1)C2]

$R^2$ is methyl or as depicted below:

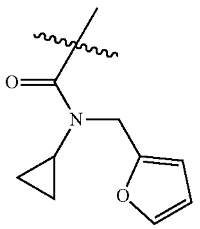 [SMILES: *C(=O)N(Cc1ccco1)C1CC1]

p is 0-2; and

X is O; or X is NR, wherein R forms a seven-membered ring with one of the carbon atoms adjacent to the nitrogen on the five-membered ring to which it is attached.

In one embodiment, the compound of Formula III is:

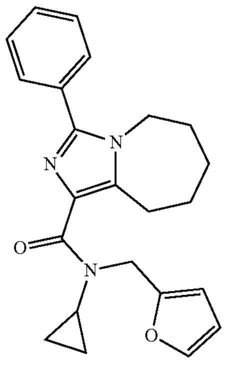

or

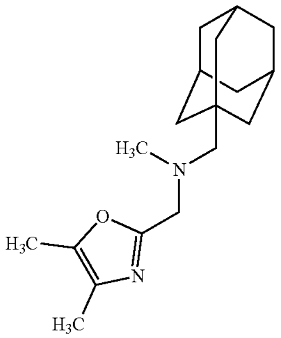

In another embodiment, the compound of Formula III is a compound of Formula IIIa:

Formula IIIa

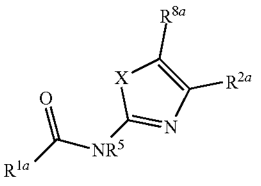

or pharmaceutically acceptable derivatives thereof, wherein $R^{1a}$ is selected from the group consisting of H, alkyl, alkenyl, alkynyl, aryl, cycloalkyl, heterocyclyl, heteroaryl, $OR^3$, and $NR^6R^7$;

wherein $R^{2a}$ is aryl or heteroaryl;

wherein $R^{8a}$ are is H or alkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula IIIa, a compound of Formula IIIa is a compound wherein:

$R^{1a}$ is selected from the group consisting of pyridinyl, isoxazolyl, phenyl, benzodioxalyl, quinoxalinyl, pyrolidinonyl, aminoalkyl, benzimidazolyl, benzyl, benzofuranyl, and one of the following:

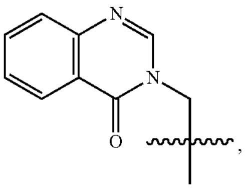,

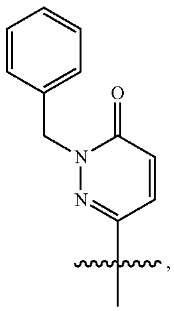,

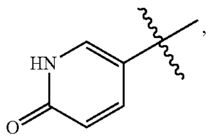,

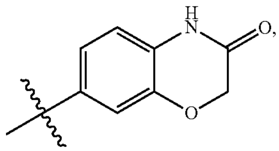, or

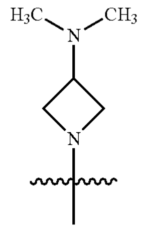

wherein pyridinyl, isoxazolyl, phenyl, furanyl and benzyl is optionally substituted with one or two substituents each selected from methyl, halogen, methoxy, benzodioxalyl, pyridinyl, tetrazolyl;

$R^{2a}$ is pyridinyl;

$R^{8a}$ is hydrogen; and $R^5$ is hydrogen.

In one embodiment, the compound of Formula IIIa is:

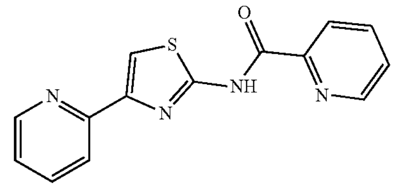

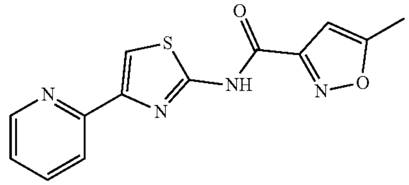

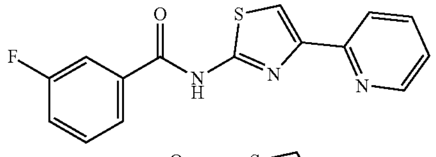

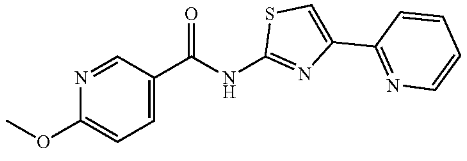

-continued
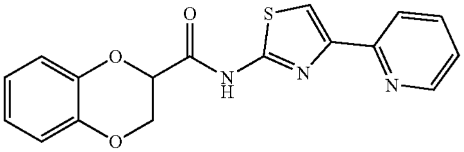
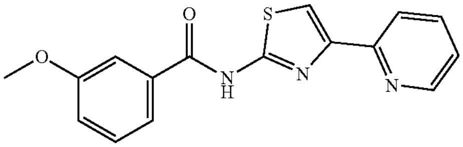
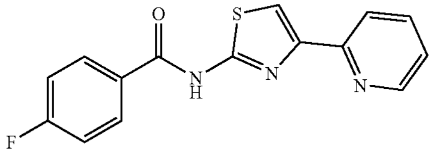
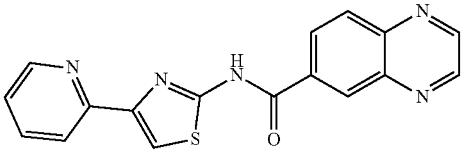
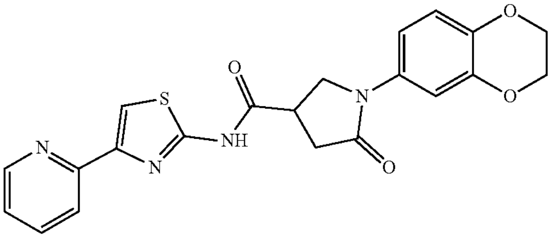
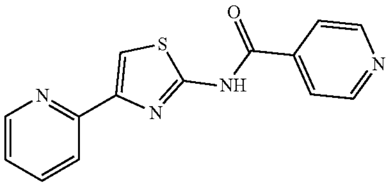
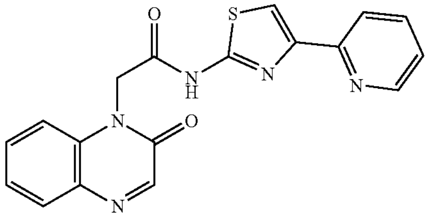
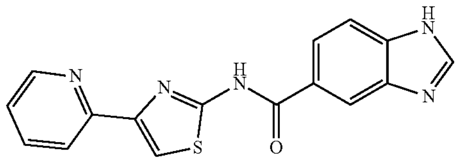
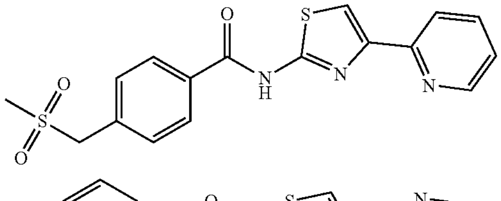
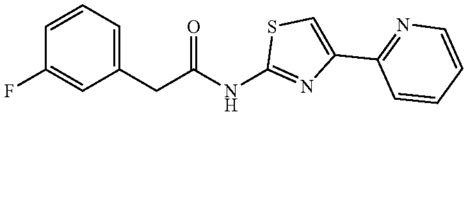
-continued
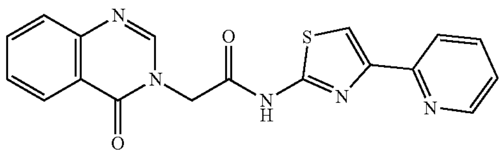
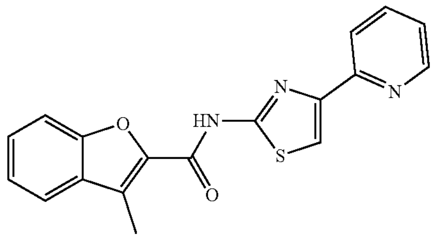
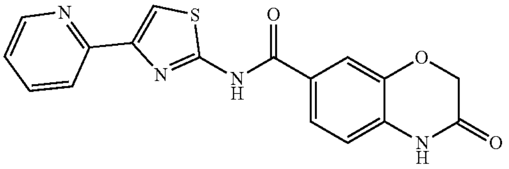
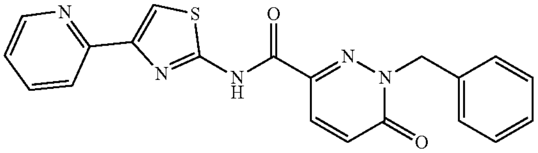
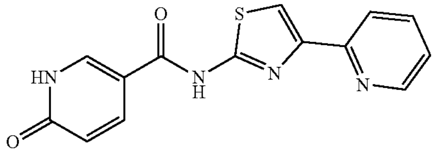
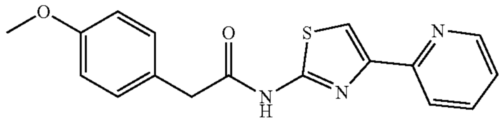
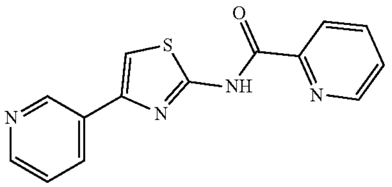
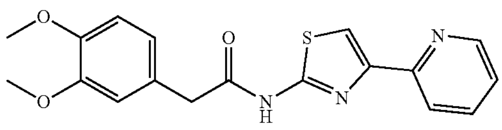
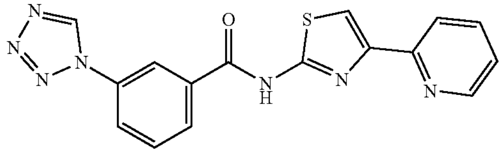
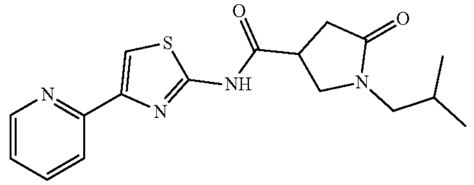

-continued

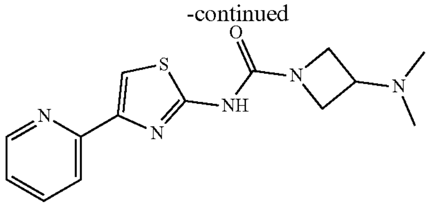

or

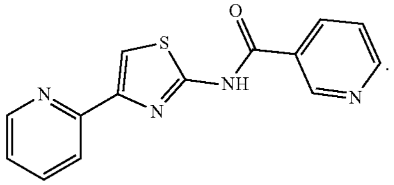

In another embodiment of Formula IIIa, a compound of Formula IIIa is a compound wherein:

$R^{1a}$ is selected from the group consisting of:

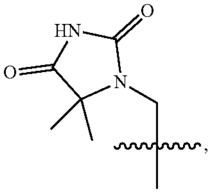

,

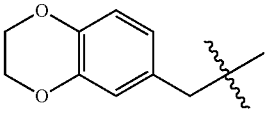

, and

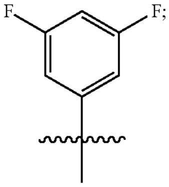

;

$R^{2a}$ is pyridinyl;

$R^{8a}$ is hydrogen; and $R^5$ is hydrogen.

In one embodiment, the compound of Formula IIIa is:

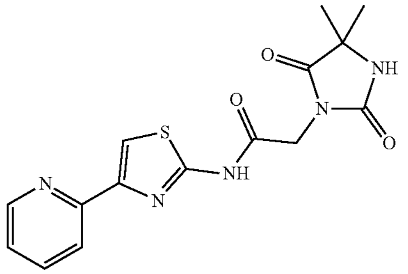

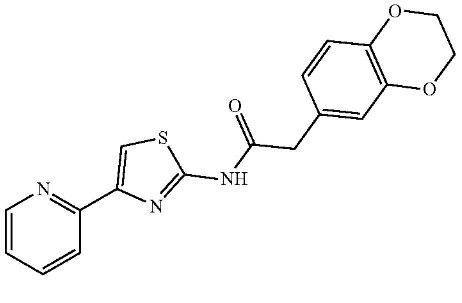

or

-continued

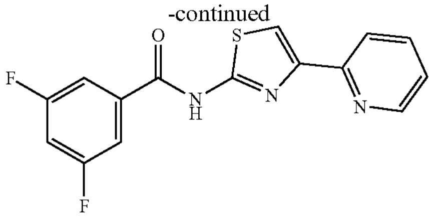

In another embodiment, the compound of Formula III is a compound of Formula IIIb:

Formula IIIb

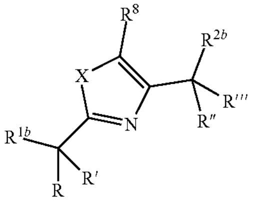

or pharmaceutically acceptable derivatives thereof, wherein $R^{1b}$ is $OR^3$, $NR^5C(O)R^4$ or $NR^6R^7$;

$R^{2b}$ is $OR^3$, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and R" and R'" are independently selected from hydrogen and alkyl, and R" and R'" are combined to form a cyclic structure including the carbon atom to which they are both attached.

In another embodiment of Formula Mb, a compound of Formula Mb is a compound wherein:

$R^{1b}$ is $OR^3$, or phenyl;

$R^{2b}$ is $OR^3$, or as follows:

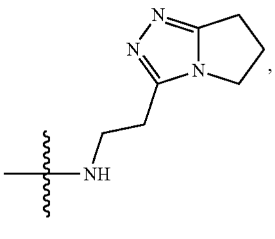

,

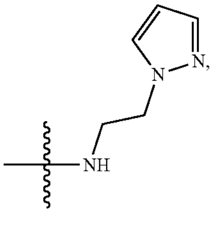

,

-continued

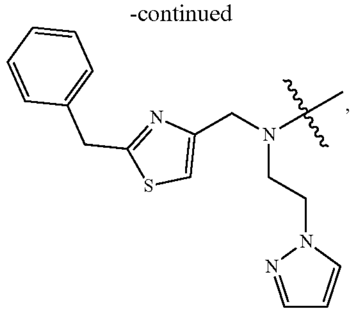

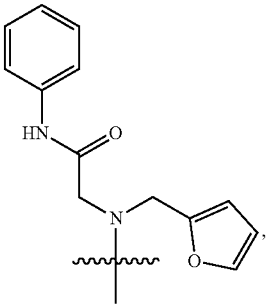

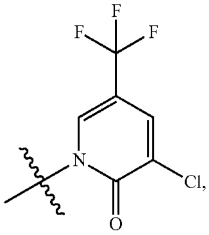

or

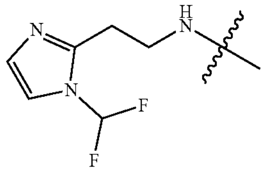

$R^3$ is phenyl, wherein phenyl is optionally substituted with one or two substituents each selected from methoxy, 1,1,1-trifluoropropan-2-ol, and halogen $R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^8$ is hydrogen; and

R and R' are hydrogen.

In one embodiment, the compound of Formula IIIb is:

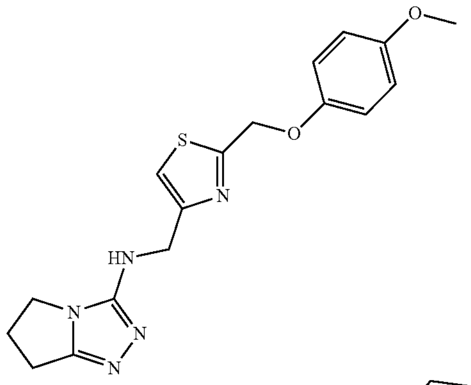

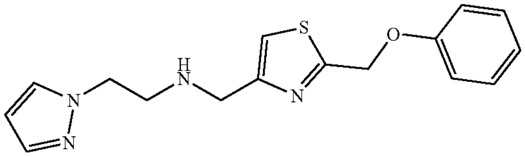

-continued

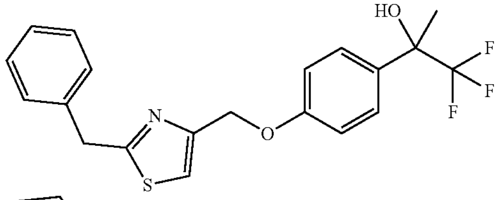

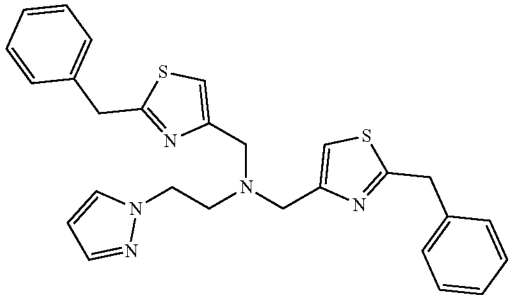

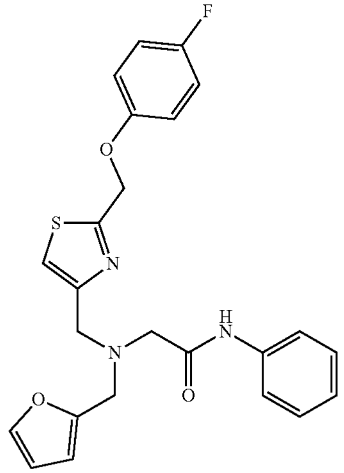

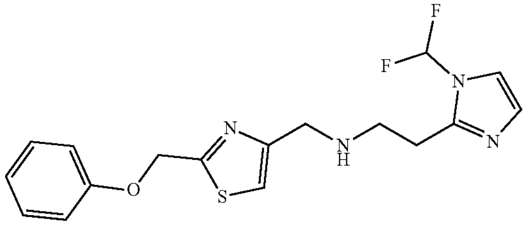

or

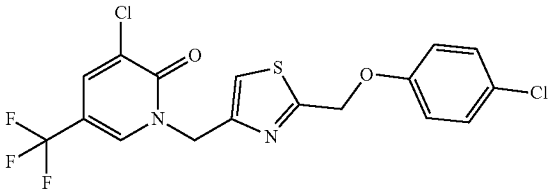

In another embodiment, the compound of Formula III is a compound of Formula IIIc:

Formula IIIc

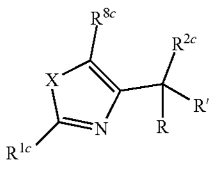

or pharmaceutically acceptable derivatives thereof, wherein $R^{1c}$ is aryl, or heteroaryl;

$R^{2c}$ is $SR^4$, $NR^5C(O)R^4$ or $NR^6R^7$;

$R^{8c}$ is H or alkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and X is O or S.

In another embodiment of Formula III, a compound of Formula IIIc is a compound wherein $R^{1c}$ is $SR^4$, phenyl, or pyridinyl, or thienyl;

wherein phenyl is optionally substituted with one or two substituents selected from methyl, methoxy, ethoxy, halogen;

$R^{2c}$ is $SR^4$, $CH_2SR^4$, or selected from the following:

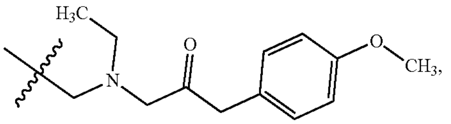

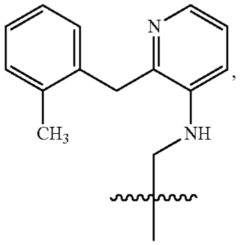

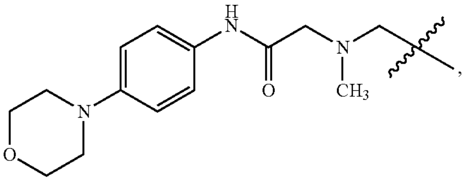

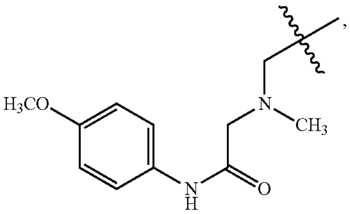

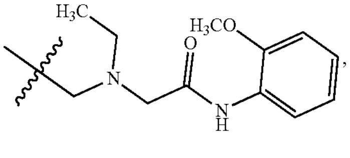

-continued

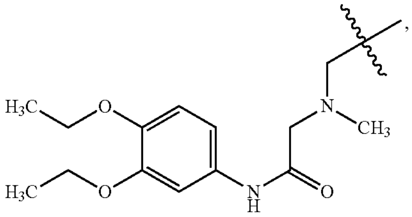

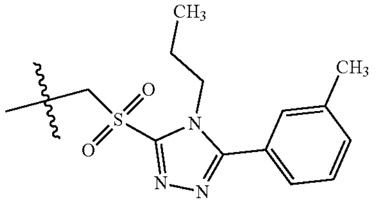

and

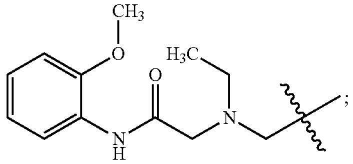

$R^{8c}$ is H or methyl;

$R^4$ is selected from the following:

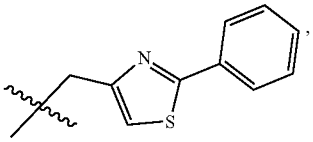

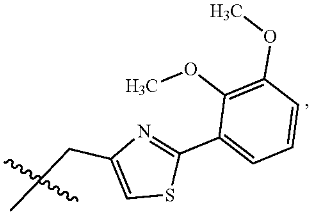

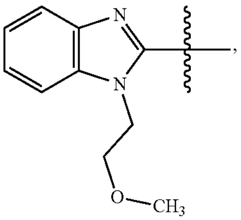

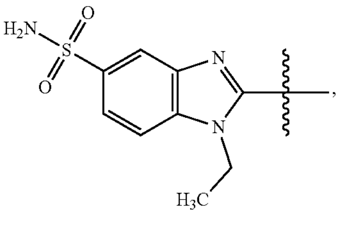

-continued

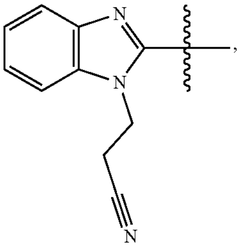

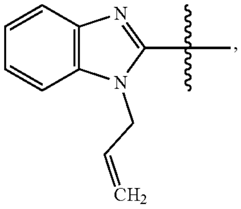

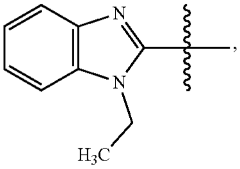

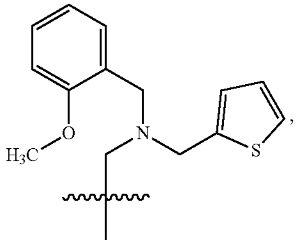

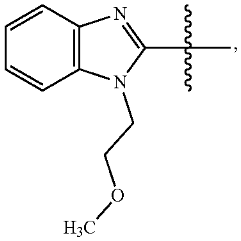

, and

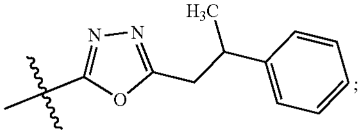

;

R and R' are hydrogen; and

X is O or S.

In another embodiment of Formula III, a compound of Formula IIIc is a compound wherein $R^{1c}$ is $SR^4$, phenyl, or pyridinyl, or thienyl;

wherein phenyl is optionally substituted with one or two substituents selected from methyl, methoxy, ethoxy, halogen;

$R^{2c}$ is $SR^4$, $CH_2SR^4$, or selected from the following:

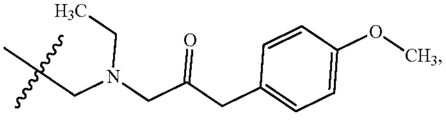

-continued

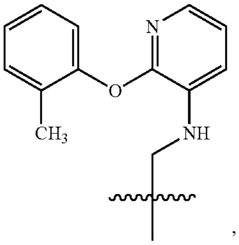

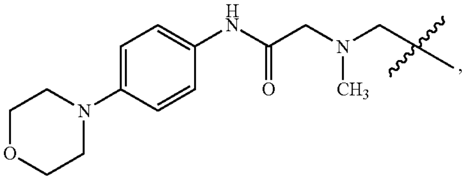

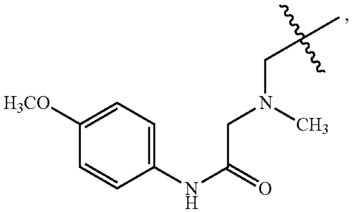

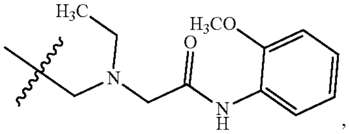

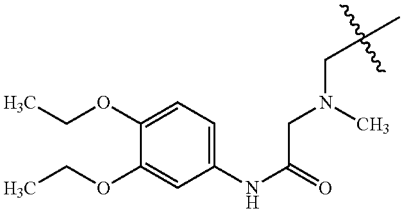

, or

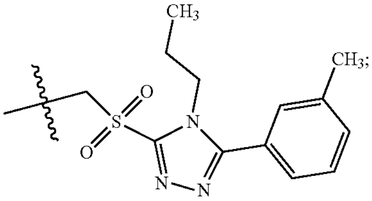

$R^{8c}$ is H or methyl;

$R^4$ is selected from the following:

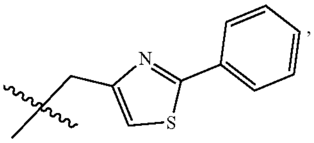

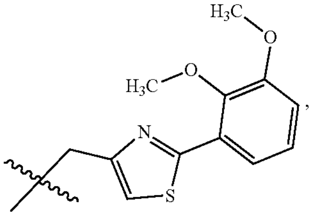

-continued
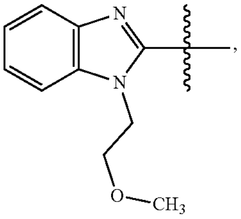
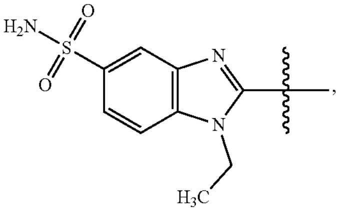
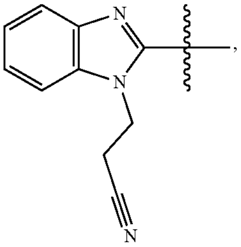
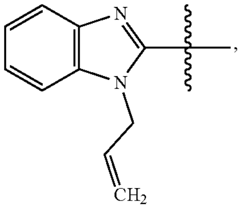
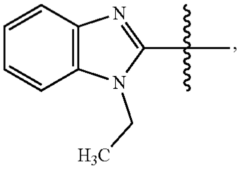
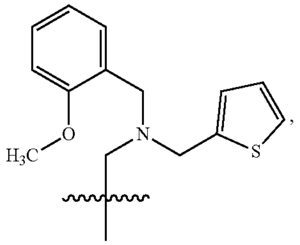
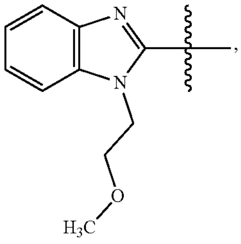
and
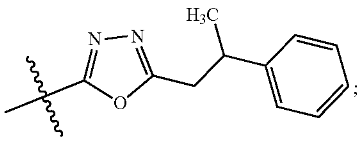
R and R' are hydrogen; and
X is O or S.
In one embodiment, the compound of Formula IIIc is:
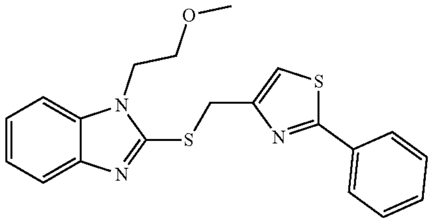
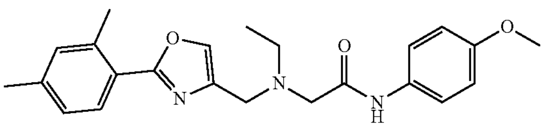
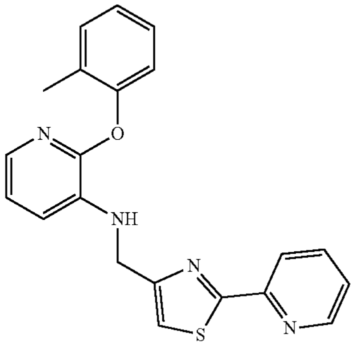
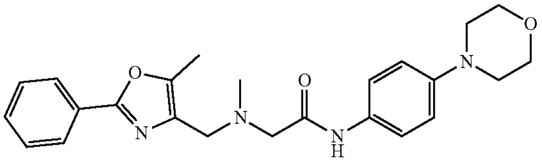
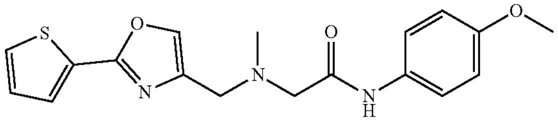
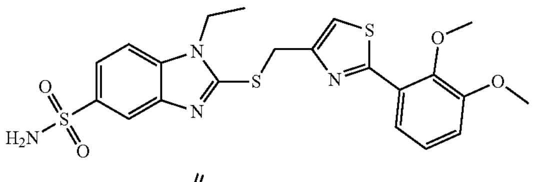
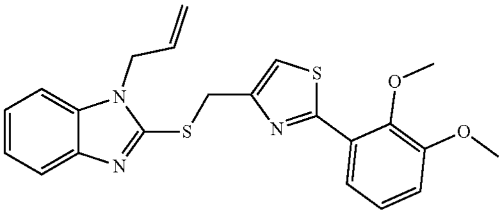
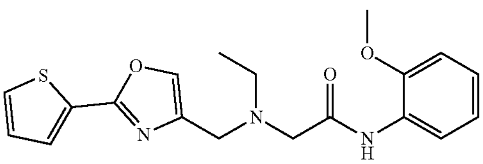
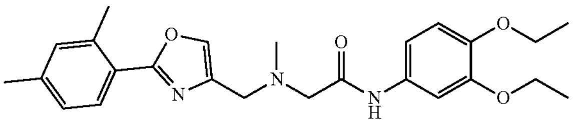

-continued

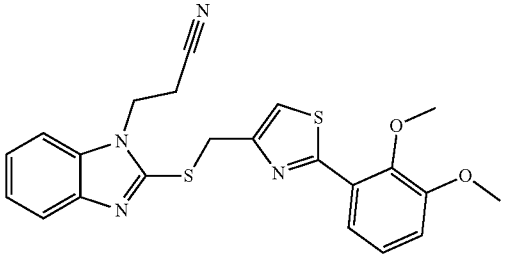

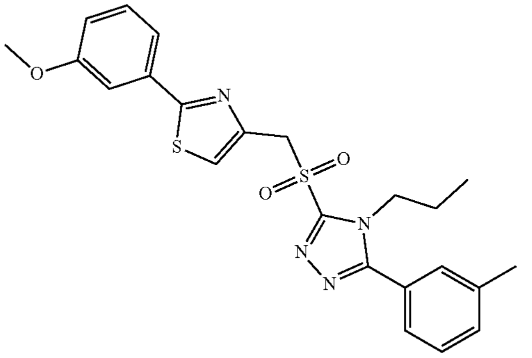

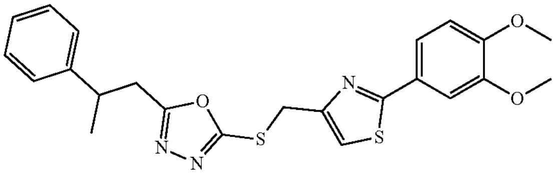

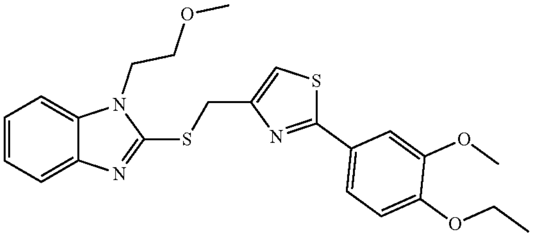

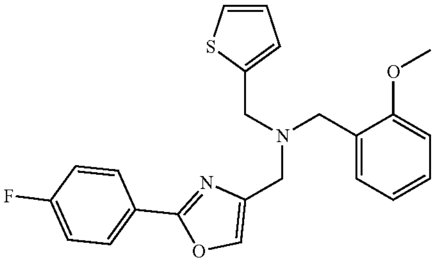

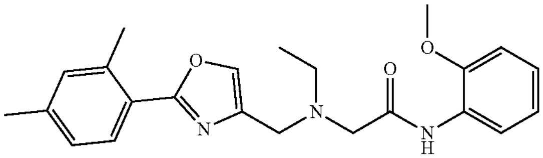

or

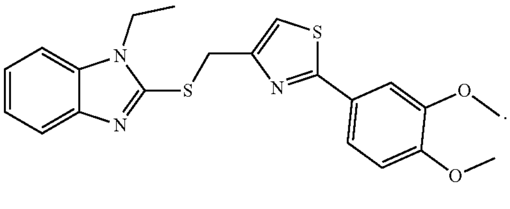

In another embodiment, the compound of Formula III is a compound of Formula IIId:

Formula IIId

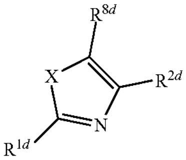

or pharmaceutically acceptable derivatives thereof, wherein $R^{1d}$ is alkyl, cycloalkyl, $S(O)_pR^4$, $NR^5C(O)R^4$, or $NR^6R^7$;

$R^{2d}$ is aryl or heteroaryl;

$R^{8d}$ is H or alkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl; and $R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula IIId, a compound of Formula IIId is a compound wherein:

wherein $R^{1d}$ is cyclopropyl, phenyl, $S(O)_2R^4$, $NR^5C(O)R^4$, or $NR^6R^7$, wherein phenyl is optionally substituted with one or two substituents each selected from hydroxyl and $CONH_2$;

$R^{2d}$ is phenyl or as depicted below:

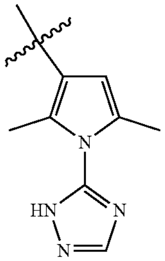

wherein phenyl is optionally substituted with 1-3 substituents each selected from methoxy, halogen, methyl, and hydroxyl;

$R^{8d}$ is hydrogen, methyl, or $CH_2CH_2CO_2CH_3$;

$R^4$ is phenyl or selected from one of the following:

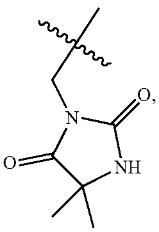

,

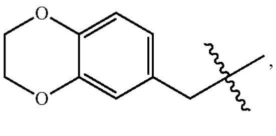

,

-continued

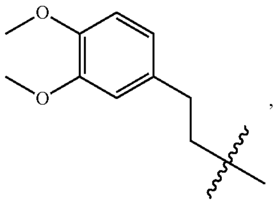

, or

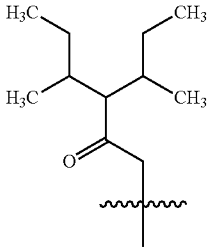

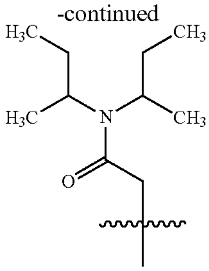

wherein phenyl is optionally substituted with two halogens;

$R^5$ is hydrogen; and $R^6$ and $R^7$ are independently selected from hydrogen, cyclohexyl, and $R^6$ and $R^7$ are combined to form a six-membered cyclic structure including the nitrogen atom to which they are both attached.

In another embodiment of Formula IIId, a compound of Formula IIId is a compound wherein:

wherein $R^{1d}$ is cyclopropyl, phenyl, $S(O)_2R^4$, $NR^5C(O)R^4$, or $NR^6R^7$, wherein phenyl is optionally substituted with one or two substituents each selected from hydroxyl and $CONH_2$;

$R^{2d}$ is phenyl or as depicted below:

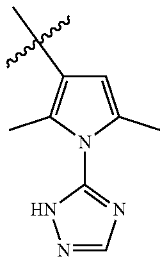

wherein phenyl is optionally substituted with 1-3 substituents each selected from methoxy, halogen, methyl, and hydroxyl;

$R^{8d}$ is hydrogen, methyl, or $CH_2CH_2CO_2CH_3$;

$R^4$ is phenyl or selected from one of the following:

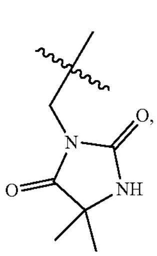

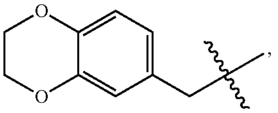

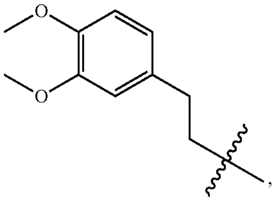

, or

-continued wherein phenyl is optionally substituted with two halogens;

$R^5$ is hydrogen; and $R^6$ and $R^7$ are independently selected from hydrogen, cyclohexyl, and $R^6$ and $R^7$ are combined to form a six-membered cyclic structure including the nitrogen atom to which they are both attached.

In one embodiment, the compound of Formula IIId is:

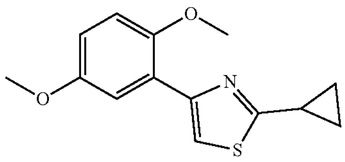

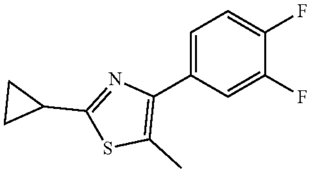

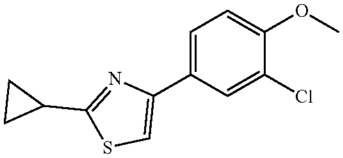

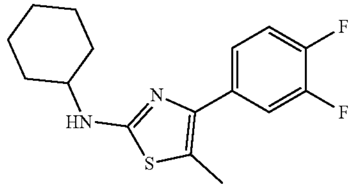

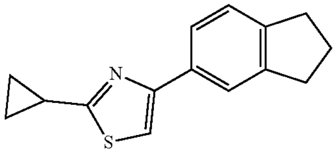

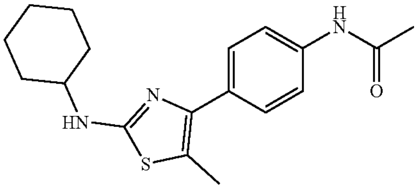

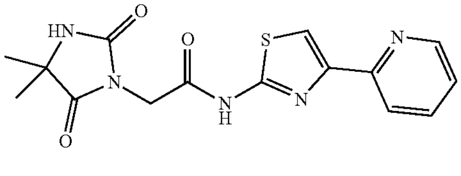

-continued
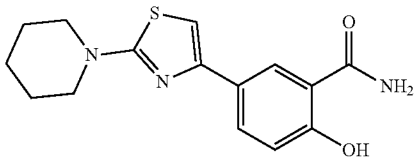
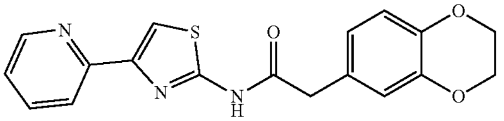
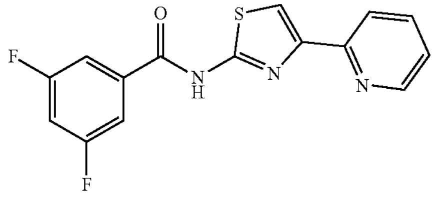
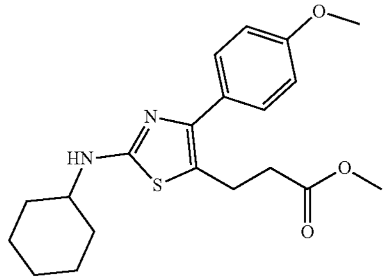
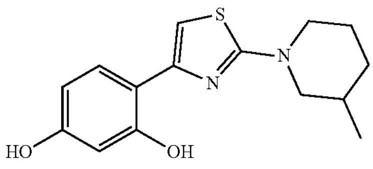
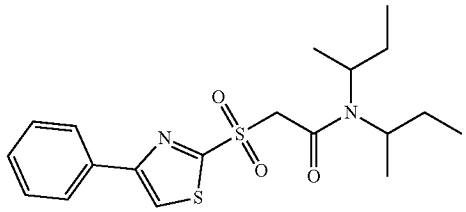
or
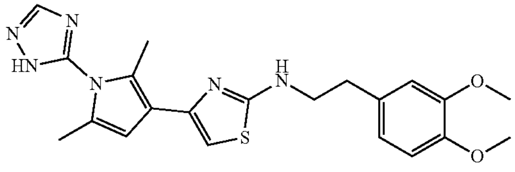
.
In one embodiment, the compound of Formula IIId is:
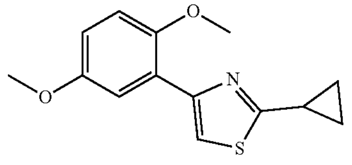
-continued
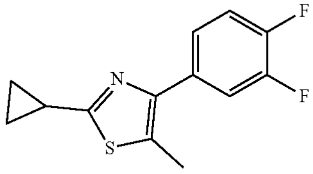
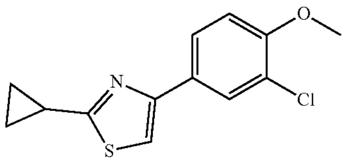
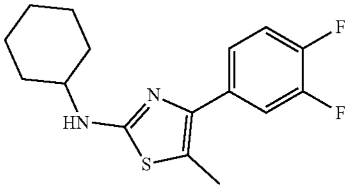
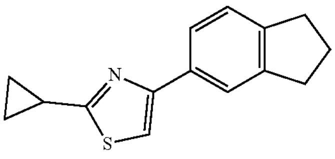
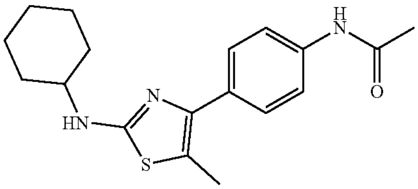
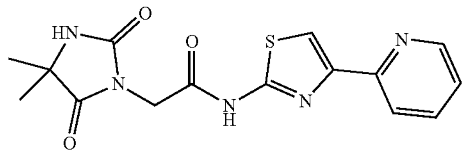
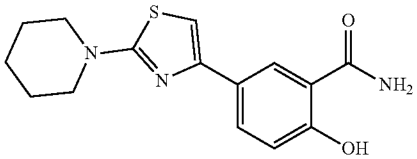
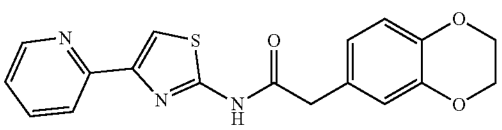
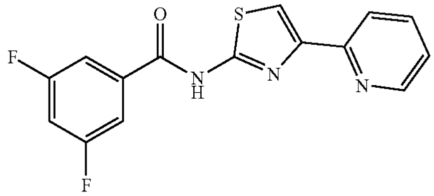
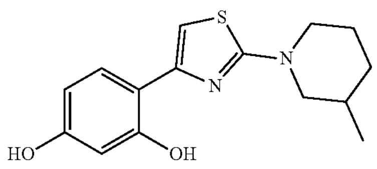

-continued

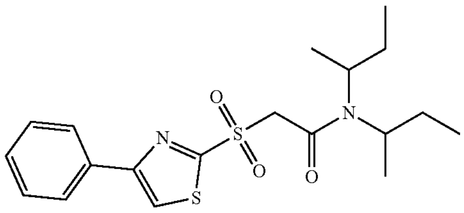

or

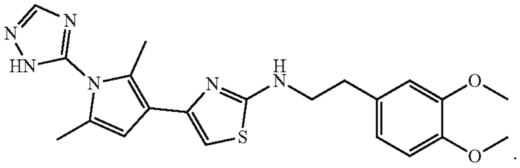

.

In another embodiment, the compound of Formula IIId is:

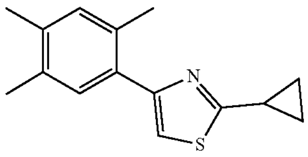 [SMILES: Cc1cc(C)c(-c2csc(C3CC3)n2)cc1C]

In another embodiment, the compound of Formula III is a compound of Formula IIIe:

Formula IIIe

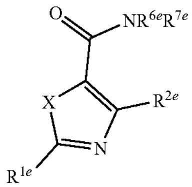

or pharmaceutically acceptable derivatives thereof, wherein $R^{1e}$ is aryl or heteroaryl;

$R^{2e}$ is H or alkyl;

$R^{6e}$ and $R^{7e}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and X is O or S.

In another embodiment of Formula IIIe, a compound of Formula IIIe is a compound wherein:

$R^{1e}$ is pyridinyl, phenyl;

wherein phenyl is optionally substituted with one substituent selected from halogen, and ethyl;

$R^{2e}$ is methyl or hydrogen;

$R^{6e}$ and $R^{7e}$ are independently selected from hydrogen or one of the following

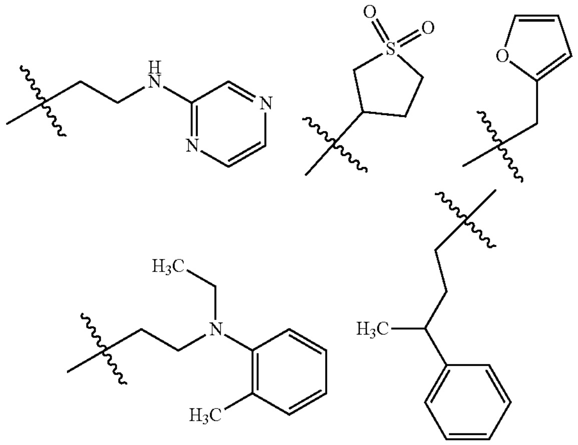

and $R^{6e}$ and $R^{7e}$ are combined to form a piperidine including the nitrogen atom to which they are both attached, and this piperidinyl ring is substituted with phenyl; and X is O or S.

In another embodiment of Formula IIIe, a compound of Formula IIIe is a compound wherein:

$R^{1e}$ is pyridinyl, phenyl;

wherein phenyl is optionally substituted with one substituent selected from halogen, and ethyl;

$R^{2e}$ is methyl or hydrogen;

$R^{6e}$ and $R^{7e}$ are independently selected from hydrogen or one of the following

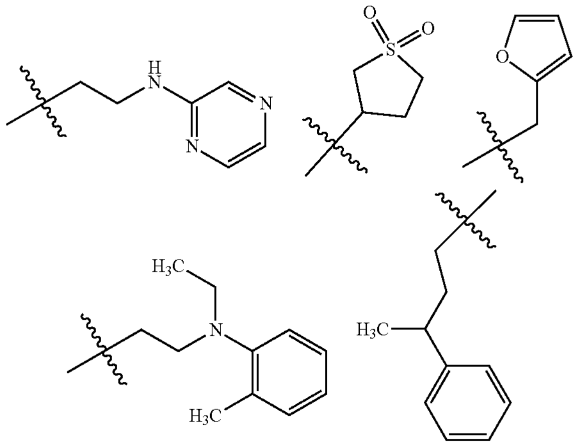

and $R^{6e}$ and $R^{7e}$ are combined to form a piperidine including the nitrogen atom to which they are both attached, and this piperidinyl ring is substituted with phenyl; and X is O or S.

In one embodiment, the compound of Formula IIIe is:

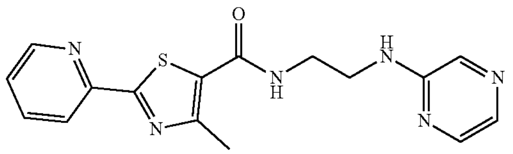

-continued

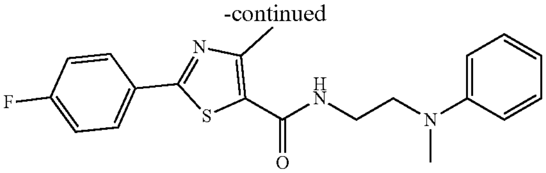

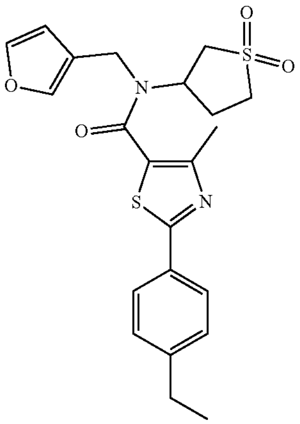

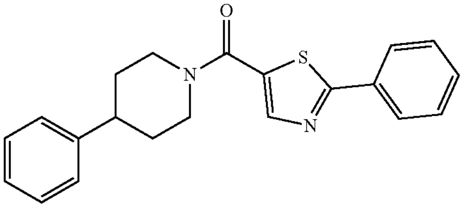

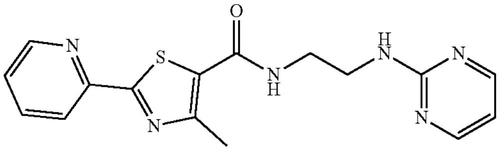

or

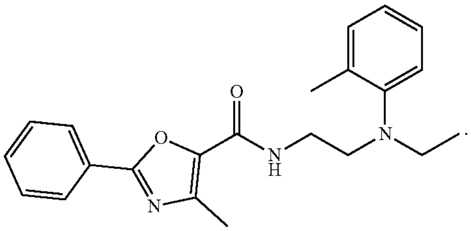

In another embodiment, the compound of Formula III is a compound of Formula IIIf:

Formula IIIf

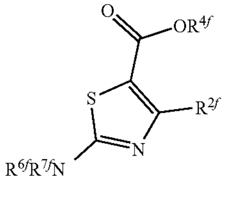

or pharmaceutically acceptable derivatives thereof, wherein $R^{2f}$ is H or alkyl;

$R^{4f}$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^{6f}$ and $R^{7f}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula IIIf, a compound of Formula IIIf is a compound wherein $R^{2f}$ is H or methyl;

$R^{4f}$ is methyl or ethyl; and $R^{6f}$ and $R^{7f}$ are independently selected from cyclopropyl, ethyl, or one of the following

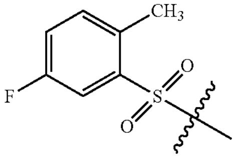

or

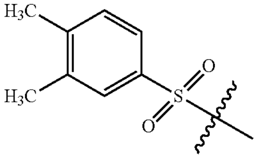

.

In one embodiment, the compound of Formula IIIf is:

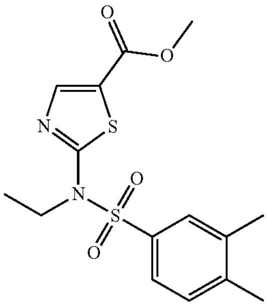

or

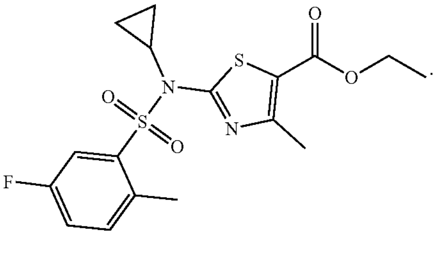

.

In another embodiment, the compound of Formula III is a compound of Formula IIIg:

Formula IIIg

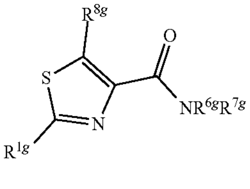

or pharmaceutically acceptable derivatives thereof, wherein $R^{1g}$ is aryl or heteroaryl;

$R^{6g}$ and $R^{7g}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^{8g}$ is H or alkyl.

In another embodiment of Formula IIIg, a compound of Formula IIIg is a compound wherein:

$R^{1g}$ is phenyl, or pyrimidinyl;

wherein phenyl is optionally substituted with one or two substituents each selected from methoxy, halogen, or propyl;

$R^{6g}$ and $R^{7g}$ are independently selected from hydrogen or one of the following:

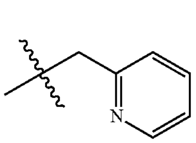

or

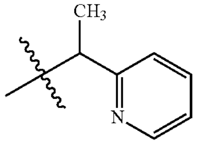

$R^6$ and $R^7$ are combined to form a cyclic structure including the nitrogen atom to which they are both attached, as depicted below:

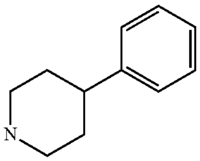

or

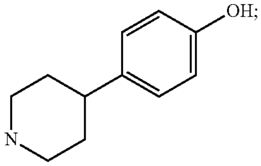

; and $R^{8g}$ is H.

In one embodiment, the compound of Formula IIIg is:

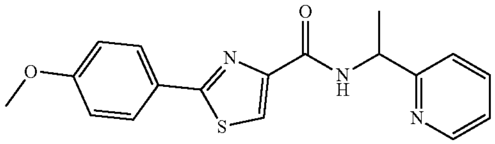

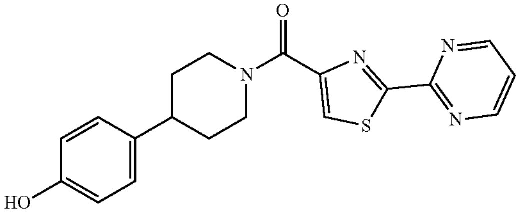

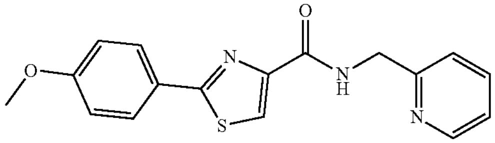

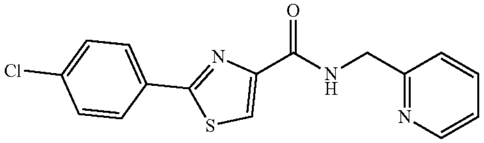

-continued

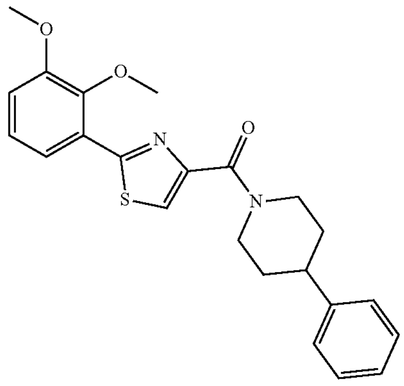

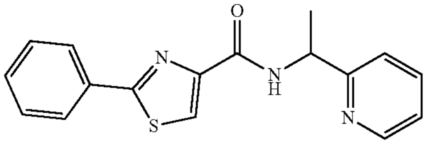

or

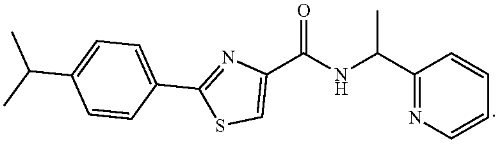

.

In one embodiment, the compound of Formula III is selected with the proviso that the compound is not

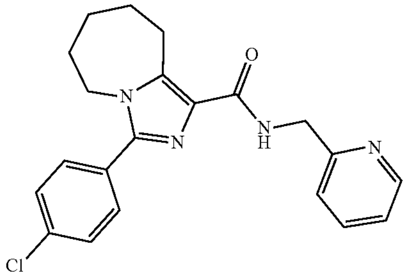

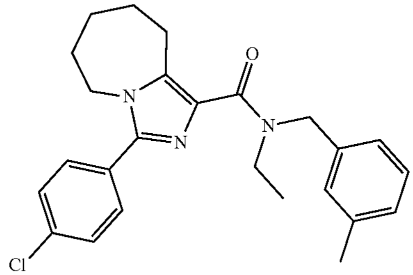

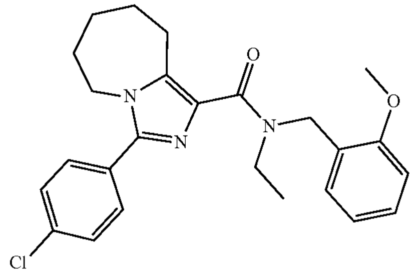

-continued

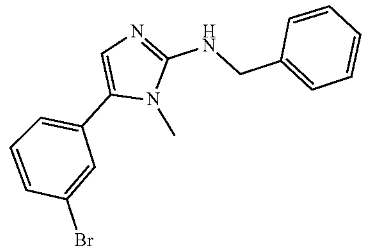

or

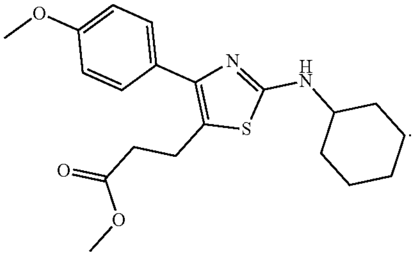

In one embodiment, the compound of Formula IIId is selected with the proviso that the compound is not

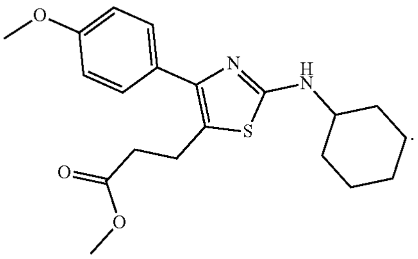 [SMILES: COC(=O)CCc1sc(NC2CCCCC2)nc1-c1ccc(OC)cc1]

In one embodiment, the compound of Formula III is selected with the proviso that if X is S, then $R^1$ is not optionally substituted morpholino, thiomorpholino, piperinyl, indolyl, pyridyl, thienyl, aminophenyl, phenyl, methoxyphenyl, chloromethyl, amido, imadazothiazolyl, piperizinyl, pyrrolidino, thiazolyl, imidazolyl, or pyrazolyl.

In one embodiment, the compound of Formula IIId is selected with the proviso that $R^{1d}$ is not optionally substituted morpholino, thiomorpholino, piperinyl, indolyl, aminophenyl, chloromethyl, amido, imadazothiazolyl, piperizinyl, pyrrolidino, imidazolyl or pyrazolyl.

In one embodiment, the compound of Formula III is selected with the proviso that if X is S, then $R^2$ is not naphthyl or tetrahydronaphthyl.

In one embodiment, the compound of Formula III is selected with the proviso that if X is O and $R^1$ is phenyl or thienyl, then $R^8$ is not morpholino.

In one embodiment, the compound of Formula III is selected with the proviso that if X is NH and $R^1$ is heteroaryl, then $R^8$ is not morpholino.

In one embodiment, the compound of Formula IIId is selected with the proviso that $R^{2d}$ is not naphthyl or tetrahydronaphthyl.

In certain embodiments, the compounds for use in the compositions and methods provided herein are of Formula IV:

Formula IV

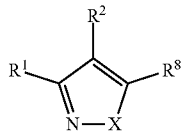

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is O or $NR^5$.

In another embodiment, the compound of Formula IV is a compound of Formula IVa:

Formula IVa

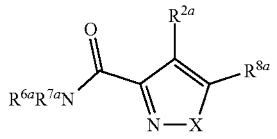

or pharmaceutically acceptable derivatives thereof, wherein $R^{2a}$ is H or alkyl;

$R^{8a}$ is aryl or heteroaryl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and X is O or $NR^5$.

In another embodiment, the compound of Formula IVa is a compound wherein $R^{2a}$ is H;

$R^{8a}$ is phenyl, pyridinyl, or as shown below

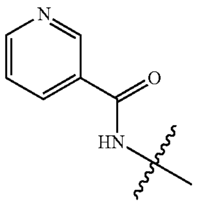 [SMILES: *NC(=O)c1cccnc1]

wherein phenyl is optionally substituted with a halogen;

$R^{6a}$ and $R^{7a}$ are independently selected from H, pyridinyl, cyclopropyl, cyclopentyl, or one of the following:

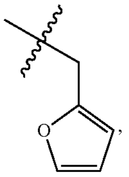
,
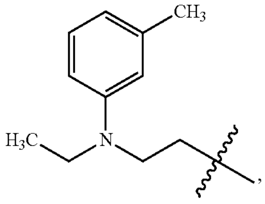
, or
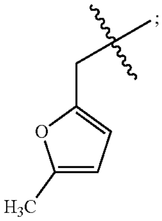
; and

X is O or NH, or $NCH_3$.

In one embodiment, the compound of Formula IVa is:

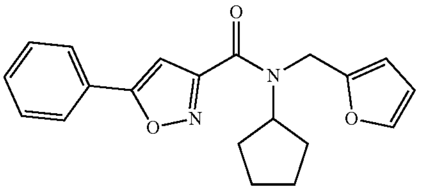

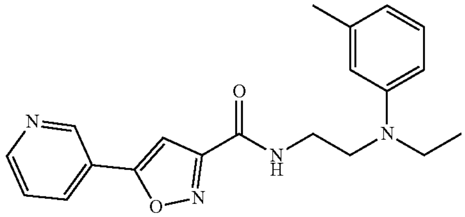

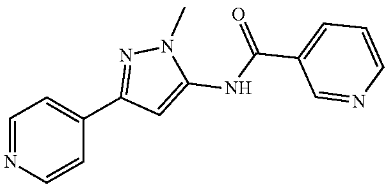

-continued

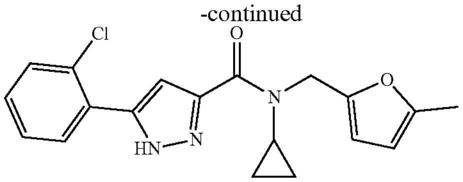
or

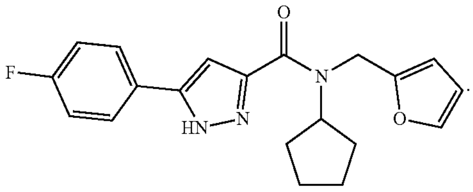
.

In another embodiment, the compound of Formula IV is a compound of Formula IVb:

Formula IVb

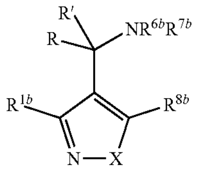

or pharmaceutically acceptable derivatives thereof, wherein $R^{1b}$ is H or alkyl;

$R^{8b}$ is H or alkyl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b}$ and $R^{7b}$ are combined to form a cyclic structure including the nitrogen atom to which they are both attached; and R and R' are independently selected from hydrogen and alkyl, and R and R' are combined to form a cyclic structure including the carbon atom to which they are both attached; and X is O or $NR^5$.

In another embodiment, Formula IVb is:

Formula IVb

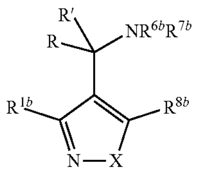

or pharmaceutically acceptable derivatives thereof, wherein $R^{1b}$ is H or alkyl;

$R^{8b}$ is H or alkyl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b}$ and $R^{7b}$ are combined to form a cyclic structure including the nitrogen atom to which they are both attached; and R and R' are independently selected from hydrogen and alkyl, and R and R' are combined to form a cyclic structure including the carbon atom to which they are both attached; and X is O or $NR^5$.

In another embodiment of Formula IVb, a compound of Formula IVb is a compound wherein $R^{1b}$ is methyl;

$R^{8b}$ is methyl;

$R^{6b}$ and $R^{7b}$ are independently selected from hydrogen, methyl, or one of the following:

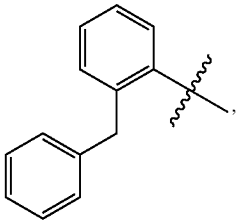

,

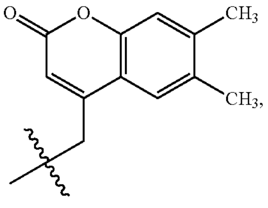

or

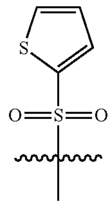

R and R' are hydrogen,

X is O or $NR^5$; and $R^5$ is benzyl wherein benzyl is substituted with a halogen.

In one embodiment, the compound of Formula IVb is:

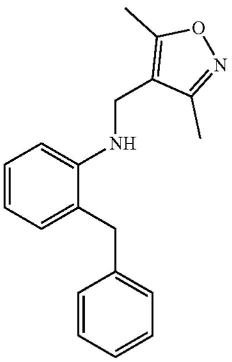

-continued

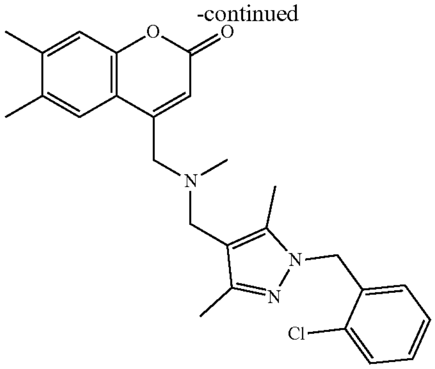

or

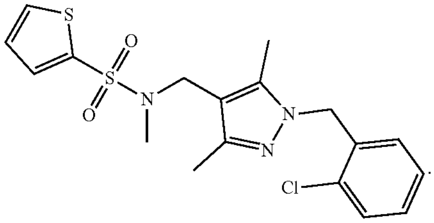

.

In another embodiment, the compound of Formula IV is a compound of Formula IVc:

Formula IVc

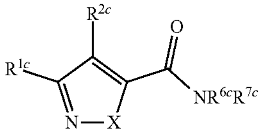

or pharmaceutically acceptable derivatives thereof, wherein $R^{1c}$ is aryl or heteroaryl;

$R^{R2c}$ is H, halo or alkyl;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6c}$ and $R^{7c}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6c}$ and $R^{7c}$ are combined to form a cyclic structure including the nitrogen atom to which they are both attached; and X is O or $NR^5$.

In another embodiment of Formula IVc, a compound of Formula IVc is a compound wherein $R^{1c}$ is phenyl wherein phenyl is optionally substituted with methyl;

$R^{2c}$ is H or a halogen;

$R^{6c}$ and $R^{7c}$ are independently selected from cyclopropyl or one of the following:

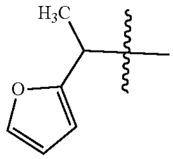

or

-continued

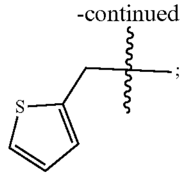

; and

X is O or NH.

In one embodiment, the compound of Formula IVc is:

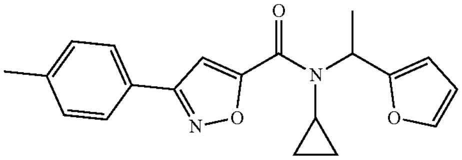

or

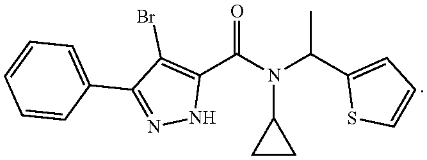

.

In another embodiment, the compound of Formula IV is a compound of Formula IVd:

Formula IVd

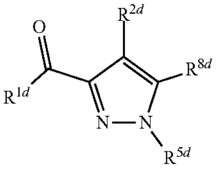

or pharmaceutically acceptable derivatives thereof, wherein $R^{1d}$ is $OR^{3a}$ or $NR^{6d}R^{7d}$;

$R^{2d}$ is H, alkyl or halo;

$R^{3d}$ is hydrogen, alkyl, alkenyl, alkynyl, aryl, heteroaryl, heterocyclyl or cycloalkyl;

$R^{5d}$ is aryl, heteroaryl, arylalkyl or heteroarylalkyl;

$R^{6d}$ and $R^{7d}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6d}$ and $R^{7d}$ are combined to form a cyclic structure including the nitrogen atom to which they are both attached;

$R^{8d}$ is H or alkyl.

In another embodiment of Formula IVd, a compound of Formula IVd is a compound wherein $R^{1d}$ is $OR^{3d}$ or $NR^{6d}R^{7d}$;

$R^{2d}$ is H, alkyl or halo;

$R^{3d}$ is hydrogen, alkyl, alkenyl, alkynyl, aryl, heteroaryl, heterocyclyl or cycloalkyl;

$R^{5d}$ is aryl, heteroaryl, arylalkyl or heteroarylalkyl;

$R^{6d}$ and $R^{7d}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6d}$ and $R^{7d}$ are combined to form a cyclic structure including the nitrogen atom to which they are both attached;

$R^{8d}$ is H or alkyl.

In another embodiment of Formula IVd, a compound of Formula IVd is a compound wherein $R^{1d}$ is $OR^{3d}$ or $NR^{6d}R^{7d}$;

$R^{2d}$ is H or Br;

$R^{3d}$ is methyl;

$R^{5d}$ is phenyl or as depicted below

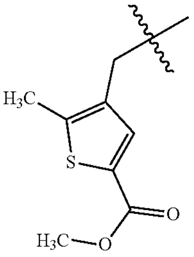 [SMILES: *Cc1cc(C(=O)OC)sc1C]

wherein phenyl is optionally substituted with one or two substituents each selected from halogen, methyl, or methoxy;

$R^{6d}$ and $R^{7d}$ are independently selected from hydrogen, pyridinylmethyl, bromophenyl, or as depicted below:

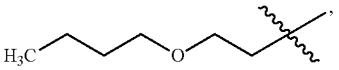

, or $R^{6d}$ and $R^{7d}$ are combined to form a cyclic structure including the nitrogen atom to which they are both attached, as shown below

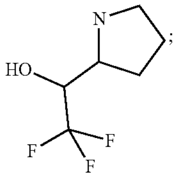

; and $R^{8d}$ is H or cyclopropyl.

In one embodiment, the compound of Formula IVd is:

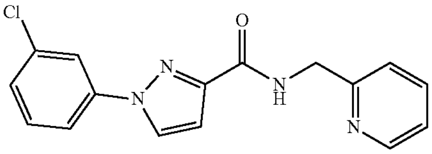

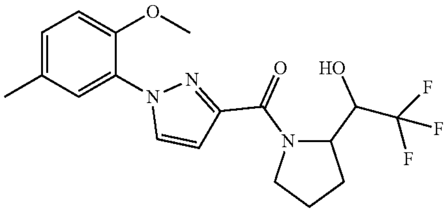

-continued

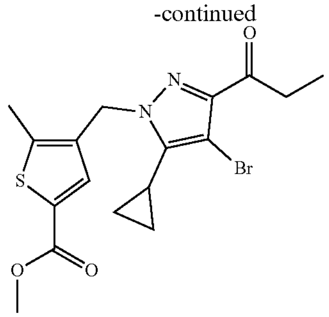

or

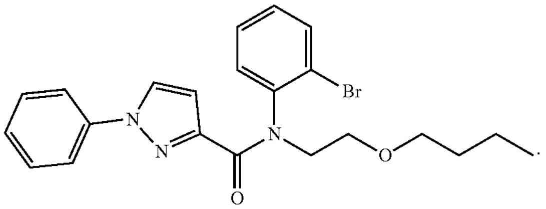

In another embodiment, the compound of Formula IV is a compound of Formula IVe:

Formula IVe

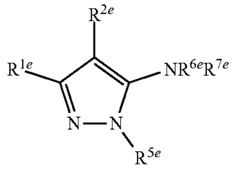

or pharmaceutically acceptable derivatives thereof, wherein $R^{1e}$ is aryl or heteroaryl;

$R^{2e}$ is H or alkyl;

$R^{5e}$ is H or alkyl; and $R^{6e}$ and $R^{7e}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6e}$ and $R^{7e}$ are combined to form a cyclic structure including the nitrogen atom to which they are both attached.

In another embodiment of Formula IV, a compound of Formula IVe is a compound wherein $R^{1e}$ is pyridinyl;

$R^{2e}$ is H;

$R^{5e}$ is H or methyl; and $R^{6e}$ and $R^{7e}$ are independently selected from hydrogen or the substituent as depicted below:

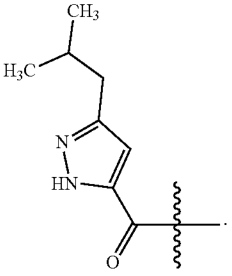 [SMILES: *C(=O)c1cc(CC(C)C)n[nH]1]

In one embodiment, the compound of Formula IVe is:

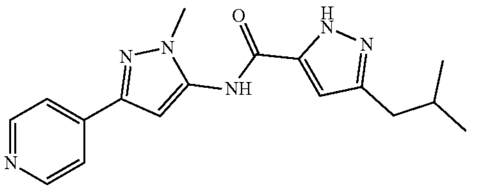

or

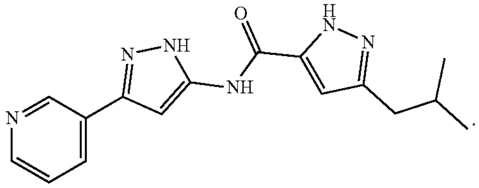

In another embodiment, the compound of Formula IV is a compound of Formula IVf:

Formula IVf

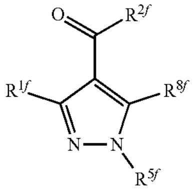

or pharmaceutically acceptable derivatives thereof, wherein $R^{1f}$ is H or alkyl;

$R^{2f}$ is aryl, heteroaryl or $NR^{6f}R^{7f}$;

$R^{5f}$ is aryl or heteroaryl;

$R^{8f}$ is H or alkyl;

$R^{6f}$ and $R^{7f}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6f}$ and $R^{7f}$ are combined to form a cyclic structure including the nitrogen atom to which they are both attached.

In another embodiment of Formula IVf, a compound of Formula IVf is a compound wherein:

$R^{1f}$ is H;

$R^{2f}$ is selected from one of the following:

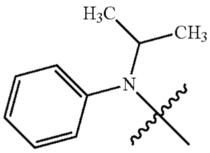

or

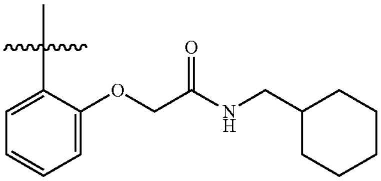

$R^{5f}$ is phenyl or pyridinyl; and $R^{8f}$ is H or methyl.

In one embodiment, the compound of Formula IVf is:

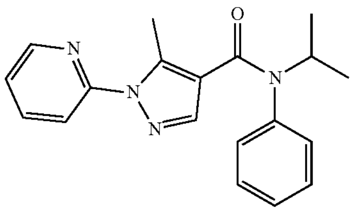

or

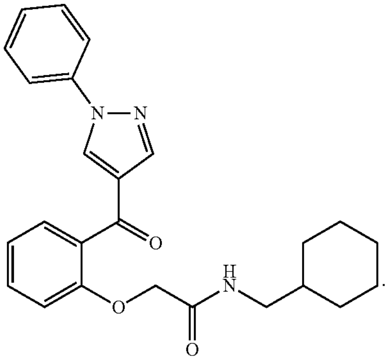

In one embodiment, the compound of Formula IV is selected with the proviso that the compound is not

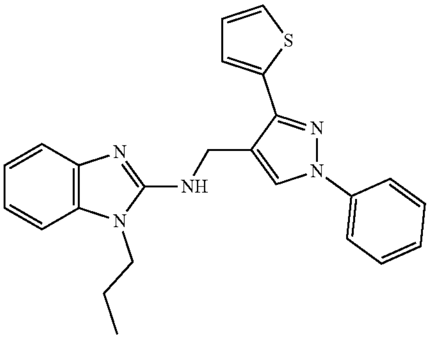

or

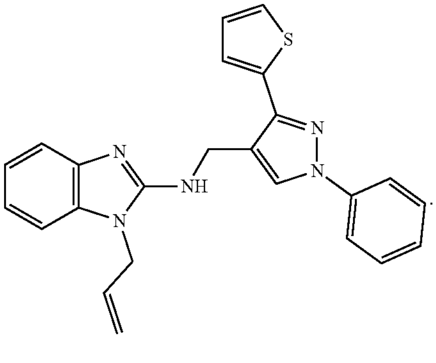

In one embodiment, the compound of Formula IVa is selected with the proviso that the compound is not

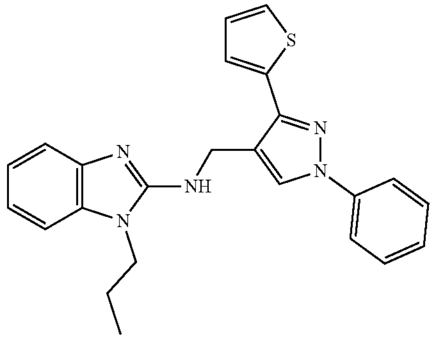

or

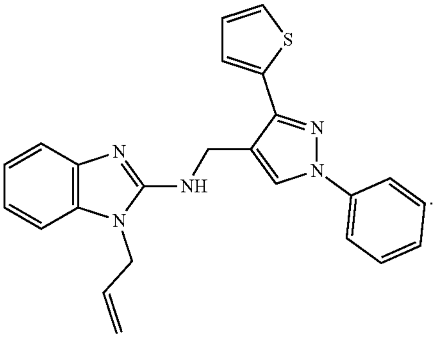

In one embodiment, the compound of Formula IV is selected with the proviso that if X is O, then $R^8$ is not optionally substituted morpholino.

In one embodiment, the compound of Formula IV is selected with the proviso that if X is N-aryl, then $R^2$ is not heteroaryl.

In certain embodiments, the compounds for use in the compositions and methods provided herein are of Formula V:

Formula V

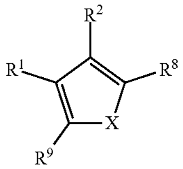

or pharmaceutically acceptable derivatives thereof, wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$; wherein $R^2$ and $R^8$ are combined to form a cyclic structure including the carbon atoms to which they are attached in the five-membered ring;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is O, S or $NR^5$.

In another embodiment, the compound of Formula V is a compound of Formula Va:

Formula Va

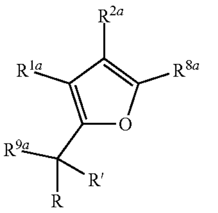

or pharmaceutically acceptable derivatives thereof, wherein $R^{1a}$ is H or alkyl;

$R^{2a}$ is H or alkyl;

$R^{8a}$ is aryl, heteroaryl, $C(O)R^4$ or $S(O)_pR^4$;

$R^{9a}$ is $OR^3$, $NR^5C(O)R^4$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R and R' are independently selected from hydrogen and alkyl, and R and R' are combined to form a cyclic structure including the carbon atom to which they are both attached; and p is 0-2.

In another embodiment of Formula V, a compound of Formula Va is a compound wherein $R^{1a}$ is H;

$R^{2a}$ is H;

$R^{8a}$ is phenyl, $C(O)R^4$ or $S(O)_pR^4$;

wherein phenyl is substituted with halogen;

$R^{9a}$ is $OR^3$, $NR^6R^7$, or selected from one of the following

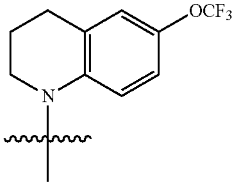

or

-continued

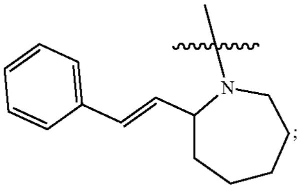

$R^3$ is phenyl, wherein phenyl is optionally substituted with one or two substituents each selected from halogen, methoxy and methyl;

$R^4$ is selected from the following:

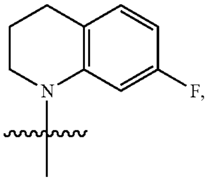

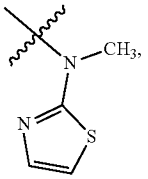

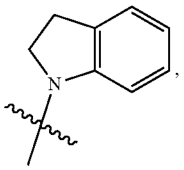

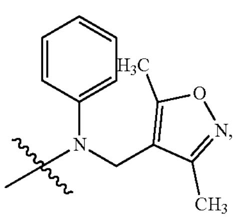

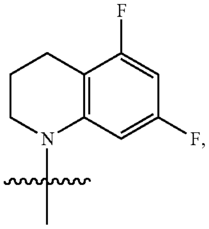

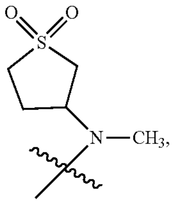

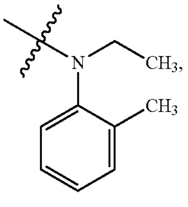

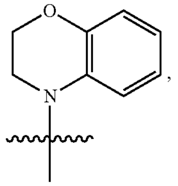

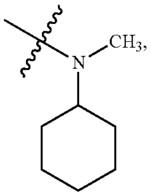

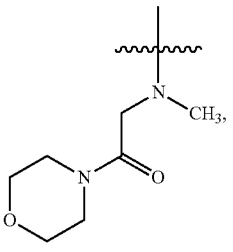

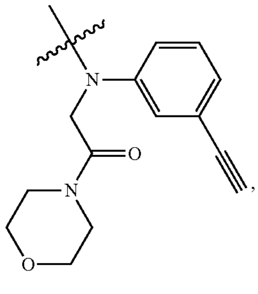

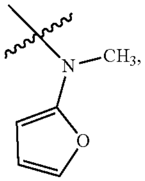

-continued

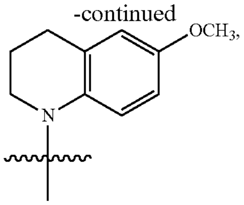

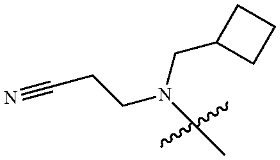

, and

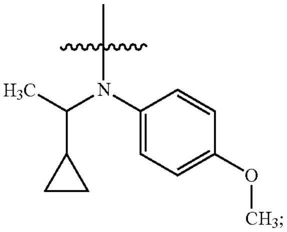

$R^6$ and $R^7$ are independently selected from ethyl, phenyl, or biphenyl;

R and R' are H; and p is 2.

In another embodiment of Formula V, a compound of Formula Va is a compound wherein $R^{1a}$ is H;

$R^{2a}$ is H;

$R^{8a}$ is phenyl, $C(O)R^4$ or $S(O)_pR^4$;

wherein phenyl is substituted with halogen;

$R^{9a}$ is $OR^3$, $NR^6R^7$, or selected from one of the following

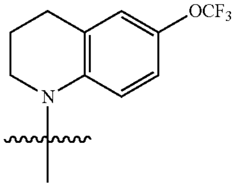

or

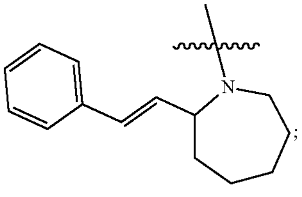

$R^3$ is phenyl, wherein phenyl is optionally substituted with one or two substituents each selected from halogen, methoxy and methyl;

$R^4$ is selected from the following:

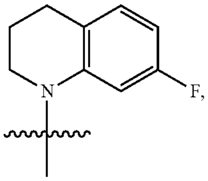

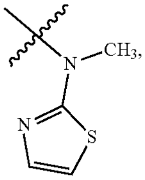

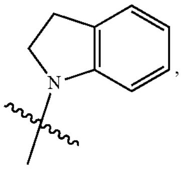

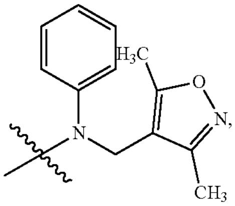

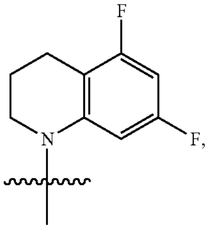

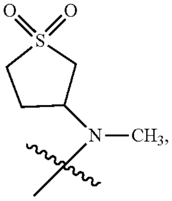

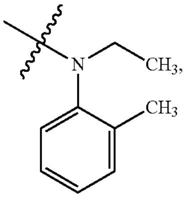

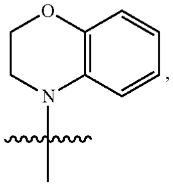

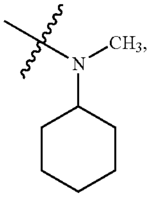

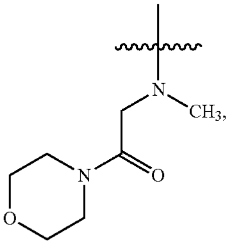

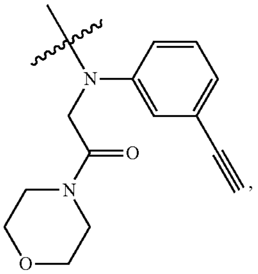

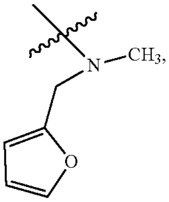

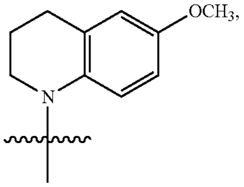

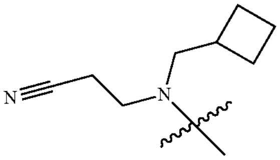

, and

-continued
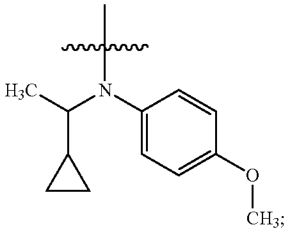
$R^6$ and $R^7$ are independently selected from ethyl, phenyl, or biphenyl;
R and R' are H; and
p is 2.
In one embodiment, the compound of Formula Va is:
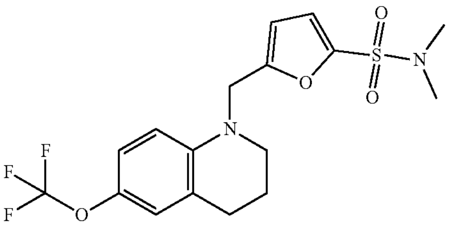
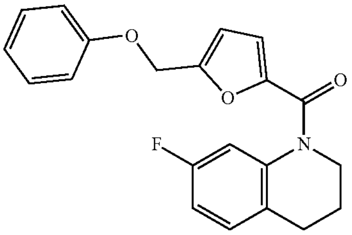
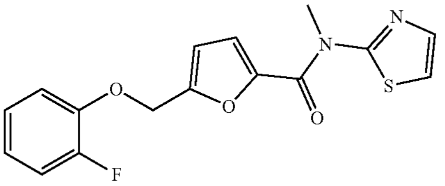
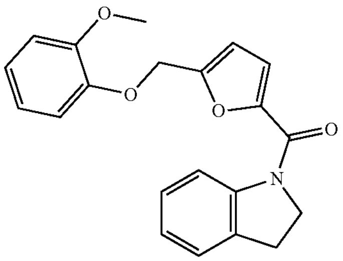
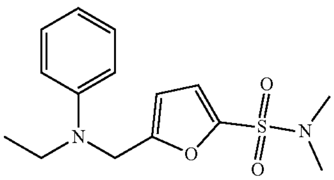
-continued
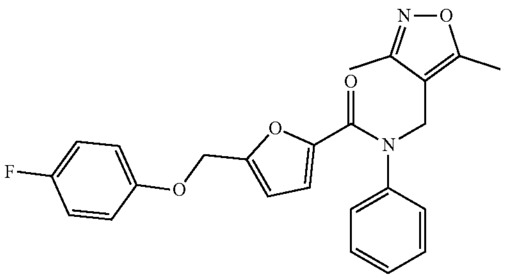
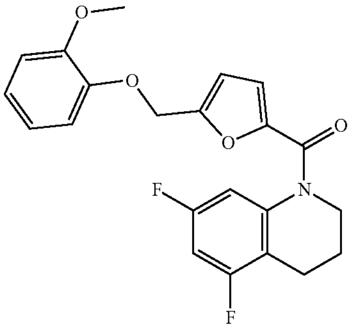
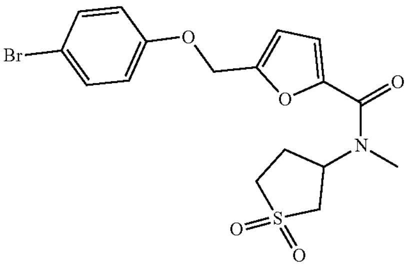
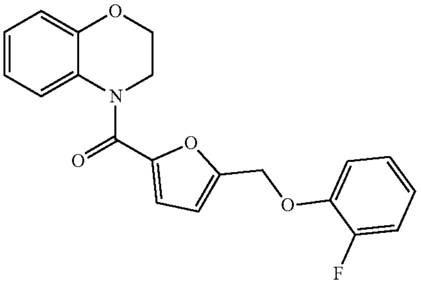
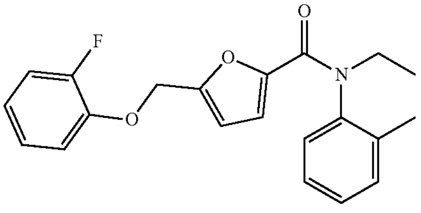
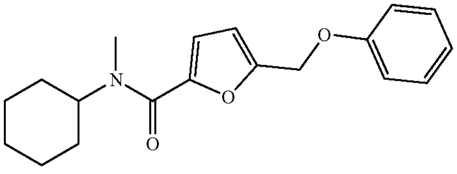
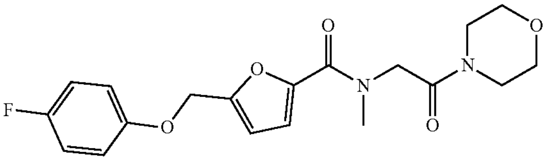

-continued

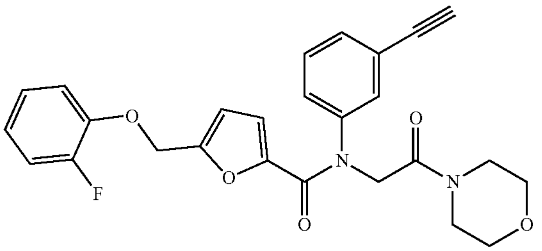

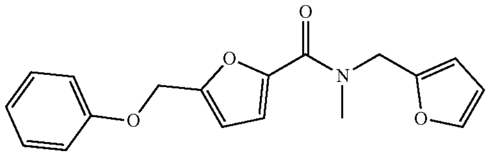

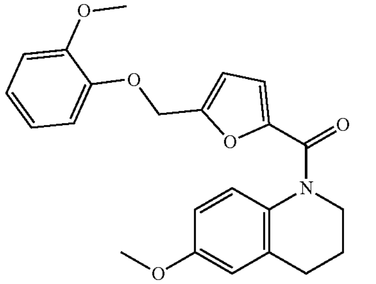

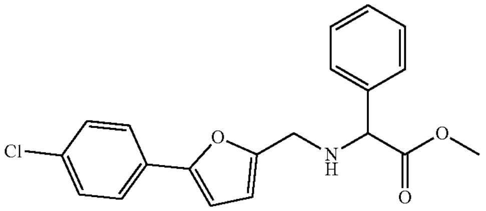

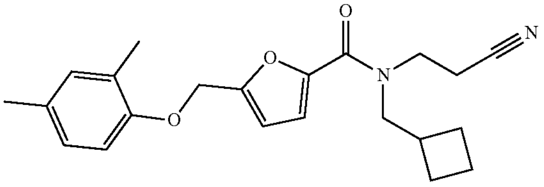

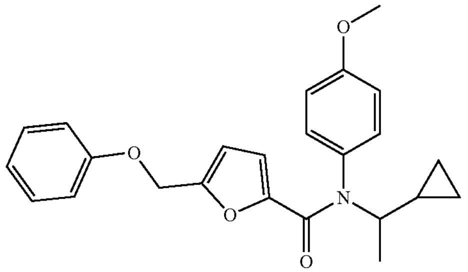

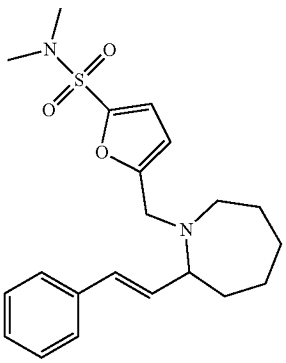

or

-continued

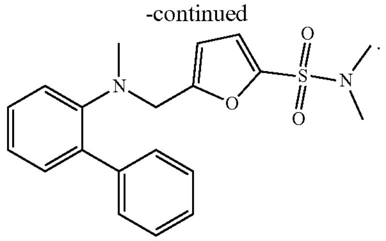

In another embodiment, the compound of Formula V is a compound of Formula Vb:

Formula Vb

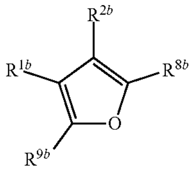

or pharmaceutically acceptable derivatives thereof, wherein $R^{1b}$ is H or alkyl;

$R^{2b}$ is H or alkyl;

$R^{8b}$ is $C(O)R^4$ or $S(O)_pR^4$;

$R^{9b}$ is aryl, heteroaryl, halo or $C(O)R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

X is O or $NR^5$; and p is 0-2.

In another embodiment, Formula Vb is:

Formula Vb

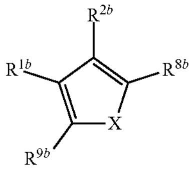

or pharmaceutically acceptable derivatives thereof, wherein $R^{1b}$ is H or alkyl;

$R^{2b}$ is H or alkyl;

$R^{8b}$ is $C(O)R^4$ or $S(O)_pR^4$;

$R^{9b}$ is aryl, heteroaryl, halo or $C(O)R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

X is O, S or $NR^5$; and p is 0-2.

In another embodiment of Formula Vb, a compound of Formula Vb is a compound wherein $R^{1b}$ is H, halogen, or $COCH_3$;

$R^{2b}$ is H, halogen, or $COCH_3$;

$R^{8b}$ is $C(O)R^4$;

$R^{9b}$ is H, halogen, phenyl, or $C(O)R^4$;

wherein phenyl is optionally substituted with halogen;

$R^4$ is $NR^6R^7$;

$R^6$ and $R^7$ are independently selected from H, cyclopropyl, thienylmethyl, furanylmethyl, cyclopentyl, methyl, and benzyl;

wherein benzyl is substituted with two methoxy substituents;

X is O, S or $NCH_3$; and p is 2.

In one embodiment, the compound of Formula Vb is:

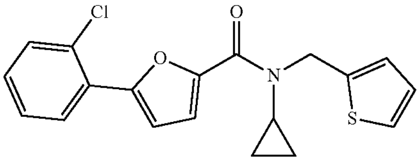

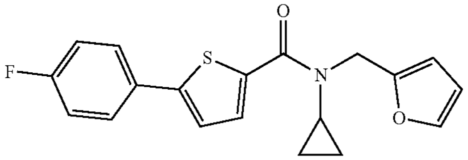

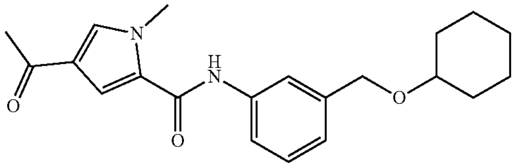

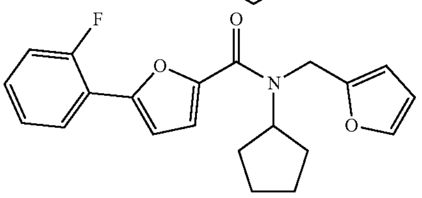

or

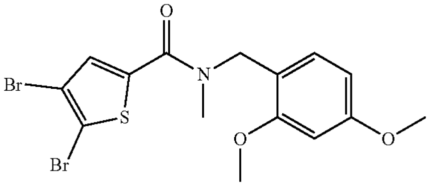

.

In another embodiment, the compound of Formula V is a compound of Formula Vc:

Formula Vc

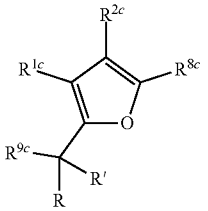

or pharmaceutically acceptable derivatives thereof, wherein $R^{1c}$ is H, alkyl or $C(O)R^4$;

$R^{2c}$ is H, alkyl or $C(O)R^4$;

$R^{8c}$ is H or alkyl;

$R^{9c}$ is $OR^3$, $NR^5C(O)R^4$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and R and R' are independently selected from hydrogen and alkyl, and R and R' are combined to form a cyclic structure including the carbon atom to which they are both attached.

In another embodiment of Formula Vc, a compound of Formula Vc is a compound wherein $R^{1c}$ is H or $C(O)R^4$;

$R^{2c}$ is H or $C(O)R^4$;

$R^{8c}$ is H or methyl;

$R^{9c}$ is $OR^3$;

$R^3$ is selected from one of the following:

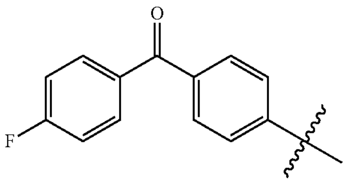

or

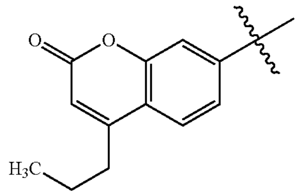

$R^4$ is methyl; and

R and R' are H.

In one embodiment, the compound of Formula Vc is:

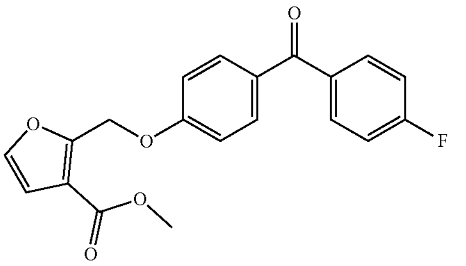

or

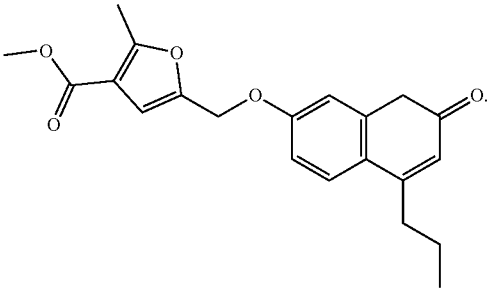

In another embodiment, the compound of Formula V is a compound of Formula Vd:

Formula Vd

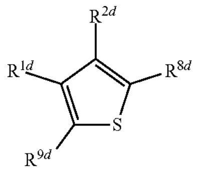

or pharmaceutically acceptable derivatives thereof, wherein $R^{1d}$ is H, alkyl, aryl or heteroaryl;

$R^{2d}$ is $C(O)R^4$;

$R^{8d}$ is $NR^5C(O)R^4$ or $N{=}C(R)NR^6R^7$;

$R^{9d}$ is H, alkyl, arylalkyl or heteroarylalkyl; wherein $R^{1d}$ and $R^{9d}$ are combined to form a cyclic structure including the carbon atoms to which they are attached in the five-membered ring;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and R and R' are independently selected from hydrogen and alkyl, or R and R' are combined to form a cyclic structure including the carbon atom to which they are both attached.

In another embodiment of Formula Vd, a compound of Formula Vd is a compound wherein wherein $R^{1d}$ is H, methyl, or phenyl, wherein phenyl is optionally substituted with methyl or halogen;

$R^{2d}$ is $C(O)R^4$, or as depicted below

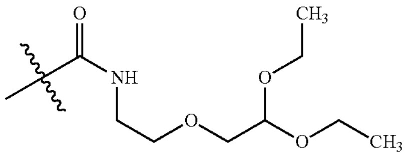 [SMILES: *C(=O)NCCOCC(OCC)OCC]

$R^{8d}$ is phenyl or $NR^5C(O)R^4$, wherein phenyl is substituted with propyl;

$R^{9d}$ is H, methyl, benzodioxylphenylmethyl, and wherein $R^{1d}$ and $R^{9d}$ are combined to form a seven-membered cyclic structure including the carbon atoms to which they are attached in the five-membered ring;

$R^4$ is ethyl, methyl, t-butyl, benzyl or as depicted below

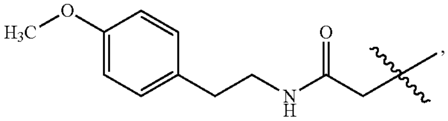

,

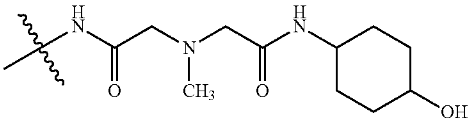

wherein benzyl is optionally substituted with 1-3 substituents each selected from methoxy $R^5$ is H; and R and R' are H.

In another embodiment of Formula Vd, a compound of Formula Vd is a compound wherein wherein $R^{1d}$ is H, methyl, or phenyl, wherein phenyl is optionally substituted with methyl or halogen;

$R^{2d}$ is $C(O)R^4$, or as depicted below

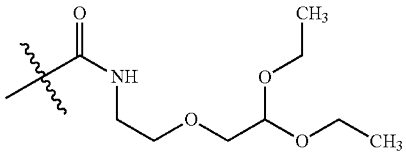

$R^{8d}$ is phenyl or $NR^5C(O)R^4$, wherein phenyl is substituted with propyl;

$R^{9d}$ is H, methyl, benzodioxylphenylmethyl, and wherein $R^{1d}$ and $R^{9d}$ are combined to form a seven-membered cyclic structure including the carbon atoms to which they are attached in the five-membered ring;

$R^4$ is ethyl, methyl, t-butyl, benzyl, p-isopropylphenyl or as depicted below

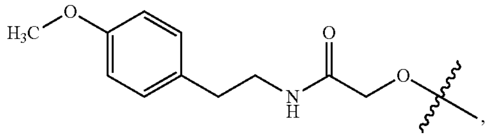

,

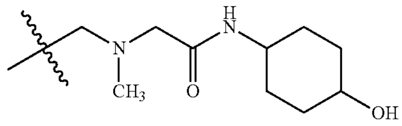

wherein benzyl is optionally substituted with 1-3 substituents each selected from methoxy $R^5$ is H; and R and R' are H.

In one embodiment, the compound of Formula Vd is:

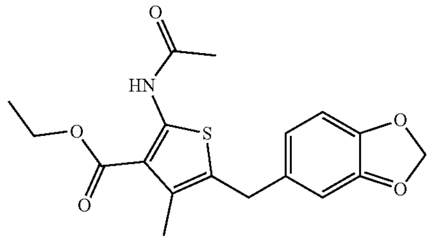

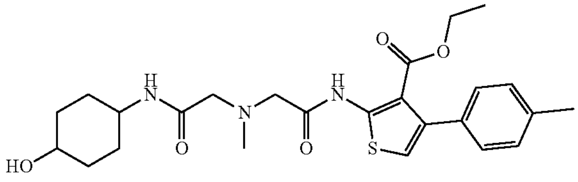

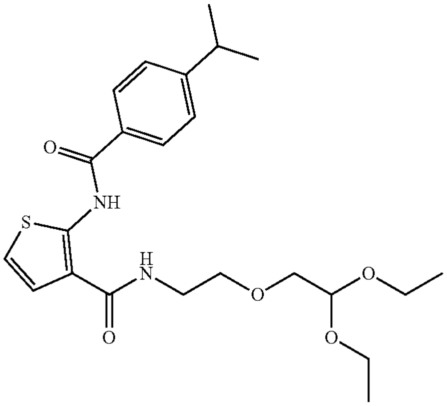

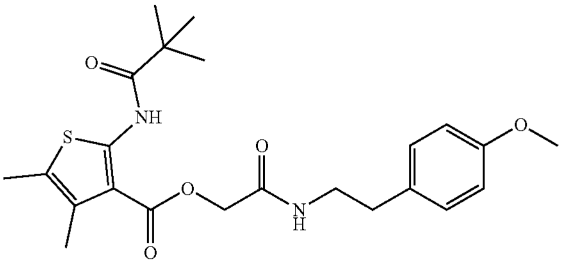

-continued

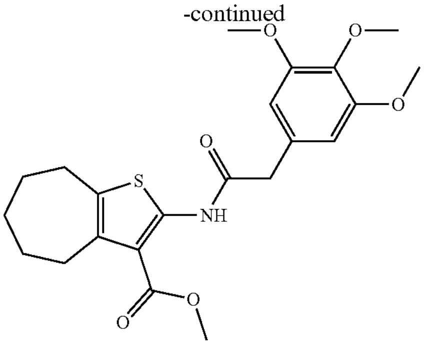

or

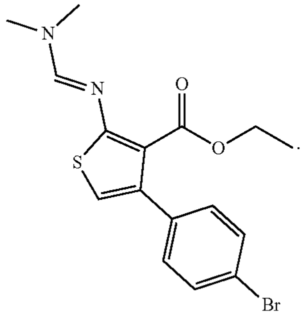

.

In another embodiment, the compound of Formula V is a compound of Formula Ve:

Formula Ve

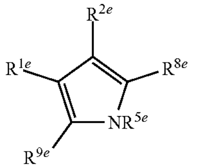

or pharmaceutically acceptable derivatives thereof, wherein $R^{1e}$ is H or alkyl;

$R^{2e}$ is $C(O)R^4$;

$R^{8e}$ is H or alkyl;

$R^{9e}$ is H or alkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5e}$ is hydrogen, alkyl, alkenyl, alkynyl, aryl, heteroaryl, heterocyclyl, cycloalkyl, alkylcarbonyl, cycloalkylcarbonyl, or arylcarbonyl; and $R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula Ve, a compound of Formula Ve is a compound wherein $R^{1e}$ is H;

$R^{2e}$ is $C(O)R^4$;

$R^{8e}$ is H or alkyl;

$R^{9e}$ is H or alkyl;

$R^4$ is selected from the following:

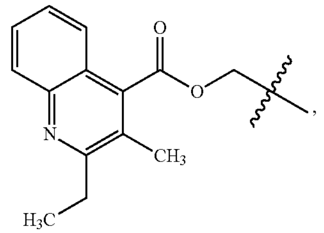

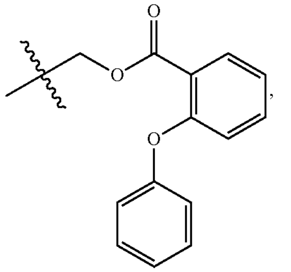

or

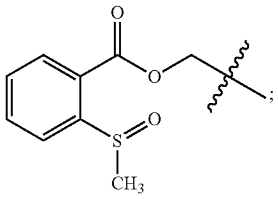

$R^{5e}$ is methoxyethyl, propenyl, or cyclohexenylpropyl.

In one embodiment, the compound of Formula Ve is:

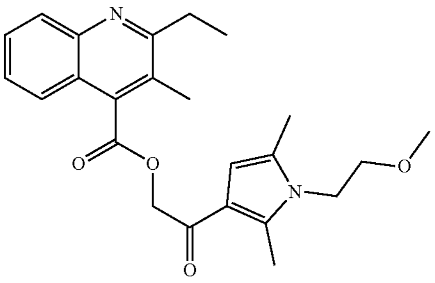

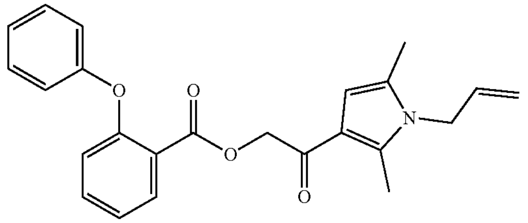

or

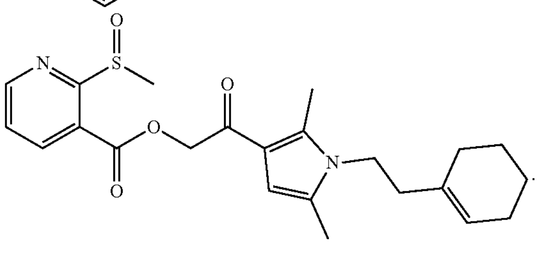

In another embodiment, the compound of Formula V is a compound of Formula Vf:

Formula Vf

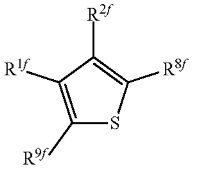

or pharmaceutically acceptable derivatives thereof, wherein $R^{1f}$ is H or alkyl;

$R^{2f}$ is $S(O)_pR^4$;

$R^{8f}$ is $C(O)R^4$;

$R^{9f}$ is aryl, H or alkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula Vf, a compound of Formula Vf is a compound wherein $R^{1f}$ is H;

$R^{2f}$ is $S(O)_pR^4$;

$R^{8f}$ is $C(O)R^4$;

$R^{9f}$ is aryl, H or alkyl;

$R^4$ is thiomorpholinyl or as depicted below

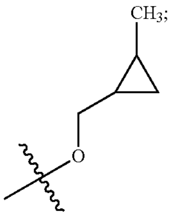

and p is 2.

In one embodiment, the compound of Formula Vf is:

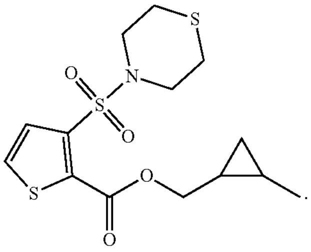 [SMILES: CC1CC1COC(=O)c1sccc1S(=O)(=O)N1CCSCC1]

In one embodiment, the compound of Formula V is selected with the proviso that the compound is not

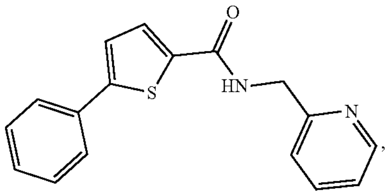
,
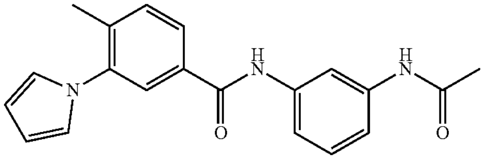
or
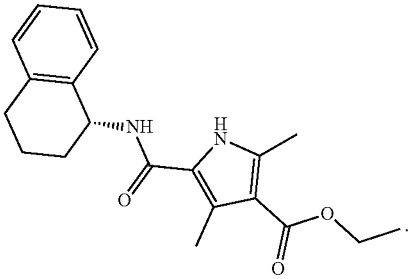
.

In one embodiment, the compound of Formula V is selected with the proviso that if X is S and $R^9$ is aryl, then neither $R^8$ nor $R^2$ is morpholino.

In one embodiment, the compound of Formula V is selected with the proviso that if X is S and $R^9$ is aryl, heteroaryl, oxazolidinonyl, arylcarbonyl, then $R^8$ is not morpholino, acyl or an ester.

In certain embodiments, the compounds for use in the compositions and methods provided herein are of Formula VI:

Formula VI

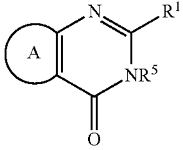

or pharmaceutically acceptable derivatives thereof, wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

A is a substituted or unsubstituted 5 or 6 membered aryl, heteroaryl, carbocyclic or heterocyclic ring.

In one embodiment, the compound of Formula VI is selected with the proviso that the compound is not
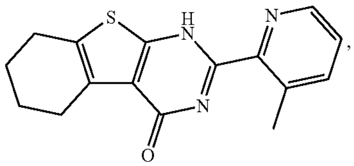
,
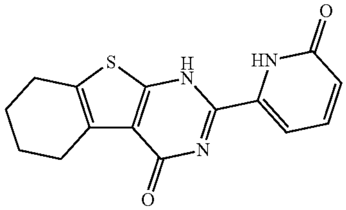
,
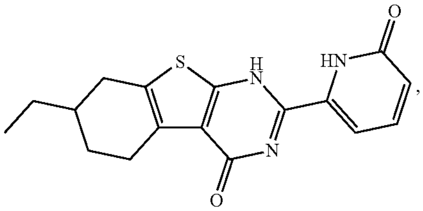
,
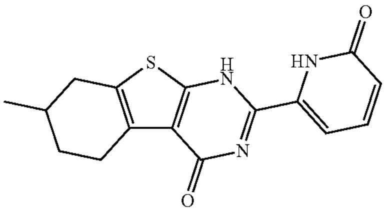
,
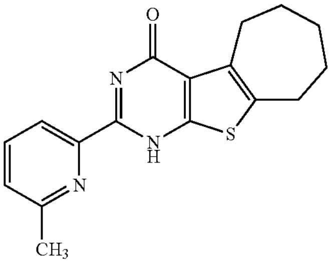
,
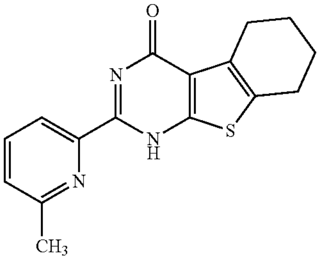
, -continued

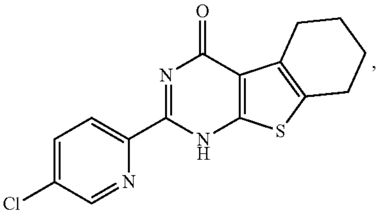
,

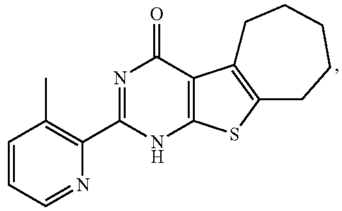
,

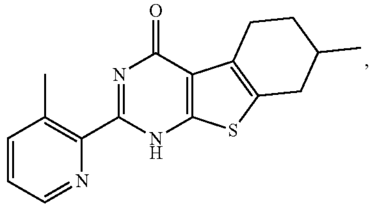
,

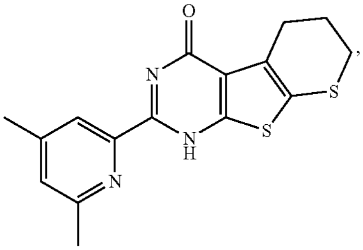
,

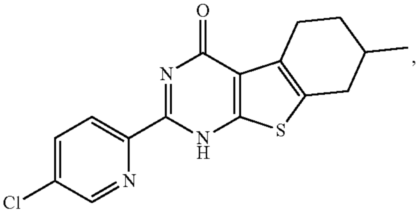
,

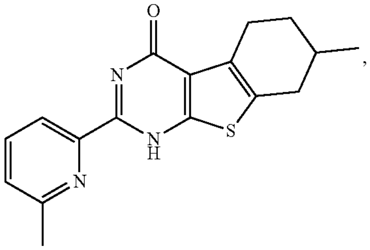
,

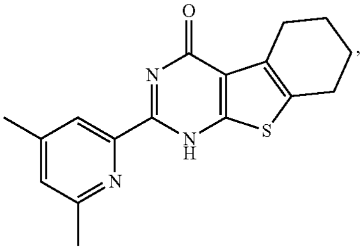
,

-continued

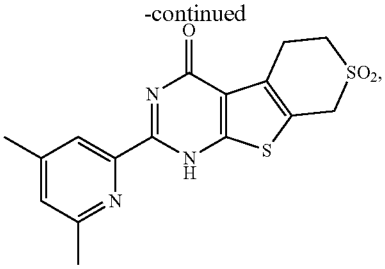
,

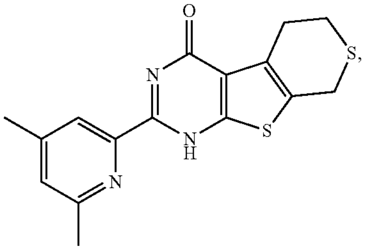
,

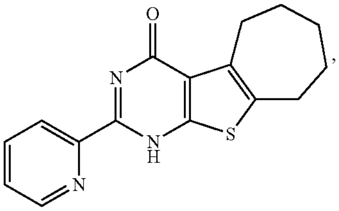
,

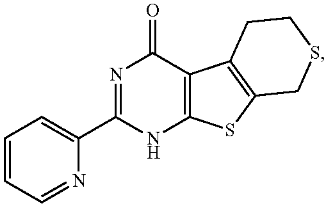
, or

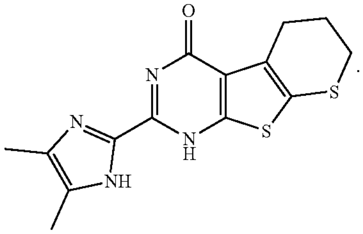
.

In certain embodiments, the compounds for use in the compositions and methods provided herein are of Formula VIt:

Formula VIt

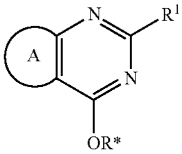

or pharmaceutically acceptable derivatives thereof, wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

R* is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

A is a substituted or unsubstituted 5 or 6 membered aryl, heteroaryl, carbocyclic or heterocyclic ring.

In one embodiment of Formula VIt, $R^1$ is aryl or heteroaryl;

R* is alkyl, alkenyl, alkynyl, aryl, heteroaryl, heterocyclyl, or cycloalkyl;

A is a substituted or unsubstituted 5 or 6 membered aryl, heteroaryl, carbocyclic or heterocyclic ring.

In one embodiment of Formula VIt, $R^1$ is 2-pyridyl;

R* is methyl;

A is a substituted or unsubstituted thienyl ring.

In one embodiment of Formula VIt, $R^1$ is 2-pyridyl;

R* is H or methyl;

A is a substituted or unsubstituted pyrazole ring.

In one embodiment of Formula VIt, the compound is

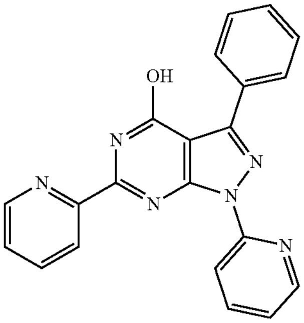

or

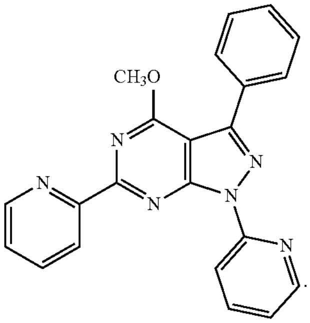

In another embodiment of Formula VIt, the compound of Formula VIt is a compound of Formula VIt1:

Formula VIt1

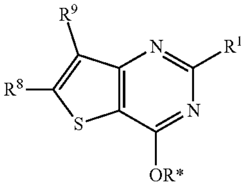

or pharmaceutically acceptable derivatives thereof, wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

R* is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^8$ is H, halo, $C(O)R^4$ or alkyl;

$R^9$ is H, alkyl, aryl, cycloalkyl, heteroaryl, heterocyclyl, halo, pseudohalo, $C(O)R^4$, or $S(O)_pR^4$; $R^8$ and $R^9$ can be combined to form a cyclic structure including the carbon atoms to which they are both attached, wherein the cyclic structure is a cycloalkyl or heterocycloalkyl;

p is 0-2.

In one embodiment of Formula VIt1, $R^1$ is aryl or heteroaryl;

R* is H or alkyl.

$R^8$ is H or $C(O)R^4$;

$R^9$ is selected from the group consisting of methyl, but-2-yl, cyclopropyl, cyclobutyl, cyclopentyl, and cyclohexyl.

In one embodiment, the compound of Formula VIt1 is:

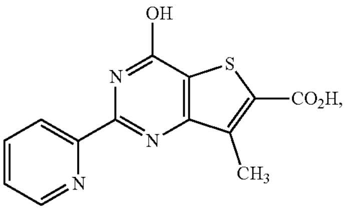

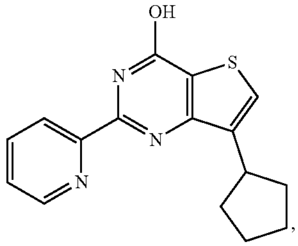

-continued

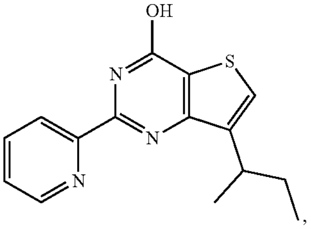

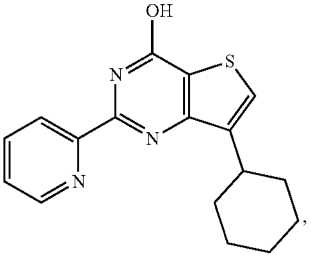

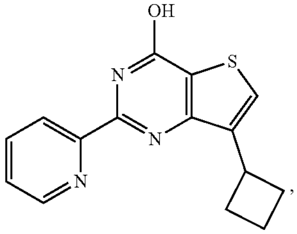

or

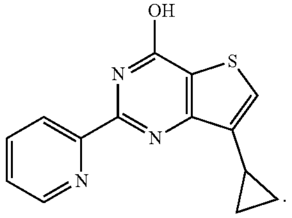

In one embodiment of Formula VIt1, $R^1$ is aryl or heteroaryl;

R* is hydrogen or alkyl.

$R^8$ and $R^9$ are combined to form a cyclic structure including the carbon atoms to which they are both attached, wherein the cyclic structure is a cycloalkyl or heterocycloalkyl.

In one embodiment, the compound of Formula VIt1 is:

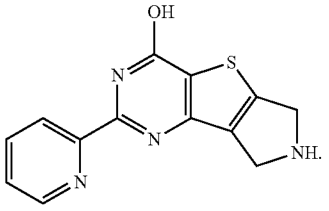 [SMILES: Oc1nc(-c2ccccn2)nc2c3c(sc12)CNC3]

In another embodiment of Formula VIt, the compound of Formula VIt is a compound of Formula VIt2:

Formula VIt2

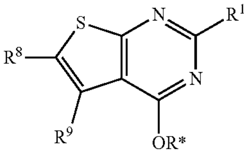

or pharmaceutically acceptable derivatives thereof, wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

R* is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^8$ is H, halo, $C(O)R^4$ or alkyl;

$R^9$ is H, alkyl, aryl, cycloalkyl, heteroaryl, heterocyclyl, halo, pseudohalo, $C(O)R^4$, or $S(O)_pR^4$; $R^8$ and $R^9$ can be combined to form a cyclic structure including the carbon atoms to which they are both attached, wherein the cyclic structure is a cycloalkyl or heterocycloalkyl;

p is 0-2.

In one embodiment of Formula VIt2, $R^1$ is aryl or heteroaryl;

R* is hydrogen or alkyl.

$R^8$ and $R^9$ are combined to form a cyclic structure including the carbon atoms to which they are both attached, wherein the cyclic structure is a cycloalkyl or heterocycloalkyl.

In one embodiment, the compound of Formula VIt2 is:

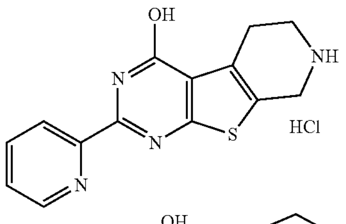

or

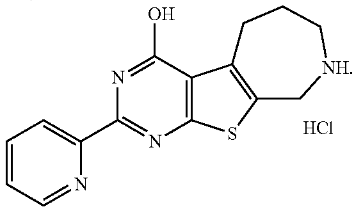

In another embodiment of Formula VIt2, a compound of Formula VIt2 is a compound wherein $R^1$ is N-methyl-imidazolyl, $R^8$ is pyridyl, phenyl, or

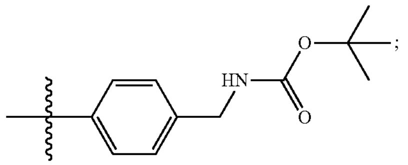 [SMILES: *c1ccc(CNC(=O)OC(C)(C)C)cc1]

$R^9$ is phenyl;

R* is H, $CH_3$, $-CH_2CH_2OEt$ or $-CH_2CH_2NEt_2$.

In one embodiment, the compound of Formula VIt2 is:

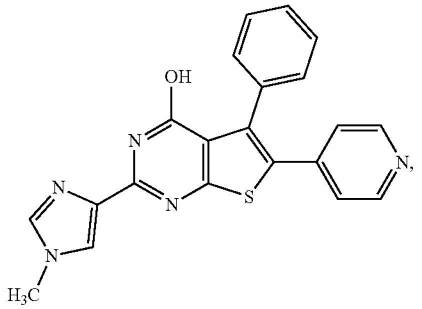

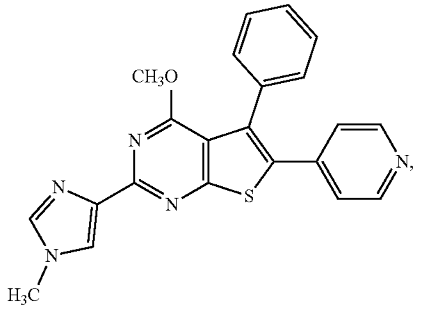

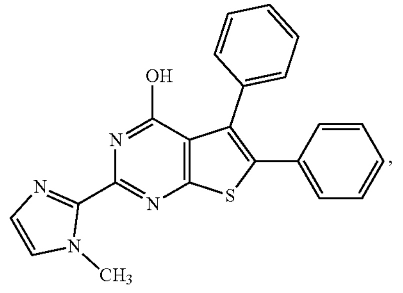

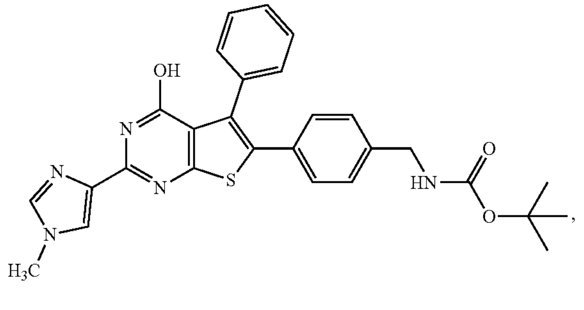

-continued

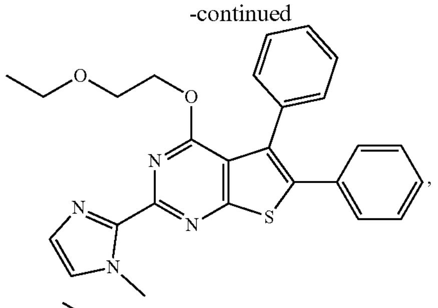

or

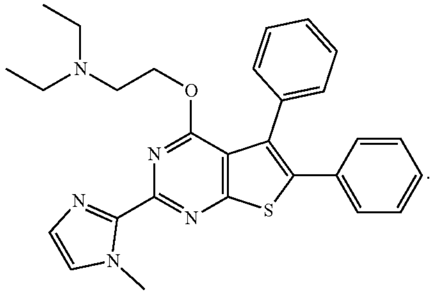

In another embodiment, the compound of Formula VI is a compound of Formula VIa:

Formula VIa

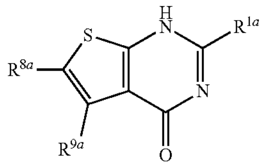

or pharmaceutically acceptable derivatives thereof, wherein $R^{1a}$ is aryl or heteroaryl;

$R^{8a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In one embodiment of Formula VIa, a compound of Formula VIa is a compound wherein $R^{1a}$ is aryl or heteroaryl;

$R^{8a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIa, a compound of Formula VIa is a compound wherein $R^{1a}$ is pyridinyl, wherein pyridinyl is optionally substituted with one or two substituents each selected from $OR^3$;

$R^3$ is difluoroethyl;

$R^{8a}$ is H, methyl, phenyl, $C(O)R^4$;

$R^{9a}$ is H, phenyl, methyl, thienyl, ethyl, furanyl, or butyl, wherein phenyl is optionally substituted with a substituent selected from halogen or methoxy;

$R^4$ is —$NR^6R^7$; and $R^6$ and $R^7$ are independently selected from H, methyl, and ethyl.

In one embodiment, the compound of Formula VIa is:

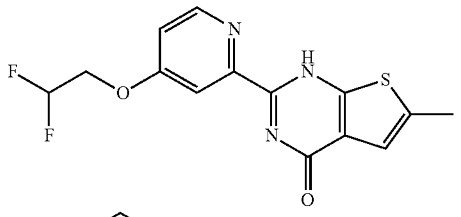

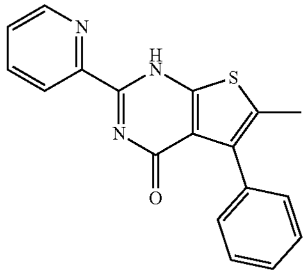

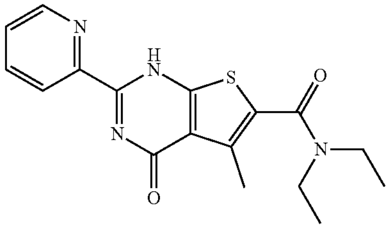

-continued

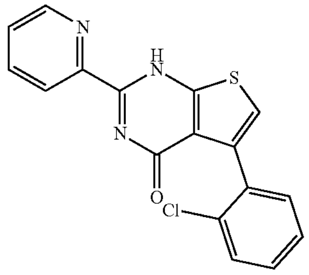

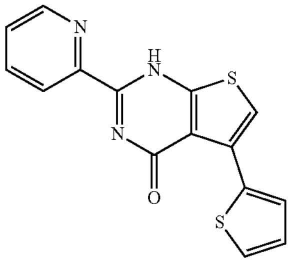

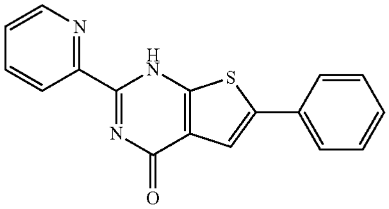

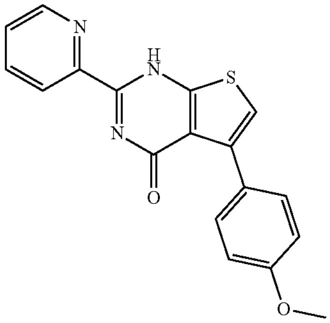

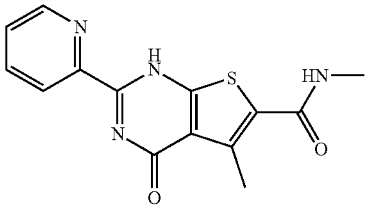

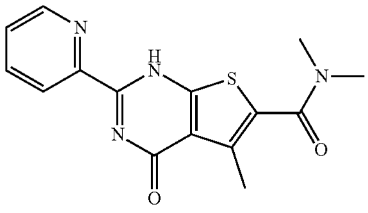

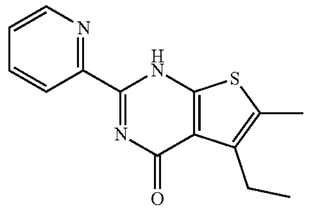

-continued
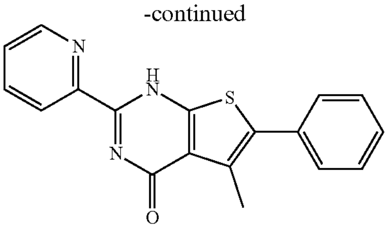
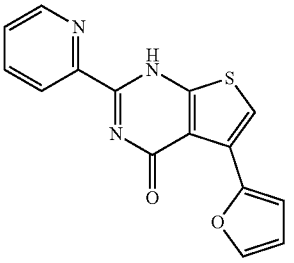
or
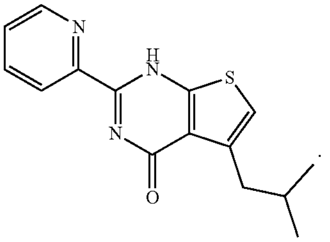 [SMILES: CC(C)Cc1csc2[nH]c(-c3ccccn3)nc(=O)c12]
In one embodiment, the compound of Formula VIa is selected with the proviso that the compound is not
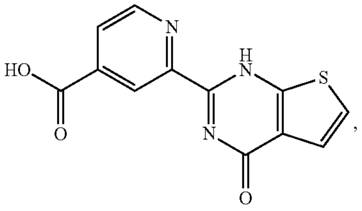
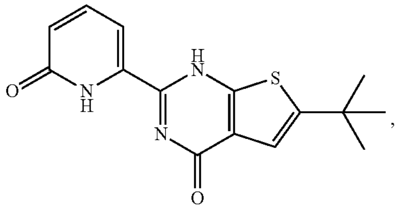
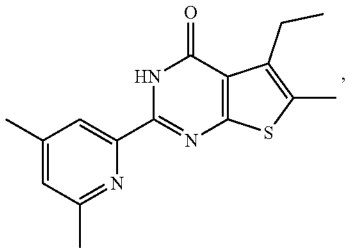
-continued
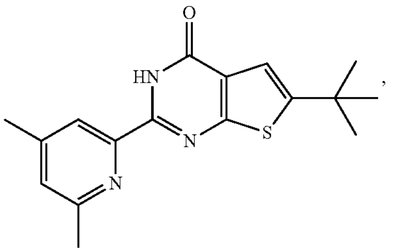
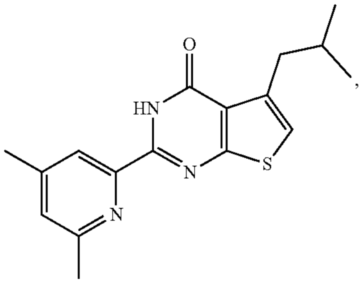
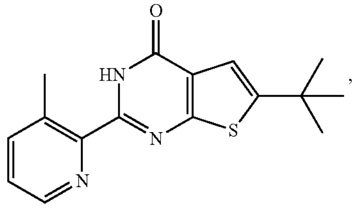
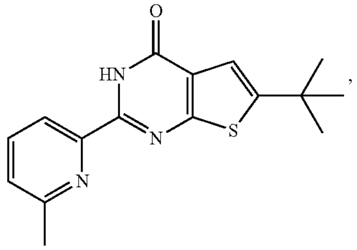
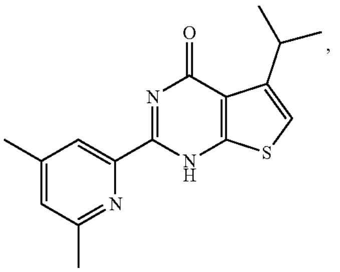
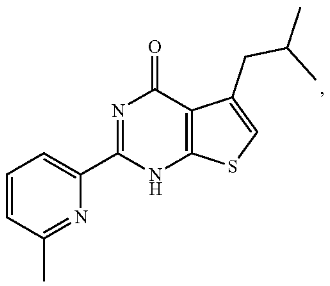

-continued

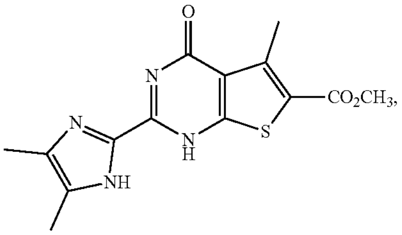

, or

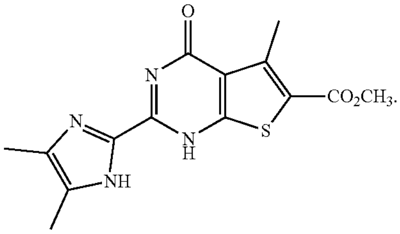

.

In another embodiment, the compound of Formula VI is a compound of Formula VIa1:

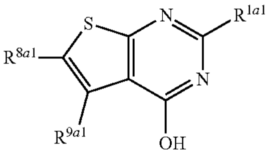

Formula VIa1 or pharmaceutically acceptable derivatives thereof, wherein $R^{1a1}$ is aryl, heteroaryl or $NR^6R^7$;

$R^{8a1}$ is H or alkyl;

$R^{9a1}$ is H, alkyl, alkenyl, carbocyclic, halo, pseudohalo, trifluoromethyl, cyano, or $C(O)NR^6R^7$; and $R^6$ and $R^7$ are independently selected from H, methyl, and ethyl.

In another embodiment of Formula VIa1, a compound of Formula VIa1 is a compound wherein $R^{1a1}$ is aryl, heteroaryl or $NR^6R^7$;

$R^{1a1}$ is H, aryl, or alkyl;

$R^{1a1}$ is H, alkyl, alkenyl, halo or pseudohalo; and $R^6$ and $R^7$ are independently selected from H, methyl, and ethyl.

In another embodiment of Formula VIa1, a compound of Formula VIa1 is a compound wherein $R^{1a1}$ is aryl, heteroaryl or $NR^6R^7$;

$R^{8a1}$ is H or alkyl;

$R^{9a1}$ is alkyl, alkenyl, halo or pseudohalo, wherein the alkyl group is not $CH_3$; and $R^6$ and $R^7$ are independently selected from H, methyl, and ethyl.

In another embodiment of Formula VIa1, a compound of Formula VIa1 is a compound wherein $R^{1a1}$ is pyridinyl or $NH_2$, $R^{1a1}$ is H or methyl;

$R^{9a1}$ is H or methyl.

In one embodiment, the compound of Formula VIa1 is:

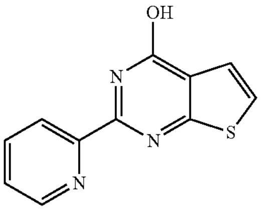

or

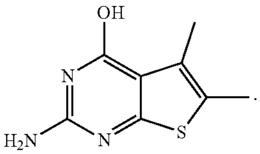

.

In one embodiment, the compound of Formula VIa1 is:

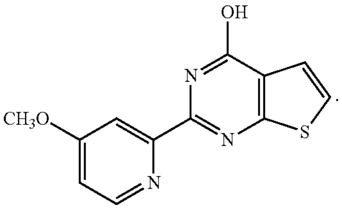

.

In another embodiment of Formula VIa1, a compound of Formula VIa1 is a compound wherein $R^{1a1}$ is pyridinyl, $R^{1a1}$ is H or methyl;

$R^{9a1}$ is fluoro, bromo, chloro or iodo.

In one embodiment, the compound of Formula VIa1 is:

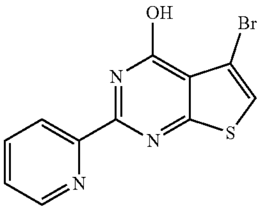 [SMILES: Oc1nc(-c2ccccn2)nc2scc(Br)c12]

In one embodiment, the compound of Formula VIa1 is:

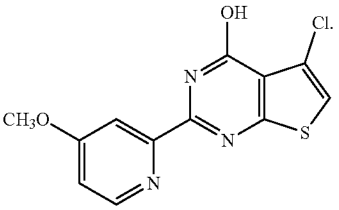

In another embodiment of Formula VIa1, a compound of Formula VIa1 is a compound wherein $R^{1a1}$ is 2-pyridinyl.

In another embodiment of Formula VIa1, a compound of Formula VIa1 is a compound wherein $R^{1a1}$ is methoxy-pyridinyl.

In another embodiment of Formula VIa1, a compound of Formula VIa1 is a compound wherein $R^{1a1}$ is 2-pyridyl;

$R^{8a1}$ is H or Ph;

$R^{9a1}$ is carbocyclic, halo, trifluoromethyl, cyano, or $C(O)NR^6R^7$;

$R^6$ is H or alkyl;

and $R^7$ is alkyl.

In another embodiment of Formula VIa1, a compound of Formula VIa1 is a compound wherein $R^{1a1}$ is 2-pyridyl;

$R^{8a1}$ is H or methyl;

$R^{9a1}$ is carbocyclic, halo, trifluoromethyl, cyano, or C(O)$NR^6R^7$;

$R^6$ is H or alkyl;

and $R^7$ is alkyl.

In another embodiment, the compound of Formula VI is a compound of Formula VIb:

Formula VIb

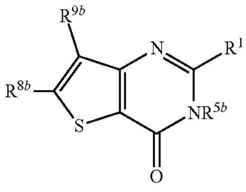

or pharmaceutically acceptable derivatives thereof, wherein $R^{1b}$ is alkyl, aryl, heteroaryl, $S(O)_pR^4$, $NR^5C(O)R^4$, or $NR^6R^7$;

$R^{8b}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$; or $R^{8b}$ and $R^{9b}$ are combined to form a cyclic structure including the carbon atoms to which they are attached in the five-membered ring;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{5b}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb, a compound of Formula VIb is a compound wherein $R^{1b}$ is pyridinyl, $S(O)_pR^4$,

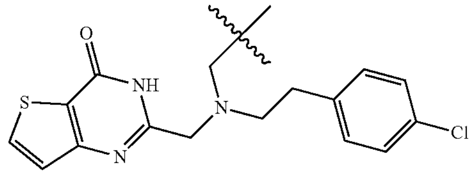

or

-continued

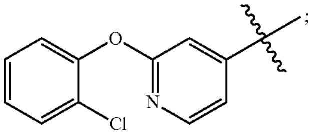

;

$R^{8b}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$; wherein $R^{8b}$ and $R^{9b}$ are combined to form a cyclic structure including the carbon atoms to which they are attached in the five-membered ring;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is depicted below

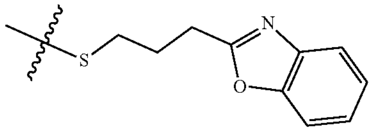

;

$R^{5b}$ is hydrogen or ethyl;

p is 0.

In one embodiment, the compound of Formula VIb is:

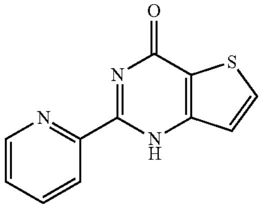

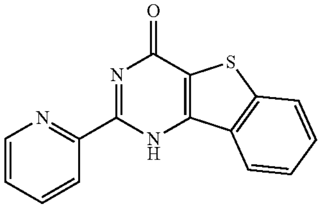

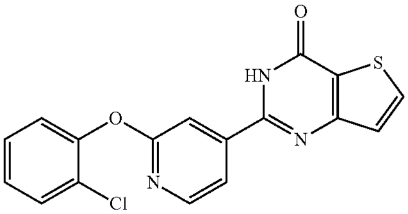

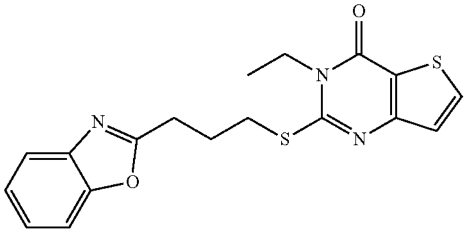

or

-continued
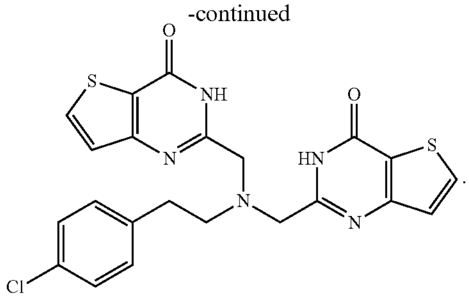
In another embodiment of Formula VIb, a compound of Formula VIb is a compound wherein
$R^{1b}$ is pyridyl, N-methyl-imidazolyl or $NH_2$;
$R^{8b}$ is phenyl, pyridyl, $C(O)R^4$,
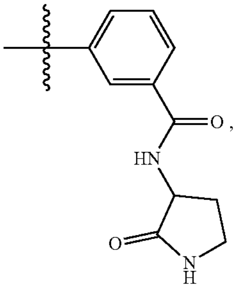
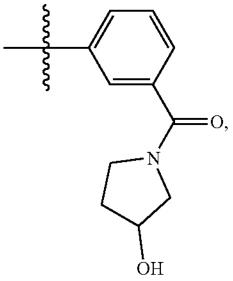
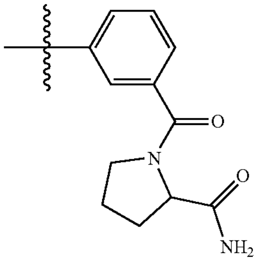
,
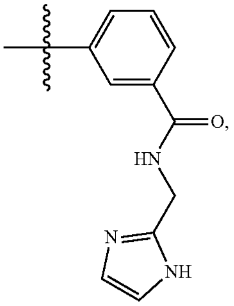
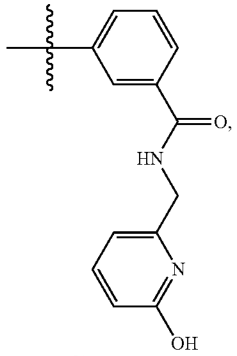
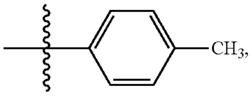
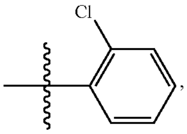
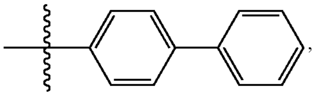
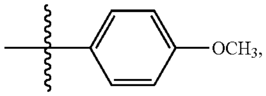
or
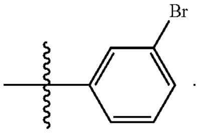
$R^{9b}$ is H, Br, phenyl, $CH_3$,
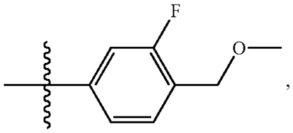
,
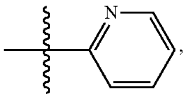
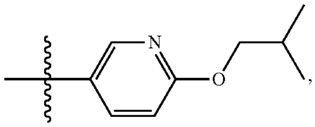
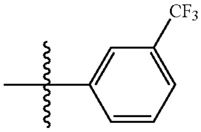
,
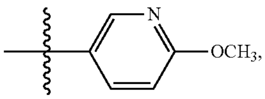
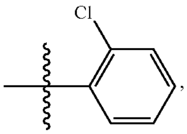
or
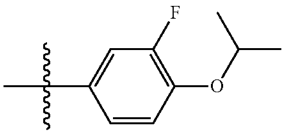
;
$R^4$ is
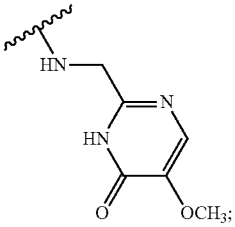
and
$R^{5b}$ is hydrogen.
In one embodiment, the compound of Formula VIb is:
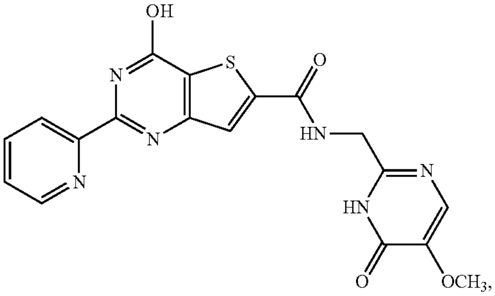
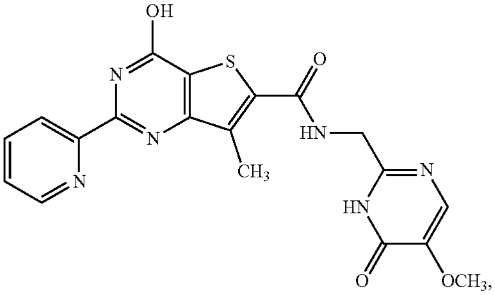

-continued
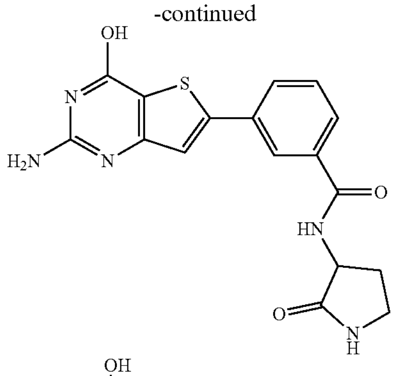
,
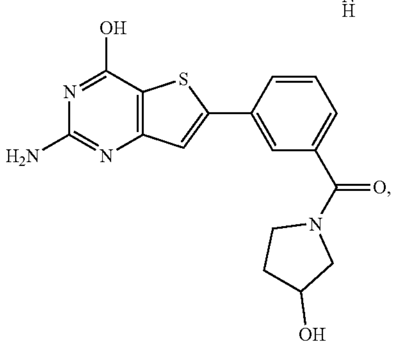
,
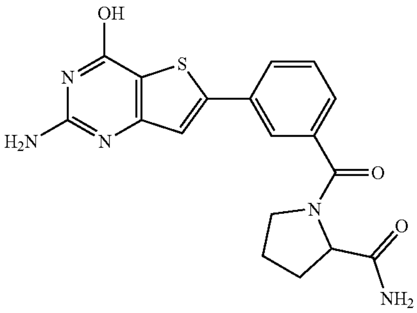
,
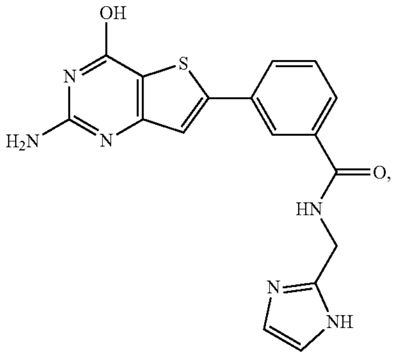
,
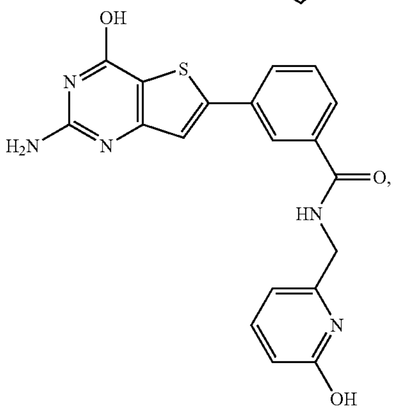
,
-continued
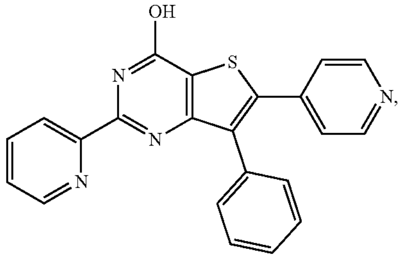
,
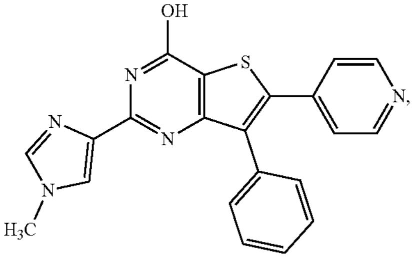
,
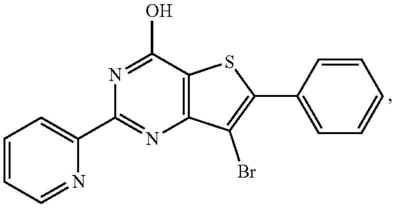
,
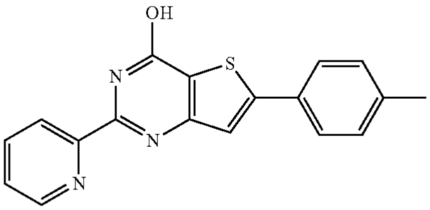
,
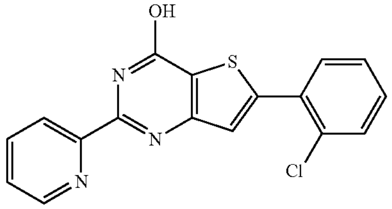
,
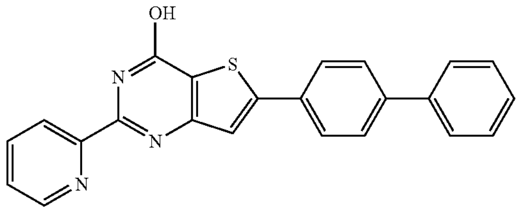
,
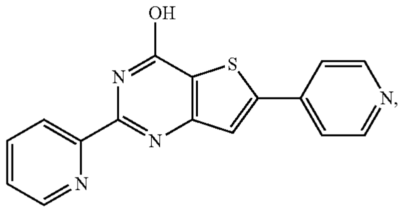
, -continued
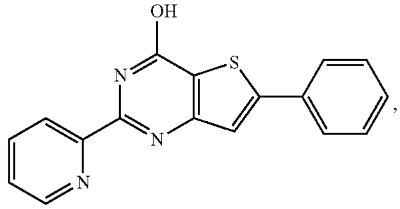
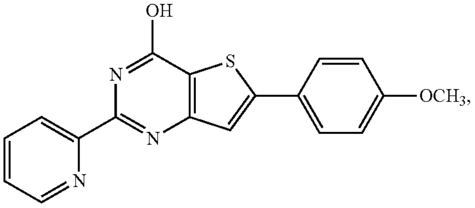
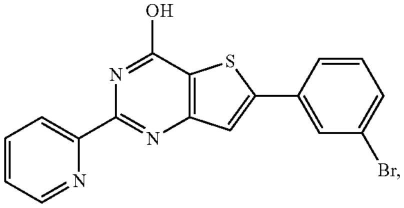
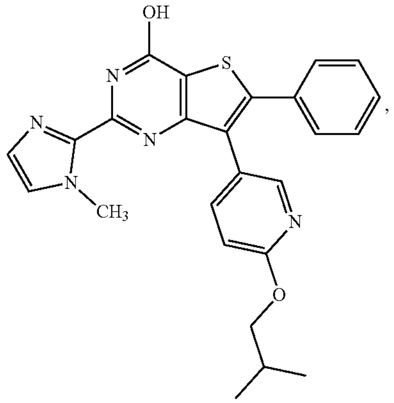
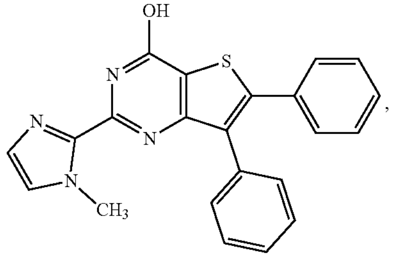
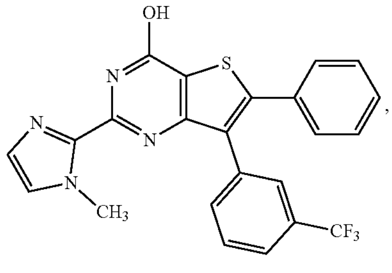
-continued
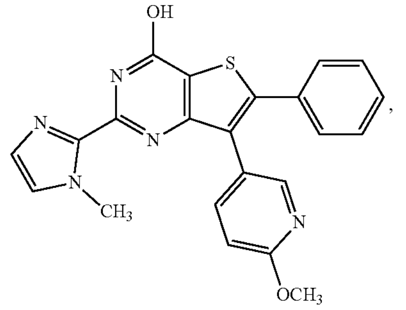
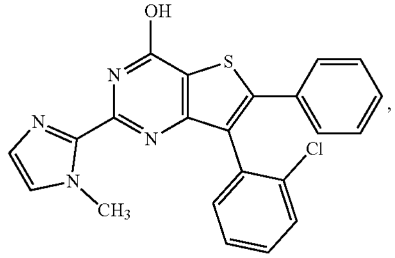
or
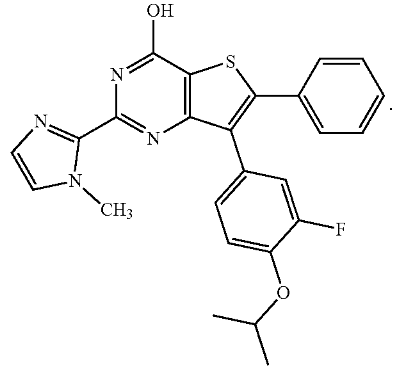 [SMILES: CC(C)Oc1ccc(-c2c(-c3ccccc3)sc3c(O)nc(-c4nccn4C)nc23)cc1F]
In one embodiment, the compound of Formula VIb is:
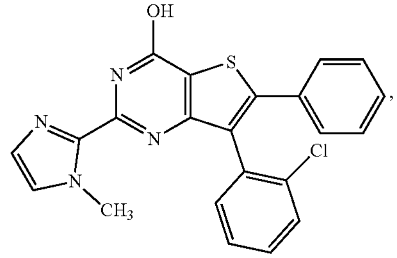
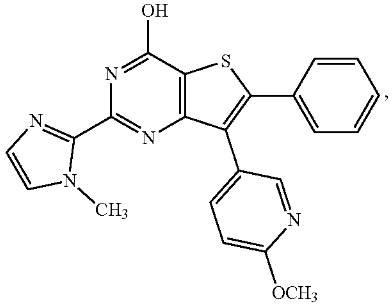
or -continued

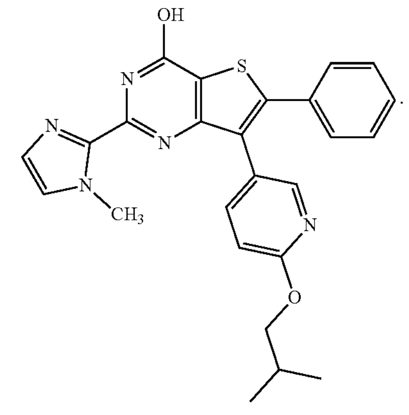

-continued

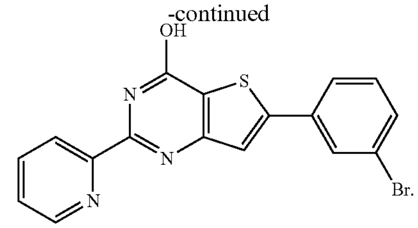

In one embodiment, the compound of Formula VIb is selected with the proviso that the compound is not

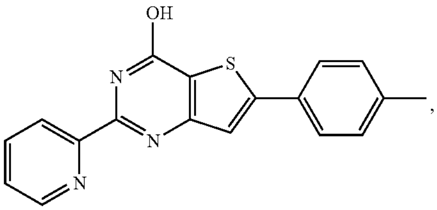
,

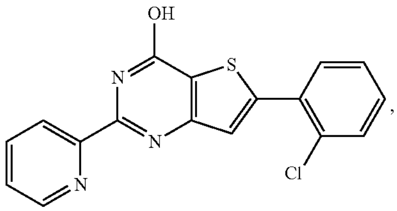
,

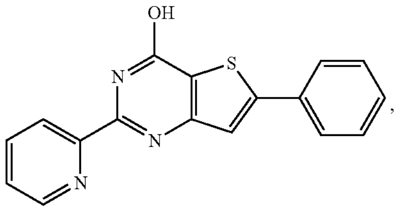
,

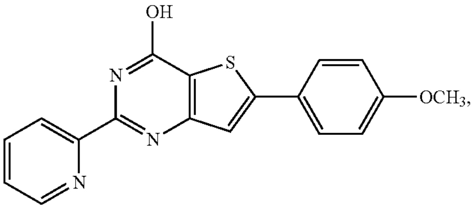

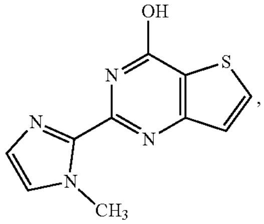
, or

In another embodiment, the compound of Formula VIb is a compound of Formula VIb 1:

Formula VIb1

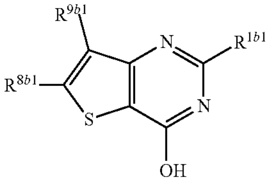

or pharmaceutically acceptable derivatives thereof, wherein $R^{1b1}$ is alkyl, aryl, heteroaryl, or $NR^6R^7$;

$R^{8b1}$ is H or alkyl;

$R^{9b1}$ is aryl, heteroaryl, heterocyclyl, halo, pseudohalo, $C(O)R^4$, or $S(O)_pR^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, $R^{1b1}$ is aryl, heteroaryl, or $NR^6R^7$;

$R^{8b1}$ is $C(O)R^4$;

$R^{9b1}$ is aryl, heteroaryl, heterocyclyl, halo, pseudohalo, $C(O)R^4$, or $S(O)_pR^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, a compound of Formula VIb1 is a compound wherein $R^{1b1}$ is pyridyl;

$R^{8b1}$ is H or alkyl;

$R^{9b1}$ is substituted phenyl, heteroaryl, heterocyclyl, fluoro, chloro, iodo, $C(O)R^4$, or $S(O)_pR^4$, wherein the heteroaryl group is not a substituted pyrazole;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, a compound of Formula VIb1 is a compound wherein $R^{1b1}$ is pyridinyl or $NH_2$;

$R^{8b1}$ is H;

$R^{9b1}$ is aryl, heteroaryl, halo, heterocyclyl or $C(O)R^4$;

$R^4$ is —$NR^6R^7$; and $R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula VIb1, a compound of Formula VIb1 is a compound wherein $R^{1b1}$ is 2-pyridyl;

$R^{8b1}$ is H or methyl;

$R^{9b1}$ is substituted phenyl, heteroaryl, heterocyclyl, C(O)$NR^6R^7$, wherein the heteroaryl group is not a substituted pyrazole; and $R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, a compound of Formula VIb1 is a compound wherein $R^{1b1}$ is 2-pyridyl;

$R^{8b1}$ is H;

$R^{9b1}$ is substituted phenyl, heteroaryl, heterocyclyl, C(O)$NR^6R^7$, wherein the heteroaryl group is not a substituted pyrazole; and $R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, $R^{1b1}$ is alkyl, aryl, heteroaryl, or $NR^6R^7$;

$R^{8b1}$ is H or alkyl;

$R^{9b1}$ is alkyl or cycloalkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, $R^{1b1}$ is aryl, heteroaryl, or $NR^6R^7$;

$R^{8b1}$ is $C(O)R^4$;

$R^{9b1}$ is alkyl or cycloalkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, a compound of Formula VIb1 is a compound wherein $R^{1b1}$ is pyridyl;

$R^{8b1}$ is H or alkyl;

$R^{9b1}$ is alkyl or cycloalkyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIb1, a compound of Formula VIb1 is a compound wherein $R^{1b1}$ is pyridinyl or $NH_2$;

$R^{8b1}$ is H;

$R^{9b1}$ is alkyl or cycloalkyl;

$R^4$ is —$NR^6R^7$; and $R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached.

In another embodiment of Formula VIb1, a compound of Formula VIb1 is a compound wherein $R^{1b1}$ is 2-pyridyl;

$R^{8b1}$ is H or methyl;

$R^{9b1}$ is substituted phenyl, heteroaryl, heterocyclyl, C(O)$NR^6R^7$, wherein the heteroaryl group is not a substituted pyrazole; and $R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, a compound of Formula VIb1 is a compound wherein $R^{1b1}$ is 2-pyridyl;

$R^{8b1}$ is H;

$R^{9b1}$ is alkyl or cycloalkyl; and $R^6$ and $R^7$ are independently selected from hydrogen, alkyl, alkenyl, alkynyl, aryl, heteroaryl, heterocyclyl, cycloalkyl, heterocycloalkyl, or $R^6$ and $R^7$ are combined to form a cyclic structure including the nitrogen atom to which they are both attached.

In another embodiment of Formula VIb1, a compound of Formula VIb1 is a compound wherein
$R^{1b1}$ is $NH_2$;
$R^{8b1}$ is H;
$R^{9b1}$ is Br,
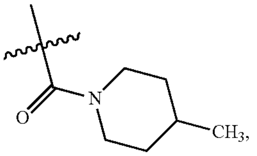
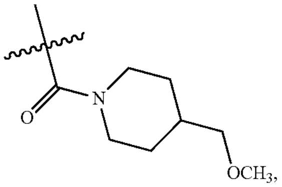
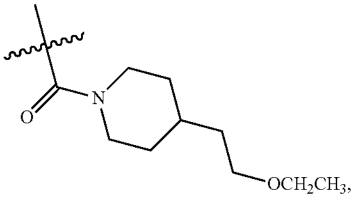
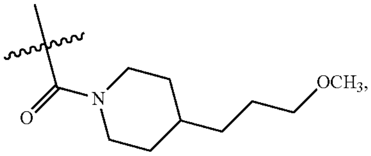
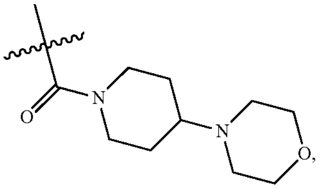
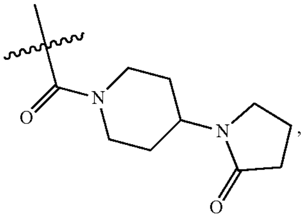
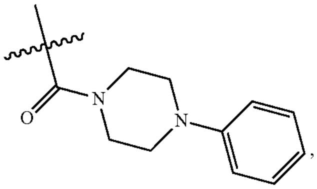
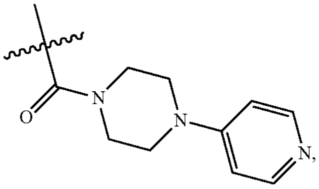
-continued
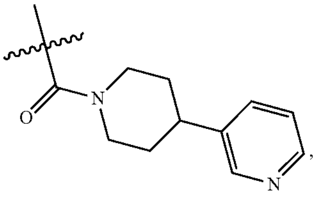
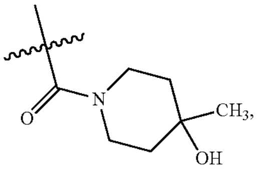
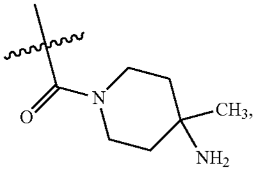
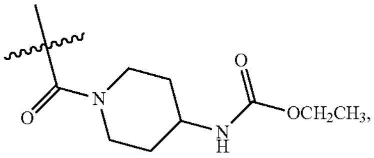
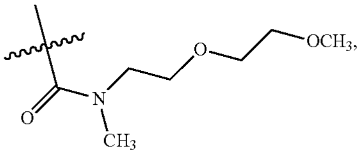
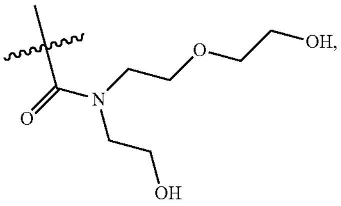
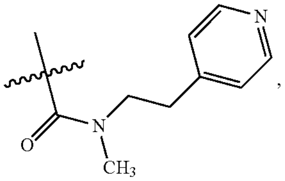
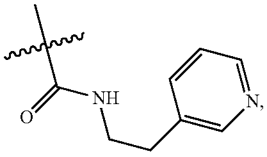
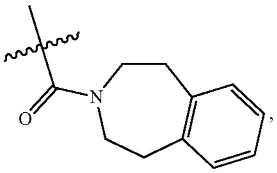
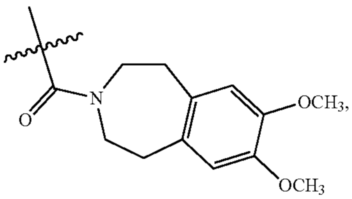
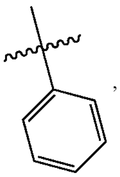
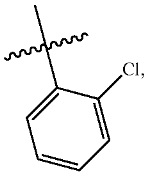
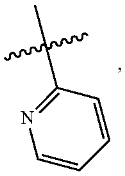
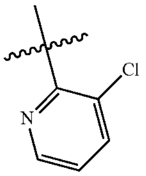
or -continued
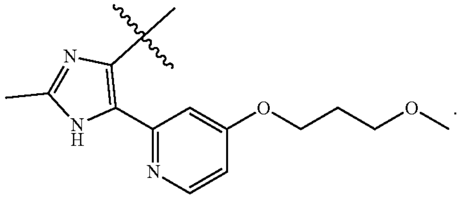
In another embodiment of Formula VIb1, a compound of Formula VIb1 is a compound wherein
$R^{1b1}$ is pyridinyl;
$R^{8b1}$ is H;
$R^{9b1}$ is Br, 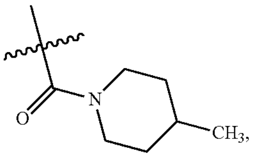
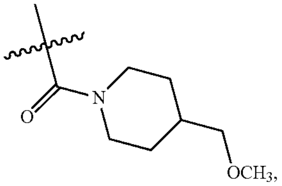
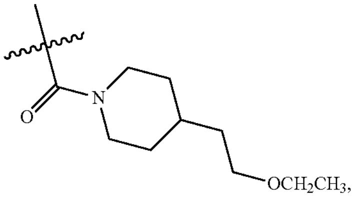
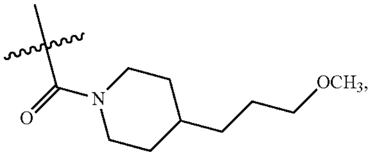
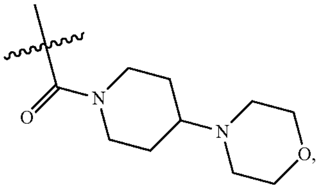
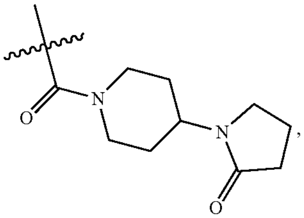
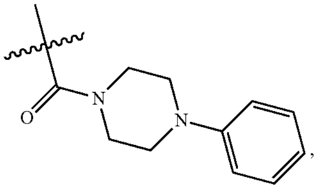
-continued
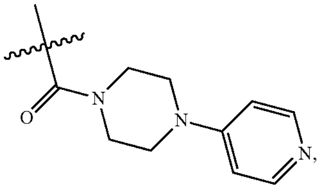
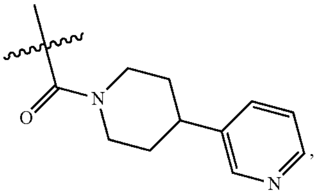
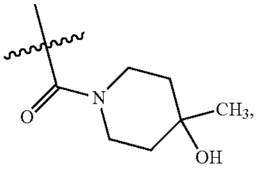
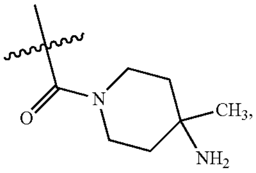
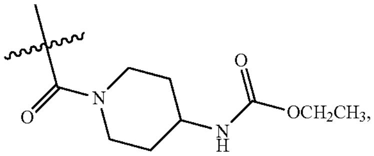
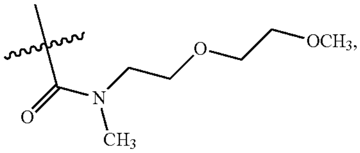
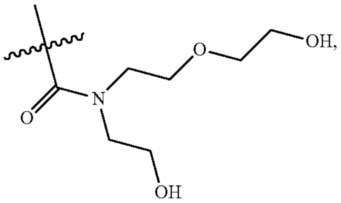
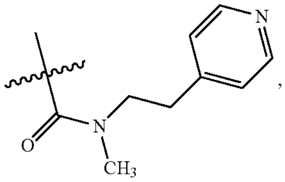
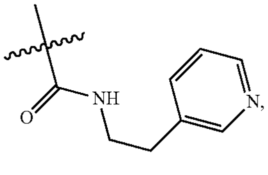
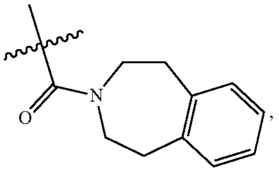
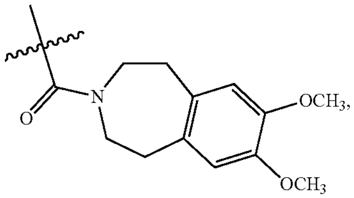
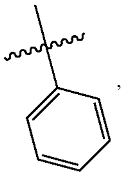

-continued
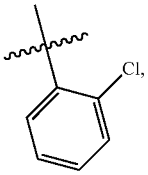
,
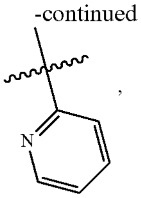
,
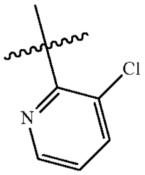
or
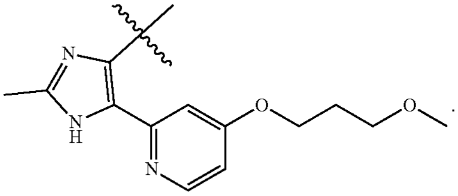
In another embodiment of Formula VIb1, a compound of Formula VIb1 is a compound wherein $R^{1b1}$ is 2-pyridyl.
In one embodiment, the compound of Formula VIb1 is:
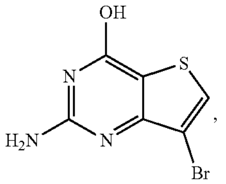
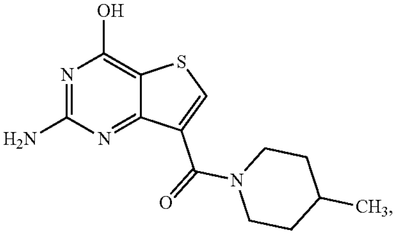
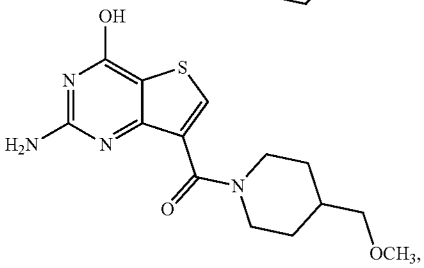
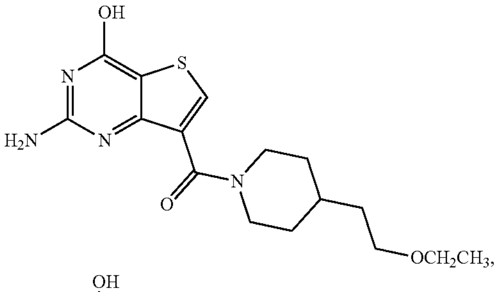
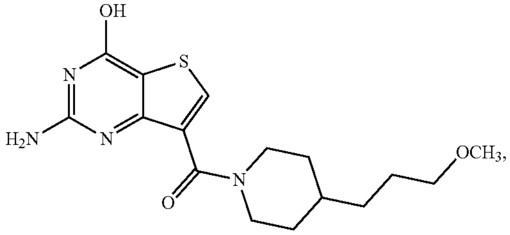
-continued
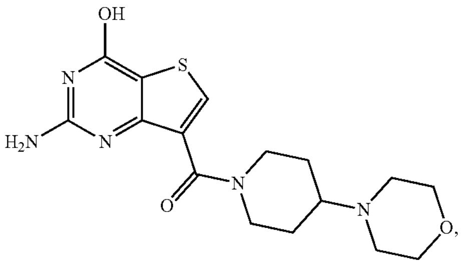
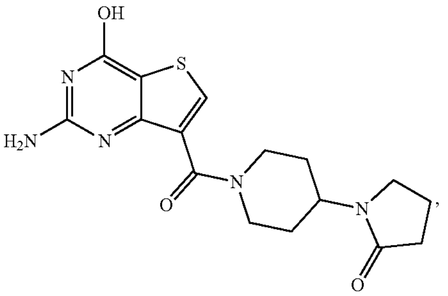
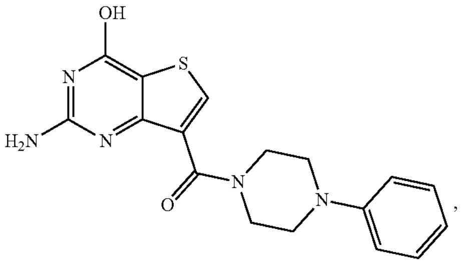
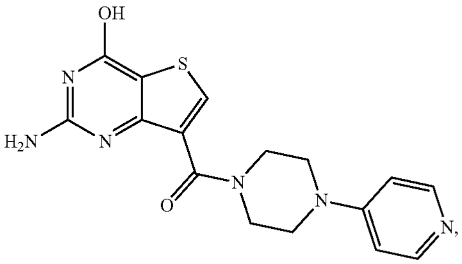
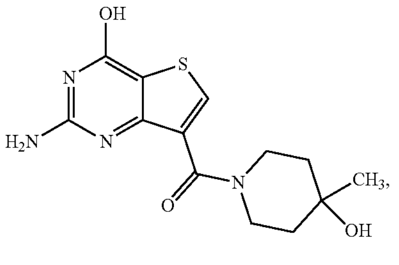
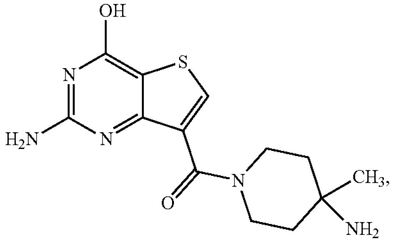

-continued
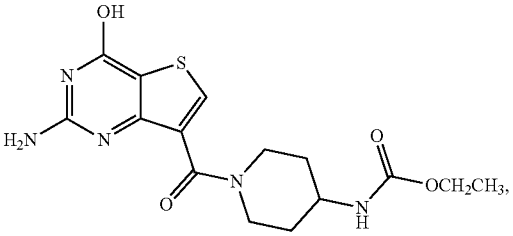
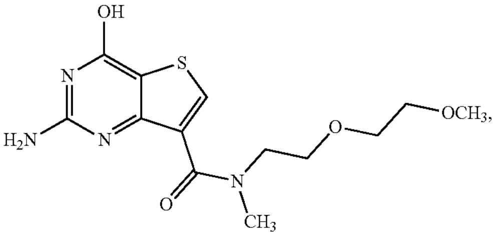
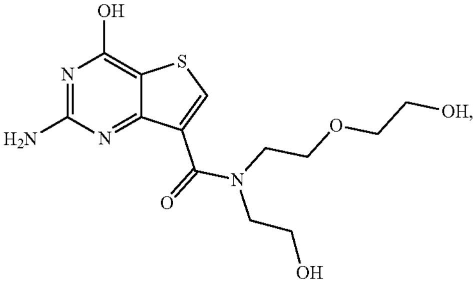
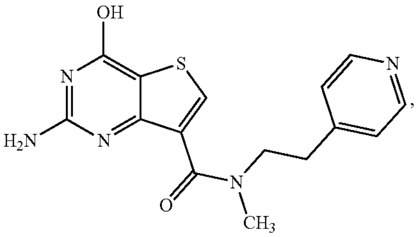
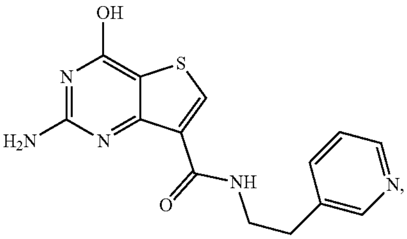
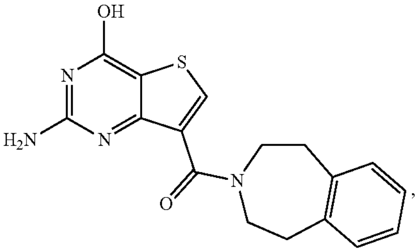
-continued
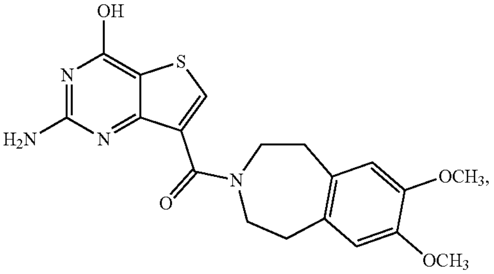
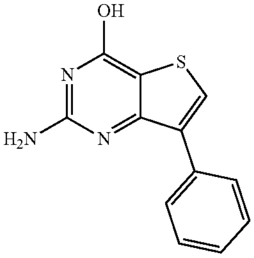
or
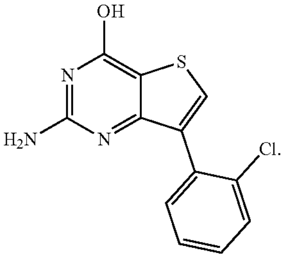
In one embodiment, the compound of Formula VIb1 is:
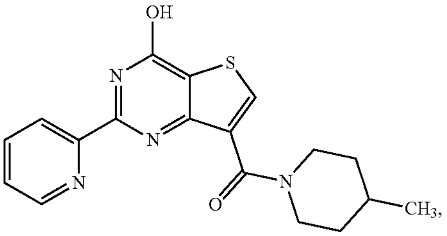
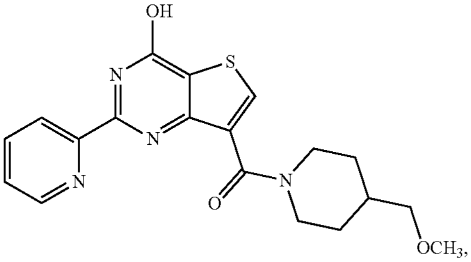
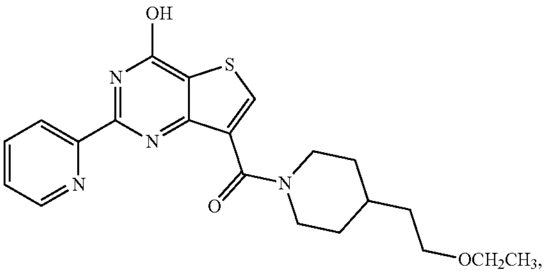

-continued
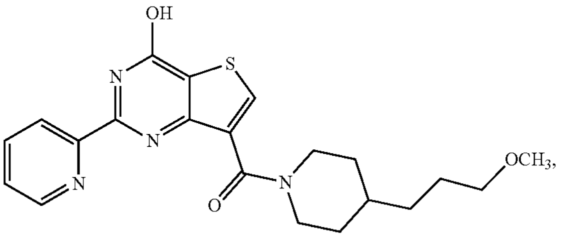
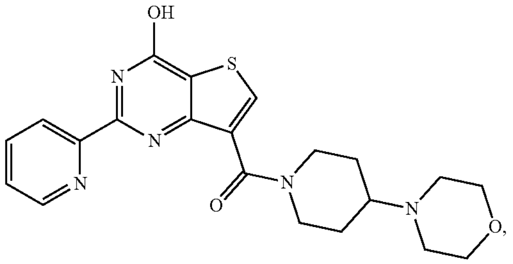
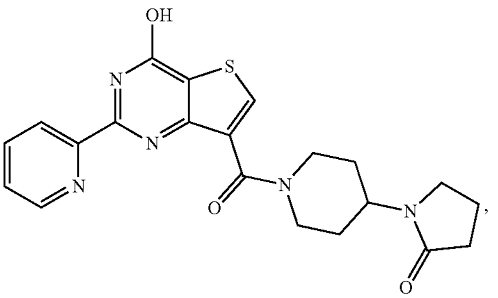
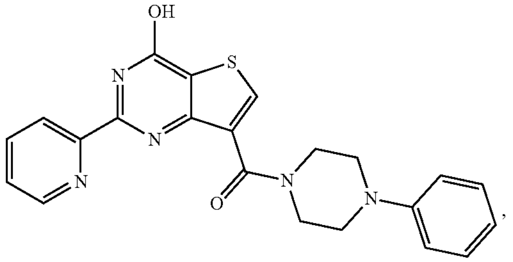
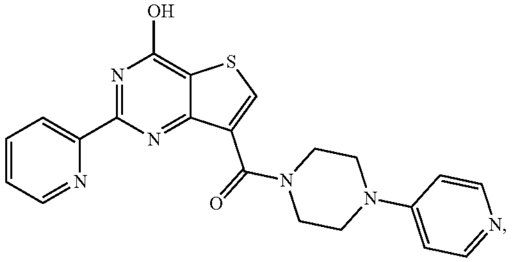
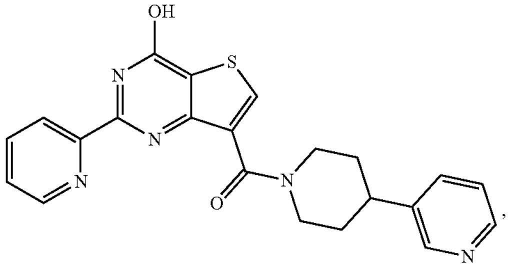
-continued
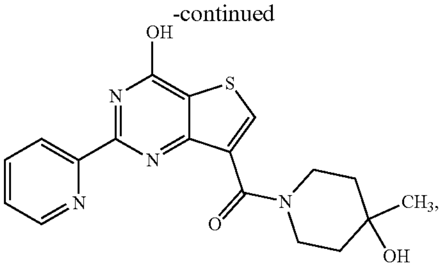
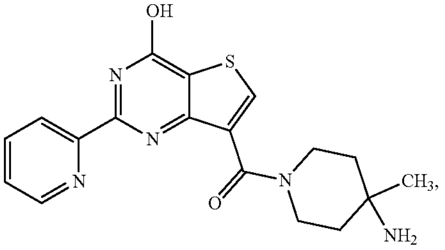
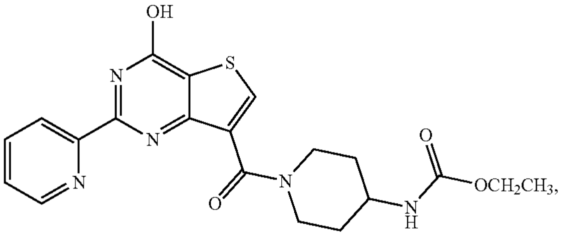
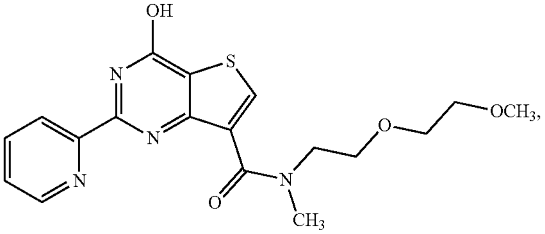
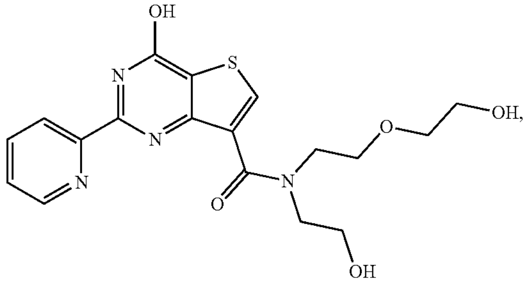
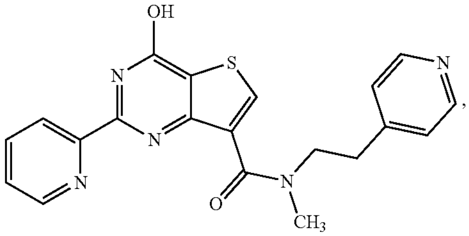
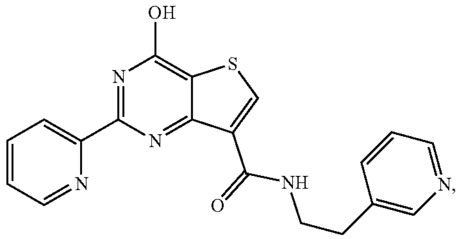

-continued
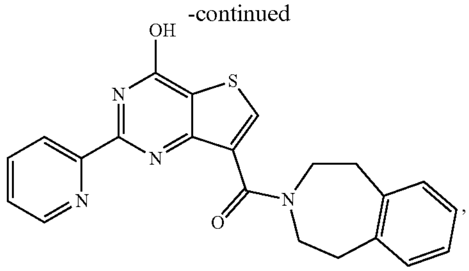
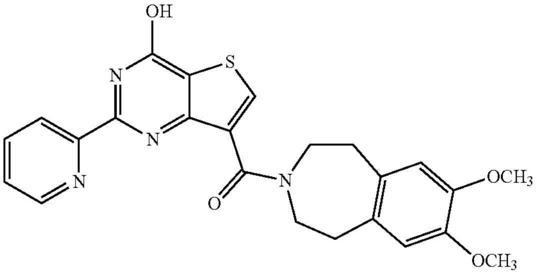
or
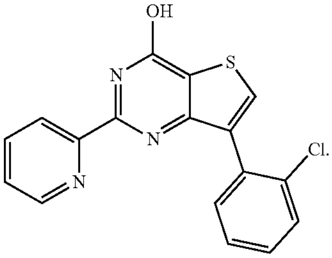
In one embodiment, the compound of Formula VIb1 is:
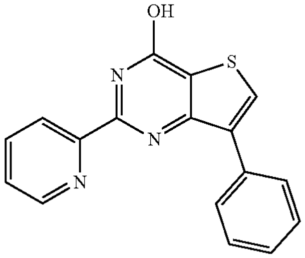
, or
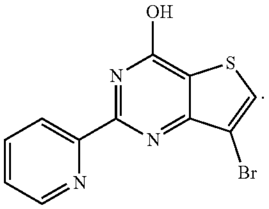
In another embodiment of Formula VIb1, a compound of Formula VIb1 is a compound wherein
$R^{1b1}$ is pyridinyl;
$R^{8b1}$ is H;
$R^{9b1}$ is
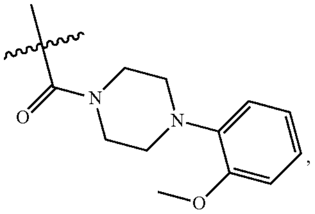
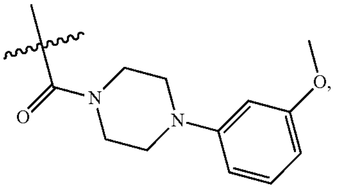
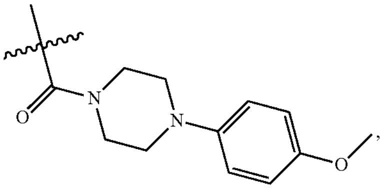
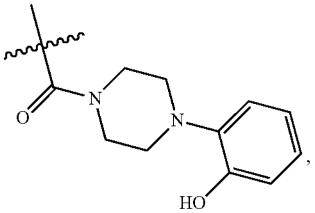
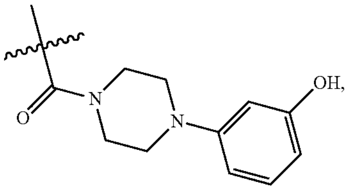
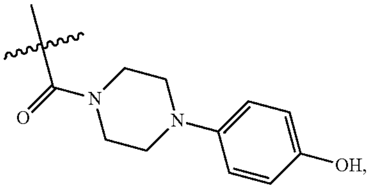
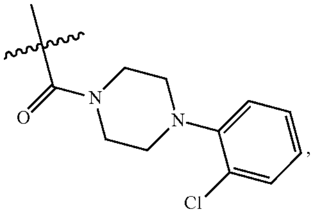
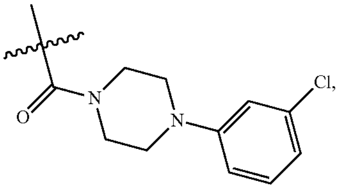

-continued
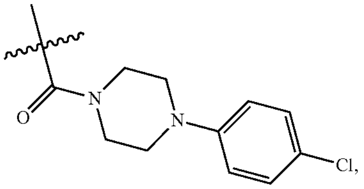
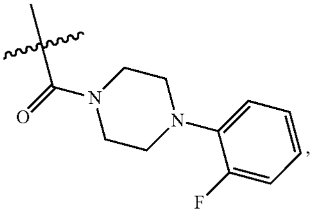
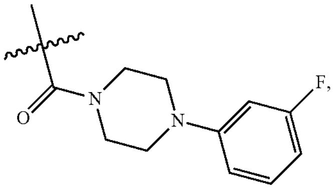
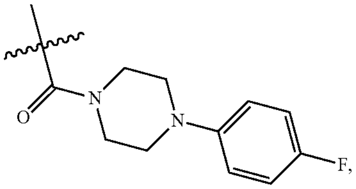
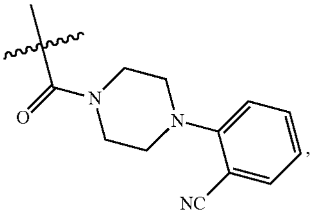
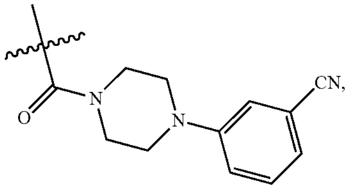
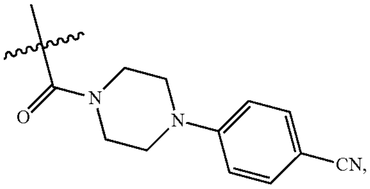
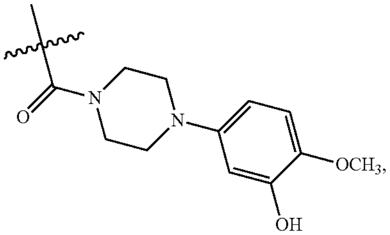
-continued
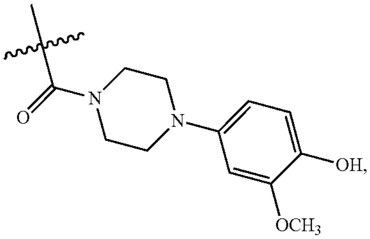
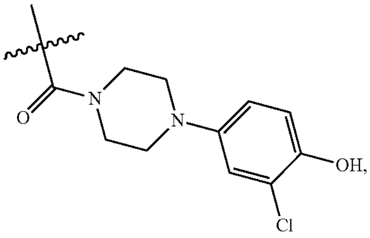
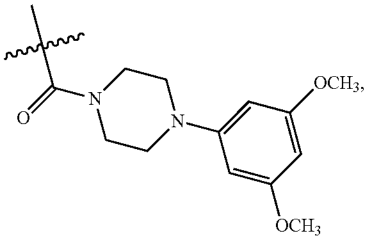
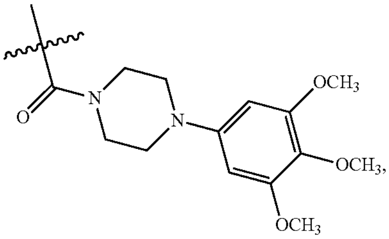
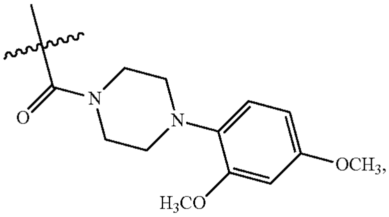
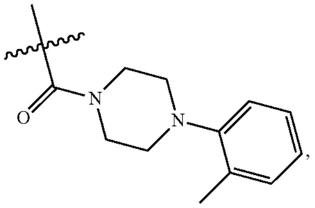
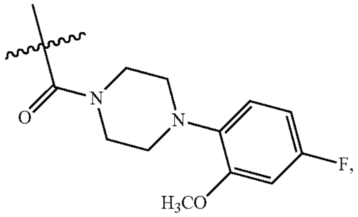

-continued
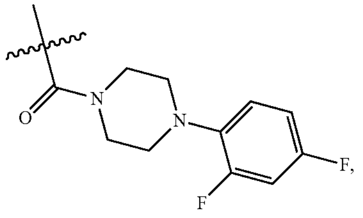
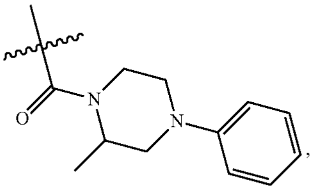
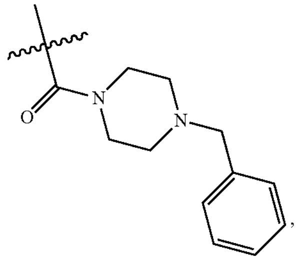
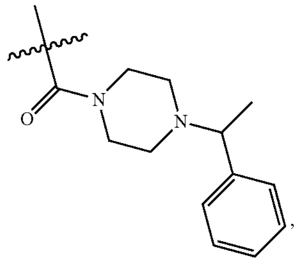
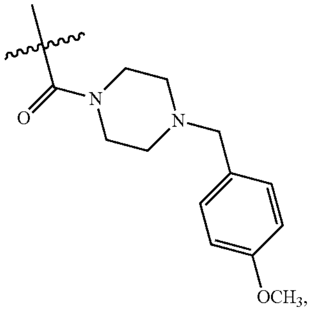
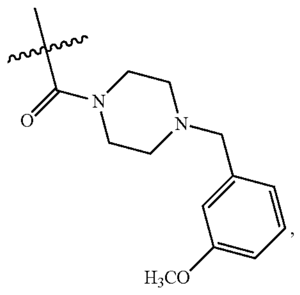
-continued
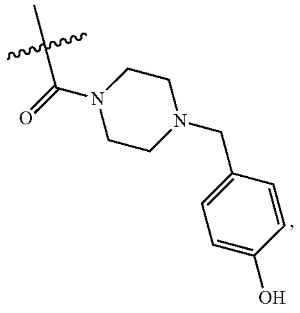
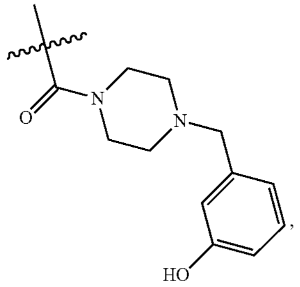
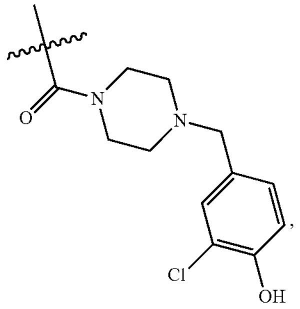
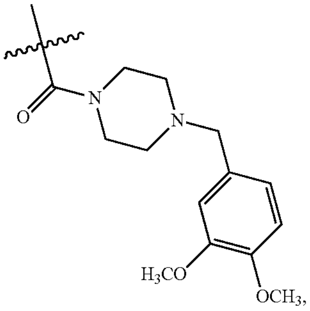
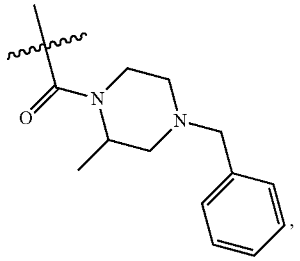
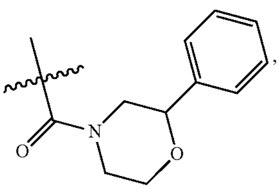
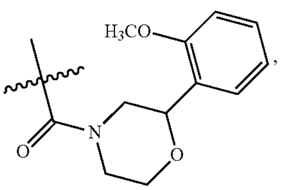

-continued
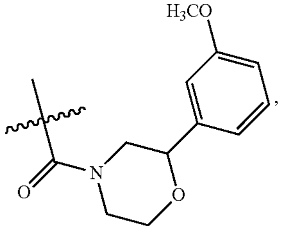,
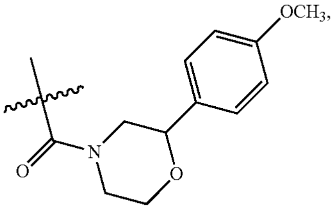,
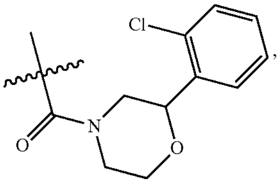, 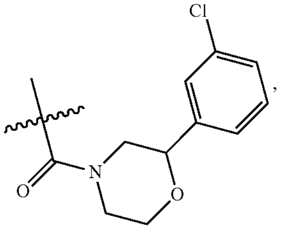,
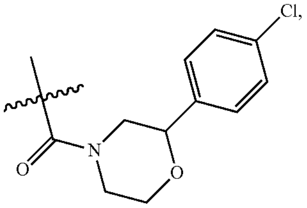,
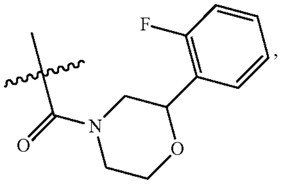, 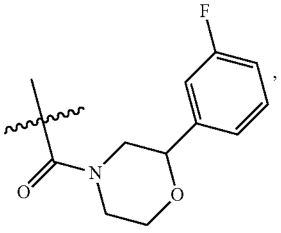,
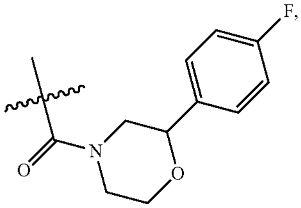,
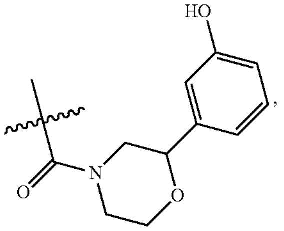, 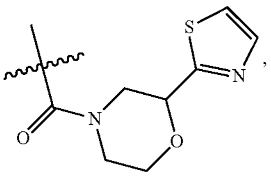,
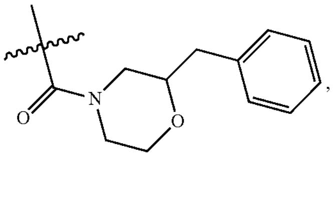,
-continued
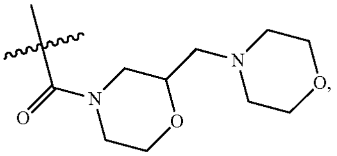,
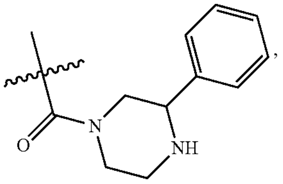, 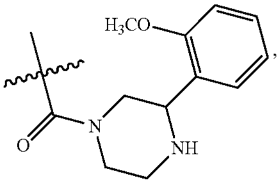,
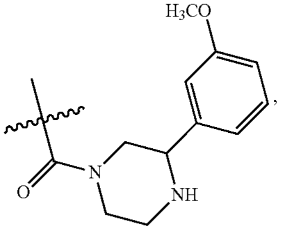,
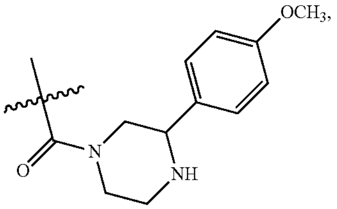,
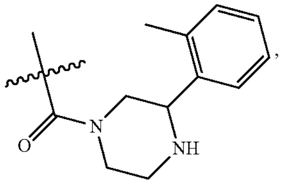, 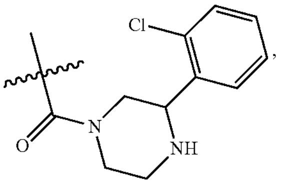,
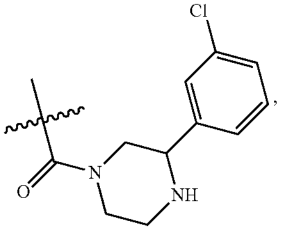,
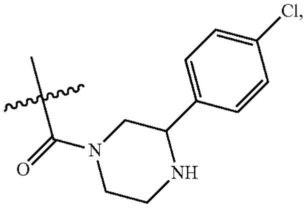,
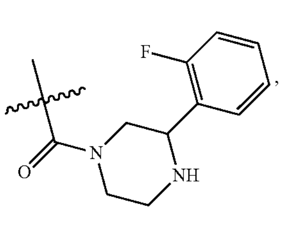, 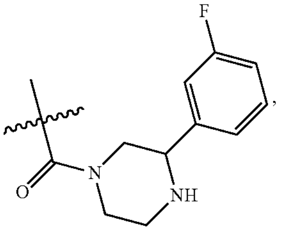, -continued
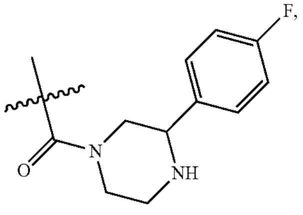
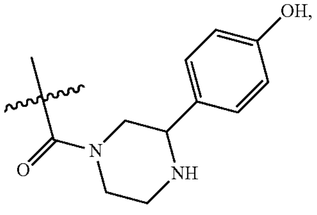
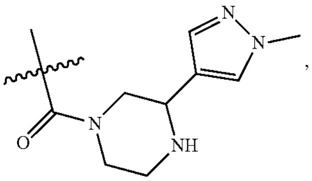
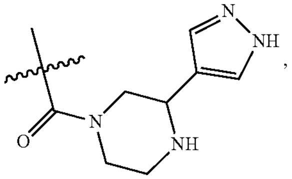
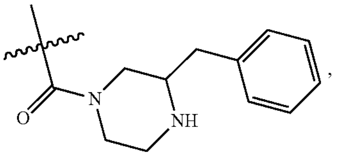
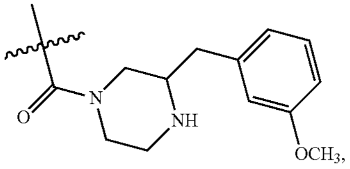
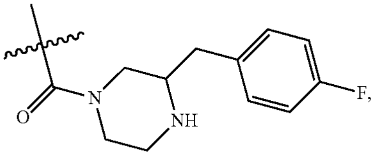
or
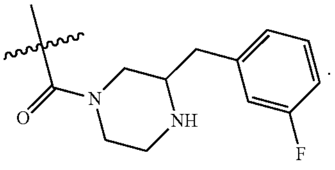
In another embodiment of Formula VIb1, a compound of Formula VIb1 is a compound wherein
$R^{1b1}$ is pyridinyl;
$R^{8b1}$ is H;
$R^{9b1}$ is
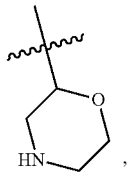
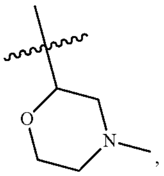
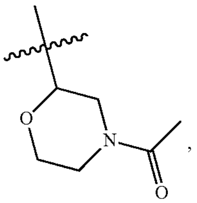
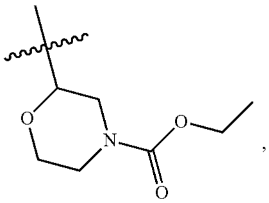
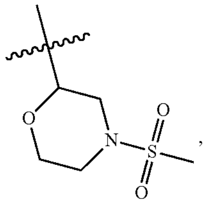
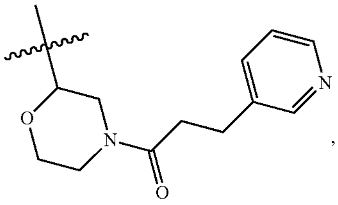
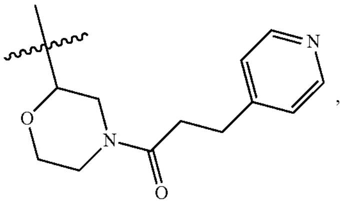
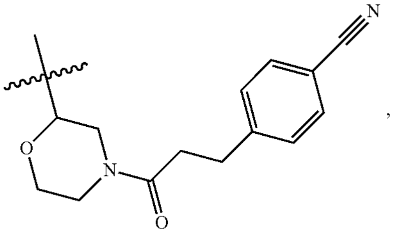
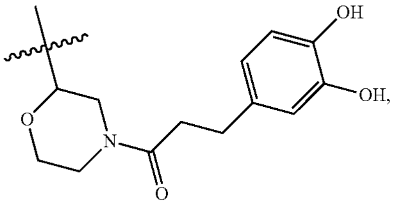
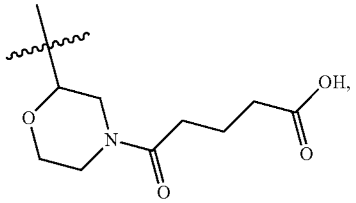
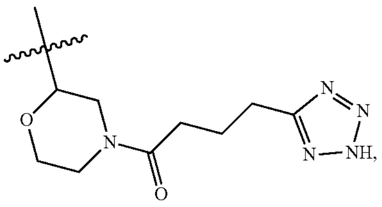

-continued
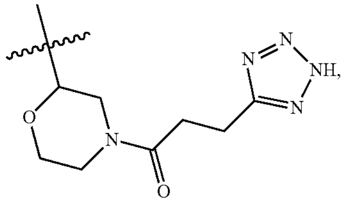
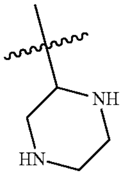
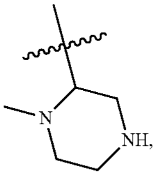
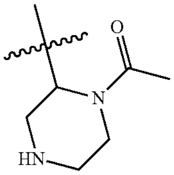
,
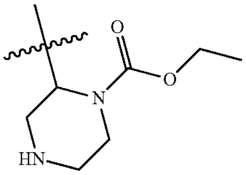
,
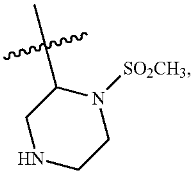
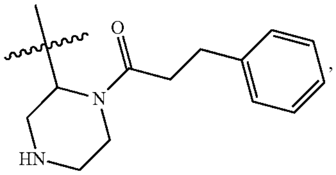
,
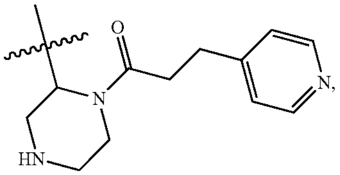
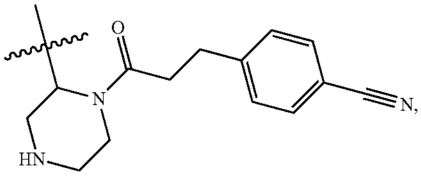
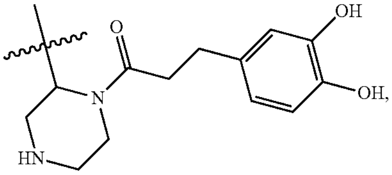
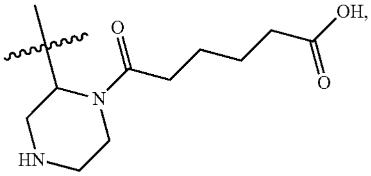
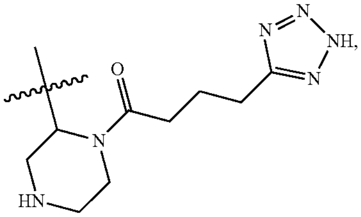
-continued
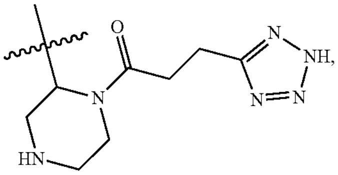
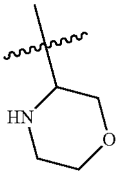
,
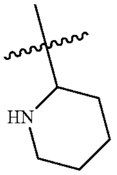
,
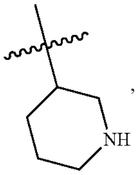
,
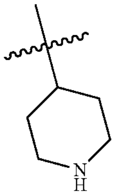
,
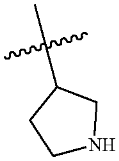
or
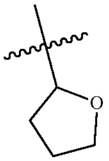
.
In another embodiment of Formula VIb1, a compound of Formula VIb1 is a compound wherein
$R^{1b1}$ is pyridinyl;
$R^{8b1}$ is H, methyl, —COOH or —$COOCH_3$;
$R^{9b1}$ is selected from the group consisting of: H, methyl, cyclobutyl, —$CO_2CH_3$, piperidin-4-ylmethyl, piperidin-3-ylmethyl, 2-chlorophenyl,
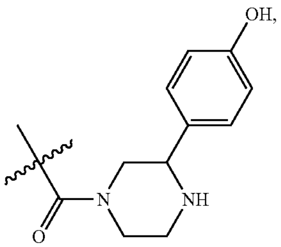
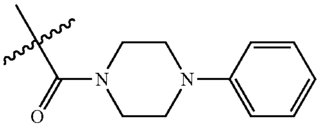
,
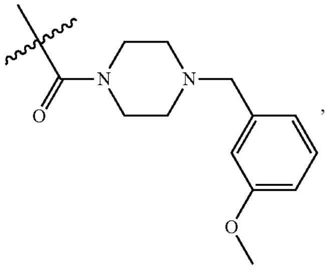
,
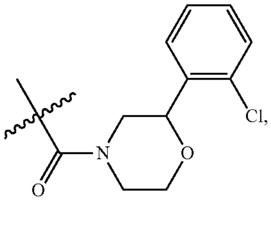

-continued
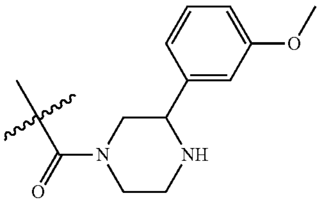,
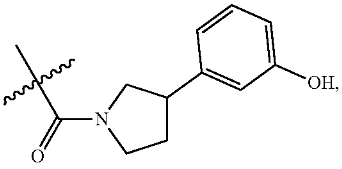,
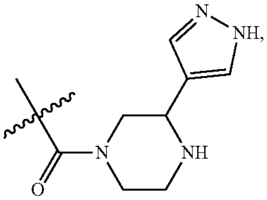,
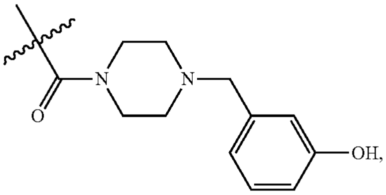,
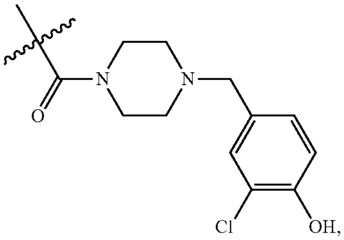,
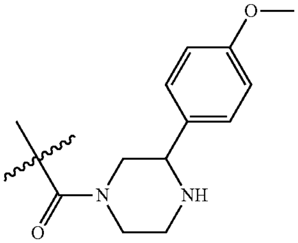,
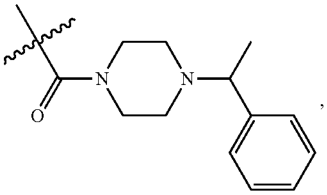,
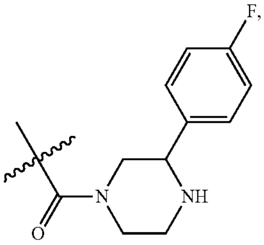
-continued
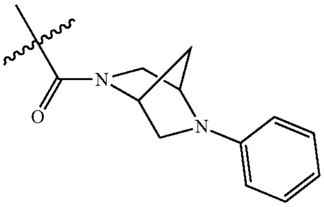,
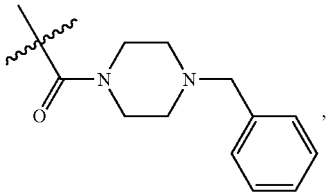,
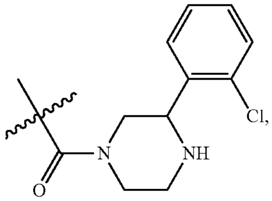,
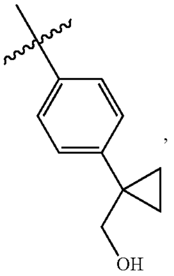,
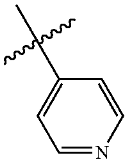,
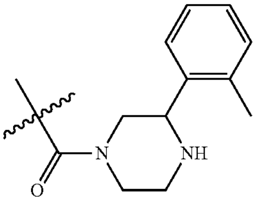,
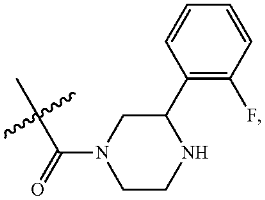,
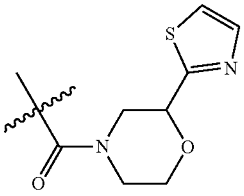,
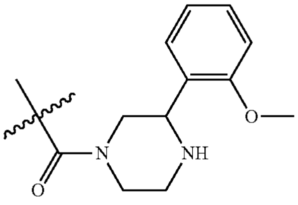, -continued
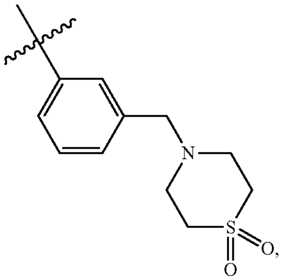
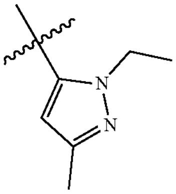
,
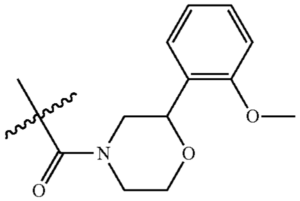
,
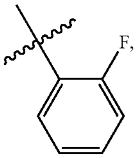
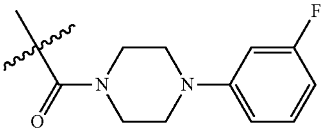
,
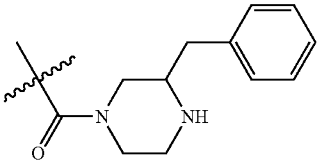
,
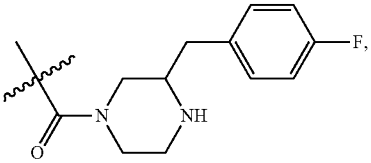
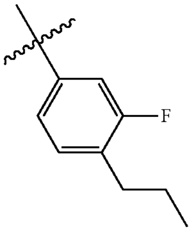
,
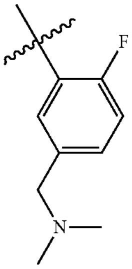
,
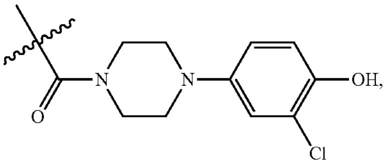
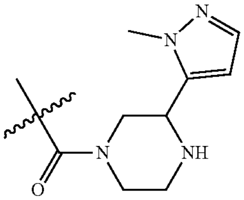
,
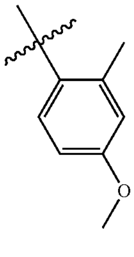
-continued
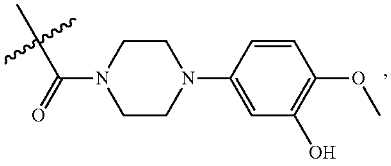
,
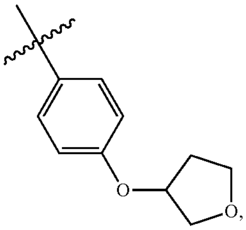
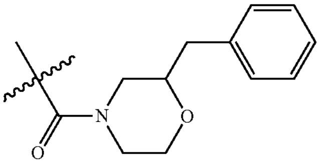
,
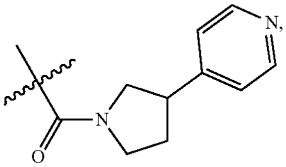
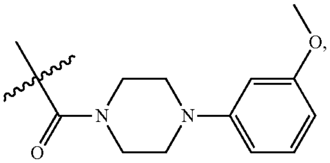
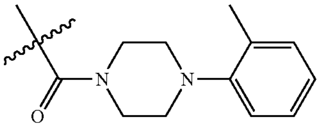
,
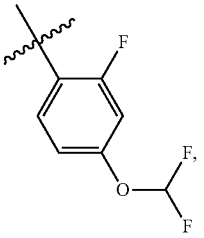
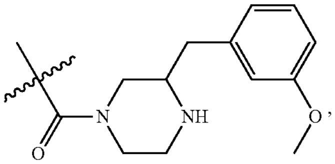
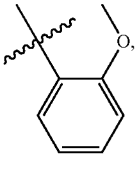
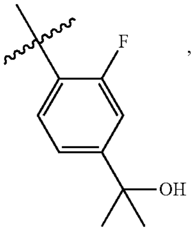
,
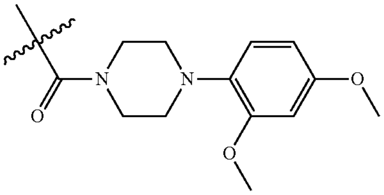
, -continued
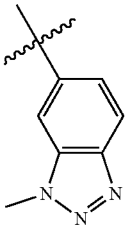
,
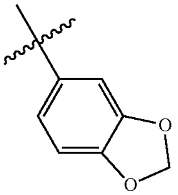
,
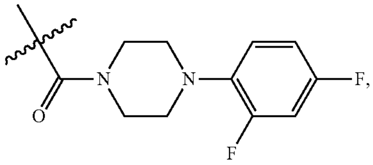
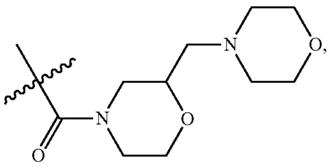
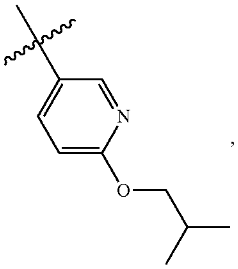
,
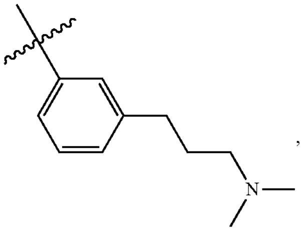
,
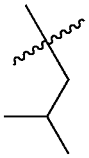
,
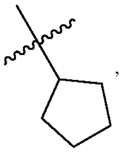
,
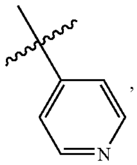
, and
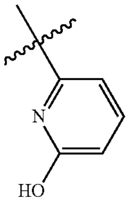
.
In one embodiment, the compound of Formula VIb1 is:
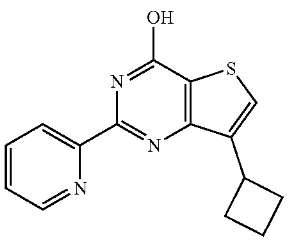
,
-continued
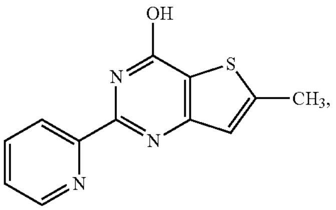
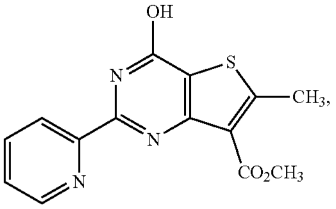
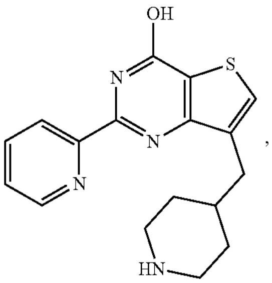
,
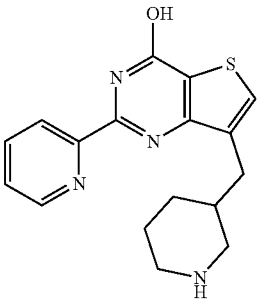
,
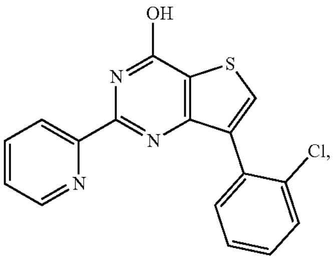
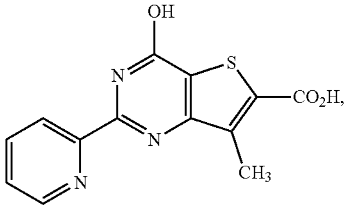
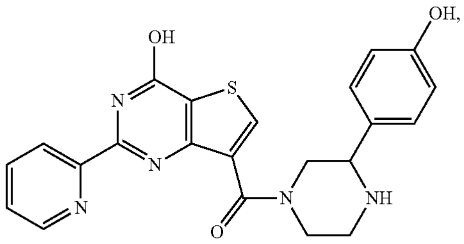
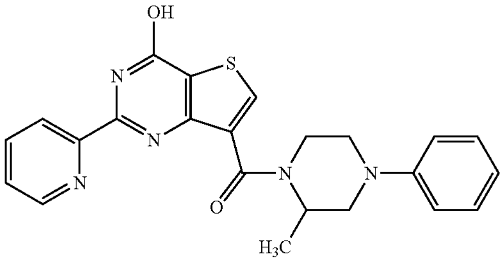
, -continued
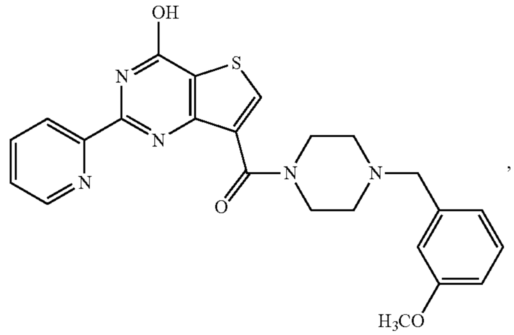
,
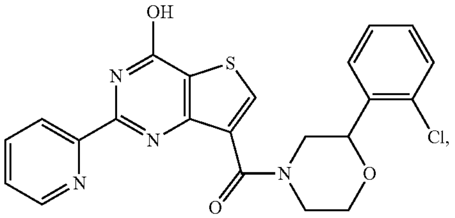
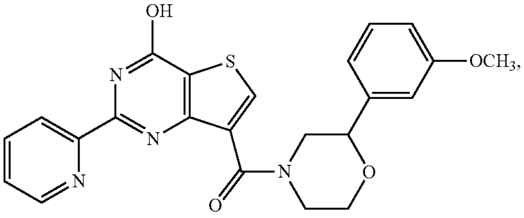
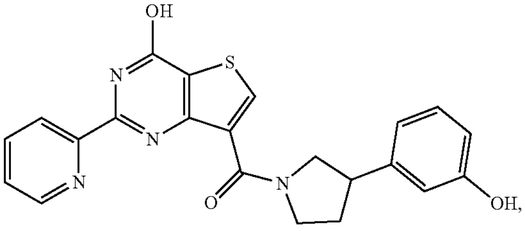
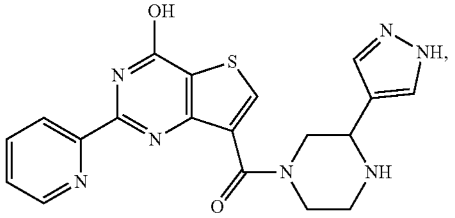
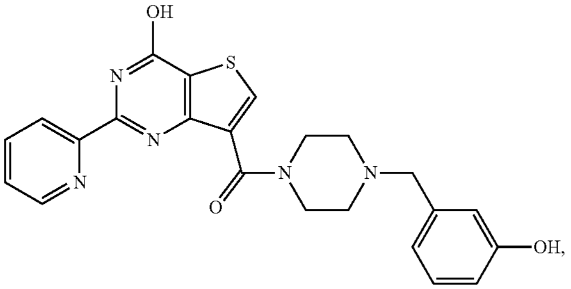
-continued
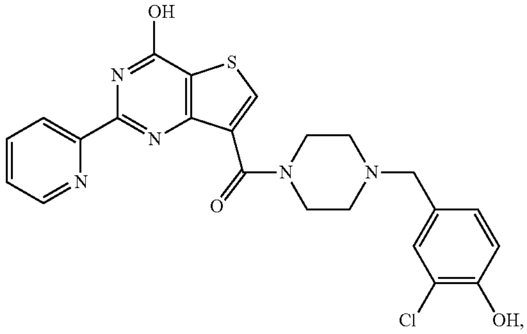
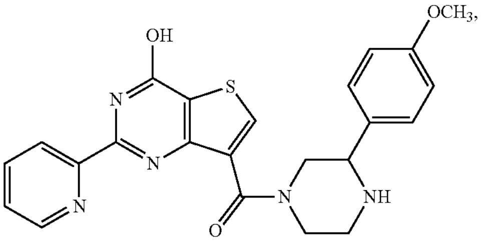
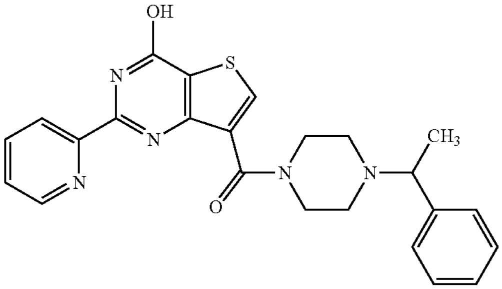
,
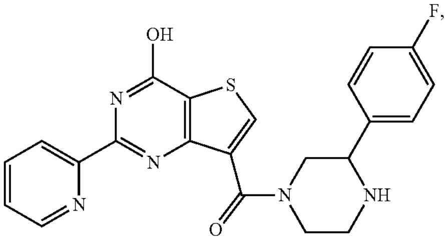
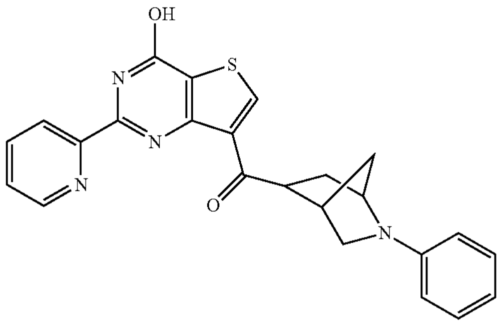
,
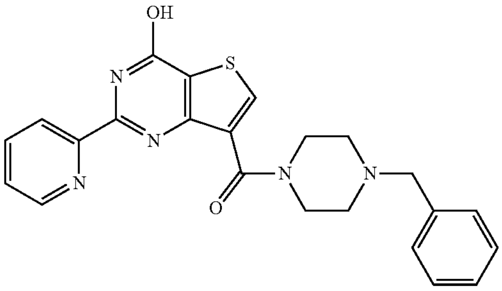
, -continued
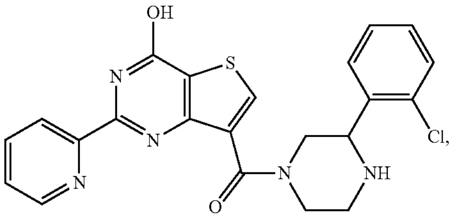
,
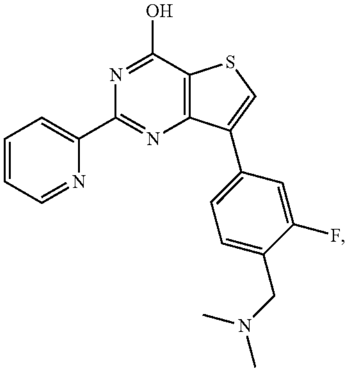
,
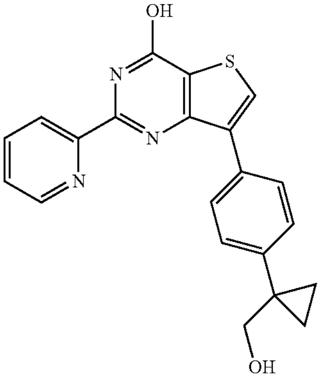
,
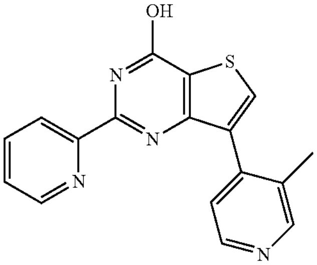
,
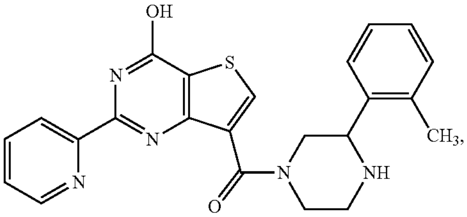
,
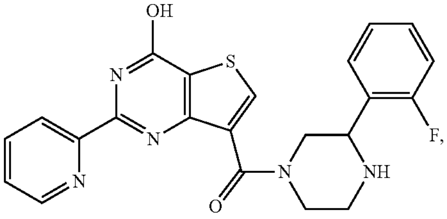
,
-continued
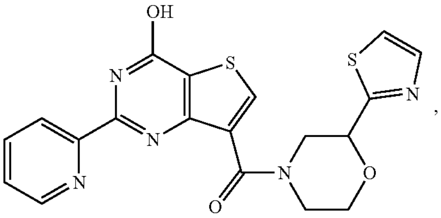
,
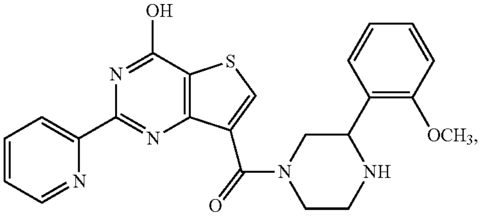
,
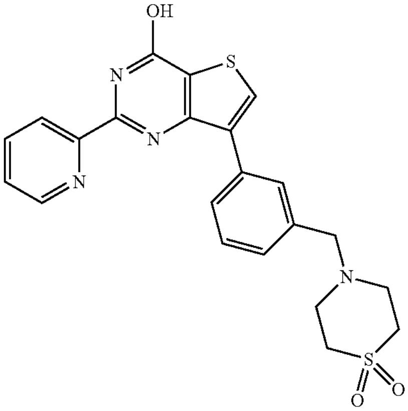
,
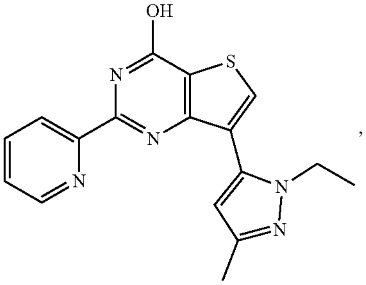
,
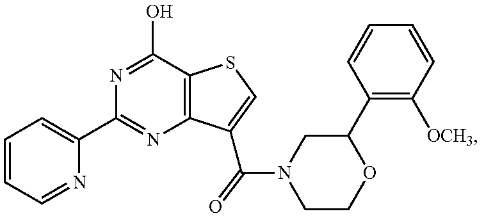
,
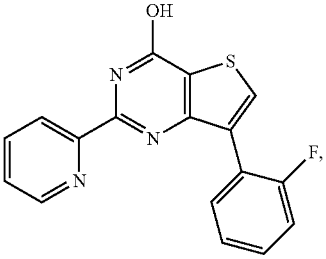
, -continued
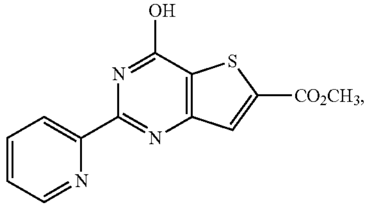
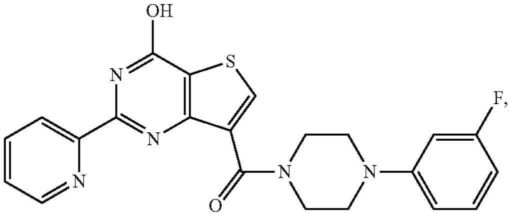
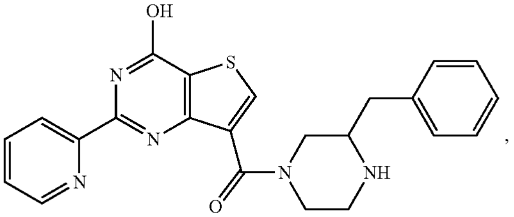
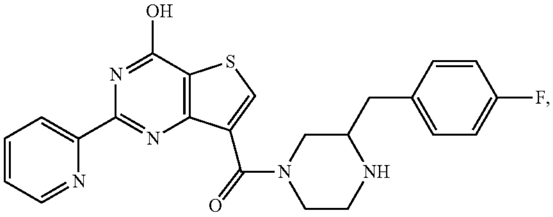
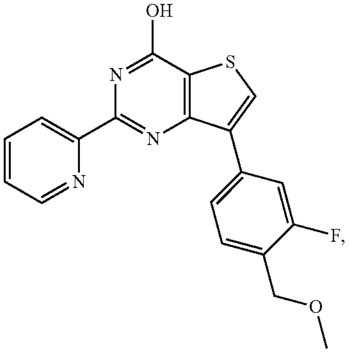
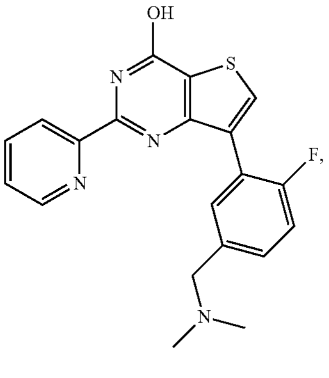
-continued
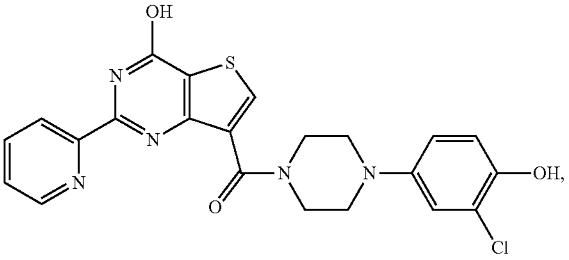
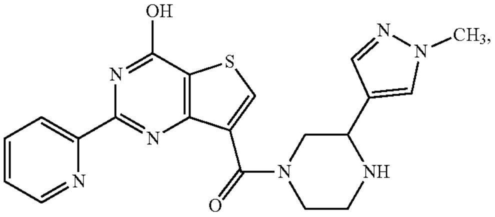
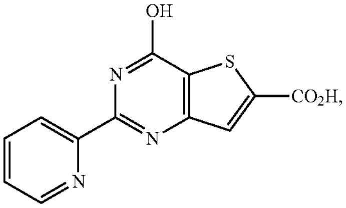
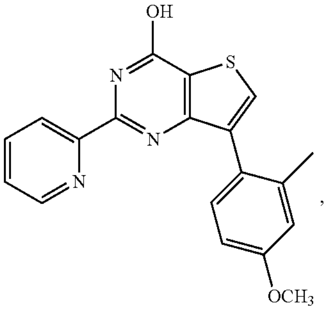
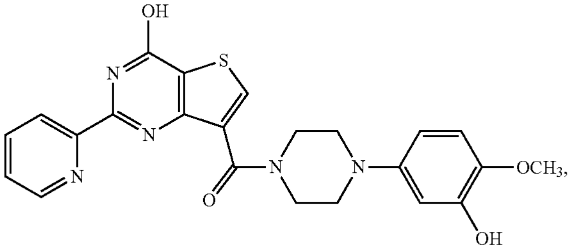
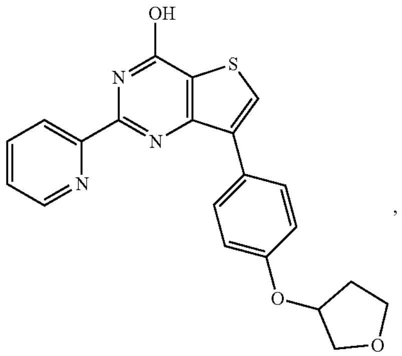

-continued
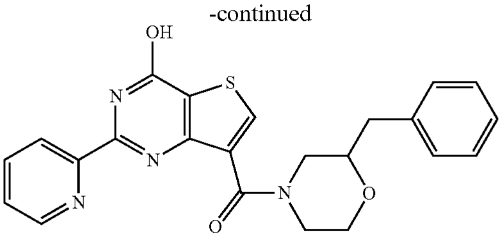
,
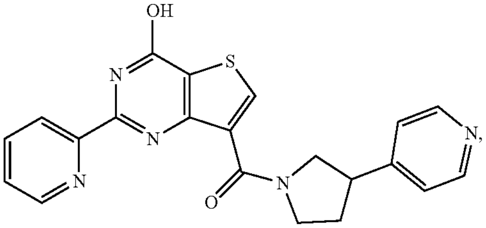
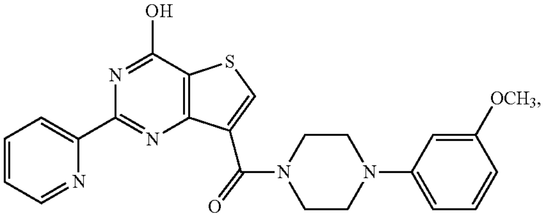
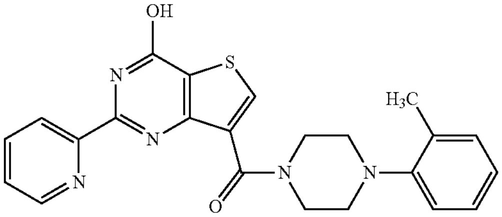
,
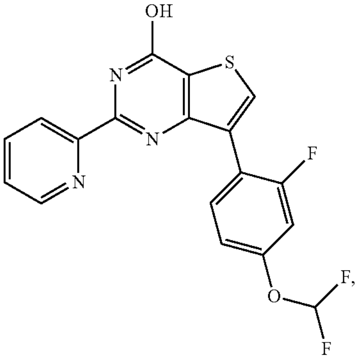
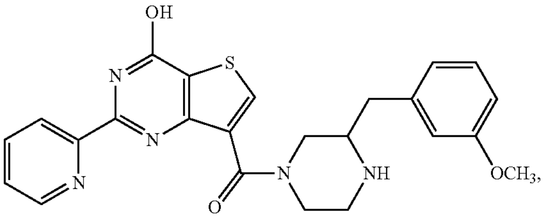
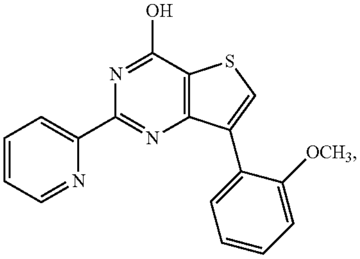
-continued
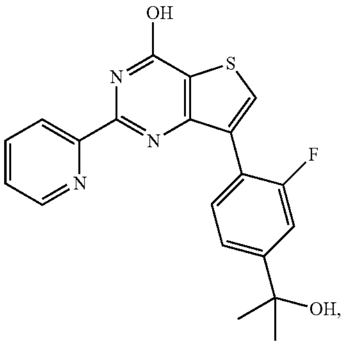
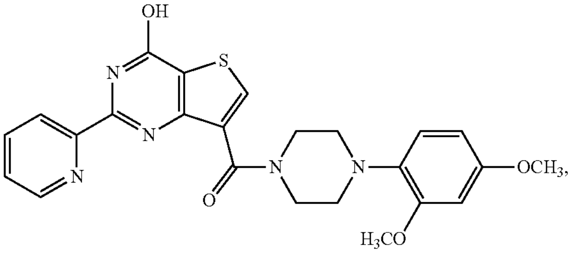
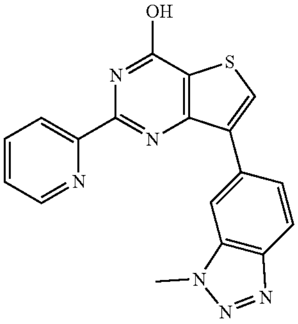
,
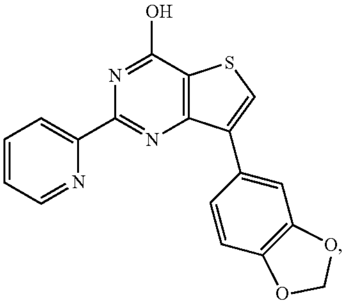
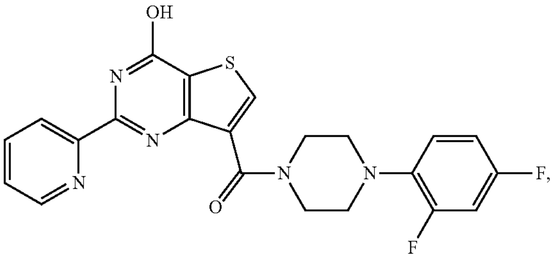
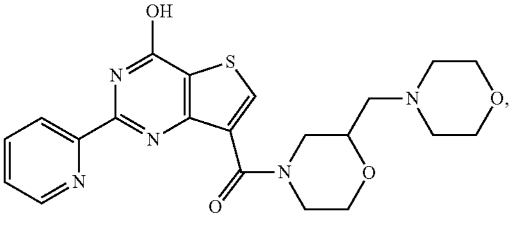

-continued
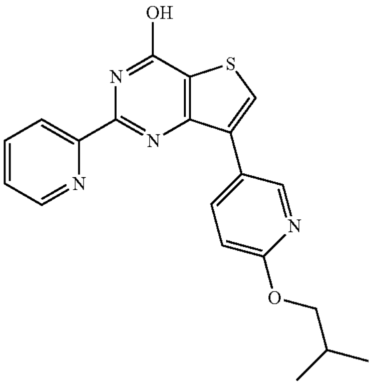
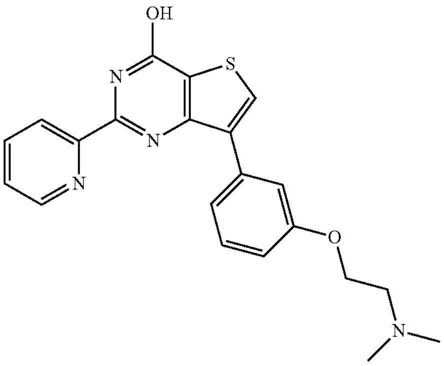
,
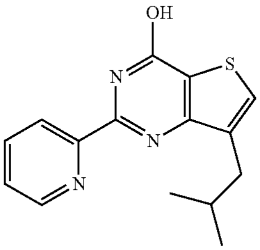
,
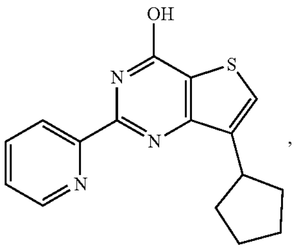
,
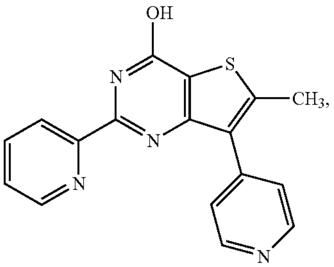
or
-continued
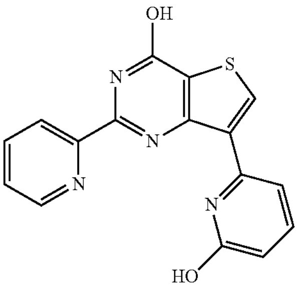
.
In another embodiment of Formula VIb1, a compound of Formula VIb1 is a compound wherein
$R^{1b1}$ is pyridinyl;
$R^{9b1}$ is H, methyl, —COOH or —$COOCH_3$;
$R^{8b1}$ is selected from the group consisting of:
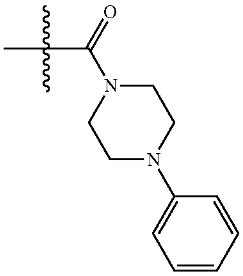
,
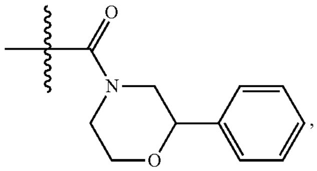
, and
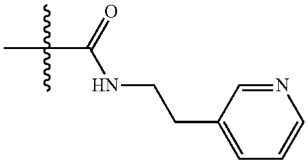
.
In one embodiment, the compound of Formula VIb1 is:
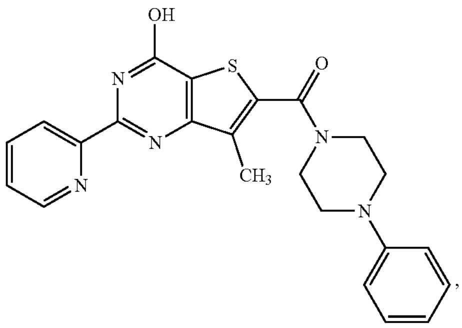
, -continued
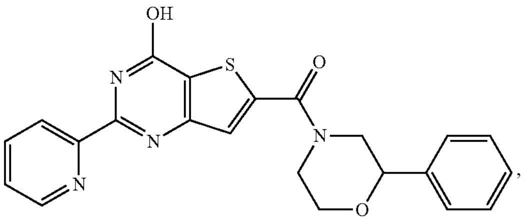
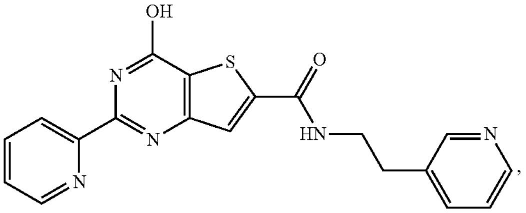
or
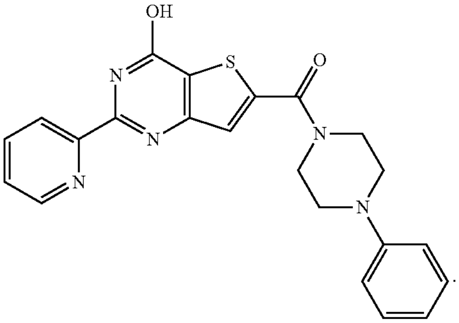
In another embodiment of Formula VIb1, a compound of Formula VIb1 is a compound wherein
$R^{1b1}$ is pyridinyl;
$R^{8b1}$ is H, t-butyl or $CH_3$;
$R^{9b1}$ is Br,
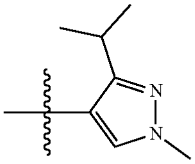
,
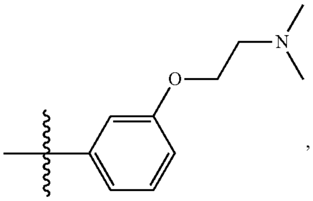
,
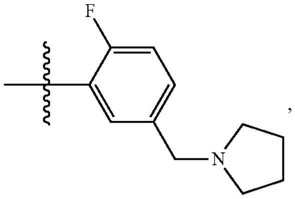
,
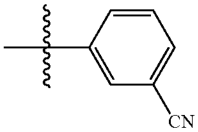
,
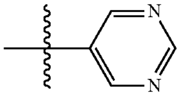
,
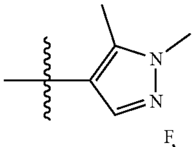
,
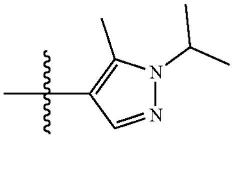
,
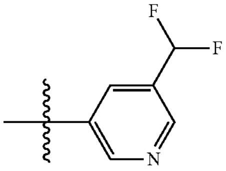
,
-continued
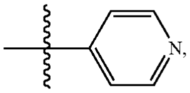
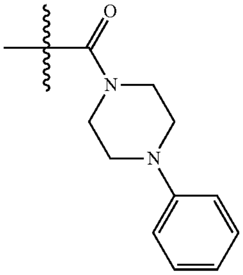
,
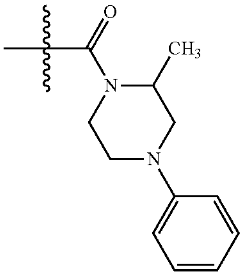
,
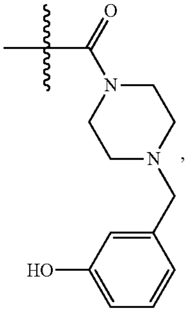
,
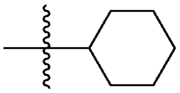
,
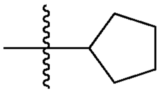
,
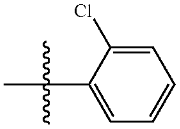
,
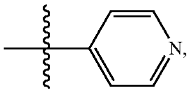
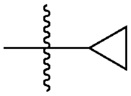
,
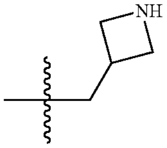
,
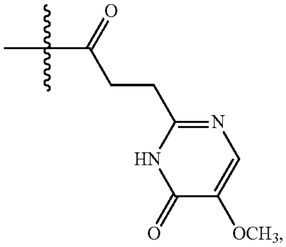
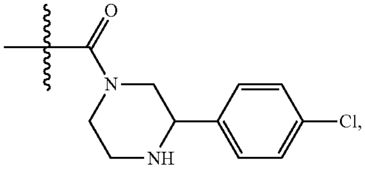
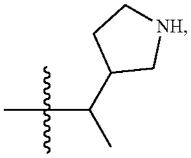
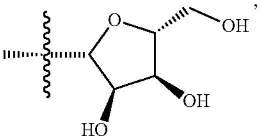
,
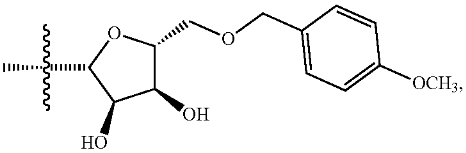
or -continued
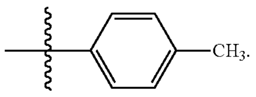
In one embodiment, the compound of Formula VIb1 is:
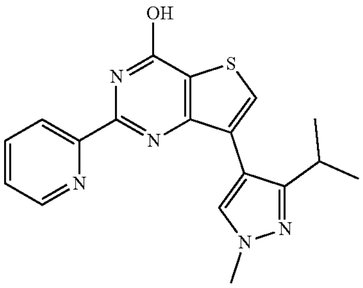
,
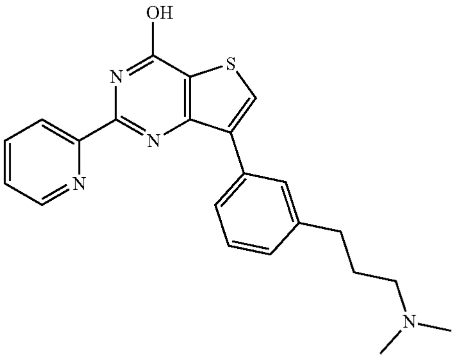
,
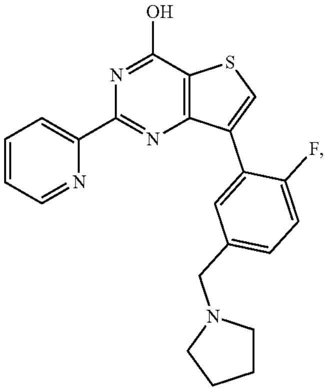
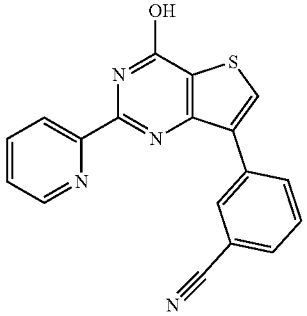
,
-continued
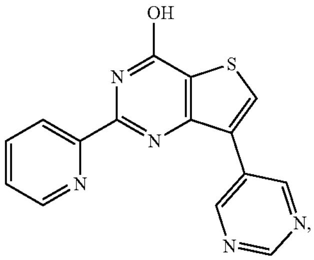
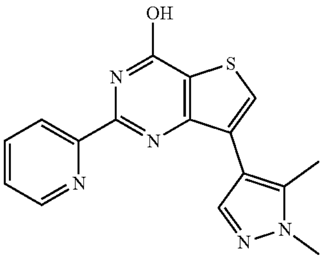
,
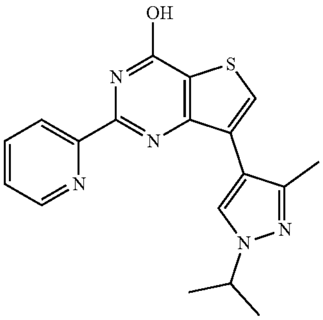
,
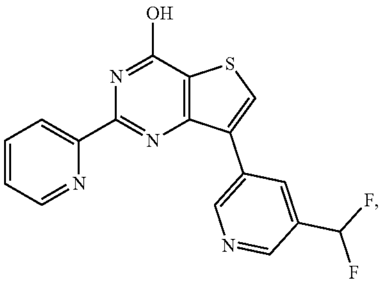
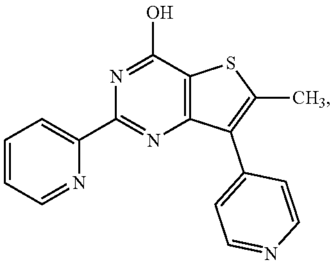
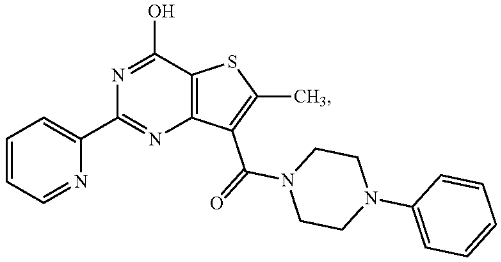
, -continued
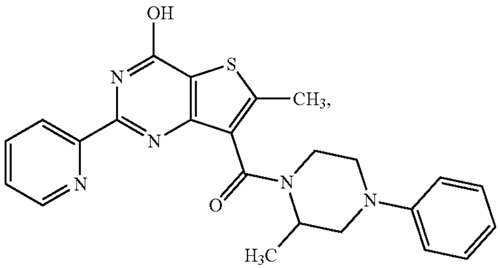
,
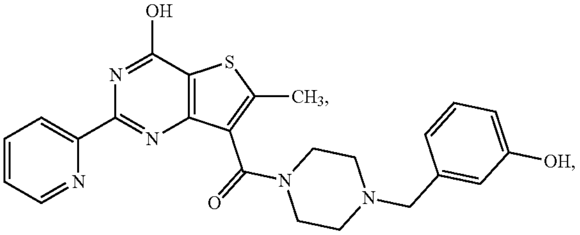
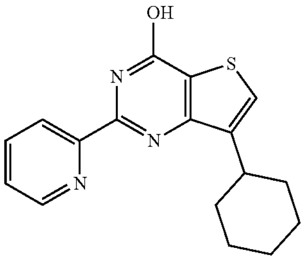
,
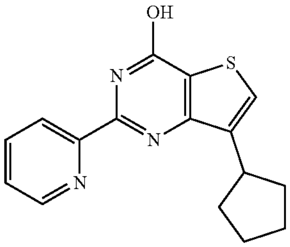
,
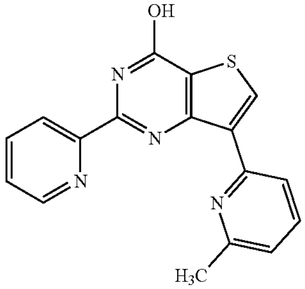
,
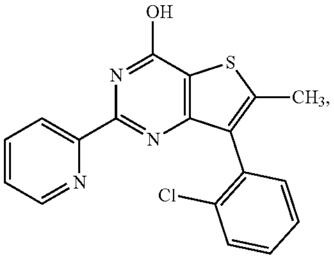
-continued
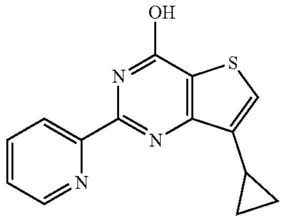
,
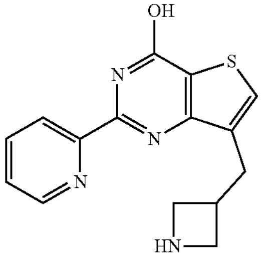
,
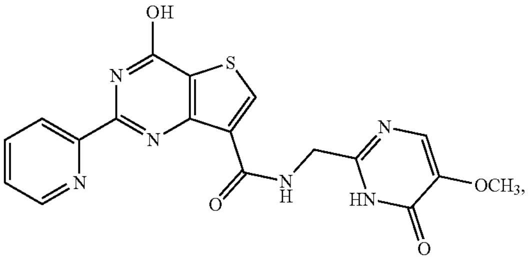
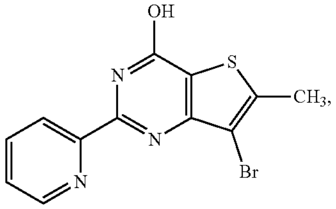
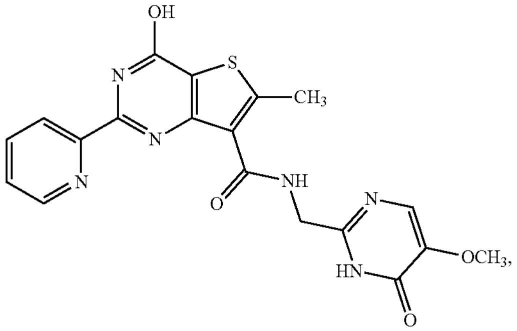
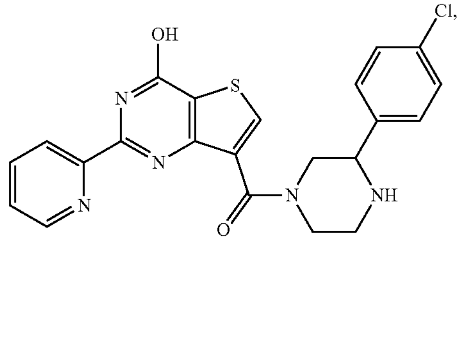

-continued
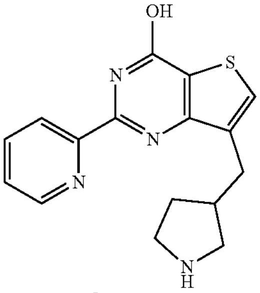
,
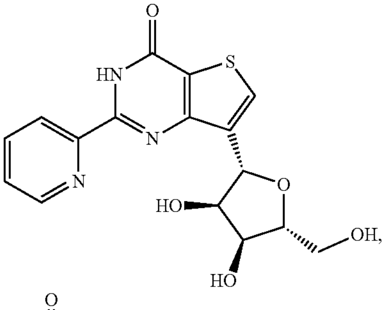
,
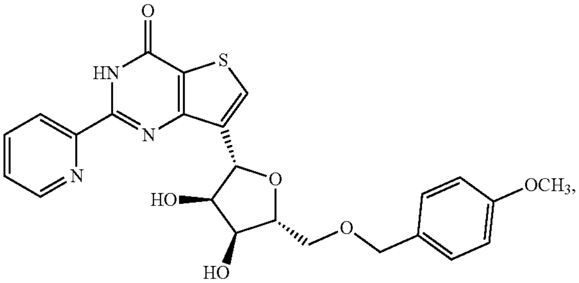
,
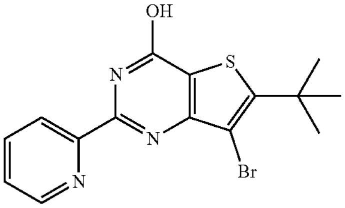
, or
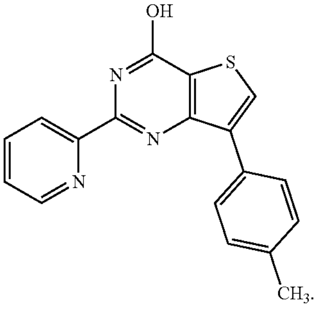
.
In another embodiment of Formula VIb1, a compound of Formula VIb1 is a compound wherein
$R^{1b1}$ is N-methyl-imidazolyl or pyrimidinyl;
$R^{8b1}$ is H or $CH_3$;
$R^{9b1}$ is Ph,
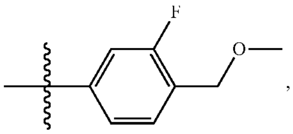
,
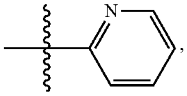
,
-continued
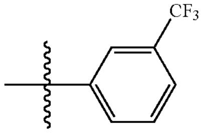
,
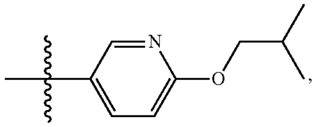
,
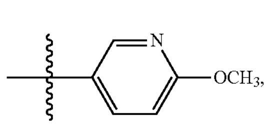
,
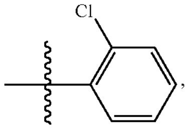
,
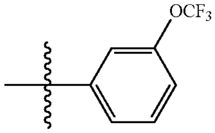
,
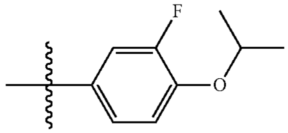
,
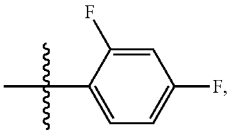
,
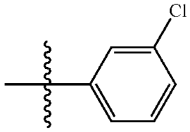
,
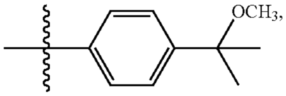
,
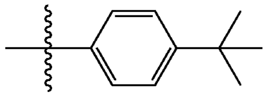
In one embodiment, the compound of Formula VIb1 is:
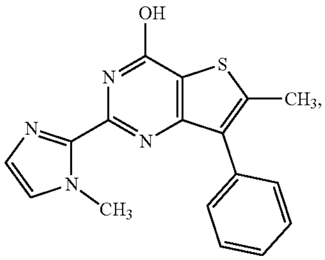
,
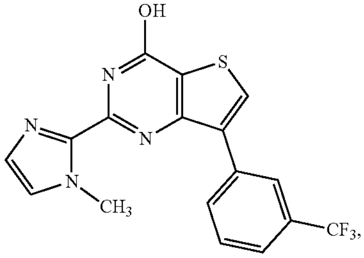
,
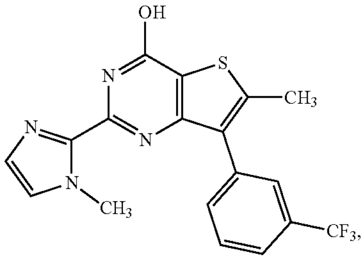
, -continued
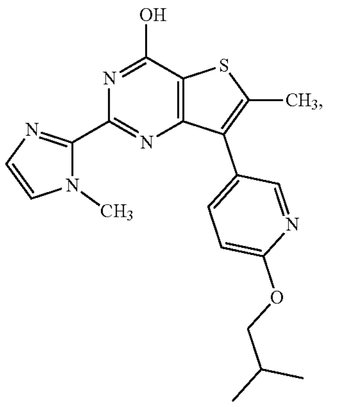
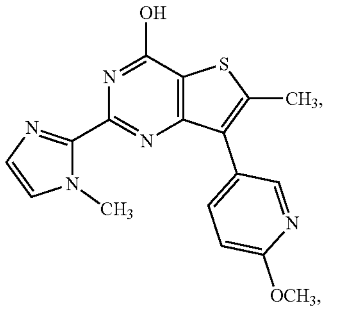
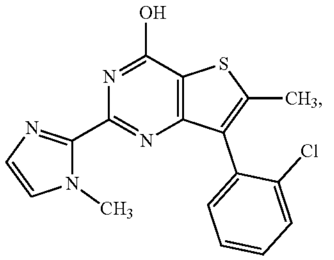
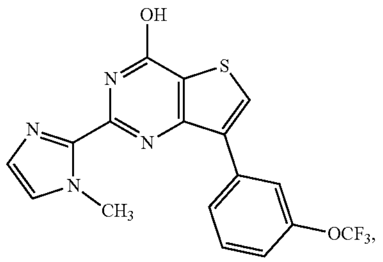
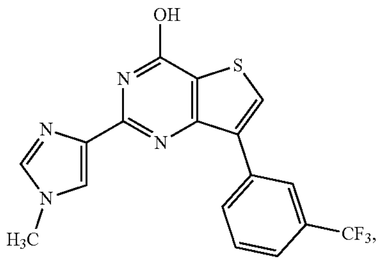
-continued
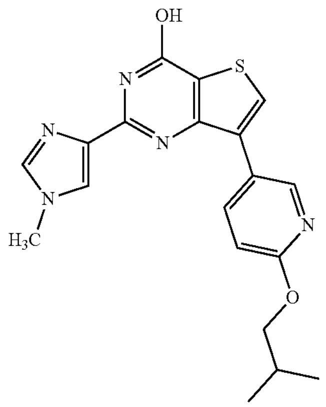
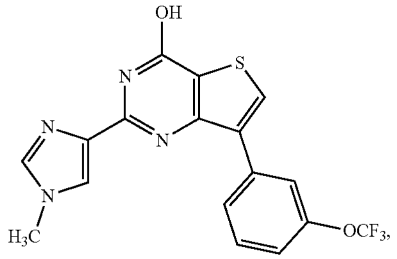
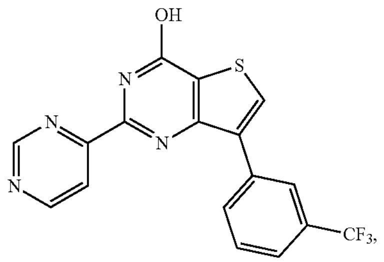
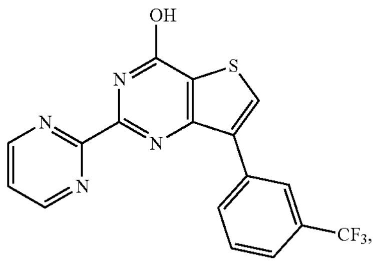
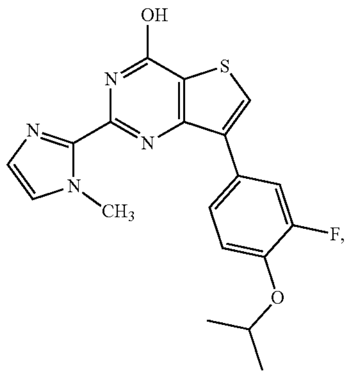

-continued
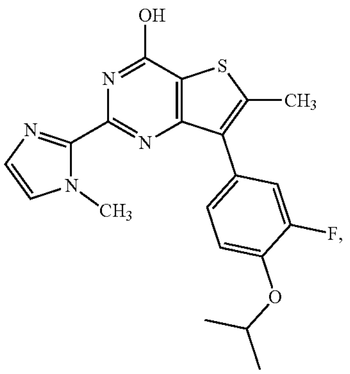
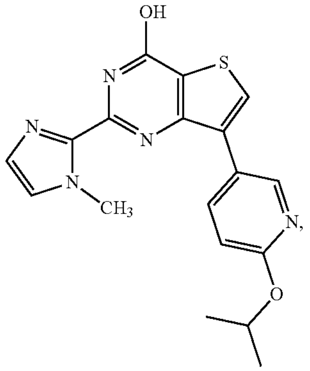
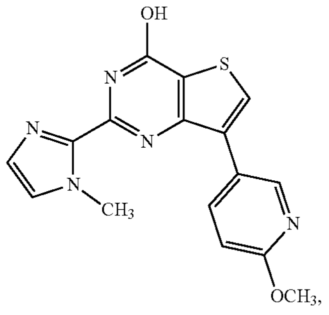
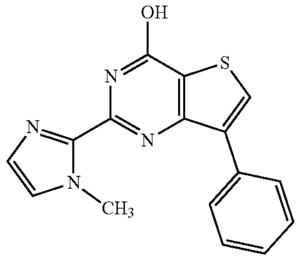
,
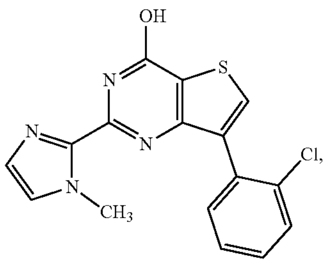
-continued
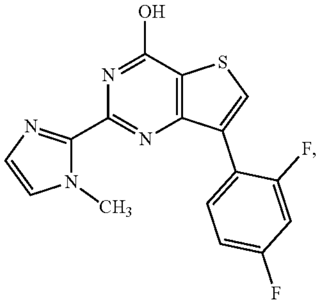
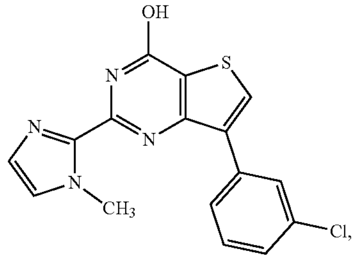
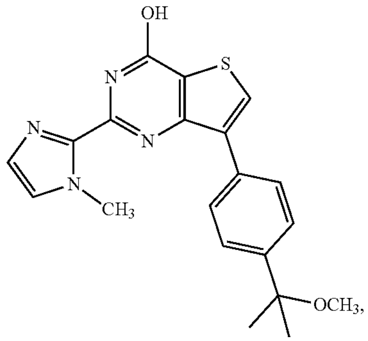
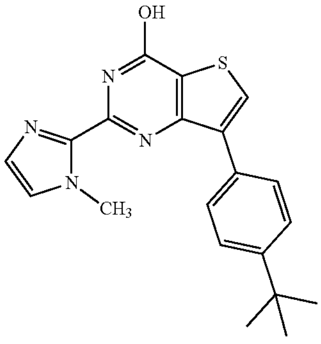
, or
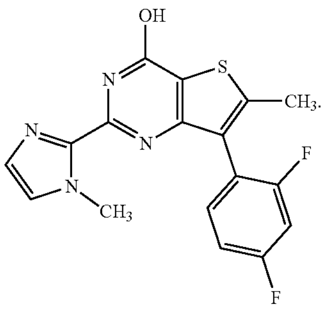
In some embodiments of Formula VIb1, $R^{1b1}$ is pyridyl, imidazolyl, N-methyl-2-imidazolyl, N-methyl-4-imdidazolyl, 2-pyrimidinyl or 4-pyrimidinyl.

In one embodiment, the compound of Formula VIb1 is:
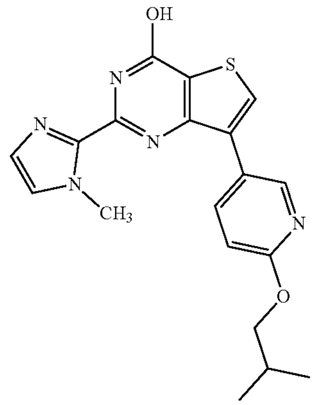
,
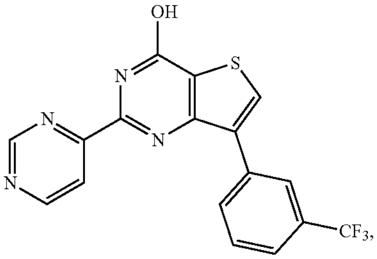
,
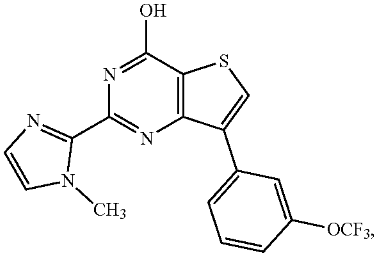
,
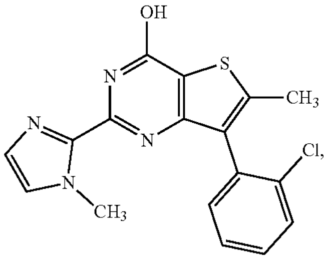
,
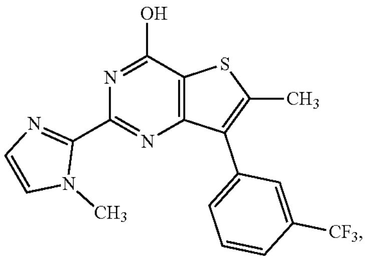
,
-continued
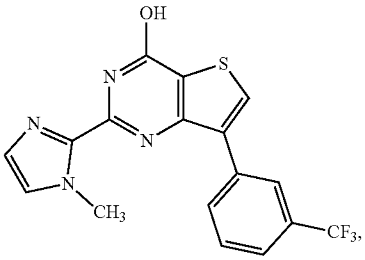
,
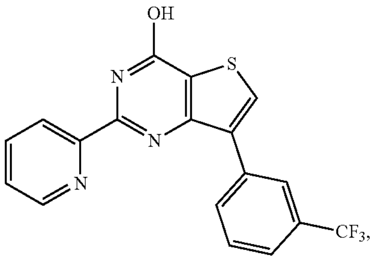
, or
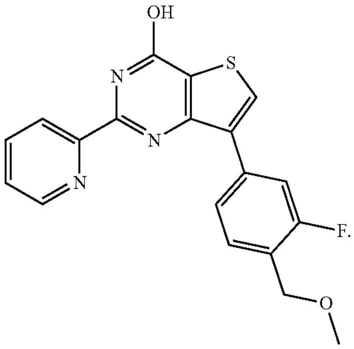
.
In one embodiment, the compound of Formula VIb1 is selected with the proviso that the compound is not
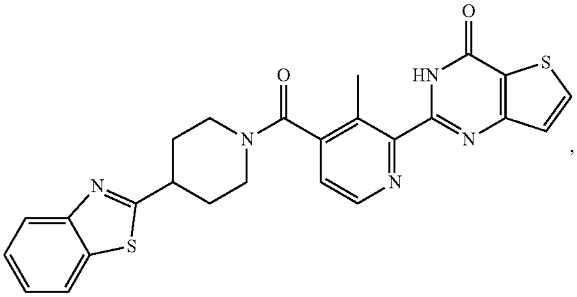
,
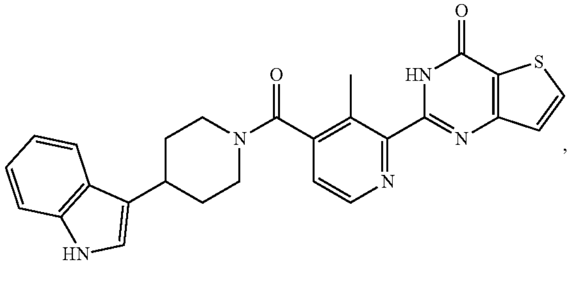
, -continued

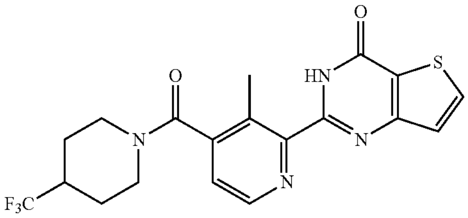

,

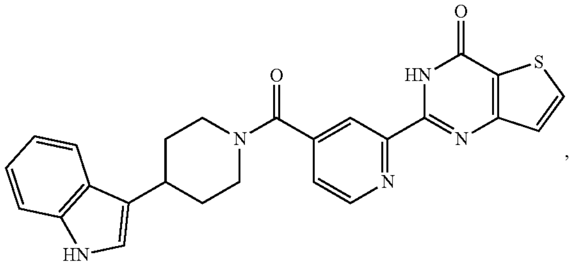

,

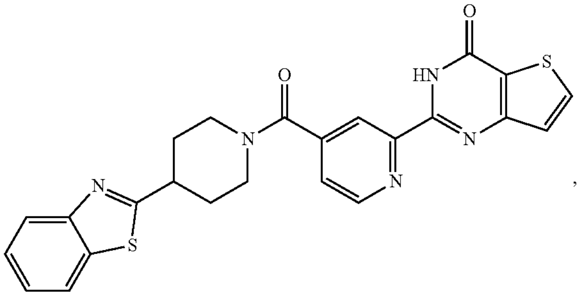

,

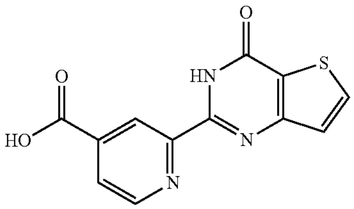

,

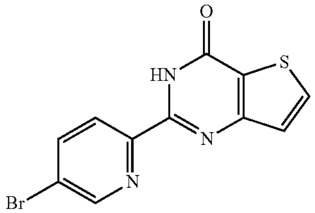

,

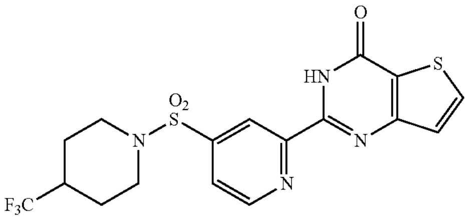

,

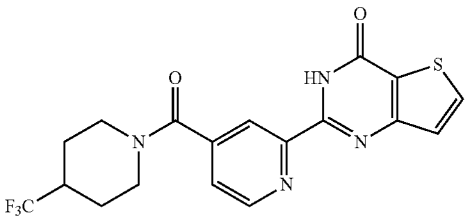

or

-continued

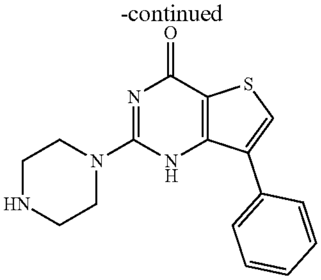

.

In one embodiment, the compound of Formula VIb1 is selected with the proviso that if $R^{91}$ is aryl and $R^{8b1}$ is H, then $R^{1b1}$ is not a saturated heterocyclic group.

In some embodiments of Formula VIb1, $R^{1b1}$ is imidazolyl.

In another embodiment, the compound of Formula VI is a compound of Formula VIc:

Formula VIc

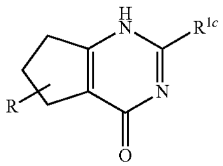

or pharmaceutically acceptable derivatives thereof, wherein $R^{1c}$ is aryl, or heteroaryl; and R may consist of 0-6 substituents independently selected from H or alkyl.

In another embodiment of Formula VIc, a compound of Formula VIc is a compound wherein $R^{1c}$ is pyridinyl; and R is H.

In one embodiment, the compound of Formula VIc is:

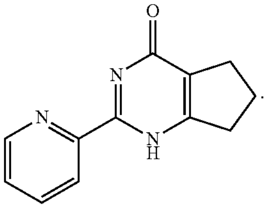 [SMILES: O=c1nc(-c2ccccn2)[nH]c2c1CCC2]

.

In another embodiment, the compound of Formula VI is a compound of Formula VId:

Formula VId

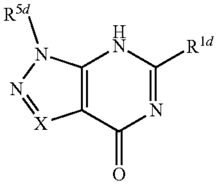

or pharmaceutically acceptable derivatives thereof, wherein $R^{1d}$ is aryl or heteroaryl;

$R^{5d}$ is hydrogen, alkyl, alkenyl, alkynyl, aryl, heteroaryl, heterocyclyl, cycloalkyl, alkylcarbonyl, cycloalkylcarbonyl, or arylcarbonyl; and X is CH or N.

In another embodiment of Formula VId, a compound of Formula VId is a compound wherein $R^{1d}$ is pyridinyl;

$R^{5d}$ is hydrogen or phenyl, wherein phenyl is substituted with $CF_3$;

X is CH or N.

In one embodiment, the compound of Formula VId is:

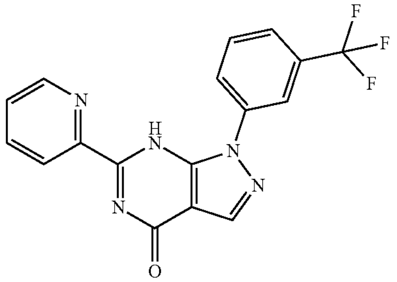

or

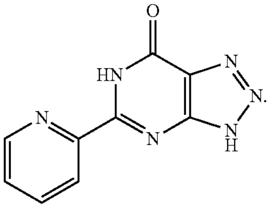

In another embodiment, the compound of Formula VI is a compound of Formula VIe:

Formula VIe

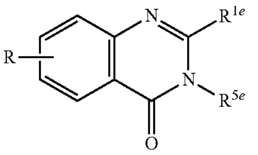

or pharmaceutically acceptable derivatives thereof, wherein $R^{1e}$ is $S(O)_pR^4$, $NR^5C(O)R^4$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5e}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

R may consist of 0-4 substituents independently selected from H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$.

In another embodiment of Formula VIe, $R^{1e}$ is heteroaryl, $S(O)_pR^4$, $NR^5C(O)R^4$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5e}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

R may consist of 0-4 substituents independently selected from H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$.

In another embodiment, the compound of Formula VI is a compound of Formula VIe:

Formula VIe

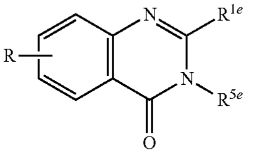

or pharmaceutically acceptable derivatives thereof, wherein $R^{1e}$ is $S(O)_pR^4$ or $NR^6R^7$;

$R^4$ is

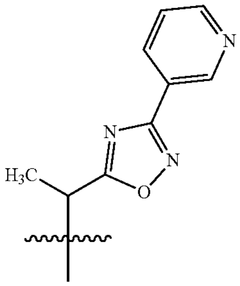

or

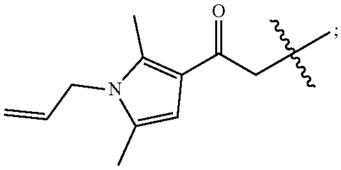

;

$R^{5e}$ is H, methoxyethyl or $CH_3OCH_2(CH_3)CH$—;

$R^6$ and $R^7$ are independently selected from hydrogen or as depicted below

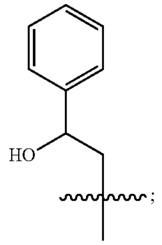 [SMILES: *CC(O)c1ccccc1]

p is 0; and

R is H or halogen.

In one embodiment, the compound of Formula VIe is:

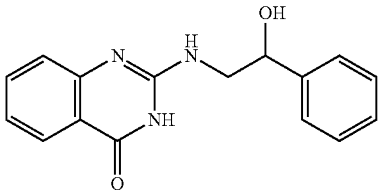

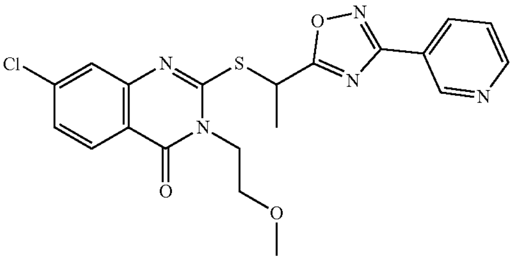

or

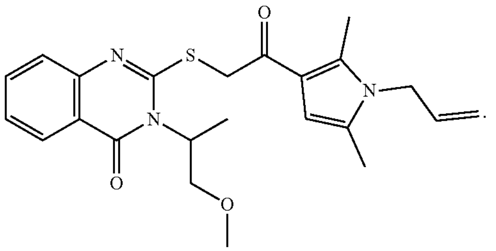

In one embodiment, the compound of Formula VIe is a compound wherein $R^{1e}$ is heteroaryl; and R is H, fluoro, bromo, chloro, or iodo.

In one embodiment, the compound of Formula VIe is:

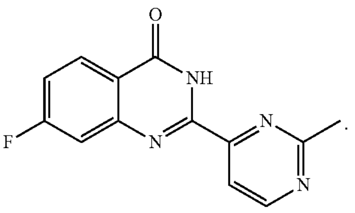 [SMILES: Cc1nccc(-c2nc3cc(F)ccc3c(=O)[nH]2)n1]

In another embodiment, the compound of Formula VI is a compound of Formula VIf:

Formula VIf

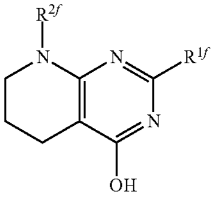

or pharmaceutically acceptable derivatives thereof, wherein $R^{1f}$ is aryl, or heteroaryl; and $R^{2f}$ is H, —C(O)R, —C(O)OR, —$S(O)_2R$, —S(O)R or alkyl, wherein R is aryl, heteroaryl or alkyl.

In another embodiment of Formula VIf, a compound of Formula VIf is a compound wherein $R^{1f}$ is 2-pyridyl; and $R^{2f}$ is —C(O)R, —C(O)OR or $SO_2R$, wherein R is aryl, heteroaryl or alkyl.

In another embodiment of Formula VIf, a compound of Formula VIf is a compound wherein $R^{1f}$ is 2-pyridyl; and $R^{2f}$ is —C(O)R, wherein R is aryl, heteroaryl or alkyl.

In another embodiment of Formula VIf, a compound of Formula VIf is a compound wherein $R^{1f}$ is pyridinyl; and $R^{2f}$ is H,

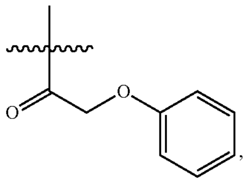

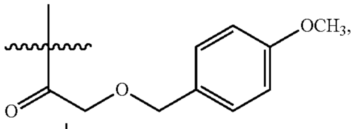

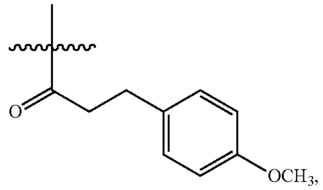

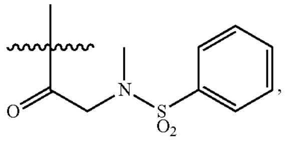

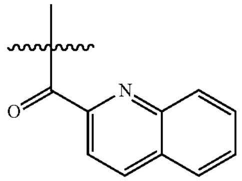

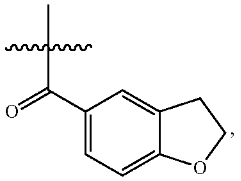

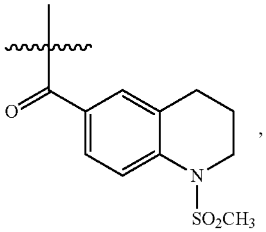

-continued
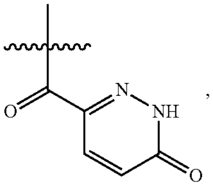
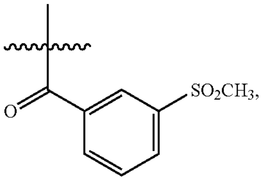
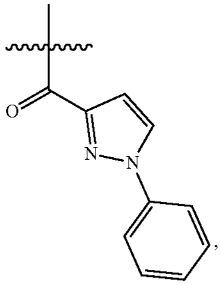
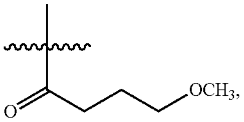
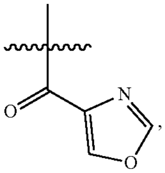
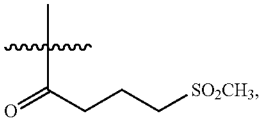
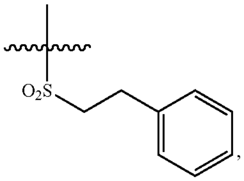
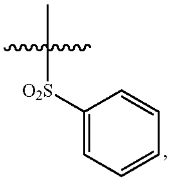
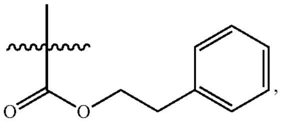
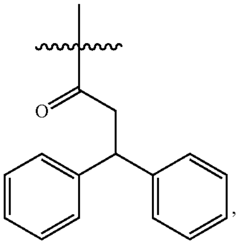
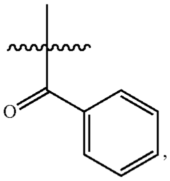
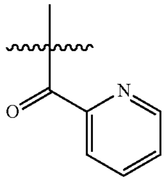
or
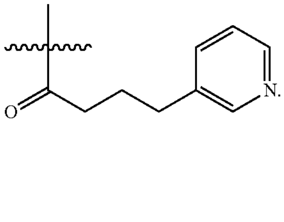
In one embodiment, the compound of Formula VIf is:
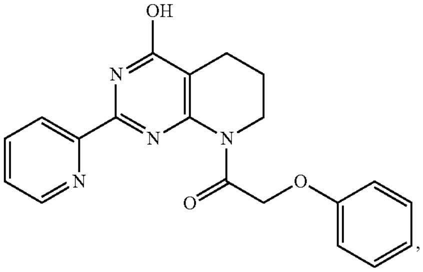
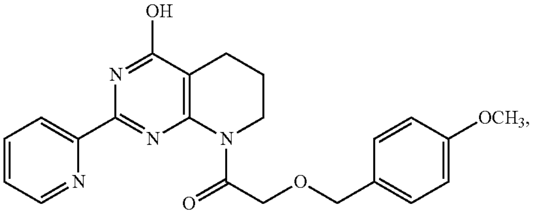
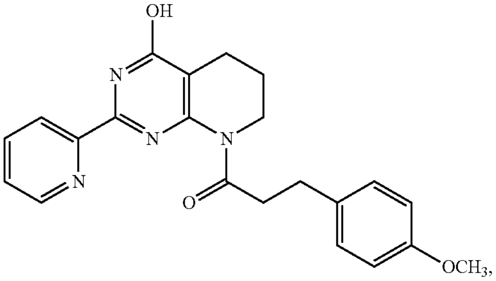
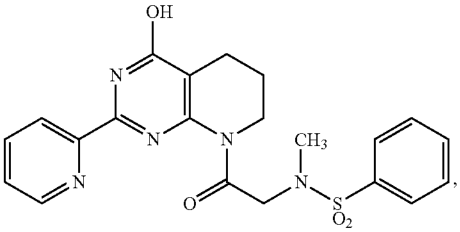
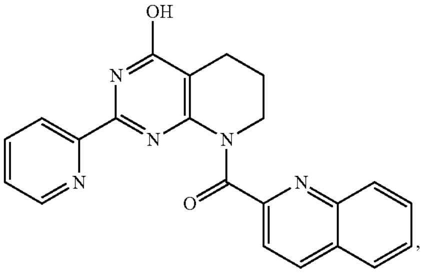
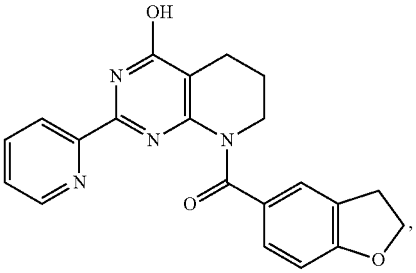

-continued
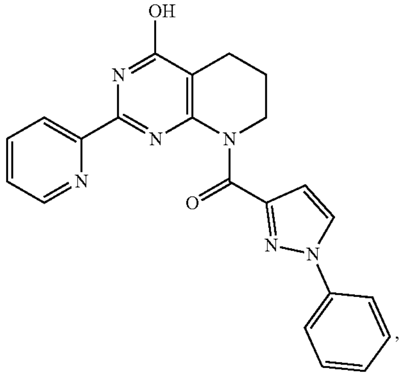
,
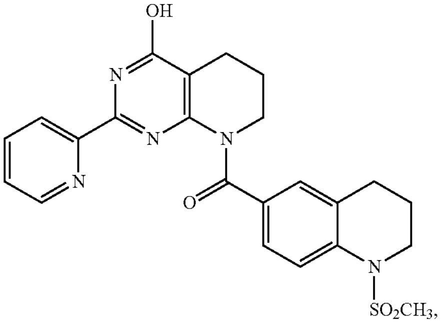
,
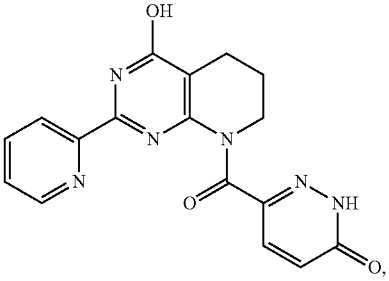
,
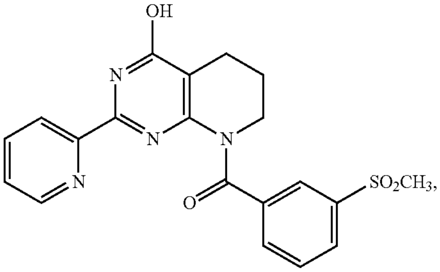
,
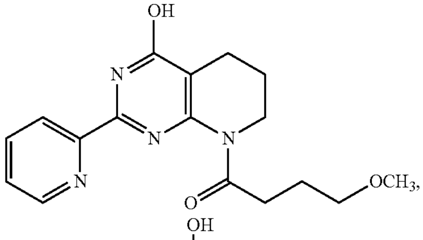
,
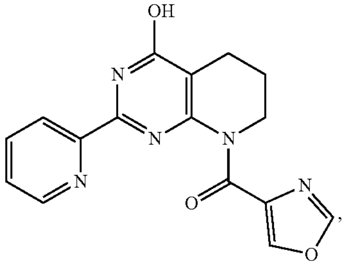
,
-continued
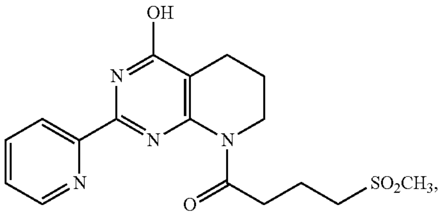
,
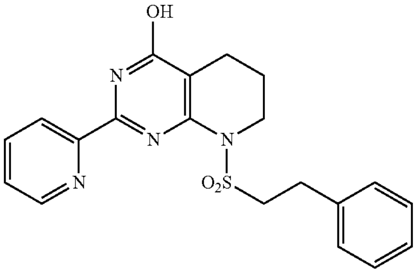
,
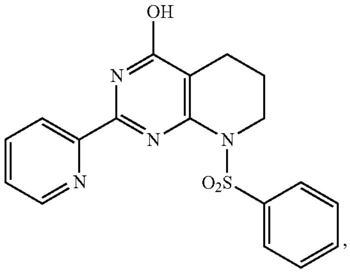
,
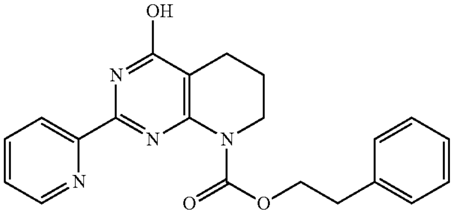
,
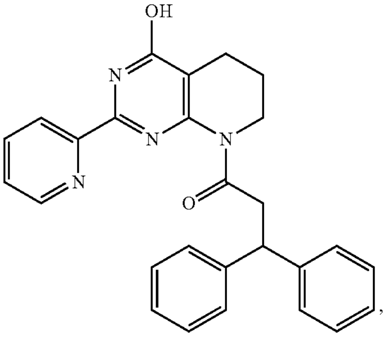
,
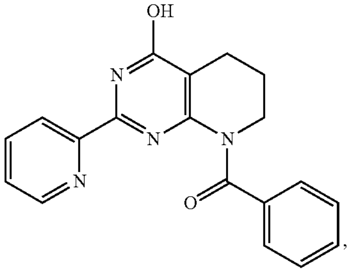
, -continued

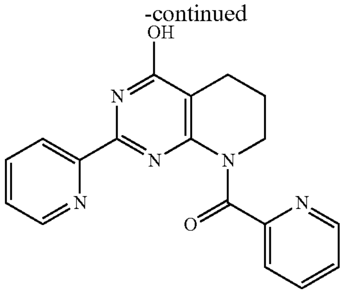

or

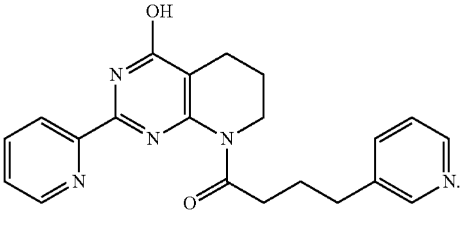

In another embodiment, the compound of Formula VI is a compound of Formula VIg:

Formula VIg

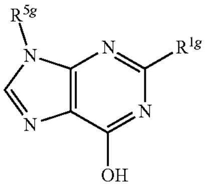

or pharmaceutically acceptable derivatives thereof, wherein $R^{1g}$ is aryl or heteroaryl; and $R^{5g}$ is hydrogen, alkyl, alkenyl, alkynyl, aryl, heteroaryl, heterocyclyl, cycloalkyl, alkylcarbonyl, cycloalkylcarbonyl, or arylcarbonyl.

In another embodiment of Formula VIg, a compound of Formula VIg is a compound wherein $R^{1g}$ is 2-pyridyl; and $R^{5g}$ is aryl, heteroaryl, heterocyclyl, cycloalkyl, $CH_2C(O)R$, wherein R is $NH_2$, NHalkyl, $N(alkyl)_2$, piperidine, OH or Oalkyl.

In another embodiment of Formula VIg, a compound of Formula VIg is a compound wherein $R^{1g}$ is pyridinyl; and $R^{5g}$ is hydrogen, phenyl, pyridyl or

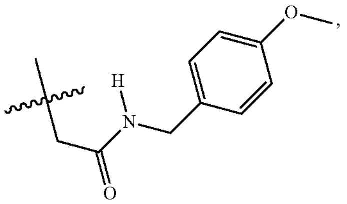

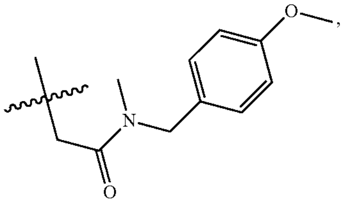

-continued

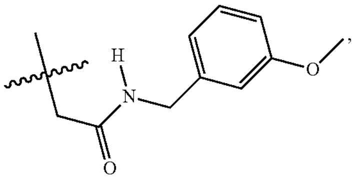

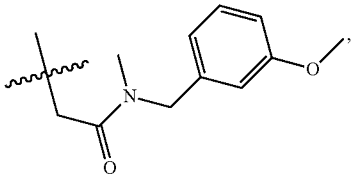

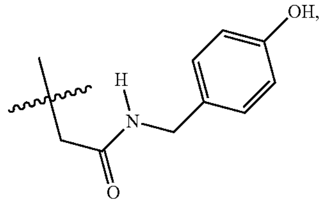

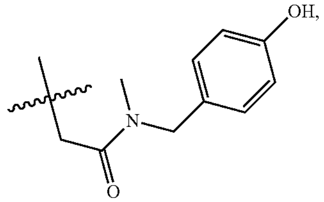

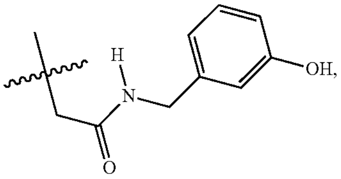

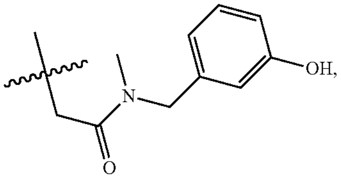

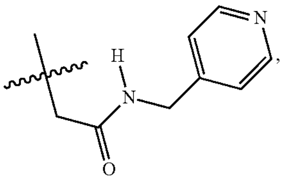

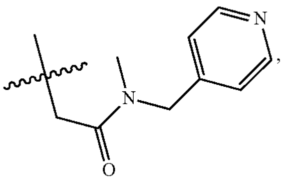

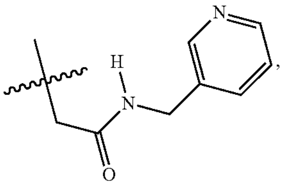

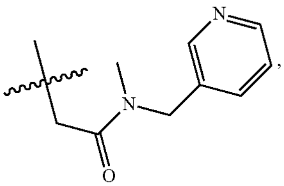

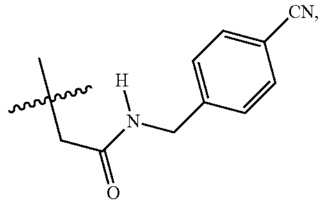

-continued
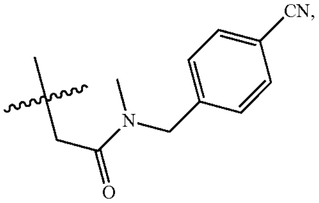
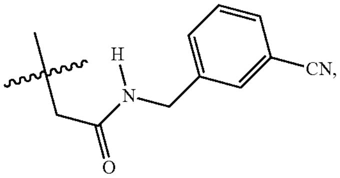
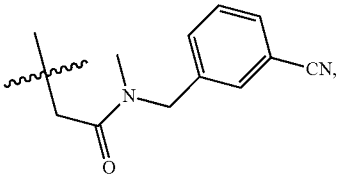
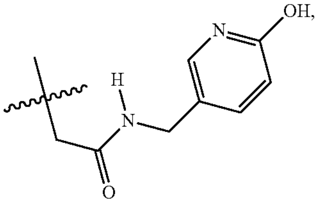
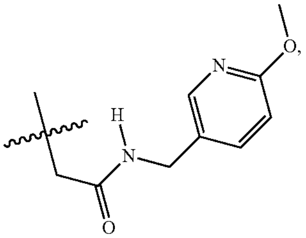
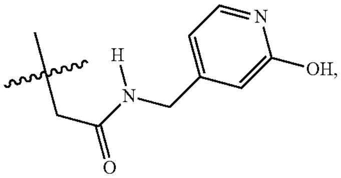
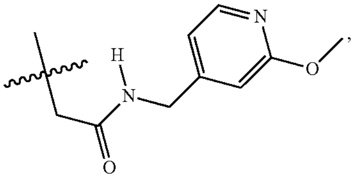
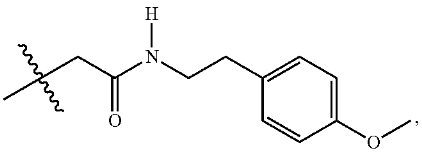
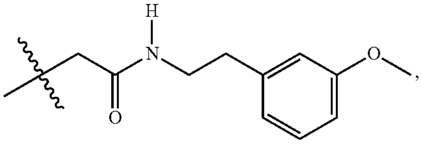
-continued
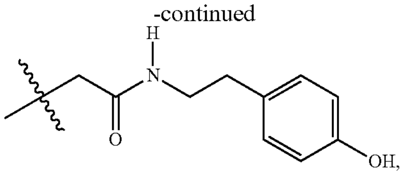
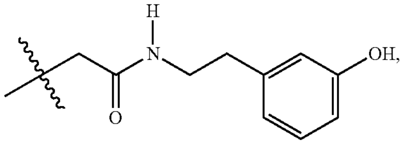
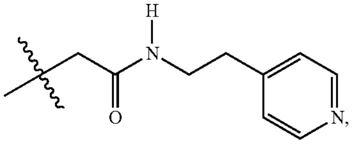
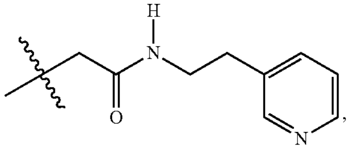
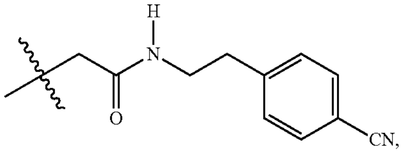
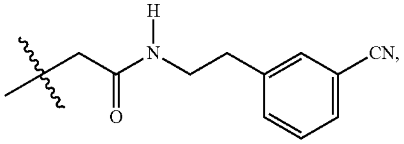
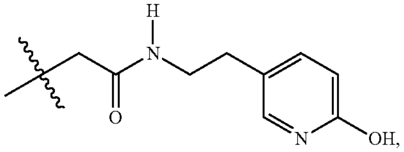
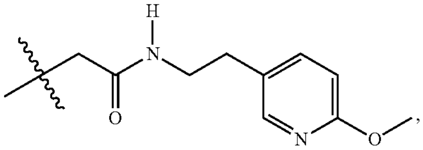
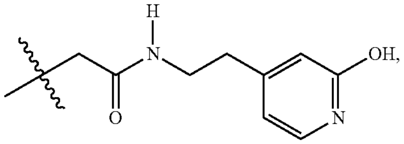
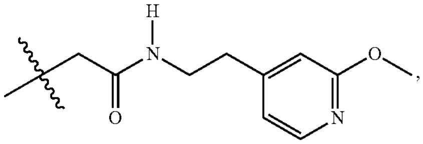
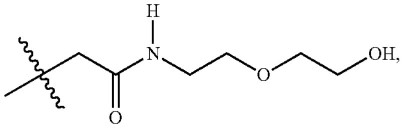
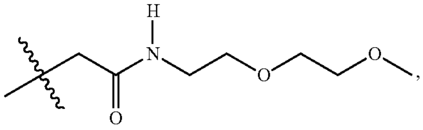

-continued

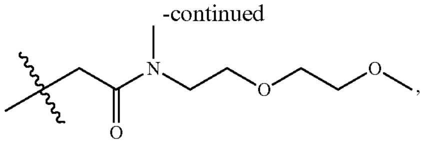

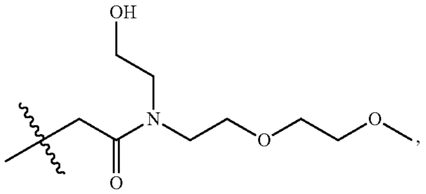

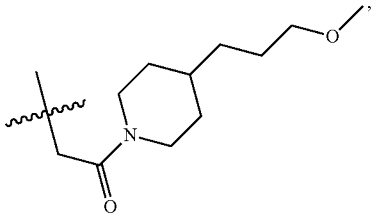

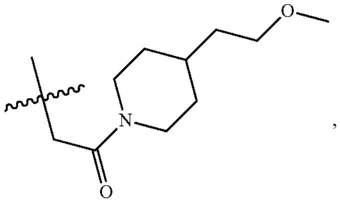

,

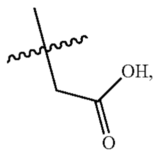

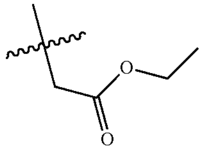

or

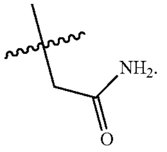

In certain embodiments, the compounds for use in the compositions and methods provided herein are of Formula VII:

Formula VII

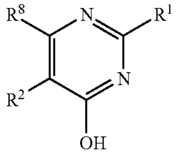

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2.

In another embodiment of Formula VII, a compound of Formula VII is a compound wherein $R^{1a}$ is pyridinyl;

$R^{2a}$ is —Oaryl, Oalkyl or —OH;

$R^{8a}$ is Oaryl, COOalkyl or unsubstituted or substituted aryl.

In one embodiment, the compound of Formula VII is:

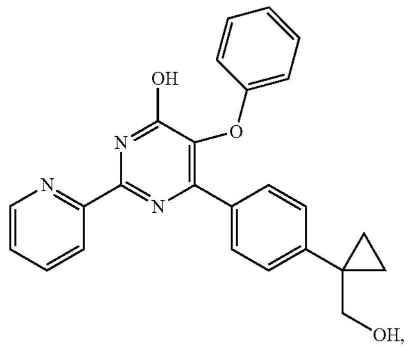

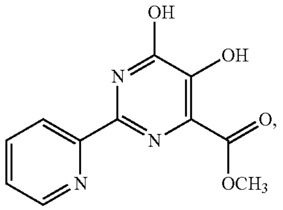

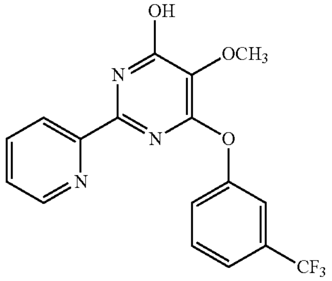

or

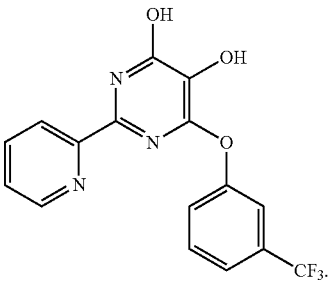

In one embodiment, the compound of Formula VII is selected with the proviso that the compound is not
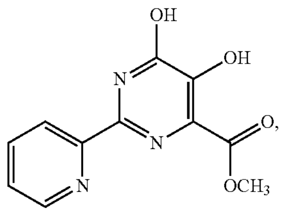
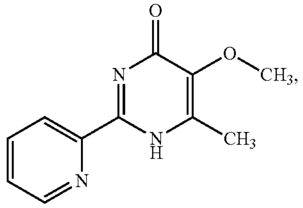
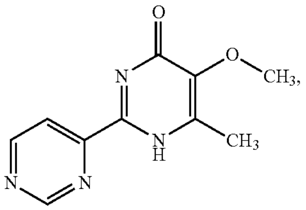
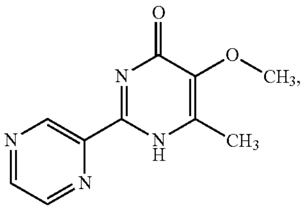
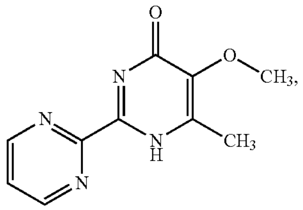
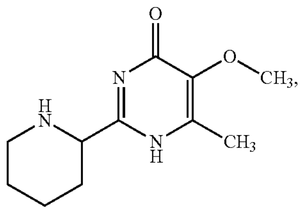
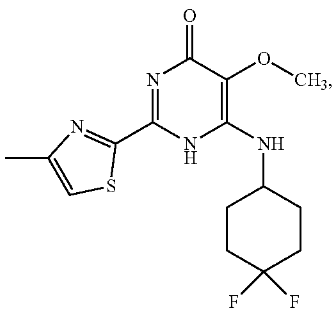
-continued
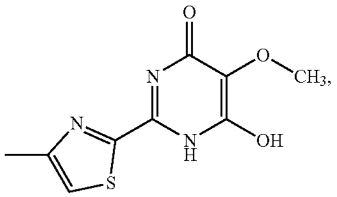
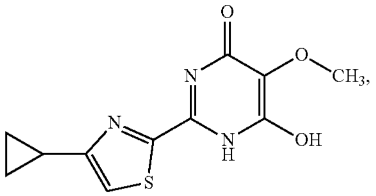
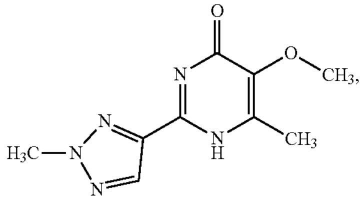
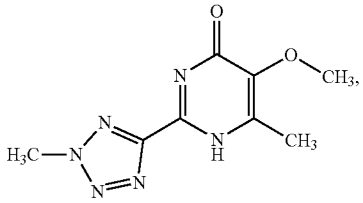
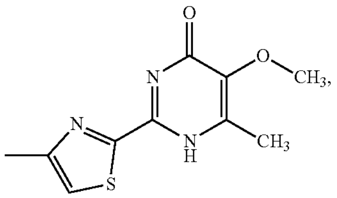
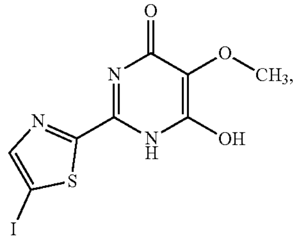
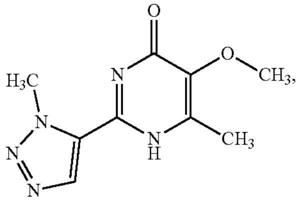
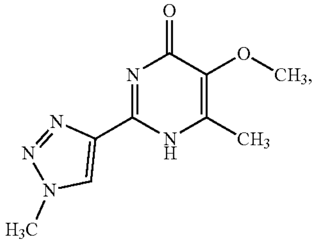

-continued
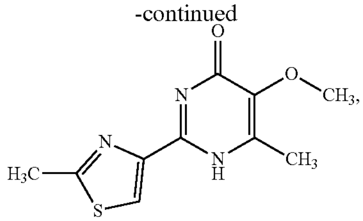
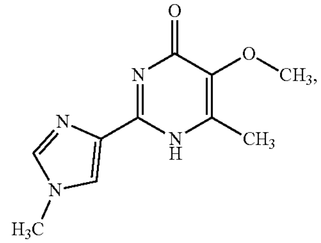
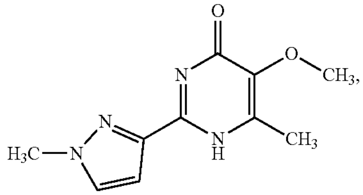
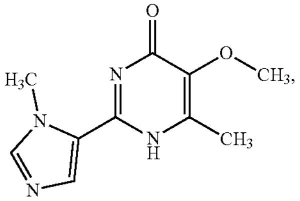
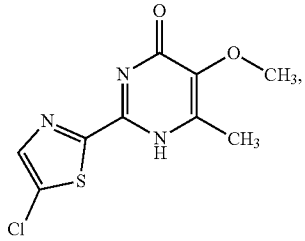
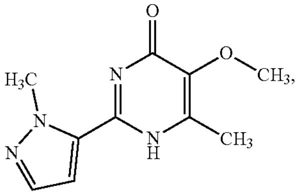
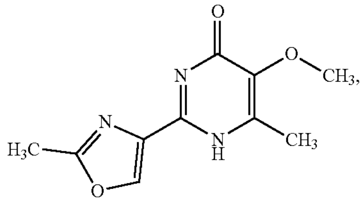
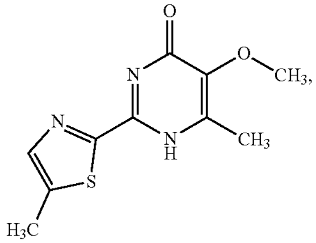
-continued
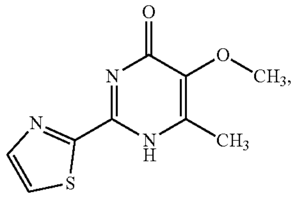
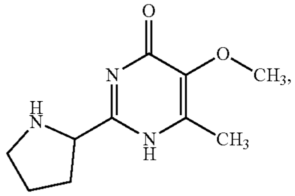
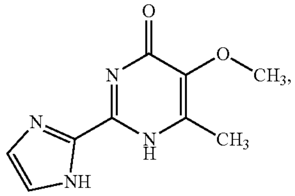
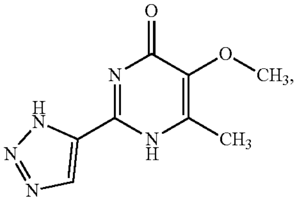
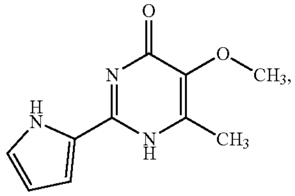
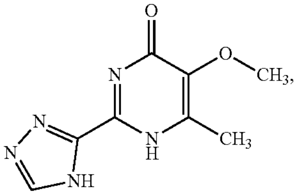
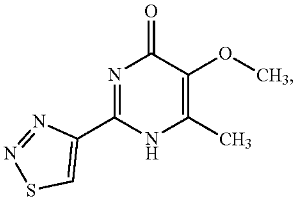
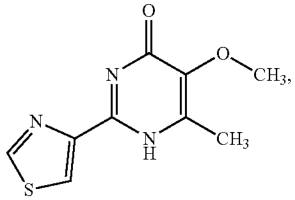

-continued

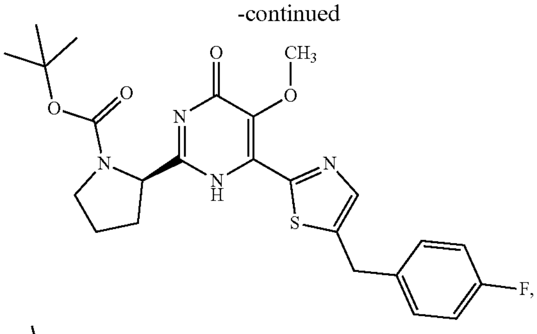

, or

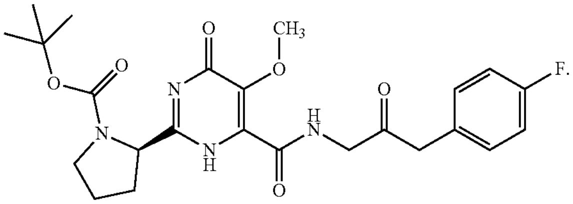

In another embodiment, the compound of Formula VII is a compound of Formula VIIa:

Formula VIIa

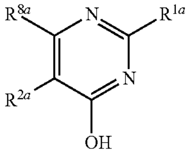

or pharmaceutically acceptable derivatives thereof, wherein $R^{1a}$ is alkyl, cycloalkyl, aryl or heteroaryl;

$R^{2a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{8a}$ is H or alkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2.

In another embodiment of Formula VIIa, $R^{1a}$ is $CH_2NR^6R^7$;

$R^{2a}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{8a}$ is H or alkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

p is 0-2.

In one embodiment of Formula VIIa, the compound of Formula VIIa is

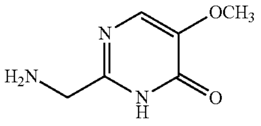 [SMILES: COc1cnc(CN)[nH]c1=O]

or its HCl salt.

In another embodiment of Formula VIIa, a compound of Formula VIIa is a compound wherein $R^{1a}$ is pyridinyl;

$R^{2a}$ is selected from one of the following:

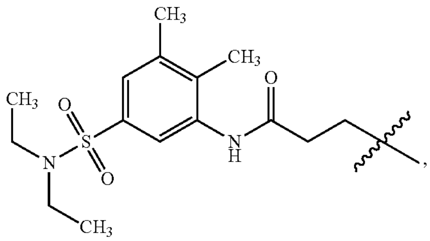

,

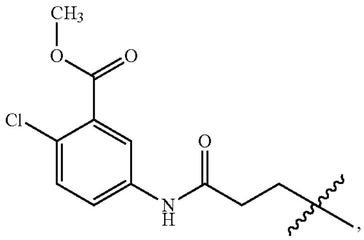

,

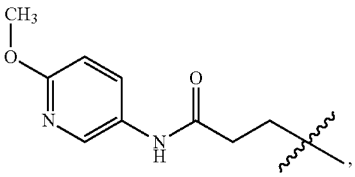

,

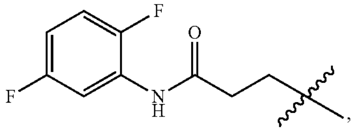

,

-continued
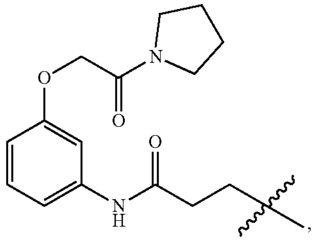,
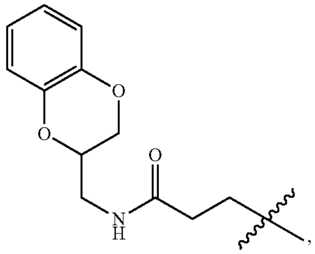,
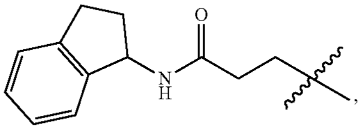,
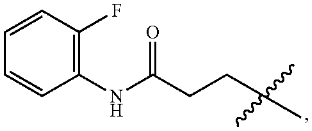,
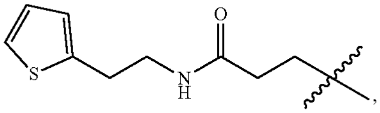,
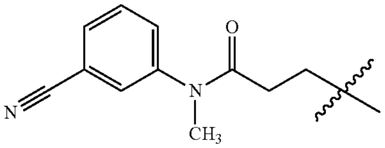 or
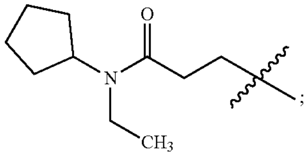;
and
$R^{8a}$ is methyl.
In another embodiment of Formula VIIa, a compound of Formula VIIa is a compound wherein
$R^{1a}$ is pyridinyl;
$R^{2a}$ is selected from one of the following:
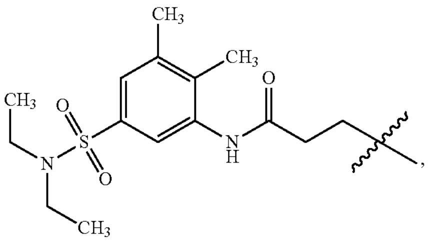,
-continued
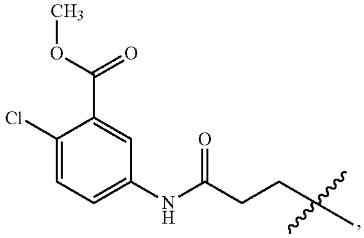,
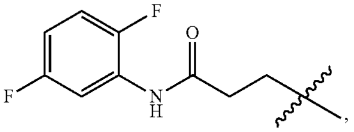,
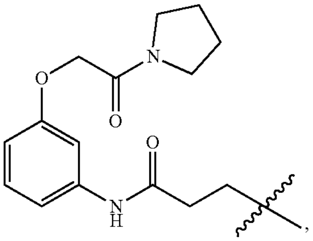,
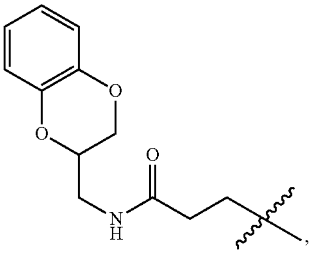,
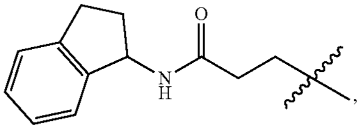,
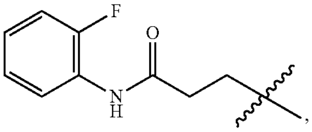,
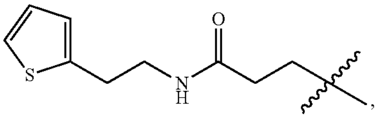,
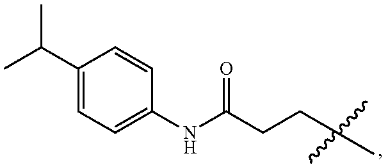,
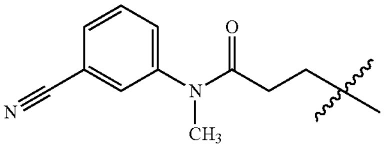 or -continued
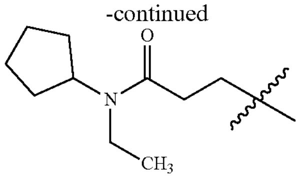;
and
$R^{8a}$ is methyl.
In one embodiment, the compound of Formula VIIa is:
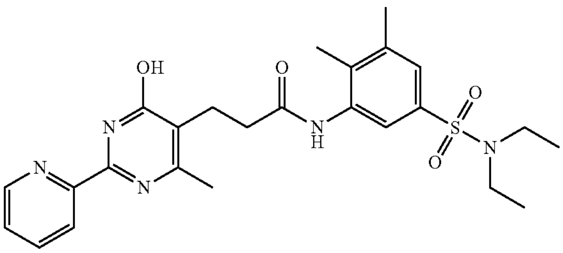,
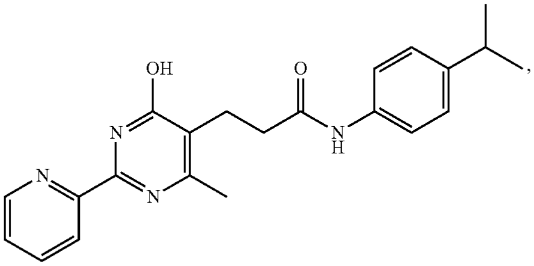,
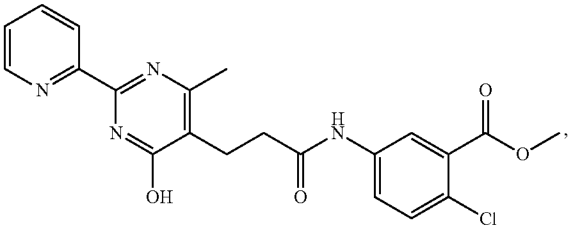,
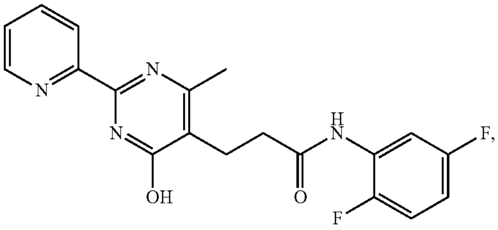,
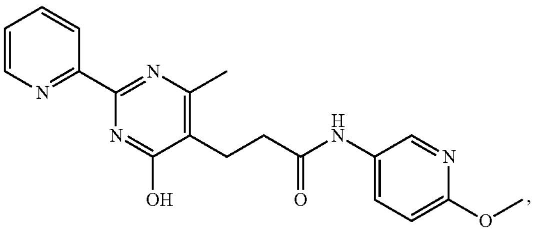,
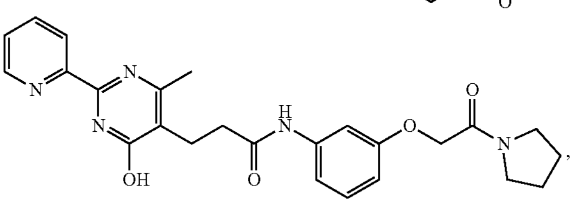,
-continued
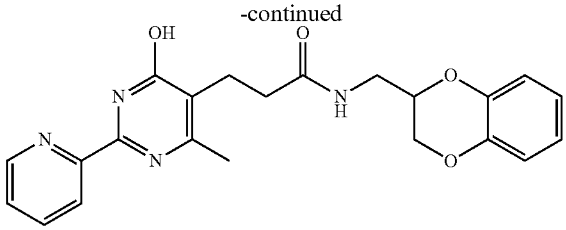,
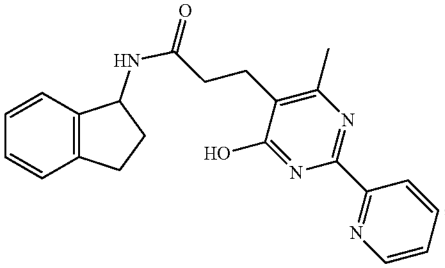,
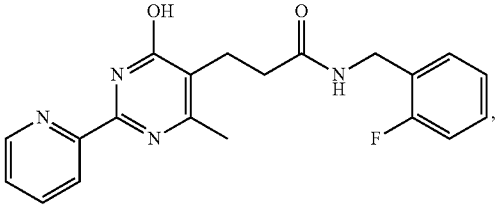,
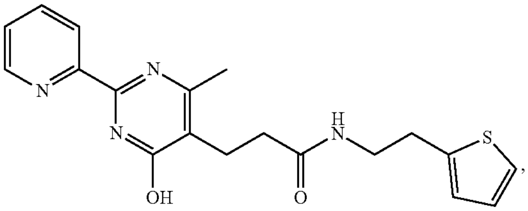,
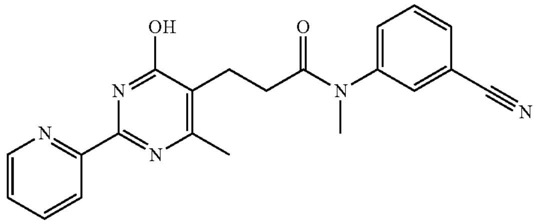 or
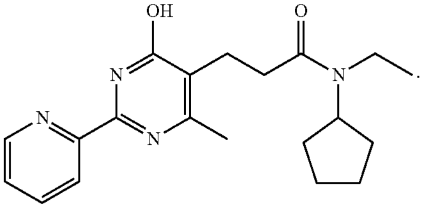.
In another embodiment of Formula VIIa, a compound of Formula VIIa is a compound wherein
$R^{1a}$ is pyridinyl or imidazolyl;
$R^{2a}$ is —Oalkyl;
$R^{8a}$ is H or alkyl.

In one embodiment, the compound of Formula VIIa is:

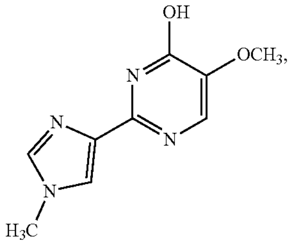

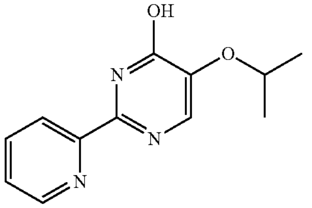

or

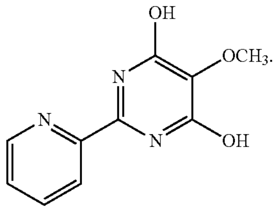

In one embodiment, the compound of Formula VIIa is:

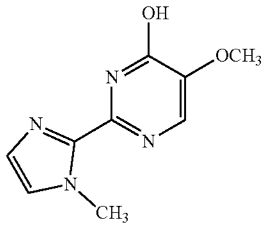

or

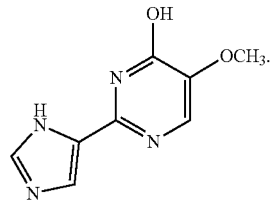

In another embodiment of Formula VIIa, a compound of Formula VIIa is a compound wherein $R^{1a}$ is aminoalkyl or aminocycloalkyl;

$R^{2a}$ is —Oalkyl;

$R^{8a}$ is H or alkyl.

In one embodiment, the compound of Formula VIIa is:

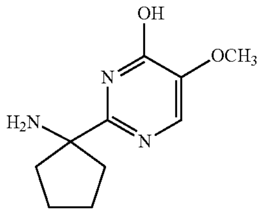

or

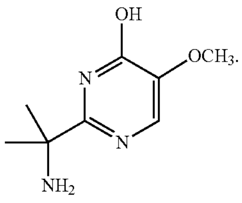

In one embodiment, the compound of Formula VIIa is selected with the proviso that the compound is not

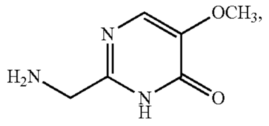

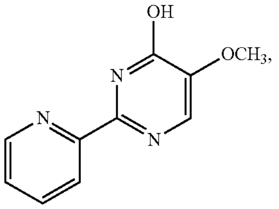

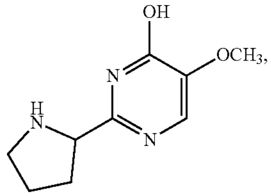

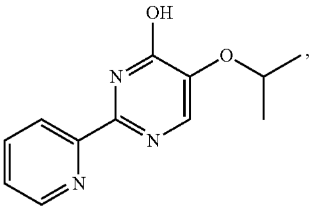

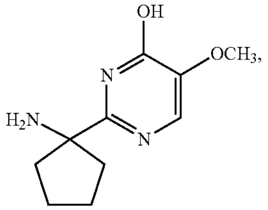

or

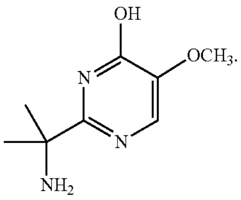

In one embodiment, the compound of Formula VIIa is selected with the proviso that the compound is not

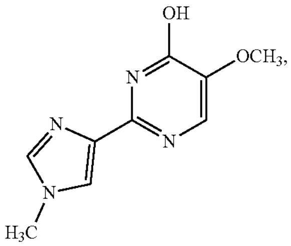

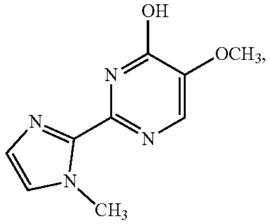

or

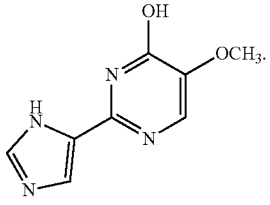

In certain embodiments, the compounds for use in the compositions and methods provided herein are of Formula VIIt:

Formula VIIt

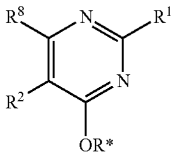

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

R* is alkyl, aryl or heteroaryl.

p is 0-2.

In one embodiment, the compound of Formula VIIt is

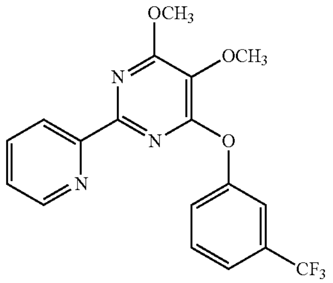

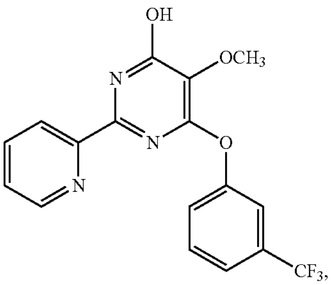

,

-continued

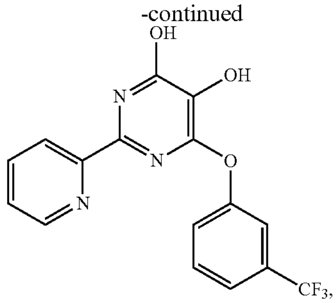

, or

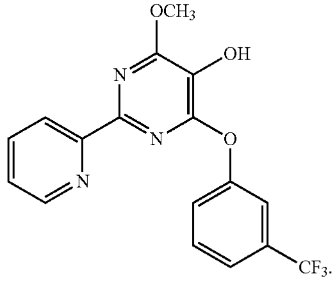

.

In certain embodiments, the compounds for use in the compositions and methods provided herein are of Formula VIIIa or Formula VIIIb:

Formula VIIIa

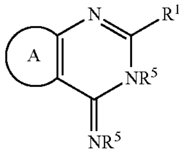

Formula VIIIb

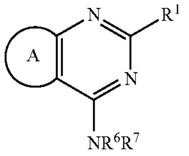

or pharmaceutically acceptable derivatives thereof, wherein $R^1$, is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

A is a substituted or unsubstituted 5 or 6 membered aryl, heteroaryl, carbocyclic or heterocyclic ring.

In one embodiment of Formula VIIIa, A is a pyrazole ring.

In one embodiment, the compound of Formula VIIIa is

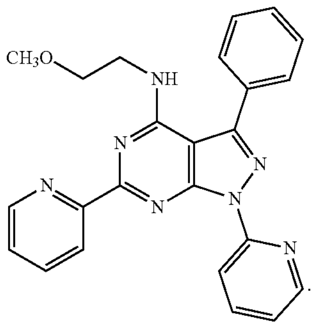

In another embodiment, the compound of Formula VIIIa is a compound of Formula VIIIa1:

Formula VIIIa1

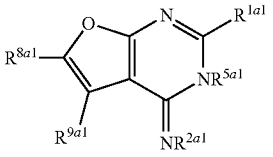

or pharmaceutically acceptable derivatives thereof, wherein $R^{1a1}$ is H, aryl or heteroaryl;

$R^{2a1}$ is H, alkyl, alkoxy or aryloxy;

$R^{8a1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9a1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5a1}$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment of Formula VIIIa1, a compound of Formula VIIIa1 is a compound wherein $R^{1a1}$ is H;

$R^{2a1}$ is H;

$R^{8a1}$ is phenyl, wherein phenyl is substituted with methoxy;

$R^{9a1}$ is phenyl, wherein phenyl is substituted with methoxy;

$R^{5a1}$ is depicted below:

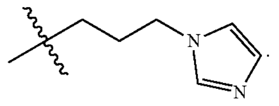 [SMILES: *CCCn1ccnc1]

In one embodiment, the compound of Formula VIIIa1 is:

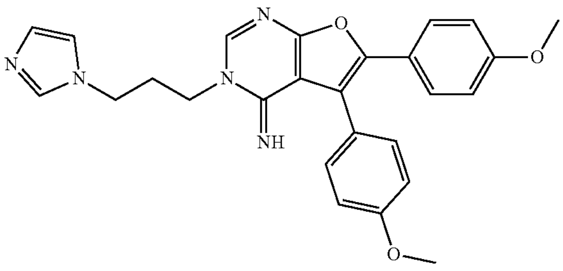

In another embodiment, the compound of Formula VIIIb is a compound of Formula VIIIb1:

Formula VIIIb1

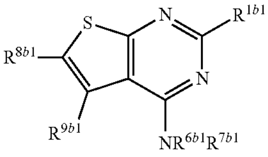

or pharmaceutically acceptable derivatives thereof, wherein $R^{1b1}$ is H, alkyl, aryl or heteroaryl;

$R^{8b1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b1}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b1}$ and $R^{7b1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or V' and $R^{7b1}$ are combined to form a cyclic structure including the nitrogen atom to which they are both attached; and p is 0-2.

In another embodiment of Formula VIIIb1, a compound of Formula VIIIb1 is a compound wherein $R^{1b1}$ is 2-pyridyl;

$R^{8b1}$ is H, methyl or phenyl;

$R^{9b1}$ is H, alkyl, alkenyl, alkynyl, substituted aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b1}$ and $R^{7b1}$ are independently selected from hydrogen, alkyl, alkenyl, alkynyl, aryl, heterocyclyl, cycloalkyl, alkylcarbonyl, cycloalkylcarbonyl, or arylcarbonyl, or $R^{6b1}$ and $R^{7b1}$ are combined to form a cyclic structure including the nitrogen atom to which they are both attached; and wherein $NR^{6b1}R^{7b1}$ is not NHMe, NHEt, NHn-Pr, NHbenzyl or NH-2-phenethyl; and wherein $NR^{6b1}R^{7b1}$ is not morpholine when $R^{8b1}$ and $R^{9b1}$ are both hydrogen; and p is 0-2.

In another embodiment of Formula VIIIb1, a compound of Formula VIIIb1 is a compound wherein $R^{1b1}$ is 2-pyridyl;

$R^{8b1}$ is H;

$R^{9b1}$ is substituted aryl, cycloalkyl, heterocyclyl, heteroaryl, halo, $C(O)NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b1}$ and $R^{7b1}$ are independently selected from hydrogen, alkyl, alkenyl, alkynyl, aryl, heterocyclyl, cycloalkyl, alkylcarbonyl, cycloalkylcarbonyl, or arylcarbonyl, or $R^{6b1}$ and $R^{7b1}$ are combined to form a cyclic structure including the nitrogen atom to which they are both attached; and wherein $NR^{6b1}R^{7b1}$ is not NHMe, NHEt, NHn-Pr, $NHCH_2CH_2OH$, NHbenzyl optionally substituted on the phenyl ring, or NH-2-phenethyl optionally substituted on the phenyl ring; and wherein $NR^{6b1}R^{7b1}$ is not morpholine when $R^{8b1}$ and $R^{9b1}$ are both hydrogen.

In another embodiment of Formula VIIIb1, a compound of Formula VIIIb1 is a compound wherein $R^{1b1}$ is H, methyl, or pyridinyl;

$R^{8b1}$ is H or methyl;

$R^{9b1}$ is H or phenyl, wherein phenyl is optionally substituted with one or two substituents selected from methoxy;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^{6b1}$ and $R^{7b1}$ are independently selected from H, methyl, hydroxypropyl, methoxypropyl, hydroxyethyl, morpholinylethyl, furanylmethyl, or one of the following:

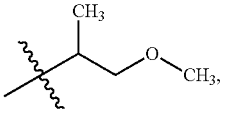

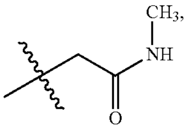

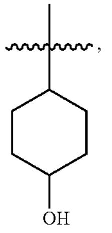

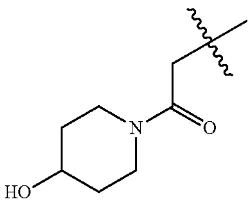

or

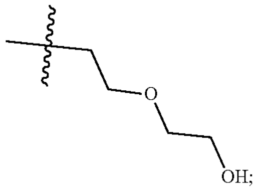

or $R^{6b1}$ and $R^{7b1}$ are combined to form a cyclic structure including the nitrogen atom to which they are both attached, as depicted below

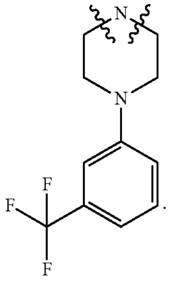

In one embodiment, the compound of Formula VIIIb1 is:
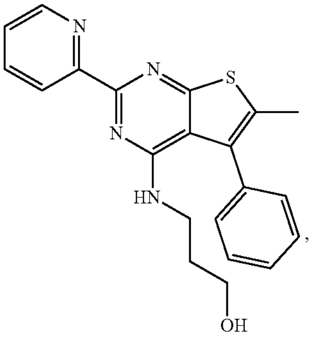
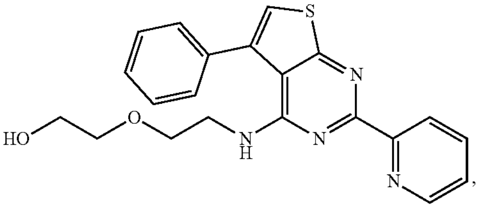
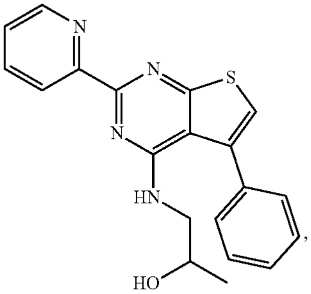
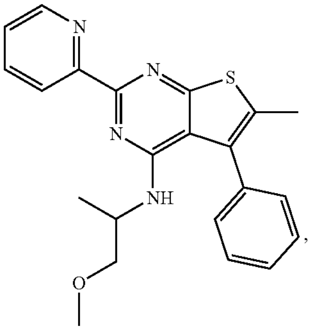
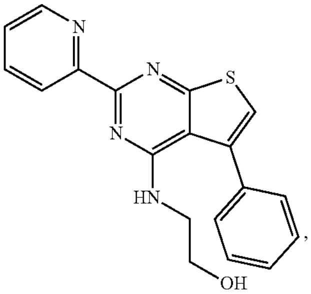
-continued
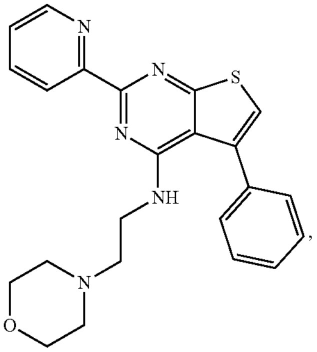
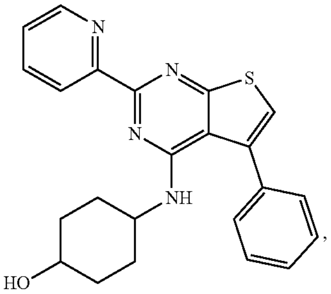
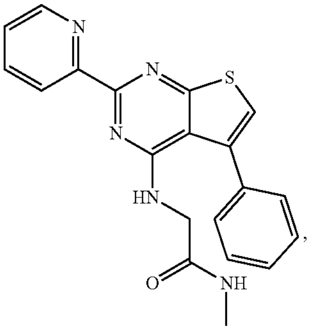
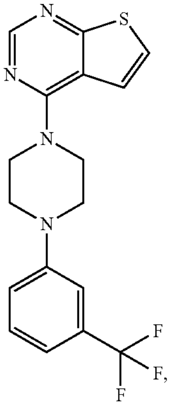
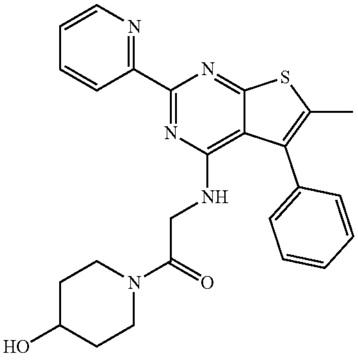
or -continued
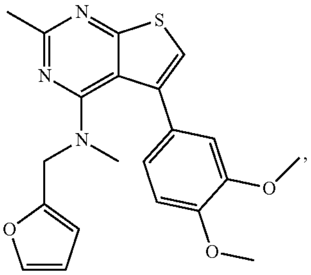
In another embodiment of Formula VIIIb1, a compound of Formula VIIIb1 is a compound wherein
$R^{1b1}$ is pyridinyl;
$R^{8b1}$ is H, methyl or phenyl;
$R^{9b1}$ is H, bromo or phenyl; and
$NR^{6b1}R^{7b1}$ is selected from
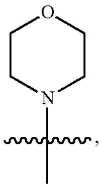, 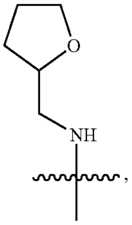, 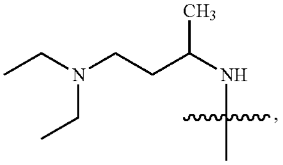,
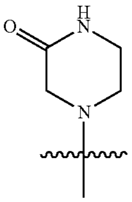, 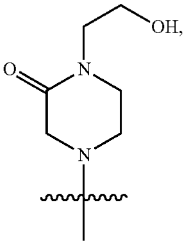, 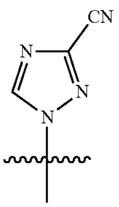
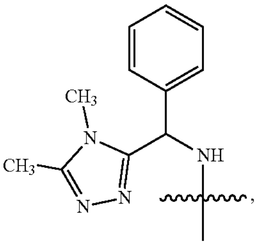, 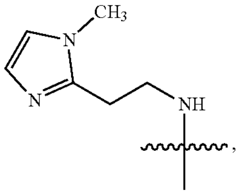,
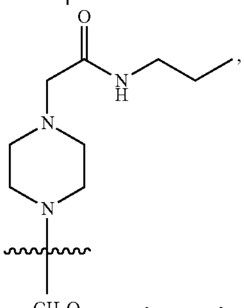
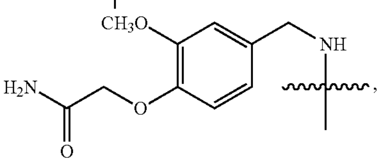,
-continued
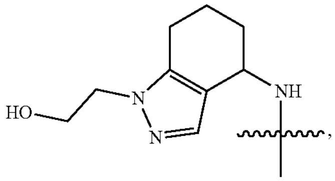,
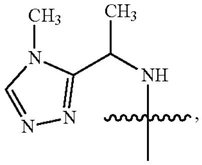, 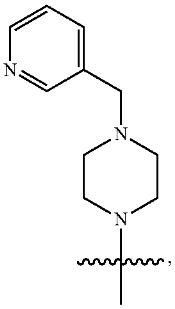, 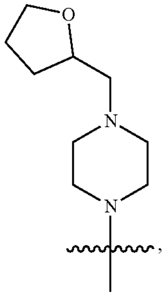,
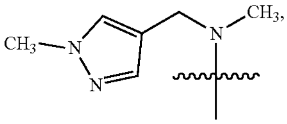
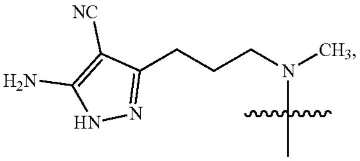
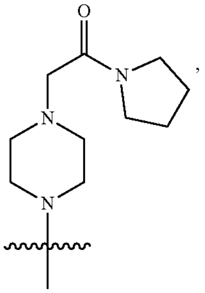, 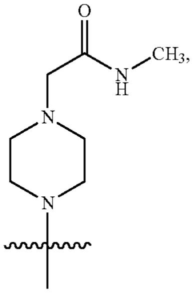
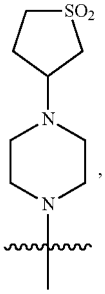, 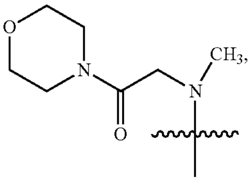 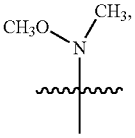
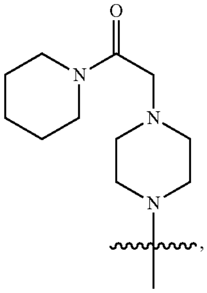, 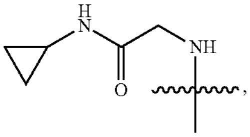, -continued
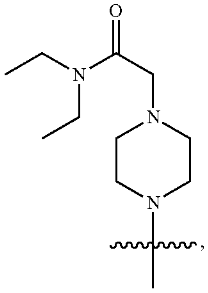,
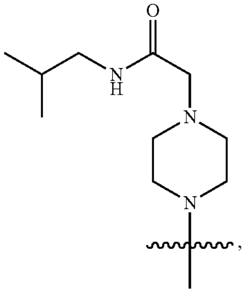,
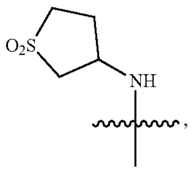,
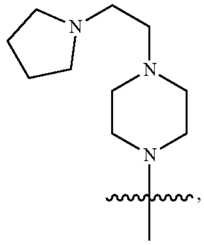,
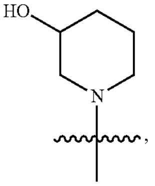,
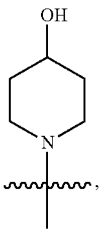,
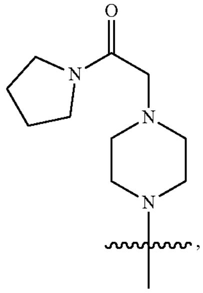,
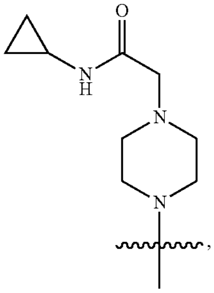,
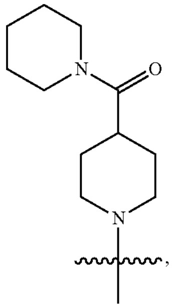,
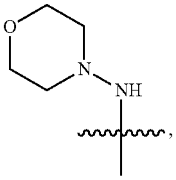,
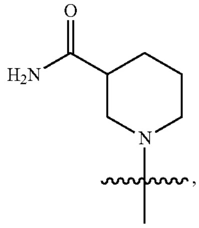,
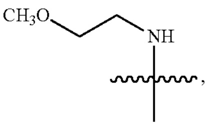,
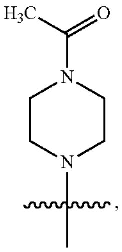,
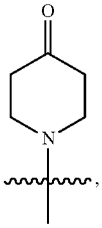,
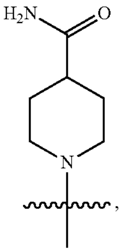,
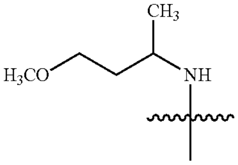
or
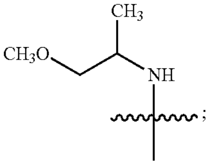;
wherein $NR^{6b1}R^{7b1}$ is not morpholine when $R^{8b1}$ and $R^{9b1}$ are both hydrogen.
In one embodiment, the compound of Formula VIIIb1 is:
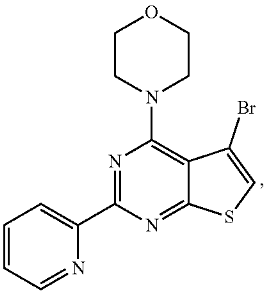,
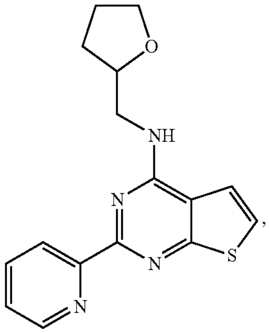,
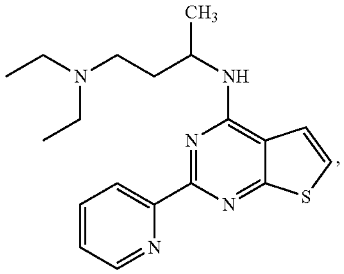,
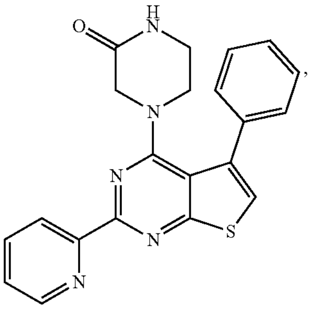,
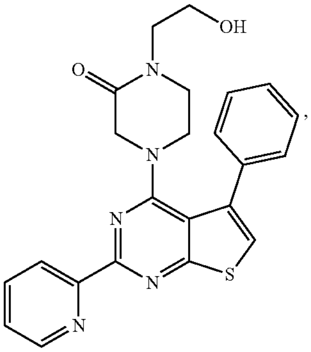,
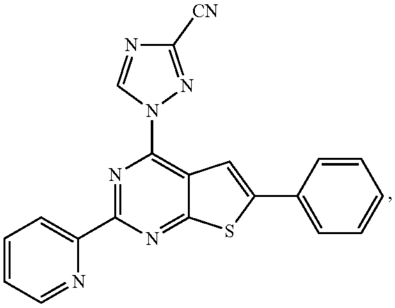, -continued
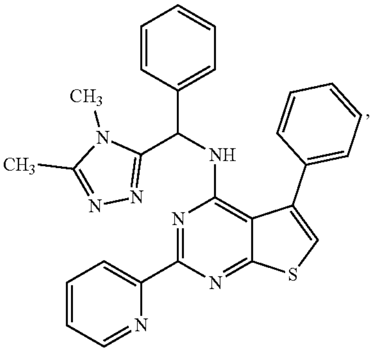
,
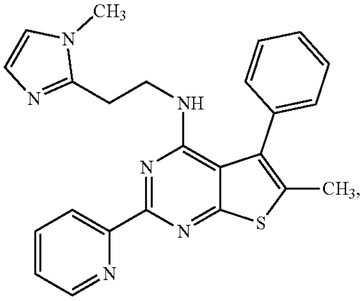
,
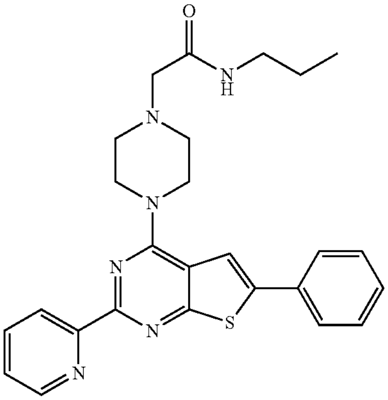
,
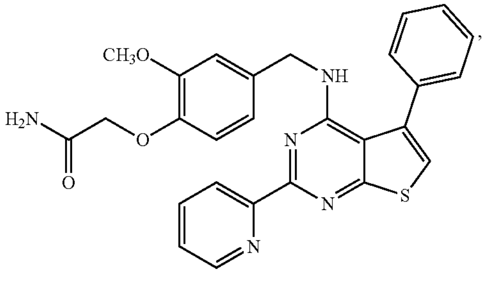
,
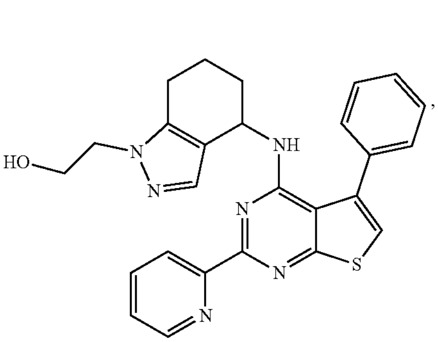
,
-continued
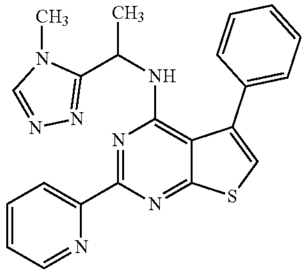
,
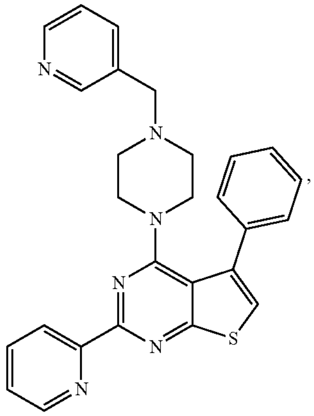
,
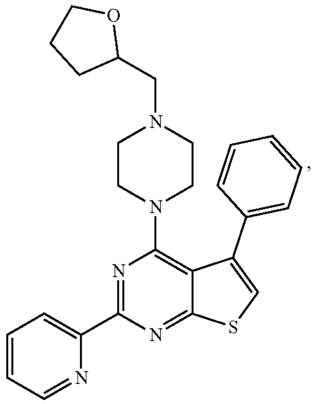
,
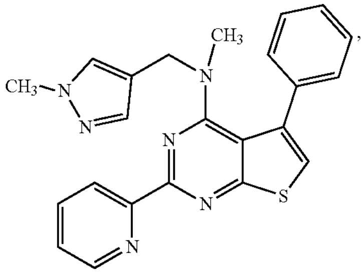
,
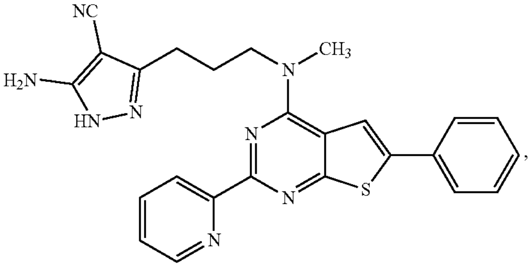
, -continued
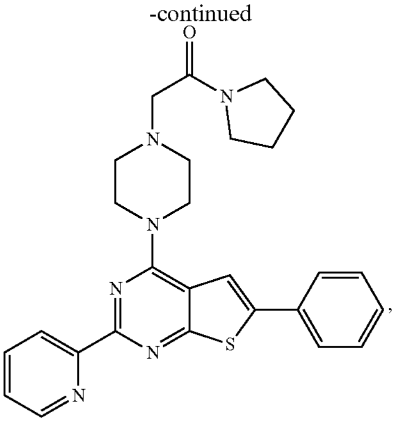
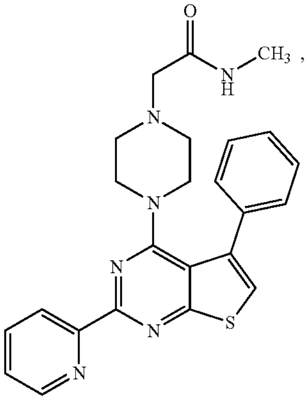
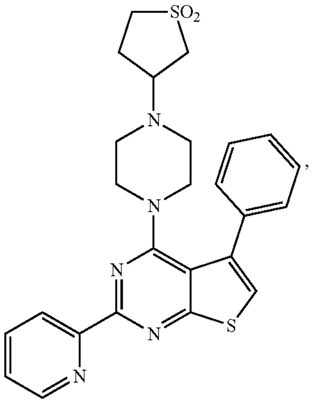
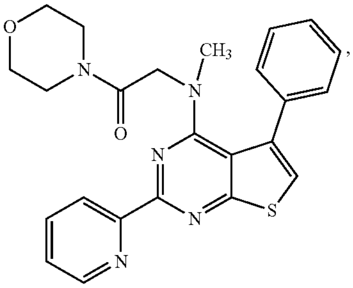
-continued
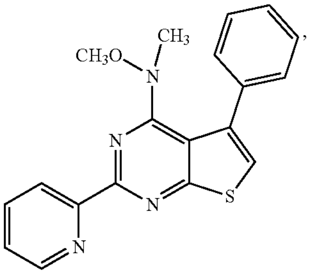
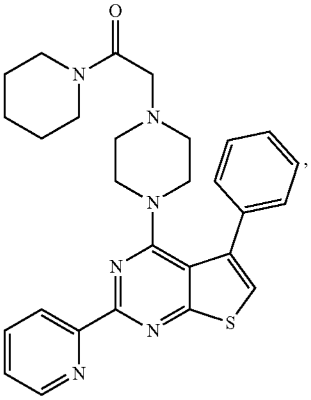
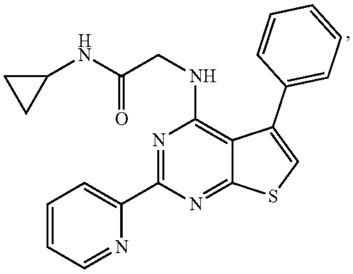
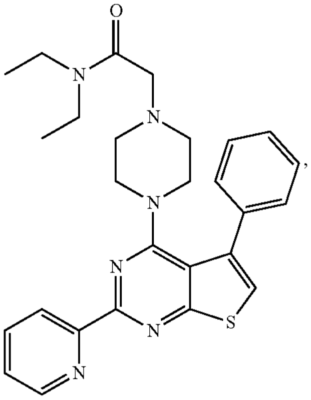

-continued
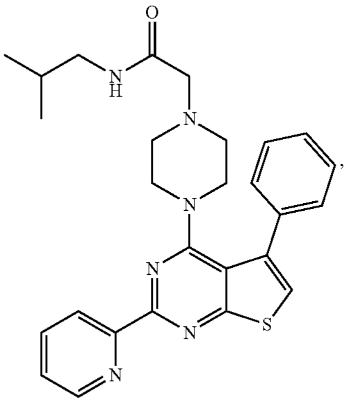
,
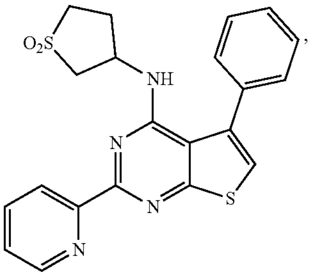
,
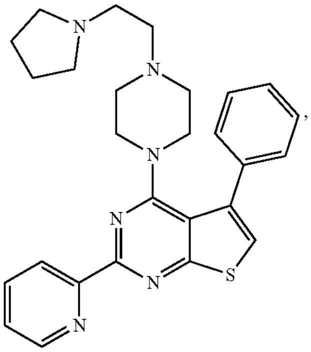
,
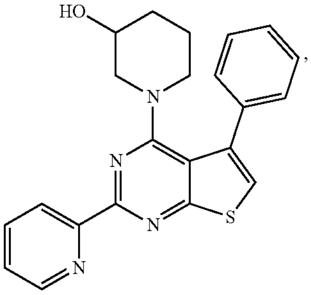
,
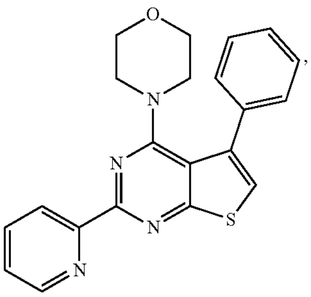
,
-continued
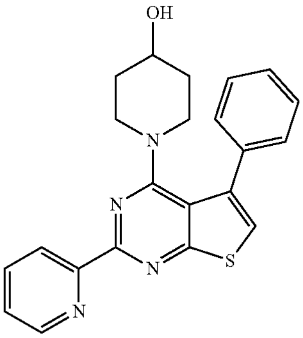
,
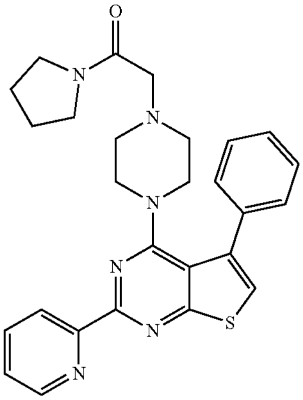
,
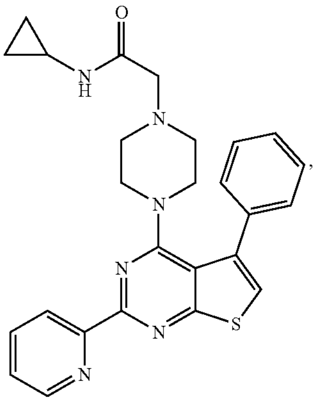
,
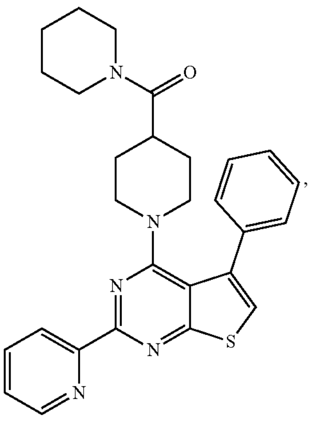
, -continued
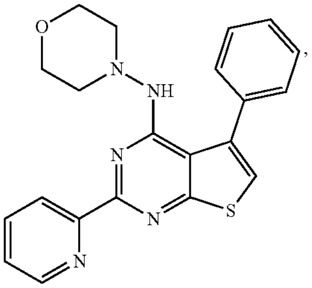
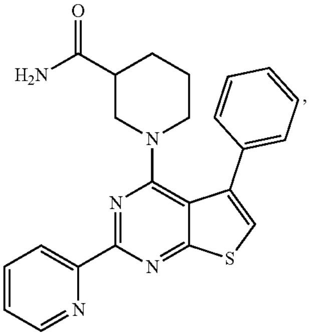
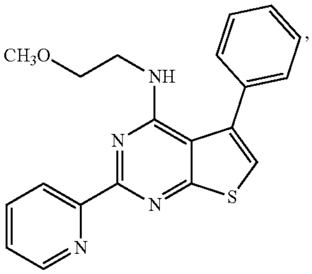
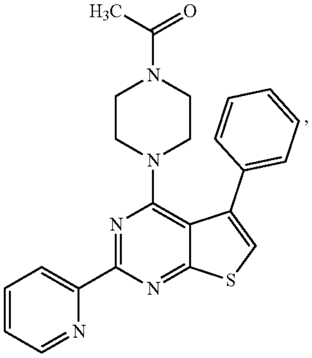
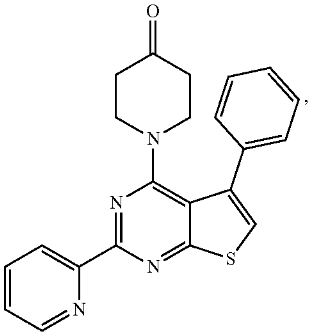
-continued
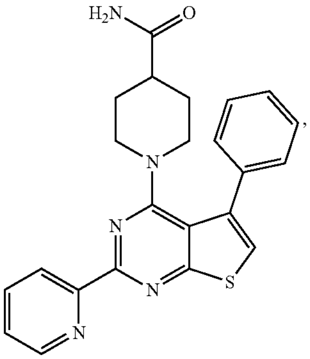
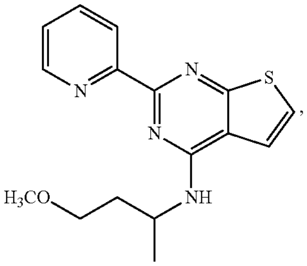
, or
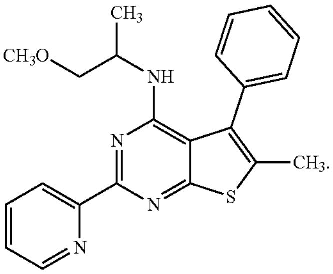
In another embodiment of Formula VIIIb1, a compound of Formula VIIIb1 is a compound wherein
$R^{1b1}$ is pyridinyl;
$R^{8b1}$ is H, methyl or phenyl;
$R^{9b1}$ is —C(O)NR$^6$R$^7$; and is selected from
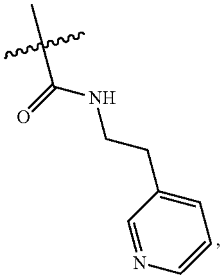
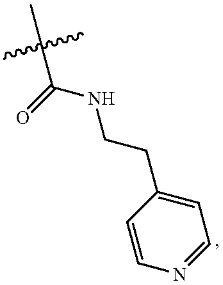

-continued
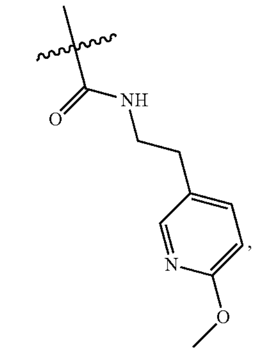,
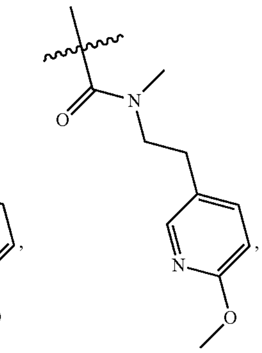,
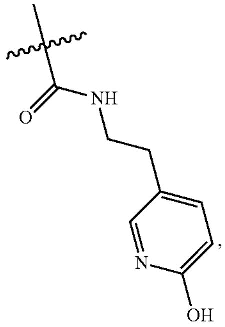,
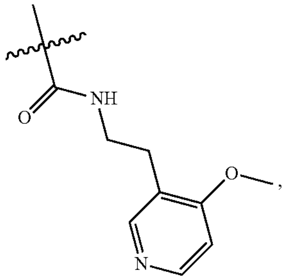,
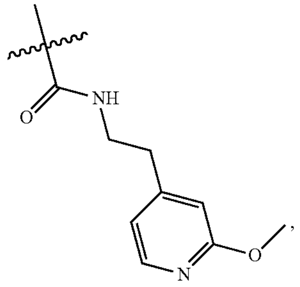,
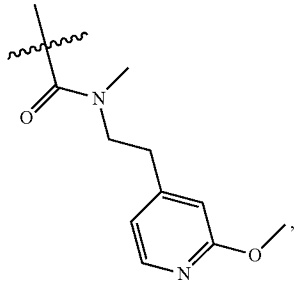,
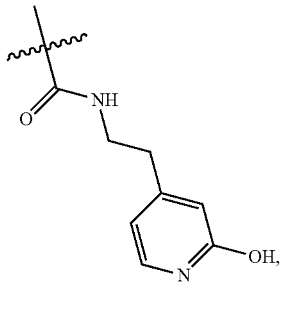
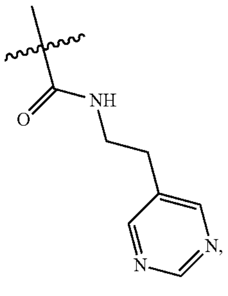
-continued
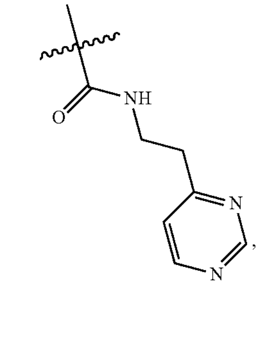,
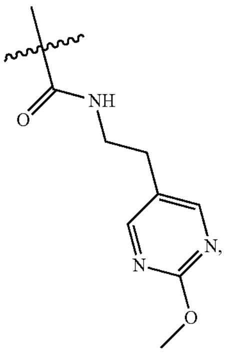
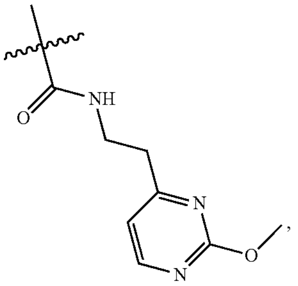,
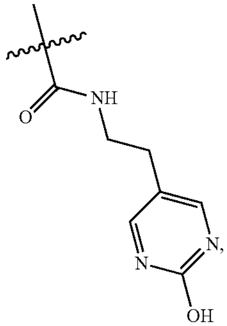
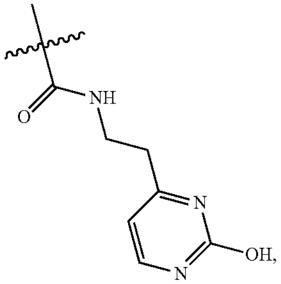
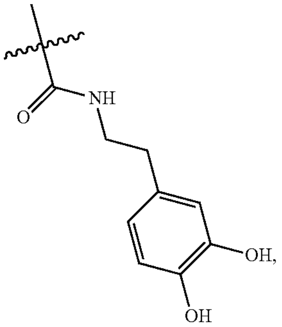
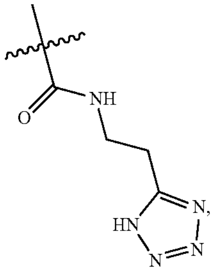
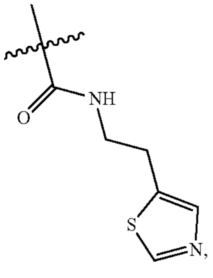
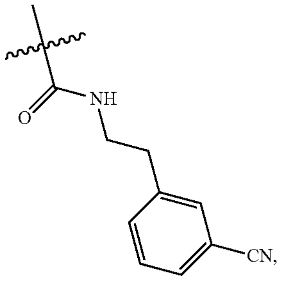

-continued
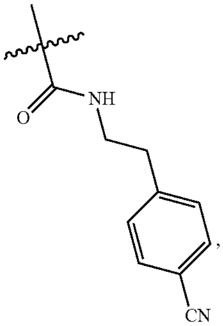,
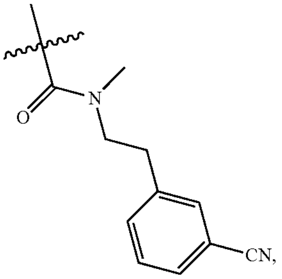,
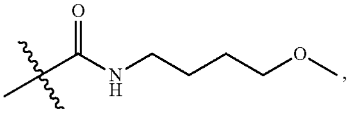,
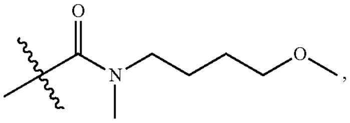,
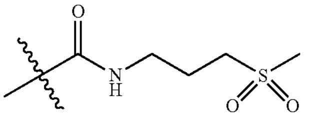 or
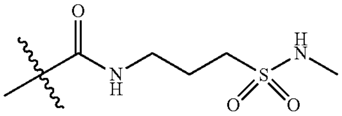;
$NR^{6b1}R^{7b1}$ is selected from
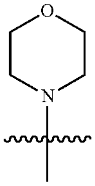 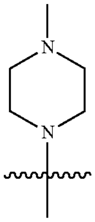 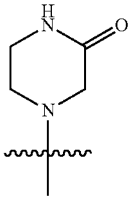 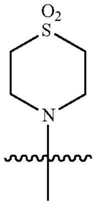
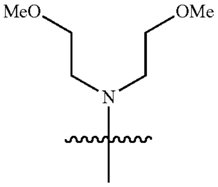 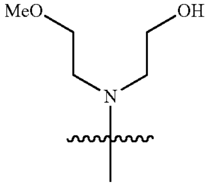
In another embodiment of Formula VIIIb1, a compound of Formula VIIIb1 is a compound wherein
$R^{1b1}$ is pyridinyl;
$R^{8b1}$ is H;
$R^{9b1}$ is H;
$R^{6b1}$ and $R^{ml}$ are independently selected from H,
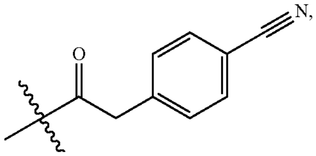,
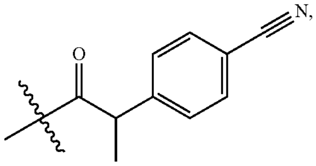,
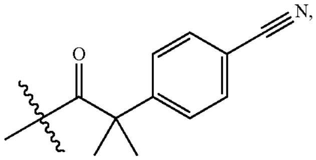,
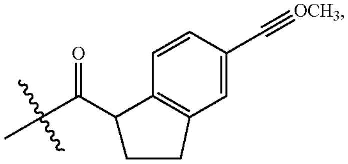,
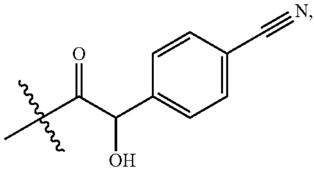,
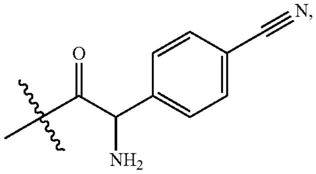,
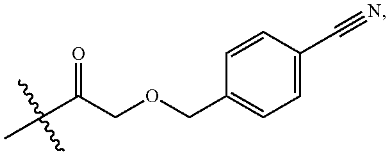,
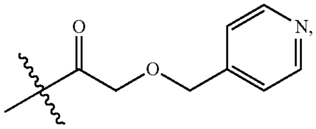,
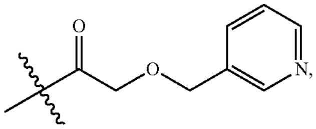,
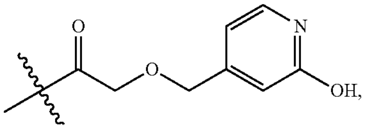,
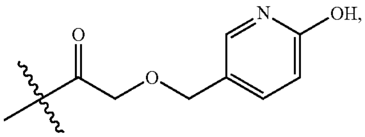, -continued

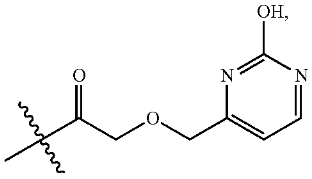

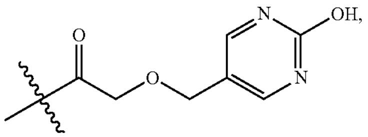

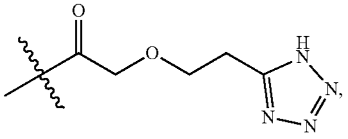

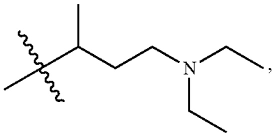

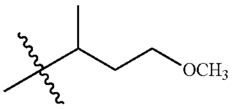

and

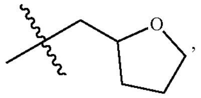

In one embodiment, the compound of Formula VIIIb1 is:

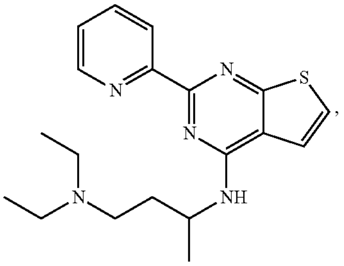

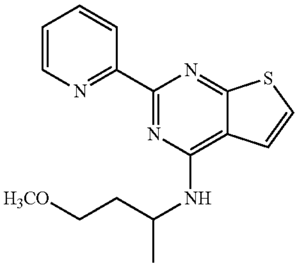

or

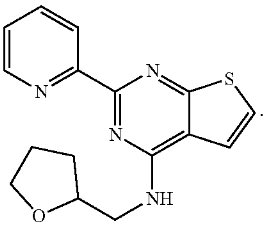

In another embodiment of Formula VIIIb1, a compound of Formula VIIIb1 is a compound wherein $R^{1b1}$ is pyridinyl or methoxypyridinyl;

$R^{8b1}$ is H;

$R^{9b1}$ is H, bromo, chloro, cyano, trifluoromethyl or phenyl; and $NR^{6b1}R^{7b1}$ is

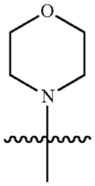 [SMILES: *N1CCOCC1]

In one embodiment, the compound of Formula VIIIb1 is:

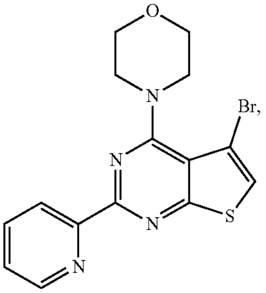

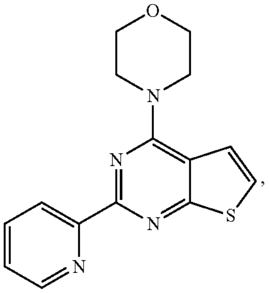

or

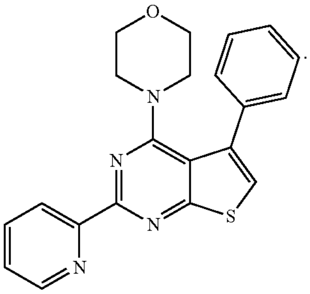

In another embodiment of Formula VIIIb1, a compound of Formula VIIIb1 is a compound wherein $R^{1b1}$ is pyridinyl;

$R^{8b1}$ is H;

$R^{9b1}$ is H; and $R^{6b1}$ and $R^{7b1}$ are independently selected from H,

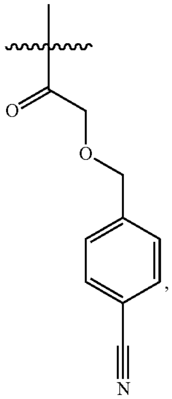
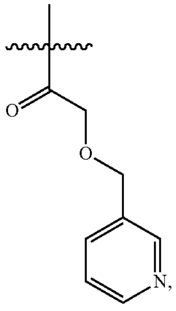
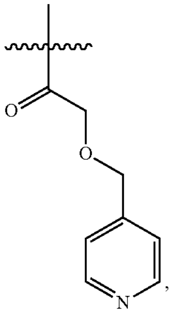
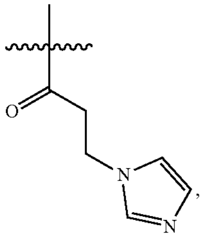
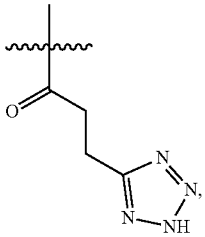
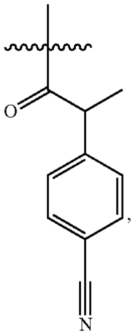
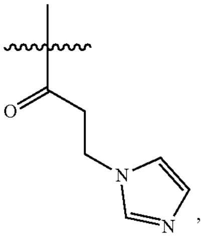
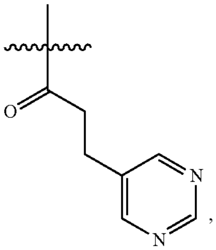
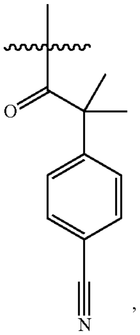
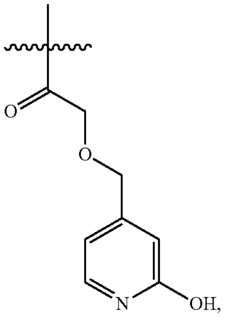
and
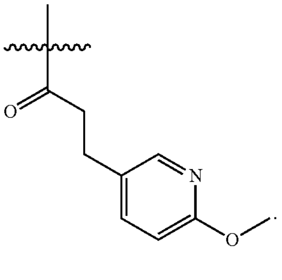
In one embodiment, the compound of Formula VIIIb1 is:
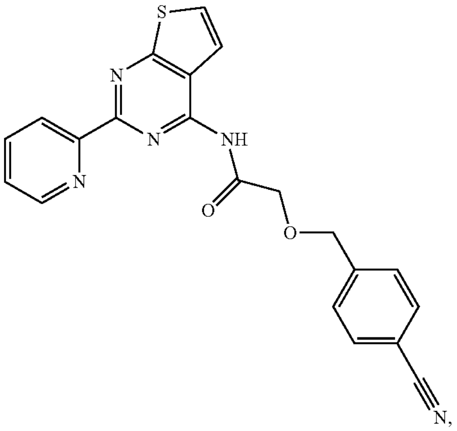
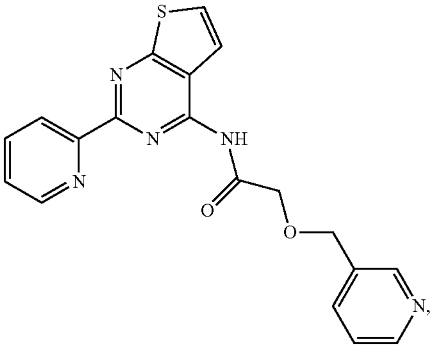
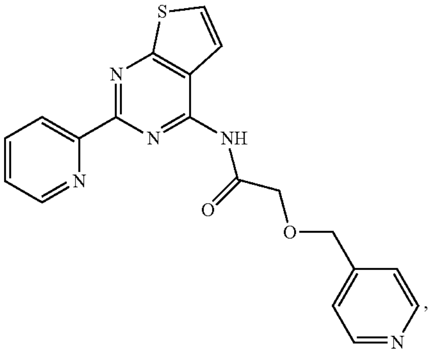
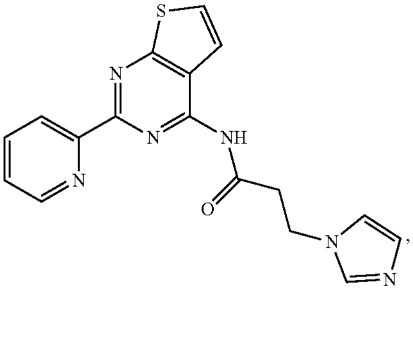

-continued
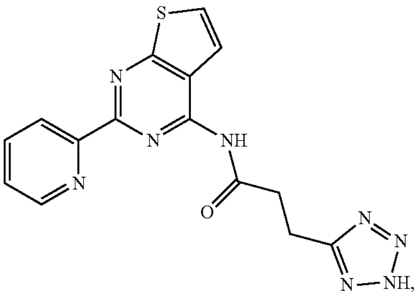
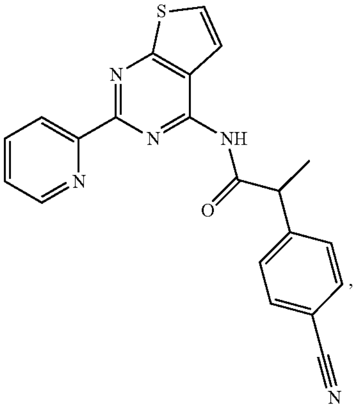
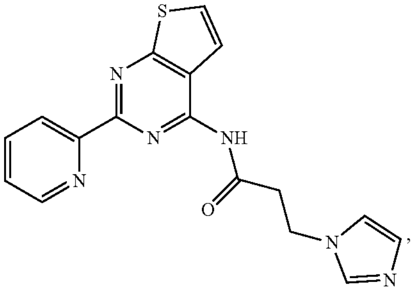
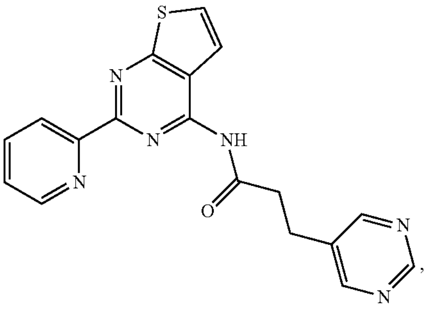
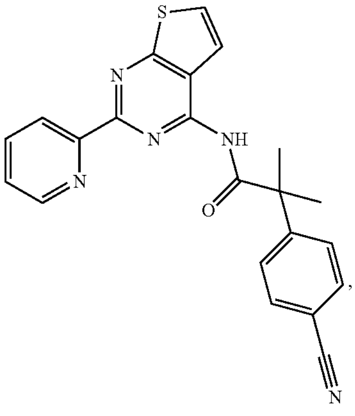
-continued
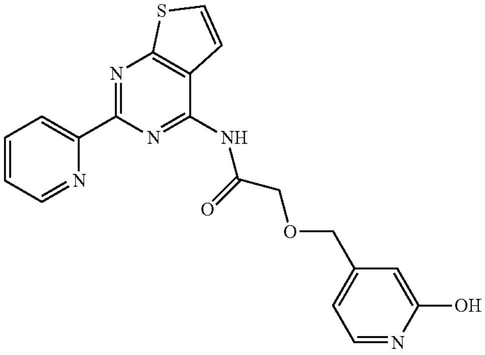
or
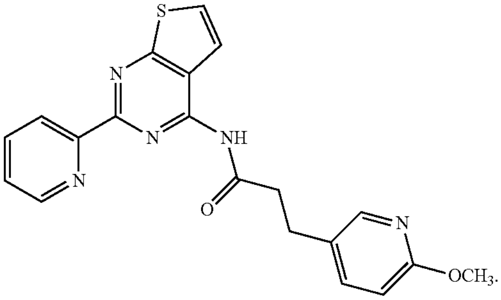
In another embodiment of Formula VIIIb1, a compound of Formula VIIIb1 is a compound wherein
$R^{1b1}$ is pyridinyl;
$R^{8b1}$ is H;
$NR^{6b1}R^{7b1}$ is morpholino or —$N(CH_2CH_2OCH_3)_2$; and
$R^{9b1}$ is —$C(O)NR^6R^7$; and is selected from
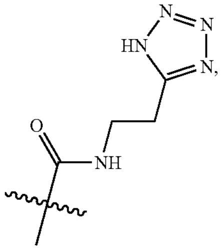
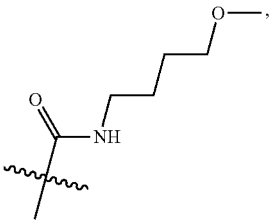
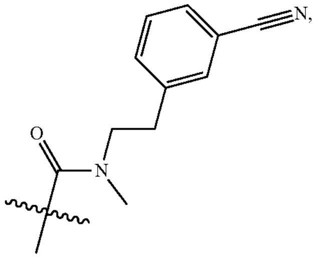
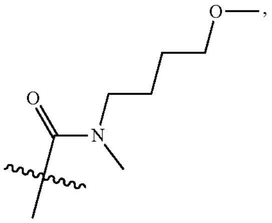
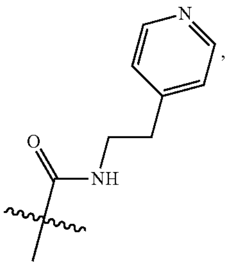

-continued
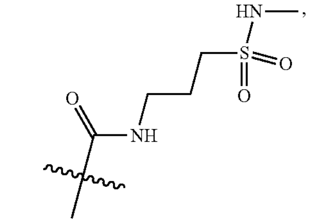
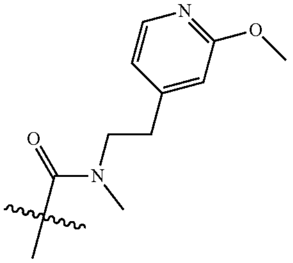
and
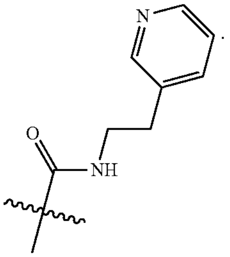
In one embodiment, the compound of Formula VIIIb1 is:
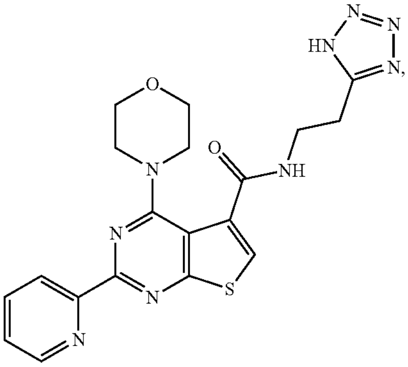
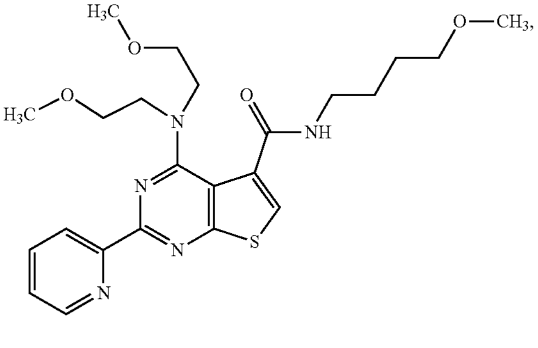
-continued
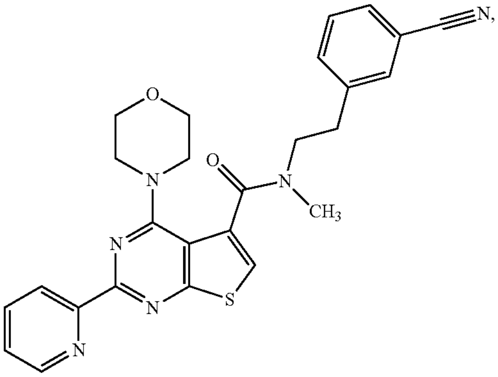
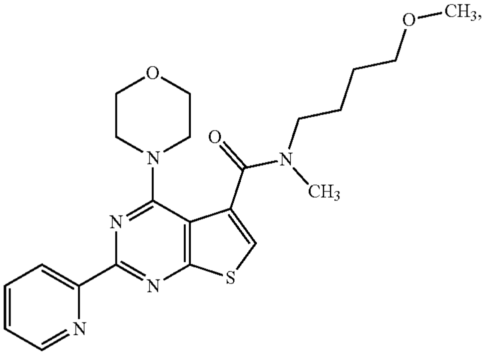
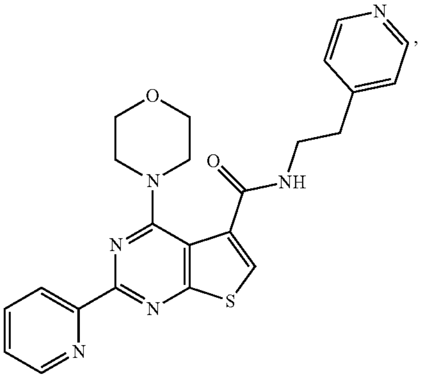
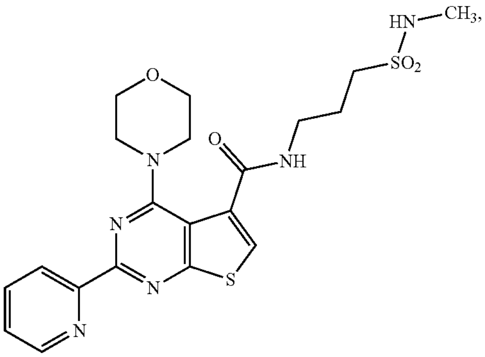

-continued
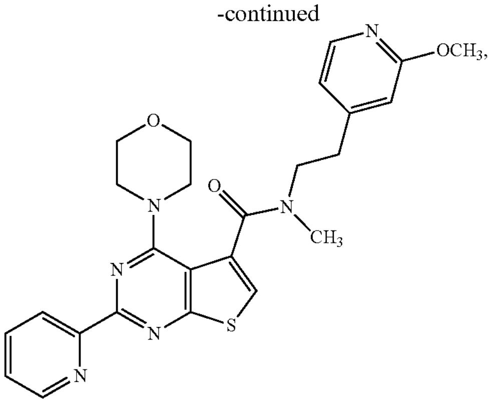
or
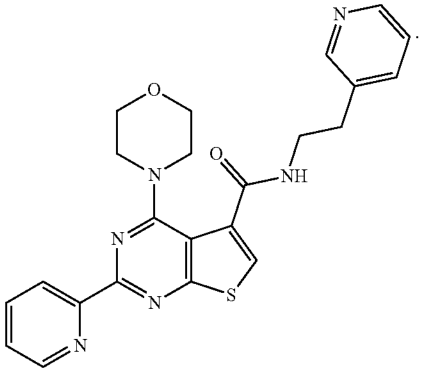
In another embodiment of Formula VIIIb1, a compound of Formula VIIIb1 is a compound wherein
$R^{1b1}$ is pyridinyl;
$R^{8b1}$ is H;
$NR^{6b1}R^{7b1}$ is $NH_2$, morpholino or $—N(CH_2CH_2OCH_3)_2$; and
$R^{9b1}$ is $—C(O)NR^6R^7$; and is selected from
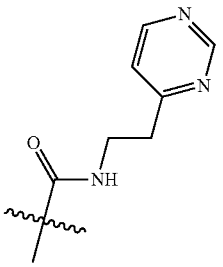
and
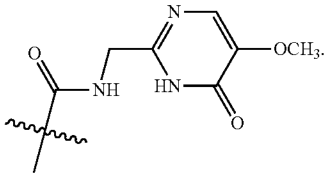
In one embodiment, the compound of Formula VIIIb1 is:
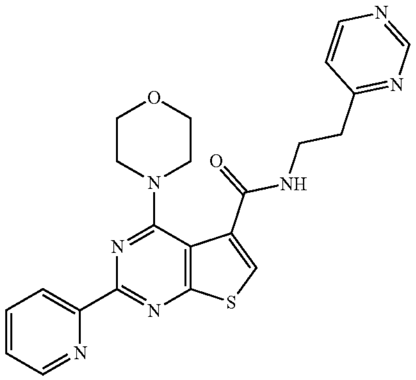
or
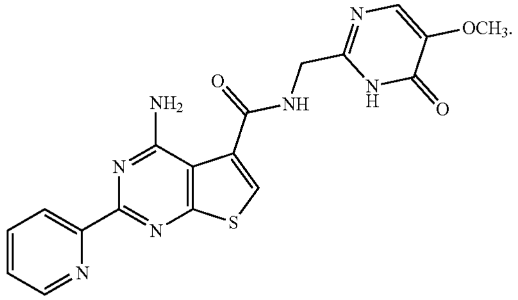
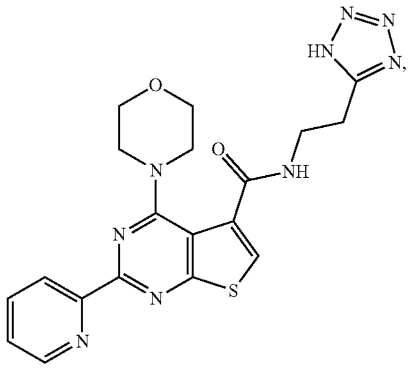
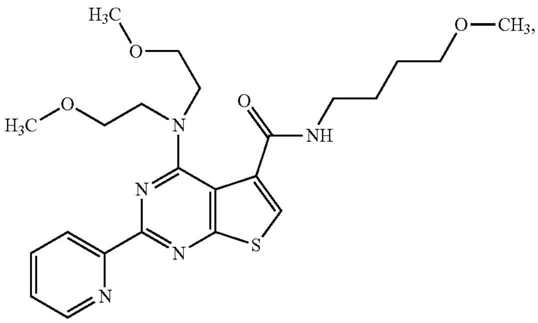

-continued

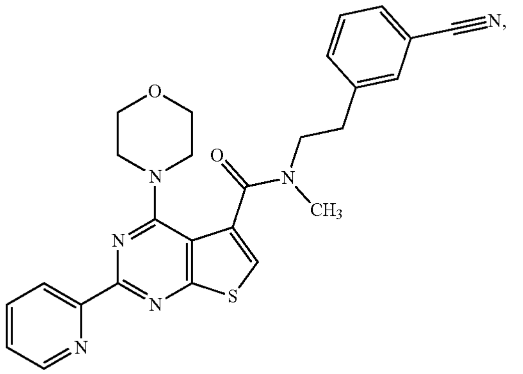

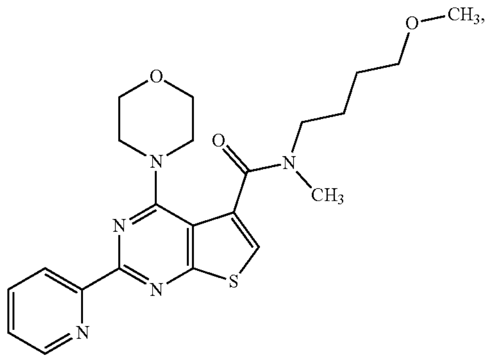

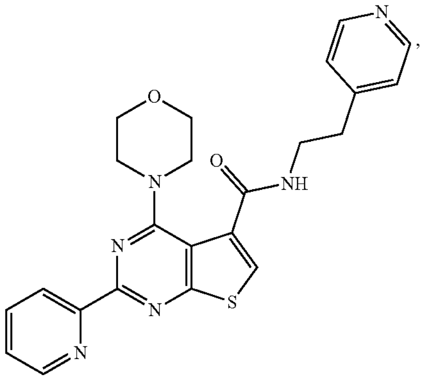

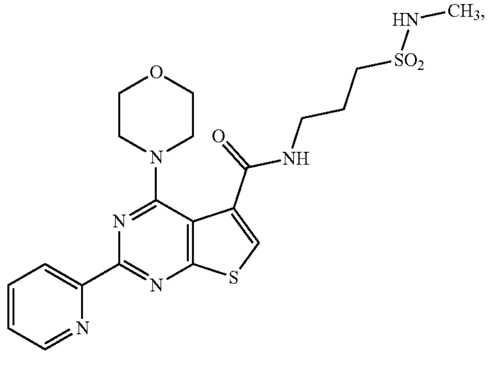

-continued

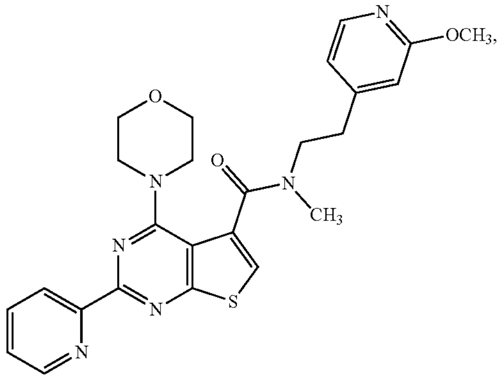

or

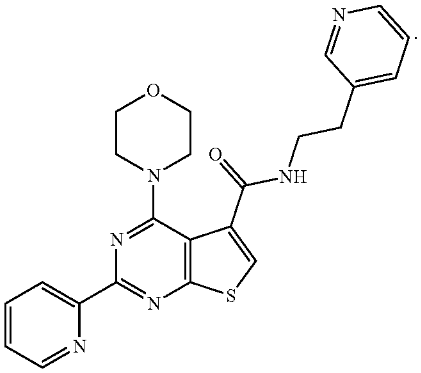

In another embodiment of Formula VIIIb1, a compound of Formula VIIIb1 is a compound wherein $R^{1b1}$ is pyridinyl, N-methyl-imidazolyl;

$R^{8b1}$ is pyridinyl, phenyl, pyrimidinyl, methyl, tetrahydropyranyl;

$NR^{6b1}R^{7b1}$ is

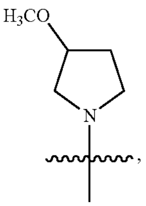

morpholino, —$NHCH_2CH_2OCH(CH_3)_2$, —$NHCH(CH_3)CH_2OCH_3$, —$NHCH(CH_3)CH_2OH$, —$N(CH_3)CH_2CH_2OCH_3$, —$NHCH_2CH_2OCF_3$, —$NHCH_2CH(CH_3)OH$, —$NHCH_2CH_2CH_2OH$, —$NHCH_2CH_2CH_2OCH_3$, —$NHCH_2CH_2O$-cPr, —$NHCH_2CH_2OCH_2CH_3$ or —$NHCH_2CH_2OCH_3$; and $R^{9b1}$ is pyridyl or phenyl.

In one embodiment, the compound of Formula VIIIb1 is:
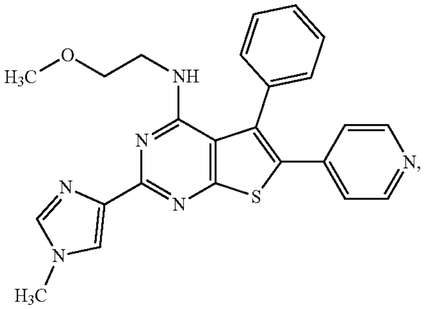
,
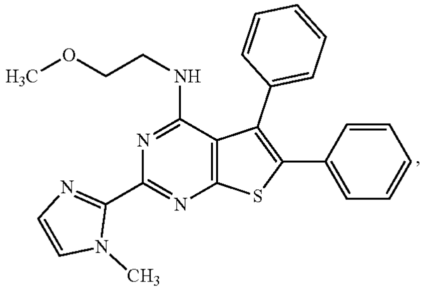
,
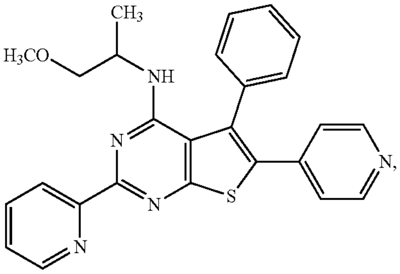
,
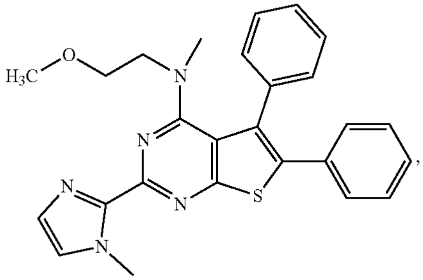
,
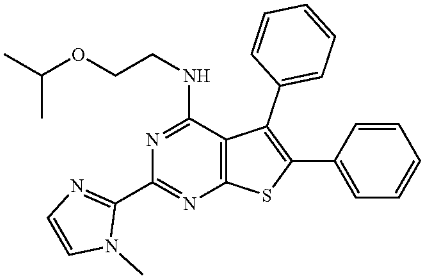
,
-continued
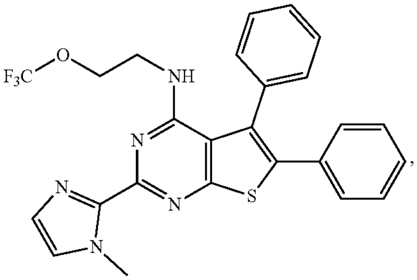
,
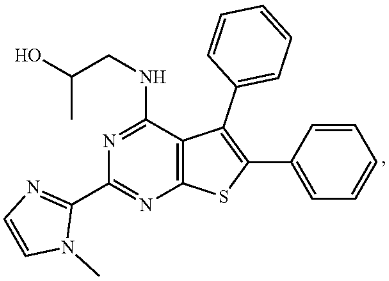
,
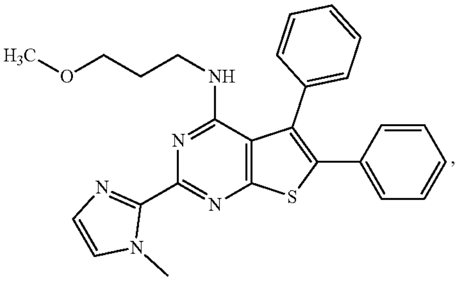
,
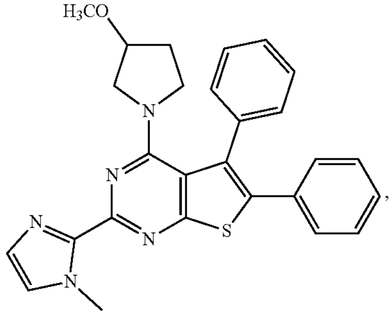
,
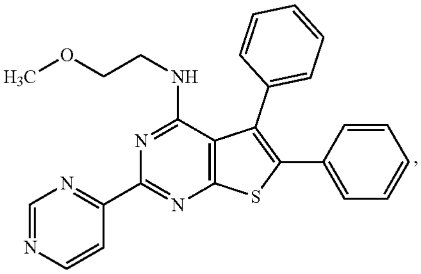
,
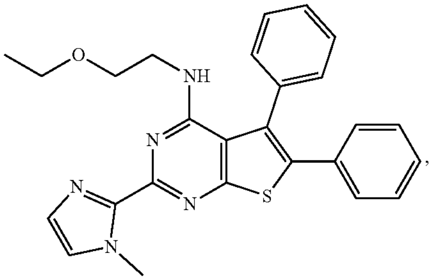
, -continued
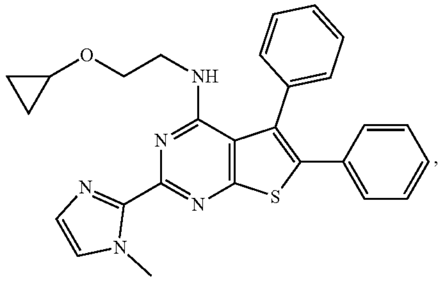,
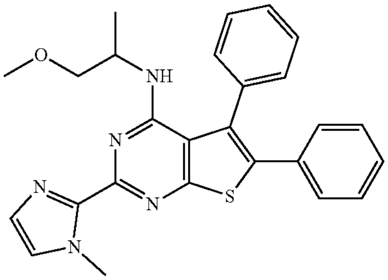,
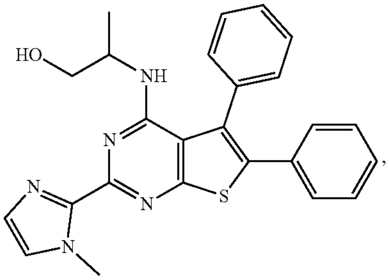,
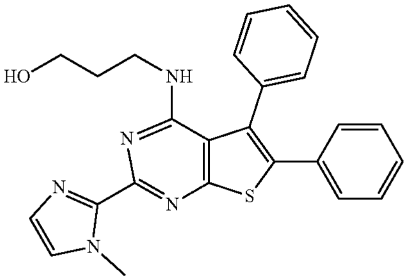,
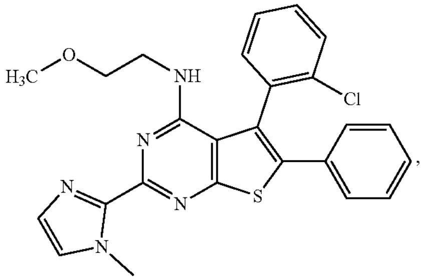,
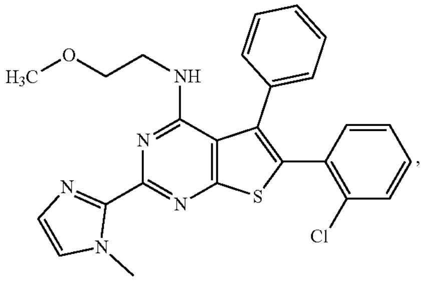,
-continued
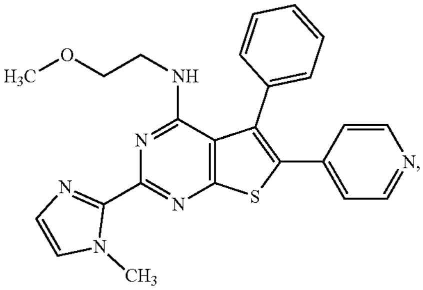,
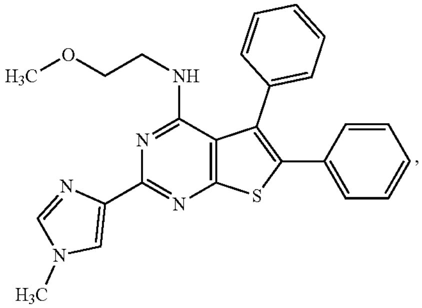,
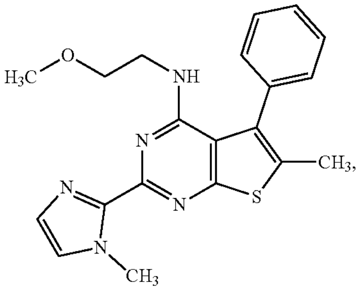,
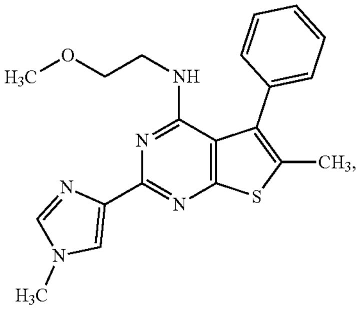,
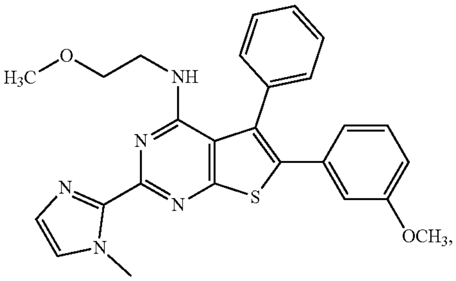, -continued

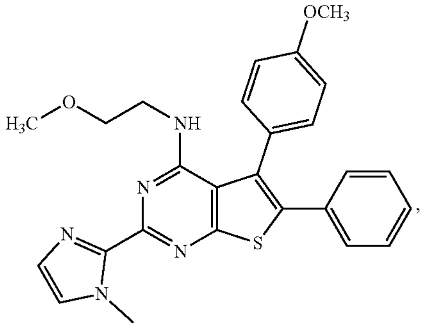

,

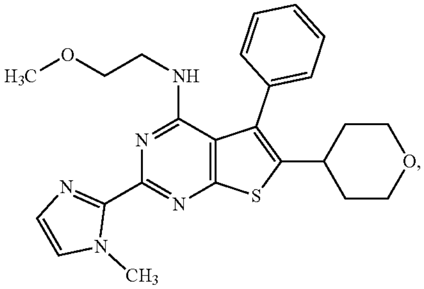

,

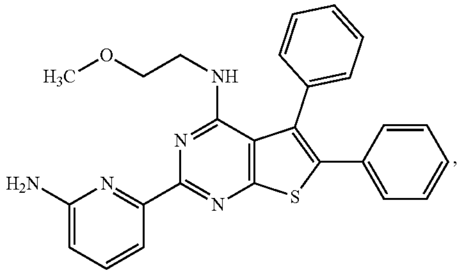

,

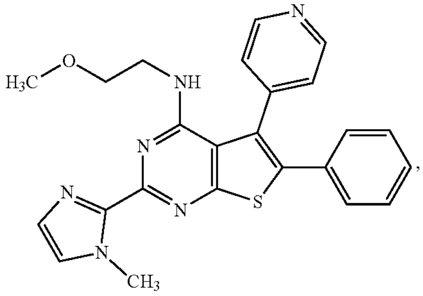

,

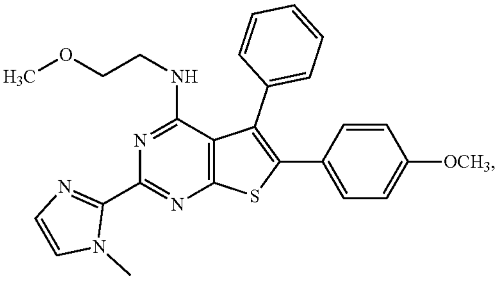

,

-continued

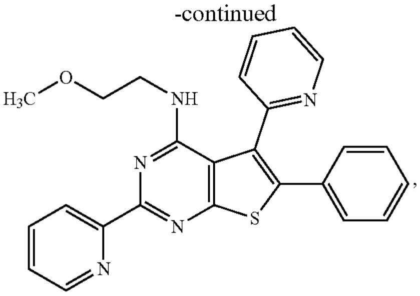

, or

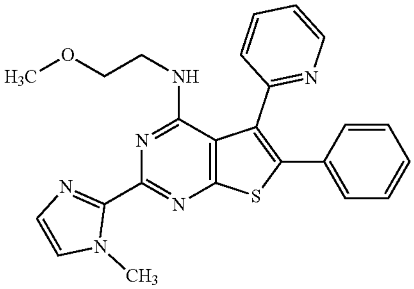

.

In another embodiment, the compound of Formula VIIIb is a compound of Formula VIIIb2:

Formula VIIIb2

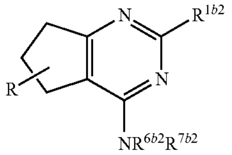

or pharmaceutically acceptable derivatives thereof, wherein $R^{1b2}$ is H, aryl or heteroaryl;

$R^{6b2}$ and $R^{7b2}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b2}$ and $R^{7b2}$ are combined to form a cyclic structure including the nitrogen atom to which they are both attached;

p is 0-2; and

R may consist of 0-6 substituents independently selected from H or alkyl.

In another embodiment, the compound of Formula VIIIb is a compound wherein $R^{1b2}$ is pyridinyl;

$R^{6b2}$ and $R^{7b2}$ are independently selected from one of the following:

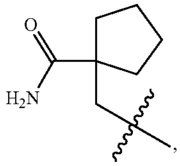

,

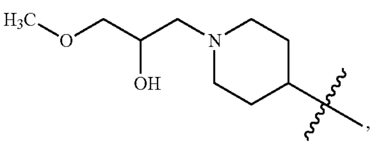

,

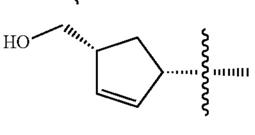

,

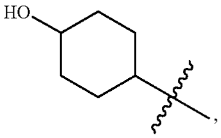

,

-continued
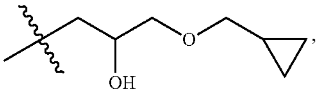
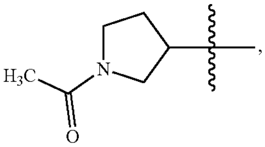
,
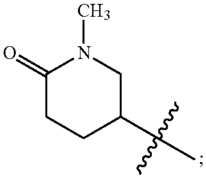
; or
$R^{6b2}$ and $R^{7b2}$ are combined to form a cyclic structure including the nitrogen atom to which they are both attached, as depicted below:
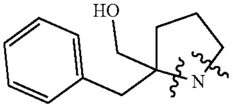
R is H.
In one embodiment, the compound of Formula VIIIb2 is:
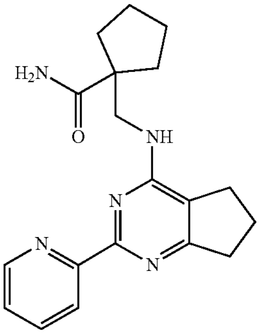
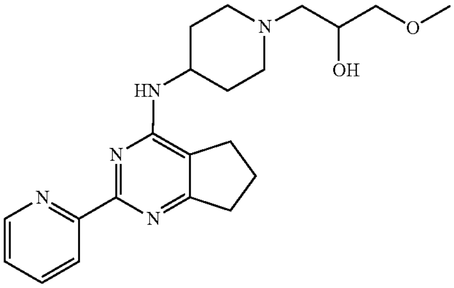
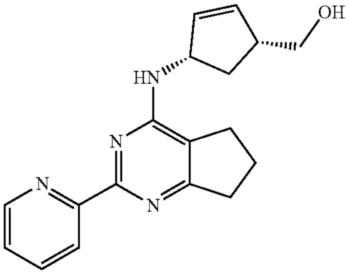
-continued
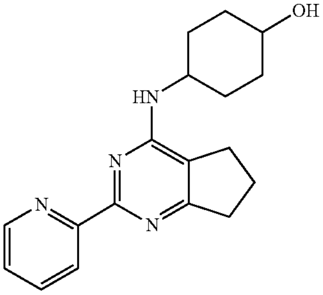
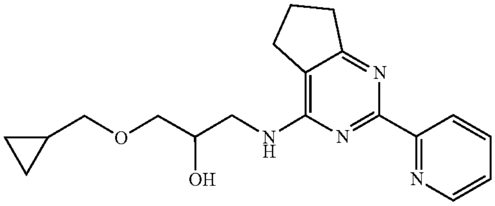
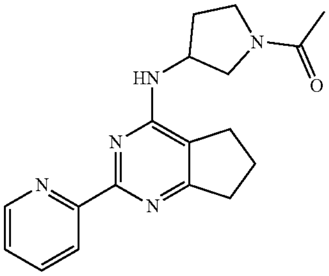
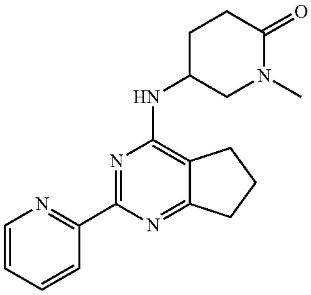
or
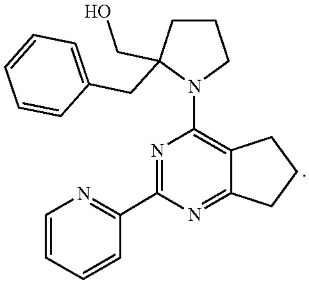
In another embodiment, the compound of Formula VIIIb is a compound of Formula VIIIb3:
Formula VIIIb3
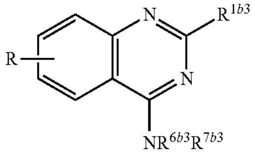

or pharmaceutically acceptable derivatives thereof, wherein $R^{1b3}$ is H, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b3}$ and $R^{7b3}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b3}$ and $R^{7b3}$ are combined to form a cyclic structure including the nitrogen atom to which they are both attached;

p is 0-2; and

R may consist of 0-4 substituents independently selected from H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$.

In another embodiment, the compound of Formula VIIIb3 is a compound wherein:

$R^{1b3}$ is thienyl;

$R^{6b3}$ and $R^{7b3}$ are combined to form a cyclic structure including the nitrogen atom to which they are both attached, as depicted below

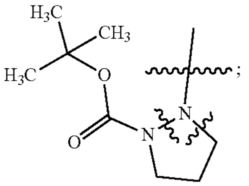

and

R is H.

In one embodiment, the compound of Formula VIIIb3 is:

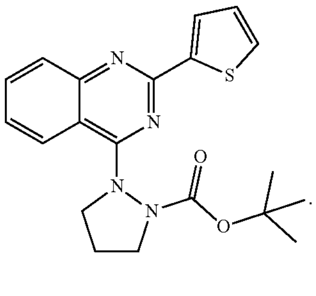 [SMILES: CC(C)(C)OC(=O)N1CCCN1c1nc(-c2cccs2)nc2ccccc12]

In another embodiment, the compound of Formula VIIIb is a compound of Formula VIIIb4:

Formula VIIIb4

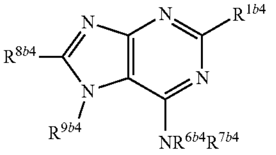

or pharmaceutically acceptable derivatives thereof, wherein $R^{1b4}$ is H, alkyl, aryl or heteroaryl;

$R^{8b4}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b4}$ is alkyl, alkenyl, alkynyl, aryl, cycloalkyl, heterocyclyl, heteroaryl, $C(O)R^4$, or $S(O)_pR^4$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b4}$ and $R^{7b4}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b4}$ and $R^{7b4}$ are combined to form a cyclic structure including the nitrogen atom to which they are both attached; and p is 0-2.

In one embodiment of Formula VIIIb4, a compound of Formula VIIIb4 is a compound wherein wherein $R^{1b4}$ is 2-pyridyl;

$R^{8b4}$ is H;

$R^{9b4}$ is $CH_2CONHR$, wherein R is H, alkyl, aryl, arylakyl, heteroaryl;

$NR^{6b4}R^{7b4}$ is a morpholine ring; and p is 0-2.

In one embodiment of Formula VIIIb4, a compound of Formula VIIIb4 is a compound wherein $R^{1b4}$ is pyridinyl;

$R^{8b4}$ is H;

$R^{9b4}$ is $CH_2CONHR$, wherein R is H,

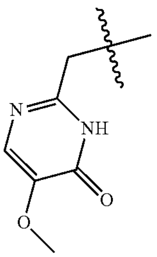

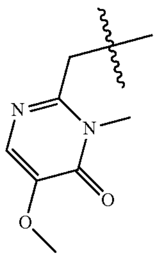

-continued

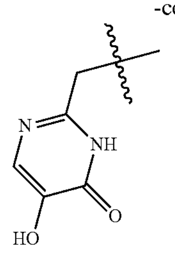

or

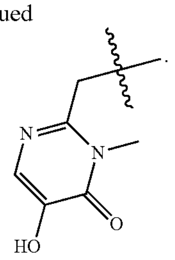

$NR^{6b4}R^{7b4}$ is

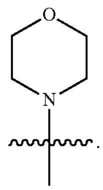

In another embodiment, the compound of Formula VIIIb is a compound of Formula VIIIb 5:

Formula VIIIb5

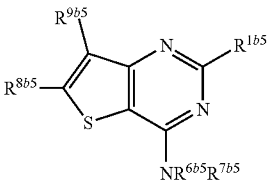

or pharmaceutically acceptable derivatives thereof, wherein $R^{1b5}$ is H, alkyl, aryl or heteroaryl;

$R^{8b5}$ is H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, or $NR^6R^7$;

$R^{9b5}$ is alkyl, alkenyl, alkynyl, aryl, cycloalkyl, heterocyclyl, heteroaryl, $C(O)R^4$, or $S(O)_pR^4$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

each $R^5$ is selected from hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b5}$ and $R^{7b5}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b5}$ and $R^{7b5}$ are combined to form a cyclic structure including the nitrogen atom to which they are both attached; and p is 0-2.

In one embodiment, the compound of Formula VIIIb5 is a compound wherein $R^{1b5}$ is pyridinyl;

$R^{6b5}$ and $R^{7b5}$ are each H;

$R^{8b5}$ is H or methyl;

$R^{9b5}$ is H or $COOCH_3$.

In one embodiment, the compound of Formula VIIIb is:

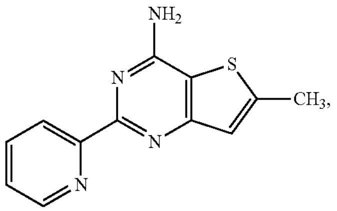

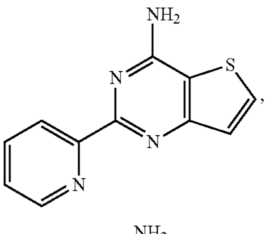

or

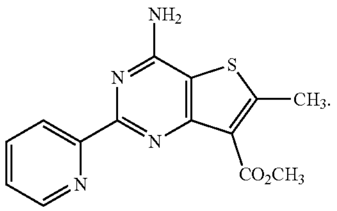

In one embodiment, the compound of Formula VIIIb1 is:

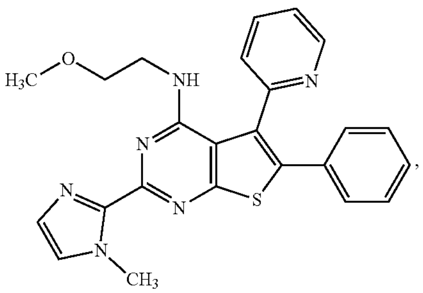

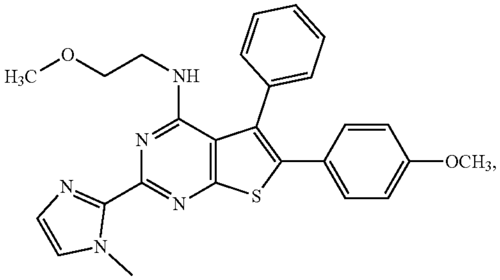

-continued
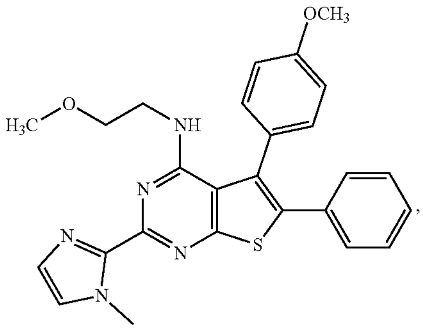
,
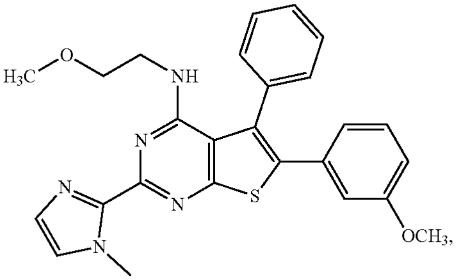
,
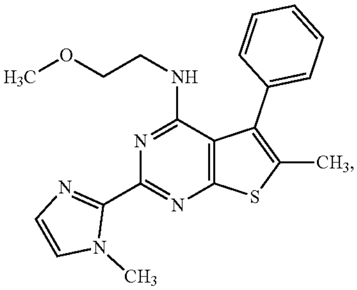
,
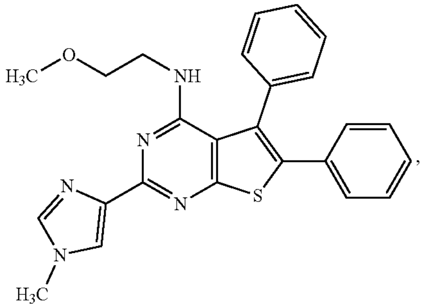
,
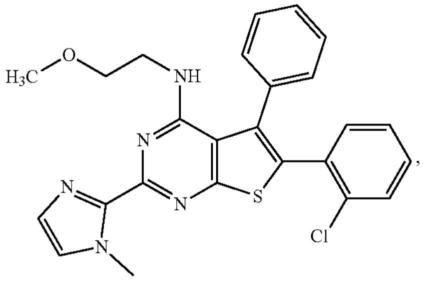
,
-continued
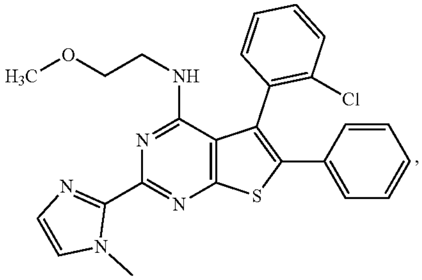
,
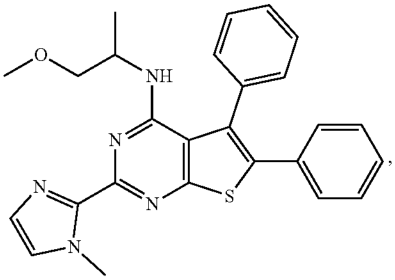
,
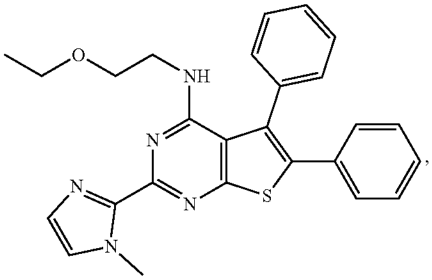
,
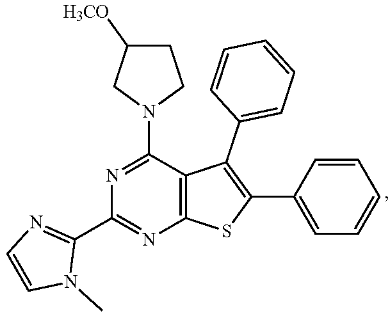
,
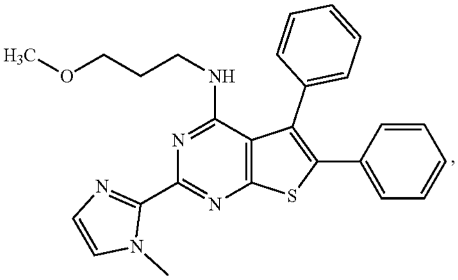
,
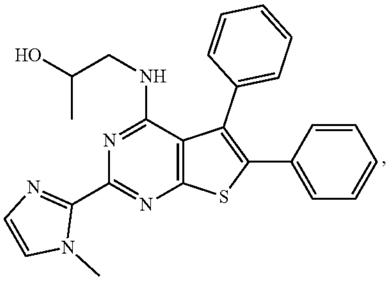
, -continued

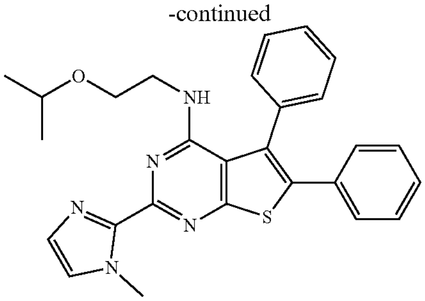

,

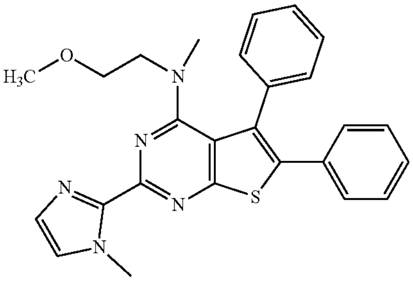

, or

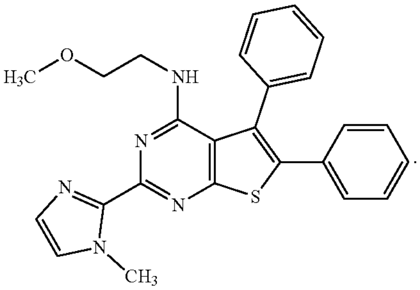

.

In some embodiments of Formula VIIIb1, $R^{1b1}$ is pyridyl, imidazolyl, N-methyl-2-imidazolyl, N-methyl-4-imdidazolyl, 2-pyrimidinyl or 4-pyrimidinyl.

In one embodiment, the compound of formula VIIIb is selected with the proviso that if A is a substituted or unsubstituted phenyl or thienyl ring, and $R^6$ is H; then $R^7$ is not 4-pyridyl, pyrimidinyl, chloropyridinyl or indazole.

In one embodiment, the compound of formula VIIIb1 is selected with the proviso that if $R^6$ is H; then $R^7$ is not 4-pyridyl, pyrimidinyl, chloropyridinyl or indazole.

In one embodiment, the compound of formula VIIIb3 is selected with the proviso that if $R^6$ is H; then $R^7$ is not 4-pyridyl, pyrimidinyl, chloropyridinyl or indazole.

In one embodiment, the compound of Formula VIIIb is selected with the proviso that the compound is not

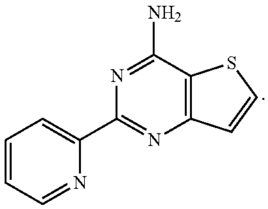 [SMILES: Nc1nc(-c2ccccn2)nc2ccsc12]

.

In one embodiment, the compound of Formula VIIIb1 is selected with the proviso that the compound is not

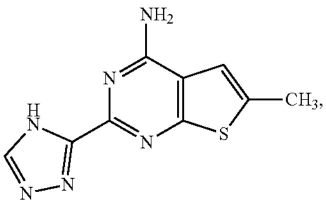

,

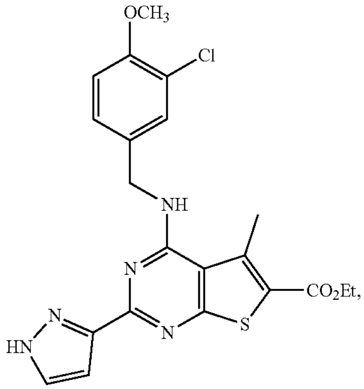

,

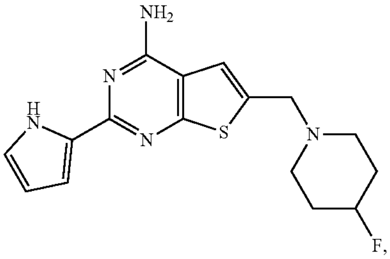

,

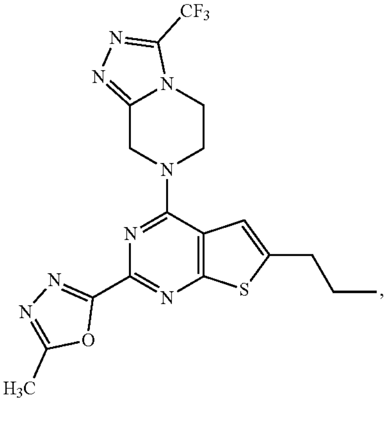

,

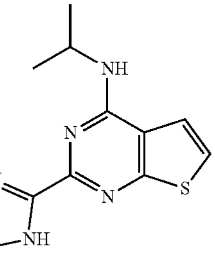

,

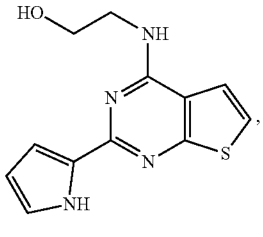

, or

-continued

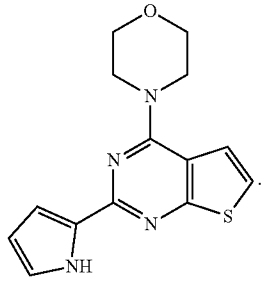

In one embodiment, the compound of Formula VIIIb1 is selected with the proviso that $NR^{6b1}R^{b1}$ is not $=NNH_2$.

In one embodiment, the compound of Formula VIIIb1 is selected with the proviso that $R^{8b1}$ and $R^{9b1}$ do not combine to form a cyclic ring structure.

In certain embodiments, the compounds for use in the compositions and methods provided herein are of Formula IXa or Formula IXb:

Formula IXa

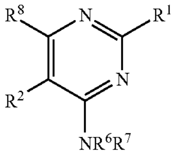

Formula IXb

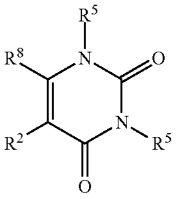

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl and alkylsulfonyl, or $R^6$ and $R^7$ are combined to form a cyclic structure including the nitrogen atom to which they are both attached; and p is 0-2.

In one embodiment, the compound of Formula IXa is

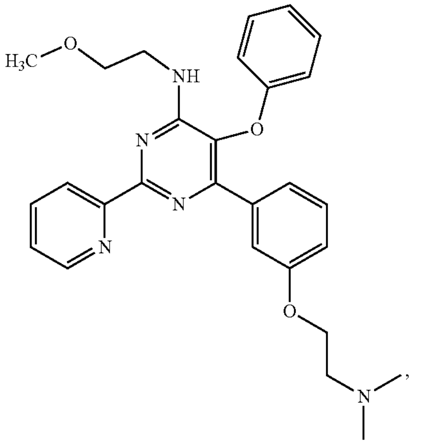

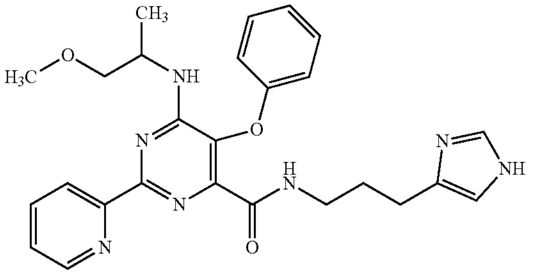

or

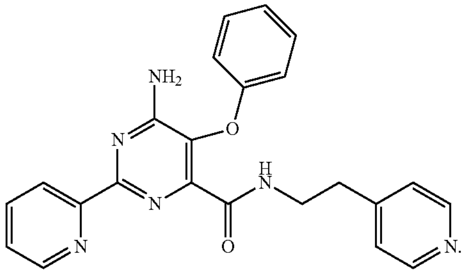

In another embodiment, the compound of Formula IXa is a compound of Formula IXa1:

Formula IXa1

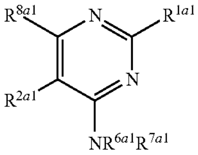

or pharmaceutically acceptable derivatives thereof, wherein $R^{1a1}$ is aryl or heteroaryl;

$R^{2a1}$ is H or alkyl;

$R^{8a1}$ is alkyl;

$R^{6a1}$ and $R^{7a1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, arylamino, alkylamino, arylcarbonylamino, heteroarylcarbonylamino, alkylcarbonylamino, heteroarylcarbonyl, aryl sulfonyl, heteroarylsulfonyl, cycloalkylsulfonyl and alkyl sulfonyl; or $R^{6a1}$ and $R^{7a1}$ are combined to form a cyclic structure including the nitrogen atom to which they are both attached.

In another embodiment of Formula IXa1, $R^{1a1}$ is aryl or heteroaryl;

$R^{2a1}$ is H or alkyl;

$R^{8a1}$ is H or alkyl;

$R^{6a1}$ and $R^{7a1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, arylamino, alkylamino, arylcarbonylamino, heteroarylcarbonylamino, alkylcarbonylamino, heteroarylcarbonyl, aryl sulfonyl, heteroarylsulfonyl, cycloalkylsulfonyl and alkyl sulfonyl; or $R^{6a1}$ and $R^{7a1}$ are combined to form a cyclic structure including the nitrogen atom to which they are both attached.

In one embodiment of Formula IXa1, $R^{1a1}$ is aryl or heteroaryl;

$R^{2a1}$ is H or alkyl;

$R^{8a1}$ is alkyl;

$R^{6a1}$ and $R^{7a1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, arylamino, alkylamino, arylcarbonylamino, heteroarylcarbonylamino, alkylcarbonylamino, heteroarylcarbonyl, aryl sulfonyl, heteroarylsulfonyl, cycloalkylsulfonyl and alkyl sulfonyl; or $R^{6a1}$ and $R^{7a1}$ are combined to form a cyclic structure including the nitrogen atom to which they are both attached.

In one embodiment of Formula IXa1, $R^{1a1}$ is 2-pyridyl;

$R^{2a1}$ is H or alkyl;

$R^{8a1}$ is alkyl;

$R^{6a1}$ and $R^{7a1}$ are independently selected from hydrogen, C(O)R, wherein R is alkyl, cycloalkyl, or heterocycloalkyl.

In one embodiment, $R^{1a1}$ is

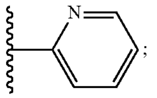

;

$R^{2a1}$ is H or methyl;

$R^{8a1}$ is methyl, ethyl, or trifluoromethyl;

$R^{6a1}$ and $R^{7a1}$ are independently selected from H,

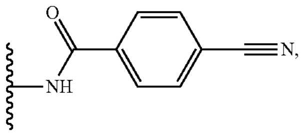

,

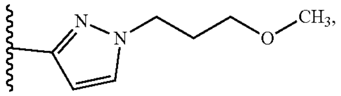

,

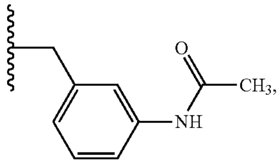

,

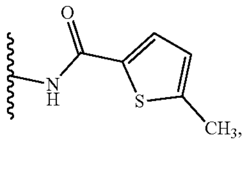

,

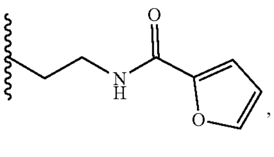

,

-continued

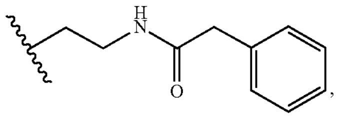

,

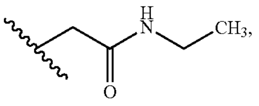

,

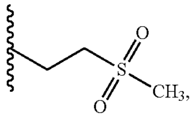

,

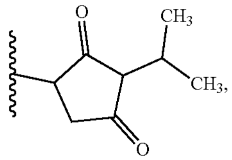

,

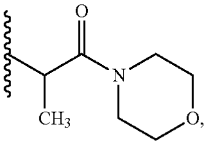

,

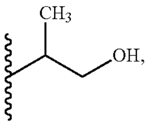

,

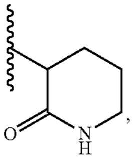

,

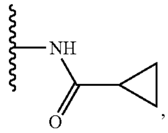

, or

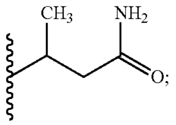

;

or $R^{6a1}$ and $R^{7a1}$ are combined to form

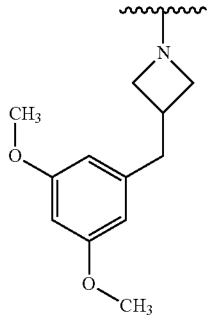 [SMILES: *N1CC(Cc2cc(OC)cc(OC)c2)C1]

including the nitrogen atom to which they are both attached.

In one embodiment of Formula IXa1, $R^{1a1}$ is

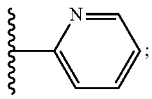 [SMILES: *c1ccccn1]

;

$R^{2a1}$ is H or methyl;

$R^{8al}$ is H;

$R^{6a1}$ and $R^{7a1}$ are independently selected from H,

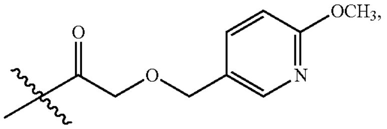
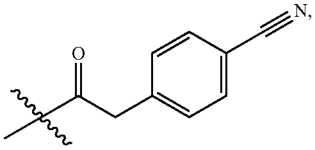
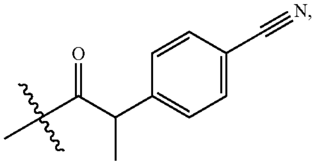
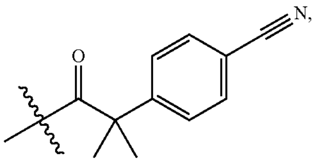
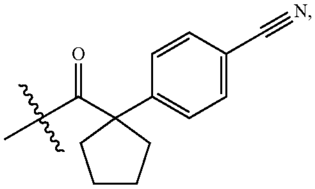
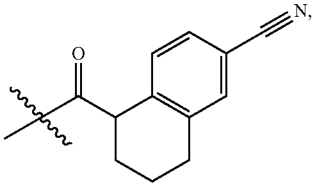
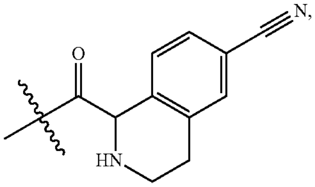
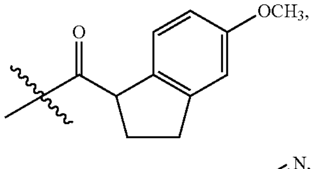
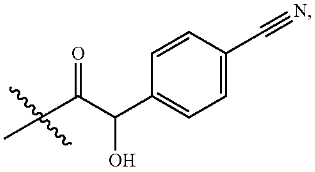
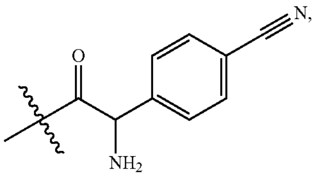
-continued
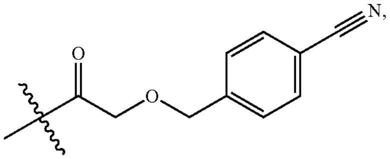
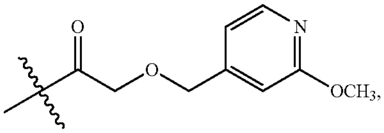
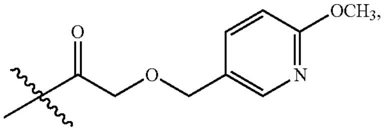
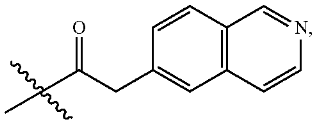
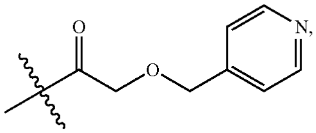
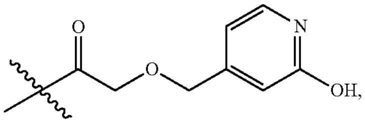
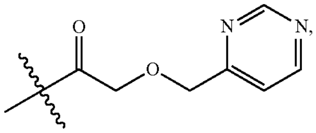
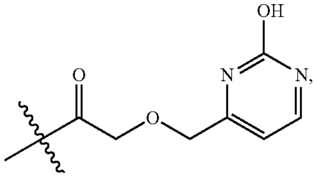
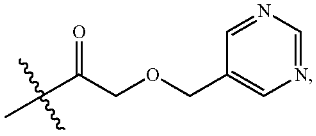
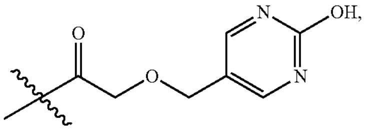
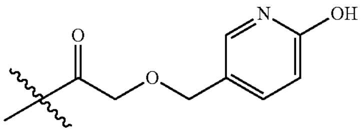
or
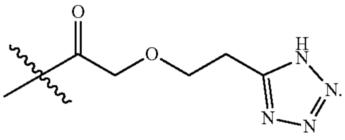

In one embodiment, the compound of Formula IXa1 is:
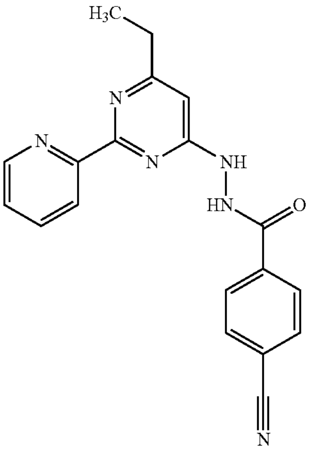
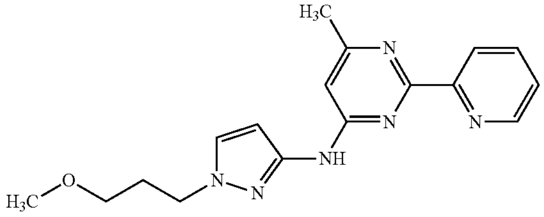
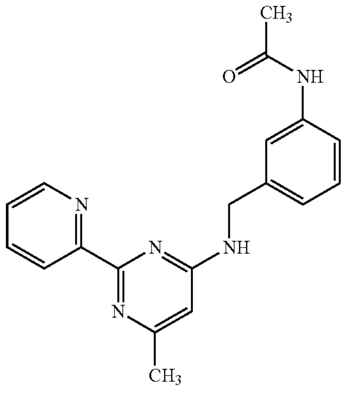
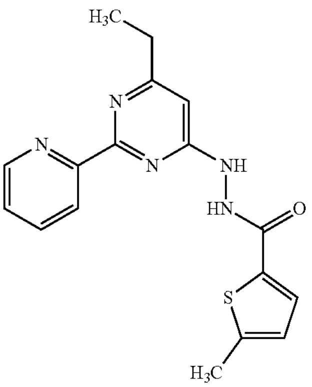
-continued
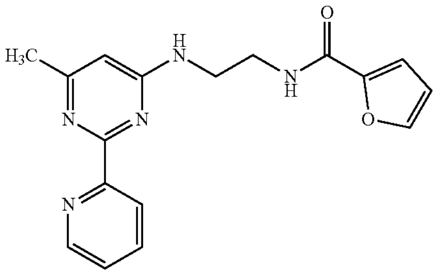
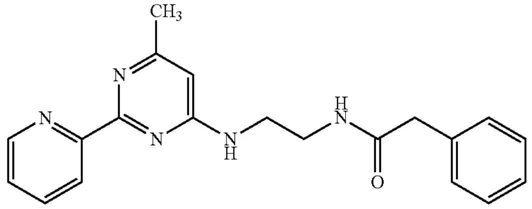
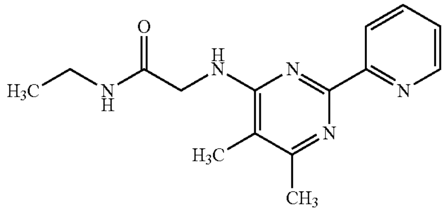
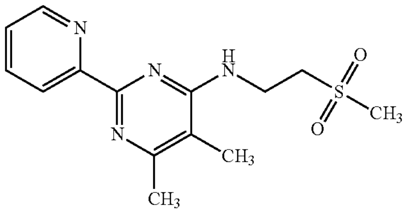
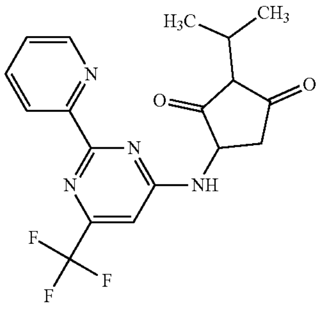
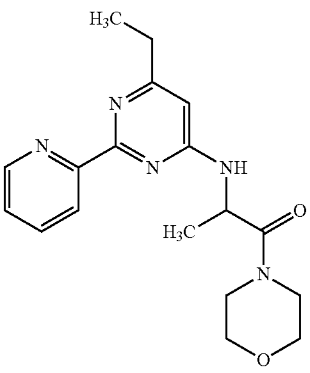

-continued
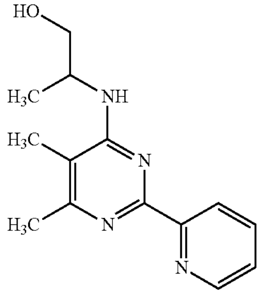
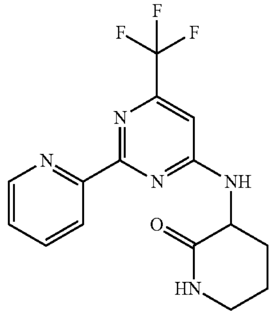
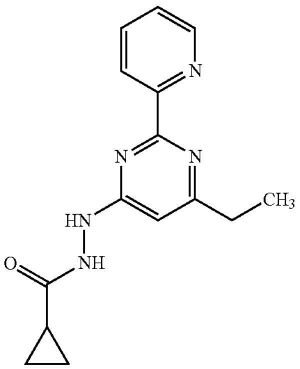
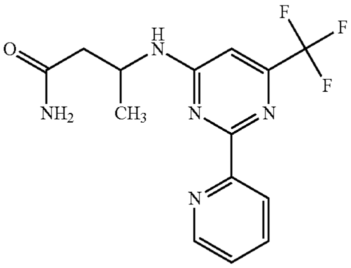
or
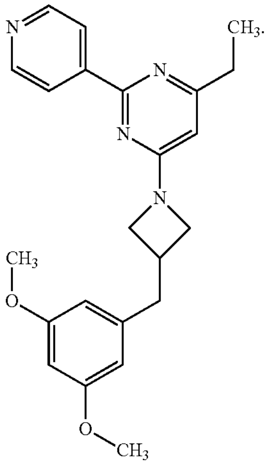
In one embodiment, the compound of Formula IXa1 is:
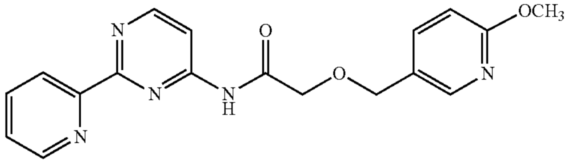
or
-continued
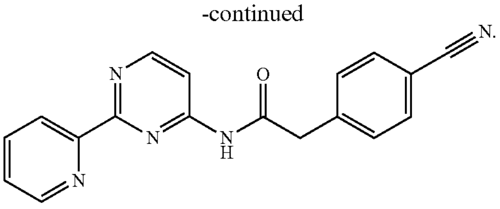
In one embodiment, $R^{1a1}$ is
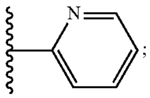 [SMILES: *c1ccccn1]
$R^{2a1}$ is H or methyl;
$R^{8a1}$ is methyl, ethyl, or trifluoromethyl;
$R^{6a1}$ and $R^{7a1}$ are independently selected from H,
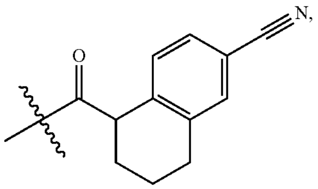
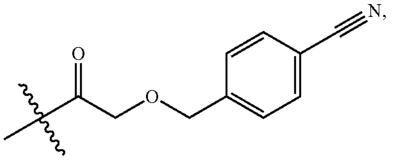
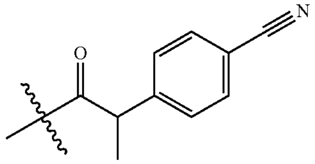
and
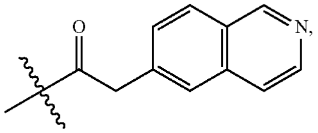
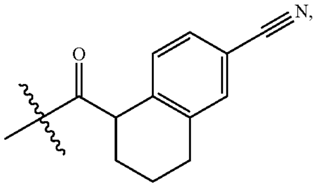
In one embodiment, the compound of Formula IXa1 is:
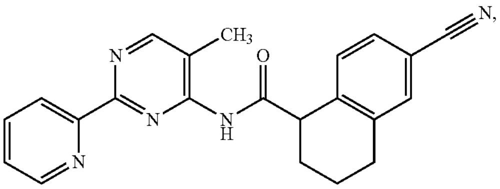

-continued

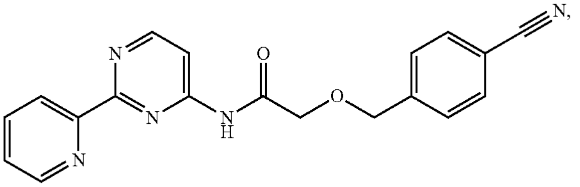

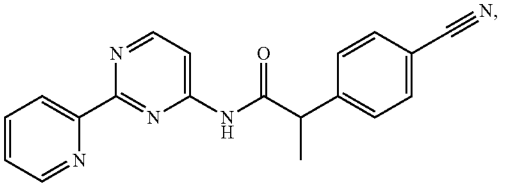

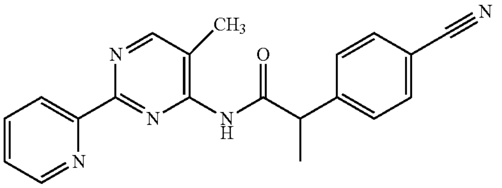

(R or S), or

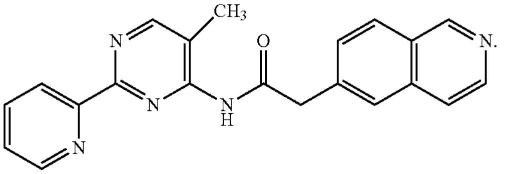

In another embodiment, the compound of Formula IXb is a compound of Formula IXb1:

Formula IXb1

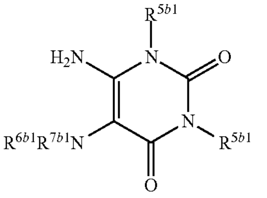

or pharmaceutically acceptable derivatives thereof, wherein each $R^{5b1}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6b1}$ and $R^{7b1}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached.

In one embodiment, each $R^{5b1}$ is methyl or

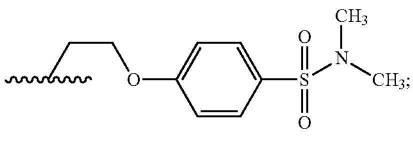 [SMILES: *CCOc1ccc(S(=O)(=O)N(C)C)cc1]

$R^{6b1}$ and $R^{7b1}$ are combined to form a piperidine structure including the nitrogen atom to which they are both attached.

In one embodiment, the compound of Formula IXb1 is:

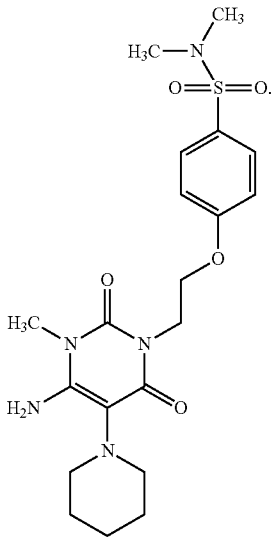 [SMILES: CN(C)S(=O)(=O)c1ccc(OCCn2c(=O)c(N3CCCCC3)c(N)n(C)c2=O)cc1]

In one embodiment, the compound of Formula IXa is selected with the proviso that if $R^1$ is heteroaryl, then $NR^6R^7$ is not morpholino.

In one embodiment, the compound of Formula IXa1 is selected with the proviso that if $R^{1a}$ is heteroaryl, then $NR^{6a}R^{7a}$ is not morpholino.

In one embodiment, the compound of Formula IXa is selected with the proviso that if $R^1$ is morpholino, then $NR^6R^7$ is not $NH_2$.

In certain embodiments, the compounds for use in the compositions and methods provided herein are of Formula X:

Formula X

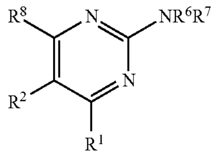

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached; and p is 0-2.

In another embodiment, the compound of Formula X is a compound of Formula Xa:

Formula Xa

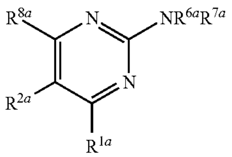

or pharmaceutically acceptable derivatives thereof, wherein $R^{1a}$ is H or alkyl;

$R^{2a}$ is H or halo;

$R^{8a}$ is H or alkyl;

$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^{6a}$ and $R^{7a}$ are combined to form a cyclic structure including the nitrogen atom to which they are both attached.

In one embodiment, $R^{1a}$ is H, methyl, or trifluoromethyl;

$R^{2a}$ is H or Br;

$R^{8a}$ is H, methyl, or trifluoromethyl;

$R^{6a}$ and $R^{7a}$ are independently selected from hydrogen,

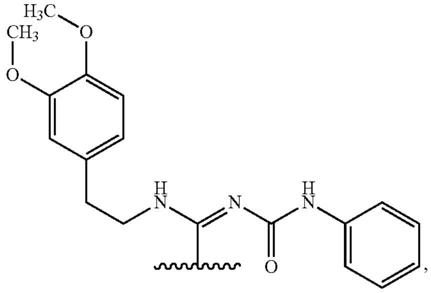,

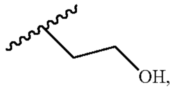, 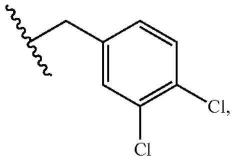, or

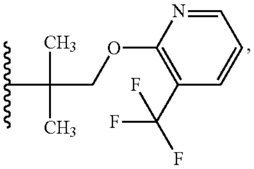, or $R^{6a}$ and $R^{7a}$ are combined to form

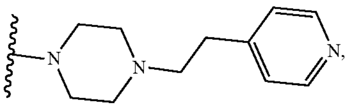

-continued

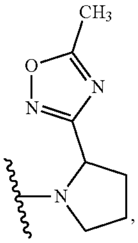, 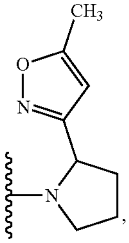, 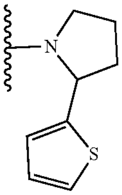,

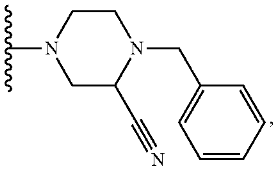, or

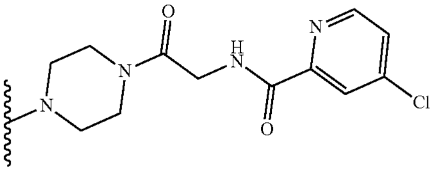

including the nitrogen atom to which they are both attached.

In one embodiment, the compound of Formula Xa is:

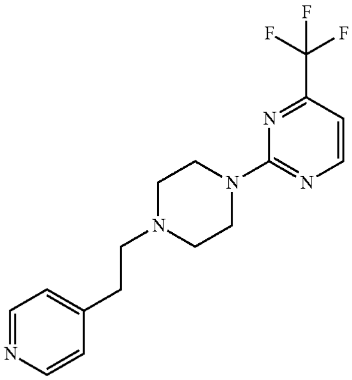

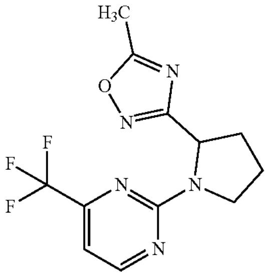

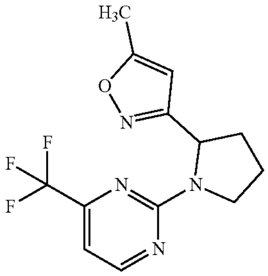

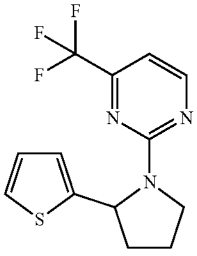

-continued

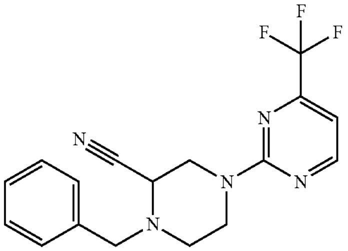

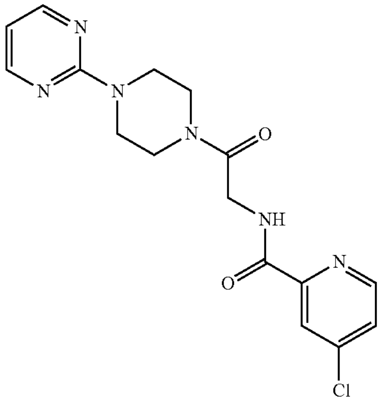

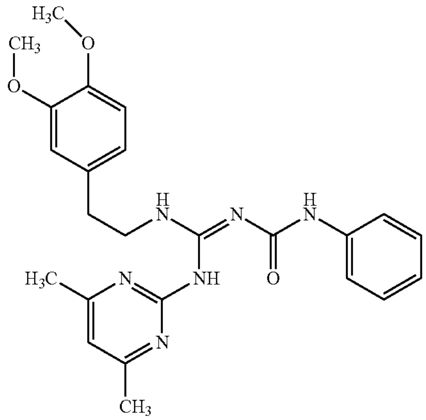

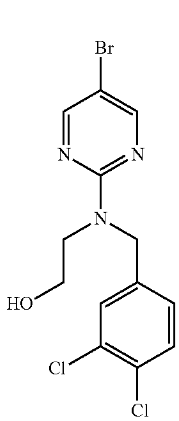

or

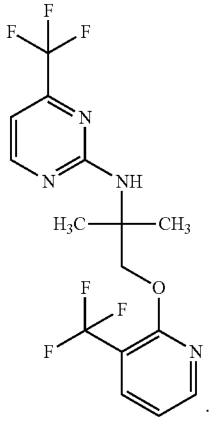

.

In one embodiment, the compound of Formula X is selected with the proviso that if $R^1$ is methyl and $NR^6R^7$ is $NH_2$, then $R^8$ is not aryl.

In certain embodiments, the compounds for use in the compositions and methods provided herein are of Formula XI:

Formula XI

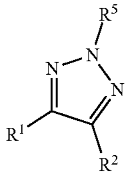

or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, C(O)$R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached; and p is 0-2.

In another embodiment, the compound of Formula XI is a compound of Formula XIa:

Formula XIa

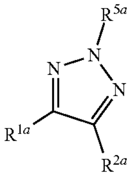

or pharmaceutically acceptable derivatives thereof, wherein $R^{1a}$ is H or alkyl;

$R^{2a}$ is C(O)$R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5a}$ is H, aryl or heteroaryl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached.

In one embodiment, $R^{1a}$ is H or methyl;

$R^{2a}$ is

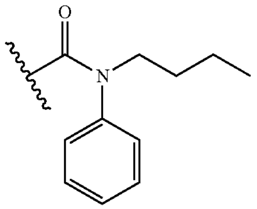

or

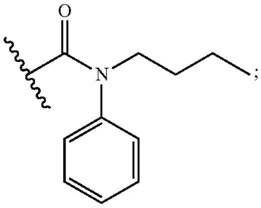

; and $R^{5a}$ is Ph.

In one embodiment, the compound of Formula XIa is:

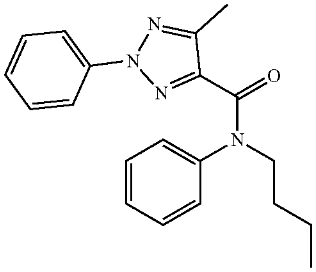

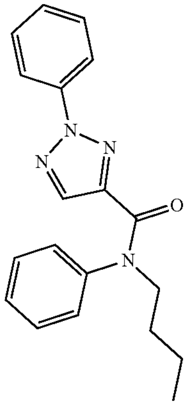

or

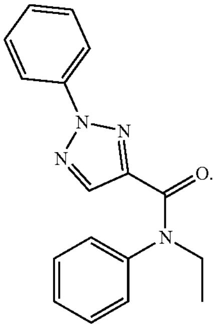

In certain embodiments, the compounds for use in the compositions and methods provided herein are of Formula XII:

Formula XII

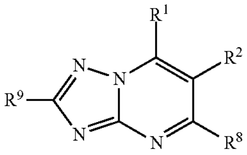

or pharmaceutically acceptable derivatives thereof, wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached; and p is 0-2.

In another embodiment, the compound of Formula XII is a compound of Formula XIIa:

Formula XIIa

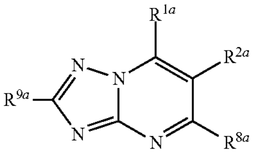

or pharmaceutically acceptable derivatives thereof, wherein $R^{1a}$ is alkyl or $NR^6R^7$;

$R^{2a}$ is H or alkyl;

$R^{8a}$ is H or alkyl;

$R^{9a}$ is H or $R^{6'}R^{7'}NC(O)alkyl$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached; and $R^{6'}$ and $R^{7'}$ are independently selected from hydrogen, alkyl, alkenyl, alkynyl, aryl, heteroaryl, heterocyclyl and cycloalkyl; or $R^{6'}$ and $R^{7'}$ are combined to form a cyclic structure including the nitrogen atom to which they are both attached.

In one embodiment, $R^{1a}$ is methyl,

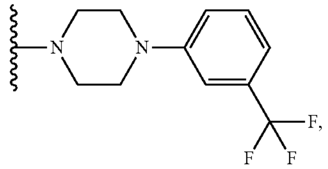

or

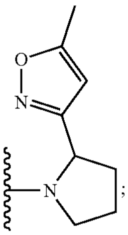

;

$R^{2a}$ is H;

$R^{8a}$ is methyl or trifluoromethyl; and $R^{9a}$ is H,

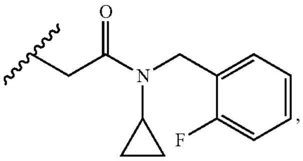

, or

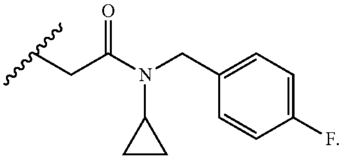

In one embodiment, the compound of Formula XIIa is:

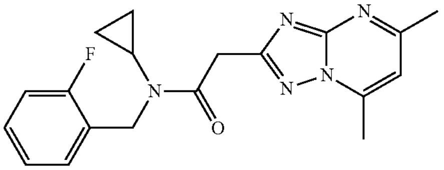

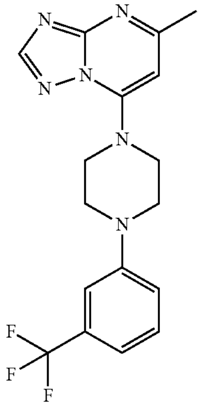

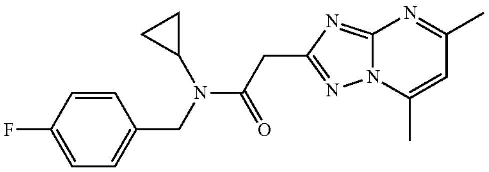

or

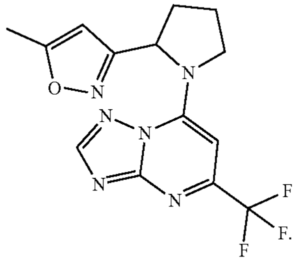

In one embodiment, the compound of Formula XII is selected with the proviso that the compound is not

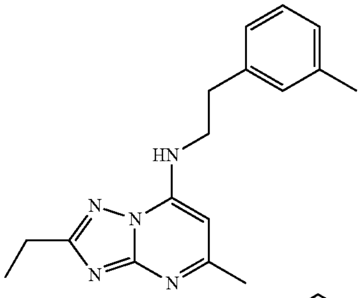

or

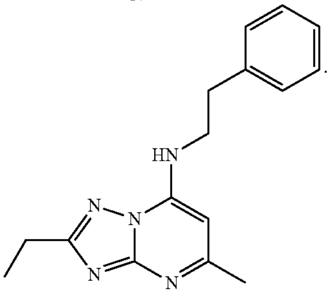

In certain embodiments, the compounds for use in the compositions and methods provided herein are of Formula XIII:

Formula XIII

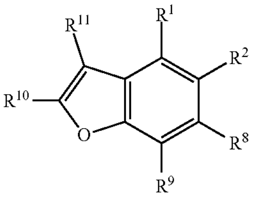

or pharmaceutically acceptable derivatives thereof, wherein $R^1$, $R^2$, $R^8$, $R^9$, $R^{10}$ and $R^{11}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached; and p is 0-2.

In another embodiment, the compound of Formula XIII is a compound of Formula XIIIa:

Formula XIIIa

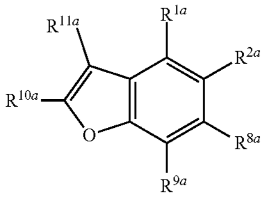

or pharmaceutically acceptable derivatives thereof, wherein $R^{1a}$ is H or alkyl;

$R^{2a}$ is H or alkyl;

$R^{8a}$ is H or alkyl;

$R^{9a}$ is H or alkyl;

$R^{10a}$ is aryl, heteroaryl or $C(O)R^4$;

$R^{11a}$ is H, -alkyl$OR^3$ or $C(O)R^4$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached.

In another embodiment, $R^{1a}$ is H or alkyl;

$R^{2a}$ is H, $OR^3$a or alkyl;

$R^{8a}$ is H or alkyl;

$R^{9a}$ is H or alkyl;

$R^{10a}$ is aryl, heteroaryl or $C(O)R^4$;

$R^{11a}$ is H, -alkyl$OR^3$ or $C(O)R^4$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached.

In one embodiment, $R^{1a}$ is H;

$R^{2a}$ is H or

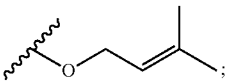 [SMILES: *OCC=C(C)C]

;

$R^{8a}$ is H;

$R^{9a}$ is H;

$R^{10a}$ is

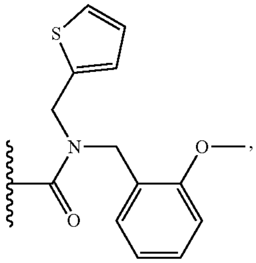

,

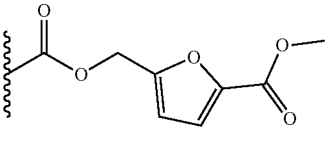

,

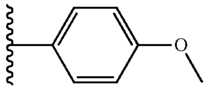

, or

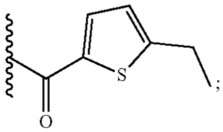

;

and $R^{11a}$ is H,

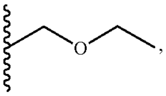

,

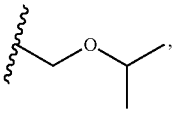

, or

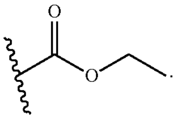

.

In one embodiment, the compound of Formula XIIIa is:

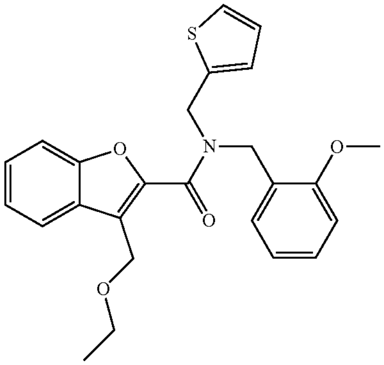

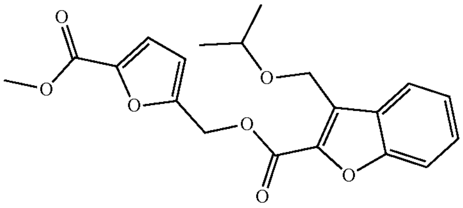

-continued

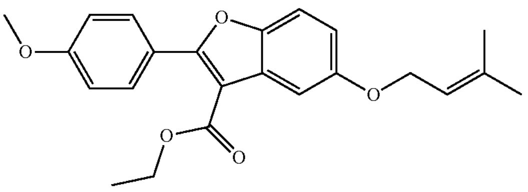

or

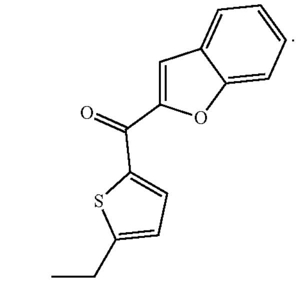

In certain embodiments, the compounds for use in the compositions and methods provided herein are of Formula XIV:

Formula XIV

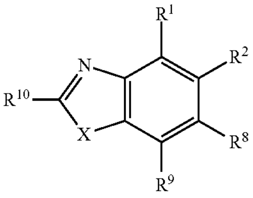

or pharmaceutically acceptable derivatives thereof, wherein $R^1$, $R^2$, $R^8$, $R^9$ and $R^{10}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is S or $NR^5$.

In another embodiment, the compound of Formula XIV is a compound of Formula XIVa:

Formula XIVa

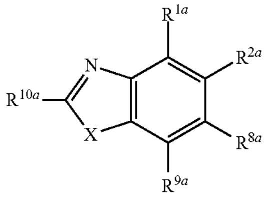

or pharmaceutically acceptable derivatives thereof, wherein $R^{1a}$, $R^{8a}$ and $R^{9a}$ are independently selected from the group consisting of H, alkyl or halo;

$R^{2a}$ is H, alkyl, halo, $C(O)R^4$ and $S(O)_pR^4$;

$R^{10a}$ is heterocyclyl, -alkyl$NR^6R^7$ or $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is S or $NR^5$.

In one embodiment, $R^{1a}$, $R^{8a}$ and $R^{9a}$ are H;

$R^{2a}$ is H or

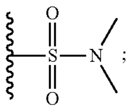 [SMILES: *S(=O)(=O)N(C)C ; ";"]

;

$R^{10a}$ is

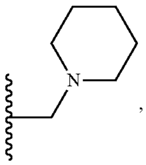

,

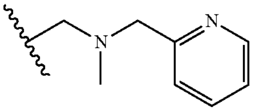

,

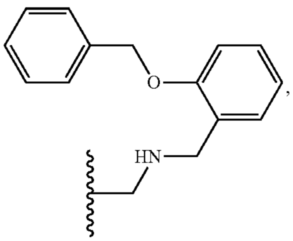

,

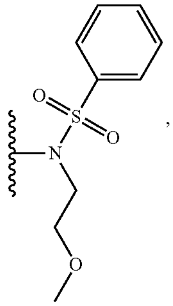

,

-continued
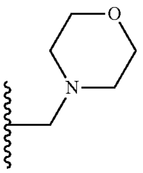
,
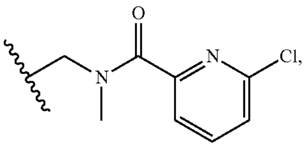
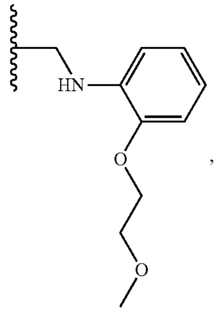
,
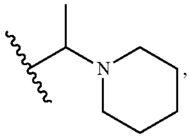
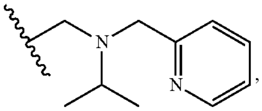
,
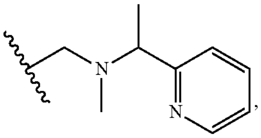
, or
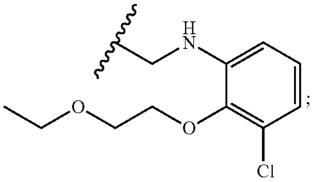
;
$R^5$ is H, methyl, n-propyl,
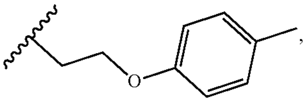
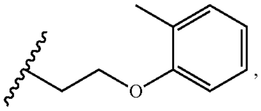
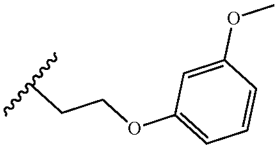
,
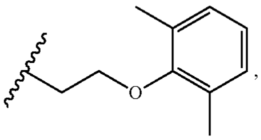
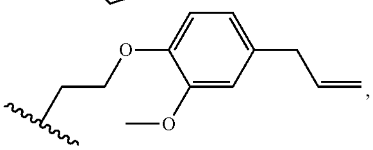
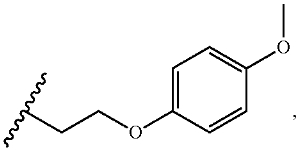
,
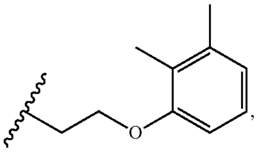
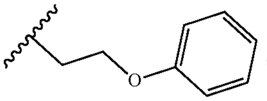
,
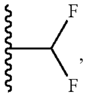
, or
-continued
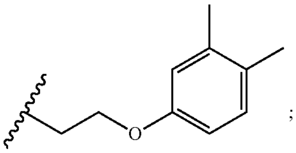
; and
X is S or $NR^5$.
In one embodiment, $R^{1a}$, $R^{8a}$ and $R^{9a}$ are H;
$R^{2a}$ is H, —CO(O)Et, or
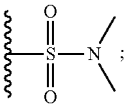 [SMILES: *S(=O)(=O)N(C)C ; ";"]
;
$R^{10a}$ is
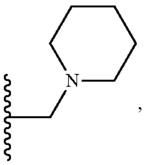
,
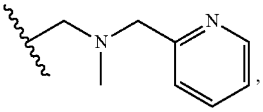
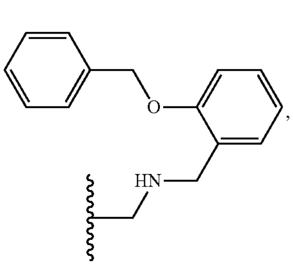
,
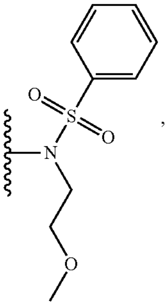
,
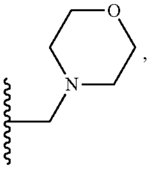
,
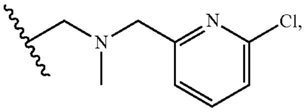
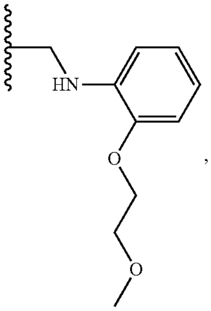
,
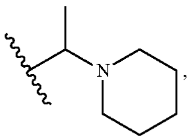
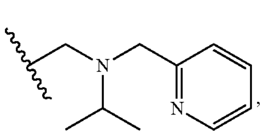
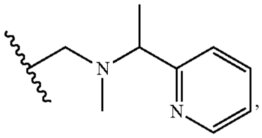

-continued
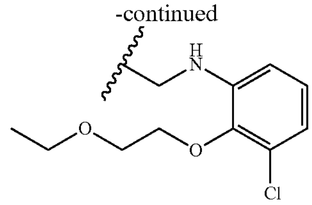
,
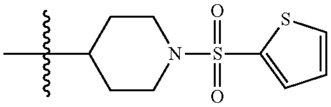
,
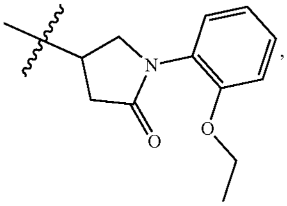
, or
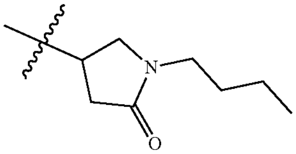
;
$R^5$ is H, methyl, n-propyl,
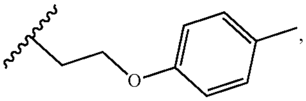
,
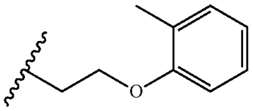
,
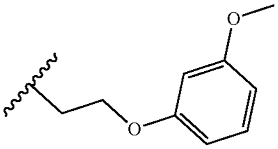
,
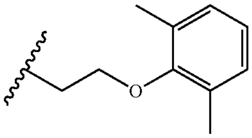
,
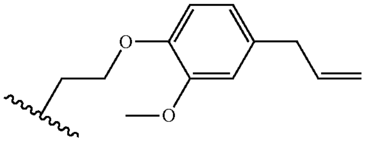
,
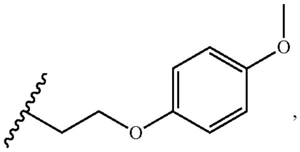
,
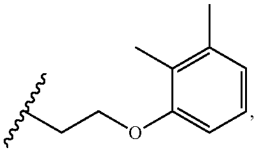
,
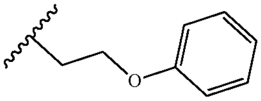
,
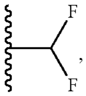
, or
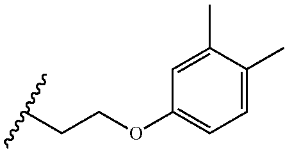
; and
X is S or $NR^5$.
In one embodiment, the compound of Formula XIVa is:
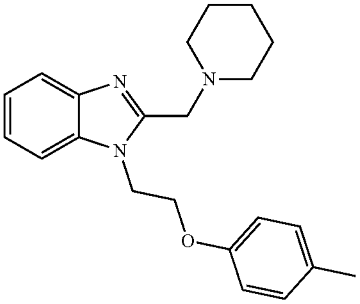
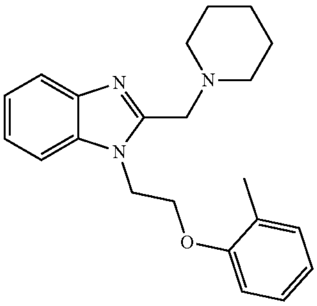
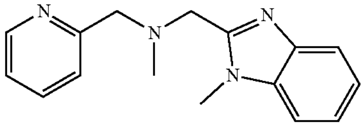
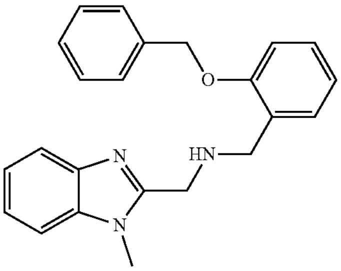
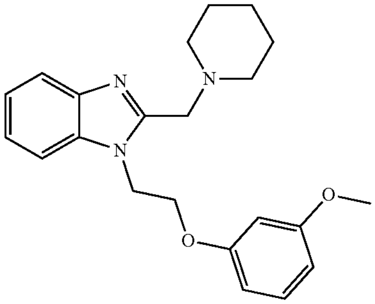
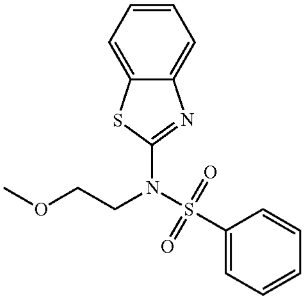

-continued
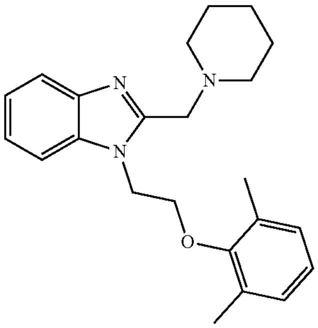
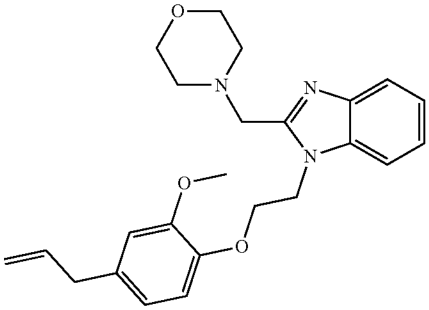
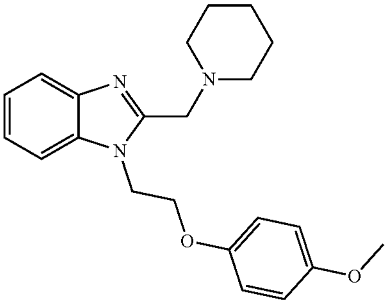
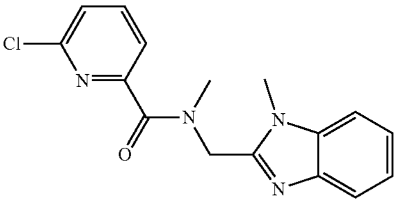
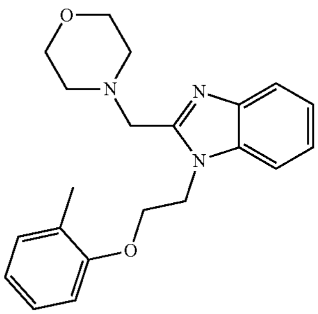
-continued
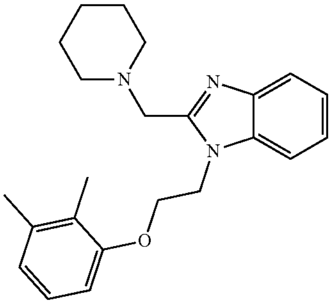
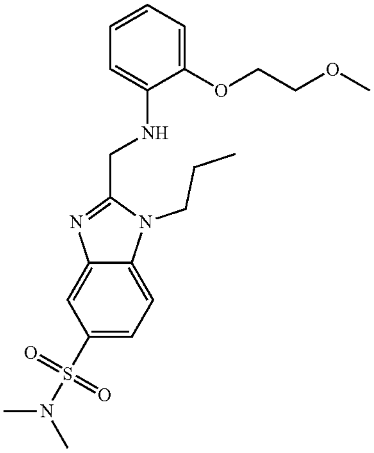
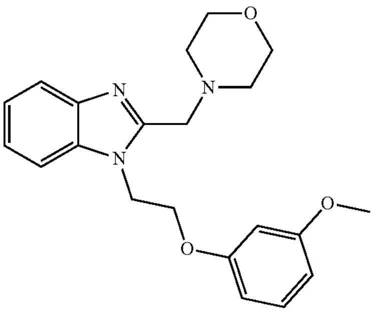
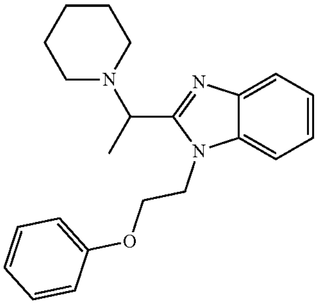
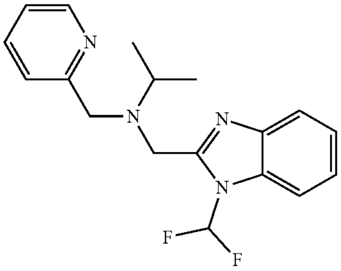

-continued

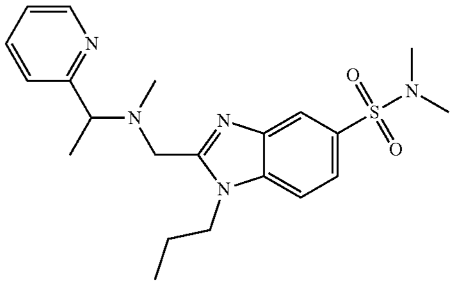

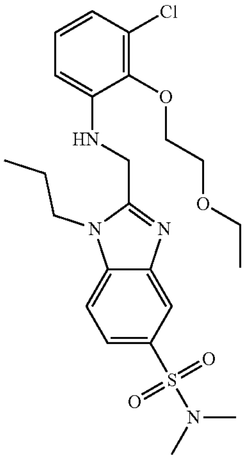

or

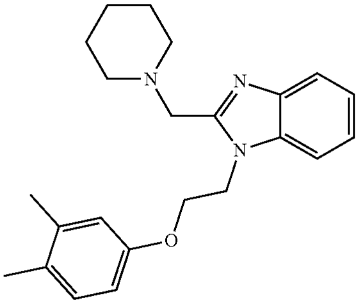

.

In another embodiment, the compound of Formula XIVa is:

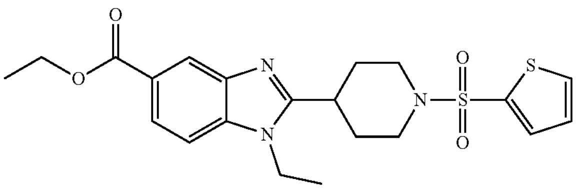

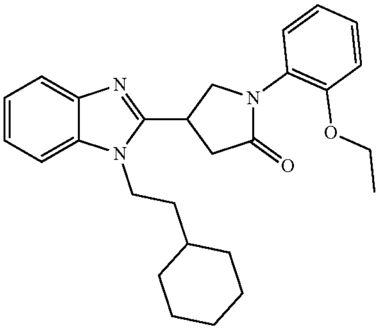

or

-continued

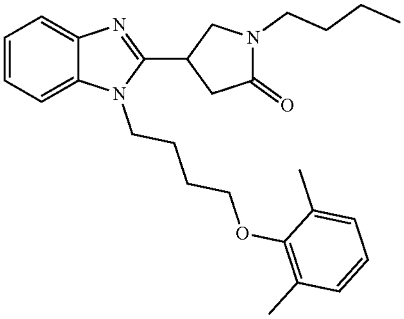

In one embodiment, the compound of formula XIV is selected with the proviso that $R^{10}$ is not morpholinomethyl, piperidinylmethyl, methylpiperizinylmethyl, morpholino-$CH(CH_3)$—, piperidinyl-$CH(CH_3)$—, methylpiperizinyl-$CH(CH_3)$—; and X is not $NR^5$ if $R^5$ is aryloxyalkyl or arylalkyl.

In another embodiment, the disease to be treated with the compounds of formula XIV is not a retinal tumor.

In one embodiment, the compound of formula XIVa is selected with the proviso that $R^{10a}$ is not morpholinomethyl, piperidinylmethyl, methylpiperizinylmethyl, morpholino-$CH(CH_3)$—, piperidinyl-$CH(CH_3)$—, methylpiperizinyl-$CH(CH_3)$—; and X is not $NR^5$ if $R^5$ is aryloxyalkyl or arylalkyl.

In another embodiment, the disease to be treated with the compounds of formula XIVa is not a retinal tumor.

In one embodiment, the compound of Formula XIV is selected with the proviso that the compound is not

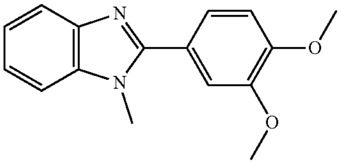

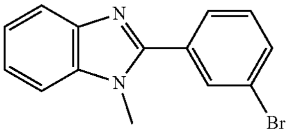

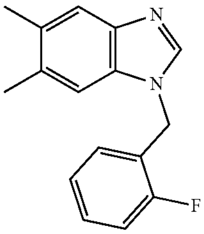

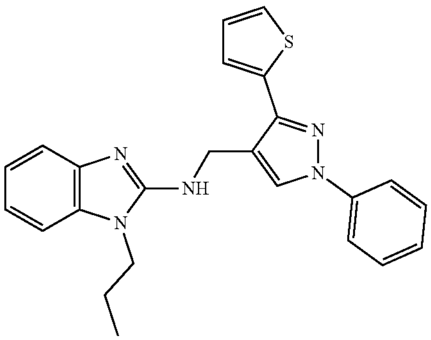

or

-continued

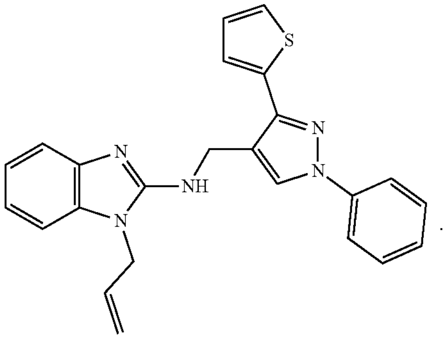

In one embodiment, the compound of Formula XIVa is selected with the proviso that the compound is not

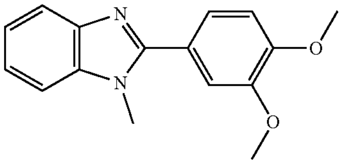

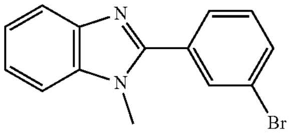

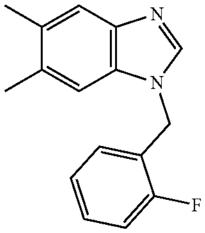

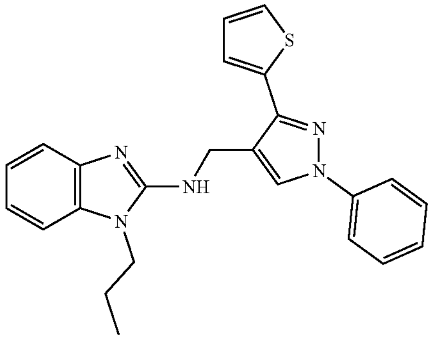

or

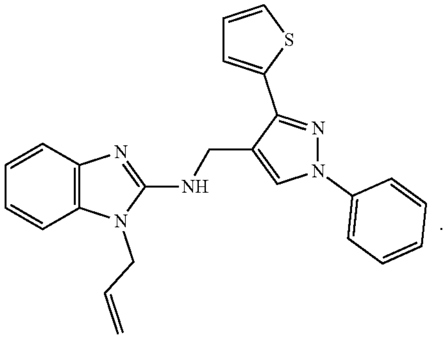

In certain embodiments, the compounds for use in the compositions and methods provided herein are of Formula XVa or Formula XVb:

Formula XVa

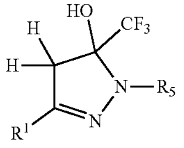

Formula XVb

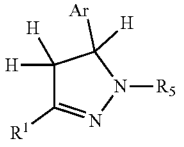

or pharmaceutically acceptable derivatives thereof, wherein $R^1$ is independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, arylcarbonyl or heteroarylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl or $R^6$ and $R^7$ are combined to form a cyclic structure including the nitrogen atom to which they are both attached;

p is 0-2; and

Ar is aryl or heteroaryl.

In another embodiment, the compound of Formula XVa is a compound of Formula XVa1:

Formula XVa1

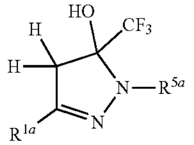

or pharmaceutically acceptable derivatives thereof, wherein $R^{1a}$ is H, aryl or heteroaryl; and $R^{5a}$ is alkylcarbonyl, cycloalkylcarbonyl, arylcarbonyl or heteroarylcarbonyl.

In one embodiment, $R^{1a}$ is H, phenyl; and $R^{5a}$ is

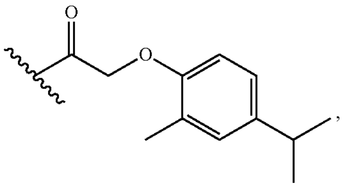

-continued
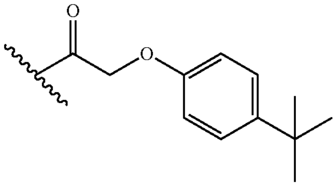,
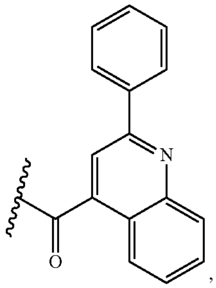,
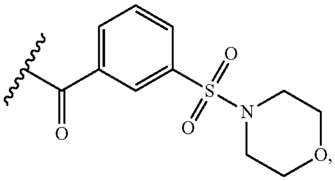,
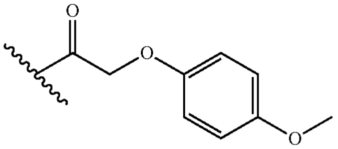,
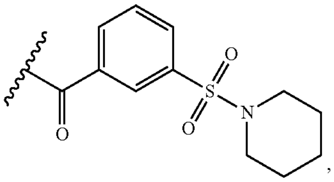,
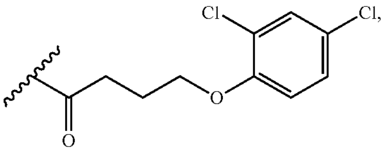,
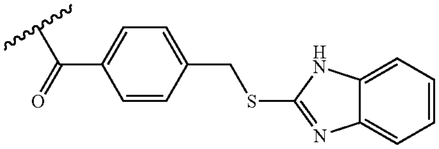,
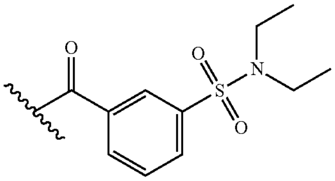, or
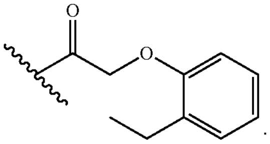.
In one embodiment, the compound of Formula XVa1 is:
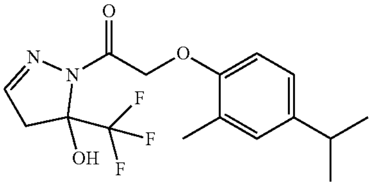
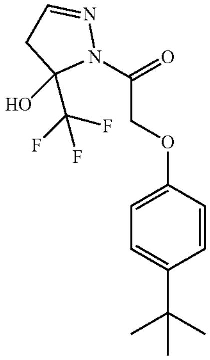
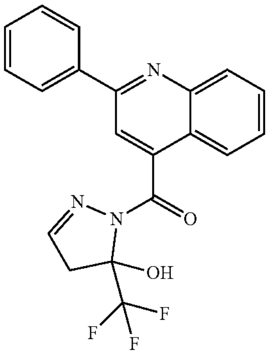
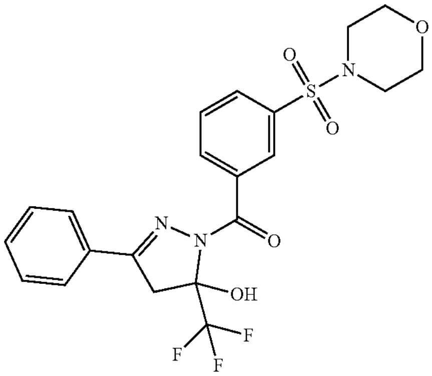
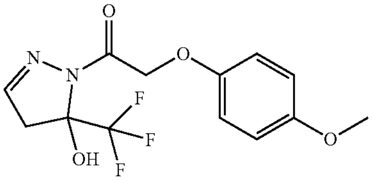

-continued

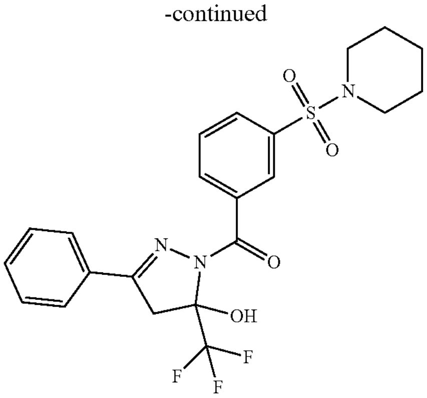

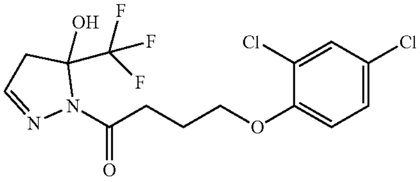

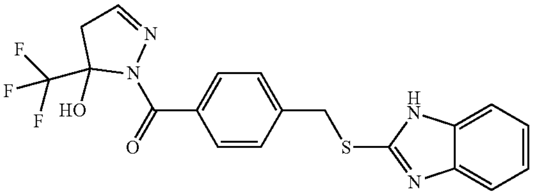

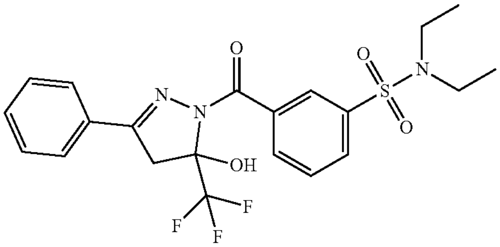

or

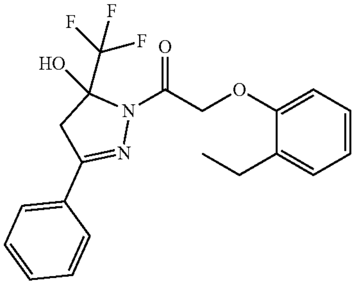

.

In another embodiment, the compound of Formula XVb is a compound of Formula XVb1:

Formula XVb1

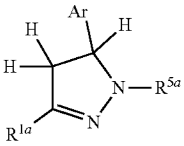

or pharmaceutically acceptable derivatives thereof, wherein $R^{1a}$ is H, aryl or heteroaryl;

$R^{5a}$ is alkylcarbonyl, cycloalkylcarbonyl, arylcarbonyl or heteroarylcarbonyl; and Ar is aryl or heteroaryl.

In one embodiment, $R^{1a}$ is

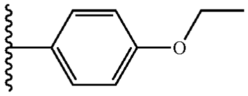

;

$R^{5a}$ is

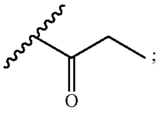 [SMILES: *C(=O)CC]

;

and

Ar is

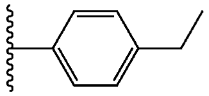

.

In one embodiment, the compound of Formula XVb1 is:

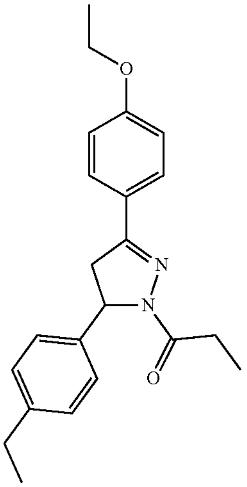

.

In certain embodiments, the compounds for use in the compositions and methods provided herein are of Formula XVI:

Formula XVI

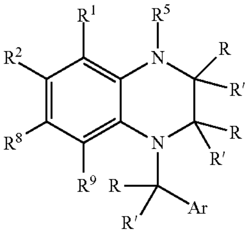

or pharmaceutically acceptable derivatives thereof, wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2;

each R and R' are independently selected from H, alkyl, or cycloalkyl; and

Ar is aryl or heteroaryl.

In another embodiment, the compound of Formula XVI is a compound of Formula XVIa:

Formula XVIa

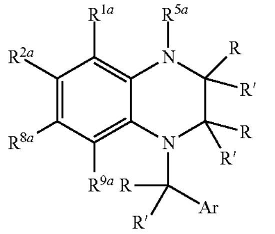

or pharmaceutically acceptable derivatives thereof, wherein $R^{1a}$, $R^{2a}$, $R^{8a}$ and $R^{9a}$ are independently selected from the group consisting of H, alkyl and halo;

$R^{5a}$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6a}$ and $R^{7a}$ are combined to form a cyclic structure including the nitrogen atom to which they are both attached;

p is 0-2;

each R and R' are independently selected from H, alkyl, or cycloalkyl; and

Ar is aryl or heteroaryl.

In one embodiment, $R^{1a}$, $R^{2a}$, $R^{8a}$ and $R^{9a}$ are independently selected from the group consisting of H, and F;

$R^{5a}$ is cyclopropyl or

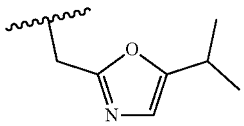

;

each R and R' are H or methyl; and

Ar is

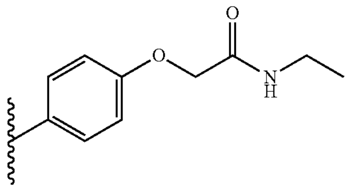

or

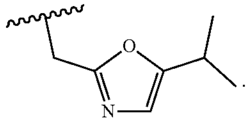

.

In one embodiment, the compound of Formula XVIa is:

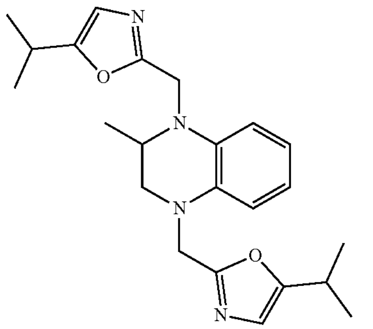

or

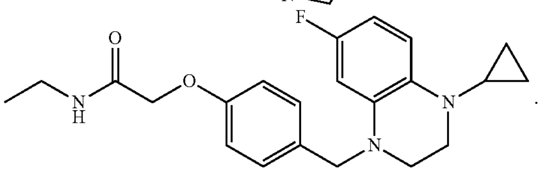

.

In certain embodiments, the compounds for use in the compositions and methods provided herein are of Formula XVII:

Formula XVII

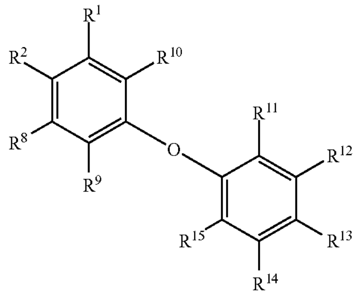

or pharmaceutically acceptable derivatives thereof, wherein $R^1$, $R^2$, $R^8$, $R^9$, $R^{10}$, $R^{11}$, $R^{12}$, $R^{13}$, $R^{14}$ and $R^{15}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment, the compound of Formula XVII is a compound of Formula XVIIa:

Formula XVIIa

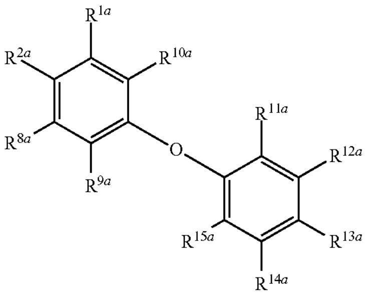

or pharmaceutically acceptable derivatives thereof, wherein $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{11a}$ is $NR^{6a}R^{7a}$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^{6'}$ is arylalkyl or heteroarylalkyl;

$R^{7'}$ is H or alkyl, and $R^6$ and $R^7$ are combined to form a cyclic structure including the nitrogen atom to which they are both attached; and p is 0-2.

In one embodiment, $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^{11a}$ is $NR^{6a}R^{7a}$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^6$ is arylalkyl or heteroarylalkyl;

$R^7$ is H or alkyl, and $R^6$ and $R^7$ are combined to form a cyclic structure including the nitrogen atom to which they are both attached; and p is 0-2.

In one embodiment, wherein $R^{1a}$, $R^{2a}$, $R^{8a}$, $R^{9a}$, $R^{10a}$, $R^{12a}$, $R^{13a}$, $R^{14a}$ and $R^{15a}$ are independently selected from the group consisting of H, methyl, F, trifluoromethyl, or OEt; and $R^{11a}$ is

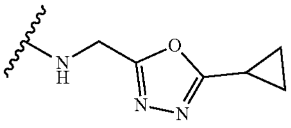,

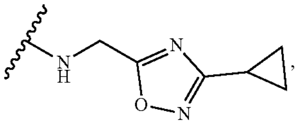, 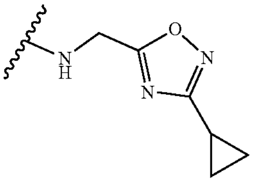,

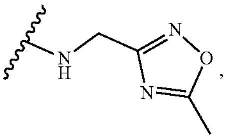, 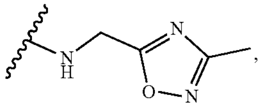, or

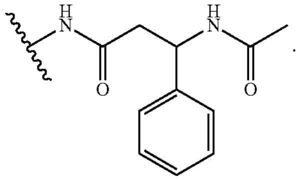.

In one embodiment, the compound of Formula XVIIa is:

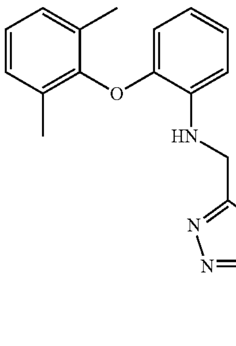

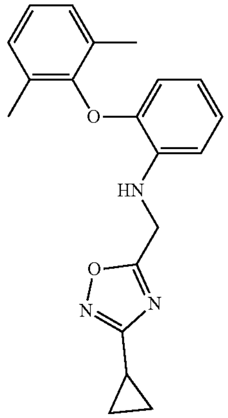

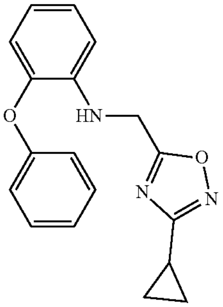

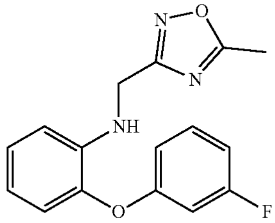

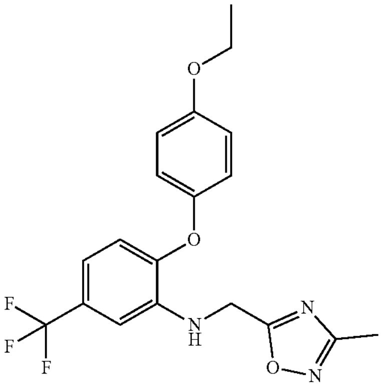

or

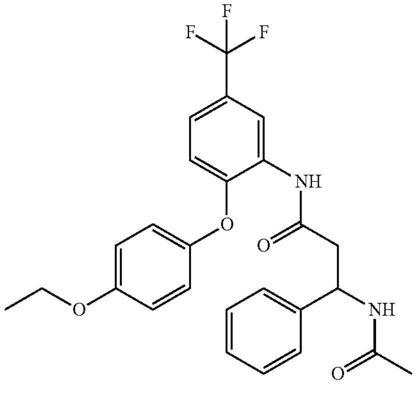

.

In another embodiment, the compound of Formula XVII is a compound of Formula XVIIb:

Formula XVIIb

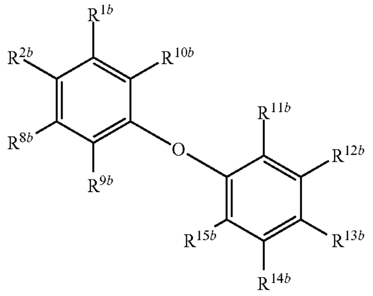

or pharmaceutically acceptable derivatives thereof, wherein $R^{1a}$, $R^{2a}$, $R^{8a}$, $R^{9a}$, $R^{10a}$ are independently selected from the group consisting of H, alkyl, halo, and $OR^3$;

$R^{11a}$, $R^{12a}$, $R^{13a}$, $R^{14a}$ and $R^{15a}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^{6'}$ is arylalkyl or heteroarylalkyl;

$R^{7'}$ is H or alkyl, and $R^6$ and $R^7$ are combined to form a cyclic structure including the nitrogen atom to which they are both attached; and p is 0-2.

In one embodiment, $R^{1b}$, $R^{2b}$, $R^{8b}$, $R^{9b}$, $R^{10b}$ are independently selected from the group consisting of H, alkyl, halo, and $OR^3$;

$R^{11b}$, $R^{12b}$, $R^{13b}$, $R^{14b}$ and $R^{15b}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and $R^6$ is arylalkyl or heteroarylalkyl;

$R^7$ is H or alkyl, and $R^6$ and $R^7$ are combined to form a cyclic structure including the nitrogen atom to which they are both attached; and p is 0-2.

In one embodiment, wherein $R^{1a}$, $R^{2a}$, $R_{8a}$, $R^{9a}$, $R^{10a}$ are independently selected from the group consisting of H, F, OMe, OPh, $CF_3$, and

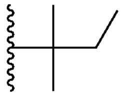;

and $R^{11a}$, $R^{12a}$, $R^{13a}$, $R^{14a}$ and $R^{15a}$ are independently selected from the group consisting of H, $CF_3$,

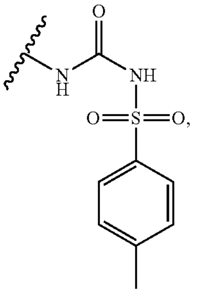

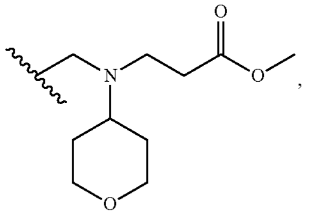

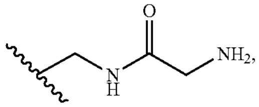

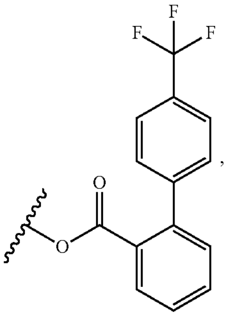

and

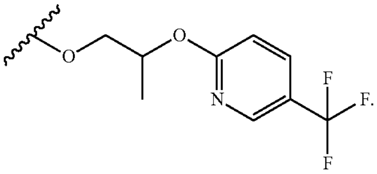

In one embodiment, wherein $R^{1b}$, $R^{2b}$, $R^{8b}$, $R^{9b}$, $R^{10b}$ are independently selected from the group consisting of H, F, OMe, OPh, $CF_3$, and

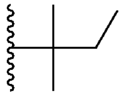;

and $R^{11b}$, $R^{12b}$, $R^{13b}$, $R^{14b}$ and $R^{15b}$ are independently selected from the group consisting of H, $CF_3$,

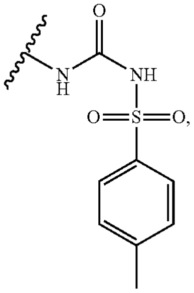

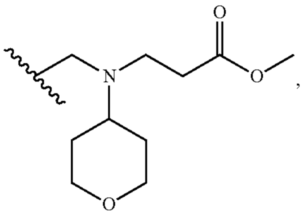

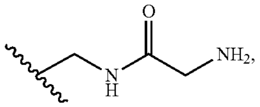

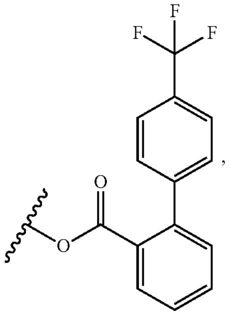

and

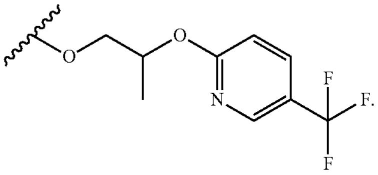

In one embodiment, the compound of Formula XVIIb is:

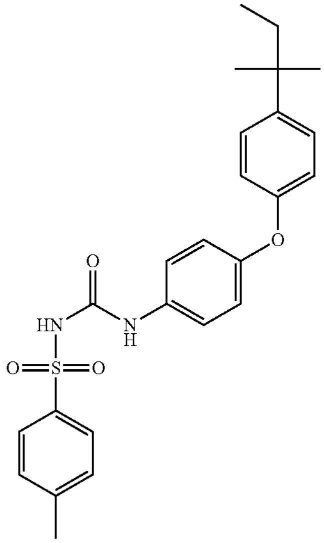

-continued

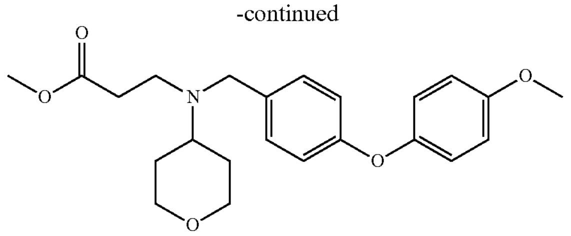

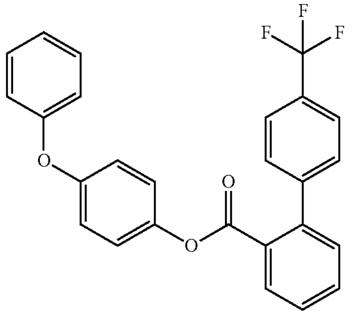

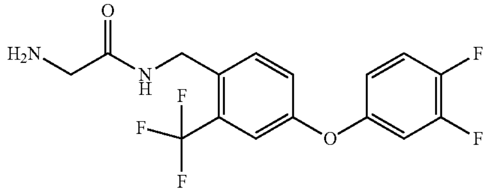

or

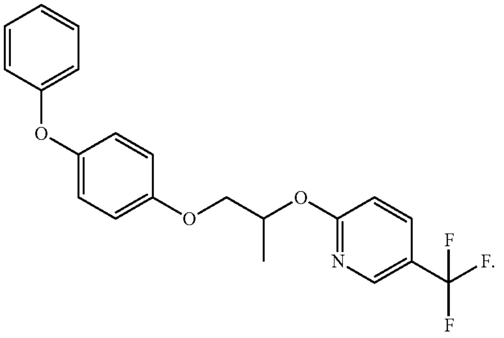

In certain embodiments, the compounds for use in the compositions and methods provided herein are of Formula XVIII:

Formula XVIII

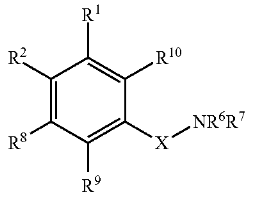

or pharmaceutically acceptable derivatives thereof, wherein $R^1$, $R^2$, $R^8$, $R^9$ and $R^{10}$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

X is $S(O)_p$ or $CR_2$, wherein each R is independently selected from hydrogen and lower alkyl.

In another embodiment, the compound of Formula XVIII is a compound of Formula XVIIIa:

Formula XVIIIa

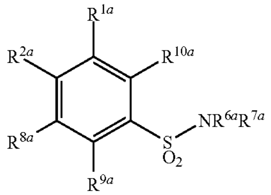

or pharmaceutically acceptable derivatives thereof, wherein $R^{1a}$, $R^{2a}$, $R^{8a}$, $R^{9a}$ and $R^{10a}$ are independently selected from the group consisting of H, alkyl, alkenyl, alkynyl, aryl, cycloalkyl, heterocyclyl, heteroaryl, nitro, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $-NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6a}$ and $R^{7a}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6a}$ and $R^{7a}$ are combined to form a cyclic structure including the nitrogen atom to which they are both attached; and p is 0-2.

In one embodiment, $R^{1a}$, $R^{2a}$, $R^{8a}$, $R^{9a}$ and $R^{10a}$ are independently selected from the group consisting of H, $CH_3$, Cl, $CF_3$, $NO_2$, $OCH_3$,

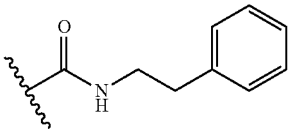,
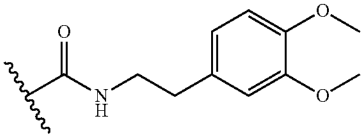,
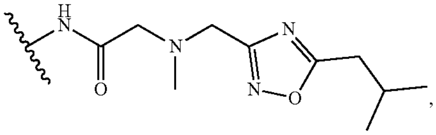,
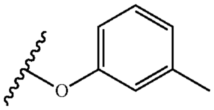, 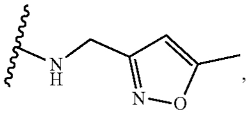,
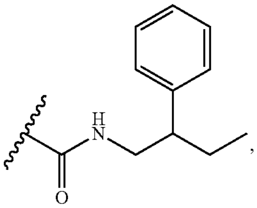,
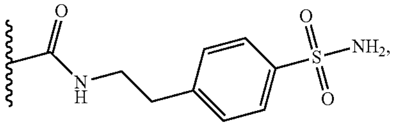
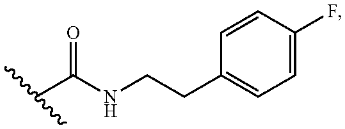
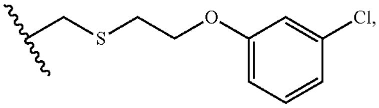
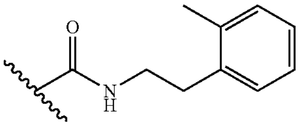,
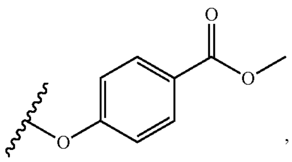, 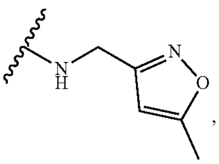, and
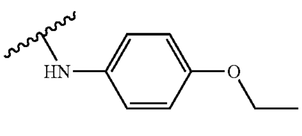;
$R^6$ and $R^7$ are independently selected from hydrogen, $CH_3$, $CH_2CH_3$ cyclopropyl,
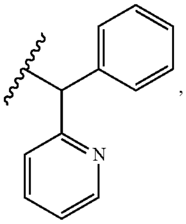, 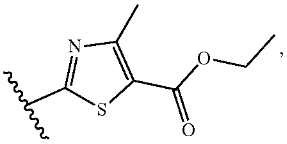,
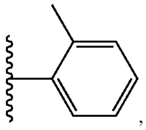, 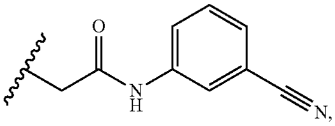
and $R^6$ and $R^7$ are combined to form
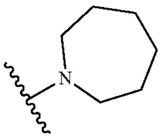, 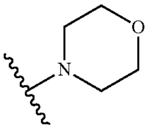, 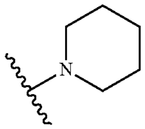,
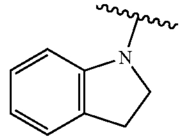,
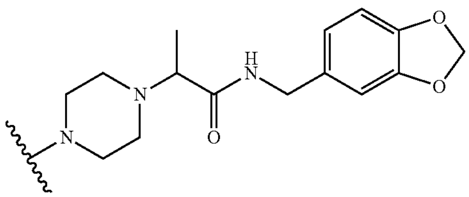,
including the nitrogen atom to which they are both attached.
In one embodiment, $R^{1a}$, $R^{2a}$, $R^{8a}$, $R^{9a}$ and $R^{10a}$ are independently selected from the group consisting of H, $CH_3$, Cl, $CF_3$, $NO_2$, $OCH_3$,
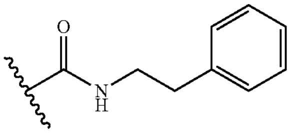,
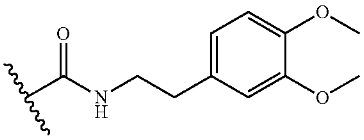,
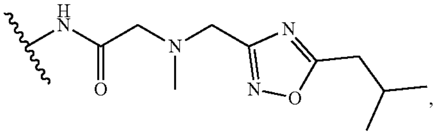,
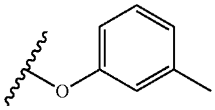, 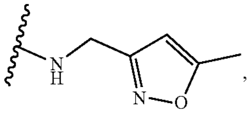, -continued
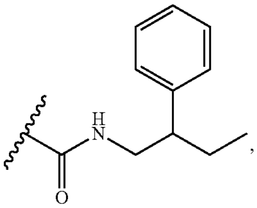
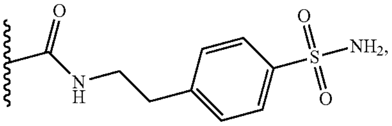
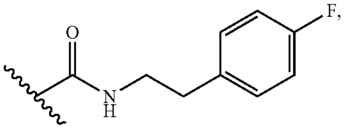
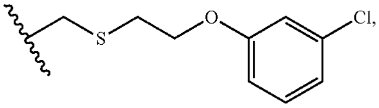
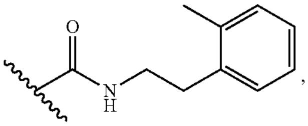
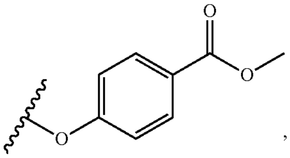
,
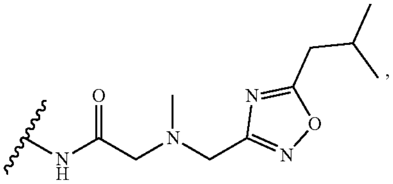
and
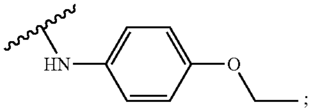
$R^{6a}$ and $R^{7a}$ are independently selected from hydrogen, $CH_3$, $CH_2CH_3$ cyclopropyl,
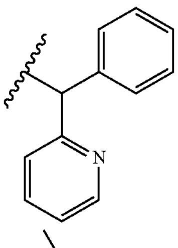
,
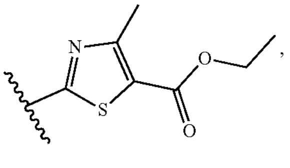
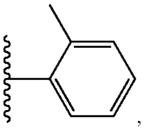
,
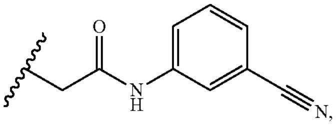
and $R^{6a}$ and $R^{7a}$ are combined to form
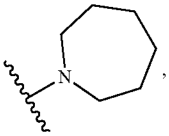
,
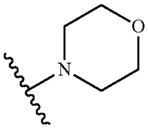
,
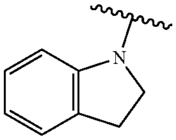
,
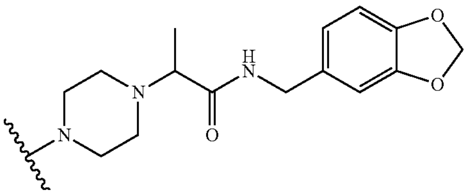
including the nitrogen atom to which they are both attached.
In one embodiment, the compound of Formula XVIIIa is:
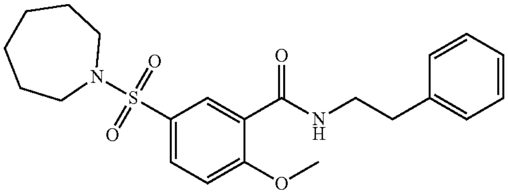
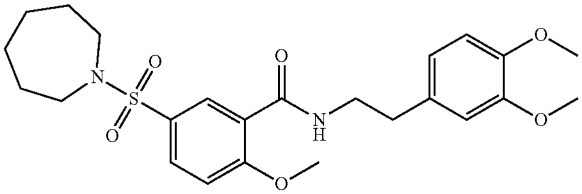
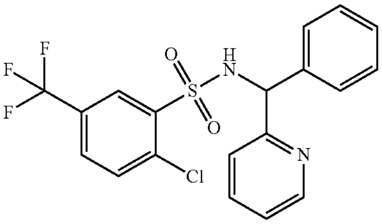
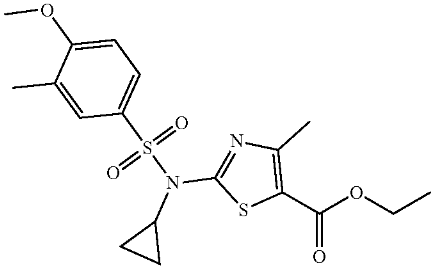
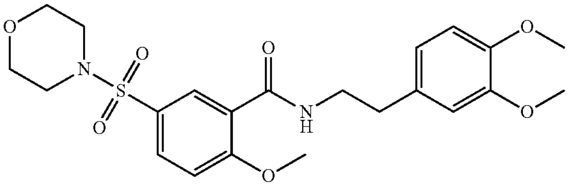

-continued

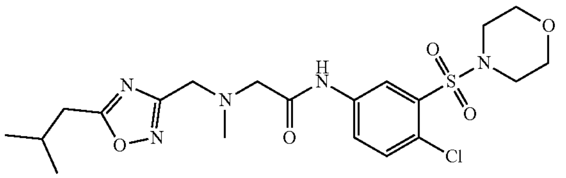

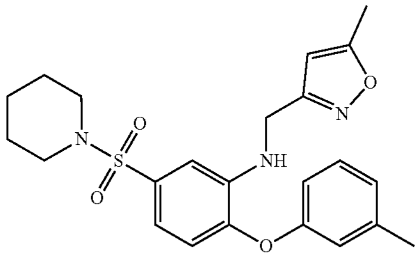

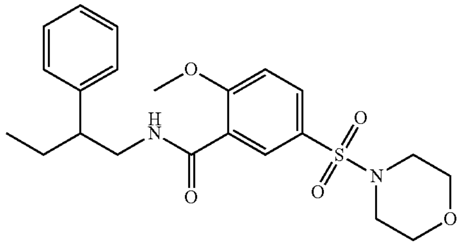

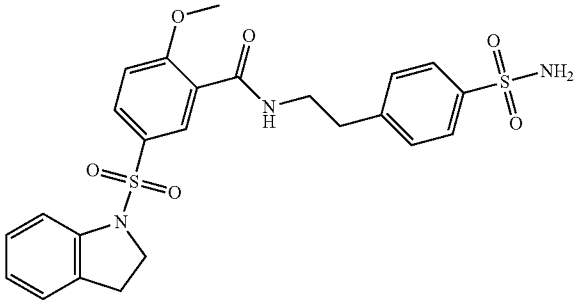

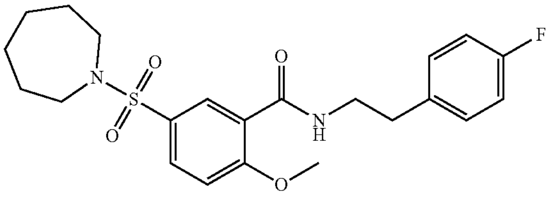

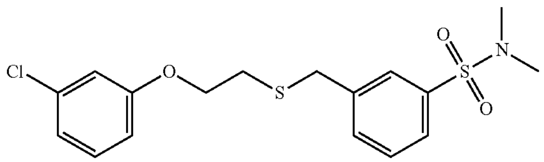

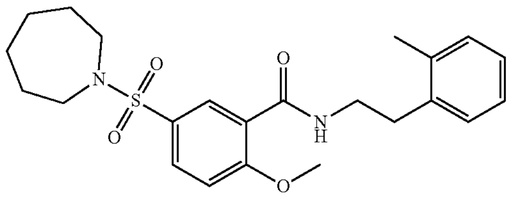

-continued

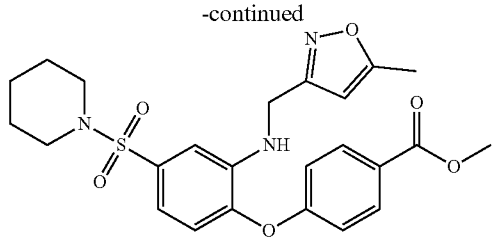

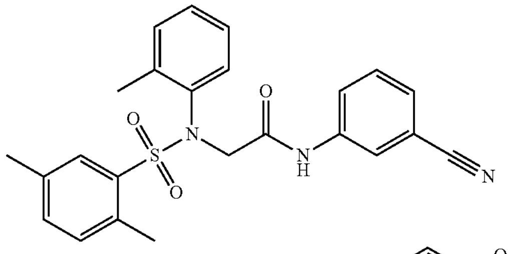

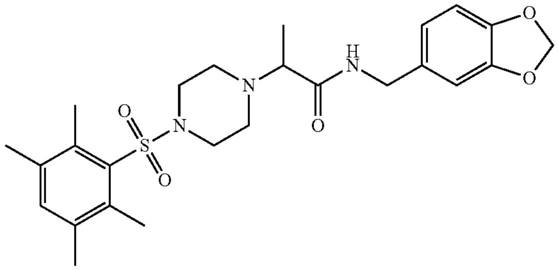

or

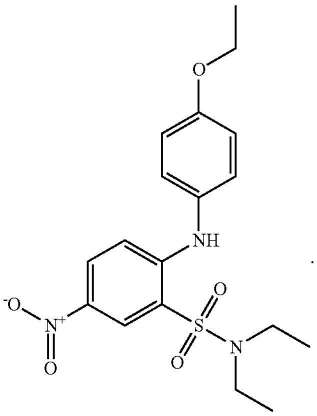

.

In another embodiment, the compound of Formula XVIII is a compound of Formula XVIIIb:

Formula XVIIIb

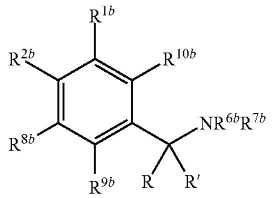

or pharmaceutically acceptable derivatives thereof, wherein $R^{1b}$, $R^{2b}$, $R^{8a}$, $R^{9b}$ and $R^{10b}$ are independently selected from the group consisting of H, alkyl, alkenyl, alkynyl, aryl, cycloalkyl, heterocyclyl, heteroaryl, nitro, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b}$ and $R^{7b}$ are combined to form a cyclic structure including the nitrogen atom to which they are both attached;

R and R' are independently selected from hydrogen and lower alkyl; and p is 0-2.

In another embodiment, $R^{1b}$, $R^{2b}$, $R^{8b}$, $R^{9b}$ and $R^{10b}$ are independently selected from the group consisting of H, alkyl, alkenyl, alkynyl, aryl, cycloalkyl, heterocyclyl, heteroaryl, nitro, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

$R^{6b}$ and $R^{7b}$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^{6b}$ and $R^{7b}$ are combined to form a cyclic structure including the nitrogen atom to which they are both attached;

R and R' are independently selected from hydrogen and lower alkyl; and p is 0-2.

In one embodiment, $R^{1b}$, $R^{2b}$, $R^{8a}$, $R^{9b}$ and $R^{10b}$ are independently selected from the group consisting of H, $OCH_3$, $SCF_3$;

$R^{6b}$ and $R^{7b}$ are independently selected from $CH_3$ and

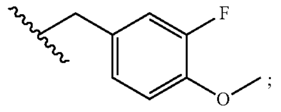 [SMILES: *Cc1ccc(OC)c(F)c1]

and

R and R' are H.

In another embodiment, $R^{1b}$, $R^{2b}$, $R^{8b}$, $R^{9b}$ and $R^{10b}$ are independently selected from the group consisting of H, $OCH_3$, $SCF_3$;

$R^{6b}$ and $R^{7b}$ are independently selected from $CH_3$ and

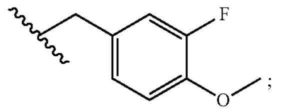 [SMILES: *Cc1ccc(OC)c(F)c1]

and

R and R' are H.

In one embodiment, the compound of Formula XVIIIb is:

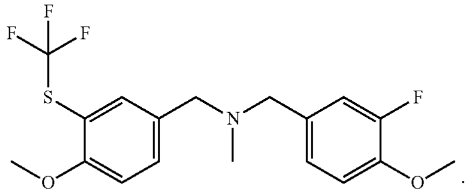 [SMILES: COc1ccc(CN(C)Cc2ccc(OC)c(SC(F)(F)F)c2)cc1F]

In one embodiment, the compound of Formula XVIII is selected with the proviso that if X is $CH_2$, then $NR^6R^7$ is not indolinone or benzoimidazolone.

In one embodiment, the compound of Formula XVIIIb is selected with the proviso that if R and R' are both H, then $NR^6R^7$ is not indolinone or benzoimidazolone.

In certain embodiments, the compounds for use in the compositions and methods provided herein are of Formula XIX:

Formula XIX

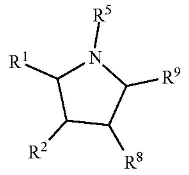

or pharmaceutically acceptable derivatives thereof, wherein $R^1$, $R^2$, $R^8$ and $R^9$ are independently selected from the group consisting of H, alkyl, alkenyl, alkynyl, aryl, cycloalkyl, heterocyclyl, heteroaryl, halo, pseudohalo, oxo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, arylalkyl, heteroarylalkyl, aryl, heteroaryl, heterocyclyl, cycloalkyl, alkylcarbonyl, cycloalkylcarbonyl, heterocyclylcarbonyl, heteroarylcarbonyl or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment, the compound of Formula XIX is a compound of Formula XIXa:

Formula XIXa

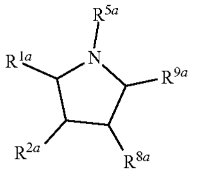

or pharmaceutically acceptable derivatives thereof, wherein $R^{1a}$, $R^{2a}$, $R^{8a}$ and $R^{9a}$ are independently selected from the group consisting of H, alkyl, aryl, cycloalkyl, heterocyclyl, heteroaryl, oxo and $C(O)R^4$;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^{5a}$ is alkyl, arylalkyl, heteroarylalkyl, aryl, heteroaryl, heterocyclyl, cycloalkyl, alkylcarbonyl, cycloalkylcarbonyl, heterocyclylcarbonyl, heteroarylcarbonyl or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, heteroarylcarbonyl, aryl sulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In one embodiment, $R^{1a}$, $R^{2a}$, $R^{8a}$ and $R^{9a}$ are independently selected from the group consisting of H, cyclopentyl, cyclohexyl, $NO_2$,

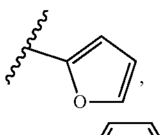,
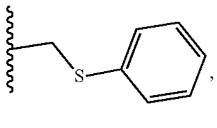,
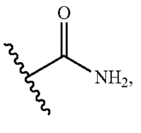,
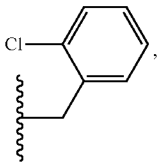,
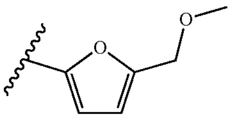, and
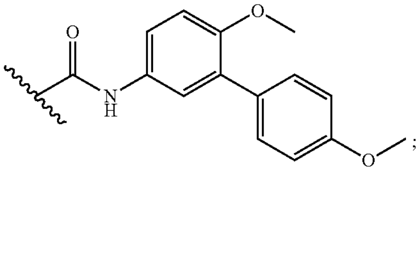;

and $R^{5a}$ is

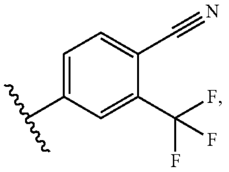,
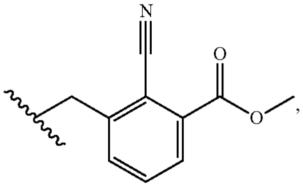,
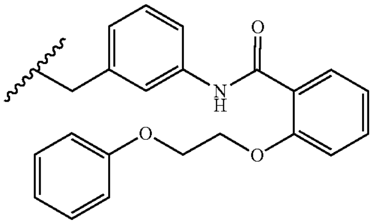,
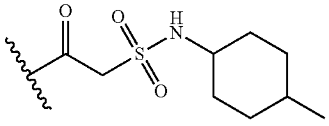,
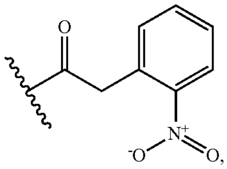,
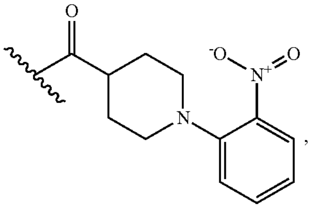, or
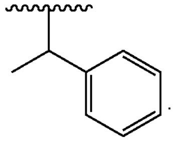.

In another embodiment, $R^{1a}$, $R^{2a}$, $R^{8a}$ and $R^{9a}$ are independently selected from the group consisting of H, cyclopentyl, cyclohexyl, oxo,

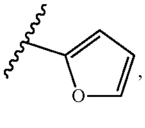,
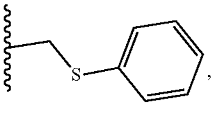,
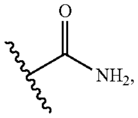,
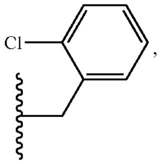,
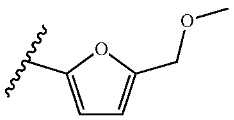, and
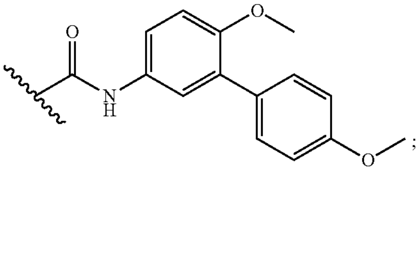; and $R^{5a}$ is

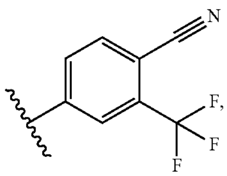

,

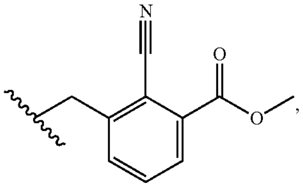

,

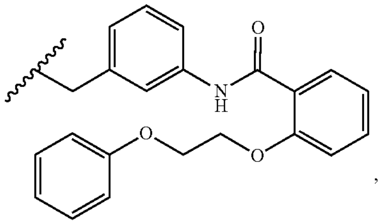

,

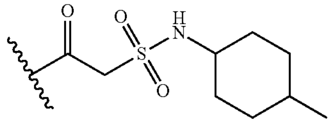

,

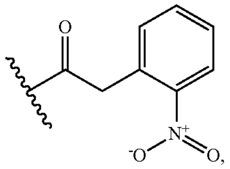

,

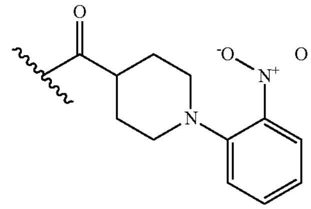

, or

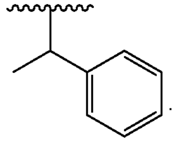

.

In one embodiment, the compound of Formula XIXa is:

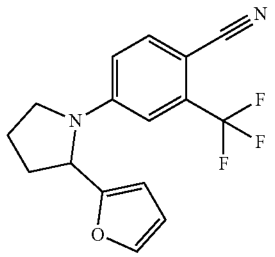

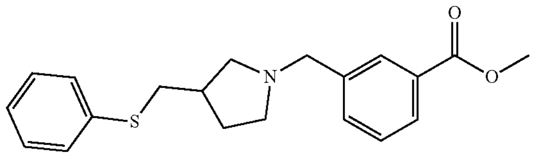

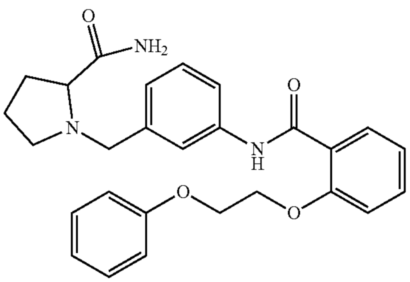

-continued

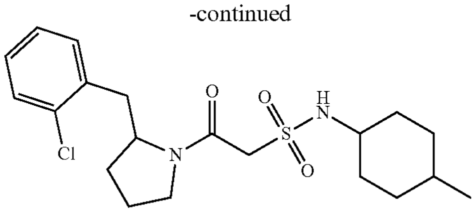

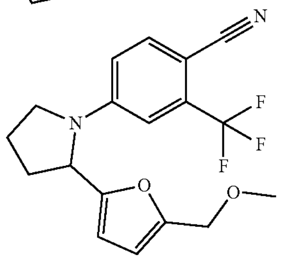

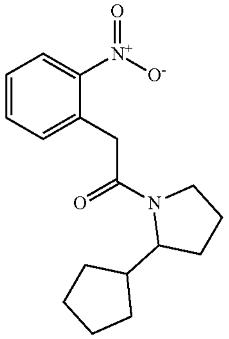

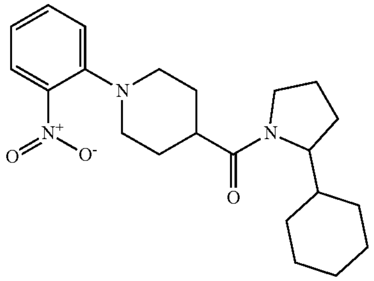

or

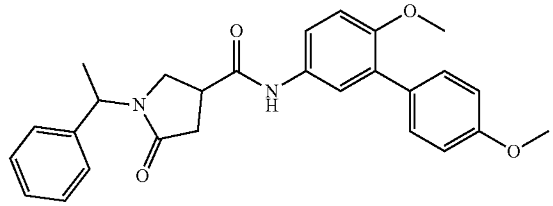

.

In one embodiment, the compound of formula XIX is selected with the proviso that the compound does not contain a hydrazide, a macrocycle, a thienopyridine or a thienopyrimidine.

In another embodiment, the disease to be treated with the compounds of formula XIX is not hepatocellular cancer.

In one embodiment, the compound of formula XIXa is selected with the proviso that the compound does not contain a hydrazide, a macrocycle, a thienopyridine or a thienopyrimidine.

In another embodiment, the disease to be treated with the compounds of formula XIXa is not hepatocellular cancer.

In certain embodiments, the compounds for use in the compositions and methods provided herein are of Formula XX:

Formula XX

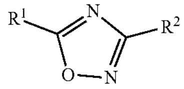

or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and p is 0-2.

In another embodiment, the compound of Formula XX is a compound of Formula XXa:

Formula XXa

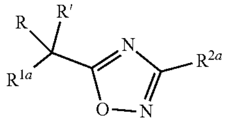

or pharmaceutically acceptable derivatives thereof, wherein $R^{1a}$ is $OR^3$, $S(O)_pR^4$, $NR^5C(O)R^4$ or $NR^6R^7$;

$R^{2a}$ is alkyl, aryl or heteroaryl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, or arylcarbonyl, or $R^6$ and $R^7$ are combined to form a cyclic structure including the nitrogen atom to which they are both attached;

R and R' are independently selected from hydrogen and lower alkyl; and p is 0-2.

In one embodiment, $R^{1a}$ is $CH_3$, Bn,

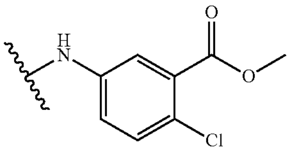
,
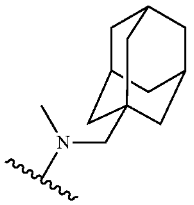
,
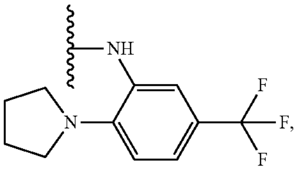

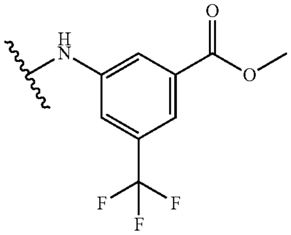
,
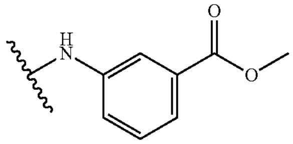
,
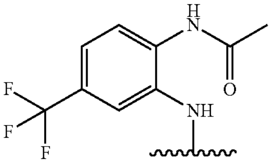
,
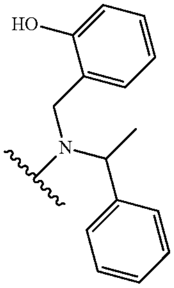
,
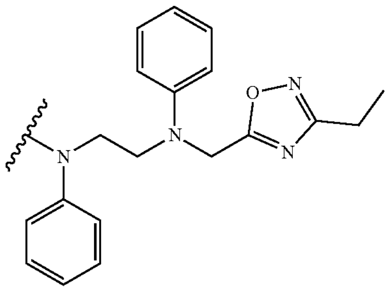
,
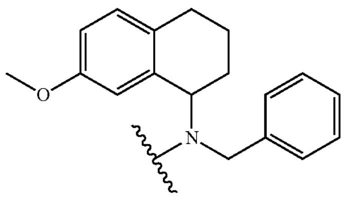
, -continued
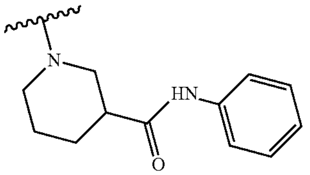
,
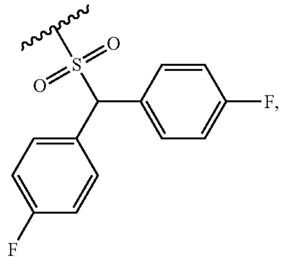
,
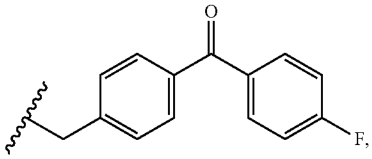
,
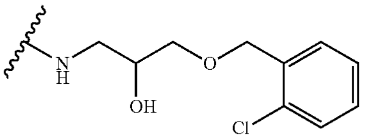
,
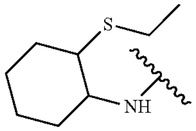
, or
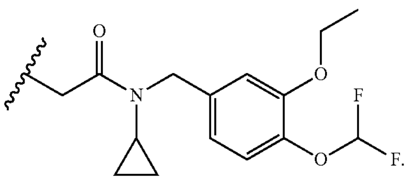
.
$R^{2a}$ is $CH_3$, $CH_2CH_3$, t-Bu, Ph,
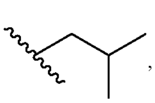
,
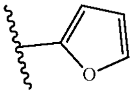
,
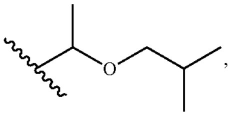
,
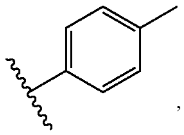
,
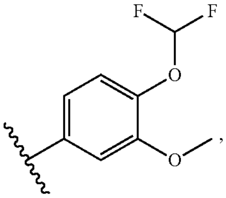
, or
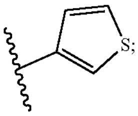
;
and
R and R' are independently selected from hydrogen and $CH_3$.
In one embodiment, the compound of Formula XXa is:
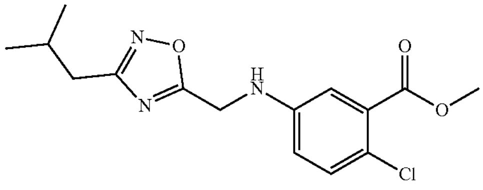
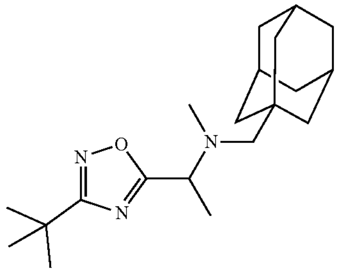
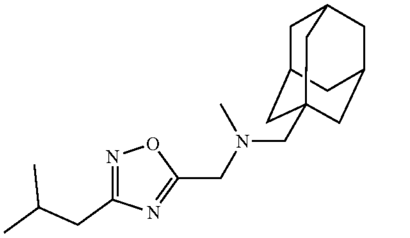
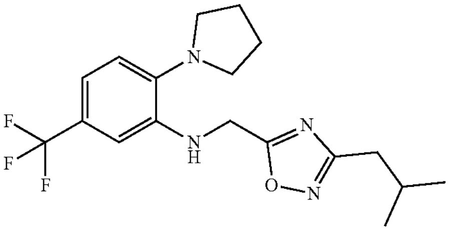
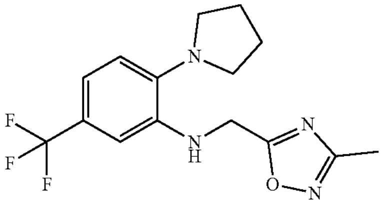
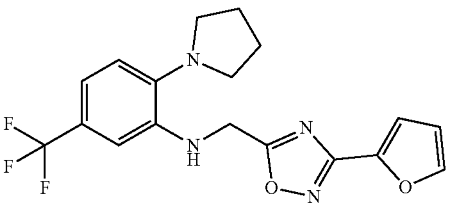
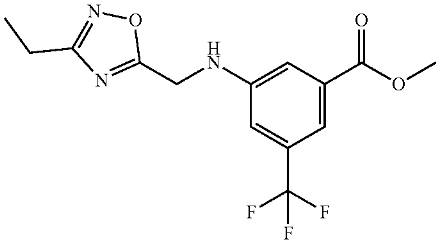

-continued

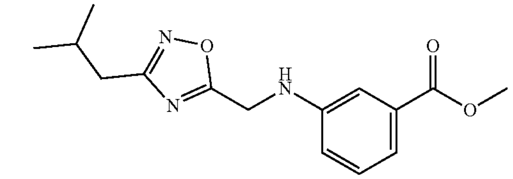

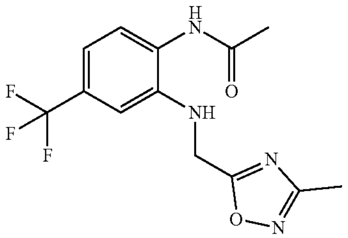

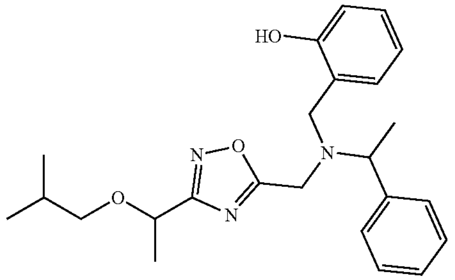

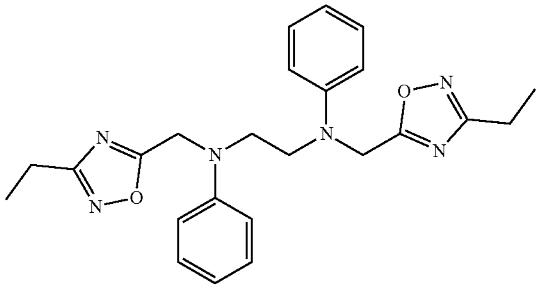

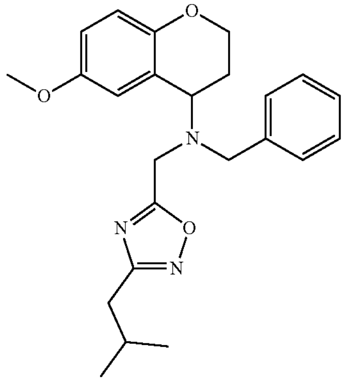

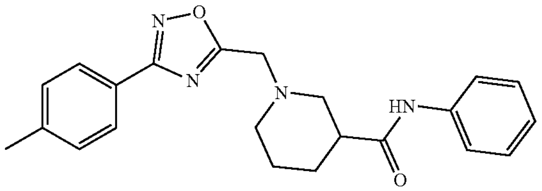

-continued

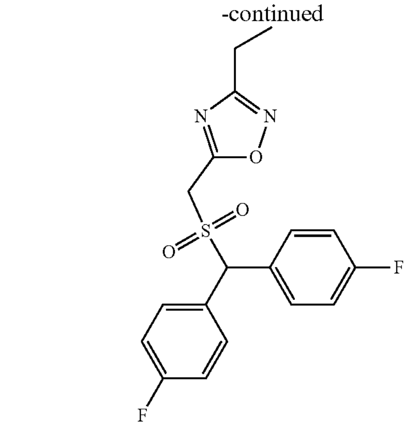

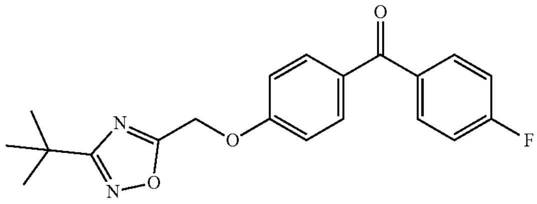

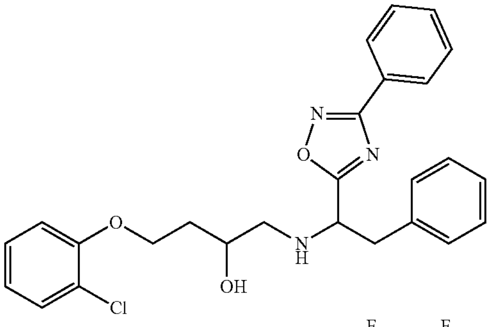

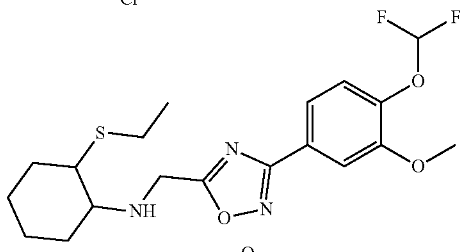

or

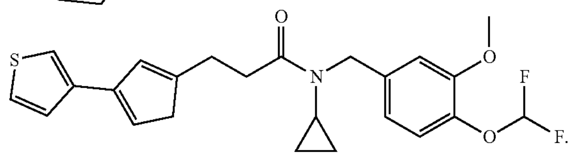

In another embodiment, the compound of Formula XX is a compound of Formula XXb:

Formula XXb

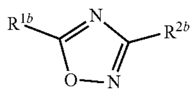

or pharmaceutically acceptable derivatives thereof, wherein $R^{1b}$ is alkyl, arylalkyl or heteroarylalkyl;

$R^{2b}$ is aryl, heteroaryl, or C(R)(R')$NR^6R^7$;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached; and R and R' are independently selected from hydrogen and lower alkyl.

In one embodiment, $R^{1b}$ is $CH_3$,

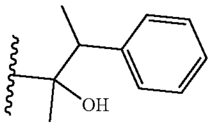,
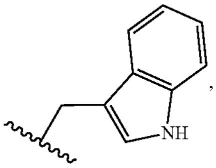,
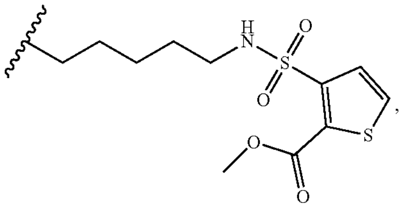, or
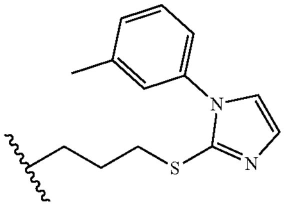;

and $R^{2b}$ is

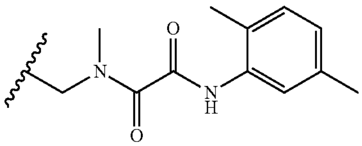,
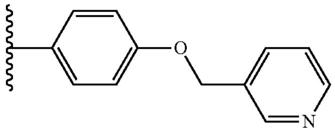,
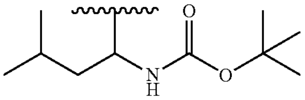,
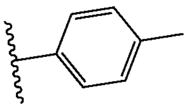, or 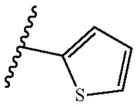.

In one embodiment, the compound of Formula XXb is:

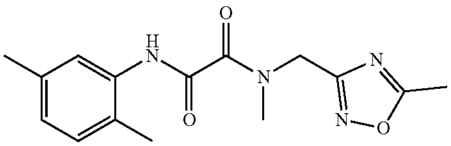

-continued

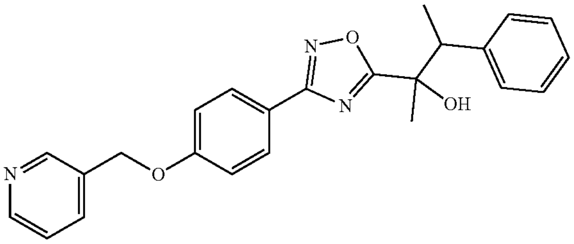

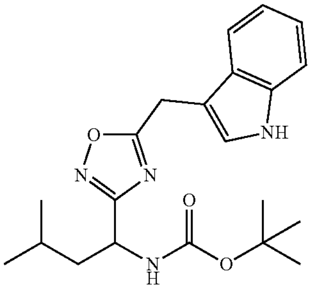

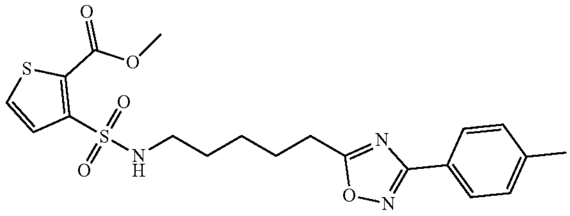

or

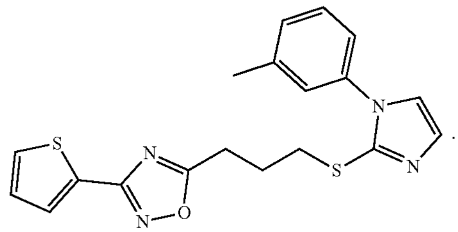.

In another embodiment, the compound of Formula XX is a compound of Formula XXc:

Formula XXc

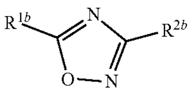

or pharmaceutically acceptable derivatives thereof, wherein $R^{1b}$ is aryl or heteroaryl; and $R^{2b}$ is heterocyclyl.

In one embodiment, $R^{1b}$ is

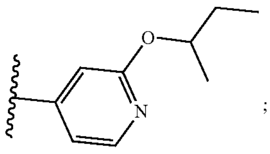 [SMILES: *c1ccnc(OC(C)CC)c1];

and $R^{2b}$ is

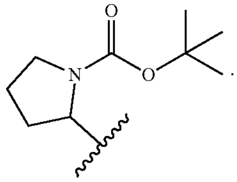 [SMILES: *C1CCCN1C(=O)OC(C)(C)C]

In one embodiment, the compound of Formula XXc is:

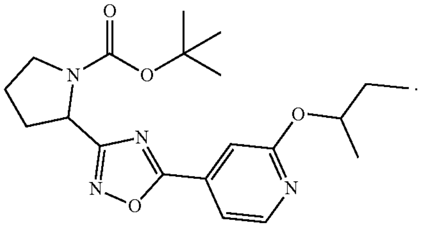 [SMILES: CCC(C)Oc1cc(-c2nc(C3CCCN3C(=O)OC(C)(C)C)no2)ccn1]

In one embodiment, the compound of Formula XX is selected with the proviso that if $R^1$ is pyridyl, then $R^2$ is not phenyl.

In one embodiment, the compound of Formula XX is selected with the proviso that if $R^2$ is pyridyl, then $R^1$ is not phenyl or cyclohexyl.

In certain embodiments, the compounds for use in the compositions and methods provided herein are of Formula XXI:

Formula XXI

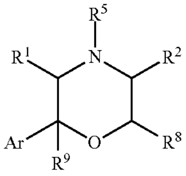

or pharmaceutically acceptable derivatives thereof, wherein $R^1$, $R^2$ and $R^8$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^9$ is H or alkyl;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or —$NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

p is 0-2; and

Ar is aryl or heteroaryl.

In another embodiment, the compound of Formula XXI is a compound of Formula XXIa:

Formula XXIa

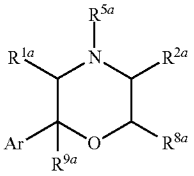

or pharmaceutically acceptable derivatives thereof, wherein $R^{1a}$, $R^{2a}$ and $R^{8a}$ are H or alkyl;

$R^{9a}$ is H or alkyl;

$R^{5a}$ is hydrogen, alkyl, alkenyl, alkynyl, aryl, heteroaryl, heterocyclyl, cycloalkyl, alkylcarbonyl, cycloalkylcarbonyl, or arylcarbonyl; and Ar is aryl or heteroaryl.

In one embodiment, $R^{1a}$, $R^{2a}$ and $R^{8a}$ are H;

$R^9$ is H or $CH_3$;

$R^{5a}$ is Bn,

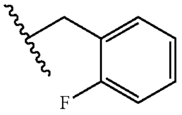,
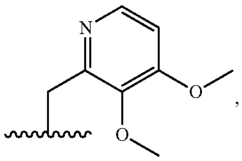,
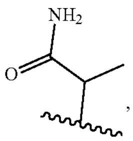,
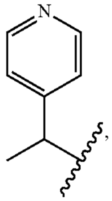,
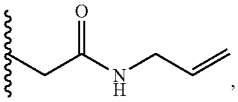,
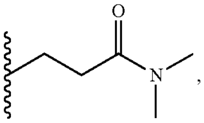,
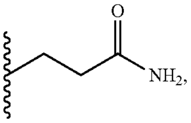,
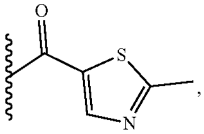,
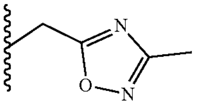,
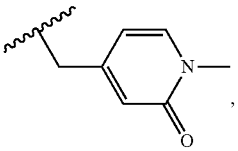,
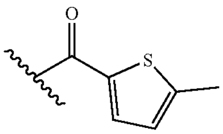, or
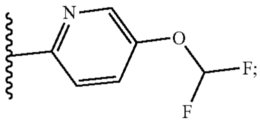;

and
Ar is Ph,
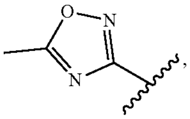,
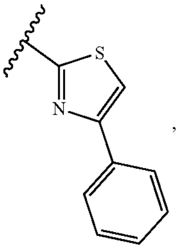,
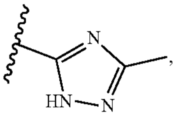,
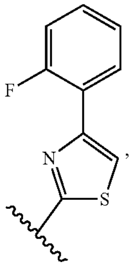,
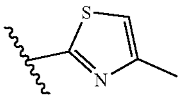,
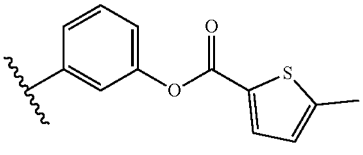,
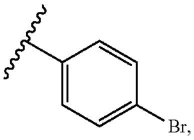, or
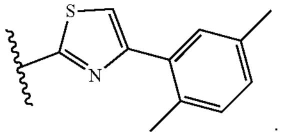.
In one embodiment, the compound of Formula XXIa is:
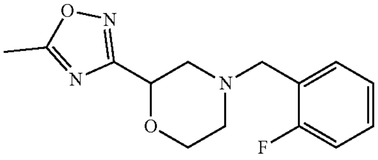
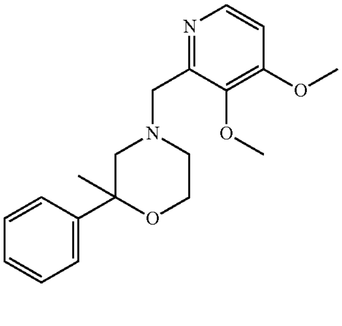
-continued
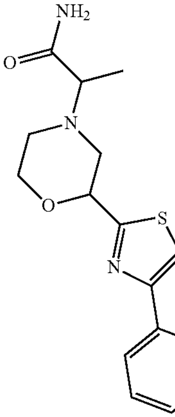
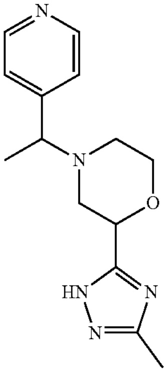
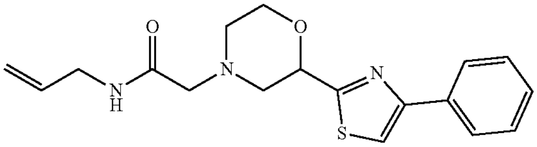
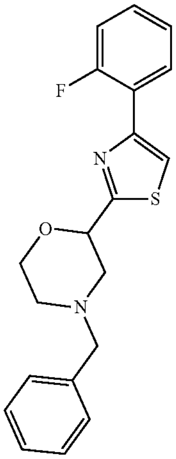
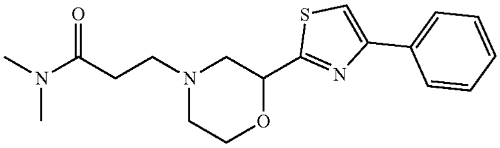
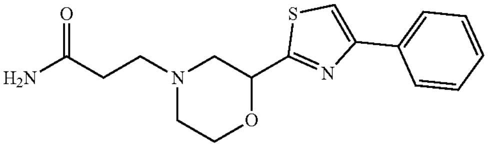
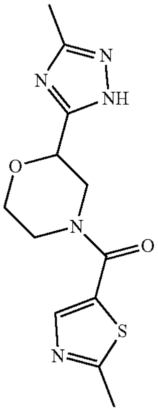

-continued

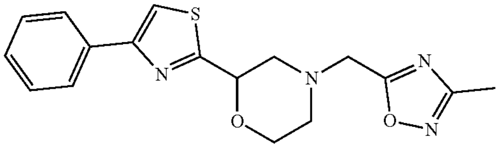

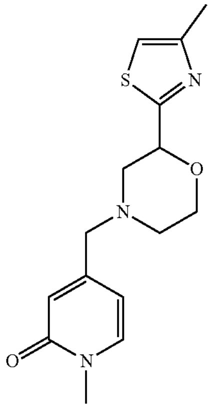

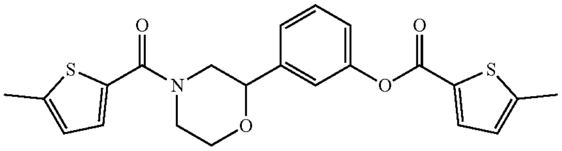

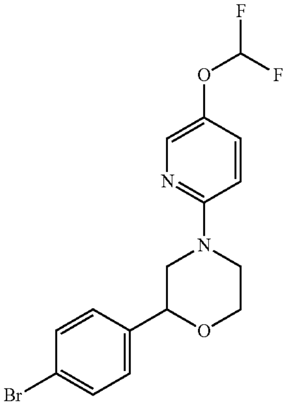

or

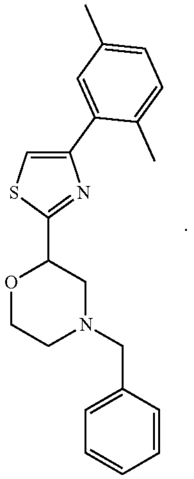

In one embodiment, the compound of Formula XXI is selected with the proviso that if Ar is pyridyl, then $R^5$ is not phenyl.

In one embodiment, the compound of Formula XXIa is selected with the proviso that if Ar is pyridyl, then $R^5$ is not phenyl.

In certain embodiments, the compounds for use in the compositions and methods provided herein are of Formula XXII:

Formula XXII

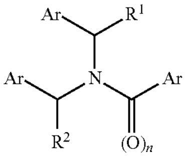

or pharmaceutically acceptable derivatives thereof, wherein $R^1$ and $R^2$ are independently selected from the group consisting of H, alkyl, alkenyl, alkynyl, aryl, cycloalkyl, heterocyclyl, heteroaryl, halo, pseudohalo, $OR^3$, $C(O)R^4$, $S(O)_pR^4$, $NR^5C(O)R^4$, and $NR^6R^7$;

$R^3$ is hydrogen, alkyl, alkenyl, alkynyl, aryl, heteroaryl, heterocyclyl, cycloalkyl, alkylcarbonyl, cycloalkylcarbonyl or arylcarbonyl;

$R^4$ is hydrogen, hydroxy, alkyl, haloalkyl, alkenyl, alkynyl, aryl, alkylaryl, heterocyclyl, cycloalkyl, aralkyl, alkoxy, alkenyloxy, alkynyloxy, aryloxy, alkylaryloxy, heterocyclyloxy, cycloalkyloxy, aralkoxy, or $—NR^6R^7$;

$R^5$ is hydrogen, alkyl, alkenyl, alkynyl, aryl, heteroaryl, heterocyclyl, cycloalkyl, alkylcarbonyl, cycloalkylcarbonyl, or arylcarbonyl;

$R^6$ and $R^7$ are independently selected from hydrogen, alkyl, alkenyl, alkynyl, aryl, heteroaryl, heterocyclyl, cycloalkyl, alkylcarbonyl, cycloalkylcarbonyl, arylcarbonyl, heteroarylcarbonyl, arylsulfonyl, heteroarylsulfonyl, cycloalkylsulfonyl or alkylsulfonyl, or $R^6$ and $R^7$ are combined to form a cyclic structure including the nitrogen atom to which they are both attached;

n is 0 or 1;

p is 0-2; and each Ar is independently selected from aryl or heteroaryl.

In another embodiment, the compound of Formula XXII is a compound of Formula XXIIa:

Formula XXIIa

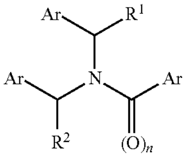

or pharmaceutically acceptable derivatives thereof, wherein $R^{1a}$ is H or alkyl;

$R^{2a}$ is H;

n is 0 or 1; and each Ar is independently selected from aryl or heteroaryl.

In another embodiment, Formula XXIIa is:

Formula XXIIa

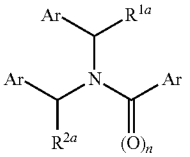

or pharmaceutically acceptable derivatives thereof,
wherein $R^{1a}$ is H or alkyl;
$R^{2a}$ is H;
n is 0 or 1; and
each Ar is independently selected from aryl or heteroaryl.
In one embodiment, $R^{1a}$ is H or $CH_3$;
$R^{2a}$ is H;
n is 0 or 1; and
Ar is independently selected from Ph,

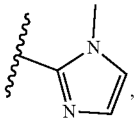, 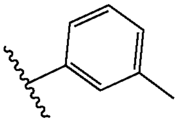, 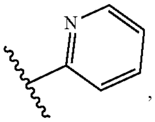,
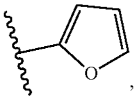, 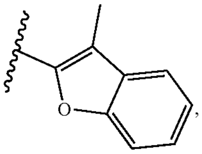, 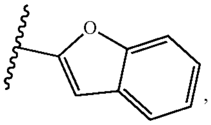,
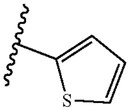, 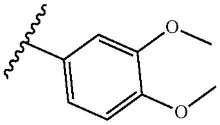,
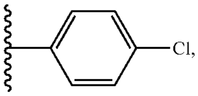, 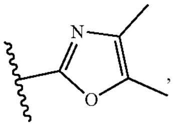,
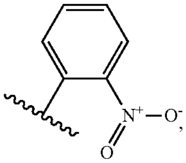, 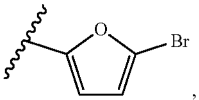, 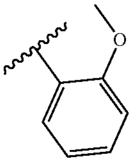,
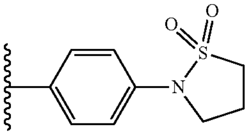, 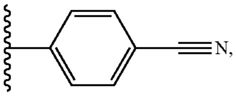,
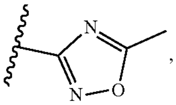, 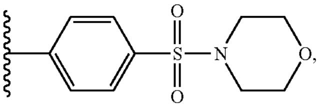,
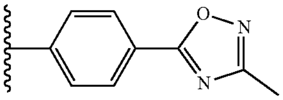, 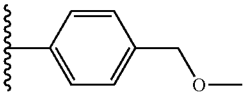,
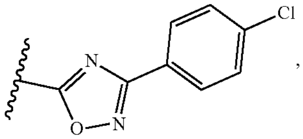, 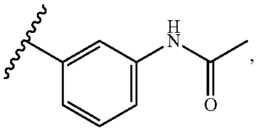, -continued

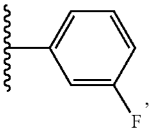, 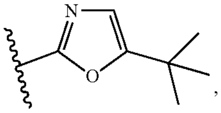,
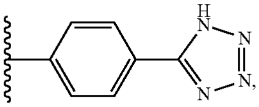, 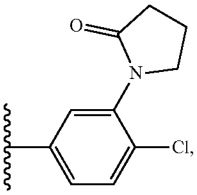,
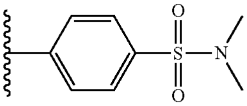, 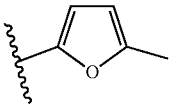,
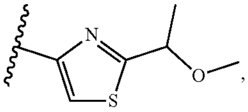, and 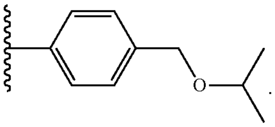.

In one embodiment, $R^{1a}$ is H or $CH_3$;
$R^{2a}$ is H;
n is 0 or 1; and
Ar is independently selected from

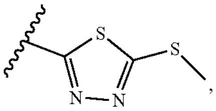, 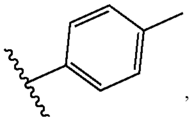, and

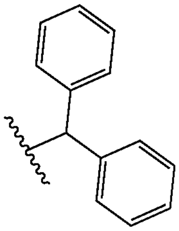,

In one embodiment, the compound of Formula XXIIa is:

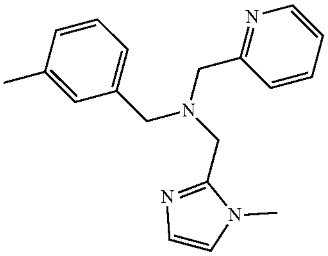

-continued
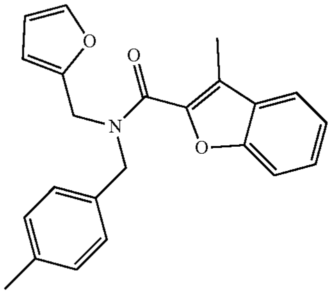
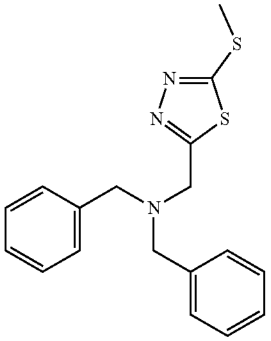
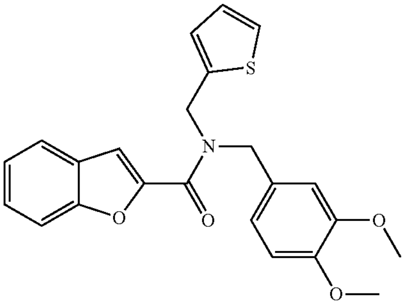
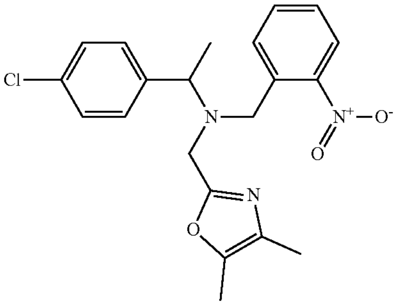
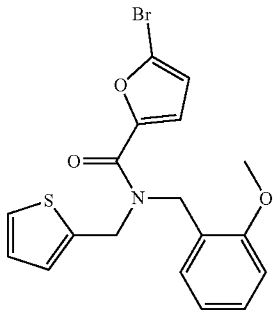
-continued
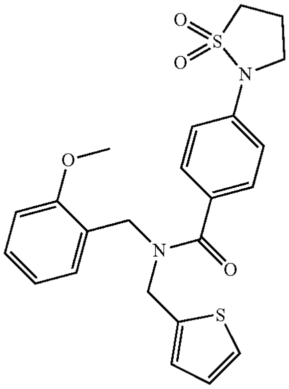
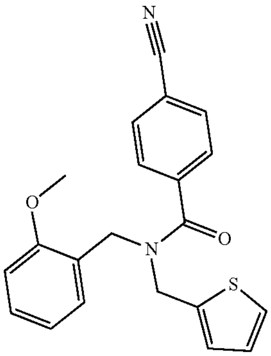
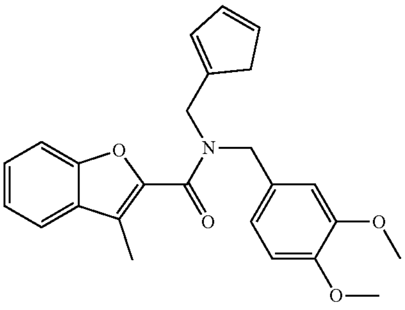
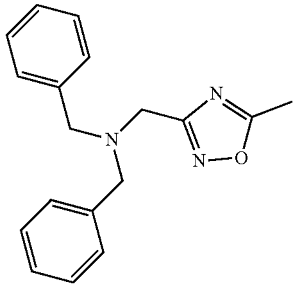

-continued
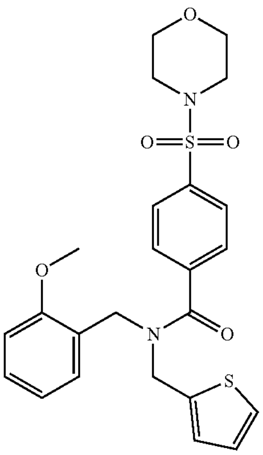
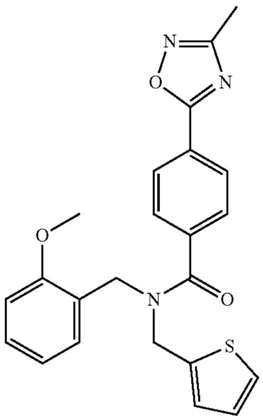
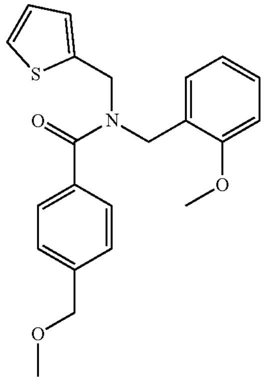
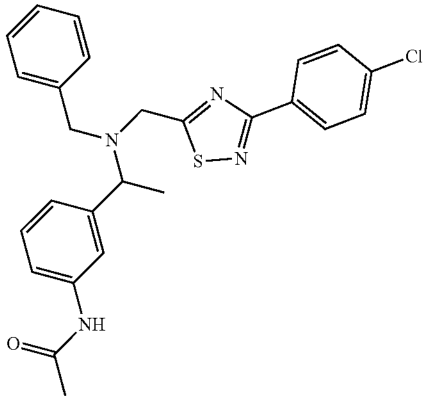
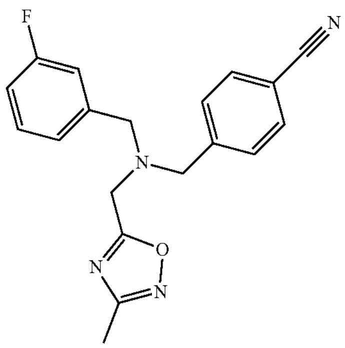
-continued
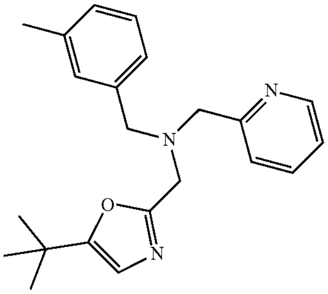
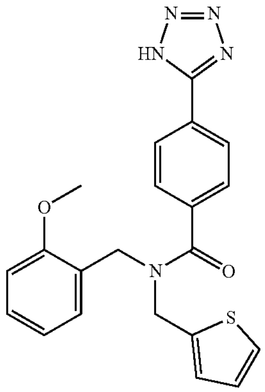
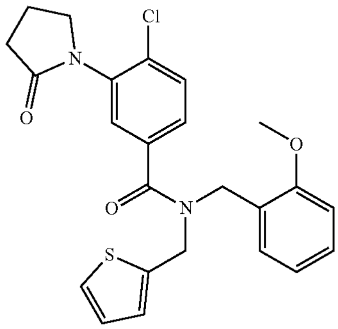
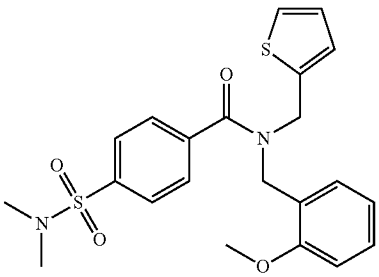
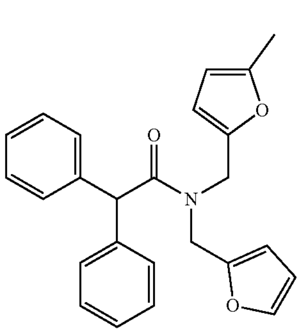

-continued
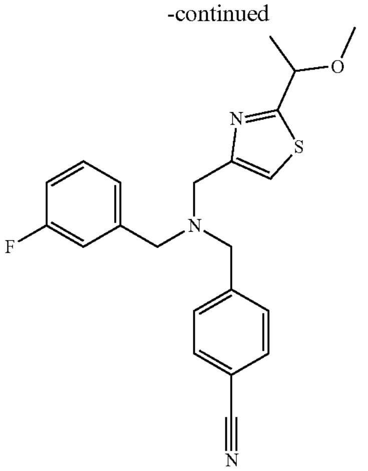
or
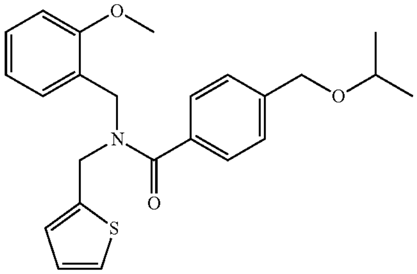
.
In certain embodiments, the compounds for use in the compositions and methods provided herein are selected from the group consisting of the following:
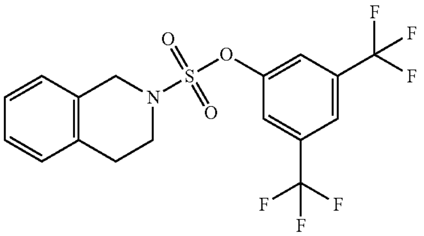
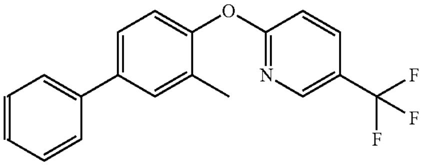
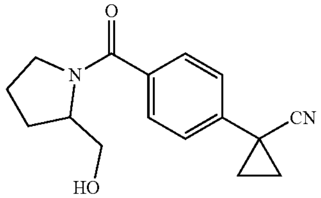
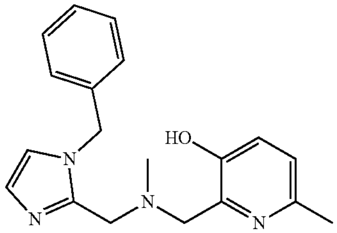
-continued
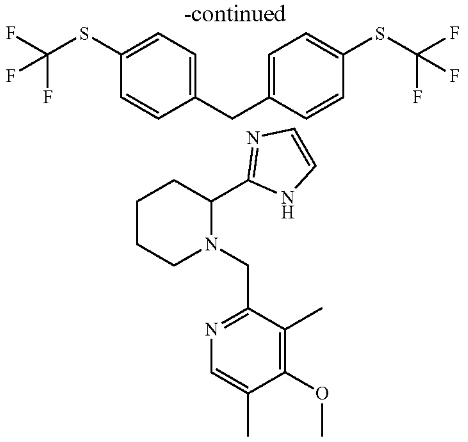
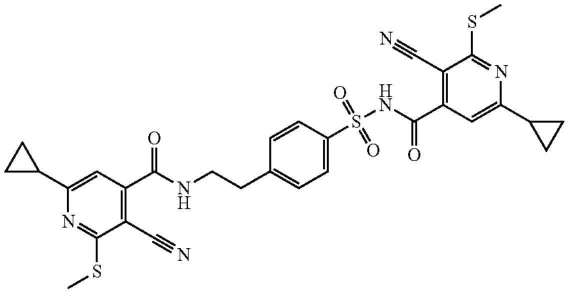
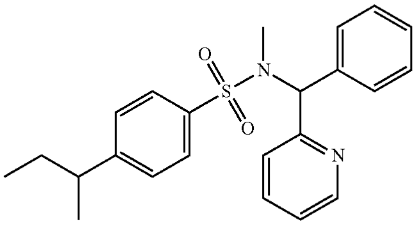
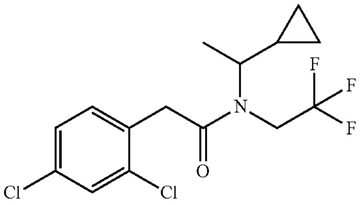
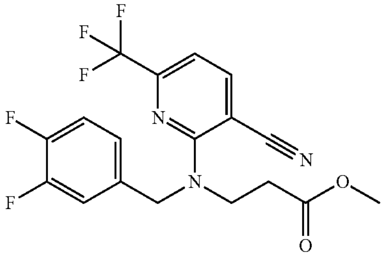
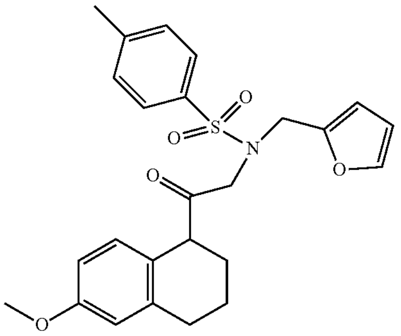

-continued
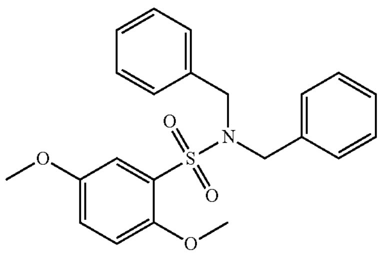
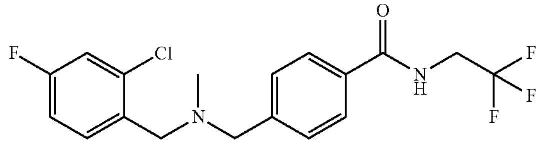
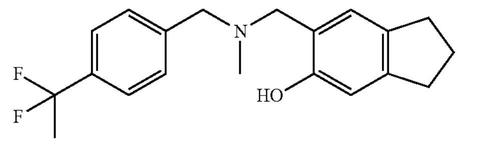
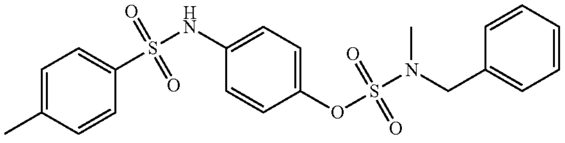
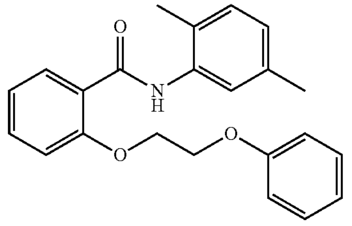
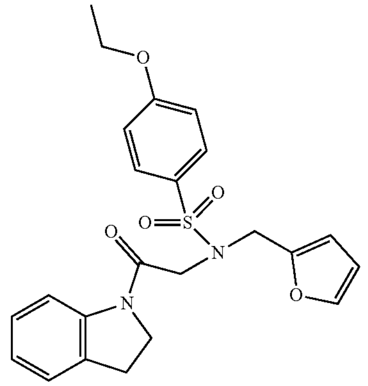
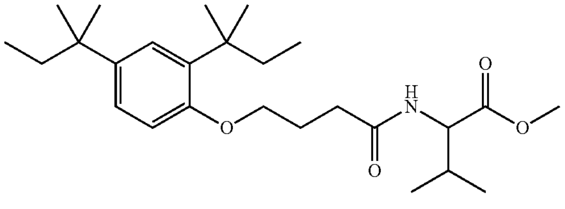
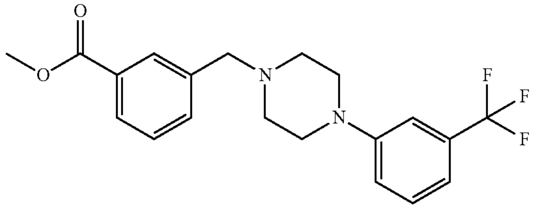
-continued
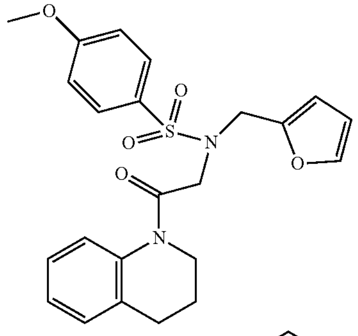
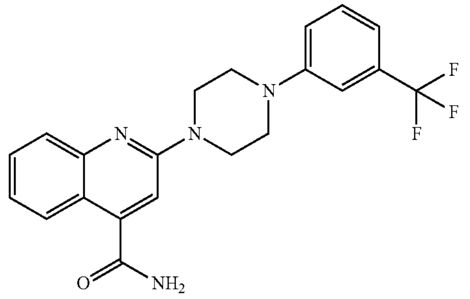
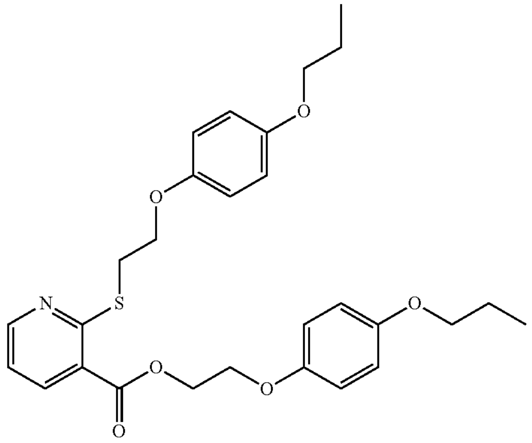
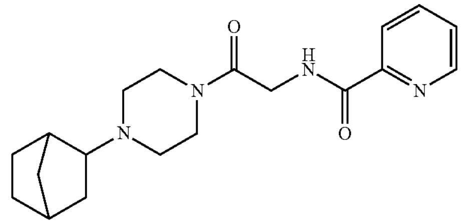
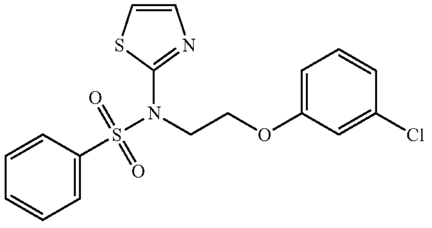
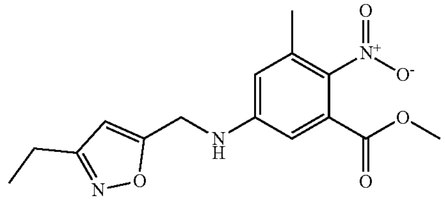

-continued
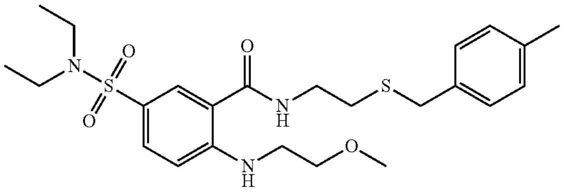
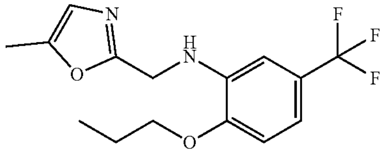
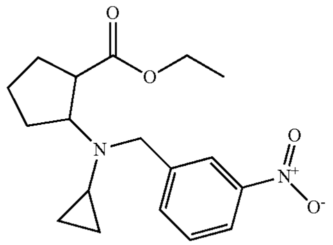
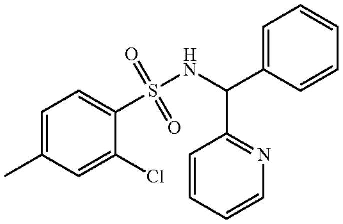
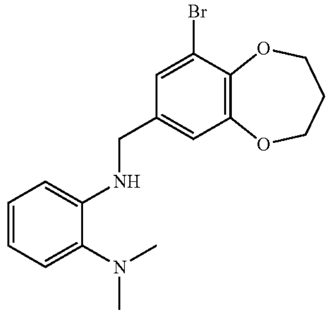
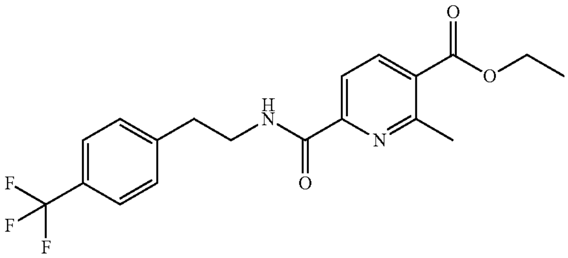
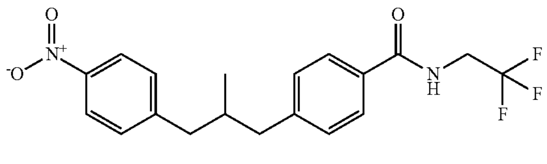
-continued
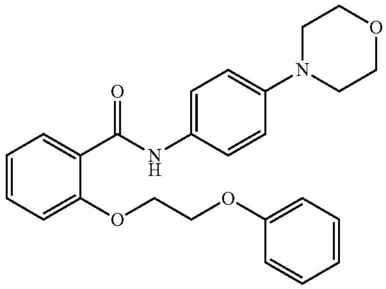
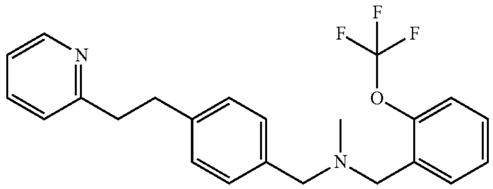
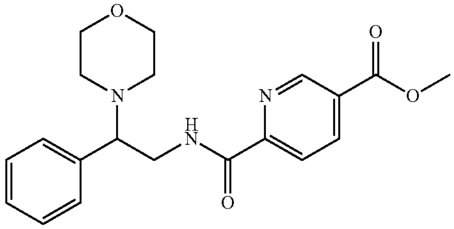
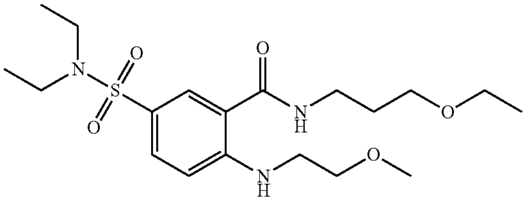
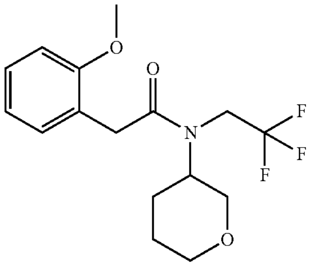
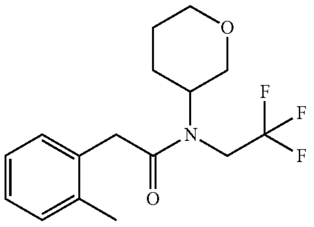
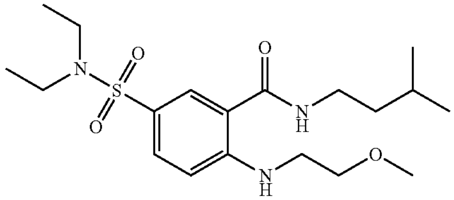

-continued
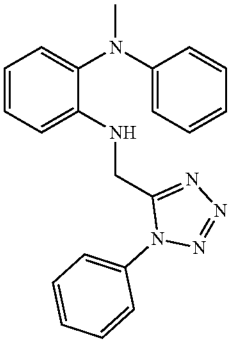
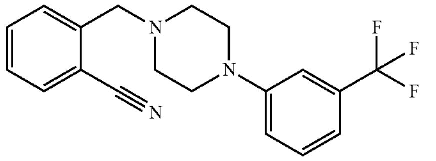
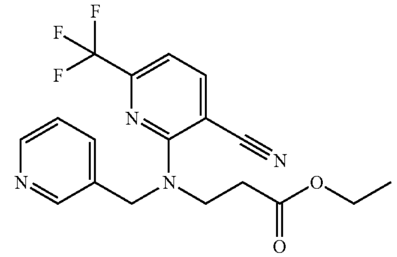
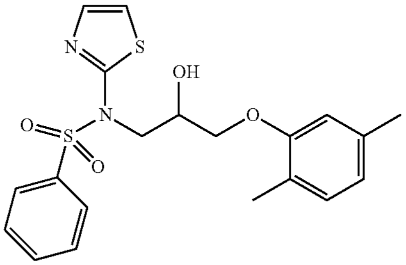
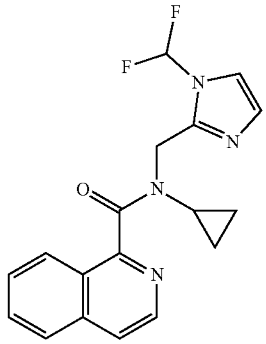
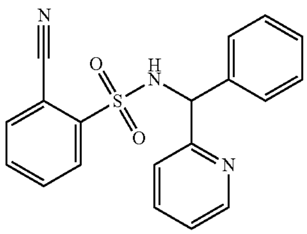
-continued
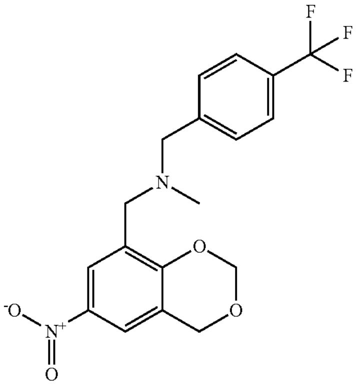
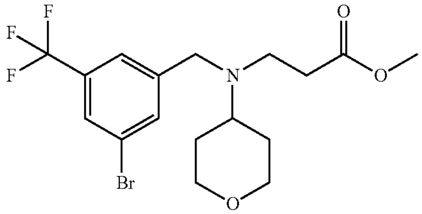
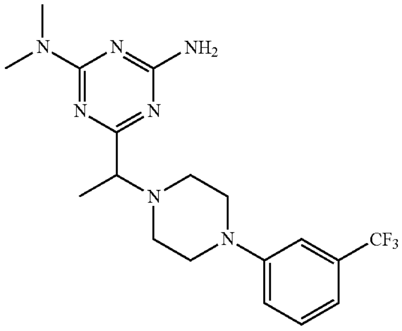
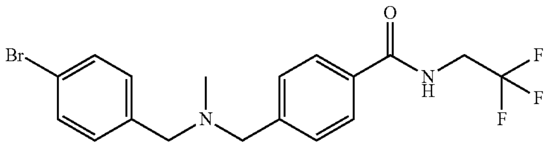
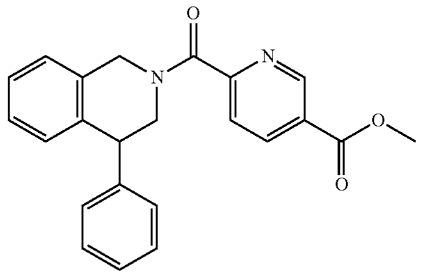
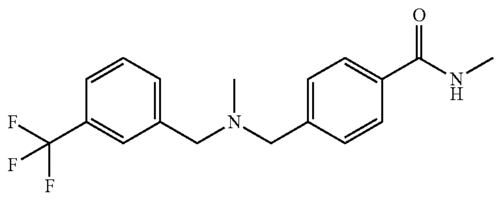

-continued
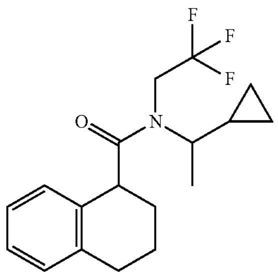
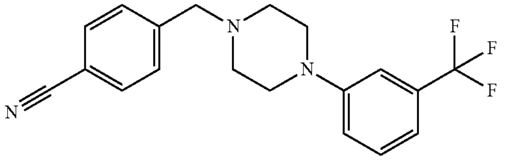
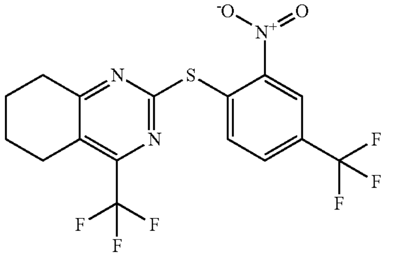
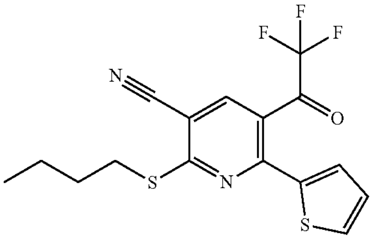
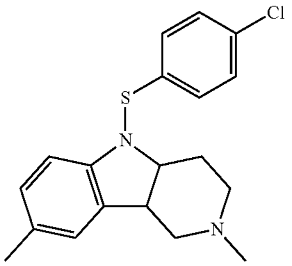
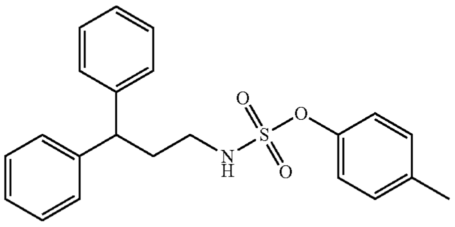
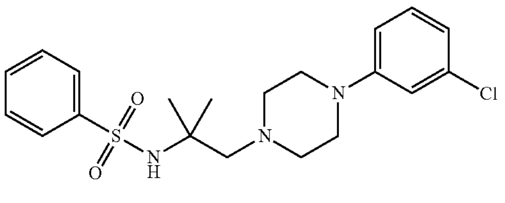
-continued
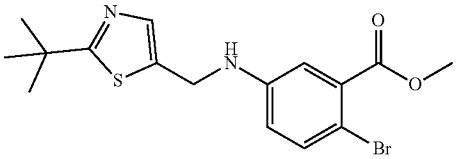
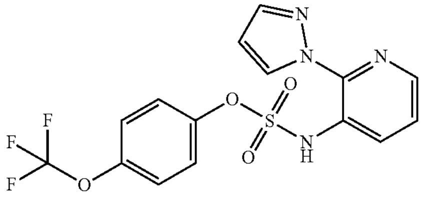
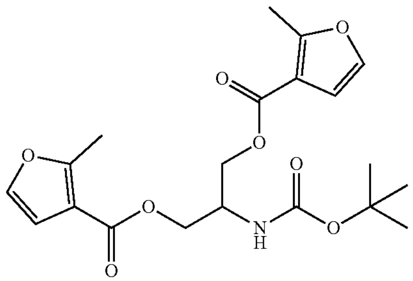
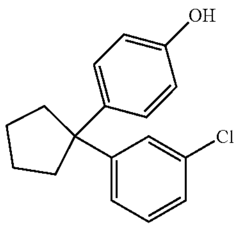
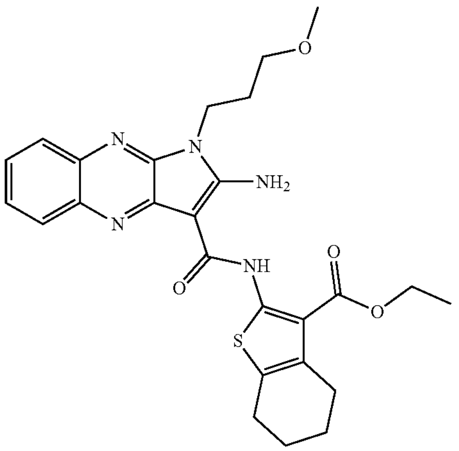
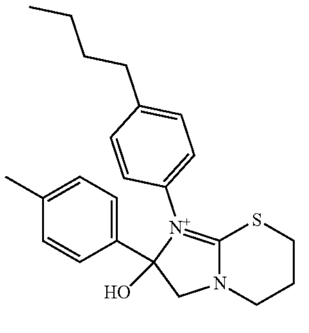
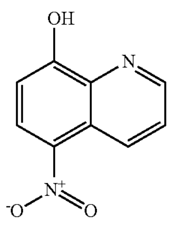

-continued
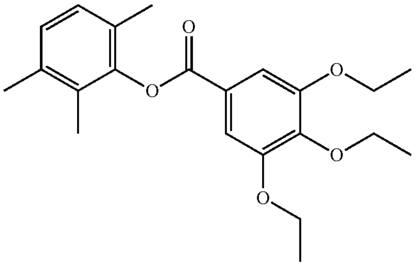
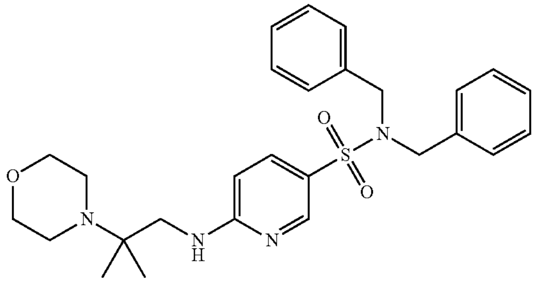
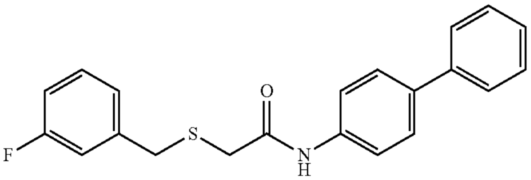
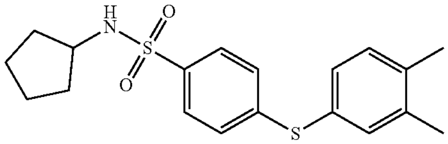
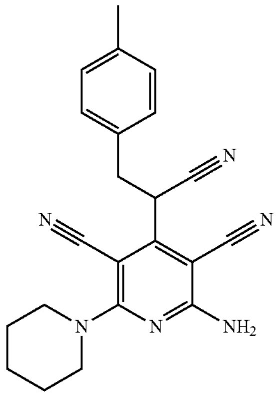
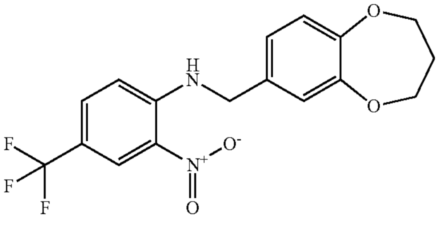
-continued
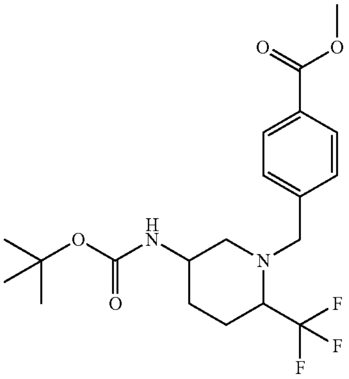
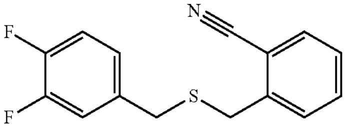
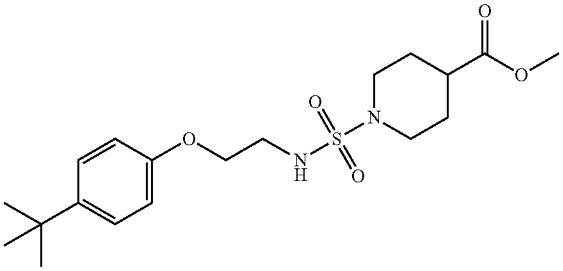
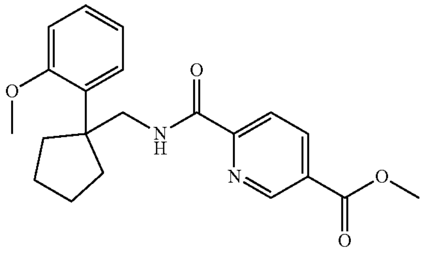
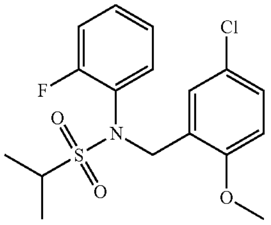
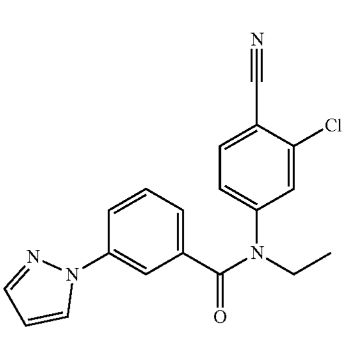

-continued
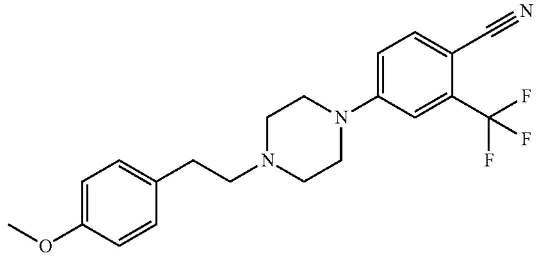
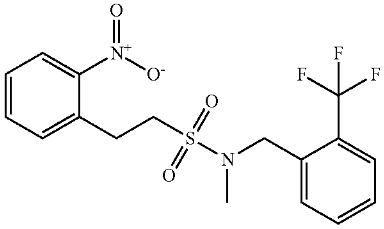
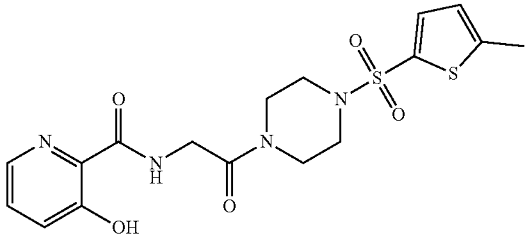
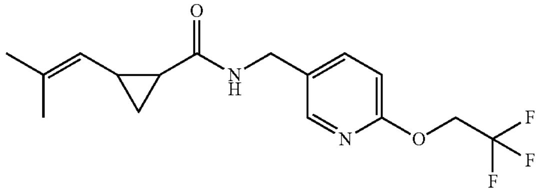
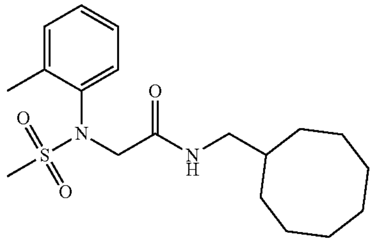
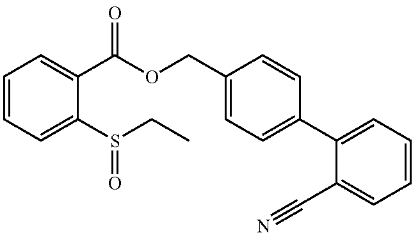
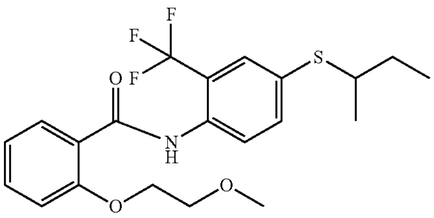
-continued
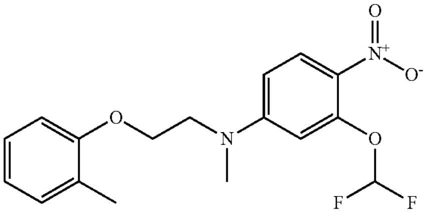
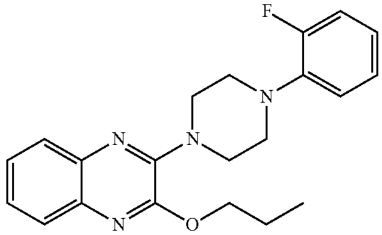
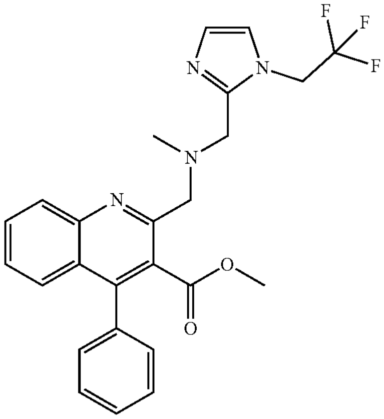
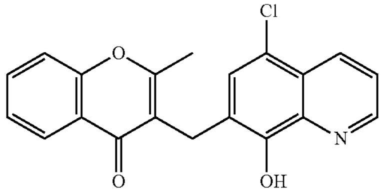
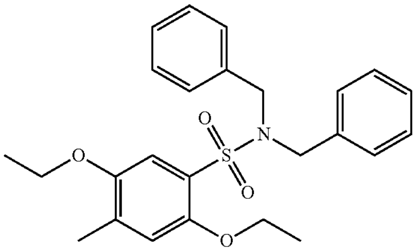
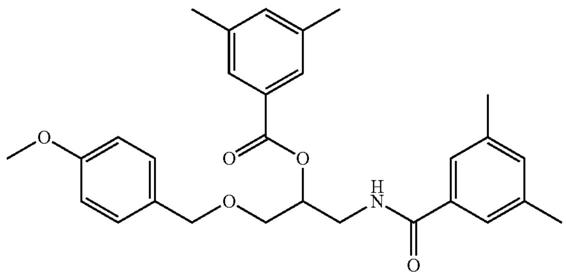

-continued
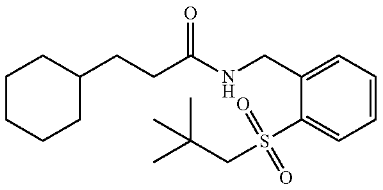
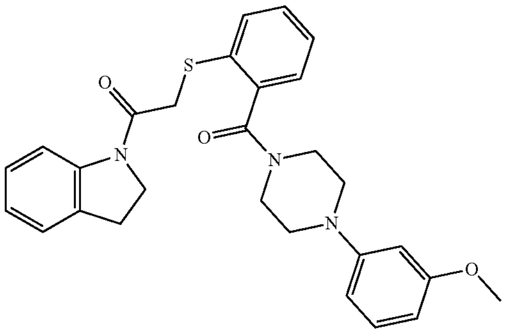
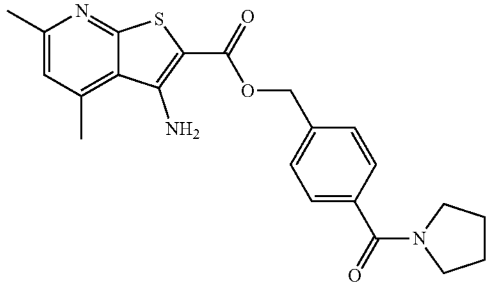
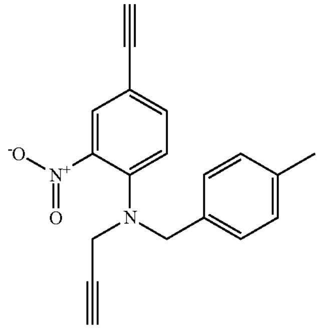
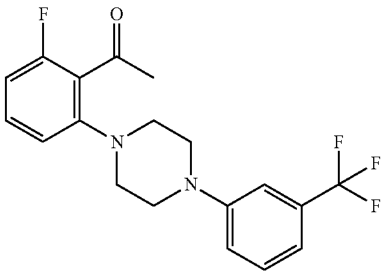
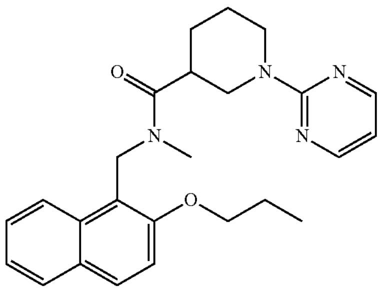
-continued
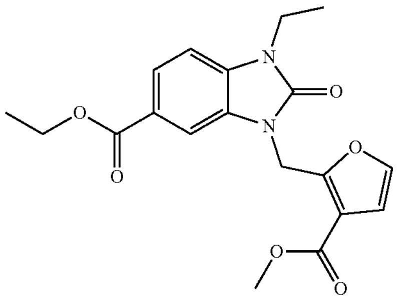
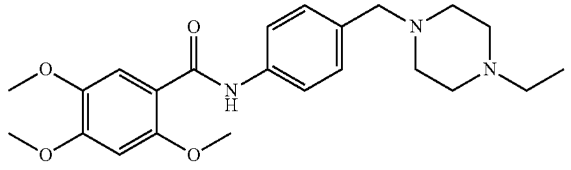
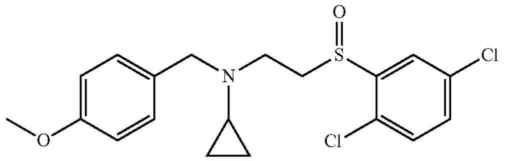
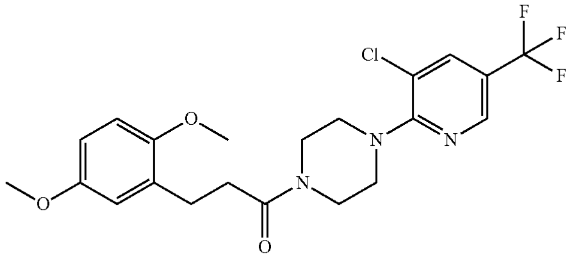
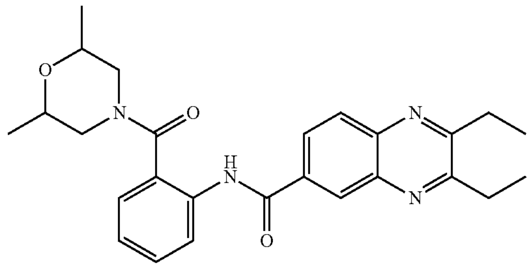
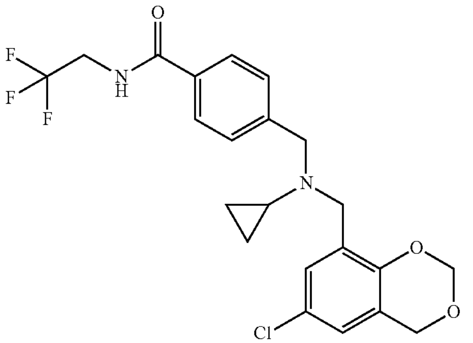

-continued
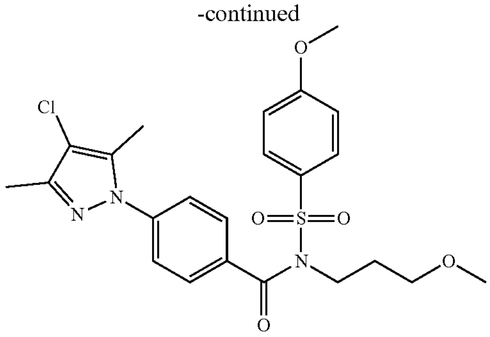
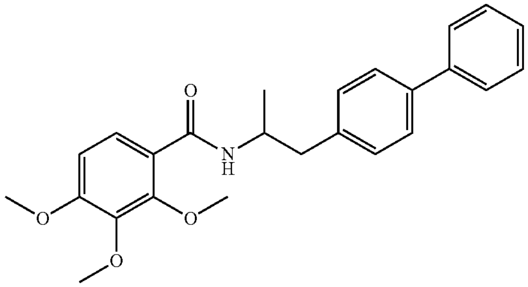
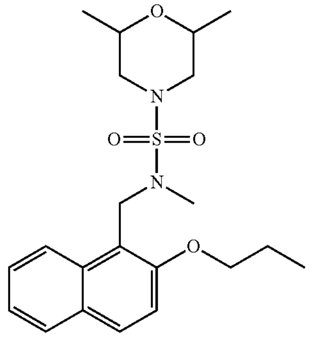
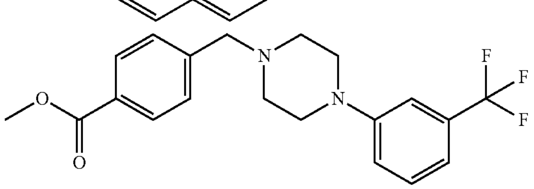
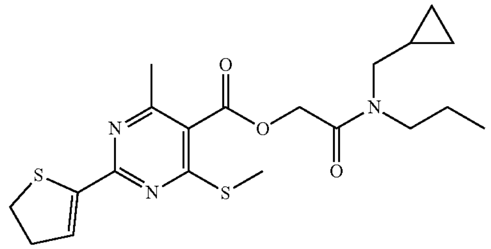
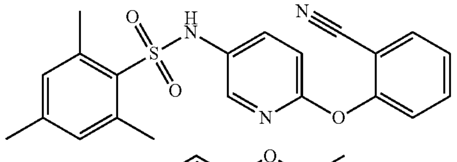
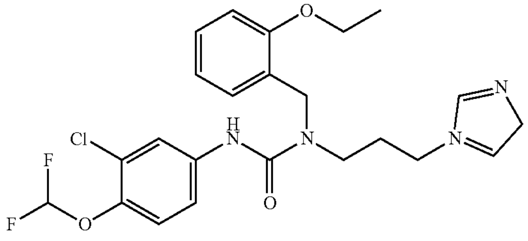
-continued
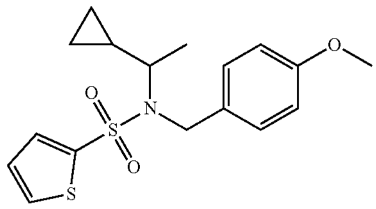
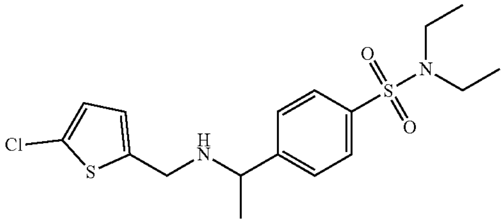
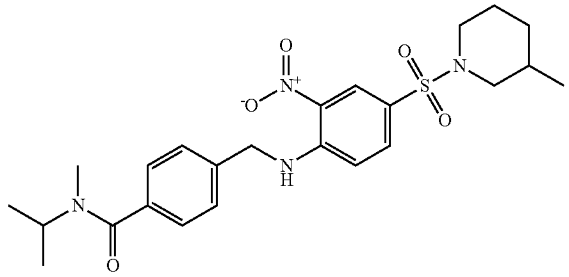
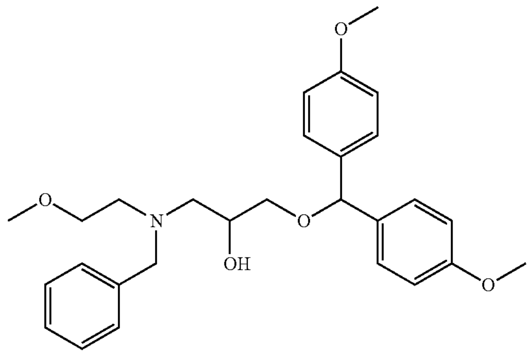
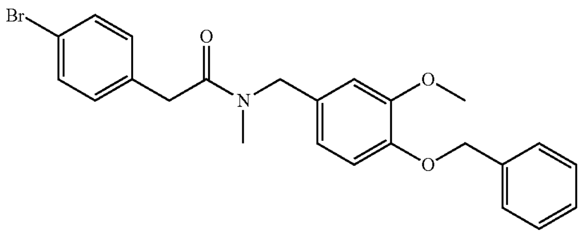
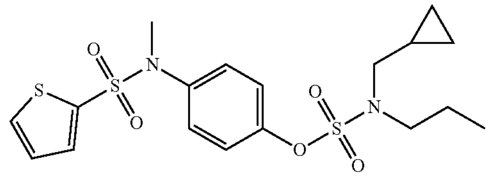
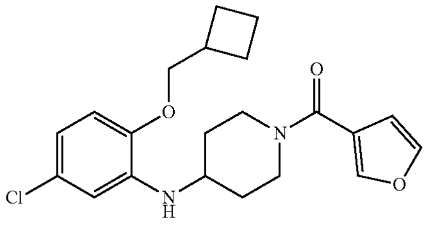

-continued
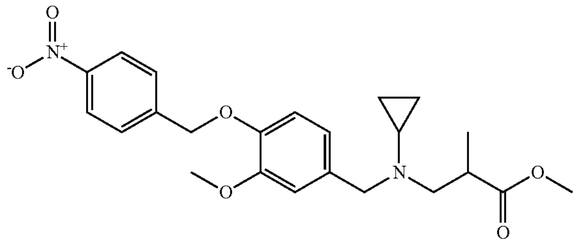
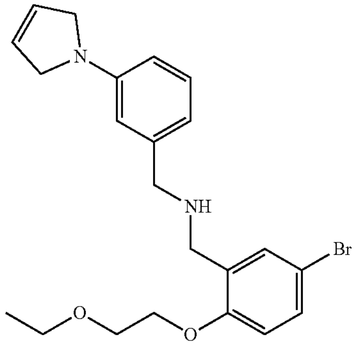
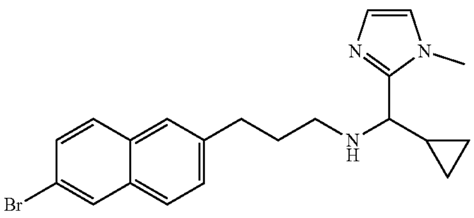
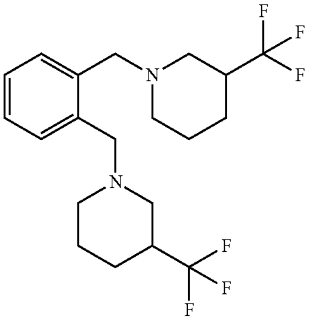
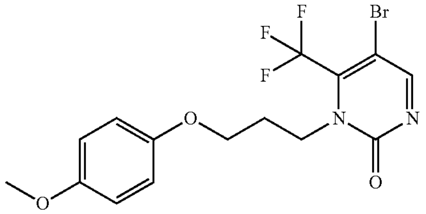
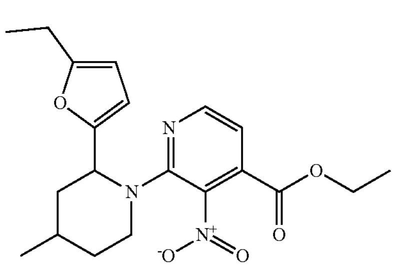
-continued
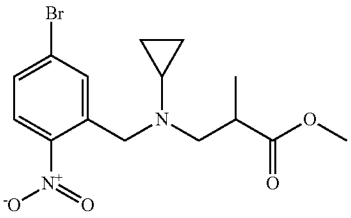
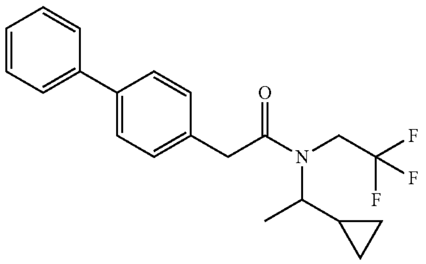
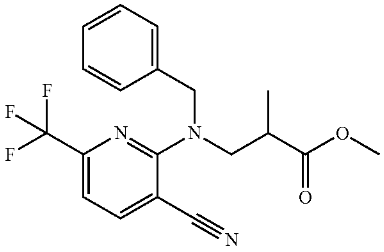
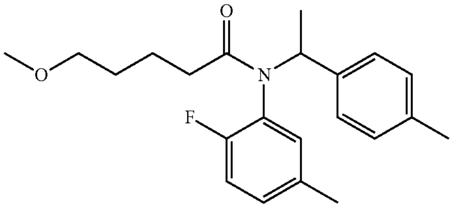
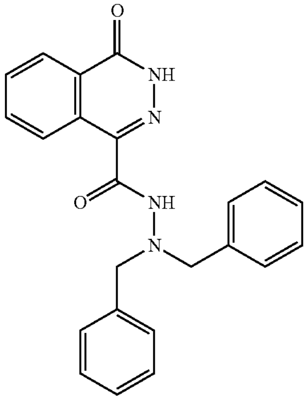
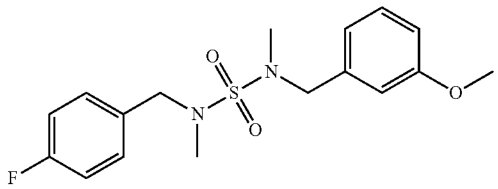

-continued
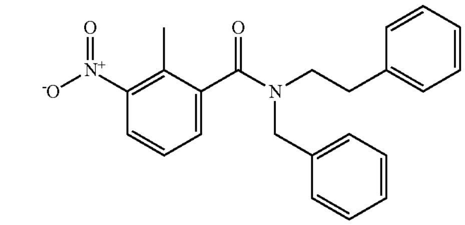
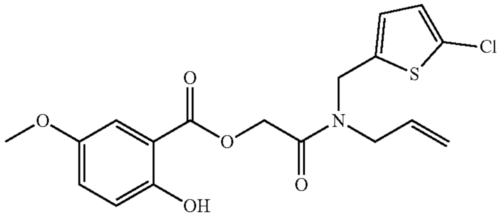
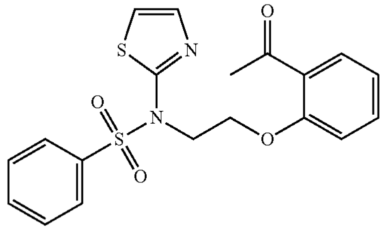
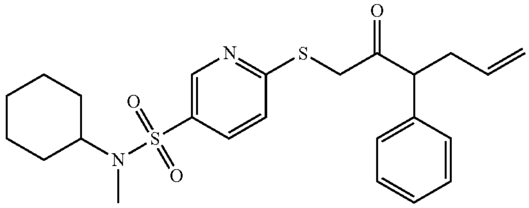
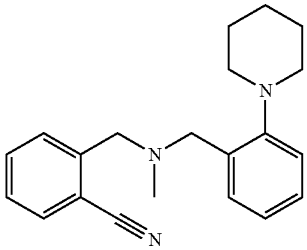
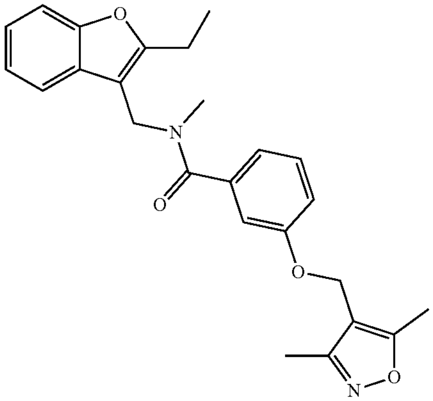
-continued
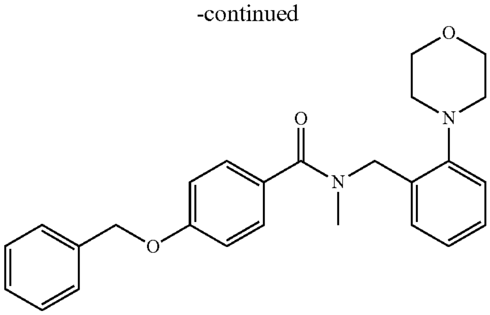
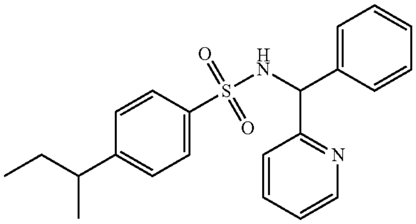
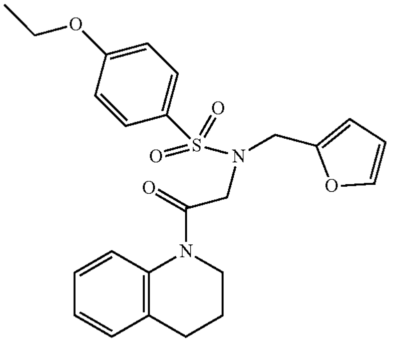
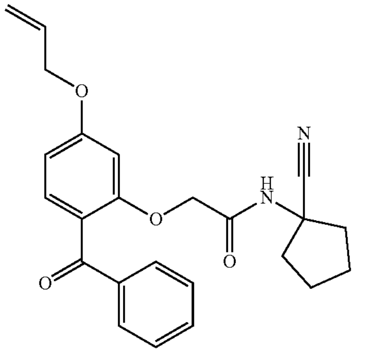
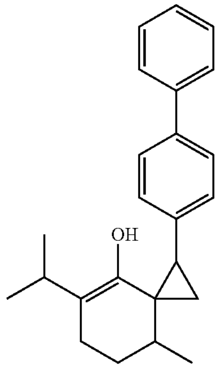
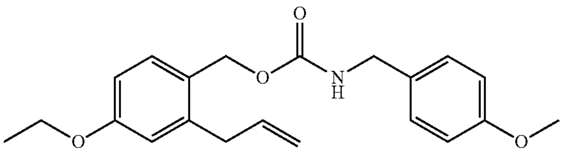

-continued

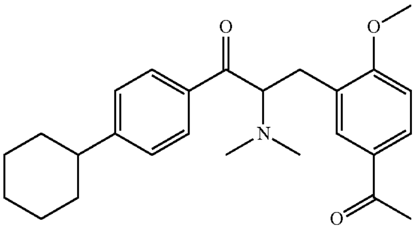

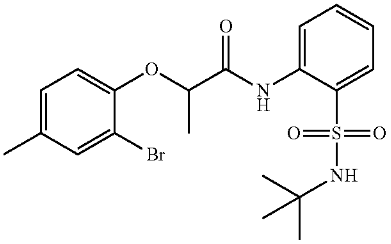

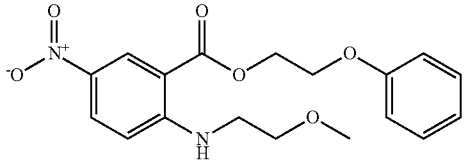

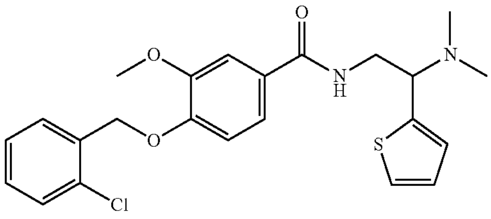

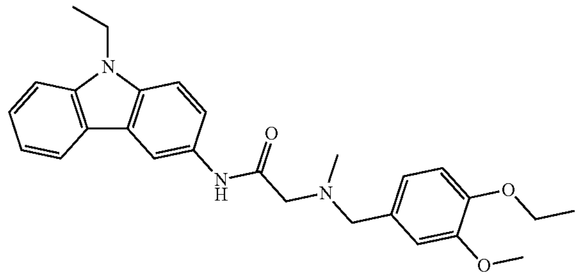

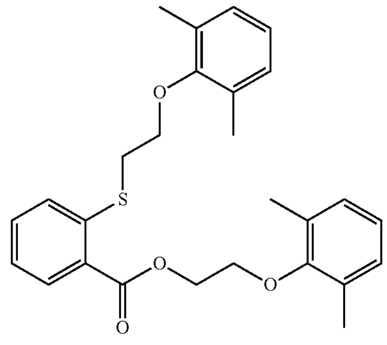

and

-continued

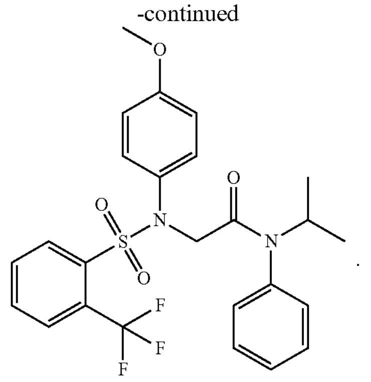

In certain embodiments, the compound for use in the compositions and methods provided herein is

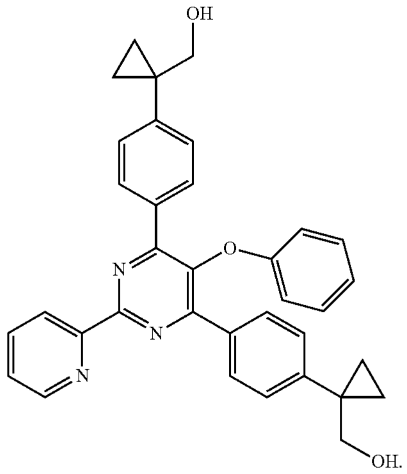 [SMILES: OCC1(c2ccc(-c3nc(-c4ccccn4)nc(-c4ccc(C5(CO)CC5)cc4)c3Oc3ccccc3)cc2)CC1]

6.5. Synthesis of the Compounds

The compounds provided herein may be obtained from commercial sources or readily synthesized by methods well known to those of skill in the art.

6.5.1 Synthetic Procedures

Amide

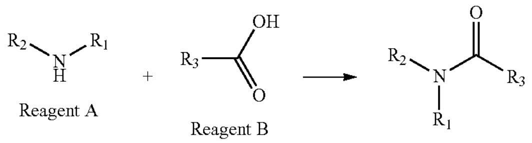

A vial was charged with 0.6 mmol of Reagent B, 1.6 mmol of DIPEA, and dry acetonitrile (1 mL). To the stirred reaction mixture 0.5 mmol of Reagent A (in case of amine salt, an additional 1.5 equivalent amount of DIPEA was added to the reaction mixture), and 0.72 mmol of 2-chloro-N-methylpyridinium iodide was added. The reaction vial was placed into a water bath and left at 100° C. for 6 hrs. Reaction mixture was cooled to room temperature and diluted by 6 mL of water. Then the vial was sonicated. If crystalline precipitate was formed it was filtered off. In case an oily product was formed the vial was left overnight, then the water layer was removed and 2-propanol (1 mL) was added to cause the crystallization. The precipitate was filtered, washed twice with a sodium carbonate solution, and then washed with methanol. Purification of the final compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

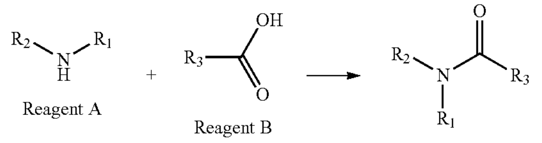

A vial was charged with 0.6 mmol of Reagent B, a solvent (1 mL of a solution of 200 g HOBt in 1 L of DMF), 0.57 mmol of Reagent A (in case of using amine salt, an additional 1.5 equivalent amount of DIPEA was added to the reaction mixture to transfer the amine to base form) and 0.66 mmol of EDC. In case the reaction mixture becomes highly viscous 0.5 mL of DMF were added. In case the reaction mixture was a homogeneous the it was kept at room temperature for 72 hrs. Otherwise the reaction mixture was sonicated at room temperature for 5 days. Reaction mixture was diluted with 6 mL of 1% sodium phosphate water solution. Then the vial was sonicated. In case a crystalline precipitate was formed it was filtered off. In case an oily product was formed the product was dissolved in methanol and precipitated by an addition of 4% hydrochloric acid. Alternatively 2-propanol (1 mL) was mixed with the crude product and the mixture was sonicated. Then the solution was diluted with 5% aqueous sodium hydrogen carbonate (the procedure repeated 2-3 times if necessary). Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

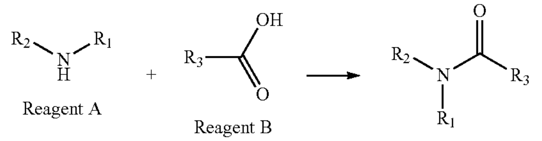

A vial was charged with 0.57 mmol of Reagent B and dry DMF (1 mL). To the stirred reaction mixture 0.57 mmol of N,N-carbodiimidazole was added. After 1 hr of stirring the vial was open and the reaction mixture was left for 2 hrs in a drying oven at 60° C. Then 0.52 mmol of Reagent A (in case of amine salt, an additional 1.5 equivalent amount of DIPEA was added to the reaction mixture) was added, the vial was firmly closed, and the reaction mixture was stirred. The reaction vial was placed into a water bath and left at 100° C. for a time specified on the vial label. Reaction mixture was cooled to room temperature and water was added until the vial was full. Then the vial was sonicated. In case a crystalline precipitate was formed the vial was passed to the filtration. In case an oily product was formed the vial was left overnight, then the water layer was removed and 2-propanol (1 mL) was added to cause the crystallization. The precipitate was filtered, washed twice with a sodium carbonate solution, and then washed with a water/2-propanol (1:1) solution. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

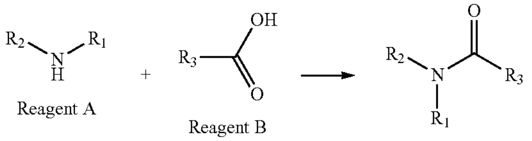

In a large vial 1.2 mmol of a Reagent B was loaded, then 1 mmol of a Reagent A (in case of amine salt, an additional 1.5 equivalent amount of DIPEA was added to the reaction mixture) and polymeric EDC (3 mmol, MW 833 g/mol) were added. 10 ml of solvent (30 g of pentafluorophenol in 1 L of dichloromethane) were added, the vial was closed and mixture was stirred. The vial was shaked continuously for 72 hours using shaker. Reaction mixture was filtered, collecting filtrate in a big tared vial. Precipitated polymer was preserved. Filtrate was evaporated, residue was weighed. If amount of the residue was low, then a small portion of methanol (about 5 ml) was added to the precipitated polymer and shaked for 4 hours. Methanol solution was filtered to the vial with dried residue after the first filtration. Filtrate was evaporated again and the residue was passed to the chromatography. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Oxadiazole synthesis

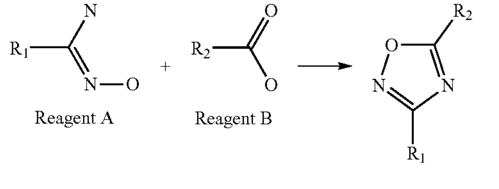

0.6 mmol of Reagent B was loaded into a small vial. 0.6 mL of solvent (a solution of 200 g N-oxybenzotriazole in 1 L of DMF) and 0.6 mmol of Reagent A (in case of amine salt, an additional 1.5 equivalent amount of DIPEA was added to the reaction mixture) were added to it. 0.9 mmol of EDC was added to the reactionary mixture after this. If the reactionary mixture was homogeneous it should be kept at the room temperature for 72 hours. If not, it should be sonicated for 5 days at the room temperature without any serious heating. 0.6 mmol of TEA was added after this and the vial with the reactionary mixture was put into bain-marie and heated at 100 C for a time indicated on the vial label (ca. 3 h). The reactionary mixture was cooled than and 3 mL of CH2CL2 with water in amount enough to fill the vial was added to it. The organic layer was washed out with water two times. All water was removed after this and the product was forwarded for the further drying. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

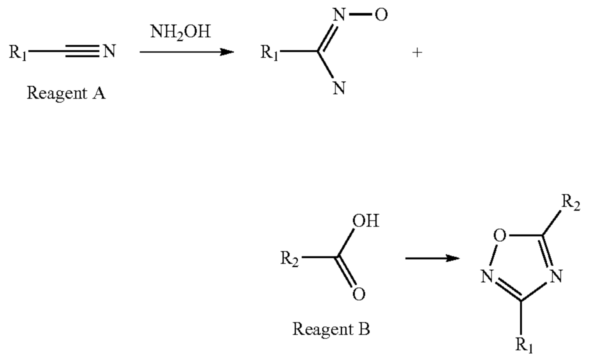

1.6 mmol of Reagent A was loaded in small vial then 2 ml of ethanol, 2.4 mmol of hydroxylamine and 3.2 mmol of TEA were added. If the reaction mixture is not homogenous then another portion of ethanol (1 mL) was added, stirred for 3-4 hours on shaker and left at rt overnight. Then it was heated at 80° C. for 3 hours and the solvent was removed under reduced pressure. The solid residue was dissolved in 1 mL of solvent (1 mL of a solution of 200 g HOBt in 1 L of DMF), 1.6 mmol of Reagent B and 2.4 mmol of CDI and sonicated for 3 days at rt. In case the reaction mixture was viscous additional 1 mL of DMF was added. Then 1.6 mmol of TEA were added and the vial was heated at 100° C. for 3 hours. The reaction mixture was cooled, diluted with 3 ml of water and extracted by 3 mL of $CH_2Cl_2$. The organic layer was washed out with water two times. All water was removed after this and the product was forwarded for the further drying. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Amino/amide synthesis

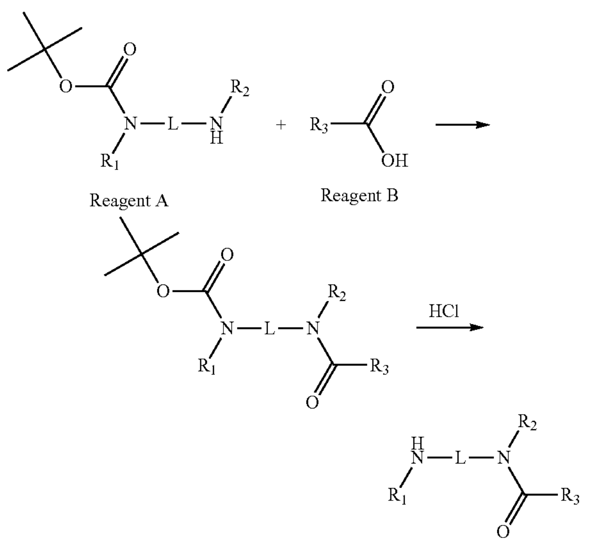

1.6 mmol of Reagent A (in case of amine salt, an additional 1.5 equivalent amount of DIPEA was added to the reaction mixture), 1.7 mmol of Reagent B, were added to 1 mL of a solution of 200 g Benzotriazole-N-oxide in 1 L of DMF. To the stirred mixture 1.9 mmol of EDC was then added. The resulting mixture was stirred at room temperature for 72 hours. The mixture was then diluted with 5 ml of 1% sodium phosphate solution, treated with ultrasound. After that 2 mL of HCl solution in 1,4-dioxane was added and the mixture was treated with ultrasound for 4 hours. The solid or oily crude product formed was isolated and purified via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Oxyprimidine synthesis

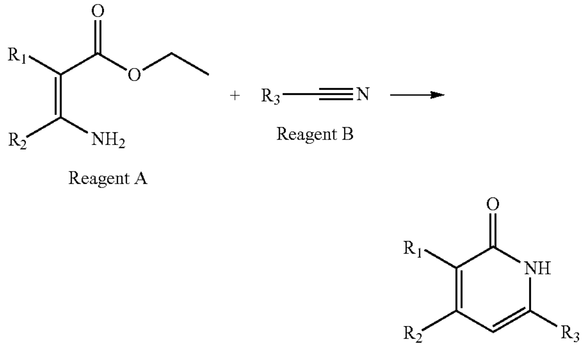

A small vial was charged with 1.6 mmol of Reagent A, 1.6 mmol of Reagent B and 1 ml of 4M dioxane solution of HCl. The vial was heated at 100° C. for 4h. In case reaction mixture was too viscous additional 0.5 ml of dioxane were added. Then it was diluted with 3 ml of water and extracted by 3 mL of $CHCl_3$. Organic layer was washed with water (2*2 mL), dried and evaporated. The solid residue was purified by preparative chromatography. In case of reasonable amount of residue formed during extraction procedure it was separated from solution and purified by preparative chromatography. Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Enamine synthesis

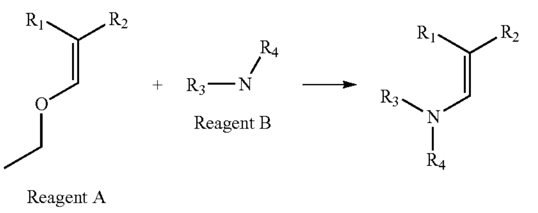

A vial was charged with 1.6 mmol of Reagent A, 1 ml of DMF and 1.6 mmol of Reagent B. The reaction mixture was stirred and heated at 100° C. for 4 h. Then it was cooled to rt. In case of residue formed it was filtered off and purified by preparative chromatography. Otherwise the reaction mixture was diluted with 3 ml of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Halogen displacement: carbon-oxygen/nitrogen/sulfur bond formation

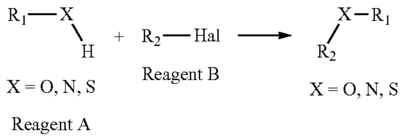

To a stirred solution containing 0.6 mmol of Reagent A (in case of amine salt, an additional 1.5 equivalent amount of DIPEA was added to the reaction mixture), 0.72 mmol of DIPEA, 80 mg of potassium iodide in 1 mL of DMF and 0.6 mmol of Reagent B was added. The reaction mixture was allowed to stir on a boiling water bath for ca. 5 min. Upon a complete dissolution of the reagents the stirred reaction mixture was heated on the water bath for the time specified on the vial label. The reaction mixture was triturated with an excess of deionized water and sonicated until a crystalline precipitate was formed. In case the trituration with water did not cause the product precipitation 1 mL of 2-propanol with the subsequent sonication were applied instead. The precipitate was filtered, washed twice with methanol, and dried. Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

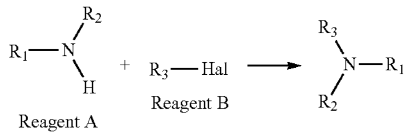

A vial was charged with 0.6 mmol of Reagent A (in case of amine salt, an additional 1.5 equivalent amount of DIPEA was added to the reaction mixture), dry DMF (2 mL), and 1.4 mmol of DIPEA. To the stirred reaction mixture 0.6 mmol of Reagent B was added. The firmly closed reaction vial was placed into a water bath and the reaction mixture was stirred at 100° C. until a complete dissolution of the reaction component occurs. Then the homogeneous reaction mixture was heated in the water bath at 100° C. for 6 hrs. The vial was passed to the polymer scavenger purification. The solvent was removed under reduced pressure. Ethyl acetate (10 mL) and then wet anion resin (5 g) were added to the residue. The stirred mixture was heated in a water bath at 70° C. for 6 hrs. Then the resin was filtered off. The solution was transferred into a pre-weighted vial and the solvent was removed under reduced pressure. Purification of the compounds was performed via preparative HPLC on Agilent 1260 Infinity systems equipped with DAD and mass-detectors. Waters Sunfire C18 OBD Prep Column, 100 Å, 5 µm, 19 mm×100 mm with SunFire C18 Prep Guard Cartridge, 100 Å, 10 µm, 19 mm×10 mm was used. Solvents used were deionized Water (phase A) and HPLC-grade Methanol (phase B). Preset chromatography gradient methods were chosen on the basis of compound properties.

Amine synthesis: Mannich Reaction

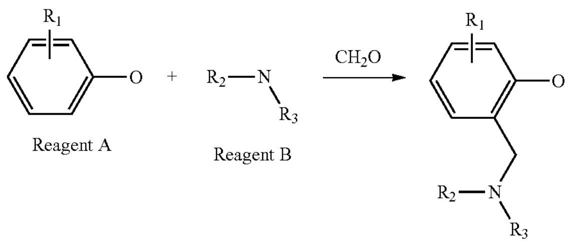

A vial was charged with 1.6 mmol of Reagent A, 2 ml of methanol and 6.4 mmol of formaline. If the solution was not homogenous additional 0.5 mL of methanol were added. The reaction mixture was sonicated for 1 h. Then 1.6 mmol of Reagent B were added and sonicated for another 1 h. In case of substantial amount of residue formed it was filtered off, washed by iPrOH (water then iPrOH if TEA is present in the reaction mixture) and purified by preparative HPLC. Otherwise the reaction mixture was diluted with 3 mL of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Oxamide synthesis

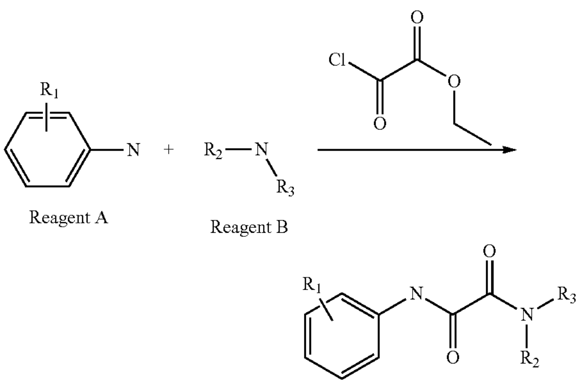

A vial was charged with 1.6 mmol of Reagent A, 1 mL of acetonitrile, 2.9 mmol of DIPEA and 1.6 mmol of ethyl chlorooxalate. The reaction mixture was stirred for 30 min at rt and 1.76 mmol of Reagent B were added. The vial was heated at 100° C. for 6 h. The reaction mixture was cooled to rt, diluted with 3 mL of water and extracted by 3 mL of $CHCl_3$. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Ether synthesis

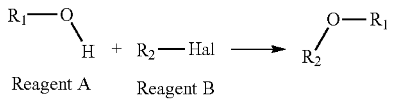

A small vial was charged with 0.6 mmol of Reagent A (in case of amine salt, an additional 1.5 equivalent amount of DIPEA was added to the reaction mixture), followed by 80 mg of potassium iodide in 0.7 mL DMF, and then 0.6 mmol of Reagent B. After stirring 1 mL 4M solution of KOH in methanol was added, the vial was closed tightly and shaked. Next the vial was sonicated for 24 h at the temperature no more than 35° C. After that the vial was filled with chloroform to the brim. After stirring the organic layer was washed twice with water and dried. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Bicyclic synthesis

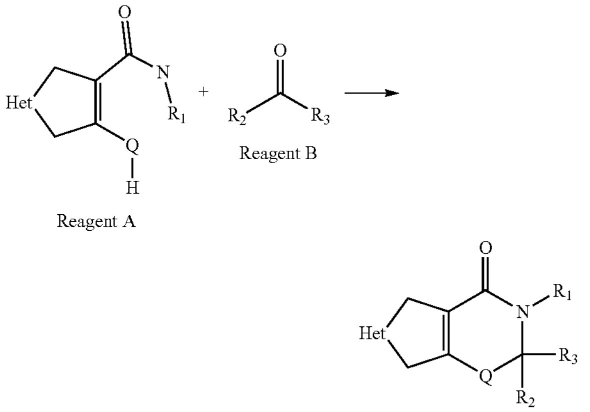

A vial was charged with 1.6 mmol of Reagent A, 1 mL of pyridine and 1.6 mmol of Reagent B, stirred. Then 6.4 mmol of $Me_3SiCl$ were added and the reaction mixture was stirred and heated at 100° C. for 8h. Then it was cooled to rt and 1.9 mmol of TEA were added and the vial was heated for another 30 min at 100° C. Then the reaction mixture was diluted with 3 ml of water and extracted by 3 mL of $CHCl_3$. The organic layer was washed with water (3*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Methyl amine synthesis: reductive amination

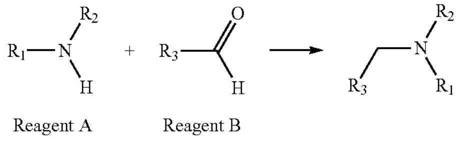

0.6 mmol of Reagent A (in case of amine salt, an additional 1.5 equivalent amount of DIPEA was added to the reaction mixture) was dissolved in 3 mL of methanol and the reaction mixture was stirred in a vial at r. t. Then 0.6 mmol of Reagent B was added to the stirred solution. The vial with the reaction mixture was sonicated at 58-60° C. for 60-90 min until a complete dissolution of the reagents. Up to 5 mL of acetonitrile could be added to complete the dissolution of the reagents. The reaction vial was cooled to 0° C. and sodium borohydride (150 mg) was added to the reaction mixture in small portions. The reaction mixture was stirred in the open vial until sodium borohydride was dissolved. The reaction vial was sonicated for 2 hrs at r. t., closed, and allowed to stand overnight at r. t. Then the open reaction vial was sonicated at 50° C. until methanol was nearly completely evaporated. The reaction mixture was triturated with 5 mL of methanol and stirred until the large part of it was dissolved. The insoluble part largely consisted of inorganic salts. The product was purified by passing the methanolic suspension through ionic polymer scavengers. In the case of an incomplete dissolution of the product in methanol 5 mL of deionized water could be added to the methanolic suspension causing precipitation of the product and dissolution of the inorganic contaminants. In the case of an emulsion formation upon addition of methanol the reaction mixture was filtered through a small chromatographic column filled with 8 g of silica gel. The product was eluted with methanol and the solvent removed under reduced pressure to yield the product. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfonamide synthesis

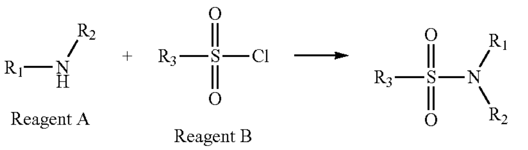

A vial was charged with 0.6 mmol of Reagent A (in case of amine salt, an additional 1.5 equivalent amount of DIPEA was added to the reaction mixture), acetonitrile (1 mL), and 0.72 mmol of triethylamine. To the stirred reaction mixture 0.6 mmol of Reagent B was added. The vial was placed in a water bath and heated at 100° C. for 2 hrs. 2% Hydrochloric acid (2 mL) was added to the reaction mixture and the vial was shaken. In case a solid precipitate was formed the vial was passed to the filtration. In case an oily product was formed the vial was sonicated to cause the crystallization. Additional measures to cause the crystallization of the oily product, e.g., varying the amount of water and an increase of the sonication time, can be taken. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfide synthesis

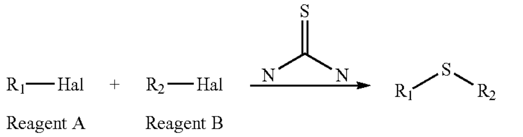

A vial was charged with 1.6 mmol of Reagent A, 0.7 ml of DMF and 1.76 mmol of thiourea. The reaction mixture was stirred and heated at 100° C. for 2h. Then it was cooled to rt and 1 mL of 4M KOH solution and 1.6 mmol of Reagent B were added. The reaction mixture was sonicated for 24 h. Then it was diluted with 3 mL of water and extracted by 3 mL of $CHCl_3$. In case of residue formed it was filtered off and purified by preparative chromatography. The organic layer was washed with water (2*2 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Sulfone synthesis

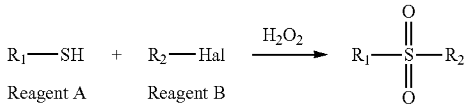

A vial was charged with 1.6 mmol of Reagent A, 1 mL of i-PrOH, 1.6 mmol of Reagent B and 1 mL of 4M KOH solution. The reaction mixture was sonicated at 50-60° C. for 2h. Then 1 ml of methanol, 0.175 mL of $CH_3COOH$, 0.45 mL of 50% $H_2O_2$ and 0.175 mL of 10% solution of ammonium molibdate were added. The reaction mixture was sonicated at 70° C. for 5 h. Then it was diluted with 3 mL of water and extracted by 3 mL of $CHCl_3$. In case of residue formed it was filtered off and purified by preparative chromatography. The organic layer was washed with 10% $NaHCO_3$ solution (5 mL), dried and evaporated. The solid residue was purified by preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Thiazole synthesis

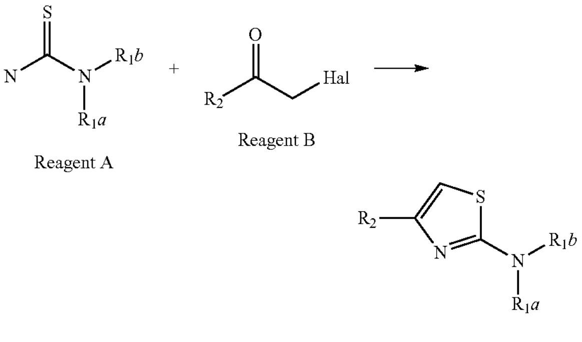

A vial was charged with 1.6 mmol of Reagent A, 1.5 mL of DMF and 1.6 mmol of Reagent B. The reaction mixture was heated at 100° C. for 2 hours. After cooling to rt 0.2 ml of DIPEA, 3 mL of water were added and extracted by 3 mL of $CHCl_3$. Organic layer was washed by water (2*1 mL), dried and evaporated. The solid residue was purified via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Urea synthesis

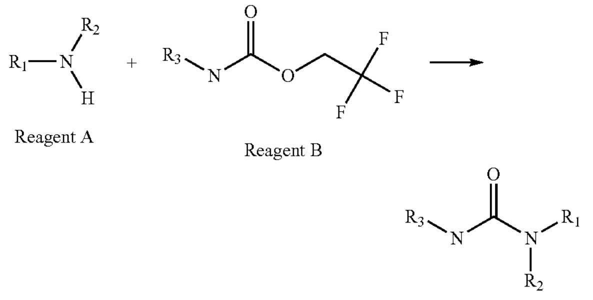

A vial was charged with 0.6 mmol of Reagent A (in case of amine salt, an additional 1.5 equivalent amount of DIPEA was added to the reaction mixture), 2 mL of acetonitrile and 0.6 mmol of DIPEA. The vial was left for 30 minutes, then 0.6 mmol of Reagent B was loaded. A vial was placed in a boiling water bath and heated up for 8 hours, then left for 30 minutes to cool down. 1 mL of water was added to the mixture and the vial was sonicated. If the residue has crystallized, the mixture was stirred until uniform and passed to filtration, otherwise the water was added until vial was full and standard workup was used. Filtered solid was washed with 1 ml of 1:1 isopropyl alcohol-water mixture 2 times. Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

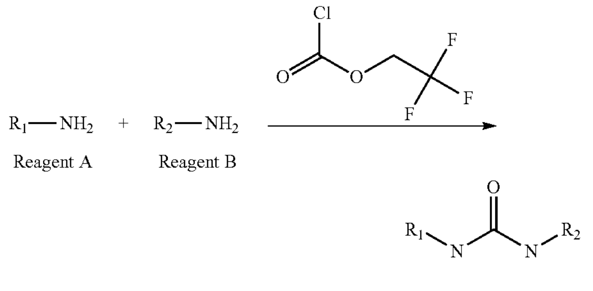

A vial was charged with 0.6 mmol of Reagent A (in case of amine salt, an additional 1.5 equivalent amount of DIPEA was added to the reaction mixture), 2 mL of acetonitrile, 0.9 mmol of DIPEA, and then 0.6 mmol of 2,2,2-trifluoroethylchloroformate dropwise. After left for 0.5 hrs, 0.73 mmol of Reagent B was added to the mixture. The vial was placed in the water boiling bath for 8 hrs. After 0.5 hrs cooling down 1 mL of water was added and the vial was passed to sonication. The outcome precipitate was filtered and washed twice with 1 ml of 50% water solution of 2-propanol). Purification of the compounds was performed via preparative HPLC on Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm was used. Solvents used were deionized Water (phase A) and HPLC-grade Methanol (phase B). Preset chromatography gradient methods were chosen on the basis of compound properties.

Piperidino-oxypyrimide synthesis
Scheme A

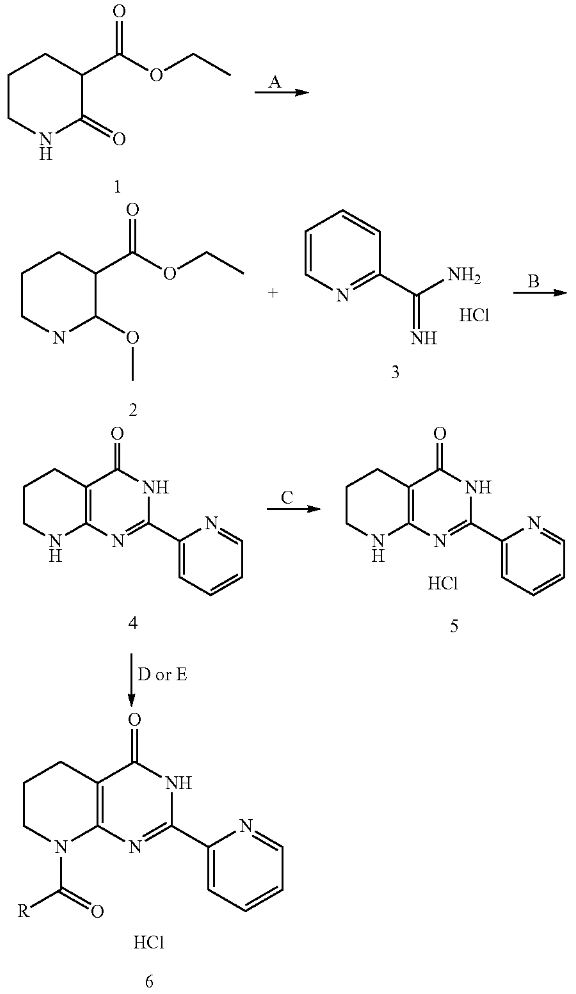

Step A: To a solution of compound 1 (50.0 g, 290 mmol) in chloroform (400 mL) $Me_3OBF_4$ (34.5 g, 220 mmol) was added. The resulting mixture was stirred at room temperature for 6 h and then washed with saturated aqueous solution of $K_2CO_3$ (2×300 mL). The organic layer was separated, dried over $MgSO_4$, and evaporated in vacuo. The residue was purified by vacuum distillation (b.p. 78° C. at 1 torr) to give 45.6 g (247 mmol, 85%) of compound 2 as a colorless oil.

Step B: Na (12.7 g, 550 mmol) was dissolved in EtOH (200 mL). Compound 3 (37.5 g, 238 mmol) was added to the solution and the resulting mixture was stirred at room temperature for 0.5 h. Then compound 2 (45.6 g, 247 mmol) was added, the reaction was refluxed for 4 h, and then evaporated under reduced pressure. The residue was dissolved in water and neutralized with 10% HCl. The precipitated solid was filtered and re-crystallized from i-PrOH to yield 40.8 g (179 mmol, 75%) of compound 4 as white solid.

Step C: To a suspension of compound 4 (0.020 g, 0.088 mmol) of in dry acetonitrile (2 mL) a solution of 10% HCl in dry dioxane was added dropwise until pH 3. After standing for 0.5 h the solvents were removed in vacuum to obtain 0.023 g (0.088 mmol, 100%) of target compound 5.

Step D: To a solution of compound 4 (0.150 g, 0.66 mmol) and DIPEA (0.256 g, 1.98 mmol) in acetonitrile the corresponding acid chloride was added (1-3 eq.). The resulting mixture was stirred under reflux for 3 hours and then evaporated in vacuo. The residue was purified by HPLC. The obtained product was suspended in dry acetonitrile. 10% HCl in dry dioxane was added dropwise until pH 3. After standing for 0.5 h the solvents were removed under reduced pressure to yield target amides 6.

Step E: To a solution of compound 4 (0.150 g, 0.66 mmol) in acetonitrile [(4-methoxybenzyl)oxy]acetic acid (0.129 g, 0.66 mmol), DIPEA (0.46 mL, 2.64 mmol), and DMAP (0.005 g, 0.04 mmol) were added. Then TBTU (0.847 g, 2.64 mmol) was added, the resulting mixture was refluxed for 8 hours, and evaporated under reduced pressure. The residue was purified by HPLC to yield the target amide 6.

-continued

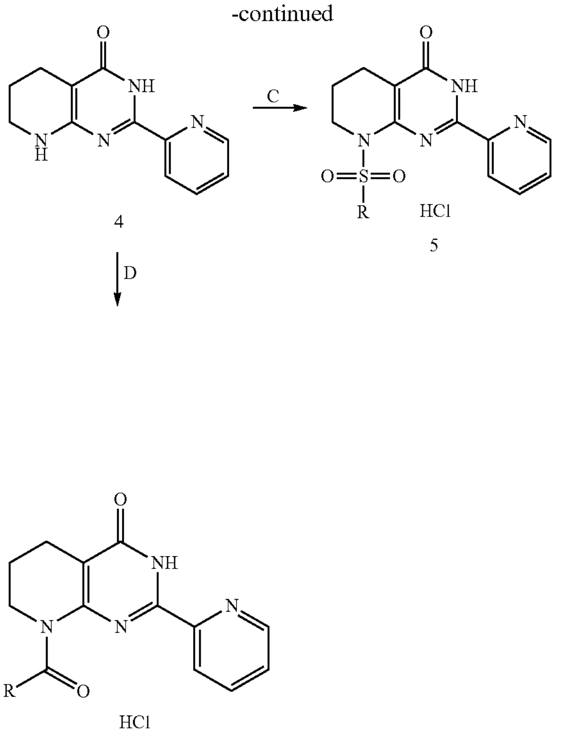

4 5 6

Scheme B

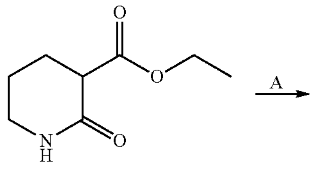

1

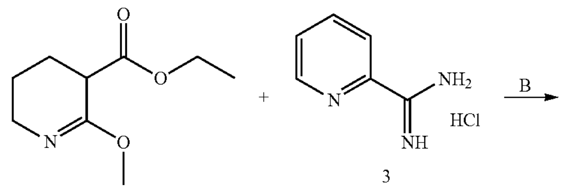

2 3

Step A: To a solution of compound 1 (50.0 g, 290 mmol) in chloroform (400 mL) $Me_3OBF_4$ (34.5 g, 220 mmol) was added. The resulting mixture was stirred at room temperature for 6 h and then washed with saturated aqueous solution of $K_2CO_3$ (2×300 mL). The organic layer was separated, dried over $MgSO_4$, and evaporated in vacuo. The residue was purified by vacuum distillation (b.p. 78° C. at 1 torr) to give 45.6 g (247 mmol, 85%) of compound 2 as a colorless oil.

Step B: Na (12.7 g, 550 mmol) was dissolved in EtOH (200 mL). Compound 3 (37.5 g, 238 mmol) was added to the solution and the resulting mixture was stirred at room temperature for 0.5 h. Then compound 2 (45.6 g, 247 mmol) was added, the reaction was refluxed for 4 h, and then evaporated under reduced pressure. The residue was dissolved in water and neutralized with 10% HCl. The precipitated solid was filtered and re-crystallized from i-PrOH to yield 40.8 g (179 mmol, 75%) of compound 4 as white solid.

Step C: To a solution of compound 4 (0.150 g, 0.66 mmol) and DIPEA (0.256 g, 1.98 mmol) in acetonitrile corresponding sulfonyl chloride (0.99 mmol, 1.5 equiv.) was added. The resulting mixture was stirred under reflux for 2 h and then evaporated in vacuo. The residue was purified by HPLC to yield the target compounds 5.

Step D: To a solution of compound 4 (0.150 g, 0.66 mmol) and DIPEA (0.256 g, 1.98 mmol) in acetonitrile the corresponding acid chloride was added (1.3-4 eq.). The resulting mixture was stirred under reflux for 3 h and then evaporated in vacuo. The residue was purified by HPLC to yield the target amides 6.

Thieno-oxypyrimide synthesis
Scheme C

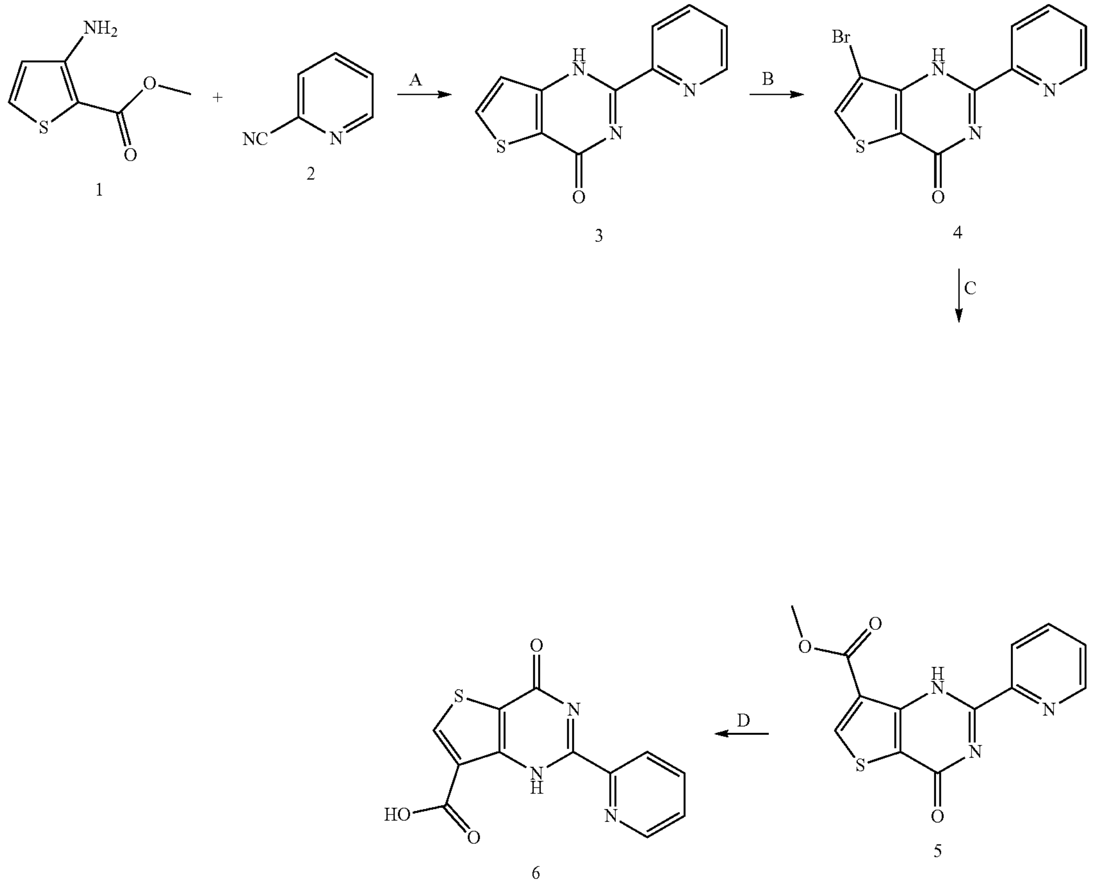

1 2 3 4 5 6

Step A: To a solution compound 1 (30 g, 0.19 mol) in 300 mL dioxane HCl was added compound 2 (23.85 g, 0.23 mol). The reaction mixture was stirred at rt overnight, diluted dioxane (300 mL), refluxed for 3h, cooled and evaporated. The resulting residue was washed by mixture EtOAc-iPrOH (1:2). The yield was 36 g (0.157 mol, 83%).

Step B: To a solution compound 3 (36 g, 0.157 mol) in 650 mL acetic acid bromine (35 mL) was added at rt. The reaction mixture was refluxed 48h, cooled, evaporated, diluted with water. The resulting precipitate was filtered, washed with water and dried. The yield was 45 g (0.146 mol, 93%).

Step C: The mixture compound 4 (35 g, 0.114 mol) and 1,1'-Bis(diphenylphosphino)ferrocene]dichloropalladium (II) complex with dichloromethane CAS95464054 (2% mol) in methanol (500 ml) was stirred overnight under CO (10 bar) in autoclave. The reaction mixture was filtered and evaporated. The resulting residue was washed with water and dried. The yield was 26 g (0.091 mol, 80%).

Step D: Compound 5 (16 g, 0.055 mol) was added to a solution NaOH (21 g, 0.525 mol) in 600 mL methanol. The reaction mixture was refluxed overnight, evaporated. The solid residue was washed by water and air-dried. The yield was 12.7 g (0.046 mol, 84%).

Scheme D

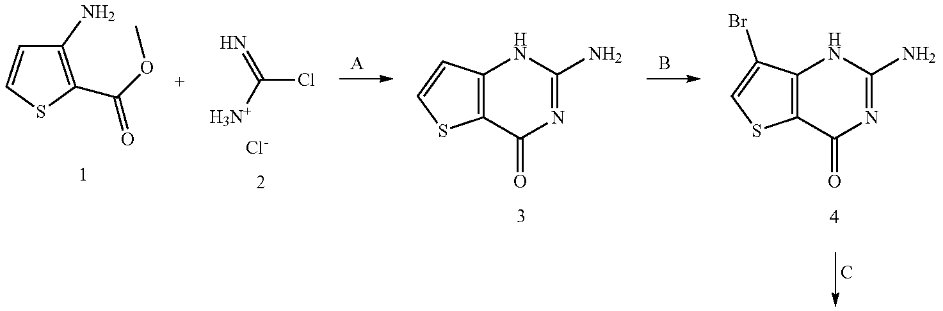

1 2 3 4

-continued

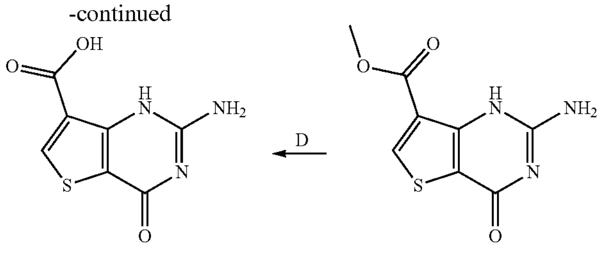

6 5

Step A: The mixture of compound 1 (50 g, 0.318 mol), compound 2 (54.86 g, 0.477 mol) and methylsulfonylmethane (150.6 g, 1.59 mol) was refluxed overnight, cooled and evaporated. The resulting residue was washed mixture EtOAc-iPrOH (1:2). The yield was 41.65 g (0.249 mol, 78%).

Step B: To a solution compound 3 (41.65 g, 0.249 mol) in 700 mL acetic acid was added bromine (42 mL) at rt. The reaction mixture was refluxed 48h, cooled, evaporated, diluted with water. The resulting precipitate was filtered, washed with water and dried. The yield was 51 g (0.207 mol, 83%).

Step C: The mixture of compound 4 (35 g, 0.142 mol) and 1,1'-Bis(diphenylphosphino)ferrocene]dichloropalladium (II) complex with dichloromethane CAS95464054 (2% mol) in methanol (500 ml) was stirred overnight under CO (10 bar) in autoclave. The reaction mixture was filtered and evaporated. The resulting residue was washed with water and dried. The yield was 28 g (0.124 mol, 88%).

Step D: Compound 5 (15 g, 0.067 mol) was added to a solution of NaOH (20 g, 0.5 mol) in 600 mL methanol. The reaction mixture was refluxed overnight, evaporated. The solid residue was washed by water and air-dried. The yield was 11.2 g (0.053 mol, 79%).

Amide synthesis from compound 6: The mixture of 1.1 eq of acid 6 and 1 eq of corresponding amine was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 mL of distilled water and left at ultrasonic bath for 30-40 min. The resulting residue was filtered off, washed by water and dried under high vacuum. If there was no residue formed the aqueous solution was extracted by 4 mL of DCM and the organic layer was washed by water (2*4 mL) and the solvent was removed under reduced pressure. In case of low purity of the final compound was subjected to preparative HPLC purification.

Scheme 1

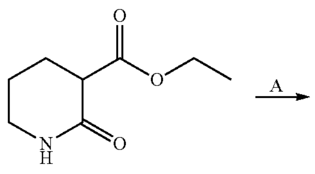

1

-continued

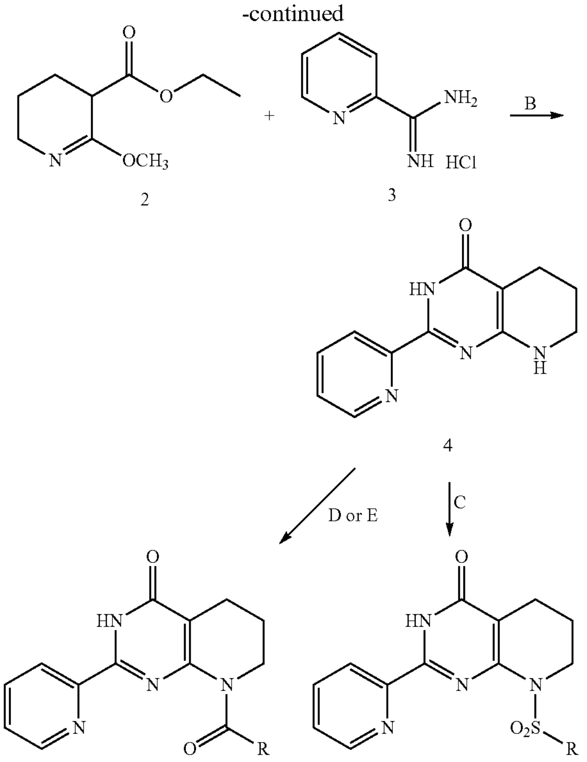

Step A: To a solution of compound 1 (50.0 g, 290 mmol) in chloroform (400 mL) $Me_3OBF_4$ (34.5 g, 220 mmol) was added. The resulting mixture was stirred at room temperature for 6 h and then washed with saturated aqueous solution of $K_2CO_3$ (2×300 mL). The organic layer was separated, dried over $MgSO_4$, and evaporated in vacuo. The residue was purified by vacuum distillation (b.p. 78° C. at 1 torr) to give 45.6 g (247 mmol, 85%) of compound 2 as a colorless oil.

Step B: Na (12.7 g, 550 mmol) was dissolved in EtOH (200 mL). Compound 3 (37.5 g, 238 mmol) was added to the solution and the resulting mixture was stirred at room temperature for 0.5 h. Then compound 2 (45.6 g, 247 mmol) was added, the reaction was refluxed for 4 h, and then evaporated under reduced pressure. The residue was dissolved in water and neutralized with 10% HCl. The precipitated solid was filtered and re-crystallized from i-PrOH to yield 40.8 g (179 mmol, 75%) of compound 4 as a white solid.

Step C: To a solution of compound 4 (0.150 g, 0.66 mmol) and DIPEA (0.256 g, 1.98 mmol) in acetonitrile corresponding sulfonyl chloride (0.99 mmol, 1.5 equiv.) was added. The resulting mixture was stirred under reflux for 2 h and then evaporated in vacuo. The residue was purified by HPLC to yield the target sulfonamides.

Step D: To a solution of compound 4 (0.150 g, 0.66 mmol) and DIPEA (0.256 g, 1.98 mmol) in acetonitrile the corresponding acid chloride was added (1-3 eq.). The resulting mixture was stirred under reflux for 3 hours and then evaporated in vacuo. The residue was purified by HPLC. The obtained product was suspended in dry acetonitrile. 10% HCl in dry dioxane was added dropwise until pH 3. After standing for 0.5 h the solvents were removed under reduced pressure to yield the target amides.

Step E: To a solution of compound 4 (0.150 g, 0.66 mmol) and DIPEA (0.256 g, 1.98 mmol) in acetonitrile the corresponding acid chloride was added (1.3-4 eq.). The resulting mixture was stirred under reflux for 3 h and then evaporated in vacuo. The residue was purified by HPLC to yield the target amides.

Step C: The mixture of compound 8 (35 g, 0.142 mol) and 1,1'-Bis(diphenylphosphino)ferrocene]dichloropalladium (II) complex with dichloromethane CAS95464054 (2% mol) in methanol (500 ml) was stirred overnight under CO (10 bar) in an autoclave. The reaction mixture was filtered and evaporated. The resulting residue was washed with water and dried. The yield of 9 was 28 g (0.124 mol, 88%).

Step D: Compound 9 (15 g, 0.067 mol) was added to a solution of NaOH (20 g, 0.5 mol) in 600 mL methanol. The reaction mixture was refluxed overnight and evaporated. The solid residue was washed by water and air-dried. The yield of 10 was 11.2 g (0.053 mol, 79%).

Step E: Amide synthesis from compound 10: 1.1 eq of acid 10 and 1 eq of corresponding amine was dissolved in 1 ml of HOBt solution in DMF (9.5% wt). Then 1.2 eq of EDC was added and reaction mixture was left stirring at rt Scheme 2

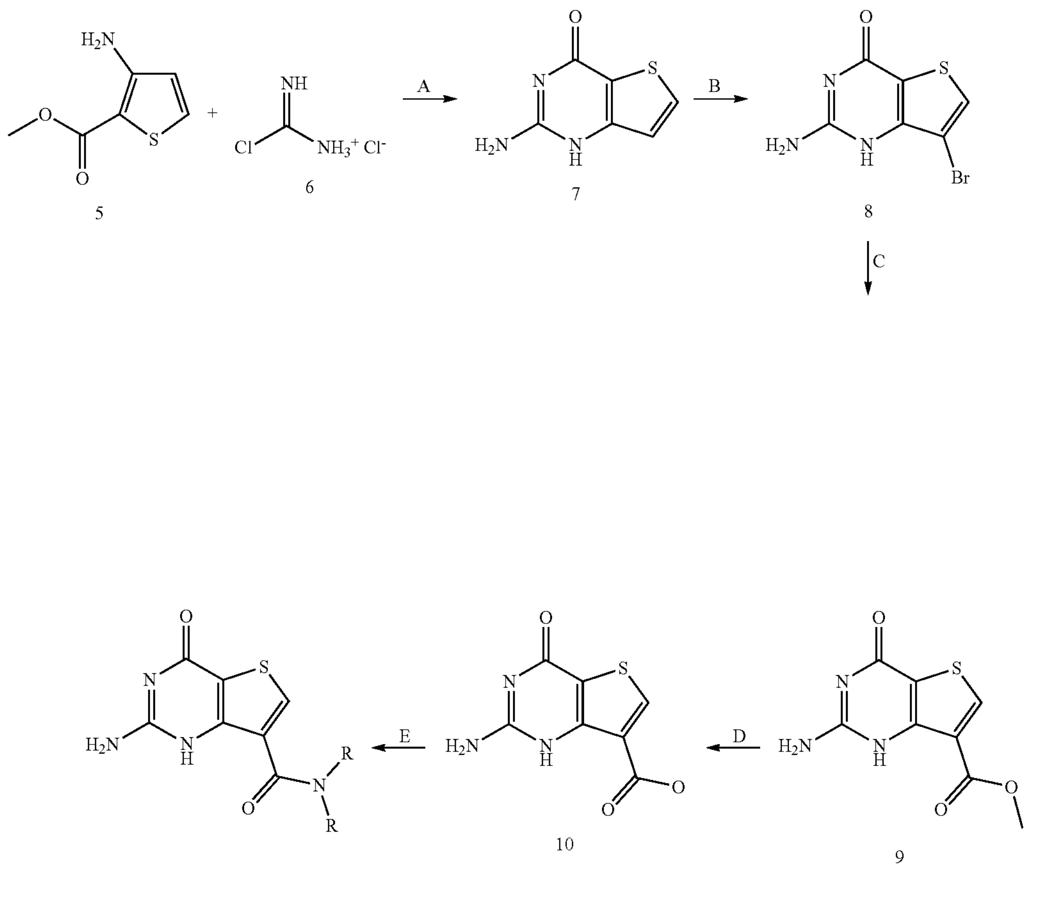

Step A: The mixture of compound 5 (50 g, 0.318 mol), compound 6 (54.86 g, 0.477 mol) and methylsulfonylmethane (150.6 g, 1.59 mol) was refluxed overnight, cooled and evaporated. The resulting residue was washed with EtOAc-iPrOH (1:2). The yield of 7 was 41.65 g (0.249 mol, 78%).

Step B: To a solution compound 7 (41.65 g, 0.249 mol) in 700 mL acetic acid was added bromine (42 mL) at rt. The reaction mixture was refluxed 48h, cooled, evaporated, diluted with water. The resulting precipitate was filtered, washed with water and dried. The yield of 8 was 51 g (0.207 mol, 83%).

overnight (16-18h). After completion of the reaction, monitored by LCMS, the reaction mixture was diluted with 4 mL of distilled water and left at ultrasonic bath for 30-40 min. The resulting residue was filtered off, washed by water and dried under high vacuum to give the target amide. If there was no residue formed the aqueous solution was extracted by 4 mL of DCM and the organic layer was washed by water (2*4 mL) and the solvent was removed under reduced pressure to give the target amide. In case of low purity of the final compound was subjected to preparative HPLC purification.

Scheme 3

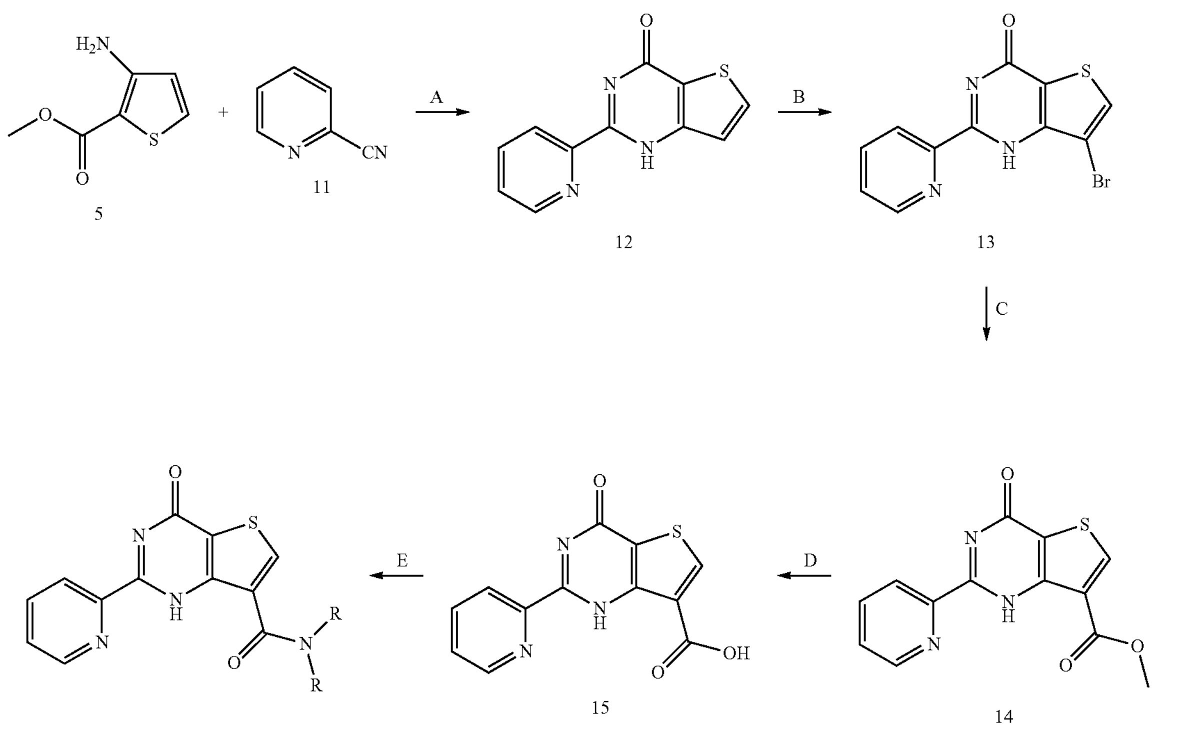

Step A: To a solution compound 5 (30 g, 0.19 mol) in 300 mL dioxane HCl was added compound 11 (23.85 g, 0.23 mol). The reaction mixture was stirred at rt overnight, diluted dioxane (300 mL), refluxed for 3h, cooled and evaporated. The resulting residue was washed with EtOAc-iPrOH (1:2). The yield of 12 was 36 g (0.157 mol, 83%).

Step B: To a solution compound 12 (36 g, 0.157 mol) in 650 mL acetic acid, bromine (35 mL) was added at rt. The reaction mixture was refluxed 48h, cooled, evaporated, diluted with water. The resulting precipitate was filtered, washed with water and dried. The yield of 13 was 45 g (0.146 mol, 93%).

Step C: The mixture of compound 13 (35 g, 0.114 mol) and 1,1'-Bis(diphenylphosphino)ferrocene]dichloropalladium(II) complex with dichloromethane CAS95464054 (2% mol) in methanol (500 ml) was stirred overnight under CO (10 bar) in an autoclave. The reaction mixture was filtered and evaporated. The resulting residue was washed with water and dried. The yield of 14 was 26 g (0.091 mol, 80%).

Step D: Compound 14 (16 g, 0.055 mol) was added to a solution NaOH (21 g, 0.525 mol) in 600 mL methanol. The reaction mixture was refluxed overnight, evaporated. The solid residue was washed by water and air-dried. The yield of 15 was 12.7 g (0.046 mol, 84%).

Step E: Amide synthesis from compound 14: 1.1 eq of acid 15 and 1 eq of corresponding amine was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 mL of distilled water and left at ultrasonic bath for 30-40 min. The resulting residue was filtered off, washed by water and dried under high vacuum to give the target amide. If there was no residue formed the aqueous solution was extracted by 4 mL of DCM and the organic layer was washed by water (2*4 mL) and the solvent was removed under reduced pressure to give the target amide. In case of low purity of the final compound was subjected to preparative HPLC purification.

Scheme 4

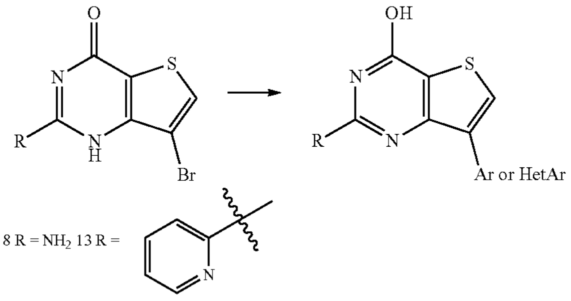

Reactions were conducted on a 100 mg scale, starting with either compound 8 (prepared in Step B, Scheme 2) or compound 13 (prepared in Step B, Scheme 3). General procedure: Compound 8 or compound 13 (1 eq.), aryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. The organic layer was evaporated and dried in vacuo. The residue was purified by HPLC to afford the target compounds.

Scheme 5

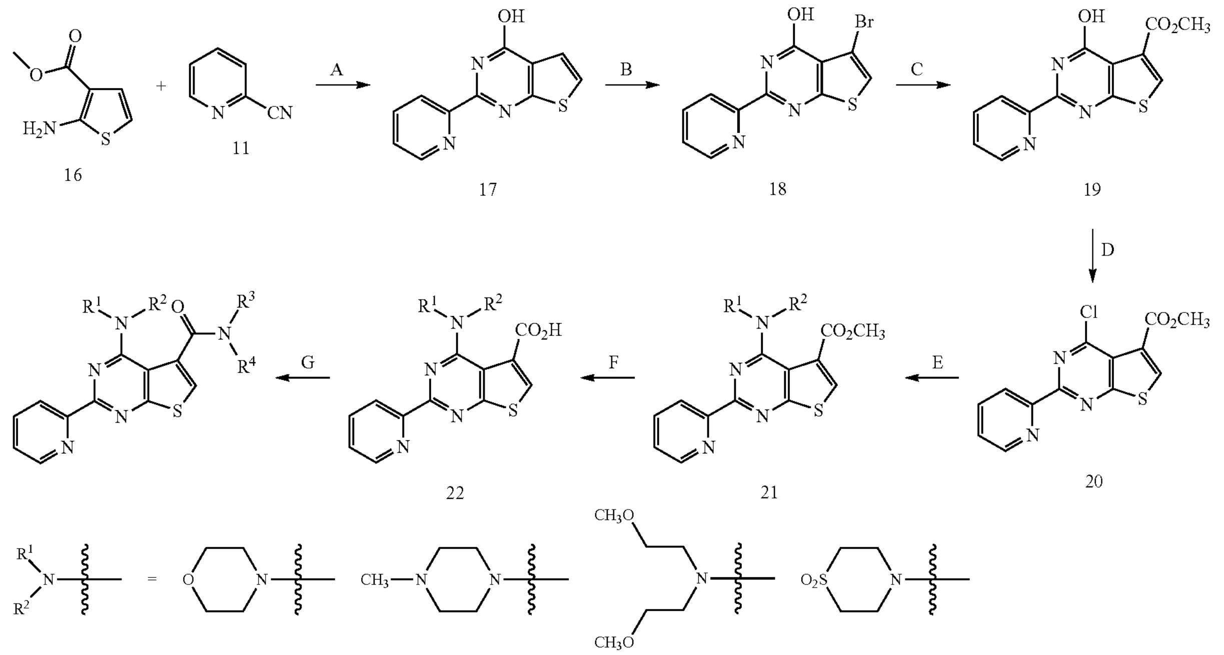

Step A: Compound 16 (10 g, 0.063 mol, 1.0 eq) and pyridine-2-carbonitrile 11 (6.62 g, 0.063 mol, 1.0 eq) were mixed in MeOH (200 mL). The mixture was cooled to 0° C., and sodium methoxide (5.1 g, 0.094 mol, 1.5 eq) was added. The reaction mixture was stirred at reflux for 24h, concentrated in vacuo, diluted with dichloromethane and poured into saturated ammonium chloride. The organic layer was washed with water, saturated sodium chloride, dried over $Na_2SO_4$, filtered and concentrated in vacuo. The solids were triturated with MTBE to give compound 17 (2.88 g, 20% yield).

Step B: To a solution compound 17 (2 g, 8.72 mmol) in 100 mL acetic acid, bromine (4.1 g, 26.16 mmol, 3.0 eq) was added at rt. The reaction mixture was refluxed 48h, cooled, evaporated, diluted with water. The resulting precipitate was filtered, washed with water and dried to give 18 as a solid (2.4 g, 90% yield).

Step C: The mixture of compound 18 (2.4 g, 7.84 mmol) and 1,1'-Bis(diphenylphosphino)ferrocene]dichloropalladium(II) complex with dichloromethane CAS95464054 (2% mol) in methanol (500 ml) was stirred overnight under CO (10 bar) in an autoclave. The reaction mixture was filtered and evaporated. The resulting residue was washed with water and dried. The yield of 19 was 1.8 g (6.27 mmol, 80% yield).

Step D: The compound 19 (5 g, 0.017 mol, 1 eq.) and phosphoryl chloride (100 mL) were heated at reflux for 24 h. The reaction mixture was then evaporated to dryness. The crude residue was dissolved in $CH_2Cl_2$ and washed carefully with ice-water and 5% $NaHCO_3$ solution. Organic layer was dried over $Na_2SO_4$ and evaporated to dryness giving sufficiently pure compound 20 as a powder (5.05 g, yield 95%).

Step E: General procedure for chlorine displacement. To a stirred solution of 20 in $CHCl_3$, was added triethylamine (1.5 eq.) and appropriate amine (1.2 eq) in one portion, and the reaction left to stir at reflux for 4 hours. The reaction mixture was washed with water twice and evaporated under reduced pressure to give crude product. The crude material was purified by column chromatography using $CHCl_3$: MeCN (1:4) as eluent to afford compounds 21.

Step F: General procedure for ester hydrolysis. Compound 21 was added to a 1M solution of NaOH in methanol. The reaction mixture was heated at reflux overnight and evaporated. The solid residue was dissolved in water and acidified by 3N HCl to pH ~4-5. The precipitate being formed was filtered and washed with water and dried in vacuo to give pure acids 22.

Step G: General procedure for amide synthesis. Reactions were conducted on a 100 mg scale. 1.1 eq of acid 22 and 1 eq of corresponding amine $R^3R^4NH$ was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 ml of distilled water and left at ultrasonic bath for 30-40 min. The resulting residue was filtered off, washed by water and dried under high vacuum to give the target compounds. If there was no residue formed the aqueous solution was extracted by 4 ml of DCM and the organic layer was washed by water (2*4 ml) and the solvent was removed under reduced pressure to give the target compounds. In cases of low purity the target compound was subjected to preparative HPLC purification.

Scheme 6

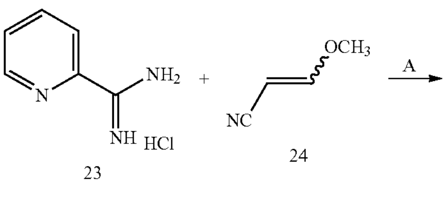

-continued

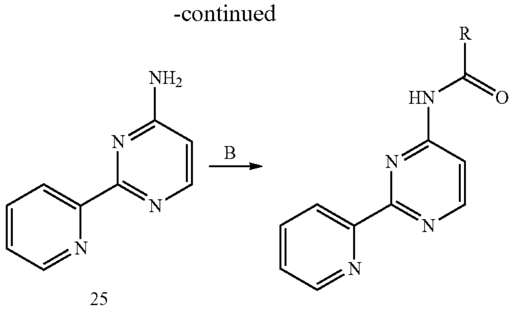

25

Step A: A mixture of 157.8 g. (1.0 mol) of 2-pyridinecarboxamidine hydrochloride 23, 54.2 g (1.0 mol) of sodium methoxide in 400 ml of dry methanol was stirred for 30 minutes. The sodium chloride was filtered and the filtrate was concentrated to dryness. The residue and 83 g (1.0 mole) of 3-methoxyacrylonitrile 24 were heated (100-160°) together for 3 hours, at this point the evolution of ethanol had stopped and the melt had started to crystallize. The product 25 was cooled to room temperature, suspended in methanol, filtered and dried to obtain 25 125.6 g, (73% yield).

Step B: Reactions were conducted on a 100 mg scale. General procedure for amide synthesis: 1.1 eq of the appropriate acid and 1 eq of 25 was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 ml of distilled water and left at ultrasonic bath for 30-40 min. The resulting residue was filtered off, washed by water and dried under high vacuum to give the target compound. If there was no residue formed the aqueous solution was extracted by 4 ml of DCM and the organic layer was washed by water (2*4 ml) and the solvent was removed under reduced pressure to give the target compound. In case of low purity of the final compound was subjected to preparative HPLC purification.

Scheme 7

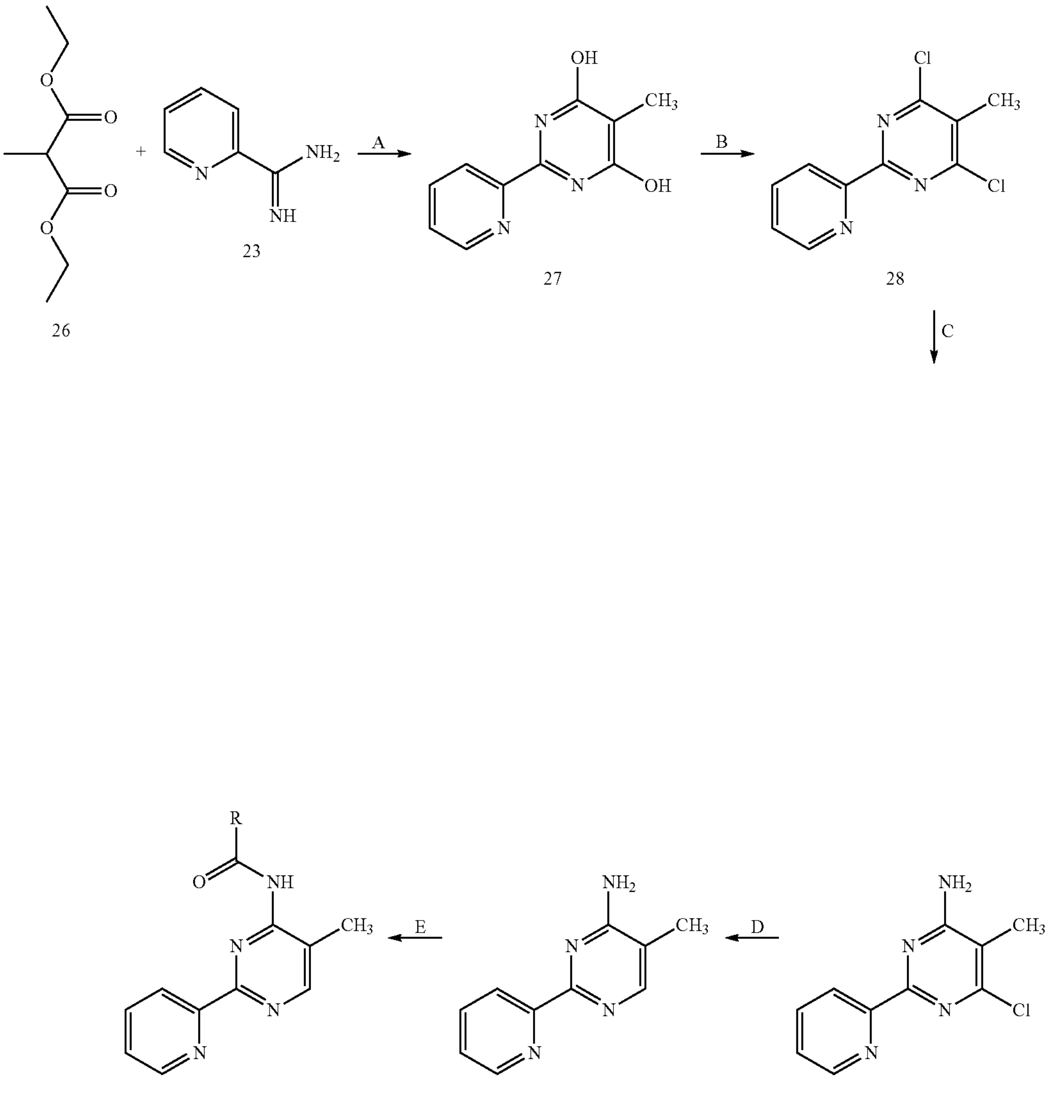

26 23 27 28

30 29

Step A: NaOMe (4.46 g, 82.64 mmol) was added to a solution of diethyl 2-methylmalonate 26 (14.34 g, 82.64 mmol) and pyridine-2-carboxamidine 23 (10 g, 82.64 mmol) in MeOH (200 ml). The reaction mixture was heated under reflux for 40 min resulting in the formation of a precipitate. The reaction mixture was diluted with MeOH (100 ml) and EtOAc (200 ml) and the precipitate was triturated and collected by filtration to give 27 (11.57 g, 57 mmol, 69% yield).

Step B: Compound 27 was heated at reflux for 24 h in phosphoryl chloride. The reaction mixture was then evaporated to dryness. The crude residue was dissolved in $CH_2Cl_2$ and washed carefully with ice-water and 5% $NaHCO_3$ solution. The organic layer was dried over $Na_2SO_4$ and evaporated to dryness to give compound 28.

Step C: A solution of 28 (2 g, 8.36 mmol) and ammonia in methanol (100 mL) was added to a 0.5 L round bottom flask. The solution was stirred at 50° C. for 5 h, The reaction mixture was cooled to room temperature. The precipitate was filtered, washed with cold methanol (20 mL) and dried under reduced pressure to give 29 (1.5 g, 81% yield) as a white solid.

Step D: The compound 29 (1.5 g, 6.81 mmol) was suspended in a mixture of methanol (10 mL), ethyl acetate (10 mL) and triethylamine (0.948 mL, 6.81 mmol). 10% Pd/C was added to the mixture and the resulting suspension was stirred at room temperature for 2 hours under a hydrogen atmosphere and then filtered. The filtrate was concentrated in vacuo, and purified by silica gel column chromatography to give the title compound 30 (0.81 g, 64% yield) as a brown solid.

Step E: Reactions were conducted on a 100 mg scale. 1.1 eq of the appropriate acid and 1 eq of 30 was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 ml of distilled water and left at ultrasonic bath for 30-40 min. The resulting residue was filtered off, washed by water and dried under high vacuum to give the target compounds. If there was no residue formed the aqueous solution was extracted by 4 ml of DCM and the organic layer was washed by water (2*4 ml) and the solvent was removed under reduced pressure to give the target compounds. In cases of low purity, the final compound was subjected to preparative HPLC purification.

Scheme 8

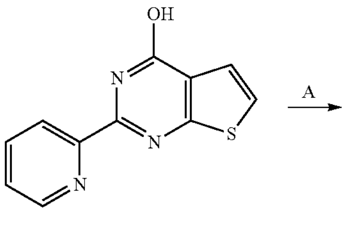

17

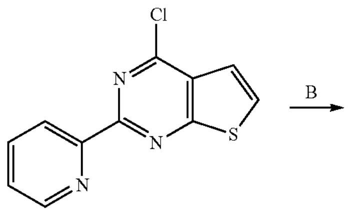

31

-continued

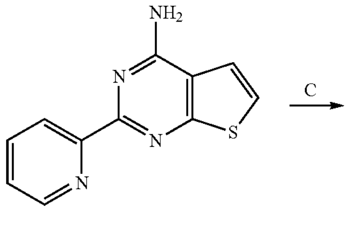

32

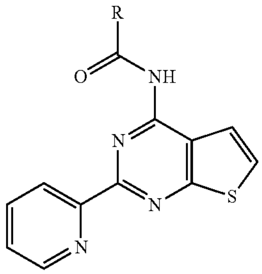

Step A: The compound 17 (20 g, 0.087 mol, 1 eq.) and phosphoryl chloride (300 mL) were heated at reflux for 24 h. The reaction mixture was then evaporated to dryness. The crude residue was dissolved in $CH_2Cl_2$ and washed carefully with ice-water and 5% $NaHCO_3$ solution. Organic layer was dried over $Na_2SO_4$ and evaporated to dryness giving sufficiently pure compound 31 as yellowish powder (20.5 g, yield 95%).

Step B: Compound 31 (10 g, 0.0405 mol, 1 eq) was stirred in 25% aqueous solution of ammonia (200 mL) at 100° C. in autoclave for 10 h. Then reaction mixture was cooled to r.t. and precipitate was filtered, washed with water and air dried to give compound 32 as white solid (8.77 g, 95% yield).

Step C: Reactions were conducted on a 100 mg scale. 1.1 eq of the appropriate acid and 1 eq of 32 was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 ml of distilled water and left at ultrasonic bath for 30-40 min. The resulting residue was filtered off, washed by water and dried under high vacuum to give the target compounds. If there was no residue formed the aqueous solution was extracted by 4 ml of DCM and the organic layer was washed by water (2*4 ml) and the solvent was removed under reduced pressure to give the target compounds. In case of low purity of the final compound was subjected to preparative HPLC purification.

Scheme 9

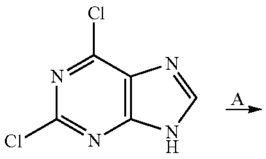

33

-continued

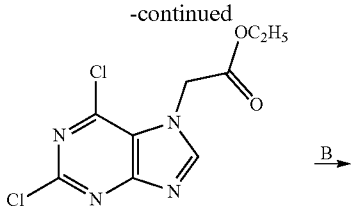

34

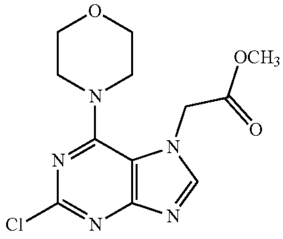

35

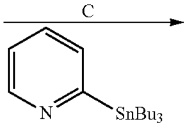

36

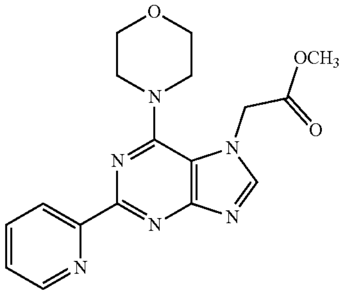

37

Step A: Compound 33 (20 g, 105.8 mmol, 1 eq.) was suspended in anhydrous THF (300 mL) and cooled to −100° C. A THF solution of 3M MeMgCl (43 mL, 1.2 eq.) was added and the reaction was stirred at ambient temperature for 30 min. Solution cooled to −78° C. and ethyl bromoacetate (13 ml, 116.4 mmol) was added dropwise and the reaction was allowed to warm to room temperature. After 18 hours the reaction was quenched with methanol and mixture was concentrated to dryness under reduced pressure. The residue was purified by silica gel column chromatography to give compound 34 (7 g, 25% yield)

Step B: To a solution of 34 (7 g, 26.8 mmol) in THF was added morpholine (7 mL, 80.4 mmol). After 24 hours the reaction was completed. The reaction mixture was filtered and washed with water to give 35 (6.5 g, 78% yield).

Step C: A solution of 2-(tributylstannyl)pyridine 36 (7.82 g, 21.25 mmol), compound 35 (6.5 g, 20.85 mmol) and $Pd(dppf)_2$ (5 mol %) in DMF (100 mL) was heated at 150° C. for 5 days. The reaction mixture was concentrated in vacuo and the residue was dissolved in MTBE (200 mL). The resulting organic solution was washed with water (2×100 mL) and saturated sodium chloride solution (100 mL). The organic layer was separated and dried over $Na_2SO_4$, filtered through $SiO_2$ pad, and evaporated to dryness. The residue was purified by column chromatography affording compound 37 (1.8 g, 24% yield)

Scheme 10

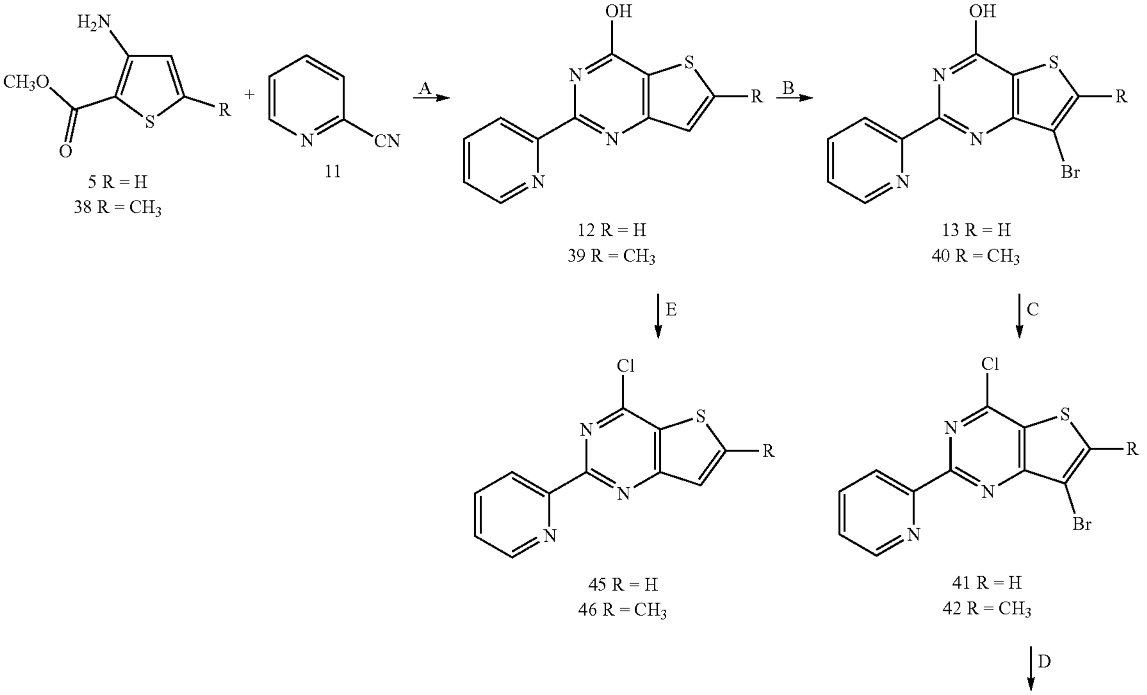

5 R = H
38 R = $CH_3$

11

12 R = H
39 R = $CH_3$

13 R = H
40 R = $CH_3$

45 R = H
46 R = $CH_3$

41 R = H
42 R = $CH_3$

-continued

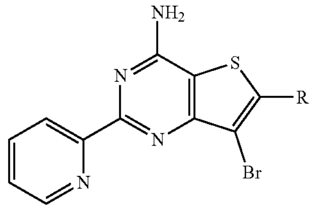

43 R = H
44 R = $CH_3$

Step A: Compound 39 was prepared analogously to 12 as described in Scheme 3, Step A.

Step B: Compound 40 was prepared analogously to 13 as described in Scheme 3, Step B.

Step C: Compound 41 was prepared from compound 13, and compound 42 was prepared from compound 40, using a procedure analogous to the procedure described in Step C of Example 65.

Step D: Compound 43 was prepared from compound 41, and compound 44 was prepared from compound 42, using a procedure analogous to the procedure described in Step B, Scheme 8 for the preparation of compound 32.

Step F: Compound 45 was prepared from compound 12, prepared as described in Scheme 3, Step A, and compound 46 was prepared from compound 39, using a procedure analogous to the procedure described in Step C of Example 65.

Scheme 11

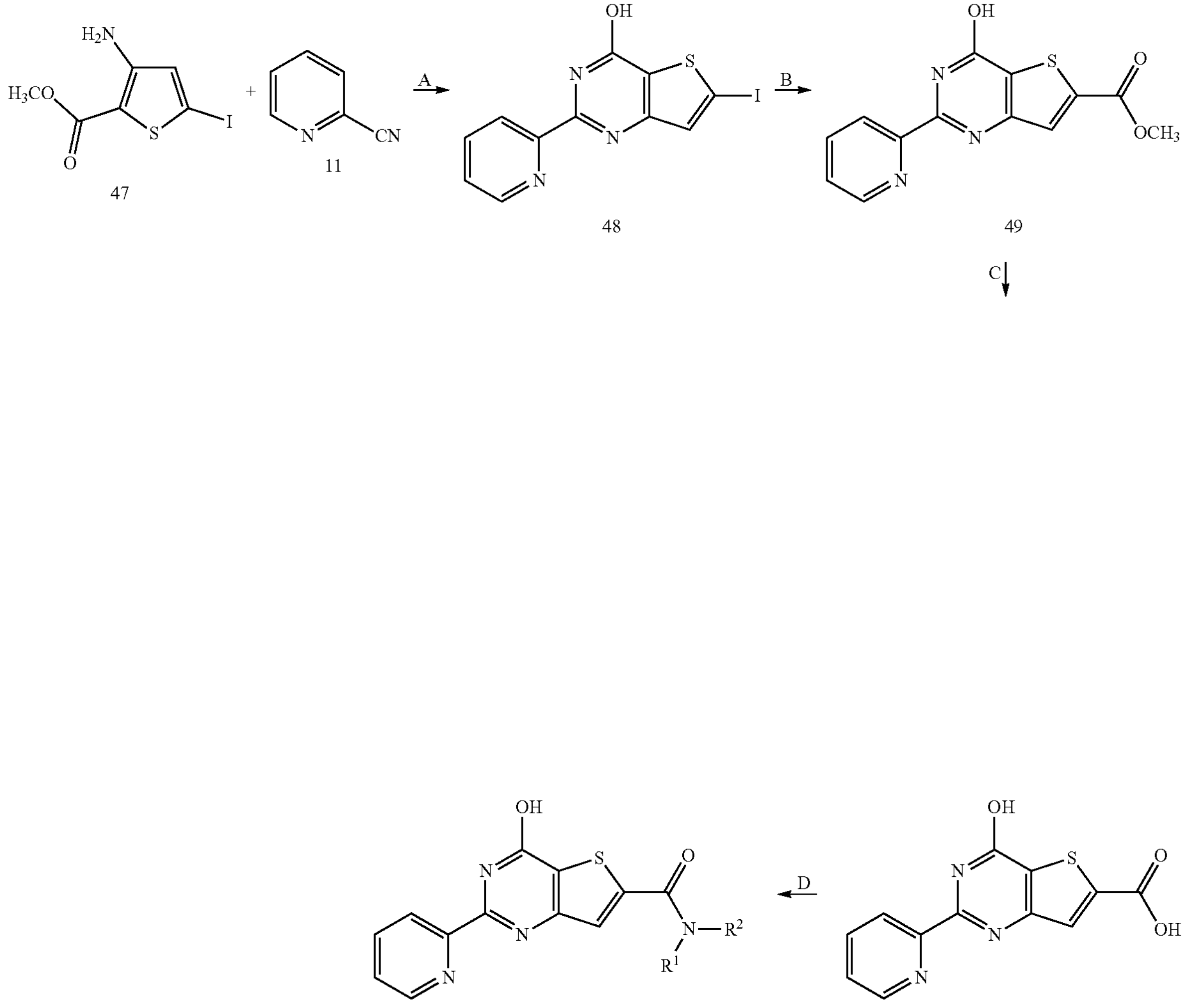

47 11 48 49 50

Step A: Compound 48 was prepared from compound 47 and compound 11 using a procedure analogous to the preparation of compound 12 in Step A, Scheme 3.

Step B: A mixture of compound 48 (4 g, 11.26 mmol) and 1,1'-Bis(diphenylphosphino)ferrocene]dichloropalladium (II) complex with dichloromethane CAS95464054 (2% mol) in methanol (100 ml) was stirred overnight under CO (10 bar) in autoclave. The reaction mixture was filtered and evaporated. The resulting residue was washed with water and dried. The yield of 49 was 2.65 g (9.24 mmol, 82% yield).

Step C: Compound 50 was prepared analogously to compound 15 in Step D of Scheme 3 using the general procedure for ester hydrolysis.

Step D: Reactions were conducted on a 100 mg scale. 1.1 eq of acid 50 and 1 eq of corresponding amine was dissolved in 1 ml of HOBt solution in DMF (9.5% wt). Then 1.2 eq of EDC was added and reaction mixture was left stirring at rt overnight (16-18h). After completion of the reaction, monitored by LCMS, the reaction mixture was diluted with 4 ml of distilled water and left at ultrasonic bath for 30-40 min. The resulting residue was filtered off, washed by water and dried under high vacuum to give the target amides. If there was no residue formed the aqueous solution was extracted by 4 ml of DCM and the organic layer was washed by water (2*4 ml) and the solvent was removed under reduced pressure to give the target amides. In case of low purity of the final compound was subjected to preparative HPLC purification.

Scheme 12

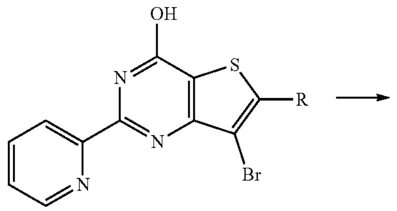

13 R = H
40 R = $CH_3$

-continued

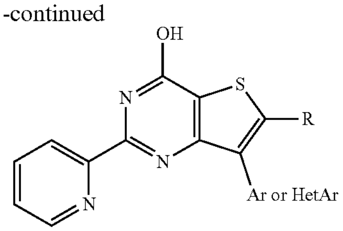

R = H
R = $CH_3$

Reactions were conducted on a 100 mg scale, starting with compound 13 (prepared in Step B, Scheme 3) or compound 40 (prepared in Step B, Scheme 10). General procedure: Compound 13 or compound 40 (1 eq.), the appropriate aryl or heteroaryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. The organic layer was evaporated and dried in vacuo. The residue was purified by HPLC to afford the target compounds.

Scheme 13

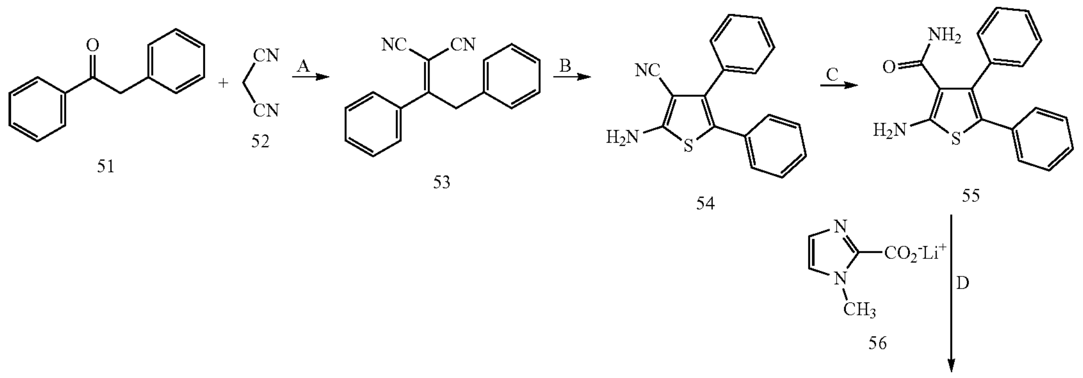

51 52 53 54 55 56

-continued

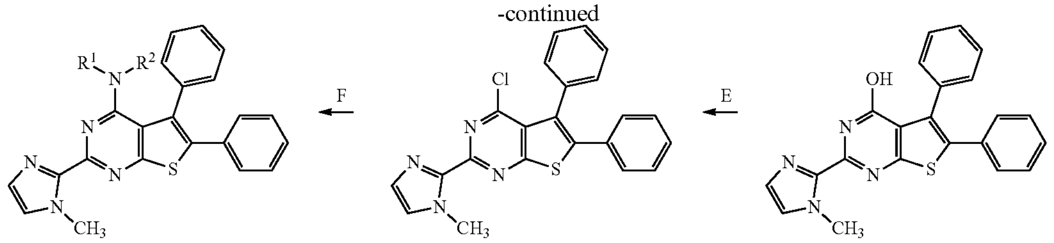

58 57

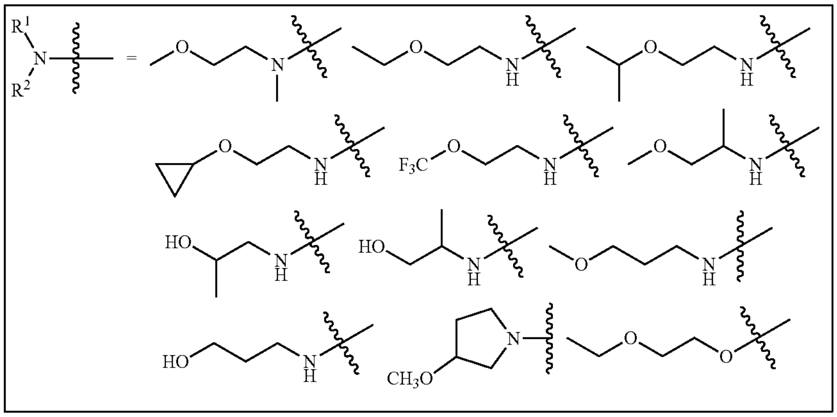

Step A: Hexamethyldisilazane (1.5 eq) was added dropwise to HOAc (7 mL). The resulting mixture was added to a suspension of malononitrile 52 (2.0 eq) and compound 51 (1.0 eq) in HOAc (5 mL). The reaction mixture was stirred with reflux overnight then, allowed to cool down to RT and diluted with toluene (30 mL) and water (20 mL). The organic layer was separated, washed with water (3.2 mL), dried over $Na_2SO_4$ and concentrated under reduced pressure affording compound 53. The scale was calculated based on a theoretical yield of 2 g of product.

Step B: Sulphur (1.2 eq) was added to a solution of compound 53 (1.0 eq) in THF (20 mL). The resulting mixture was stirred at 50° C. for 30 min and then $NaHCO_3$ (1.0 eq) was added. Then, the reaction mixture was stirred at 50° C. overnight and diluted with EtOAc. The organic phase was dried with $Na_2SO_4$ and evaporated in vacuo to obtain compound 54. The scale was calculated based on a theoretical yield of 1.4 g of product.

Step C: The compound 54 (1.0 eq) and 80% $H_2SO_4$ (10 mL) were stirred at RT for 18 h. After completion (monitored by LCMS), the reaction mixture was poured in ice and aqueous ammonia (5 mL) was added. The precipitate formed was filtered off, washed with water and air-dried. The scale was calculated based on a theoretical yield of 0.5 g of product.

Step D: Lithium 1-methyl-1H-imidazole-2-carboxylate 56 (1.3 eq), triethylamine (1.4 eq) and 1-methyl-1H-imidazole (2.5 eq) were dissolved in $CH_2Cl_2$ (15 mL). The resulting mixture was cooled to 0° C. and methanesulfonyl chloride (1.2 eq) was added dropwise. Then, the resulting suspension was stirred for 30 min and compound 55 (1.0 eq) was added in one portion. The reaction mixture was stirred overnight and evaporated in vacuo. The residue was dissolved in DMSO and potassium tert-butoxide (2.0 eq) was added. The resulting suspension was stirred overnight at 80° C. and HOAc (5 mL) was added. The resulting precipitate was filtered off, washed with water and dried to give 57. The scale was calculated based on a theoretical yield of 300 mg of product.

Step E: The compound 57 (1.0 eq.) and phosphoryl chloride (7 mL) were stirred at 90° c. for 18 h. The reaction mixture was poured into ice and extracted with EtOAc. The organic layer was dried ($Na_2SO_4$), filtered and the solvent was removed under reduced pressure to give the compound 58. The scale was calculated based on a theoretical yield of 170 mg of product.

Step F: To a solution of compound 58 (1.0 eq) in DMSO (3 mL), the appropriate amine (1.0 eq) and DIPEA (1.3 eq) were added. The resulting mixture was stirred overnight at 60° C. Then, the reaction suspension was poured into water and extracted with EtOAc. The solvent was evaporated and the residue was purified by HPLC to obtain the target compounds. The scale was calculated based on a theoretical yield of 100 mg of final product.

Scheme 14

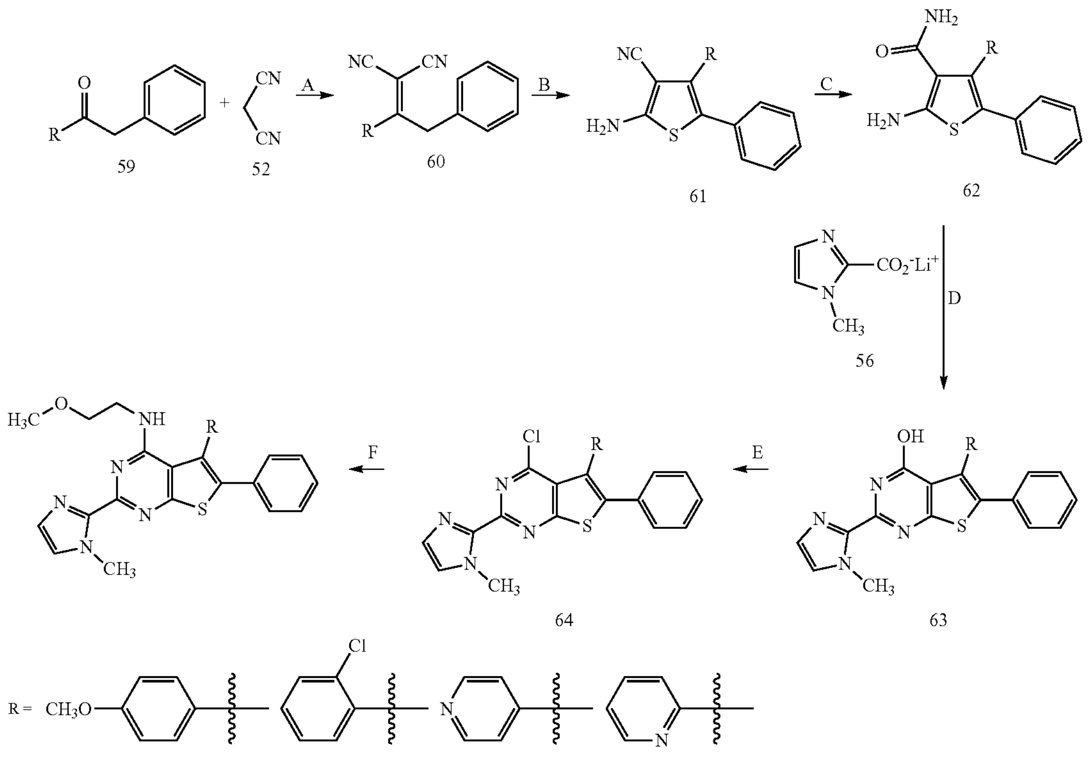

Step A: Hexamethyldisilazane (1.5 eq) was added dropwise to HOAc (7 mL). The resulting mixture was added to a suspension of malononitrile 52 (2.0 eq) and compound 59 (1.0 eq) in HOAc (5 mL). The reaction mixture was stirred with reflux overnight then, allowed to cool down to RT and diluted with toluene (30 mL) and water (20 mL). The organic layer was separated, washed with water (3.2 mL), dried over $Na_2SO_4$ and concentrated under reduced pressure affording compound 60. The scale was calculated based on a theoretical yield of 2 g of product.

Step B: Sulphur (1.2 eq) was added to a solution of compound 60 (1.0 eq) in THF (20 mL). The resulting mixture was stirred at 50° C. for 30 min and then $NaHCO_3$ (1.0 eq) was added. Then, the reaction mixture was stirred at 50° C. overnight and diluted with EtOAc. The organic phase was dried with $Na_2SO_4$ and evaporated in vacuo to obtain compound 61. The scale was calculated based on a theoretical yield of 0.5 g of product.

Step C when R=4-methoxyphenyl: The compound 61 (1.0 eq) and polyphosphoric acid (10 mL) were stirred at 80° C. for 18 h. After completion of the reaction (monitored by LCMS) the reaction mixture was poured in ice and sodium hydroxide (5 mL) was added. The resulting precipitate was filtered off, washed with water and dried. The yield was 61%. The scale was calculated based on a theoretical yield of 0.5 g of product.

Step C when R=2-chlorophenyl: The compound 61 (1.0 eq) and 80% $H_2SO_4$ (10 mL) were stirred at RT for 18 h. After completion (monitored by LCMS), the reaction mixture was poured in ice and aqueous ammonia (5 mL) was added. The precipitate formed was filtered off, washed with water and air-dried. The scale was calculated based on a theoretical yield of 0.5 g of product.

Step C when R=4-pyridinyl or 2-pyridinyl: The compound 61 (1.0 eq) and 80% $H_2SO_4$ (10 mL) were stirred at 80° C. for 24 h. After completion of the reaction (monitored by LCMS) the reaction mixture was poured in ice and ammonia (5 mL) was added. The resulting precipitate was filtered off, washed with water and air-dried. The yield was 72%. The scale was calculated based on a theoretical yield of 0.5 g of product.

Step D: Lithium 1-methyl-1H-imidazole-2-carboxylate 56 (1.3 eq), triethylamine (1.4 eq) and 1-methyl-1H-imidazole (2.5 eq) were dissolved in $CH_2Cl_2$ (15 mL). The resulting mixture was cooled to 0° C. and methanesulfonyl chloride (1.2 eq) was added dropwise. Then, the resulting suspension was stirred for 30 min and compound 62 (1.0 eq) was added in one portion. The reaction mixture was stirred overnight and evaporated in vacuo. The residue was dissolved in DMSO and potassium tert-butoxide (2.0 eq) was added. The resulting suspension was stirred overnight at 80° C. and HOAc (5 mL) was added. The resulting precipitate was filtered off, washed with water and dried to give 63. The scale was calculated based on a theoretical yield of 300 mg of product.

Step E: The compound 63 (1.0 eq.) and phosphoryl chloride (7 mL) were stirred at 90° c. for 18 h. The reaction mixture was poured into ice and extracted with EtOAc. The organic layer was dried ($Na_2SO_4$), filtered and the solvent was removed under reduced pressure to give the compound 64. The scale was calculated based on a theoretical yield of 180 mg of product.

Step F: To a solution of compound 64 (1.0 eq) in DMSO (3 mL), 2-methoxyethanamine (1.0 eq) and DIPEA (1.3 eq) were added. The resulting mixture was stirred overnight at 60° C. Then, the reaction suspension was poured into water and extracted with EtOAc. The solvent was evaporated and the residue was purified by HPLC to obtain the target compounds. The scale was calculated based on a theoretical yield of 100 mg of final product.

added. The precipitate formed was filtered off, washed with water and air-dried to give 68. The scale was calculated based on a theoretical yield of 0.5 g of product.

Scheme 15

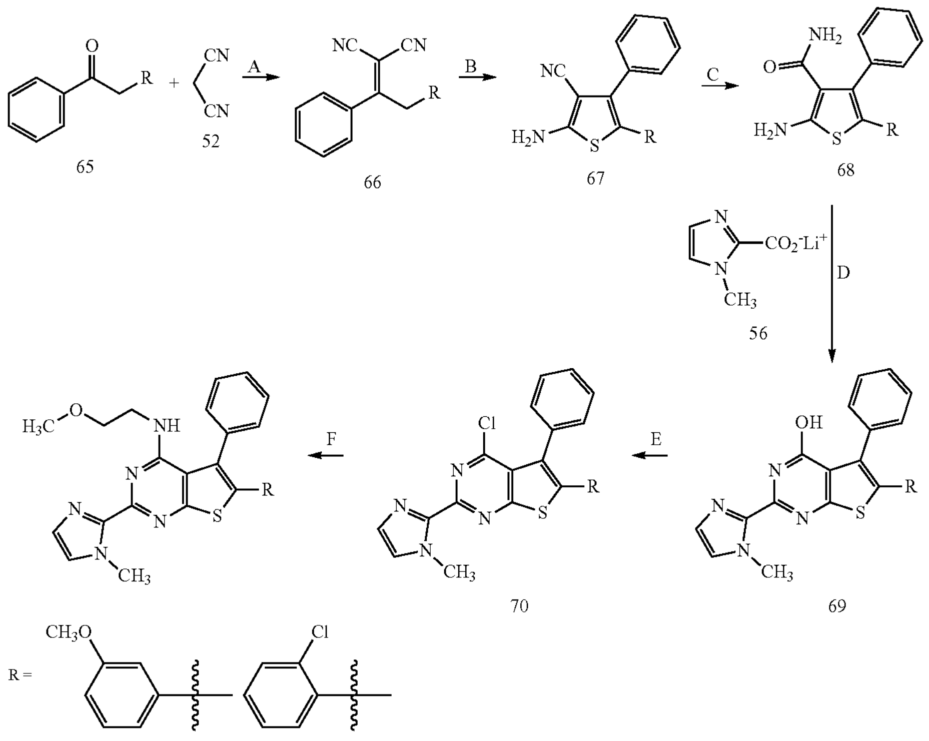

Step A: Hexamethyldisilazane (1.5 eq) was added dropwise to HOAc (7 mL). The resulting mixture was added to a suspension of malononitrile 52 (2.0 eq) and compound 65 (1.0 eq) in HOAc (5 mL). The reaction mixture was stirred with reflux overnight then, allowed to cool down to RT and diluted with toluene (30 mL) and water (20 mL). The organic layer was separated, washed with water (3.2 mL), dried over $Na_2SO_4$ and concentrated under reduced pressure affording compound 66. The scale was calculated based on a theoretical yield of 2 g of product.

Step B: Sulphur (1.2 eq) was added to a solution of compound 66 (1.0 eq) in THF (20 mL). The resulting mixture was stirred at 50° C. for 30 min and then $NaHCO_3$ (1.0 eq) was added. Then, the reaction mixture was stirred at 50° C. overnight and diluted with EtOAc. The organic phase was dried with $Na_2SO_4$ and evaporated in vacuo to obtain compound 67. The scale was calculated based on a theoretical yield of 1.5 g of product.

Step C when R=3-methoxyphenyl: The compound 67 (1.0 eq) and polyphosphoric acid (10 mL) were stirred at 80° C. for 18 h. After completion of the reaction (monitored by LCMS) the reaction mixture was poured in ice and sodium hydroxide (5 mL) was added. The resulting precipitate was filtered off, washed with water and dried to give 68. The scale was calculated based on a theoretical yield of 0.5 g of product.

Step C when R=2-chlorophenyl: The compound 67 (1.0 eq) and 80% $H_2SO_4$ (10 mL) were stirred at RT for 18 h. After completion (monitored by LCMS), the reaction mixture was poured in ice and aqueous ammonia (5 mL) was Step D: Lithium 1-methyl-1H-imidazole-2-carboxylate 56 (1.3 eq), triethylamine (1.4 eq) and 1-methyl-1H-imidazole (2.5 eq) were dissolved in $CH_2Cl_2$ (15 mL). The resulting mixture was cooled to 0° C. and methanesulfonyl chloride (1.2 eq) was added dropwise. Then, the resulting suspension was stirred for 30 min and compound 68 (1.0 eq) was added in one portion. The reaction mixture was stirred overnight and evaporated in vacuo. The residue was dissolved in DMSO and potassium tert-butoxide (2.0 eq) was added. The resulting suspension was stirred overnight at 80° C. and HOAc (5 mL) was added. The resulting precipitate was filtered off, washed with water and dried to give 69. The scale was calculated based on a theoretical yield of 300 mg of product.

Step E: The compound 69 (1.0 eq.) and phosphoryl chloride (7 mL) were stirred at 90° c. for 18 h. The reaction mixture was poured into ice and extracted with EtOAc. The organic layer was dried ($Na_2SO_4$), filtered and the solvent was removed under reduced pressure to give the compound 70. The scale was calculated based on a theoretical yield of 170 mg of product.

Step F: To a solution of compound 70 (1.0 eq) in DMSO (3 mL), 2-methoxyethanamine (1.0 eq) and DIPEA (1.3 eq) were added. The resulting mixture was stirred overnight at 60° C. Then, the reaction suspension was poured into water and extracted with EtOAc. The solvent was evaporated and the residue was purified by HPLC to obtain the target compounds. The scale was calculated based on a theoretical yield of 100 mg of final product.

Scheme 16

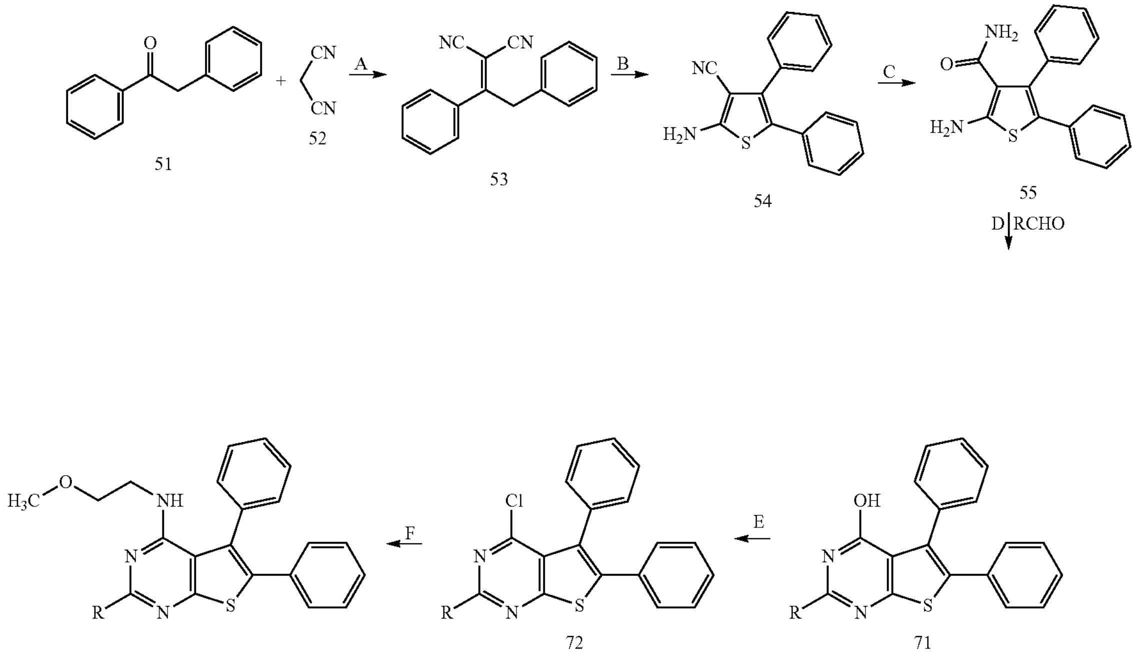

R =

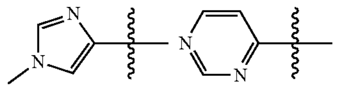

Step A: Hexamethyldisilazane (1.5 eq) was added dropwise to HOAc (7 mL). The resulting mixture was added to a suspension of malononitrile 52 (2.0 eq) and compound 51 (1.0 eq) in HOAc (5 mL). The reaction mixture was stirred with reflux overnight then, allowed to cool down to RT and diluted with toluene (30 mL) and water (20 mL). The organic layer was separated, washed with water (3.2 mL), dried over $Na_2SO_4$ and concentrated under reduced pressure affording compound 53. The scale was calculated based on a theoretical yield of 2 g of product.

Step B: Sulphur (1.2 eq) was added to a solution of compound 53 (1.0 eq) in THF (20 mL). The resulting mixture was stirred at 50° C. for 30 min and then $NaHCO_3$ (1.0 eq) was added. Then, the reaction mixture was stirred at 50° C. overnight and diluted with EtOAc. The organic phase was dried with $Na_2SO_4$ and evaporated in vacuo to obtain compound 54. The scale was calculated based on a theoretical yield of 1.5 g of product.

Step C: The compound 54 (1.0 eq) and 80% $H_2SO_4$ (10 mL) were stirred at RT for 18 h. After completion (monitored by LCMS), the reaction mixture was poured in ice and aqueous ammonia (5 mL) was added. The precipitate formed was filtered off, washed with water and air-dried to give 55. The scale was calculated based on a theoretical yield of 0.5 g of product.

Step D: To a solution of compound 55 (1.0 eq) in DMF (5 mL), the appropriate aldehyde (1.5 eq) was added. The resulting mixture was stirred at 90° C. overnight. Then, the mixture was diluted with water (5 mL) and the product was extracted with $CH_2Cl_2$ (3*2 mL). The organic phase was dried with $Na_2SO_4$ and evaporated in vacuo affording crude product. The residue was recrystallized from MeOH to obtain pure product 71 (51% yield). The scale was calculated based on a theoretical yield of 300 mg of product.

Step E: The compound 71 (1.0 eq.) and phosphoryl chloride (7 mL) were stirred at 90° c. for 18 h. The reaction mixture was poured into ice and extracted with EtOAc. The organic layer was dried ($Na_2SO_4$), filtered and the solvent was removed under reduced pressure to give the compound 72. The scale was calculated based on a theoretical yield of 160 mg of product.

Step F: To a solution of compound 72 (1.0 eq) in DMSO (3 mL), 2-methoxyethanamine (1.0 eq) and DIPEA (1.3 eq) were added. The resulting mixture was stirred overnight at 60° C. Then, the reaction suspension was poured into water and extracted with EtOAc. The solvent was evaporated and the residue was purified by HPLC to obtain the target compounds. The scale was calculated based on a theoretical yield of 100 mg of final product.

Scheme 17

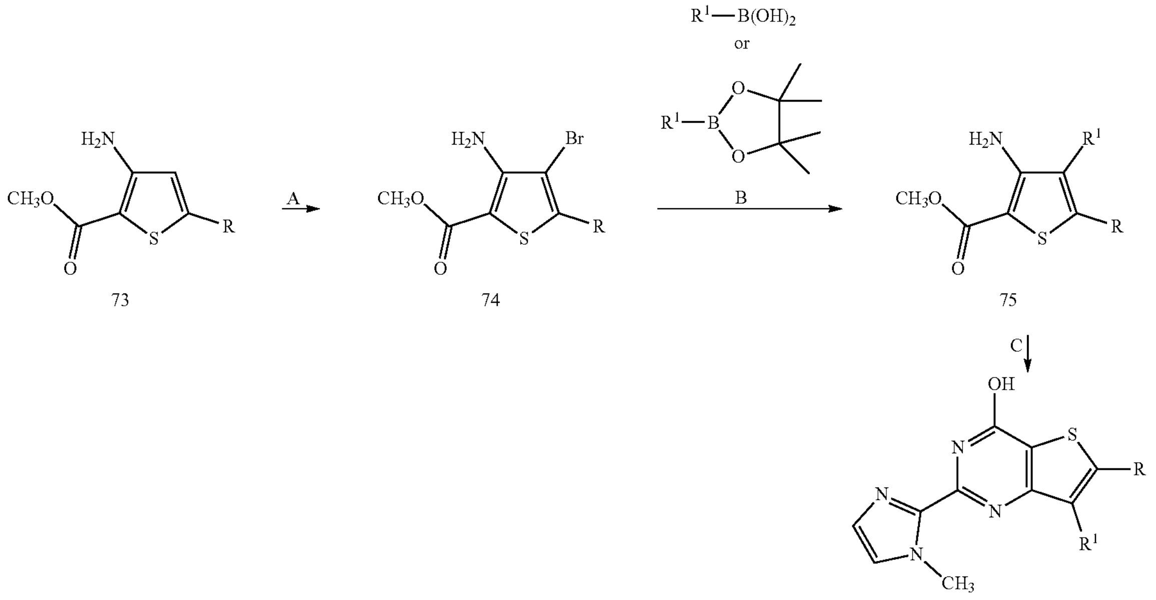

73 74 75 76

R = H, $CH_3$, Ph
$R^1$ = Ar, HetAr

Step A: To a solution of compound 73 (1.0 eq) in HOAc (15.0 mL) was added $Br_2$ (3.0 eq). The reaction was heated to 60° C. and allowed to stir approximately 45 minutes. The excess $Br_2$ was neutralized with excess of $Na_2S_2O_3$, and the crude product was extracted (3*25 mL) of DCM. The combined organic layers were dried over $MgSO_4$ and concentrated in vacuo, affording crude compound 74 as a light yellow solid. The products were used in the next step without purification. The scale of the reaction was calculated based on a theoretical yield of 1 g of 74.

Step B: Compound 74 (1.0 eq), the corresponding boronic acid (1.1 eq), Pd(dppf)$Cl_2$.$CH_2Cl_2$ (0.02 eq) and potassium carbonate (2.0 eq) in dioxane (2 mL) and water (1 mL) was heated at 90° C. overnight under Ar atmosphere. After cooling, the mixture was purified by flash chromatography on silica gel using 1:4 ethyl acetate/hexanes to give the target compounds 75. The scale of the reaction was calculated based on a theoretical yield of 0.5 g of 75.

Step C: Compound 75 (1.0 eq), 1-methyl-2-cyanoimidazole (1.1 eq) and sodium tert-butoxide (2.0 eq) in dry THF (2 ml) was heated at reflux for 12 hours. After cooling, the mixture was poured into water (2 ml). The formed precipitated solid was collected and purified by HPLC to give the target compounds 76. The scale of the reaction was calculated based on a theoretical yield of 200 mg of 76.

Scheme 18

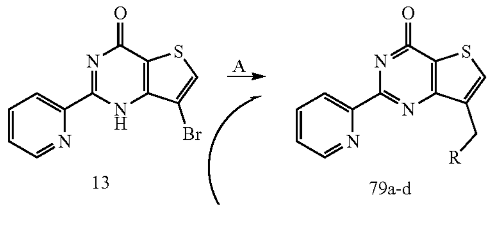

13 79a-d

-continued

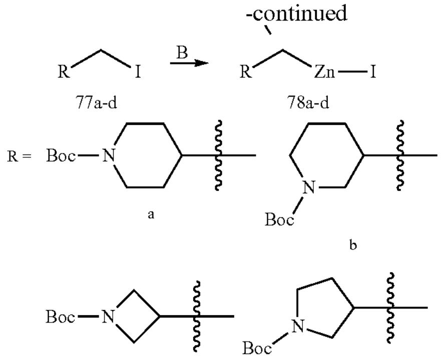

77a-d 78a-d a b c d

Step A-Step B: Into a 500 mL flask were charged 13 (1 g, 3.25 mmol, 1 eq.), [1,1' bis(diphenylphosphino)-ferrocene] dichloropalladium(II)-dichloromethane complex (0.132 g, 0.16 mmol, 0.05 eq.), cuprous iodide (0.061 g, 0.32 mmol, 0.1 eq.), and THF (50 mL). The resulting mixture was degassed with alternating vacuum/nitrogen purges. The filtered organozinc reagent 78 (9.75 mmol, prepared as described in *J. Org. Chem.* 2004, 69, 5120-5123 from iodide 77) was then added. The mixture was degassed one more time and then heated at reflux for 24 h. The reaction mixture was then cooled to 20° C. and treated with MTBE (methyl tert-butyl ether, 130 mL) and 1 N ammonium chloride (130 mL). The mixture was stirred at 20-30° C. for 30 min and then filtered. The lower aqueous layer was drawn off, and the remaining organic layer was treated with saturated aqueous $NH_4Cl$ (50 mL) and stirred for 30 min. After settling, the lower aqueous layer was removed and the organic layer was collected. The resulting organic solution was then filtered through a small pad of $SiO_2$. The $SiO_2$ pad was washed with MTBE (25 mL). The solvent was evaporated, and the residue was purified by HPLC to give the products 79.

Scheme 19

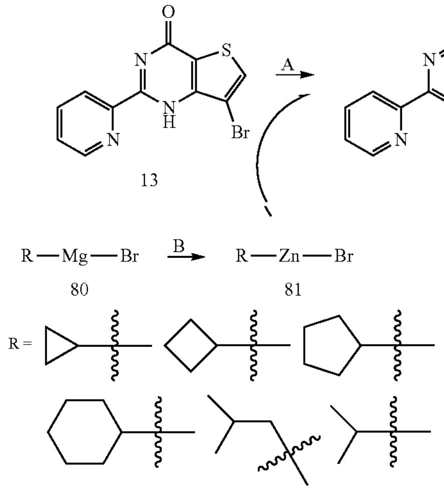

13 80 81

Into a 500 mL flask were charged 13 (1 g, 3.25 mmol, 1 eq.), [1,1' bis(diphenylphosphino)-ferrocene]dichloropalladium(II)-dichloromethane complex (0.132 g, 0.16 mmol, 0.05 eq.), cuprous iodide (0.061 g, 0.32 mmol, 0.1 eq.), and THF (50 mL). The resulting mixture was degassed with alternating vacuum/nitrogen purges. The filtered organozinc reagent 81 (9.75 mmol, prepared as described in *J. Org. Chem.* 2004, 69, 5120-5123 from 80) was then added. The mixture was degassed one more time and then heated at reflux for 24 h. The reaction mixture was then cooled to 20° C. and treated with MTBE (methyl tert-butyl ether, 130 mL) and 1 N ammonium chloride (130 mL). The mixture was stirred at 20-30° C. for 30 min and then filtered. The lower aqueous layer was drawn off, and the remaining organic layer was treated with saturated aqueous $NH_4Cl$ (50 mL) and stirred for 30 min. After settling, the lower aqueous layer was removed and the organic layer was collected. The resulting organic solution was then filtered through a small pad of $SiO_2$. The $SiO_2$ pad was washed with MTBE (25 mL). The solvent was evaporated, and the residue was purified by HPLC to give the target compounds.

Purification and Analytical Procedures:

Purification was performed using HPLC ($H_2O$-MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the $N_2$ flow upon heating to 80° C. On the basis of post-chromatography LCMS analysis fractions were united. Solid fractions were dissolved in 0.5 mL MeOH and transferred into a pre-weighted marked vials. Obtained solutions were again evaporated under the $N_2$ flow upon heating to 80° C. After drying, products were finally characterized by LCMS and $^1$H NMR.

NMR Instrument specifications: Bruker AVANCE DRX 500, Varian UNITYplus 400.

LC/MS Instrument specifications: Agilent 1100 Series LC/MSD system with DAD\ELSD and Agilent LC\MSD VL (G1956A), SL (G1956B) mass-spectrometer. Agilent 1200 Series LC/MSD system with DAD\ELSD and Agilent LC\MSD SL (G6130A), SL (G6140A) mass-spectrometer. All the LC/MS data were obtained using positive/negative mode switching. Column Zorbax SB-C18 1.8 μm 4.6×15 mm Rapid Resolution cartridge (PN 821975-932) Mobile phase A—acetonitrile, 0.1% formic acid, B—water (0.1% formic acid) Flow rate 3 ml/min Gradient 0 min-100% B, 0.01 min-100% B, 1.5 min-0% B, 1.8 min-0% B, 1.81 min-100% B. Injection volume 1 μl. Ionization mode atmospheric pressure chemical ionization (APCI). Scan range m/z 80-1000

TABLE 3

Mass Spectral Data

| Compound | MW | M + H (calculated) | M + H (observed) |
|---|---|---|---|
| 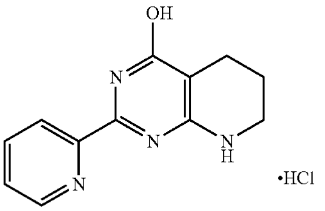 [SMILES: Oc1nc(-c2ccccn2)nc2c1CCCN2 ; Cl] | 265 | 229.1 | 229.2 |
| 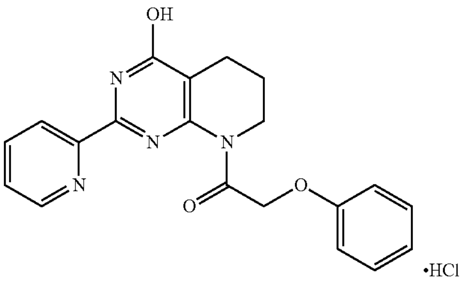 [SMILES: O=C(COc1ccccc1)N1CCCc2c(O)nc(-c3ccccn3)nc21 ; Cl] | 399 | 363.1 | 363.0 |

TABLE 3-continued
| Mass Spectral Data | | | |
|---|---|---|---|
| Compound | MW | M + H (calculated) | M + H (observed) |
| 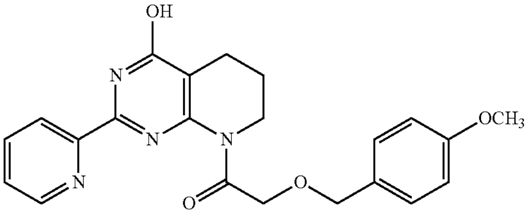 [SMILES: COc1ccc(COCC(=O)N2CCCc3c(O)nc(-c4ccccn4)nc32)cc1] | 406 | 407.2 | 407.2 |
| 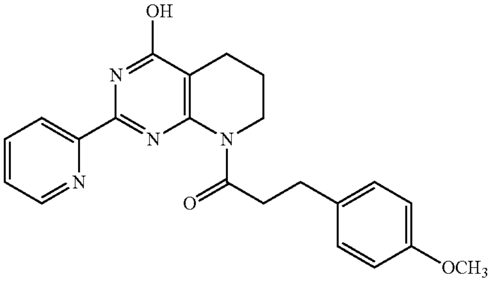 •HCl | 427 | 391.2 | 391.2 |
| 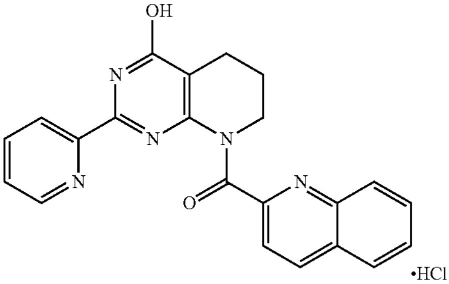 [SMILES: O=C(c1ccc2ccccc2n1)N1CCCc2c(O)nc(-c3ccccn3)nc21 ; Cl] •HCl | 420 | 384.2 | 384.0 |
| 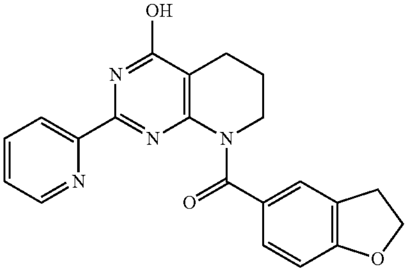 •HCl | 411 | 375.2 | 375.1 |
| 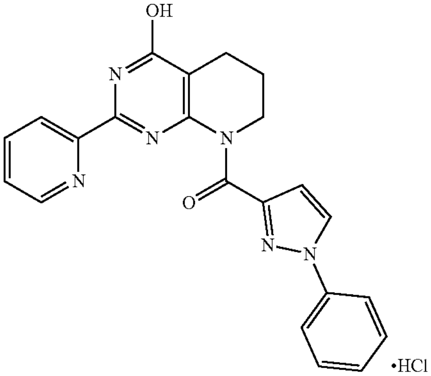 [SMILES: O=C(c1ccn(-c2ccccc2)n1)N1CCCc2c(O)nc(-c3ccccn3)nc21 ; Cl] •HCl | 435 | 399.2 | 399.2 |

TABLE 3-continued
| Mass Spectral Data | | | |
|---|---|---|---|
| Compound | MW | M + H (calculated) | M + H (observed) |
| 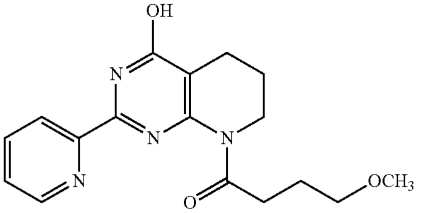 [SMILES: COCCCC(=O)N1CCCc2c(O)nc(-c3ccccn3)nc21] | 328 | 329.2 | 329.2 |
| 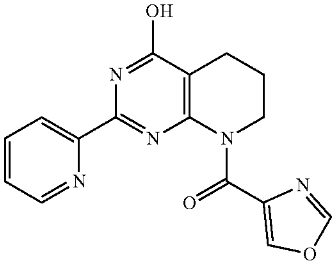 [SMILES: O=C(c1cocn1)N1CCCc2c(O)nc(-c3ccccn3)nc21] | 323 | 324.1 | 324.2 |
| 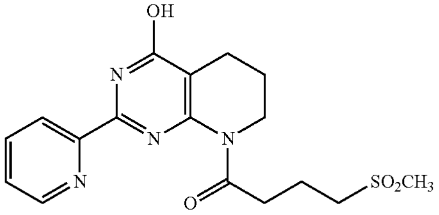 [SMILES: CS(=O)(=O)CCCC(=O)N1CCCc2c(O)nc(-c3ccccn3)nc21] | 376 | 377.1 | 377.2 |
| 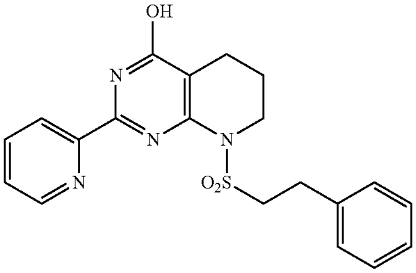 [SMILES: O=S(=O)(CCc1ccccc1)N1CCCc2c(O)nc(-c3ccccn3)nc21] | 396 | 397.1 | 397.2 |
| 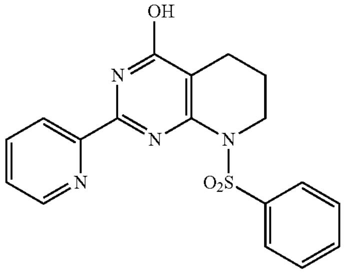 [SMILES: O=S(=O)(c1ccccc1)N1CCCc2c(O)nc(-c3ccccn3)nc21] | 368 | 369.1 | 369.2 |
| 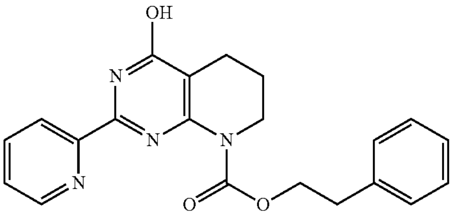 [SMILES: O=C(OCCc1ccccc1)N1CCCc2c(O)nc(-c3ccccn3)nc21] | 376 | 377.2 | 377.2 |

TABLE 3-continued
| Mass Spectral Data | | | |
|---|---|---|---|
| Compound | MW | M + H (calculated) | M + H (observed) |
| 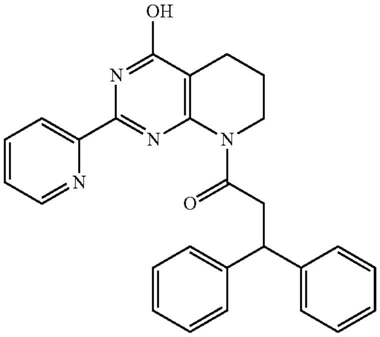 [SMILES: O=C(CC(c1ccccc1)c1ccccc1)N1CCCc2c(O)nc(-c3ccccn3)nc21] | 437 | 437.2 | 437.1 |
| 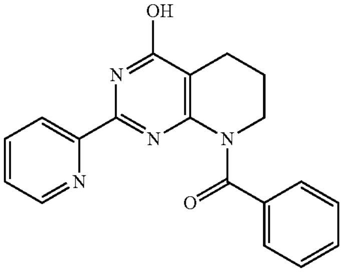 [SMILES: O=C(c1ccccc1)N1CCCc2c(O)nc(-c3ccccn3)nc21] | 332 | 333.1 | 333.2 |
| 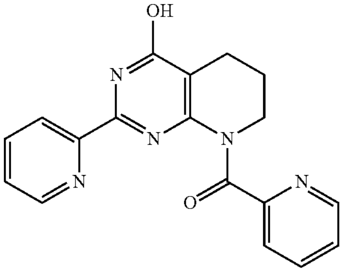 [SMILES: O=C(c1ccccn1)N1CCCc2c(O)nc(-c3ccccn3)nc21] | 333 | 334.1 | 334.0 |
| 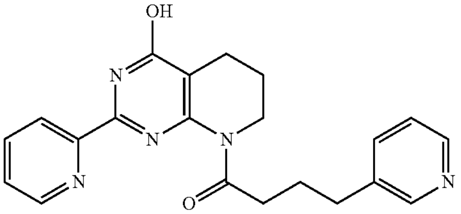 [SMILES: O=C(CCCc1cccnc1)N1CCCc2c(O)nc(-c3ccccn3)nc21] | 375 | 376.2 | 376.2 |
| 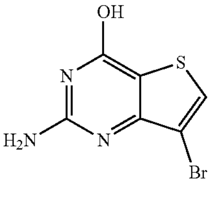 [SMILES: Nc1nc(O)c2scc(Br)c2n1] | 246 | 245.9 | 246.0 |

TABLE 3-continued
| Mass Spectral Data | | | |
|---|---|---|---|
| Compound | MW | M + H (calculated) | M + H (observed) |
| 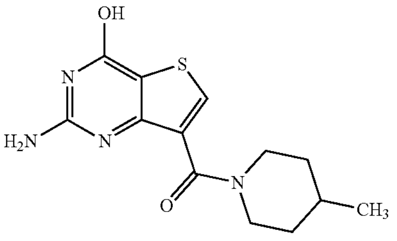 [SMILES: CC1CCN(C(=O)c2csc3c(O)nc(N)nc23)CC1] | 292 | 293.1 | 293.0 |
| 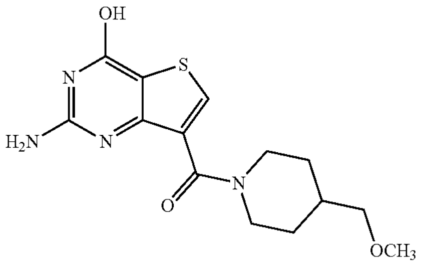 [SMILES: COCC1CCN(C(=O)c2csc3c(O)nc(N)nc23)CC1] | 322 | 323.1 | 323.0 |
| 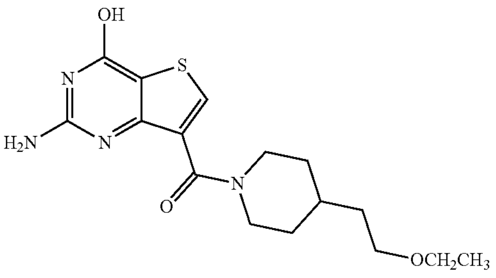 [SMILES: CCOCCC1CCN(C(=O)c2csc3c(O)nc(N)nc23)CC1] | 350 | 351.1 | 351.0 |
| 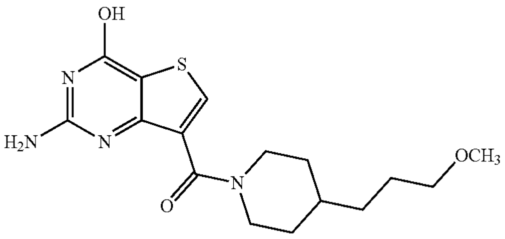 [SMILES: COCCCC1CCN(C(=O)c2csc3c(O)nc(N)nc23)CC1] | 350 | 351.2 | 351.2 |
| 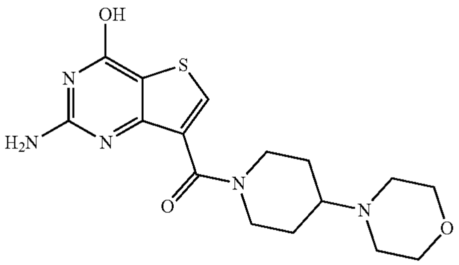 [SMILES: Nc1nc(O)c2scc(C(=O)N3CCC(N4CCOCC4)CC3)c2n1] | 363 | 364.1 | 364.2 |

TABLE 3-continued
| Mass Spectral Data | | | |
|---|---|---|---|
| Compound | MW | M + H (calculated) | M + H (observed) |
| 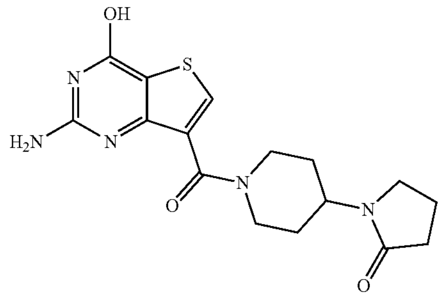 [SMILES: Nc1nc(O)c2scc(C(=O)N3CCC(N4CCCC4=O)CC3)c2n1] | 361 | 362.1 | 362.2 |
| 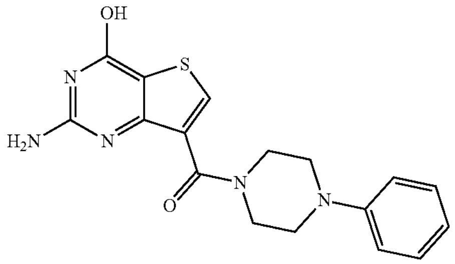 [SMILES: Nc1nc(O)c2scc(C(=O)N3CCN(c4ccccc4)CC3)c2n1] | 355 | 356.1 | 356.1 |
| 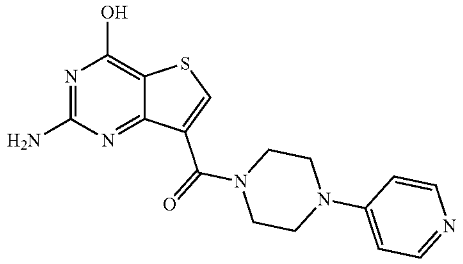 [SMILES: Nc1nc(O)c2scc(C(=O)N3CCN(c4ccncc4)CC3)c2n1] | 356 | 357.1 | 357 |
| 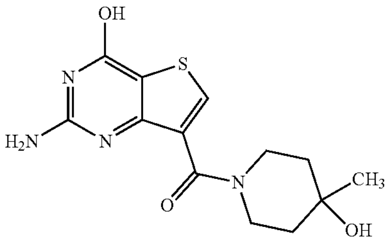 [SMILES: CC1(O)CCN(C(=O)c2csc3c(O)nc(N)nc23)CC1] | 308 | 309.1 | 309.0 |
| 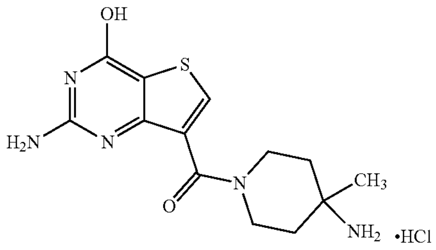 [SMILES: CC1(N)CCN(C(=O)c2csc3c(O)nc(N)nc23)CC1 ; Cl] | 344 | 308.1 | 308.2 |

TABLE 3-continued
| Mass Spectral Data | | | |
|---|---|---|---|
| Compound | MW | M + H (calculated) | M + H (observed) |
| 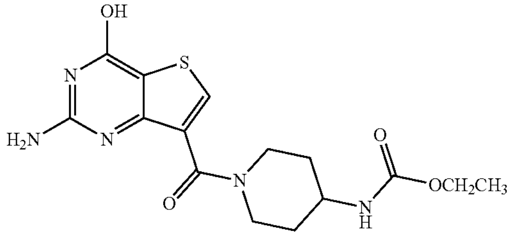 [SMILES: CCOC(=O)NC1CCN(C(=O)c2csc3c(O)nc(N)nc23)CC1] | 365 | 366.1 | 366.0 |
| 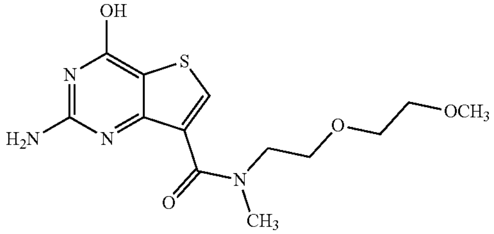 [SMILES: COCCOCCN(C)C(=O)c1csc2c(O)nc(N)nc12] | 326 | 327.1 | 327.0 |
| 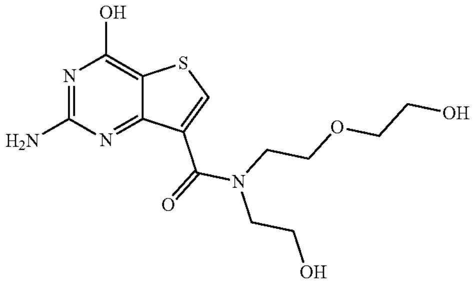 [SMILES: Nc1nc(O)c2scc(C(=O)N(CCO)CCOCCO)c2n1] | 342 | 343.1 | 343.2 |
| 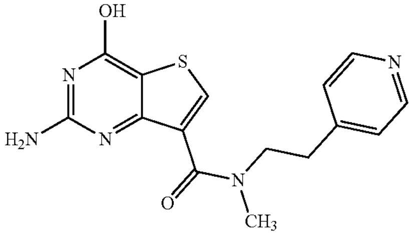 [SMILES: CN(CCc1ccncc1)C(=O)c1csc2c(O)nc(N)nc12] | 329 | 330.1 | 330.2 |
| 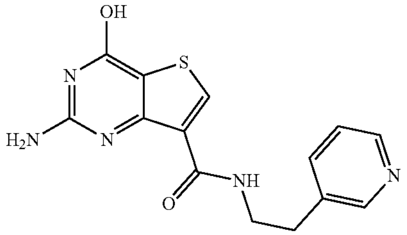 [SMILES: Nc1nc(O)c2scc(C(=O)NCCc3cccnc3)c2n1] | 315 | 316.1 | 316.0 |
| 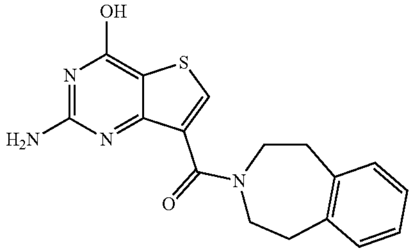 [SMILES: Nc1nc(O)c2scc(C(=O)N3CCc4ccccc4CC3)c2n1] | 340 | 341.1 | 341.2 |

TABLE 3-continued
| Mass Spectral Data | | | |
|---|---|---|---|
| Compound | MW | M + H (calculated) | M + H (observed) |
| 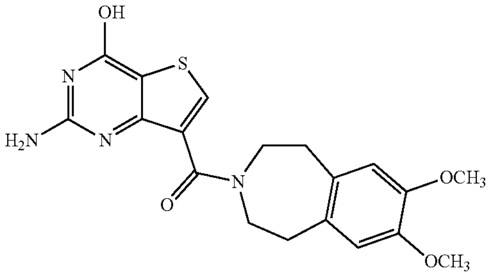 [SMILES: COc1cc2c(cc1OC)CCN(C(=O)c1csc3c(O)nc(N)nc13)CC2] | 400 | 401.1 | 401.0 |
| 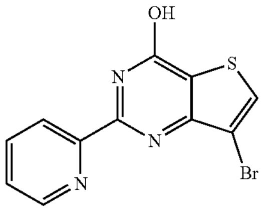 [SMILES: Oc1nc(-c2ccccn2)nc2c(Br)csc12] | 308 | 307.9 | 308.0 |
| 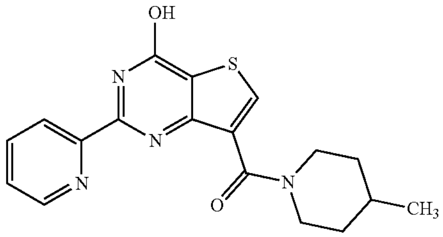 [SMILES: CC1CCN(C(=O)c2csc3c(O)nc(-c4ccccn4)nc23)CC1] | 354 | 355.1 | 355.2 |
| 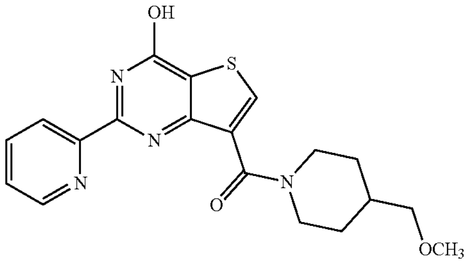 | 384 | 385.1 | 385.0 |
| 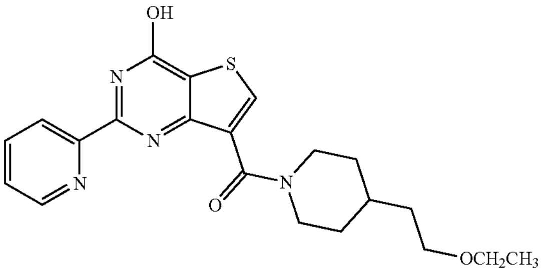 [SMILES: CCOCCC1CCN(C(=O)c2csc3c(O)nc(-c4ccccn4)nc23)CC1] | 413 | 413.2 | 413.2 |
| 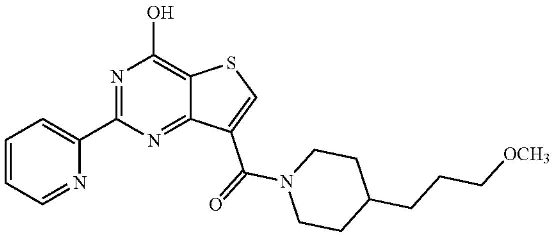 [SMILES: COCCCC1CCN(C(=O)c2csc3c(O)nc(-c4ccccn4)nc23)CC1] | 413 | 413.2 | 413.2 |

TABLE 3-continued
Mass Spectral Data
| Compound | MW | M + H (calculated) | M + H (observed) |
|---|---|---|---|
| 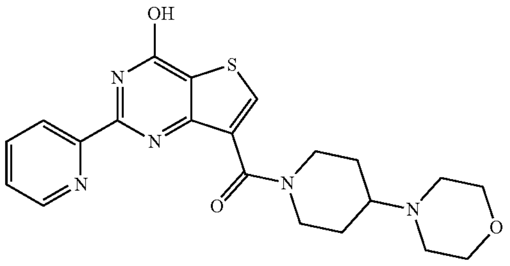 [SMILES: O=C(c1csc2c(O)nc(-c3ccccn3)nc12)N1CCC(N2CCOCC2)CC1] | 426 | 426.2 | 426.0 |
| 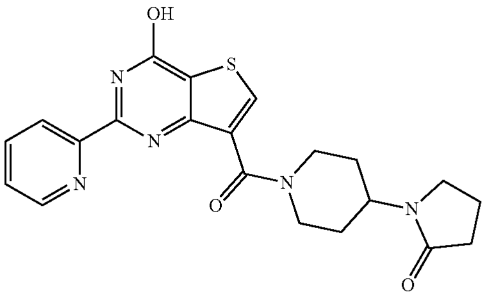 [SMILES: O=C(c1csc2c(O)nc(-c3ccccn3)nc12)N1CCC(N2CCCC2=O)CC1] | 423 | 424.2 | 424.2 |
| 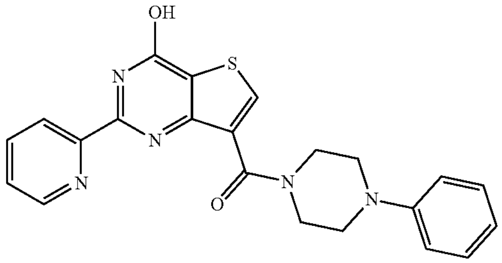 [SMILES: O=C(c1csc2c(O)nc(-c3ccccn3)nc12)N1CCN(c2ccccc2)CC1] | 417 | 418.1 | 418.2 |
| 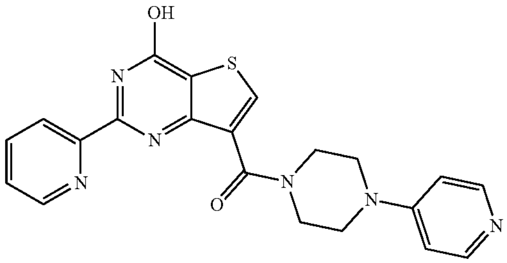 [SMILES: O=C(c1csc2c(O)nc(-c3ccccn3)nc12)N1CCN(c2ccncc2)CC1] | 418 | 419.1 | 419.0 |
| 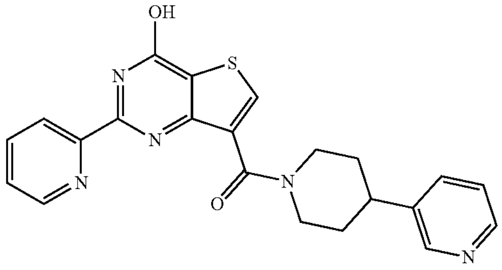 [SMILES: O=C(c1csc2c(O)nc(-c3ccccn3)nc12)N1CCC(c2cccnc2)CC1] | 417 | 418.1 | 418.2 |

TABLE 3-continued
| Mass Spectral Data | | | |
|---|---|---|---|
| Compound | MW | M + H (calculated) | M + H (observed) |
| 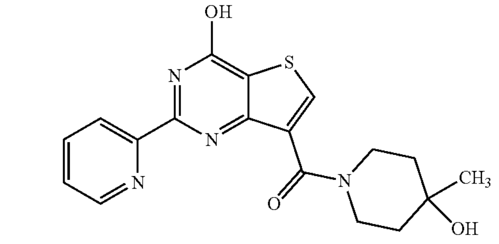 [SMILES: CC1(O)CCN(C(=O)c2csc3c(O)nc(-c4ccccn4)nc23)CC1] | 370 | 371.1 | 371.0 |
| 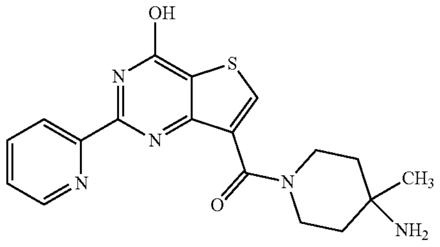 •2 HCl | 442 | 370.1 | 370.2 |
| 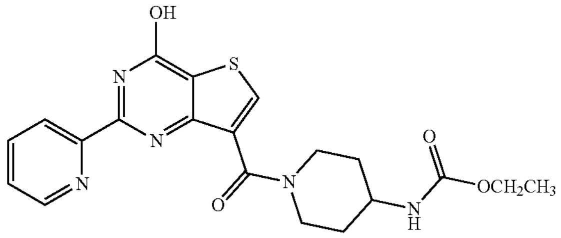 [SMILES: CCOC(=O)NC1CCN(C(=O)c2csc3c(O)nc(-c4ccccn4)nc23)CC1] | 427 | 428.1 | 428.0 |
| 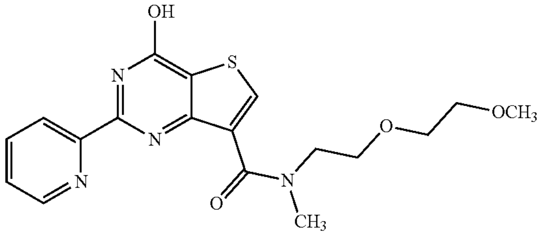 [SMILES: COCCOCCN(C)C(=O)c1csc2c(O)nc(-c3ccccn3)nc12] | 388 | 389.1 | 389.2 |
| 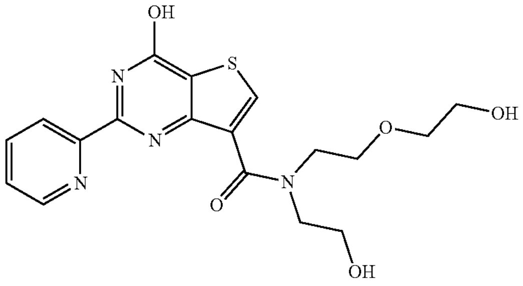 [SMILES: O=C(c1csc2c(O)nc(-c3ccccn3)nc12)N(CCO)CCOCCO] | 404 | 405.1 | 405.0 |
| 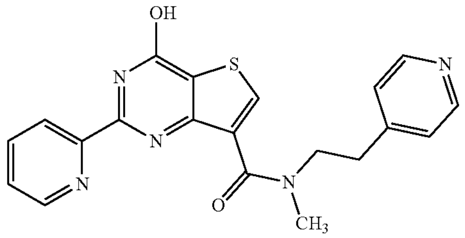 [SMILES: CN(CCc1ccncc1)C(=O)c1csc2c(O)nc(-c3ccccn3)nc12] | 391 | 392.1 | 392.2 |

TABLE 3-continued
| Mass Spectral Data | | | |
|---|---|---|---|
| Compound | MW | M + H (calculated) | M + H (observed) |
| 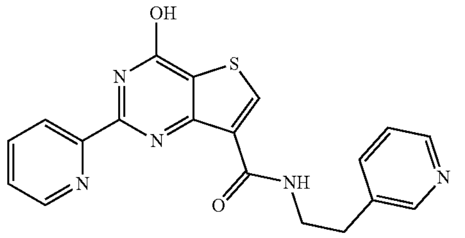 [SMILES: O=C(NCCc1cccnc1)c1csc2c(O)nc(-c3ccccn3)nc12] | 377 | 378.1 | 378.2 |
| 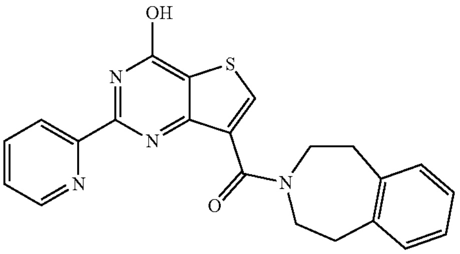 [SMILES: O=C(c1csc2c(O)nc(-c3ccccn3)nc12)N1CCc2ccccc2CC1] | 402 | 403.1 | 403.0 |
| 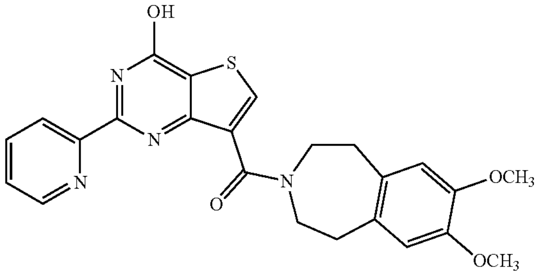 [SMILES: COc1cc2c(cc1OC)CCN(C(=O)c1csc3c(O)nc(-c4ccccn4)nc13)CC2] | 463 | 463.2 | 463.2 |
| 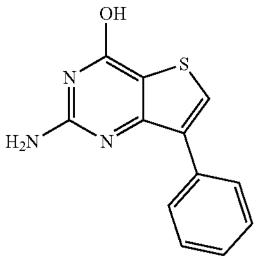 [SMILES: Nc1nc(O)c2scc(-c3ccccc3)c2n1] | 243 | 244.3 | 244.0 |
| 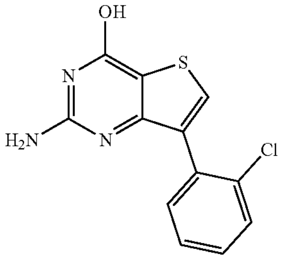 [SMILES: Nc1nc(O)c2scc(-c3ccccc3Cl)c2n1] | 278 | 278.0 | 278.0 |

TABLE 3-continued
| Mass Spectral Data | | | |
|---|---|---|---|
| Compound | MW | M + H (calculated) | M + H (observed) |
| 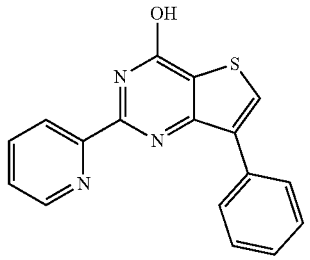 [SMILES: Oc1nc(-c2ccccn2)nc2c(-c3ccccc3)csc12] | 305 | 306.1 | 306.0 |
| 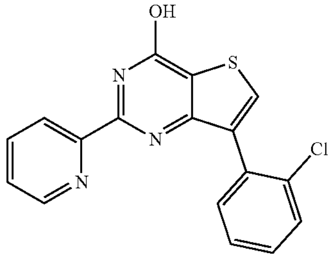 [SMILES: Oc1nc(-c2ccccn2)nc2c(-c3ccccc3Cl)csc12] | 340 | 340.0 | 339.9 |
| 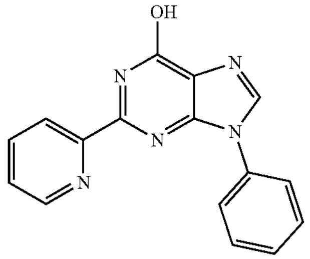 [SMILES: Oc1nc(-c2ccccn2)nc2c1ncn2-c1ccccc1] | 289 | 290.1 | 290.2 |
| 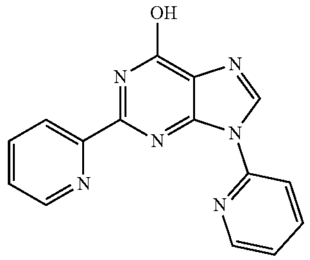 [SMILES: Oc1nc(-c2ccccn2)nc2c1ncn2-c1ccccn1] | 290 | 291.1 | 291.0 |
| 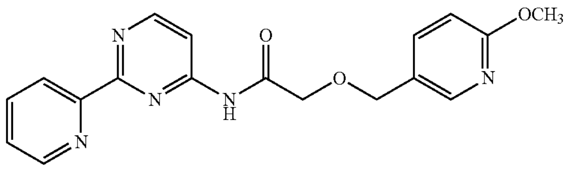 [SMILES: COc1ccc(COCC(=O)Nc2ccnc(-c3ccccn3)n2)cn1] | 351 | 352.1 | 352.2 |
| 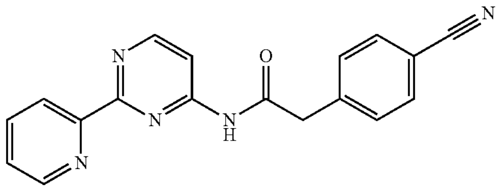 [SMILES: N#Cc1ccc(CC(=O)Nc2ccnc(-c3ccccn3)n2)cc1] | 315 | 316.1 | 316.0 |

TABLE 3-continued
| Mass Spectral Data | | | |
|---|---|---|---|
| Compound | MW | M + H (calculated) | M + H (observed) |
| 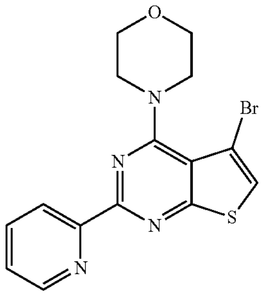 [SMILES: Brc1csc2nc(-c3ccccn3)nc(N3CCOCC3)c12] | 377 | 377.0 | 377.0 |
| 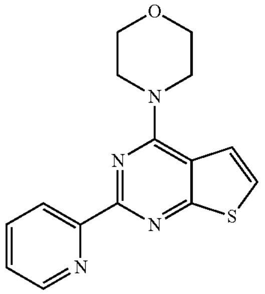 [SMILES: c1ccc(-c2nc(N3CCOCC3)c3ccsc3n2)nc1] | 298 | 299.1 | 299.1 |
| 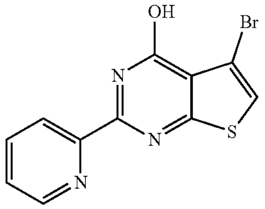 [SMILES: Oc1nc(-c2ccccn2)nc2scc(Br)c12] | 308 | 307.9 | 308.0 |
| 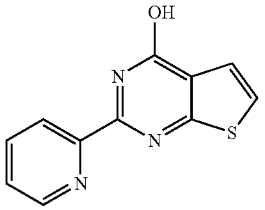 [SMILES: Oc1nc(-c2ccccn2)nc2sccc12] | 229 | 230.0 | 230.0 |
| 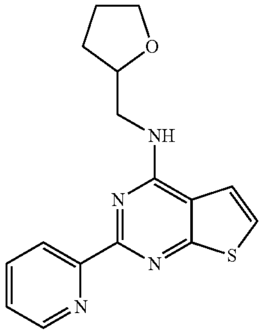 [SMILES: c1ccc(-c2nc(NCC3CCCO3)c3ccsc3n2)nc1] | 312 | 313.1 | 313.0 |

TABLE 3-continued
| Mass Spectral Data | | | |
|---|---|---|---|
| Compound | MW | M + H (calculated) | M + H (observed) |
| 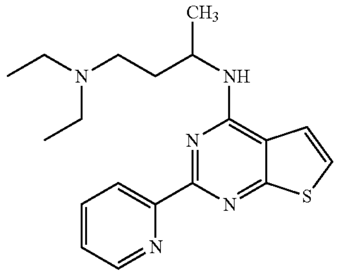 [SMILES: CCN(CC)CCC(C)Nc1nc(-c2ccccn2)nc2sccc12] | 356 | 356.2 | 356.2 |
| 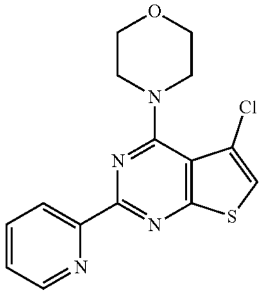 [SMILES: Clc1csc2nc(-c3ccccn3)nc(N3CCOCC3)c12] | 333 | 333.1 | 333.0 |
| 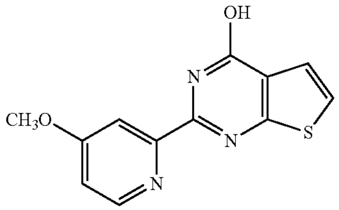 | 259 | 260.0 | 260.2 |
| 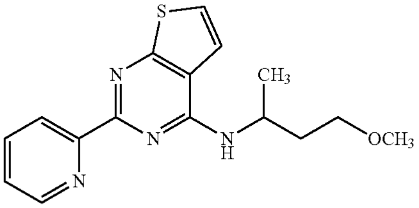 [SMILES: COCCC(C)Nc1nc(-c2ccccn2)nc2sccc12] | 314 | 315.1 | 315.1 |
| 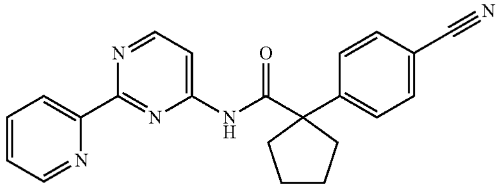 [SMILES: N#Cc1ccc(C2(C(=O)Nc3ccnc(-c4ccccn4)n3)CCCC2)cc1] | 369 | 370.2 | 370.2 |
| 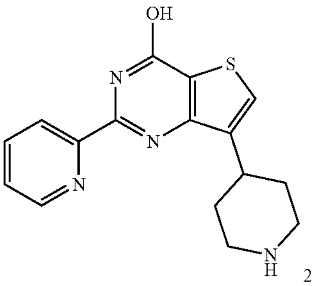 2 HCl | 385 | 313.1 | 313.2 |

TABLE 3-continued
| Mass Spectral Data | | | |
|---|---|---|---|
| Compound | MW | M + H (calculated) | M + H (observed) |
| 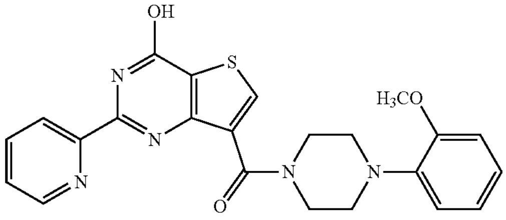 [SMILES: COc1ccccc1N1CCN(C(=O)c2csc3c(O)nc(-c4ccccn4)nc23)CC1] | 448 | 448.2 | 448.0 |
| 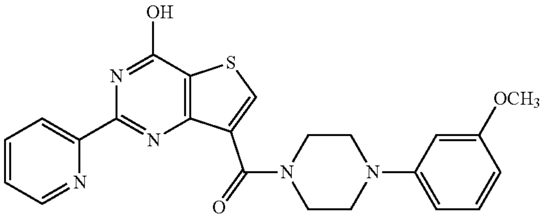 [SMILES: COc1cccc(N2CCN(C(=O)c3csc4c(O)nc(-c5ccccn5)nc34)CC2)c1] | 448 | 448.2 | 448.2 |
| 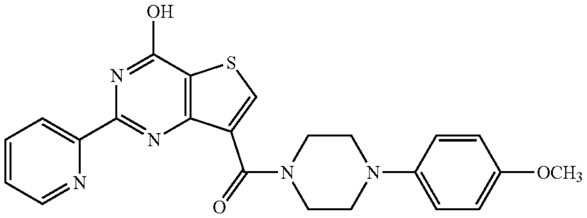 [SMILES: COc1ccc(N2CCN(C(=O)c3csc4c(O)nc(-c5ccccn5)nc34)CC2)cc1] | 448 | 448.2 | 448.2 |
| 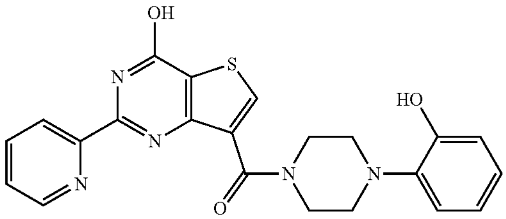 | 433 | 434.1 | 434.0 |
| 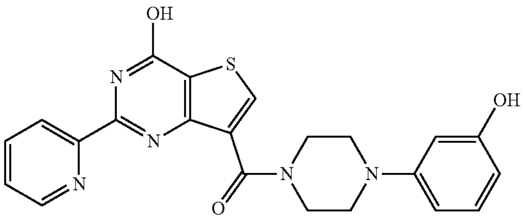 | 433 | 434.1 | 434.0 |
| 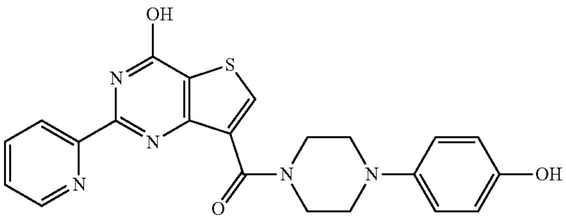 | 433 | 434.1 | 434.0 |

TABLE 3-continued
| Mass Spectral Data | | | |
|---|---|---|---|
| Compound | MW | M + H (calculated) | M + H (observed) |
| 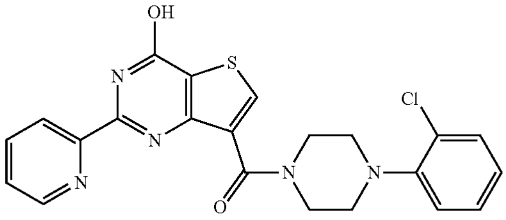 | 452 | 452.1 | 452.0 |
| 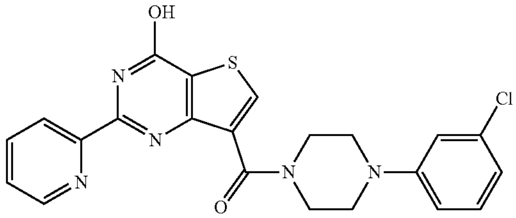 [SMILES: O=C(c1csc2c(O)nc(-c3ccccn3)nc12)N1CCN(c2cccc(Cl)c2)CC1] | 452 | 452.1 | 452.1 |
| 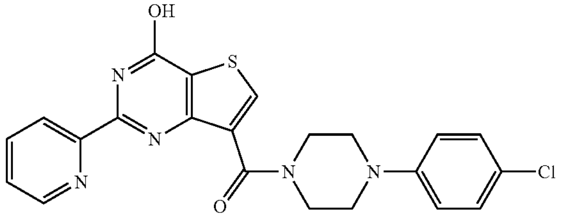 [SMILES: O=C(c1csc2c(O)nc(-c3ccccn3)nc12)N1CCN(c2ccc(Cl)cc2)CC1] | 452 | 452.1 | 452.0 |
| 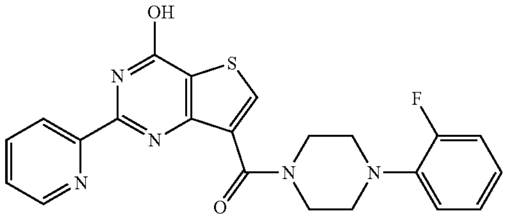 [SMILES: O=C(c1csc2c(O)nc(-c3ccccn3)nc12)N1CCN(c2ccccc2F)CC1] | 435 | 436.1 | 436.0 |
| 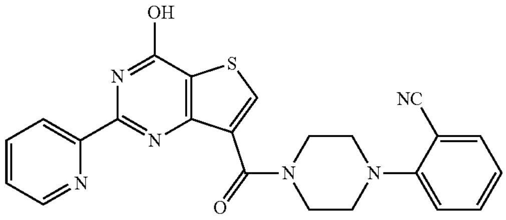 [SMILES: N#Cc1ccccc1N1CCN(C(=O)c2csc3c(O)nc(-c4ccccn4)nc23)CC1] | 442 | 443.1 | 443.0 |
| 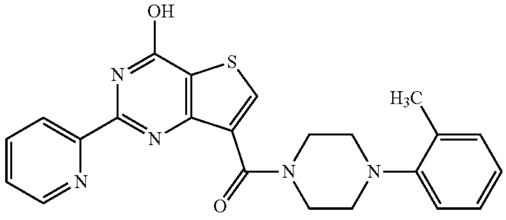 | 432 | 432.2 | 432.2 |

TABLE 3-continued
| Mass Spectral Data | | | |
|---|---|---|---|
| Compound | MW | M + H (calculated) | M + H (observed) |
| 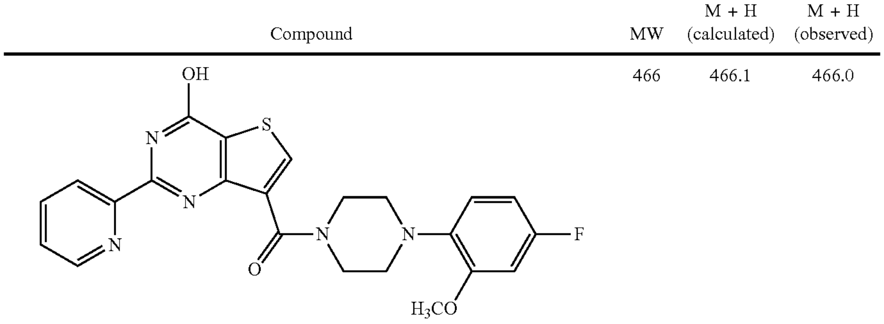 | 466 | 466.1 | 466.0 |
| 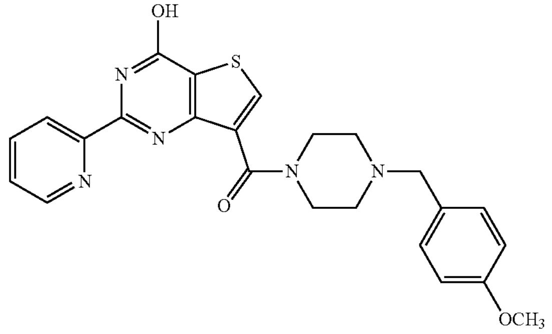 [SMILES: COc1ccc(CN2CCN(C(=O)c3csc4c(O)nc(-c5ccccn5)nc34)CC2)cc1] | 462 | 462.2 | 462.2 |
| 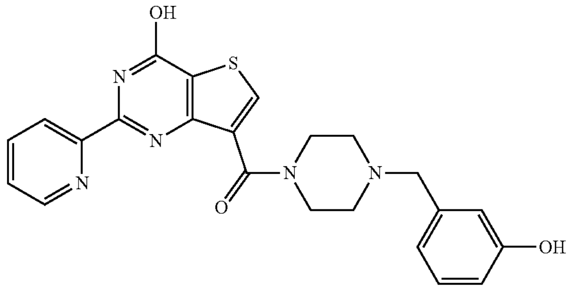 [SMILES: O=C(c1csc2c(O)nc(-c3ccccn3)nc12)N1CCN(Cc2cccc(O)c2)CC1] | 448 | 448.2 | 448.2 |
| 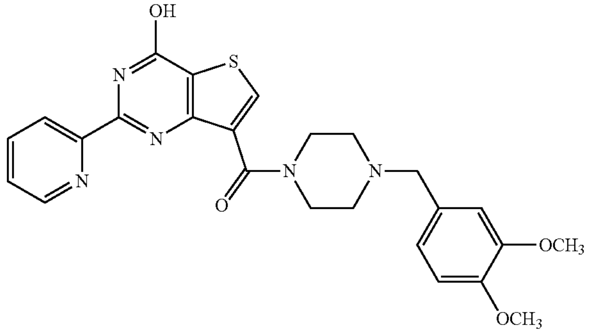 [SMILES: COc1ccc(CN2CCN(C(=O)c3csc4c(O)nc(-c5ccccn5)nc34)CC2)cc1OC] | 492 | 492.2 | 492.2 |
| 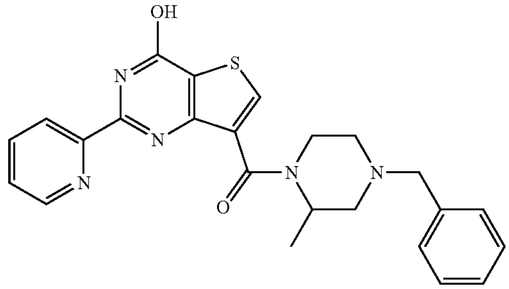 [SMILES: CC1CN(Cc2ccccc2)CCN1C(=O)c1csc2c(O)nc(-c3ccccn3)nc12] | 446 | 446.2 | 446.2 |

TABLE 3-continued
| Mass Spectral Data | | | |
|---|---|---|---|
| Compound | MW | M + H (calculated) | M + H (observed) |
| 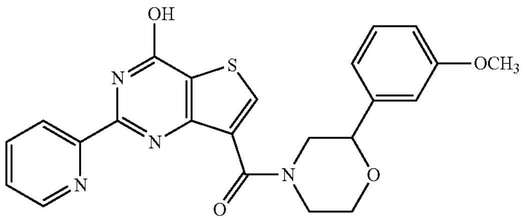 [SMILES: COc1cccc(C2CN(C(=O)c3csc4c(O)nc(-c5ccccn5)nc34)CCO2)c1] | 448 | 449.1 | 449.0 |
| 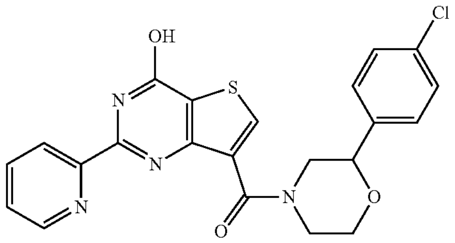 [SMILES: O=C(c1csc2c(O)nc(-c3ccccn3)nc12)N1CCOC(c2ccc(Cl)cc2)C1] | 453 | 453.1 | 453.0 |
| 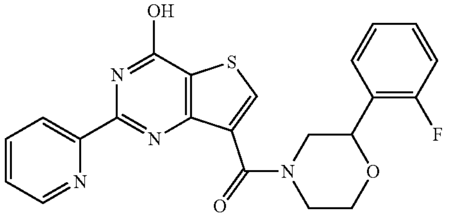 [SMILES: O=C(c1csc2c(O)nc(-c3ccccn3)nc12)N1CCOC(c2ccccc2F)C1] | 436 | 437.1 | 437.0 |
| 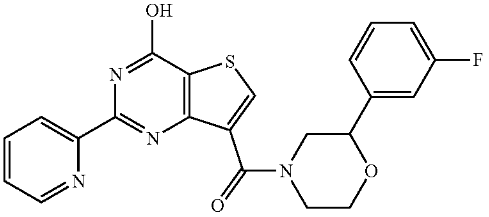 [SMILES: O=C(c1csc2c(O)nc(-c3ccccn3)nc12)N1CCOC(c2cccc(F)c2)C1] | 436 | 437.1 | 437.0 |
| 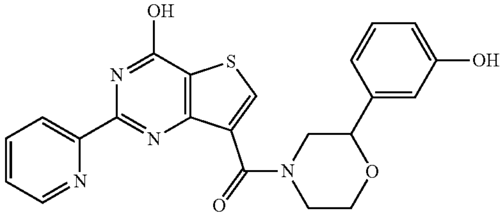 [SMILES: O=C(c1csc2c(O)nc(-c3ccccn3)nc12)N1CCOC(c2cccc(O)c2)C1] | 434 | 435.1 | 435.0 |
| 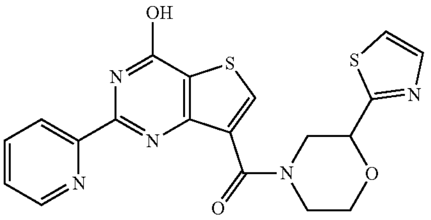 [SMILES: O=C(c1csc2c(O)nc(-c3ccccn3)nc12)N1CCOC(c2nccs2)C1] | 425 | 426.1 | 426.0 |

TABLE 3-continued
| Mass Spectral Data | | | |
|---|---|---|---|
| Compound | MW | M + H (calculated) | M + H (observed) |
| 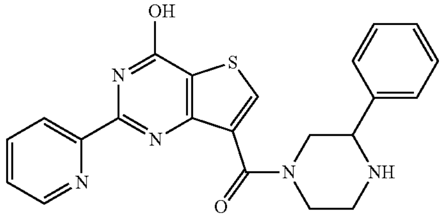 | 417 | 418.1 | 418.2 |
| 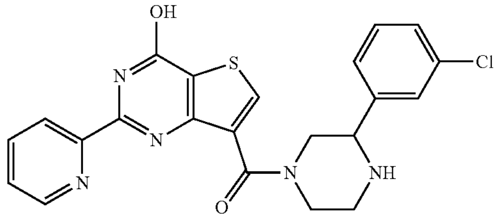 [SMILES: O=C(c1csc2c(O)nc(-c3ccccn3)nc12)N1CCNC(c2cccc(Cl)c2)C1] | 452 | 452.1 | 452.0 |
| 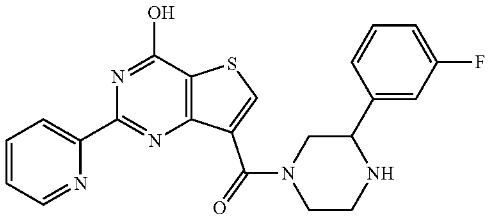 | 435 | 436.1 | 436.0 |
| 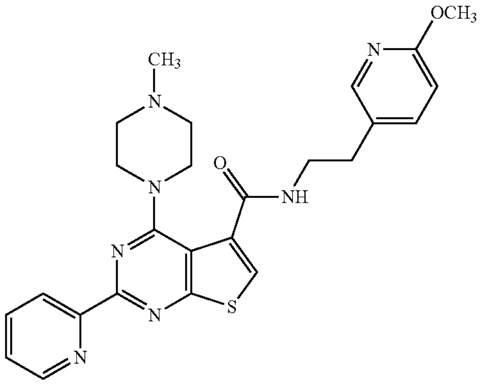 [SMILES: COc1ccc(CCNC(=O)c2csc3nc(-c4ccccn4)nc(N4CCN(C)CC4)c23)cn1] | 490 | 490.2 | 490.2 |
| 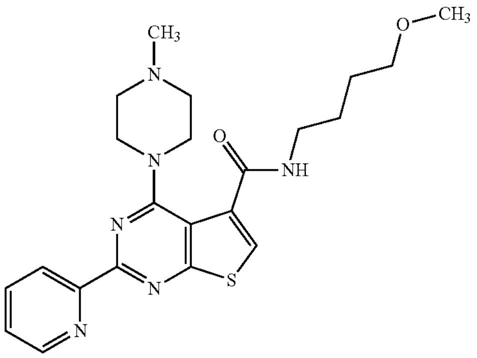 [SMILES: COCCCCNC(=O)c1csc2nc(-c3ccccn3)nc(N3CCN(C)CC3)c12] | 441 | 441.2 | 441.2 |

TABLE 3-continued
| Mass Spectral Data | | | |
|---|---|---|---|
| Compound | MW | M + H (calculated) | M + H (observed) |
| 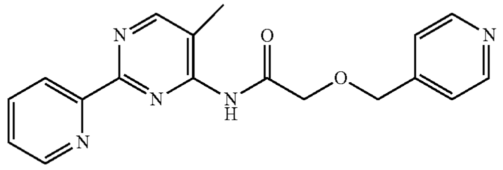 [SMILES: Cc1cnc(-c2ccccn2)nc1NC(=O)COCc1ccncc1] | 335 | 336.2 | 336.2 |
| 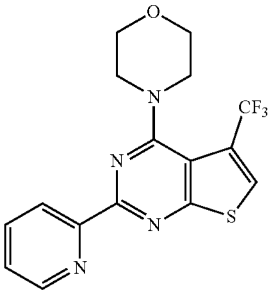 [SMILES: FC(F)(F)c1csc2nc(-c3ccccn3)nc(N3CCOCC3)c12] | 366 | 367.1 | 367.0 |
| 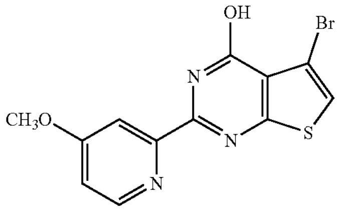 | 338 | 338.0 | 338.0 |
| 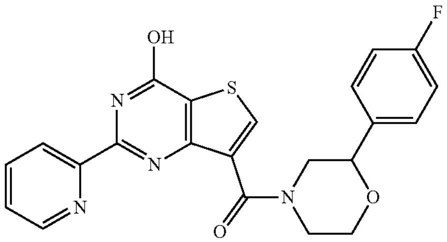 [SMILES: O=C(c1csc2c(O)nc(-c3ccccn3)nc12)N1CCOC(c2ccc(F)cc2)C1] | 436 | 437.1 | 437.2 |
| 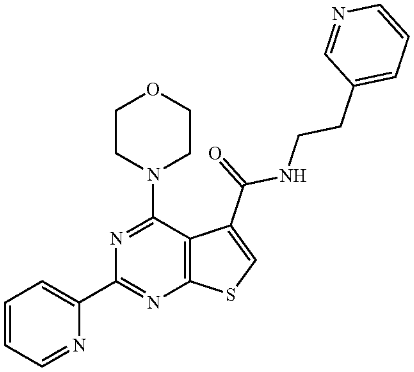 [SMILES: O=C(NCCc1cccnc1)c1csc2nc(-c3ccccn3)nc(N3CCOCC3)c12] | 447 | 447.2 | 447.1 |

TABLE 3-continued
| Mass Spectral Data | | | |
|---|---|---|---|
| Compound | MW | M + H (calculated) | M + H (observed) |
| 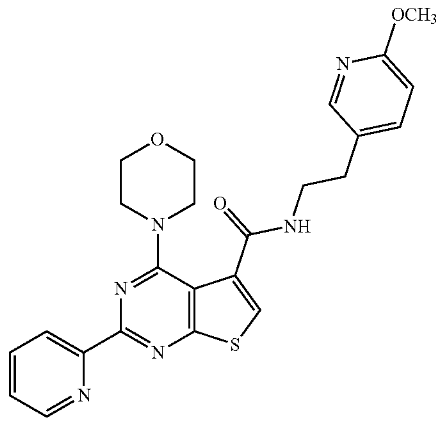 [SMILES: COc1ccc(CCNC(=O)c2csc3nc(-c4ccccn4)nc(N4CCOCC4)c23)cn1] | 477 | 477.2 | 477.1 |
| 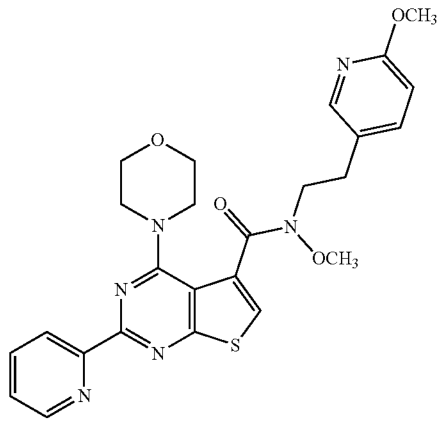 [SMILES: COc1ccc(CCN(OC)C(=O)c2csc3nc(-c4ccccn4)nc(N4CCOCC4)c23)cn1] | 491 | 491.2 | 491.1 |
| 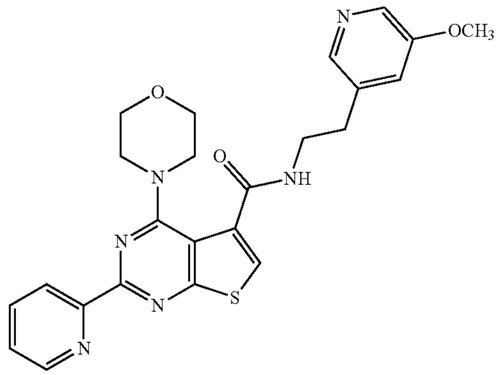 [SMILES: COc1cncc(CCNC(=O)c2csc3nc(-c4ccccn4)nc(N4CCOCC4)c23)c1] | 477 | 477.2 | 477.1 |

TABLE 3-continued
| Mass Spectral Data | | | |
|---|---|---|---|
| Compound | MW | M + H (calculated) | M + H (observed) |
| 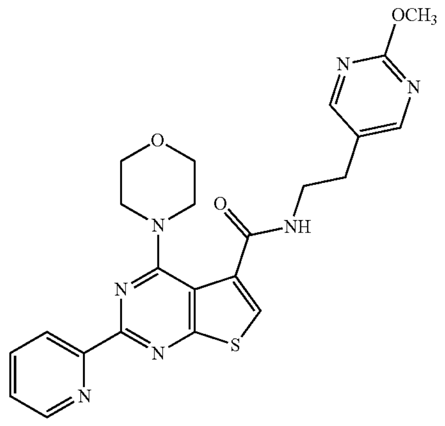 [SMILES: COc1ncc(CCNC(=O)c2csc3nc(-c4ccccn4)nc(N4CCOCC4)c23)cn1] | 478 | 478.2 | 478.0 |
| 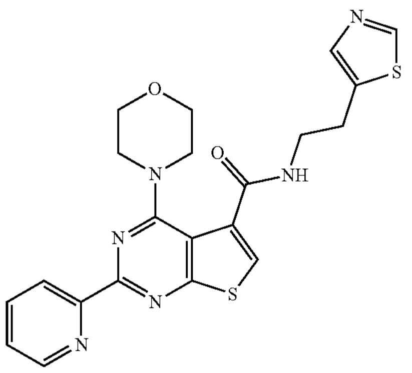 [SMILES: O=C(NCCc1cncs1)c1csc2nc(-c3ccccn3)nc(N3CCOCC3)c12] | 453 | 453.1 | 453.1 |
| 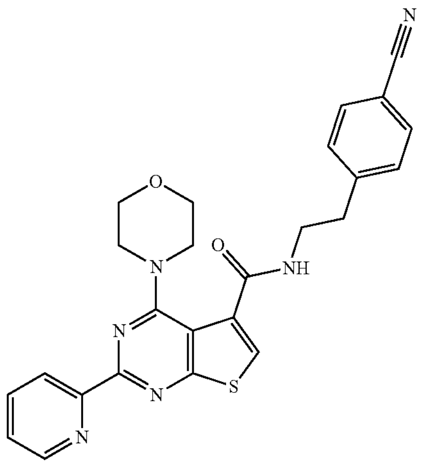 [SMILES: N#Cc1ccc(CCNC(=O)c2csc3nc(-c4ccccn4)nc(N4CCOCC4)c23)cc1] | 471 | 471.2 | 471.1 |
| 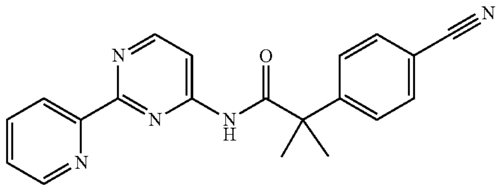 [SMILES: CC(C)(C(=O)Nc1ccnc(-c2ccccn2)n1)c1ccc(C#N)cc1] | 343 | 344.2 | 344.3 |

TABLE 3-continued
| Mass Spectral Data | | | |
|---|---|---|---|
| Compound | MW | M + H (calculated) | M + H (observed) |
| 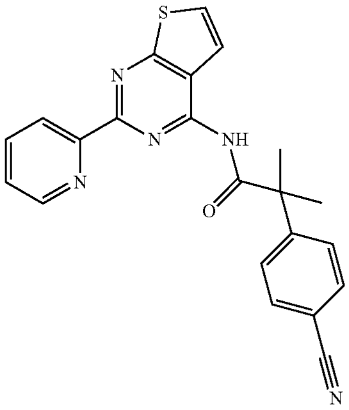 [SMILES: CC(C)(C(=O)Nc1nc(-c2ccccn2)nc2sccc12)c1ccc(C#N)cc1] | 399 | 400.1 | 400.2 |
| 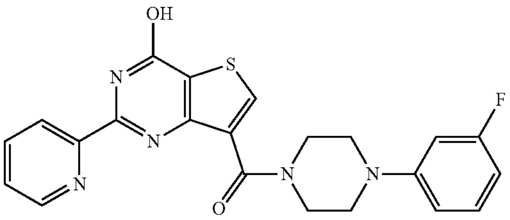 [SMILES: O=C(c1csc2c(O)nc(-c3ccccn3)nc12)N1CCN(c2cccc(F)c2)CC1] | 435 | 436.1 | 436.0 |
| 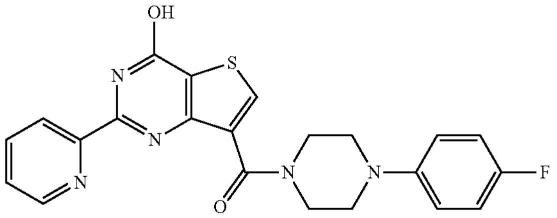 [SMILES: O=C(c1csc2c(O)nc(-c3ccccn3)nc12)N1CCN(c2ccc(F)cc2)CC1] | 435 | 436.1 | 436.0 |
| 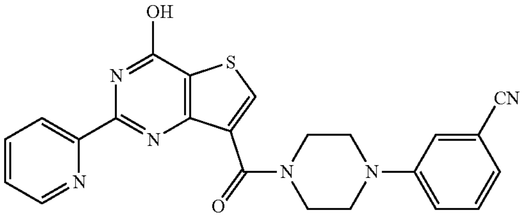 [SMILES: N#Cc1cccc(N2CCN(C(=O)c3csc4c(O)nc(-c5ccccn5)nc34)CC2)c1] | 442 | 443.1 | 443.1 |
| 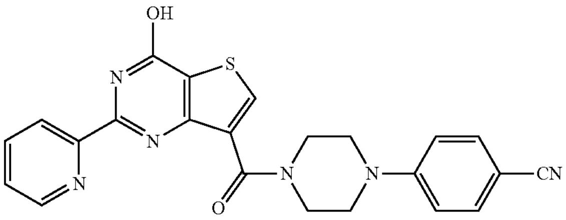 [SMILES: N#Cc1ccc(N2CCN(C(=O)c3csc4c(O)nc(-c5ccccn5)nc34)CC2)cc1] | 442 | 443.1 | 443.1 |

TABLE 3-continued
| Mass Spectral Data | | | |
|---|---|---|---|
| Compound | MW | M + H (calculated) | M + H (observed) |
| 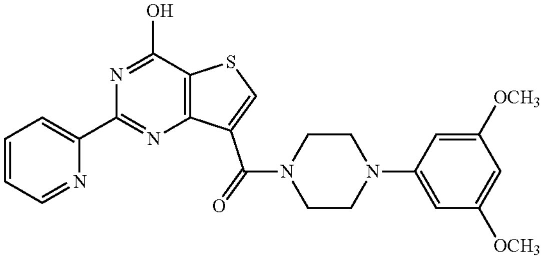 [SMILES: COc1cc(OC)cc(N2CCN(C(=O)c3csc4c(O)nc(-c5ccccn5)nc34)CC2)c1] | 478 | 478.2 | 478.0 |
| 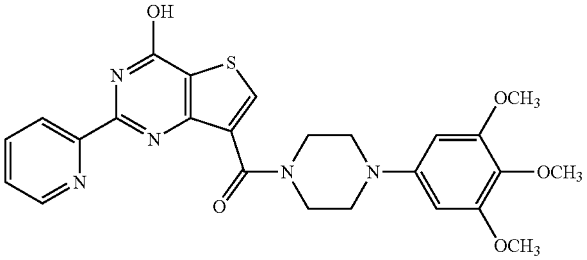 [SMILES: COc1cc(N2CCN(C(=O)c3csc4c(O)nc(-c5ccccn5)nc34)CC2)cc(OC)c1OC] | 508 | 508.2 | 508.2 |
| 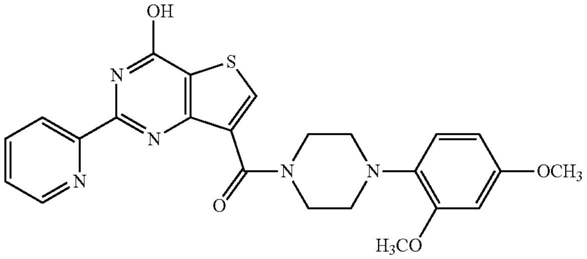 [SMILES: COc1ccc(N2CCN(C(=O)c3csc4c(O)nc(-c5ccccn5)nc34)CC2)c(OC)c1] | 478 | 478.2 | 478.2 |
| 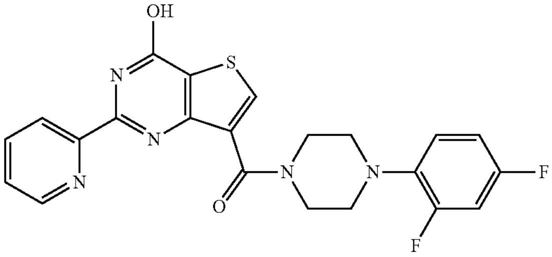 [SMILES: O=C(c1csc2c(O)nc(-c3ccccn3)nc12)N1CCN(c2ccc(F)cc2F)CC1] | 453 | 454.1 | 454.2 |
| 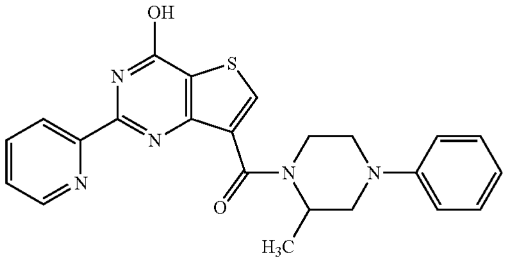 [SMILES: CC1CN(c2ccccc2)CCN1C(=O)c1csc2c(O)nc(-c3ccccn3)nc12] | 432 | 432.2 | 432.2 |

TABLE 3-continued
| Mass Spectral Data | | | |
| --- | --- | --- | --- |
| Compound | MW | M + H (calculated) | M + H (observed) |
| 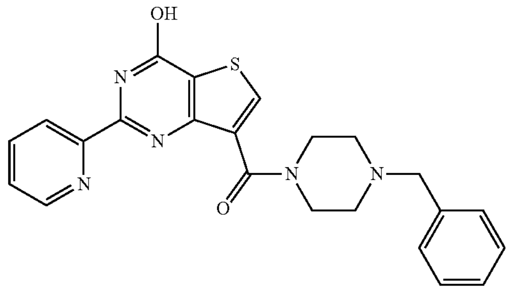 [SMILES: O=C(c1csc2c(O)nc(-c3ccccn3)nc12)N1CCN(Cc2ccccc2)CC1] | 432 | 432.2 | 432.2 |
| 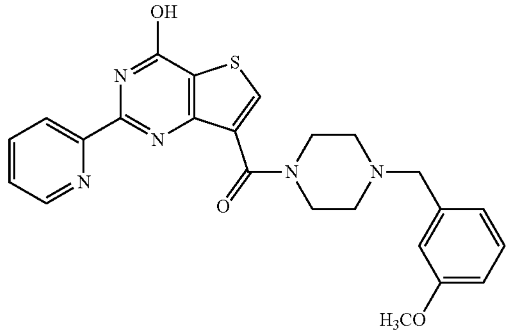 [SMILES: COc1cccc(CN2CCN(C(=O)c3csc4c(O)nc(-c5ccccn5)nc34)CC2)c1] | 462 | 462.2 | 462.2 |
| 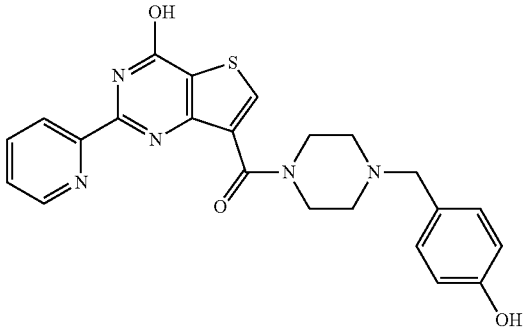 [SMILES: O=C(c1csc2c(O)nc(-c3ccccn3)nc12)N1CCN(Cc2ccc(O)cc2)CC1] | 448 | 448.2 | 448.0 |
| 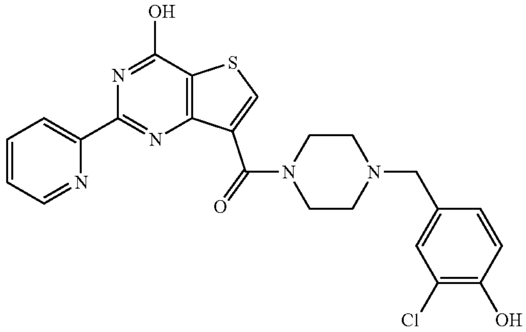 [SMILES: O=C(c1csc2c(O)nc(-c3ccccn3)nc12)N1CCN(Cc2ccc(O)c(Cl)c2)CC1] | 482 | 482.1 | 482.1 |
| 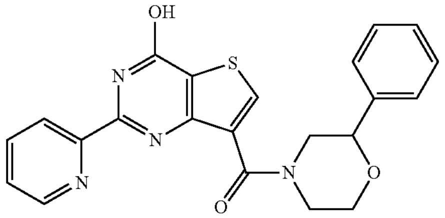 [SMILES: O=C(c1csc2c(O)nc(-c3ccccn3)nc12)N1CCOC(c2ccccc2)C1] | 418 | 419.1 | 419.0 |

TABLE 3-continued
| Mass Spectral Data | | | |
|---|---|---|---|
| Compound | MW | M + H (calculated) | M + H (observed) |
| 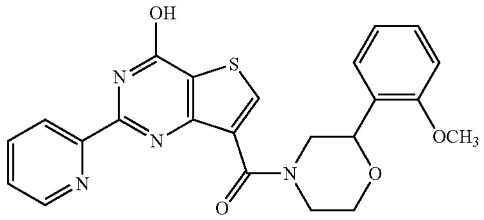 | 448 | 449.1 | 449.2 |
| 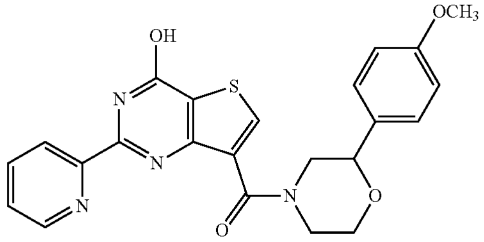 [SMILES: COc1ccc(C2CN(C(=O)c3csc4c(O)nc(-c5ccccn5)nc34)CCO2)cc1] | 448 | 449.1 | 449.1 |
| 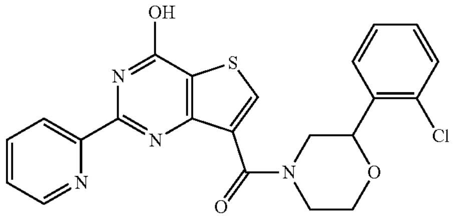 [SMILES: O=C(c1csc2c(O)nc(-c3ccccn3)nc12)N1CCOC(c2ccccc2Cl)C1] | 453 | 453.1 | 453.2 |
| 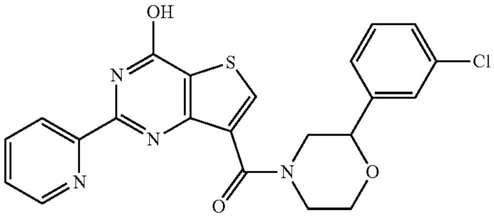 [SMILES: O=C(c1csc2c(O)nc(-c3ccccn3)nc12)N1CCOC(c2cccc(Cl)c2)C1] | 453 | 453.1 | 453.2 |
| 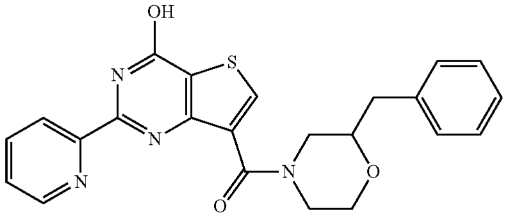 [SMILES: O=C(c1csc2c(O)nc(-c3ccccn3)nc12)N1CCOC(Cc2ccccc2)C1] | 432 | 433.1 | 433.2 |
| 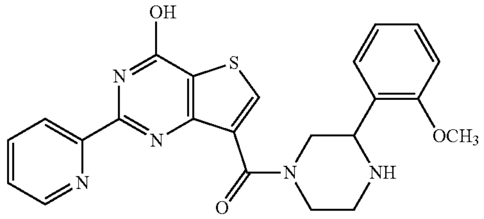 [SMILES: COc1ccccc1C1CN(C(=O)c2csc3c(O)nc(-c4ccccn4)nc23)CCN1] | 448 | 448.2 | 448.0 |

TABLE 3-continued
| Mass Spectral Data | | | |
|---|---|---|---|
| Compound | MW | M + H (calculated) | M + H (observed) |
| 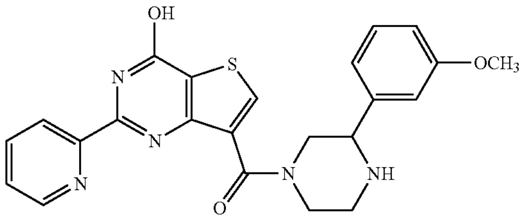 | 448 | 448.2 | 448.0 |
| 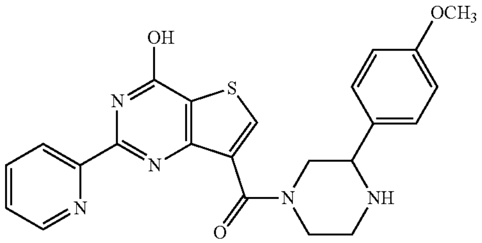 | 448 | 448.2 | 448.0 |
| 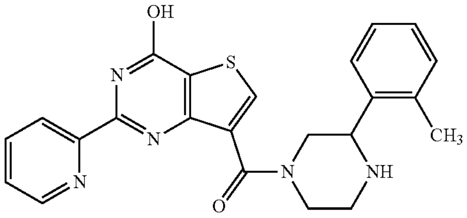 [SMILES: Cc1ccccc1C1CN(C(=O)c2csc3c(O)nc(-c4ccccn4)nc23)CCN1] | 432 | 432.1 | 432.1 |
| 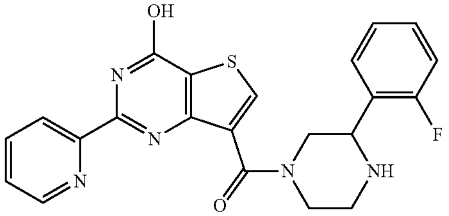 [SMILES: O=C(c1csc2c(O)nc(-c3ccccn3)nc12)N1CCNC(c2ccccc2F)C1] | 435 | 436.1 | 436.0 |
| 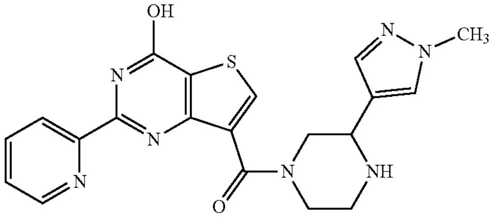 [SMILES: Cn1cc(C2CN(C(=O)c3csc4c(O)nc(-c5ccccn5)nc34)CCN2)cn1] | 421 | 422.1 | 422.1 |
| 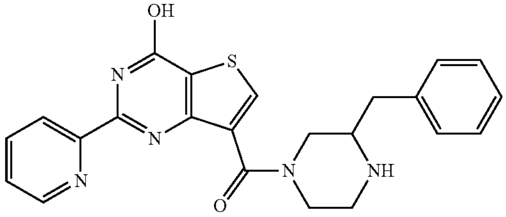 | 432 | 432.2 | 432.1 |

TABLE 3-continued
| Mass Spectral Data | | | |
|---|---|---|---|
| Compound | MW | M + H (calculated) | M + H (observed) |
| 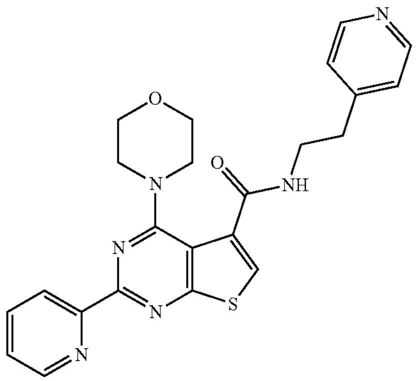 [SMILES: O=C(NCCc1ccncc1)c1csc2nc(-c3ccccn3)nc(N3CCOCC3)c12] | 447 | 447.2 | 447.2 |
| 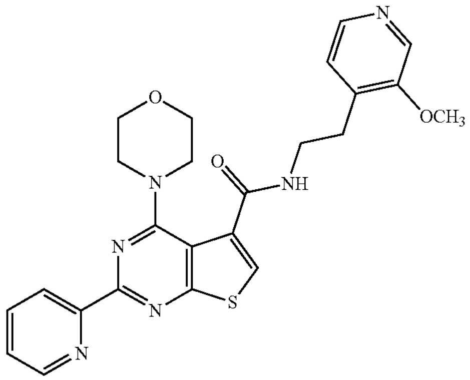 [SMILES: COc1cnccc1CCNC(=O)c1csc2nc(-c3ccccn3)nc(N3CCOCC3)c12] | 477 | 477.2 | 477.2 |
| 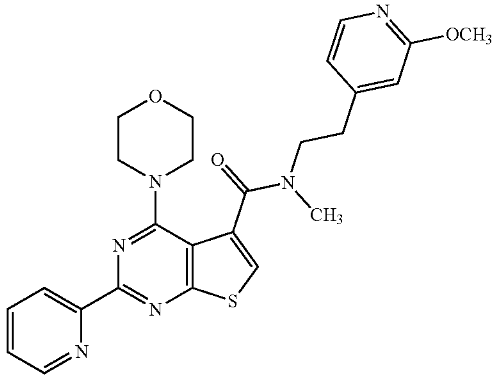 [SMILES: COc1cc(CCN(C)C(=O)c2csc3nc(-c4ccccn4)nc(N4CCOCC4)c23)ccn1] | 491 | 491.2 | 491.2 |
| 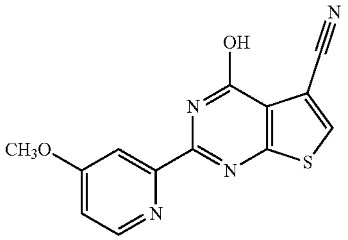 | 284 | 285.0 | 285.0 |

TABLE 3-continued
| Mass Spectral Data | | | |
|---|---|---|---|
| Compound | MW | M + H (calculated) | M + H (observed) |
| 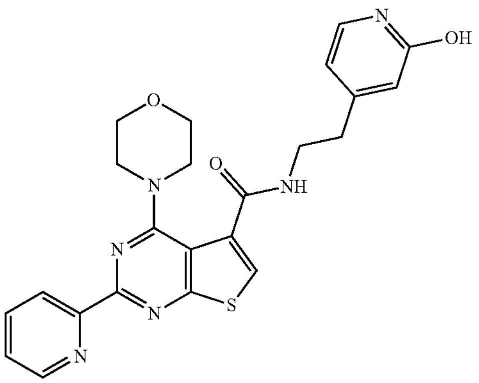 [SMILES: O=C(NCCc1ccnc(O)c1)c1csc2nc(-c3ccccn3)nc(N3CCOCC3)c12] | 463 | 463.2 | 463.2 |
| 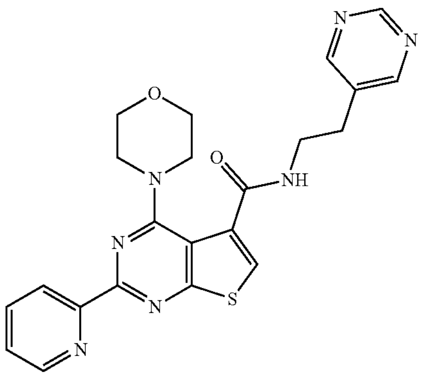 [SMILES: O=C(NCCc1cncnc1)c1csc2nc(-c3ccccn3)nc(N3CCOCC3)c12] | 448 | 448.2 | 448.2 |
| 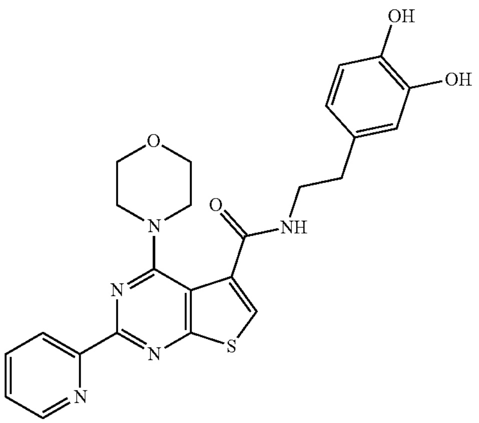 [SMILES: O=C(NCCc1ccc(O)c(O)c1)c1csc2nc(-c3ccccn3)nc(N3CCOCC3)c12] | 478 | 478.2 | 478.2 |
| 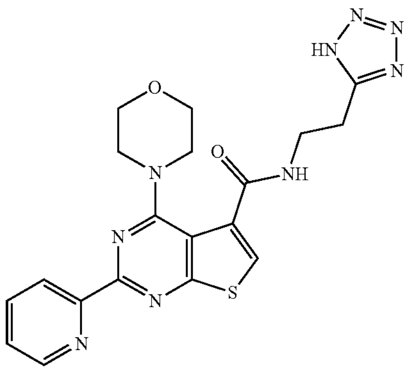 [SMILES: O=C(NCCc1nnn[nH]1)c1csc2nc(-c3ccccn3)nc(N3CCOCC3)c12] | 437 | 438.1 | 438.2 |

TABLE 3-continued
| Mass Spectral Data | | | |
|---|---|---|---|
| Compound | MW | M + H (calculated) | M + H (observed) |
| 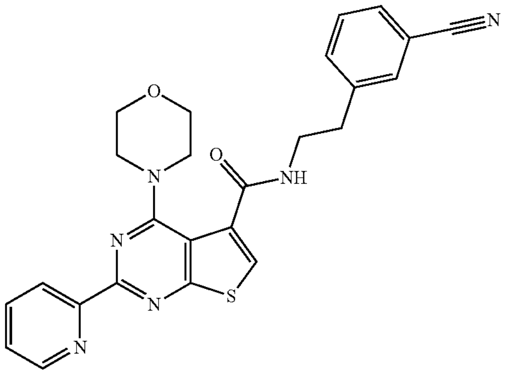 [SMILES: N#Cc1cccc(CCNC(=O)c2csc3nc(-c4ccccn4)nc(N4CCOCC4)c23)c1] | 471 | 471.2 | 471.1 |
| 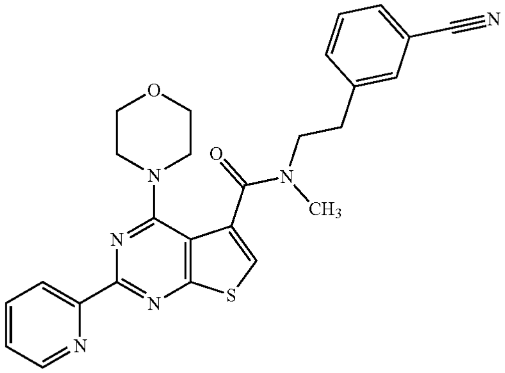 [SMILES: CN(CCc1cccc(C#N)c1)C(=O)c1csc2nc(-c3ccccn3)nc(N3CCOCC3)c12] | 485 | 485.2 | 485.2 |
| 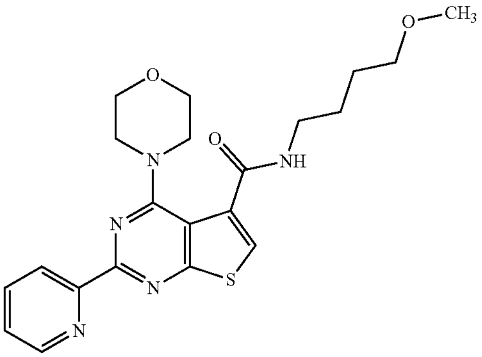 [SMILES: COCCCCNC(=O)c1csc2nc(-c3ccccn3)nc(N3CCOCC3)c12] | 428 | 428.2 | 428.2 |
| 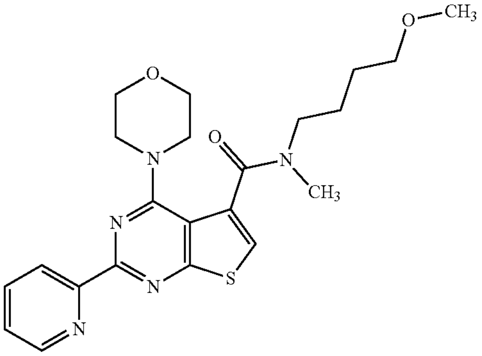 [SMILES: COCCCCN(C)C(=O)c1csc2nc(-c3ccccn3)nc(N3CCOCC3)c12] | 442 | 442.2 | 442.2 |

TABLE 3-continued
| Mass Spectral Data | | | |
|---|---|---|---|
| Compound | MW | M + H (calculated) | M + H (observed) |
| 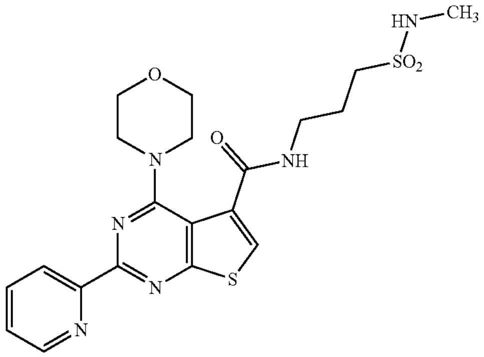 [SMILES: CNS(=O)(=O)CCCNC(=O)c1csc2nc(-c3ccccn3)nc(N3CCOCC3)c12] | 477 | 477.1 | 477.2 |
| 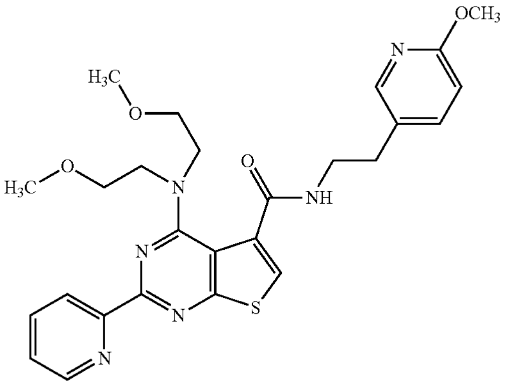 [SMILES: COCCN(CCOC)c1nc(-c2ccccn2)nc2scc(C(=O)NCCc3ccc(OC)nc3)c12] | 523 | 523.2 | 523.2 |
| 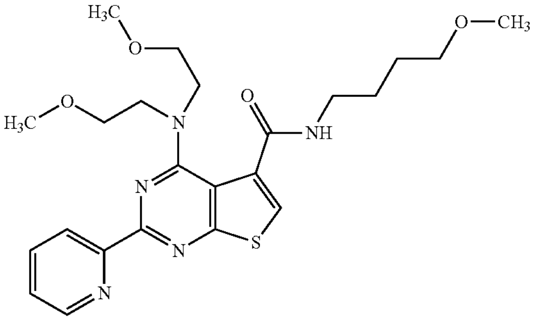 [SMILES: COCCCCNC(=O)c1csc2nc(-c3ccccn3)nc(N(CCOC)CCOC)c12] | 474 | 474.2 | 474.2 |
| 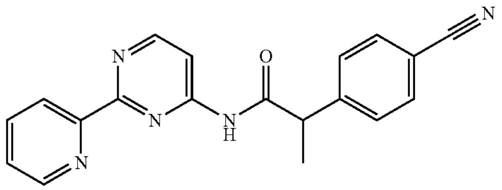 [SMILES: CC(C(=O)Nc1ccnc(-c2ccccn2)n1)c1ccc(C#N)cc1] | 329 | 330.1 | 330.1 |
| 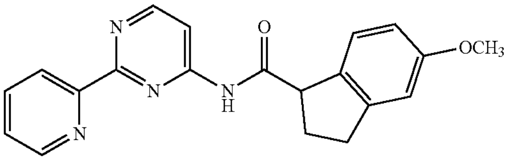 [SMILES: COc1ccc2c(c1)CCC2C(=O)Nc1ccnc(-c2ccccn2)n1] | 346 | 347.2 | 347.2 |

TABLE 3-continued
| Mass Spectral Data | | | |
|---|---|---|---|
| Compound | MW | M + H (calculated) | M + H (observed) |
| 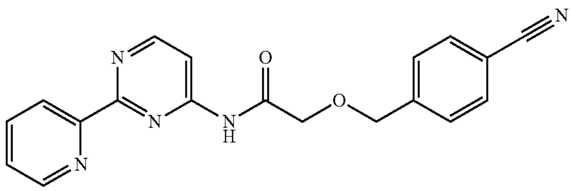 [SMILES: N#Cc1ccc(COCC(=O)Nc2ccnc(-c3ccccn3)n2)cc1] | 345 | 346.1 | 346.2 |
| 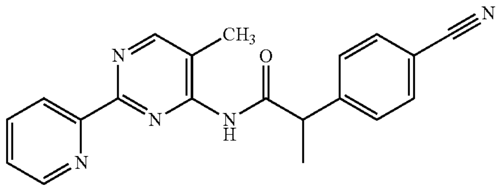 [SMILES: Cc1cnc(-c2ccccn2)nc1NC(=O)C(C)c1ccc(C#N)cc1] | 343 | 344.2 | 344.1 |
| 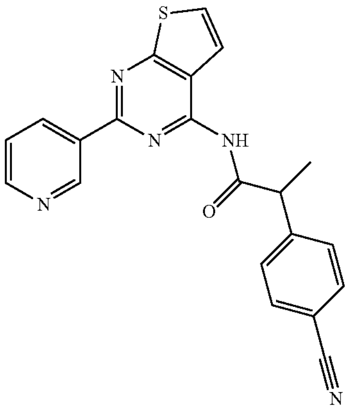 [SMILES: CC(C(=O)Nc1nc(-c2cccnc2)nc2sccc12)c1ccc(C#N)cc1] | 385 | 386.1 | 386.0 |
| 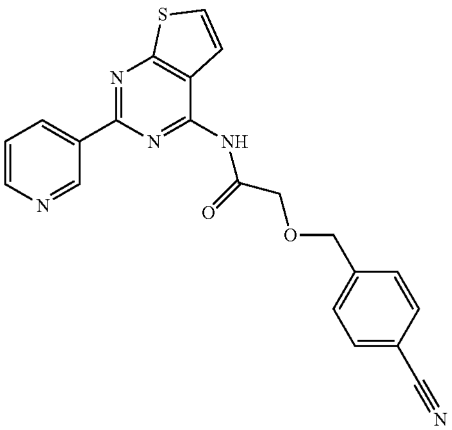 [SMILES: N#Cc1ccc(COCC(=O)Nc2nc(-c3cccnc3)nc3sccc23)cc1] | 401 | 402.1 | 402.2 |
| 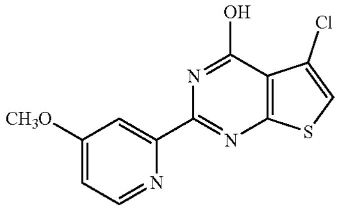 | 294 | 294.0 | 294.0 |

TABLE 3-continued
| Mass Spectral Data | | | |
|---|---|---|---|
| Compound | MW | M + H (calculated) | M + H (observed) |
| 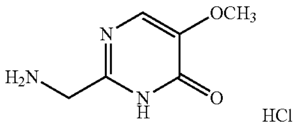 [SMILES: COc1cnc(CN)[nH]c1=O ; Cl] | 192 | 156.1 | 156.2 |
| 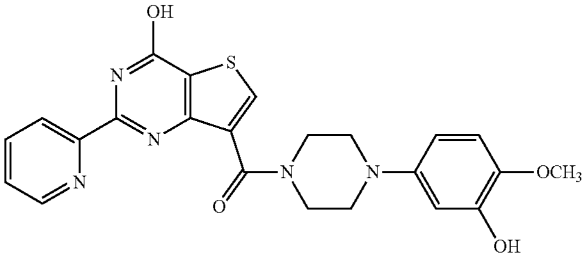 [SMILES: COc1ccc(N2CCN(C(=O)c3csc4c(O)nc(-c5ccccn5)nc34)CC2)cc1O] | 464 | 464.1 | 464.0 |
| 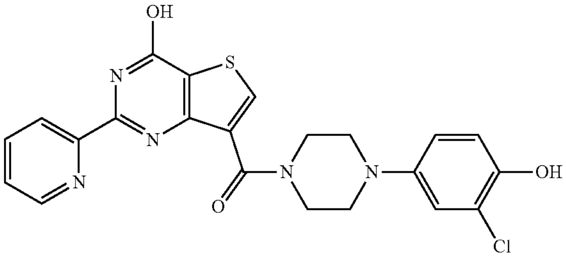 [SMILES: O=C(c1csc2c(O)nc(-c3ccccn3)nc12)N1CCN(c2ccc(O)c(Cl)c2)CC1] | 468 | 468.1 | 468.2 |
| 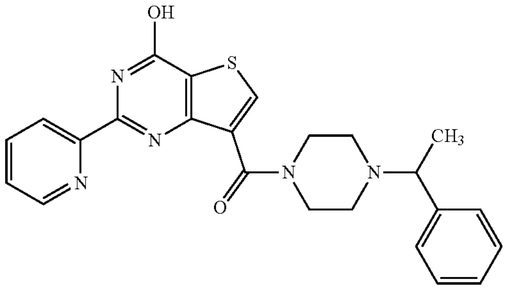 [SMILES: CC(c1ccccc1)N1CCN(C(=O)c2csc3c(O)nc(-c4ccccn4)nc23)CC1] | 446 | 446.2 | 446.2 |
| 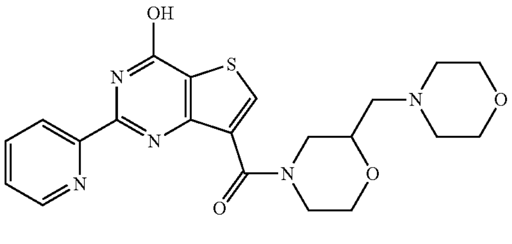 [SMILES: O=C(c1csc2c(O)nc(-c3ccccn3)nc12)N1CCOC(CN2CCOCC2)C1] | 442 | 442.2 | 442.2 |
| 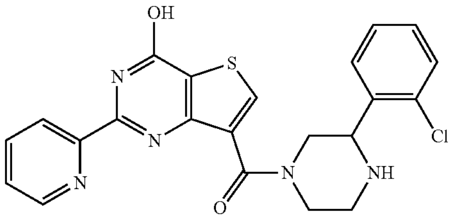 [SMILES: O=C(c1csc2c(O)nc(-c3ccccn3)nc12)N1CCNC(c2ccccc2Cl)C1] | 452 | 452.1 | 452.2 |

TABLE 3-continued
| Mass Spectral Data | | | |
|---|---|---|---|
| Compound | MW | M + H (calculated) | M + H (observed) |
| 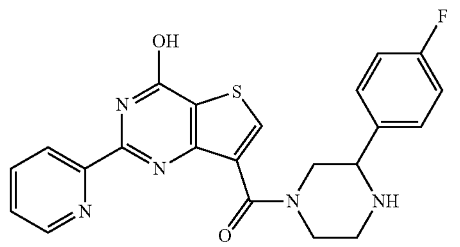 [SMILES: O=C(c1csc2c(O)nc(-c3ccccn3)nc12)N1CCNC(c2ccc(F)cc2)C1] | 435 | 436.1 | 436.0 |
| 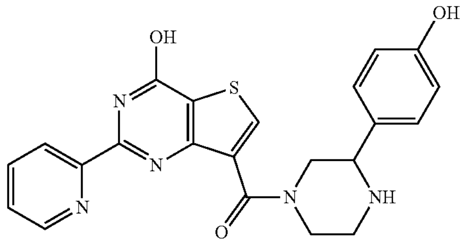 [SMILES: O=C(c1csc2c(O)nc(-c3ccccn3)nc12)N1CCNC(c2ccc(O)cc2)C1] | 433 | 434.1 | 434.0 |
| 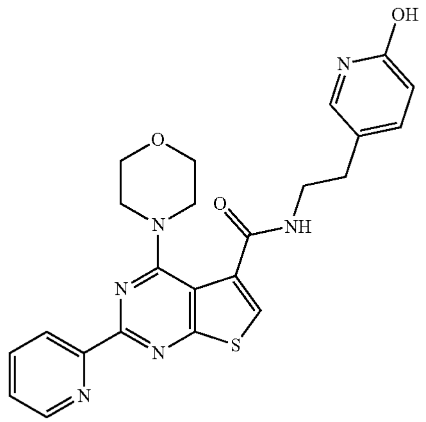 [SMILES: O=C(NCCc1ccc(O)nc1)c1csc2nc(-c3ccccn3)nc(N3CCOCC3)c12] | 463 | 463.2 | 463.2 |
| 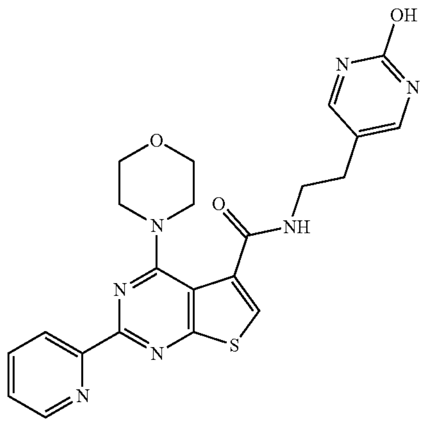 [SMILES: O=C(NCCc1cnc(O)nc1)c1csc2nc(-c3ccccn3)nc(N3CCOCC3)c12] | 464 | 464.2 | 464.2 |

TABLE 3-continued
| Mass Spectral Data | | | |
|---|---|---|---|
| Compound | MW | M + H (calculated) | M + H (observed) |
| 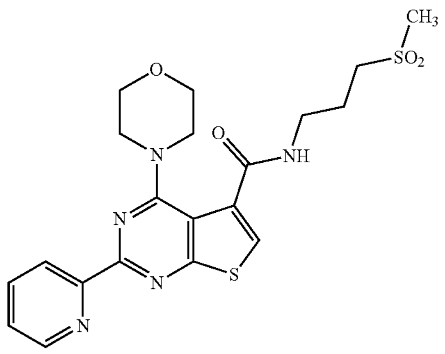 [SMILES: CS(=O)(=O)CCCNC(=O)c1csc2nc(-c3ccccn3)nc(N3CCOCC3)c12] | 462 | 462.1 | 462.1 |
| 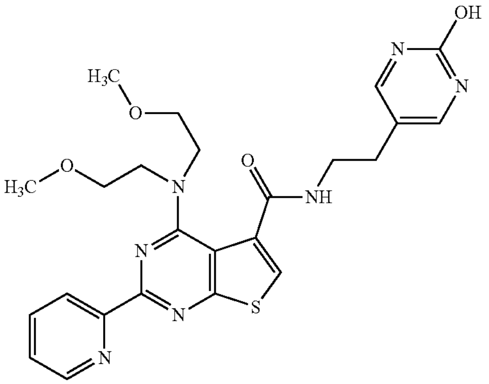 [SMILES: COCCN(CCOC)c1nc(-c2ccccn2)nc2scc(C(=O)NCCc3cnc(O)nc3)c12] | 510 | 510.2 | 510.2 |
| 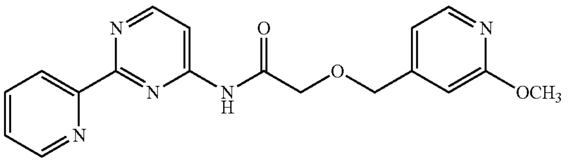 [SMILES: COc1cc(COCC(=O)Nc2ccnc(-c3ccccn3)n2)ccn1] | 351 | 352.1 | 352.2 |
| 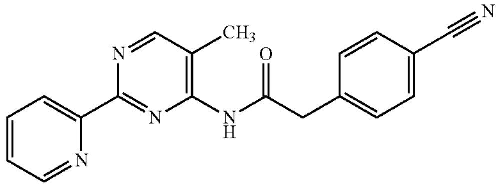 [SMILES: Cc1cnc(-c2ccccn2)nc1NC(=O)Cc1ccc(C#N)cc1] | 329 | 330.1 | 330.0 |
| 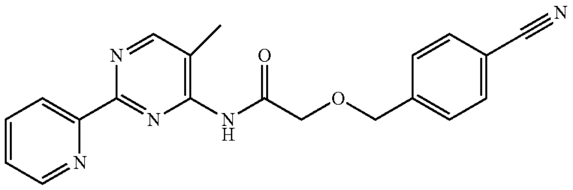 [SMILES: Cc1cnc(-c2ccccn2)nc1NC(=O)COCc1ccc(C#N)cc1] | 359 | 360.2 | 360.0 |
| 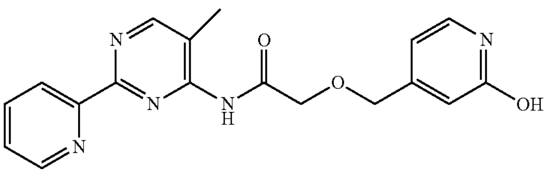 [SMILES: Cc1cnc(-c2ccccn2)nc1NC(=O)COCc1ccnc(O)c1] | 351 | 352.1 | 352.2 |

TABLE 3-continued
| Mass Spectral Data | | | |
|---|---|---|---|
| Compound | MW | M + H (calculated) | M + H (observed) |
| 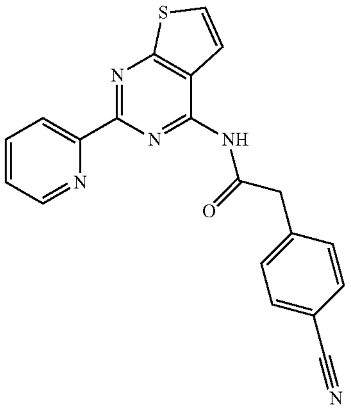 [SMILES: N#Cc1ccc(CC(=O)Nc2nc(-c3ccccn3)nc3sccc23)cc1] | 371 | 372.1 | 372.0 |
| 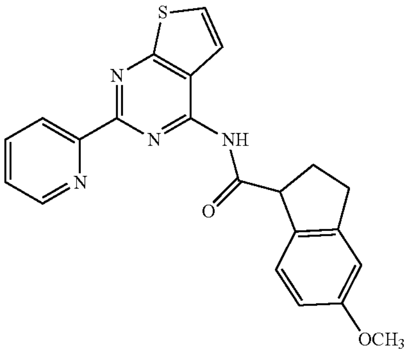 [SMILES: COc1ccc2c(c1)CCC2C(=O)Nc1nc(-c2ccccn2)nc2sccc12] | 402 | 403.1 | 403.0 |
| 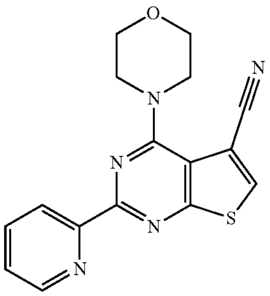 [SMILES: N#Cc1csc2nc(-c3ccccn3)nc(N3CCOCC3)c12] | 323 | 324.1 | 324.0 |
| 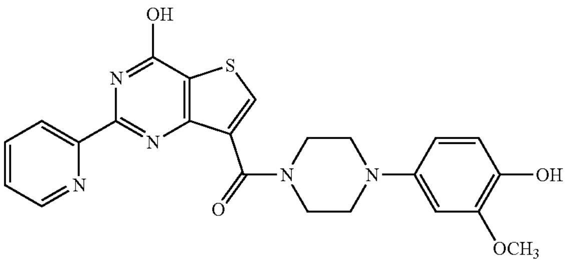 [SMILES: COc1cc(N2CCN(C(=O)c3csc4c(O)nc(-c5ccccn5)nc34)CC2)ccc1O] | 464 | 464.1 | 464.2 |

TABLE 3-continued
| Mass Spectral Data | | | |
|---|---|---|---|
| Compound | MW | M + H (calculated) | M + H (observed) |
| 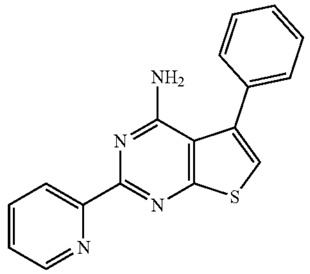 [SMILES: Nc1nc(-c2ccccn2)nc2scc(-c3ccccc3)c12] | 304 | 305.1 | 305.0 |
| 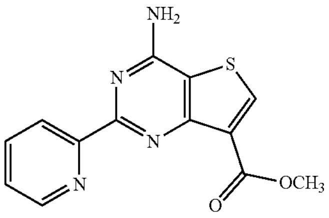 | 287 | 288.0 | 288.0 |
| 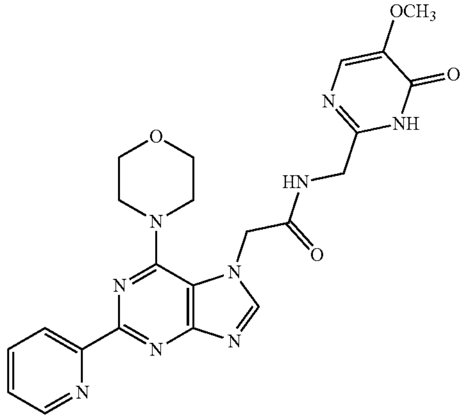 [SMILES: COc1cnc(CNC(=O)Cn2cnc3nc(-c4ccccn4)nc(N4CCOCC4)c32)[nH]c1=O] | 477 | 478.2 | 478.2 |
| 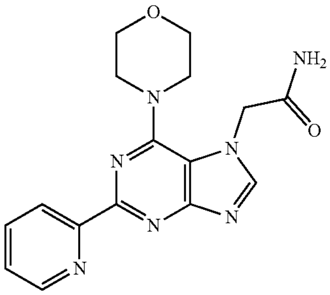 [SMILES: NC(=O)Cn1cnc2nc(-c3ccccn3)nc(N3CCOCC3)c21] | 339 | 340.1 | 340.2 |
| 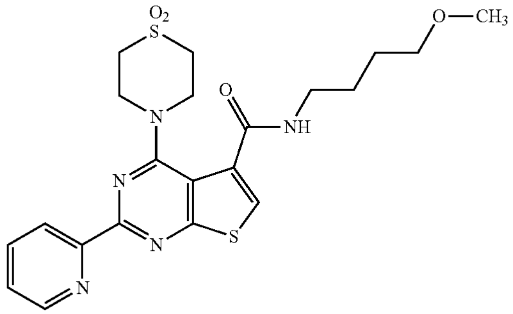 [SMILES: COCCCCNC(=O)c1csc2nc(-c3ccccn3)nc(N3CCS(=O)(=O)CC3)c12] | 476 | 476.2 | 476.2 |

TABLE 3-continued
| Mass Spectral Data | | | |
|---|---|---|---|
| Compound | MW | M + H (calculated) | M + H (observed) |
| 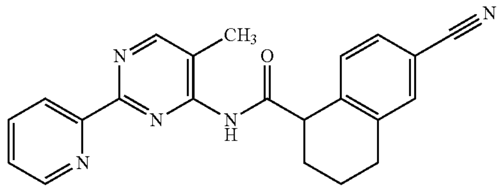 [SMILES: Cc1cnc(-c2ccccn2)nc1NC(=O)C1CCCc2cc(C#N)ccc21] | 369 | 370.2 | 370.2 |
| 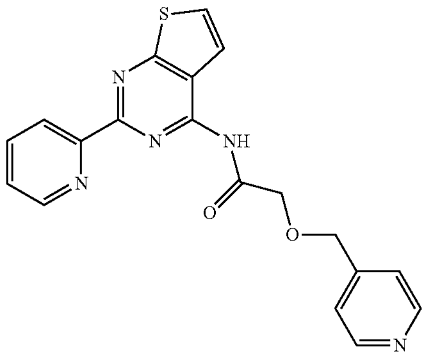 [SMILES: O=C(COCc1ccncc1)Nc1nc(-c2ccccn2)nc2sccc12] | 377 | 378.1 | 378.0 |
| 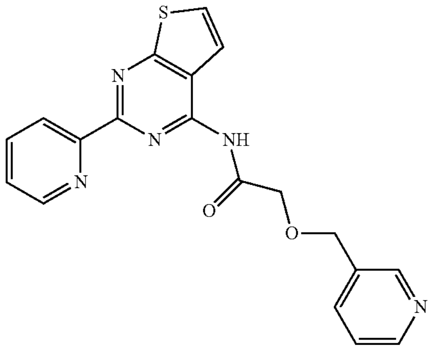 [SMILES: O=C(COCc1cccnc1)Nc1nc(-c2ccccn2)nc2sccc12] | 377 | 378.1 | 378.0 |
| 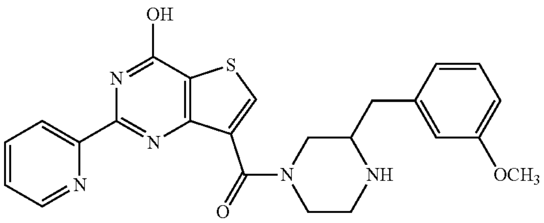 [SMILES: COc1cccc(CC2CN(C(=O)c3csc4c(O)nc(-c5ccccn5)nc34)CCN2)c1] | 462 | 462.2 | 462.2 |
| 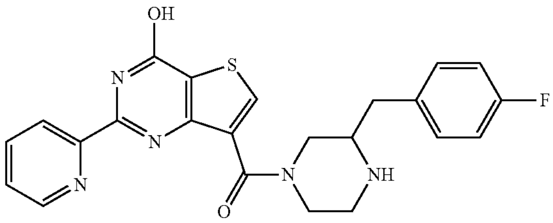 [SMILES: O=C(c1csc2c(O)nc(-c3ccccn3)nc12)N1CCNC(Cc2ccc(F)cc2)C1] | 450 | 450.2 | 450.0 |

TABLE 3-continued
| Mass Spectral Data | | | |
|---|---|---|---|
| Compound | MW | M + H (calculated) | M + H (observed) |
| 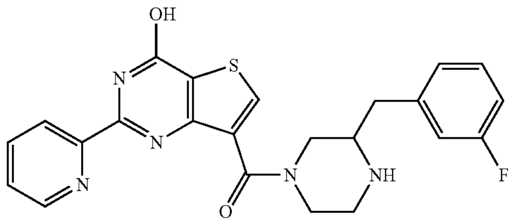 [SMILES: O=C(c1csc2c(O)nc(-c3ccccn3)nc12)N1CCNC(Cc2cccc(F)c2)C1] | 450 | 450.2 | 450.0 |
| 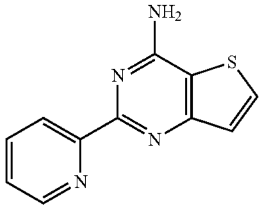 [SMILES: Nc1nc(-c2ccccn2)nc2ccsc12] | 228 | 229.1 | 229.0 |
| 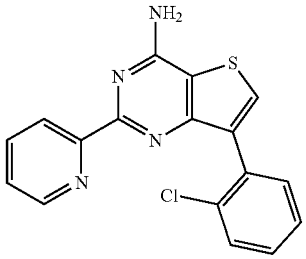 [SMILES: Nc1nc(-c2ccccn2)nc2c(-c3ccccc3Cl)csc12] | 339 | 339.1 | 339.2 |
| 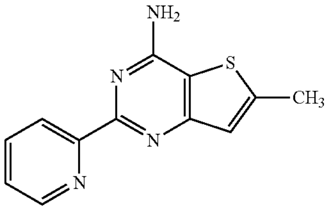 | 242 | 243.1 | 243.0 |
| 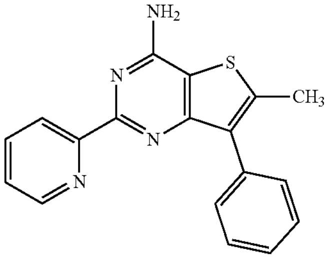 | 318 | 319.1 | 319.2 |
| 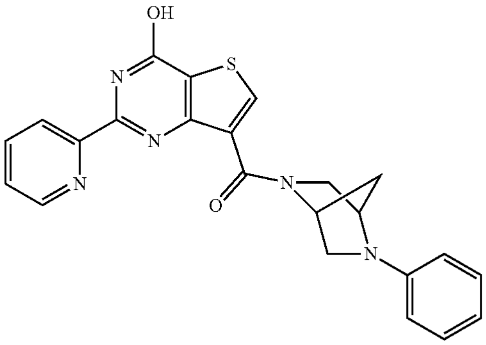 [SMILES: O=C(c1csc2c(O)nc(-c3ccccn3)nc12)N1CC2CC1CN2c1ccccc1] | 429 | 430.1 | 430.2 |

TABLE 3-continued
| Mass Spectral Data | | | |
|---|---|---|---|
| Compound | MW | M + H (calculated) | M + H (observed) |
| 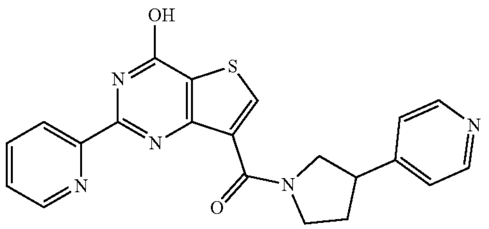 [SMILES: O=C(c1csc2c(O)nc(-c3ccccn3)nc12)N1CCC(c2ccncc2)C1] | 403 | 404.1 | 404.1 |
| 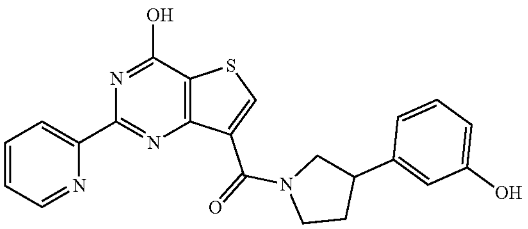 [SMILES: O=C(c1csc2c(O)nc(-c3ccccn3)nc12)N1CCC(c2cccc(O)c2)C1] | 418 | 419.1 | 419.0 |
| 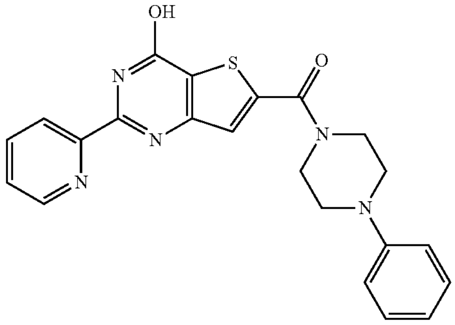 [SMILES: O=C(c1cc2nc(-c3ccccn3)nc(O)c2s1)N1CCN(c2ccccc2)CC1] | 417 | 418.1 | 418.2 |
| 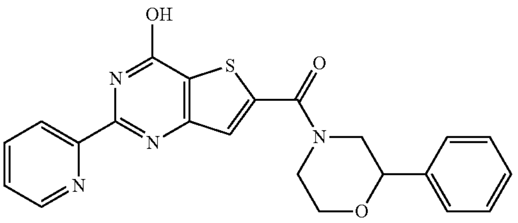 [SMILES: O=C(c1cc2nc(-c3ccccn3)nc(O)c2s1)N1CCOC(c2ccccc2)C1] | 418 | 419.1 | 419.0 |
| 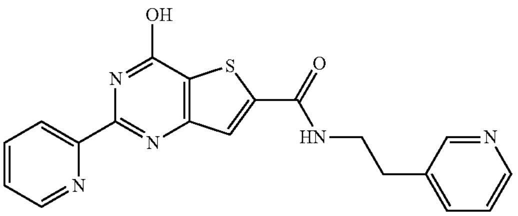 [SMILES: O=C(NCCc1cccnc1)c1cc2nc(-c3ccccn3)nc(O)c2s1] | 377 | 378.1 | 378.2 |
| 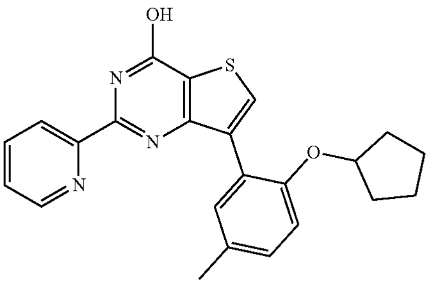 [SMILES: Cc1ccc(OC2CCCC2)c(-c2csc3c(O)nc(-c4ccccn4)nc23)c1] | 403 | 404.2 | 404.0 |

TABLE 3-continued
| Mass Spectral Data | | | |
|---|---|---|---|
| Compound | MW | M + H (calculated) | M + H (observed) |
| 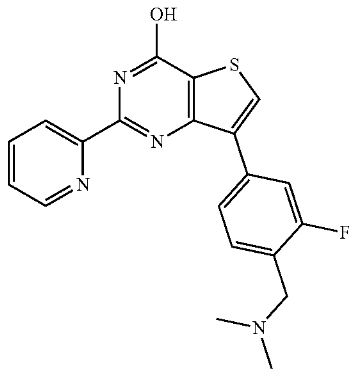 [SMILES: CN(C)Cc1ccc(-c2csc3c(O)nc(-c4ccccn4)nc23)cc1F] | 380 | 381.1 | 381.0 |
| 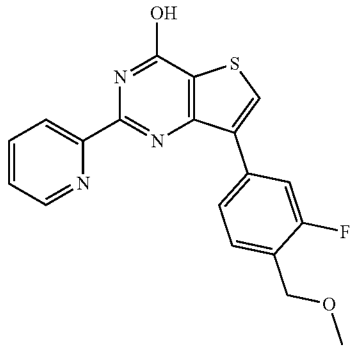 [SMILES: COCc1ccc(-c2csc3c(O)nc(-c4ccccn4)nc23)cc1F] | 367 | 368.1 | 368.1 |
| 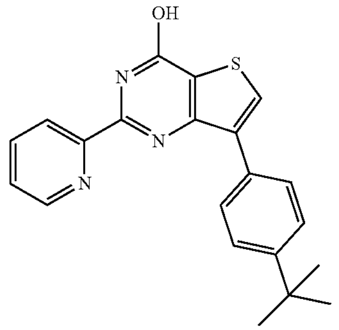 [SMILES: CC(C)(C)c1ccc(-c2csc3c(O)nc(-c4ccccn4)nc23)cc1] | 361 | 362.2 | 362.2 |
| 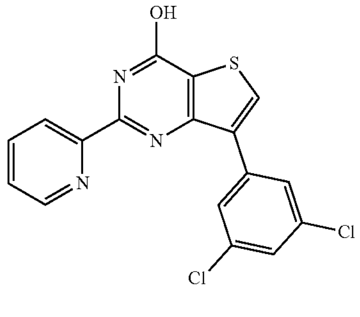 [SMILES: Oc1nc(-c2ccccn2)nc2c(-c3cc(Cl)cc(Cl)c3)csc12] | 374 | 374.0 | 374.0 |

TABLE 3-continued
| Mass Spectral Data | | | |
|---|---|---|---|
| Compound | MW | M + H (calculated) | M + H (observed) |
| 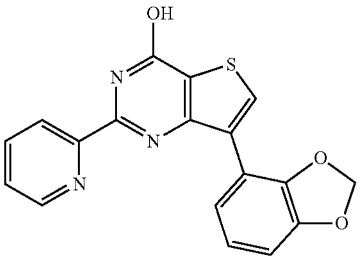 [SMILES: Oc1nc(-c2ccccn2)nc2c(-c3cccc4c3OCO4)csc12] | 349 | 350.1 | 350.1 |
| 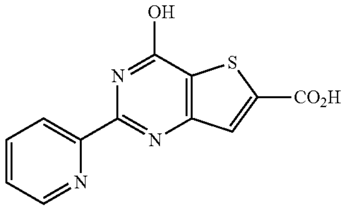 [SMILES: O=C(O)c1cc2nc(-c3ccccn3)nc(O)c2s1] | 273 | 274.0 | 274.0 |
| 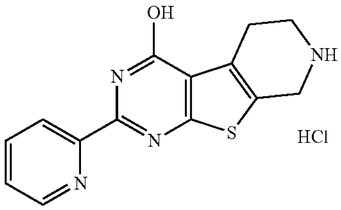 [SMILES: Oc1nc(-c2ccccn2)nc2sc3c(c12)CCNC3 ; Cl] HCl | 321 | 285.1 | 285.1 |
| 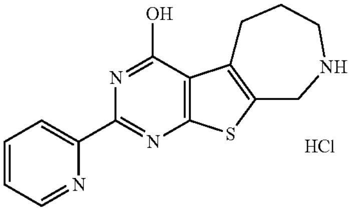 [SMILES: Oc1nc(-c2ccccn2)nc2sc3c(c12)CCCNC3 ; Cl] HCl | 335 | 299.1 | 299.1 |
| 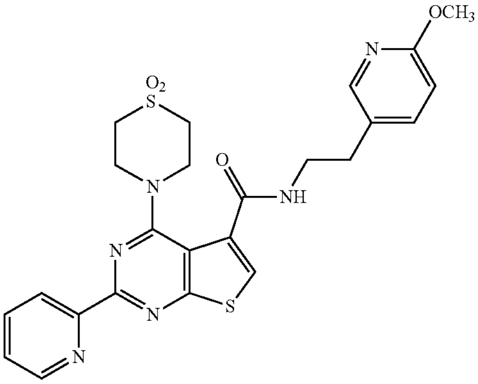 [SMILES: COc1ccc(CCNC(=O)c2csc3nc(-c4ccccn4)nc(N4CCS(=O)(=O)CC4)c23)cn1] | 525 | 525.1 | 525.2 |

TABLE 3-continued
| Mass Spectral Data | | | |
|---|---|---|---|
| Compound | MW | M + H (calculated) | M + H (observed) |
| 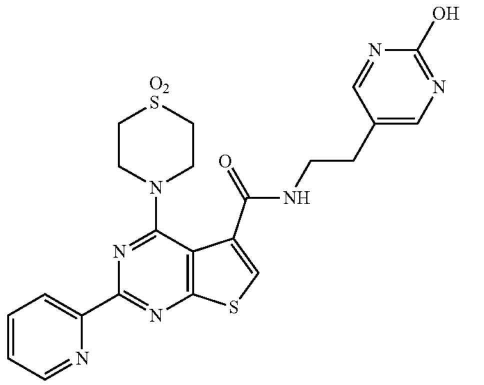 | 512 | 512.1 | 512 |
| 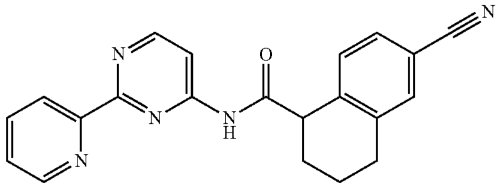 [SMILES: N#Cc1ccc2c(c1)CCCC2C(=O)Nc1ccnc(-c2ccccn2)n1] | 355 | 356.2 | 356.0 |
| 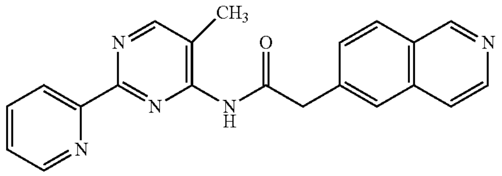 [SMILES: Cc1cnc(-c2ccccn2)nc1NC(=O)Cc1ccc2cnccc2c1] | 355 | 356.1 | 356.3 |
| 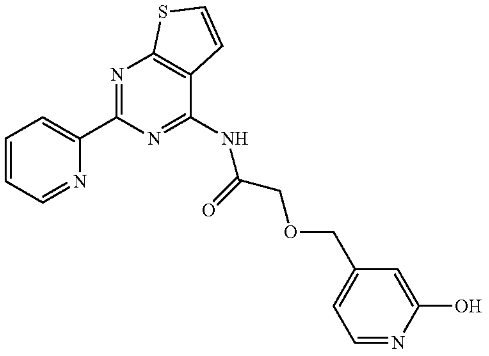 [SMILES: O=C(COCc1ccnc(O)c1)Nc1nc(-c2ccccn2)nc2sccc12] | 393 | 394.1 | 394.0 |
| 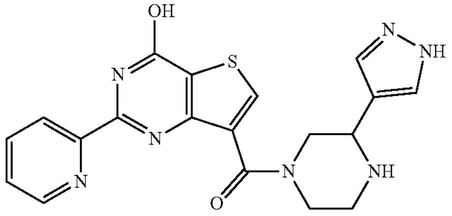 [SMILES: O=C(c1csc2c(O)nc(-c3ccccn3)nc12)N1CCNC(c2cn[nH]c2)C1] | 407 | 408.1 | 408.0 |

TABLE 3-continued
| Mass Spectral Data | | | |
|---|---|---|---|
| Compound | MW | M + H (calculated) | M + H (observed) |
| 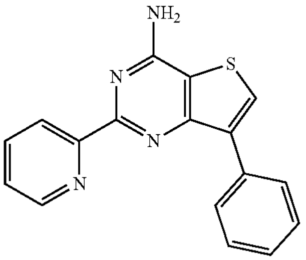 [SMILES: Nc1nc(-c2ccccn2)nc2c(-c3ccccc3)csc12] | 304 | 305.1 | 305.2 |
| 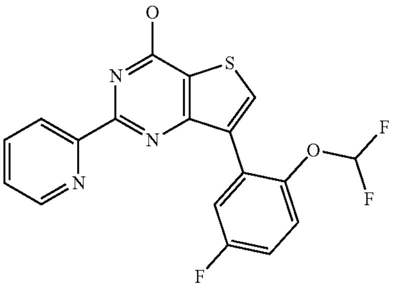 [SMILES: Oc1nc(-c2ccccn2)nc2c(-c3cc(F)ccc3OC(F)F)csc12] | 389 | 390.1 | 390.0 |
| 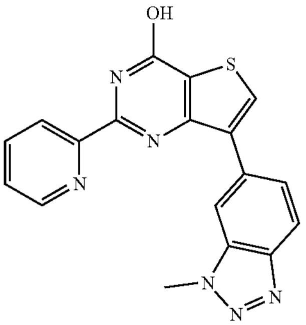 [SMILES: Cn1nnc2ccc(-c3csc4c(O)nc(-c5ccccn5)nc34)cc21] | 360 | 361.1 | 361.0 |
| 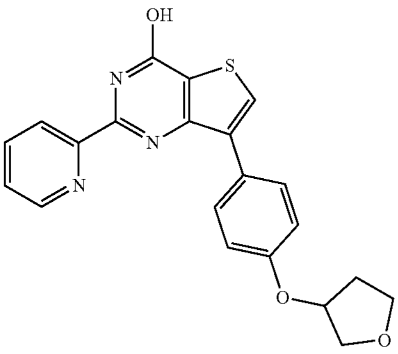 [SMILES: Oc1nc(-c2ccccn2)nc2c(-c3ccc(OC4CCOC4)cc3)csc12] | 391 | 392.1 | 392.2 |

TABLE 3-continued
| Mass Spectral Data | | | |
|---|---|---|---|
| Compound | MW | M + H (calculated) | M + H (observed) |
| 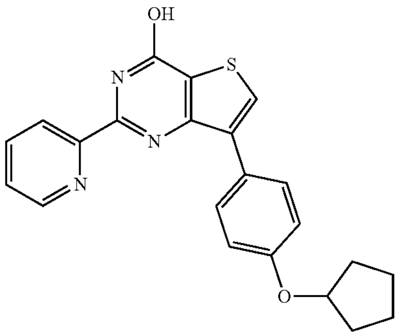 [SMILES: Oc1nc(-c2ccccn2)nc2c(-c3ccc(OC4CCCC4)cc3)csc12] | 389 | 390.1 | 390.0 |
| 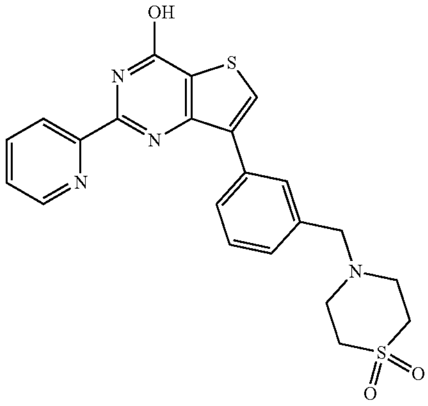 [SMILES: O=S1(=O)CCN(Cc2cccc(-c3csc4c(O)nc(-c5ccccn5)nc34)c2)CC1] | 453 | 453.1 | 453.0 |
| 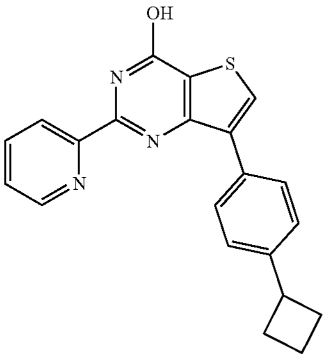 [SMILES: Oc1nc(-c2ccccn2)nc2c(-c3ccc(C4CCC4)cc3)csc12] | 359 | 360.1 | 360.0 |
| 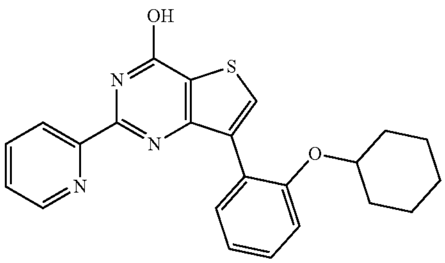 [SMILES: Oc1nc(-c2ccccn2)nc2c(-c3ccccc3OC3CCCCC3)csc12] | 403 | 404.2 | 404.2 |

TABLE 3-continued
| Mass Spectral Data | | | |
|---|---|---|---|
| Compound | MW | M + H (calculated) | M + H (observed) |
| 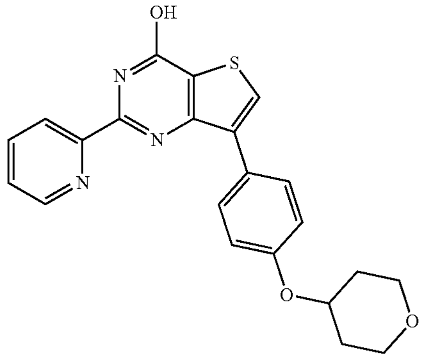 [SMILES: Oc1nc(-c2ccccn2)nc2c(-c3ccc(OC4CCOCC4)cc3)csc12] | 405 | 406.1 | 406.2 |
| 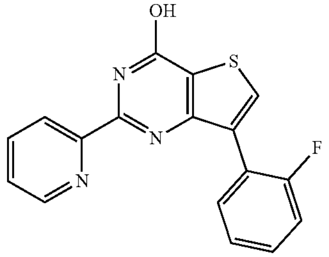 [SMILES: Oc1nc(-c2ccccn2)nc2c(-c3ccccc3F)csc12] | 323 | 324.1 | 324.1 |
| 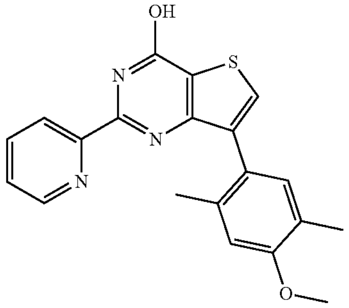 [SMILES: COc1cc(C)c(-c2csc3c(O)nc(-c4ccccn4)nc23)cc1C] | 363 | 364.1 | 364.2 |
| 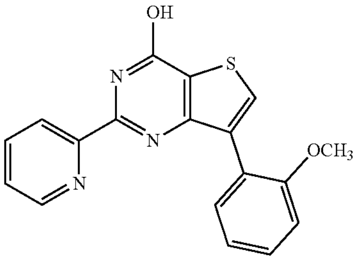 [SMILES: COc1ccccc1-c1csc2c(O)nc(-c3ccccn3)nc12] | 335 | 336.1 | 336.0 |
| 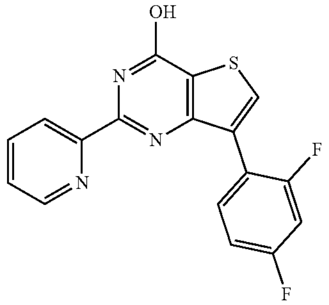 [SMILES: Oc1nc(-c2ccccn2)nc2c(-c3ccc(F)cc3F)csc12] | 341 | 342.1 | 342.0 |

TABLE 3-continued
Mass Spectral Data
| Compound | MW | M + H (calculated) | M + H (observed) |
|---|---|---|---|
| 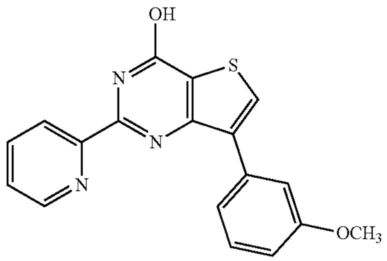 [SMILES: COc1cccc(-c2csc3c(O)nc(-c4ccccn4)nc23)c1] | 335 | 336.1 | 336.2 |
| 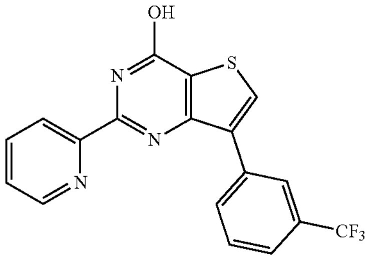 | 373 | 374.1 | 374.2 |
| 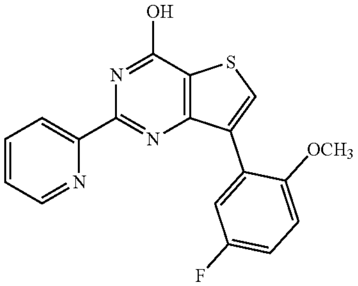 [SMILES: COc1ccc(F)cc1-c1csc2c(O)nc(-c3ccccn3)nc12] | 353 | 354.1 | 354.0 |
| 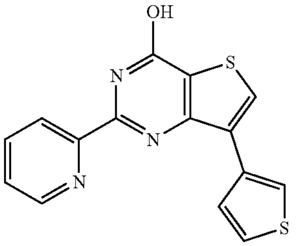 [SMILES: Oc1nc(-c2ccccn2)nc2c(-c3ccsc3)csc12] | 311 | 312.0 | 312.0 |
| 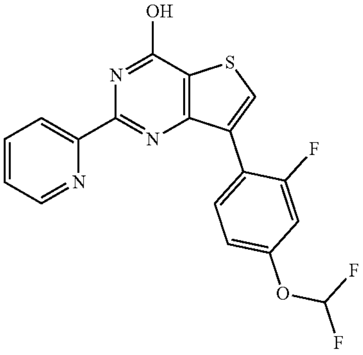 [SMILES: Oc1nc(-c2ccccn2)nc2c(-c3ccc(OC(F)F)cc3F)csc12] | 389 | 390.1 | 390.2 |

TABLE 3-continued
| Mass Spectral Data | | | |
|---|---|---|---|
| Compound | MW | M + H (calculated) | M + H (observed) |
| 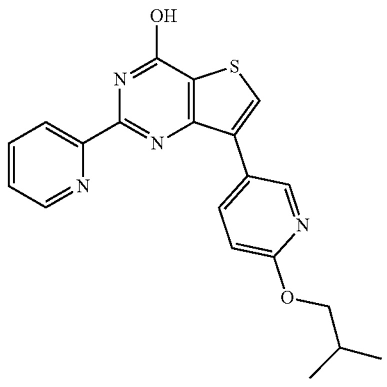 [SMILES: CC(C)COc1ccc(-c2csc3c(O)nc(-c4ccccn4)nc23)cn1] | 378 | 379.1 | 379.2 |
| 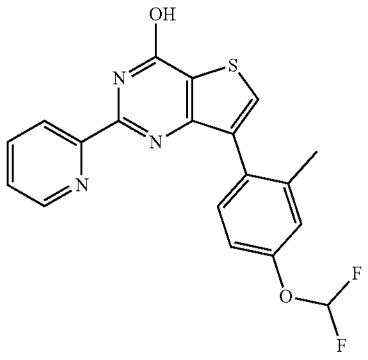 [SMILES: Cc1cc(OC(F)F)ccc1-c1csc2c(O)nc(-c3ccccn3)nc12] | 385 | 386.1 | 386.2 |
| 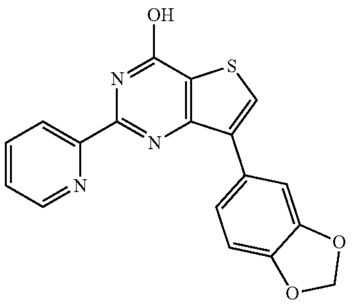 [SMILES: Oc1nc(-c2ccccn2)nc2c(-c3ccc4c(c3)OCO4)csc12] | 349 | 350.1 | 350.2 |
| 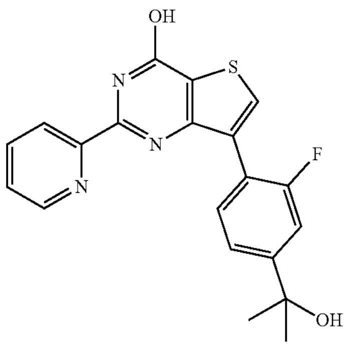 [SMILES: CC(C)(O)c1ccc(-c2csc3c(O)nc(-c4ccccn4)nc23)c(F)c1] | 381 | 382.1 | 382.0 |

TABLE 3-continued
| Mass Spectral Data | | | |
|---|---|---|---|
| Compound | MW | M + H (calculated) | M + H (observed) |
| 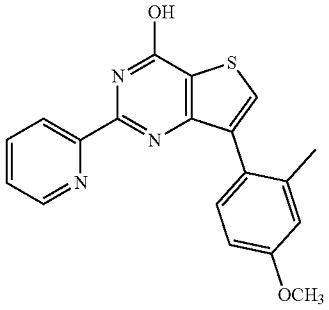 [SMILES: COc1ccc(-c2csc3c(O)nc(-c4ccccn4)nc23)c(C)c1] | 349 | 350.1 | 350.1 |
| 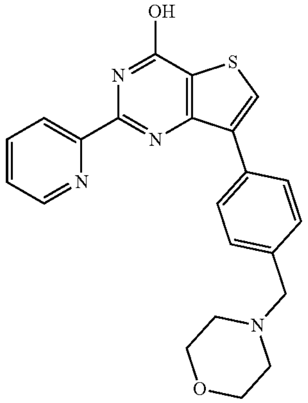 [SMILES: Oc1nc(-c2ccccn2)nc2c(-c3ccc(CN4CCOCC4)cc3)csc12] | 404 | 405.2 | 405.2 |
| 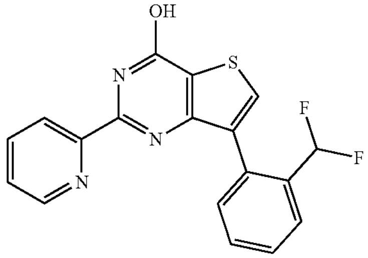 [SMILES: Oc1nc(-c2ccccn2)nc2c(-c3ccccc3C(F)F)csc12] | 355 | 356.1 | 356.2 |
| 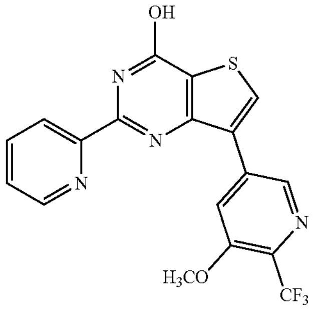 [SMILES: COc1cc(-c2csc3c(O)nc(-c4ccccn4)nc23)cnc1C(F)(F)F] | 404 | 405.1 | 405.0 |

TABLE 3-continued
| Mass Spectral Data | | | |
|---|---|---|---|
| Compound | MW | M + H (calculated) | M + H (observed) |
| 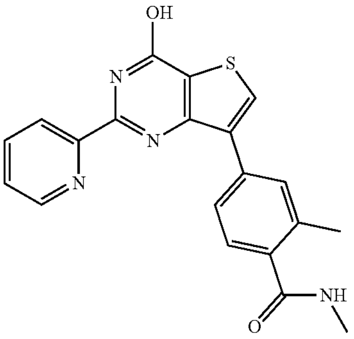 [SMILES: CNC(=O)c1ccc(-c2csc3c(O)nc(-c4ccccn4)nc23)cc1C] | 376 | 377.1 | 377.0 |
| 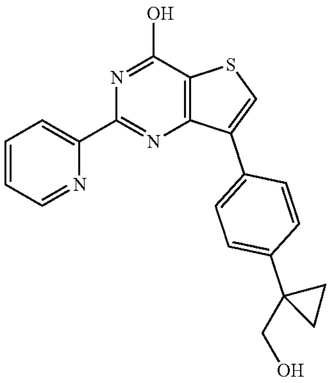 [SMILES: OCC1(c2ccc(-c3csc4c(O)nc(-c5ccccn5)nc34)cc2)CC1] | 375 | 376.1 | 376.0 |
| 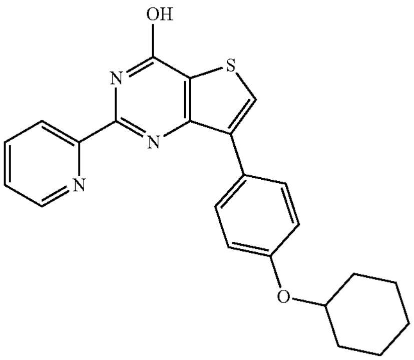 [SMILES: Oc1nc(-c2ccccn2)nc2c(-c3ccc(OC4CCCCC4)cc3)csc12] | 403 | 404.2 | 404.2 |
| 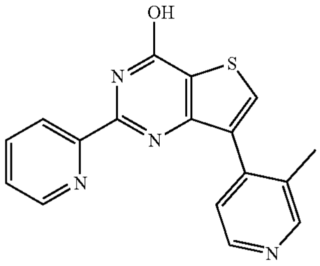 [SMILES: Cc1cnccc1-c1csc2c(O)nc(-c3ccccn3)nc12] | 320 | 321.1 | 321.1 |

TABLE 3-continued
| Mass Spectral Data | | | |
|---|---|---|---|
| Compound | MW | M + H (calculated) | M + H (observed) |
| 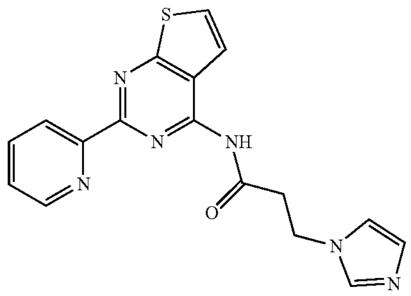 [SMILES: O=C(CCn1ccnc1)Nc1nc(-c2ccccn2)nc2sccc12] | 350 | 351.1 | 351.2 |
| 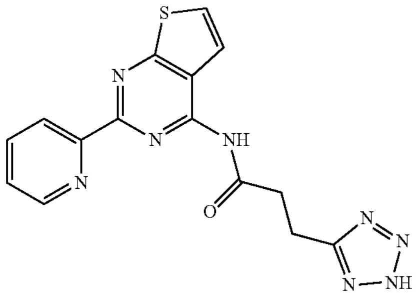 [SMILES: O=C(CCc1nn[nH]n1)Nc1nc(-c2ccccn2)nc2sccc12] | 352 | [M − 1] 351.1 | [M − 1] 351.0 |
| 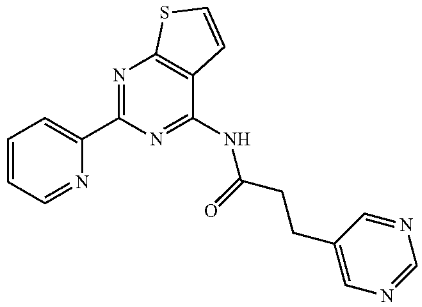 [SMILES: O=C(CCc1cncnc1)Nc1nc(-c2ccccn2)nc2sccc12] | 362 | 363.1 | 363.0 |
| 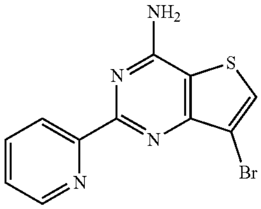 [SMILES: Nc1nc(-c2ccccn2)nc2c(Br)csc12] | 307 | 307.0 | 307.0 |
| 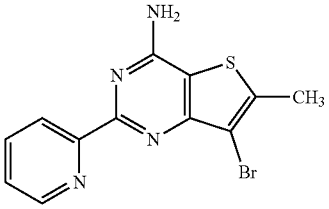 [SMILES: Cc1sc2c(N)nc(-c3ccccn3)nc2c1Br] | 321 | 321.0 | 321.0 |

TABLE 3-continued
Mass Spectral Data
| Compound | MW | M + H (calculated) | M + H (observed) |
|---|---|---|---|
| 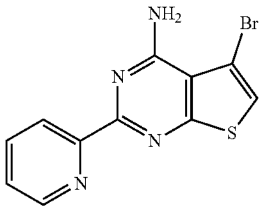 [SMILES: Nc1nc(-c2ccccn2)nc2scc(Br)c12] | 307 | 307.0 | 307.0 |
| 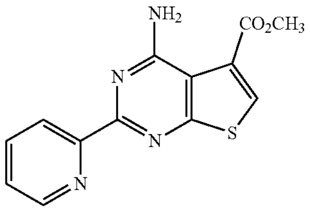 [SMILES: COC(=O)c1csc2nc(-c3ccccn3)nc(N)c12] | 286 | 287.1 | 287.0 |
| 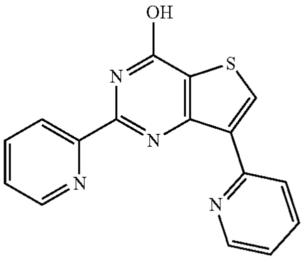 [SMILES: Oc1nc(-c2ccccn2)nc2c(-c3ccccn3)csc12] | 468 | 307.1 | 307.0 |
| 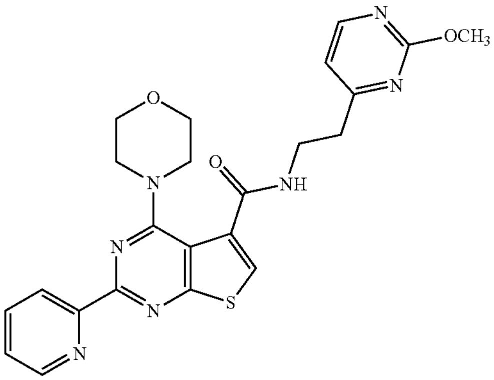 [SMILES: COc1nccc(CCNC(=O)c2csc3nc(-c4ccccn4)nc(N4CCOCC4)c23)n1] | 478 | 478.2 | 478.2 |
| 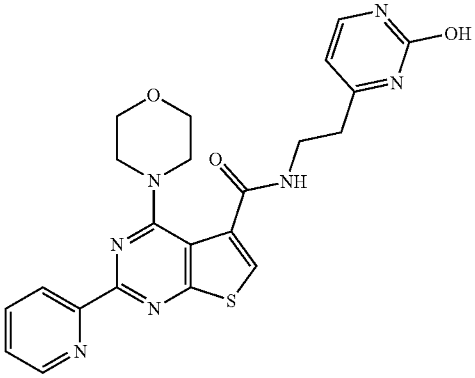 | 464 | 464.1 | 464.2 |

TABLE 3-continued
| Mass Spectral Data | | | |
|---|---|---|---|
| Compound | MW | M + H (calculated) | M + H (observed) |
| 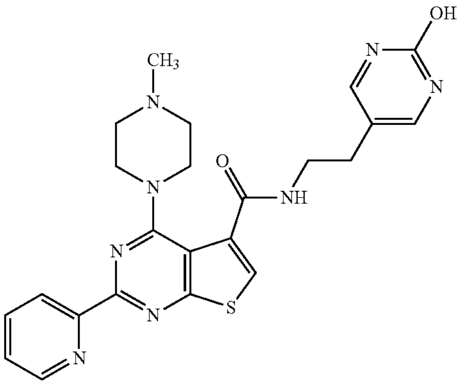 [SMILES: CN1CCN(c2nc(-c3ccccn3)nc3scc(C(=O)NCCc4cnc(O)nc4)c23)CC1] | 477 | 477.2 | 477.2 |
| 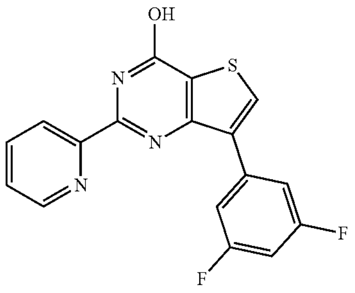 [SMILES: Oc1nc(-c2ccccn2)nc2c(-c3cc(F)cc(F)c3)csc12] | 341 | 342.1 | 342.2 |
| 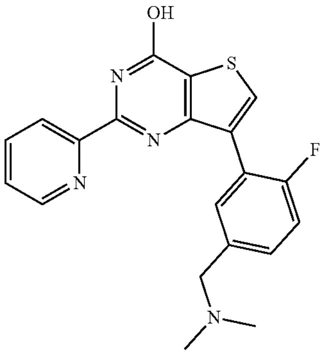 [SMILES: CN(C)Cc1ccc(F)c(-c2csc3c(O)nc(-c4ccccn4)nc23)c1] | 380 | 381.1 | 381.2 |
| 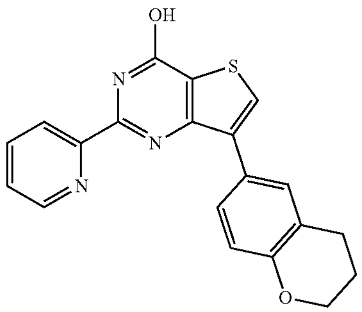 [SMILES: Oc1nc(-c2ccccn2)nc2c(-c3ccc4c(c3)CCCO4)csc12] | 361 | 362.1 | 362.2 |

TABLE 3-continued
| Mass Spectral Data | | | |
|---|---|---|---|
| Compound | MW | M + H (calculated) | M + H (observed) |
| 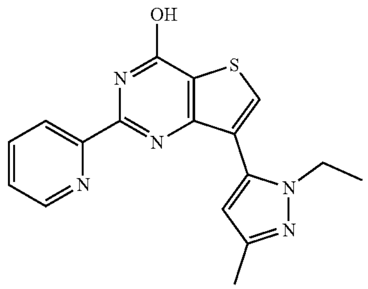 [SMILES: CCn1nc(C)cc1-c1csc2c(O)nc(-c3ccccn3)nc12] | 337 | 338.1 | 338.1 |
| 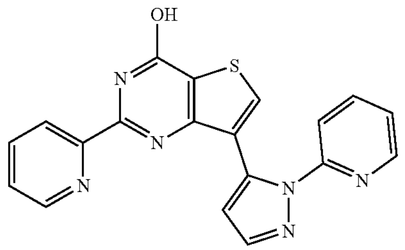 [SMILES: Oc1nc(-c2ccccn2)nc2c(-c3ccnn3-c3ccccn3)csc12] | 372 | 373.1 | 373.0 |
| 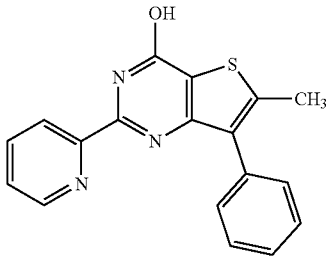 [SMILES: Cc1sc2c(O)nc(-c3ccccn3)nc2c1-c1ccccc1] | 319 | 320.1 | 320.0 |
| 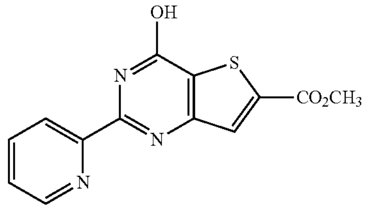 [SMILES: COC(=O)c1cc2nc(-c3ccccn3)nc(O)c2s1] | 287 | 288.0 | 288.1 |
| 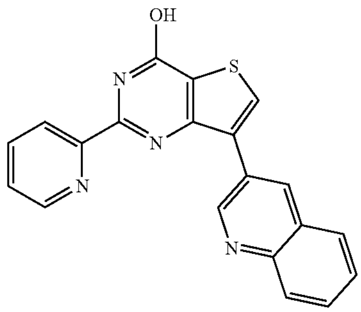 [SMILES: Oc1nc(-c2ccccn2)nc2c(-c3cnc4ccccc4c3)csc12] | 356 | 357.1 | 357.0 |

TABLE 3-continued
| Mass Spectral Data | | | |
|---|---|---|---|
| Compound | MW | M + H (calculated) | M + H (observed) |
| 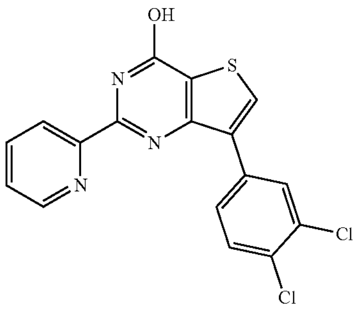 [SMILES: Oc1nc(-c2ccccn2)nc2c(-c3ccc(Cl)c(Cl)c3)csc12] | 374 | 374.0 | 374.0 |
| 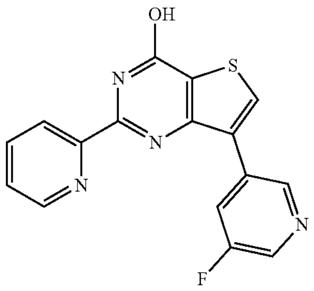 [SMILES: Oc1nc(-c2ccccn2)nc2c(-c3cncc(F)c3)csc12] | 324 | 325.1 | 325.2 |
| 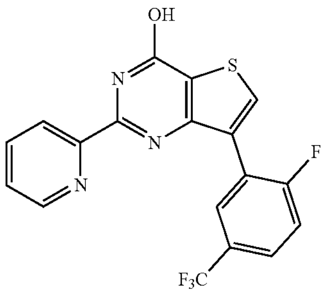 [SMILES: Oc1nc(-c2ccccn2)nc2c(-c3cc(C(F)(F)F)ccc3F)csc12] | 391 | 392.1 | 392.0 |
| 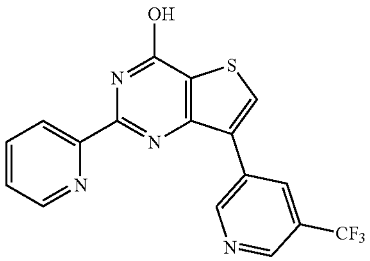 [SMILES: Oc1nc(-c2ccccn2)nc2c(-c3cncc(C(F)(F)F)c3)csc12] | 374 | 375.1 | 375.2 |
| 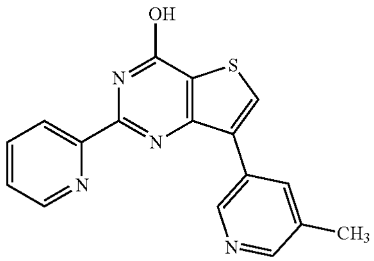 [SMILES: Cc1cncc(-c2csc3c(O)nc(-c4ccccn4)nc23)c1] | 320 | 321.1 | 321.2 |

TABLE 3-continued
| Mass Spectral Data | | | |
|---|---|---|---|
| Compound | MW | M + H (calculated) | M + H (observed) |
| 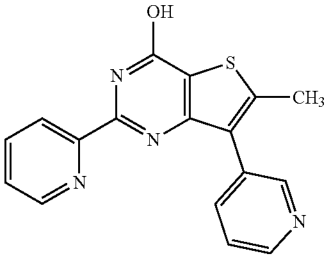 [SMILES: Cc1sc2c(O)nc(-c3ccccn3)nc2c1-c1cccnc1] | 320 | 321.1 | 321.0 |
| 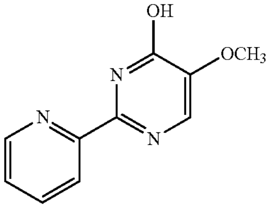 [SMILES: COc1cnc(-c2ccccn2)nc1O] | 203 | 204.1 | 204.2 |
| 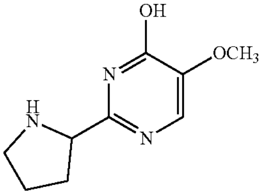 [SMILES: COc1cnc(C2CCCN2)nc1O] | 232 | 196.1 | 196.2 |
| 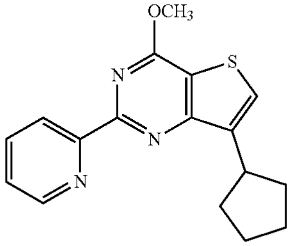 [SMILES: COc1nc(-c2ccccn2)nc2c(C3CCCC3)csc12] | 311 | 312.1 | 312.0 |
| 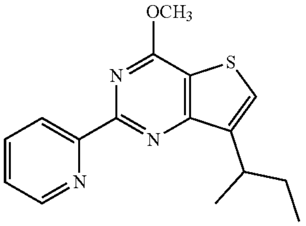 [SMILES: CCC(C)c1csc2c(OC)nc(-c3ccccn3)nc12] | 299 | 300.1 | 300.0 |
| 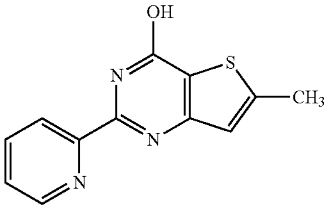 [SMILES: Cc1cc2nc(-c3ccccn3)nc(O)c2s1] | 243 | 244.1 | 244.2 |

TABLE 3-continued
| Mass Spectral Data | | | |
|---|---|---|---|
| Compound | MW | M + H (calculated) | M + H (observed) |
| 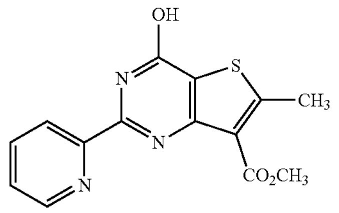 [SMILES: COC(=O)c1c(C)sc2c(O)nc(-c3ccccn3)nc12] | 301 | 302.1 | 302.0 |
| 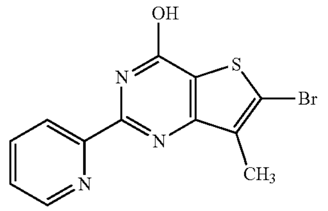 [SMILES: Cc1c(Br)sc2c(O)nc(-c3ccccn3)nc12] | 322 | 322.0 | 322.0 |
| 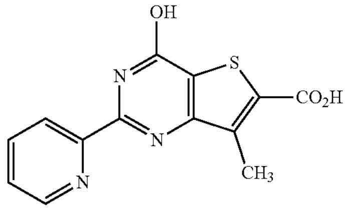 [SMILES: Cc1c(C(=O)O)sc2c(O)nc(-c3ccccn3)nc12] | 287 | 288.0 | 288.0 |
| 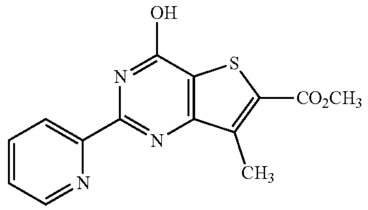 [SMILES: COC(=O)c1sc2c(O)nc(-c3ccccn3)nc2c1C] | 301 | 302.1 | 302.0 |
| 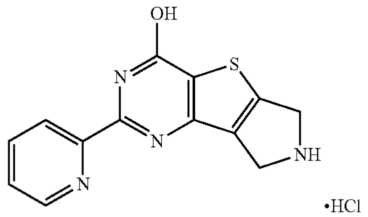 [SMILES: Oc1nc(-c2ccccn2)nc2c3c(sc12)CNC3 ; Cl] | 307 | 271.1 | 271.0 |
| 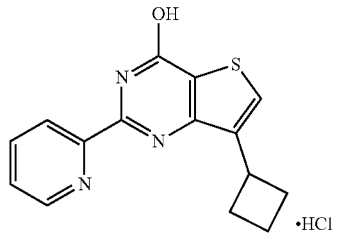 [SMILES: Oc1nc(-c2ccccn2)nc2c(C3CCC3)csc12 ; Cl] | 320 | 284.1 | 284.1 |

TABLE 3-continued
Mass Spectral Data
| Compound | MW | M + H (calculated) | M + H (observed) |
|---|---|---|---|
| 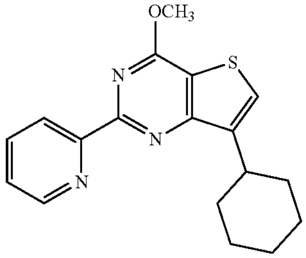 [SMILES: COc1nc(-c2ccccn2)nc2c(C3CCCCC3)csc12] | 325 | 326.2 | 326.2 |
| 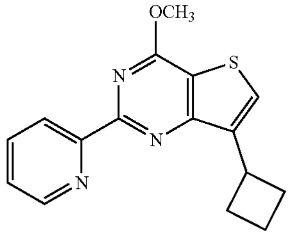 [SMILES: COc1nc(-c2ccccn2)nc2c(C3CCC3)csc12] | 297 | 298.1 | 298.0 |
| 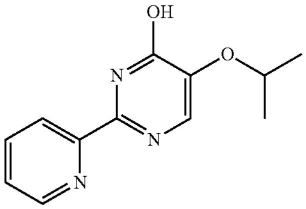 [SMILES: CC(C)Oc1cnc(-c2ccccn2)nc1O] | 231 | 232.1 | 232.2 |
| 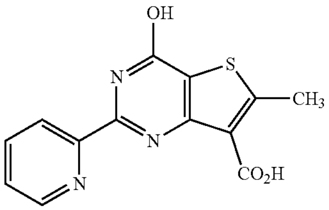 [SMILES: Cc1sc2c(O)nc(-c3ccccn3)nc2c1C(=O)O] | 287 | 288.0 | 288.0 |
| 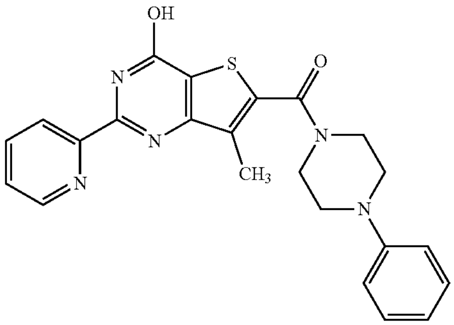 [SMILES: Cc1c(C(=O)N2CCN(c3ccccc3)CC2)sc2c(O)nc(-c3ccccn3)nc12] | 432 | 432.2 | 432.2 |
| 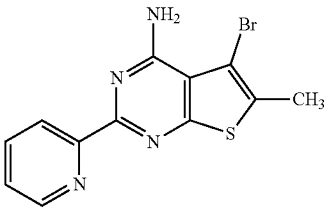 [SMILES: Cc1sc2nc(-c3ccccn3)nc(N)c2c1Br] | 321 | 322.2 | 322.0 |

TABLE 3-continued
| Mass Spectral Data | | | |
|---|---|---|---|
| Compound | MW | M + H (calculated) | M + H (observed) |
| 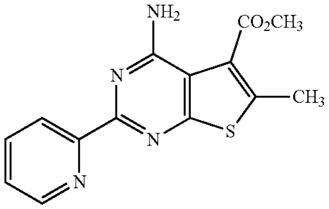 [SMILES: COC(=O)c1c(C)sc2nc(-c3ccccn3)nc(N)c12] | 300 | 301.1 | 301.0 |
| 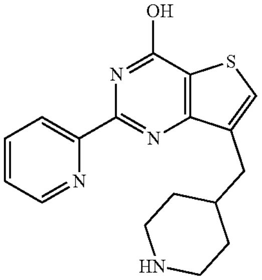 •2HCl | 399 | 327.1 | 327.0 |
| 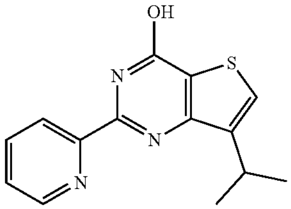 •HCl | 308 | 272.1 | 272.0 |
| 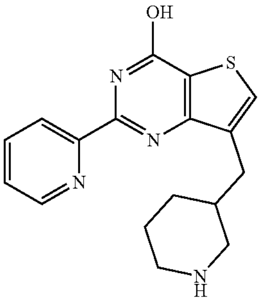 •HCl | 399 | 327.1 | 327.0 |
| 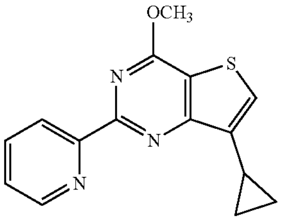 [SMILES: COc1nc(-c2ccccn2)nc2c(C3CC3)csc12] | 283 | 284.1 | 284.0 |
| 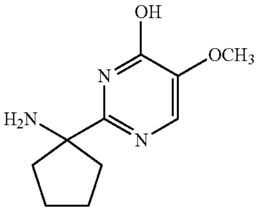 •HCl | 246 | 210.1 | 210.2 |

TABLE 3-continued
| Mass Spectral Data | | | |
|---|---|---|---|
| Compound | MW | M + H (calculated) | M + H (observed) |
| 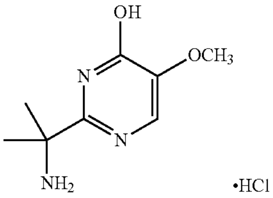 •HCl | 220 | 184.1 | 184.2 |
| 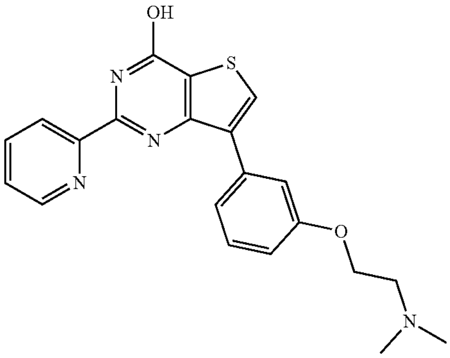 [SMILES: CN(C)CCOc1cccc(-c2csc3c(O)nc(-c4ccccn4)nc23)c1] | 392 | 393.2 | 393.0 |
| 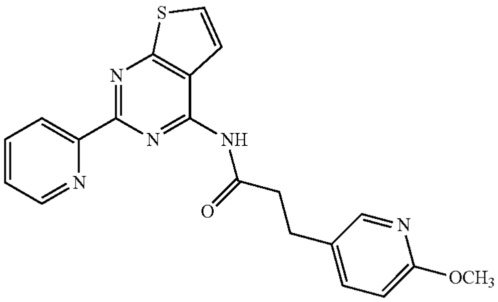 [SMILES: COc1ccc(CCC(=O)Nc2nc(-c3ccccn3)nc3sccc23)cn1] | 391 | 392.1 | 392.0 |
| 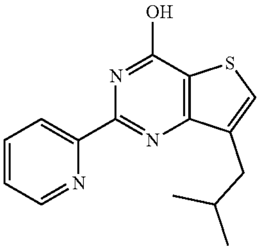 [SMILES: CC(C)Cc1csc2c(O)nc(-c3ccccn3)nc12] | 285 | 286.1 | 286.0 |
| 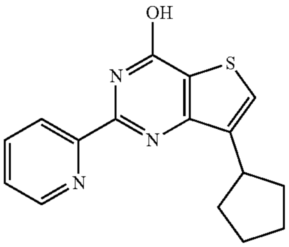 [SMILES: Oc1nc(-c2ccccn2)nc2c(C3CCCC3)csc12] | 297 | 298.1 | 298.0 |

TABLE 3-continued
| Mass Spectral Data | | | |
|---|---|---|---|
| Compound | MW | M + H (calculated) | M + H (observed) |
| 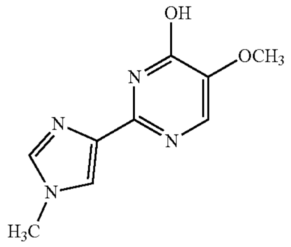 | 206 | 207.1 | 207.0 |
| 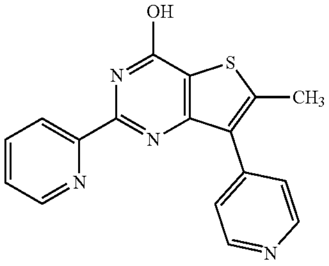 [SMILES: Cc1sc2c(O)nc(-c3ccccn3)nc2c1-c1ccncc1] | 320 | 321.1 | 321.0 |
| 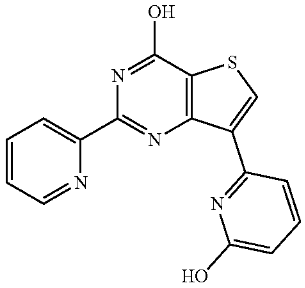 •HCl | 322 | 323.1 | 323.1 |
| 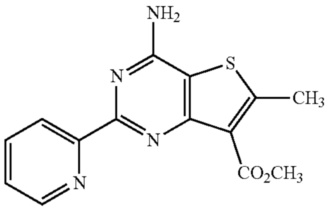 [SMILES: COC(=O)c1c(C)sc2c(N)nc(-c3ccccn3)nc12] | 300 | 301.1 | 301.0 |
| 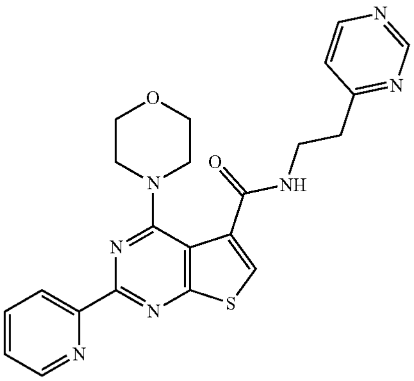 [SMILES: O=C(NCCc1ccncn1)c1csc2nc(-c3ccccn3)nc(N3CCOCC3)c12] | 448 | 448.2 | 448.0 |

TABLE 3-continued
| Mass Spectral Data | | | |
|---|---|---|---|
| Compound | MW | M + H (calculated) | M + H (observed) |
| 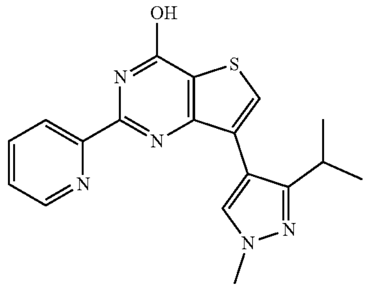 [SMILES: CC(C)c1nn(C)cc1-c1csc2c(O)nc(-c3ccccn3)nc12] | 351 | 352.1 | 352.2 |
| 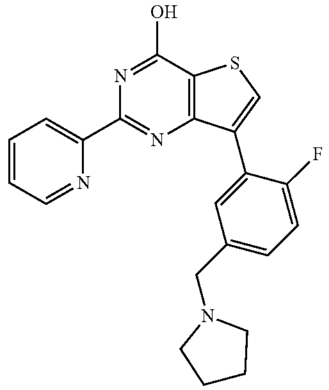 [SMILES: Oc1nc(-c2ccccn2)nc2c(-c3cc(CN4CCCC4)ccc3F)csc12] | 406 | 407.2 | 407.2 |
| 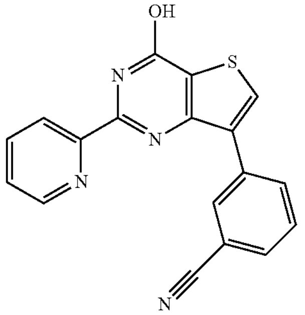 [SMILES: N#Cc1cccc(-c2csc3c(O)nc(-c4ccccn4)nc23)c1] | 330 | 331.1 | 331.0 |
| 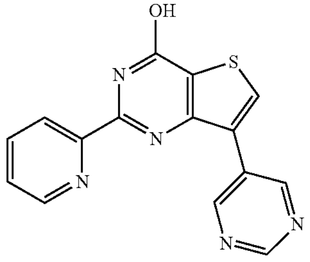 [SMILES: Oc1nc(-c2ccccn2)nc2c(-c3cncnc3)csc12] | 307 | 308.1 | 308.0 |
| 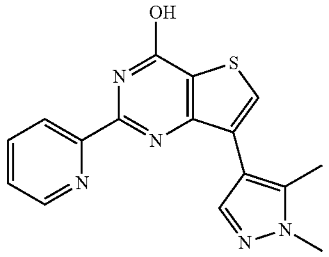 [SMILES: Cc1c(-c2csc3c(O)nc(-c4ccccn4)nc23)cnn1C] | 323 | 324.1 | 324.0 |

TABLE 3-continued
| Mass Spectral Data | | | |
|---|---|---|---|
| Compound | MW | M + H (calculated) | M + H (observed) |
| 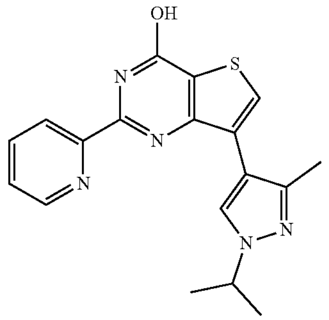 [SMILES: Cc1nn(C(C)C)cc1-c1csc2c(O)nc(-c3ccccn3)nc12] | 351 | 352.1 | 352.2 |
| 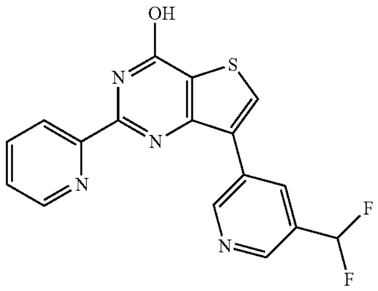 [SMILES: Oc1nc(-c2ccccn2)nc2c(-c3cncc(C(F)F)c3)csc12] | 356 | 357.1 | 357.0 |
| 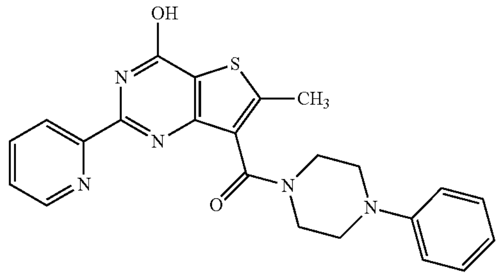 [SMILES: Cc1sc2c(O)nc(-c3ccccn3)nc2c1C(=O)N1CCN(c2ccccc2)CC1] | 432 | 432.2 | 432.2 |
| 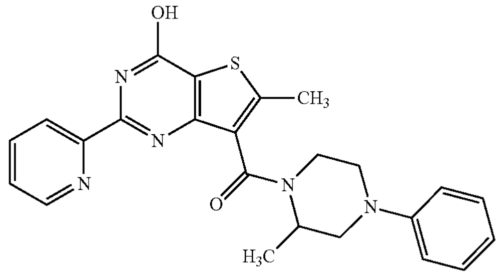 [SMILES: Cc1sc2c(O)nc(-c3ccccn3)nc2c1C(=O)N1CCN(c2ccccc2)CC1C] | 446 | 446.2 | 446.0 |
| 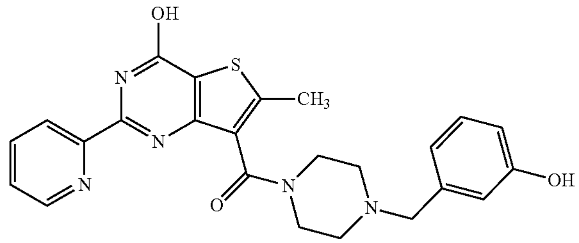 [SMILES: Cc1sc2c(O)nc(-c3ccccn3)nc2c1C(=O)N1CCN(Cc2cccc(O)c2)CC1] | 462 | 462.2 | 462.0 |

TABLE 3-continued
| Mass Spectral Data | | | |
|---|---|---|---|
| Compound | MW | M + H (calculated) | M + H (observed) |
| 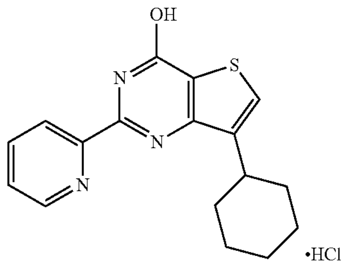 [SMILES: Oc1nc(-c2ccccn2)nc2c(C3CCCCC3)csc12 ; Cl] | 348 | 311.1 | 312.0 |
| 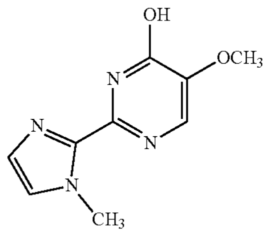 | 206 | 207.1 | 207.2 |
| 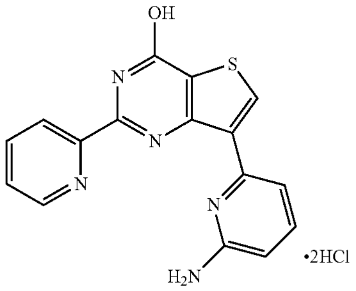 [SMILES: Nc1cccc(-c2csc3c(O)nc(-c4ccccn4)nc23)n1] | 394 | 322.1 | 322.0 |
| 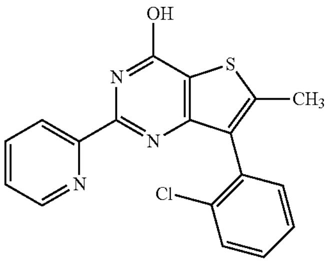 [SMILES: Cc1sc2c(O)nc(-c3ccccn3)nc2c1-c1ccccc1Cl] | 354 | 354.0 | 354.0 |
| 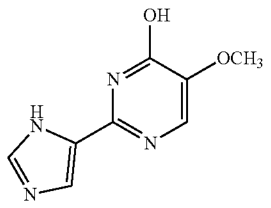 [SMILES: COc1cnc(-c2cnc[nH]2)nc1O] | 192 | 193.1 | 193.2 |

TABLE 3-continued
| Mass Spectral Data | | | |
|---|---|---|---|
| Compound | MW | M + H (calculated) | M + H (observed) |
| 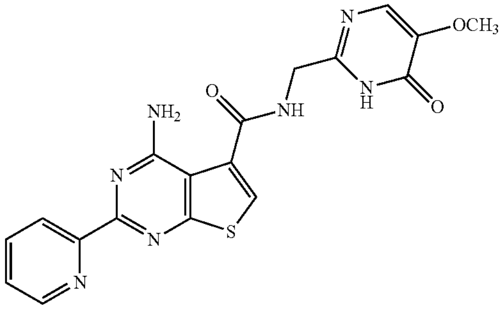 [SMILES: COc1cnc(CNC(=O)c2csc3nc(-c4ccccn4)nc(N)c23)[nH]c1=O] | 409 | 410.1 | 410.0 |
| 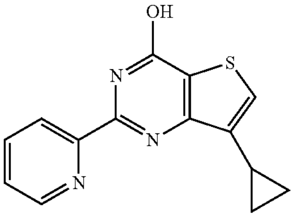 [SMILES: Oc1nc(-c2ccccn2)nc2c(C3CC3)csc12] | 269 | 270.1 | 270.0 |
| 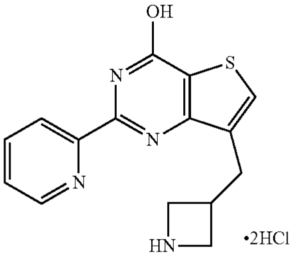 [SMILES: Oc1nc(-c2ccccn2)nc2c(CC3CNC3)csc12] | 371 | 299.1 | 299.0 |
| 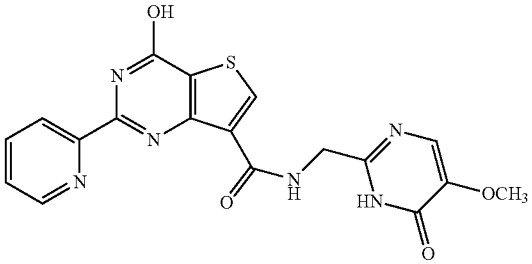 [SMILES: COc1cnc(CNC(=O)c2csc3c(O)nc(-c4ccccn4)nc23)[nH]c1=O] | 410 | 411.1 | 411.1 |
| 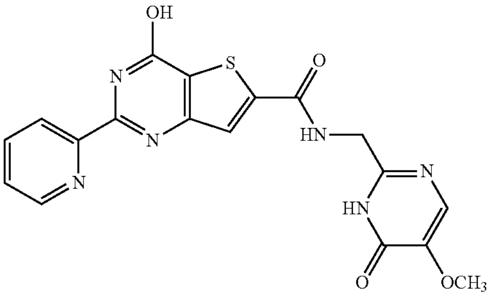 [SMILES: COc1cnc(CNC(=O)c2cc3nc(-c4ccccn4)nc(O)c3s2)[nH]c1=O] | 410 | 411.1 | 411.0 |

TABLE 3-continued
| Mass Spectral Data | | | |
|---|---|---|---|
| Compound | MW | M + H (calculated) | M + H (observed) |
| 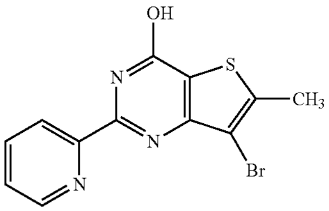 [SMILES: Cc1sc2c(O)nc(-c3ccccn3)nc2c1Br] | 322 | 322.0 | 321.9 |
| 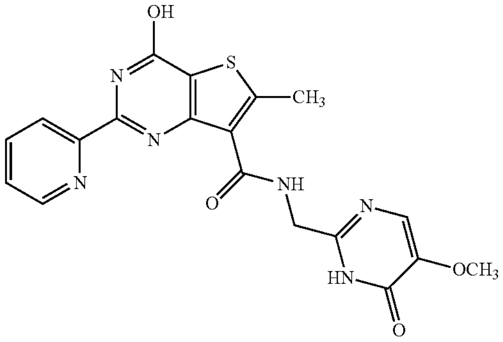 [SMILES: COc1cnc(CNC(=O)c2c(C)sc3c(O)nc(-c4ccccn4)nc23)[nH]c1=O] | 424 | 425.1 | 425.2 |
| 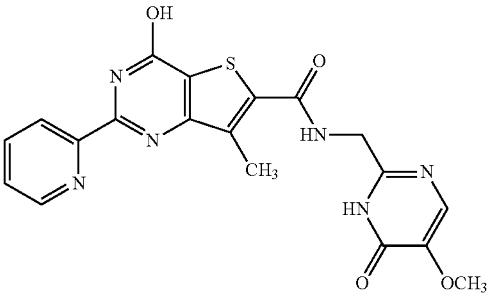 [SMILES: COc1cnc(CNC(=O)c2sc3c(O)nc(-c4ccccn4)nc3c2C)[nH]c1=O] | 424 | 425.1 | 425.2 |
| 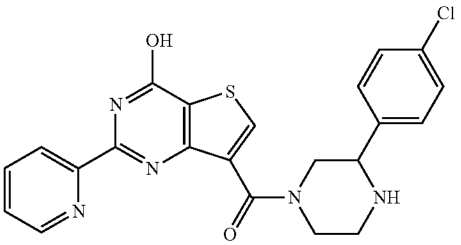 [SMILES: O=C(c1csc2c(O)nc(-c3ccccn3)nc12)N1CCNC(c2ccc(Cl)cc2)C1] | 452 | 452.1 | 452.0 |
| 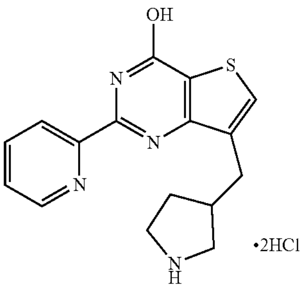 [SMILES: Oc1nc(-c2ccccn2)nc2c(CC3CCNC3)csc12] •2HCl | 385 | 313.1 | 313.2 |

TABLE 3-continued
| Mass Spectral Data | | | |
|---|---|---|---|
| Compound | MW | M + H (calculated) | M + H (observed) |
| 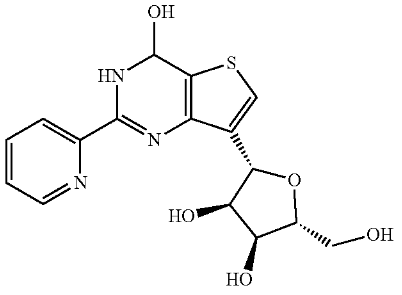 [SMILES: OC[C@H]1O[C@@H](c2csc3c2N=C(c2ccccn2)NC3O)[C@H](O)[C@@H]1O] | 361 | 362.1 | 362.0 |
| 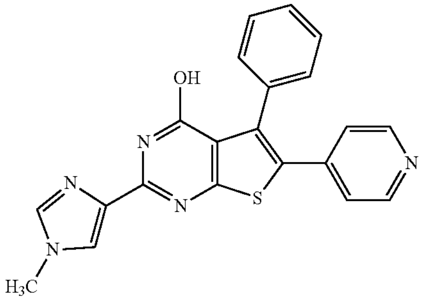 [SMILES: Cn1cnc(-c2nc(O)c3c(-c4ccccc4)c(-c4ccncc4)sc3n2)c1] | 458 | 386.1 | 386.2 |
| 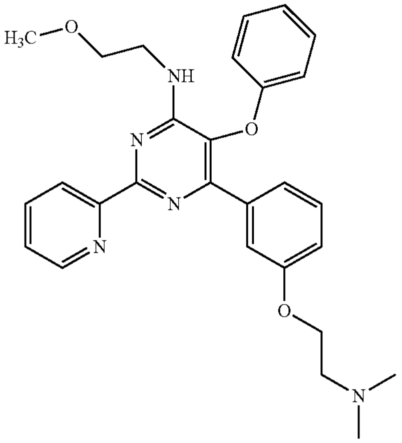 [SMILES: COCCNc1nc(-c2ccccn2)nc(-c2cccc(OCCN(C)C)c2)c1Oc1ccccc1] | 486 | 486.2 | 486.2 |
| 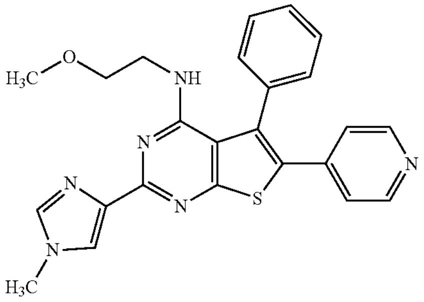 [SMILES: COCCNc1nc(-c2cn(C)cn2)nc2sc(-c3ccncc3)c(-c3ccccc3)c12] | 443 | 443.2 | 443.2 |

TABLE 3-continued
| Mass Spectral Data | | | |
|---|---|---|---|
| Compound | MW | M + H (calculated) | M + H (observed) |
| 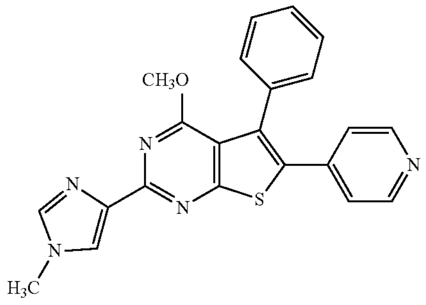 | 399 | 400.1 | 400.2 |
| 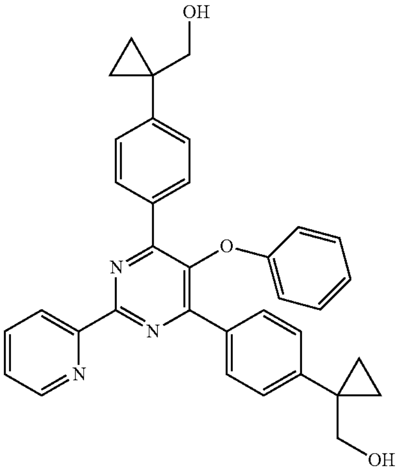 [SMILES: OCC1(c2ccc(-c3nc(-c4ccccn4)nc(-c4ccc(C5(CO)CC5)cc4)c3Oc3ccccc3)cc2)CC1] | 542 | 542.2 | 542.3 |
| 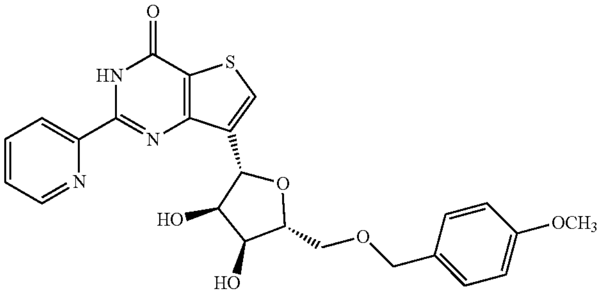 [SMILES: COc1ccc(COC[C@H]2O[C@@H](c3csc4c(=O)[nH]c(-c5ccccn5)nc34)[C@H](O)[C@@H]2O)cc1] | 482 | 482.1 | 482.2 |
| 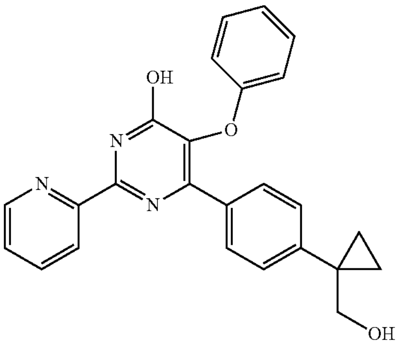 [SMILES: OCC1(c2ccc(-c3nc(-c4ccccn4)nc(O)c3Oc3ccccc3)cc2)CC1] | 411 | 412.2 | 412.0 |

TABLE 3-continued
| Mass Spectral Data | | | |
|---|---|---|---|
| Compound | MW | M + H (calculated) | M + H (observed) |
| 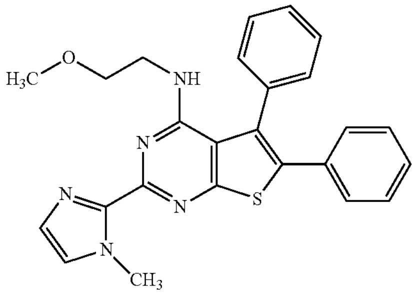 [SMILES: COCCNc1nc(-c2nccn2C)nc2sc(-c3ccccc3)c(-c3ccccc3)c12] | 442 | 442.2 | 442.2 |
| 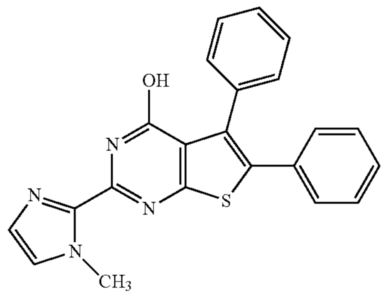 [SMILES: Cn1ccnc1-c1nc(O)c2c(-c3ccccc3)c(-c3ccccc3)sc2n1] | 384 | 385.1 | 385.0 |
| 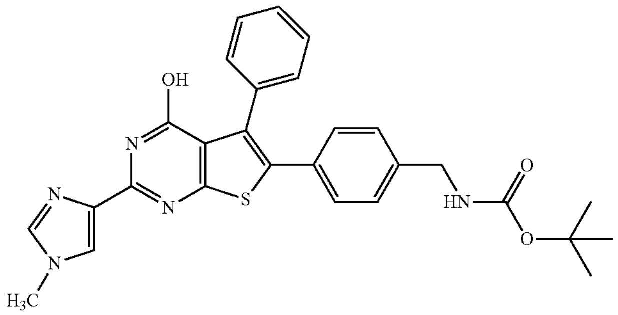 [SMILES: Cn1cnc(-c2nc(O)c3c(-c4ccccc4)c(-c4ccc(CNC(=O)OC(C)(C)C)cc4)sc3n2)c1] | 514 | 514.2 | 514.2 |
| 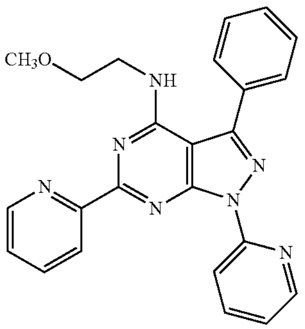 | 423 | 424.2 | 424.2 |

TABLE 3-continued
| Mass Spectral Data | | | |
|---|---|---|---|
| Compound | MW | M + H (calculated) | M + H (observed) |
| 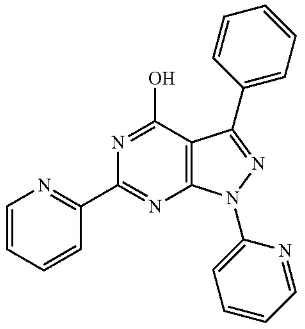 [SMILES: Oc1nc(-c2ccccn2)nc2c1c(-c1ccccc1)nn2-c1ccccn1] | 366 | 367.1 | 367.1 |
| 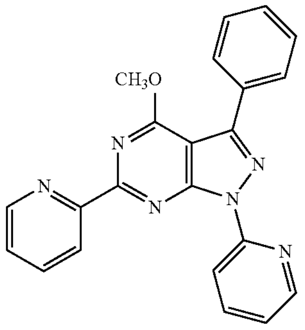 | 380 | 381.1 | 381.2 |
| 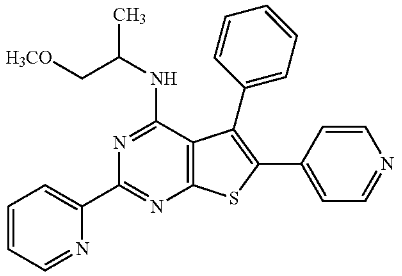 [SMILES: COCC(C)Nc1nc(-c2ccccn2)nc2sc(-c3ccncc3)c(-c3ccccc3)c12] | 454 | 454.2 | 454.2 |
| 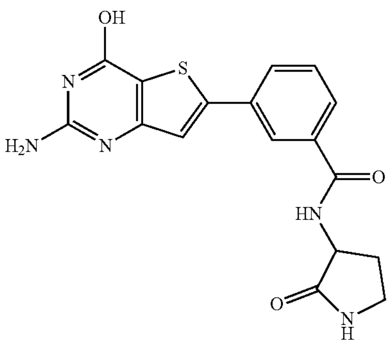 [SMILES: Nc1nc(O)c2sc(-c3cccc(C(=O)NC4CCNC4=O)c3)cc2n1] | 369 | 370.1 | 370.0 |

TABLE 3-continued
| Mass Spectral Data | | | |
|---|---|---|---|
| Compound | MW | M + H (calculated) | M + H (observed) |
| 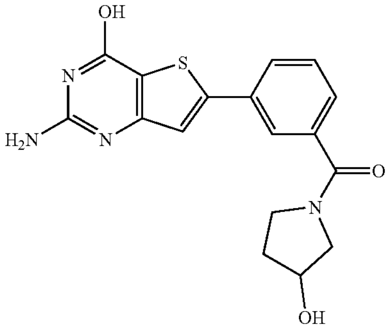 [SMILES: Nc1nc(O)c2sc(-c3cccc(C(=O)N4CCC(O)C4)c3)cc2n1] | 356 | 357.1 | 357.0 |
| 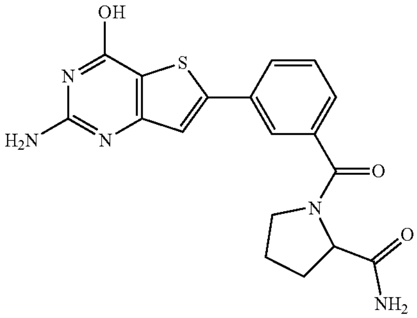 [SMILES: NC(=O)C1CCCN1C(=O)c1cccc(-c2cc3nc(N)nc(O)c3s2)c1] | 383 | 384.1 | 384.2 |
| 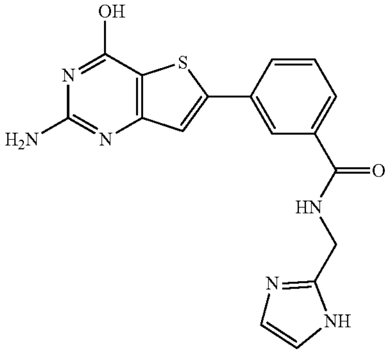 [SMILES: Nc1nc(O)c2sc(-c3cccc(C(=O)NCc4ncc[nH]4)c3)cc2n1] | 366 | 367.1 | 367.0 |
| 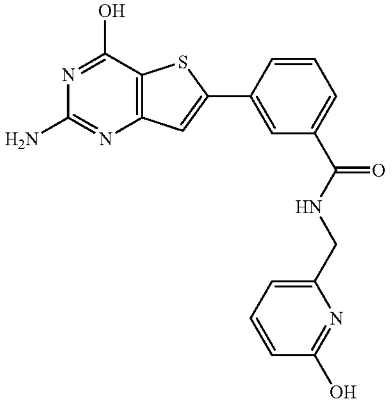 [SMILES: Nc1nc(O)c2sc(-c3cccc(C(=O)NCc4cccc(O)n4)c3)cc2n1] | 393 | 394.1 | 394.2 |

TABLE 3-continued
| Mass Spectral Data | | | |
|---|---|---|---|
| Compound | MW | M + H (calculated) | M + H (observed) |
| 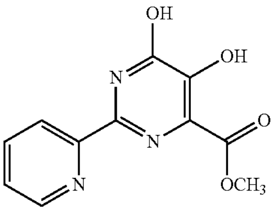 [SMILES: COC(=O)c1nc(-c2ccccn2)nc(O)c1O] | 247 | 248.1 | 247.9 |
| 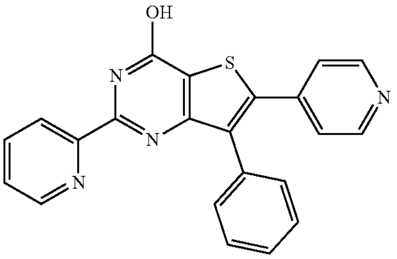 [SMILES: Oc1nc(-c2ccccn2)nc2c(-c3ccccc3)c(-c3ccncc3)sc12] | 382 | 383.1 | 383.2 |
| 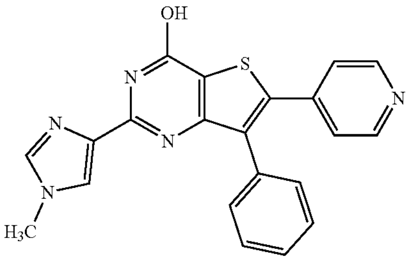 [SMILES: Cn1cnc(-c2nc(O)c3sc(-c4ccncc4)c(-c4ccccc4)c3n2)c1] | 385 | 386.1 | 386.2 |
| 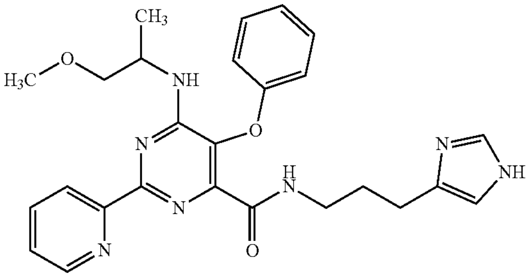 [SMILES: COCC(C)Nc1nc(-c2ccccn2)nc(C(=O)NCCCc2c[nH]cn2)c1Oc1ccccc1] | 488 | 488.2 | 488.2 |
| 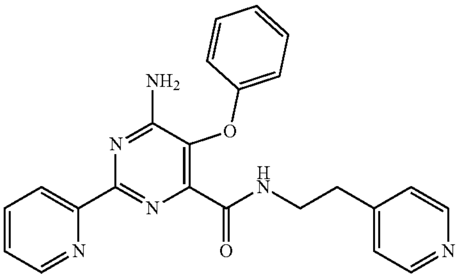 [SMILES: Nc1nc(-c2ccccn2)nc(C(=O)NCCc2ccncc2)c1Oc1ccccc1] | 412 | 413.2 | 413.2 |

TABLE 3-continued
| Mass Spectral Data | | | |
|---|---|---|---|
| Compound | MW | M + H (calculated) | M + H (observed) |
| 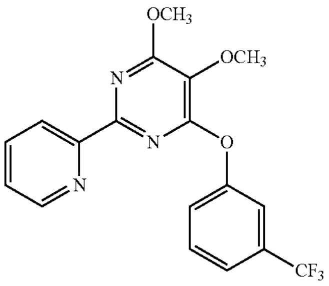 [SMILES: COc1nc(-c2ccccn2)nc(Oc2cccc(C(F)(F)F)c2)c1OC] | 377 | 378.1 | 378.0 |
| 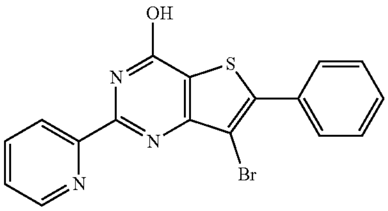 [SMILES: Oc1nc(-c2ccccn2)nc2c(Br)c(-c3ccccc3)sc12] | 384 | 384.0 | 384.0 |
| 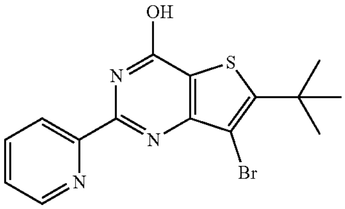 [SMILES: CC(C)(C)c1sc2c(O)nc(-c3ccccn3)nc2c1Br] | 364 | 364.0 | 364.0 |
| 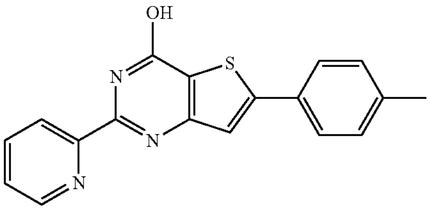 [SMILES: Cc1ccc(-c2cc3nc(-c4ccccn4)nc(O)c3s2)cc1] | 319 | 320.1 | 320.0 |
| 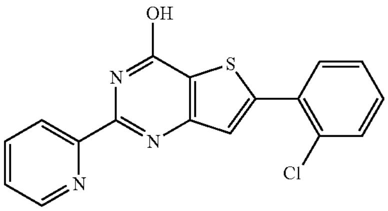 [SMILES: Oc1nc(-c2ccccn2)nc2cc(-c3ccccc3Cl)sc12] | 340 | 340.0 | 340.0 |
| 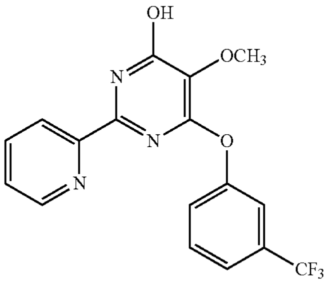 | 363 | 364.1 | 364.0 |

TABLE 3-continued
Mass Spectral Data
| Compound | MW | M + H (calculated) | M + H (observed) |
|---|---|---|---|
| 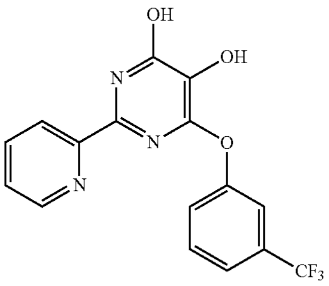 [SMILES: Oc1nc(-c2ccccn2)nc(Oc2cccc(C(F)(F)F)c2)c1O] | 349 | 350.1 | 350.1 |
| 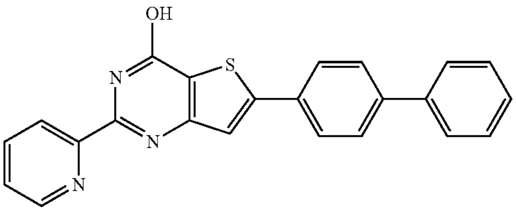 [SMILES: Oc1nc(-c2ccccn2)nc2cc(-c3ccc(-c4ccccc4)cc3)sc12] | 381 | 382.1 | 382.0 |
| 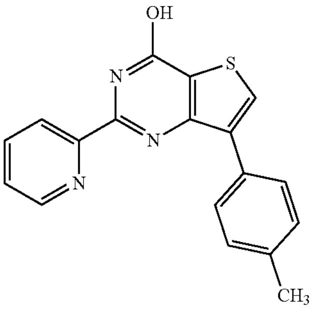 [SMILES: Cc1ccc(-c2csc3c(O)nc(-c4ccccn4)nc23)cc1] | 319 | 320.1 | 320.0 |
| 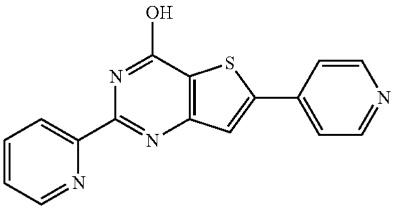 [SMILES: Oc1nc(-c2ccccn2)nc2cc(-c3ccncc3)sc12] | 306 | 307.1 | 307.0 |
| 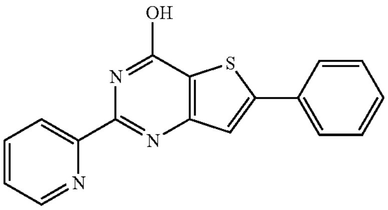 [SMILES: Oc1nc(-c2ccccn2)nc2cc(-c3ccccc3)sc12] | 305 | 306.1 | 306.0 |
| 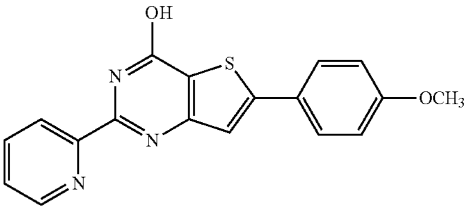 [SMILES: COc1ccc(-c2cc3nc(-c4ccccn4)nc(O)c3s2)cc1] | 335 | 336.1 | 336.0 |

TABLE 3-continued
| Mass Spectral Data | | | |
|---|---|---|---|
| Compound | MW | M + H (calculated) | M + H (observed) |
| 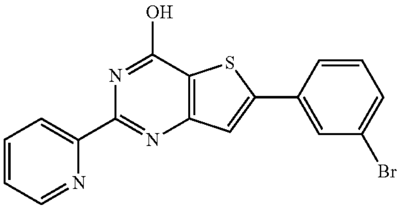 [SMILES: Oc1nc(-c2ccccn2)nc2cc(-c3cccc(Br)c3)sc12] | 384 | 384.0 | 384.0 |
| 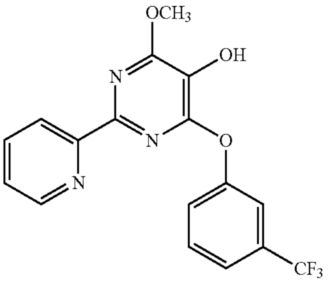 [SMILES: COc1nc(-c2ccccn2)nc(Oc2cccc(C(F)(F)F)c2)c1O] | 363 | 364.1 | 364.0 |
| 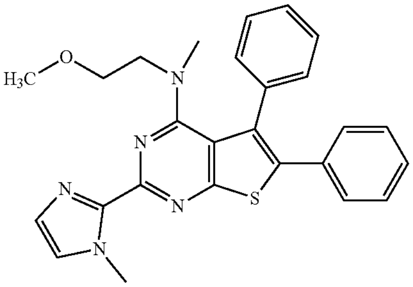 [SMILES: COCCN(C)c1nc(-c2nccn2C)nc2sc(-c3ccccc3)c(-c3ccccc3)c12] | 456 | 456.2 | 456.2 |
| 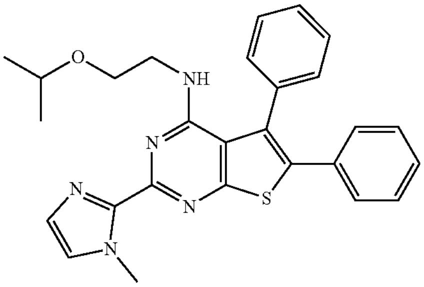 [SMILES: CC(C)OCCNc1nc(-c2nccn2C)nc2sc(-c3ccccc3)c(-c3ccccc3)c12] | 470 | 470.2 | 470.2 |
| 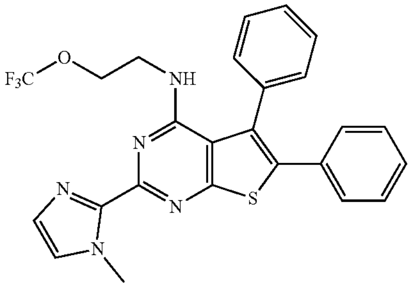 [SMILES: Cn1ccnc1-c1nc(NCCOC(F)(F)F)c2c(-c3ccccc3)c(-c3ccccc3)sc2n1] | 496 | 410.2 calculated [M − 85.0] | 410.2 |

TABLE 3-continued
| Mass Spectral Data | | | |
|---|---|---|---|
| Compound | MW | M + H (calculated) | M + H (observed) |
| 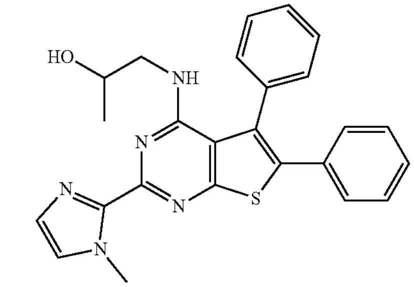 [SMILES: CC(O)CNc1nc(-c2nccn2C)nc2sc(-c3ccccc3)c(-c3ccccc3)c12] | 442 | 442.2 | 422.2 |
| 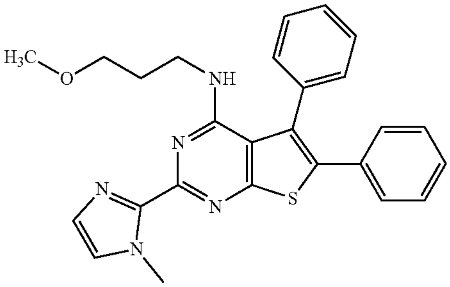 [SMILES: COCCCNc1nc(-c2nccn2C)nc2sc(-c3ccccc3)c(-c3ccccc3)c12] | 456 | 456.2 | 456.2 |
| 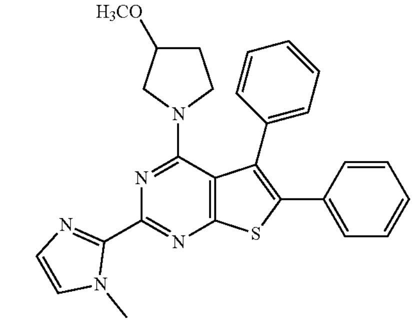 [SMILES: COC1CCN(c2nc(-c3nccn3C)nc3sc(-c4ccccc4)c(-c4ccccc4)c23)C1] | 468 | 468.2 | 468.2 |
| 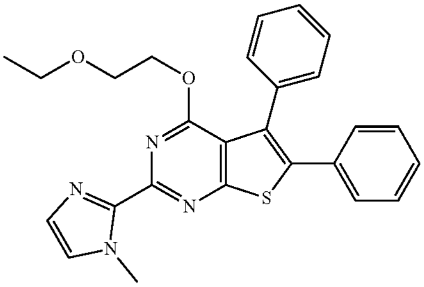 [SMILES: CCOCCOc1nc(-c2nccn2C)nc2sc(-c3ccccc3)c(-c3ccccc3)c12] | 457 | 457.2 | 457.0 |
| 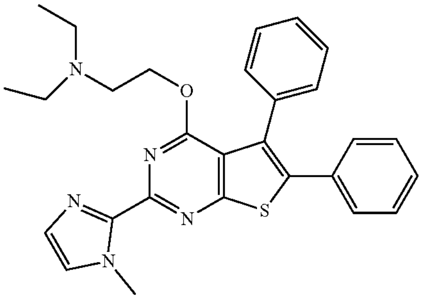 [SMILES: CCN(CC)CCOc1nc(-c2nccn2C)nc2sc(-c3ccccc3)c(-c3ccccc3)c12] | 484 | 484.3 | 484.0 |

TABLE 3-continued
| Mass Spectral Data | | | |
|---|---|---|---|
| Compound | MW | M + H (calculated) | M + H (observed) |
| 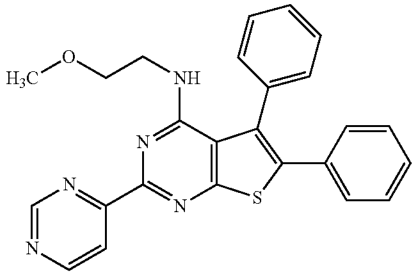 [SMILES: COCCNc1nc(-c2ccncn2)nc2sc(-c3ccccc3)c(-c3ccccc3)c12] | 440 | 440.2 | 440.2 |
| 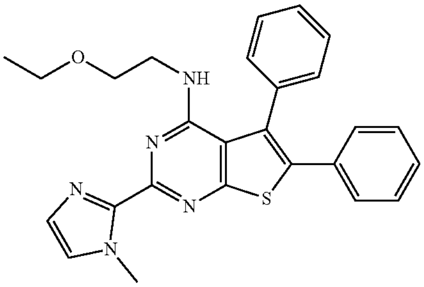 [SMILES: CCOCCNc1nc(-c2nccn2C)nc2sc(-c3ccccc3)c(-c3ccccc3)c12] | 456 | 456.2 | 456.2 |
| 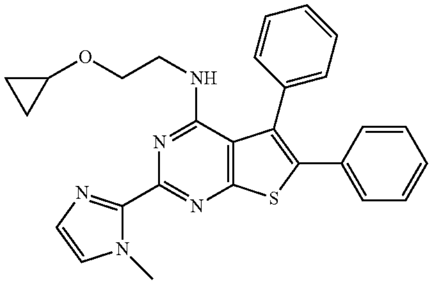 [SMILES: Cn1ccnc1-c1nc(NCCOC2CC2)c2c(-c3ccccc3)c(-c3ccccc3)sc2n1] | 468 | 468.2 | 468.2 |
| 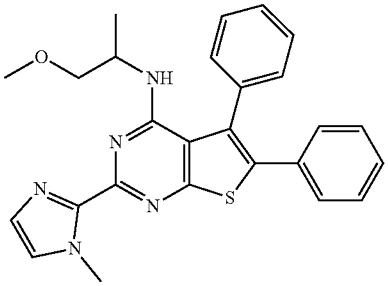 [SMILES: COCC(C)Nc1nc(-c2nccn2C)nc2sc(-c3ccccc3)c(-c3ccccc3)c12] | 456 | 456.2 | 456.2 |
| 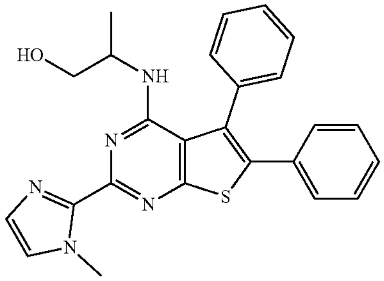 [SMILES: CC(CO)Nc1nc(-c2nccn2C)nc2sc(-c3ccccc3)c(-c3ccccc3)c12] | 442 | 442.2 | 442.2 |

TABLE 3-continued
| Mass Spectral Data | | | |
|---|---|---|---|
| Compound | MW | M + H (calculated) | M + H (observed) |
| 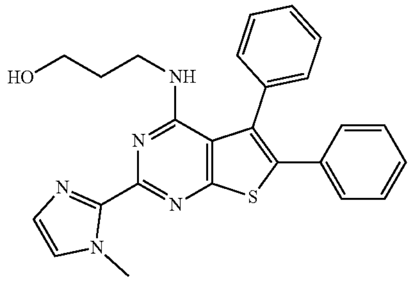 [SMILES: Cn1ccnc1-c1nc(NCCCO)c2c(-c3ccccc3)c(-c3ccccc3)sc2n1] | 442 | 442.2 | 442.0 |
| 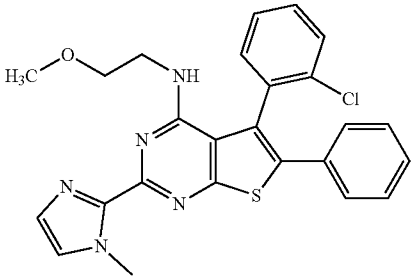 [SMILES: COCCNc1nc(-c2nccn2C)nc2sc(-c3ccccc3)c(-c3ccccc3Cl)c12] | 476 | 476.2 | 476.2 |
| 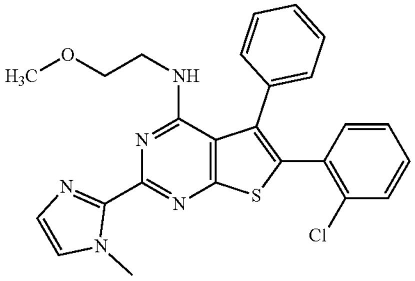 | 476 | 476.2 | 476.2 |
| 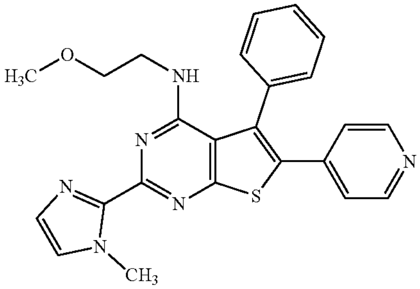 [SMILES: COCCNc1nc(-c2nccn2C)nc2sc(-c3ccncc3)c(-c3ccccc3)c12] | 443 | 443.2 | 443.2 |
| 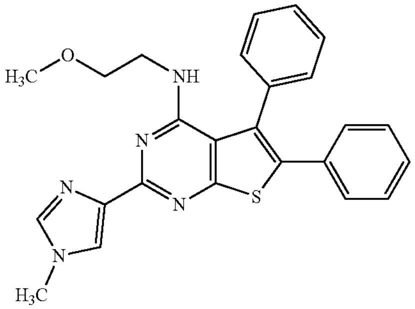 [SMILES: COCCNc1nc(-c2cn(C)cn2)nc2sc(-c3ccccc3)c(-c3ccccc3)c12] | 442 | 442.2 | 442.2 |

TABLE 3-continued
| Mass Spectral Data | | | |
|---|---|---|---|
| Compound | MW | M + H (calculated) | M + H (observed) |
| 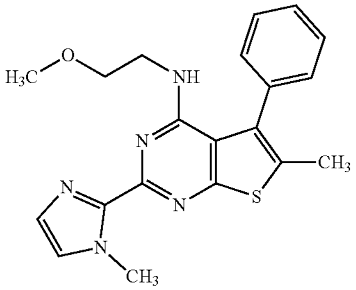 | 379 | 380.2 | 380.2 |
| 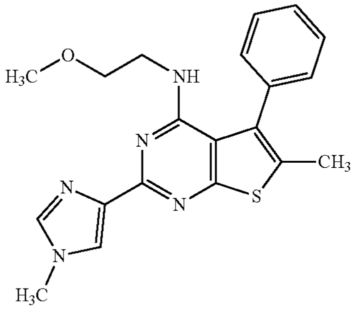 [SMILES: COCCNc1nc(-c2cn(C)cn2)nc2sc(C)c(-c3ccccc3)c12] | 379 | 380.2 | 380.2 |
| 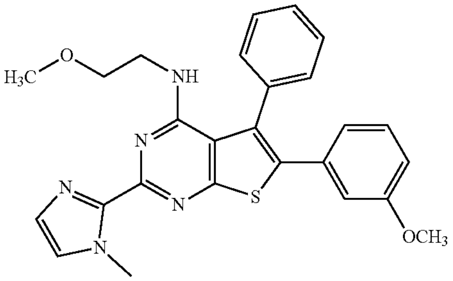 [SMILES: COCCNc1nc(-c2nccn2C)nc2sc(-c3cccc(OC)c3)c(-c3ccccc3)c12] | 472 | 472.2 | 472.2 |
| 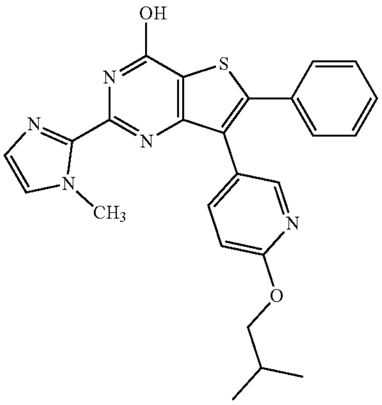 [SMILES: CC(C)COc1ccc(-c2c(-c3ccccc3)sc3c(O)nc(-c4nccn4C)nc23)cn1] | 458 | 458.2 | 458.2 |

TABLE 3-continued
| Mass Spectral Data | | | |
|---|---|---|---|
| Compound | MW | M + H (calculated) | M + H (observed) |
| 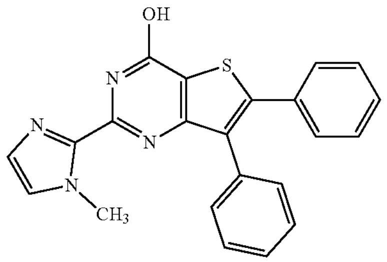 [SMILES: Cn1ccnc1-c1nc(O)c2sc(-c3ccccc3)c(-c3ccccc3)c2n1] | 384 | 384.1 | 385.2 |
| 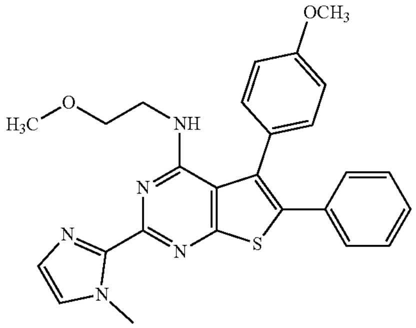 [SMILES: COCCNc1nc(-c2nccn2C)nc2sc(-c3ccccc3)c(-c3ccc(OC)cc3)c12] | 472 | 472.2 | 472.2 |
| 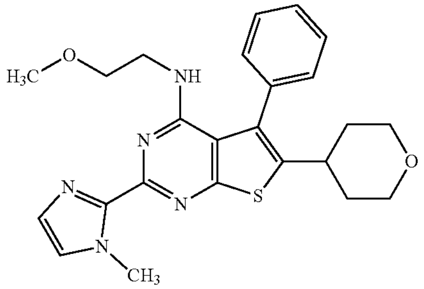 | 450 | 450.2 | 450.2 |
| 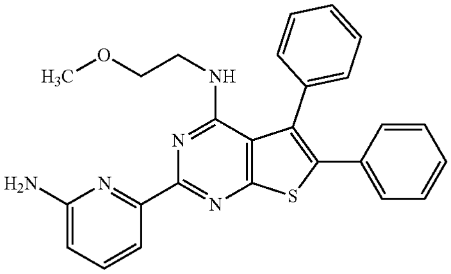 [SMILES: COCCNc1nc(-c2cccc(N)n2)nc2sc(-c3ccccc3)c(-c3ccccc3)c12] | 454 | 454.2 | 454.2 |
| 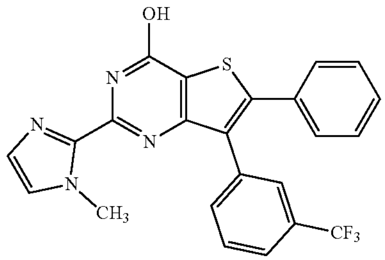 [SMILES: Cn1ccnc1-c1nc(O)c2sc(-c3ccccc3)c(-c3cccc(C(F)(F)F)c3)c2n1] | 452 | 453.1 | 453.0 |

TABLE 3-continued
| Mass Spectral Data | | | |
|---|---|---|---|
| Compound | MW | M + H (calculated) | M + H (observed) |
| 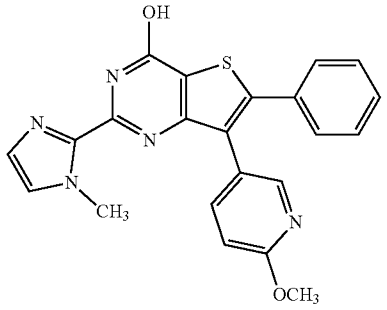 [SMILES: COc1ccc(-c2c(-c3ccccc3)sc3c(O)nc(-c4nccn4C)nc23)cn1] | 415 | 416.1 | 416.0 |
| 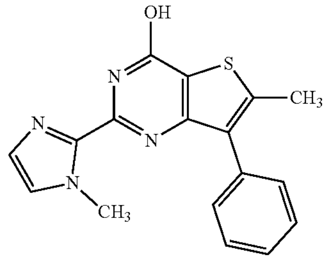 [SMILES: Cc1sc2c(O)nc(-c3nccn3C)nc2c1-c1ccccc1] | 322 | 323.1 | 323.1 |
| 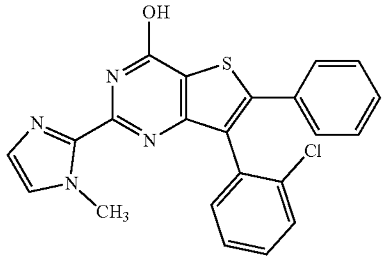 [SMILES: Cn1ccnc1-c1nc(O)c2sc(-c3ccccc3)c(-c3ccccc3Cl)c2n1] | 419 | 419.1 | 419.0 |
| 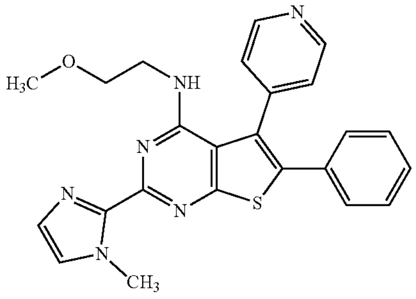 [SMILES: COCCNc1nc(-c2nccn2C)nc2sc(-c3ccccc3)c(-c3ccncc3)c12] | 443 | 443.2 | 443.2 |
| 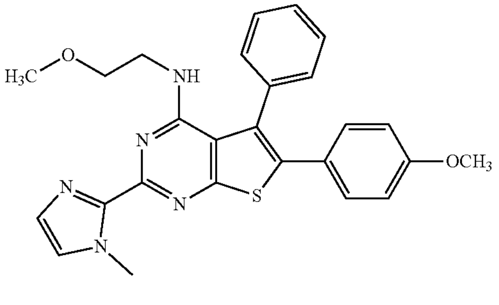 [SMILES: COCCNc1nc(-c2nccn2C)nc2sc(-c3ccc(OC)cc3)c(-c3ccccc3)c12] | 472 | 472.2 | 472.2 |

TABLE 3-continued
| Mass Spectral Data | | | |
|---|---|---|---|
| Compound | MW | M + H (calculated) | M + H (observed) |
| 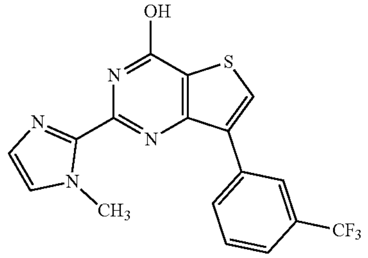 [SMILES: Cn1ccnc1-c1nc(O)c2scc(-c3cccc(C(F)(F)F)c3)c2n1] | 376 | 377.1 | 377.0 |
| 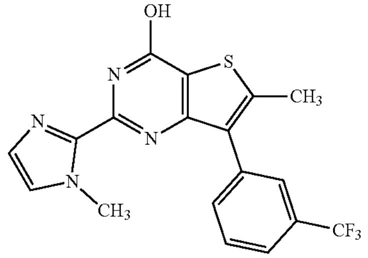 [SMILES: Cc1sc2c(O)nc(-c3nccn3C)nc2c1-c1cccc(C(F)(F)F)c1] | 390 | 391.1 | 391.0 |
| 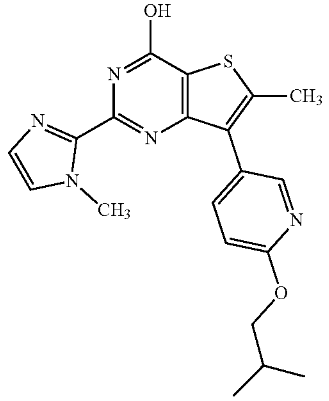 [SMILES: Cc1sc2c(O)nc(-c3nccn3C)nc2c1-c1ccc(OCC(C)C)nc1] | 395 | 396.2 | 396.2 |
| 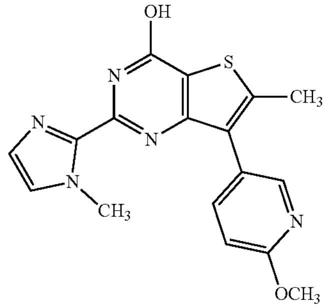 [SMILES: COc1ccc(-c2c(C)sc3c(O)nc(-c4nccn4C)nc23)cn1] | 353 | 354.4 | need |
| 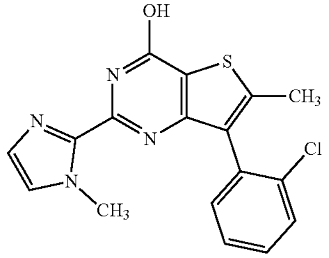 [SMILES: Cc1sc2c(O)nc(-c3nccn3C)nc2c1-c1ccccc1Cl] | 357 | 357.1 | 357.0 |

TABLE 3-continued
| Mass Spectral Data | | | |
| --- | --- | --- | --- |
| Compound | MW | M + H (calculated) | M + H (observed) |
| 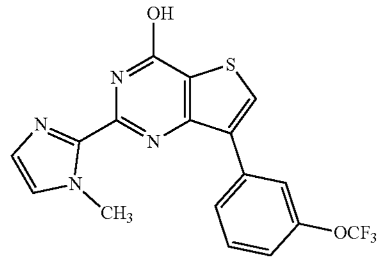 [SMILES: Cn1ccnc1-c1nc(O)c2scc(-c3cccc(OC(F)(F)F)c3)c2n1] | 392 | 393.1 | 393.0 |
| 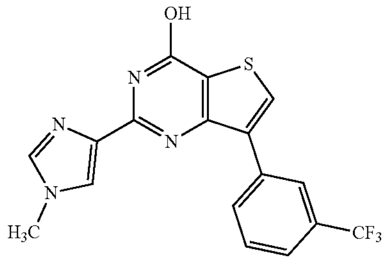 [SMILES: Cn1cnc(-c2nc(O)c3scc(-c4cccc(C(F)(F)F)c4)c3n2)c1] | 376 | 377.1 | 377.0 |
| 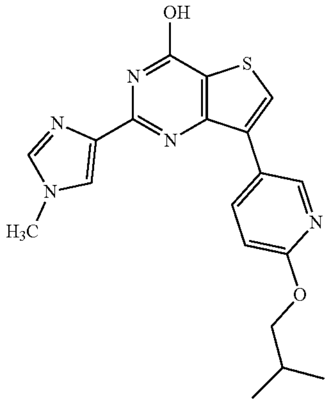 [SMILES: CC(C)COc1ccc(-c2csc3c(O)nc(-c4cn(C)cn4)nc23)cn1] | 381 | 382.1 | 382.2 |
| 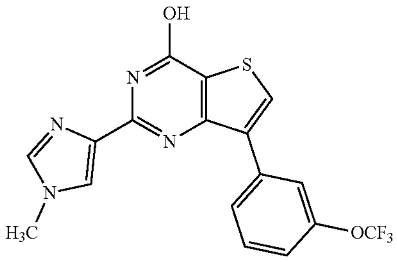 [SMILES: Cn1cnc(-c2nc(O)c3scc(-c4cccc(OC(F)(F)F)c4)c3n2)c1] | 392 | 393.1 | 393.0 |
| 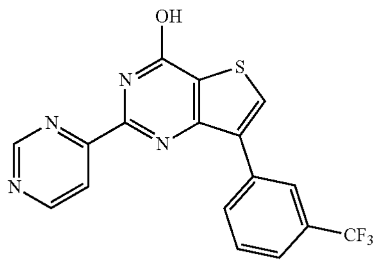 [SMILES: Oc1nc(-c2ccncn2)nc2c(-c3cccc(C(F)(F)F)c3)csc12] | 374 | 375.1 | 375.0 |

TABLE 3-continued
| Mass Spectral Data | | | |
|---|---|---|---|
| Compound | MW | M + H (calculated) | M + H (observed) |
| 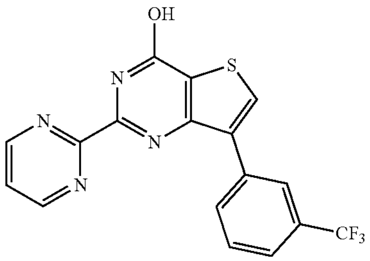 [SMILES: Oc1nc(-c2ncccn2)nc2c(-c3cccc(C(F)(F)F)c3)csc12] | 374 | 375.1 | 375.0 |
| 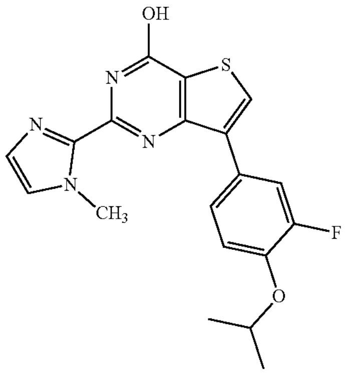 [SMILES: CC(C)Oc1ccc(-c2csc3c(O)nc(-c4nccn4C)nc23)cc1F] | 384 | 385.1 | 385.0 |
| 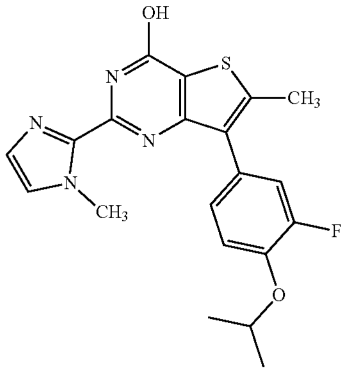 [SMILES: Cc1sc2c(O)nc(-c3nccn3C)nc2c1-c1ccc(OC(C)C)c(F)c1] | 398 | 399.1 | 399.1 |
| 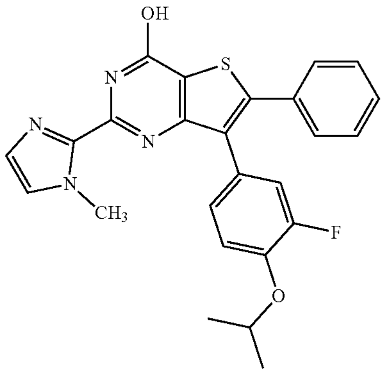 [SMILES: CC(C)Oc1ccc(-c2c(-c3ccccc3)sc3c(O)nc(-c4nccn4C)nc23)cc1F] | 460 | 461.2 | 461.1 |

TABLE 3-continued
| Mass Spectral Data | | | |
|---|---|---|---|
| Compound | MW | M + H (calculated) | M + H (observed) |
| 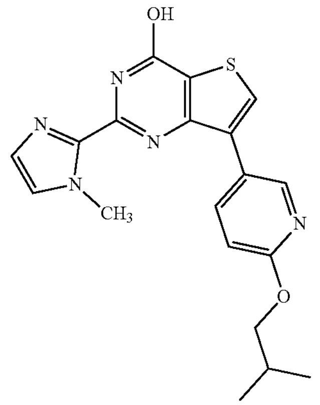 [SMILES: CC(C)COc1ccc(-c2csc3c(O)nc(-c4nccn4C)nc23)cn1] | 381 | 382.1 | 382.2 |
| 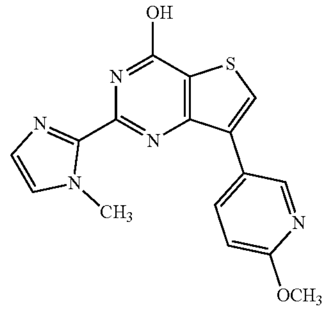 [SMILES: COc1ccc(-c2csc3c(O)nc(-c4nccn4C)nc23)cn1] | 339 | 340.1 | 340.0 |
| 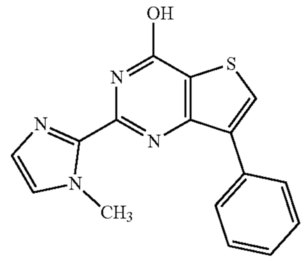 [SMILES: Cn1ccnc1-c1nc(O)c2scc(-c3ccccc3)c2n1] | 308 | 309.1 | 309.0 |
| 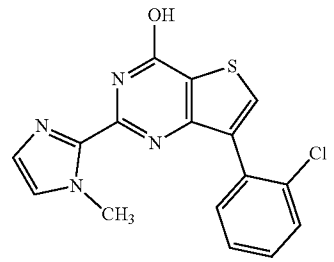 [SMILES: Cn1ccnc1-c1nc(O)c2scc(-c3ccccc3Cl)c2n1] | 342 | 343.0 | 343.0 |

TABLE 3-continued
| Mass Spectral Data | | | |
|---|---|---|---|
| Compound | MW | M + H (calculated) | M + H (observed) |
| 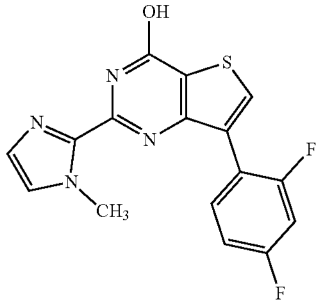 [SMILES: Cn1ccnc1-c1nc(O)c2scc(-c3ccc(F)cc3F)c2n1] | 344 | 345.1 | 345.0 |
| 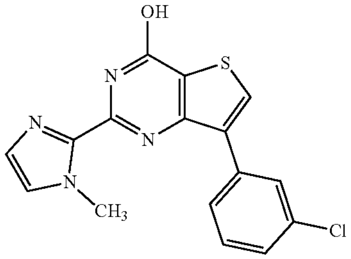 [SMILES: Cn1ccnc1-c1nc(O)c2scc(-c3cccc(Cl)c3)c2n1] | 342 | 343.0 | 343.0 |
| 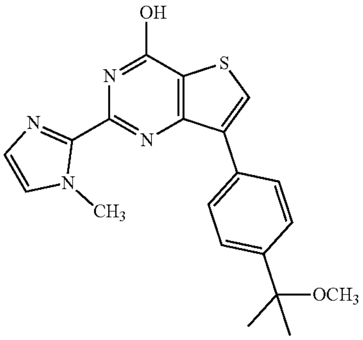 [SMILES: COC(C)(C)c1ccc(-c2csc3c(O)nc(-c4nccn4C)nc23)cc1] | 380 | 383.1 | 381.2 |
| 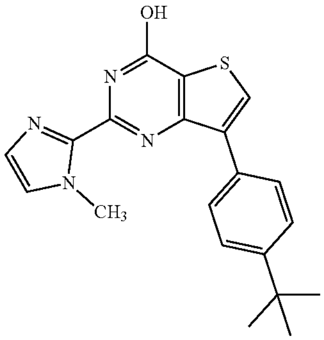 [SMILES: Cn1ccnc1-c1nc(O)c2scc(-c3ccc(C(C)(C)C)cc3)c2n1] | 364 | 365.1 | 365.2 |
| 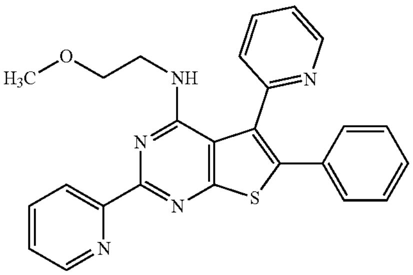 | 440 | 440.2 | 440.2 |

TABLE 3-continued

| Mass Spectral Data | | | |
|---|---|---|---|
| Compound | MW | M + H (calculated) | M + H (observed) |
| 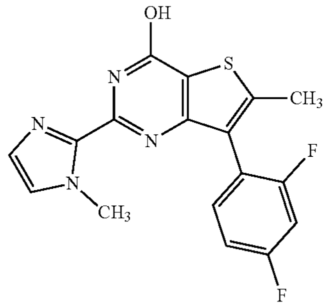 [SMILES: Cc1sc2c(O)nc(-c3nccn3C)nc2c1-c1ccc(F)cc1F] | 358 | 359.1 | 359.2 |
| 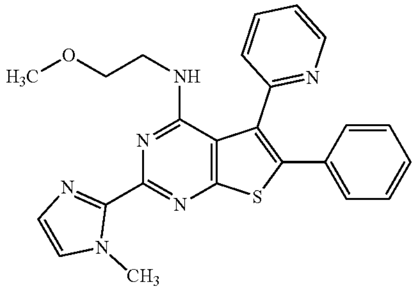 | 443 | 443.2 | 443.2 |

6.6. Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and then extrapolated therefrom for dosages for humans. In some embodiments, the active compound is administered in a method to achieve a therapeutically effective concentration of the drug. In some embodiments, a companion diagnostic (see, e.g., Olsen D and Jorgensen J T, *Front. Oncol.,* 2014 May 16, 4:105, doi: 10.3389/fonc.2014.00105) is used to determine the therapeutic concentration and safety profile of the active compound in specific subjects or subject populations.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 μg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil. In some embodiments, the suspension is a suspension of microparticles or nanoparticles. In some embodiments, the emulsion is an emulsion of microparticles or nanoparticles.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. In some embodiments, the suspension is a suspension of microparticles or nanoparticles. In some embodiments, the emulsion is an emulsion of microparticles or nanoparticles. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased subject compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Targeted Formulations

The compounds provided herein, or pharmaceutically acceptable salts thereof, may also be formulated to be targeted to a particular tissue, receptor, or other area of the body of the subject to be treated, including liposome-, resealed erythrocyte-, and antibody-based delivery systems. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, the antibody-based delivery system is an antibody-drug conjugate ("ADC"), e.g., as described in Hamilton G S, *Biologicals,* 2015 September, 43(5):318-32; Kim E G and Kim K M, *Biomol. Ther.* (*Seoul*), 2015 November, 23(6):493-509; and Peters C and Brown S, *Biosci. Rep.,* 2015 Jun. 12, 35(4) pii: e00225, each of which is incorporated herein by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms or progression of a disease or disorder disclosed herein, and a label that indicates that the compound or pharmaceutically acceptable salt thereof is used for treatment, prevention or amelioration of one or more symptoms or progression of a disease or disorder disclosed herein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

6.7. Dosing

The compounds and pharmaceutical compositions provided herein may be dosed in certain therapeutically or prohylactically effective amounts, certain time intervals, certain dosage forms, and certain dosage administration methods as described below.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The methods provided herein encompass treating a patient regardless of subject's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancers, inflammatory diseases, rasopathies, or fibrotic disease.

In one embodiment, provided herein is a method of treating, preventing, or managing cancers, inflammatory diseases, rasopathies, and fibrotic disease, comprising administering to a subject a compound provided herein, or a derivative thereof; in combination with one or more second active agents.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease or disorder being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the subject.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent, prior to, during, or after the use of conventional therapy.

7. EXAMPLES

The following examples are offered to illustrate but not to limit the disclosure.

Example 1

Computational Procedure for Modeling

The protein structures used in this work were obtained from the RCSB PDB (www.rcsb.org).

These structures were prepared for modeling using a suite of structure preparation tools available in the Molecular Operating Environment software (MOE). MOE is a state of the art molecular modeling package licensed by Chemical Computing Group (Molecular Operating Environment (MOE), 2016.08; Chemical Computing Group Inc., 1010 Sherbrooke St. West, Suite #910, Montreal, QC, Canada, H3A 2R7, 2016). It is used extensively in the pharmaceutical industry to carry out a wide range of computer-aided drug design activities. Specifically, each structure was examined for missing atoms and chain breaks. Where possible these were corrected by modeling in incomplete residues or capping. The ligand was also evaluated to ensure the correct structure and bond orders. All titratable residues and the ligand were subjected to Protonate3D (Labute, P.; Protonate3D: Assignment of Ionization States and Hydrogen Coordinates to Macromolecular Structures; Proteins 75 (2008) 187-205) to determine the most probably protonation states at pH 7. Finally, the environment around the ligand was subjected to restrained optimization to remove bad intermolecular contacts and reduce the strain energy for the ligand.

Compounds of interest were modeled in the appropriate binding site using a variety of methods all available in MOE. In many cases the ligands had to be docked into the site. Docking is an automated approach to examine all of the possible ways a ligand might fit into a protein binding site of interest and score the possibilities. These scored structures were used to suggest the best overall protein-ligand complex structure. Docked structures can be evaluated further using other energetic or structural evaluations. In many cases, we also computed the location and contributions of water molecules to binding. This analysis based on 3D-RISM calculations (Luchko, T., Gurasov, S., Roe, D. R., Simmerling, C., Case, D. A., Tuszynski, J., Kovalenko, A.; Three-Dimensional Molecular Theory of Solvation Coupled with Molecular Dynamics in Amber; J. Chem. Theory Comput. 6 (2010) 607-624) can be very helpful for understanding water mediated interactions, and new potential binding sites in the protein that might be exploited with appropriate substitution of the putative ligand.

The ability to build computational models before undertaking their synthesis is a powerful tool for improving the speed and success of drug discovery (Merz, Kenneth M.; Ringe, Dagmar; Reynolds, Charles H., Editors, Drug design: ligand and structure based approaches, Cambridge University Press, 2010).

The docking models displayed in the figures include residues with any atom in close proximity to within a 2.5 angstrom distance from any atom in the ligand. In addition, residues within approximately 2.5 angstroms from the ligand with specific interactions (i.e., a hydrogen bond) are included, and highlighted in the 2D interaction maps.

FIG. 1 displays GDP bound to the GTP binding site of KRas as determined by the crystal structure of GDP with KRas, PDB code: 4epr. The KRas residues within 2.5 angstroms of the ligand or approximately 2.5 angstroms from the ligand with specific interactions are Gly13, Gly15, Lys16, Ser17, Ala18, Val29, Asp30, Asn116, Asp119, Leu120, Ser145, Ala146 and Lys147.

Figure 2:
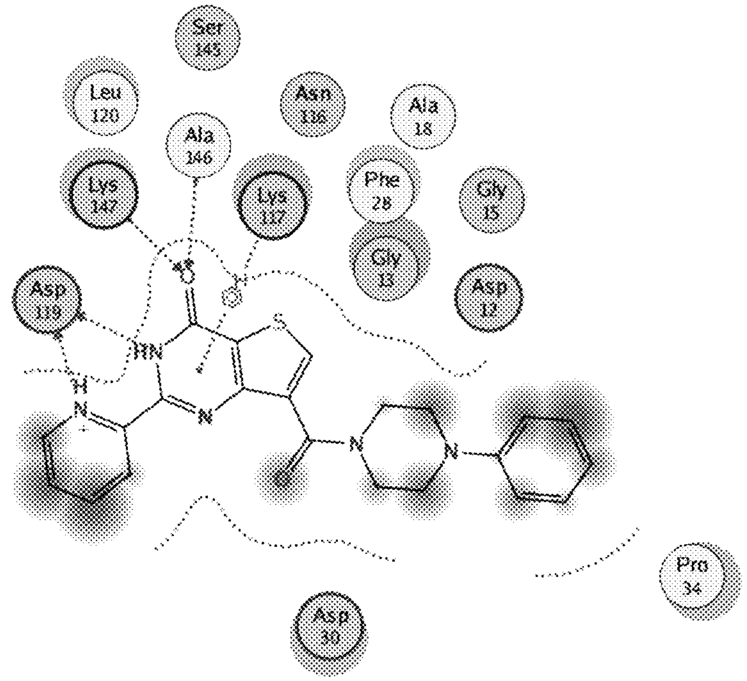
FIG. 2 depicts a compound disclosed herein binding to the guanosine binding region of the GTP binding site of KRas as determined through molecular modeling of a compound disclosed herein with KRas crystal structure PDB code: 4epr.

FIG. 2 depicts a compound disclosed herein binding to the guanosine binding region of the GTP binding site of KRas as determined through molecular modeling of a compound disclosed herein with KRas crystal structure PDB code: 4epr. The KRas residues within 2.5 angstroms of the ligand or approximately 2.5 angstroms from the ligand with specific interactions are Ala18, Asp30, Pro34, Lys117, Asp119, Leu120, Ala146 and Lys147.

Figure 3:
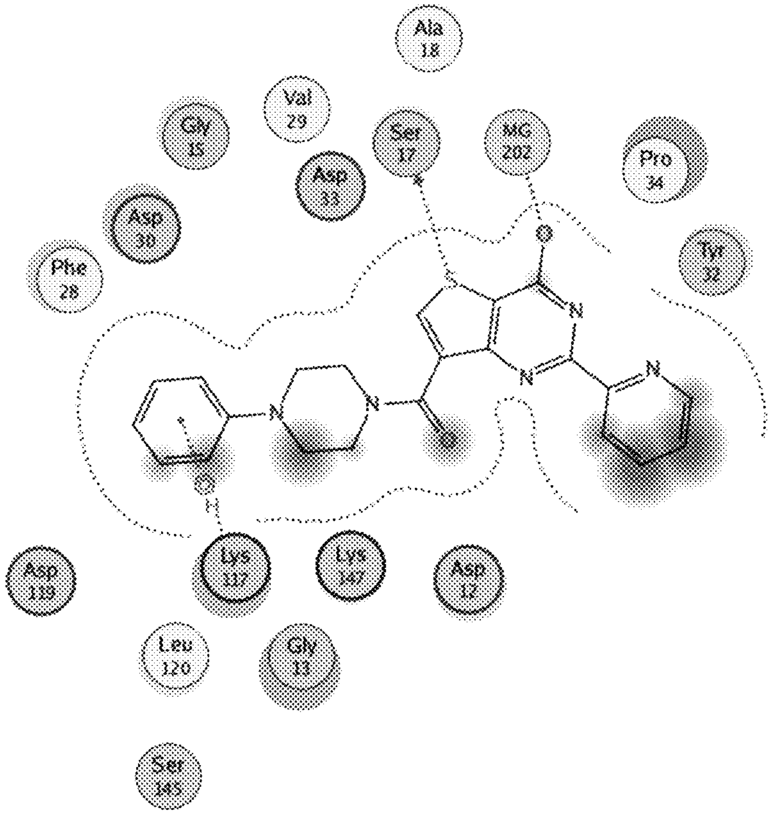
FIG. 3 depicts a compound disclosed herein binding to the metal region of the GTP binding site of KRas as determined through molecular modeling of a compound disclosed herein with KRas crystal structure PDB code: 4epr.

FIG. 3 depicts a compound disclosed herein binding to the metal region of the GTP binding site of KRas as determined through molecular modeling of a compound disclosed herein with KRas crystal structure PDB code: 4epr. The KRas residues within 2.5 angstroms of the ligand or approximately 2.5 angstroms from the ligand with specific interactions are Asp12, Gly13, Ala18, Pro34, Asp119, Leu120, Lys147 and Mg202.

Figure 4:
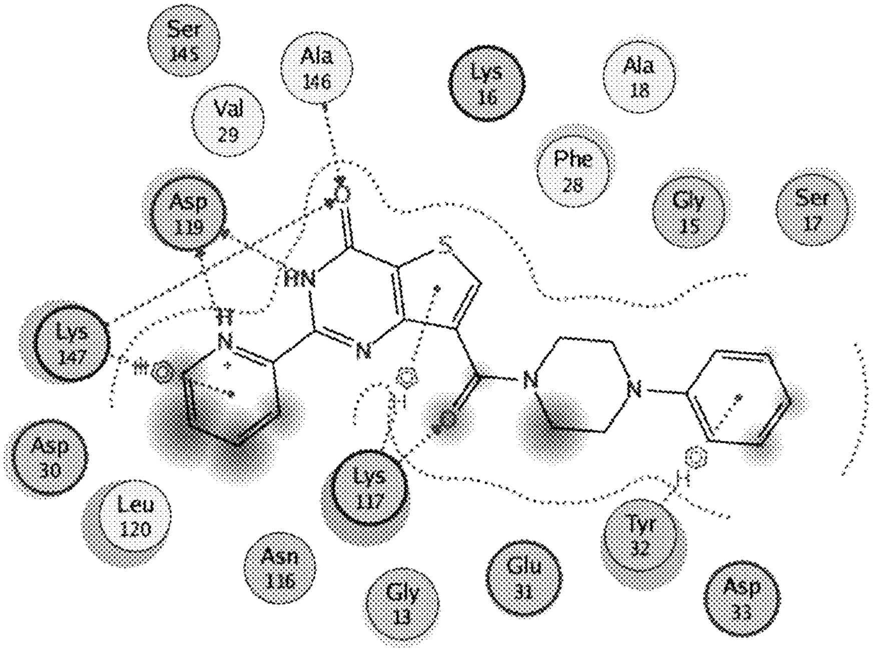
FIG. 4 depicts a compound disclosed herein binding to the guanosine binding region of the alternative Tyr32 conformation in the GTP binding site of KRas as determined through molecular modeling of a compound disclosed herein with KRas crystal structure PDB code: 3gft.

FIG. 4 depicts a compound disclosed herein binding to the guanosine binding site of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Gly15, Ser17, Ala18, Phe28, Asp30, Tyr32, Asp119, Ala146 and Lys147.

Figure 5:
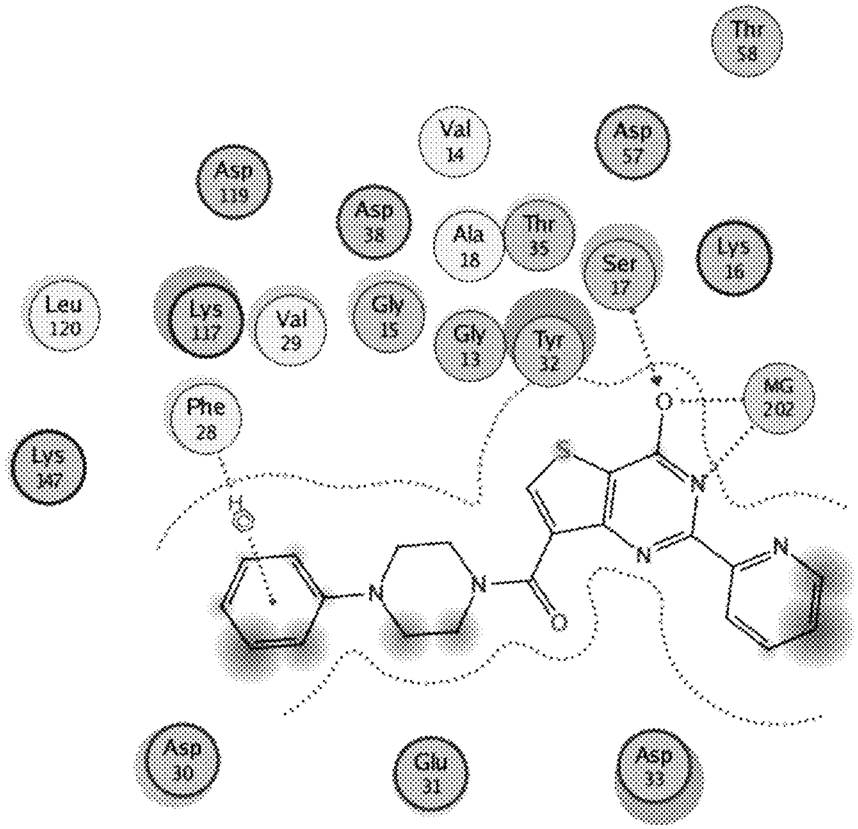
FIG. 5 depicts a compound disclosed herein binding to the metal region of the alternative Tyr32 conformation in the GTP binding site of KRas as determined through molecular modeling of a compound disclosed herein with KRas crystal structure PDB code: 3gft.

FIG. 5 depicts a compound disclosed herein binding to the metal region of the alternative Tyr32 conformation "Tyr conformation" in the GTP binding site of KRAS as determined through molecular modeling of a compound disclosed herein with KRas crystal structure PDB code: 3gft. The KRas residues within 2.5 angstroms or approximately 2.5 angstroms from the ligand with specific interactions of the ligand are Gly13, Gly15, Ser17, Ala18, Tyr32, Asp33, Lys117, Lys147 and Mg202.

Figure 6:
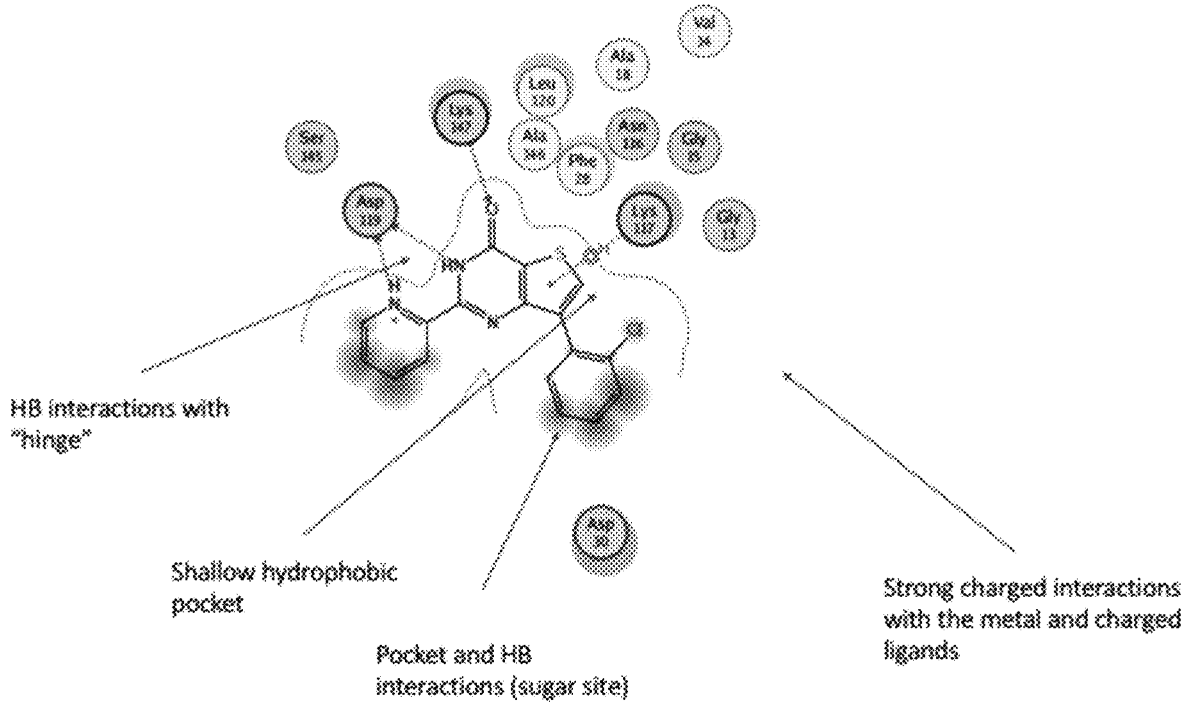
FIG. 6 depicts a compound disclosed herein binding to the guanosine binding region of the GTP binding site of KRas as determined through molecular modeling of a compound disclosed herein with KRas crystal structure PDB code: 4epr.

FIG. 6 depicts a compound disclosed herein binding to the guanosine binding site of the GTP binding site of KRas as determined through molecular modeling of a compound disclosed herein with KRas crystal structure PDB code: 4epr. The KRas residues within 2.5 angstroms or approximately 2.5 angstroms from the ligand with specific interactions of the ligand are Gly15, Phe28, Asn116, Asp119, Leu120, and Lys147.

Figure 7:
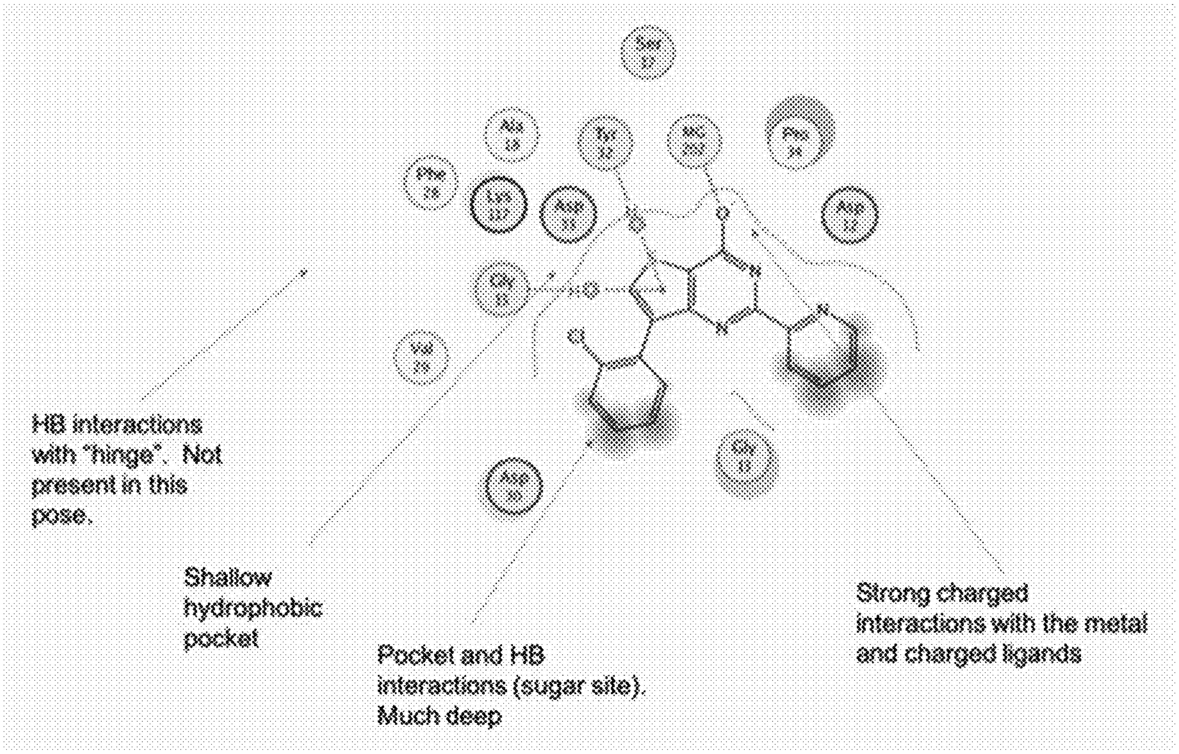
FIG. 7 depicts a compound disclosed herein binding to the metal region of the GTP binding site of KRas as determined through molecular modeling of a compound disclosed herein with KRas crystal structure PDB code: 4epr.

FIG. 7 depicts a compound disclosed herein binding to the metal region of the GTP binding site of KRas as determined through molecular modeling of a compound disclosed herein with KRAS crystal structure PDB code: 4epr. The KRas residues within 2.5 angstroms or approximately 2.5 angstroms from the ligand with specific interactions of the ligand are Asp12, Gly13, Ala18, Pro34 and Mg202.

Figure 8:
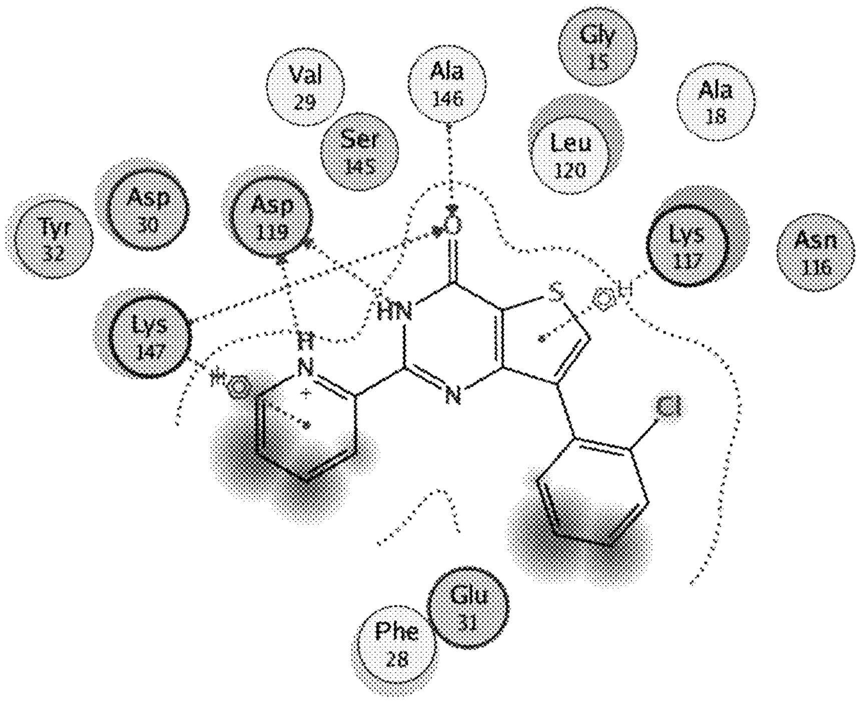
FIG. 8 depicts a compound disclosed herein binding to the guanosine binding region of the alternative Tyr32 conformation in the GTP binding site of KRas as determined through molecular modeling of a compound disclosed herein with KRas crystal structure PDB code: 3gft.

FIG. 8 depicts a compound disclosed herein binding to the guanosine binding site of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Gly15, Tyr32, Lys117, Asp119, Ala146 and Lys147.

Figure 9:
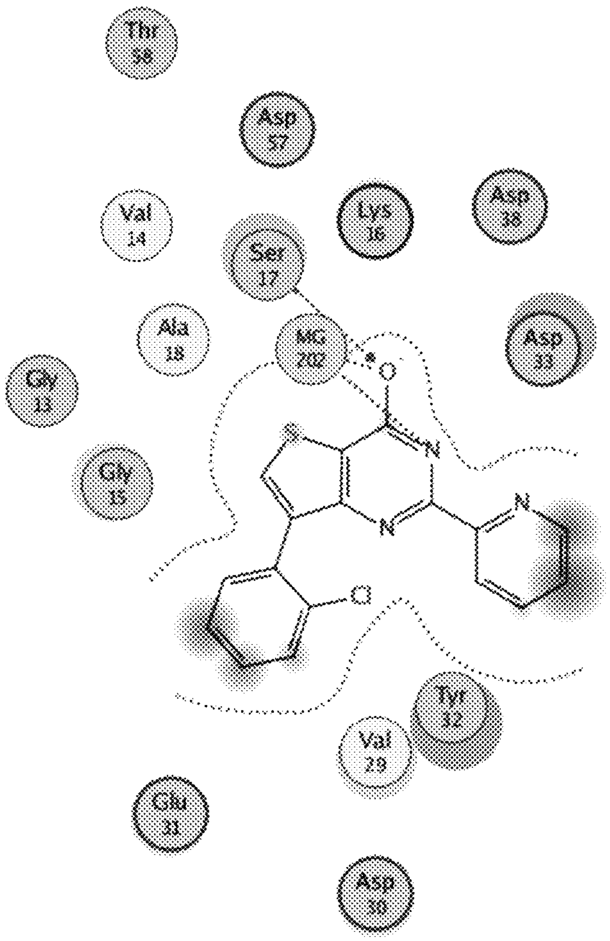
FIG. 9 depicts a compound disclosed herein binding to the metal region of the alternative Tyr32 conformation in the GTP binding site of KRas as determined through molecular modeling of a compound disclosed herein with KRas crystal structure PDB code: 3gft.

FIG. 9 depicts a compound disclosed herein binding to the metal region of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Gly13, Gly15, Ser17, Ala18, Asp30, Tyr32, Asp33 and Mg 202.

Figure 10:
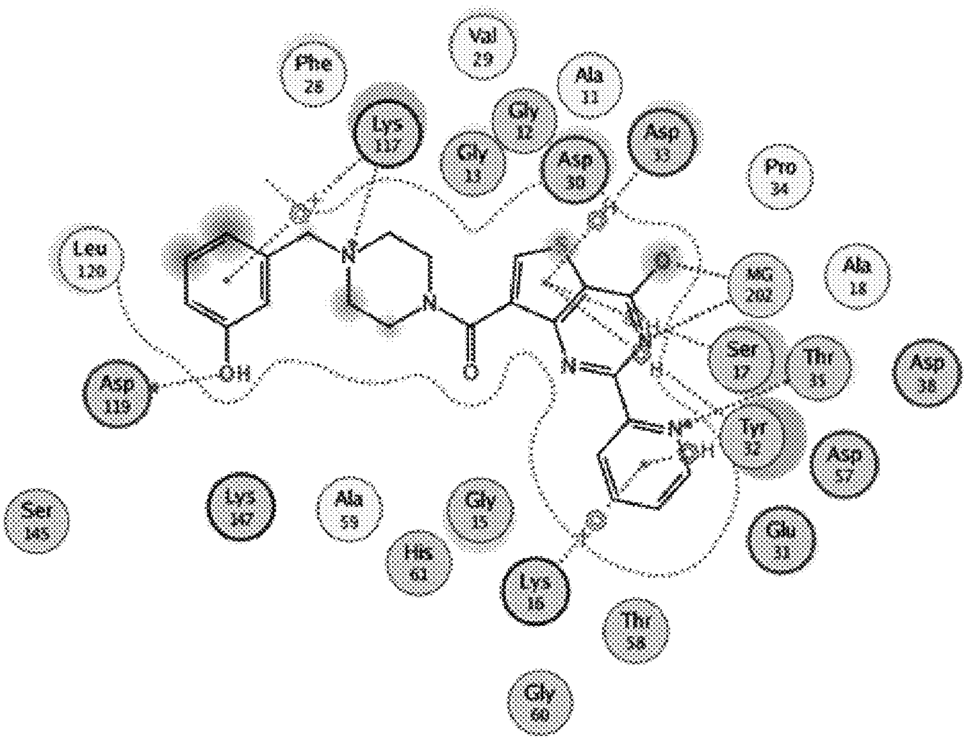
FIG. 10 depicts a compound disclosed herein binding to the metal region of the alternative Tyr32 conformation in the GTP binding site of KRas as determined through molecular modeling of a compound disclosed herein with KRas crystal structure PDB code: 3gft.

FIG. 10 depicts a compound disclosed herein binding to the metal region of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Ala11, Gly12, Lys16, Ser17, Tyr32, Thr35, Lys36, Lys117, Asp119 and Mg 202.

Figure 11:
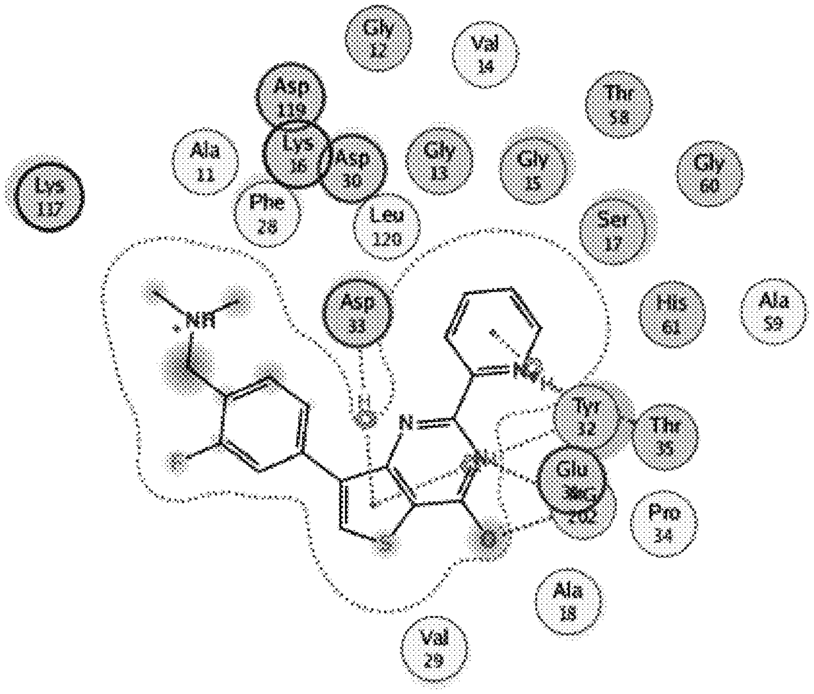
FIG. 11 depicts a compound disclosed herein binding to the metal region of the alternative Tyr32 conformation in the GTP binding site of KRas as determined through molecular modeling of a compound disclosed herein with KRas crystal structure PDB code: 3gft.

FIG. 11 depicts a compound disclosed herein binding to the metal region of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Gly12, Val14, Gly15, Lys16, Ser17, Phe28, Val29, Glu31, Thr35, Gly60, Lys117, Leu120 and Mg 202.

Figure 12:
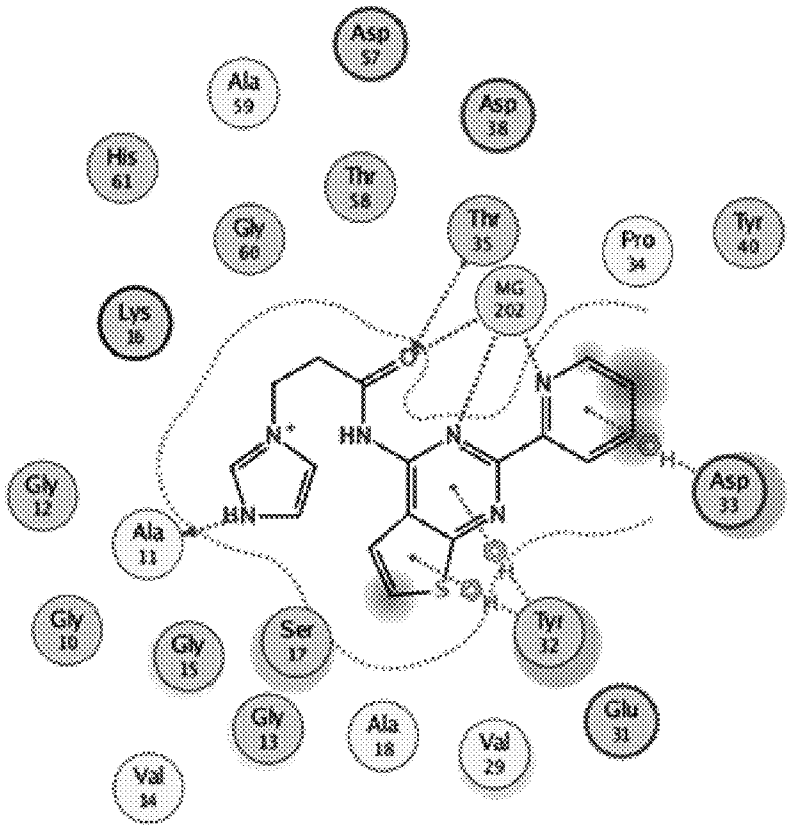
FIG. 12 depicts a compound disclosed herein binding to the metal region of the alternative Tyr32 conformation in the GTP binding site of KRas as determined through molecular modeling of a compound disclosed herein with KRas crystal structure PDB code: 3 gft.

FIG. 12 depicts a compound disclosed herein binding to the metal region of the alternative Tyr32 conformation in the GTP binding site of KRas as determined through molecular modeling of a compound disclosed herein with KRas crystal structure PDB code: 3gft. The KRas residues within 2.5 angstroms or approximately 2.5 angstroms from the ligand with specific interactions of the ligand are Ala11, Gly12, Gly15, Ser17, Ala18, Val29, Tyr32, Asp33, Thr35 and Mg 202.

Figure 13:
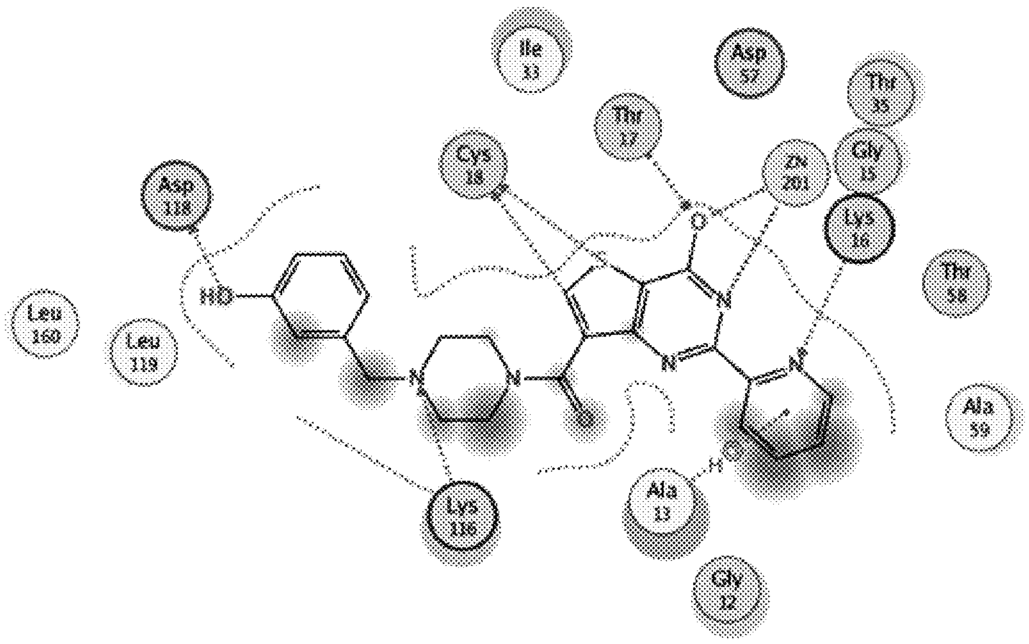
FIG. 13 depicts a compound disclosed herein binding to the metal region of the GTP binding site of Rac-1 as determined through molecular modeling of a compound disclosed herein with Rac-1 crystal structure PDB code: 2p2l.

FIG. 13 depicts a compound disclosed herein binding to the metal region of the GTP binding site of Rac-1 as determined through molecular modeling of a compound disclosed herein with Rac-1 crystal structure PDB code: 2p2l. The Rac-1 residues within 2.5 angstroms or approximately 2.5 angstroms from the ligand with specific interactions of the ligand are Ala13, Gly15, Lys16, Thr17, Cys18, Lys116, Asp118, Leu119 and Mg 202.

Figure 14:
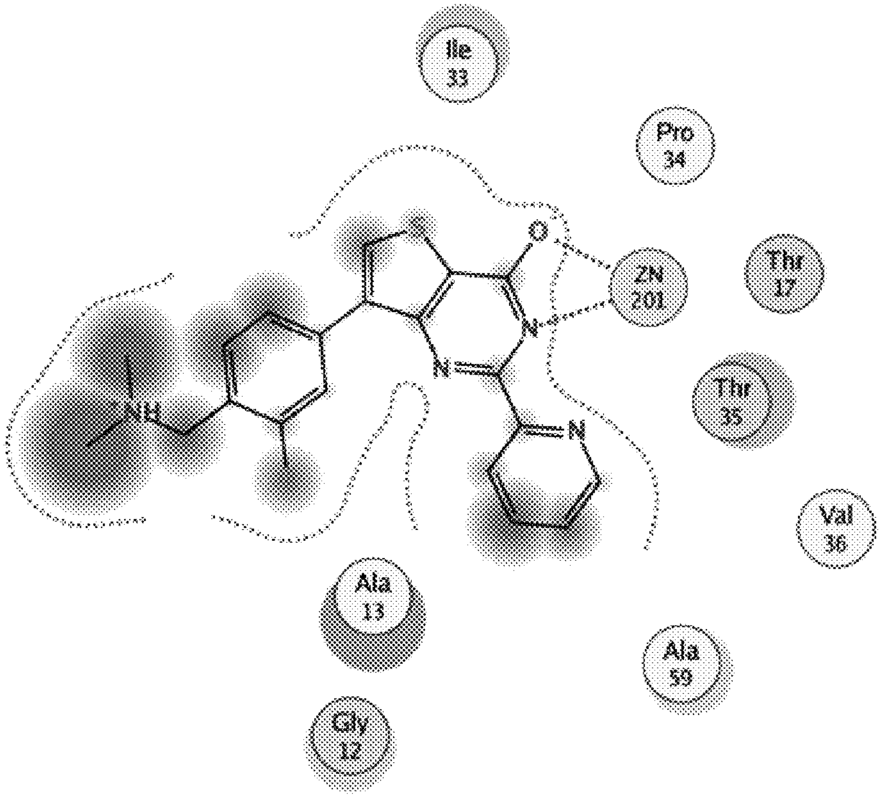
FIG. 14 depicts a compound disclosed herein binding to the metal region of the GTP binding site of Rac-1 as determined through molecular modeling of a compound disclosed herein with Rac-1 crystal structure PDB code: 2p2l.

FIG. 14 depicts a compound disclosed herein binding to the metal region of the GTP binding site of Rac-1 as determined through molecular modeling of a compound disclosed herein with Rac-1 crystal structure PDB code: 2p2l. The Rac-1 residues within 2.5 angstroms or approximately 2.5 angstroms from the ligand with specific interactions of the ligand are Gly12, Ala13, Thr17, Ile33, Pro34, Val36, Ala59 and Mg 202.

Figure 15:
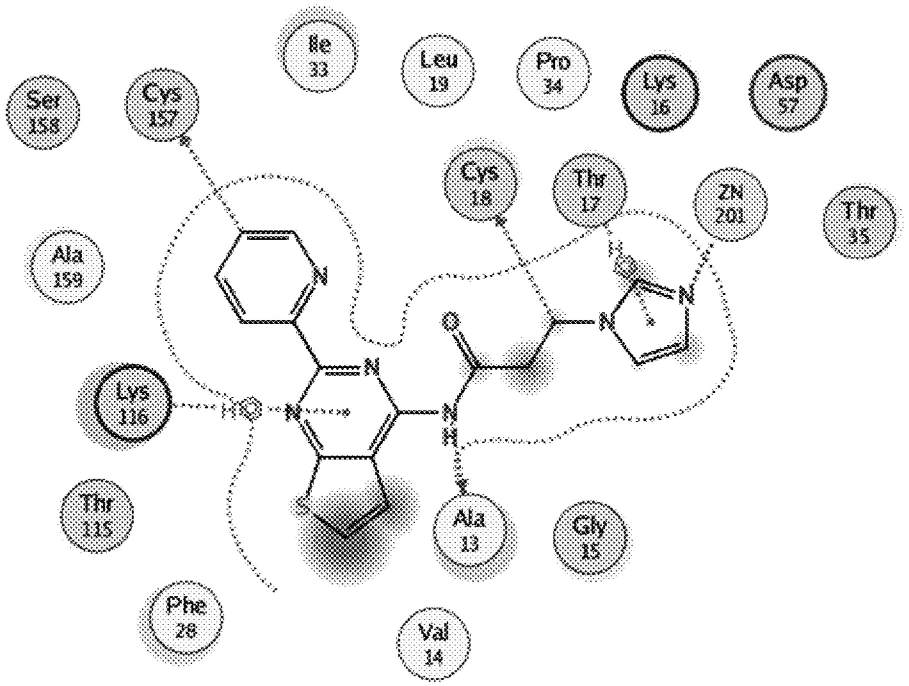
FIG. 15 depicts a compound disclosed herein binding to the metal region of the GTP binding site of Rac-1 as determined through molecular modeling of a compound disclosed herein with Rac-1 crystal structure PDB code: 2p2l.

FIG. 15 depicts a compound disclosed herein binding to the metal region of the GTP binding site of Rac-1 as determined through molecular modeling of a compound disclosed herein with Rac-1 crystal structure PDB code: 2p2l. The Rac-1 residues within 2.5 angstroms or approximately 2.5 angstroms from the ligand with specific interactions of the ligand are Ala13, Gly15, Lys16, Thr17, Cys18, Leu19, Phe28, Ile33, Thr115, Cys157, Ala159 and Mg 202.

Figure 16:
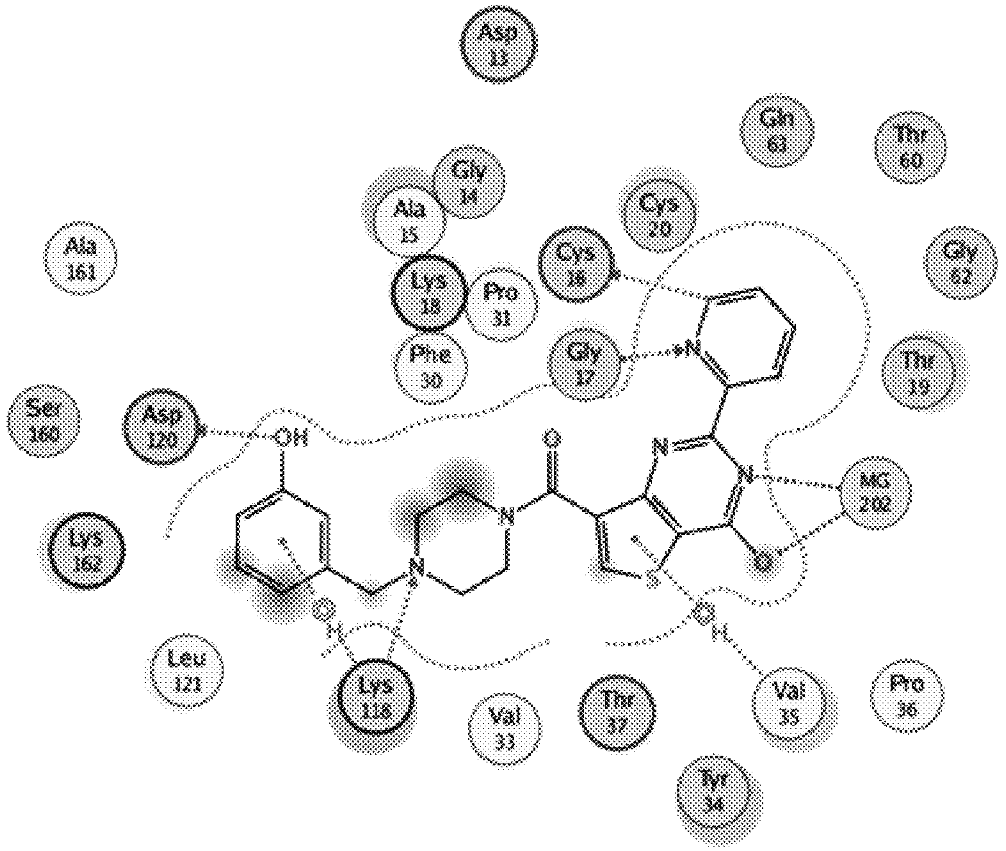
FIG. 16 depicts a compound disclosed herein binding to the metal region of the GTP binding site of Rho-A as determined through molecular modeling of a compound disclosed herein with Rho-A crystal structure PDB code: 5hpy.

FIG. 16 depicts a compound disclosed herein binding to the metal region of the GTP binding site of Rho-A as determined through molecular modeling of a compound disclosed herein with Rho-A crystal structure PDB code: 5hpy. The Rho-A residues within 2.5 angstroms or approximately 2.5 angstroms from the ligand with specific interactions of the ligand are Cys16, Gly17, Lys18, Thr19, Phe30, Pro31, Val35, Lys118, Asp120 and Mg 202.

Figure 17:
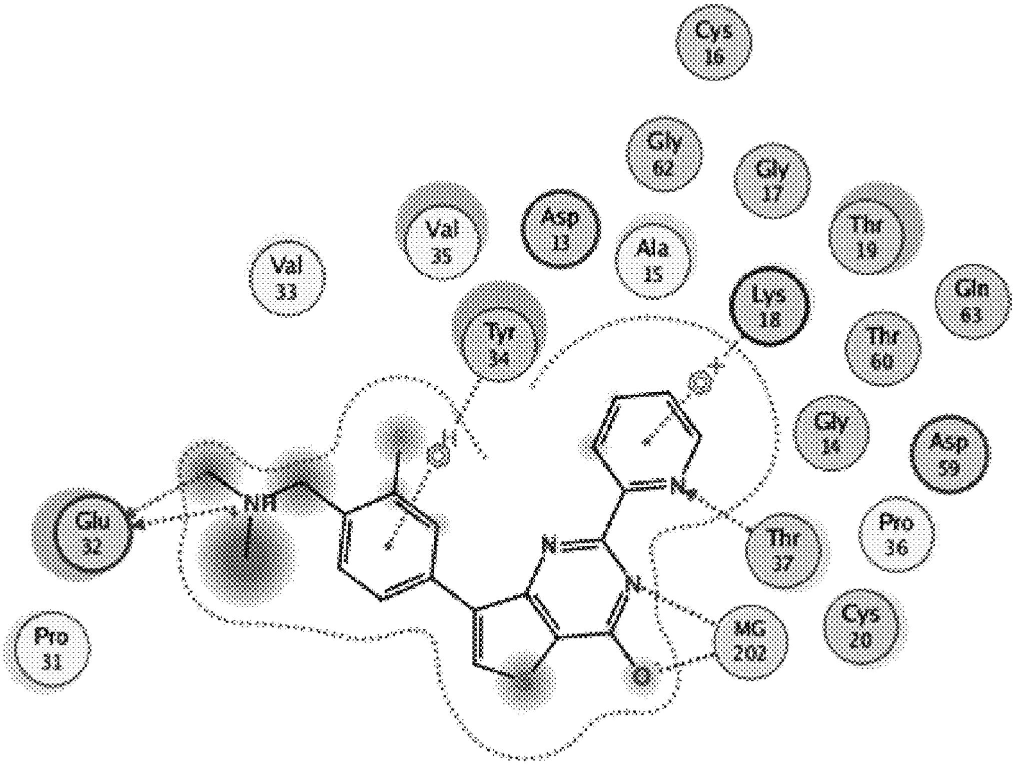
FIG. 17 depicts a compound disclosed herein binding to the metal region of the GTP binding site of Rho-A as determined through molecular modeling of a compound disclosed herein with Rho-A crystal structure PDB code: 5hpy.

FIG. 17 depicts a compound disclosed herein binding to the metal region of the GTP binding site of Rho-A as determined through molecular modeling of a compound disclosed herein with Rho-A crystal structure PDB code: 5hpy. The Rho-A residues within 2.5 angstroms or approximately 2.5 angstroms from the ligand with specific interactions of the ligand are Gly14, Ala15, Lys18, Thr19, Cys20, Pro31, Glu32, Tyr34, Val35, Pro36, Thr37 and Mg 202.

Figure 18:
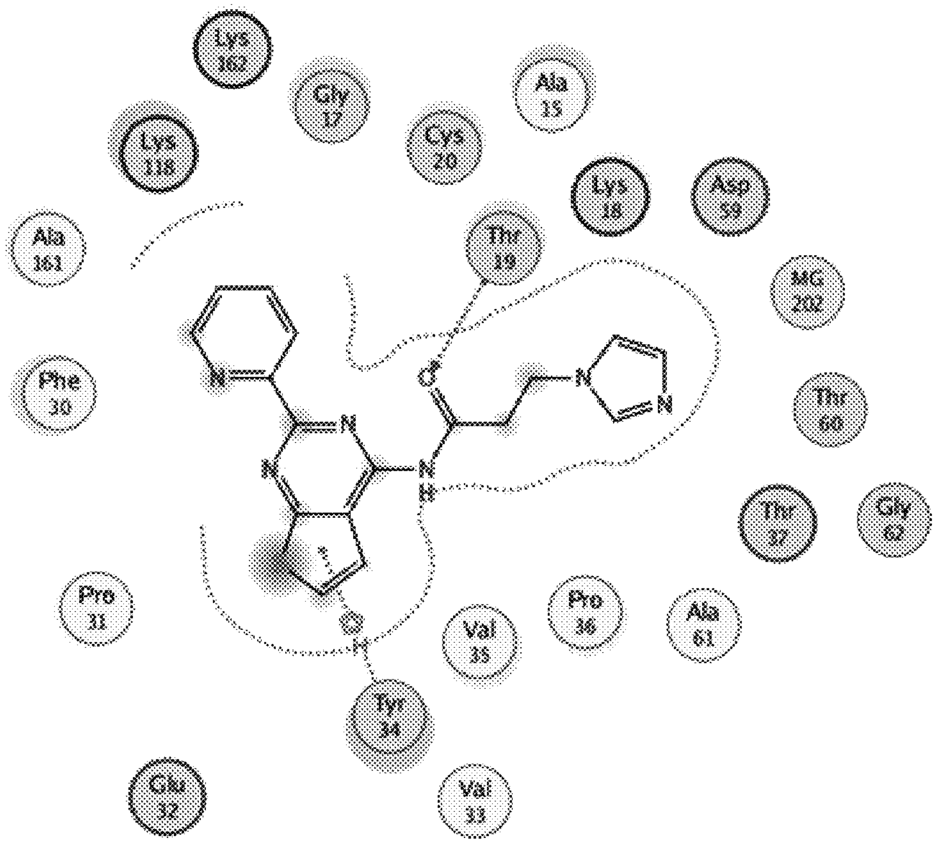
FIG. 18 depicts a compound disclosed herein binding to the metal region of the GTP binding site of Rho-A as determined through molecular modeling of a compound disclosed herein with Rho-A crystal structure PDB code: 5hpy.

FIG. 18 depicts a compound disclosed herein binding to the metal region of the GTP binding site of Rho-A as determined through molecular modeling of a compound disclosed herein with Rho-A crystal structure PDB code: 5hpy. The Rho-A residues within 2.5 angstroms or approximately 2.5 angstroms from the ligand with specific interactions of the ligand are Gly17, Thr19, Phe30, Tyr34, Pro36, Thr37, Asp59, Lys118, Lys162 and Mg 202.

Example 2

Protocol for MAPK Cell-Based Phosphorylation Assay

Cell lines: Tumor-derived pancreatic cancer cell lines PANC-1 were purchased from ATCC and were maintained according to ATCC recommendation.

Method: Cells were plated at 7500 cells/well density in 96-wells plate, starved over night, and the small molecules to be tested were added to the cells in the final concentration of 30 μM with 0.3% DMSO for 6 hours incubation at 37° C. For $IC_{50}$ value determination, serial dilutions of compounds were added to cells under the same conditions. Next, cells were stimulated with 1.5 ng/ml EGF for 15 min. followed by cell fixation with 4% Formaldehyde in PBS at RT for 20 min. Phosphorylation level of MAPK was determined by Cell-direct ELISA.

Cell-direct ELISA: For each well, cells were permeabilized with PBS-Triton 0.1%, quenched with $H_2O_2$ 0.6% in PBS-Triton 0.1%, and probed with anti-phospho-MAPK antibodies (R&D Systems) followed by HRP-conjugated secondary antibody (Jackson Immunoresearch, West Grove, Pa.). Next, a solution 50 μM of the fluorescent substrate AmpliFlu Red (Sigma) was added and incubated at RT for 20 min. At the end of the incubation time, fluorescence was measured at 595 nm on a microplate reader (AF2200; Eppendorf, Inc., Hamburg, Germany).

Table 4 shows inhibition data for selected compounds tested in the cellular assay described above.

TABLE 4

% Inhibition of MAPK phosphorylation at 30 μM in the PANC-1 pancreatic cancer cell line, and select $IC_{50}$ data

| Compound | PANC-1 | $IC_{50}$ (μM) |
|---|---|---|
| 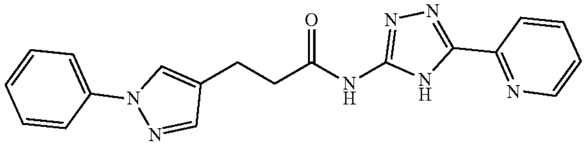 [SMILES: O=C(CCc1cnn(-c2ccccc2)c1)Nc1nnc(-c2ccccn2)[nH]1] | B | |
| 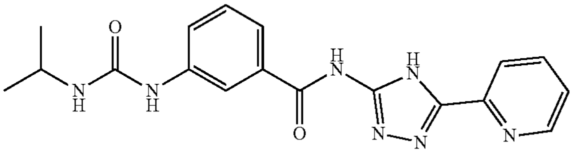 [SMILES: CC(C)NC(=O)Nc1cccc(C(=O)Nc2nnc(-c3ccccn3)[nH]2)c1] | A | |
| 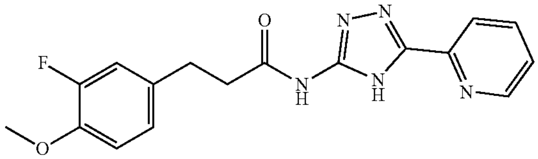 [SMILES: COc1ccc(CCC(=O)Nc2nnc(-c3ccccn3)[nH]2)cc1F] | C | |
| 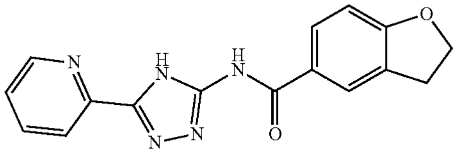 [SMILES: O=C(Nc1nnc(-c2ccccn2)[nH]1)c1ccc2c(c1)CCO2] | A | |
| 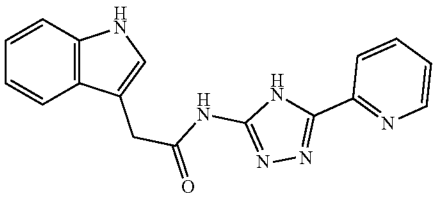 [SMILES: O=C(Cc1c[nH]c2ccccc12)Nc1nnc(-c2ccccn2)[nH]1] | C | |
| 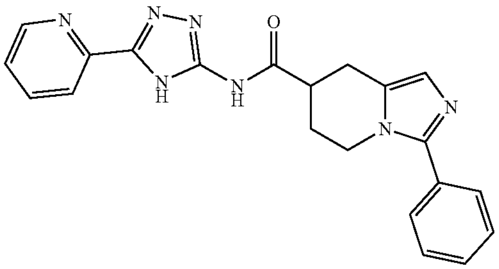 [SMILES: O=C(Nc1nnc(-c2ccccn2)[nH]1)C1CCn2c(cnc2-c2ccccc2)C1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 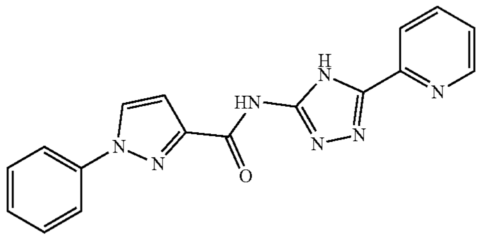 [SMILES: O=C(Nc1nnc(-c2ccccn2)[nH]1)c1ccn(-c2ccccc2)n1] | A | |
| 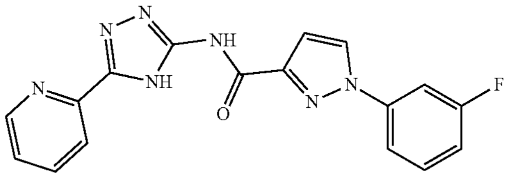 [SMILES: O=C(Nc1nnc(-c2ccccn2)[nH]1)c1ccn(-c2cccc(F)c2)n1] | A | |
| 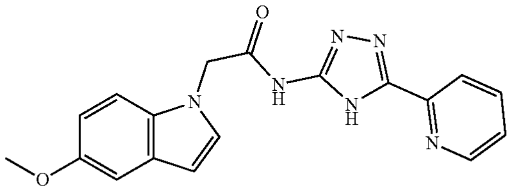 [SMILES: COc1ccc2c(ccn2CC(=O)Nc2nnc(-c3ccccn3)[nH]2)c1] | A | |
| 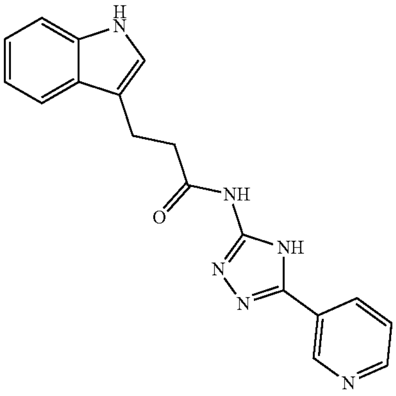 [SMILES: O=C(CCc1c[nH]c2ccccc12)Nc1nnc(-c2cccnc2)[nH]1] | B | |
| 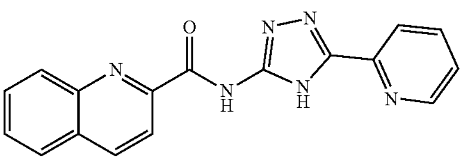 [SMILES: O=C(Nc1nnc(-c2ccccn2)[nH]1)c1ccc2ccccc2n1] | A | |
| 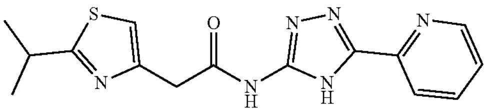 [SMILES: CC(C)c1nc(CC(=O)Nc2nnc(-c3ccccn3)[nH]2)cs1] | A | |
| 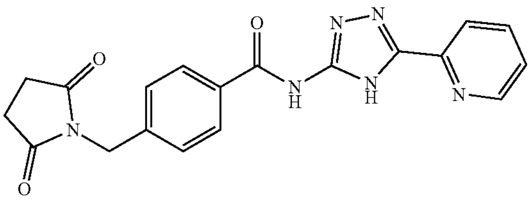 [SMILES: O=C(Nc1nnc(-c2ccccn2)[nH]1)c1ccc(CN2C(=O)CCC2=O)cc1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 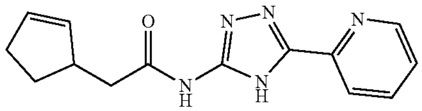 [SMILES: O=C(CC1C=CCC1)Nc1nnc(-c2ccccn2)[nH]1] | A | |
| 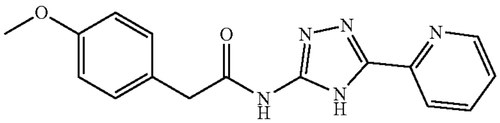 [SMILES: COc1ccc(CC(=O)Nc2nnc(-c3ccccn3)[nH]2)cc1] | A | |
| 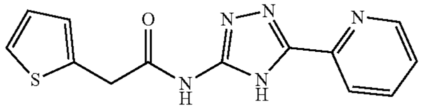 [SMILES: O=C(Cc1cccs1)Nc1nnc(-c2ccccn2)[nH]1] | B | |
| 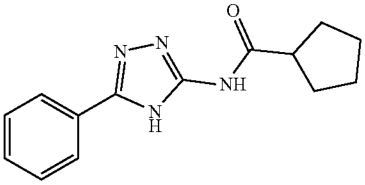 [SMILES: O=C(Nc1nnc(-c2ccccc2)[nH]1)C1CCCC1] | A | |
| 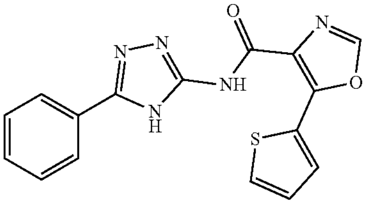 [SMILES: O=C(Nc1nnc(-c2ccccc2)[nH]1)c1ncoc1-c1cccs1] | B | |
| 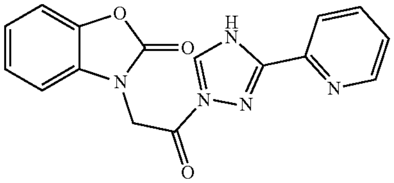 | A | |
| 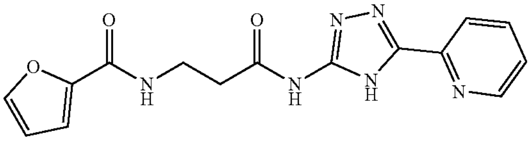 [SMILES: O=C(CCNC(=O)c1ccco1)Nc1nnc(-c2ccccn2)[nH]1] | A | |
| 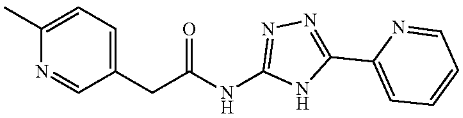 [SMILES: Cc1ccc(CC(=O)Nc2nnc(-c3ccccn3)[nH]2)cn1] | A | |
| 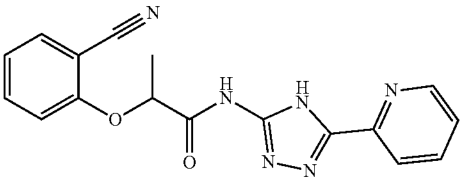 [SMILES: CC(Oc1ccccc1C#N)C(=O)Nc1nnc(-c2ccccn2)[nH]1] | C | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 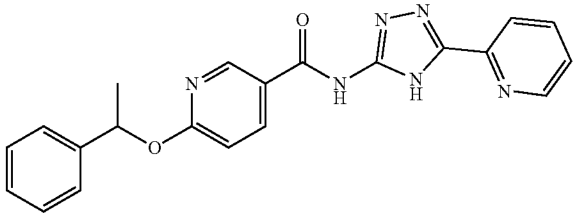 [SMILES: CC(Oc1ccc(C(=O)Nc2nnc(-c3ccccn3)[nH]2)cn1)c1ccccc1] | B | |
| 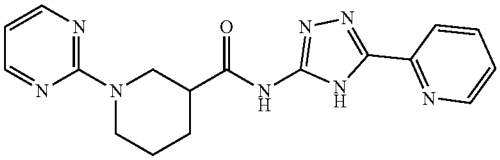 [SMILES: O=C(Nc1nnc(-c2ccccn2)[nH]1)C1CCCN(c2ncccn2)C1] | A | |
| 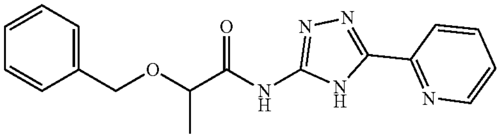 [SMILES: CC(OCc1ccccc1)C(=O)Nc1nnc(-c2ccccn2)[nH]1] | A | |
| 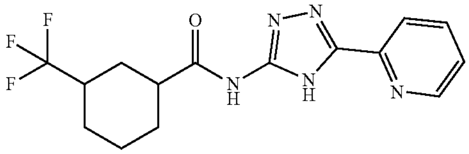 [SMILES: O=C(Nc1nnc(-c2ccccn2)[nH]1)C1CCCC(C(F)(F)F)C1] | C | |
| 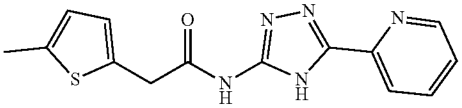 [SMILES: Cc1ccc(CC(=O)Nc2nnc(-c3ccccn3)[nH]2)s1] | A | |
| 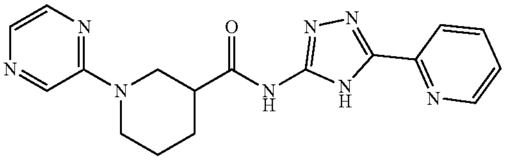 [SMILES: O=C(Nc1nnc(-c2ccccn2)[nH]1)C1CCCN(c2cnccn2)C1] | A | |
| 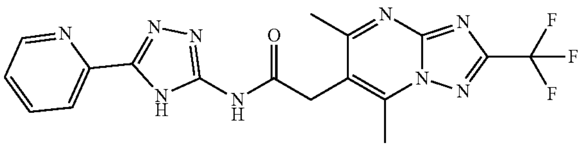 [SMILES: Cc1nc2nc(C(F)(F)F)nn2c(C)c1CC(=O)Nc1nnc(-c2ccccn2)[nH]1] | A | |
| 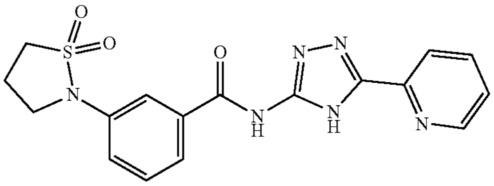 [SMILES: O=C(Nc1nnc(-c2ccccn2)[nH]1)c1cccc(N2CCCS2(=O)=O)c1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 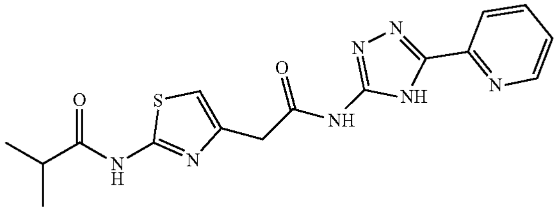 [SMILES: CC(C)C(=O)Nc1nc(CC(=O)Nc2nnc(-c3ccccn3)[nH]2)cs1] | A | |
| 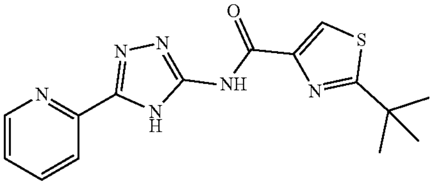 [SMILES: CC(C)(C)c1nc(C(=O)Nc2nnc(-c3ccccn3)[nH]2)cs1] | A | |
| 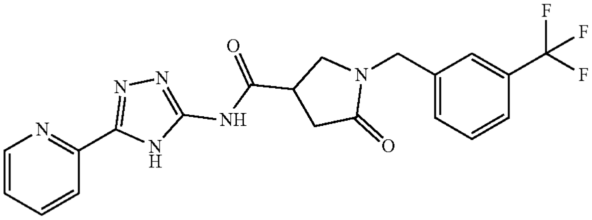 [SMILES: O=C(Nc1nnc(-c2ccccn2)[nH]1)C1CC(=O)N(Cc2cccc(C(F)(F)F)c2)C1] | B | |
| 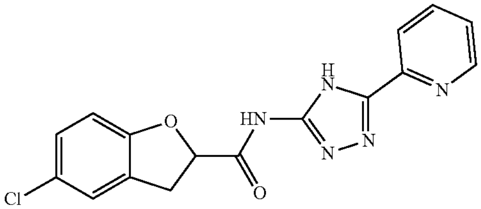 [SMILES: O=C(Nc1nnc(-c2ccccn2)[nH]1)C1Cc2cc(Cl)ccc2O1] | A | |
| 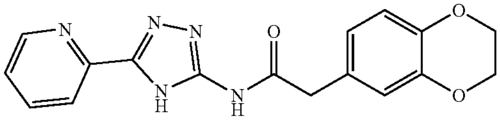 [SMILES: O=C(Cc1ccc2c(c1)OCCO2)Nc1nnc(-c2ccccn2)[nH]1] | A | |
| 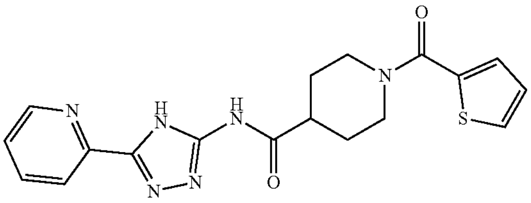 [SMILES: O=C(Nc1nnc(-c2ccccn2)[nH]1)C1CCN(C(=O)c2cccs2)CC1] | A | |
| 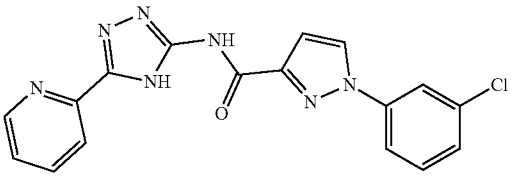 [SMILES: O=C(Nc1nnc(-c2ccccn2)[nH]1)c1ccn(-c2cccc(Cl)c2)n1] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 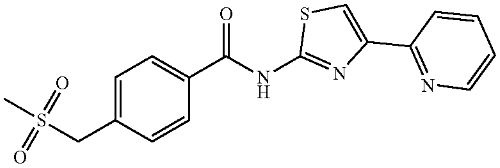 [SMILES: CS(=O)(=O)Cc1ccc(C(=O)Nc2nc(-c3ccccn3)cs2)cc1] | A | |
| 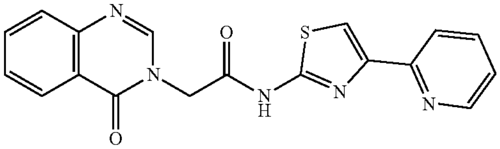 [SMILES: O=C(Cn1cnc2ccccc2c1=O)Nc1nc(-c2ccccn2)cs1] | A | |
| 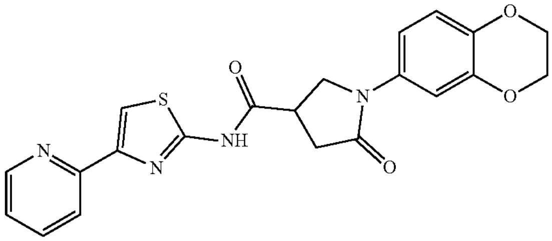 [SMILES: O=C(Nc1nc(-c2ccccn2)cs1)C1CC(=O)N(c2ccc3c(c2)OCCO3)C1] | B | |
| 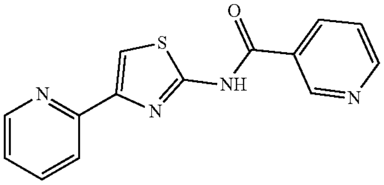 [SMILES: O=C(Nc1nc(-c2ccccn2)cs1)c1cccnc1] | A | |
| 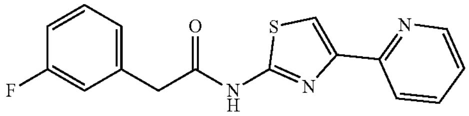 [SMILES: O=C(Cc1cccc(F)c1)Nc1nc(-c2ccccn2)cs1] | A | |
| 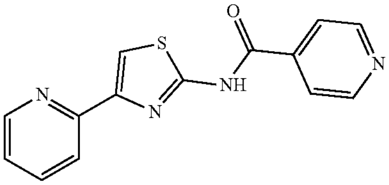 [SMILES: O=C(Nc1nc(-c2ccccn2)cs1)c1ccncc1] | B | |
| 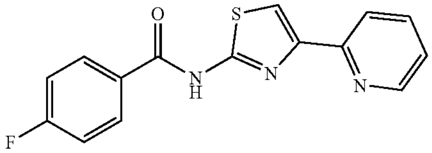 [SMILES: O=C(Nc1nc(-c2ccccn2)cs1)c1ccc(F)cc1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 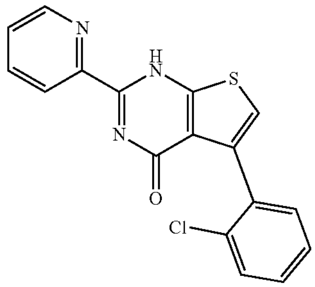 [SMILES: O=c1nc(-c2ccccn2)[nH]c2scc(-c3ccccc3Cl)c12] | B | |
| 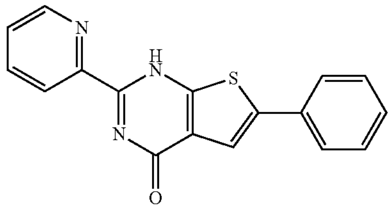 [SMILES: O=c1nc(-c2ccccn2)[nH]c2sc(-c3ccccc3)cc12] | B | |
| 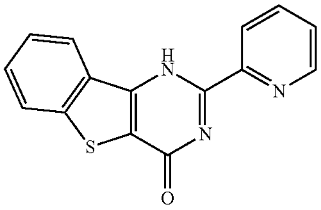 [SMILES: O=c1nc(-c2ccccn2)[nH]c2c1sc1ccccc12] | D | |
| 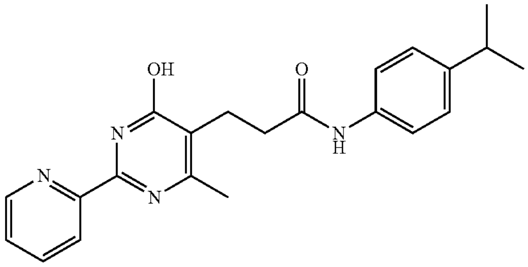 [SMILES: Cc1nc(-c2ccccn2)nc(O)c1CCC(=O)Nc1ccc(C(C)C)cc1] | A | |
| 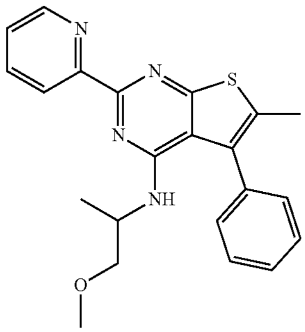 [SMILES: COCC(C)Nc1nc(-c2ccccn2)nc2sc(C)c(-c3ccccc3)c12] | D | F |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 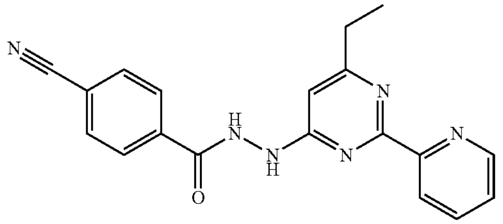 [SMILES: CCc1cc(NNC(=O)c2ccc(C#N)cc2)nc(-c2ccccn2)n1] | D | G |
| 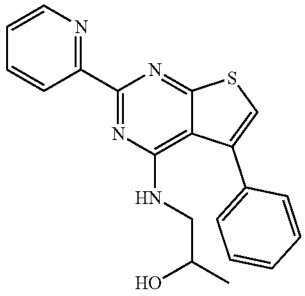 [SMILES: CC(O)CNc1nc(-c2ccccn2)nc2scc(-c3ccccc3)c12] | B | |
| 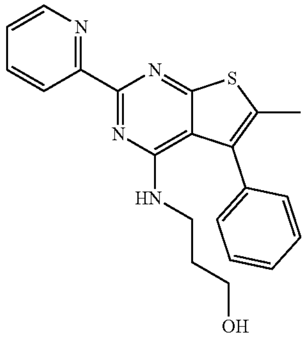 [SMILES: Cc1sc2nc(-c3ccccn3)nc(NCCCO)c2c1-c1ccccc1] | A | |
| 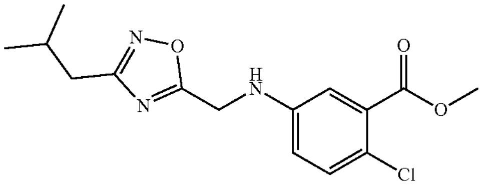 [SMILES: COC(=O)c1cc(NCc2nc(CC(C)C)no2)ccc1Cl] | A | |
| 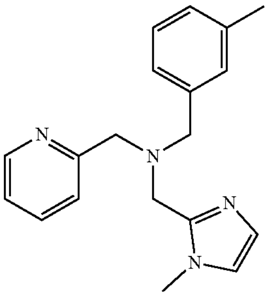 [SMILES: Cc1cccc(CN(Cc2ccccn2)Cc2nccn2C)c1] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 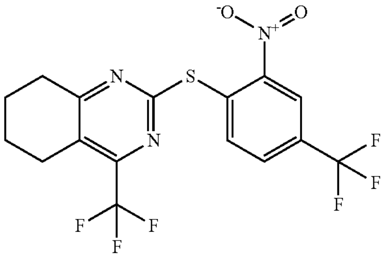 | A | |
| 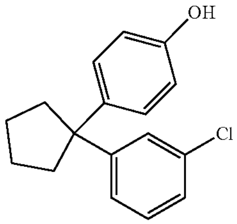 [SMILES: Oc1ccc(C2(c3cccc(Cl)c3)CCCC2)cc1] | D | |
| 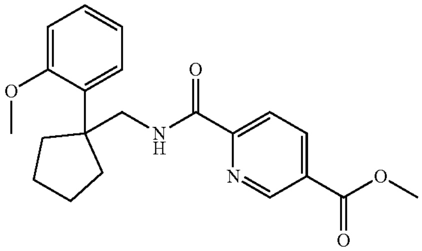 [SMILES: COC(=O)c1ccc(C(=O)NCC2(c3ccccc3OC)CCCC2)nc1] | A | |
| 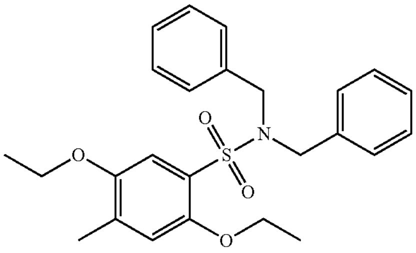 [SMILES: CCOc1cc(S(=O)(=O)N(Cc2ccccc2)Cc2ccccc2)c(OCC)cc1C] | A | |
| 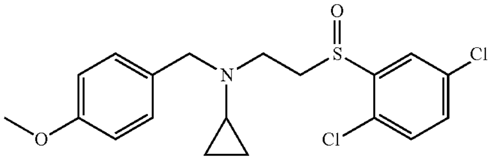 [SMILES: COc1ccc(CN(CCS(=O)c2cc(Cl)ccc2Cl)C2CC2)cc1] | B | |
| 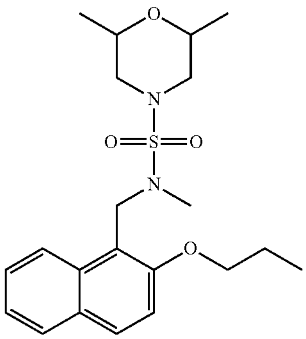 [SMILES: CCCOc1ccc2ccccc2c1CN(C)S(=O)(=O)N1CC(C)OC(C)C1] | A | |

TABLE 4-continued
% Inhibition of MAPK phosphorylation at 30 μM in the PANC-1 pancreatic cancer cell line, and select $IC_{50}$ data
| Compound | PANC-1 $IC_{50}$ (μM) |
|---|---|
| 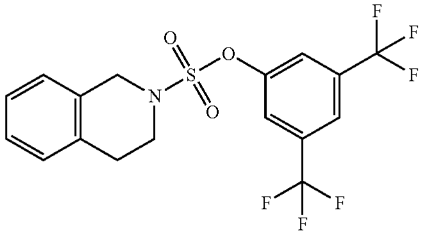 [SMILES: O=S(=O)(Oc1cc(C(F)(F)F)cc(C(F)(F)F)c1)N1CCc2ccccc2C1] | A |
| 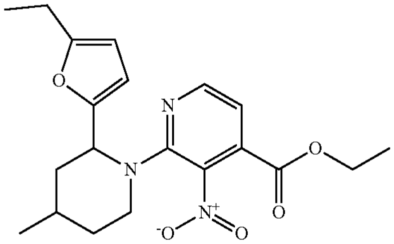 | B |
| 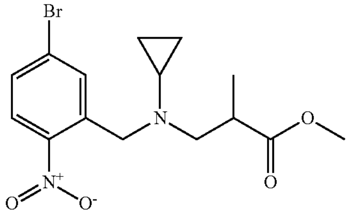 [SMILES: COC(=O)C(C)CN(Cc1cc(Br)ccc1[N+](=O)[O-])C1CC1] | A |
| 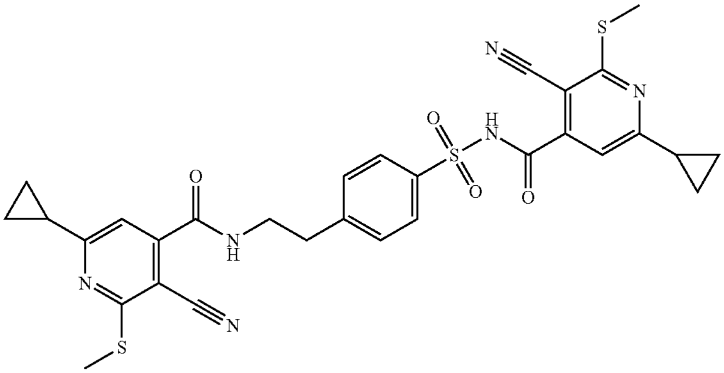 [SMILES: CSc1nc(C2CC2)cc(C(=O)NCCc2ccc(S(=O)(=O)NC(=O)c3cc(C4CC4)nc(SC)c3C#N)cc2)c1C#N] | D |
| 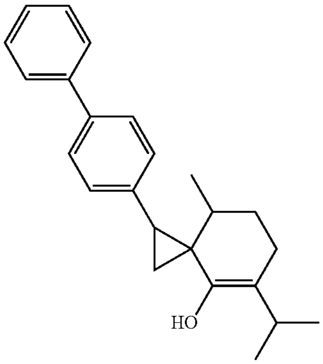 [SMILES: CC(C)C1=C(O)C2(CC2c2ccc(-c3ccccc3)cc2)C(C)CC1] | A |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 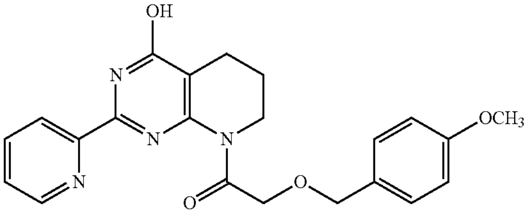 [SMILES: COc1ccc(COCC(=O)N2CCCc3c(O)nc(-c4ccccn4)nc32)cc1] | A | |
| 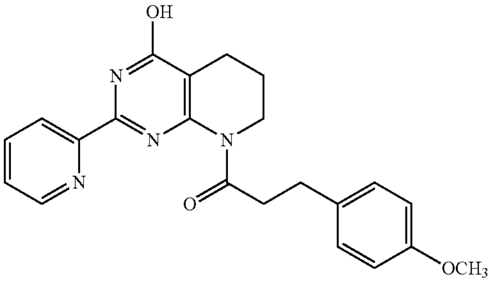 [SMILES: COc1ccc(CCC(=O)N2CCCc3c(O)nc(-c4ccccn4)nc32)cc1] | B | |
| 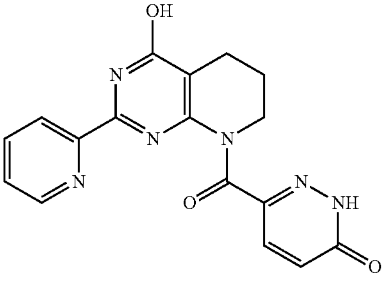 [SMILES: O=C(c1ccc(=O)[nH]n1)N1CCCc2c(O)nc(-c3ccccn3)nc21] | A | |
| 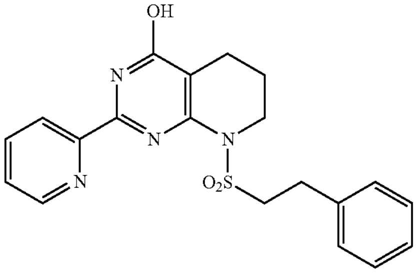 [SMILES: O=S(=O)(CCc1ccccc1)N1CCCc2c(O)nc(-c3ccccn3)nc21] | B | |
| 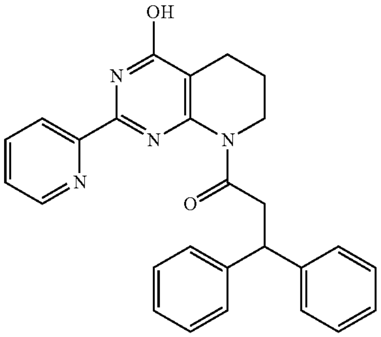 [SMILES: O=C(CC(c1ccccc1)c1ccccc1)N1CCCc2c(O)nc(-c3ccccn3)nc21] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 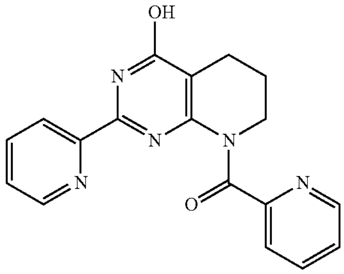 [SMILES: O=C(c1ccccn1)N1CCCc2c(O)nc(-c3ccccn3)nc21] | A | |
| 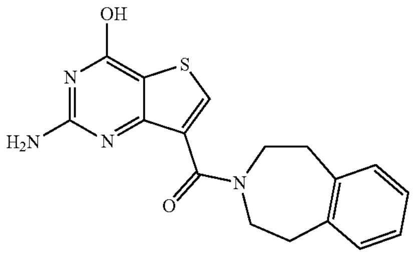 [SMILES: Nc1nc(O)c2scc(C(=O)N3CCc4ccccc4CC3)c2n1] | A | |
| 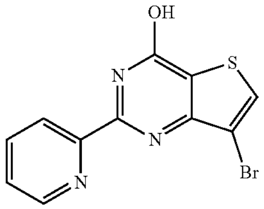 [SMILES: Oc1nc(-c2ccccn2)nc2c(Br)csc12] | D | G |
| 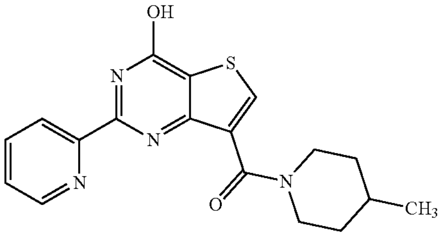 [SMILES: CC1CCN(C(=O)c2csc3c(O)nc(-c4ccccn4)nc23)CC1] | A | |
| 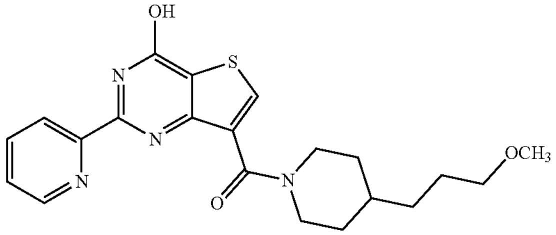 [SMILES: COCCCC1CCN(C(=O)c2csc3c(O)nc(-c4ccccn4)nc23)CC1] | A | |
| 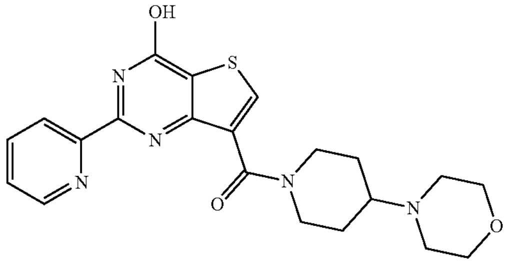 [SMILES: O=C(c1csc2c(O)nc(-c3ccccn3)nc12)N1CCC(N2CCOCC2)CC1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 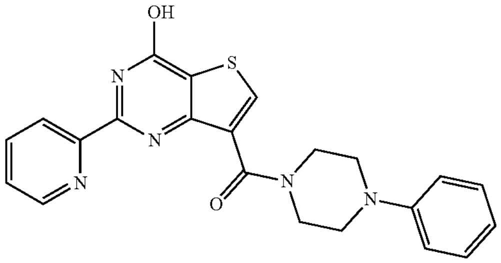 [SMILES: O=C(c1csc2c(O)nc(-c3ccccn3)nc12)N1CCN(c2ccccc2)CC1] | D | G |
| 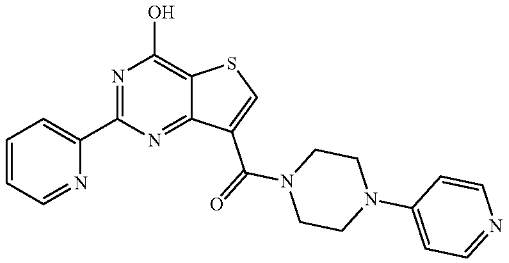 [SMILES: O=C(c1csc2c(O)nc(-c3ccccn3)nc12)N1CCN(c2ccncc2)CC1] | B | |
| 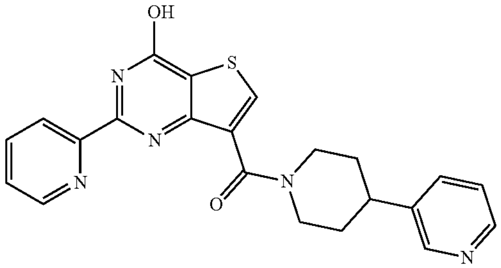 [SMILES: O=C(c1csc2c(O)nc(-c3ccccn3)nc12)N1CCC(c2cccnc2)CC1] | A | |
| 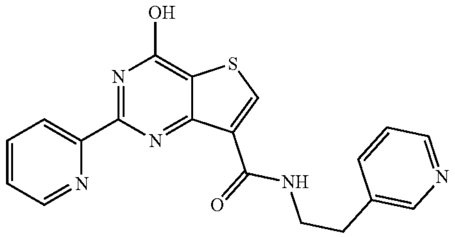 [SMILES: O=C(NCCc1cccnc1)c1csc2c(O)nc(-c3ccccn3)nc12] | A | |
| 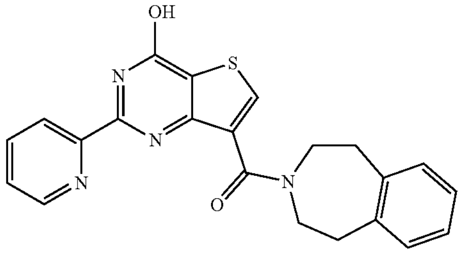 [SMILES: O=C(c1csc2c(O)nc(-c3ccccn3)nc12)N1CCc2ccccc2CC1] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 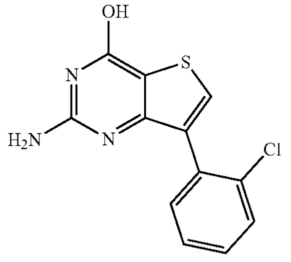 [SMILES: Nc1nc(O)c2scc(-c3ccccc3Cl)c2n1] | A | |
| 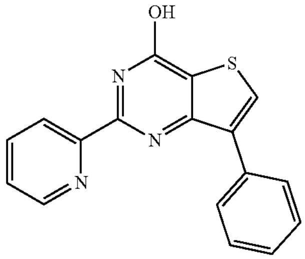 [SMILES: Oc1nc(-c2ccccn2)nc2c(-c3ccccc3)csc12] | D | H |
| 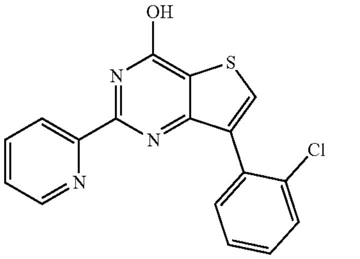 [SMILES: Oc1nc(-c2ccccn2)nc2c(-c3ccccc3Cl)csc12] | D | H |
| 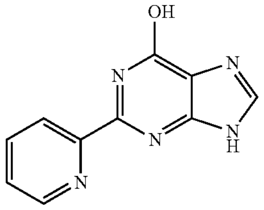 [SMILES: Oc1nc(-c2ccccn2)nc2[nH]cnc12] | A | |
| 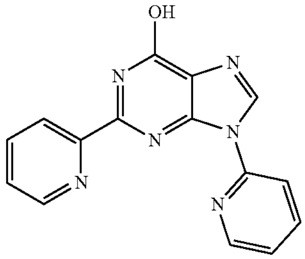 [SMILES: Oc1nc(-c2ccccn2)nc2c1ncn2-c1ccccn1] | A | |
| 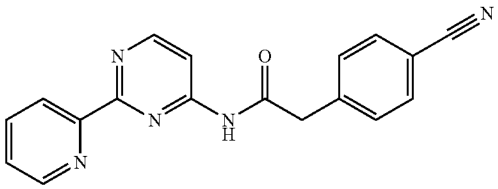 [SMILES: N#Cc1ccc(CC(=O)Nc2ccnc(-c3ccccn3)n2)cc1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 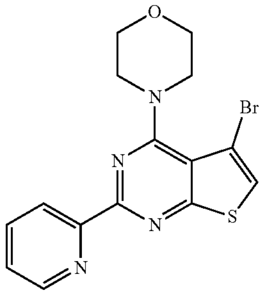 [SMILES: Brc1csc2nc(-c3ccccn3)nc(N3CCOCC3)c12] | A | |
| 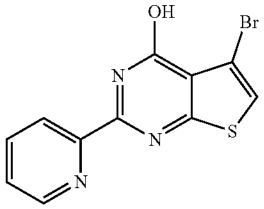 [SMILES: Oc1nc(-c2ccccn2)nc2scc(Br)c12] | D | G |
| 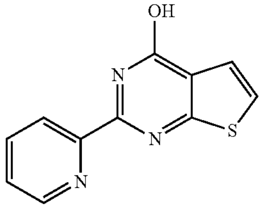 [SMILES: Oc1nc(-c2ccccn2)nc2sccc12] | A | F |
| 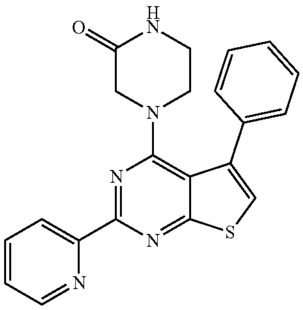 [SMILES: O=C1CN(c2nc(-c3ccccn3)nc3scc(-c4ccccc4)c23)CCN1] | A | |
| 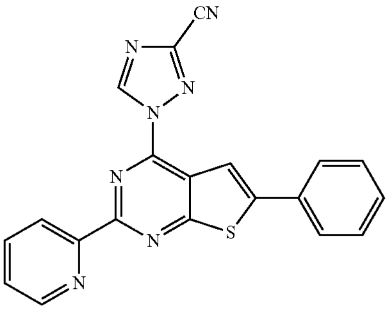 [SMILES: N#Cc1ncn(-c2nc(-c3ccccn3)nc3sc(-c4ccccc4)cc23)n1] | D | G |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 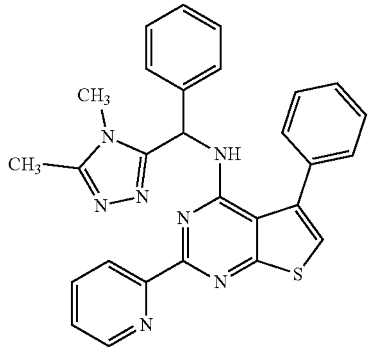 [SMILES: Cc1nnc(C(Nc2nc(-c3ccccn3)nc3scc(-c4ccccc4)c23)c2ccccc2)n1C] | C | |
| 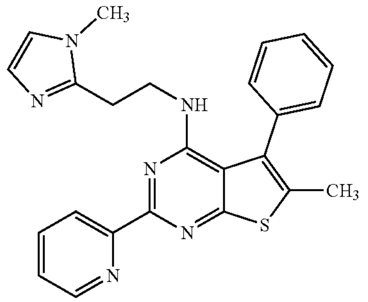 [SMILES: Cc1sc2nc(-c3ccccn3)nc(NCCc3nccn3C)c2c1-c1ccccc1] | A | |
| 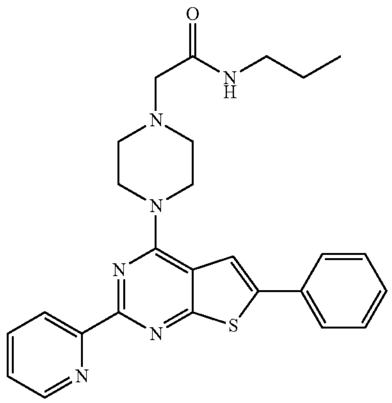 [SMILES: CCCNC(=O)CN1CCN(c2nc(-c3ccccn3)nc3sc(-c4ccccc4)cc23)CC1] | D | |
| 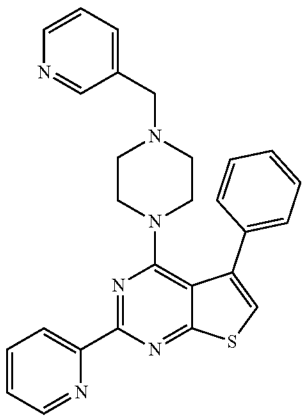 [SMILES: c1ccc(-c2csc3nc(-c4ccccn4)nc(N4CCN(Cc5cccnc5)CC4)c23)cc1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 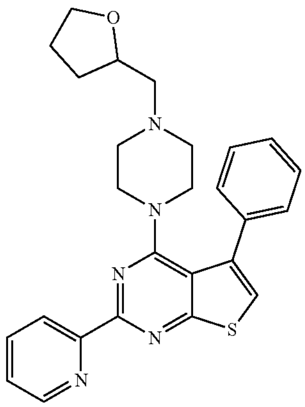 [SMILES: c1ccc(-c2csc3nc(-c4ccccn4)nc(N4CCN(CC5CCCO5)CC4)c23)cc1] | A | |
| 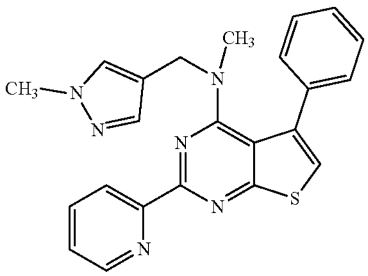 [SMILES: CN(Cc1cnn(C)c1)c1nc(-c2ccccn2)nc2scc(-c3ccccc3)c12] | B | |
| 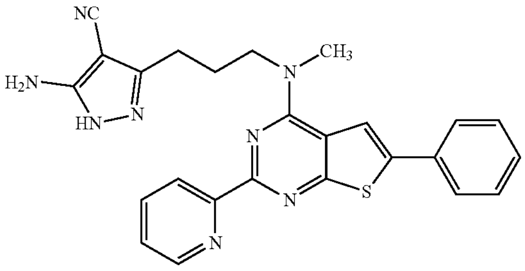 [SMILES: CN(CCCc1n[nH]c(N)c1C#N)c1nc(-c2ccccn2)nc2sc(-c3ccccc3)cc12] | B | |
| 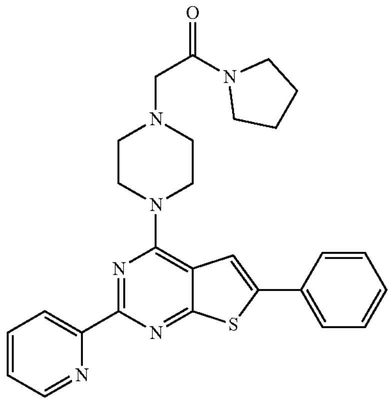 [SMILES: O=C(CN1CCN(c2nc(-c3ccccn3)nc3sc(-c4ccccc4)cc23)CC1)N1CCCC1] | D | G |

TABLE 4-continued
| % Inhibition of MAPK phosphorylation at 30 μM in the PANC-1 pancreatic cancer cell line, and select $IC_{50}$ data | |
|---|---|
| Compound | PANC-1 $IC_{50}$ (μM) |
| 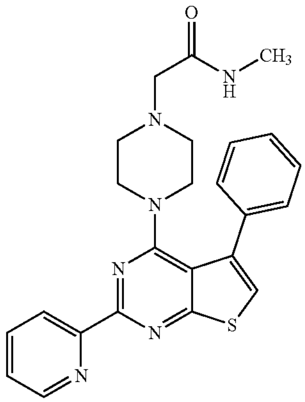 [SMILES: CNC(=O)CN1CCN(c2nc(-c3ccccn3)nc3scc(-c4ccccc4)c23)CC1] | A |
| 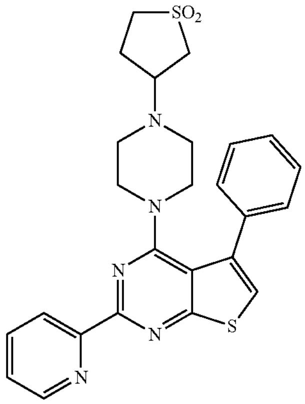 [SMILES: O=S1(=O)CCC(N2CCN(c3nc(-c4ccccn4)nc4scc(-c5ccccc5)c34)CC2)C1] | A |
| 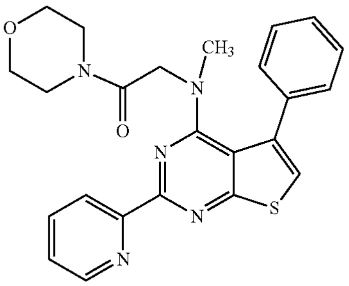 [SMILES: CN(CC(=O)N1CCOCC1)c1nc(-c2ccccn2)nc2scc(-c3ccccc3)c12] | A |
| 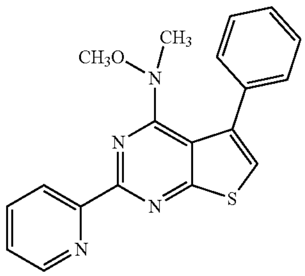 | B |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 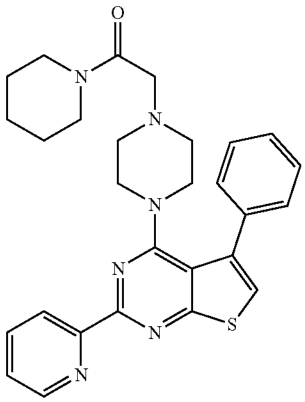 [SMILES: O=C(CN1CCN(c2nc(-c3ccccn3)nc3scc(-c4ccccc4)c23)CC1)N1CCCCC1] | B | |
| 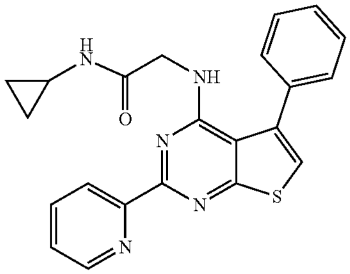 [SMILES: O=C(CNc1nc(-c2ccccn2)nc2scc(-c3ccccc3)c12)NC1CC1] | B | |
| 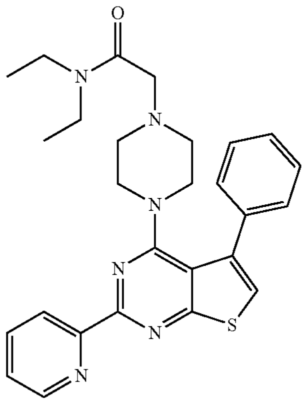 [SMILES: CCN(CC)C(=O)CN1CCN(c2nc(-c3ccccn3)nc3scc(-c4ccccc4)c23)CC1] | B | |
| 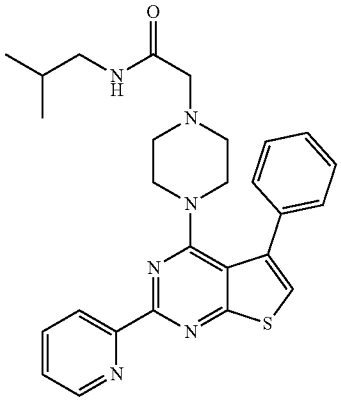 [SMILES: CC(C)CNC(=O)CN1CCN(c2nc(-c3ccccn3)nc3scc(-c4ccccc4)c23)CC1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 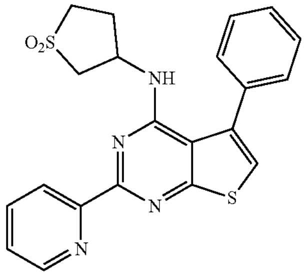 [SMILES: O=S1(=O)CCC(Nc2nc(-c3ccccn3)nc3scc(-c4ccccc4)c23)C1] | A | |
| 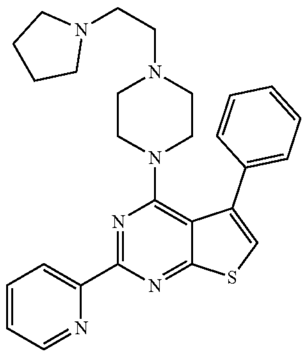 [SMILES: c1ccc(-c2csc3nc(-c4ccccn4)nc(N4CCN(CCN5CCCC5)CC4)c23)cc1] | D | |
| 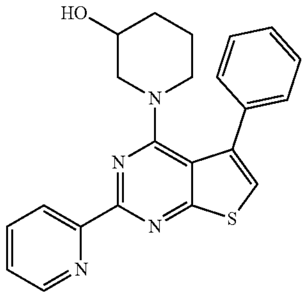 [SMILES: OC1CCCN(c2nc(-c3ccccn3)nc3scc(-c4ccccc4)c23)C1] | C | |
| 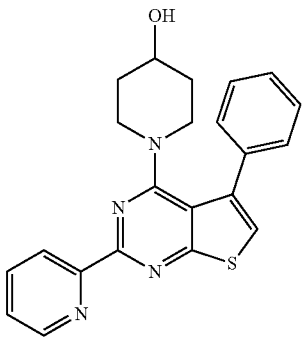 [SMILES: OC1CCN(c2nc(-c3ccccn3)nc3scc(-c4ccccc4)c23)CC1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 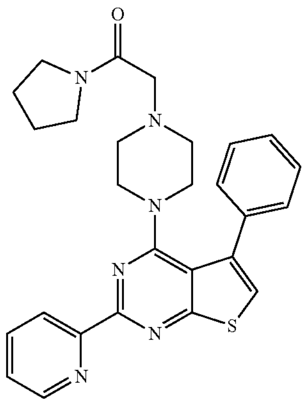 [SMILES: O=C(CN1CCN(c2nc(-c3ccccn3)nc3scc(-c4ccccc4)c23)CC1)N1CCCC1] | A | |
| 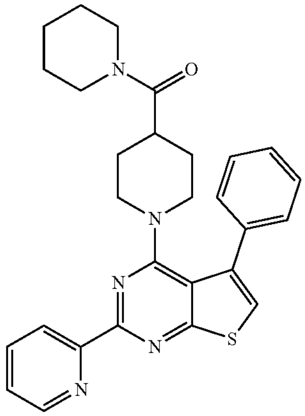 [SMILES: O=C(C1CCN(c2nc(-c3ccccn3)nc3scc(-c4ccccc4)c23)CC1)N1CCCCC1] | A | |
| 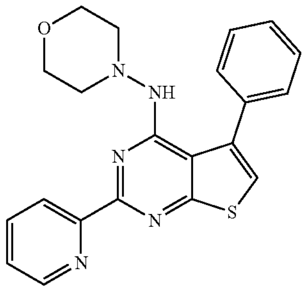 [SMILES: c1ccc(-c2csc3nc(-c4ccccn4)nc(NN4CCOCC4)c23)cc1] | A | |
| 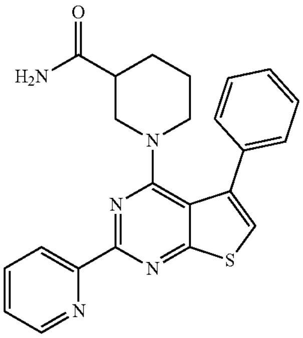 [SMILES: NC(=O)C1CCCN(c2nc(-c3ccccn3)nc3scc(-c4ccccc4)c23)C1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 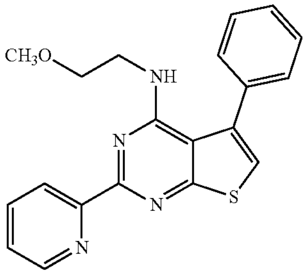 | D | |
| 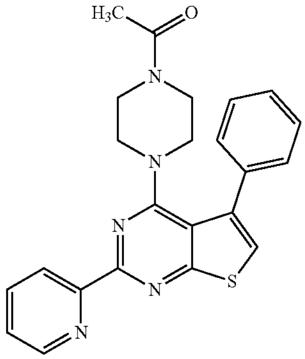 [SMILES: CC(=O)N1CCN(c2nc(-c3ccccn3)nc3scc(-c4ccccc4)c23)CC1] | B | |
| 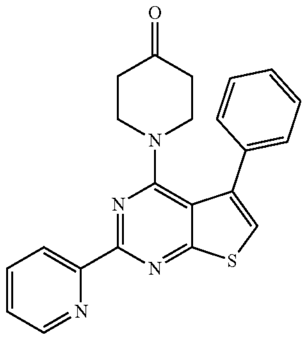 [SMILES: O=C1CCN(c2nc(-c3ccccn3)nc3scc(-c4ccccc4)c23)CC1] | B | |
| 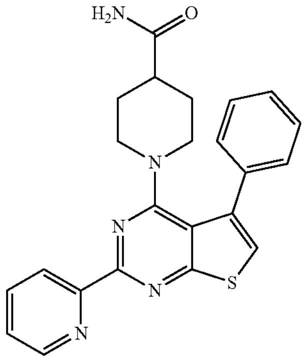 [SMILES: NC(=O)C1CCN(c2nc(-c3ccccn3)nc3scc(-c4ccccc4)c23)CC1] | A | |
| 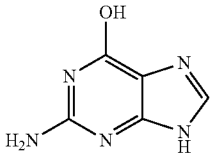 [SMILES: Nc1nc(O)c2nc[nH]c2n1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 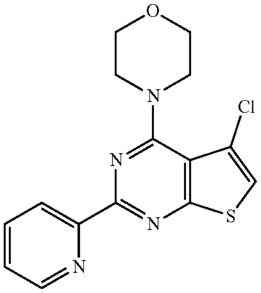 [SMILES: Clc1csc2nc(-c3ccccn3)nc(N3CCOCC3)c12] | A | |
| 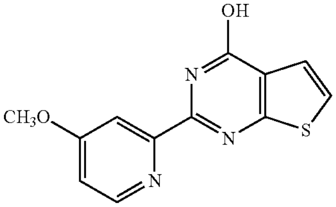 | C | E |
| 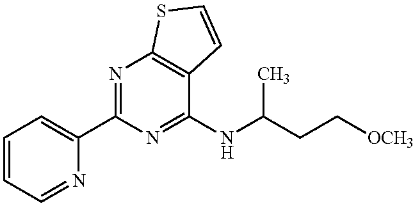 [SMILES: COCCC(C)Nc1nc(-c2ccccn2)nc2sccc12] | B | |
| 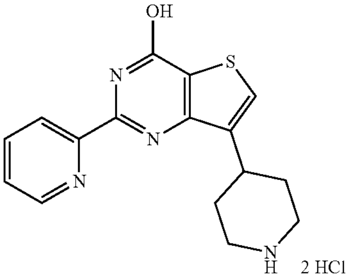 [SMILES: Oc1nc(-c2ccccn2)nc2c(C3CCNCC3)csc12] | A | |
| 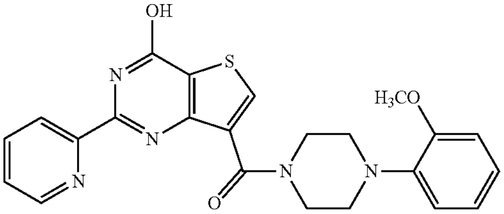 [SMILES: COc1ccccc1N1CCN(C(=O)c2csc3c(O)nc(-c4ccccn4)nc23)CC1] | A | |
| 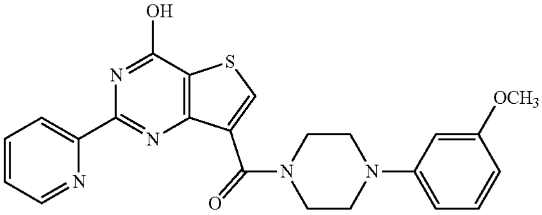 [SMILES: COc1cccc(N2CCN(C(=O)c3csc4c(O)nc(-c5ccccn5)nc34)CC2)c1] | D | E |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 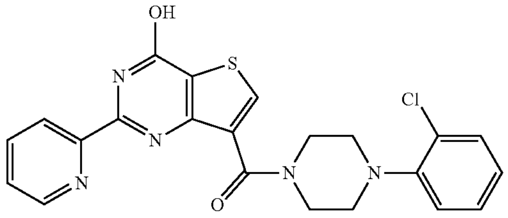 | A | |
| 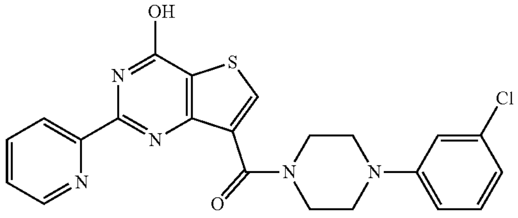 [SMILES: O=C(c1csc2c(O)nc(-c3ccccn3)nc12)N1CCN(c2cccc(Cl)c2)CC1] | B | |
| 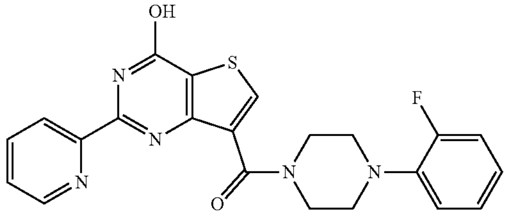 [SMILES: O=C(c1csc2c(O)nc(-c3ccccn3)nc12)N1CCN(c2ccccc2F)CC1] | A | |
| 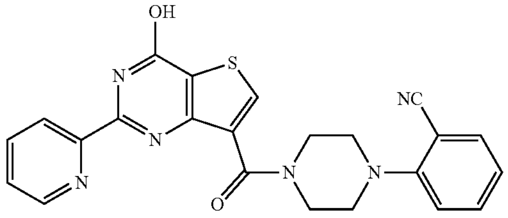 | A | |
| 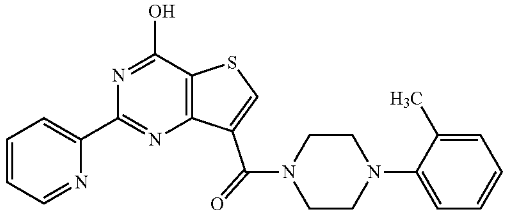 [SMILES: Cc1ccccc1N1CCN(C(=O)c2csc3c(O)nc(-c4ccccn4)nc23)CC1] | B | E |
| 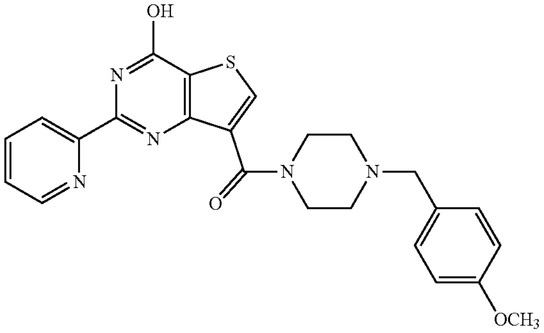 [SMILES: COc1ccc(CN2CCN(C(=O)c3csc4c(O)nc(-c5ccccn5)nc34)CC2)cc1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 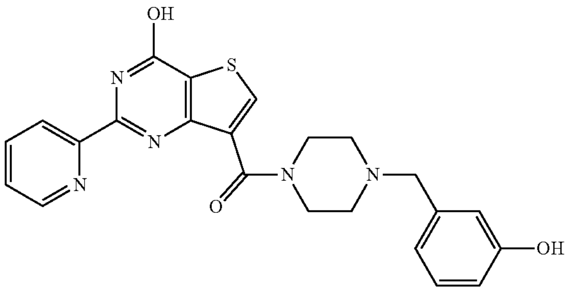 [SMILES: O=C(c1csc2c(O)nc(-c3ccccn3)nc12)N1CCN(Cc2cccc(O)c2)CC1] | C | E |
| 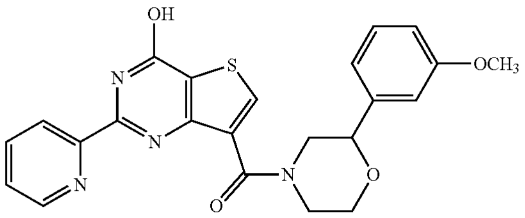 [SMILES: COc1cccc(C2CN(C(=O)c3csc4c(O)nc(-c5ccccn5)nc34)CCO2)c1] | A | |
| 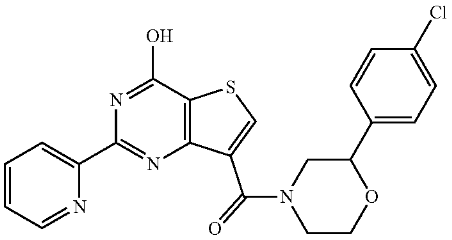 [SMILES: O=C(c1csc2c(O)nc(-c3ccccn3)nc12)N1CCOC(c2ccc(Cl)cc2)C1] | A | |
| 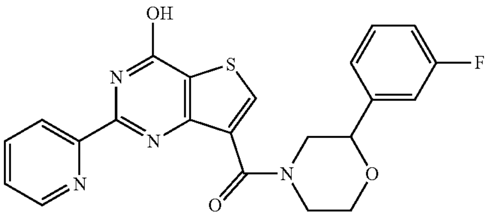 [SMILES: O=C(c1csc2c(O)nc(-c3ccccn3)nc12)N1CCOC(c2cccc(F)c2)C1] | A | E |
| 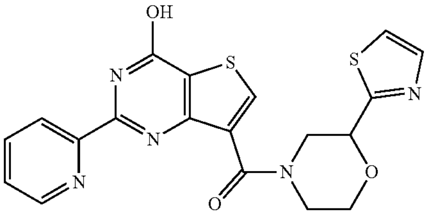 [SMILES: O=C(c1csc2c(O)nc(-c3ccccn3)nc12)N1CCOC(c2nccs2)C1] | B | E |
| 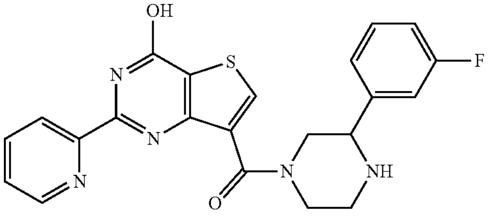 [SMILES: O=C(c1csc2c(O)nc(-c3ccccn3)nc12)N1CCNC(c2cccc(F)c2)C1] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 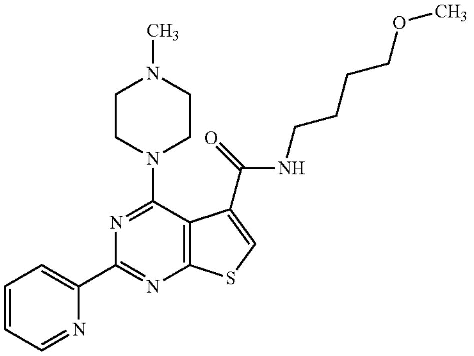 [SMILES: COCCCCNC(=O)c1csc2nc(-c3ccccn3)nc(N3CCN(C)CC3)c12] | A | |
| 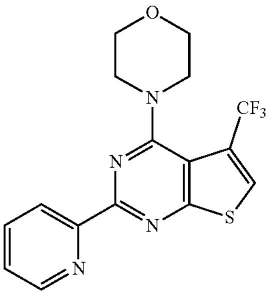 [SMILES: FC(F)(F)c1csc2nc(-c3ccccn3)nc(N3CCOCC3)c12] | A | |
| 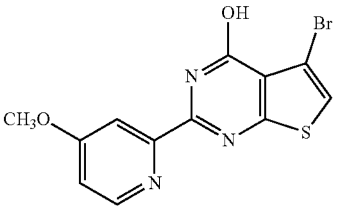 | D | G |
| 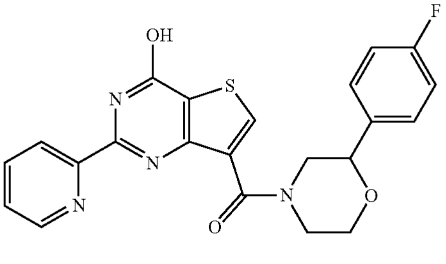 [SMILES: O=C(c1csc2c(O)nc(-c3ccccn3)nc12)N1CCOC(c2ccc(F)cc2)C1] | A | |
| 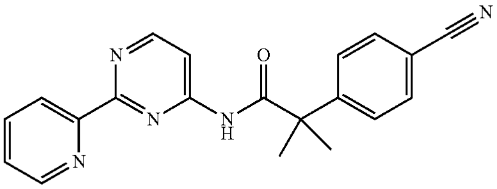 [SMILES: CC(C)(C(=O)Nc1ccnc(-c2ccccn2)n1)c1ccc(C#N)cc1] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 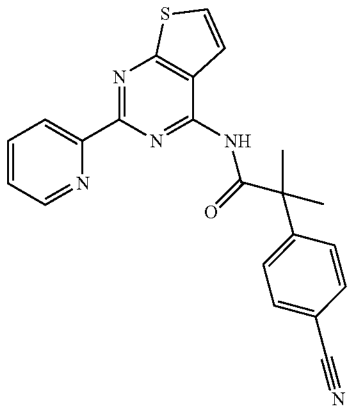 [SMILES: CC(C)(C(=O)Nc1nc(-c2ccccn2)nc2sccc12)c1ccc(C#N)cc1] | A | |
| 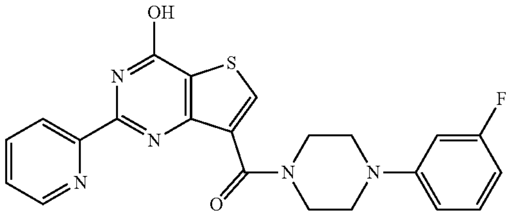 [SMILES: O=C(c1csc2c(O)nc(-c3ccccn3)nc12)N1CCN(c2cccc(F)c2)CC1] | A | |
| 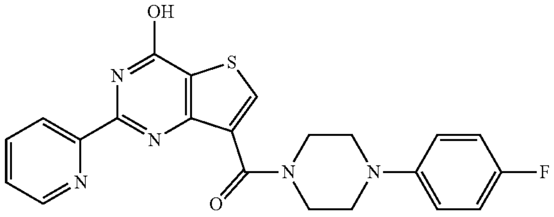 [SMILES: O=C(c1csc2c(O)nc(-c3ccccn3)nc12)N1CCN(c2ccc(F)cc2)CC1] | A | |
| 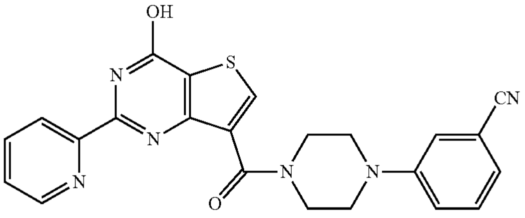 [SMILES: N#Cc1cccc(N2CCN(C(=O)c3csc4c(O)nc(-c5ccccn5)nc34)CC2)c1] | A | |
| 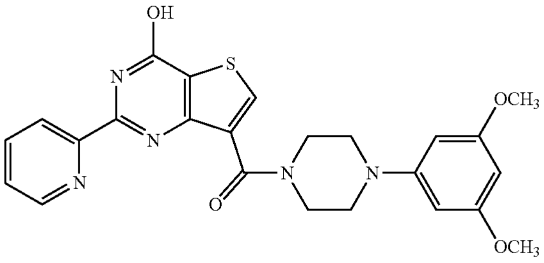 [SMILES: COc1cc(OC)cc(N2CCN(C(=O)c3csc4c(O)nc(-c5ccccn5)nc34)CC2)c1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 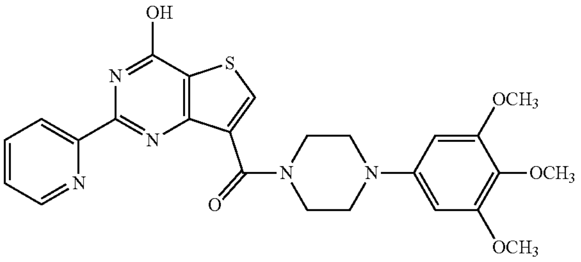 [SMILES: COc1cc(N2CCN(C(=O)c3csc4c(O)nc(-c5ccccn5)nc34)CC2)cc(OC)c1OC] | A | |
| 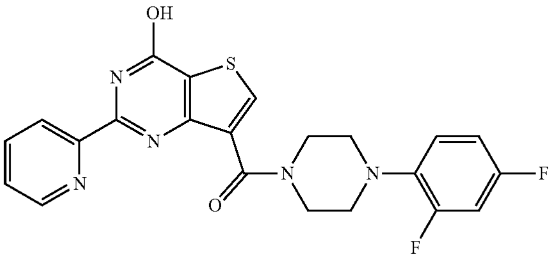 [SMILES: O=C(c1csc2c(O)nc(-c3ccccn3)nc12)N1CCN(c2ccc(F)cc2F)CC1] | A | |
| 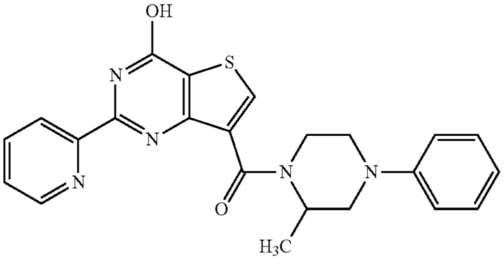 [SMILES: CC1CN(c2ccccc2)CCN1C(=O)c1csc2c(O)nc(-c3ccccn3)nc12] | C | E |
| 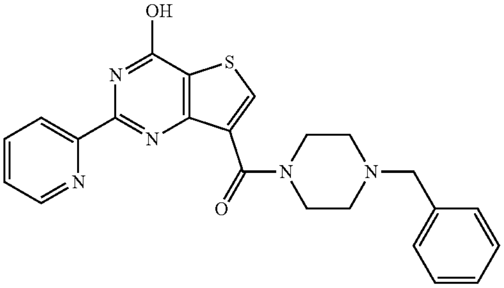 [SMILES: O=C(c1csc2c(O)nc(-c3ccccn3)nc12)N1CCN(Cc2ccccc2)CC1] | A | |
| 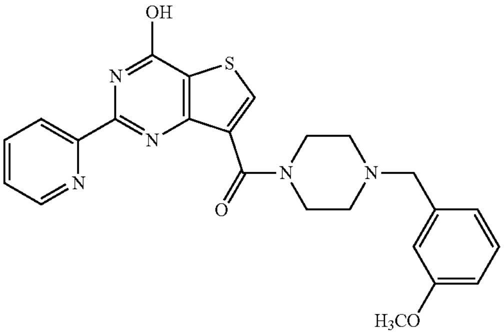 [SMILES: COc1cccc(CN2CCN(C(=O)c3csc4c(O)nc(-c5ccccn5)nc34)CC2)c1] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 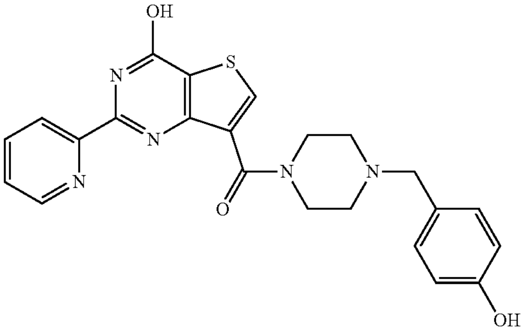 [SMILES: O=C(c1csc2c(O)nc(-c3ccccn3)nc12)N1CCN(Cc2ccc(O)cc2)CC1] | B | |
| 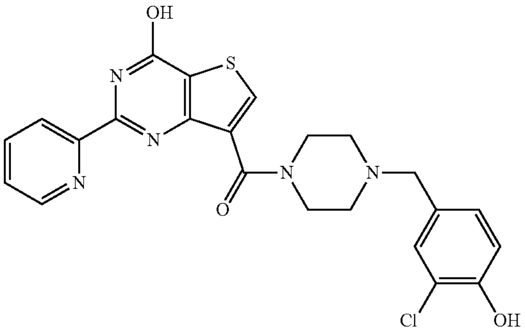 [SMILES: O=C(c1csc2c(O)nc(-c3ccccn3)nc12)N1CCN(Cc2ccc(O)c(Cl)c2)CC1] | B | |
| 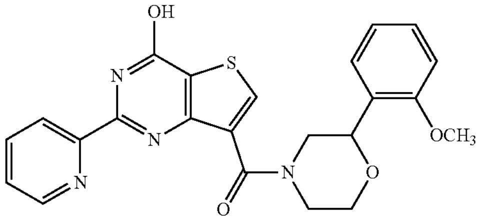 | A | |
| 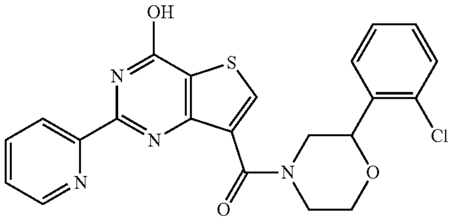 [SMILES: O=C(c1csc2c(O)nc(-c3ccccn3)nc12)N1CCOC(c2ccccc2Cl)C1] | A | |
| 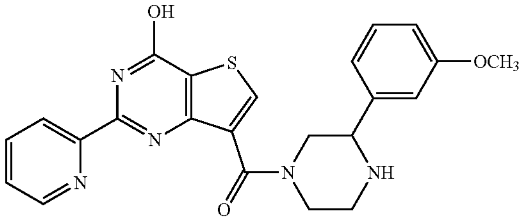 [SMILES: COc1cccc(C2CN(C(=O)c3csc4c(O)nc(-c5ccccn5)nc34)CCN2)c1] | A | |

TABLE 4-continued
| % Inhibition of MAPK phosphorylation at 30 μM in the PANC-1 pancreatic cancer cell line, and select $IC_{50}$ data | |
|---|---|
| Compound | PANC-1 $IC_{50}$ (μM) |
| 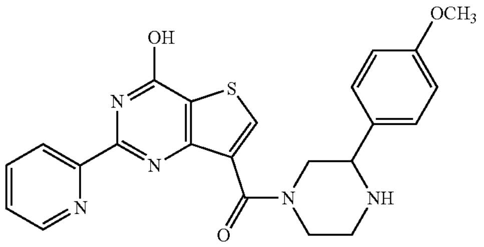 | B |
| 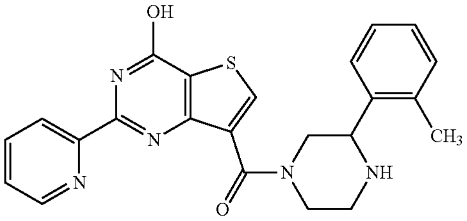 [SMILES: Cc1ccccc1C1CN(C(=O)c2csc3c(O)nc(-c4ccccn4)nc23)CCN1] | A |
| 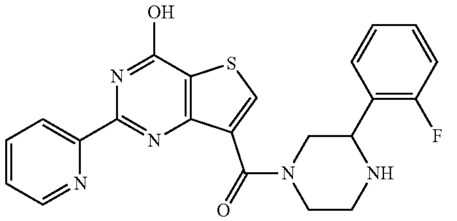 [SMILES: O=C(c1csc2c(O)nc(-c3ccccn3)nc12)N1CCNC(c2ccccc2F)C1] | A |
| 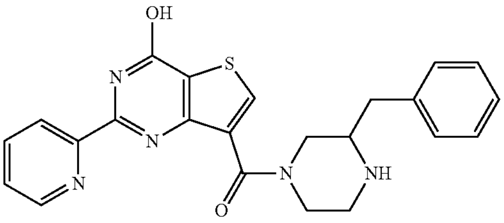 [SMILES: O=C(c1csc2c(O)nc(-c3ccccn3)nc12)N1CCNC(Cc2ccccc2)C1] | A |
| 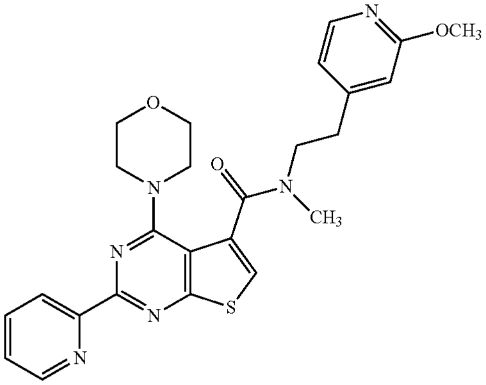 [SMILES: COc1cc(CCN(C)C(=O)c2csc3nc(-c4ccccn4)nc(N4CCOCC4)c23)ccn1] | A |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 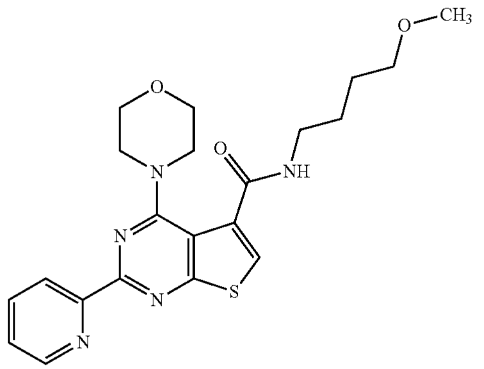 [SMILES: COCCCCNC(=O)c1csc2nc(-c3ccccn3)nc(N3CCOCC3)c12] | A | |
| 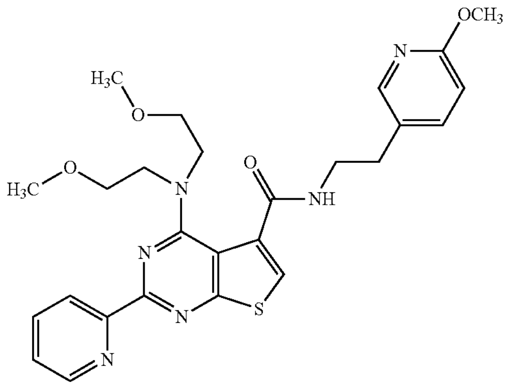 [SMILES: COCCN(CCOC)c1nc(-c2ccccn2)nc2scc(C(=O)NCCc3ccc(OC)nc3)c12] | A | |
| 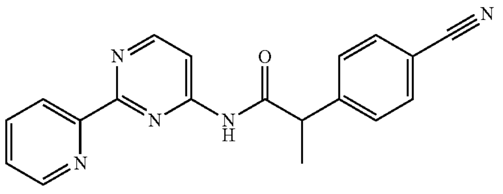 [SMILES: CC(C(=O)Nc1ccnc(-c2ccccn2)n1)c1ccc(C#N)cc1] | A | |
| 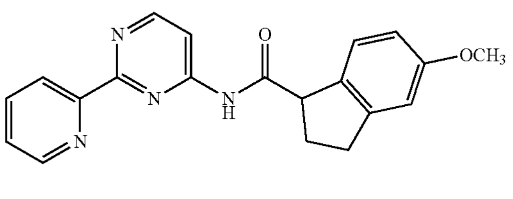 [SMILES: COc1ccc2c(c1)CCC2C(=O)Nc1ccnc(-c2ccccn2)n1] | A | |
| 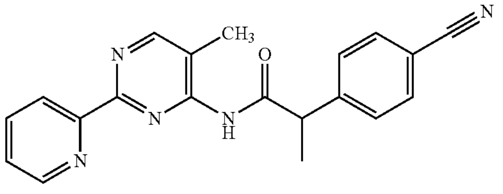 [SMILES: Cc1cnc(-c2ccccn2)nc1NC(=O)C(C)c1ccc(C#N)cc1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 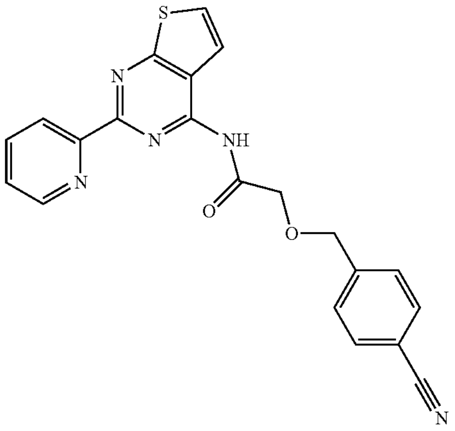 [SMILES: N#Cc1ccc(COCC(=O)Nc2nc(-c3ccccn3)nc3sccc23)cc1] | A | |
| 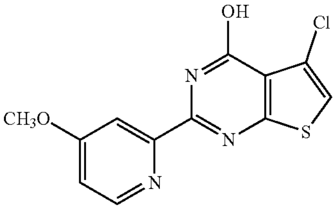 | A | |
| 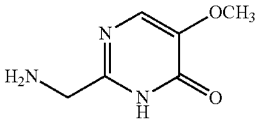 HCl | A | |
| 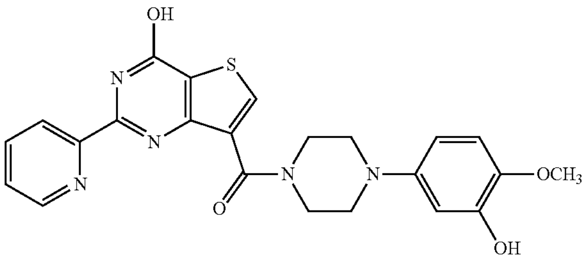 [SMILES: COc1ccc(N2CCN(C(=O)c3csc4c(O)nc(-c5ccccn5)nc34)CC2)cc1O] | A | |
| 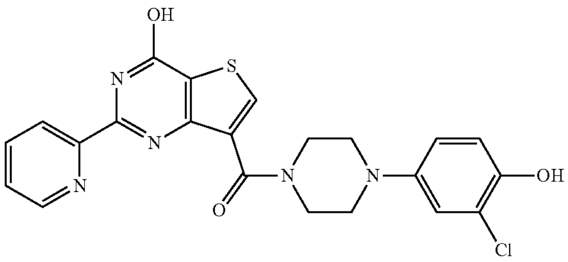 [SMILES: O=C(c1csc2c(O)nc(-c3ccccn3)nc12)N1CCN(c2ccc(O)c(Cl)c2)CC1] | A | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 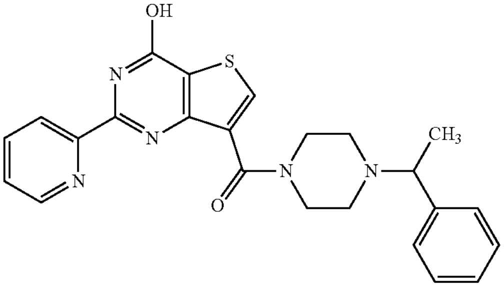 [SMILES: CC(c1ccccc1)N1CCN(C(=O)c2csc3c(O)nc(-c4ccccn4)nc23)CC1] | A | |
| 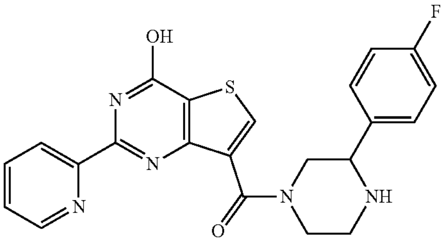 [SMILES: O=C(c1csc2c(O)nc(-c3ccccn3)nc12)N1CCNC(c2ccc(F)cc2)C1] | A | |
| 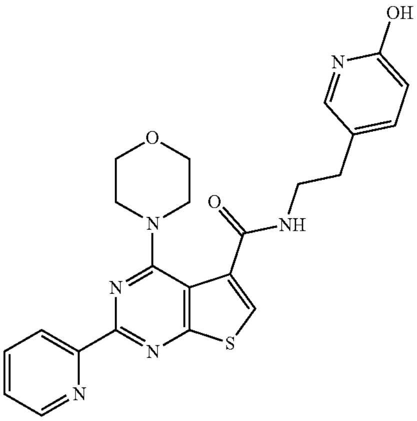 [SMILES: O=C(NCCc1ccc(O)nc1)c1csc2nc(-c3ccccn3)nc(N3CCOCC3)c12] | A | |
| 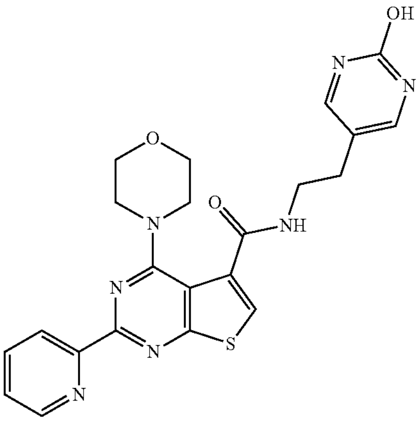 [SMILES: O=C(NCCc1cnc(O)nc1)c1csc2nc(-c3ccccn3)nc(N3CCOCC3)c12] | B | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 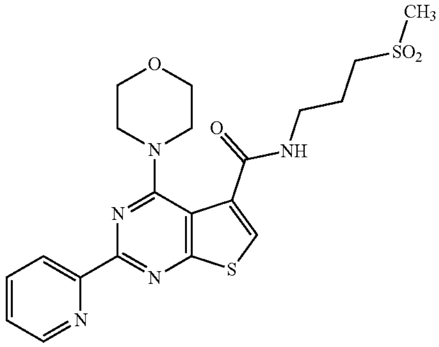 [SMILES: CS(=O)(=O)CCCNC(=O)c1csc2nc(-c3ccccn3)nc(N3CCOCC3)c12] | B | |
| 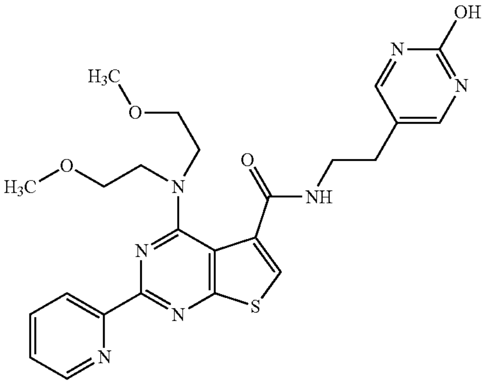 [SMILES: COCCN(CCOC)c1nc(-c2ccccn2)nc2scc(C(=O)NCCc3cnc(O)nc3)c12] | B | |
| 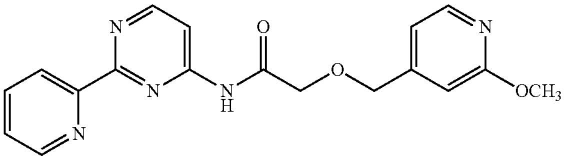 [SMILES: COc1cc(COCC(=O)Nc2ccnc(-c3ccccn3)n2)ccn1] | B | |
| 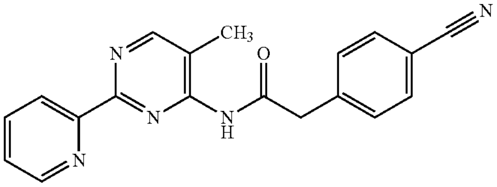 [SMILES: Cc1cnc(-c2ccccn2)nc1NC(=O)Cc1ccc(C#N)cc1] | C | |
| 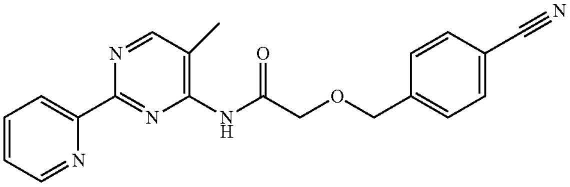 [SMILES: Cc1cnc(-c2ccccn2)nc1NC(=O)COCc1ccc(C#N)cc1] | A | |
| 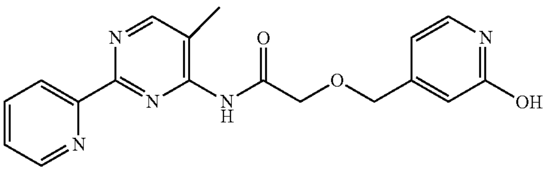 [SMILES: Cc1cnc(-c2ccccn2)nc1NC(=O)COCc1ccnc(O)c1] | B | |

TABLE 4-continued
| % Inhibition of MAPK phosphorylation at 30 μM in the PANC-1 pancreatic cancer cell line, and select $IC_{50}$ data | |
|---|---|
| Compound | $IC_{50}$ PANC-1 (μM) |
| 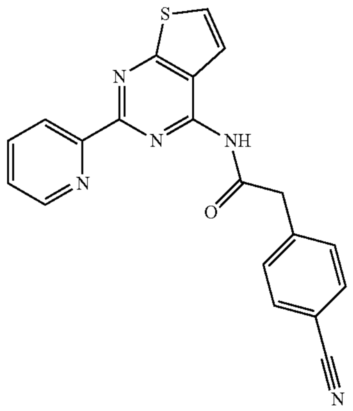 [SMILES: N#Cc1ccc(CC(=O)Nc2nc(-c3ccccn3)nc3sccc23)cc1] | D |
| 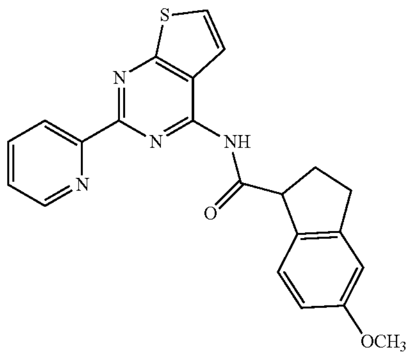 [SMILES: COc1ccc2c(c1)CCC2C(=O)Nc1nc(-c2ccccn2)nc2sccc12] | A |
| 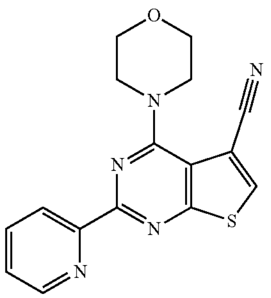 [SMILES: N#Cc1csc2nc(-c3ccccn3)nc(N3CCOCC3)c12] | A |
| 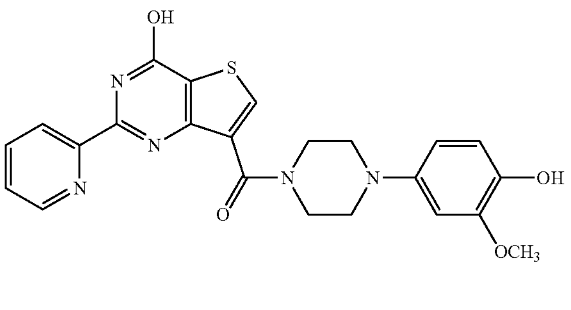 [SMILES: COc1cc(N2CCN(C(=O)c3csc4c(O)nc(-c5ccccn5)nc34)CC2)ccc1O] | B |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 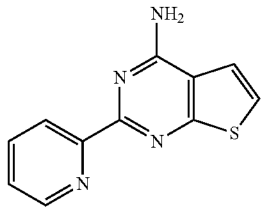 [SMILES: Nc1nc(-c2ccccn2)nc2sccc12] | A | |
| 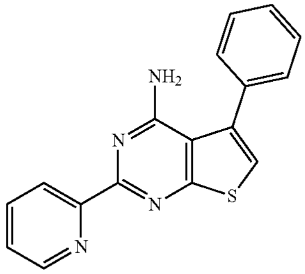 [SMILES: Nc1nc(-c2ccccn2)nc2scc(-c3ccccc3)c12] | A | |
| 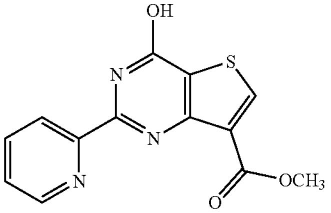 [SMILES: COC(=O)c1csc2c(O)nc(-c3ccccn3)nc12] | B | |
| 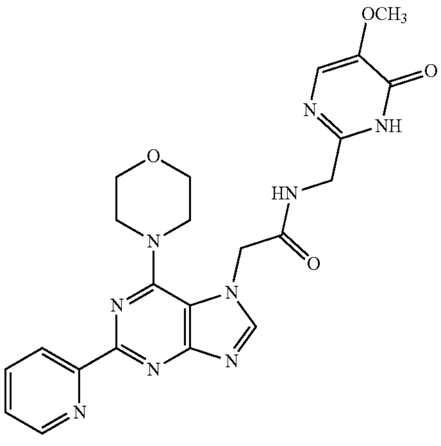 [SMILES: COc1cnc(CNC(=O)Cn2cnc3nc(-c4ccccn4)nc(N4CCOCC4)c32)[nH]c1=O] | A | |
| 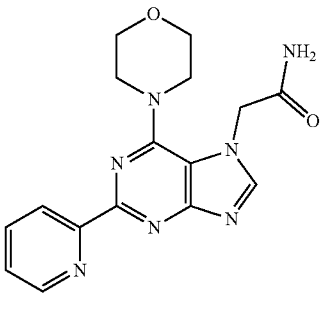 [SMILES: NC(=O)Cn1cnc2nc(-c3ccccn3)nc(N3CCOCC3)c21] | A | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 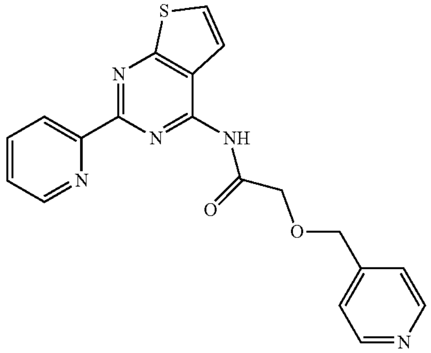 [SMILES: O=C(COCc1ccncc1)Nc1nc(-c2ccccn2)nc2sccc12] | A* | |
| 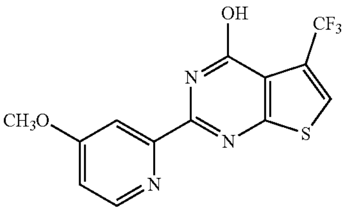 | A* | |
| 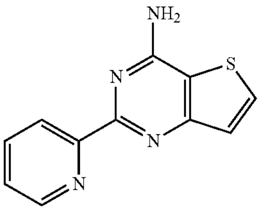 [SMILES: Nc1nc(-c2ccccn2)nc2ccsc12] | A* | |
| 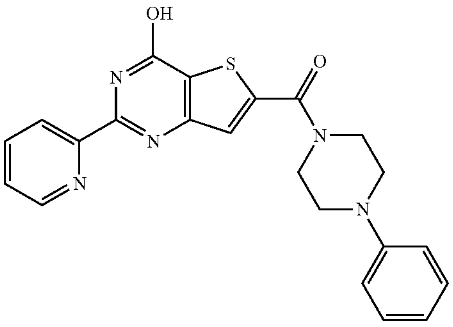 [SMILES: O=C(c1cc2nc(-c3ccccn3)nc(O)c2s1)N1CCN(c2ccccc2)CC1] | A* | |
| 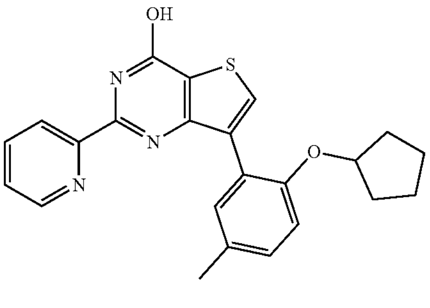 [SMILES: Cc1ccc(OC2CCCC2)c(-c2csc3c(O)nc(-c4ccccn4)nc23)c1] | B* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 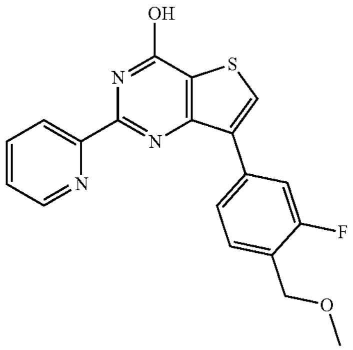 [SMILES: COCc1ccc(-c2csc3c(O)nc(-c4ccccn4)nc23)cc1F] | D* | G |
| 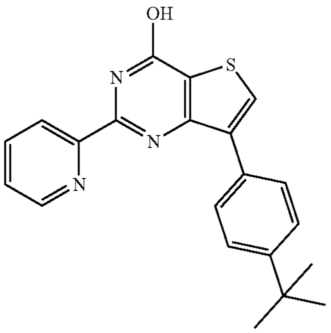 [SMILES: CC(C)(C)c1ccc(-c2csc3c(O)nc(-c4ccccn4)nc23)cc1] | D* | G |
| 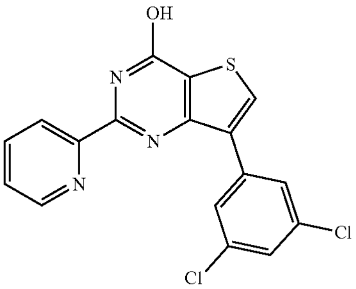 [SMILES: Oc1nc(-c2ccccn2)nc2c(-c3cc(Cl)cc(Cl)c3)csc12] | A* | E |
| 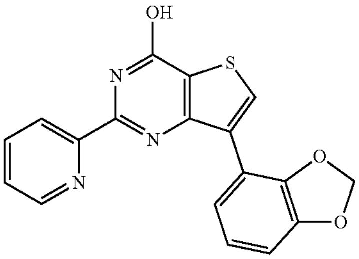 [SMILES: Oc1nc(-c2ccccn2)nc2c(-c3cccc4c3OCO4)csc12] | D* | H |
| 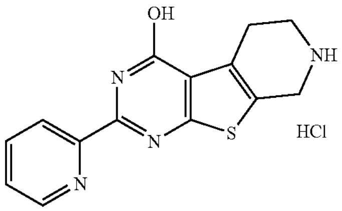 [SMILES: Oc1nc(-c2ccccn2)nc2sc3c(c12)CCNC3 ; Cl] | B* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 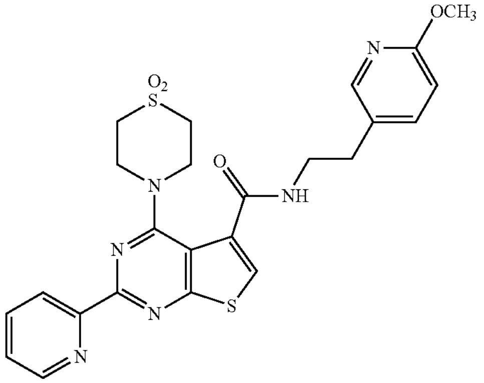 [SMILES: COc1ccc(CCNC(=O)c2csc3nc(-c4ccccn4)nc(N4CCS(=O)(=O)CC4)c23)cn1] | A* | |
| 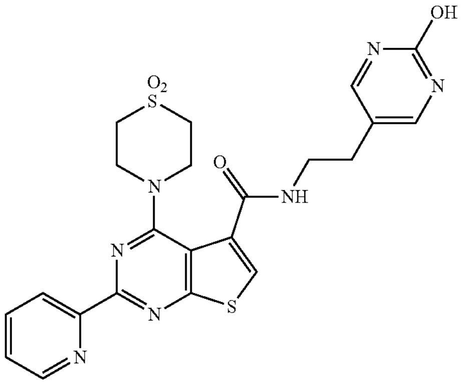 | A* | |
| 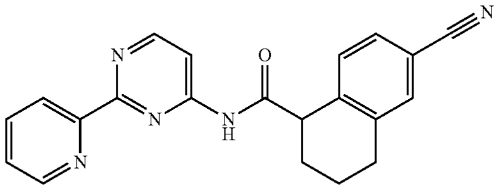 [SMILES: N#Cc1ccc2c(c1)CCCC2C(=O)Nc1ccnc(-c2ccccn2)n1] | A* | |
| 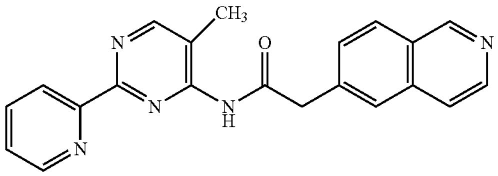 [SMILES: Cc1cnc(-c2ccccn2)nc1NC(=O)Cc1ccc2cnccc2c1] | B* | |
| 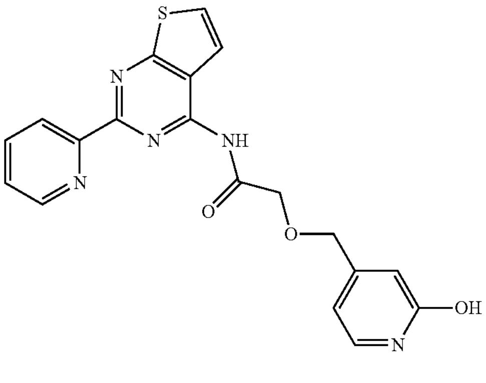 [SMILES: O=C(COCc1ccnc(O)c1)Nc1nc(-c2ccccn2)nc2sccc12] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 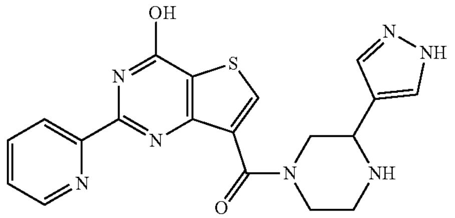 [SMILES: O=C(c1csc2c(O)nc(-c3ccccn3)nc12)N1CCNC(c2cn[nH]c2)C1] | B* | |
| 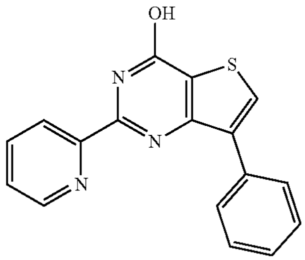 | B* | |
| 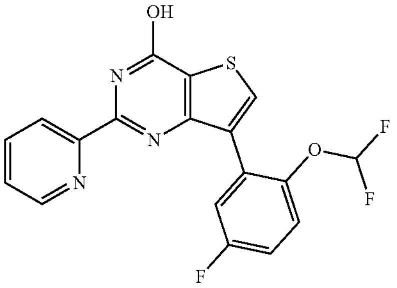 [SMILES: Oc1nc(-c2ccccn2)nc2c(-c3cc(F)ccc3OC(F)F)csc12] | A* | |
| 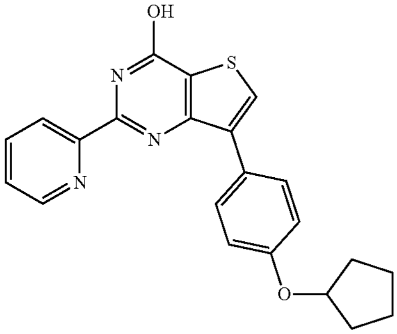 [SMILES: Oc1nc(-c2ccccn2)nc2c(-c3ccc(OC4CCCC4)cc3)csc12] | B* | |
| 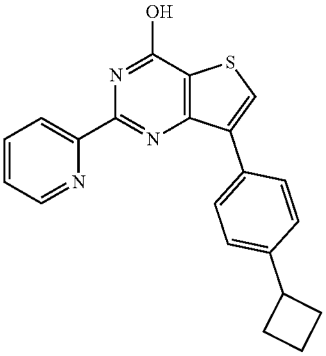 [SMILES: Oc1nc(-c2ccccn2)nc2c(-c3ccc(C4CCC4)cc3)csc12] | C* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 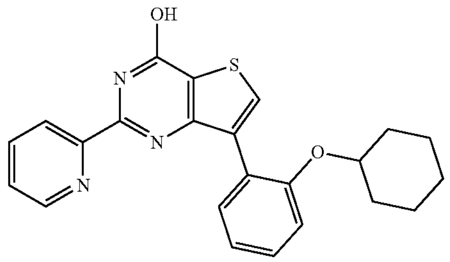 [SMILES: Oc1nc(-c2ccccn2)nc2c(-c3ccccc3OC3CCCCC3)csc12] | A* | |
| 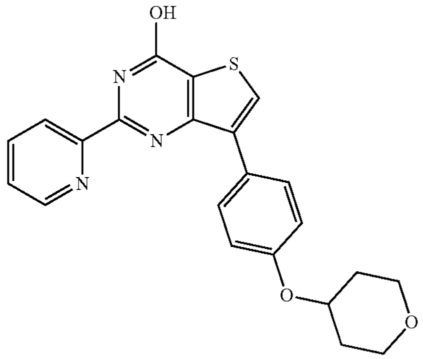 [SMILES: Oc1nc(-c2ccccn2)nc2c(-c3ccc(OC4CCOCC4)cc3)csc12] | A* | |
| 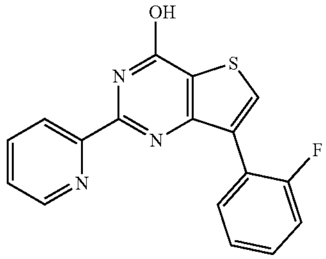 [SMILES: Oc1nc(-c2ccccn2)nc2c(-c3ccccc3F)csc12] | D* | G |
| 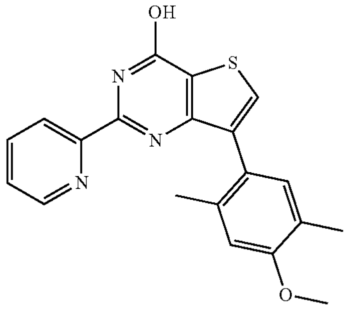 [SMILES: COc1cc(C)c(-c2csc3c(O)nc(-c4ccccn4)nc23)cc1C] | A* | |
| 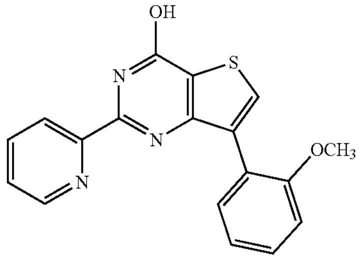 [SMILES: COc1ccccc1-c1csc2c(O)nc(-c3ccccn3)nc12] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 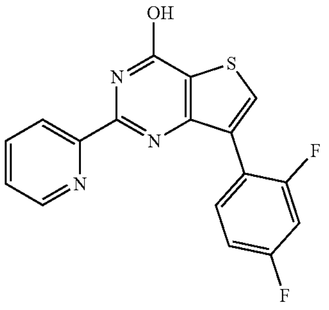 [SMILES: Oc1nc(-c2ccccn2)nc2c(-c3ccc(F)cc3F)csc12] | D* | G |
| 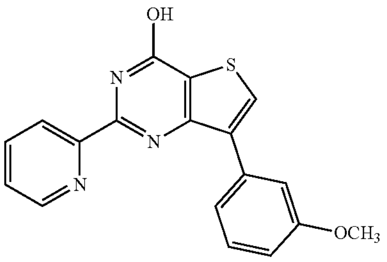 [SMILES: COc1cccc(-c2csc3c(O)nc(-c4ccccn4)nc23)c1] | A* | |
| 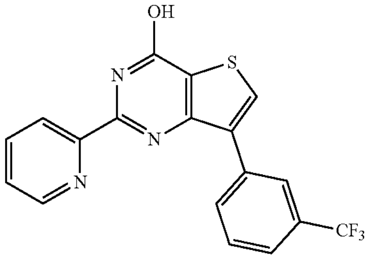 | D* | H |
| 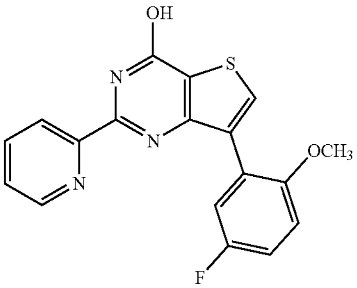 [SMILES: COc1ccc(F)cc1-c1csc2c(O)nc(-c3ccccn3)nc12] | B* | |
| 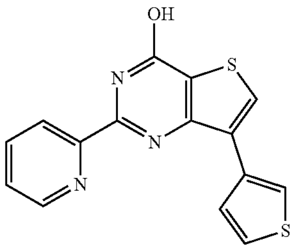 [SMILES: Oc1nc(-c2ccccn2)nc2c(-c3ccsc3)csc12] | D* | H |

TABLE 4-continued
| % Inhibition of MAPK phosphorylation at 30 μM in the PANC-1 pancreatic cancer cell line, and select $IC_{50}$ data | |
|---|---|
| Compound | PANC-1 $IC_{50}$ (μM) |
| 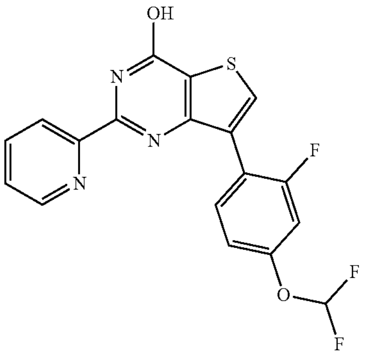 [SMILES: Oc1nc(-c2ccccn2)nc2c(-c3ccc(OC(F)F)cc3F)csc12] | C* |
| 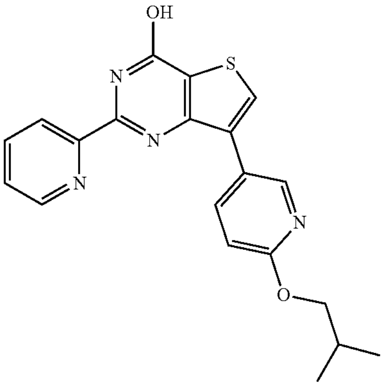 [SMILES: CC(C)COc1ccc(-c2csc3c(O)nc(-c4ccccn4)nc23)cn1] | C* |
| 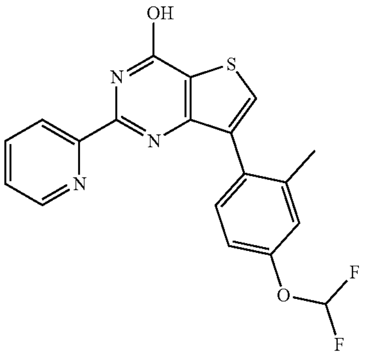 [SMILES: Cc1cc(OC(F)F)ccc1-c1csc2c(O)nc(-c3ccccn3)nc12] | A* |
| 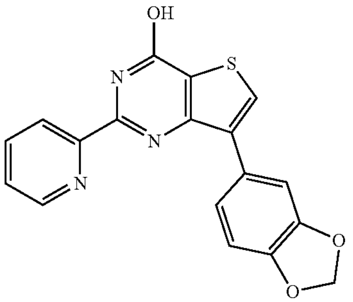 [SMILES: Oc1nc(-c2ccccn2)nc2c(-c3ccc4c(c3)OCO4)csc12] | D* |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 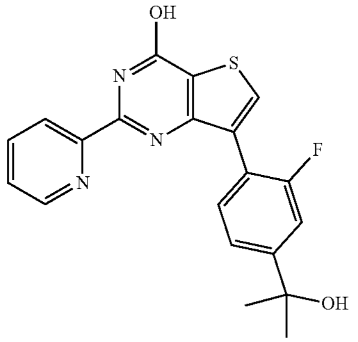 [SMILES: CC(C)(O)c1ccc(-c2csc3c(O)nc(-c4ccccn4)nc23)c(F)c1] | D* | |
| 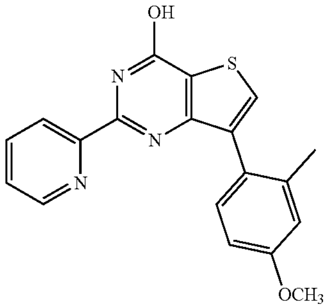 [SMILES: COc1ccc(-c2csc3c(O)nc(-c4ccccn4)nc23)c(C)c1] | D* | |
| 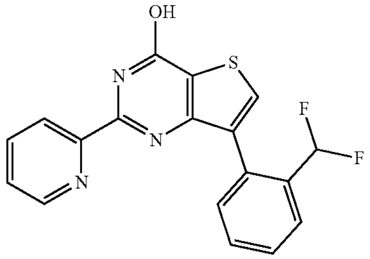 [SMILES: Oc1nc(-c2ccccn2)nc2c(-c3ccccc3C(F)F)csc12] | D* | |
| 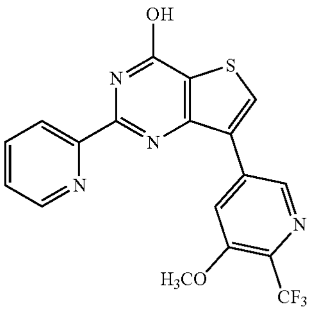 [SMILES: COc1cc(-c2csc3c(O)nc(-c4ccccn4)nc23)cnc1C(F)(F)F] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 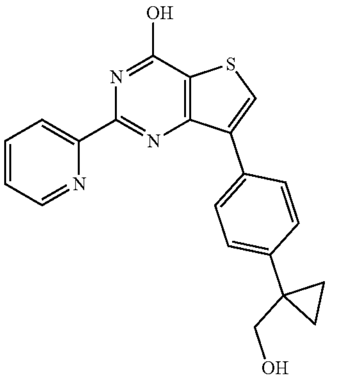 [SMILES: OCC1(c2ccc(-c3csc4c(O)nc(-c5ccccn5)nc34)cc2)CC1] | C* | |
| 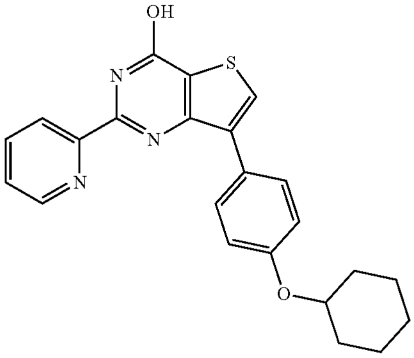 [SMILES: Oc1nc(-c2ccccn2)nc2c(-c3ccc(OC4CCCCC4)cc3)csc12] | B* | |
| 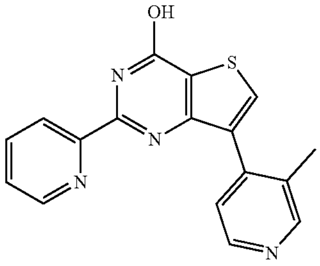 [SMILES: Cc1cnccc1-c1csc2c(O)nc(-c3ccccn3)nc12] | A* | |
| 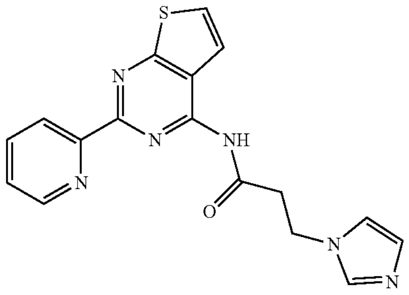 [SMILES: O=C(CCn1ccnc1)Nc1nc(-c2ccccn2)nc2sccc12] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 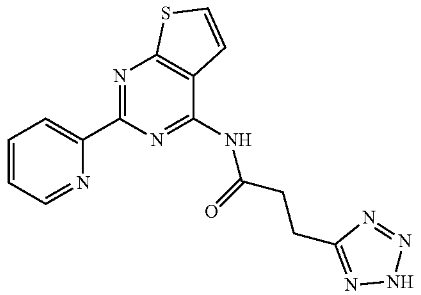 [SMILES: O=C(CCc1nn[nH]n1)Nc1nc(-c2ccccn2)nc2sccc12] | B* | |
| 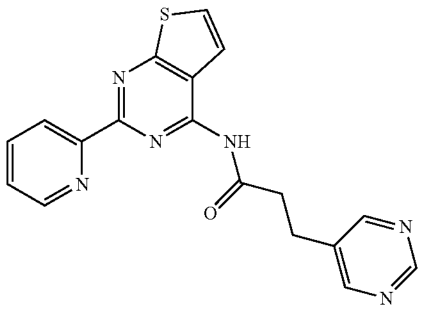 [SMILES: O=C(CCc1cncnc1)Nc1nc(-c2ccccn2)nc2sccc12] | A* | |
| 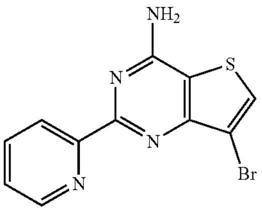 [SMILES: Nc1nc(-c2ccccn2)nc2c(Br)csc12] | B* | |
| 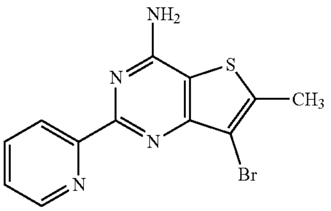 | A* | |
| 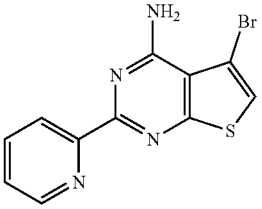 [SMILES: Nc1nc(-c2ccccn2)nc2scc(Br)c12] | A* | |
| 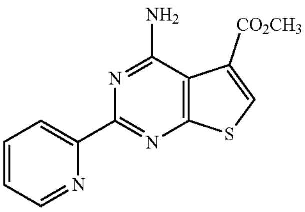 [SMILES: COC(=O)c1csc2nc(-c3ccccn3)nc(N)c12] | B* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 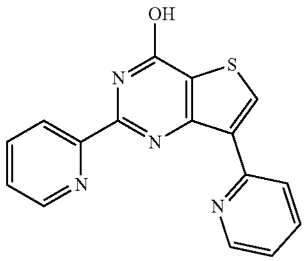 | D* | |
| 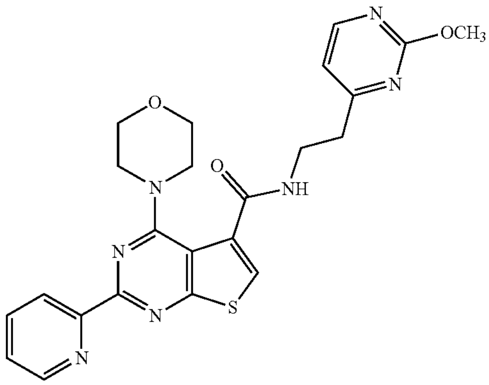 [SMILES: COc1nccc(CCNC(=O)c2csc3nc(-c4ccccn4)nc(N4CCOCC4)c23)n1] | B* | |
| 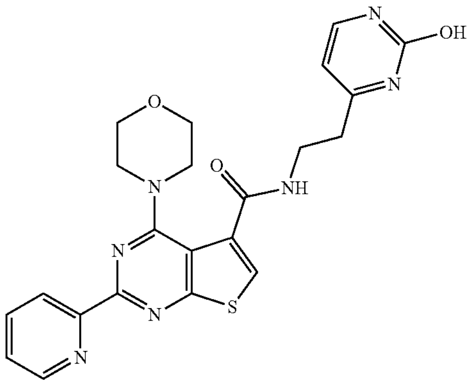 [SMILES: O=C(NCCc1ccnc(O)n1)c1csc2nc(-c3ccccn3)nc(N3CCOCC3)c12] | A* | |
| 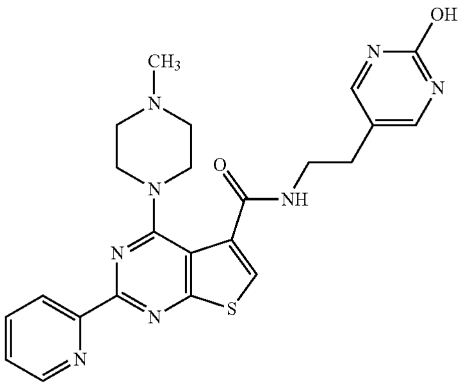 [SMILES: CN1CCN(c2nc(-c3ccccn3)nc3scc(C(=O)NCCc4cnc(O)nc4)c23)CC1] | B* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 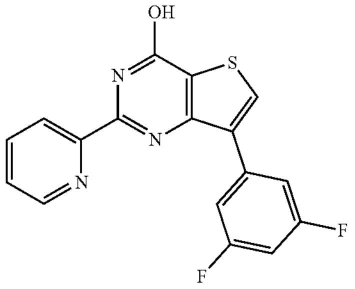 [SMILES: Oc1nc(-c2ccccn2)nc2c(-c3cc(F)cc(F)c3)csc12] | D* | |
| 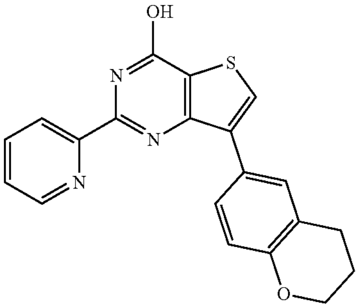 [SMILES: Oc1nc(-c2ccccn2)nc2c(-c3ccc4c(c3)CCCO4)csc12] | D* | |
| 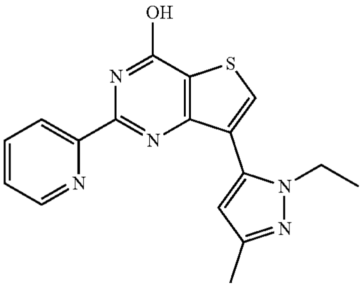 [SMILES: CCn1nc(C)cc1-c1csc2c(O)nc(-c3ccccn3)nc12] | A* | |
| 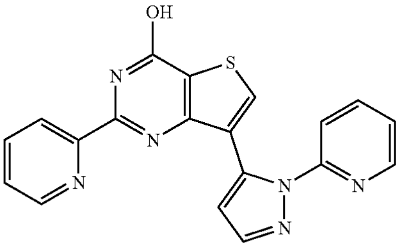 [SMILES: Oc1nc(-c2ccccn2)nc2c(-c3ccnn3-c3ccccn3)csc12] | A* | |
| 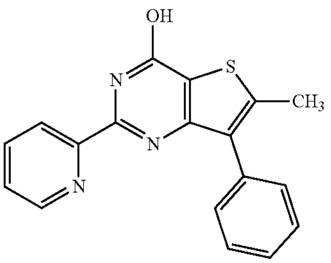 [SMILES: Cc1sc2c(O)nc(-c3ccccn3)nc2c1-c1ccccc1] | D* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 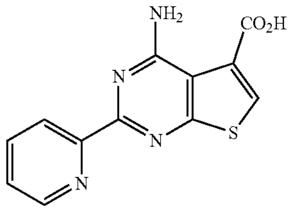 [SMILES: Nc1nc(-c2ccccn2)nc2scc(C(=O)O)c12] | A* | |
| 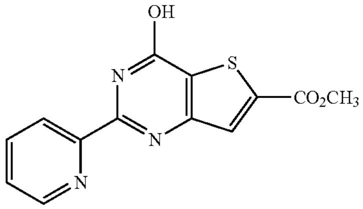 [SMILES: COC(=O)c1cc2nc(-c3ccccn3)nc(O)c2s1] | B* | |
| 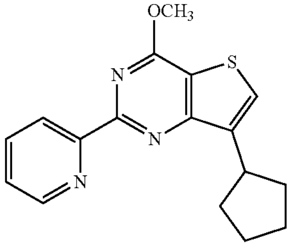 [SMILES: COc1nc(-c2ccccn2)nc2c(C3CCCC3)csc12] | A* | |
| 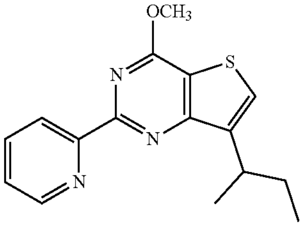 [SMILES: CCC(C)c1csc2c(OC)nc(-c3ccccn3)nc12] | B* | |
| 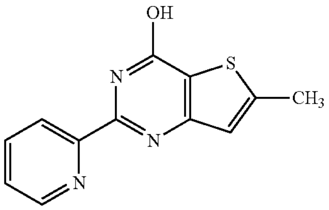 [SMILES: Cc1cc2nc(-c3ccccn3)nc(O)c2s1] | B* | |
| 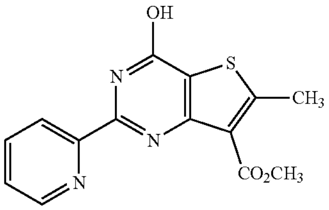 [SMILES: COC(=O)c1c(C)sc2c(O)nc(-c3ccccn3)nc12] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 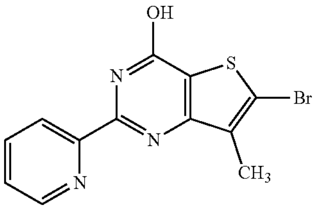 [SMILES: Cc1c(Br)sc2c(O)nc(-c3ccccn3)nc12] | A* | |
| 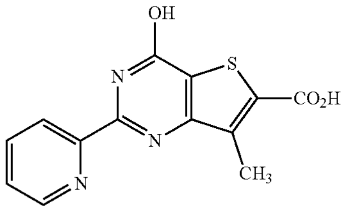 [SMILES: Cc1c(C(=O)O)sc2c(O)nc(-c3ccccn3)nc12] | B* | |
| 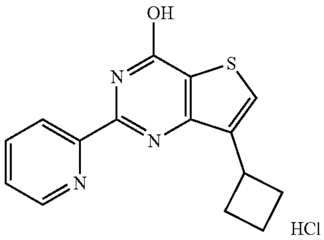 [SMILES: Oc1nc(-c2ccccn2)nc2c(C3CCC3)csc12 ; Cl] | D* | |
| 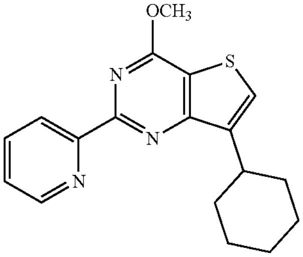 [SMILES: COc1nc(-c2ccccn2)nc2c(C3CCCCC3)csc12] | A* | |
| 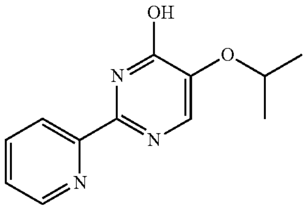 [SMILES: CC(C)Oc1cnc(-c2ccccn2)nc1O] | A* | |
| 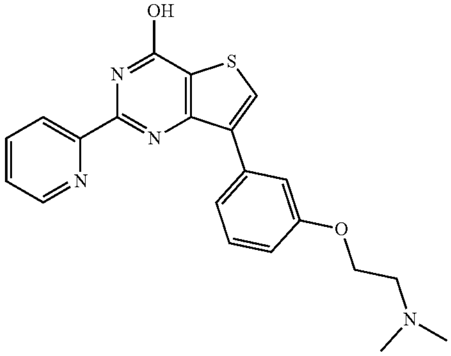 [SMILES: CN(C)CCOc1cccc(-c2csc3c(O)nc(-c4ccccn4)nc23)c1] | D* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 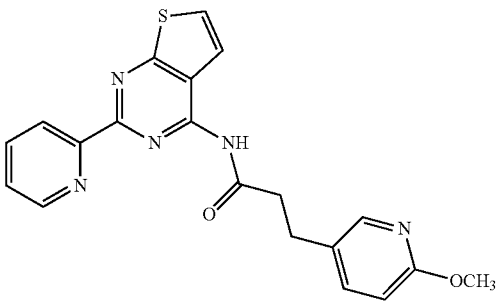 [SMILES: COc1ccc(CCC(=O)Nc2nc(-c3ccccn3)nc3sccc23)cn1] | D* | |
| 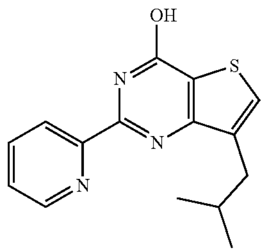 [SMILES: CC(C)Cc1csc2c(O)nc(-c3ccccn3)nc12] | D* | |
| 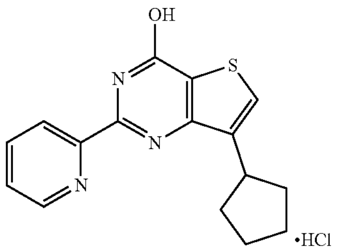 [SMILES: Oc1nc(-c2ccccn2)nc2c(C3CCCC3)csc12 ; Cl] | D* | |
| 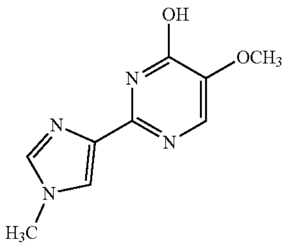 | C* | |
| 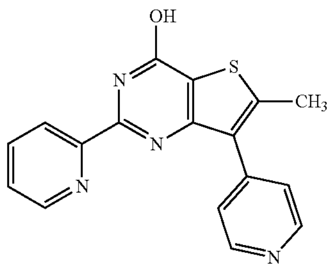 [SMILES: Cc1sc2c(O)nc(-c3ccccn3)nc2c1-c1ccncc1] | C* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 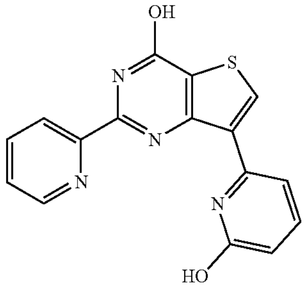 [SMILES: Oc1cccc(-c2csc3c(O)nc(-c4ccccn4)nc23)n1] | C* | |
| 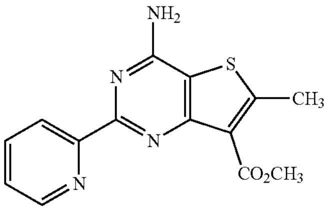 | B* | |
| 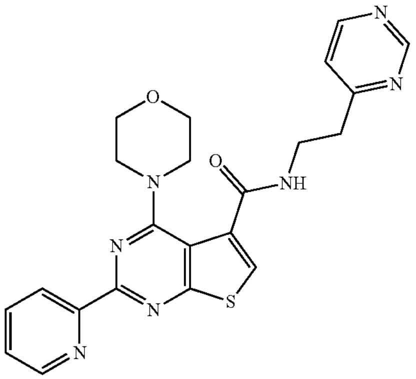 | 0* | |
| 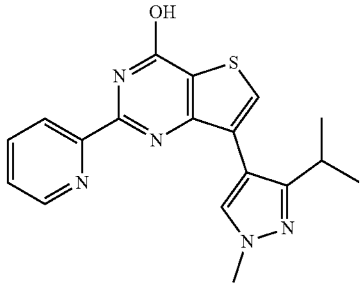 [SMILES: CC(C)c1nn(C)cc1-c1csc2c(O)nc(-c3ccccn3)nc12] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 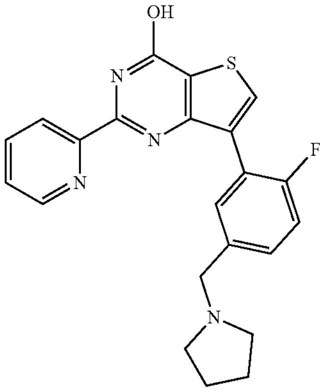 [SMILES: Oc1nc(-c2ccccn2)nc2c(-c3cc(CN4CCCC4)ccc3F)csc12] | 0* | |
| 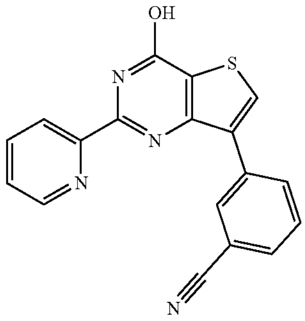 [SMILES: N#Cc1cccc(-c2csc3c(O)nc(-c4ccccn4)nc23)c1] | 0* | |
| 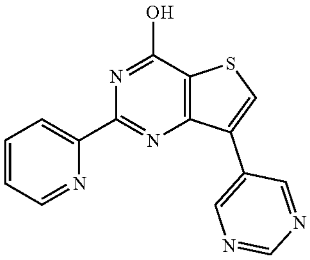 [SMILES: Oc1nc(-c2ccccn2)nc2c(-c3cncnc3)csc12] | 0* | |
| 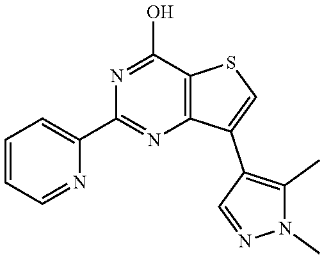 [SMILES: Cc1c(-c2csc3c(O)nc(-c4ccccn4)nc23)cnn1C] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 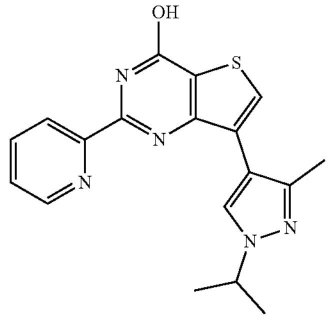 [SMILES: Cc1nn(C(C)C)cc1-c1csc2c(O)nc(-c3ccccn3)nc12] | 0* | |
| 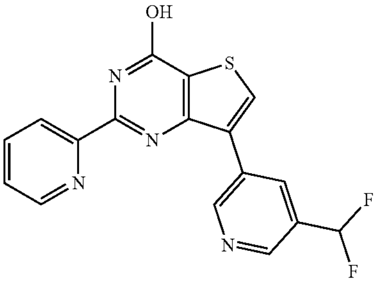 [SMILES: Oc1nc(-c2ccccn2)nc2c(-c3cncc(C(F)F)c3)csc12] | 0* | |
| 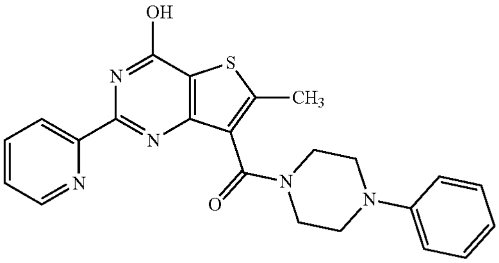 [SMILES: Cc1sc2c(O)nc(-c3ccccn3)nc2c1C(=O)N1CCN(c2ccccc2)CC1] | A* | |
| 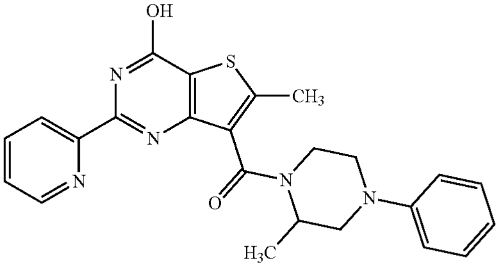 [SMILES: Cc1sc2c(O)nc(-c3ccccn3)nc2c1C(=O)N1CCN(c2ccccc2)CC1C] | A* | |
| 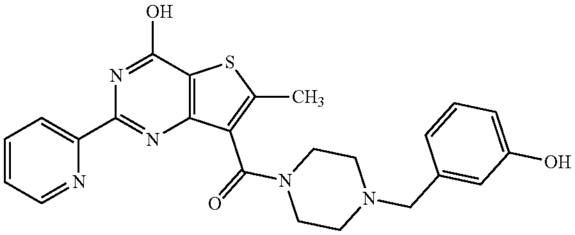 [SMILES: Cc1sc2c(O)nc(-c3ccccn3)nc2c1C(=O)N1CCN(Cc2cccc(O)c2)CC1] | B* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 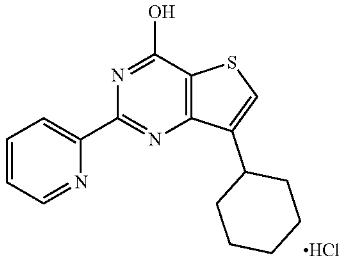 [SMILES: Oc1nc(-c2ccccn2)nc2c(C3CCCCC3)csc12 ; Cl] | B* | |
| 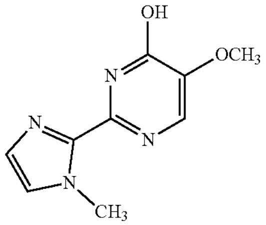 | B* | |
| 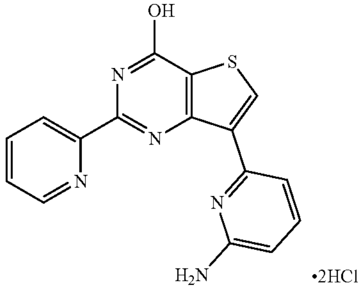 [SMILES: Nc1cccc(-c2csc3c(O)nc(-c4ccccn4)nc23)n1] | C* | |
| 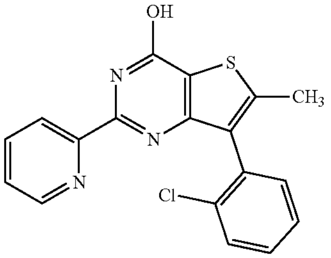 [SMILES: Cc1sc2c(O)nc(-c3ccccn3)nc2c1-c1ccccc1Cl] | D* | |
| 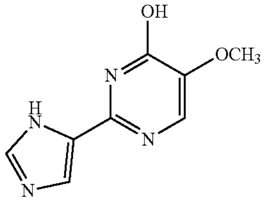 [SMILES: COc1cnc(-c2cnc[nH]2)nc1O] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 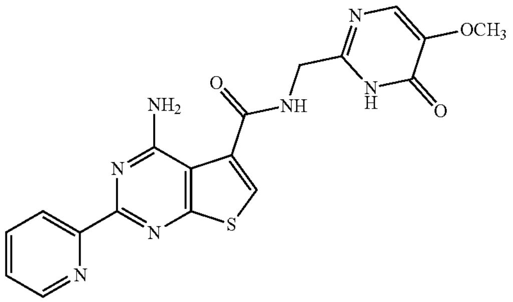 [SMILES: COc1cnc(CNC(=O)c2csc3nc(-c4ccccn4)nc(N)c23)[nH]c1=O] | B* | |
| 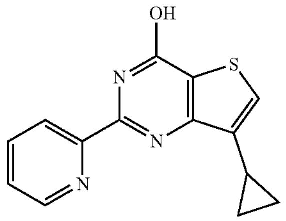 [SMILES: Oc1nc(-c2ccccn2)nc2c(C3CC3)csc12] | C* | |
| 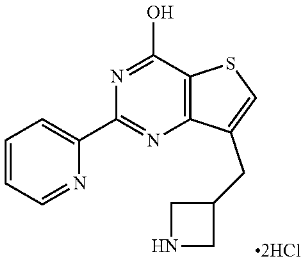 [SMILES: Oc1nc(-c2ccccn2)nc2c(CC3CNC3)csc12] | 0* | |
| 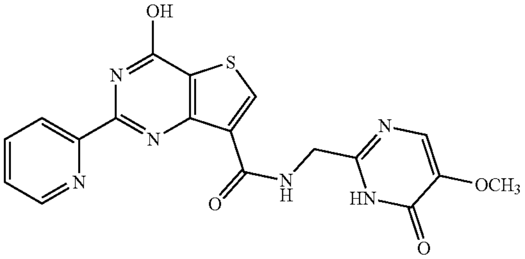 [SMILES: COc1cnc(CNC(=O)c2csc3c(O)nc(-c4ccccn4)nc23)[nH]c1=O] | 0* | |
| 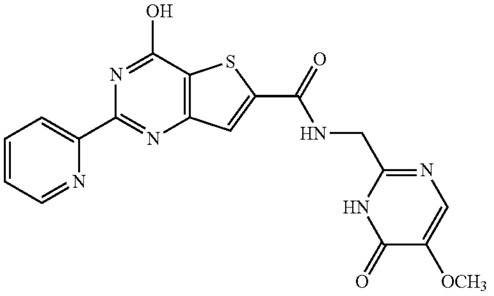 [SMILES: COc1cnc(CNC(=O)c2cc3nc(-c4ccccn4)nc(O)c3s2)[nH]c1=O] | C* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 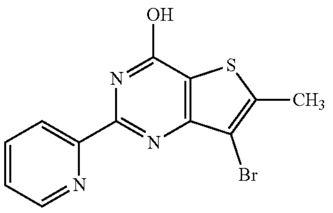 [SMILES: Cc1sc2c(O)nc(-c3ccccn3)nc2c1Br] | D* | |
| 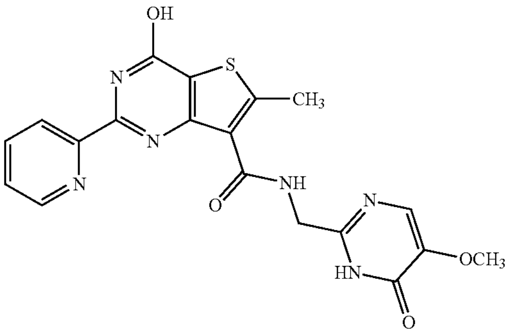 [SMILES: COc1cnc(CNC(=O)c2c(C)sc3c(O)nc(-c4ccccn4)nc23)[nH]c1=O] | 0* | |
| 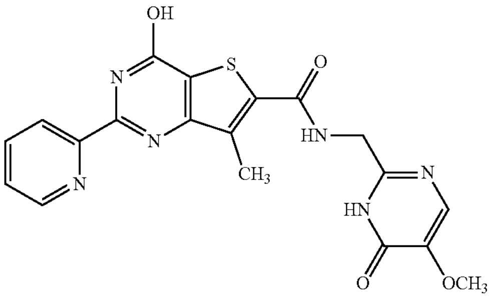 [SMILES: COc1cnc(CNC(=O)c2sc3c(O)nc(-c4ccccn4)nc3c2C)[nH]c1=O] | 0* | |
| 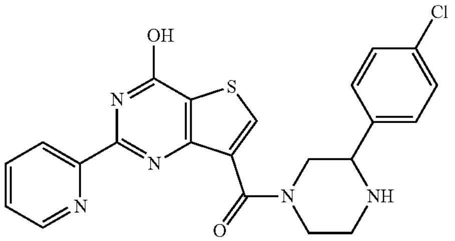 [SMILES: O=C(c1csc2c(O)nc(-c3ccccn3)nc12)N1CCNC(c2ccc(Cl)cc2)C1] | 0* | |
| 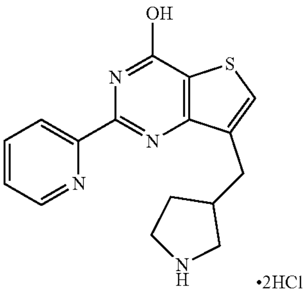 [SMILES: Oc1nc(-c2ccccn2)nc2c(CC3CCNC3)csc12] •2HCl | A* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 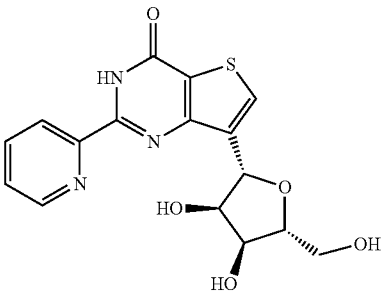 [SMILES: O=c1[nH]c(-c2ccccn2)nc2c([C@@H]3O[C@H](CO)[C@@H](O)[C@H]3O)csc12] | A* | |
| 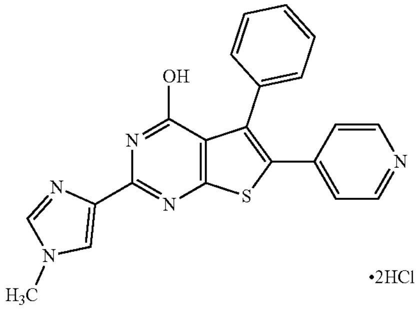 [SMILES: Cn1cnc(-c2nc(O)c3c(-c4ccccc4)c(-c4ccncc4)sc3n2)c1] •2HCl | B* | |
| 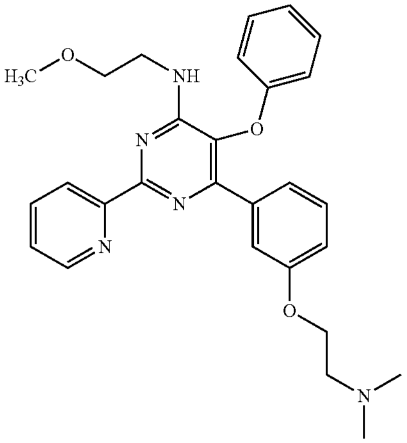 [SMILES: COCCNc1nc(-c2ccccn2)nc(-c2cccc(OCCN(C)C)c2)c1Oc1ccccc1] | B* | |
| 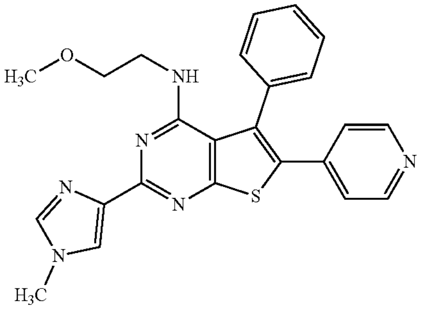 [SMILES: COCCNc1nc(-c2cn(C)cn2)nc2sc(-c3ccncc3)c(-c3ccccc3)c12] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 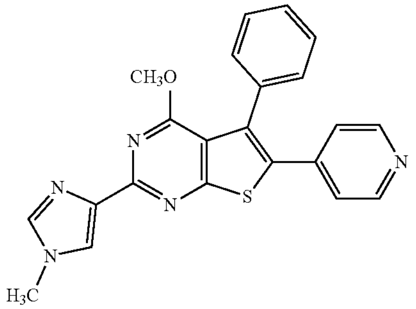 | A* | |
| 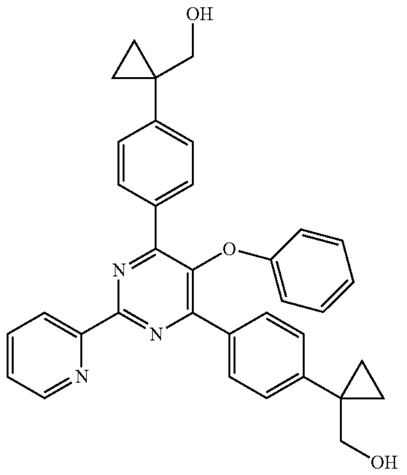 [SMILES: OCC1(c2ccc(-c3nc(-c4ccccn4)nc(-c4ccc(C5(CO)CC5)cc4)c3Oc3ccccc3)cc2)CC1] | C* | |
| 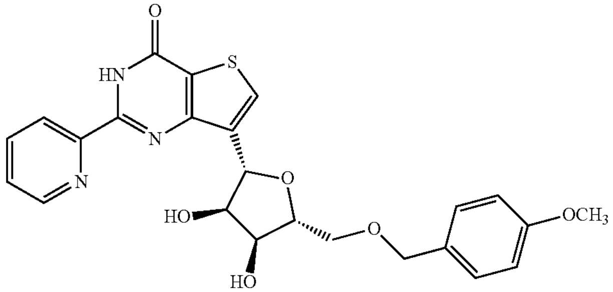 [SMILES: COc1ccc(COC[C@H]2O[C@@H](c3csc4c(=O)[nH]c(-c5ccccn5)nc34)[C@H](O)[C@@H]2O)cc1] | 0* | |
| 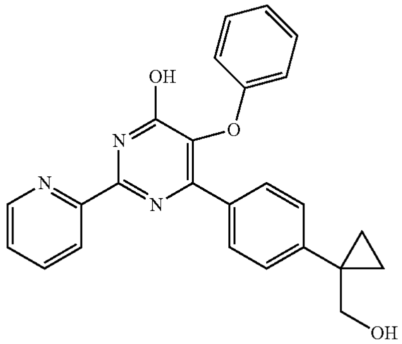 [SMILES: OCC1(c2ccc(-c3nc(-c4ccccn4)nc(O)c3Oc3ccccc3)cc2)CC1] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 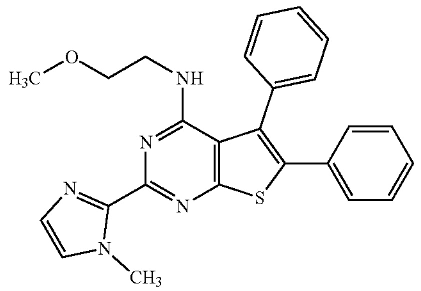 | D* | |
| 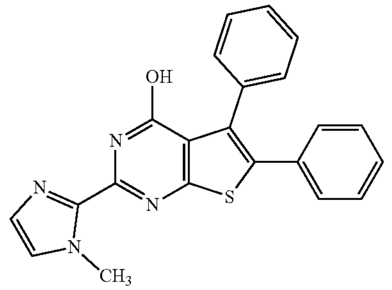 | 0* | |
| 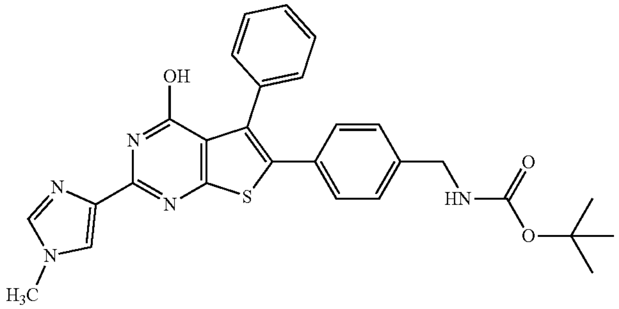 | 0* | |
| 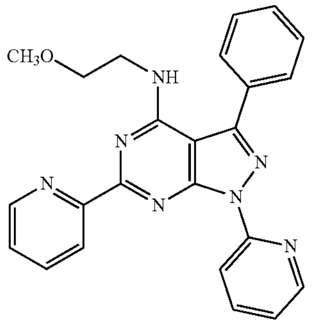 | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 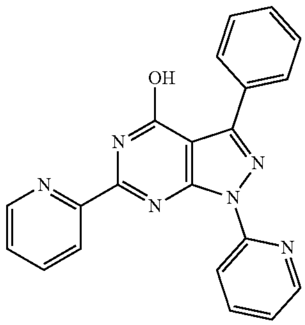 [SMILES: Oc1nc(-c2ccccn2)nc2c1c(-c1ccccc1)nn2-c1ccccn1] | 0* | |
| 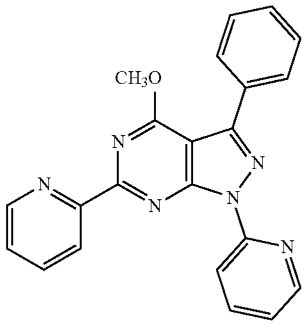 | B* | |
| 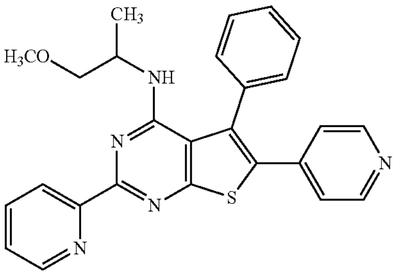 [SMILES: COCC(C)Nc1nc(-c2ccccn2)nc2sc(-c3ccncc3)c(-c3ccccc3)c12] | 0* | |
| 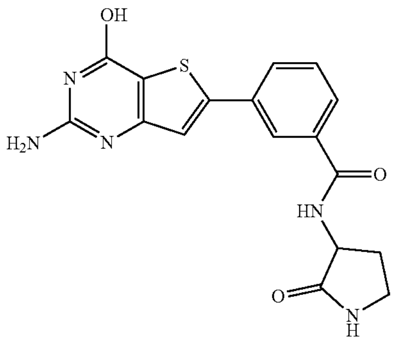 [SMILES: Nc1nc(O)c2sc(-c3cccc(C(=O)NC4CCNC4=O)c3)cc2n1] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 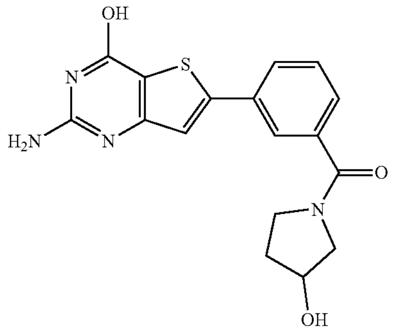 [SMILES: Nc1nc(O)c2sc(-c3cccc(C(=O)N4CCC(O)C4)c3)cc2n1] | 0* | |
| 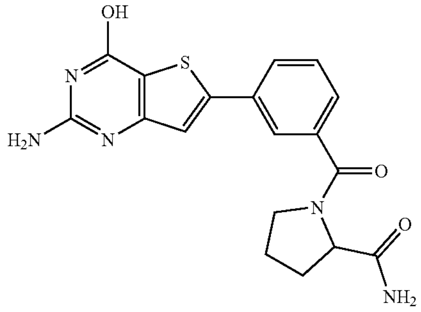 [SMILES: NC(=O)C1CCCN1C(=O)c1cccc(-c2cc3nc(N)nc(O)c3s2)c1] | A* | |
| 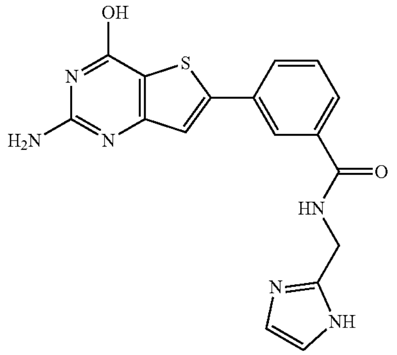 [SMILES: Nc1nc(O)c2sc(-c3cccc(C(=O)NCc4ncc[nH]4)c3)cc2n1] | 0* | |
| 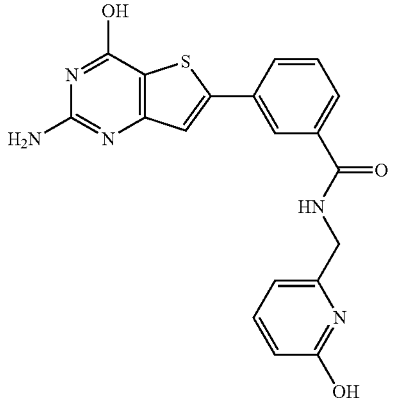 [SMILES: Nc1nc(O)c2sc(-c3cccc(C(=O)NCc4cccc(O)n4)c3)cc2n1] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 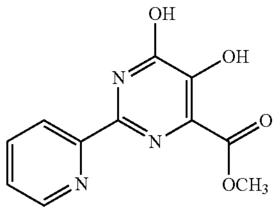 [SMILES: COC(=O)c1nc(-c2ccccn2)nc(O)c1O] | 0* | |
| 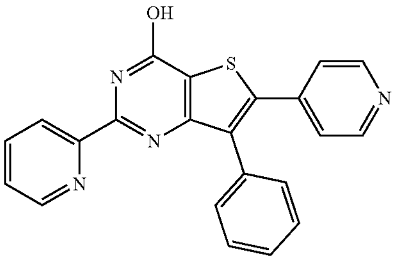 [SMILES: Oc1nc(-c2ccccn2)nc2c(-c3ccccc3)c(-c3ccncc3)sc12] | 0* | |
| 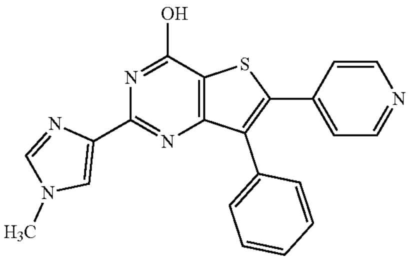 [SMILES: Cn1cnc(-c2nc(O)c3sc(-c4ccncc4)c(-c4ccccc4)c3n2)c1] | 0* | |
| 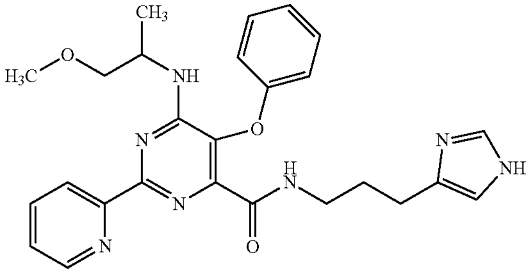 [SMILES: COCC(C)Nc1nc(-c2ccccn2)nc(C(=O)NCCCc2c[nH]cn2)c1Oc1ccccc1] | A* | |
| 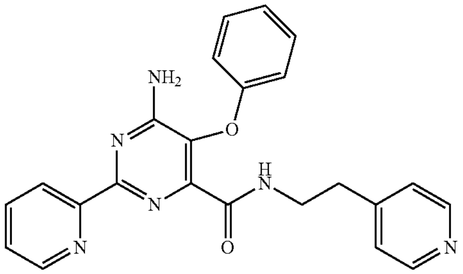 [SMILES: Nc1nc(-c2ccccn2)nc(C(=O)NCCc2ccncc2)c1Oc1ccccc1] | A* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 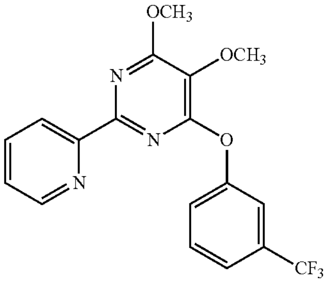 [SMILES: COc1nc(-c2ccccn2)nc(Oc2cccc(C(F)(F)F)c2)c1OC] | 0* | |
| 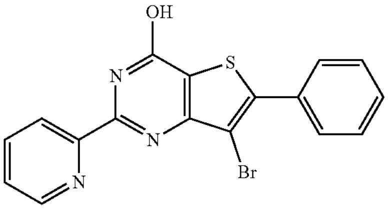 [SMILES: Oc1nc(-c2ccccn2)nc2c(Br)c(-c3ccccc3)sc12] | 0* | |
| 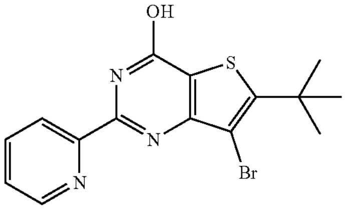 [SMILES: CC(C)(C)c1sc2c(O)nc(-c3ccccn3)nc2c1Br] | A* | |
| 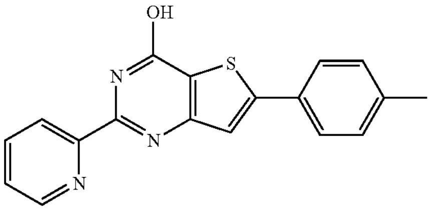 [SMILES: Cc1ccc(-c2cc3nc(-c4ccccn4)nc(O)c3s2)cc1] | D* | |
| 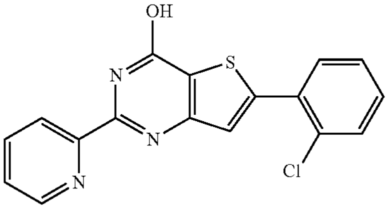 [SMILES: Oc1nc(-c2ccccn2)nc2cc(-c3ccccc3Cl)sc12] | A* | |
| 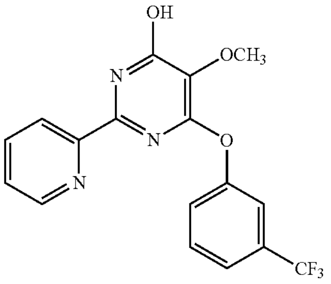 [SMILES: COc1c(O)nc(-c2ccccn2)nc1Oc1cccc(C(F)(F)F)c1] | A* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 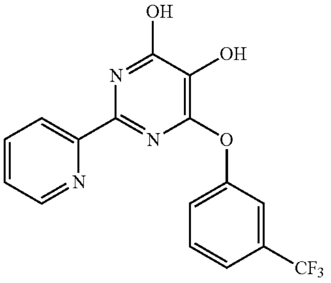 [SMILES: Oc1nc(-c2ccccn2)nc(Oc2cccc(C(F)(F)F)c2)c1O] | A* | |
| 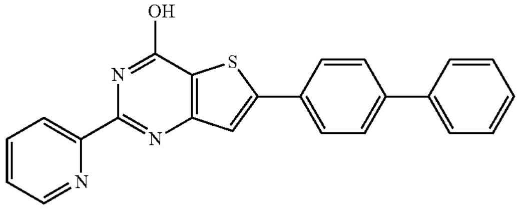 [SMILES: Oc1nc(-c2ccccn2)nc2cc(-c3ccc(-c4ccccc4)cc3)sc12] | B* | |
| 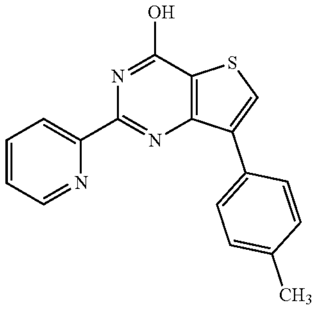 [SMILES: Cc1ccc(-c2csc3c(O)nc(-c4ccccn4)nc23)cc1] | A* | |
| 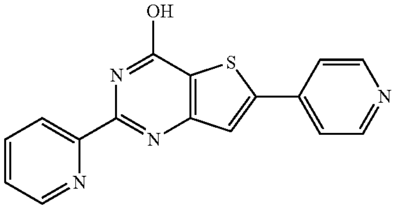 [SMILES: Oc1nc(-c2ccccn2)nc2cc(-c3ccncc3)sc12] | 0* | |
| 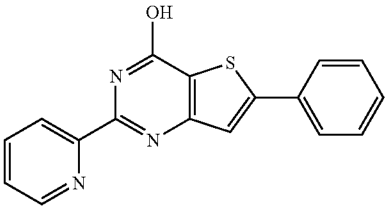 [SMILES: Oc1nc(-c2ccccn2)nc2cc(-c3ccccc3)sc12] | B* | |
| 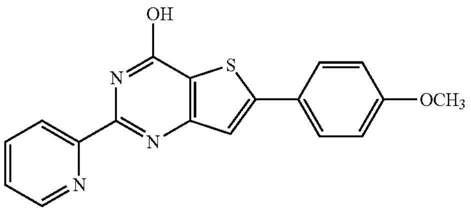 [SMILES: COc1ccc(-c2cc3nc(-c4ccccn4)nc(O)c3s2)cc1] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 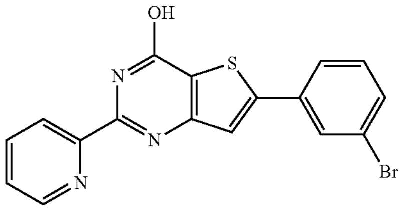 [SMILES: Oc1nc(-c2ccccn2)nc2cc(-c3cccc(Br)c3)sc12] | B* | |
| 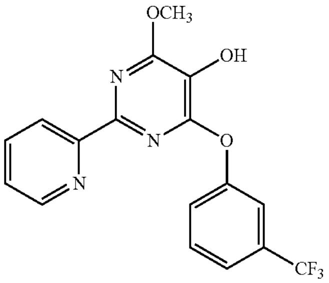 [SMILES: COc1nc(-c2ccccn2)nc(Oc2cccc(C(F)(F)F)c2)c1O] | A* | |
| 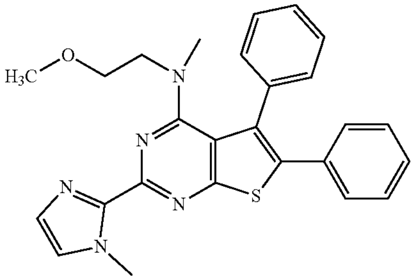 [SMILES: COCCN(C)c1nc(-c2nccn2C)nc2sc(-c3ccccc3)c(-c3ccccc3)c12] | D* | |
| 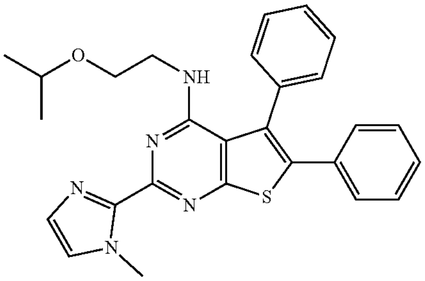 [SMILES: CC(C)OCCNc1nc(-c2nccn2C)nc2sc(-c3ccccc3)c(-c3ccccc3)c12] | D* | |
| 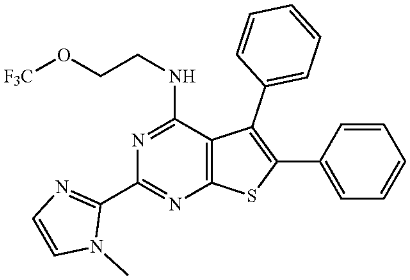 [SMILES: Cn1ccnc1-c1nc(NCCOC(F)(F)F)c2c(-c3ccccc3)c(-c3ccccc3)sc2n1] | D* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 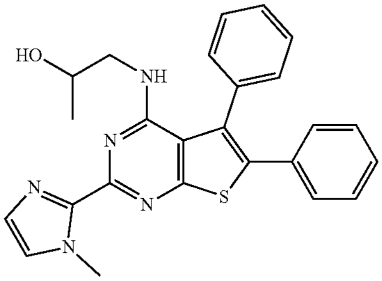 | A* | |
| 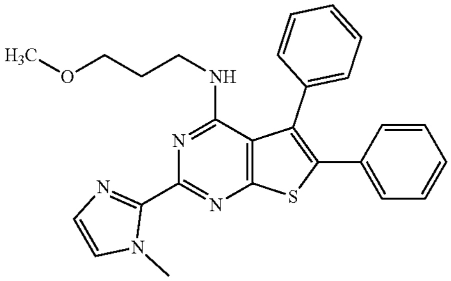 [SMILES: COCCCNc1nc(-c2nccn2C)nc2sc(-c3ccccc3)c(-c3ccccc3)c12] | D* | |
| 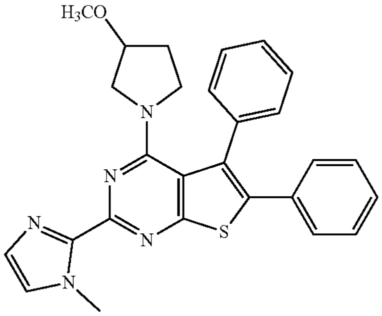 [SMILES: COC1CCN(c2nc(-c3nccn3C)nc3sc(-c4ccccc4)c(-c4ccccc4)c23)C1] | D* | |
| 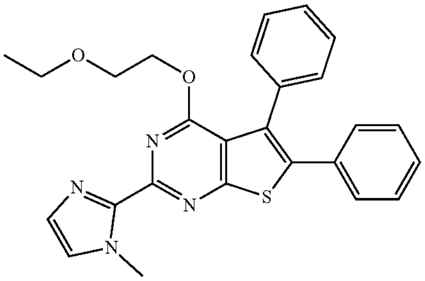 [SMILES: CCOCCOc1nc(-c2nccn2C)nc2sc(-c3ccccc3)c(-c3ccccc3)c12] | 0* | |
| 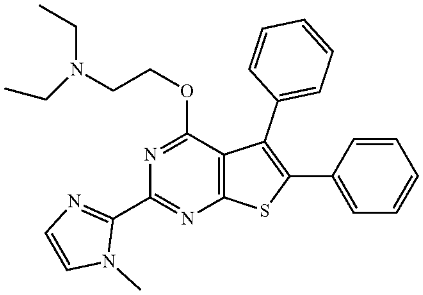 [SMILES: CCN(CC)CCOc1nc(-c2nccn2C)nc2sc(-c3ccccc3)c(-c3ccccc3)c12] | D* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 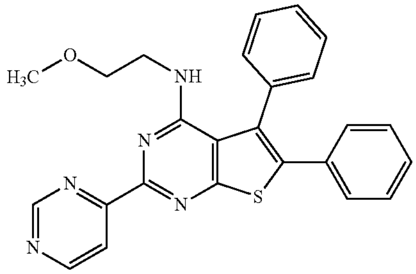 [SMILES: COCCNc1nc(-c2ccncn2)nc2sc(-c3ccccc3)c(-c3ccccc3)c12] | A* | |
| 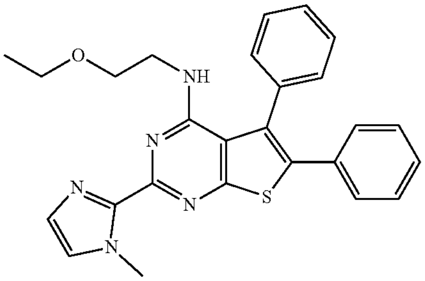 [SMILES: CCOCCNc1nc(-c2nccn2C)nc2sc(-c3ccccc3)c(-c3ccccc3)c12] | D* | |
| 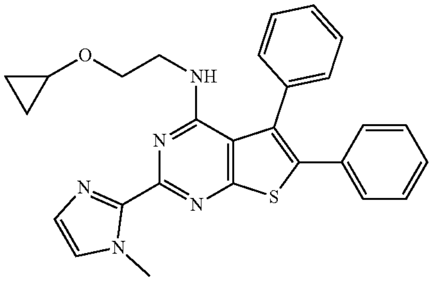 [SMILES: Cn1ccnc1-c1nc(NCCOC2CC2)c2c(-c3ccccc3)c(-c3ccccc3)sc2n1] | D* | |
| 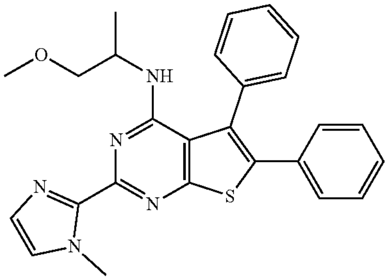 [SMILES: COCC(C)Nc1nc(-c2nccn2C)nc2sc(-c3ccccc3)c(-c3ccccc3)c12] | D* | |
| 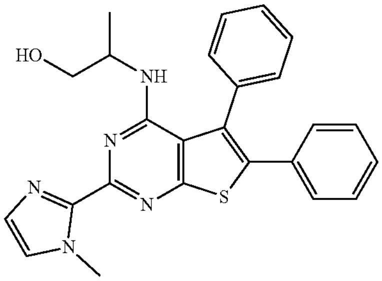 [SMILES: CC(CO)Nc1nc(-c2nccn2C)nc2sc(-c3ccccc3)c(-c3ccccc3)c12] | B* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 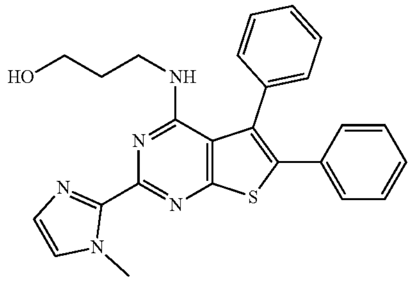 [SMILES: Cn1ccnc1-c1nc(NCCCO)c2c(-c3ccccc3)c(-c3ccccc3)sc2n1] | A* | |
| 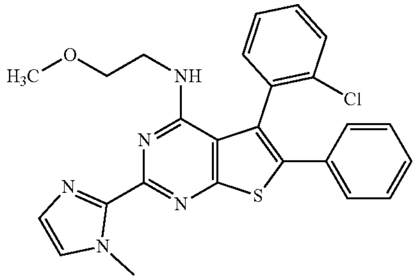 [SMILES: COCCNc1nc(-c2nccn2C)nc2sc(-c3ccccc3)c(-c3ccccc3Cl)c12] | D* | |
| 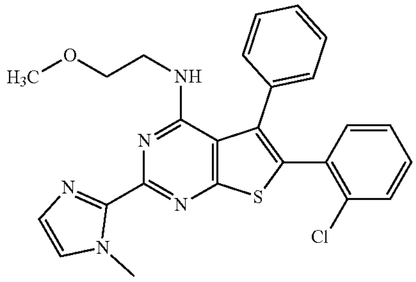 [SMILES: COCCNc1nc(-c2nccn2C)nc2sc(-c3ccccc3Cl)c(-c3ccccc3)c12] | D* | |
| 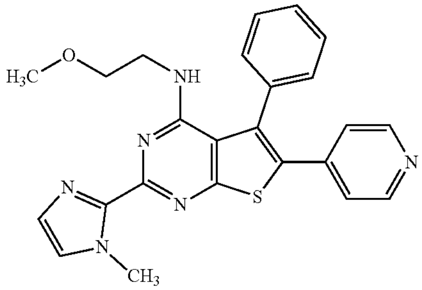 [SMILES: COCCNc1nc(-c2nccn2C)nc2sc(-c3ccncc3)c(-c3ccccc3)c12] | 0* | |
| 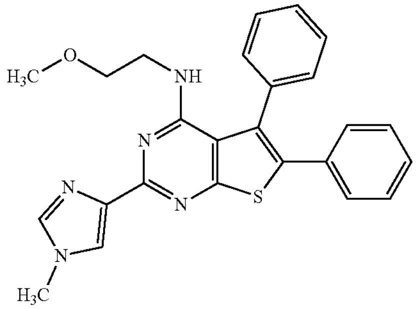 [SMILES: COCCNc1nc(-c2cn(C)cn2)nc2sc(-c3ccccc3)c(-c3ccccc3)c12] | D* | |

TABLE 4-continued
% Inhibition of MAPK phosphorylation at 30 μM in the PANC-1 pancreatic cancer cell line, and select $IC_{50}$ data
| Compound | $IC_{50}$ PANC-1 (μM) |
|---|---|
| 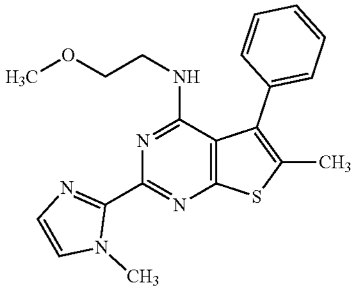 | C* |
| 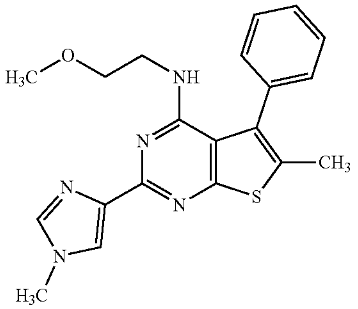 [SMILES: COCCNc1nc(-c2cn(C)cn2)nc2sc(C)c(-c3ccccc3)c12] | B* |
| 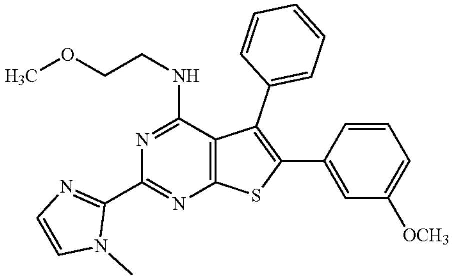 [SMILES: COCCNc1nc(-c2nccn2C)nc2sc(-c3cccc(OC)c3)c(-c3ccccc3)c12] | D* |
| 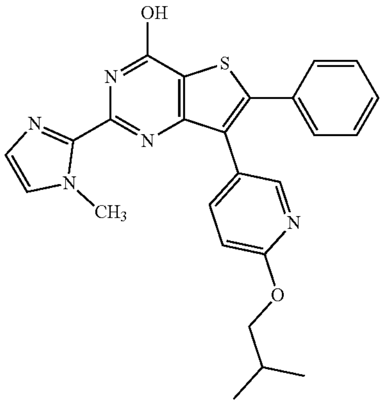 [SMILES: CC(C)COc1ccc(-c2c(-c3ccccc3)sc3c(O)nc(-c4nccn4C)nc23)cn1] | C* |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
| --- | --- | --- |
| 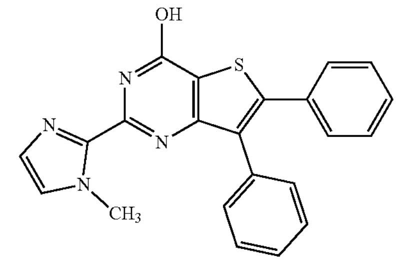 [SMILES: Cn1ccnc1-c1nc(O)c2sc(-c3ccccc3)c(-c3ccccc3)c2n1] | C* | |
| 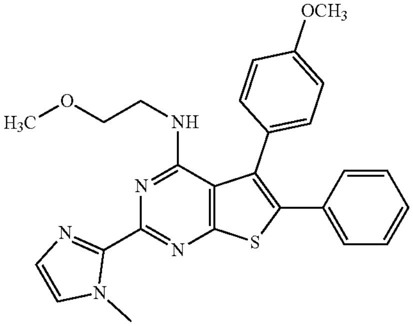 [SMILES: COCCNc1nc(-c2nccn2C)nc2sc(-c3ccccc3)c(-c3ccc(OC)cc3)c12] | D* | |
| 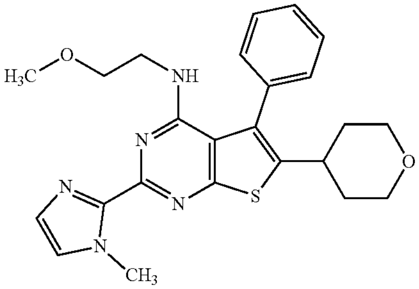 | C* | |
| 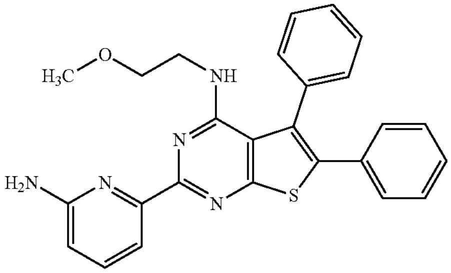 [SMILES: COCCNc1nc(-c2cccc(N)n2)nc2sc(-c3ccccc3)c(-c3ccccc3)c12] | C* | |
| 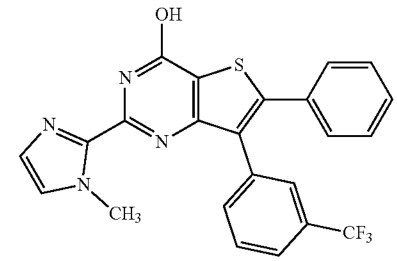 [SMILES: Cn1ccnc1-c1nc(O)c2sc(-c3ccccc3)c(-c3cccc(C(F)(F)F)c3)c2n1] | 0* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 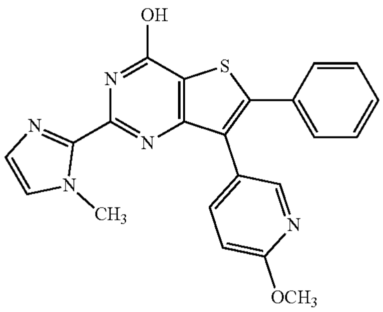 [SMILES: COc1ccc(-c2c(-c3ccccc3)sc3c(O)nc(-c4nccn4C)nc23)cn1] | C* | |
| 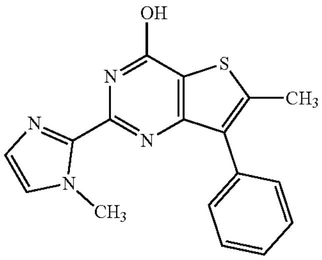 [SMILES: Cc1sc2c(O)nc(-c3nccn3C)nc2c1-c1ccccc1] | 0* | |
| 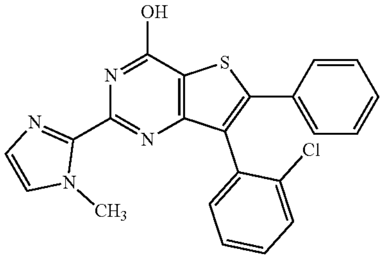 [SMILES: Cn1ccnc1-c1nc(O)c2sc(-c3ccccc3)c(-c3ccccc3Cl)c2n1] | C* | |
| 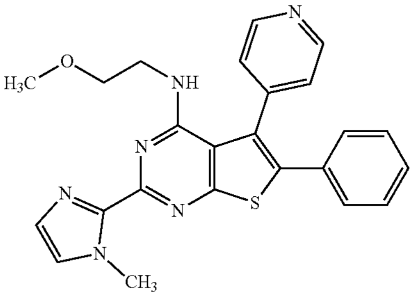 [SMILES: COCCNc1nc(-c2nccn2C)nc2sc(-c3ccccc3)c(-c3ccncc3)c12] | B* | |
| 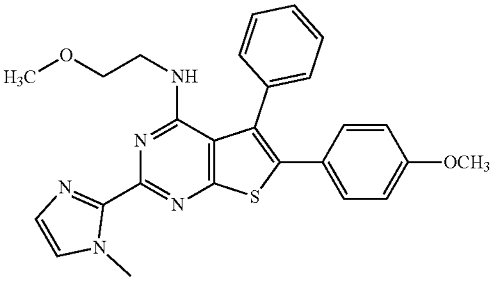 [SMILES: COCCNc1nc(-c2nccn2C)nc2sc(-c3ccc(OC)cc3)c(-c3ccccc3)c12] | C* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 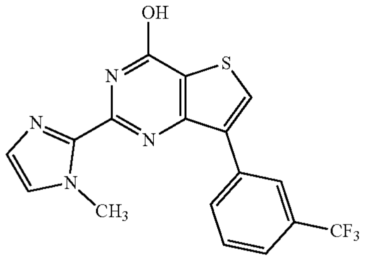 [SMILES: Cn1ccnc1-c1nc(O)c2scc(-c3cccc(C(F)(F)F)c3)c2n1] | B* | |
| 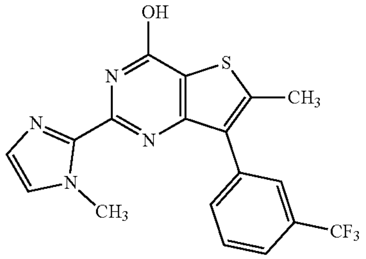 [SMILES: Cc1sc2c(O)nc(-c3nccn3C)nc2c1-c1cccc(C(F)(F)F)c1] | A* | |
| 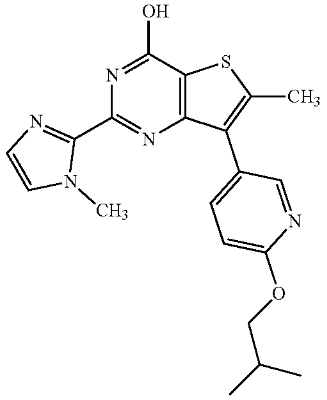 [SMILES: Cc1sc2c(O)nc(-c3nccn3C)nc2c1-c1ccc(OCC(C)C)nc1] | B* | |
| 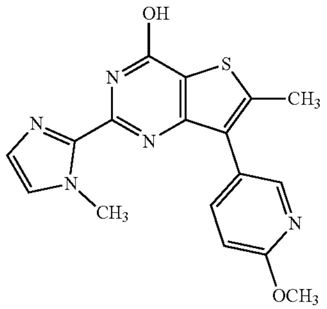 [SMILES: COc1ccc(-c2c(C)sc3c(O)nc(-c4nccn4C)nc23)cn1] | B* | |
| 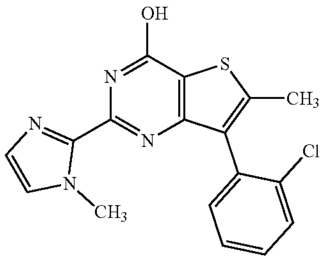 [SMILES: Cc1sc2c(O)nc(-c3nccn3C)nc2c1-c1ccccc1Cl] | A* | |

TABLE 4-continued
| % Inhibition of MAPK phosphorylation at 30 μM in the PANC-1 pancreatic cancer cell line, and select $IC_{50}$ data | | |
|---|---|---|
| Compound | PANC-1 | $IC_{50}$ (μM) |
| 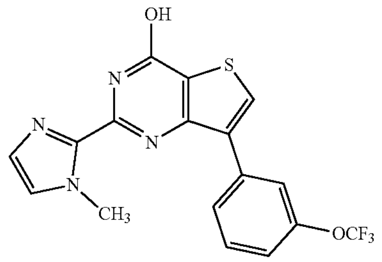 [SMILES: Cn1ccnc1-c1nc(O)c2scc(-c3cccc(OC(F)(F)F)c3)c2n1] | B* | |
| 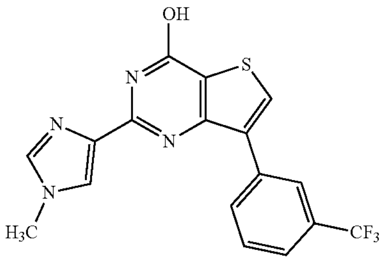 [SMILES: Cn1cnc(-c2nc(O)c3scc(-c4cccc(C(F)(F)F)c4)c3n2)c1] | A* | |
| 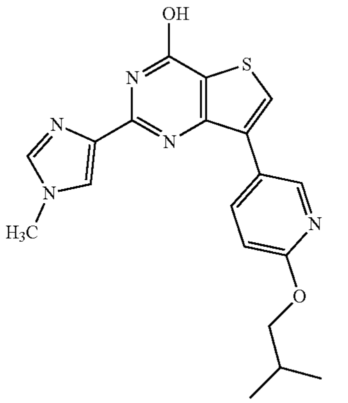 [SMILES: CC(C)COc1ccc(-c2csc3c(O)nc(-c4cn(C)cn4)nc23)cn1] | A* | |
| 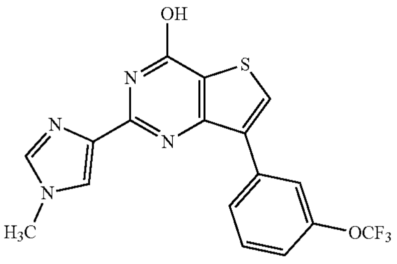 [SMILES: Cn1cnc(-c2nc(O)c3scc(-c4cccc(OC(F)(F)F)c4)c3n2)c1] | A* | |
| 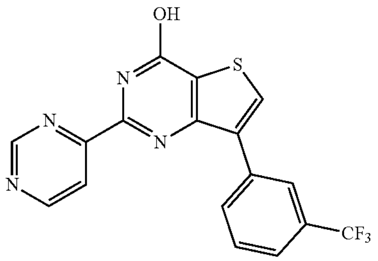 [SMILES: Oc1nc(-c2ccncn2)nc2c(-c3cccc(C(F)(F)F)c3)csc12] | A* | |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 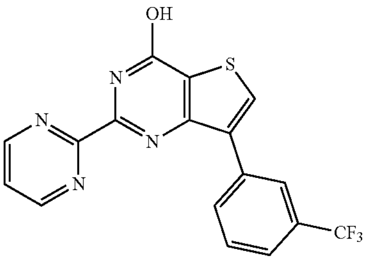 [SMILES: Oc1nc(-c2ncccn2)nc2c(-c3cccc(C(F)(F)F)c3)csc12] | A* | |
| 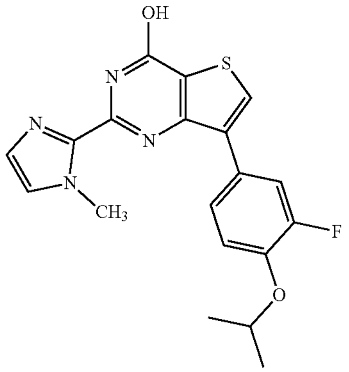 [SMILES: CC(C)Oc1ccc(-c2csc3c(O)nc(-c4nccn4C)nc23)cc1F] | B* | |
| 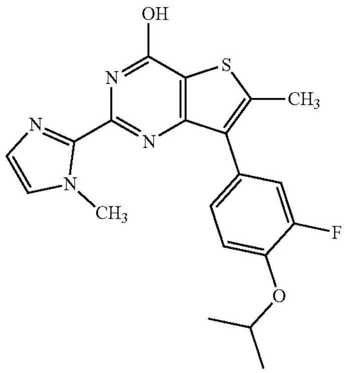 [SMILES: Cc1sc2c(O)nc(-c3nccn3C)nc2c1-c1ccc(OC(C)C)c(F)c1] | B* | |
| 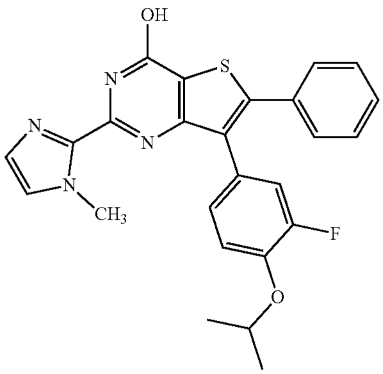 [SMILES: CC(C)Oc1ccc(-c2c(-c3ccccc3)sc3c(O)nc(-c4nccn4C)nc23)cc1F] | B* | |

TABLE 4-continued
| % Inhibition of MAPK phosphorylation at 30 μM in the PANC-1 pancreatic cancer cell line, and select $IC_{50}$ data | |
|---|---|
| Compound | PANC-1 $IC_{50}$ (μM) |
| 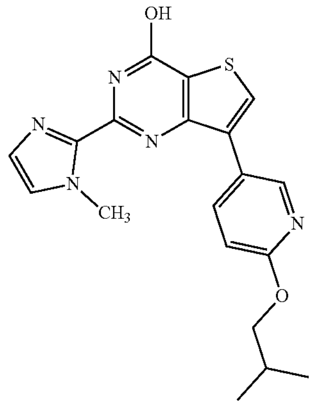 [SMILES: CC(C)COc1ccc(-c2csc3c(O)nc(-c4nccn4C)nc23)cn1] | B* |
| 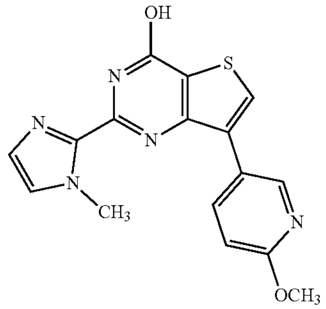 [SMILES: COc1ccc(-c2csc3c(O)nc(-c4nccn4C)nc23)cn1] | C* |
| 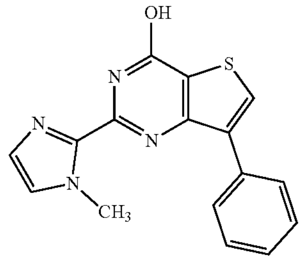 [SMILES: Cn1ccnc1-c1nc(O)c2scc(-c3ccccc3)c2n1] | D* |
| 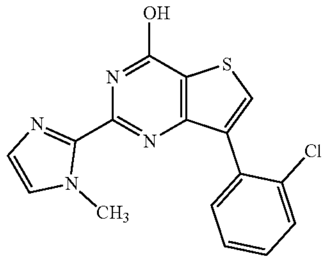 [SMILES: Cn1ccnc1-c1nc(O)c2scc(-c3ccccc3Cl)c2n1] | B* |

TABLE 4-continued
% Inhibition of MAPK phosphorylation at 30 μM in the PANC-1 pancreatic cancer cell line, and select $IC_{50}$ data
| Compound | PANC-1 | $IC_{50}$ (μM) |
|---|---|---|
| 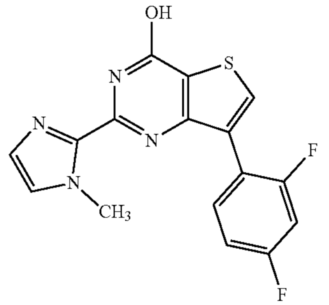 [SMILES: Cn1ccnc1-c1nc(O)c2scc(-c3ccc(F)cc3F)c2n1] | 0* | |
| 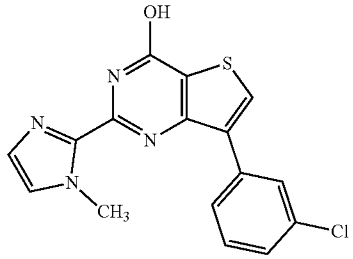 [SMILES: Cn1ccnc1-c1nc(O)c2scc(-c3cccc(Cl)c3)c2n1] | B* | |
| 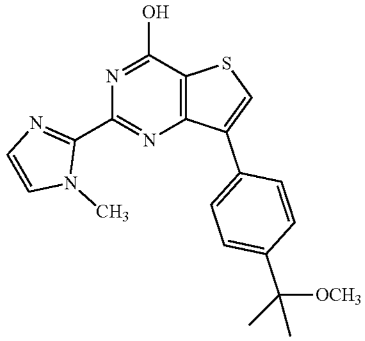 [SMILES: COC(C)(C)c1ccc(-c2csc3c(O)nc(-c4nccn4C)nc23)cc1] | B* | |
| 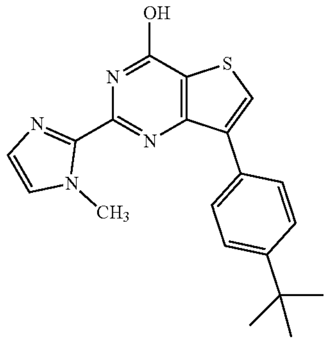 [SMILES: Cn1ccnc1-c1nc(O)c2scc(-c3ccc(C(C)(C)C)cc3)c2n1] | B* | |

TABLE 4-continued

% Inhibition of MAPK phosphorylation at 30 μM in the PANC-1 pancreatic cancer cell line, and select $IC_{50}$ data

| Compound | PANC-1 | $IC_{50}$ (μM) |
|---|---|---|
| 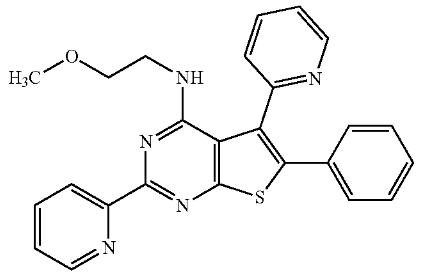 [SMILES: COCCNc1nc(-c2ccccn2)nc2sc(-c3ccccc3)c(-c3ccccn3)c12] | 0* | |
| 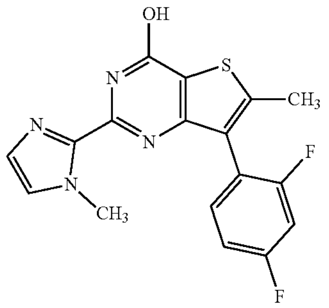 [SMILES: Cc1sc2c(O)nc(-c3nccn3C)nc2c1-c1ccc(F)cc1F] | 0* | |
| 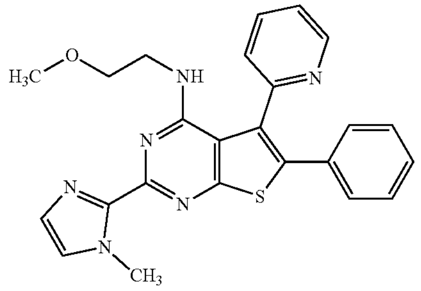 | C* | |

*= tested at 10 μM.
A = 1-25% inhibition,
B = 25-50% inhibition,
C = 51-75% inhibition,
D = 76-100% inhibition.
E = >30 μM $IC_{50}$,
F = 11-30 μM $IC_{50}$,
G = 2-10 μM $IC_{50}$,
H = <2 μM $IC_{50}$.

Example 3

Protocol for Cell Proliferation Assay

Cell lines: Tumor-derived pancreatic cancer cell lines MIA-PACA2 were purchased from ATCC and grown in complete DMEM-High Glucose medium supplemented with penicillin (100 U/mL), streptomycin (100 μg/mL), and 10% heat-inactivated FBS at 37° C. in a humidified incubator with 5% CO2.

Method: Cells are plated at 1000 cells/well density in 96-wells plate, starved ON, and the next day tested small molecules are added to the cells in the final concentration of 30 μM with 0.3% DMSO 3 hours prior to 10% FBS addition. After serum addition cells are incubated for 6 days at 37° C. in a humidified incubator with 5% $CO_2$. For $IC_{50}$ value determination, serial dilutions of compounds were added to cells under the same conditions.

Assay: At the end of the incubation period, cell cultures are tested using the CellTiter 96® AQueous One Solution Cell Proliferation Assay kit (Promega Corporation, Madison, Wis.) according to the manufacturer specifications. Briefly, assay is performed by adding 20 μl of the CellTiter 96 Aqueous One Solution Reagent directly to culture wells, followed by for 1-4 hours incubation at 37° C. in a humidified incubator with 5% $CO_2$. At the end of incubation time, absorbance at 492 nm is recorded with the 96-well plate reader Eppendorf AF2200, and degree of small molecule-dependent proliferation inhibition is calculated from raw data assuming No Serum cells value as 100%.

Alternate Assay Conditions

Cell lines: Tumor-derived pancreatic cancer cell lines MIA-PACA2 were purchased from ATCC and grown in complete DMEM-High Glucose medium supplemented with penicillin (100 U/mL), streptomycin (100 μg/mL), and 10% heat-inactivated FBS at 37° C. in a humidified incubator with 5% $CO_2$.

Method: Cells are plated at 4000 cells/well density in 96-wells plate. The next day tested small molecules are added to the cells in the final concentration of 10 μM in the presence of 0.3% DMSO and 10% FBS. After small molecules addition, cells are incubated for 4 days at 37° C. in a humidified incubator with 5% $CO_2$. For $IC_{50}$ value determination, serial dilutions of compounds were added to cells under the same conditions.

Assay: At the end of the incubation period, cell cultures are fixed with a 50-50 mixture (v/v) acetone-methanol for 10 minutes at −20° C., followed by rehydration in PBS for 10 minutes at room temperature. After rehydration, cells are stained with DAPI (1 μg/ml) in PBS for 10 minutes at room temperature, followed by 3 washes with PBS. After staining, DAPI fluorescence is recorded (358 nm excitation/461 nm emission) with the 96-well plate reader Molecular Devices Spectramax M3; degree of small mole-cule-dependent proliferation inhibition is calculated from raw data assuming No Serum cells value as 100%.

Table 5 shows inhibition data for selected compounds tested in the cellular assay conditions described above.

TABLE 5

% Inhibition of cell proliferation at 30 μM or 10 μM in MIA-PACA2 pancreatic cancer cell lines, with select $IC_{50}$ values

| Compound | MIA-PACA2 | MIA-PACA2 (alternate conditions) | $IC_{50}$ (nM) |
|---|---|---|---|
| 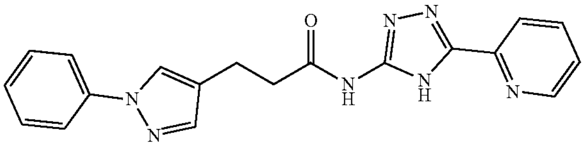 [SMILES: O=C(CCc1cnn(-c2ccccc2)c1)Nc1nnc(-c2ccccn2)[nH]1] | D | | |
| 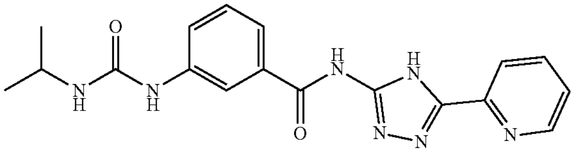 [SMILES: CC(C)NC(=O)Nc1cccc(C(=O)Nc2nnc(-c3ccccn3)[nH]2)c1] | B | | |
| 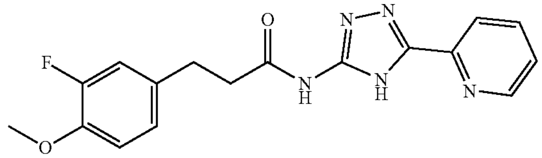 [SMILES: COc1ccc(CCC(=O)Nc2nnc(-c3ccccn3)[nH]2)cc1F] | A | | |
| 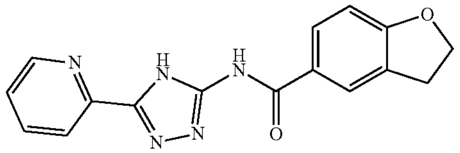 [SMILES: O=C(Nc1nnc(-c2ccccn2)[nH]1)c1ccc2c(c1)CCO2] | D | | |
| 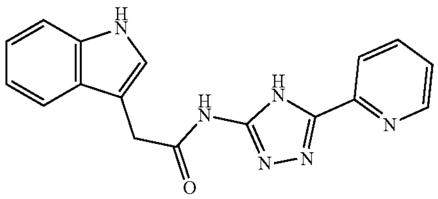 [SMILES: O=C(Cc1c[nH]c2ccccc12)Nc1nnc(-c2ccccn2)[nH]1] | A | | |
| 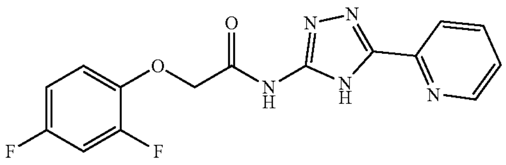 [SMILES: O=C(COc1ccc(F)cc1F)Nc1nnc(-c2ccccn2)[nH]1] | C | | |

TABLE 5-continued
| Compound | MIA-PACA2 | MIA-PACA2 (alternate conditions) | $IC_{50}$ (nM) |
|---|---|---|---|
| % Inhibition of cell proliferation at 30 μM or 10 μM in MIA-PACA2 pancreatic cancer cell lines, with select $IC_{50}$ values | | | |
| 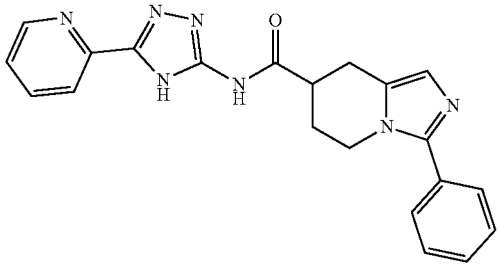 [SMILES: O=C(Nc1nnc(-c2ccccn2)[nH]1)C1CCn2c(cnc2-c2ccccc2)C1] | A | | |
| 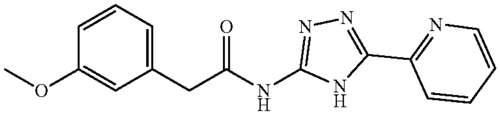 [SMILES: COc1cccc(CC(=O)Nc2nnc(-c3ccccn3)[nH]2)c1] | B | | |
| 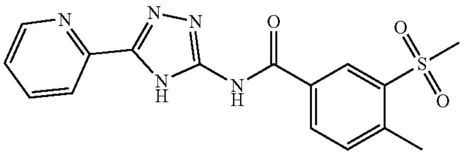 [SMILES: Cc1ccc(C(=O)Nc2nnc(-c3ccccn3)[nH]2)cc1S(C)(=O)=O] | C | | |
| 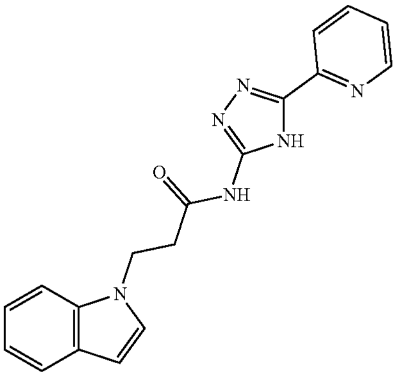 [SMILES: O=C(CCn1ccc2ccccc21)Nc1nnc(-c2ccccn2)[nH]1] | C | | |
| 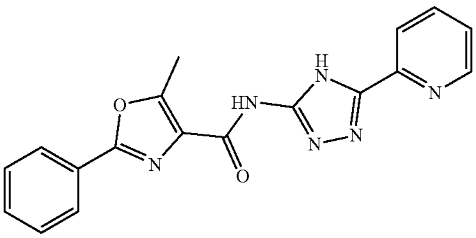 [SMILES: Cc1oc(-c2ccccc2)nc1C(=O)Nc1nnc(-c2ccccn2)[nH]1] | D | | |
| 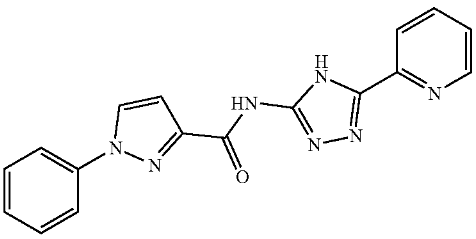 [SMILES: O=C(Nc1nnc(-c2ccccn2)[nH]1)c1ccn(-c2ccccc2)n1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 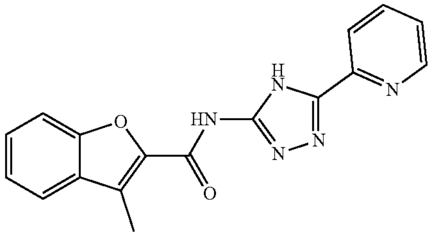 [SMILES: Cc1c(C(=O)Nc2nnc(-c3ccccn3)[nH]2)oc2ccccc12] | D | | |
| 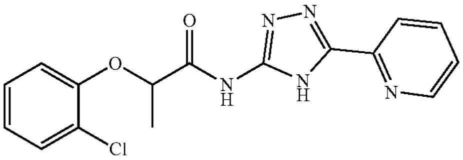 [SMILES: CC(Oc1ccccc1Cl)C(=O)Nc1nnc(-c2ccccn2)[nH]1] | D | | |
| 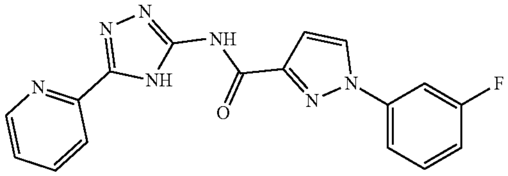 [SMILES: O=C(Nc1nnc(-c2ccccn2)[nH]1)c1ccn(-c2cccc(F)c2)n1] | D | | |
| 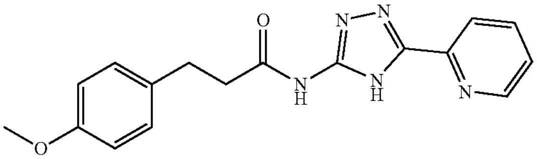 [SMILES: COc1ccc(CCC(=O)Nc2nnc(-c3ccccn3)[nH]2)cc1] | C | | |
| 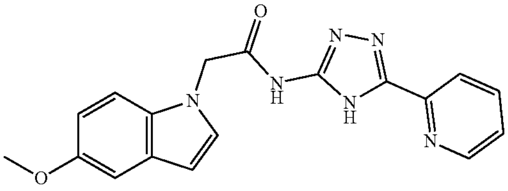 [SMILES: COc1ccc2c(ccn2CC(=O)Nc2nnc(-c3ccccn3)[nH]2)c1] | D | | |
| 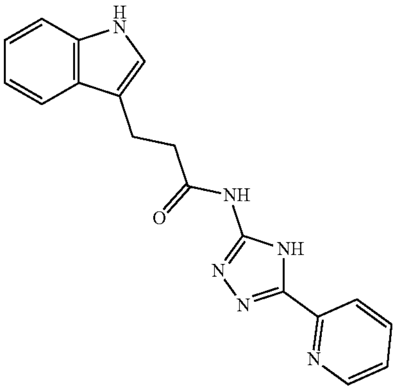 [SMILES: O=C(CCc1c[nH]c2ccccc12)Nc1nnc(-c2ccccn2)[nH]1] | C | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 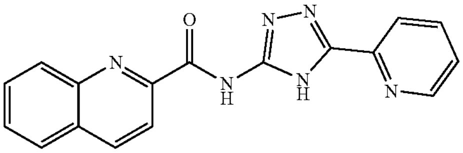 [SMILES: O=C(Nc1nnc(-c2ccccn2)[nH]1)c1ccc2ccccc2n1] | B | | |
| 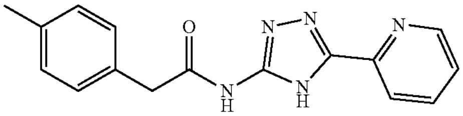 [SMILES: Cc1ccc(CC(=O)Nc2nnc(-c3ccccn3)[nH]2)cc1] | B | | |
| 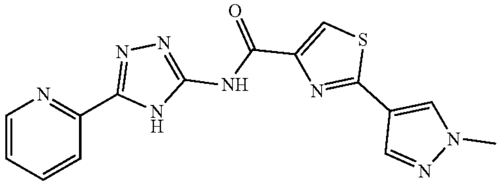 [SMILES: Cn1cc(-c2nc(C(=O)Nc3nnc(-c4ccccn4)[nH]3)cs2)cn1] | D | | |
| 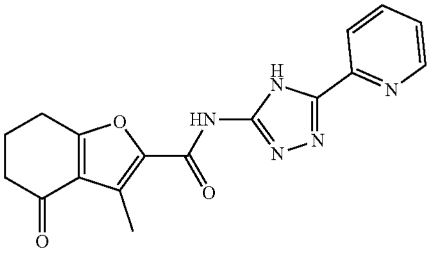 [SMILES: Cc1c(C(=O)Nc2nnc(-c3ccccn3)[nH]2)oc2c1C(=O)CCC2] | D | | |
| 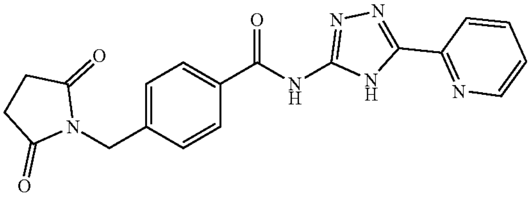 [SMILES: O=C(Nc1nnc(-c2ccccn2)[nH]1)c1ccc(CN2C(=O)CCC2=O)cc1] | A | | |
| 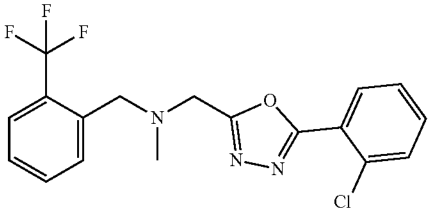 [SMILES: CN(Cc1nnc(-c2ccccc2Cl)o1)Cc1ccccc1C(F)(F)F] | B | | |
| 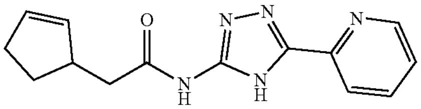 [SMILES: O=C(CC1C=CCC1)Nc1nnc(-c2ccccn2)[nH]1] | C | | |
| 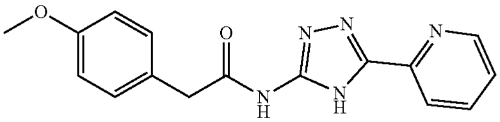 [SMILES: COc1ccc(CC(=O)Nc2nnc(-c3ccccn3)[nH]2)cc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 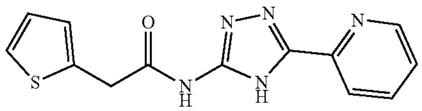 [SMILES: O=C(Cc1cccs1)Nc1nnc(-c2ccccn2)[nH]1] | A | | |
| 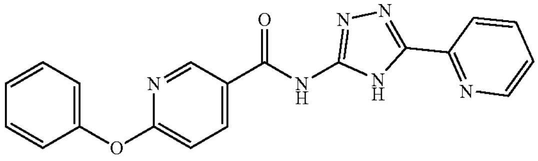 [SMILES: O=C(Nc1nnc(-c2ccccn2)[nH]1)c1ccc(Oc2ccccc2)nc1] | C | | |
| 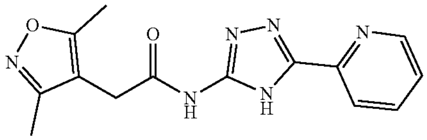 [SMILES: Cc1noc(C)c1CC(=O)Nc1nnc(-c2ccccn2)[nH]1] | B | | |
| 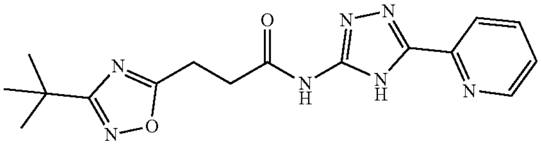 [SMILES: CC(C)(C)c1noc(CCC(=O)Nc2nnc(-c3ccccn3)[nH]2)n1] | B | | |
| 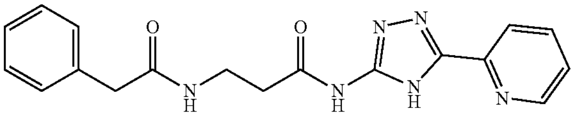 [SMILES: O=C(Cc1ccccc1)NCCC(=O)Nc1nnc(-c2ccccn2)[nH]1] | A | | |
| 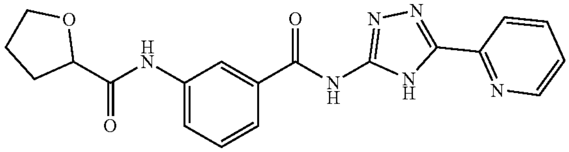 [SMILES: O=C(Nc1nnc(-c2ccccn2)[nH]1)c1cccc(NC(=O)C2CCCO2)c1] | C | | |
| 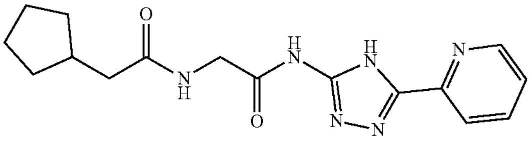 [SMILES: O=C(CC1CCCC1)NCC(=O)Nc1nnc(-c2ccccn2)[nH]1] | A | | |
| 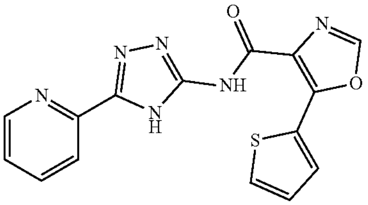 [SMILES: O=C(Nc1nnc(-c2ccccn2)[nH]1)c1ncoc1-c1cccs1] | D | | |
| 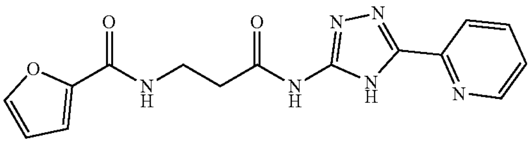 [SMILES: O=C(CCNC(=O)c1ccco1)Nc1nnc(-c2ccccn2)[nH]1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 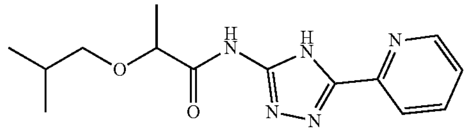 [SMILES: CC(C)COC(C)C(=O)Nc1nnc(-c2ccccn2)[nH]1] | D | | |
| 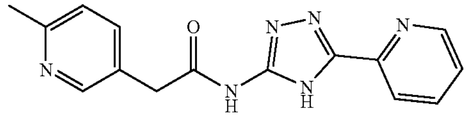 [SMILES: Cc1ccc(CC(=O)Nc2nnc(-c3ccccn3)[nH]2)cn1] | C | | |
| 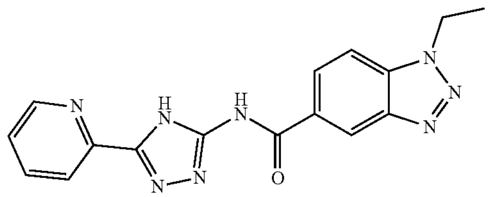 [SMILES: CCn1nnc2cc(C(=O)Nc3nnc(-c4ccccn4)[nH]3)ccc21] | C | | |
| 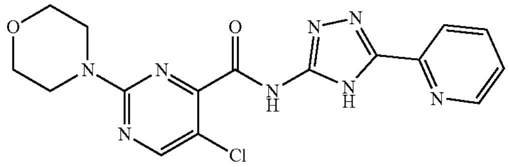 [SMILES: O=C(Nc1nnc(-c2ccccn2)[nH]1)c1nc(N2CCOCC2)ncc1Cl] | D | | |
| 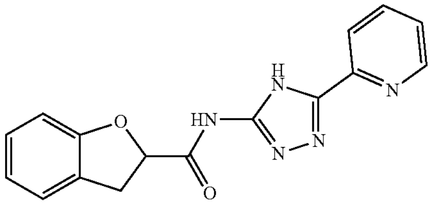 [SMILES: O=C(Nc1nnc(-c2ccccn2)[nH]1)C1Cc2ccccc2O1] | A | | |
| 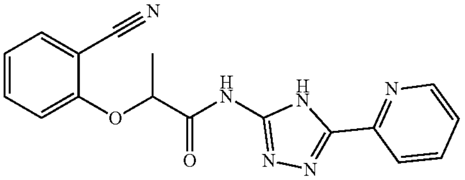 | D | | |
| 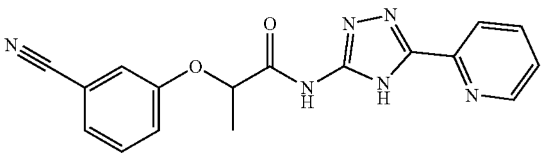 | D | | |
| 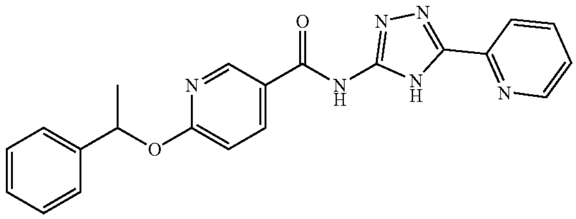 [SMILES: CC(Oc1ccc(C(=O)Nc2nnc(-c3ccccn3)[nH]2)cn1)c1ccccc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 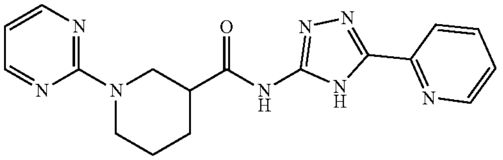 [SMILES: O=C(Nc1nnc(-c2ccccn2)[nH]1)C1CCCN(c2ncccn2)C1] | D | | |
| 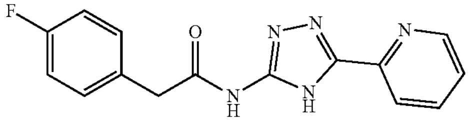 [SMILES: O=C(Cc1ccc(F)cc1)Nc1nnc(-c2ccccn2)[nH]1] | C | | |
| 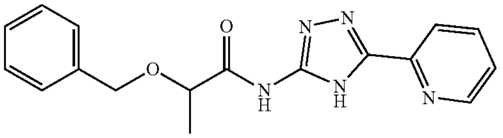 [SMILES: CC(OCc1ccccc1)C(=O)Nc1nnc(-c2ccccn2)[nH]1] | C | | |
| 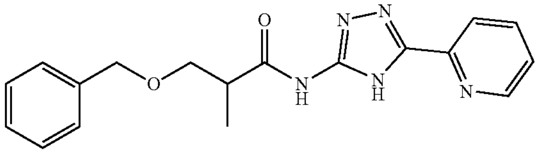 [SMILES: CC(COCc1ccccc1)C(=O)Nc1nnc(-c2ccccn2)[nH]1] | B | | |
| 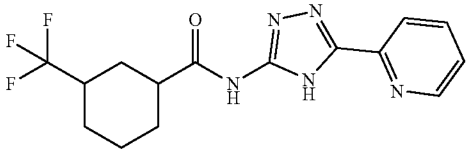 [SMILES: O=C(Nc1nnc(-c2ccccn2)[nH]1)C1CCCC(C(F)(F)F)C1] | D | | |
| 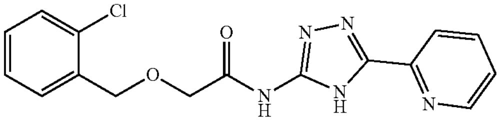 [SMILES: O=C(COCc1ccccc1Cl)Nc1nnc(-c2ccccn2)[nH]1] | D | | |
| 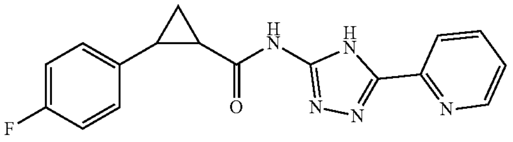 [SMILES: O=C(Nc1nnc(-c2ccccn2)[nH]1)C1CC1c1ccc(F)cc1] | C | | |
| 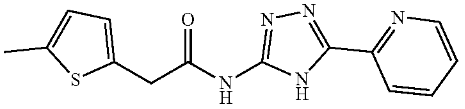 [SMILES: Cc1ccc(CC(=O)Nc2nnc(-c3ccccn3)[nH]2)s1] | D | | |
| 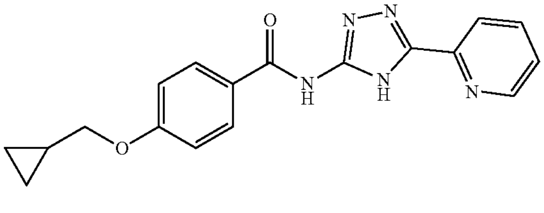 [SMILES: O=C(Nc1nnc(-c2ccccn2)[nH]1)c1ccc(OCC2CC2)cc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 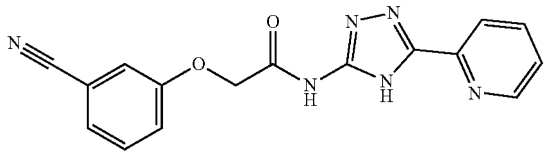 [SMILES: N#Cc1cccc(OCC(=O)Nc2nnc(-c3ccccn3)[nH]2)c1] | B | | |
| 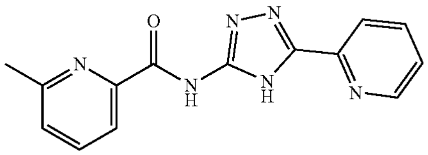 [SMILES: Cc1cccc(C(=O)Nc2nnc(-c3ccccn3)[nH]2)n1] | C | | |
| 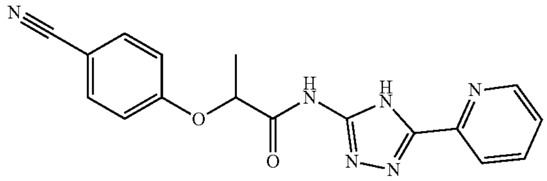 [SMILES: CC(Oc1ccc(C#N)cc1)C(=O)Nc1nnc(-c2ccccn2)[nH]1] | D | | |
| 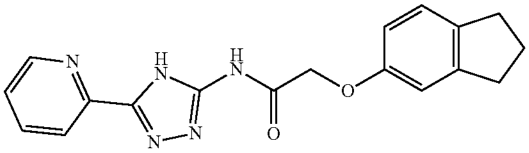 [SMILES: O=C(COc1ccc2c(c1)CCC2)Nc1nnc(-c2ccccn2)[nH]1] | A | | |
| 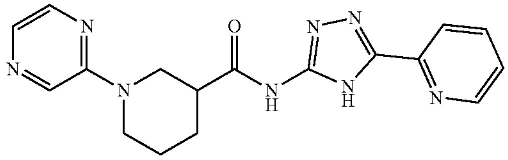 [SMILES: O=C(Nc1nnc(-c2ccccn2)[nH]1)C1CCCN(c2cnccn2)C1] | D | | |
| 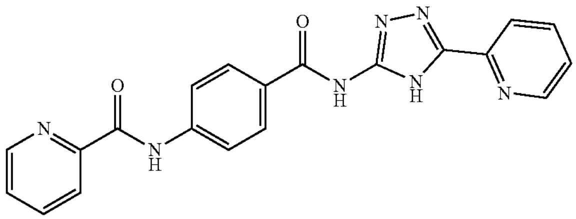 [SMILES: O=C(Nc1nnc(-c2ccccn2)[nH]1)c1ccc(NC(=O)c2ccccn2)cc1] | B | | |
| 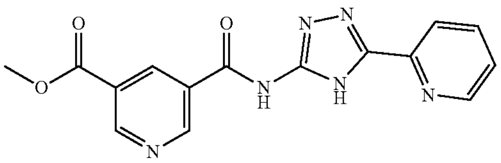 [SMILES: COC(=O)c1cncc(C(=O)Nc2nnc(-c3ccccn3)[nH]2)c1] | B | | |
| 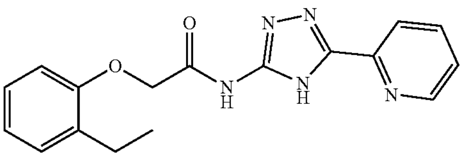 [SMILES: CCc1ccccc1OCC(=O)Nc1nnc(-c2ccccn2)[nH]1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 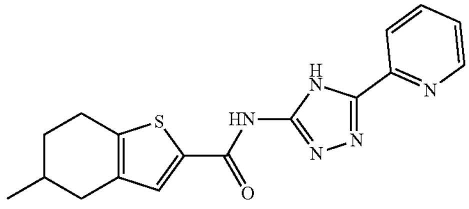 [SMILES: CC1CCc2sc(C(=O)Nc3nnc(-c4ccccn4)[nH]3)cc2C1] | D | | |
| 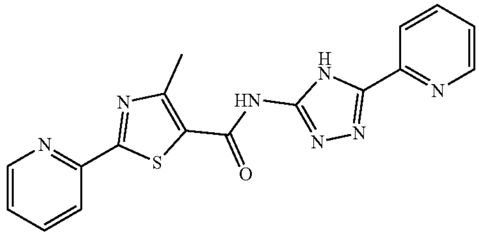 [SMILES: Cc1nc(-c2ccccn2)sc1C(=O)Nc1nnc(-c2ccccn2)[nH]1] | D | | |
| 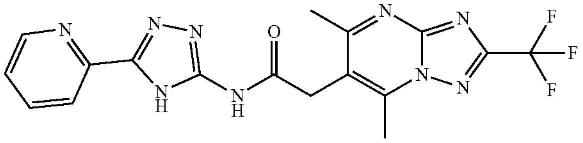 [SMILES: Cc1nc2nc(C(F)(F)F)nn2c(C)c1CC(=O)Nc1nnc(-c2ccccn2)[nH]1] | C | | |
| 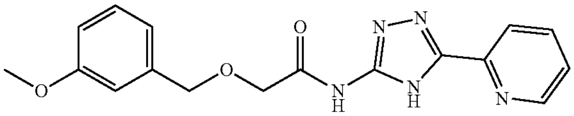 [SMILES: COc1cccc(COCC(=O)Nc2nnc(-c3ccccn3)[nH]2)c1] | C | | |
| 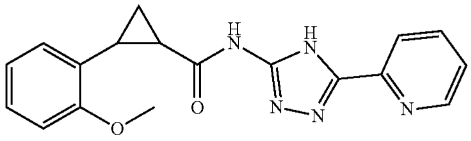 [SMILES: COc1ccccc1C1CC1C(=O)Nc1nnc(-c2ccccn2)[nH]1] | B | | |
| 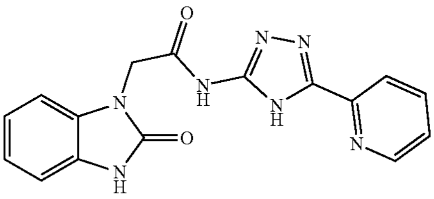 [SMILES: O=C(Cn1c(=O)[nH]c2ccccc21)Nc1nnc(-c2ccccn2)[nH]1] | B | | |
| 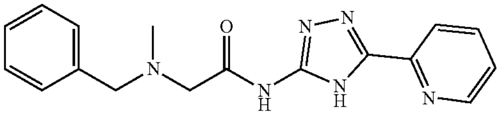 [SMILES: CN(CC(=O)Nc1nnc(-c2ccccn2)[nH]1)Cc1ccccc1] | C | | |
| 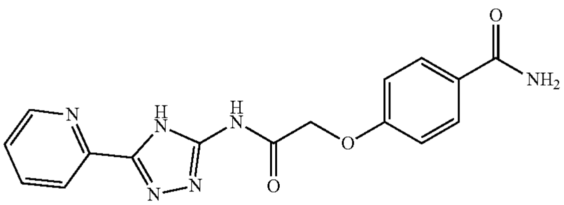 [SMILES: NC(=O)c1ccc(OCC(=O)Nc2nnc(-c3ccccn3)[nH]2)cc1] | A | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 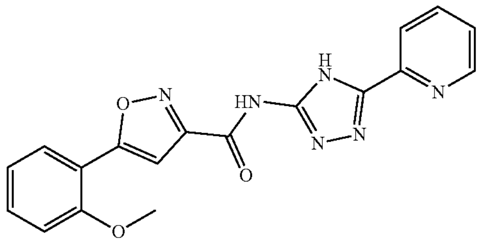 [SMILES: COc1ccccc1-c1cc(C(=O)Nc2nnc(-c3ccccn3)[nH]2)no1] | D | | |
| 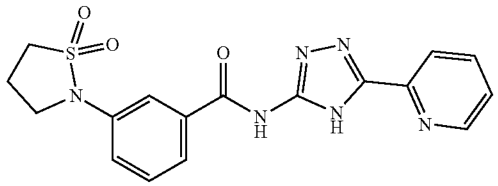 [SMILES: O=C(Nc1nnc(-c2ccccn2)[nH]1)c1cccc(N2CCCS2(=O)=O)c1] | A | | |
| 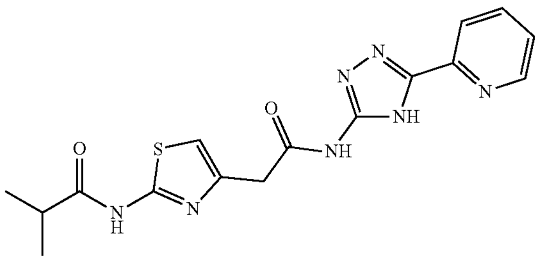 [SMILES: CC(C)C(=O)Nc1nc(CC(=O)Nc2nnc(-c3ccccn3)[nH]2)cs1] | D | | |
| 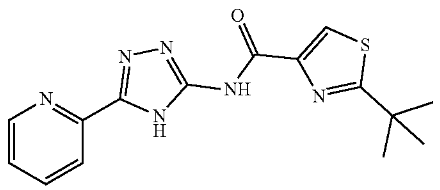 [SMILES: CC(C)(C)c1nc(C(=O)Nc2nnc(-c3ccccn3)[nH]2)cs1] | D | | |
| 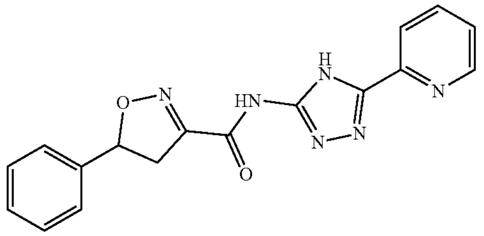 [SMILES: O=C(Nc1nnc(-c2ccccn2)[nH]1)C1=NOC(c2ccccc2)C1] | B | | |
| 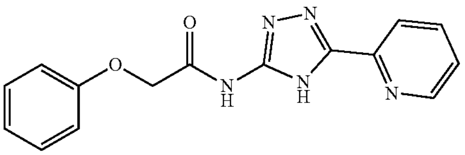 [SMILES: O=C(COc1ccccc1)Nc1nnc(-c2ccccn2)[nH]1] | B | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 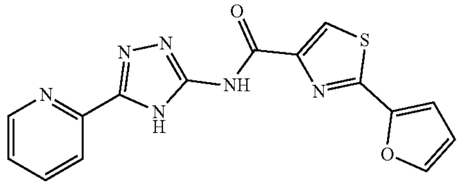 [SMILES: O=C(Nc1nnc(-c2ccccn2)[nH]1)c1csc(-c2ccco2)n1] | D | | |
| 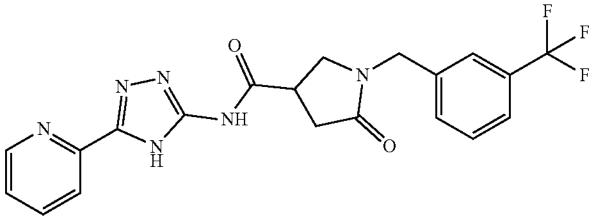 [SMILES: O=C(Nc1nnc(-c2ccccn2)[nH]1)C1CC(=O)N(Cc2cccc(C(F)(F)F)c2)C1] | D | | |
| 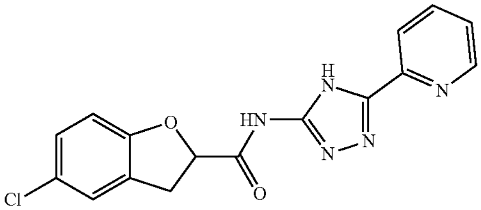 [SMILES: O=C(Nc1nnc(-c2ccccn2)[nH]1)C1Cc2cc(Cl)ccc2O1] | D | | |
| 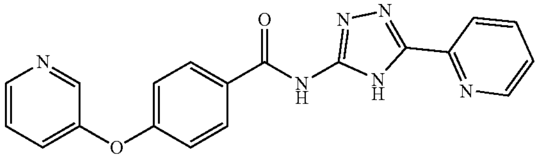 [SMILES: O=C(Nc1nnc(-c2ccccn2)[nH]1)c1ccc(Oc2cccnc2)cc1] | D | | |
| 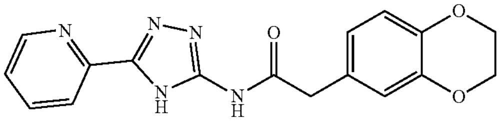 [SMILES: O=C(Cc1ccc2c(c1)OCCO2)Nc1nnc(-c2ccccn2)[nH]1] | C | | |
| 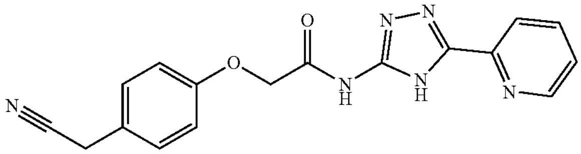 [SMILES: N#CCc1ccc(OCC(=O)Nc2nnc(-c3ccccn3)[nH]2)cc1] | A | | |
| 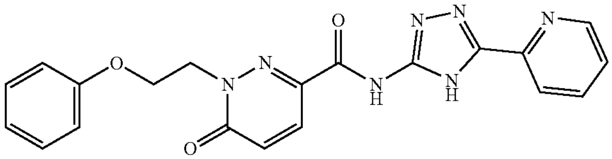 [SMILES: O=C(Nc1nnc(-c2ccccn2)[nH]1)c1ccc(=O)n(CCOc2ccccc2)n1] | D | | |
| 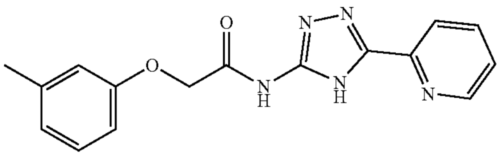 [SMILES: Cc1cccc(OCC(=O)Nc2nnc(-c3ccccn3)[nH]2)c1] | C | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 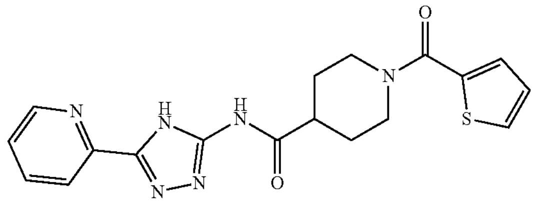 [SMILES: O=C(Nc1nnc(-c2ccccn2)[nH]1)C1CCN(C(=O)c2cccs2)CC1] | D | | |
| 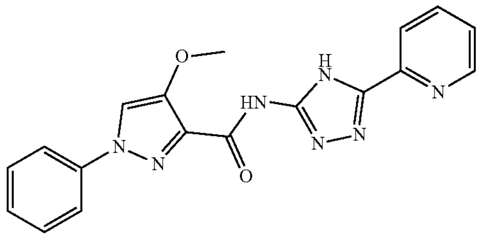 [SMILES: COc1cn(-c2ccccc2)nc1C(=O)Nc1nnc(-c2ccccn2)[nH]1] | C | | |
| 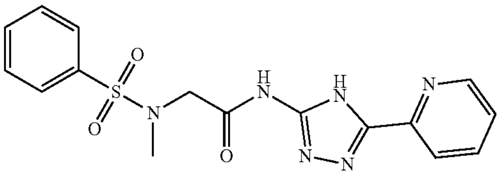 [SMILES: CN(CC(=O)Nc1nnc(-c2ccccn2)[nH]1)S(=O)(=O)c1ccccc1] | A | | |
| 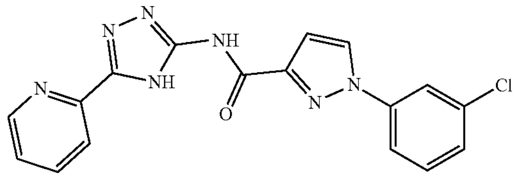 [SMILES: O=C(Nc1nnc(-c2ccccn2)[nH]1)c1ccn(-c2cccc(Cl)c2)n1] | D | | |
| 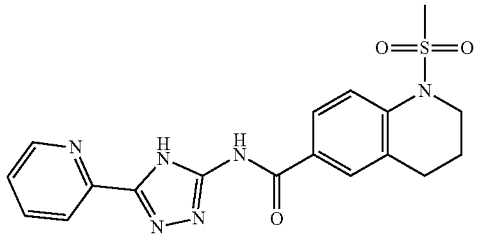 [SMILES: CS(=O)(=O)N1CCCc2cc(C(=O)Nc3nnc(-c4ccccn4)[nH]3)ccc21] | D | | |
| 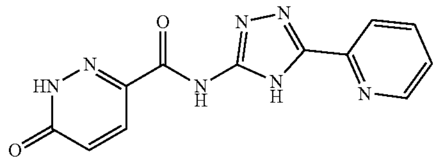 [SMILES: O=C(Nc1nnc(-c2ccccn2)[nH]1)c1ccc(=O)[nH]n1] | B | | |
| 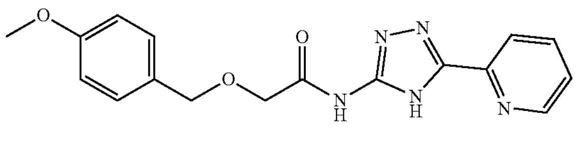 [SMILES: COc1ccc(COCC(=O)Nc2nnc(-c3ccccn3)[nH]2)cc1] | A | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 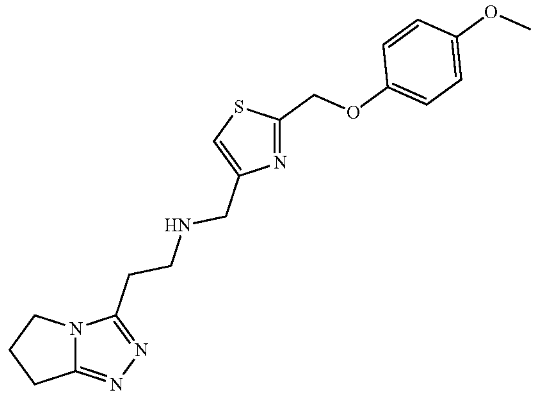 [SMILES: COc1ccc(OCc2nc(CNCCc3nnc4n3CCC4)cs2)cc1] | D | | |
| 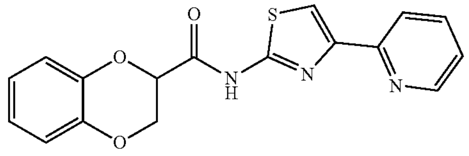 [SMILES: O=C(Nc1nc(-c2ccccn2)cs1)C1COc2ccccc2O1] | D | | |
| 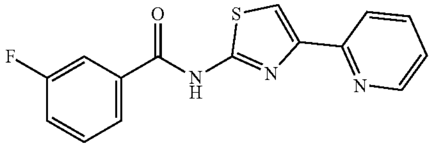 [SMILES: O=C(Nc1nc(-c2ccccn2)cs1)c1cccc(F)c1] | D | | |
| 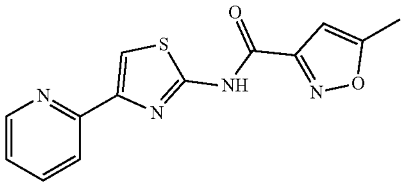 [SMILES: Cc1cc(C(=O)Nc2nc(-c3ccccn3)cs2)no1] | D | | |
| 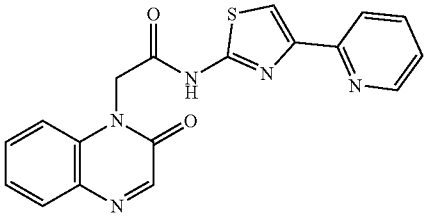 [SMILES: O=C(Cn1c(=O)cnc2ccccc21)Nc1nc(-c2ccccn2)cs1] | D | | |
| 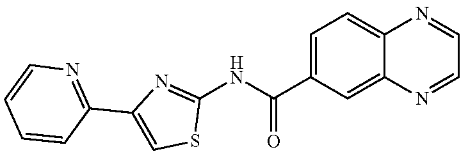 [SMILES: O=C(Nc1nc(-c2ccccn2)cs1)c1ccc2nccnc2c1] | D | | |
| 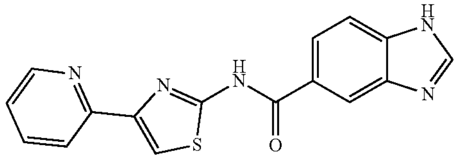 [SMILES: O=C(Nc1nc(-c2ccccn2)cs1)c1ccc2[nH]cnc2c1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 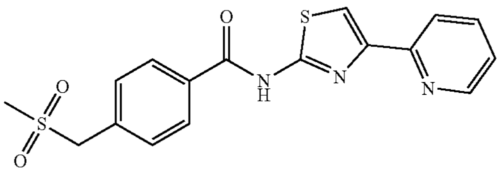 [SMILES: CS(=O)(=O)Cc1ccc(C(=O)Nc2nc(-c3ccccn3)cs2)cc1] | D | | |
| 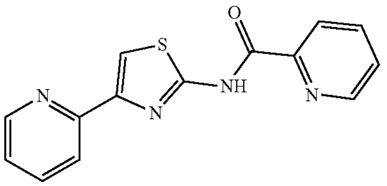 [SMILES: O=C(Nc1nc(-c2ccccn2)cs1)c1ccccn1] | D | | |
| 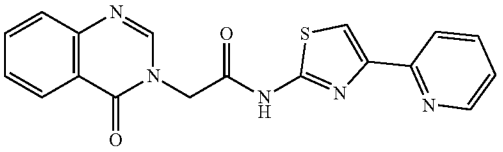 [SMILES: O=C(Cn1cnc2ccccc2c1=O)Nc1nc(-c2ccccn2)cs1] | D | | |
| 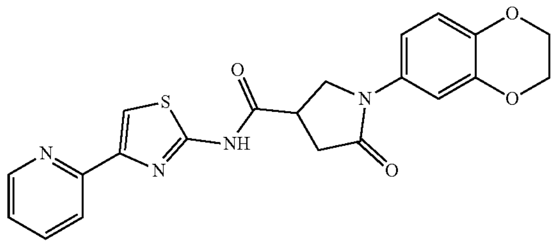 [SMILES: O=C(Nc1nc(-c2ccccn2)cs1)C1CC(=O)N(c2ccc3c(c2)OCCO3)C1] | D | | |
| 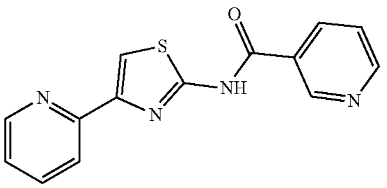 [SMILES: O=C(Nc1nc(-c2ccccn2)cs1)c1cccnc1] | D | | |
| 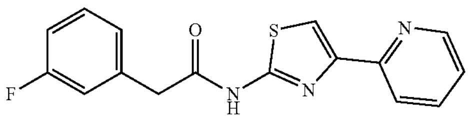 [SMILES: O=C(Cc1cccc(F)c1)Nc1nc(-c2ccccn2)cs1] | D | | |
| 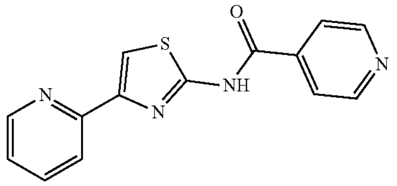 [SMILES: O=C(Nc1nc(-c2ccccn2)cs1)c1ccncc1] | D | | |
| 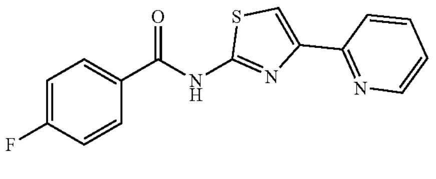 [SMILES: O=C(Nc1nc(-c2ccccn2)cs1)c1ccc(F)cc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 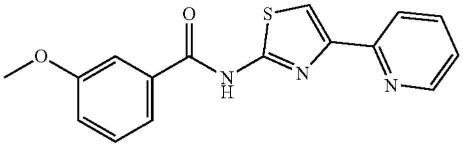 [SMILES: COc1cccc(C(=O)Nc2nc(-c3ccccn3)cs2)c1] | D | | |
| 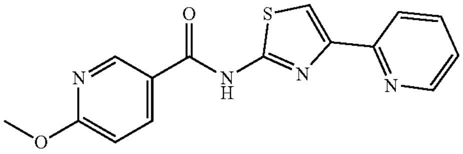 [SMILES: COc1ccc(C(=O)Nc2nc(-c3ccccn3)cs2)cn1] | D | | |
| 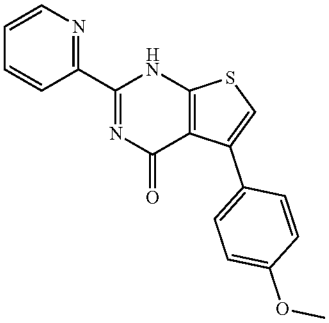 [SMILES: COc1ccc(-c2csc3[nH]c(-c4ccccn4)nc(=O)c23)cc1] | D | | |
| 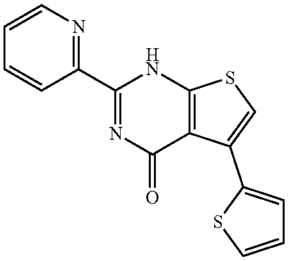 [SMILES: O=c1nc(-c2ccccn2)[nH]c2scc(-c3cccs3)c12] | D | | |
| 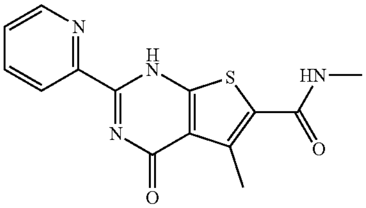 [SMILES: CNC(=O)c1sc2[nH]c(-c3ccccn3)nc(=O)c2c1C] | C | | |
| 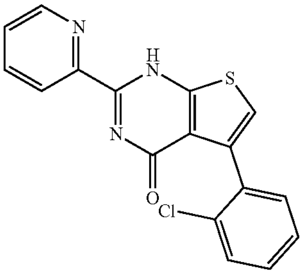 [SMILES: O=c1nc(-c2ccccn2)[nH]c2scc(-c3ccccc3Cl)c12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 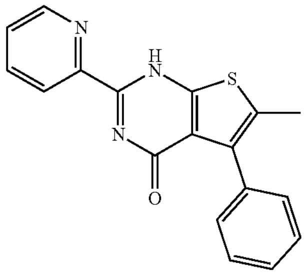 [SMILES: Cc1sc2[nH]c(-c3ccccn3)nc(=O)c2c1-c1ccccc1] | D | | |
| 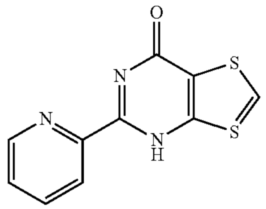 | A | | E |
| 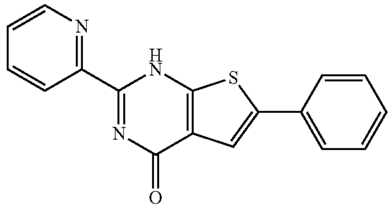 [SMILES: O=c1nc(-c2ccccn2)[nH]c2sc(-c3ccccc3)cc12] | D | | |
| 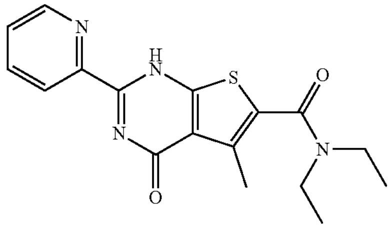 [SMILES: CCN(CC)C(=O)c1sc2[nH]c(-c3ccccn3)nc(=O)c2c1C] | D | | |
| 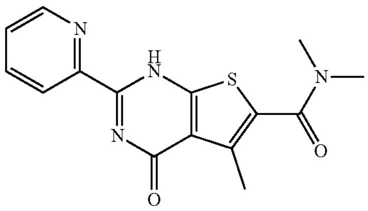 [SMILES: Cc1c(C(=O)N(C)C)sc2[nH]c(-c3ccccn3)nc(=O)c12] | C | | |
| 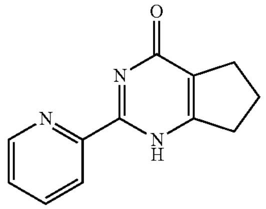 [SMILES: O=c1nc(-c2ccccn2)[nH]c2c1CCC2] | A | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 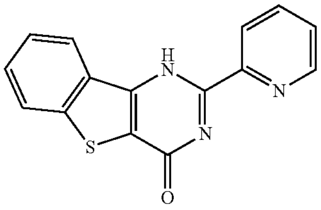 [SMILES: O=c1nc(-c2ccccn2)[nH]c2c1sc1ccccc12] | D | | |
| 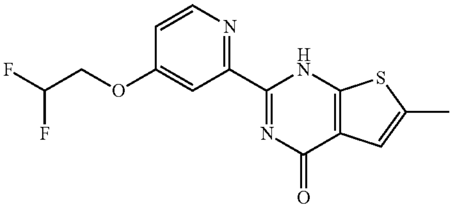 [SMILES: Cc1cc2c(=O)nc(-c3cc(OCC(F)F)ccn3)[nH]c2s1] | D | | |
| 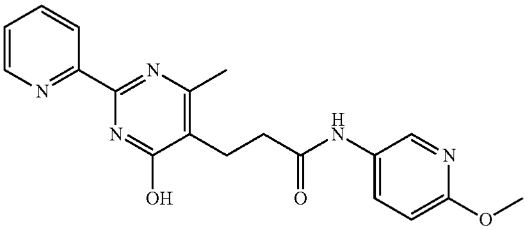 [SMILES: COc1ccc(NC(=O)CCc2c(C)nc(-c3ccccn3)nc2O)cn1] | D | | |
| 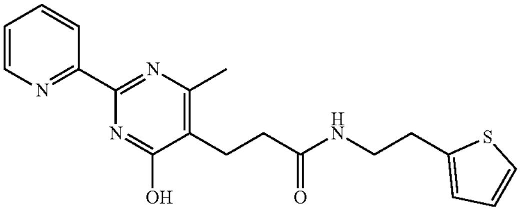 [SMILES: Cc1nc(-c2ccccn2)nc(O)c1CCC(=O)NCCc1cccs1] | D | | |
| 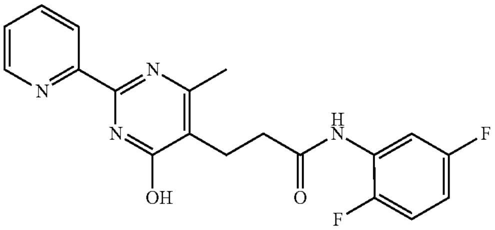 [SMILES: Cc1nc(-c2ccccn2)nc(O)c1CCC(=O)Nc1cc(F)ccc1F] | D | | |
| 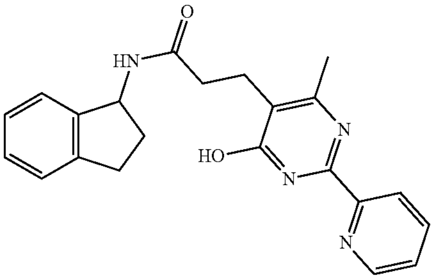 [SMILES: Cc1nc(-c2ccccn2)nc(O)c1CCC(=O)NC1CCc2ccccc21] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 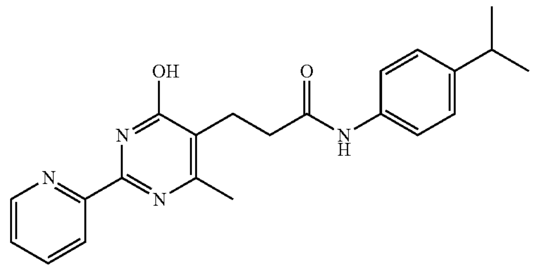 [SMILES: Cc1nc(-c2ccccn2)nc(O)c1CCC(=O)Nc1ccc(C(C)C)cc1] | D | | |
| 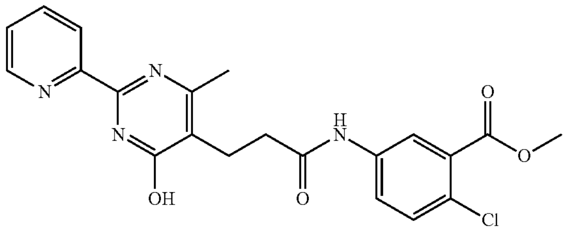 [SMILES: COC(=O)c1cc(NC(=O)CCc2c(C)nc(-c3ccccn3)nc2O)ccc1Cl] | D | | |
| 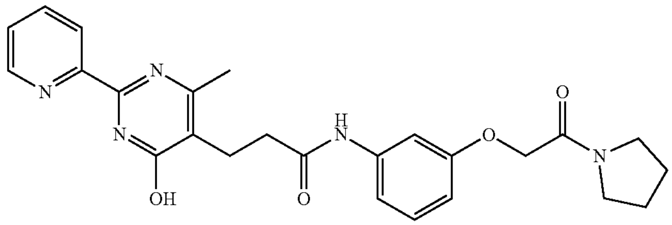 [SMILES: Cc1nc(-c2ccccn2)nc(O)c1CCC(=O)Nc1cccc(OCC(=O)N2CCCC2)c1] | A | | |
| 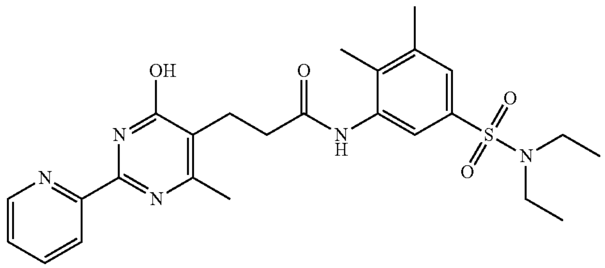 [SMILES: CCN(CC)S(=O)(=O)c1cc(C)c(C)c(NC(=O)CCc2c(C)nc(-c3ccccn3)nc2O)c1] | D | | |
| 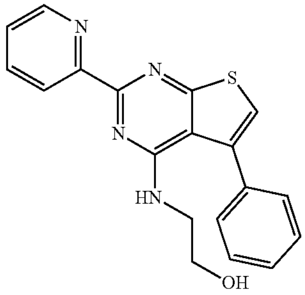 [SMILES: OCCNc1nc(-c2ccccn2)nc2scc(-c3ccccc3)c12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 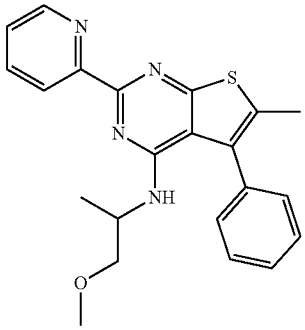 [SMILES: COCC(C)Nc1nc(-c2ccccn2)nc2sc(C)c(-c3ccccc3)c12] | D | | E |
| 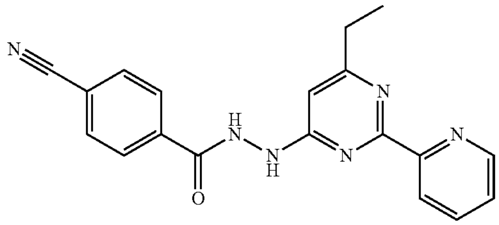 [SMILES: CCc1cc(NNC(=O)c2ccc(C#N)cc2)nc(-c2ccccn2)n1] | D | | |
| 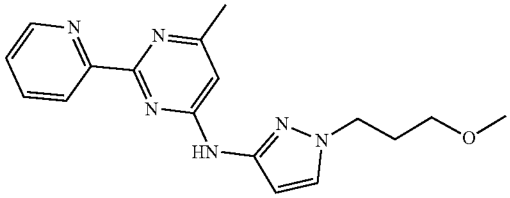 [SMILES: COCCCn1ccc(Nc2cc(C)nc(-c3ccccn3)n2)n1] | B | | |
| 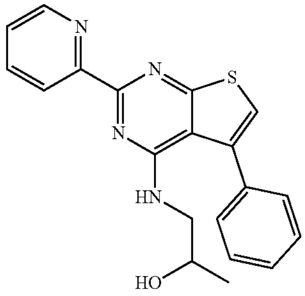 [SMILES: CC(O)CNc1nc(-c2ccccn2)nc2scc(-c3ccccc3)c12] | D | | |
| 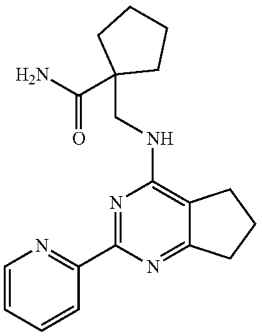 [SMILES: NC(=O)C1(CNc2nc(-c3ccccn3)nc3c2CCC3)CCCC1] | D | | |

TABLE 5-continued
| Compound | MIA-PACA2 | MIA-PACA2 (alternate conditions) | $IC_{50}$ (nM) |
|---|---|---|---|
| % Inhibition of cell proliferation at 30 μM or 10 μM in MIA-PACA2 pancreatic cancer cell lines, with select $IC_{50}$ values | | | |
| 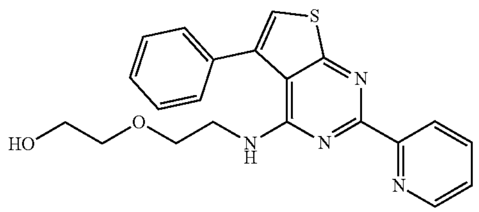 [SMILES: OCCOCCNc1nc(-c2ccccn2)nc2scc(-c3ccccc3)c12] | D | | |
| 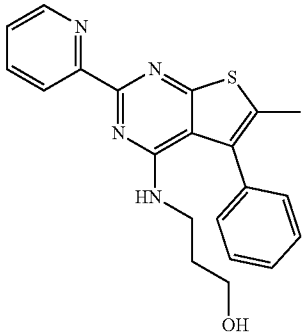 [SMILES: Cc1sc2nc(-c3ccccn3)nc(NCCCO)c2c1-c1ccccc1] | D | | |
| 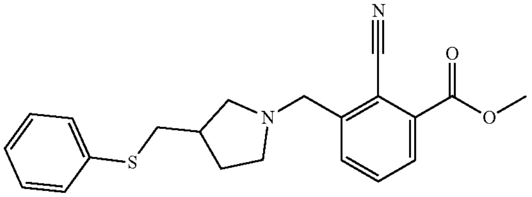 [SMILES: COC(=O)c1cccc(CN2CCC(CSc3ccccc3)C2)c1C#N] | D | | |
| 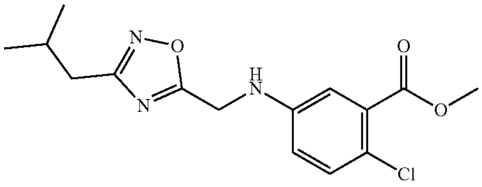 [SMILES: COC(=O)c1cc(NCc2nc(CC(C)C)no2)ccc1Cl] | D | | |
| 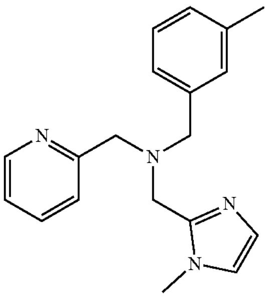 [SMILES: Cc1cccc(CN(Cc2ccccn2)Cc2nccn2C)c1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 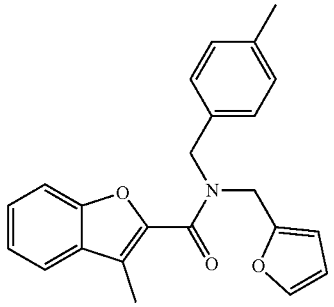 [SMILES: Cc1ccc(CN(Cc2ccco2)C(=O)c2oc3ccccc3c2C)cc1] | A | | |
| 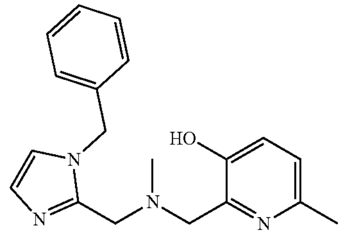 [SMILES: Cc1ccc(O)c(CN(C)Cc2nccn2Cc2ccccc2)n1] | D | | |
| 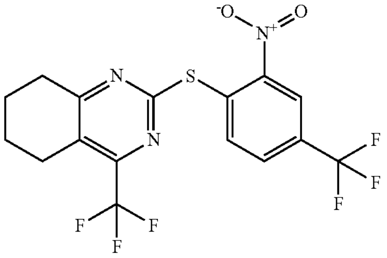 | D | | |
| 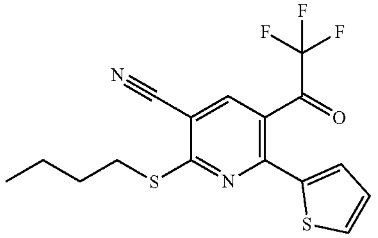 [SMILES: CCCCSc1nc(-c2cccs2)c(C(=O)C(F)(F)F)cc1C#N] | D | | |
| 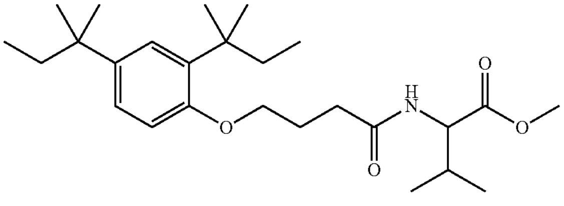 [SMILES: CCC(C)(C)c1ccc(OCCCC(=O)NC(C(=O)OC)C(C)C)c(C(C)(C)CC)c1] | D | | |
| 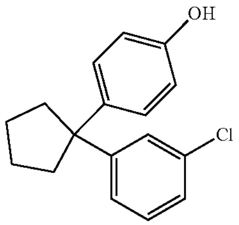 [SMILES: Oc1ccc(C2(c3cccc(Cl)c3)CCCC2)cc1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 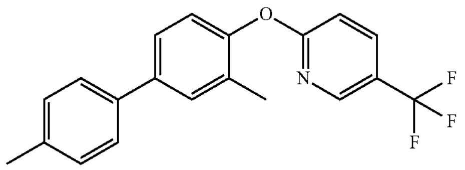 [SMILES: Cc1ccc(-c2ccc(Oc3ccc(C(F)(F)F)cn3)c(C)c2)cc1] | D | | |
| 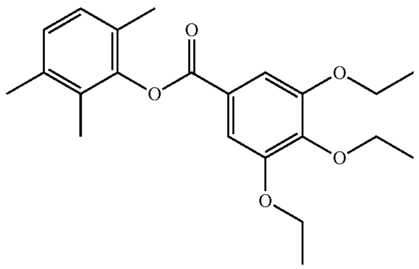 [SMILES: CCOc1cc(C(=O)Oc2c(C)ccc(C)c2C)cc(OCC)c1OCC] | D | | |
| 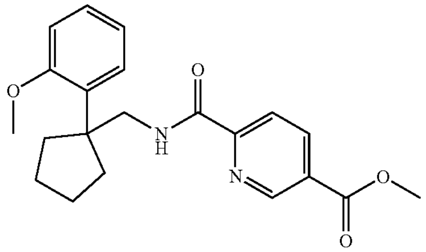 [SMILES: COC(=O)c1ccc(C(=O)NCC2(c3ccccc3OC)CCCC2)nc1] | D | | |
| 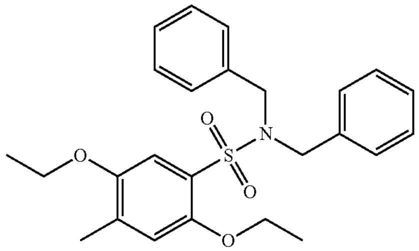 [SMILES: CCOc1cc(S(=O)(=O)N(Cc2ccccc2)Cc2ccccc2)c(OCC)cc1C] | D | | |
| 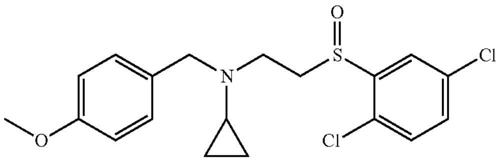 [SMILES: COc1ccc(CN(CCS(=O)c2cc(Cl)ccc2Cl)C2CC2)cc1] | C | | |
| 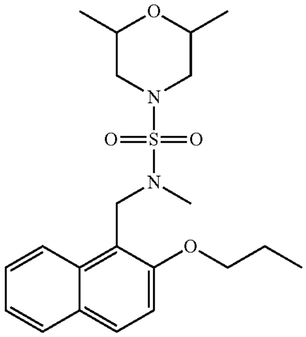 [SMILES: CCCOc1ccc2ccccc2c1CN(C)S(=O)(=O)N1CC(C)OC(C)C1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 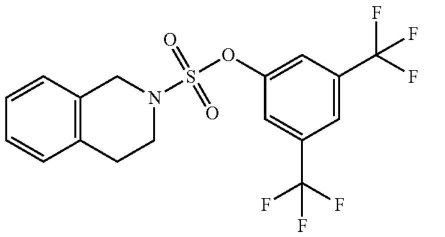 [SMILES: O=S(=O)(Oc1cc(C(F)(F)F)cc(C(F)(F)F)c1)N1CCc2ccccc2C1] | B | | |
| 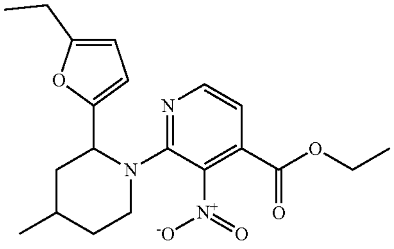 | D | | |
| 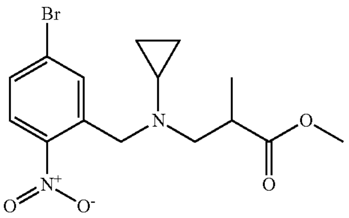 [SMILES: COC(=O)C(C)CN(Cc1cc(Br)ccc1[N+](=O)[O-])C1CC1] | A | | |
| 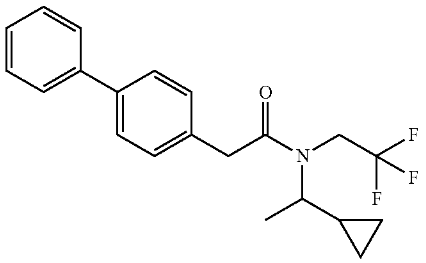 [SMILES: CC(C1CC1)N(CC(F)(F)F)C(=O)Cc1ccc(-c2ccccc2)cc1] | D | | |
| 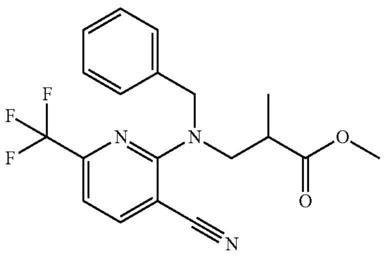 [SMILES: COC(=O)C(C)CN(Cc1ccccc1)c1nc(C(F)(F)F)ccc1C#N] | C | | |
| 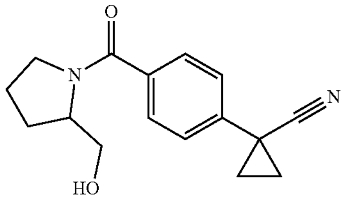 [SMILES: N#CC1(c2ccc(C(=O)N3CCCC3CO)cc2)CC1] | C | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 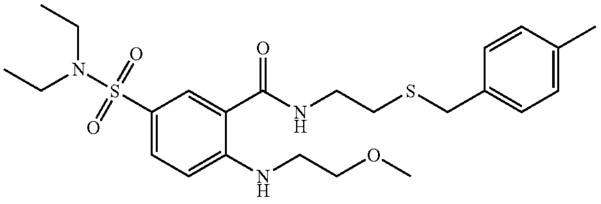 [SMILES: CCN(CC)S(=O)(=O)c1ccc(NCCOC)c(C(=O)NCCSCc2ccc(C)cc2)c1] | D | | |
| 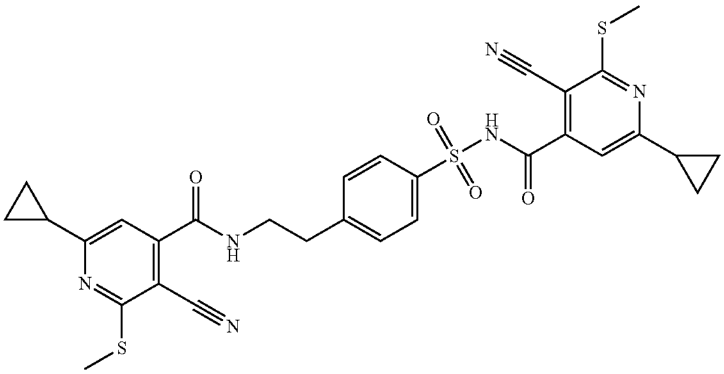 [SMILES: CSc1nc(C2CC2)cc(C(=O)NCCc2ccc(S(=O)(=O)NC(=O)c3cc(C4CC4)nc(SC)c3C#N)cc2)c1C#N] | A | | |
| 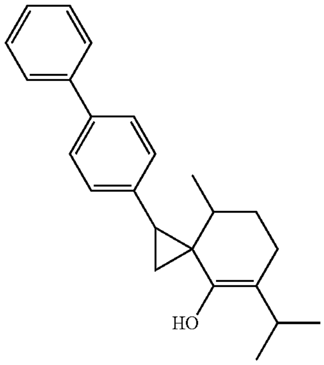 [SMILES: CC(C)C1=C(O)C2(CC2c2ccc(-c3ccccc3)cc2)C(C)CC1] | D | | |
| 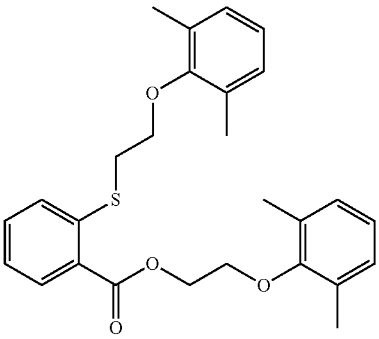 [SMILES: Cc1cccc(C)c1OCCOC(=O)c1ccccc1SCCOc1c(C)cccc1C] | C | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 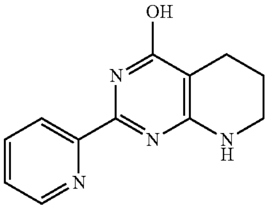 [SMILES: Oc1nc(-c2ccccn2)nc2c1CCCN2] | A | | |
| 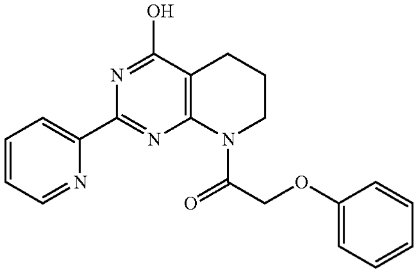 [SMILES: O=C(COc1ccccc1)N1CCCc2c(O)nc(-c3ccccn3)nc21] | D | | |
| 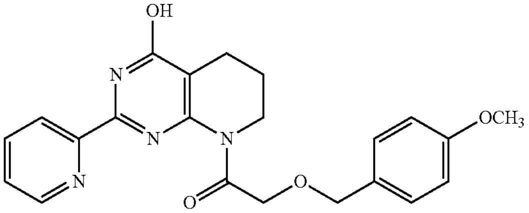 [SMILES: COc1ccc(COCC(=O)N2CCCc3c(O)nc(-c4ccccn4)nc32)cc1] | D | | |
| 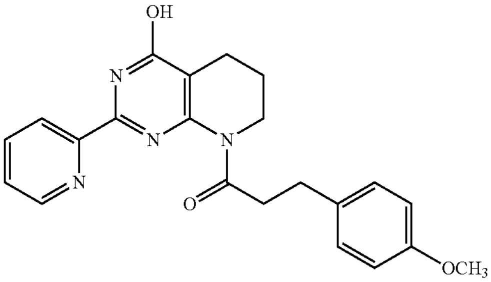 [SMILES: COc1ccc(CCC(=O)N2CCCc3c(O)nc(-c4ccccn4)nc32)cc1] | D | | |
| 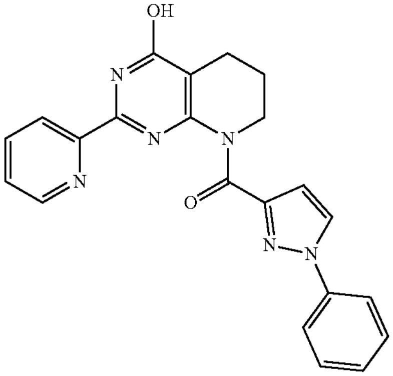 [SMILES: O=C(c1ccn(-c2ccccc2)n1)N1CCCc2c(O)nc(-c3ccccn3)nc21] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 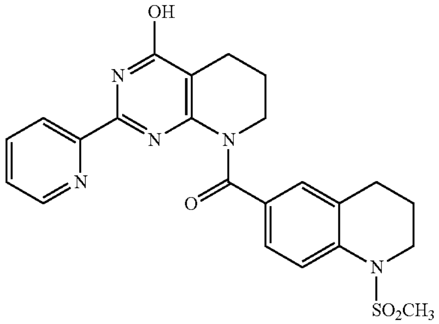 [SMILES: CS(=O)(=O)N1CCCc2cc(C(=O)N3CCCc4c(O)nc(-c5ccccn5)nc43)ccc21] | D | | |
| 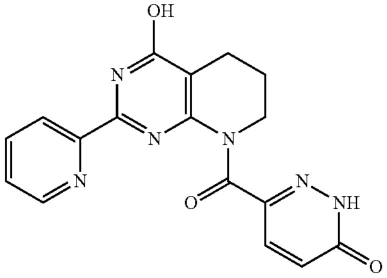 [SMILES: O=C(c1ccc(=O)[nH]n1)N1CCCc2c(O)nc(-c3ccccn3)nc21] | D | | |
| 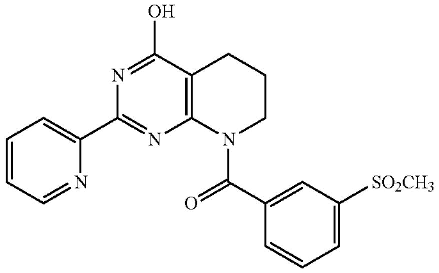 [SMILES: CS(=O)(=O)c1cccc(C(=O)N2CCCc3c(O)nc(-c4ccccn4)nc32)c1] | A | | |
| 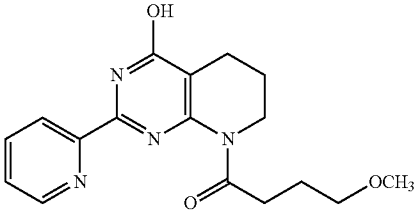 [SMILES: COCCCC(=O)N1CCCc2c(O)nc(-c3ccccn3)nc21] | D | | |
| 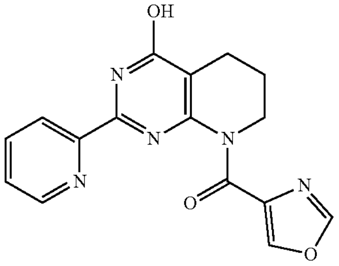 [SMILES: O=C(c1cocn1)N1CCCc2c(O)nc(-c3ccccn3)nc21] | A | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 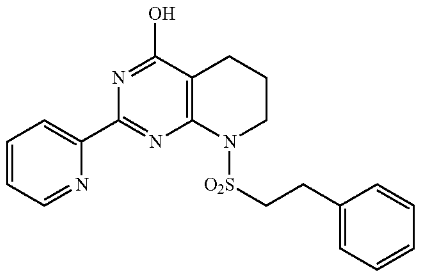 [SMILES: O=S(=O)(CCc1ccccc1)N1CCCc2c(O)nc(-c3ccccn3)nc21] | A | | |
| 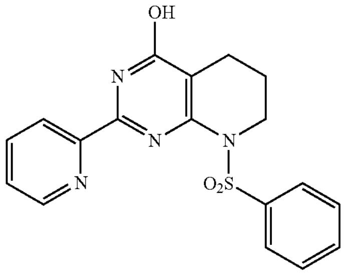 [SMILES: O=S(=O)(c1ccccc1)N1CCCc2c(O)nc(-c3ccccn3)nc21] | B | | |
| 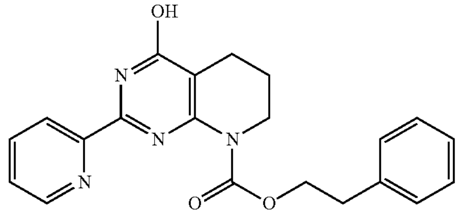 [SMILES: O=C(OCCc1ccccc1)N1CCCc2c(O)nc(-c3ccccn3)nc21] | D | | |
| 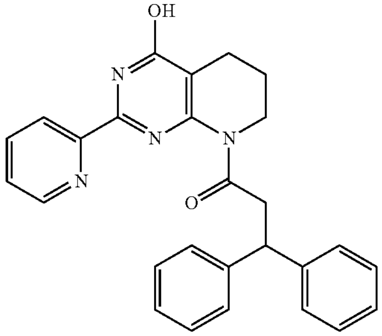 [SMILES: O=C(CC(c1ccccc1)c1ccccc1)N1CCCc2c(O)nc(-c3ccccn3)nc21] | D | | |
| 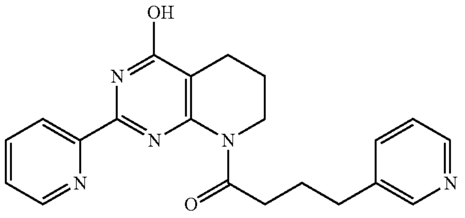 [SMILES: O=C(CCCc1cccnc1)N1CCCc2c(O)nc(-c3ccccn3)nc21] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 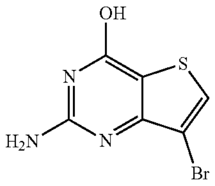 [SMILES: Nc1nc(O)c2scc(Br)c2n1] | A | | |
| 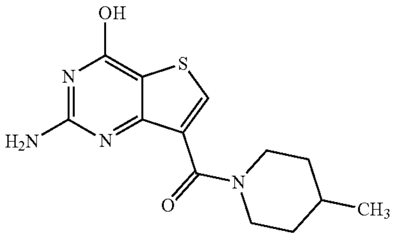 [SMILES: CC1CCN(C(=O)c2csc3c(O)nc(N)nc23)CC1] | A | | |
| 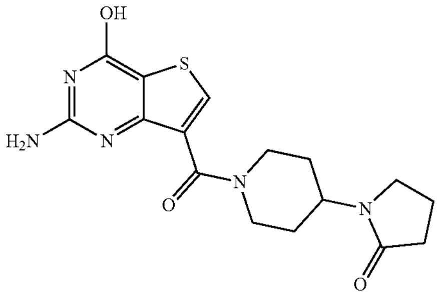 [SMILES: Nc1nc(O)c2scc(C(=O)N3CCC(N4CCCC4=O)CC3)c2n1] | B | | |
| 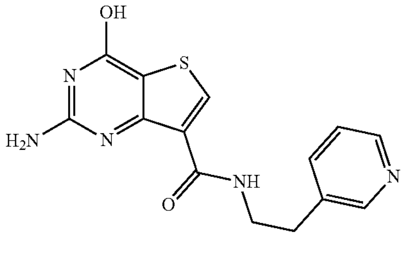 [SMILES: Nc1nc(O)c2scc(C(=O)NCCc3cccnc3)c2n1] | A | | |
| 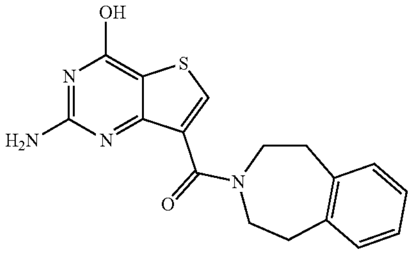 [SMILES: Nc1nc(O)c2scc(C(=O)N3CCc4ccccc4CC3)c2n1] | A | | |
| 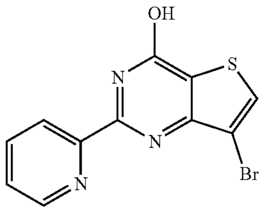 [SMILES: Oc1nc(-c2ccccn2)nc2c(Br)csc12] | D | | F |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 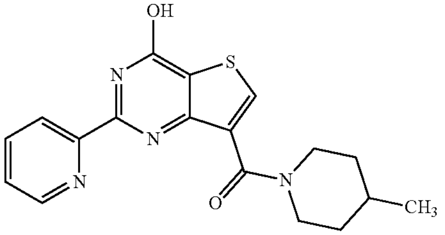 [SMILES: CC1CCN(C(=O)c2csc3c(O)nc(-c4ccccn4)nc23)CC1] | D | | |
| 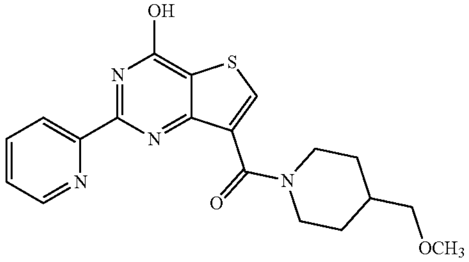 [SMILES: COCC1CCN(C(=O)c2csc3c(O)nc(-c4ccccn4)nc23)CC1] | D | | |
| 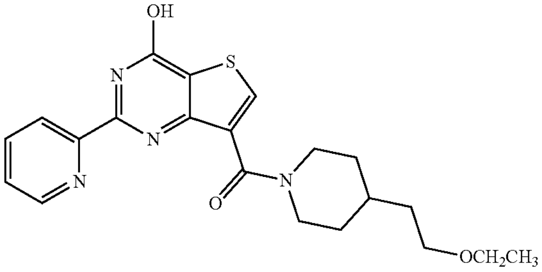 [SMILES: CCOCCC1CCN(C(=O)c2csc3c(O)nc(-c4ccccn4)nc23)CC1] | D | | |
| 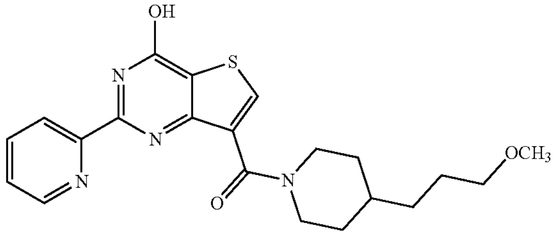 [SMILES: COCCCC1CCN(C(=O)c2csc3c(O)nc(-c4ccccn4)nc23)CC1] | D | | |
| 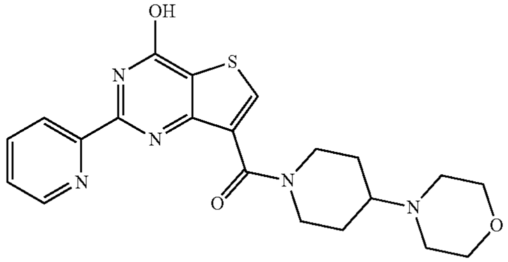 [SMILES: O=C(c1csc2c(O)nc(-c3ccccn3)nc12)N1CCC(N2CCOCC2)CC1] | A | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 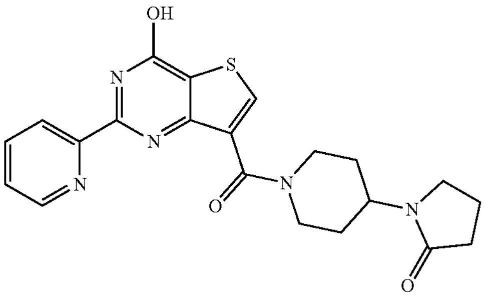 [SMILES: O=C(c1csc2c(O)nc(-c3ccccn3)nc12)N1CCC(N2CCCC2=O)CC1] | A | | |
| 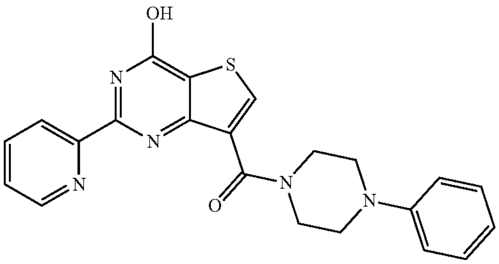 [SMILES: O=C(c1csc2c(O)nc(-c3ccccn3)nc12)N1CCN(c2ccccc2)CC1] | D | | G |
| 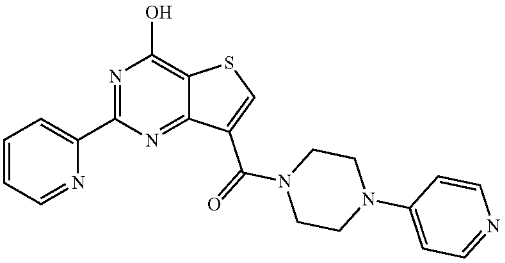 [SMILES: O=C(c1csc2c(O)nc(-c3ccccn3)nc12)N1CCN(c2ccncc2)CC1] | D | | |
| 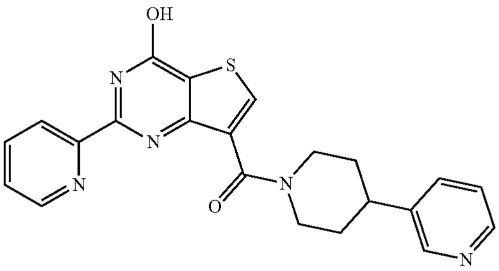 [SMILES: O=C(c1csc2c(O)nc(-c3ccccn3)nc12)N1CCC(c2cccnc2)CC1] | D | | |
| 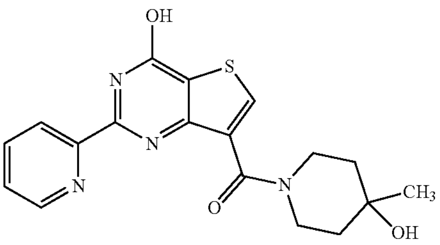 [SMILES: CC1(O)CCN(C(=O)c2csc3c(O)nc(-c4ccccn4)nc23)CC1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 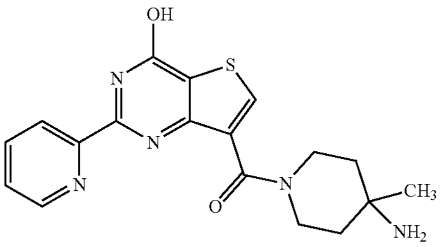 [SMILES: CC1(N)CCN(C(=O)c2csc3c(O)nc(-c4ccccn4)nc23)CC1] | A | | |
| 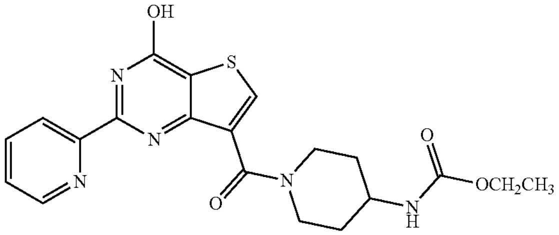 [SMILES: CCOC(=O)NC1CCN(C(=O)c2csc3c(O)nc(-c4ccccn4)nc23)CC1] | C | | |
| 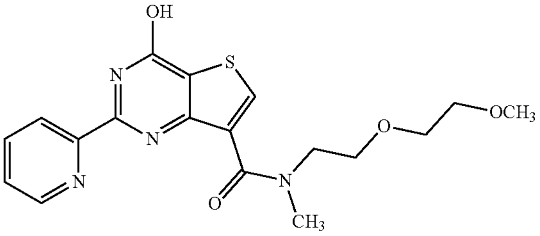 [SMILES: COCCOCCN(C)C(=O)c1csc2c(O)nc(-c3ccccn3)nc12] | B | | |
| 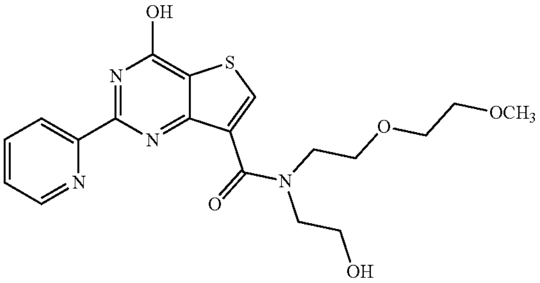 [SMILES: COCCOCCN(CCO)C(=O)c1csc2c(O)nc(-c3ccccn3)nc12] | A | | |
| 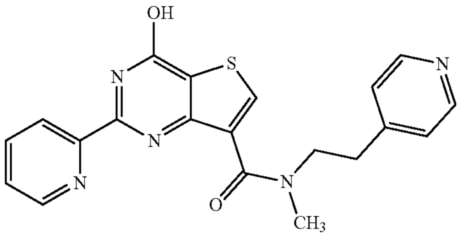 [SMILES: CN(CCc1ccncc1)C(=O)c1csc2c(O)nc(-c3ccccn3)nc12] | B | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 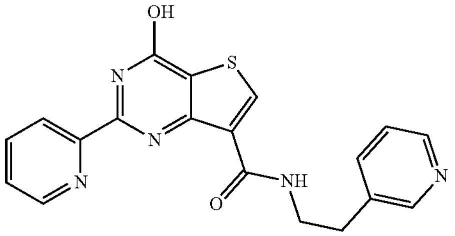 [SMILES: O=C(NCCc1cccnc1)c1csc2c(O)nc(-c3ccccn3)nc12] | D | | |
| 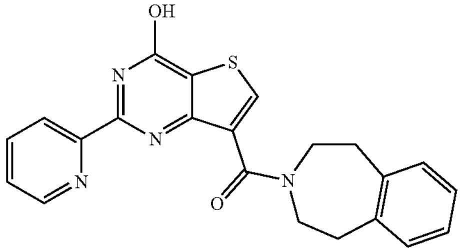 [SMILES: O=C(c1csc2c(O)nc(-c3ccccn3)nc12)N1CCc2ccccc2CC1] | D | | |
| 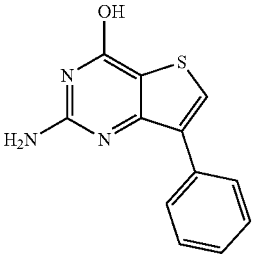 [SMILES: Nc1nc(O)c2scc(-c3ccccc3)c2n1] | B | | |
| 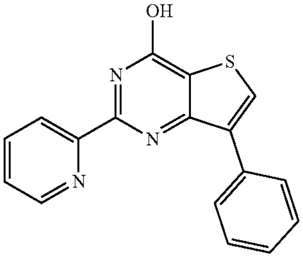 [SMILES: Oc1nc(-c2ccccn2)nc2c(-c3ccccc3)csc12] | D | | G |
| 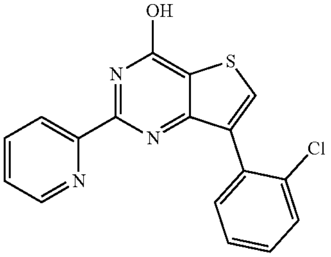 [SMILES: Oc1nc(-c2ccccn2)nc2c(-c3ccccc3Cl)csc12] | D | | G |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 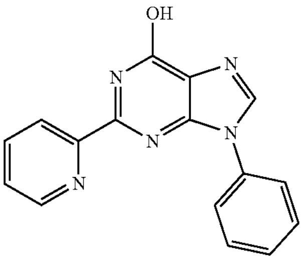 [SMILES: Oc1nc(-c2ccccn2)nc2c1ncn2-c1ccccc1] | B | | |
| 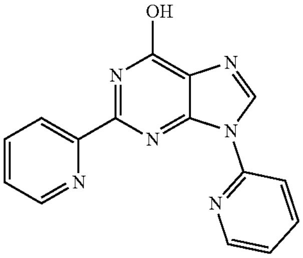 [SMILES: Oc1nc(-c2ccccn2)nc2c1ncn2-c1ccccn1] | D | | |
| 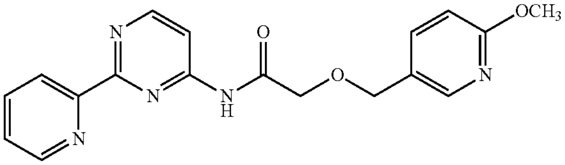 [SMILES: COc1ccc(COCC(=O)Nc2ccnc(-c3ccccn3)n2)cn1] | A | | |
| 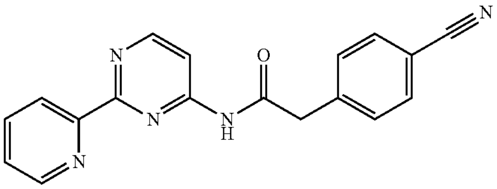 [SMILES: N#Cc1ccc(CC(=O)Nc2ccnc(-c3ccccn3)n2)cc1] | D | | |
| 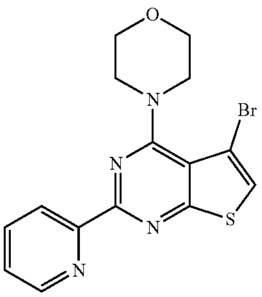 [SMILES: Brc1csc2nc(-c3ccccn3)nc(N3CCOCC3)c12] | B | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 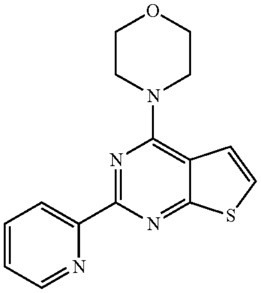 [SMILES: c1ccc(-c2nc(N3CCOCC3)c3ccsc3n2)nc1] | C | | |
| 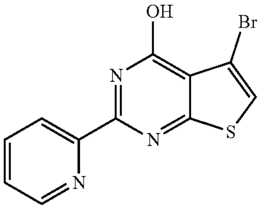 [SMILES: Oc1nc(-c2ccccn2)nc2scc(Br)c12] | D | | G |
| 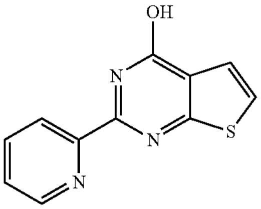 [SMILES: Oc1nc(-c2ccccn2)nc2sccc12] | D | | |
| 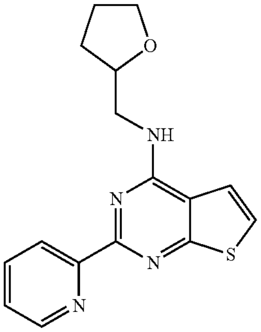 [SMILES: c1ccc(-c2nc(NCC3CCCO3)c3ccsc3n2)nc1] | D | | |
| 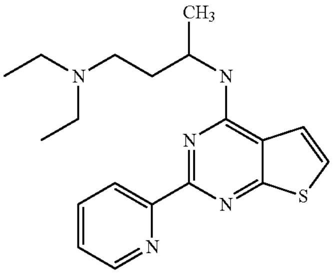 [SMILES: CCN(CC)CCC(C)Nc1nc(-c2ccccn2)nc2sccc12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 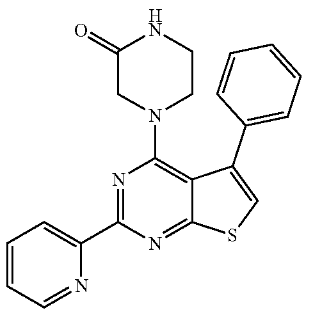 [SMILES: O=C1CN(c2nc(-c3ccccn3)nc3scc(-c4ccccc4)c23)CCN1] | A | | |
| 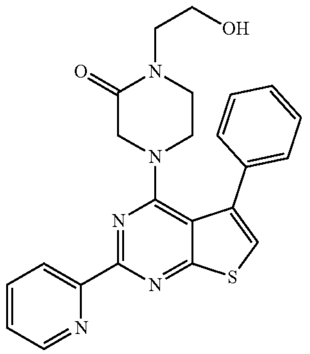 [SMILES: O=C1CN(c2nc(-c3ccccn3)nc3scc(-c4ccccc4)c23)CCN1CCO] | C | | |
| 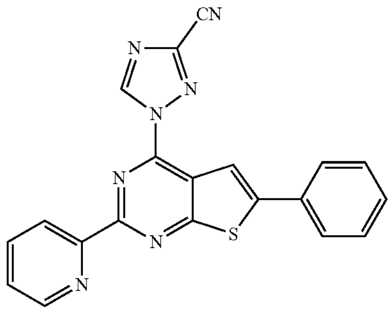 [SMILES: N#Cc1ncn(-c2nc(-c3ccccn3)nc3sc(-c4ccccc4)cc23)n1] | D | | F |
| 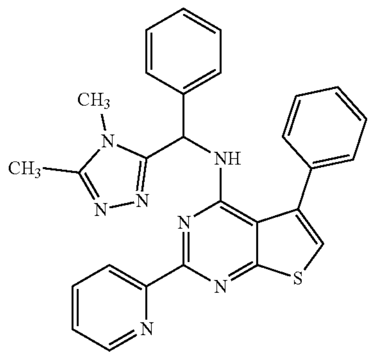 [SMILES: Cc1nnc(C(Nc2nc(-c3ccccn3)nc3scc(-c4ccccc4)c23)c2ccccc2)n1C] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 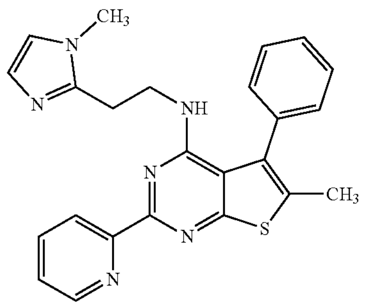 [SMILES: Cc1sc2nc(-c3ccccn3)nc(NCCc3nccn3C)c2c1-c1ccccc1] | D | | |
| 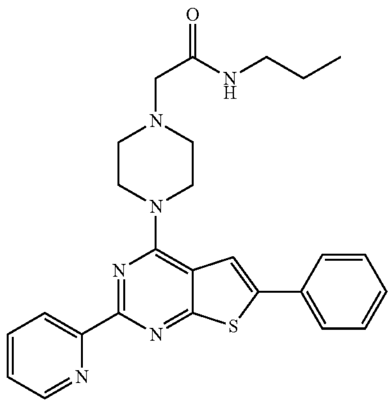 [SMILES: CCCNC(=O)CN1CCN(c2nc(-c3ccccn3)nc3sc(-c4ccccc4)cc23)CC1] | D | | |
| 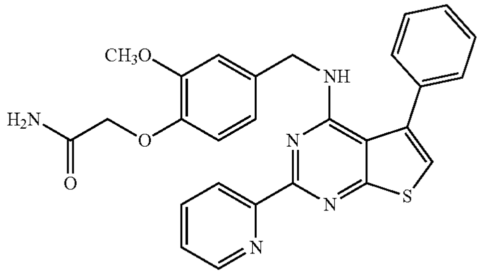 | D | | |
| 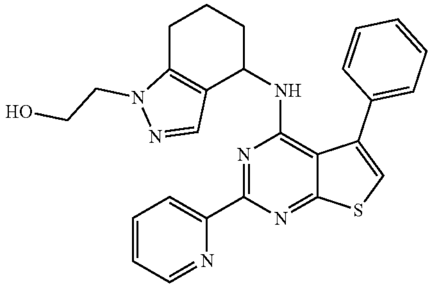 [SMILES: OCCn1ncc2c1CCCC2Nc1nc(-c2ccccn2)nc2scc(-c3ccccc3)c12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 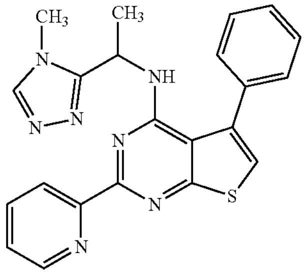 [SMILES: CC(Nc1nc(-c2ccccn2)nc2scc(-c3ccccc3)c12)c1nncn1C] | D | | |
| 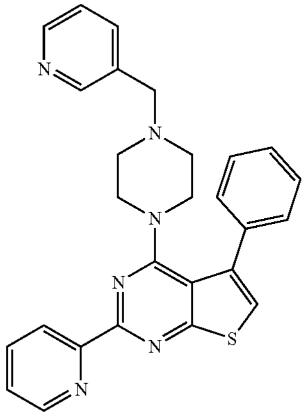 [SMILES: c1ccc(-c2csc3nc(-c4ccccn4)nc(N4CCN(Cc5cccnc5)CC4)c23)cc1] | D | | |
| 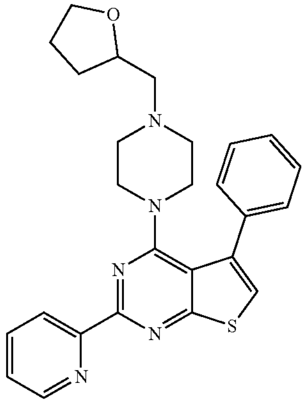 [SMILES: c1ccc(-c2csc3nc(-c4ccccn4)nc(N4CCN(CC5CCCO5)CC4)c23)cc1] | D | | |
| 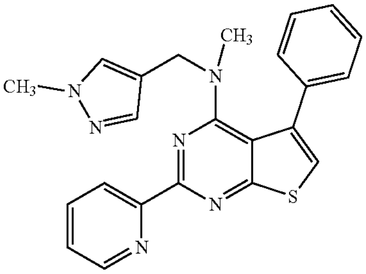 [SMILES: CN(Cc1cnn(C)c1)c1nc(-c2ccccn2)nc2scc(-c3ccccc3)c12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 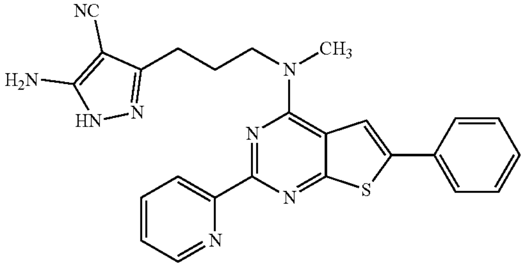 [SMILES: CN(CCCc1n[nH]c(N)c1C#N)c1nc(-c2ccccn2)nc2sc(-c3ccccc3)cc12] | D | | |
| 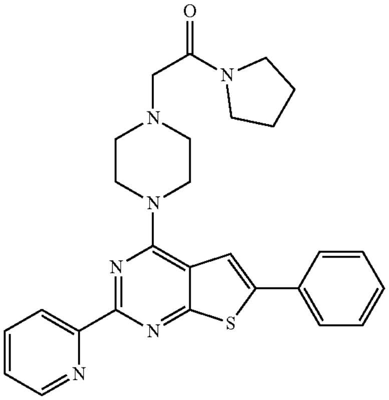 [SMILES: O=C(CN1CCN(c2nc(-c3ccccn3)nc3sc(-c4ccccc4)cc23)CC1)N1CCCC1] | D | | E |
| 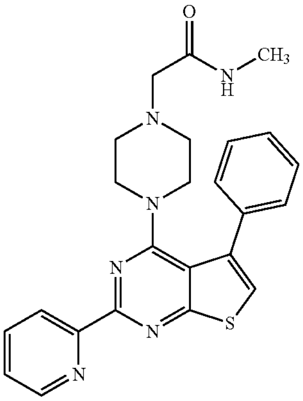 [SMILES: CNC(=O)CN1CCN(c2nc(-c3ccccn3)nc3scc(-c4ccccc4)c23)CC1] | A | | |
| 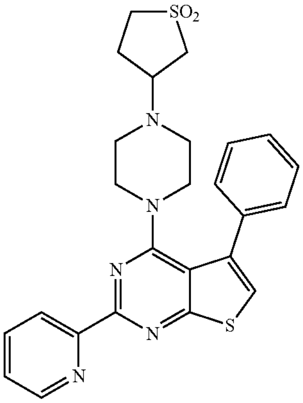 [SMILES: O=S1(=O)CCC(N2CCN(c3nc(-c4ccccn4)nc4scc(-c5ccccc5)c34)CC2)C1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 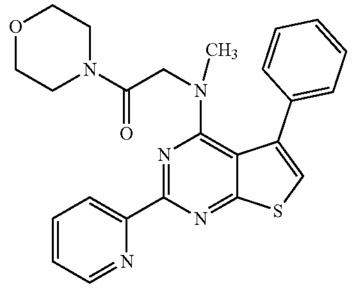 [SMILES: CN(CC(=O)N1CCOCC1)c1nc(-c2ccccn2)nc2scc(-c3ccccc3)c12] | C | | |
| 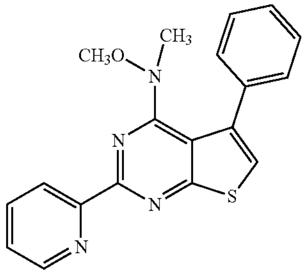 | D | | |
| 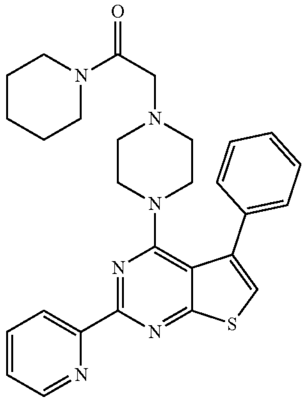 [SMILES: O=C(CN1CCN(c2nc(-c3ccccn3)nc3scc(-c4ccccc4)c23)CC1)N1CCCCC1] | D | | |
| 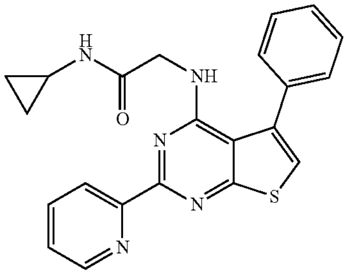 [SMILES: O=C(CNc1nc(-c2ccccn2)nc2scc(-c3ccccc3)c12)NC1CC1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 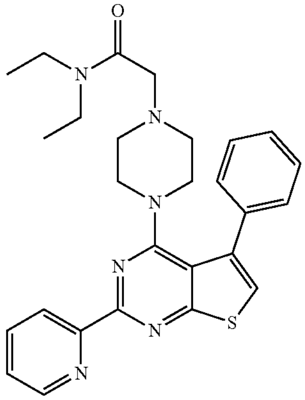 [SMILES: CCN(CC)C(=O)CN1CCN(c2nc(-c3ccccn3)nc3scc(-c4ccccc4)c23)CC1] | D | | |
| 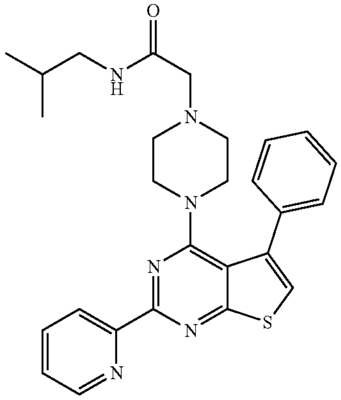 [SMILES: CC(C)CNC(=O)CN1CCN(c2nc(-c3ccccn3)nc3scc(-c4ccccc4)c23)CC1] | D | | |
| 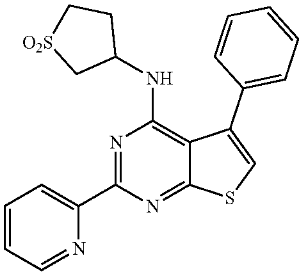 [SMILES: O=S1(=O)CCC(Nc2nc(-c3ccccn3)nc3scc(-c4ccccc4)c23)C1] | D | | |
| 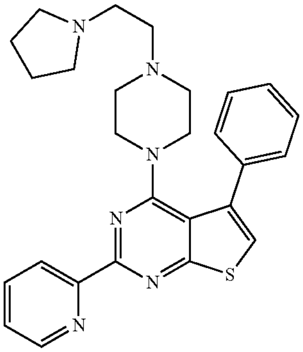 [SMILES: c1ccc(-c2csc3nc(-c4ccccn4)nc(N4CCN(CCN5CCCC5)CC4)c23)cc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 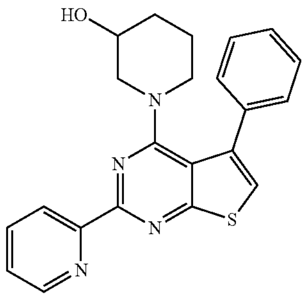 [SMILES: OC1CCCN(c2nc(-c3ccccn3)nc3scc(-c4ccccc4)c23)C1] | D | | |
| 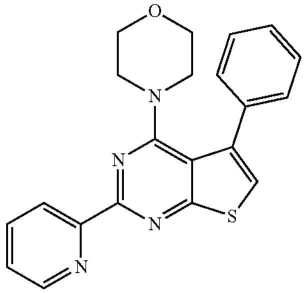 [SMILES: c1ccc(-c2csc3nc(-c4ccccn4)nc(N4CCOCC4)c23)cc1] | D | | |
| 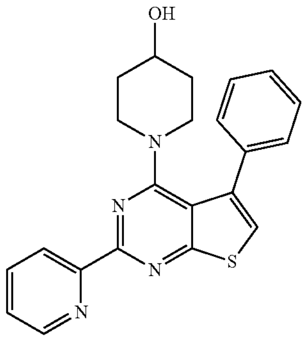 [SMILES: OC1CCN(c2nc(-c3ccccn3)nc3scc(-c4ccccc4)c23)CC1] | D | | |
| 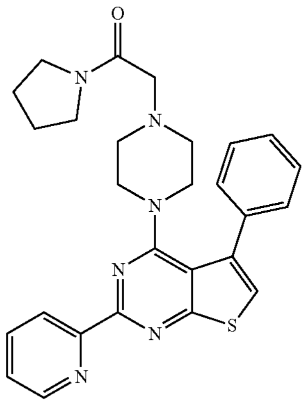 [SMILES: O=C(CN1CCN(c2nc(-c3ccccn3)nc3scc(-c4ccccc4)c23)CC1)N1CCCC1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 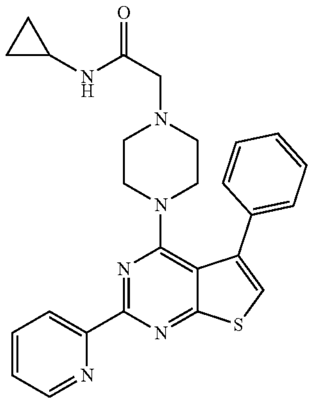 [SMILES: O=C(CN1CCN(c2nc(-c3ccccn3)nc3scc(-c4ccccc4)c23)CC1)NC1CC1] | D | | |
| 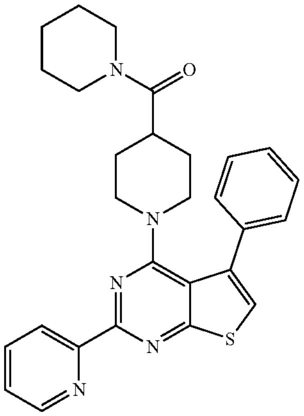 [SMILES: O=C(C1CCN(c2nc(-c3ccccn3)nc3scc(-c4ccccc4)c23)CC1)N1CCCCC1] | D | | |
| 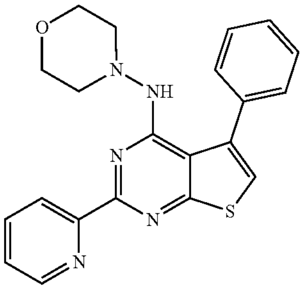 [SMILES: c1ccc(-c2csc3nc(-c4ccccn4)nc(NN4CCOCC4)c23)cc1] | D | | |
| 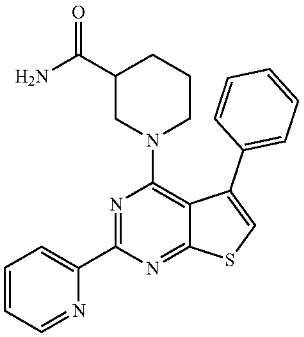 [SMILES: NC(=O)C1CCCN(c2nc(-c3ccccn3)nc3scc(-c4ccccc4)c23)C1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 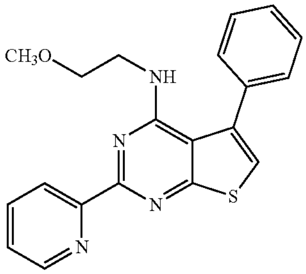 | D | | |
| 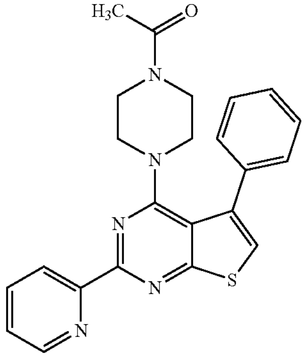 [SMILES: CC(=O)N1CCN(c2nc(-c3ccccn3)nc3scc(-c4ccccc4)c23)CC1] | D | | |
| 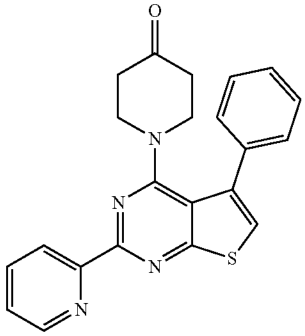 [SMILES: O=C1CCN(c2nc(-c3ccccn3)nc3scc(-c4ccccc4)c23)CC1] | D | | |
| 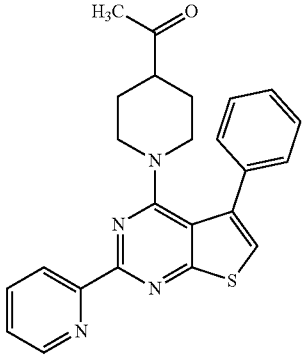 [SMILES: CC(=O)C1CCN(c2nc(-c3ccccn3)nc3scc(-c4ccccc4)c23)CC1] | D | | |
| 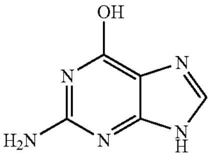 [SMILES: Nc1nc(O)c2nc[nH]c2n1] | A | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 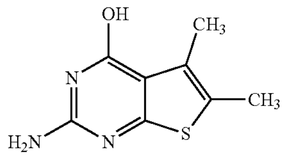 | A | | |
| 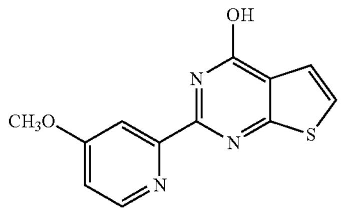 | D | | G |
| 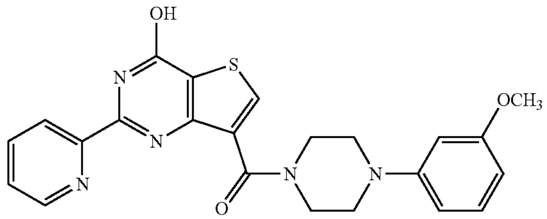 [SMILES: COc1cccc(N2CCN(C(=O)c3csc4c(O)nc(-c5ccccn5)nc34)CC2)c1] | D | | G |
| 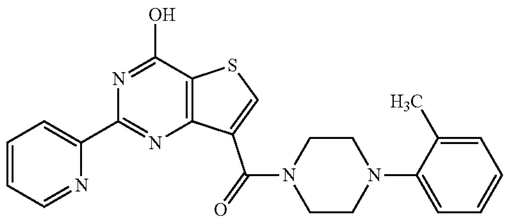 | D | | |
| 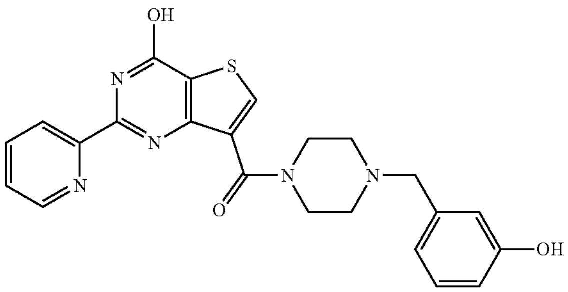 [SMILES: O=C(c1csc2c(O)nc(-c3ccccn3)nc12)N1CCN(Cc2cccc(O)c2)CC1] | D | | |
| 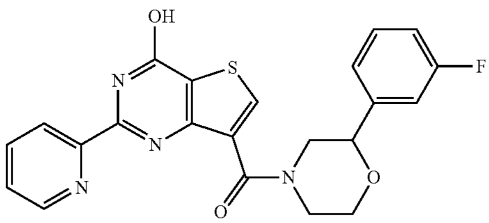 [SMILES: O=C(c1csc2c(O)nc(-c3ccccn3)nc12)N1CCOC(c2cccc(F)c2)C1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 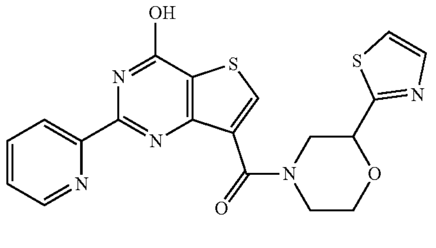 [SMILES: O=C(c1csc2c(O)nc(-c3ccccn3)nc12)N1CCOC(c2nccs2)C1] | D | | |
| 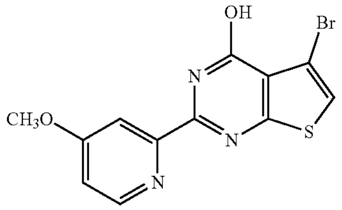 | D | | G |
| 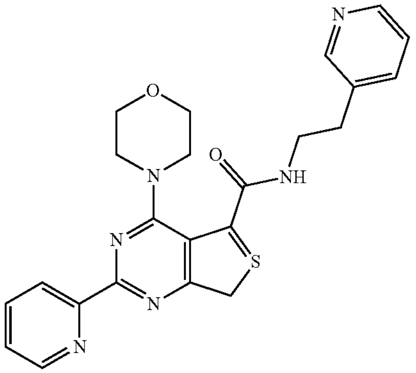 | D | | |
| 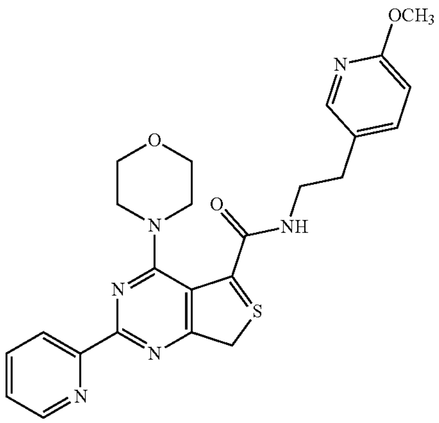 | C | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 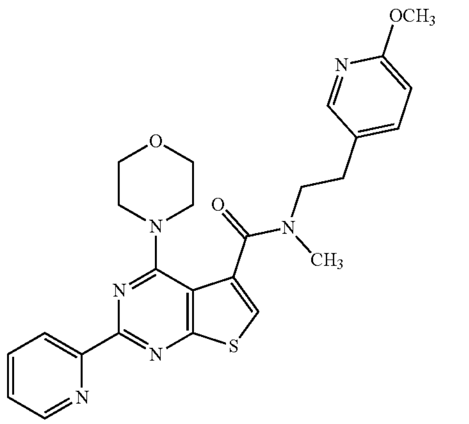 [SMILES: COc1ccc(CCN(C)C(=O)c2csc3nc(-c4ccccn4)nc(N4CCOCC4)c23)cn1] | D | | |
| 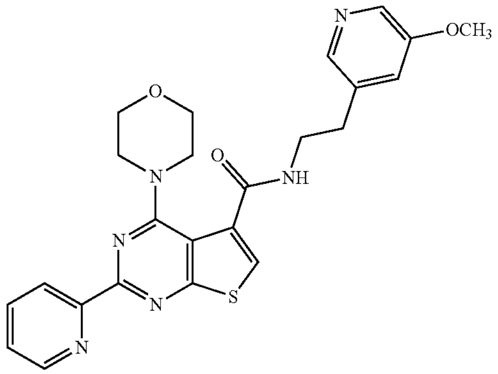 [SMILES: COc1cncc(CCNC(=O)c2csc3nc(-c4ccccn4)nc(N4CCOCC4)c23)c1] | C | | |
| 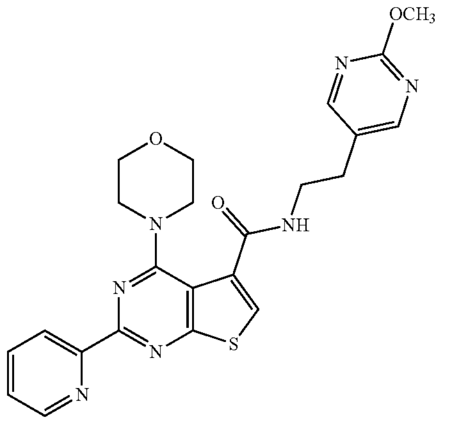 [SMILES: COc1ncc(CCNC(=O)c2csc3nc(-c4ccccn4)nc(N4CCOCC4)c23)cn1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 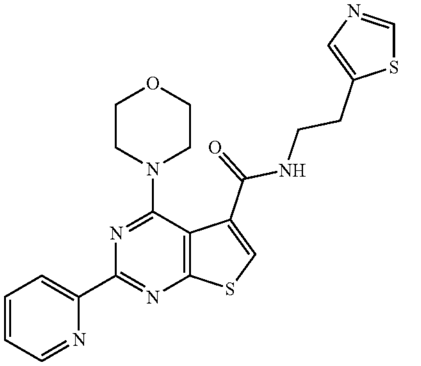 [SMILES: O=C(NCCc1cncs1)c1csc2nc(-c3ccccn3)nc(N3CCOCC3)c12] | D | | |
| 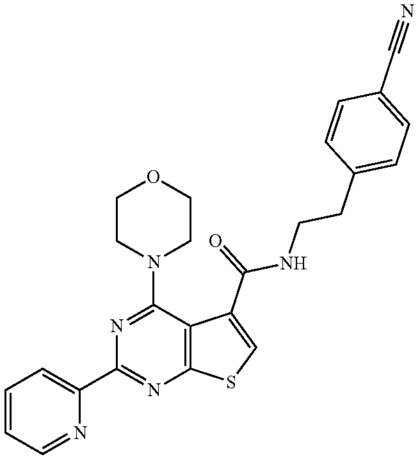 [SMILES: N#Cc1ccc(CCNC(=O)c2csc3nc(-c4ccccn4)nc(N4CCOCC4)c23)cc1] | B | | |
| 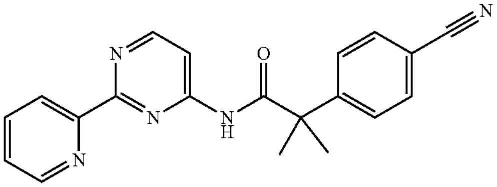 [SMILES: CC(C)(C(=O)Nc1ccnc(-c2ccccn2)n1)c1ccc(C#N)cc1] | D | | |
| 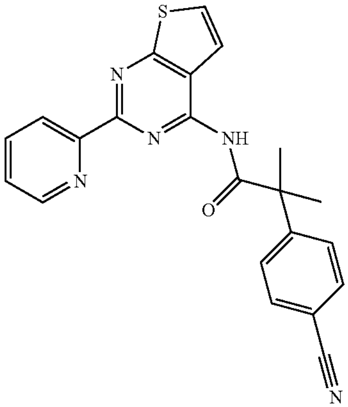 [SMILES: CC(C)(C(=O)Nc1nc(-c2ccccn2)nc2sccc12)c1ccc(C#N)cc1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 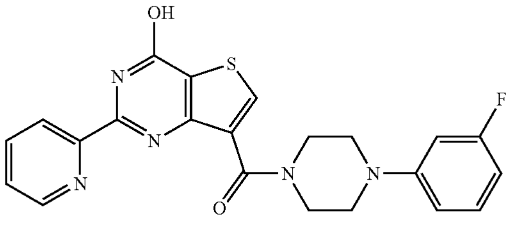 [SMILES: O=C(c1csc2c(O)nc(-c3ccccn3)nc12)N1CCN(c2cccc(F)c2)CC1] | D | | |
| 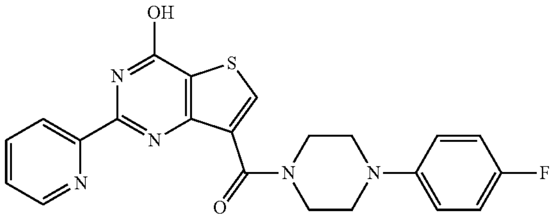 [SMILES: O=C(c1csc2c(O)nc(-c3ccccn3)nc12)N1CCN(c2ccc(F)cc2)CC1] | D | | |
| 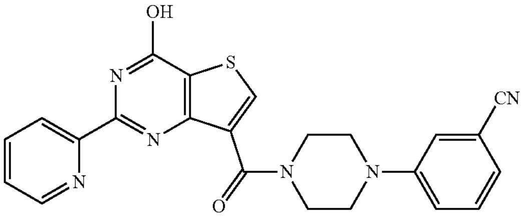 | D | | |
| 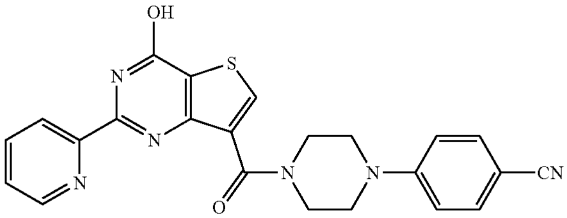 [SMILES: N#Cc1ccc(N2CCN(C(=O)c3csc4c(O)nc(-c5ccccn5)nc34)CC2)cc1] | B | | |
| 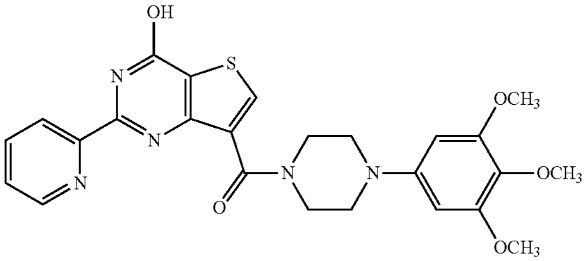 [SMILES: COc1cc(N2CCN(C(=O)c3csc4c(O)nc(-c5ccccn5)nc34)CC2)cc(OC)c1OC] | C | | |
| 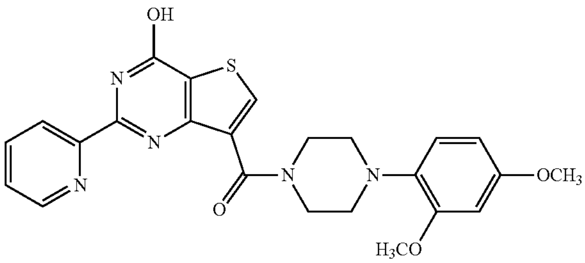 [SMILES: COc1ccc(N2CCN(C(=O)c3csc4c(O)nc(-c5ccccn5)nc34)CC2)c(OC)c1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 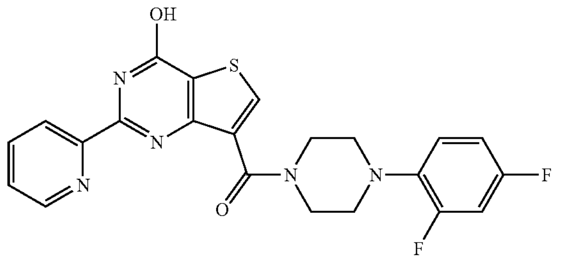 [SMILES: O=C(c1csc2c(O)nc(-c3ccccn3)nc12)N1CCN(c2ccc(F)cc2F)CC1] | D | | |
| 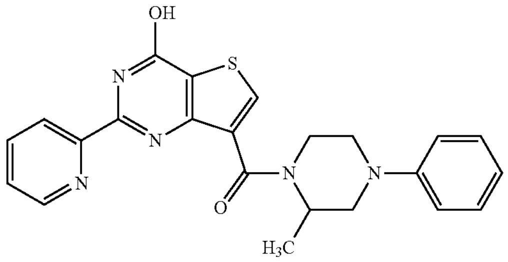 [SMILES: CC1CN(c2ccccc2)CCN1C(=O)c1csc2c(O)nc(-c3ccccn3)nc12] | D | | F |
| 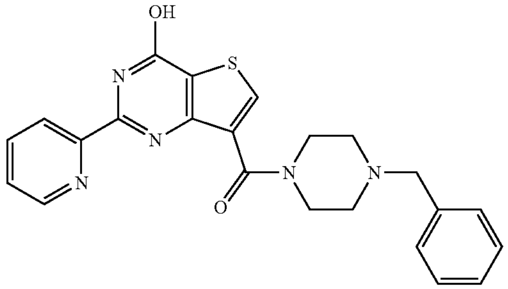 [SMILES: O=C(c1csc2c(O)nc(-c3ccccn3)nc12)N1CCN(Cc2ccccc2)CC1] | D | | |
| 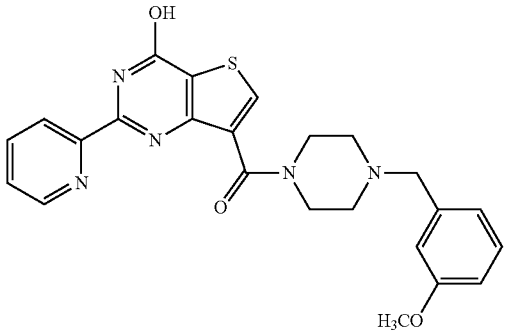 [SMILES: COc1cccc(CN2CCN(C(=O)c3csc4c(O)nc(-c5ccccn5)nc34)CC2)c1] | D | | |
| 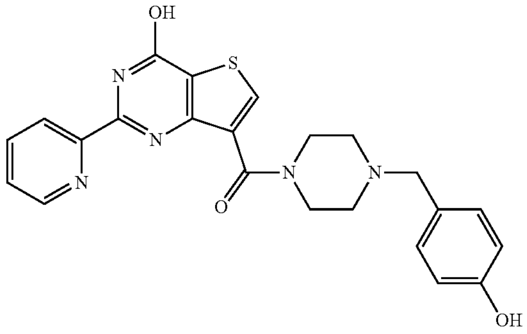 [SMILES: O=C(c1csc2c(O)nc(-c3ccccn3)nc12)N1CCN(Cc2ccc(O)cc2)CC1] | A | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 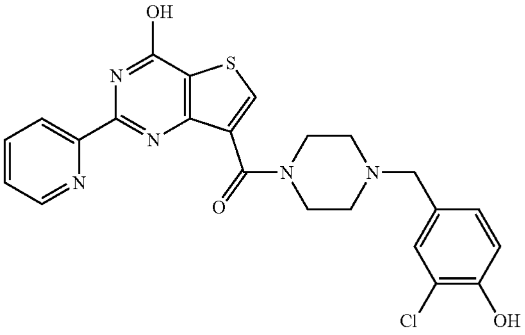 [SMILES: O=C(c1csc2c(O)nc(-c3ccccn3)nc12)N1CCN(Cc2ccc(O)c(Cl)c2)CC1] | D | | |
| 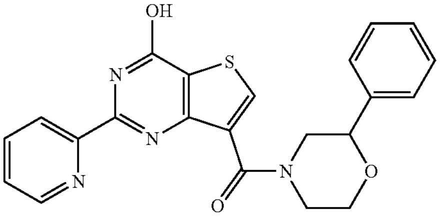 | D | | |
| 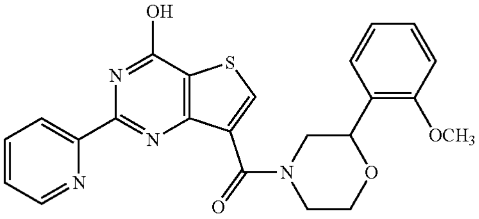 [SMILES: COc1ccccc1C1CN(C(=O)c2csc3c(O)nc(-c4ccccn4)nc23)CCO1] | D | | |
| 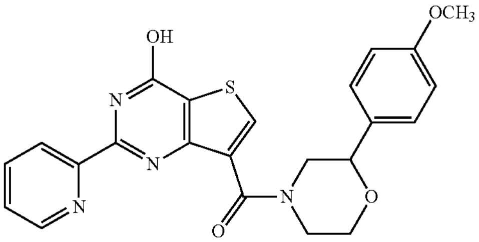 [SMILES: COc1ccc(C2CN(C(=O)c3csc4c(O)nc(-c5ccccn5)nc34)CCO2)cc1] | D | | |
| 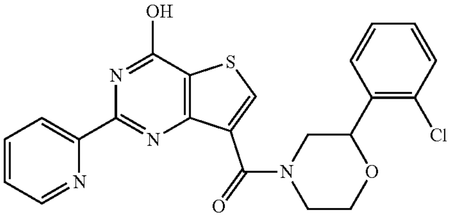 [SMILES: O=C(c1csc2c(O)nc(-c3ccccn3)nc12)N1CCOC(c2ccccc2Cl)C1] | D | | |
| 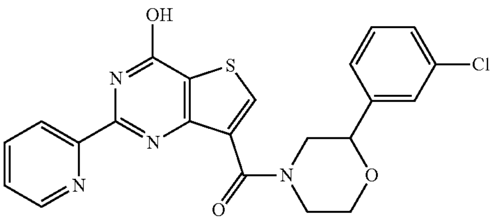 [SMILES: O=C(c1csc2c(O)nc(-c3ccccn3)nc12)N1CCOC(c2cccc(Cl)c2)C1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 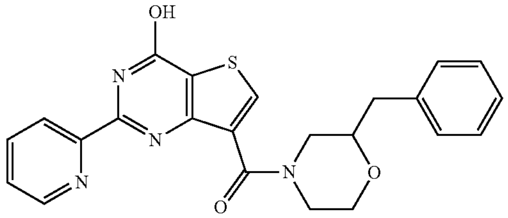 | D | | |
| 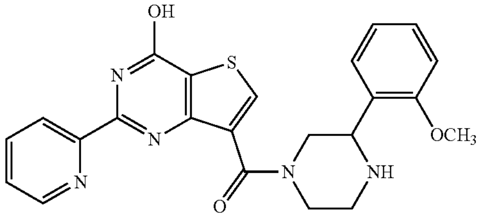 [SMILES: COc1ccccc1C1CN(C(=O)c2csc3c(O)nc(-c4ccccn4)nc23)CCN1] | D | | |
| 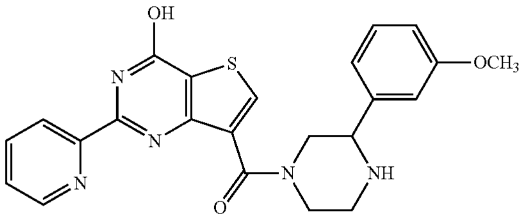 [SMILES: COc1cccc(C2CN(C(=O)c3csc4c(O)nc(-c5ccccn5)nc34)CCN2)c1] | D | | |
| 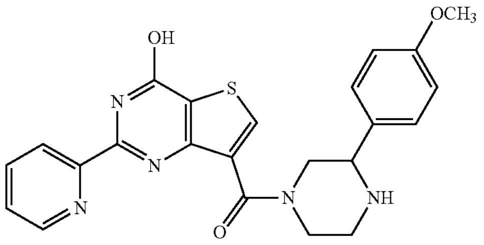 [SMILES: COc1ccc(C2CN(C(=O)c3csc4c(O)nc(-c5ccccn5)nc34)CCN2)cc1] | B | | |
| 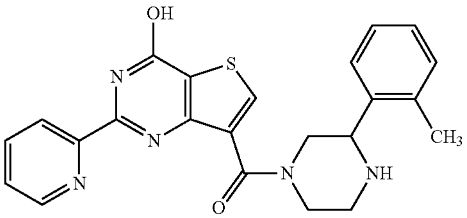 [SMILES: Cc1ccccc1C1CN(C(=O)c2csc3c(O)nc(-c4ccccn4)nc23)CCN1] | D | | |
| 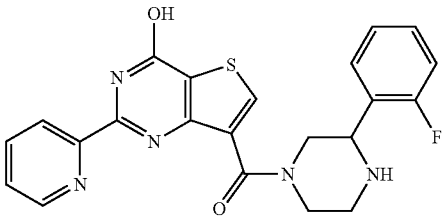 [SMILES: O=C(c1csc2c(O)nc(-c3ccccn3)nc12)N1CCNC(c2ccccc2F)C1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 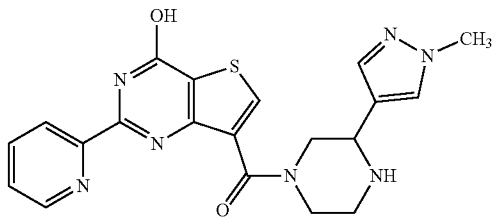 [SMILES: Cn1cc(C2CN(C(=O)c3csc4c(O)nc(-c5ccccn5)nc34)CCN2)cn1] | A | | |
| 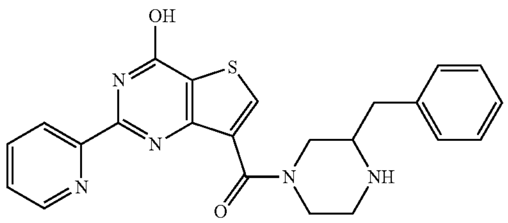 [SMILES: O=C(c1csc2c(O)nc(-c3ccccn3)nc12)N1CCNC(Cc2ccccc2)C1] | D | | |
| 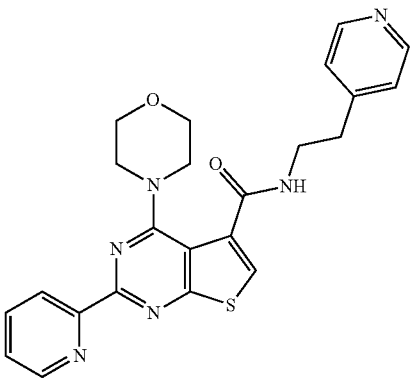 [SMILES: O=C(NCCc1ccncc1)c1csc2nc(-c3ccccn3)nc(N3CCOCC3)c12] | D | | |
| 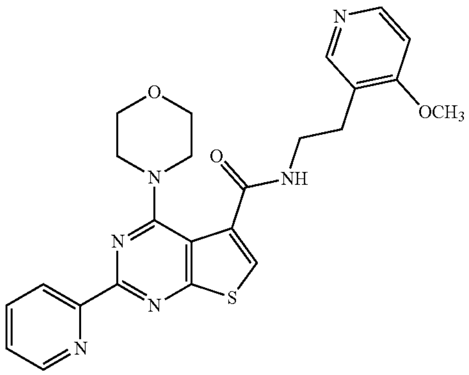 [SMILES: COc1ccncc1CCNC(=O)c1csc2nc(-c3ccccn3)nc(N3CCOCC3)c12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 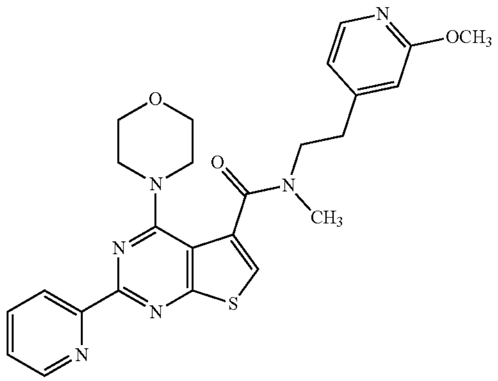 [SMILES: COc1cc(CCN(C)C(=O)c2csc3nc(-c4ccccn4)nc(N4CCOCC4)c23)ccn1] | D | | |
| 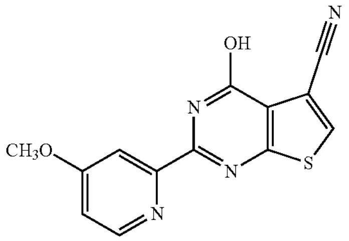 | D | | |
| 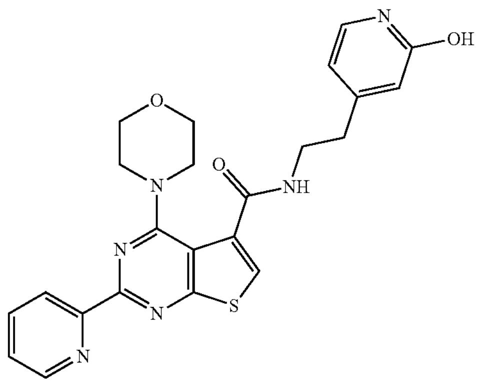 [SMILES: O=C(NCCc1ccnc(O)c1)c1csc2nc(-c3ccccn3)nc(N3CCOCC3)c12] | C | | |
| 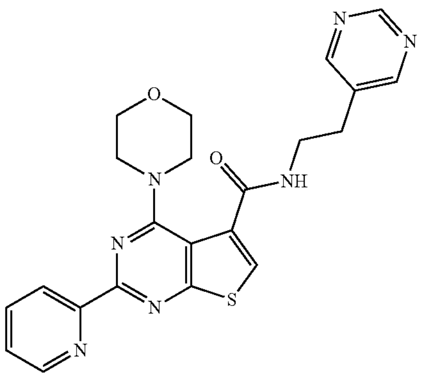 [SMILES: O=C(NCCc1cncnc1)c1csc2nc(-c3ccccn3)nc(N3CCOCC3)c12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 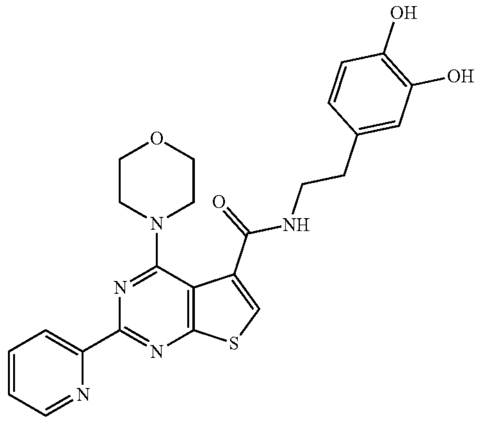 [SMILES: O=C(NCCc1ccc(O)c(O)c1)c1csc2nc(-c3ccccn3)nc(N3CCOCC3)c12] | D | | |
| 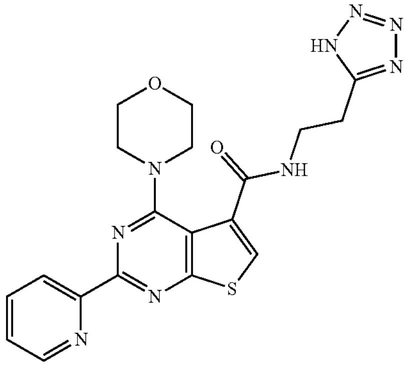 [SMILES: O=C(NCCc1nnn[nH]1)c1csc2nc(-c3ccccn3)nc(N3CCOCC3)c12] | C | | |
| 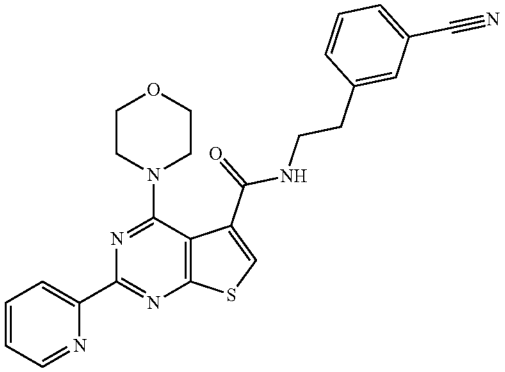 [SMILES: N#Cc1cccc(CCNC(=O)c2csc3nc(-c4ccccn4)nc(N4CCOCC4)c23)c1] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 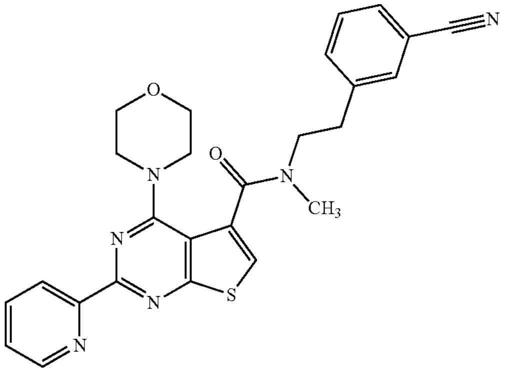 [SMILES: CN(CCc1cccc(C#N)c1)C(=O)c1csc2nc(-c3ccccn3)nc(N3CCOCC3)c12] | D | | |
| 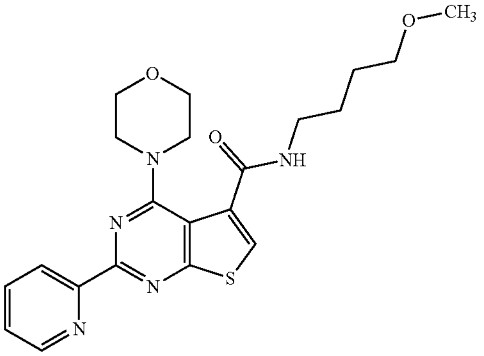 [SMILES: COCCCCNC(=O)c1csc2nc(-c3ccccn3)nc(N3CCOCC3)c12] | D | | |
| 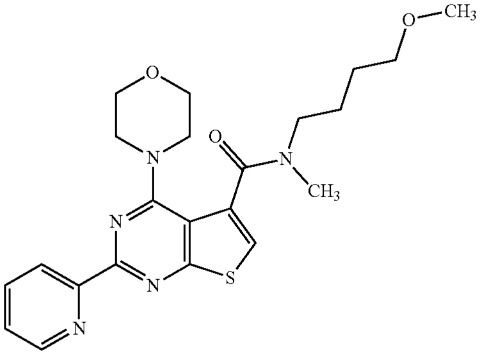 [SMILES: COCCCCN(C)C(=O)c1csc2nc(-c3ccccn3)nc(N3CCOCC3)c12] | D | | |
| 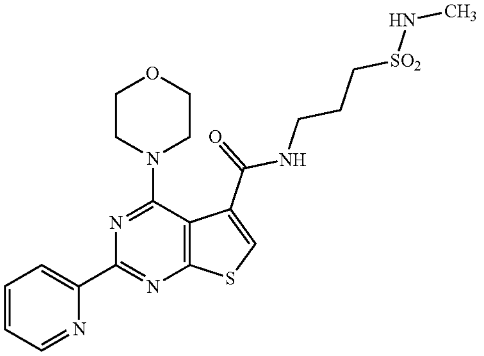 [SMILES: CNS(=O)(=O)CCCNC(=O)c1csc2nc(-c3ccccn3)nc(N3CCOCC3)c12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 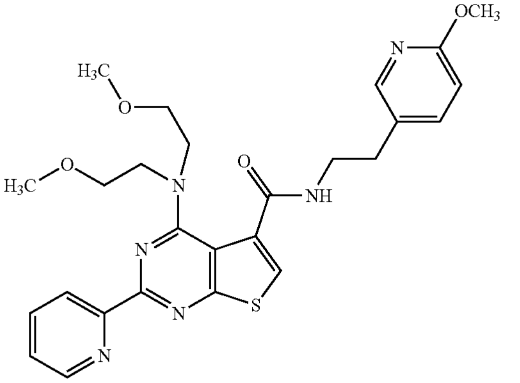 [SMILES: COCCN(CCOC)c1nc(-c2ccccn2)nc2scc(C(=O)NCCc3ccc(OC)nc3)c12] | D | | |
| 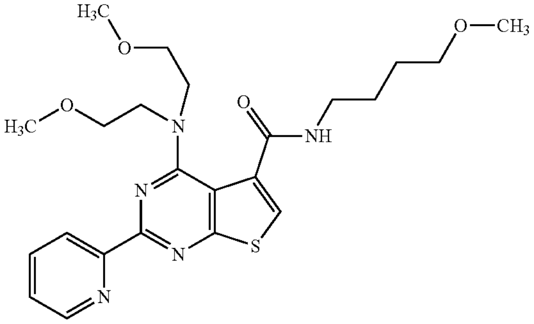 | D | | |
| 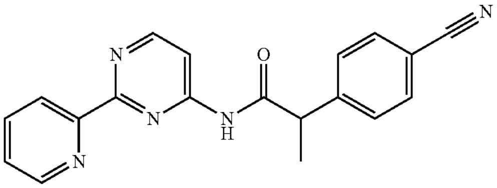 [SMILES: CC(C(=O)Nc1ccnc(-c2ccccn2)n1)c1ccc(C#N)cc1] | D | | |
| 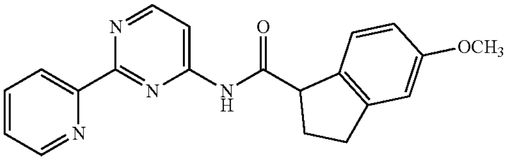 [SMILES: COc1ccc2c(c1)CCC2C(=O)Nc1ccnc(-c2ccccn2)n1] | D | | |
| 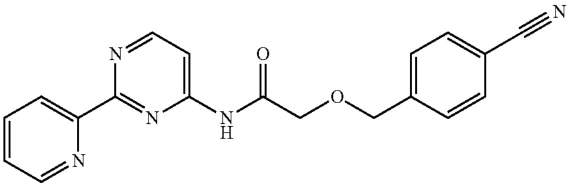 [SMILES: N#Cc1ccc(COCC(=O)Nc2ccnc(-c3ccccn3)n2)cc1] | D | | |
| 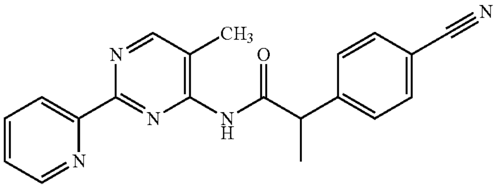 [SMILES: Cc1cnc(-c2ccccn2)nc1NC(=O)C(C)c1ccc(C#N)cc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 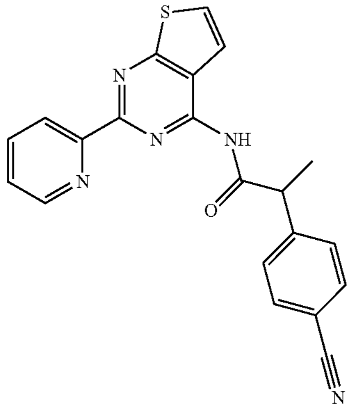 [SMILES: CC(C(=O)Nc1nc(-c2ccccn2)nc2sccc12)c1ccc(C#N)cc1] | D | | |
| 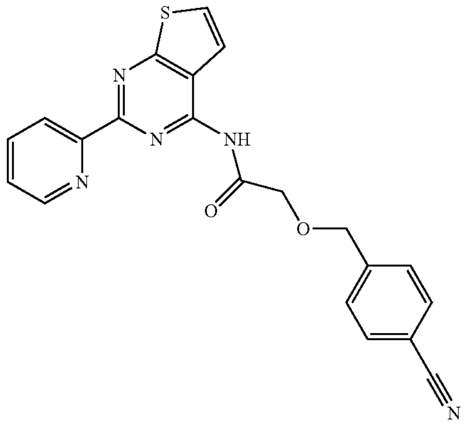 [SMILES: N#Cc1ccc(COCC(=O)Nc2nc(-c3ccccn3)nc3sccc23)cc1] | D | | |
| 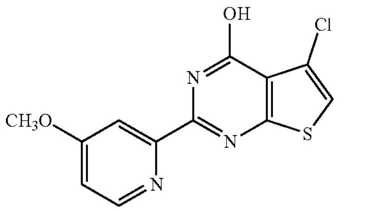 | D | | |
| 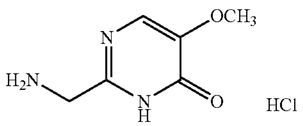 [SMILES: COc1cnc(CN)[nH]c1=O ; Cl] | C | | |
| 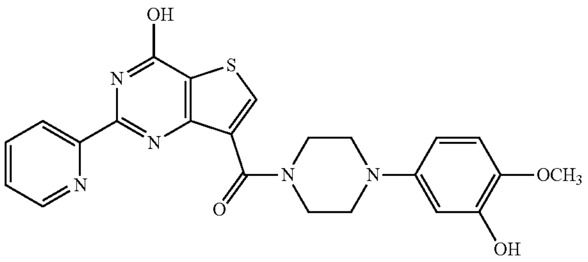 [SMILES: COc1ccc(N2CCN(C(=O)c3csc4c(O)nc(-c5ccccn5)nc34)CC2)cc1O] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 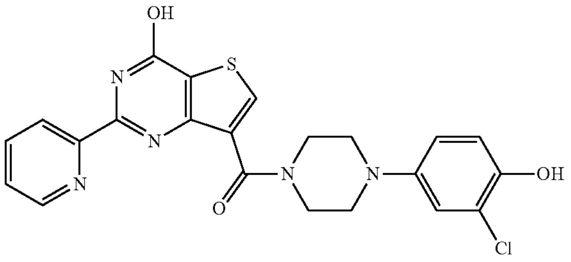 [SMILES: O=C(c1csc2c(O)nc(-c3ccccn3)nc12)N1CCN(c2ccc(O)c(Cl)c2)CC1] | D | | |
| 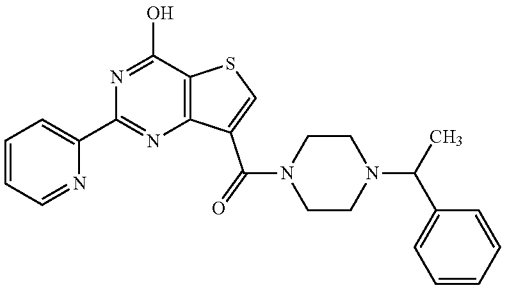 [SMILES: CC(c1ccccc1)N1CCN(C(=O)c2csc3c(O)nc(-c4ccccn4)nc23)CC1] | D | | |
| 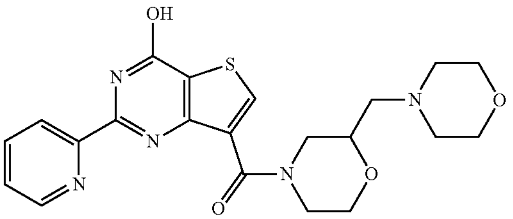 [SMILES: O=C(c1csc2c(O)nc(-c3ccccn3)nc12)N1CCOC(CN2CCOCC2)C1] | C | | |
| 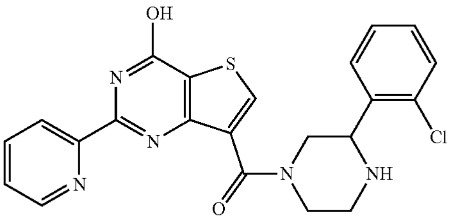 | D | | |
| 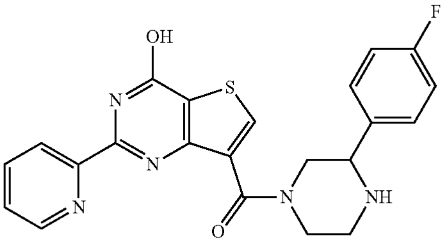 | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 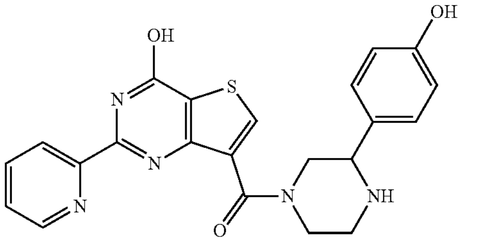 [SMILES: O=C(c1csc2c(O)nc(-c3ccccn3)nc12)N1CCNC(c2ccc(O)cc2)C1] | D | | |
| 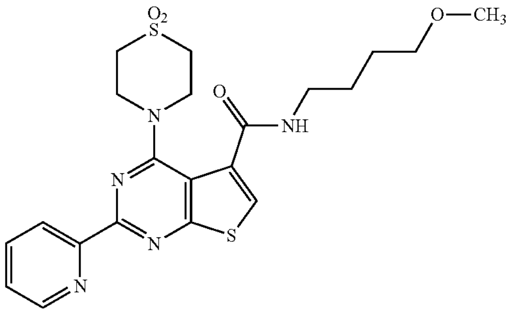 | A | | |
| 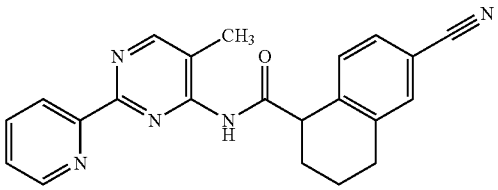 [SMILES: Cc1cnc(-c2ccccn2)nc1NC(=O)C1CCCc2cc(C#N)ccc21] | D | | |
| 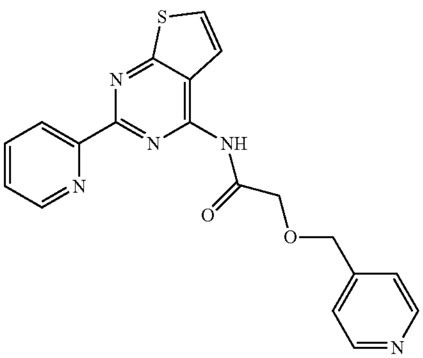 [SMILES: O=C(COCc1ccncc1)Nc1nc(-c2ccccn2)nc2sccc12] | D | | |
| 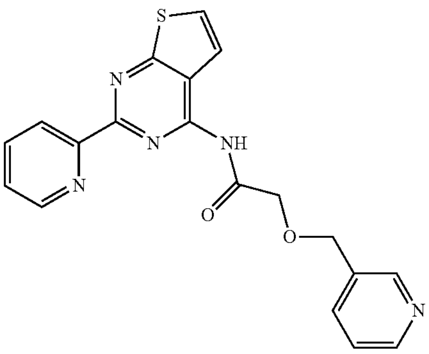 [SMILES: O=C(COCc1cccnc1)Nc1nc(-c2ccccn2)nc2sccc12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 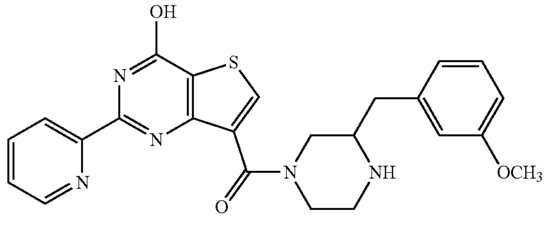 [SMILES: COc1cccc(CC2CN(C(=O)c3csc4c(O)nc(-c5ccccn5)nc34)CCN2)c1] | A | | |
| 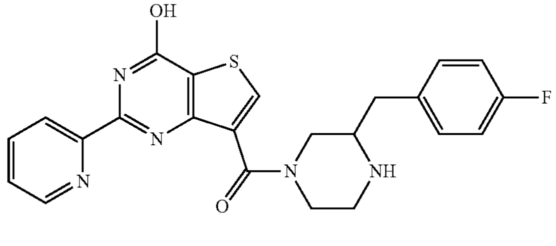 [SMILES: O=C(c1csc2c(O)nc(-c3ccccn3)nc12)N1CCNC(Cc2ccc(F)cc2)C1] | C | | |
| 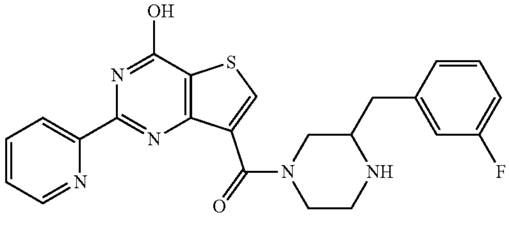 [SMILES: O=C(c1csc2c(O)nc(-c3ccccn3)nc12)N1CCNC(Cc2cccc(F)c2)C1] | B | | |
| 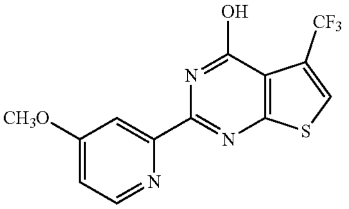 | D | | |
| 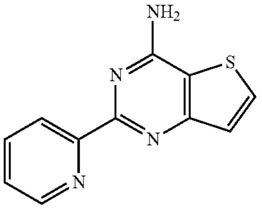 [SMILES: Nc1nc(-c2ccccn2)nc2ccsc12] | A | | |
| 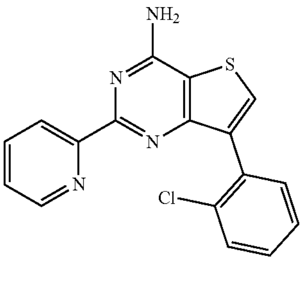 [SMILES: Nc1nc(-c2ccccn2)nc2c(-c3ccccc3Cl)csc12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 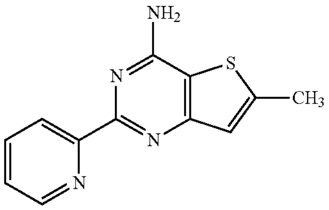 | D | | |
| 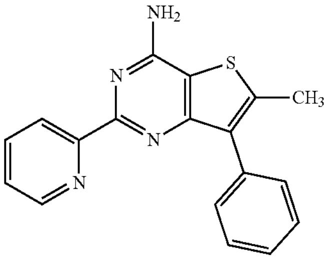 [SMILES: Cc1sc2c(N)nc(-c3ccccn3)nc2c1-c1ccccc1] | D | | |
| 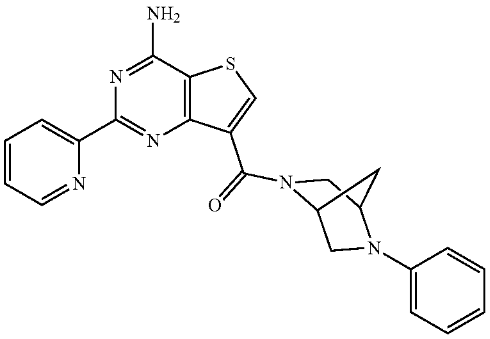 [SMILES: Nc1nc(-c2ccccn2)nc2c(C(=O)N3CC4CC3CN4c3ccccc3)csc12] | D | | |
| 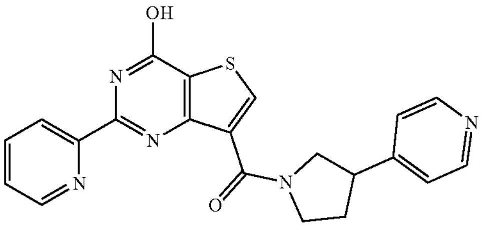 [SMILES: O=C(c1csc2c(O)nc(-c3ccccn3)nc12)N1CCC(c2ccncc2)C1] | D | | |
| 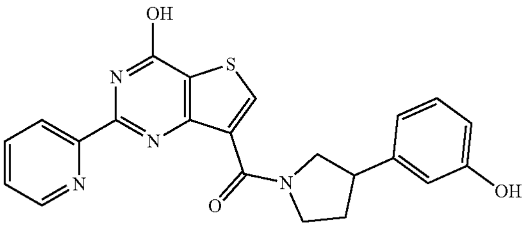 [SMILES: O=C(c1csc2c(O)nc(-c3ccccn3)nc12)N1CCC(c2cccc(O)c2)C1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 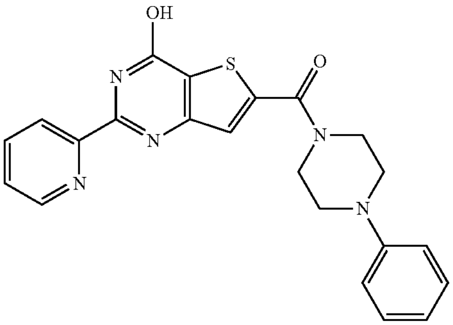 [SMILES: O=C(c1cc2nc(-c3ccccn3)nc(O)c2s1)N1CCN(c2ccccc2)CC1] | D | | |
| 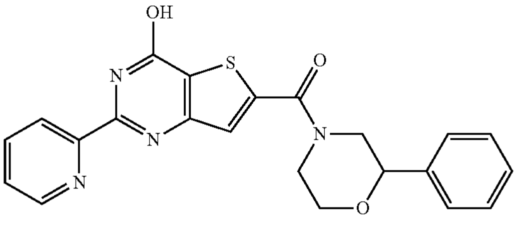 [SMILES: O=C(c1cc2nc(-c3ccccn3)nc(O)c2s1)N1CCOC(c2ccccc2)C1] | D | | |
| 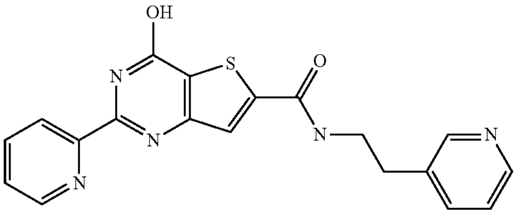 [SMILES: O=C(NCCc1cccnc1)c1cc2nc(-c3ccccn3)nc(O)c2s1] | D | | |
| 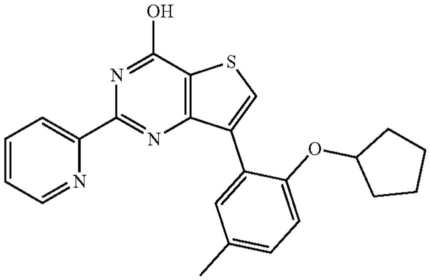 [SMILES: Cc1ccc(OC2CCCC2)c(-c2csc3c(O)nc(-c4ccccn4)nc23)c1] | D | | |
| 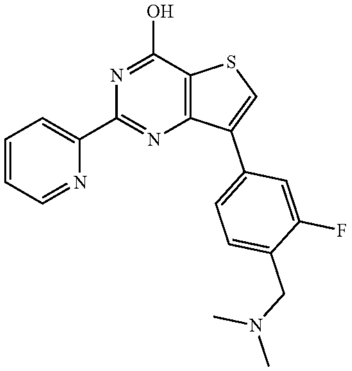 [SMILES: CN(C)Cc1ccc(-c2csc3c(O)nc(-c4ccccn4)nc23)cc1F] | D | | G |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 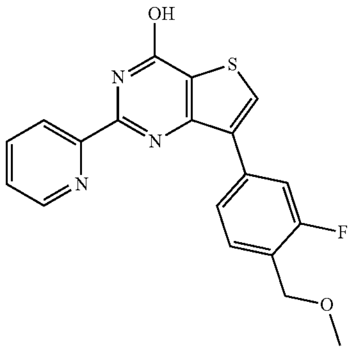 [SMILES: COCc1ccc(-c2csc3c(O)nc(-c4ccccn4)nc23)cc1F] | D | D* | H |
| 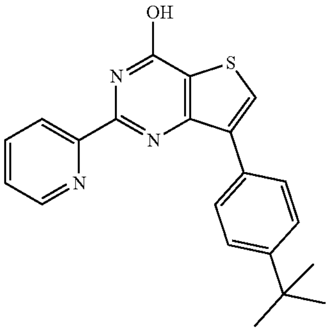 [SMILES: CC(C)(C)c1ccc(-c2csc3c(O)nc(-c4ccccn4)nc23)cc1] | D | | G |
| 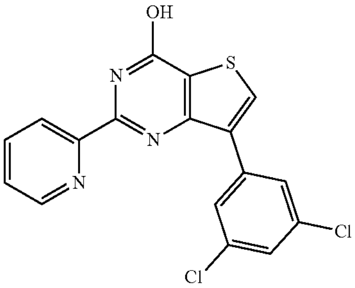 [SMILES: Oc1nc(-c2ccccn2)nc2c(-c3cc(Cl)cc(Cl)c3)csc12] | D | | G |
| 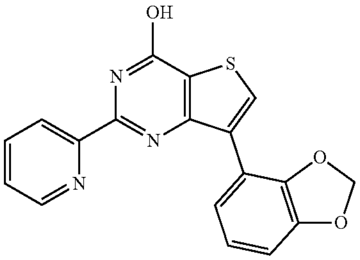 [SMILES: Oc1nc(-c2ccccn2)nc2c(-c3cccc4c3OCO4)csc12] | D | | G |
| 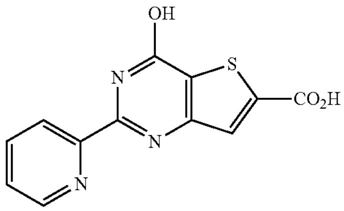 [SMILES: O=C(O)c1cc2nc(-c3ccccn3)nc(O)c2s1] | C | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 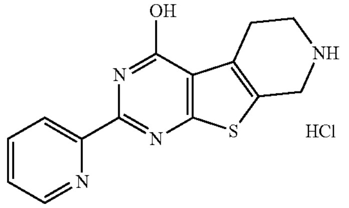 [SMILES: Oc1nc(-c2ccccn2)nc2sc3c(c12)CCNC3 ; Cl] | D | | |
| 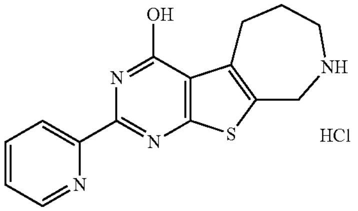 [SMILES: Oc1nc(-c2ccccn2)nc2sc3c(c12)CCCNC3 ; Cl] | B | | |
| 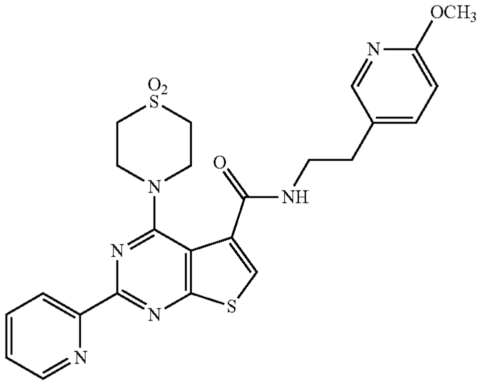 | C | | |
| 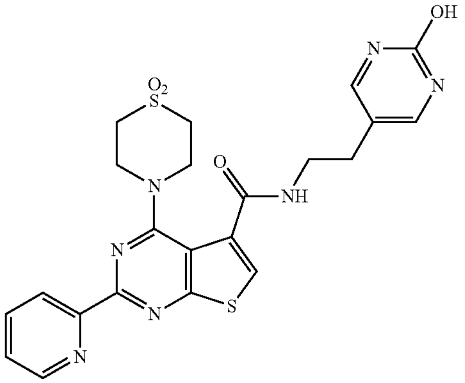 | A | | |
| 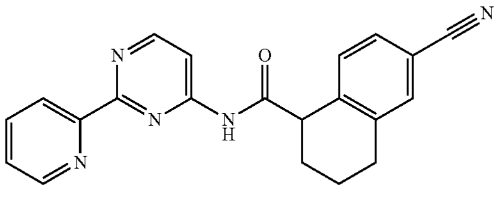 [SMILES: N#Cc1ccc2c(c1)CCCC2C(=O)Nc1ccnc(-c2ccccn2)n1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 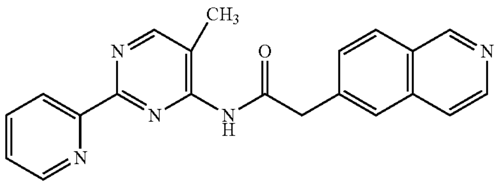 [SMILES: Cc1cnc(-c2ccccn2)nc1NC(=O)Cc1ccc2cnccc2c1] | D | | |
| 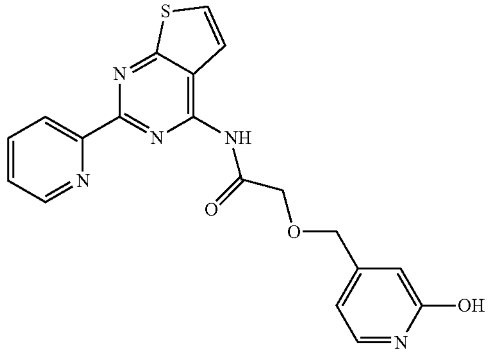 [SMILES: O=C(COCc1ccnc(O)c1)Nc1nc(-c2ccccn2)nc2sccc12] | C | | |
| 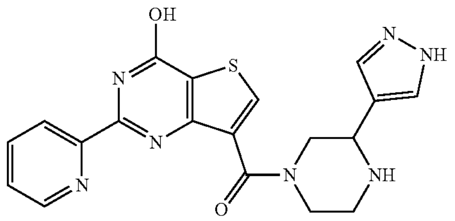 [SMILES: O=C(c1csc2c(O)nc(-c3ccccn3)nc12)N1CCNC(c2cn[nH]c2)C1] | A | | |
| 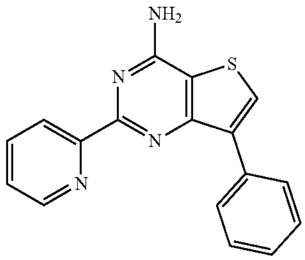 | D | | |
| 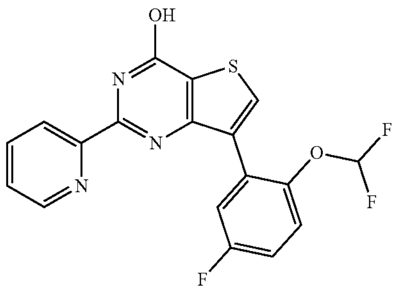 [SMILES: Oc1nc(-c2ccccn2)nc2c(-c3cc(F)ccc3OC(F)F)csc12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 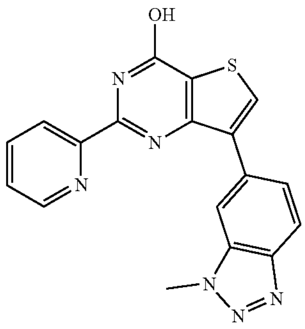 [SMILES: Cn1nnc2ccc(-c3csc4c(O)nc(-c5ccccn5)nc34)cc21] | D | | |
| 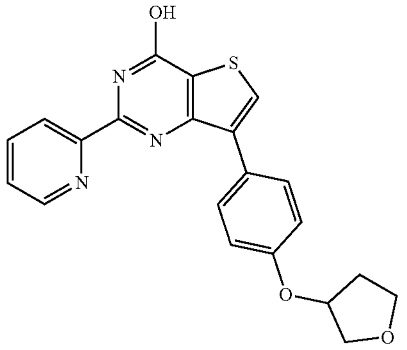 [SMILES: Oc1nc(-c2ccccn2)nc2c(-c3ccc(OC4CCOC4)cc3)csc12] | D | | |
| 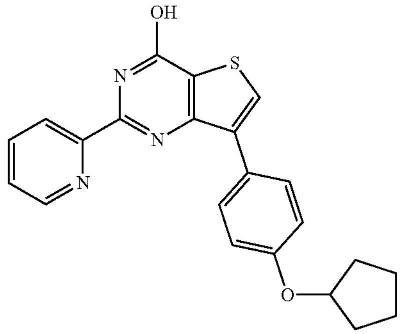 [SMILES: Oc1nc(-c2ccccn2)nc2c(-c3ccc(OC4CCCC4)cc3)csc12] | D | | |
| 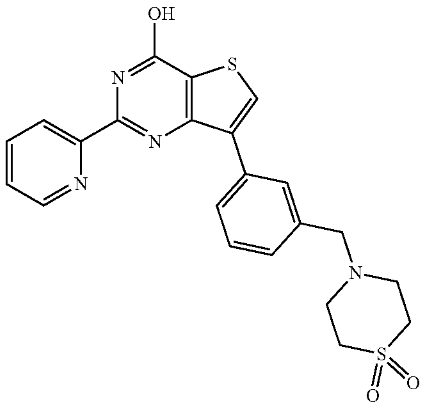 [SMILES: O=S1(=O)CCN(Cc2cccc(-c3csc4c(O)nc(-c5ccccn5)nc34)c2)CC1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 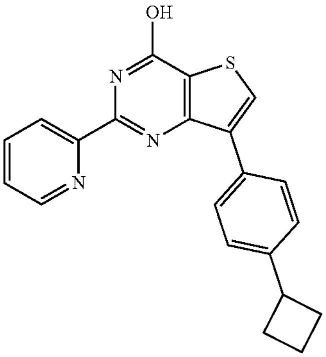 [SMILES: Oc1nc(-c2ccccn2)nc2c(-c3ccc(C4CCC4)cc3)csc12] | D | | |
| 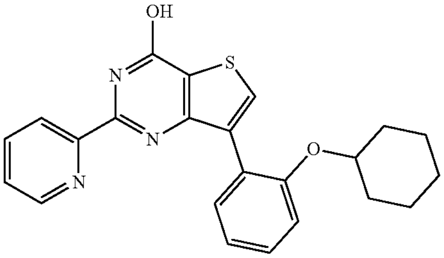 [SMILES: Oc1nc(-c2ccccn2)nc2c(-c3ccccc3OC3CCCCC3)csc12] | D | | |
| 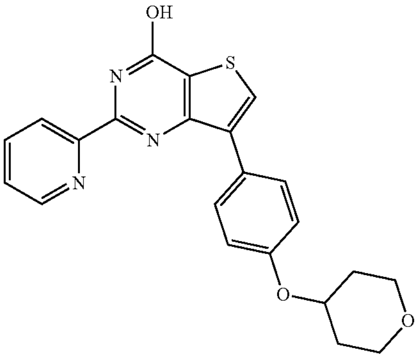 [SMILES: Oc1nc(-c2ccccn2)nc2c(-c3ccc(OC4CCOCC4)cc3)csc12] | D | | |
| 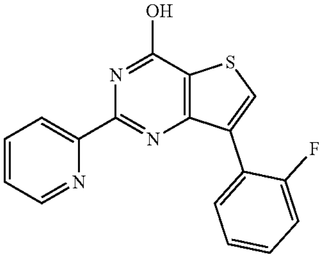 [SMILES: Oc1nc(-c2ccccn2)nc2c(-c3ccccc3F)csc12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 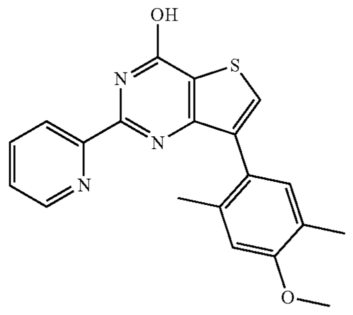 [SMILES: COc1cc(C)c(-c2csc3c(O)nc(-c4ccccn4)nc23)cc1C] | D | | |
| 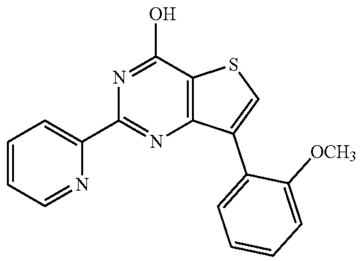 [SMILES: COc1ccccc1-c1csc2c(O)nc(-c3ccccn3)nc12] | D | | |
| 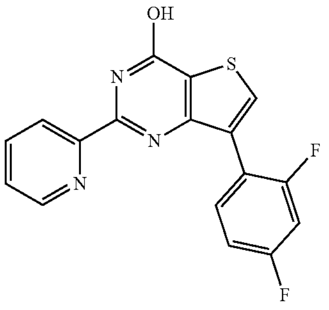 [SMILES: Oc1nc(-c2ccccn2)nc2c(-c3ccc(F)cc3F)csc12] | D | | |
| 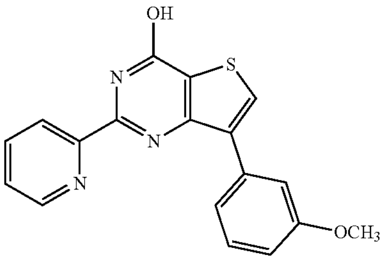 [SMILES: COc1cccc(-c2csc3c(O)nc(-c4ccccn4)nc23)c1] | D | | |
| 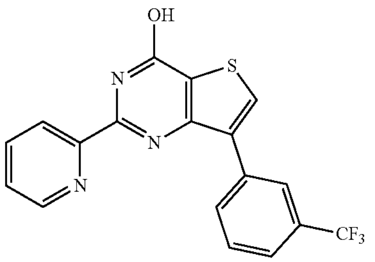 [SMILES: Oc1nc(-c2ccccn2)nc2c(-c3cccc(C(F)(F)F)c3)csc12] | D | D* | G |

TABLE 5-continued
| Compound | MIA-PACA2 | MIA-PACA2 (alternate conditions) | $IC_{50}$ (nM) |
|---|---|---|---|
| % Inhibition of cell proliferation at 30 μM or 10 μM in MIA-PACA2 pancreatic cancer cell lines, with select $IC_{50}$ values | | | |
| 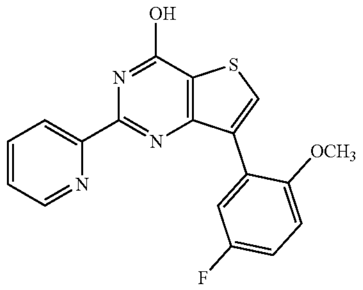 [SMILES: COc1ccc(F)cc1-c1csc2c(O)nc(-c3ccccn3)nc12] | D | | |
| 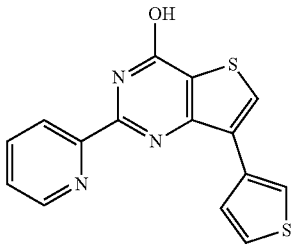 [SMILES: Oc1nc(-c2ccccn2)nc2c(-c3ccsc3)csc12] | D | | |
| 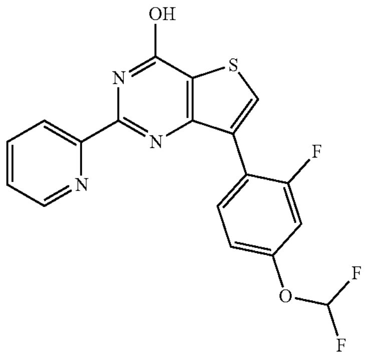 | D | | |
| 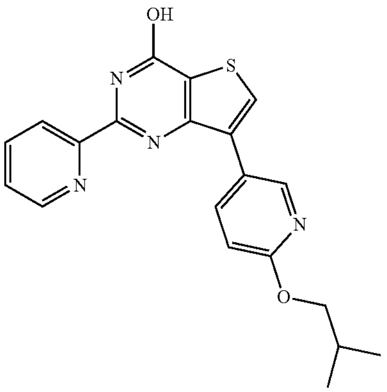 [SMILES: CC(C)COc1ccc(-c2csc3c(O)nc(-c4ccccn4)nc23)cn1] | D | D* | F |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 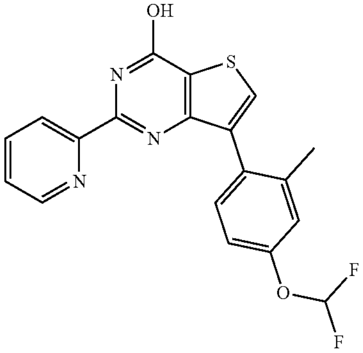 [SMILES: Cc1cc(OC(F)F)ccc1-c1csc2c(O)nc(-c3ccccn3)nc12] | D | | |
| 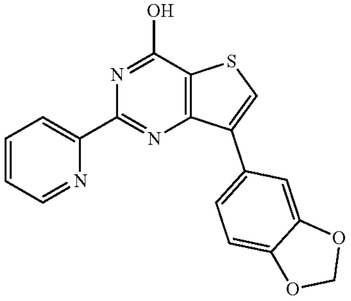 [SMILES: Oc1nc(-c2ccccn2)nc2c(-c3ccc4c(c3)OCO4)csc12] | D | | |
| 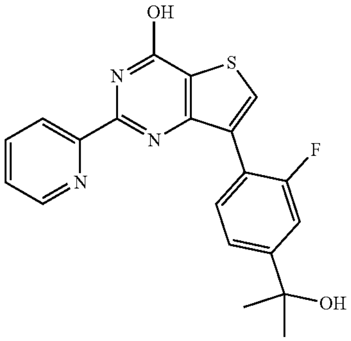 [SMILES: CC(C)(O)c1ccc(-c2csc3c(O)nc(-c4ccccn4)nc23)c(F)c1] | D | | |
| 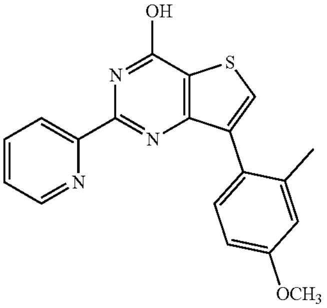 [SMILES: COc1ccc(-c2csc3c(O)nc(-c4ccccn4)nc23)c(C)c1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 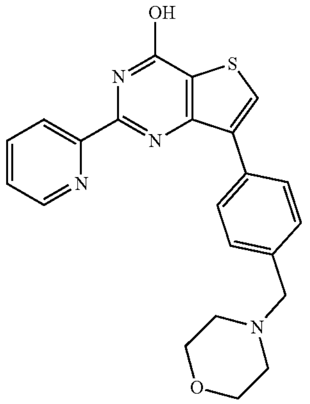 [SMILES: Oc1nc(-c2ccccn2)nc2c(-c3ccc(CN4CCOCC4)cc3)csc12] | D | | |
| 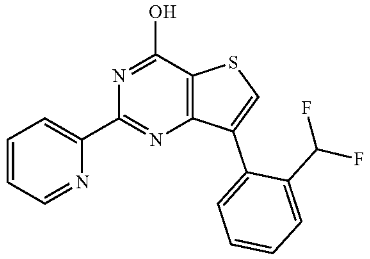 [SMILES: Oc1nc(-c2ccccn2)nc2c(-c3ccccc3C(F)F)csc12] | D | | |
| 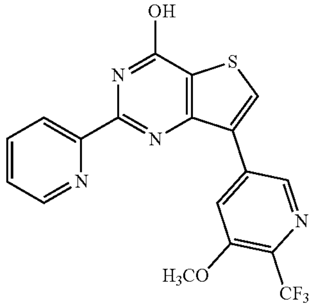 [SMILES: COc1cc(-c2csc3c(O)nc(-c4ccccn4)nc23)cnc1C(F)(F)F] | D | | |
| 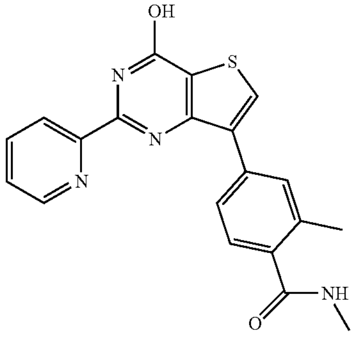 [SMILES: CNC(=O)c1ccc(-c2csc3c(O)nc(-c4ccccn4)nc23)cc1C] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 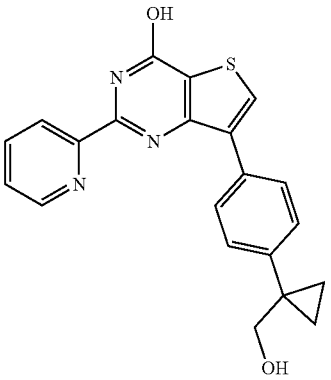 [SMILES: OCC1(c2ccc(-c3csc4c(O)nc(-c5ccccn5)nc34)cc2)CC1] | D | | |
| 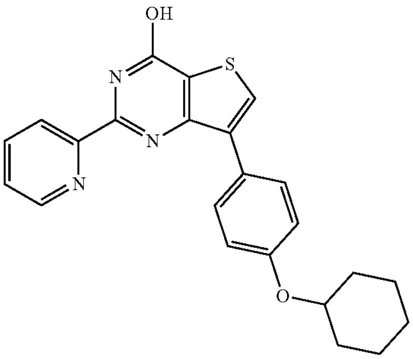 [SMILES: Oc1nc(-c2ccccn2)nc2c(-c3ccc(OC4CCCCC4)cc3)csc12] | D | | |
| 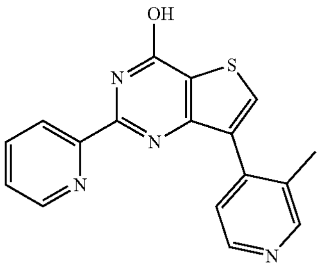 [SMILES: Cc1cnccc1-c1csc2c(O)nc(-c3ccccn3)nc12] | D | | |
| 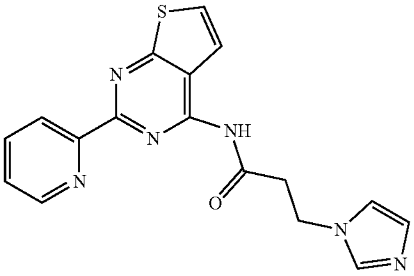 [SMILES: O=C(CCn1ccnc1)Nc1nc(-c2ccccn2)nc2sccc12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 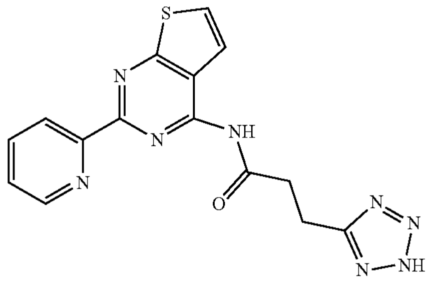 [SMILES: O=C(CCc1nn[nH]n1)Nc1nc(-c2ccccn2)nc2sccc12] | C | | |
| 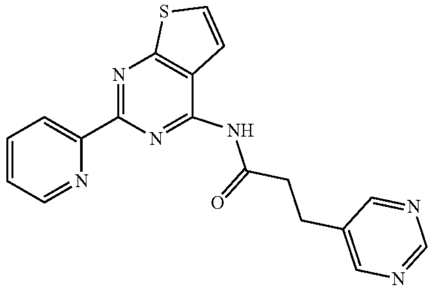 [SMILES: O=C(CCc1cncnc1)Nc1nc(-c2ccccn2)nc2sccc12] | D | | |
| 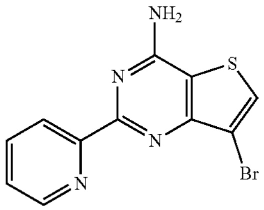 [SMILES: Nc1nc(-c2ccccn2)nc2c(Br)csc12] | B | | |
| 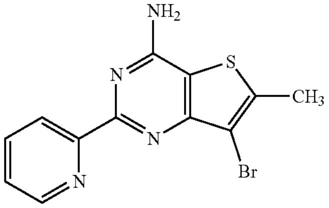 | D | | |
| 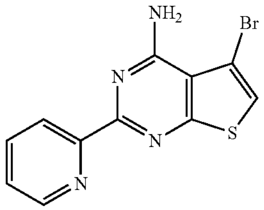 [SMILES: Nc1nc(-c2ccccn2)nc2scc(Br)c12] | A | | |
| 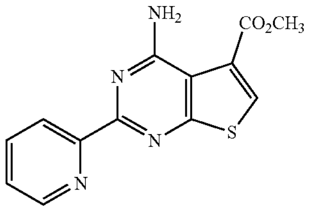 [SMILES: COC(=O)c1csc2nc(-c3ccccn3)nc(N)c12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 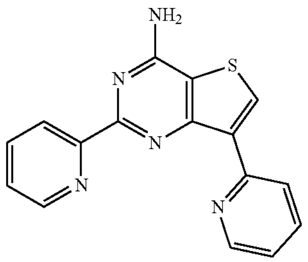 [SMILES: Nc1nc(-c2ccccn2)nc2c(-c3ccccn3)csc12] | D | D* | E |
| 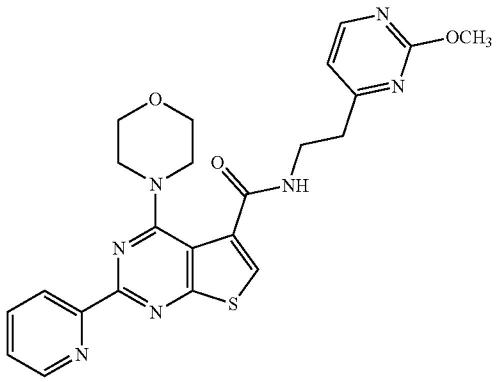 [SMILES: COc1nccc(CCNC(=O)c2csc3nc(-c4ccccn4)nc(N4CCOCC4)c23)n1] | D | | |
| 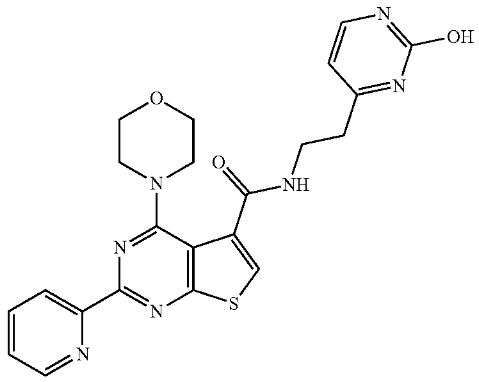 [SMILES: O=C(NCCc1ccnc(O)n1)c1csc2nc(-c3ccccn3)nc(N3CCOCC3)c12] | A | | |
| 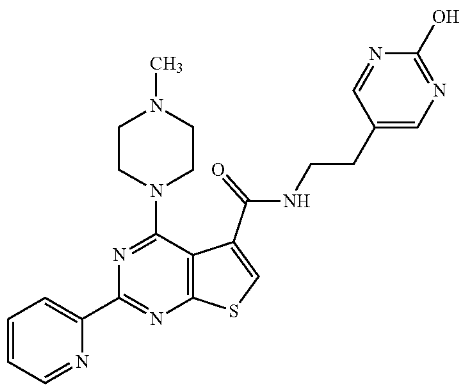 [SMILES: CN1CCN(c2nc(-c3ccccn3)nc3scc(C(=O)NCCc4cnc(O)nc4)c23)CC1] | B | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 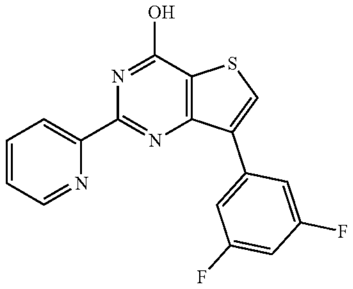 [SMILES: Oc1nc(-c2ccccn2)nc2c(-c3cc(F)cc(F)c3)csc12] | D | | |
| 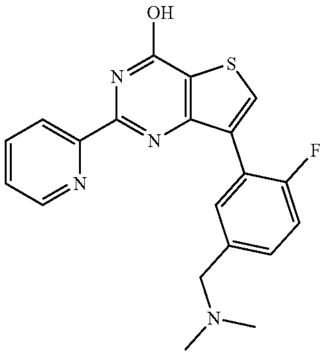 [SMILES: CN(C)Cc1ccc(F)c(-c2csc3c(O)nc(-c4ccccn4)nc23)c1] | D | | |
| 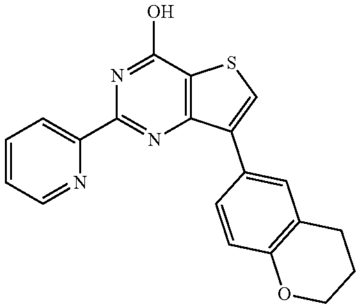 [SMILES: Oc1nc(-c2ccccn2)nc2c(-c3ccc4c(c3)CCCO4)csc12] | D | | |
| 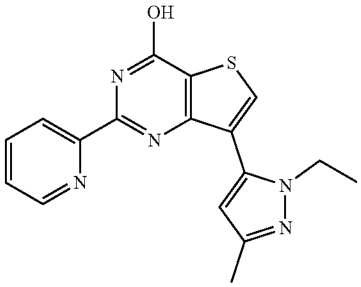 [SMILES: CCn1nc(C)cc1-c1csc2c(O)nc(-c3ccccn3)nc12] | D | | |
| 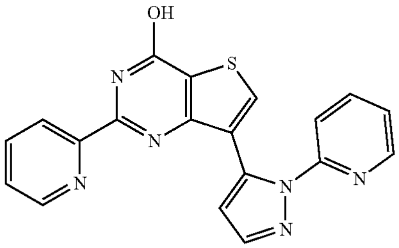 [SMILES: Oc1nc(-c2ccccn2)nc2c(-c3ccnn3-c3ccccn3)csc12] | D | | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 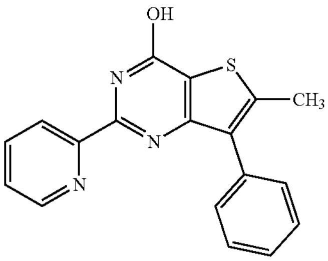 [SMILES: Cc1sc2c(O)nc(-c3ccccn3)nc2c1-c1ccccc1] | D | | |
| 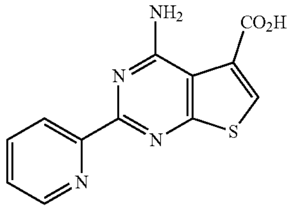 [SMILES: Nc1nc(-c2ccccn2)nc2scc(C(=O)O)c12] | A | | |
| 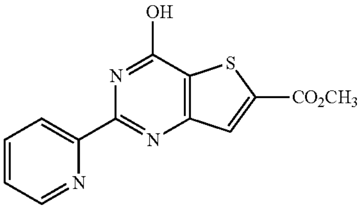 [SMILES: COC(=O)c1cc2nc(-c3ccccn3)nc(O)c2s1] | D | | |
| 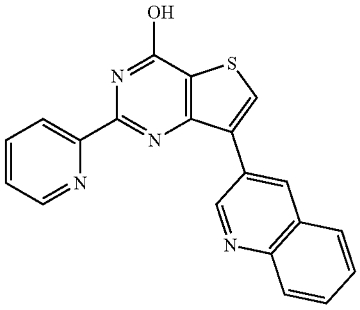 [SMILES: Oc1nc(-c2ccccn2)nc2c(-c3cnc4ccccc4c3)csc12] | D | | |
| 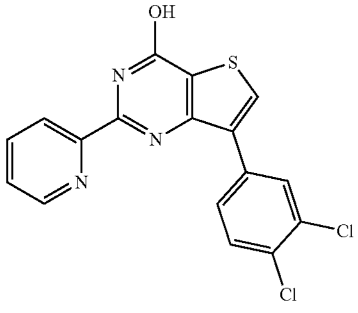 [SMILES: Oc1nc(-c2ccccn2)nc2c(-c3ccc(Cl)c(Cl)c3)csc12] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 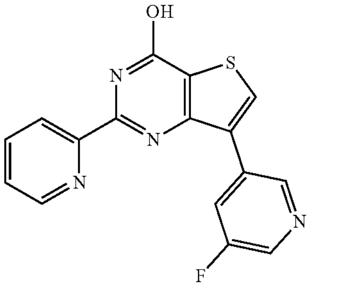 [SMILES: Oc1nc(-c2ccccn2)nc2c(-c3cncc(F)c3)csc12] | D | | |
| 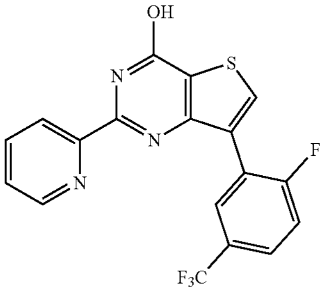 [SMILES: Oc1nc(-c2ccccn2)nc2c(-c3cc(C(F)(F)F)ccc3F)csc12] | D | | |
| 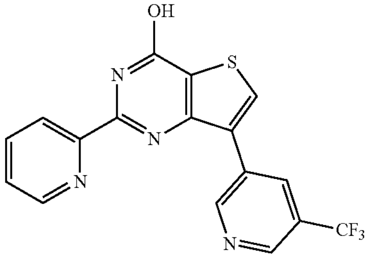 [SMILES: Oc1nc(-c2ccccn2)nc2c(-c3cncc(C(F)(F)F)c3)csc12] | D | | |
| 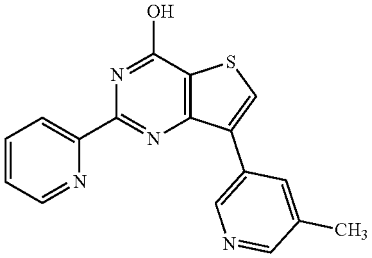 [SMILES: Cc1cncc(-c2csc3c(O)nc(-c4ccccn4)nc23)c1] | D | | |
| 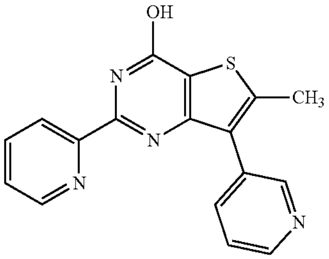 [SMILES: Cc1sc2c(O)nc(-c3ccccn3)nc2c1-c1cccnc1] | D | | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 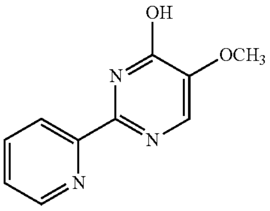 [SMILES: COc1cnc(-c2ccccn2)nc1O] | D | | |
| 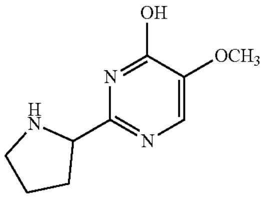 •HCl | C | | |
| 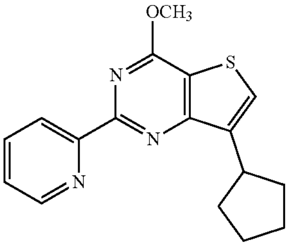 [SMILES: COc1nc(-c2ccccn2)nc2c(C3CCCC3)csc12] | D | | |
| 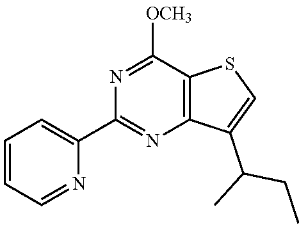 [SMILES: CCC(C)c1csc2c(OC)nc(-c3ccccn3)nc12] | D | | |
| 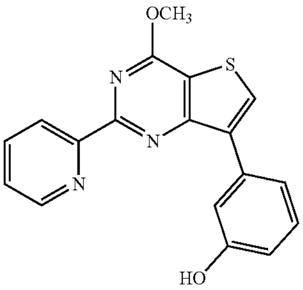 •HCl | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 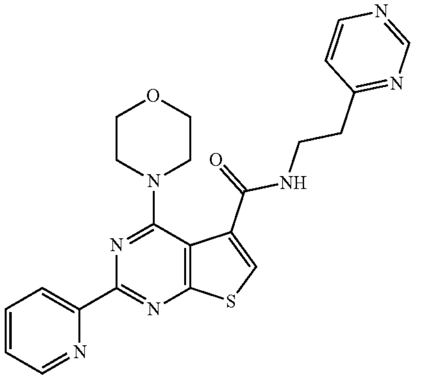 | | A* | |
| 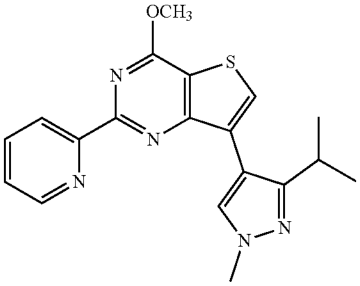 | | D* | |
| 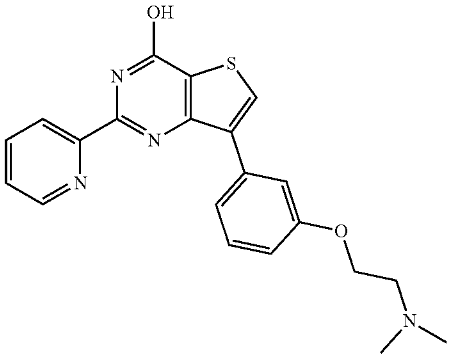 [SMILES: CN(C)CCOc1cccc(-c2csc3c(O)nc(-c4ccccn4)nc23)c1] | | D* | |
| 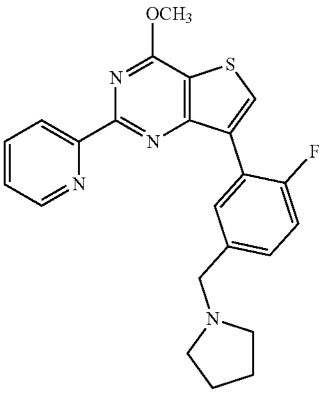 [SMILES: COc1nc(-c2ccccn2)nc2c(-c3cc(CN4CCCC4)ccc3F)csc12] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 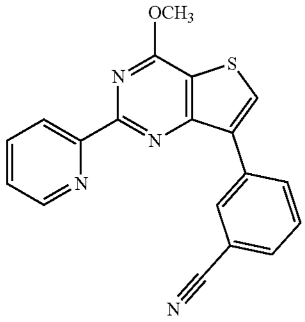 [SMILES: COc1nc(-c2ccccn2)nc2c(-c3cccc(C#N)c3)csc12] | | D* | |
| 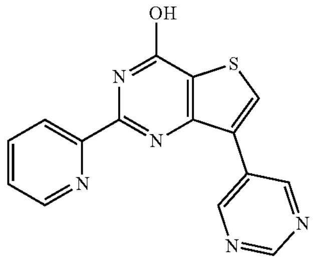 [SMILES: Oc1nc(-c2ccccn2)nc2c(-c3cncnc3)csc12] | | 0* | |
| 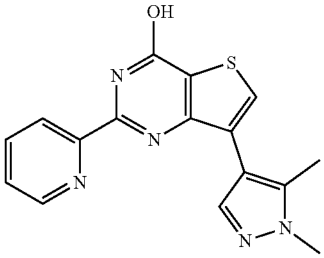 [SMILES: Cc1c(-c2csc3c(O)nc(-c4ccccn4)nc23)cnn1C] | | D* | |
| 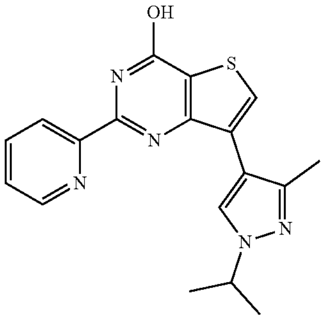 [SMILES: Cc1nn(C(C)C)cc1-c1csc2c(O)nc(-c3ccccn3)nc12] | | D* | |
| 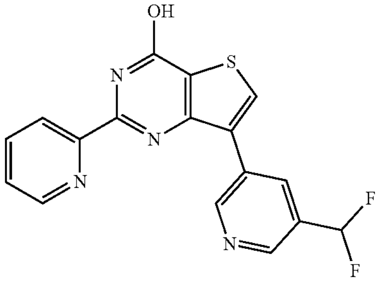 [SMILES: Oc1nc(-c2ccccn2)nc2c(-c3cncc(C(F)F)c3)csc12] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
| --- | --- | --- | --- |
| 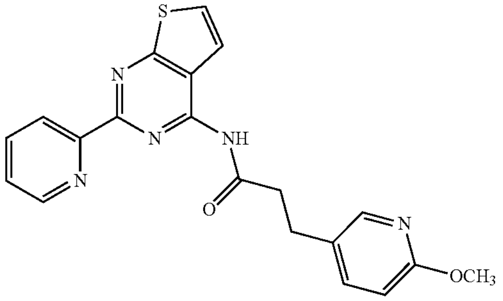 [SMILES: COc1ccc(CCC(=O)Nc2nc(-c3ccccn3)nc3sccc23)cn1] | | D* | |
| 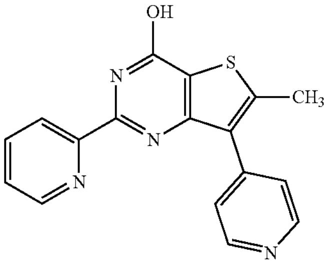 [SMILES: Cc1sc2c(O)nc(-c3ccccn3)nc2c1-c1ccncc1] | | D* | |
| 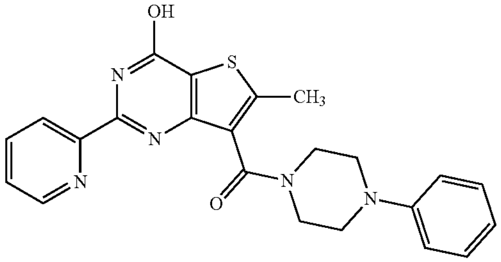 [SMILES: Cc1sc2c(O)nc(-c3ccccn3)nc2c1C(=O)N1CCN(c2ccccc2)CC1] | | D* | |
| 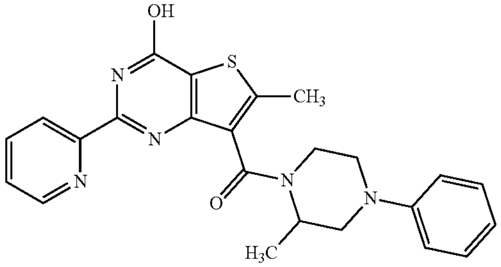 [SMILES: Cc1sc2c(O)nc(-c3ccccn3)nc2c1C(=O)N1CCN(c2ccccc2)CC1C] | | D* | |
| 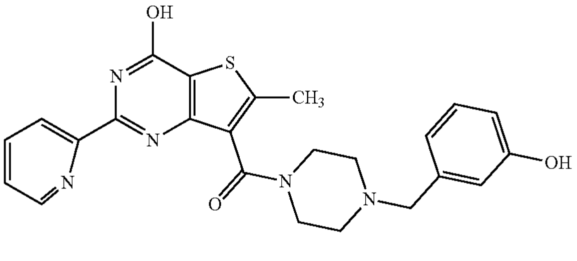 [SMILES: Cc1sc2c(O)nc(-c3ccccn3)nc2c1C(=O)N1CCN(Cc2cccc(O)c2)CC1] | | B* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 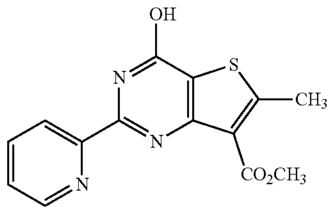 [SMILES: COC(=O)c1c(C)sc2c(O)nc(-c3ccccn3)nc12] | | B* | |
| 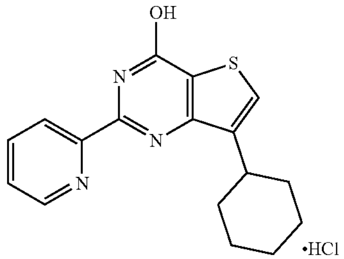 [SMILES: Oc1nc(-c2ccccn2)nc2c(C3CCCCC3)csc12 ; Cl] | | D* | |
| 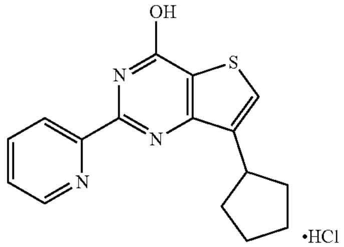 [SMILES: Oc1nc(-c2ccccn2)nc2c(C3CCCC3)csc12 ; Cl] | | D* | |
| 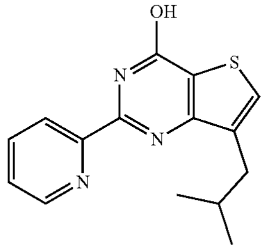 [SMILES: CC(C)Cc1csc2c(O)nc(-c3ccccn3)nc12] | | D* | |
| 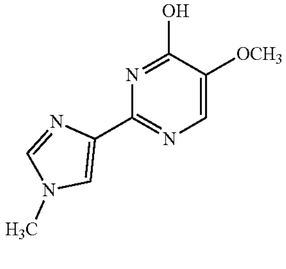 | | A* | |
| 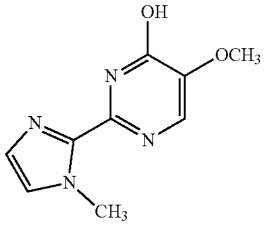 | | C* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 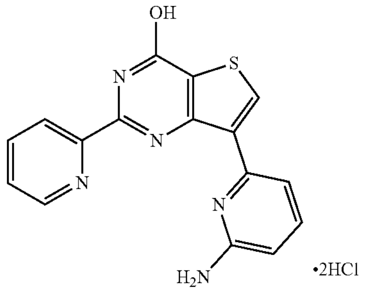 [SMILES: Nc1cccc(-c2csc3c(O)nc(-c4ccccn4)nc23)n1] | | D* | |
| 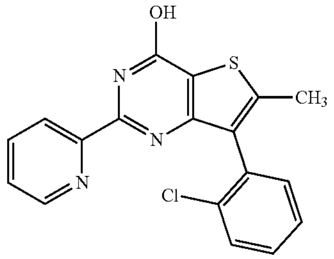 [SMILES: Cc1sc2c(O)nc(-c3ccccn3)nc2c1-c1ccccc1Cl] | | D* | |
| 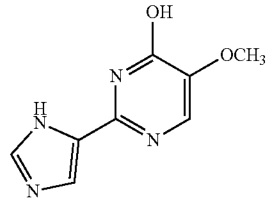 [SMILES: COc1cnc(-c2cnc[nH]2)nc1O] | | 0* | |
| 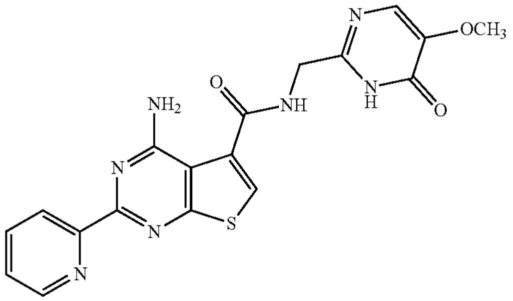 [SMILES: COc1cnc(CNC(=O)c2csc3nc(-c4ccccn4)nc(N)c23)[nH]c1=O] | | 0* | |
| 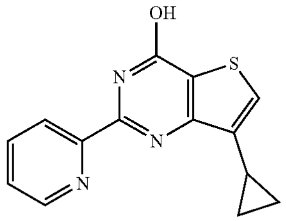 [SMILES: Oc1nc(-c2ccccn2)nc2c(C3CC3)csc12] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 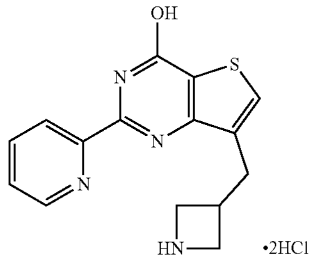 [SMILES: Oc1nc(-c2ccccn2)nc2c(CC3CNC3)csc12] •2HCl | | B* | |
| 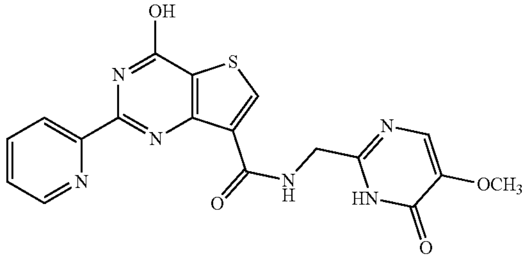 [SMILES: COc1cnc(CNC(=O)c2csc3c(O)nc(-c4ccccn4)nc23)[nH]c1=O] | | C* | |
| 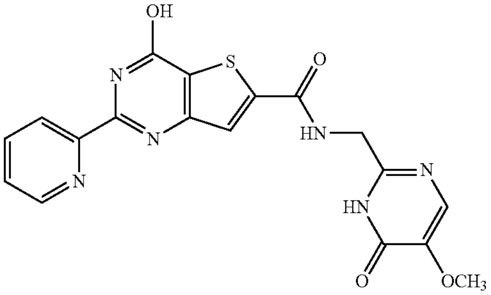 [SMILES: COc1cnc(CNC(=O)c2cc3nc(-c4ccccn4)nc(O)c3s2)[nH]c1=O] | | B* | |
| 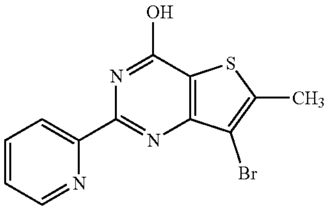 [SMILES: Cc1sc2c(O)nc(-c3ccccn3)nc2c1Br] | | D* | |
| 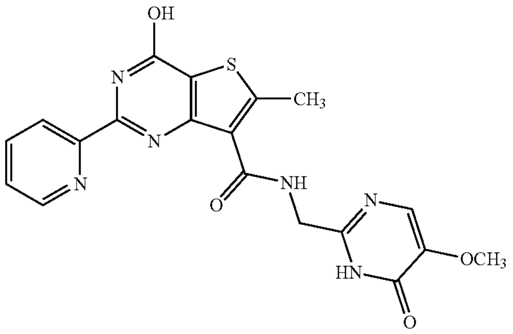 [SMILES: COc1cnc(CNC(=O)c2c(C)sc3c(O)nc(-c4ccccn4)nc23)[nH]c1=O] | | 0* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 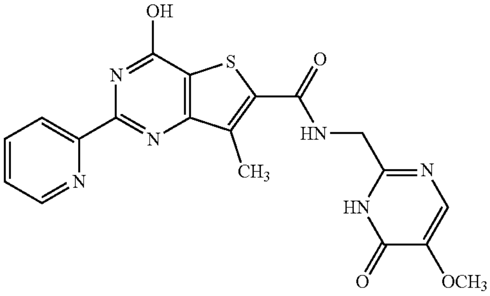 [SMILES: COc1cnc(CNC(=O)c2sc3c(O)nc(-c4ccccn4)nc3c2C)[nH]c1=O] | | 0* | |
| 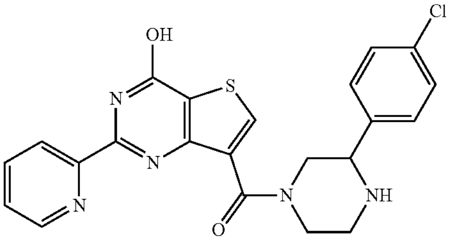 [SMILES: O=C(c1csc2c(O)nc(-c3ccccn3)nc12)N1CCNC(c2ccc(Cl)cc2)C1] | | D* | |
| 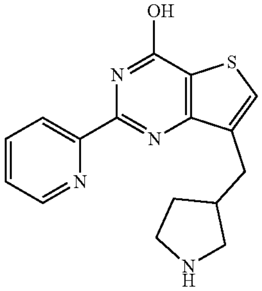 •2HCl | | 0* | |
| 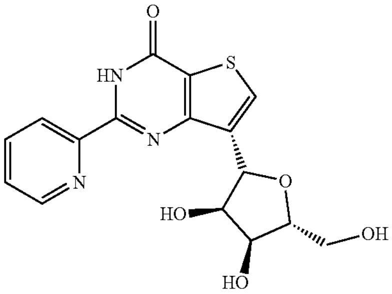 | | D* | |
| 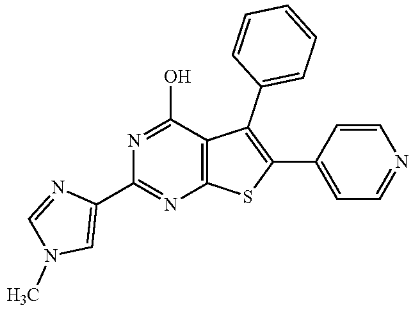 •2HCl | | D* | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 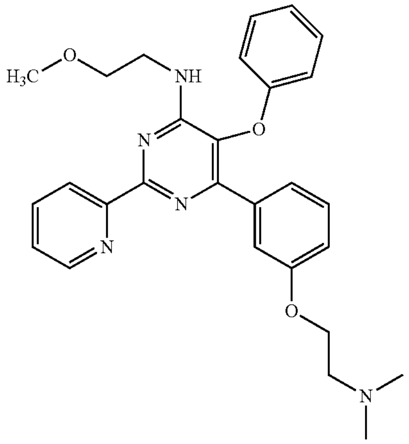 [SMILES: COCCNc1nc(-c2ccccn2)nc(-c2cccc(OCCN(C)C)c2)c1Oc1ccccc1] | | D* | |
| 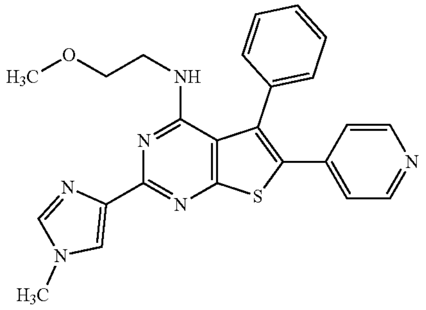 [SMILES: COCCNc1nc(-c2cn(C)cn2)nc2sc(-c3ccncc3)c(-c3ccccc3)c12] | | D* | |
| 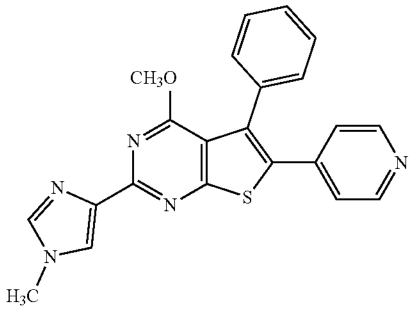 | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 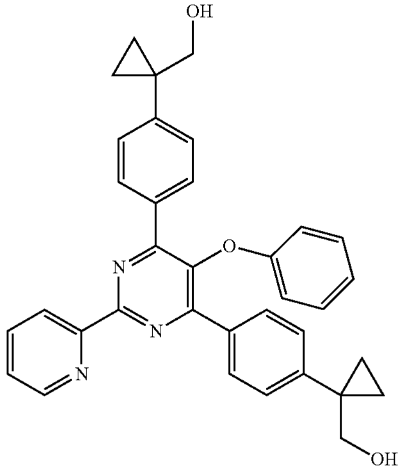 [SMILES: OCC1(c2ccc(-c3nc(-c4ccccn4)nc(-c4ccc(C5(CO)CC5)cc4)c3Oc3ccccc3)cc2)CC1] | | D* | |
| 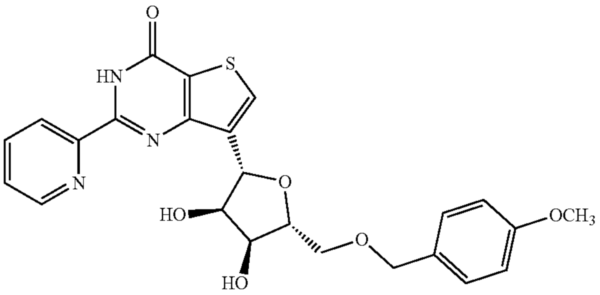 [SMILES: COc1ccc(COC[C@H]2O[C@@H](c3csc4c(=O)[nH]c(-c5ccccn5)nc34)[C@H](O)[C@@H]2O)cc1] | | A* | |
| 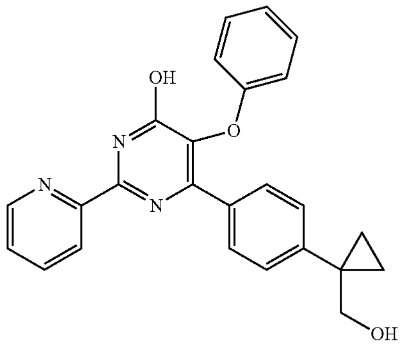 [SMILES: OCC1(c2ccc(-c3nc(-c4ccccn4)nc(O)c3Oc3ccccc3)cc2)CC1] | | D* | |
| 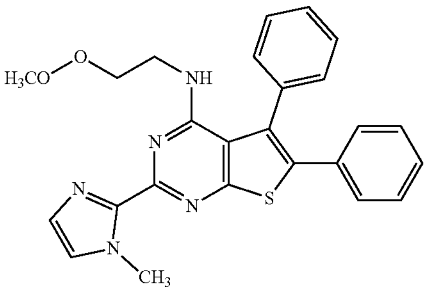 [SMILES: COOCCNc1nc(-c2nccn2C)nc2sc(-c3ccccc3)c(-c3ccccc3)c12] | | D* | F |

TABLE 5-continued
| Compound | MIA-PACA2 | MIA-PACA2 (alternate conditions) | $IC_{50}$ (nM) |
|---|---|---|---|
| % Inhibition of cell proliferation at 30 μM or 10 μM in MIA-PACA2 pancreatic cancer cell lines, with select $IC_{50}$ values | | | |
| 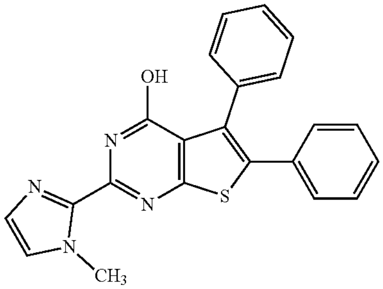 | | D* | |
| 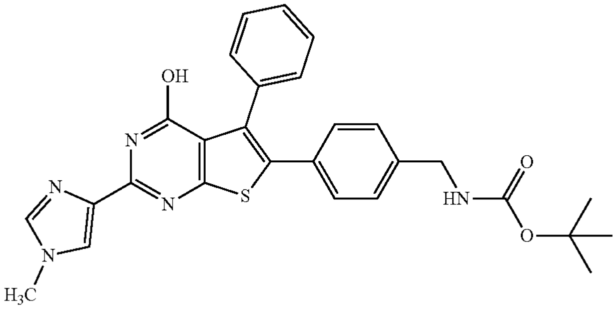 | | B* | |
| 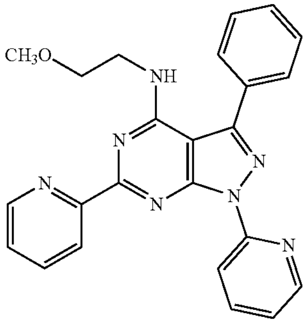 | | D* | |
| 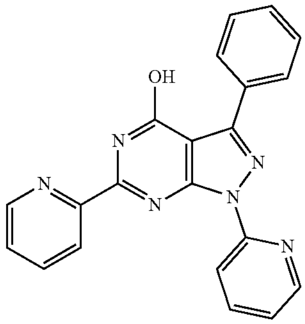 [SMILES: Oc1nc(-c2ccccn2)nc2c1c(-c1ccccc1)nn2-c1ccccn1] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 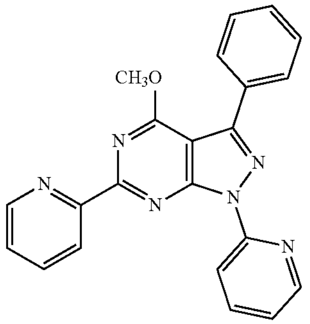 | | D* | |
| 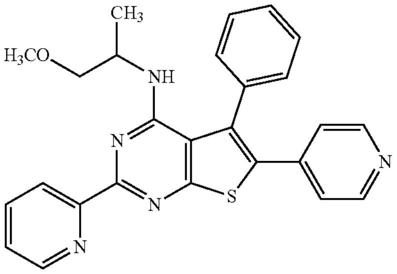 [SMILES: COCC(C)Nc1nc(-c2ccccn2)nc2sc(-c3ccncc3)c(-c3ccccc3)c12] | | C* | |
| 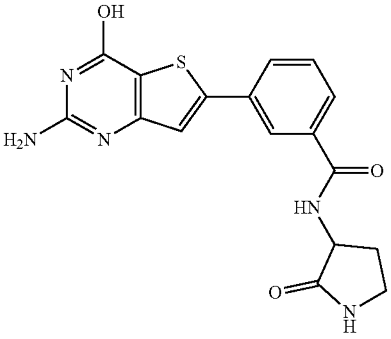 [SMILES: Nc1nc(O)c2sc(-c3cccc(C(=O)NC4CCNC4=O)c3)cc2n1] | | 0* | |
| 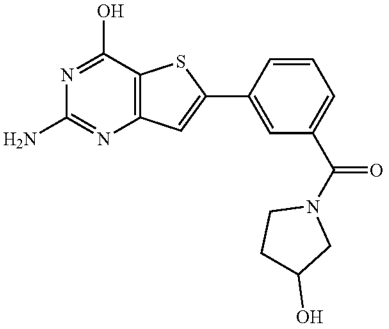 [SMILES: Nc1nc(O)c2sc(-c3cccc(C(=O)N4CCC(O)C4)c3)cc2n1] | | A* | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 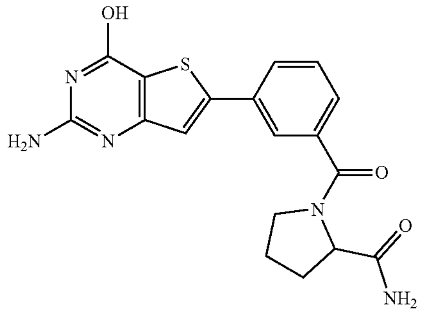 [SMILES: NC(=O)C1CCCN1C(=O)c1cccc(-c2cc3nc(N)nc(O)c3s2)c1] | | C* | |
| 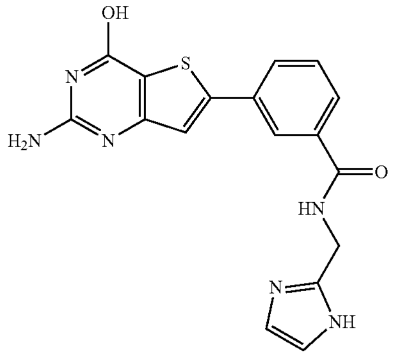 [SMILES: Nc1nc(O)c2sc(-c3cccc(C(=O)NCc4ncc[nH]4)c3)cc2n1] | | A* | |
| 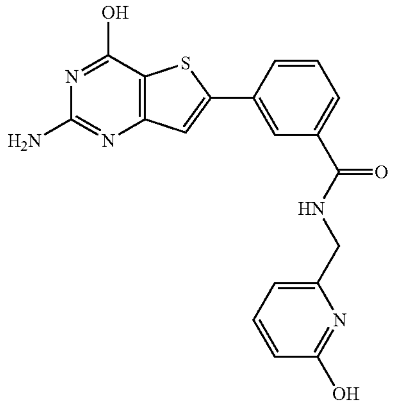 [SMILES: Nc1nc(O)c2sc(-c3cccc(C(=O)NCc4cccc(O)n4)c3)cc2n1] | | A* | |
| 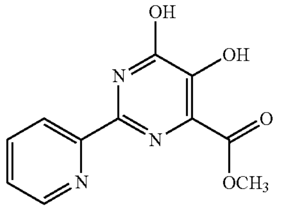 [SMILES: COC(=O)c1nc(-c2ccccn2)nc(O)c1O] | | B* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 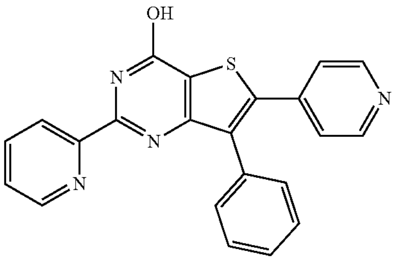 [SMILES: Oc1nc(-c2ccccn2)nc2c(-c3ccccc3)c(-c3ccncc3)sc12] | | D* | |
| 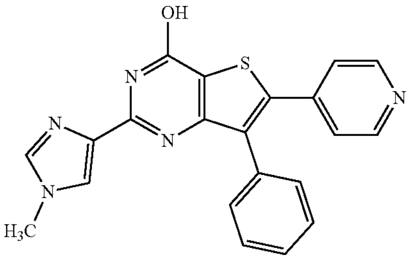 [SMILES: Cn1cnc(-c2nc(O)c3sc(-c4ccncc4)c(-c4ccccc4)c3n2)c1] | | D* | |
| 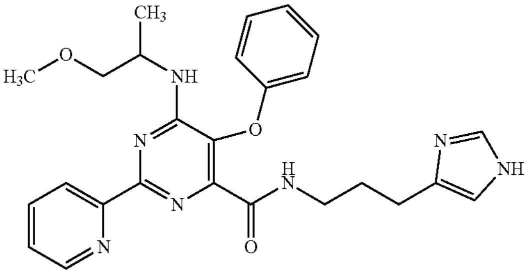 [SMILES: COCC(C)Nc1nc(-c2ccccn2)nc(C(=O)NCCCc2c[nH]cn2)c1Oc1ccccc1] | | D* | |
| 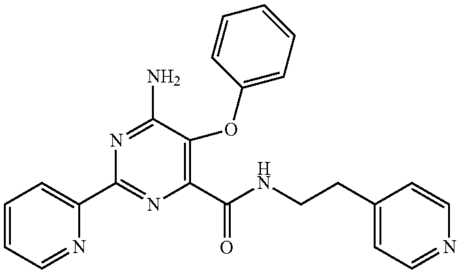 [SMILES: Nc1nc(-c2ccccn2)nc(C(=O)NCCc2ccncc2)c1Oc1ccccc1] | | D* | |
| 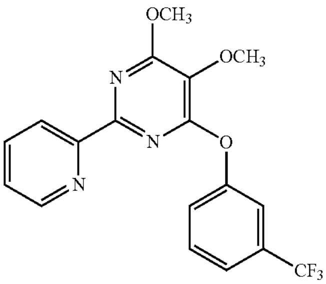 [SMILES: COc1nc(-c2ccccn2)nc(Oc2cccc(C(F)(F)F)c2)c1OC] | | D* | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 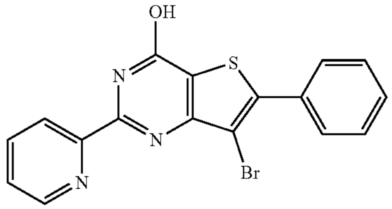 [SMILES: Oc1nc(-c2ccccn2)nc2c(Br)c(-c3ccccc3)sc12] | | D* | |
| 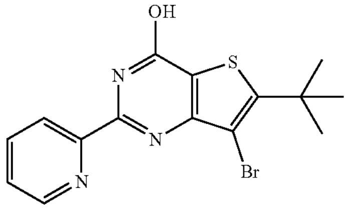 [SMILES: CC(C)(C)c1sc2c(O)nc(-c3ccccn3)nc2c1Br] | | D* | |
| 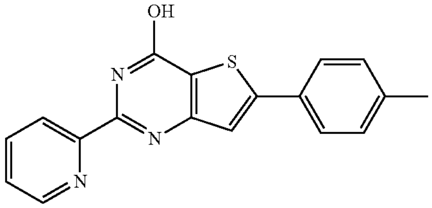 [SMILES: Cc1ccc(-c2cc3nc(-c4ccccn4)nc(O)c3s2)cc1] | | D* | |
| 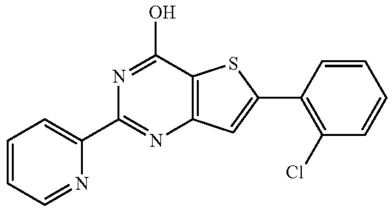 [SMILES: Oc1nc(-c2ccccn2)nc2cc(-c3ccccc3Cl)sc12] | | D* | |
| 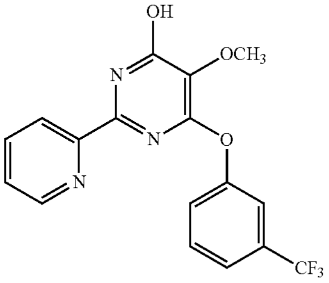 | | D* | |
| 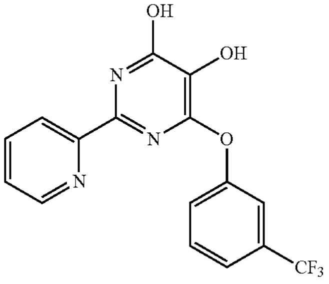 [SMILES: Oc1nc(-c2ccccn2)nc(Oc2cccc(C(F)(F)F)c2)c1O] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 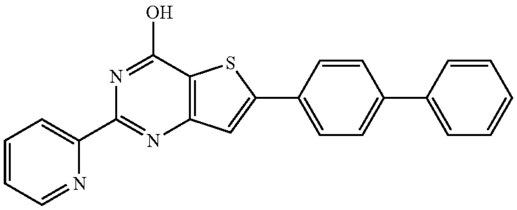 [SMILES: Oc1nc(-c2ccccn2)nc2cc(-c3ccc(-c4ccccc4)cc3)sc12] | | D* | |
| 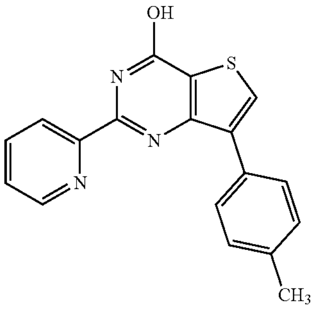 [SMILES: Cc1ccc(-c2csc3c(O)nc(-c4ccccn4)nc23)cc1] | | D* | |
| 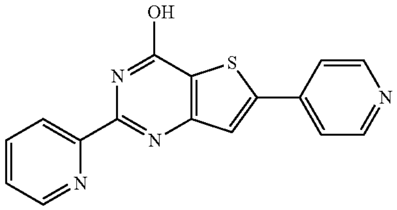 [SMILES: Oc1nc(-c2ccccn2)nc2cc(-c3ccncc3)sc12] | | D* | |
| 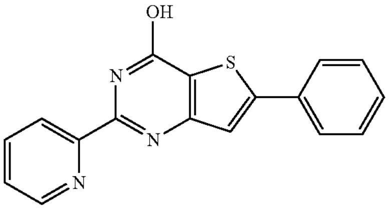 [SMILES: Oc1nc(-c2ccccn2)nc2cc(-c3ccccc3)sc12] | | D* | |
| 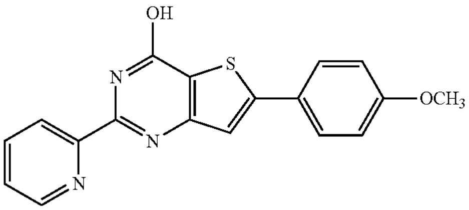 [SMILES: COc1ccc(-c2cc3nc(-c4ccccn4)nc(O)c3s2)cc1] | | D* | |
| 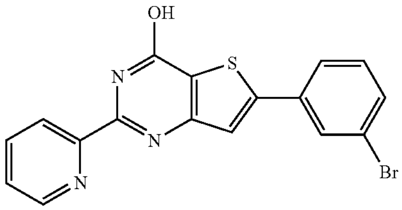 [SMILES: Oc1nc(-c2ccccn2)nc2cc(-c3cccc(Br)c3)sc12] | | D* | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 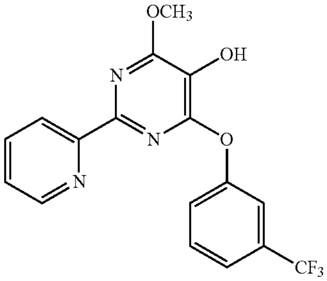 [SMILES: COc1nc(-c2ccccn2)nc(Oc2cccc(C(F)(F)F)c2)c1O] | | A* | |
| 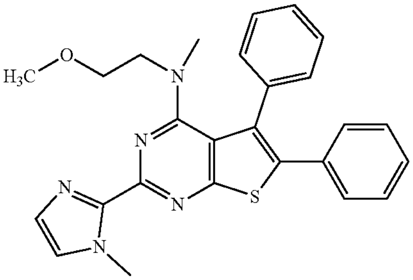 [SMILES: COCCN(C)c1nc(-c2nccn2C)nc2sc(-c3ccccc3)c(-c3ccccc3)c12] | | D* | E |
| 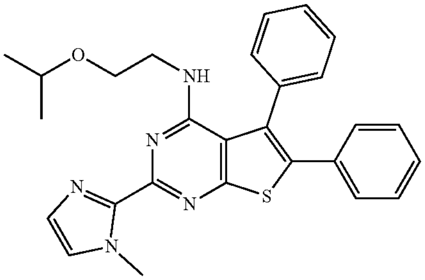 [SMILES: CC(C)OCCNc1nc(-c2nccn2C)nc2sc(-c3ccccc3)c(-c3ccccc3)c12] | | D* | |
| 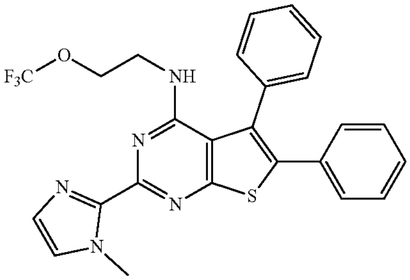 [SMILES: Cn1ccnc1-c1nc(NCCOC(F)(F)F)c2c(-c3ccccc3)c(-c3ccccc3)sc2n1] | | D* | |
| 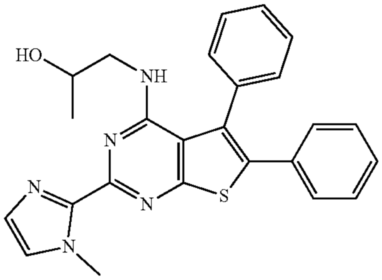 | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 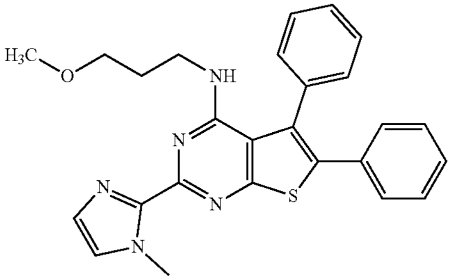 [SMILES: COCCCNc1nc(-c2nccn2C)nc2sc(-c3ccccc3)c(-c3ccccc3)c12] | | D* | F |
| 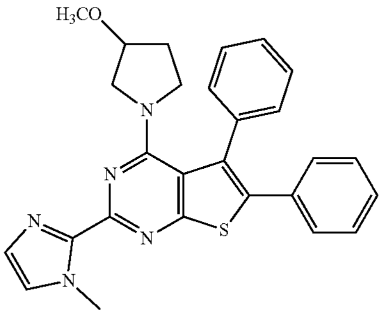 [SMILES: COC1CCN(c2nc(-c3nccn3C)nc3sc(-c4ccccc4)c(-c4ccccc4)c23)C1] | | D* | F |
| 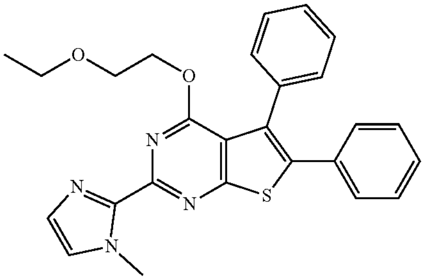 [SMILES: CCOCCOc1nc(-c2nccn2C)nc2sc(-c3ccccc3)c(-c3ccccc3)c12] | | D* | |
| 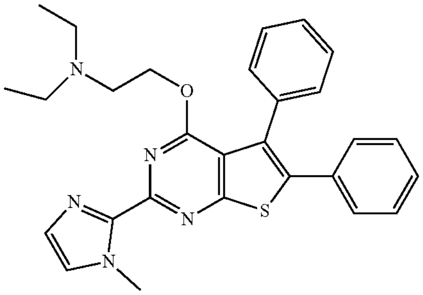 [SMILES: CCN(CC)CCOc1nc(-c2nccn2C)nc2sc(-c3ccccc3)c(-c3ccccc3)c12] | | D* | |
| 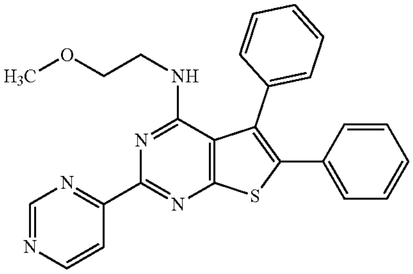 [SMILES: COCCNc1nc(-c2ccncn2)nc2sc(-c3ccccc3)c(-c3ccccc3)c12] | | C* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 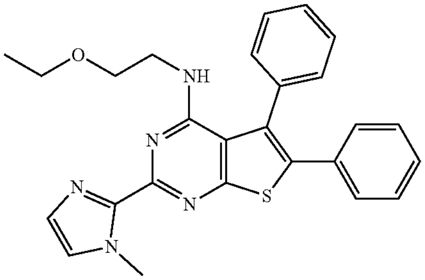 [SMILES: CCOCCNc1nc(-c2nccn2C)nc2sc(-c3ccccc3)c(-c3ccccc3)c12] | | D* | F |
| 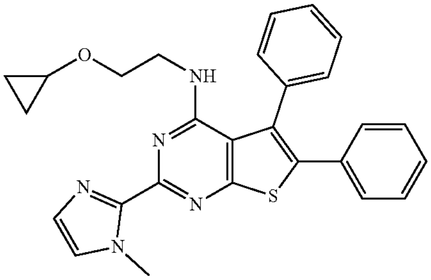 [SMILES: Cn1ccnc1-c1nc(NCCOC2CC2)c2c(-c3ccccc3)c(-c3ccccc3)sc2n1] | | D* | |
| 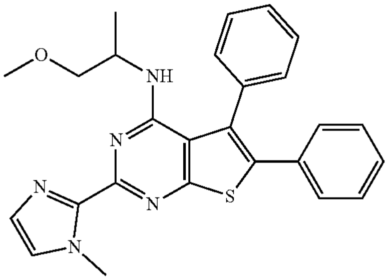 [SMILES: COCC(C)Nc1nc(-c2nccn2C)nc2sc(-c3ccccc3)c(-c3ccccc3)c12] | | D* | F |
| 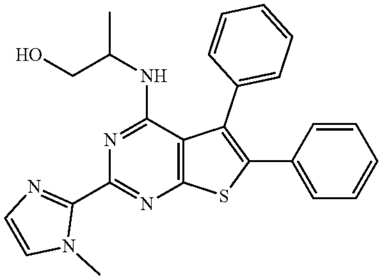 [SMILES: CC(CO)Nc1nc(-c2nccn2C)nc2sc(-c3ccccc3)c(-c3ccccc3)c12] | | D* | |
| 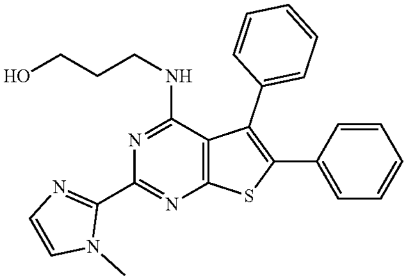 [SMILES: Cn1ccnc1-c1nc(NCCCO)c2c(-c3ccccc3)c(-c3ccccc3)sc2n1] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 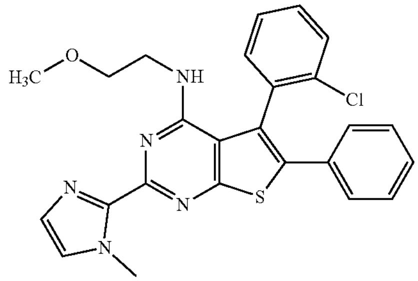 [SMILES: COCCNc1nc(-c2nccn2C)nc2sc(-c3ccccc3)c(-c3ccccc3Cl)c12] | | D* | E |
| 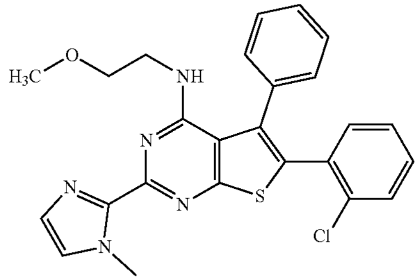 [SMILES: COCCNc1nc(-c2nccn2C)nc2sc(-c3ccccc3Cl)c(-c3ccccc3)c12] | | D* | F |
| 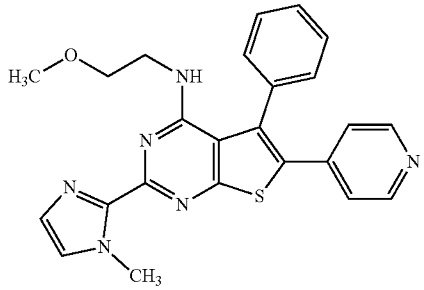 [SMILES: COCCNc1nc(-c2nccn2C)nc2sc(-c3ccncc3)c(-c3ccccc3)c12] | | D* | |
| 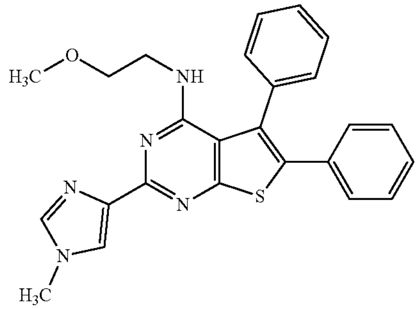 [SMILES: COCCNc1nc(-c2cn(C)cn2)nc2sc(-c3ccccc3)c(-c3ccccc3)c12] | | D* | E |
| 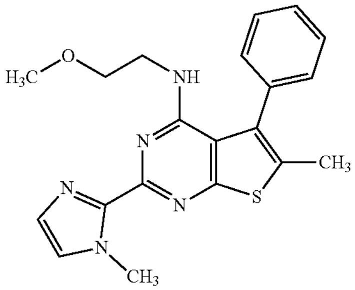 [SMILES: COCCNc1nc(-c2nccn2C)nc2sc(C)c(-c3ccccc3)c12] | | D* | F |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 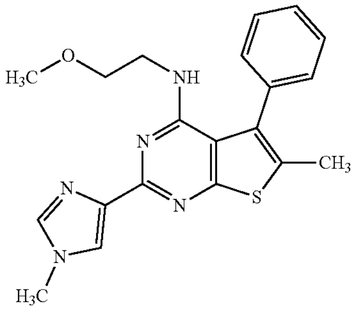 [SMILES: COCCNc1nc(-c2cn(C)cn2)nc2sc(C)c(-c3ccccc3)c12] | | D* | |
| 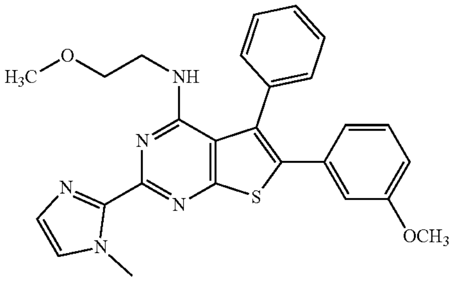 [SMILES: COCCNc1nc(-c2nccn2C)nc2sc(-c3cccc(OC)c3)c(-c3ccccc3)c12] | | D* | |
| 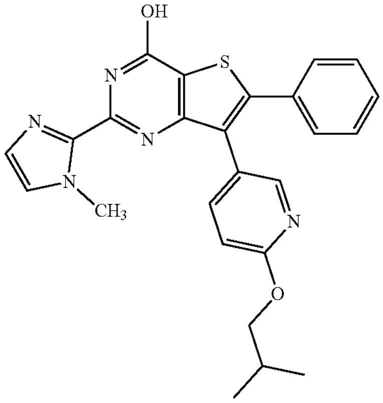 [SMILES: CC(C)COc1ccc(-c2c(-c3ccccc3)sc3c(O)nc(-c4nccn4C)nc23)cn1] | | D* | G |
| 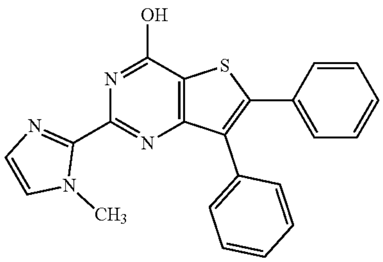 [SMILES: Cn1ccnc1-c1nc(O)c2sc(-c3ccccc3)c(-c3ccccc3)c2n1] | | C* | |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 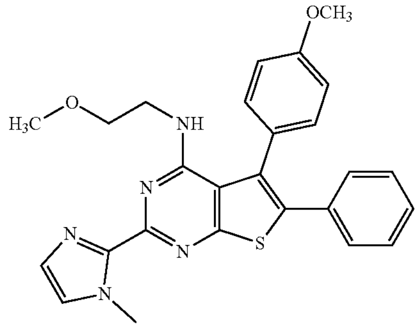 [SMILES: COCCNc1nc(-c2nccn2C)nc2sc(-c3ccccc3)c(-c3ccc(OC)cc3)c12] | | D* | F |
| 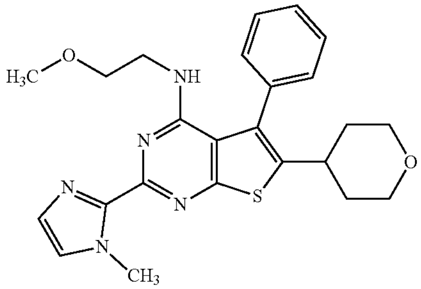 [SMILES: COCCNc1nc(-c2nccn2C)nc2sc(C3CCOCC3)c(-c3ccccc3)c12] | | D* | |
| 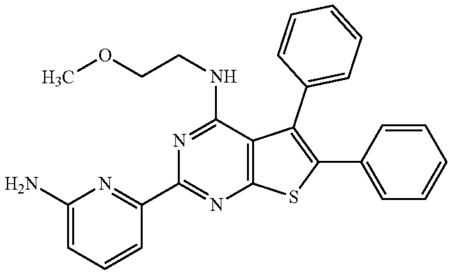 [SMILES: COCCNc1nc(-c2cccc(N)n2)nc2sc(-c3ccccc3)c(-c3ccccc3)c12] | | D* | |
| 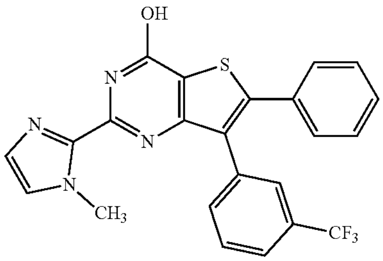 [SMILES: Cn1ccnc1-c1nc(O)c2sc(-c3ccccc3)c(-c3cccc(C(F)(F)F)c3)c2n1] | | B* | |
| 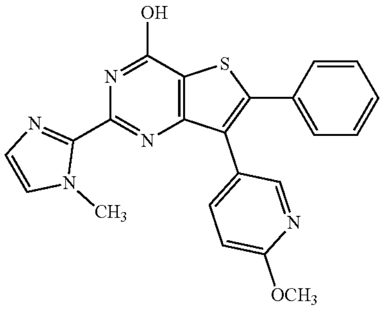 [SMILES: COc1ccc(-c2c(-c3ccccc3)sc3c(O)nc(-c4nccn4C)nc23)cn1] | | D* | F |

TABLE 5-continued
| % Inhibition of cell proliferation at 30 μM or 10 μM in MIA-PACA2 pancreatic cancer cell lines, with select $IC_{50}$ values | | | |
|---|---|---|---|
| Compound | MIA-PACA2 | MIA-PACA2 (alternate conditions) | $IC_{50}$ (nM) |
| 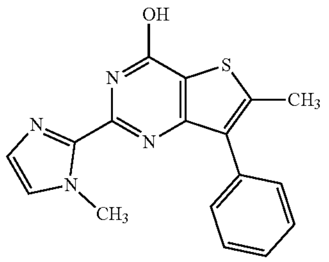 [SMILES: Cc1sc2c(O)nc(-c3nccn3C)nc2c1-c1ccccc1] | | D* | |
| 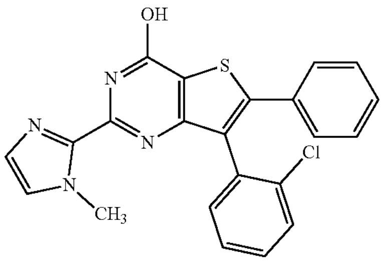 [SMILES: Cn1ccnc1-c1nc(O)c2sc(-c3ccccc3)c(-c3ccccc3Cl)c2n1] | | D* | G |
| 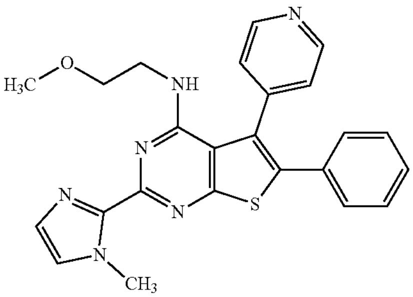 [SMILES: COCCNc1nc(-c2nccn2C)nc2sc(-c3ccccc3)c(-c3ccncc3)c12] | | D* | |
| 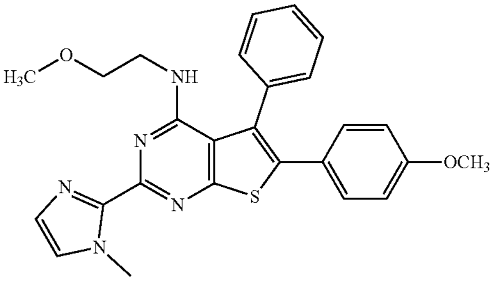 [SMILES: COCCNc1nc(-c2nccn2C)nc2sc(-c3ccc(OC)cc3)c(-c3ccccc3)c12] | | D* | G |
| 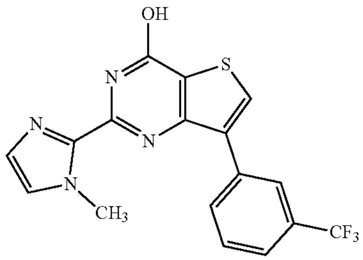 [SMILES: Cn1ccnc1-c1nc(O)c2scc(-c3cccc(C(F)(F)F)c3)c2n1] | | D* | E |

TABLE 5-continued
| Compound | MIA-PACA2 | MIA-PACA2 (alternate conditions) | $IC_{50}$ (nM) |
|---|---|---|---|
| % Inhibition of cell proliferation at 30 μM or 10 μM in MIA-PACA2 pancreatic cancer cell lines, with select $IC_{50}$ values | | | |
| 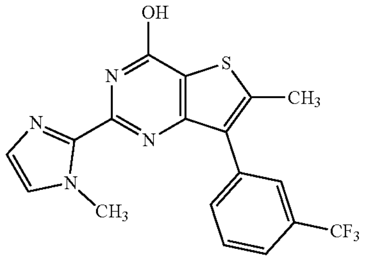 [SMILES: Cc1sc2c(O)nc(-c3nccn3C)nc2c1-c1cccc(C(F)(F)F)c1] | | D* | G |
| 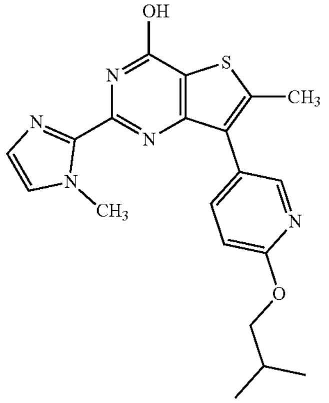 [SMILES: Cc1sc2c(O)nc(-c3nccn3C)nc2c1-c1ccc(OCC(C)C)nc1] | | D* | |
| 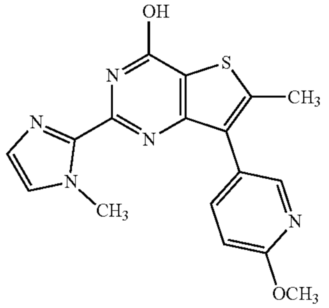 [SMILES: COc1ccc(-c2c(C)sc3c(O)nc(-c4nccn4C)nc23)cn1] | | B* | |
| 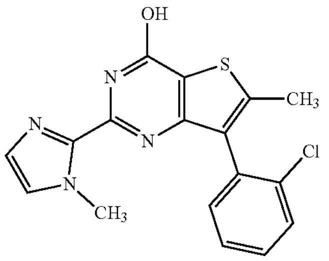 [SMILES: Cc1sc2c(O)nc(-c3nccn3C)nc2c1-c1ccccc1Cl] | | D* | G |

TABLE 5-continued
% Inhibition of cell proliferation at 30 µM or 10 µM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 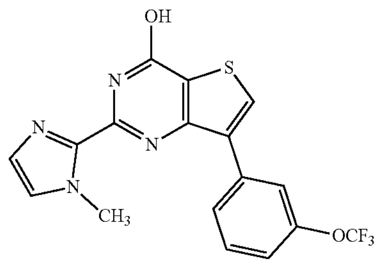 [SMILES: Cn1ccnc1-c1nc(O)c2scc(-c3cccc(OC(F)(F)F)c3)c2n1] | | D* | G |
| 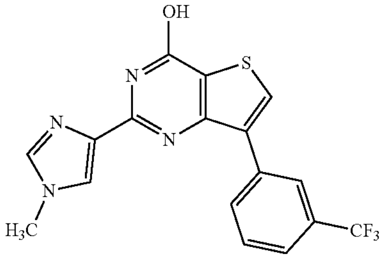 [SMILES: Cn1cnc(-c2nc(O)c3scc(-c4cccc(C(F)(F)F)c4)c3n2)c1] | | D* | |
| 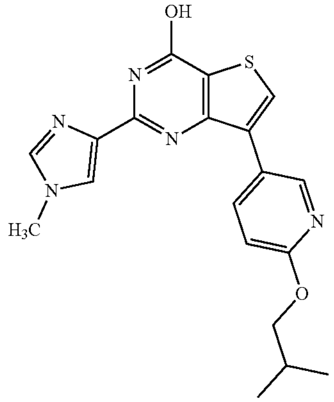 [SMILES: CC(C)COc1ccc(-c2csc3c(O)nc(-c4cn(C)cn4)nc23)cn1] | | D* | |
| 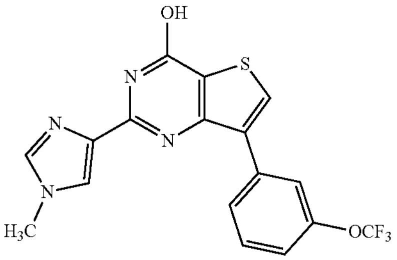 [SMILES: Cn1cnc(-c2nc(O)c3scc(-c4cccc(OC(F)(F)F)c4)c3n2)c1] | | D* | |
| 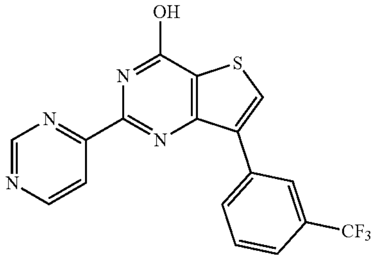 [SMILES: Oc1nc(-c2ccncn2)nc2c(-c3cccc(C(F)(F)F)c3)csc12] | | D* | E |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 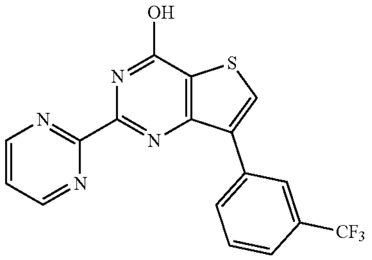 [SMILES: Oc1nc(-c2ncccn2)nc2c(-c3cccc(C(F)(F)F)c3)csc12] | | D* | |
| 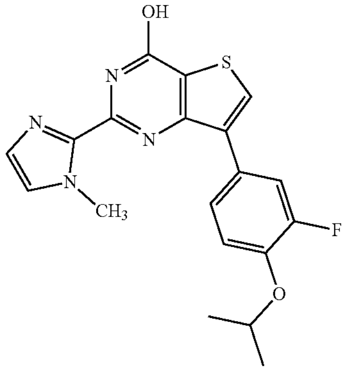 [SMILES: CC(C)Oc1ccc(-c2csc3c(O)nc(-c4nccn4C)nc23)cc1F] | | D* | |
| 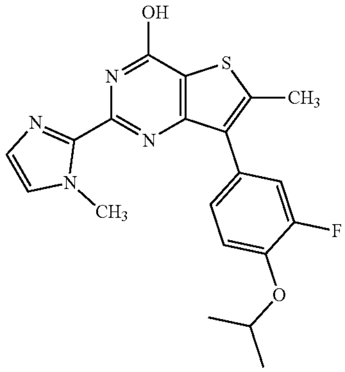 [SMILES: Cc1sc2c(O)nc(-c3nccn3C)nc2c1-c1ccc(OC(C)C)c(F)c1] | | D* | |
| 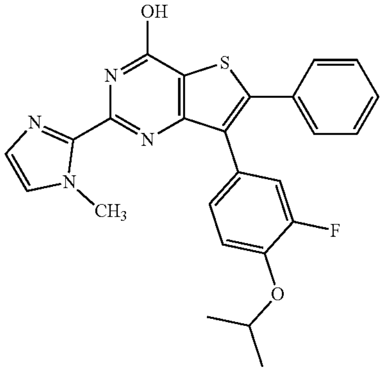 [SMILES: CC(C)Oc1ccc(-c2c(-c3ccccc3)sc3c(O)nc(-c4nccn4C)nc23)cc1F] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 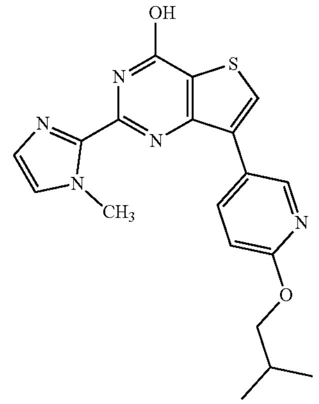 [SMILES: CC(C)COc1ccc(-c2csc3c(O)nc(-c4nccn4C)nc23)cn1] | | D* | G |
| 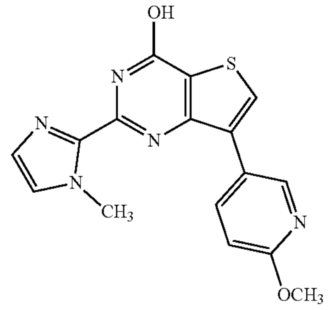 [SMILES: COc1ccc(-c2csc3c(O)nc(-c4nccn4C)nc23)cn1] | | D* | |
| 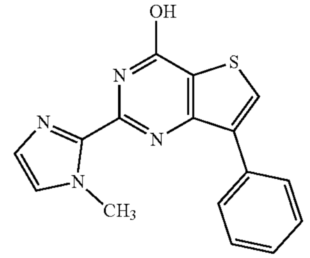 [SMILES: Cn1ccnc1-c1nc(O)c2scc(-c3ccccc3)c2n1] | | D* | |
| 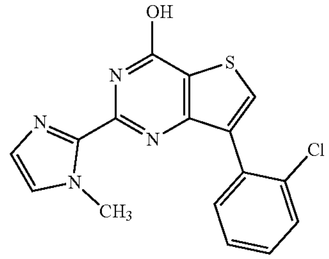 [SMILES: Cn1ccnc1-c1nc(O)c2scc(-c3ccccc3Cl)c2n1] | | D* | |

TABLE 5-continued
% Inhibition of cell proliferation at 30 μM or 10 μM in MIA-PACA2 pancreatic cancer cell lines, with select $IC_{50}$ values
| Compound | MIA-PACA2 | MIA-PACA2 (alternate conditions) | $IC_{50}$ (nM) |
|---|---|---|---|
| 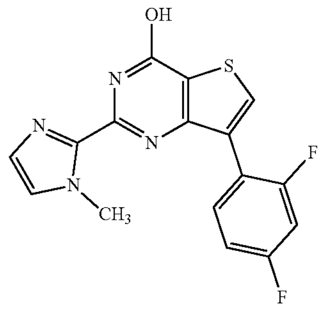 [SMILES: Cn1ccnc1-c1nc(O)c2scc(-c3ccc(F)cc3F)c2n1] | | D* | |
| 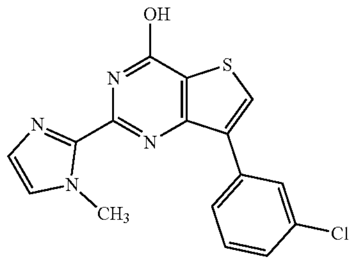 [SMILES: Cn1ccnc1-c1nc(O)c2scc(-c3cccc(Cl)c3)c2n1] | | D* | |
| 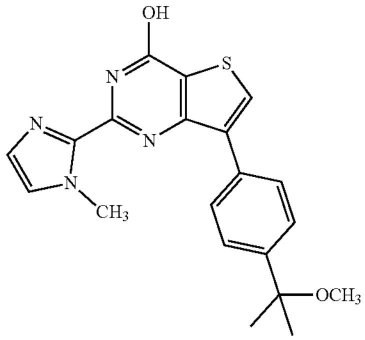 [SMILES: COC(C)(C)c1ccc(-c2csc3c(O)nc(-c4nccn4C)nc23)cc1] | | D* | |
| 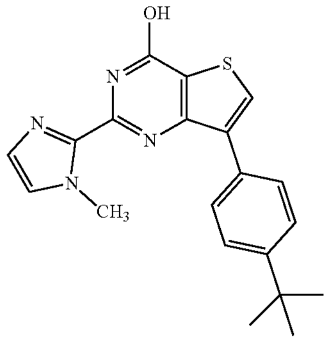 [SMILES: Cn1ccnc1-c1nc(O)c2scc(-c3ccc(C(C)(C)C)cc3)c2n1] | | D* | |

TABLE 5-continued

% Inhibition of cell proliferation at 30 μM or 10 μM in MIA-PACA2 pancreatic cancer cell lines, with select $IC_{50}$ values

| Compound | MIA-PACA2 | MIA-PACA2 (alternate conditions) | $IC_{50}$ (nM) |
|---|---|---|---|
| 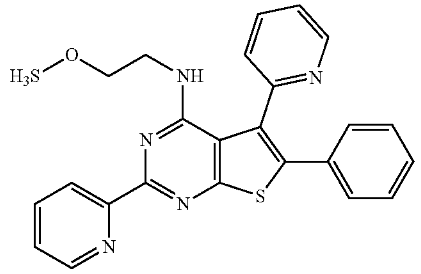 [SMILES: SOCCNc1nc(-c2ccccn2)nc2sc(-c3ccccc3)c(-c3ccccn3)c12] | | D* | |
| 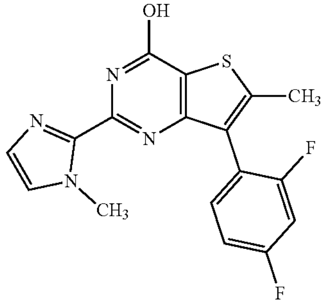 [SMILES: Cc1sc2c(O)nc(-c3nccn3C)nc2c1-c1ccc(F)cc1F] | | D* | |
| 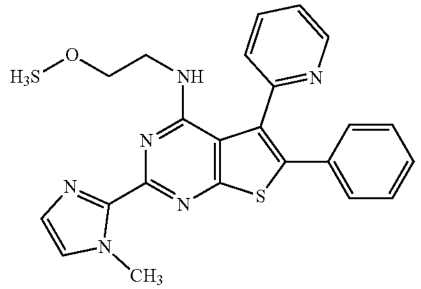 | | D* | F |

*= tested at 10 μM.

Note: $IC_{50}$ values were determined via the same assay as was used for the % inhibition determination for each compound reported.

A=1-25% inhibition, B=25-50% inhibition, C=51-75% inhibition, D=76-100% inhibition. E=>1000 nM $IC_{50}$, F=501-1000 nM $IC_{50}$, G=100-500 nM $IC_{50}$, H=<100 nM $IC_{50}$.

Example 4

Protocol for Mouse TNF Alpha and IL6 Quantification Assay

Cell lines: Abelson murine leukemia virus transformed macrophage cell line RAW 264.7 was purchased from ATCC and grown in complete DMEM-High Glucose medium supplemented with penicillin (100 U/mL), streptomycin (100 μg/mL), and 10% heat-inactivated FBS at 37° C. in a humidified incubator with 5% $CO_2$.

Method: Cells were plated at 40000 cells/well density in a 96-wells plate. After a 3-hour incubation, macrophages were starved with DMEM plus 0.5% FBS o/n. The next day the small molecules to be tested were added to the cells in the final concentration of 30 μM (with 0.3% DMSO) 3 hours prior to LPS stimulation (100 ng/ml). After LPS stimulation cells were incubated at 37° C. for 16h. At the end of the incubation period, culture media were collected and production of LPS-induced TNFα and IL6 cytokine was measured using ELISA detection kits.

Sandwich ELISA: The ELISA Immunoassays Quantikine Mouse TNF-alpha (catalog number MTA00B) and IL6 (catalog number M6000B) were purchased from R&D Systems Inc., Minneapolis, Minn. These 4.5 hours solid phase ELISAs were used to measure mouse TNFα or IL6 levels in macrophages culture supernatants. Assays were executed according to the manufacturer specifications.

Table 6 shows inhibition data for selected compounds tested in the cellular assay described above.

TABLE 6
| IL-6 and TNFα % Inhibition at 30 μM in RAW 264.7 murine leukemia virus transformed macrophage cell lines | | |
|---|---|---|
| Compound | IL-6 | TNF-α |
| 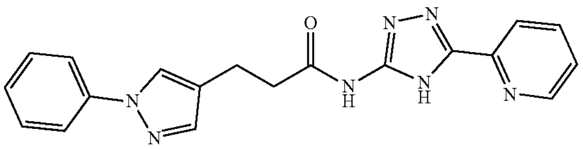 [SMILES: O=C(CCc1cnn(-c2ccccc2)c1)Nc1nnc(-c2ccccn2)[nH]1] | B | A |
| 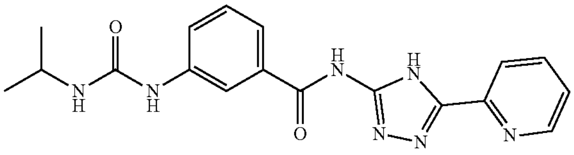 [SMILES: CC(C)NC(=O)Nc1cccc(C(=O)Nc2nnc(-c3ccccn3)[nH]2)c1] | 0 | A |
| 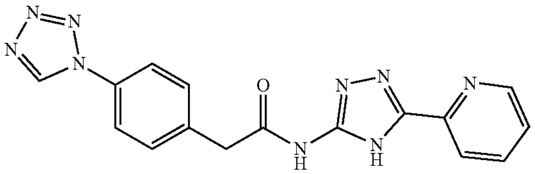 [SMILES: O=C(Cc1ccc(-n2cnnn2)cc1)Nc1nnc(-c2ccccn2)[nH]1] | 0 | A |
| 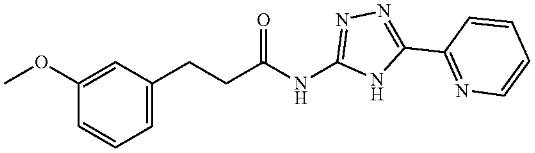 [SMILES: COc1cccc(CCC(=O)Nc2nnc(-c3ccccn3)[nH]2)c1] | 0 | A |
| 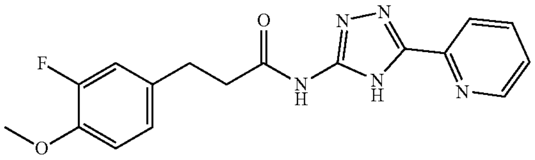 [SMILES: COc1ccc(CCC(=O)Nc2nnc(-c3ccccn3)[nH]2)cc1F] | A | B |
| 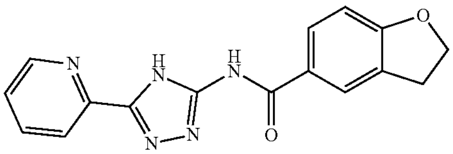 [SMILES: O=C(Nc1nnc(-c2ccccn2)[nH]1)c1ccc2c(c1)CCO2] | A | 0 |
| 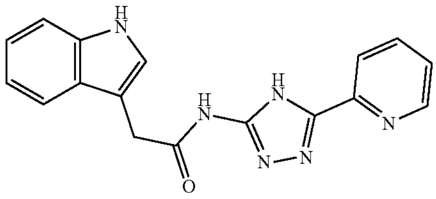 [SMILES: O=C(Cc1c[nH]c2ccccc12)Nc1nnc(-c2ccccn2)[nH]1] | B | A |
| 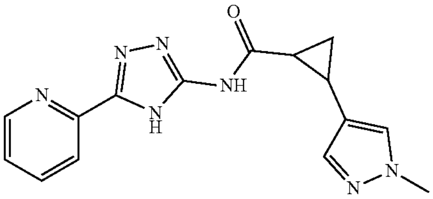 [SMILES: Cn1cc(C2CC2C(=O)Nc2nnc(-c3ccccn3)[nH]2)cn1] | 0 | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 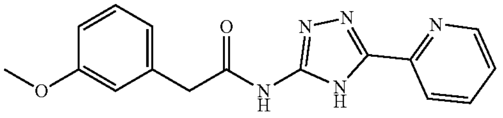 [SMILES: COc1cccc(CC(=O)Nc2nnc(-c3ccccn3)[nH]2)c1] | B | A |
| 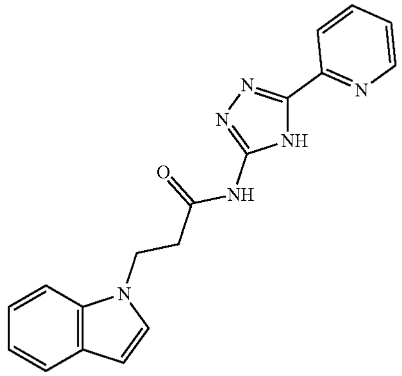 [SMILES: O=C(CCn1ccc2ccccc21)Nc1nnc(-c2ccccn2)[nH]1] | A | A |
| 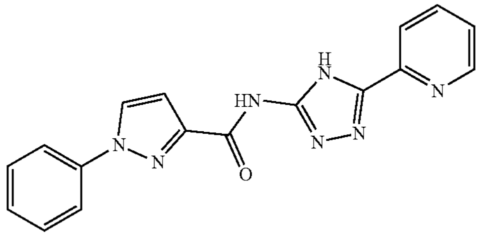 [SMILES: O=C(Nc1nnc(-c2ccccn2)[nH]1)c1ccn(-c2ccccc2)n1] | A | A |
| 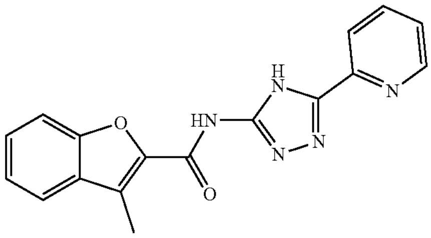 [SMILES: Cc1c(C(=O)Nc2nnc(-c3ccccn3)[nH]2)oc2ccccc12] | 0 | A |
| 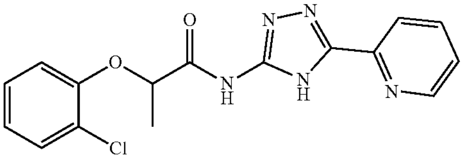 [SMILES: CC(Oc1ccccc1Cl)C(=O)Nc1nnc(-c2ccccn2)[nH]1] | B | A |
| 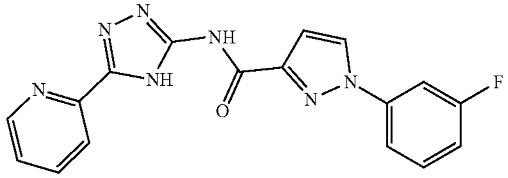 [SMILES: O=C(Nc1nnc(-c2ccccn2)[nH]1)c1ccn(-c2cccc(F)c2)n1] | B | 0 |
| 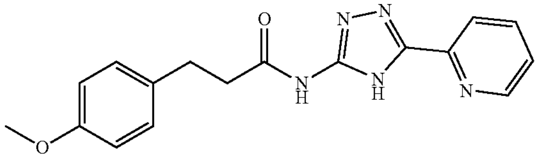 [SMILES: COc1ccc(CCC(=O)Nc2nnc(-c3ccccn3)[nH]2)cc1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 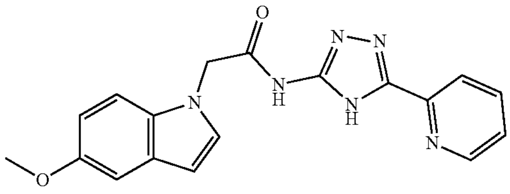 [SMILES: COc1ccc2c(ccn2CC(=O)Nc2nnc(-c3ccccn3)[nH]2)c1] | B | A |
| 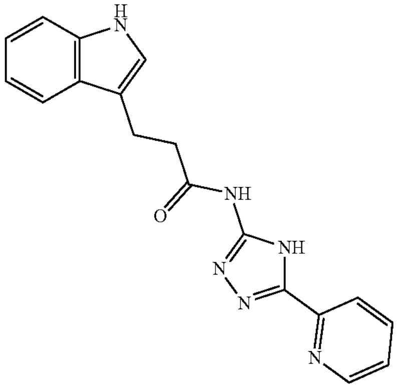 [SMILES: O=C(CCc1c[nH]c2ccccc12)Nc1nnc(-c2ccccn2)[nH]1] | C | 0 |
| 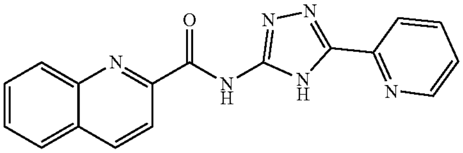 [SMILES: O=C(Nc1nnc(-c2ccccn2)[nH]1)c1ccc2ccccc2n1] | A | 0 |
| 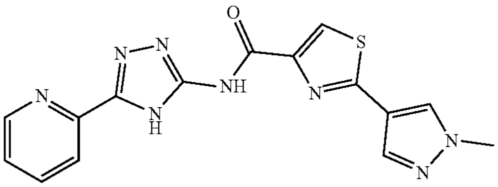 [SMILES: Cn1cc(-c2nc(C(=O)Nc3nnc(-c4ccccn4)[nH]3)cs2)cn1] | A | 0 |
| 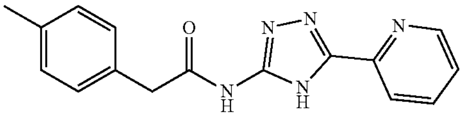 [SMILES: Cc1ccc(CC(=O)Nc2nnc(-c3ccccn3)[nH]2)cc1] | C | A |
| 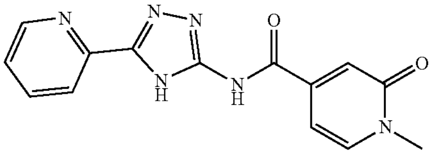 [SMILES: Cn1ccc(C(=O)Nc2nnc(-c3ccccn3)[nH]2)cc1=O] | 0 | A |
| 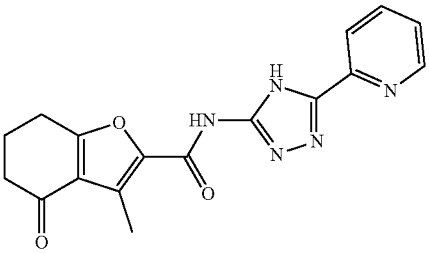 [SMILES: Cc1c(C(=O)Nc2nnc(-c3ccccn3)[nH]2)oc2c1C(=O)CCC2] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 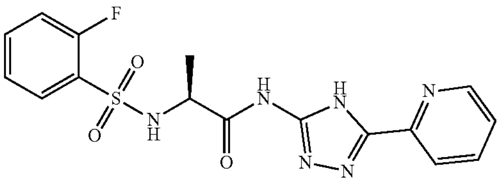 [SMILES: C[C@H](NS(=O)(=O)c1ccccc1F)C(=O)Nc1nnc(-c2ccccn2)[nH]1] | C | A |
| 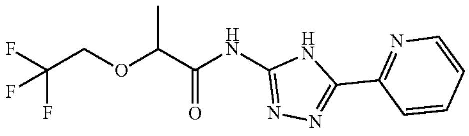 [SMILES: CC(OCC(F)(F)F)C(=O)Nc1nnc(-c2ccccn2)[nH]1] | 0 | A |
| 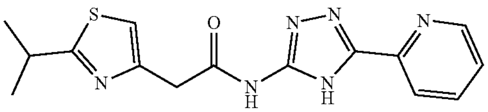 [SMILES: CC(C)c1nc(CC(=O)Nc2nnc(-c3ccccn3)[nH]2)cs1] | A | 0 |
| 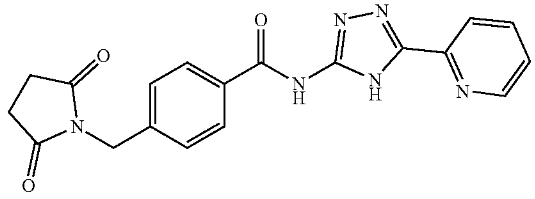 [SMILES: O=C(Nc1nnc(-c2ccccn2)[nH]1)c1ccc(CN2C(=O)CCC2=O)cc1] | 0 | A |
| 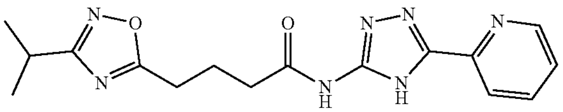 [SMILES: CC(C)c1noc(CCCC(=O)Nc2nnc(-c3ccccn3)[nH]2)n1] | 0 | A |
| 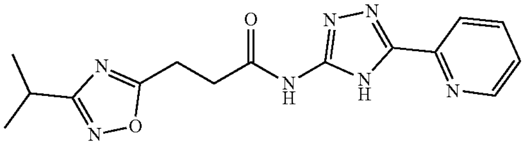 [SMILES: CC(C)c1noc(CCC(=O)Nc2nnc(-c3ccccn3)[nH]2)n1] | A | 0 |
| 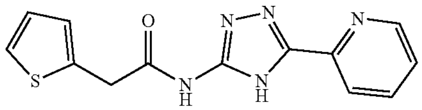 [SMILES: O=C(Cc1cccs1)Nc1nnc(-c2ccccn2)[nH]1] | A | A |
| 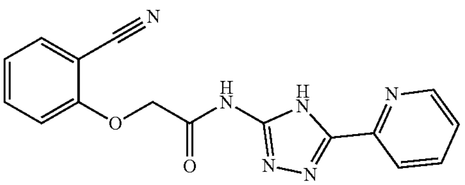 [SMILES: N#Cc1ccccc1OCC(=O)Nc1nnc(-c2ccccn2)[nH]1] | A | 0 |
| 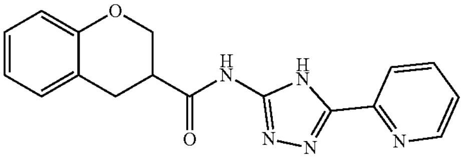 [SMILES: O=C(Nc1nnc(-c2ccccn2)[nH]1)C1COc2ccccc2C1] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 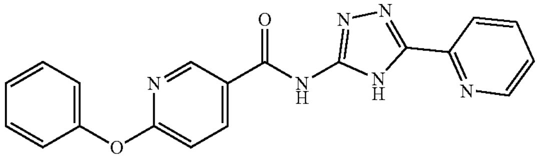 [SMILES: O=C(Nc1nnc(-c2ccccn2)[nH]1)c1ccc(Oc2ccccc2)nc1] | B | A |
| 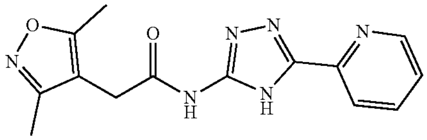 [SMILES: Cc1noc(C)c1CC(=O)Nc1nnc(-c2ccccn2)[nH]1] | A | 0 |
| 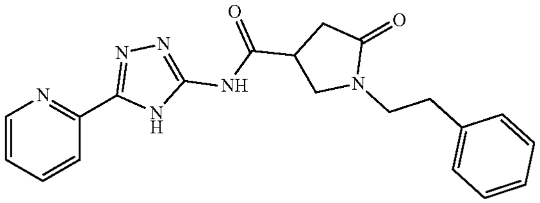 [SMILES: O=C(Nc1nnc(-c2ccccn2)[nH]1)C1CC(=O)N(CCc2ccccc2)C1] | A | 0 |
| 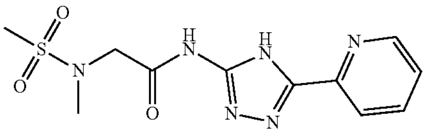 [SMILES: CN(CC(=O)Nc1nnc(-c2ccccn2)[nH]1)S(C)(=O)=O] | 0 | A |
| 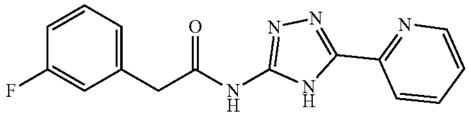 [SMILES: O=C(Cc1cccc(F)c1)Nc1nnc(-c2ccccn2)[nH]1] | A | 0 |
| 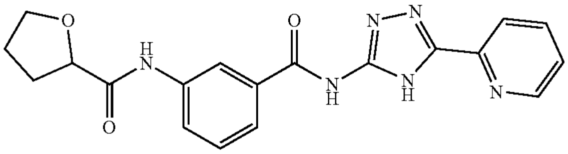 [SMILES: O=C(Nc1nnc(-c2ccccn2)[nH]1)c1cccc(NC(=O)C2CCCO2)c1] | A | 0 |
| 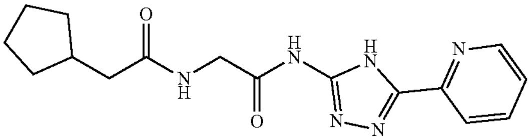 [SMILES: O=C(CC1CCCC1)NCC(=O)Nc1nnc(-c2ccccn2)[nH]1] | A | A |
| 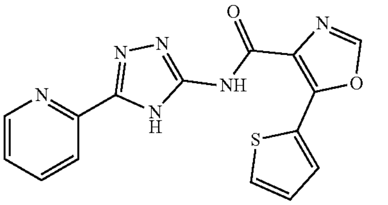 [SMILES: O=C(Nc1nnc(-c2ccccn2)[nH]1)c1ncoc1-c1cccs1] | B | A |
| 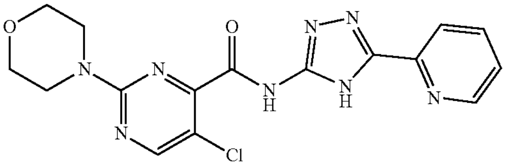 [SMILES: O=C(Nc1nnc(-c2ccccn2)[nH]1)c1nc(N2CCOCC2)ncc1Cl] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 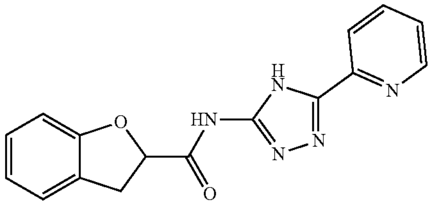 [SMILES: O=C(Nc1nnc(-c2ccccn2)[nH]1)C1Cc2ccccc2O1] | A | 0 |
| 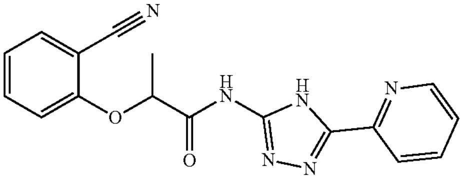 [SMILES: CC(Oc1ccccc1C#N)C(=O)Nc1nnc(-c2ccccn2)[nH]1] | 0 | A |
| 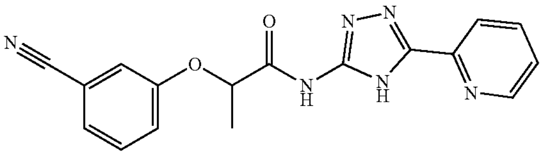 [SMILES: CC(Oc1cccc(C#N)c1)C(=O)Nc1nnc(-c2ccccn2)[nH]1] | A | 0 |
| 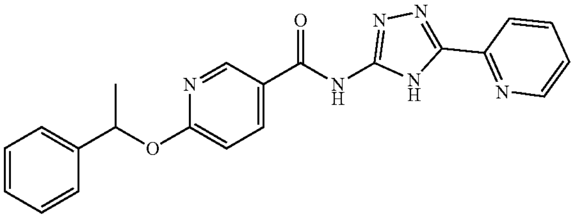 [SMILES: CC(Oc1ccc(C(=O)Nc2nnc(-c3ccccn3)[nH]2)cn1)c1ccccc1] | A | 0 |
| 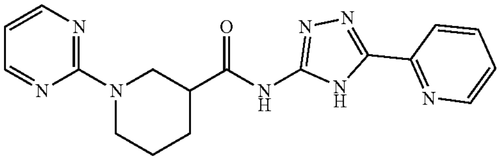 [SMILES: O=C(Nc1nnc(-c2ccccn2)[nH]1)C1CCCN(c2ncccn2)C1] | 0 | A |
| 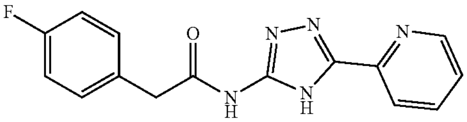 [SMILES: O=C(Cc1ccc(F)cc1)Nc1nnc(-c2ccccn2)[nH]1] | A | A |
| 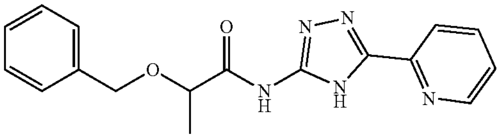 [SMILES: CC(OCc1ccccc1)C(=O)Nc1nnc(-c2ccccn2)[nH]1] | A | 0 |
| 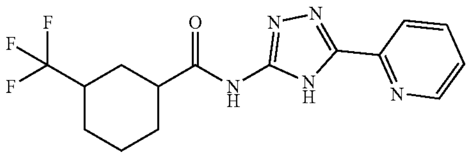 [SMILES: O=C(Nc1nnc(-c2ccccn2)[nH]1)C1CCCC(C(F)(F)F)C1] | A | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 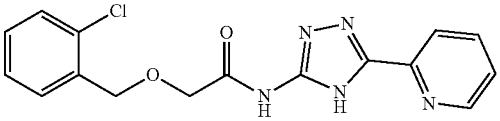 [SMILES: O=C(COCc1ccccc1Cl)Nc1nnc(-c2ccccn2)[nH]1] | B | A |
| 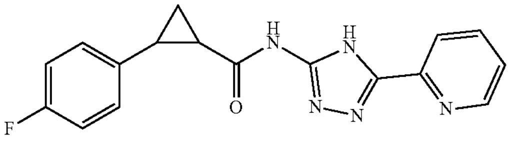 [SMILES: O=C(Nc1nnc(-c2ccccn2)[nH]1)C1CC1c1ccc(F)cc1] | A | A |
| 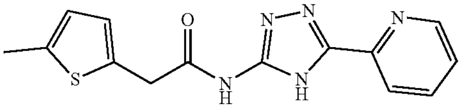 [SMILES: Cc1ccc(CC(=O)Nc2nnc(-c3ccccn3)[nH]2)s1] | A | 0 |
| 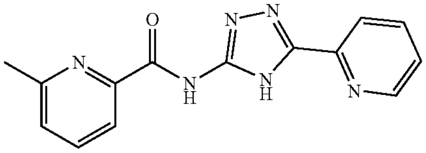 [SMILES: Cc1cccc(C(=O)Nc2nnc(-c3ccccn3)[nH]2)n1] | A | 0 |
| 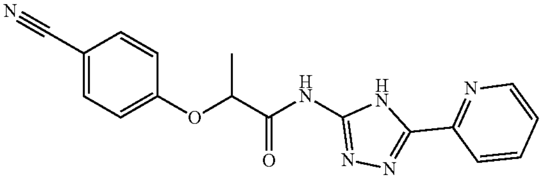 [SMILES: CC(Oc1ccc(C#N)cc1)C(=O)Nc1nnc(-c2ccccn2)[nH]1] | A | A |
| 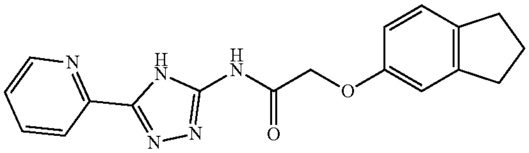 [SMILES: O=C(COc1ccc2c(c1)CCC2)Nc1nnc(-c2ccccn2)[nH]1] | A | 0 |
| 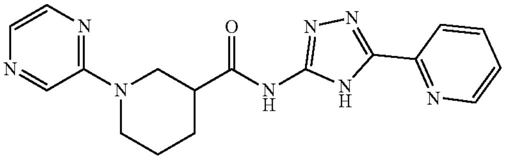 [SMILES: O=C(Nc1nnc(-c2ccccn2)[nH]1)C1CCCN(c2cnccn2)C1] | A | A |
| 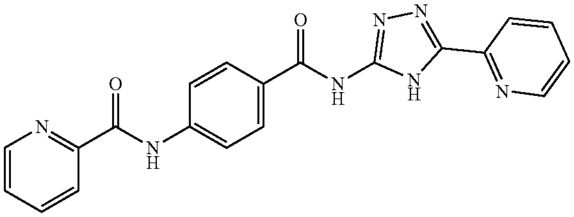 [SMILES: O=C(Nc1nnc(-c2ccccn2)[nH]1)c1ccc(NC(=O)c2ccccn2)cc1] | 0 | A |
| 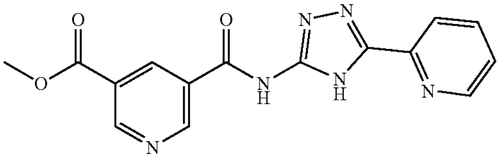 [SMILES: COC(=O)c1cncc(C(=O)Nc2nnc(-c3ccccn3)[nH]2)c1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 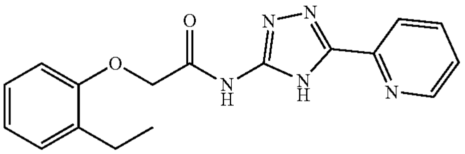 [SMILES: CCc1ccccc1OCC(=O)Nc1nnc(-c2ccccn2)[nH]1] | B | 0 |
| 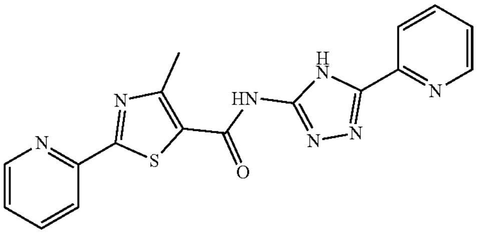 [SMILES: Cc1nc(-c2ccccn2)sc1C(=O)Nc1nnc(-c2ccccn2)[nH]1] | A | 0 |
| 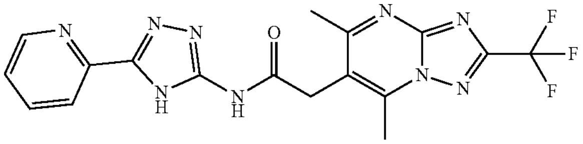 [SMILES: Cc1nc2nc(C(F)(F)F)nn2c(C)c1CC(=O)Nc1nnc(-c2ccccn2)[nH]1] | 0 | A |
| 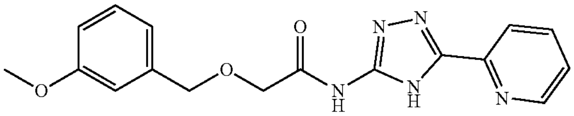 [SMILES: COc1cccc(COCC(=O)Nc2nnc(-c3ccccn3)[nH]2)c1] | B | A |
| 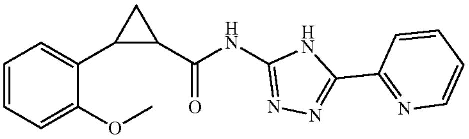 [SMILES: COc1ccccc1C1CC1C(=O)Nc1nnc(-c2ccccn2)[nH]1] | B | A |
| 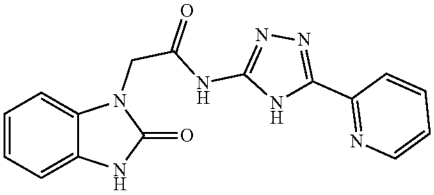 [SMILES: O=C(Cn1c(=O)[nH]c2ccccc21)Nc1nnc(-c2ccccn2)[nH]1] | A | A |
| 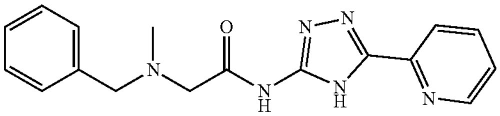 [SMILES: CN(CC(=O)Nc1nnc(-c2ccccn2)[nH]1)Cc1ccccc1] | B | A |
| 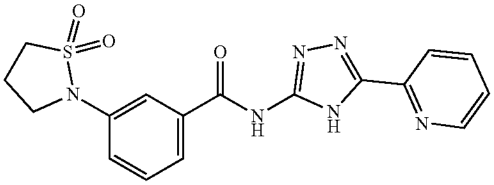 [SMILES: O=C(Nc1nnc(-c2ccccn2)[nH]1)c1cccc(N2CCCS2(=O)=O)c1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 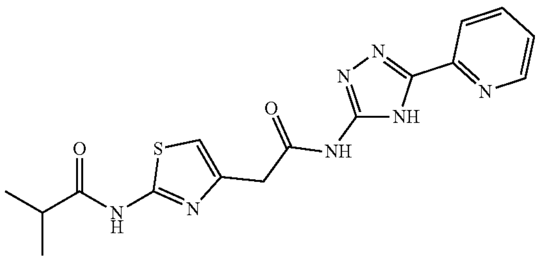 [SMILES: CC(C)C(=O)Nc1nc(CC(=O)Nc2nnc(-c3ccccn3)[nH]2)cs1] | 0 | A |
| 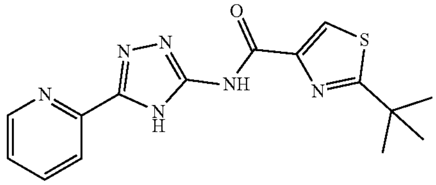 [SMILES: CC(C)(C)c1nc(C(=O)Nc2nnc(-c3ccccn3)[nH]2)cs1] | A | 0 |
| 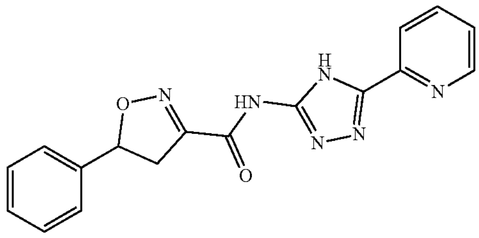 [SMILES: O=C(Nc1nnc(-c2ccccn2)[nH]1)C1=NOC(c2ccccc2)C1] | B | A |
| 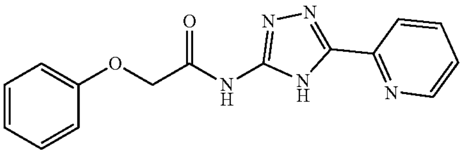 [SMILES: O=C(COc1ccccc1)Nc1nnc(-c2ccccn2)[nH]1] | A | 0 |
| 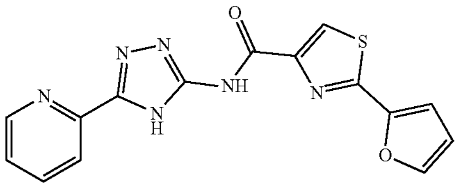 [SMILES: O=C(Nc1nnc(-c2ccccn2)[nH]1)c1csc(-c2ccco2)n1] | C | 0 |
| 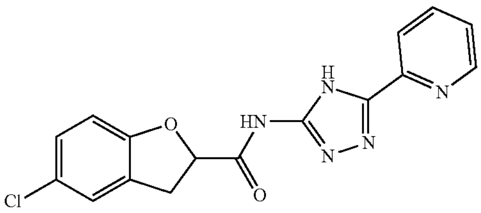 [SMILES: O=C(Nc1nnc(-c2ccccn2)[nH]1)C1Cc2cc(Cl)ccc2O1] | C | A |
| 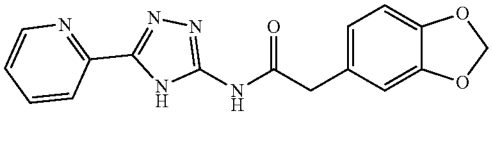 [SMILES: O=C(Cc1ccc2c(c1)OCO2)Nc1nnc(-c2ccccn2)[nH]1] | B | A |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 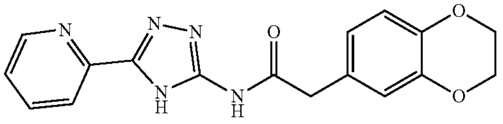 [SMILES: O=C(Cc1ccc2c(c1)OCCO2)Nc1nnc(-c2ccccn2)[nH]1] | 0 | A |
| 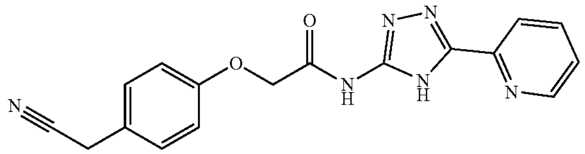 [SMILES: N#CCc1ccc(OCC(=O)Nc2nnc(-c3ccccn3)[nH]2)cc1] | 0 | A |
| 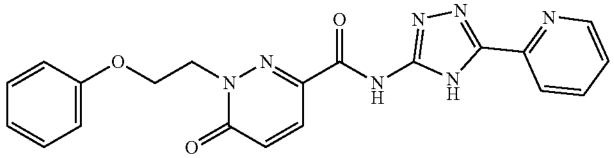 [SMILES: O=C(Nc1nnc(-c2ccccn2)[nH]1)c1ccc(=O)n(CCOc2ccccc2)n1] | B | 0 |
| 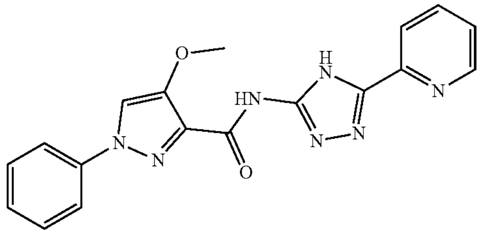 [SMILES: COc1cn(-c2ccccc2)nc1C(=O)Nc1nnc(-c2ccccn2)[nH]1] | B | 0 |
| 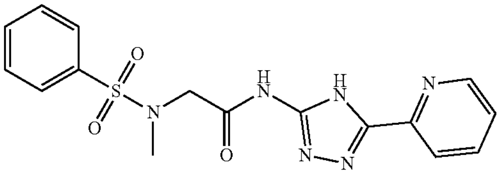 [SMILES: CN(CC(=O)Nc1nnc(-c2ccccn2)[nH]1)S(=O)(=O)c1ccccc1] | A | 0 |
| 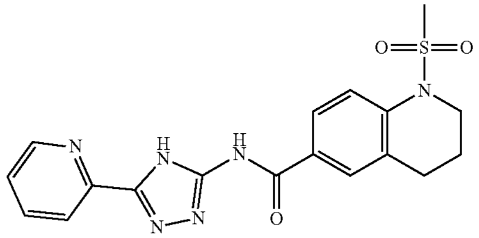 [SMILES: CS(=O)(=O)N1CCCc2cc(C(=O)Nc3nnc(-c4ccccn4)[nH]3)ccc21] | B | A |
| 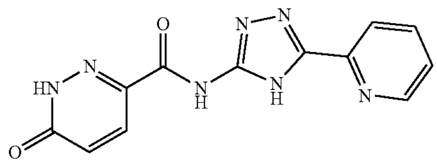 [SMILES: O=C(Nc1nnc(-c2ccccn2)[nH]1)c1ccc(=O)[nH]n1] | B | A |
| 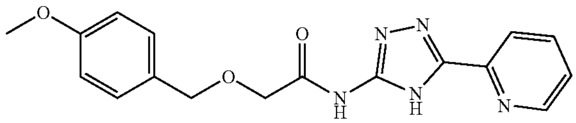 [SMILES: COc1ccc(COCC(=O)Nc2nnc(-c3ccccn3)[nH]2)cc1] | B | A |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 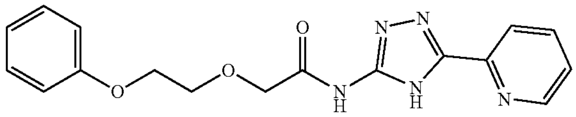 [SMILES: O=C(COCCOc1ccccc1)Nc1nnc(-c2ccccn2)[nH]1] | 0 | A |
| 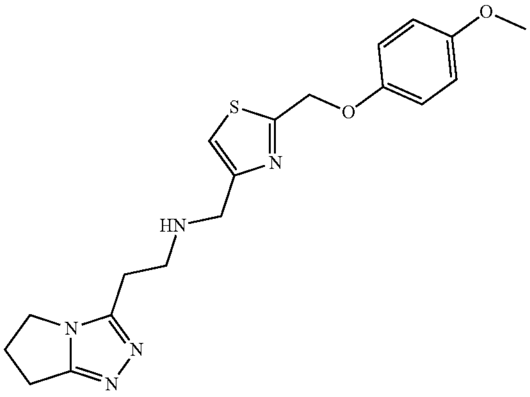 [SMILES: COc1ccc(OCc2nc(CNCCc3nnc4n3CCC4)cs2)cc1] | A | 0 |
| 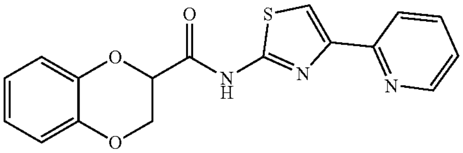 [SMILES: O=C(Nc1nc(-c2ccccn2)cs1)C1COc2ccccc2O1] | 0 | A |
| 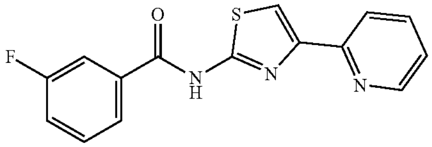 [SMILES: O=C(Nc1nc(-c2ccccn2)cs1)c1cccc(F)c1] | A | 0 |
| 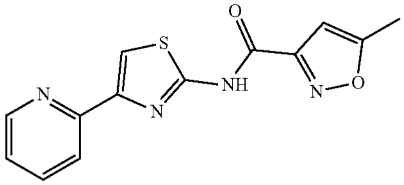 [SMILES: Cc1cc(C(=O)Nc2nc(-c3ccccn3)cs2)no1] | D | 0 |
| 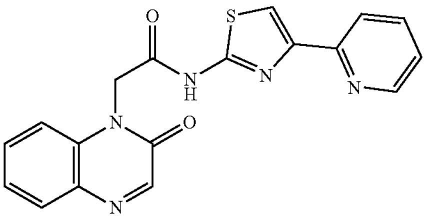 [SMILES: O=C(Cn1c(=O)cnc2ccccc21)Nc1nc(-c2ccccn2)cs1] | C | 0 |
| 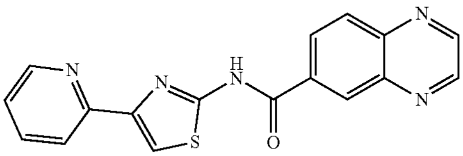 [SMILES: O=C(Nc1nc(-c2ccccn2)cs1)c1ccc2nccnc2c1] | C | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 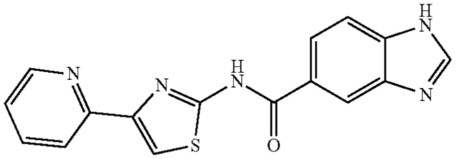 [SMILES: O=C(Nc1nc(-c2ccccn2)cs1)c1ccc2[nH]cnc2c1] | B | A |
| 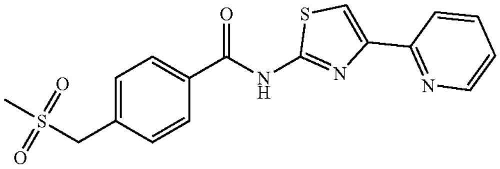 [SMILES: CS(=O)(=O)Cc1ccc(C(=O)Nc2nc(-c3ccccn3)cs2)cc1] | 0 | A |
| 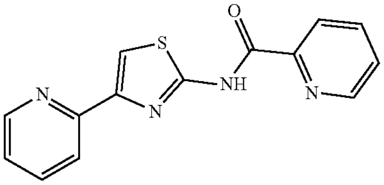 [SMILES: O=C(Nc1nc(-c2ccccn2)cs1)c1ccccn1] | C | A |
| 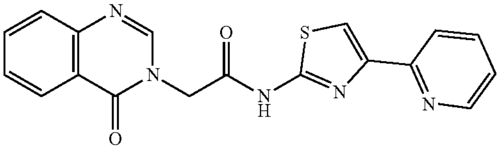 [SMILES: O=C(Cn1cnc2ccccc2c1=O)Nc1nc(-c2ccccn2)cs1] | C | A |
| 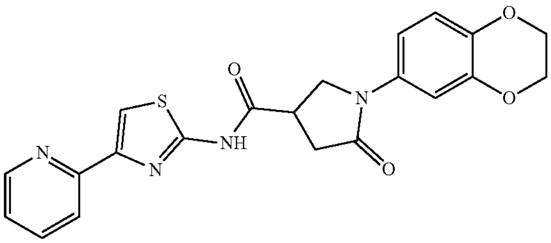 [SMILES: O=C(Nc1nc(-c2ccccn2)cs1)C1CC(=O)N(c2ccc3c(c2)OCCO3)C1] | B | A |
| 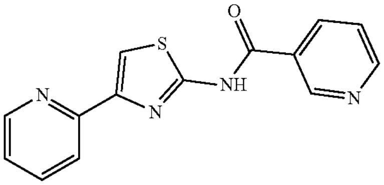 [SMILES: O=C(Nc1nc(-c2ccccn2)cs1)c1cccnc1] | A | A |
| 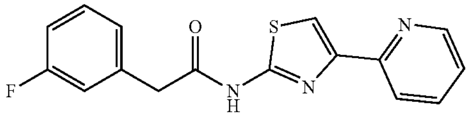 [SMILES: O=C(Cc1cccc(F)c1)Nc1nc(-c2ccccn2)cs1] | A | A |
| 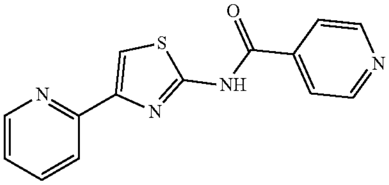 [SMILES: O=C(Nc1nc(-c2ccccn2)cs1)c1ccncc1] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 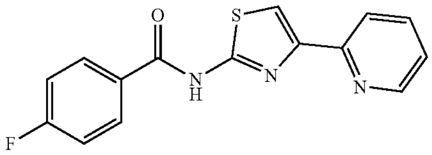 [SMILES: O=C(Nc1nc(-c2ccccn2)cs1)c1ccc(F)cc1] | B | B |
| 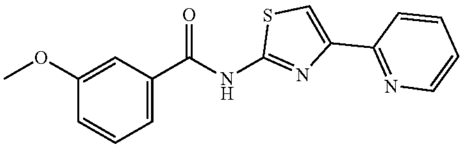 [SMILES: COc1cccc(C(=O)Nc2nc(-c3ccccn3)cs2)c1] | A | 0 |
| 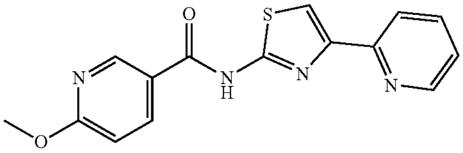 [SMILES: COc1ccc(C(=O)Nc2nc(-c3ccccn3)cs2)cn1] | D | C |
| 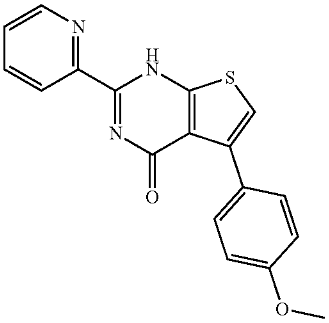 [SMILES: COc1ccc(-c2csc3[nH]c(-c4ccccn4)nc(=O)c23)cc1] | B | A |
| 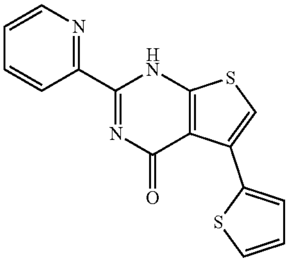 [SMILES: O=c1nc(-c2ccccn2)[nH]c2scc(-c3cccs3)c12] | 0 | A |
| 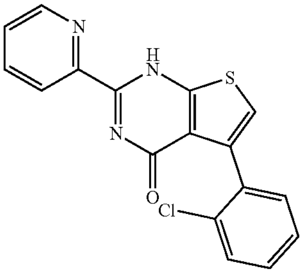 [SMILES: O=c1nc(-c2ccccn2)[nH]c2scc(-c3ccccc3Cl)c12] | 0 | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 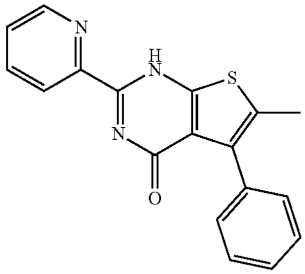 [SMILES: Cc1sc2[nH]c(-c3ccccn3)nc(=O)c2c1-c1ccccc1] | 0 | A |
| 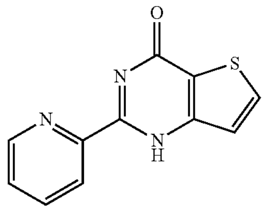 [SMILES: O=c1nc(-c2ccccn2)[nH]c2ccsc12] | A | 0 |
| 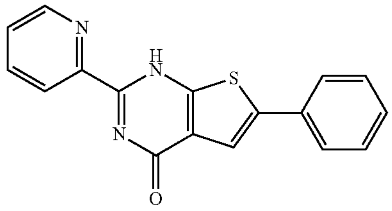 [SMILES: O=c1nc(-c2ccccn2)[nH]c2sc(-c3ccccc3)cc12] | C | D |
| 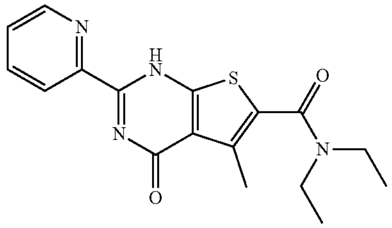 [SMILES: CCN(CC)C(=O)c1sc2[nH]c(-c3ccccn3)nc(=O)c2c1C] | A | A |
| 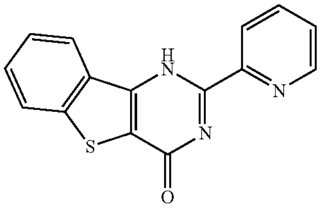 [SMILES: O=c1nc(-c2ccccn2)[nH]c2c1sc1ccccc12] | D | D |
| 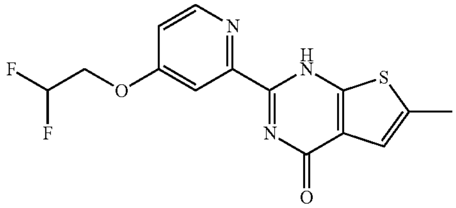 [SMILES: Cc1cc2c(=O)nc(-c3cc(OCC(F)F)ccn3)[nH]c2s1] | A | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 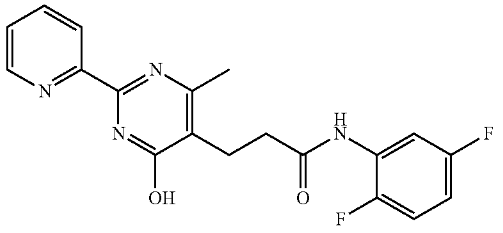 [SMILES: Cc1nc(-c2ccccn2)nc(O)c1CCC(=O)Nc1cc(F)ccc1F] | A | A |
| 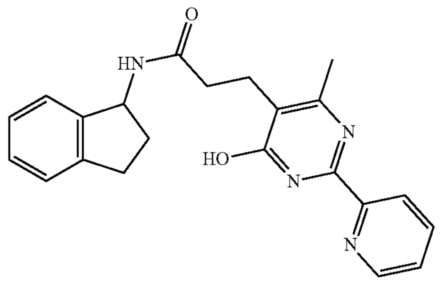 [SMILES: Cc1nc(-c2ccccn2)nc(O)c1CCC(=O)NC1CCc2ccccc21] | B | B |
| 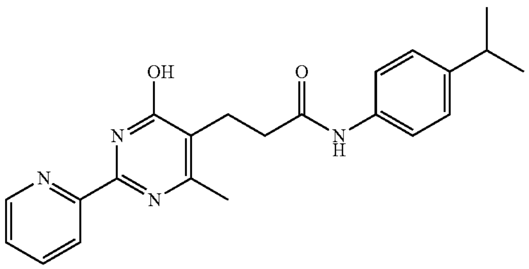 [SMILES: Cc1nc(-c2ccccn2)nc(O)c1CCC(=O)Nc1ccc(C(C)C)cc1] | 0 | A |
| 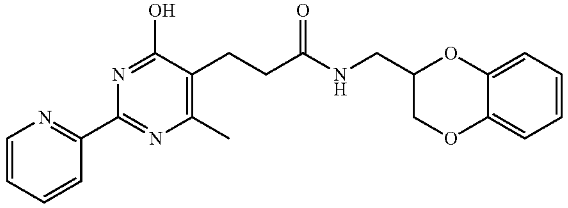 [SMILES: Cc1nc(-c2ccccn2)nc(O)c1CCC(=O)NCC1COc2ccccc2O1] | 0 | A |
| 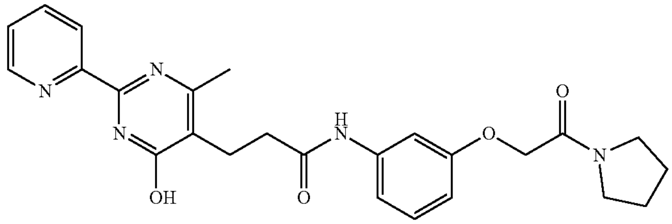 [SMILES: Cc1nc(-c2ccccn2)nc(O)c1CCC(=O)Nc1cccc(OCC(=O)N2CCCC2)c1] | 0 | A |
| 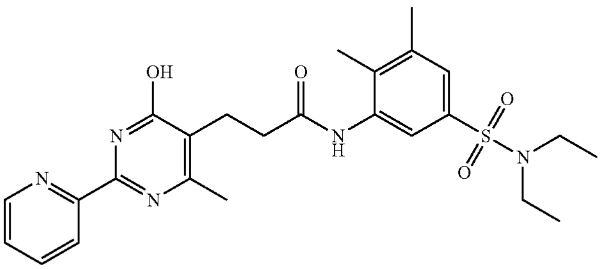 [SMILES: CCN(CC)S(=O)(=O)c1cc(C)c(C)c(NC(=O)CCc2c(C)nc(-c3ccccn3)nc2O)c1] | 0 | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 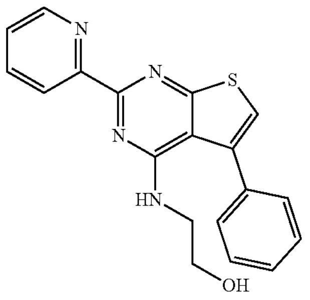 [SMILES: OCCNc1nc(-c2ccccn2)nc2scc(-c3ccccc3)c12] | A | 0 |
| 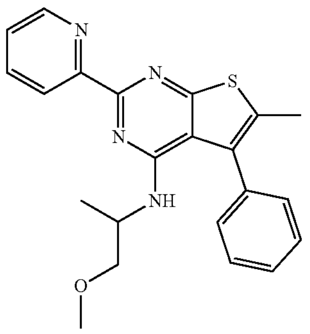 [SMILES: COCC(C)Nc1nc(-c2ccccn2)nc2sc(C)c(-c3ccccc3)c12] | D | D |
| 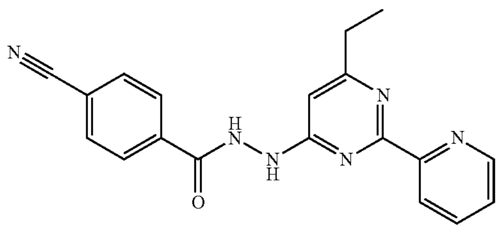 [SMILES: CCc1cc(NNC(=O)c2ccc(C#N)cc2)nc(-c2ccccn2)n1] | D | D |
| 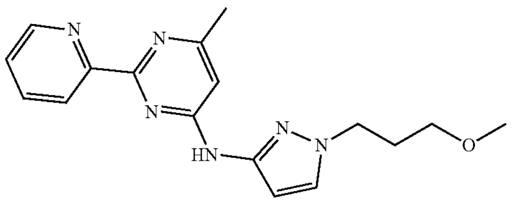 [SMILES: COCCCn1ccc(Nc2cc(C)nc(-c3ccccn3)n2)n1] | B | 0 |
| 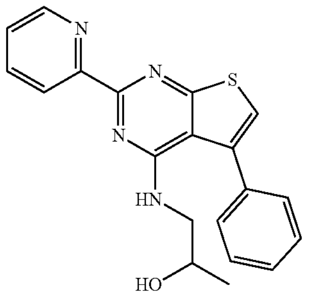 [SMILES: CC(O)CNc1nc(-c2ccccn2)nc2scc(-c3ccccc3)c12] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 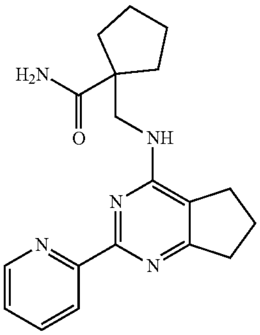 [SMILES: NC(=O)C1(CNc2nc(-c3ccccn3)nc3c2CCC3)CCCC1] | B | A |
| 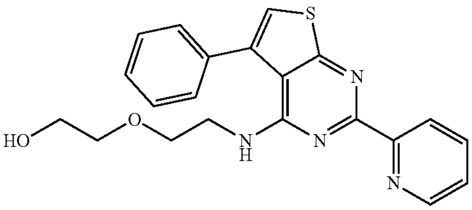 [SMILES: OCCOCCNc1nc(-c2ccccn2)nc2scc(-c3ccccc3)c12] | A | A |
| 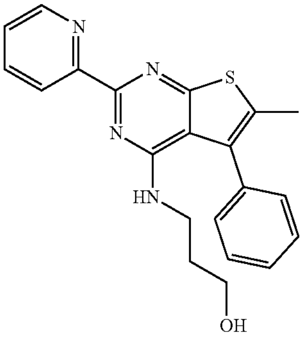 [SMILES: Cc1sc2nc(-c3ccccn3)nc(NCCCO)c2c1-c1ccccc1] | A | A |
| 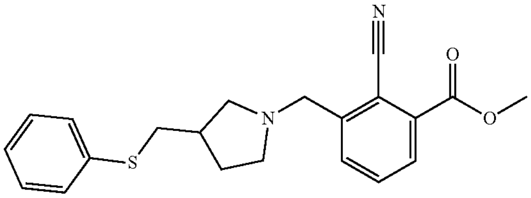 [SMILES: COC(=O)c1cccc(CN2CCC(CSc3ccccc3)C2)c1C#N] | B | 0 |
| 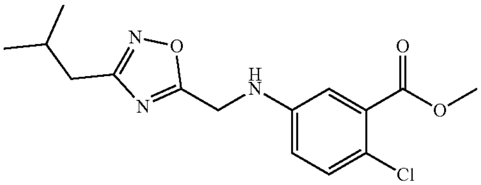 [SMILES: COC(=O)c1cc(NCc2nc(CC(C)C)no2)ccc1Cl] | B | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 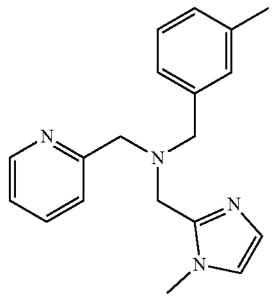 [SMILES: Cc1cccc(CN(Cc2ccccn2)Cc2nccn2C)c1] | B | A |
| 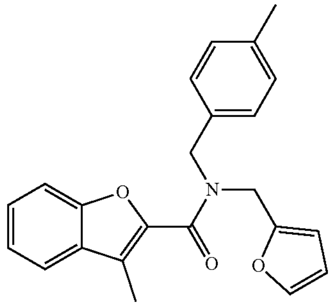 [SMILES: Cc1ccc(CN(Cc2ccco2)C(=O)c2oc3ccccc3c2C)cc1] | A | 0 |
| 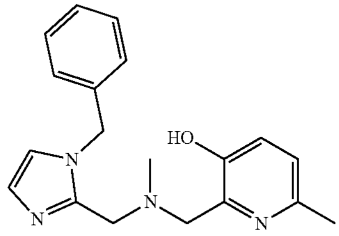 [SMILES: Cc1ccc(O)c(CN(C)Cc2nccn2Cc2ccccc2)n1] | A | 0 |
| 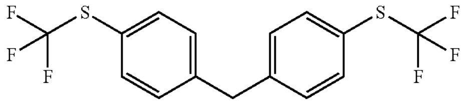 [SMILES: FC(F)(F)Sc1ccc(Cc2ccc(SC(F)(F)F)cc2)cc1] | A | 0 |
| 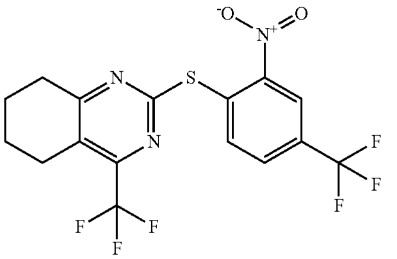 | 0 | A |
| 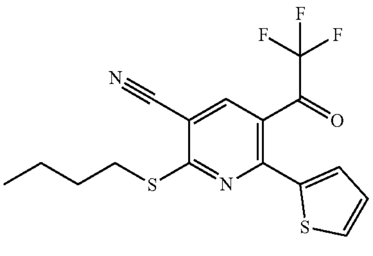 [SMILES: CCCCSc1nc(-c2cccs2)c(C(=O)C(F)(F)F)cc1C#N] | C | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 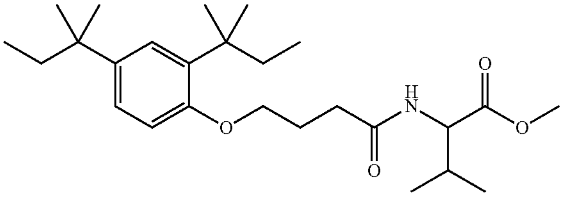 [SMILES: CCC(C)(C)c1ccc(OCCCC(=O)NC(C(=O)OC)C(C)C)c(C(C)(C)CC)c1] | B | B |
| 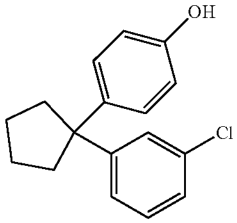 [SMILES: Oc1ccc(C2(c3cccc(Cl)c3)CCCC2)cc1] | D | D |
| 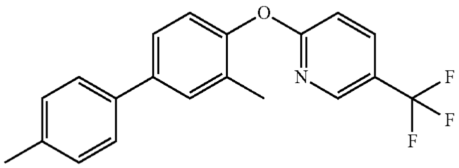 [SMILES: Cc1ccc(-c2ccc(Oc3ccc(C(F)(F)F)cn3)c(C)c2)cc1] | 0 | A |
| 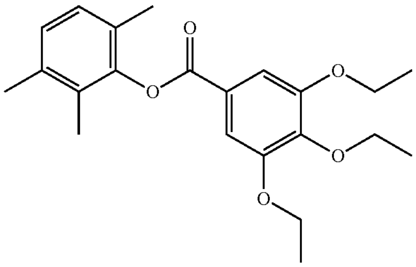 [SMILES: CCOc1cc(C(=O)Oc2c(C)ccc(C)c2C)cc(OCC)c1OCC] | C | A |
| 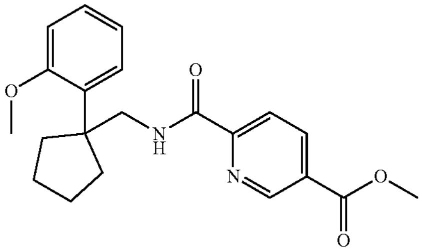 [SMILES: COC(=O)c1ccc(C(=O)NCC2(c3ccccc3OC)CCCC2)nc1] | 0 | A |
| 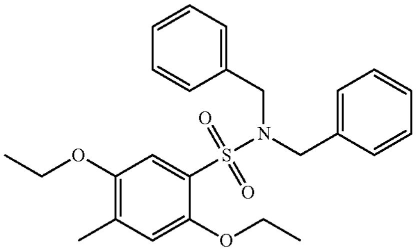 [SMILES: CCOc1cc(S(=O)(=O)N(Cc2ccccc2)Cc2ccccc2)c(OCC)cc1C] | A | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 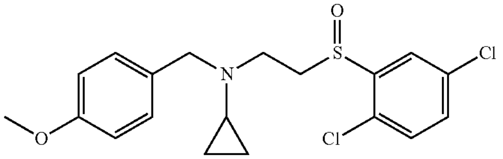 [SMILES: COc1ccc(CN(CCS(=O)c2cc(Cl)ccc2Cl)C2CC2)cc1] | 0 | A |
| 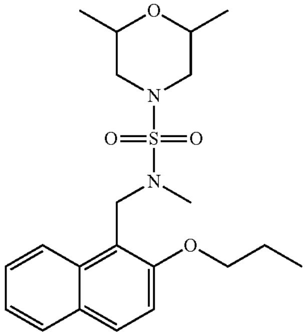 [SMILES: CCCOc1ccc2ccccc2c1CN(C)S(=O)(=O)N1CC(C)OC(C)C1] | A | C |
| 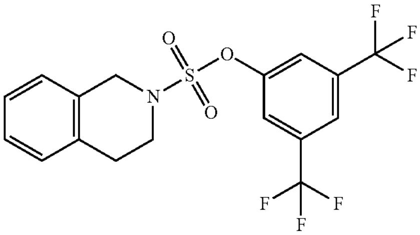 [SMILES: O=S(=O)(Oc1cc(C(F)(F)F)cc(C(F)(F)F)c1)N1CCc2ccccc2C1] | C | 0 |
| 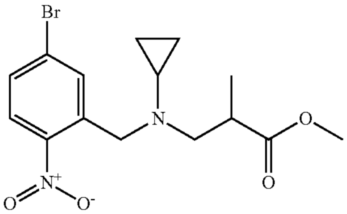 [SMILES: COC(=O)C(C)CN(Cc1cc(Br)ccc1[N+](=O)[O-])C1CC1] | B | 0 |
| 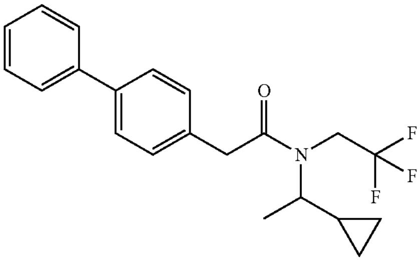 [SMILES: CC(C1CC1)N(CC(F)(F)F)C(=O)Cc1ccc(-c2ccccc2)cc1] | A | A |
| 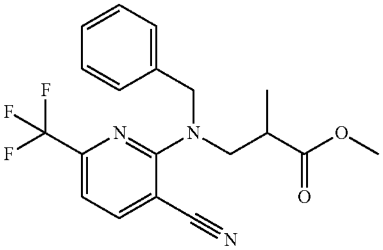 [SMILES: COC(=O)C(C)CN(Cc1ccccc1)c1nc(C(F)(F)F)ccc1C#N] | B | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 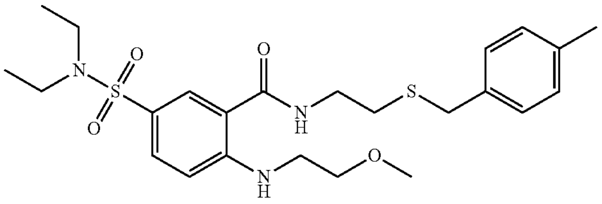 [SMILES: CCN(CC)S(=O)(=O)c1ccc(NCCOC)c(C(=O)NCCSCc2ccc(C)cc2)c1] | B | B |
| 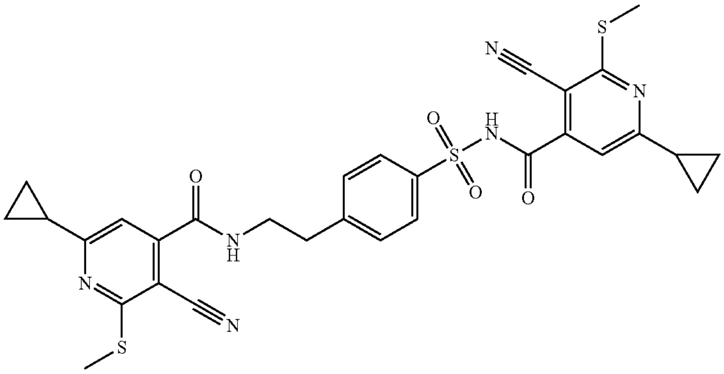 [SMILES: CSc1nc(C2CC2)cc(C(=O)NCCc2ccc(S(=O)(=O)NC(=O)c3cc(C4CC4)nc(SC)c3C#N)cc2)c1C#N] | A | B |
| 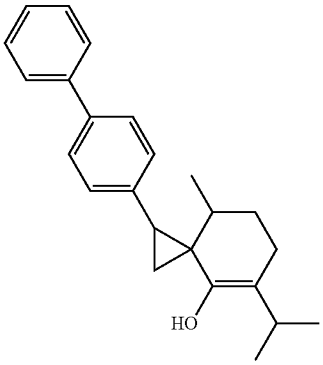 [SMILES: CC(C)C1=C(O)C2(CC2c2ccc(-c3ccccc3)cc2)C(C)CC1] | 0 | A |
| 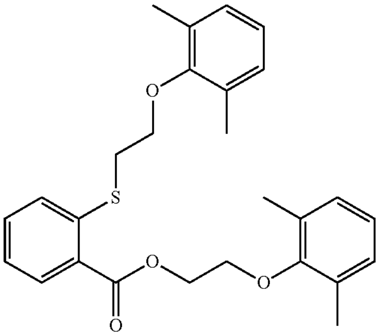 [SMILES: Cc1cccc(C)c1OCCOC(=O)c1ccccc1SCCOc1c(C)cccc1C] | A | 0 |
| 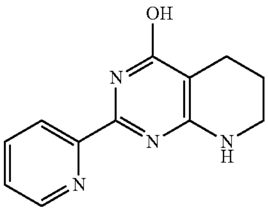 [SMILES: Oc1nc(-c2ccccn2)nc2c1CCCN2] | B | A |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 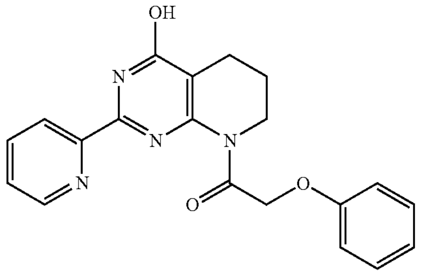 [SMILES: O=C(COc1ccccc1)N1CCCc2c(O)nc(-c3ccccn3)nc21] | D | A |
| 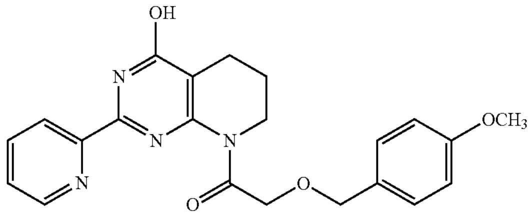 [SMILES: COc1ccc(COCC(=O)N2CCCc3c(O)nc(-c4ccccn4)nc32)cc1] | C | A |
| 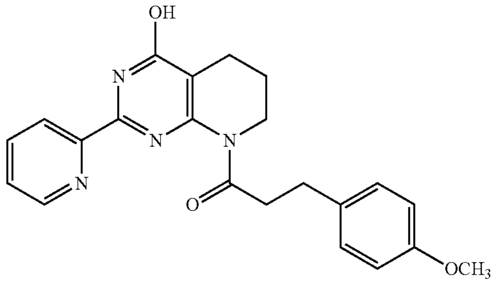 [SMILES: COc1ccc(CCC(=O)N2CCCc3c(O)nc(-c4ccccn4)nc32)cc1] | D | B |
| 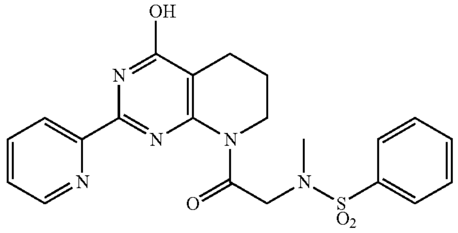 [SMILES: CN(CC(=O)N1CCCc2c(O)nc(-c3ccccn3)nc21)S(=O)(=O)c1ccccc1] | A | 0 |
| 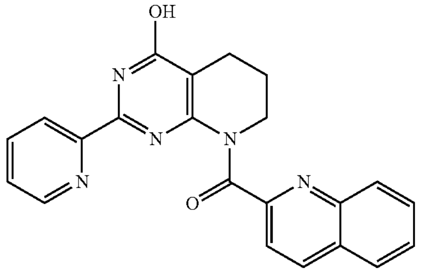 [SMILES: O=C(c1ccc2ccccc2n1)N1CCCc2c(O)nc(-c3ccccn3)nc21] | D | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 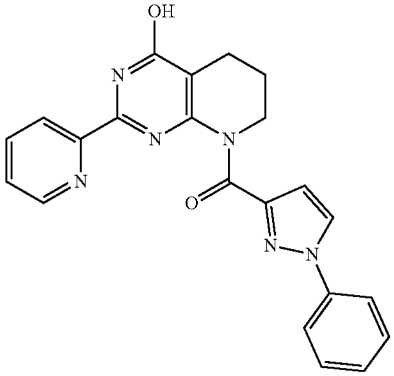 [SMILES: O=C(c1ccn(-c2ccccc2)n1)N1CCCc2c(O)nc(-c3ccccn3)nc21] | D | B |
| 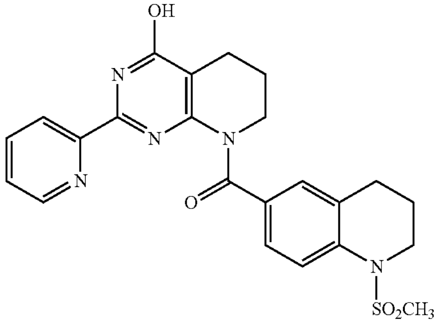 [SMILES: CS(=O)(=O)N1CCCc2cc(C(=O)N3CCCc4c(O)nc(-c5ccccn5)nc43)ccc21] | D | A |
| 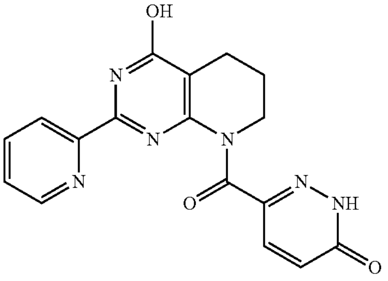 [SMILES: O=C(c1ccc(=O)[nH]n1)N1CCCc2c(O)nc(-c3ccccn3)nc21] | D | A |
| 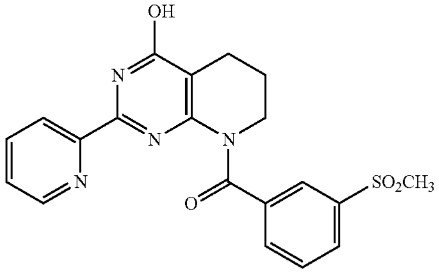 [SMILES: CS(=O)(=O)c1cccc(C(=O)N2CCCc3c(O)nc(-c4ccccn4)nc32)c1] | C | 0 |
| 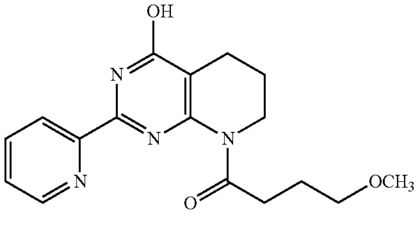 [SMILES: COCCCC(=O)N1CCCc2c(O)nc(-c3ccccn3)nc21] | D | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 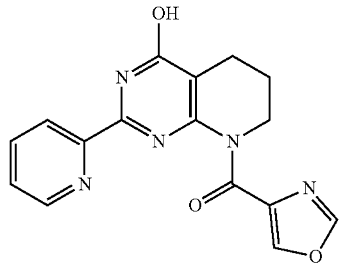 [SMILES: O=C(c1cocn1)N1CCCc2c(O)nc(-c3ccccn3)nc21] | A | A |
| 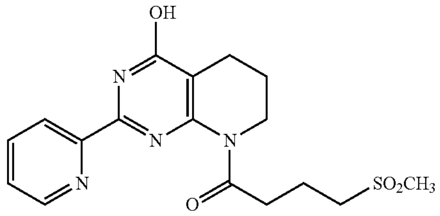 [SMILES: CS(=O)(=O)CCCC(=O)N1CCCc2c(O)nc(-c3ccccn3)nc21] | B | 0 |
| 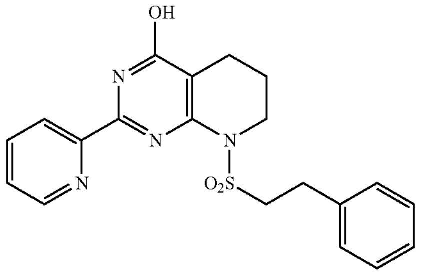 [SMILES: O=S(=O)(CCc1ccccc1)N1CCCc2c(O)nc(-c3ccccn3)nc21] | B | 0 |
| 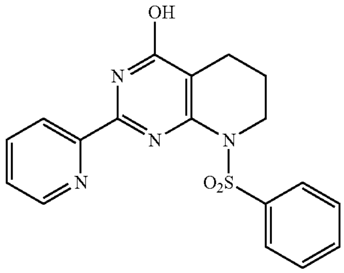 [SMILES: O=S(=O)(c1ccccc1)N1CCCc2c(O)nc(-c3ccccn3)nc21] | 0 | A |
| 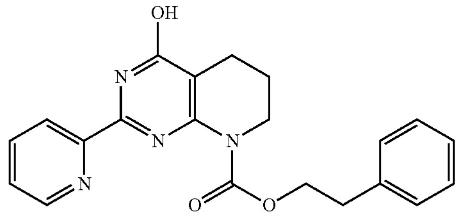 [SMILES: O=C(OCCc1ccccc1)N1CCCc2c(O)nc(-c3ccccn3)nc21] | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 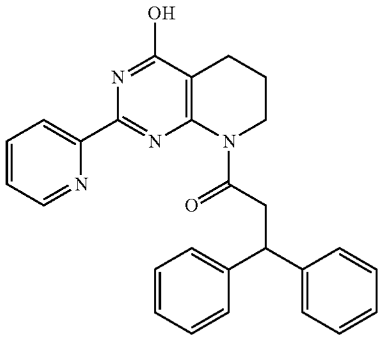 [SMILES: O=C(CC(c1ccccc1)c1ccccc1)N1CCCc2c(O)nc(-c3ccccn3)nc21] | B | 0 |
| 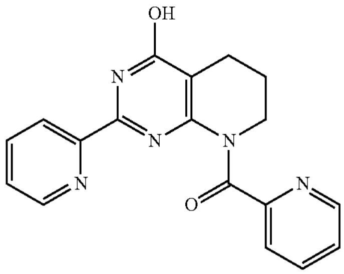 [SMILES: O=C(c1ccccn1)N1CCCc2c(O)nc(-c3ccccn3)nc21] | A | A |
| 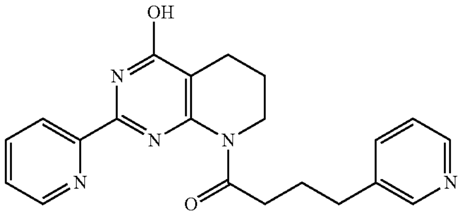 [SMILES: O=C(CCCc1cccnc1)N1CCCc2c(O)nc(-c3ccccn3)nc21] | D | A |
| 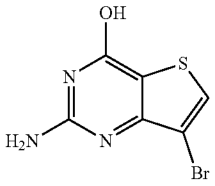 [SMILES: Nc1nc(O)c2scc(Br)c2n1] | A | A |
| 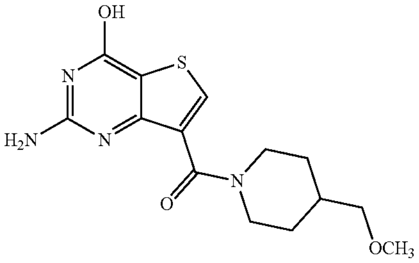 [SMILES: COCC1CCN(C(=O)c2csc3c(O)nc(N)nc23)CC1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 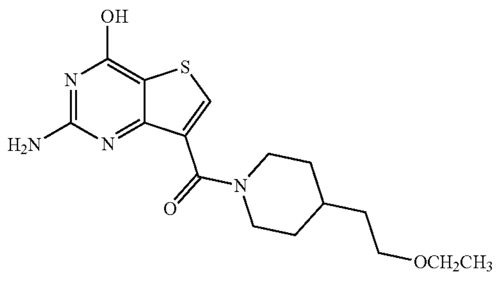 [SMILES: CCOCCC1CCN(C(=O)c2csc3c(O)nc(N)nc23)CC1] | 0 | A |
| 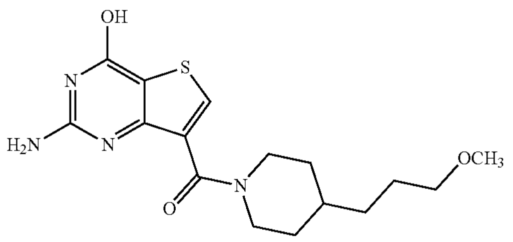 [SMILES: COCCCC1CCN(C(=O)c2csc3c(O)nc(N)nc23)CC1] | 0 | A |
| 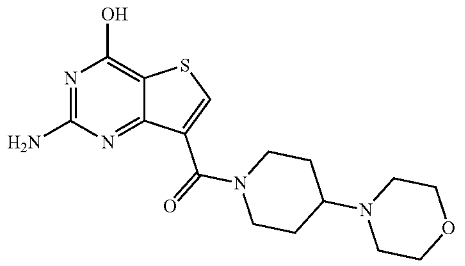 [SMILES: Nc1nc(O)c2scc(C(=O)N3CCC(N4CCOCC4)CC3)c2n1] | 0 | A |
| 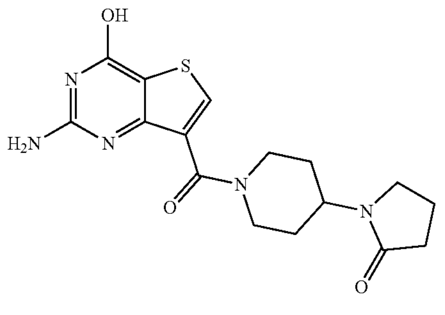 [SMILES: Nc1nc(O)c2scc(C(=O)N3CCC(N4CCCC4=O)CC3)c2n1] | A | 0 |
| 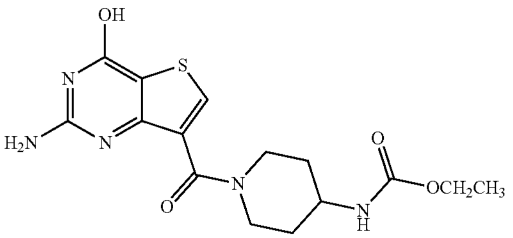 [SMILES: CCOC(=O)NC1CCN(C(=O)c2csc3c(O)nc(N)nc23)CC1] | 0 | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 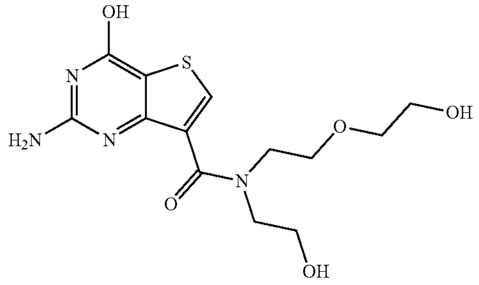 [SMILES: Nc1nc(O)c2scc(C(=O)N(CCO)CCOCCO)c2n1] | A | 0 |
| 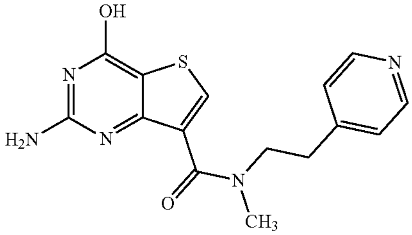 [SMILES: CN(CCc1ccncc1)C(=O)c1csc2c(O)nc(N)nc12] | A | 0 |
| 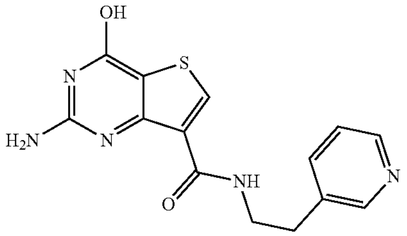 [SMILES: Nc1nc(O)c2scc(C(=O)NCCc3cccnc3)c2n1] | A | A |
| 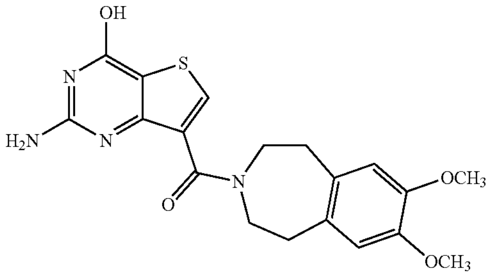 [SMILES: COc1cc2c(cc1OC)CCN(C(=O)c1csc3c(O)nc(N)nc13)CC2] | A | A |
| 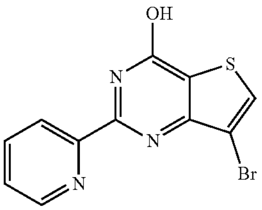 [SMILES: Oc1nc(-c2ccccn2)nc2c(Br)csc12] | D | D |
| 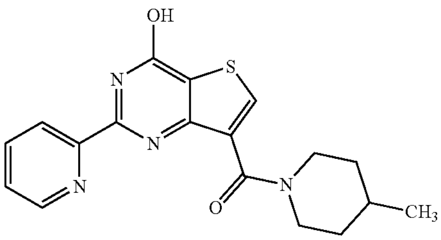 [SMILES: CC1CCN(C(=O)c2csc3c(O)nc(-c4ccccn4)nc23)CC1] | B | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 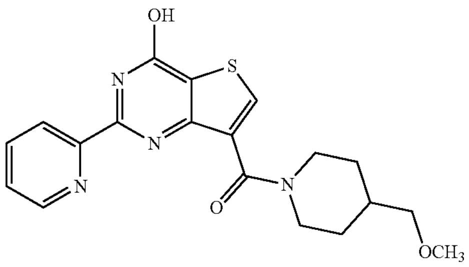 [SMILES: COCC1CCN(C(=O)c2csc3c(O)nc(-c4ccccn4)nc23)CC1] | D | A |
| 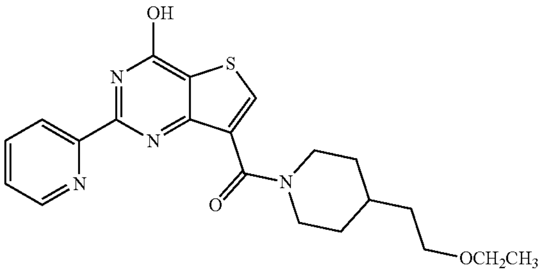 [SMILES: CCOCCC1CCN(C(=O)c2csc3c(O)nc(-c4ccccn4)nc23)CC1] | D | A |
| 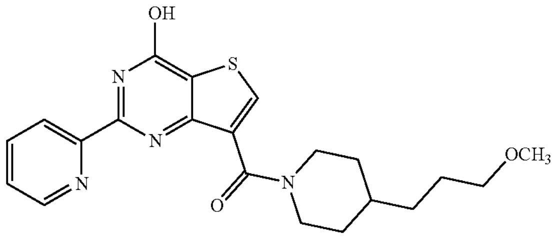 [SMILES: COCCCC1CCN(C(=O)c2csc3c(O)nc(-c4ccccn4)nc23)CC1] | C | A |
| 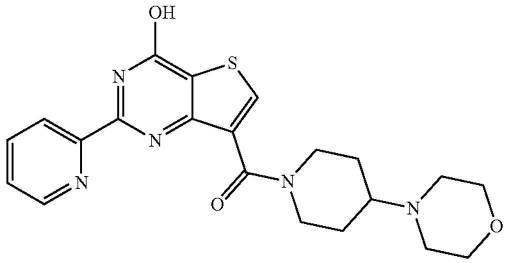 [SMILES: O=C(c1csc2c(O)nc(-c3ccccn3)nc12)N1CCC(N2CCOCC2)CC1] | A | 0 |
| 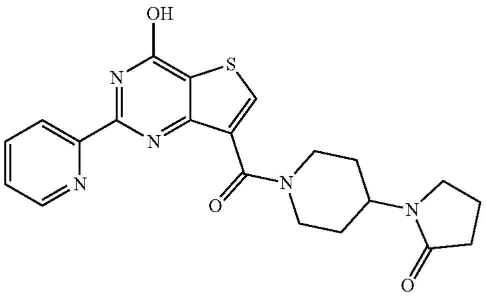 [SMILES: O=C(c1csc2c(O)nc(-c3ccccn3)nc12)N1CCC(N2CCCC2=O)CC1] | A | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 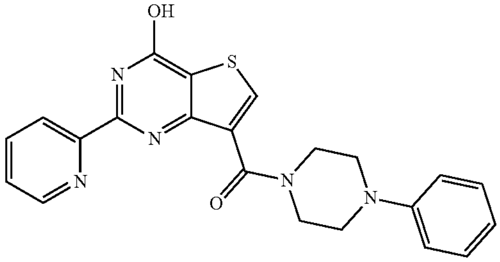 [SMILES: O=C(c1csc2c(O)nc(-c3ccccn3)nc12)N1CCN(c2ccccc2)CC1] | D | C |
| 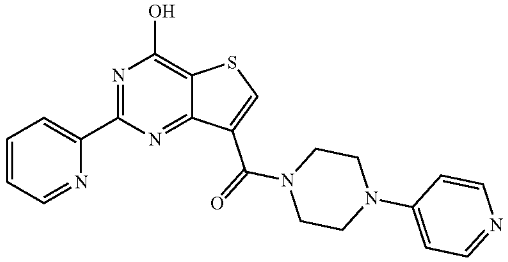 [SMILES: O=C(c1csc2c(O)nc(-c3ccccn3)nc12)N1CCN(c2ccncc2)CC1] | A | 0 |
| 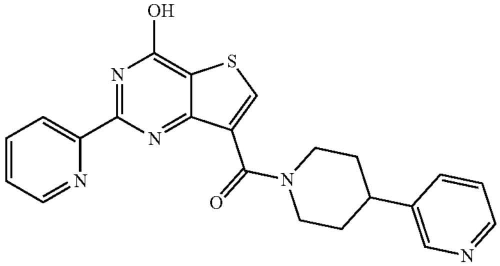 [SMILES: O=C(c1csc2c(O)nc(-c3ccccn3)nc12)N1CCC(c2cccnc2)CC1] | D | A |
| 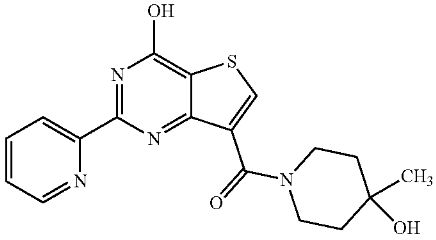 [SMILES: CC1(O)CCN(C(=O)c2csc3c(O)nc(-c4ccccn4)nc23)CC1] | C | 0 |
| 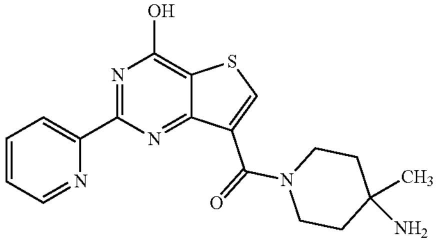 [SMILES: CC1(N)CCN(C(=O)c2csc3c(O)nc(-c4ccccn4)nc23)CC1] | A | 0 |
| 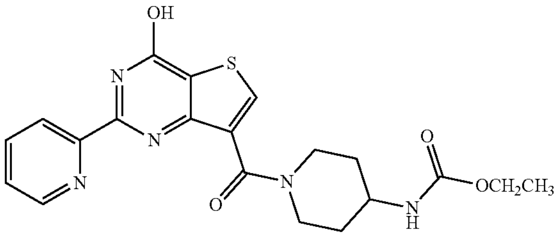 [SMILES: CCOC(=O)NC1CCN(C(=O)c2csc3c(O)nc(-c4ccccn4)nc23)CC1] | C | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 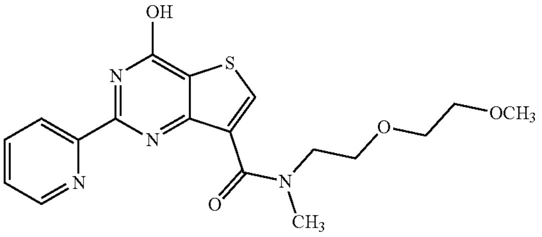 [SMILES: COCCOCCN(C)C(=O)c1csc2c(O)nc(-c3ccccn3)nc12] | B | 0 |
| 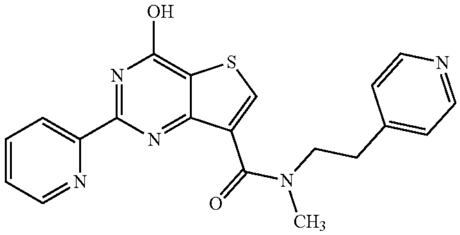 [SMILES: CN(CCc1ccncc1)C(=O)c1csc2c(O)nc(-c3ccccn3)nc12] | C | 0 |
| 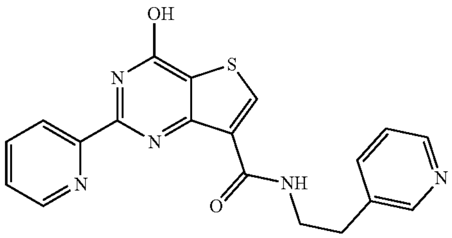 [SMILES: O=C(NCCc1cccnc1)c1csc2c(O)nc(-c3ccccn3)nc12] | B | 0 |
| 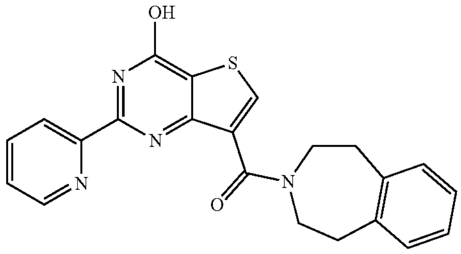 [SMILES: O=C(c1csc2c(O)nc(-c3ccccn3)nc12)N1CCc2ccccc2CC1] | C | 0 |
| 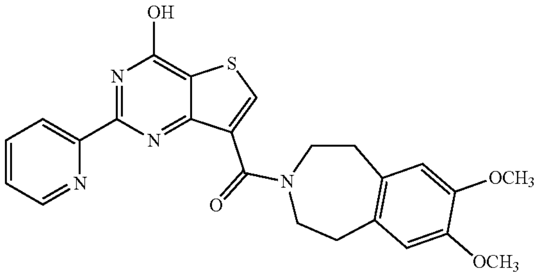 [SMILES: COc1cc2c(cc1OC)CCN(C(=O)c1csc3c(O)nc(-c4ccccn4)nc13)CC2] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 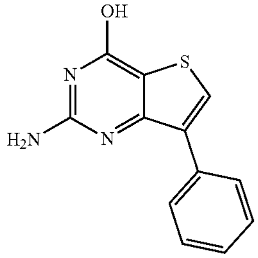 [SMILES: Nc1nc(O)c2scc(-c3ccccc3)c2n1] | A | 0 |
| 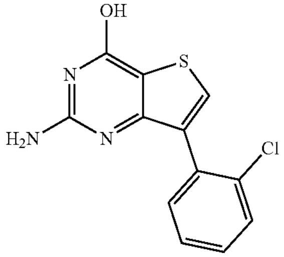 [SMILES: Nc1nc(O)c2scc(-c3ccccc3Cl)c2n1] | B | 0 |
| 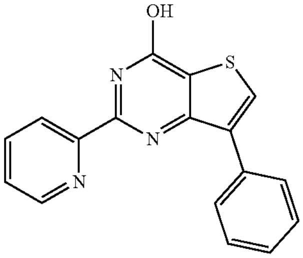 [SMILES: Oc1nc(-c2ccccn2)nc2c(-c3ccccc3)csc12] | D | C |
| 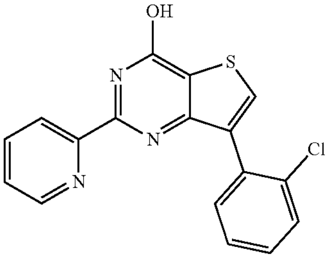 [SMILES: Oc1nc(-c2ccccn2)nc2c(-c3ccccc3Cl)csc12] | D | D |
| 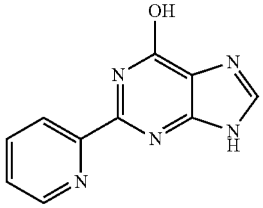 [SMILES: Oc1nc(-c2ccccn2)nc2[nH]cnc12] | D | D |
| 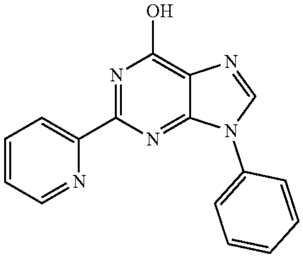 [SMILES: Oc1nc(-c2ccccn2)nc2c1ncn2-c1ccccc1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 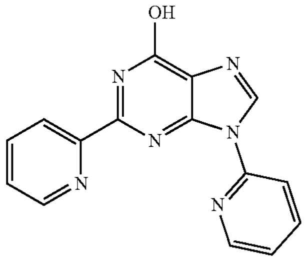 [SMILES: Oc1nc(-c2ccccn2)nc2c1ncn2-c1ccccn1] | B | 0 |
| 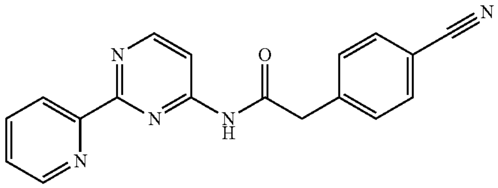 [SMILES: N#Cc1ccc(CC(=O)Nc2ccnc(-c3ccccn3)n2)cc1] | A | A |
| 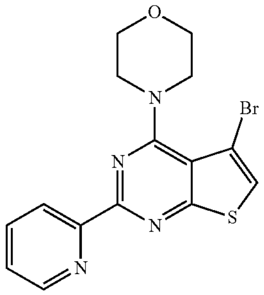 [SMILES: Brc1csc2nc(-c3ccccn3)nc(N3CCOCC3)c12] | C | 0 |
| 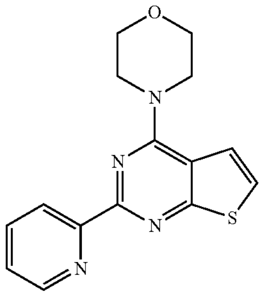 [SMILES: c1ccc(-c2nc(N3CCOCC3)c3ccsc3n2)nc1] | A | A |
| 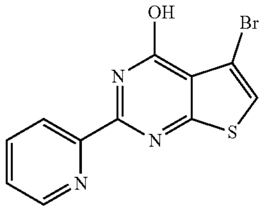 [SMILES: Oc1nc(-c2ccccn2)nc2scc(Br)c12] | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 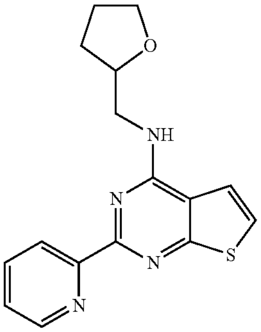 [SMILES: c1ccc(-c2nc(NCC3CCCO3)c3ccsc3n2)nc1] | C | A |
| 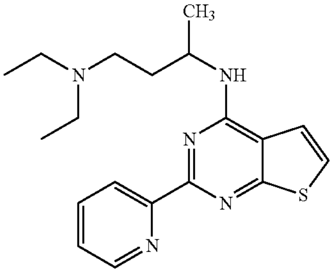 [SMILES: CCN(CC)CCC(C)Nc1nc(-c2ccccn2)nc2sccc12] | A | 0 |
| 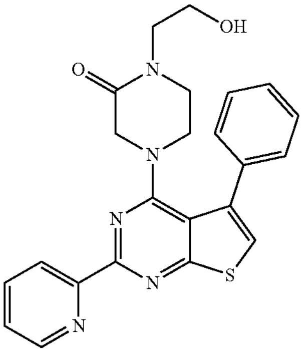 [SMILES: O=C1CN(c2nc(-c3ccccn3)nc3scc(-c4ccccc4)c23)CCN1CCO] | A | A |
| 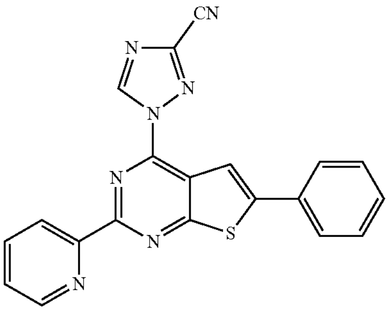 [SMILES: N#Cc1ncn(-c2nc(-c3ccccn3)nc3sc(-c4ccccc4)cc23)n1] | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 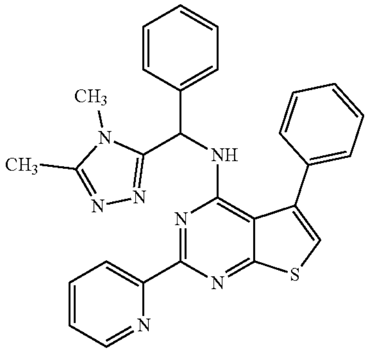 [SMILES: Cc1nnc(C(Nc2nc(-c3ccccn3)nc3scc(-c4ccccc4)c23)c2ccccc2)n1C] | D | D |
| 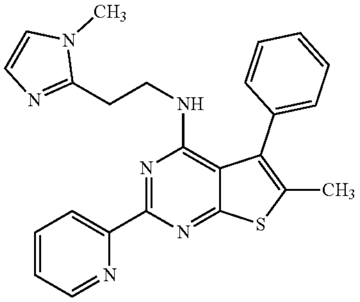 [SMILES: Cc1sc2nc(-c3ccccn3)nc(NCCc3nccn3C)c2c1-c1ccccc1] | A | 0 |
| 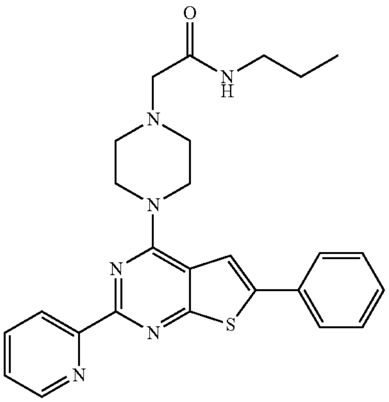 [SMILES: CCCNC(=O)CN1CCN(c2nc(-c3ccccn3)nc3sc(-c4ccccc4)cc23)CC1] | D | D |
| 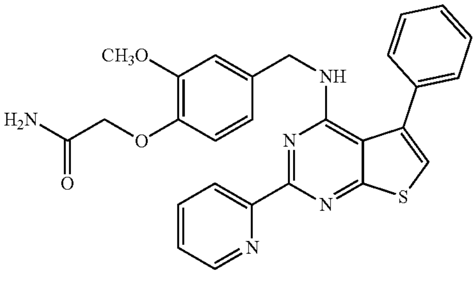 | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 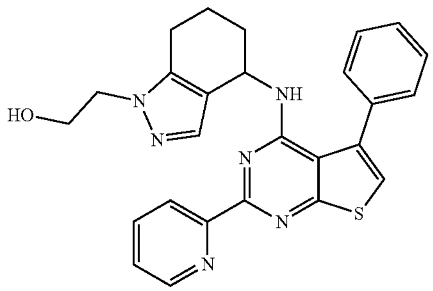 [SMILES: OCCn1ncc2c1CCCC2Nc1nc(-c2ccccn2)nc2scc(-c3ccccc3)c12] | B | B |
| 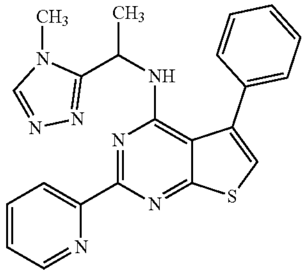 [SMILES: CC(Nc1nc(-c2ccccn2)nc2scc(-c3ccccc3)c12)c1nncn1C] | A | A |
| 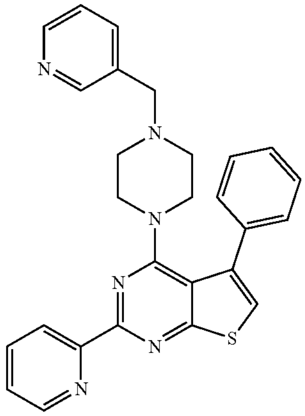 [SMILES: c1ccc(-c2csc3nc(-c4ccccn4)nc(N4CCN(Cc5cccnc5)CC4)c23)cc1] | D | C |
| 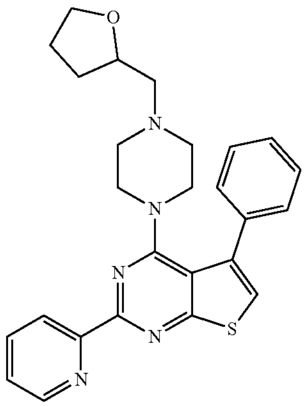 [SMILES: c1ccc(-c2csc3nc(-c4ccccn4)nc(N4CCN(CC5CCCO5)CC4)c23)cc1] | C | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 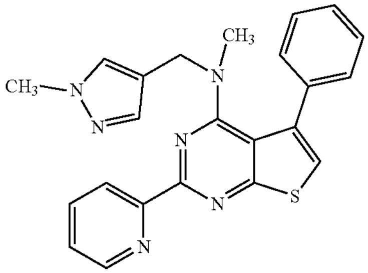 [SMILES: CN(Cc1cnn(C)c1)c1nc(-c2ccccn2)nc2scc(-c3ccccc3)c12] | D | B |
| 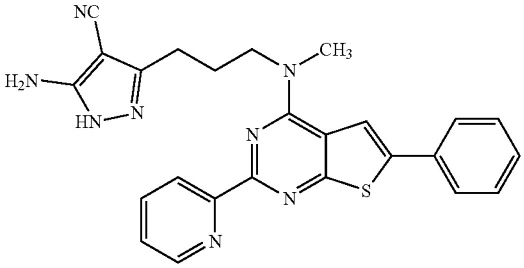 [SMILES: CN(CCCc1n[nH]c(N)c1C#N)c1nc(-c2ccccn2)nc2sc(-c3ccccc3)cc12] | D | C |
| 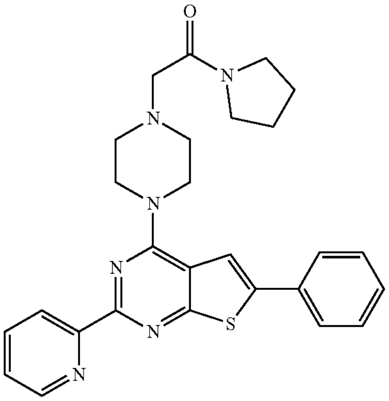 [SMILES: O=C(CN1CCN(c2nc(-c3ccccn3)nc3sc(-c4ccccc4)cc23)CC1)N1CCCC1] | D | D |
| 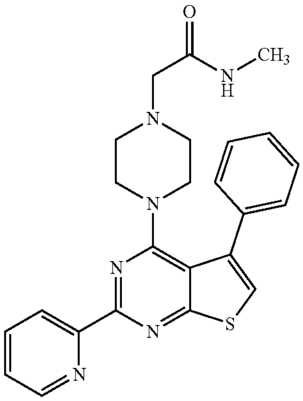 [SMILES: CNC(=O)CN1CCN(c2nc(-c3ccccn3)nc3scc(-c4ccccc4)c23)CC1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 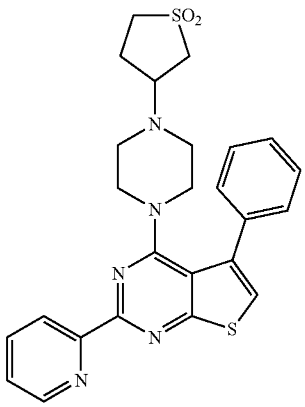 [SMILES: O=S1(=O)CCC(N2CCN(c3nc(-c4ccccn4)nc4scc(-c5ccccc5)c34)CC2)C1] | A | A |
| 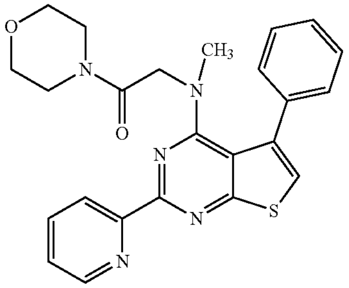 [SMILES: CN(CC(=O)N1CCOCC1)c1nc(-c2ccccn2)nc2scc(-c3ccccc3)c12] | A | A |
| 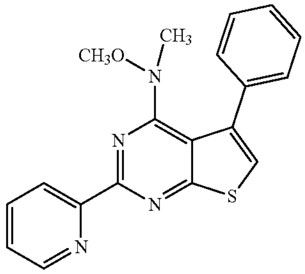 | B | A |
| 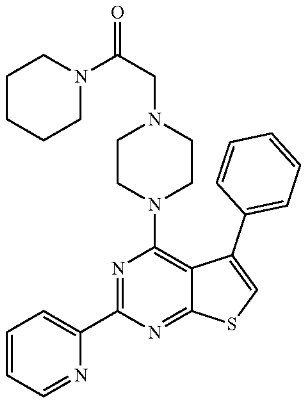 [SMILES: O=C(CN1CCN(c2nc(-c3ccccn3)nc3scc(-c4ccccc4)c23)CC1)N1CCCCC1] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 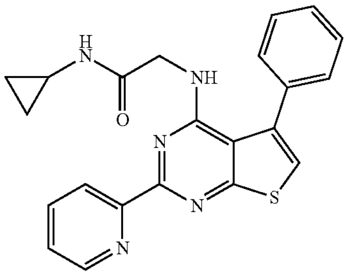 [SMILES: O=C(CNc1nc(-c2ccccn2)nc2scc(-c3ccccc3)c12)NC1CC1] | B | B |
| 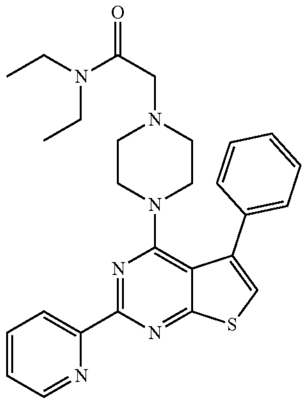 [SMILES: CCN(CC)C(=O)CN1CCN(c2nc(-c3ccccn3)nc3scc(-c4ccccc4)c23)CC1] | D | C |
| 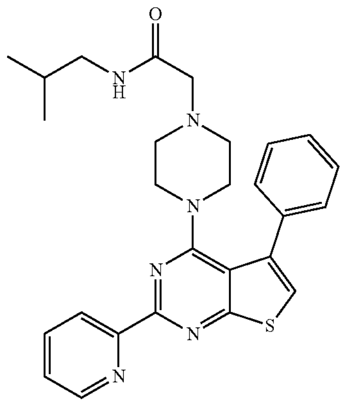 [SMILES: CC(C)CNC(=O)CN1CCN(c2nc(-c3ccccn3)nc3scc(-c4ccccc4)c23)CC1] | D | B |
| 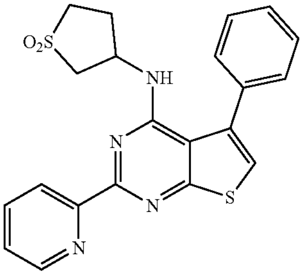 [SMILES: O=S1(=O)CCC(Nc2nc(-c3ccccn3)nc3scc(-c4ccccc4)c23)C1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 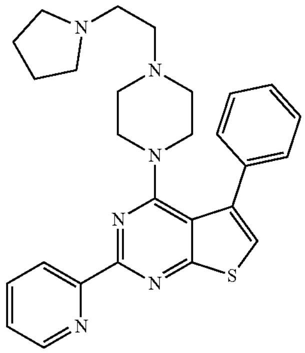 [SMILES: c1ccc(-c2csc3nc(-c4ccccn4)nc(N4CCN(CCN5CCCC5)CC4)c23)cc1] | B | 0 |
| 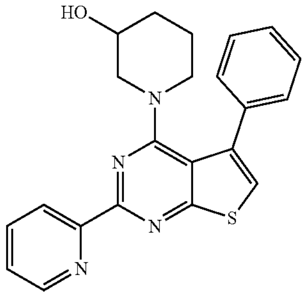 [SMILES: OC1CCCN(c2nc(-c3ccccn3)nc3scc(-c4ccccc4)c23)C1] | B | A |
| 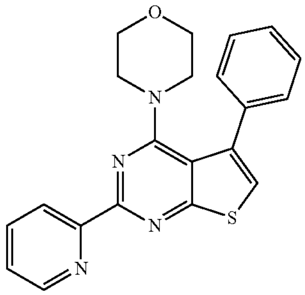 [SMILES: c1ccc(-c2csc3nc(-c4ccccn4)nc(N4CCOCC4)c23)cc1] | A | A |
| 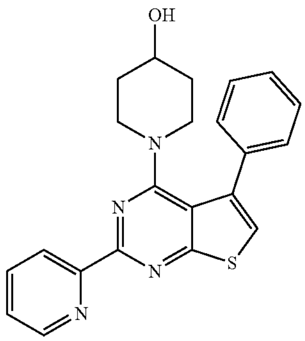 [SMILES: OC1CCN(c2nc(-c3ccccn3)nc3scc(-c4ccccc4)c23)CC1] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 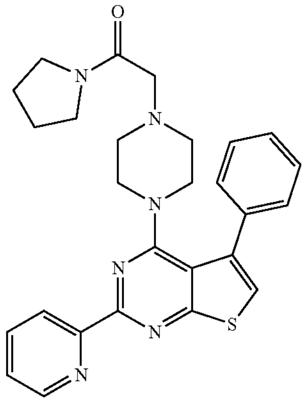 [SMILES: O=C(CN1CCN(c2nc(-c3ccccn3)nc3scc(-c4ccccc4)c23)CC1)N1CCCC1] | A | A |
| 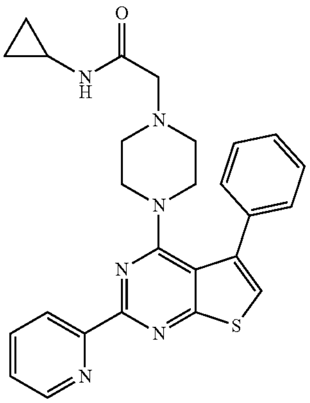 [SMILES: O=C(CN1CCN(c2nc(-c3ccccn3)nc3scc(-c4ccccc4)c23)CC1)NC1CC1] | D | B |
| 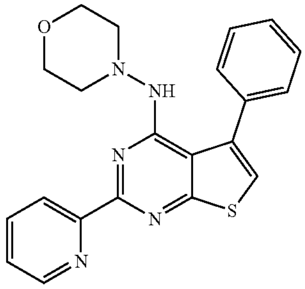 [SMILES: c1ccc(-c2csc3nc(-c4ccccn4)nc(NN4CCOCC4)c23)cc1] | C | B |
| 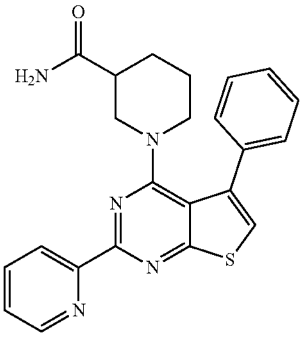 [SMILES: NC(=O)C1CCCN(c2nc(-c3ccccn3)nc3scc(-c4ccccc4)c23)C1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 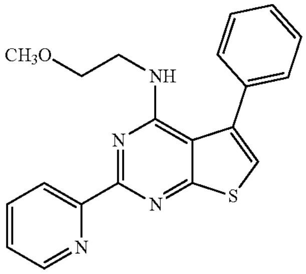 | D | D |
| 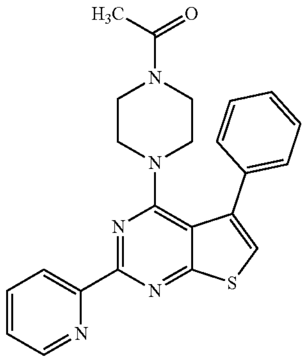 [SMILES: CC(=O)N1CCN(c2nc(-c3ccccn3)nc3scc(-c4ccccc4)c23)CC1] | B | B |
| 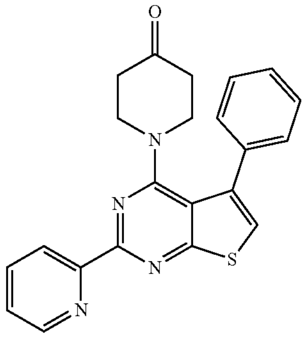 [SMILES: O=C1CCN(c2nc(-c3ccccn3)nc3scc(-c4ccccc4)c23)CC1] | A | A |
| 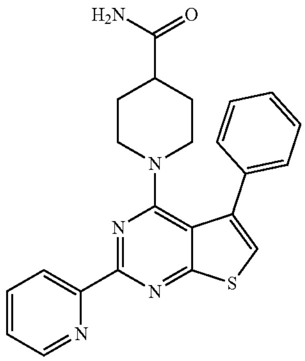 | A | A |
| 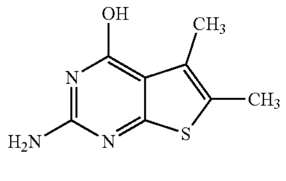 | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 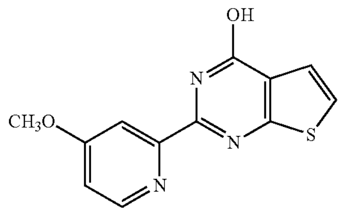 | A | A |
| 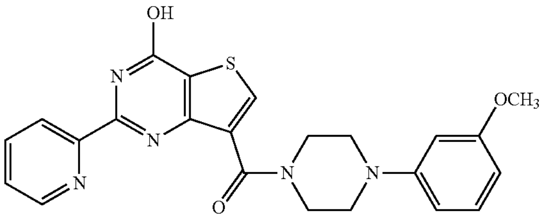 [SMILES: COc1cccc(N2CCN(C(=O)c3csc4c(O)nc(-c5ccccn5)nc34)CC2)c1] | B | 0 |
| 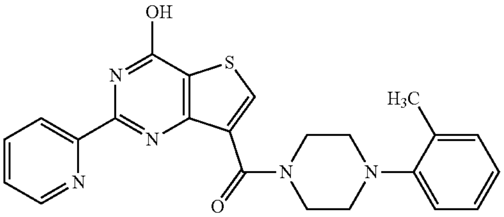 | C | A |
| 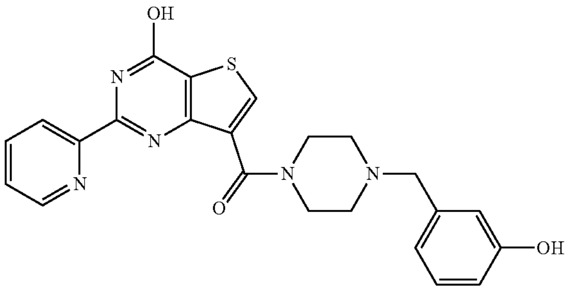 [SMILES: O=C(c1csc2c(O)nc(-c3ccccn3)nc12)N1CCN(Cc2cccc(O)c2)CC1] | B | A |
| 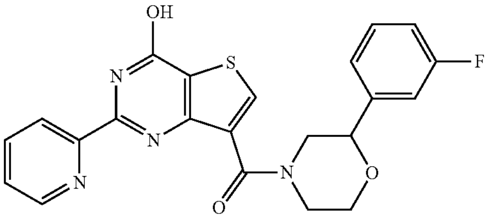 [SMILES: O=C(c1csc2c(O)nc(-c3ccccn3)nc12)N1CCOC(c2cccc(F)c2)C1] | B | A |
| 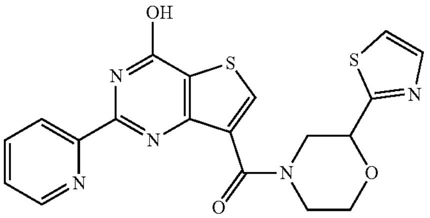 [SMILES: O=C(c1csc2c(O)nc(-c3ccccn3)nc12)N1CCOC(c2nccs2)C1] | C | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 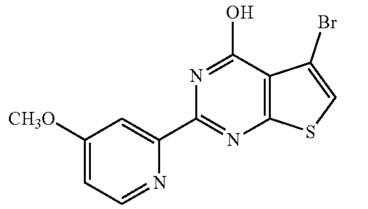 | D | B |
| 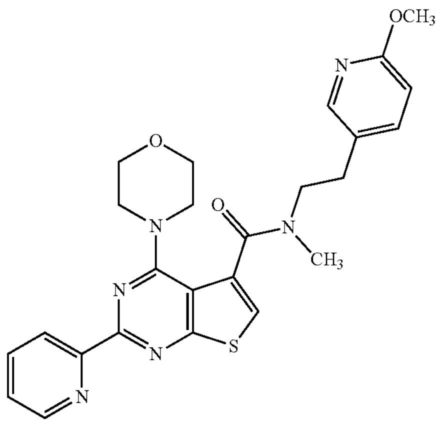 [SMILES: COc1ccc(CCN(C)C(=O)c2csc3nc(-c4ccccn4)nc(N4CCOCC4)c23)cn1] | B | 0 |
| 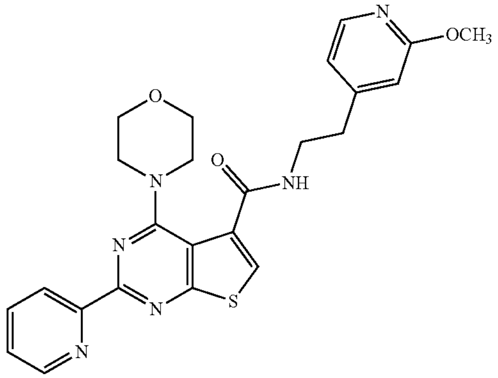 [SMILES: COc1cc(CCNC(=O)c2csc3nc(-c4ccccn4)nc(N4CCOCC4)c23)ccn1] | A | 0 |
| 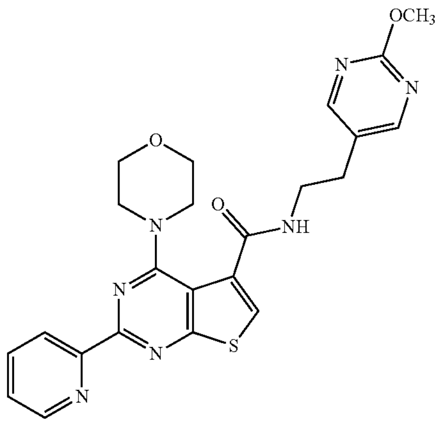 [SMILES: COc1ncc(CCNC(=O)c2csc3nc(-c4ccccn4)nc(N4CCOCC4)c23)cn1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 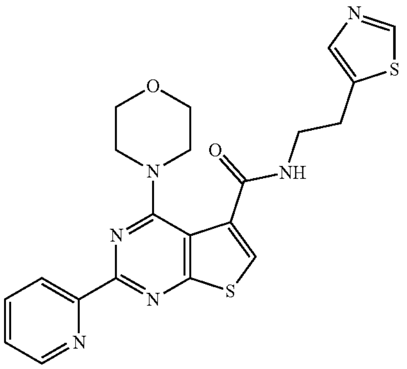 [SMILES: O=C(NCCc1cncs1)c1csc2nc(-c3ccccn3)nc(N3CCOCC3)c12] | A | 0 |
| 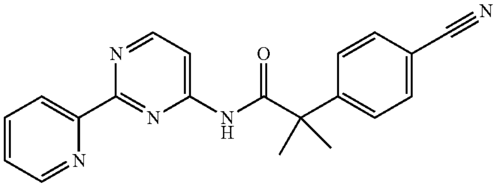 [SMILES: CC(C)(C(=O)Nc1ccnc(-c2ccccn2)n1)c1ccc(C#N)cc1] | A | 0 |
| 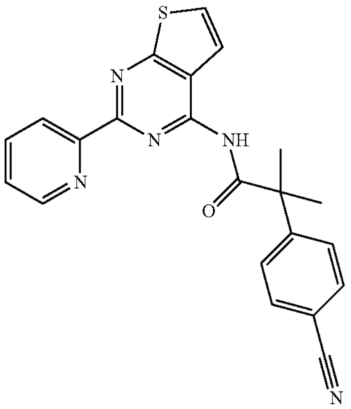 [SMILES: CC(C)(C(=O)Nc1nc(-c2ccccn2)nc2sccc12)c1ccc(C#N)cc1] | D | A |
| 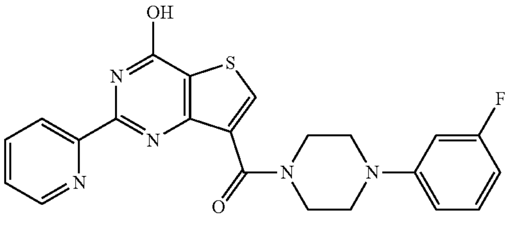 [SMILES: O=C(c1csc2c(O)nc(-c3ccccn3)nc12)N1CCN(c2cccc(F)c2)CC1] | D | 0 |
| 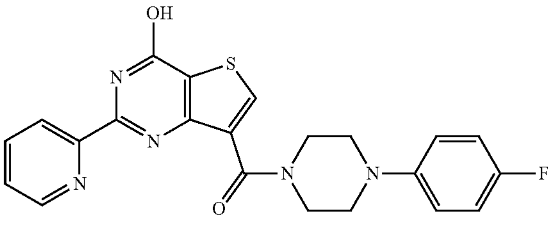 [SMILES: O=C(c1csc2c(O)nc(-c3ccccn3)nc12)N1CCN(c2ccc(F)cc2)CC1] | B | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 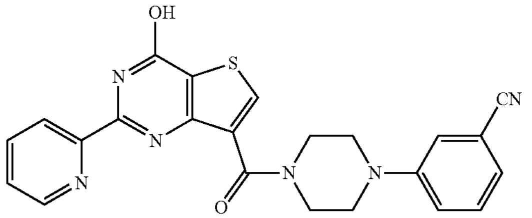 | C | 0 |
| 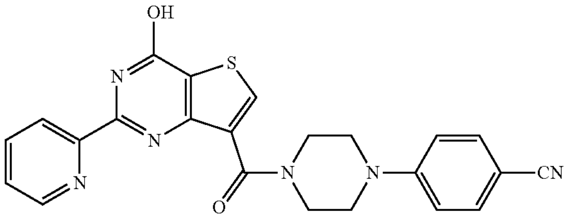 | B | 0 |
| 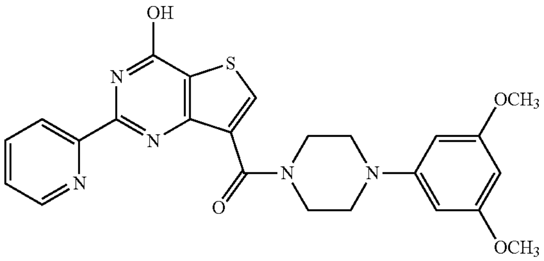 [SMILES: COc1cc(OC)cc(N2CCN(C(=O)c3csc4c(O)nc(-c5ccccn5)nc34)CC2)c1] | B | A |
| 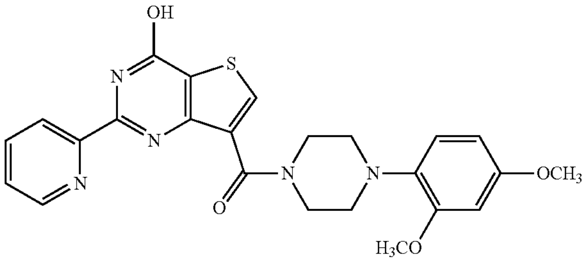 [SMILES: COc1ccc(N2CCN(C(=O)c3csc4c(O)nc(-c5ccccn5)nc34)CC2)c(OC)c1] | D | 0 |
| 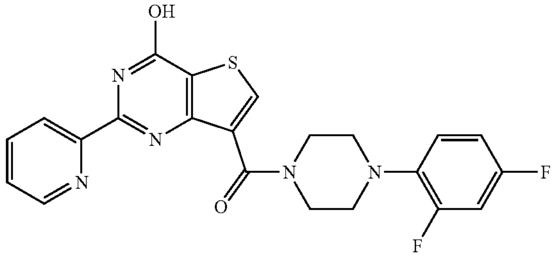 [SMILES: O=C(c1csc2c(O)nc(-c3ccccn3)nc12)N1CCN(c2ccc(F)cc2F)CC1] | D | 0 |
| 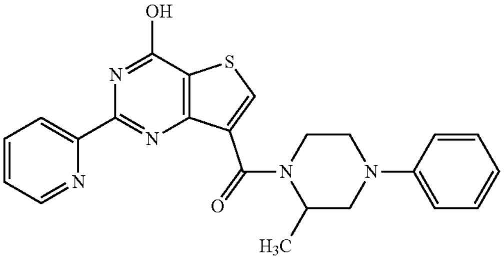 [SMILES: CC1CN(c2ccccc2)CCN1C(=O)c1csc2c(O)nc(-c3ccccn3)nc12] | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 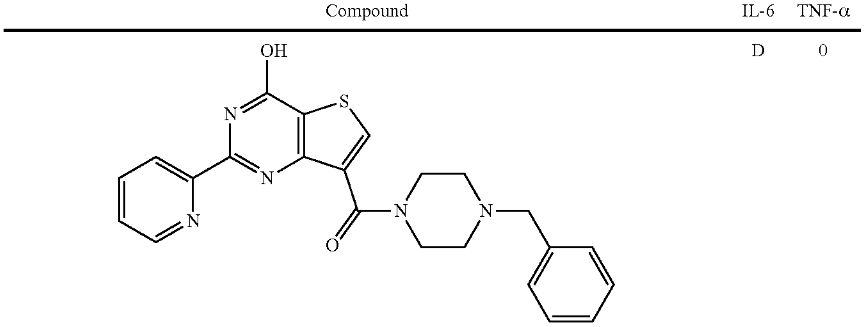 | D | 0 |
| 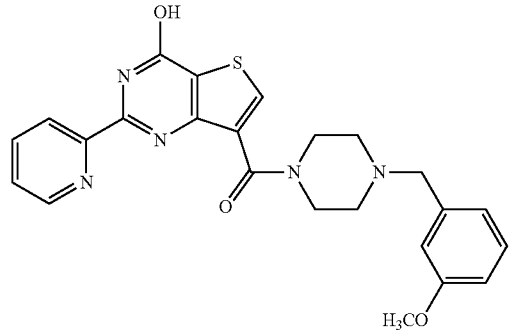 [SMILES: COc1cccc(CN2CCN(C(=O)c3csc4c(O)nc(-c5ccccn5)nc34)CC2)c1] | C | 0 |
| 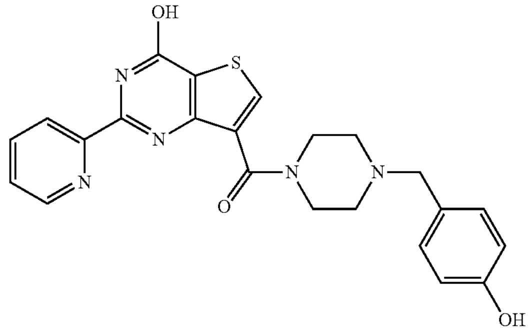 [SMILES: O=C(c1csc2c(O)nc(-c3ccccn3)nc12)N1CCN(Cc2ccc(O)cc2)CC1] | A | A |
| 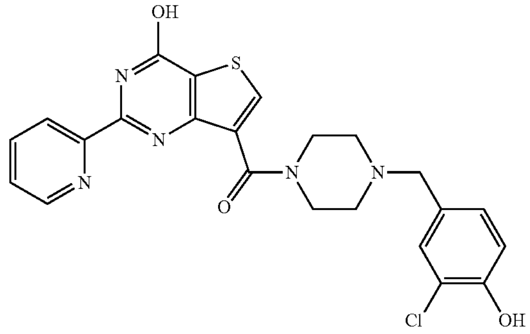 [SMILES: O=C(c1csc2c(O)nc(-c3ccccn3)nc12)N1CCN(Cc2ccc(O)c(Cl)c2)CC1] | D | A |
| 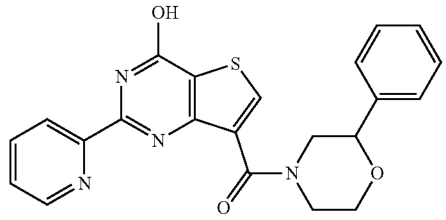 [SMILES: O=C(c1csc2c(O)nc(-c3ccccn3)nc12)N1CCOC(c2ccccc2)C1] | C | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 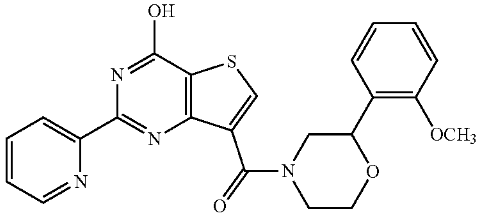 [SMILES: COc1ccccc1C1CN(C(=O)c2csc3c(O)nc(-c4ccccn4)nc23)CCO1] | D | C |
| 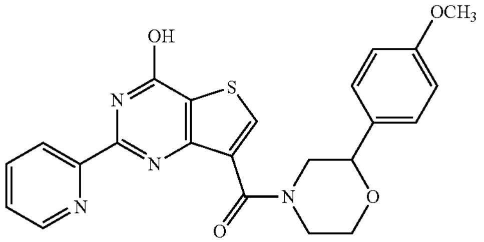 [SMILES: COc1ccc(C2CN(C(=O)c3csc4c(O)nc(-c5ccccn5)nc34)CCO2)cc1] | D | A |
| 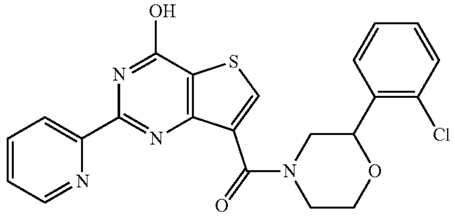 [SMILES: O=C(c1csc2c(O)nc(-c3ccccn3)nc12)N1CCOC(c2ccccc2Cl)C1] | D | A |
| 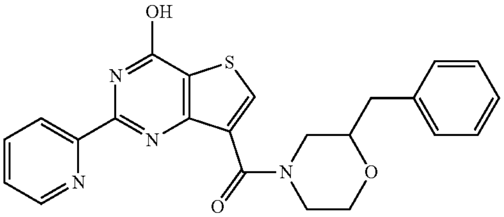 [SMILES: O=C(c1csc2c(O)nc(-c3ccccn3)nc12)N1CCOC(Cc2ccccc2)C1] | D | 0 |
| 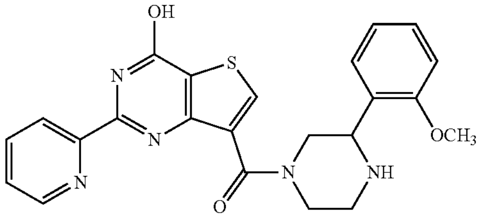 [SMILES: COc1ccccc1C1CN(C(=O)c2csc3c(O)nc(-c4ccccn4)nc23)CCN1] | B | 0 |
| 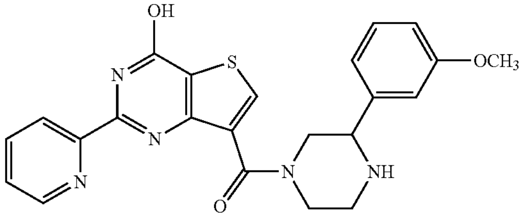 [SMILES: COc1cccc(C2CN(C(=O)c3csc4c(O)nc(-c5ccccn5)nc34)CCN2)c1] | D | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 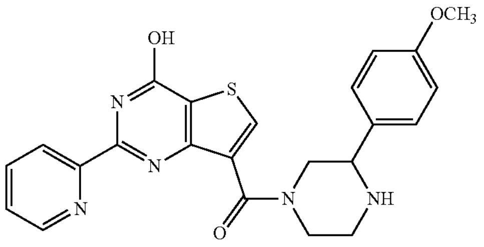 | C | 0 |
| 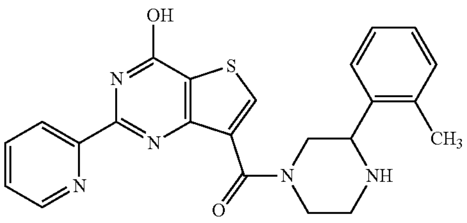 [SMILES: Cc1ccccc1C1CN(C(=O)c2csc3c(O)nc(-c4ccccn4)nc23)CCN1] | D | A |
| 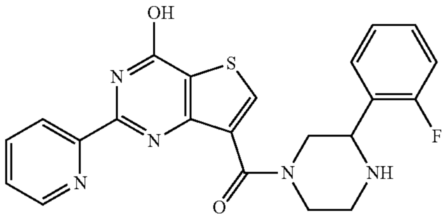 | D | A |
| 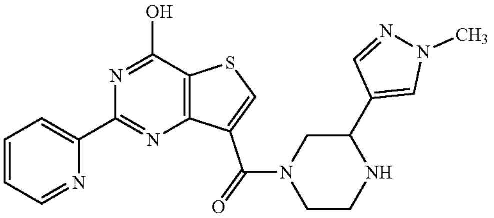 [SMILES: Cn1cc(C2CN(C(=O)c3csc4c(O)nc(-c5ccccn5)nc34)CCN2)cn1] | D | D |
| 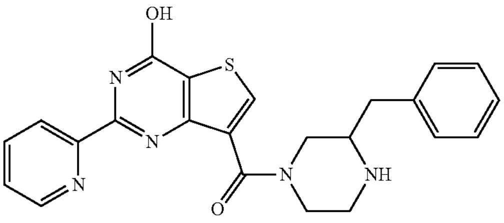 | D | A |
| 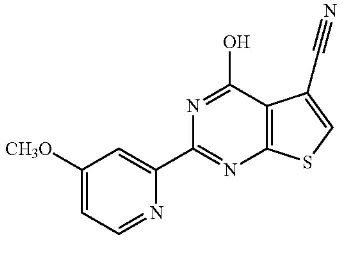 | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 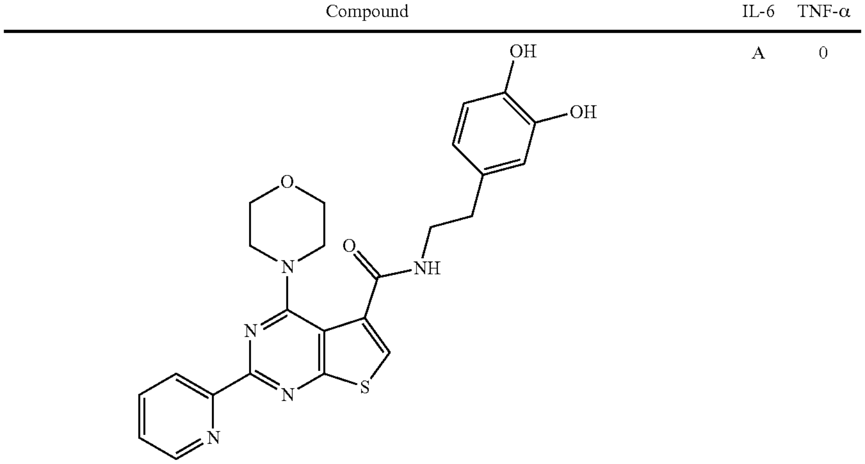 | A | 0 |
| 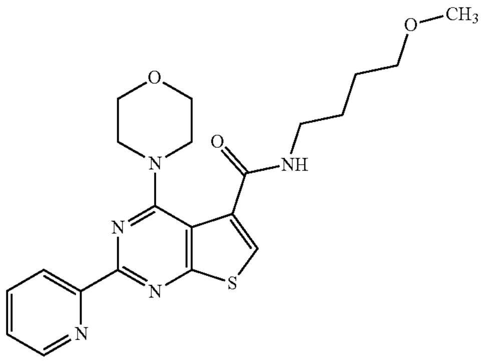 [SMILES: COCCCCNC(=O)c1csc2nc(-c3ccccn3)nc(N3CCOCC3)c12] | A | A |
| 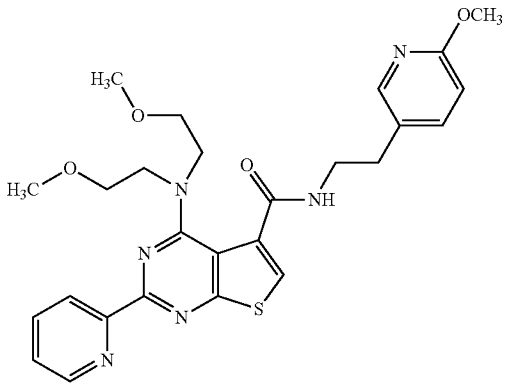 [SMILES: COCCN(CCOC)c1nc(-c2ccccn2)nc2scc(C(=O)NCCc3ccc(OC)nc3)c12] | A | 0 |
| 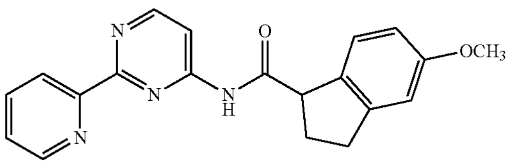 [SMILES: COc1ccc2c(c1)CCC2C(=O)Nc1ccnc(-c2ccccn2)n1] | B | 0 |
| 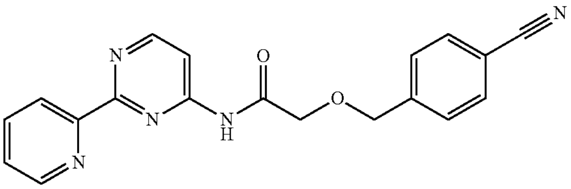 [SMILES: N#Cc1ccc(COCC(=O)Nc2ccnc(-c3ccccn3)n2)cc1] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 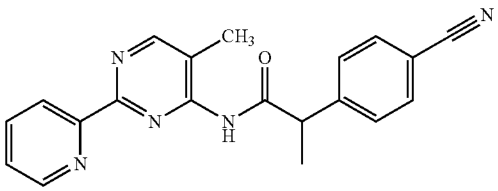 [SMILES: Cc1cnc(-c2ccccn2)nc1NC(=O)C(C)c1ccc(C#N)cc1] | A | A |
| 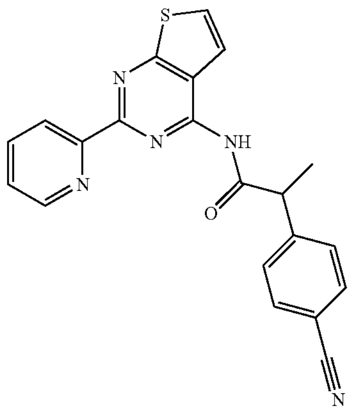 [SMILES: CC(C(=O)Nc1nc(-c2ccccn2)nc2sccc12)c1ccc(C#N)cc1] | C | 0 |
| 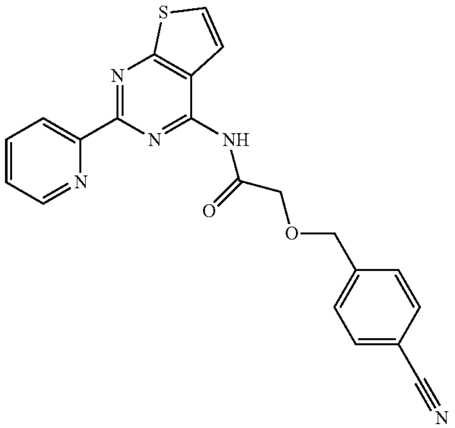 [SMILES: N#Cc1ccc(COCC(=O)Nc2nc(-c3ccccn3)nc3sccc23)cc1] | C | A |
| 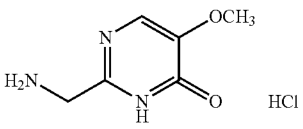 | 0 | A |
| 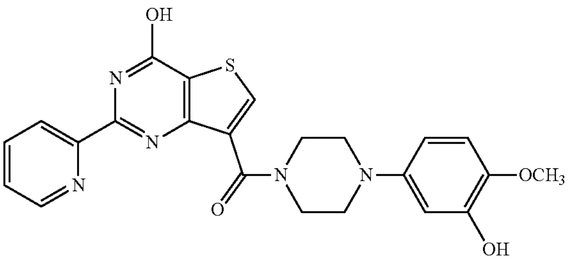 [SMILES: COc1ccc(N2CCN(C(=O)c3csc4c(O)nc(-c5ccccn5)nc34)CC2)cc1O] | B | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 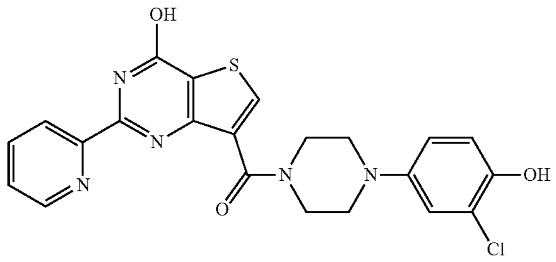 [SMILES: O=C(c1csc2c(O)nc(-c3ccccn3)nc12)N1CCN(c2ccc(O)c(Cl)c2)CC1] | B | 0 |
| 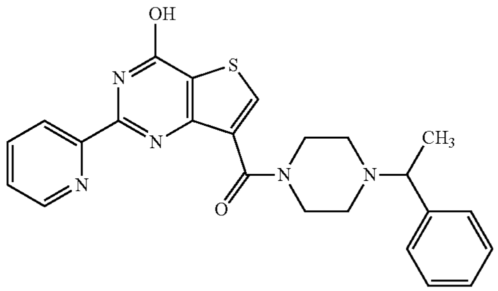 [SMILES: CC(c1ccccc1)N1CCN(C(=O)c2csc3c(O)nc(-c4ccccn4)nc23)CC1] | C | 0 |
| 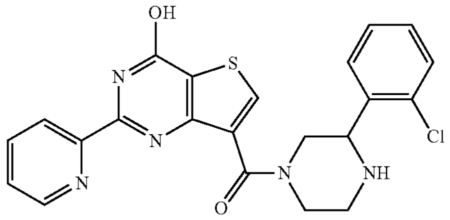 [SMILES: O=C(c1csc2c(O)nc(-c3ccccn3)nc12)N1CCNC(c2ccccc2Cl)C1] | C | 0 |
| 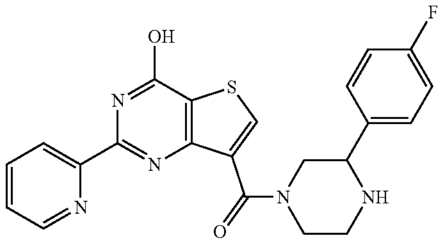 [SMILES: O=C(c1csc2c(O)nc(-c3ccccn3)nc12)N1CCNC(c2ccc(F)cc2)C1] | A | 0 |
| 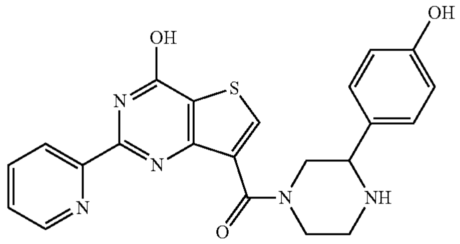 [SMILES: O=C(c1csc2c(O)nc(-c3ccccn3)nc12)N1CCNC(c2ccc(O)cc2)C1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 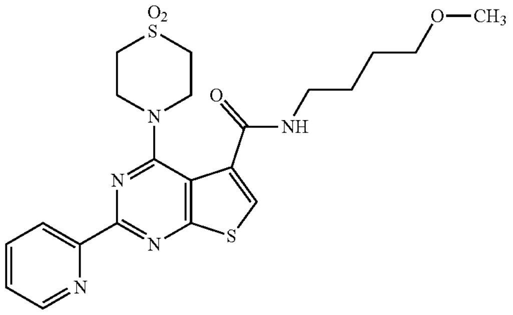 [SMILES: COCCCCNC(=O)c1csc2nc(-c3ccccn3)nc(N3CCS(=O)(=O)CC3)c12] | B | 0 |
| 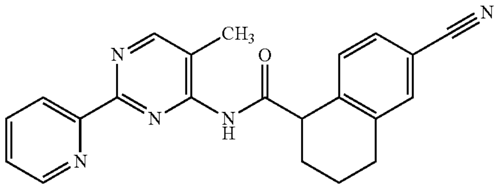 [SMILES: Cc1cnc(-c2ccccn2)nc1NC(=O)C1CCCc2cc(C#N)ccc21] | D | C |
| 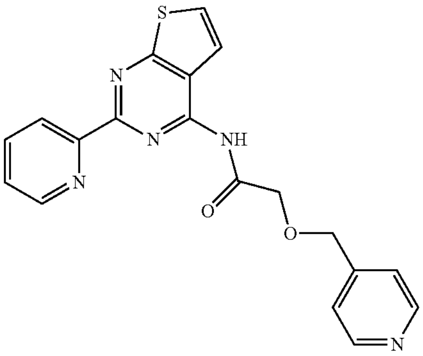 [SMILES: O=C(COCc1ccncc1)Nc1nc(-c2ccccn2)nc2sccc12] | D | A |
| 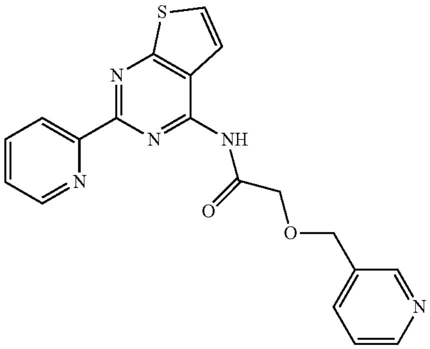 [SMILES: O=C(COCc1cccnc1)Nc1nc(-c2ccccn2)nc2sccc12] | C | A |
| 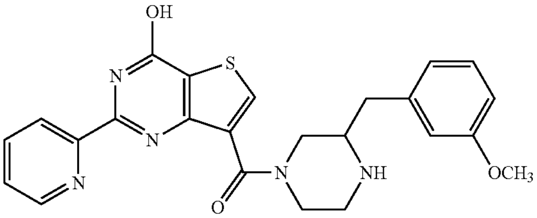 [SMILES: COc1cccc(CC2CN(C(=O)c3csc4c(O)nc(-c5ccccn5)nc34)CCN2)c1] | A | A |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 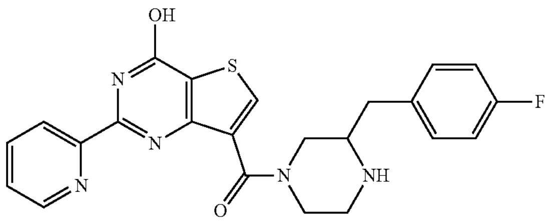 [SMILES: O=C(c1csc2c(O)nc(-c3ccccn3)nc12)N1CCNC(Cc2ccc(F)cc2)C1] | B | A |
| 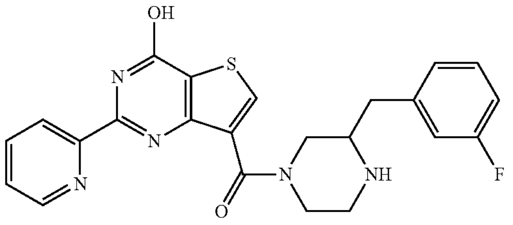 [SMILES: O=C(c1csc2c(O)nc(-c3ccccn3)nc12)N1CCNC(Cc2cccc(F)c2)C1] | B | A |
| 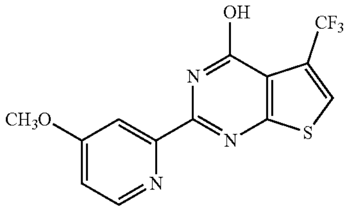 | C | A |
| 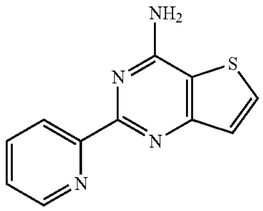 [SMILES: Nc1nc(-c2ccccn2)nc2ccsc12] | 0 | A |
| 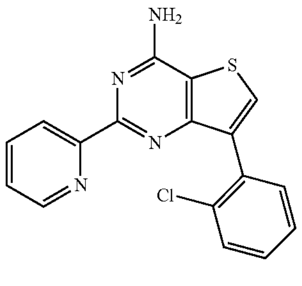 [SMILES: Nc1nc(-c2ccccn2)nc2c(-c3ccccc3Cl)csc12] | D | A |
| 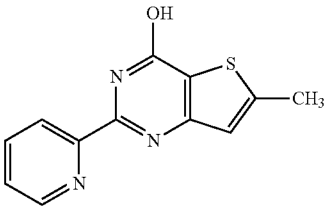 | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 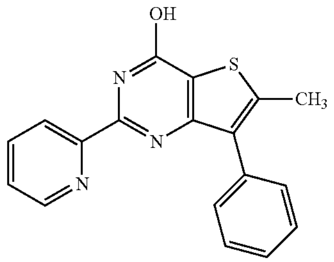 [SMILES: Cc1sc2c(O)nc(-c3ccccn3)nc2c1-c1ccccc1] | C | A |
| 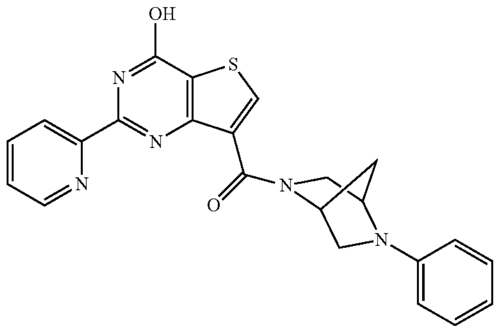 [SMILES: O=C(c1csc2c(O)nc(-c3ccccn3)nc12)N1CC2CC1CN2c1ccccc1] | C | 0 |
| 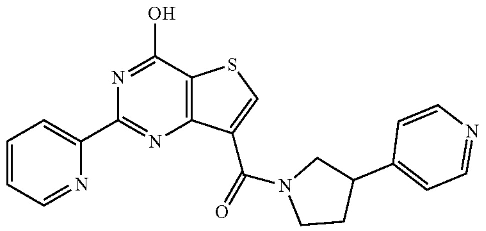 [SMILES: O=C(c1csc2c(O)nc(-c3ccccn3)nc12)N1CCC(c2ccncc2)C1] | D | A |
| 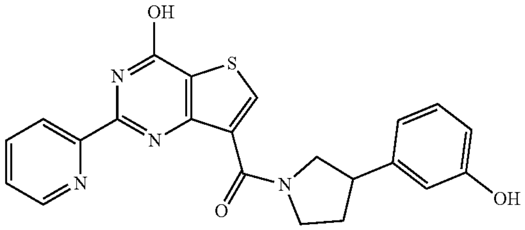 [SMILES: O=C(c1csc2c(O)nc(-c3ccccn3)nc12)N1CCC(c2cccc(O)c2)C1] | D | B |
| 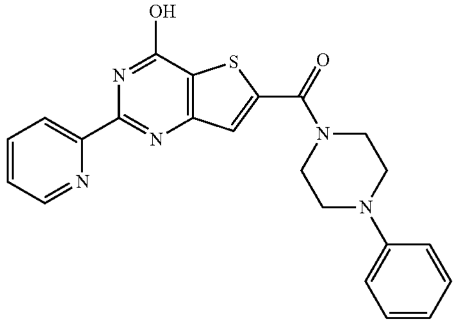 [SMILES: O=C(c1cc2nc(-c3ccccn3)nc(O)c2s1)N1CCN(c2ccccc2)CC1] | B | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 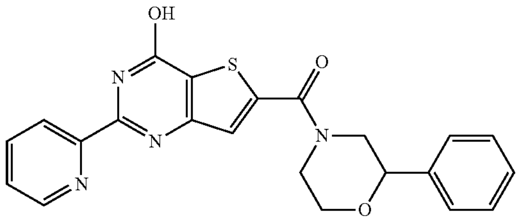 [SMILES: O=C(c1cc2nc(-c3ccccn3)nc(O)c2s1)N1CCOC(c2ccccc2)C1] | A | A |
| 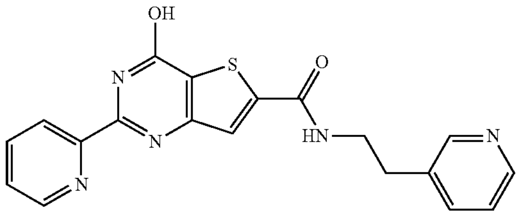 [SMILES: O=C(NCCc1cccnc1)c1cc2nc(-c3ccccn3)nc(O)c2s1] | B | A |
| 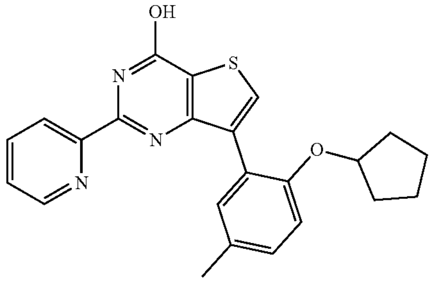 [SMILES: Cc1ccc(OC2CCCC2)c(-c2csc3c(O)nc(-c4ccccn4)nc23)c1] | D | C |
| 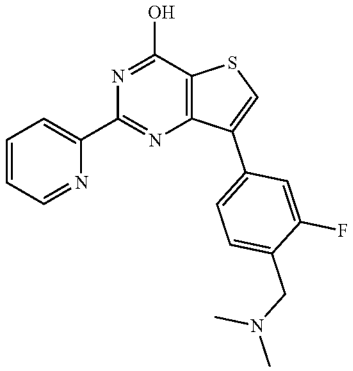 [SMILES: CN(C)Cc1ccc(-c2csc3c(O)nc(-c4ccccn4)nc23)cc1F] | D | C |
| 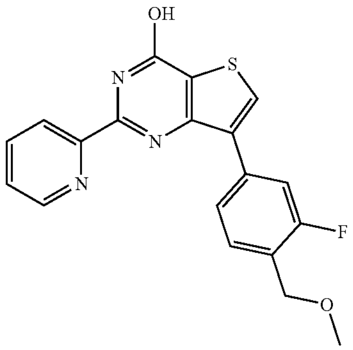 [SMILES: COCc1ccc(-c2csc3c(O)nc(-c4ccccn4)nc23)cc1F] | D | C |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 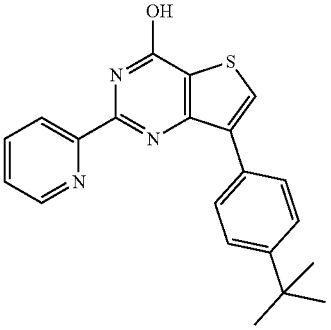 [SMILES: CC(C)(C)c1ccc(-c2csc3c(O)nc(-c4ccccn4)nc23)cc1] | D | D |
| 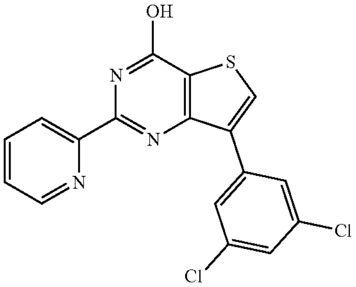 [SMILES: Oc1nc(-c2ccccn2)nc2c(-c3cc(Cl)cc(Cl)c3)csc12] | 0 | A |
| 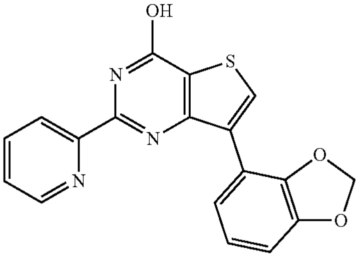 [SMILES: Oc1nc(-c2ccccn2)nc2c(-c3cccc4c3OCO4)csc12] | C | C |
| 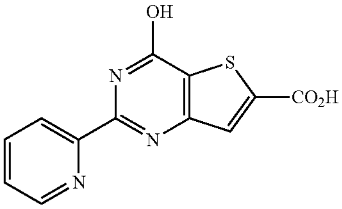 [SMILES: O=C(O)c1cc2nc(-c3ccccn3)nc(O)c2s1] | A | A |
| 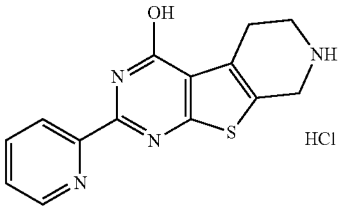 [SMILES: Oc1nc(-c2ccccn2)nc2sc3c(c12)CCNC3 ; Cl] | B | B |
| 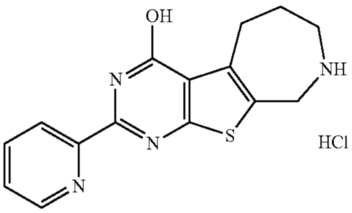 [SMILES: Oc1nc(-c2ccccn2)nc2sc3c(c12)CCCNC3 ; Cl] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 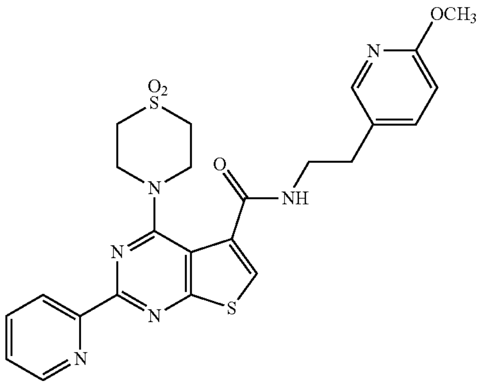 | B | 0 |
| 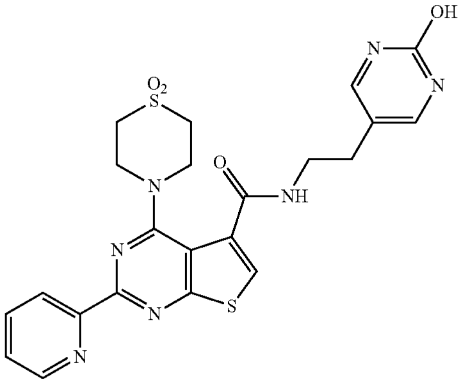 | C | 0 |
| 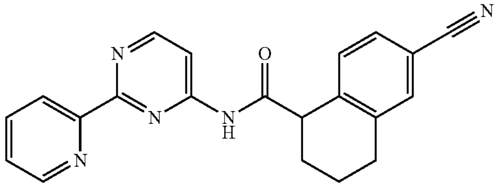 [SMILES: N#Cc1ccc2c(c1)CCCC2C(=O)Nc1ccnc(-c2ccccn2)n1] | A | 0 |
| 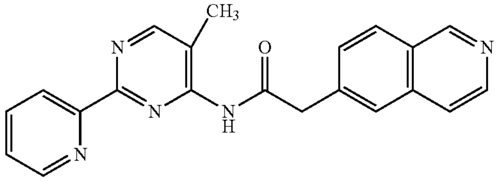 [SMILES: Cc1cnc(-c2ccccn2)nc1NC(=O)Cc1ccc2cnccc2c1] | D | 0 |
| 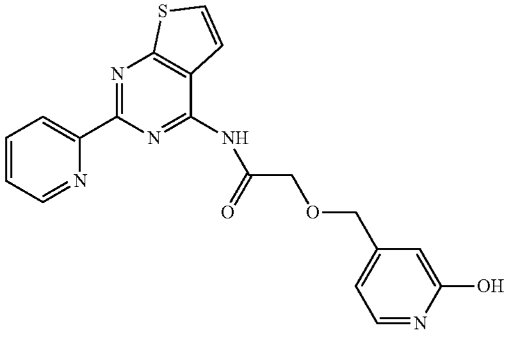 [SMILES: O=C(COCc1ccnc(O)c1)Nc1nc(-c2ccccn2)nc2sccc12] | B | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 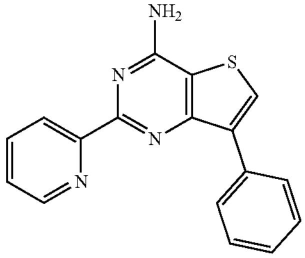 [SMILES: Nc1nc(-c2ccccn2)nc2c(-c3ccccc3)csc12] | D | C |
| 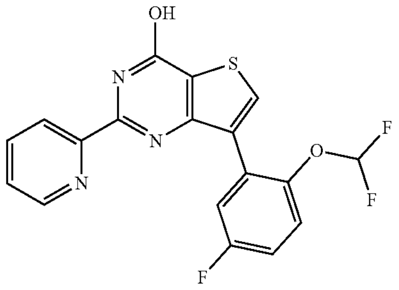 [SMILES: Oc1nc(-c2ccccn2)nc2c(-c3cc(F)ccc3OC(F)F)csc12] | D | B |
| 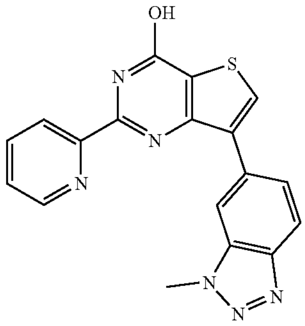 [SMILES: Cn1nnc2ccc(-c3csc4c(O)nc(-c5ccccn5)nc34)cc21] | D | A |
| 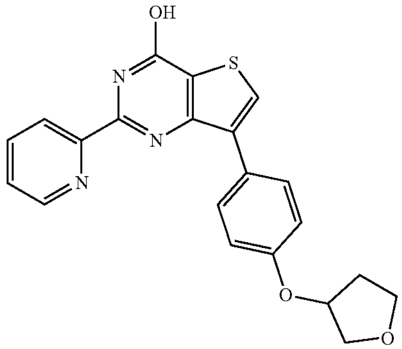 [SMILES: Oc1nc(-c2ccccn2)nc2c(-c3ccc(OC4CCOC4)cc3)csc12] | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 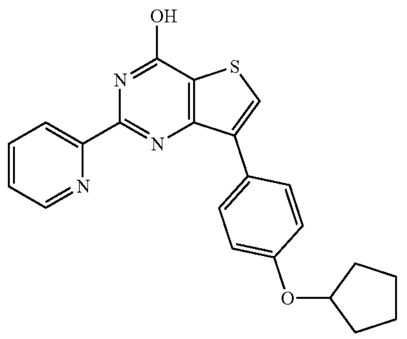 [SMILES: Oc1nc(-c2ccccn2)nc2c(-c3ccc(OC4CCCC4)cc3)csc12] | D | 0 |
| 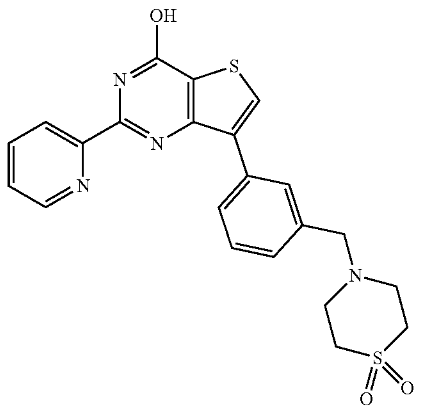 [SMILES: O=S1(=O)CCN(Cc2cccc(-c3csc4c(O)nc(-c5ccccn5)nc34)c2)CC1] | D | A |
| 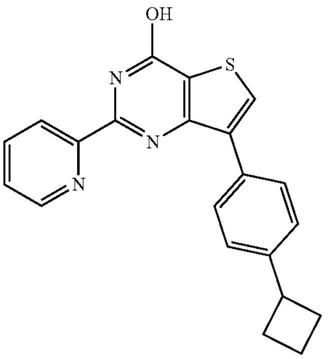 [SMILES: Oc1nc(-c2ccccn2)nc2c(-c3ccc(C4CCC4)cc3)csc12] | C | 0 |
| 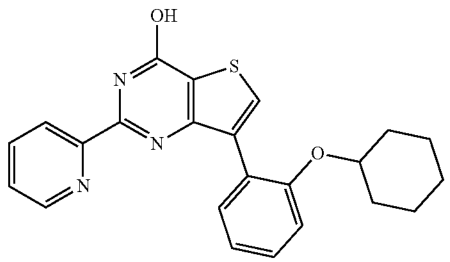 [SMILES: Oc1nc(-c2ccccn2)nc2c(-c3ccccc3OC3CCCCC3)csc12] | D | B |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 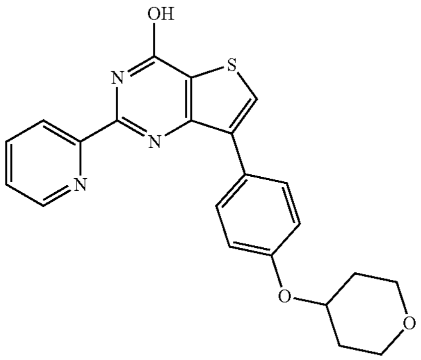 [SMILES: Oc1nc(-c2ccccn2)nc2c(-c3ccc(OC4CCOCC4)cc3)csc12] | D | 0 |
| 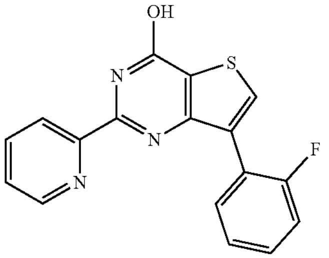 [SMILES: Oc1nc(-c2ccccn2)nc2c(-c3ccccc3F)csc12] | D | C |
| 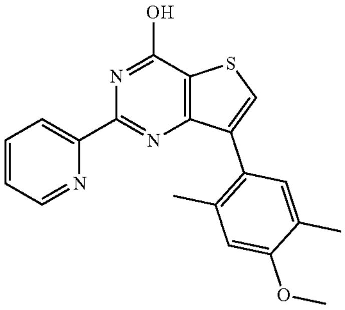 [SMILES: COc1cc(C)c(-c2csc3c(O)nc(-c4ccccn4)nc23)cc1C] | C | 0 |
| 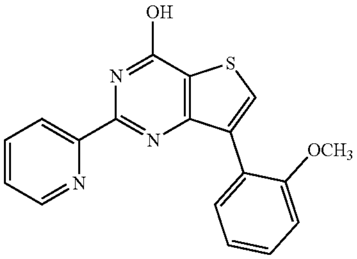 [SMILES: COc1ccccc1-c1csc2c(O)nc(-c3ccccn3)nc12] | D | C |
| 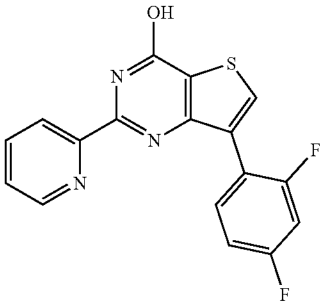 [SMILES: Oc1nc(-c2ccccn2)nc2c(-c3ccc(F)cc3F)csc12] | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 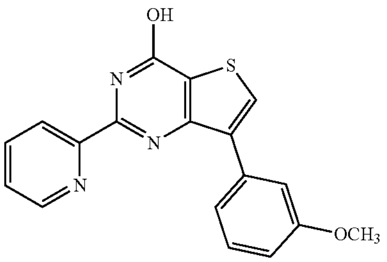 [SMILES: COc1cccc(-c2csc3c(O)nc(-c4ccccn4)nc23)c1] | D | B |
| 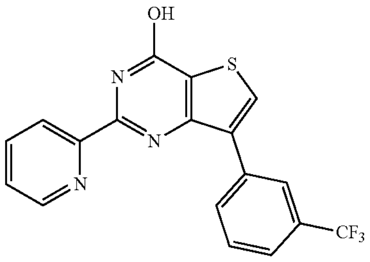 | D | D |
| 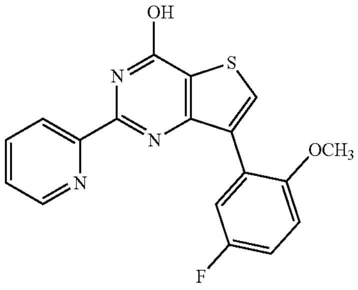 [SMILES: COc1ccc(F)cc1-c1csc2c(O)nc(-c3ccccn3)nc12] | D | B |
| 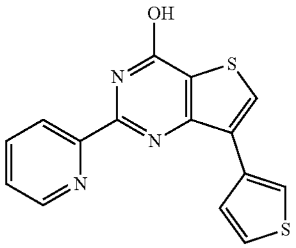 [SMILES: Oc1nc(-c2ccccn2)nc2c(-c3ccsc3)csc12] | D | D |
| 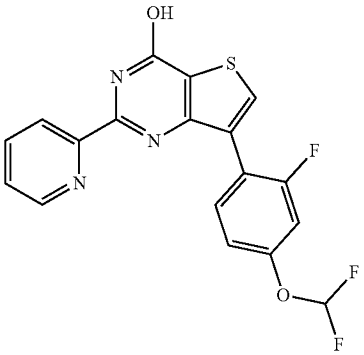 | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 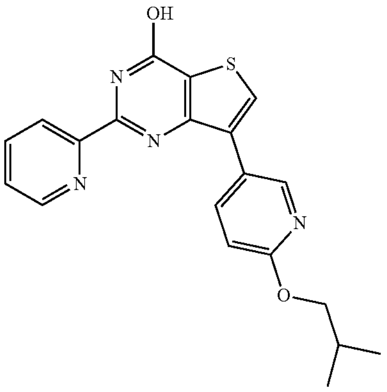 [SMILES: CC(C)COc1ccc(-c2csc3c(O)nc(-c4ccccn4)nc23)cn1] | D | C |
| 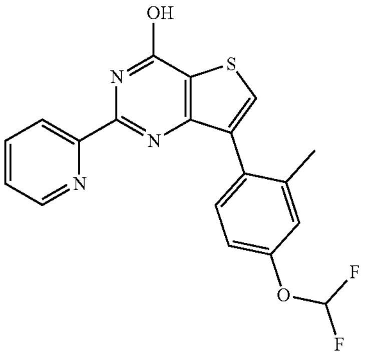 | D | 0 |
| 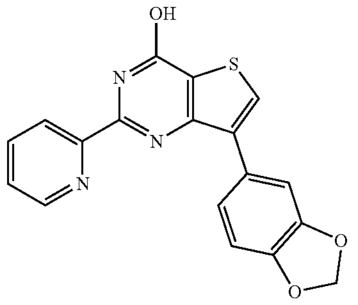 [SMILES: Oc1nc(-c2ccccn2)nc2c(-c3ccc4c(c3)OCO4)csc12] | D | D |
| 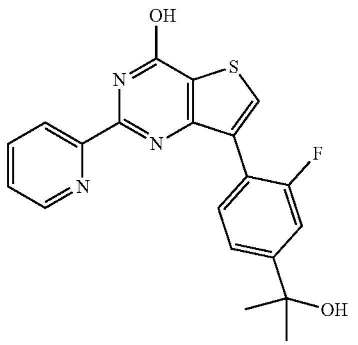 [SMILES: CC(C)(O)c1ccc(-c2csc3c(O)nc(-c4ccccn4)nc23)c(F)c1] | D | D |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 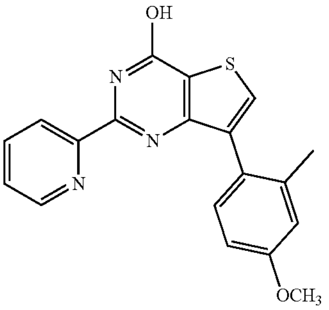 [SMILES: COc1ccc(-c2csc3c(O)nc(-c4ccccn4)nc23)c(C)c1] | D | D |
| 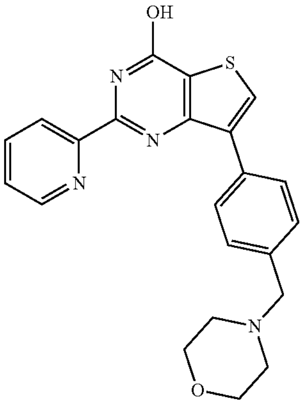 [SMILES: Oc1nc(-c2ccccn2)nc2c(-c3ccc(CN4CCOCC4)cc3)csc12] | B | 0 |
| 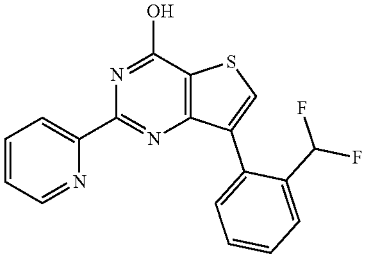 [SMILES: Oc1nc(-c2ccccn2)nc2c(-c3ccccc3C(F)F)csc12] | D | D |
| 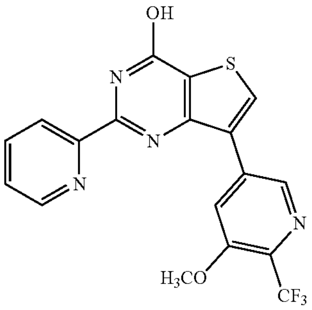 [SMILES: COc1cc(-c2csc3c(O)nc(-c4ccccn4)nc23)cnc1C(F)(F)F] | C | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 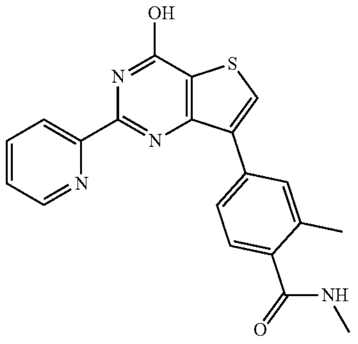 [SMILES: CNC(=O)c1ccc(-c2csc3c(O)nc(-c4ccccn4)nc23)cc1C] | B | 0 |
| 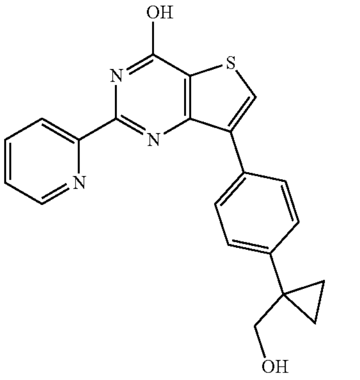 [SMILES: OCC1(c2ccc(-c3csc4c(O)nc(-c5ccccn5)nc34)cc2)CC1] | D | A |
| 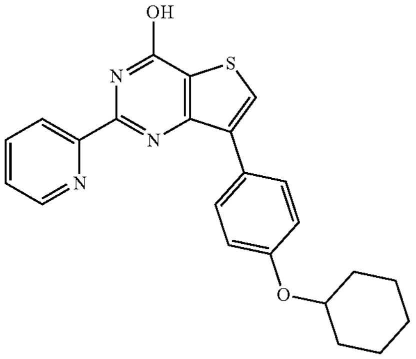 [SMILES: Oc1nc(-c2ccccn2)nc2c(-c3ccc(OC4CCCCC4)cc3)csc12] | D | D |
| 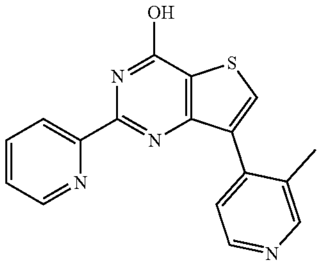 [SMILES: Cc1cnccc1-c1csc2c(O)nc(-c3ccccn3)nc12] | D | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 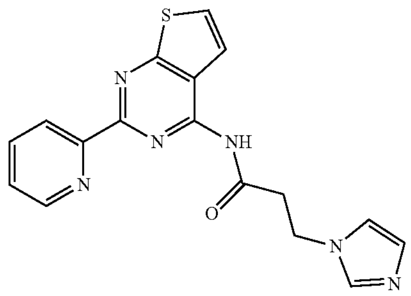 [SMILES: O=C(CCn1ccnc1)Nc1nc(-c2ccccn2)nc2sccc12] | C | 0 |
| 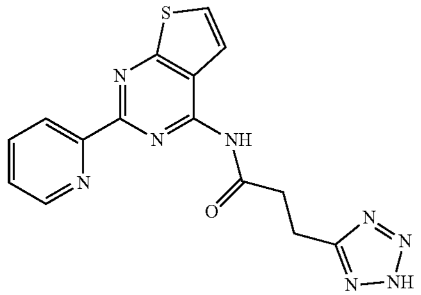 [SMILES: O=C(CCc1nn[nH]n1)Nc1nc(-c2ccccn2)nc2sccc12] | A | 0 |
| 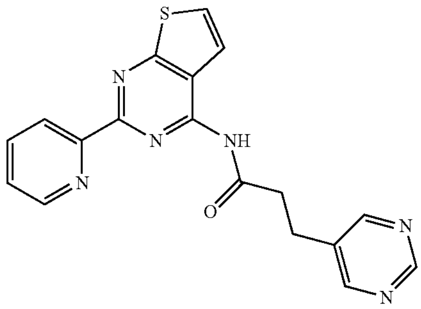 [SMILES: O=C(CCc1cncnc1)Nc1nc(-c2ccccn2)nc2sccc12] | B | 0 |
| 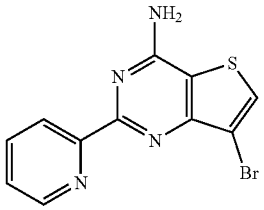 [SMILES: Nc1nc(-c2ccccn2)nc2c(Br)csc12] | B | 0 |
| 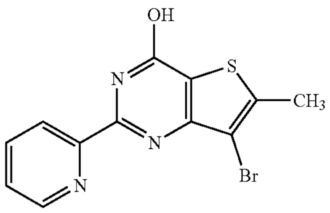 [SMILES: Cc1sc2c(O)nc(-c3ccccn3)nc2c1Br] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 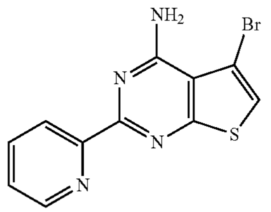 [SMILES: Nc1nc(-c2ccccn2)nc2scc(Br)c12] | A | 0 |
| 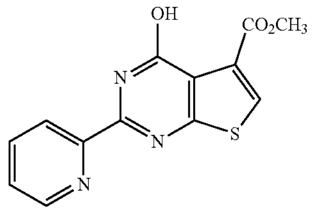 | C | 0 |
| 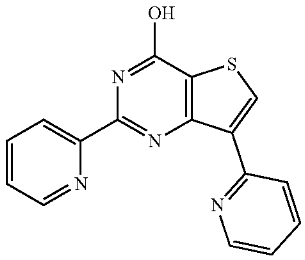 | D | D |
| 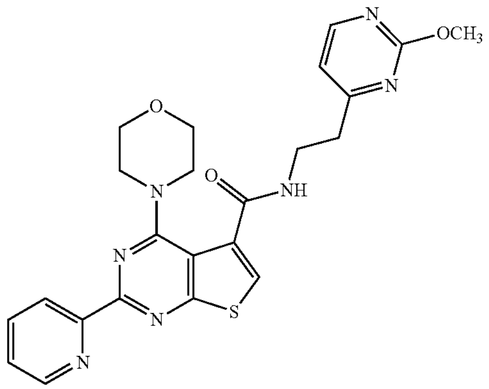 [SMILES: COc1nccc(CCNC(=O)c2csc3nc(-c4ccccn4)nc(N4CCOCC4)c23)n1] | B | 0 |
| 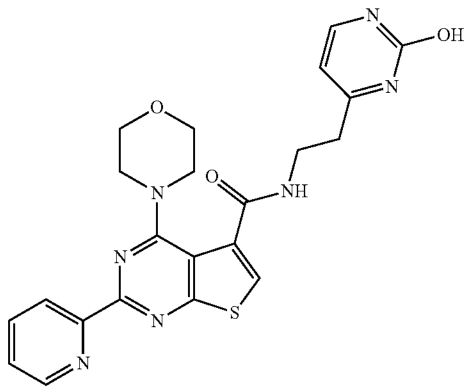 [SMILES: O=C(NCCc1ccnc(O)n1)c1csc2nc(-c3ccccn3)nc(N3CCOCC3)c12] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 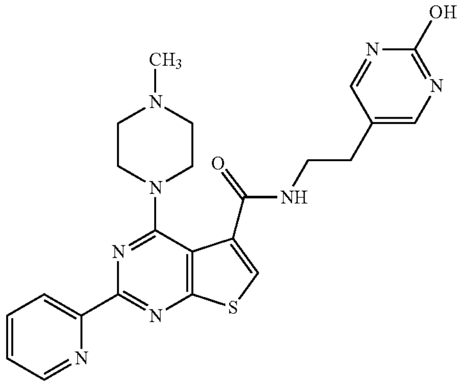 [SMILES: CN1CCN(c2nc(-c3ccccn3)nc3scc(C(=O)NCCc4cnc(O)nc4)c23)CC1] | B | B |
| 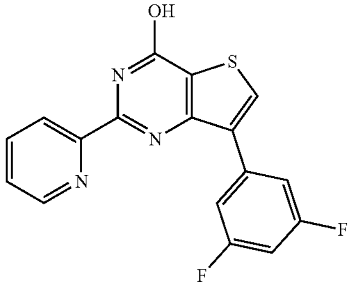 [SMILES: Oc1nc(-c2ccccn2)nc2c(-c3cc(F)cc(F)c3)csc12] | D | C |
| 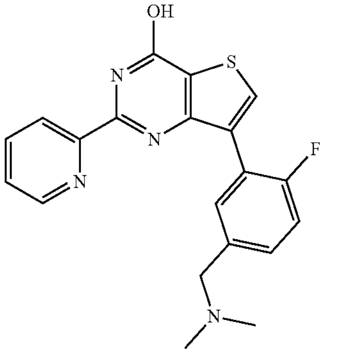 [SMILES: CN(C)Cc1ccc(F)c(-c2csc3c(O)nc(-c4ccccn4)nc23)c1] | D | C |
| 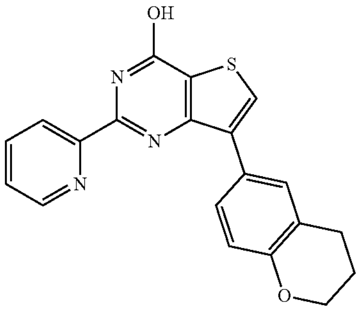 [SMILES: Oc1nc(-c2ccccn2)nc2c(-c3ccc4c(c3)CCCO4)csc12] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 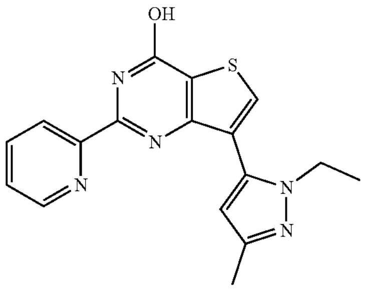 [SMILES: CCn1nc(C)cc1-c1csc2c(O)nc(-c3ccccn3)nc12] | D | C |
| 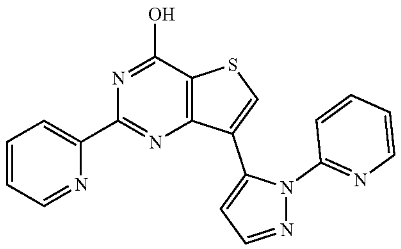 [SMILES: Oc1nc(-c2ccccn2)nc2c(-c3ccnn3-c3ccccn3)csc12] | C | 0 |
| 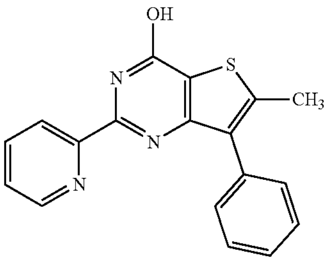 [SMILES: Cc1sc2c(O)nc(-c3ccccn3)nc2c1-c1ccccc1] | D | D |
| 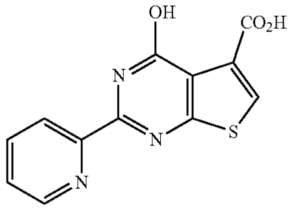 [SMILES: O=C(O)c1csc2nc(-c3ccccn3)nc(O)c12] | A | A |
| 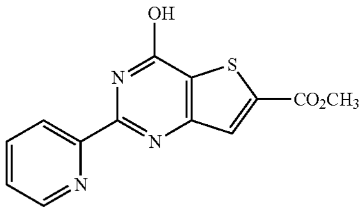 [SMILES: COC(=O)c1cc2nc(-c3ccccn3)nc(O)c2s1] | D | C |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 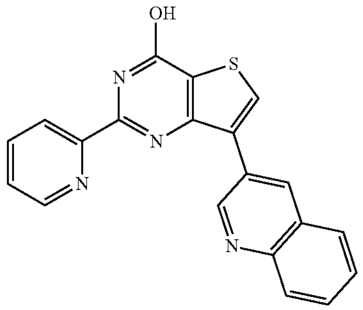 [SMILES: Oc1nc(-c2ccccn2)nc2c(-c3cnc4ccccc4c3)csc12] | D | A |
| 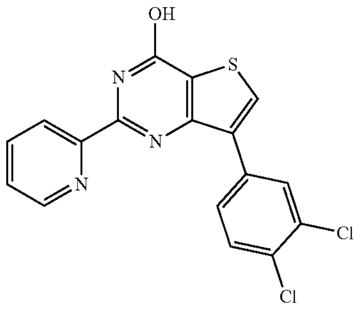 [SMILES: Oc1nc(-c2ccccn2)nc2c(-c3ccc(Cl)c(Cl)c3)csc12] | B | 0 |
| 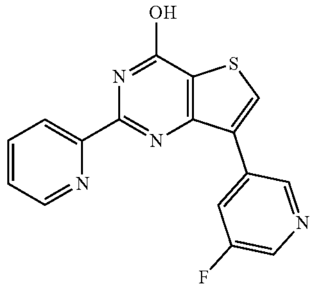 [SMILES: Oc1nc(-c2ccccn2)nc2c(-c3cncc(F)c3)csc12] | C | 0 |
| 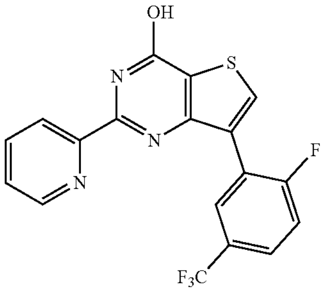 [SMILES: Oc1nc(-c2ccccn2)nc2c(-c3cc(C(F)(F)F)ccc3F)csc12] | D | A |
| 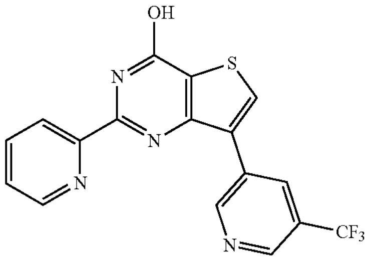 [SMILES: Oc1nc(-c2ccccn2)nc2c(-c3cncc(C(F)(F)F)c3)csc12] | A | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 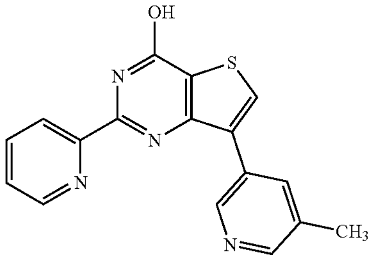 [SMILES: Cc1cncc(-c2csc3c(O)nc(-c4ccccn4)nc23)c1] | D | A |
| 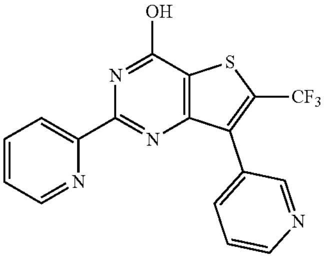 [SMILES: Oc1nc(-c2ccccn2)nc2c(-c3cccnc3)c(C(F)(F)F)sc12] | C | 0 |
| 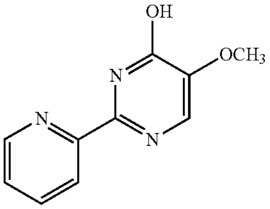 [SMILES: COc1cnc(-c2ccccn2)nc1O] | D | A |
| 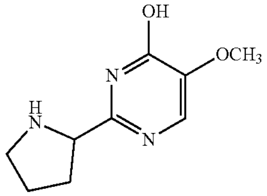 HCl | A | A |
| 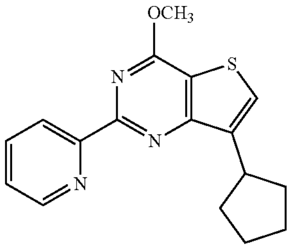 [SMILES: COc1nc(-c2ccccn2)nc2c(C3CCCC3)csc12] | 0 | 0 |
| 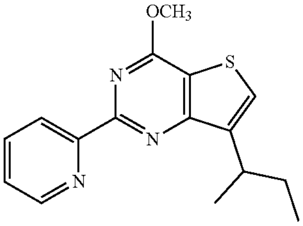 [SMILES: CCC(C)c1csc2c(OC)nc(-c3ccccn3)nc12] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 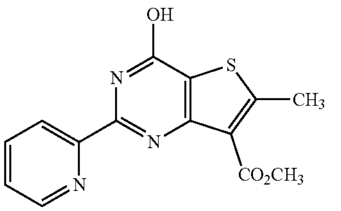 [SMILES: COC(=O)c1c(C)sc2c(O)nc(-c3ccccn3)nc12] | D | A |
| 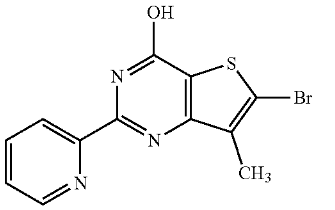 [SMILES: Cc1c(Br)sc2c(O)nc(-c3ccccn3)nc12] | D | C |
| 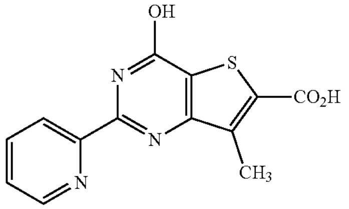 [SMILES: Cc1c(C(=O)O)sc2c(O)nc(-c3ccccn3)nc12] | D | D |
| 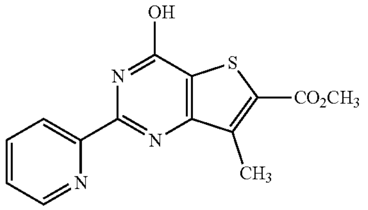 [SMILES: COC(=O)c1sc2c(O)nc(-c3ccccn3)nc2c1C] | A | 0 |
| 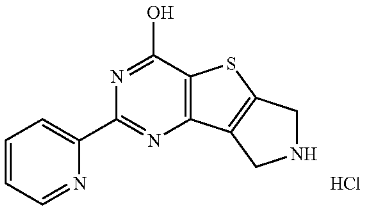 [SMILES: Oc1nc(-c2ccccn2)nc2c3c(sc12)CNC3 ; Cl] | 0 | A |
| 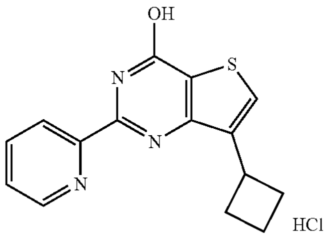 [SMILES: Oc1nc(-c2ccccn2)nc2c(C3CCC3)csc12 ; Cl] | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 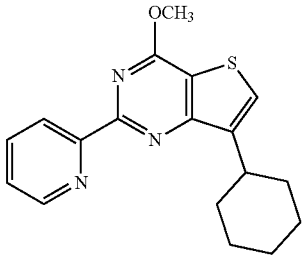 [SMILES: COc1nc(-c2ccccn2)nc2c(C3CCCCC3)csc12] | B | A |
| 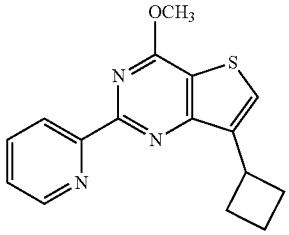 [SMILES: COc1nc(-c2ccccn2)nc2c(C3CCC3)csc12] | A | A |
| 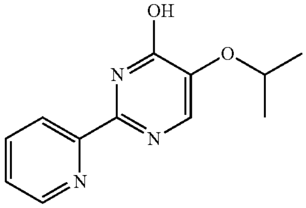 [SMILES: CC(C)Oc1cnc(-c2ccccn2)nc1O] | D | A |
| 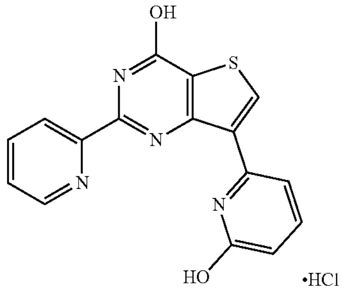 [SMILES: Oc1cccc(-c2csc3c(O)nc(-c4ccccn4)nc23)n1 ; Cl] •HCl | C | 0 |
| 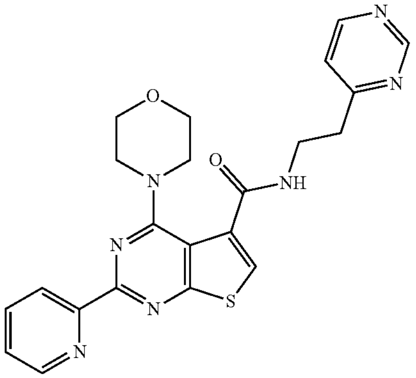 [SMILES: O=C(NCCc1ccncn1)c1csc2nc(-c3ccccn3)nc(N3CCOCC3)c12] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 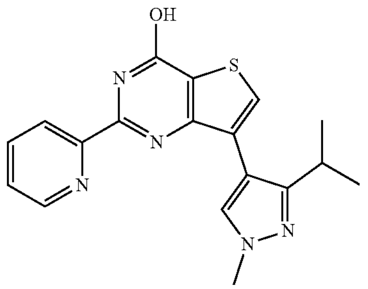 [SMILES: CC(C)c1nn(C)cc1-c1csc2c(O)nc(-c3ccccn3)nc12] | D | A |
| 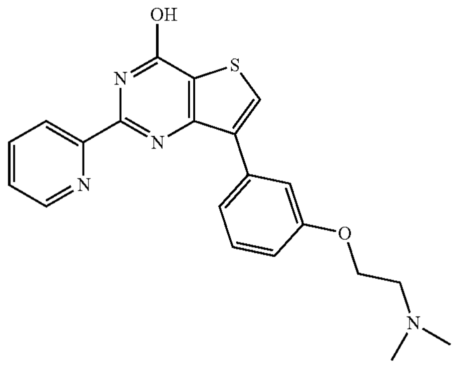 [SMILES: CN(C)CCOc1cccc(-c2csc3c(O)nc(-c4ccccn4)nc23)c1] | D | D |
| 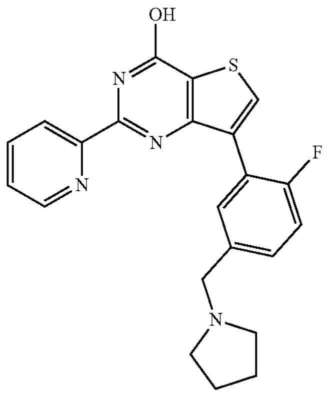 [SMILES: Oc1nc(-c2ccccn2)nc2c(-c3cc(CN4CCCC4)ccc3F)csc12] | C | 0 |
| 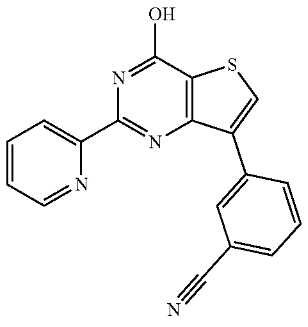 [SMILES: N#Cc1cccc(-c2csc3c(O)nc(-c4ccccn4)nc23)c1] | B | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 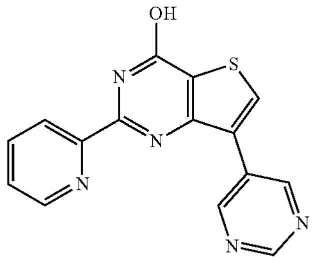 [SMILES: Oc1nc(-c2ccccn2)nc2c(-c3cncnc3)csc12] | B | 0 |
| 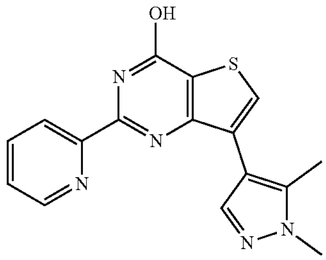 [SMILES: Cc1c(-c2csc3c(O)nc(-c4ccccn4)nc23)cnn1C] | D | C |
| 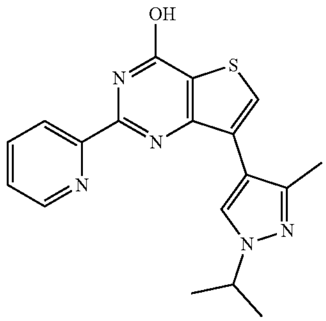 [SMILES: Cc1nn(C(C)C)cc1-c1csc2c(O)nc(-c3ccccn3)nc12] | D | B |
| 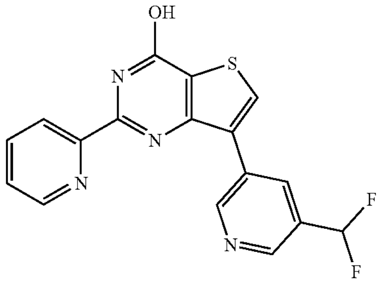 [SMILES: Oc1nc(-c2ccccn2)nc2c(-c3cncc(C(F)F)c3)csc12] | B | 0 |
| 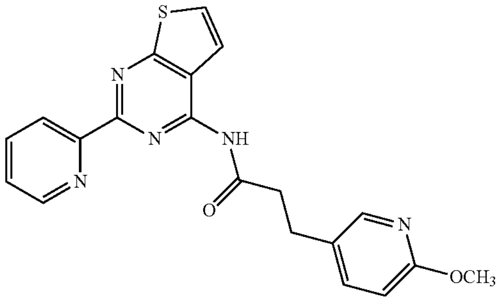 [SMILES: COc1ccc(CCC(=O)Nc2nc(-c3ccccn3)nc3sccc23)cn1] | D | C |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 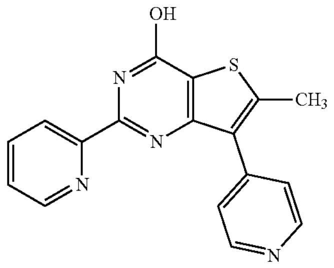 [SMILES: Cc1sc2c(O)nc(-c3ccccn3)nc2c1-c1ccncc1] | B | 0 |
| 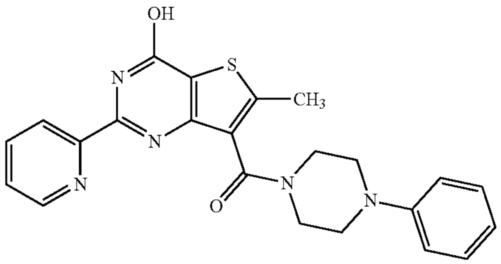 [SMILES: Cc1sc2c(O)nc(-c3ccccn3)nc2c1C(=O)N1CCN(c2ccccc2)CC1] | B | A |
| 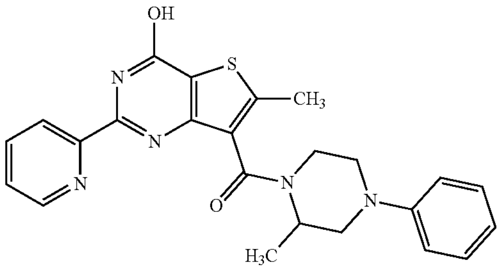 [SMILES: Cc1sc2c(O)nc(-c3ccccn3)nc2c1C(=O)N1CCN(c2ccccc2)CC1C] | A | 0 |
| 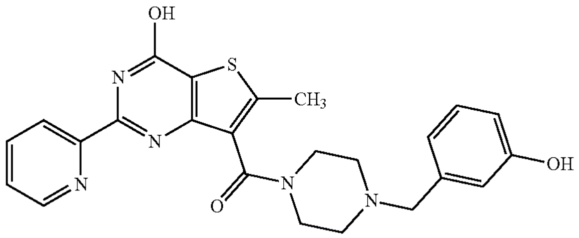 [SMILES: Cc1sc2c(O)nc(-c3ccccn3)nc2c1C(=O)N1CCN(Cc2cccc(O)c2)CC1] | B | 0 |
| 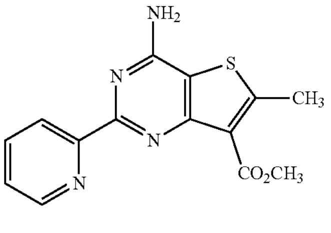 | D | A |
| 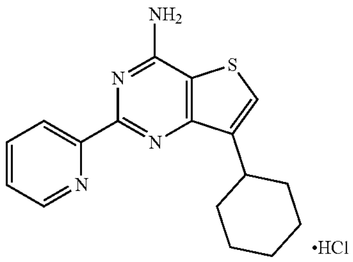 [SMILES: Nc1nc(-c2ccccn2)nc2c(C3CCCCC3)csc12 ; Cl] | 0 | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 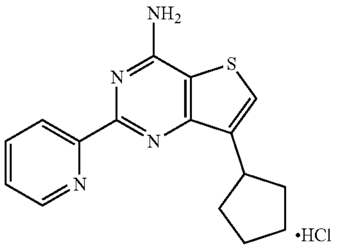 [SMILES: Nc1nc(-c2ccccn2)nc2c(C3CCCC3)csc12 ; Cl] | C | B |
| 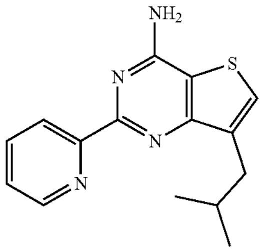 [SMILES: CC(C)Cc1csc2c(N)nc(-c3ccccn3)nc12] | D | D |
| 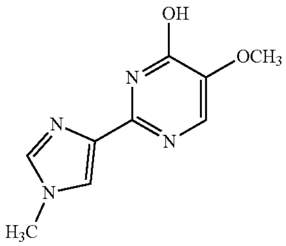 | B | 0 |
| 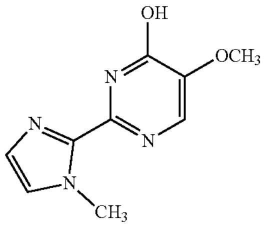 | A | 0 |
| 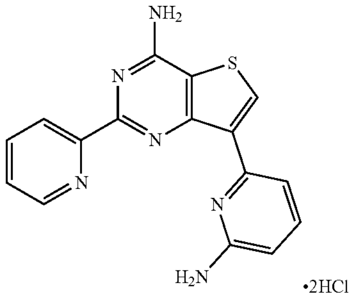 [SMILES: Nc1cccc(-c2csc3c(N)nc(-c4ccccn4)nc23)n1 ; "·2HCl"] | D | B |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 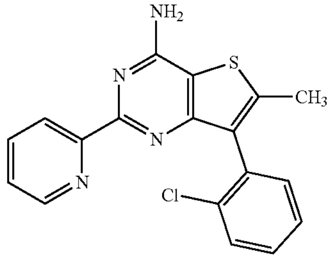 | C | C |
| 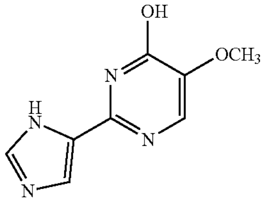 [SMILES: COc1cnc(-c2cnc[nH]2)nc1O] | A | 0 |
| 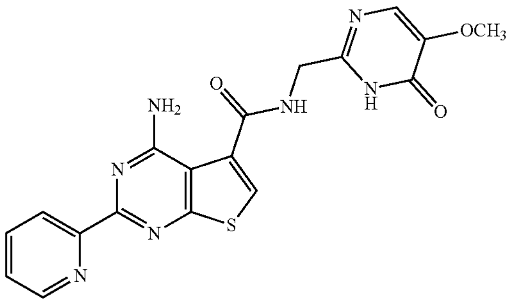 [SMILES: COc1cnc(CNC(=O)c2csc3nc(-c4ccccn4)nc(N)c23)[nH]c1=O] | A | A |
| 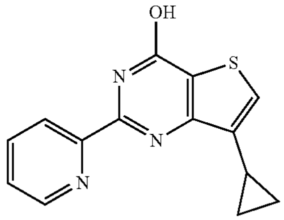 [SMILES: Oc1nc(-c2ccccn2)nc2c(C3CC3)csc12] | A | A |
| 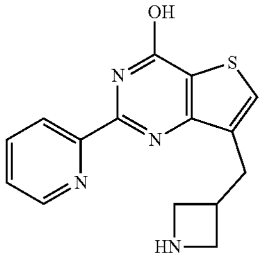 [SMILES: Oc1nc(-c2ccccn2)nc2c(CC3CNC3)csc12] | D | A |
| 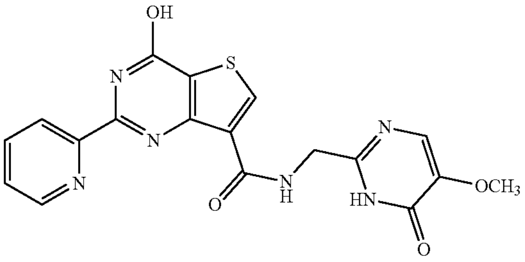 [SMILES: COc1cnc(CNC(=O)c2csc3c(O)nc(-c4ccccn4)nc23)[nH]c1=O] | A | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 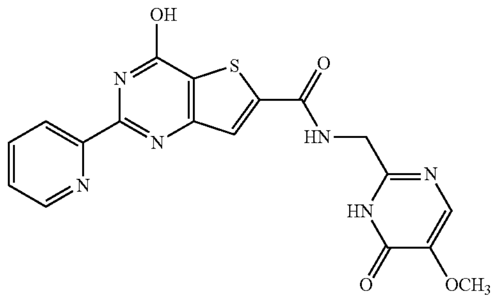 [SMILES: COc1cnc(CNC(=O)c2cc3nc(-c4ccccn4)nc(O)c3s2)[nH]c1=O] | 0 | A |
| 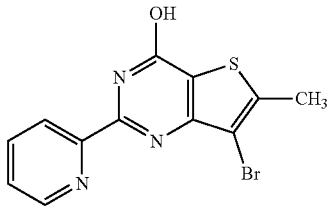 [SMILES: Cc1sc2c(O)nc(-c3ccccn3)nc2c1Br] | B | 0 |
| 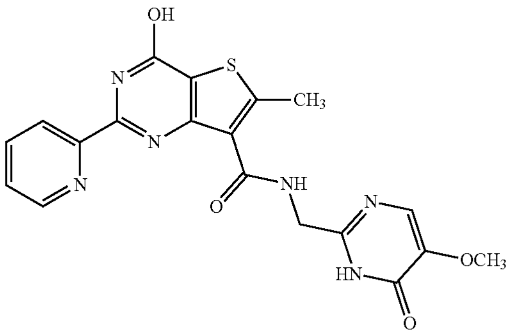 [SMILES: COc1cnc(CNC(=O)c2c(C)sc3c(O)nc(-c4ccccn4)nc23)[nH]c1=O] | 0 | A |
| 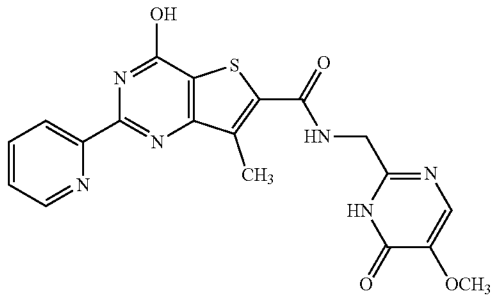 [SMILES: COc1cnc(CNC(=O)c2sc3c(O)nc(-c4ccccn4)nc3c2C)[nH]c1=O] | A | A |
| 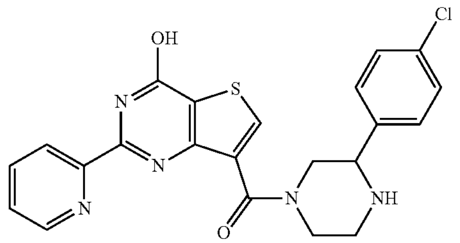 [SMILES: O=C(c1csc2c(O)nc(-c3ccccn3)nc12)N1CCNC(c2ccc(Cl)cc2)C1] | D | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 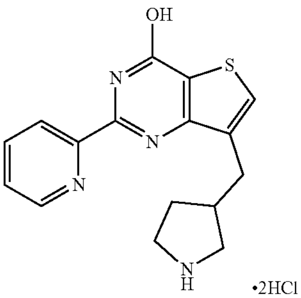 [SMILES: Oc1nc(-c2ccccn2)nc2c(CC3CCNC3)csc12] •2HCl | C | A |
| 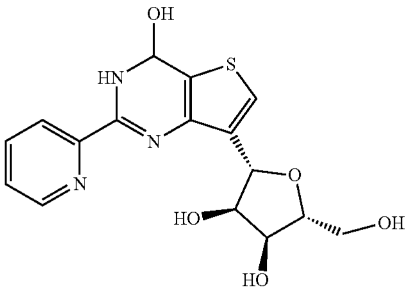 [SMILES: OC[C@H]1O[C@@H](c2csc3c2N=C(c2ccccn2)NC3O)[C@H](O)[C@@H]1O] | A | B |
| 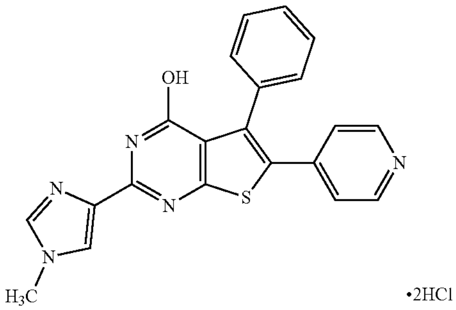 [SMILES: Cn1cnc(-c2nc(O)c3c(-c4ccccc4)c(-c4ccncc4)sc3n2)c1] •2HCl | 0 | A |
| 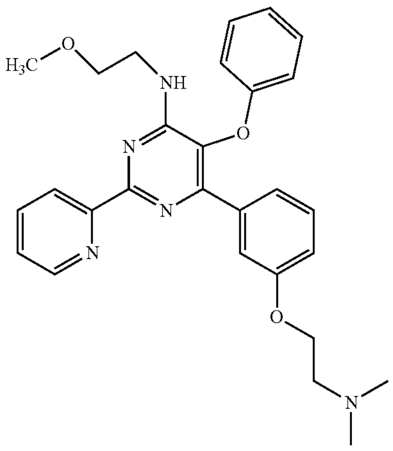 [SMILES: COCCNc1nc(-c2ccccn2)nc(-c2cccc(OCCN(C)C)c2)c1Oc1ccccc1] | 0 | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 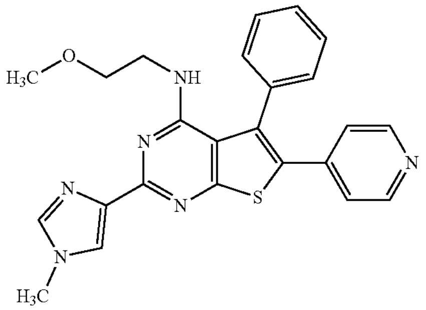 [SMILES: COCCNc1nc(-c2cn(C)cn2)nc2sc(-c3ccncc3)c(-c3ccccc3)c12] | C | A |
| 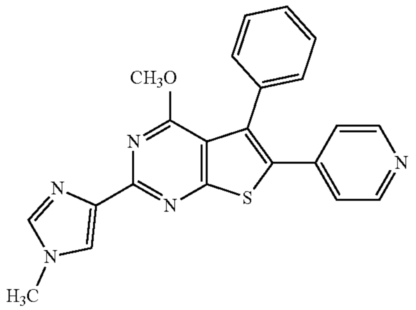 | C | A |
| 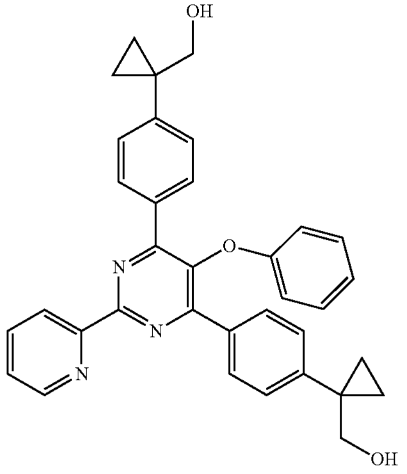 [SMILES: OCC1(c2ccc(-c3nc(-c4ccccn4)nc(-c4ccc(C5(CO)CC5)cc4)c3Oc3ccccc3)cc2)CC1] | 0 | 0 |
| 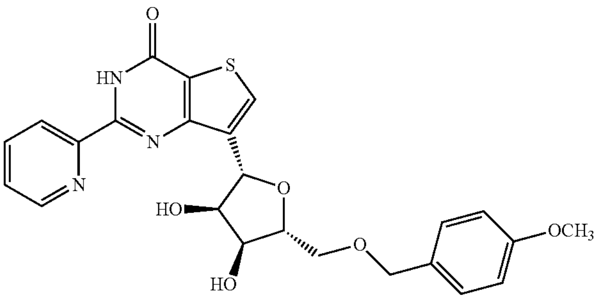 [SMILES: COc1ccc(COC[C@H]2O[C@@H](c3csc4c(=O)[nH]c(-c5ccccn5)nc34)[C@H](O)[C@@H]2O)cc1] | A | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 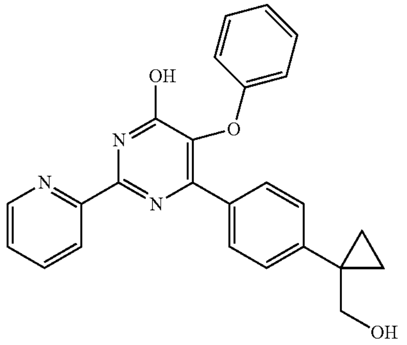 [SMILES: OCC1(c2ccc(-c3nc(-c4ccccn4)nc(O)c3Oc3ccccc3)cc2)CC1] | 0 | B |
| 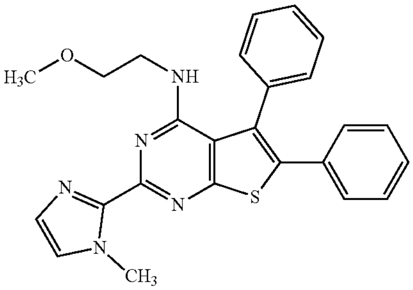 | C | B |
| 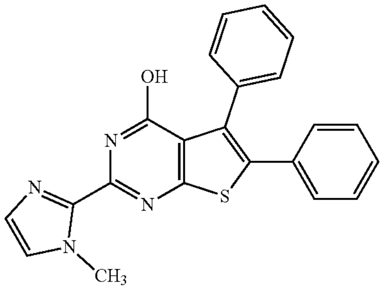 | A | B |
| 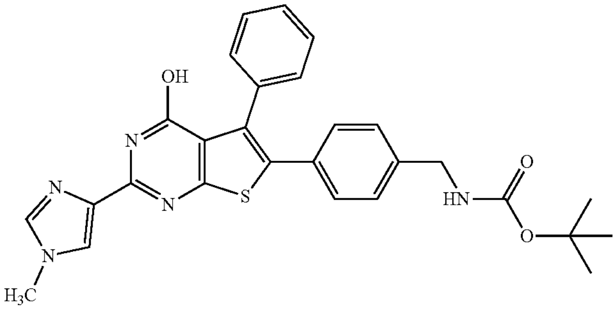 | A | 0 |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 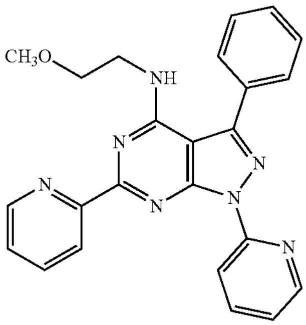 | D | C |
| 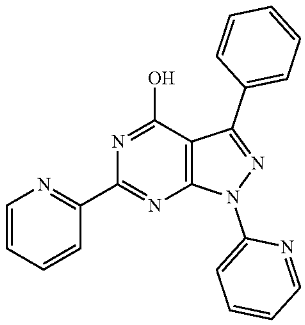 [SMILES: Oc1nc(-c2ccccn2)nc2c1c(-c1ccccc1)nn2-c1ccccn1] | C | A |
| 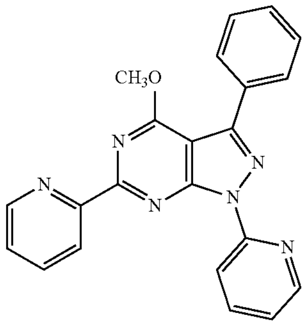 | D | D |
| 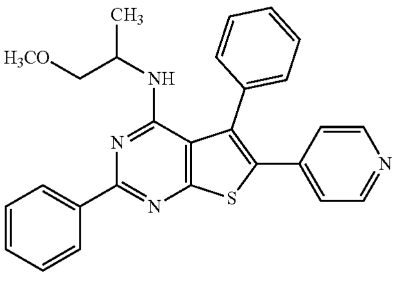 | 0 | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 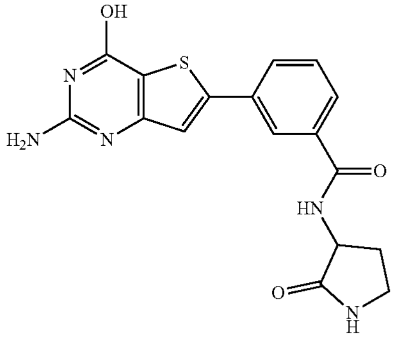 [SMILES: Nc1nc(O)c2sc(-c3cccc(C(=O)NC4CCNC4=O)c3)cc2n1] | A | A |
| 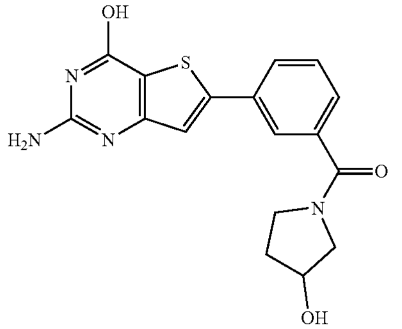 [SMILES: Nc1nc(O)c2sc(-c3cccc(C(=O)N4CCC(O)C4)c3)cc2n1] | 0 | 0 |
| 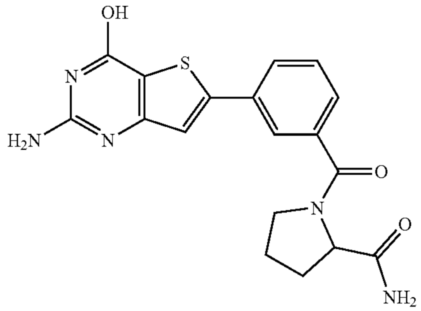 [SMILES: NC(=O)C1CCCN1C(=O)c1cccc(-c2cc3nc(N)nc(O)c3s2)c1] | 0 | 0 |
| 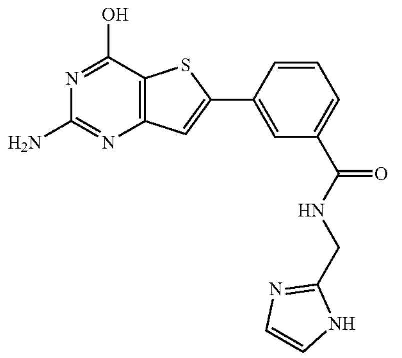 [SMILES: Nc1nc(O)c2sc(-c3cccc(C(=O)NCc4ncc[nH]4)c3)cc2n1] | 0 | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 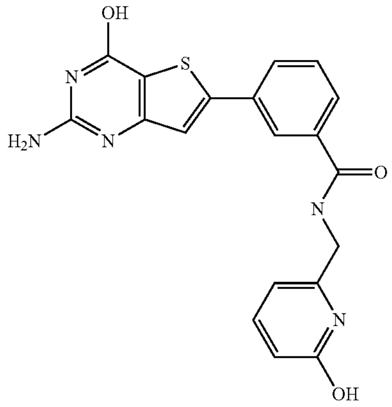 [SMILES: Nc1nc(O)c2sc(-c3cccc(C(=O)NCc4cccc(O)n4)c3)cc2n1] | C | 0 |
| 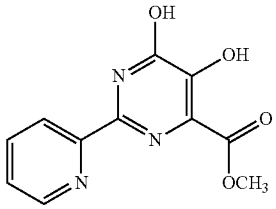 [SMILES: COC(=O)c1nc(-c2ccccn2)nc(O)c1O] | 0 | 0 |
| 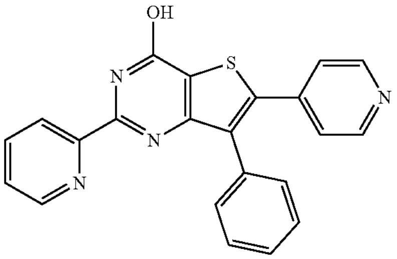 [SMILES: Oc1nc(-c2ccccn2)nc2c(-c3ccccc3)c(-c3ccncc3)sc12] | A | 0 |
| 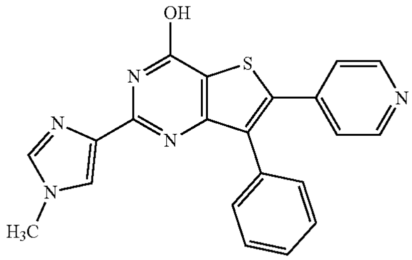 [SMILES: Cn1cnc(-c2nc(O)c3sc(-c4ccncc4)c(-c4ccccc4)c3n2)c1] | A | 0 |
| 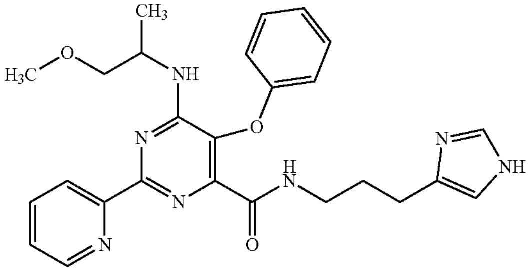 [SMILES: COCC(C)Nc1nc(-c2ccccn2)nc(C(=O)NCCCc2c[nH]cn2)c1Oc1ccccc1] | A | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 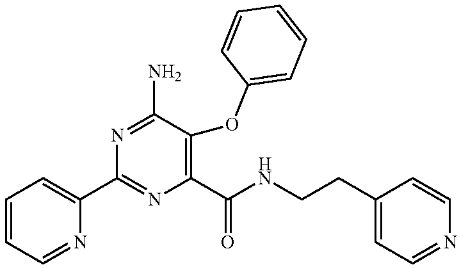 [SMILES: Nc1nc(-c2ccccn2)nc(C(=O)NCCc2ccncc2)c1Oc1ccccc1] | 0 | 0 |
| 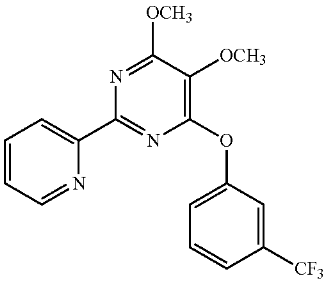 | A | A |
| 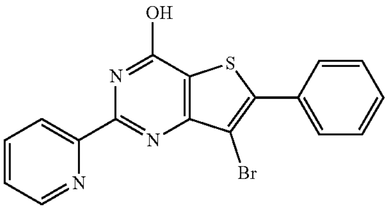 [SMILES: Oc1nc(-c2ccccn2)nc2c(Br)c(-c3ccccc3)sc12] | A | 0 |
| 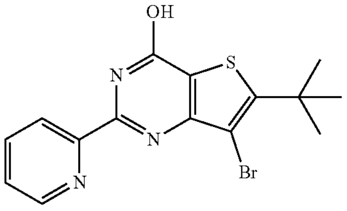 [SMILES: CC(C)(C)c1sc2c(O)nc(-c3ccccn3)nc2c1Br] | 0 | A |
| 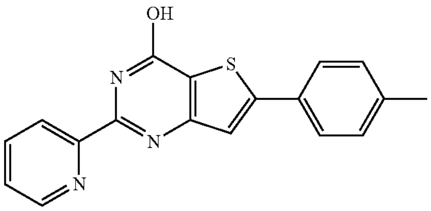 [SMILES: Cc1ccc(-c2cc3nc(-c4ccccn4)nc(O)c3s2)cc1] | A | A |
| 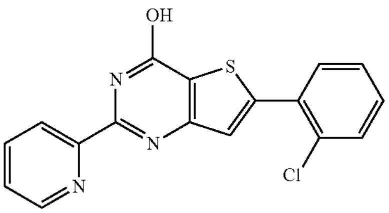 [SMILES: Oc1nc(-c2ccccn2)nc2cc(-c3ccccc3Cl)sc12] | B | 0 |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 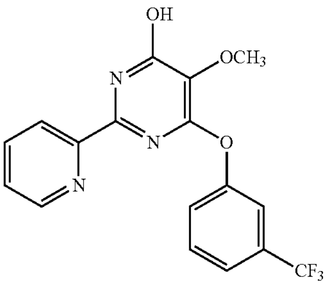 | A | B |
| 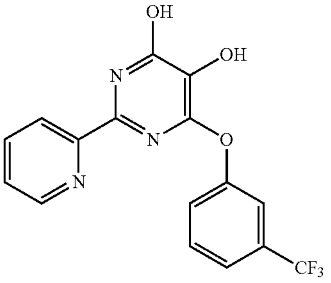 [SMILES: Oc1nc(-c2ccccn2)nc(Oc2cccc(C(F)(F)F)c2)c1O] | A | A |
| 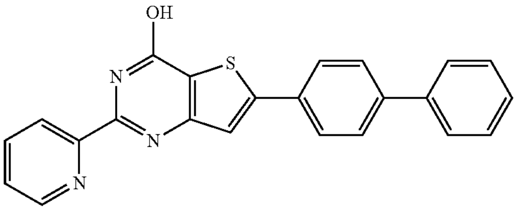 [SMILES: Oc1nc(-c2ccccn2)nc2cc(-c3ccc(-c4ccccc4)cc3)sc12] | C | A |
| 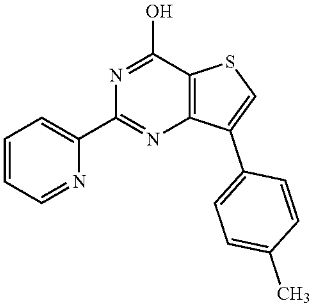 [SMILES: Cc1ccc(-c2csc3c(O)nc(-c4ccccn4)nc23)cc1] | 0 | A |
| 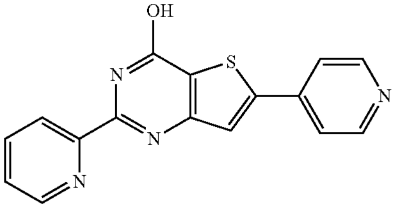 [SMILES: Oc1nc(-c2ccccn2)nc2cc(-c3ccncc3)sc12] | B | A |
| 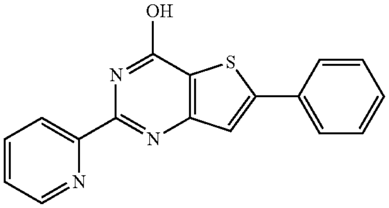 [SMILES: Oc1nc(-c2ccccn2)nc2cc(-c3ccccc3)sc12] | B | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 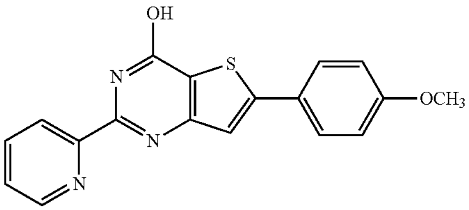 [SMILES: COc1ccc(-c2cc3nc(-c4ccccn4)nc(O)c3s2)cc1] | 0 | A |
| 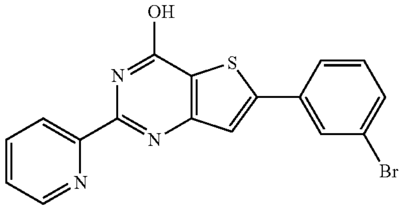 [SMILES: Oc1nc(-c2ccccn2)nc2cc(-c3cccc(Br)c3)sc12] | A | A |
| 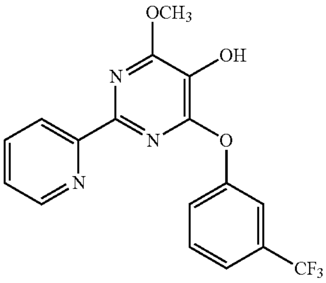 | 0 | A |
| 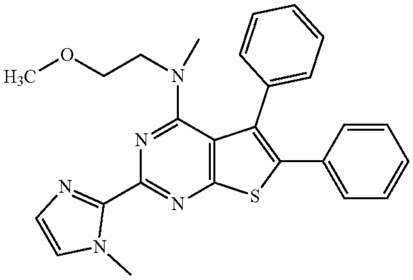 [SMILES: COCCN(C)c1nc(-c2nccn2C)nc2sc(-c3ccccc3)c(-c3ccccc3)c12] | D | D |
| 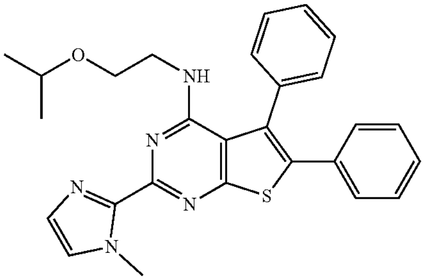 [SMILES: CC(C)OCCNc1nc(-c2nccn2C)nc2sc(-c3ccccc3)c(-c3ccccc3)c12] | A | A |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 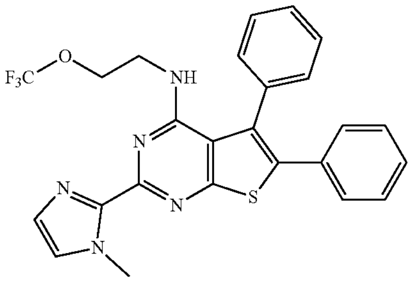 [SMILES: Cn1ccnc1-c1nc(NCCOC(F)(F)F)c2c(-c3ccccc3)c(-c3ccccc3)sc2n1] | B | A |
| 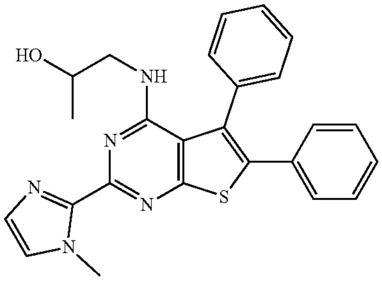 [SMILES: CC(O)CNc1nc(-c2nccn2C)nc2sc(-c3ccccc3)c(-c3ccccc3)c12] | B | 0 |
| 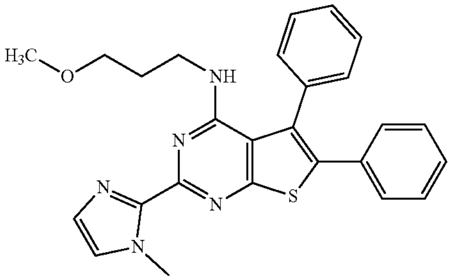 [SMILES: COCCCNc1nc(-c2nccn2C)nc2sc(-c3ccccc3)c(-c3ccccc3)c12] | D | D |
| 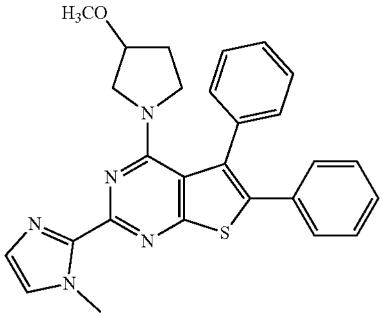 [SMILES: COC1CCN(c2nc(-c3nccn3C)nc3sc(-c4ccccc4)c(-c4ccccc4)c23)C1] | D | D |
| 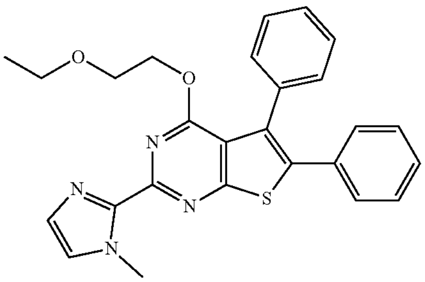 [SMILES: CCOCCOc1nc(-c2nccn2C)nc2sc(-c3ccccc3)c(-c3ccccc3)c12] | A | B |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 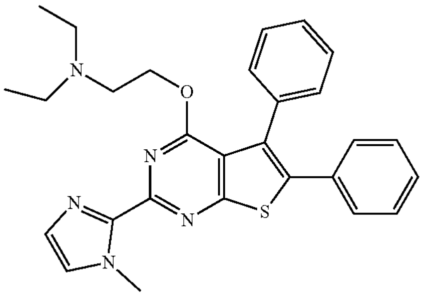 [SMILES: CCN(CC)CCOc1nc(-c2nccn2C)nc2sc(-c3ccccc3)c(-c3ccccc3)c12] | D | D |
| 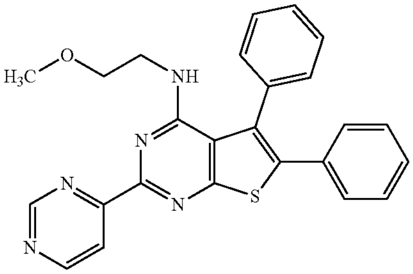 | D | C |
| 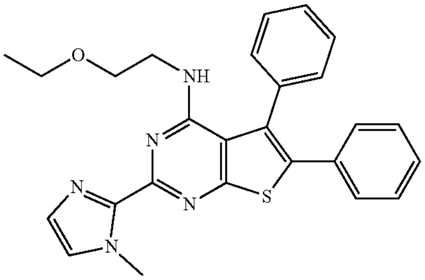 [SMILES: CCOCCNc1nc(-c2nccn2C)nc2sc(-c3ccccc3)c(-c3ccccc3)c12] | D | D |
| 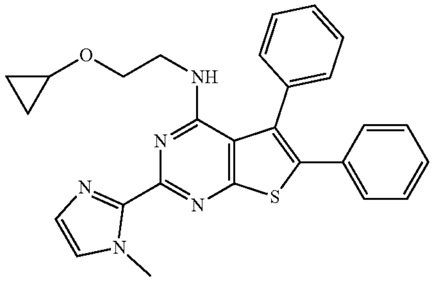 [SMILES: Cn1ccnc1-c1nc(NCCOC2CC2)c2c(-c3ccccc3)c(-c3ccccc3)sc2n1] | D | D |
| 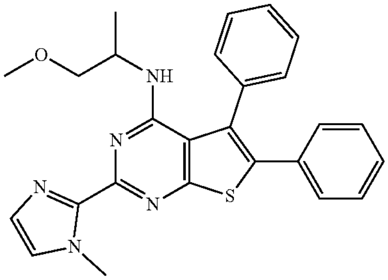 [SMILES: COCC(C)Nc1nc(-c2nccn2C)nc2sc(-c3ccccc3)c(-c3ccccc3)c12] | D | D |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 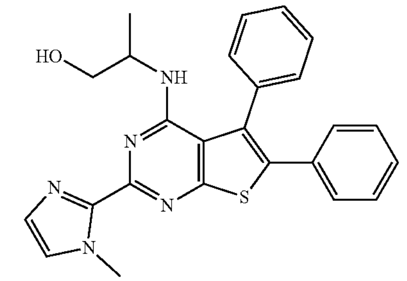 [SMILES: CC(CO)Nc1nc(-c2nccn2C)nc2sc(-c3ccccc3)c(-c3ccccc3)c12] | C | A |
| 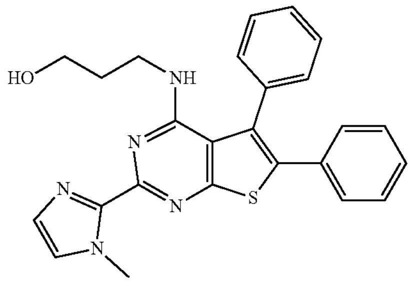 [SMILES: Cn1ccnc1-c1nc(NCCCO)c2c(-c3ccccc3)c(-c3ccccc3)sc2n1] | C | B |
| 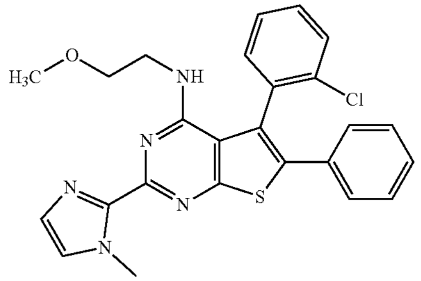 [SMILES: COCCNc1nc(-c2nccn2C)nc2sc(-c3ccccc3)c(-c3ccccc3Cl)c12] | C | A |
| 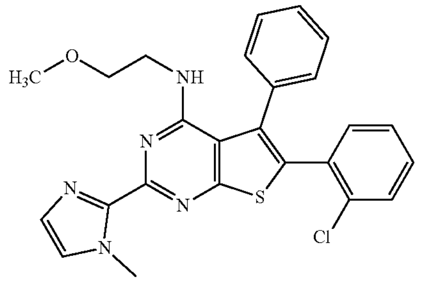 [SMILES: COCCNc1nc(-c2nccn2C)nc2sc(-c3ccccc3Cl)c(-c3ccccc3)c12] | A | A |
| 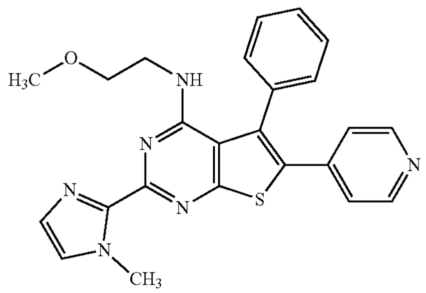 [SMILES: COCCNc1nc(-c2nccn2C)nc2sc(-c3ccncc3)c(-c3ccccc3)c12] | D | C |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 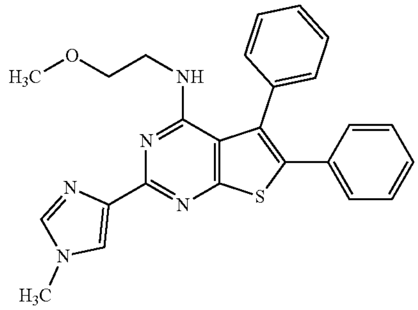 [SMILES: COCCNc1nc(-c2cn(C)cn2)nc2sc(-c3ccccc3)c(-c3ccccc3)c12] | D | D |
| 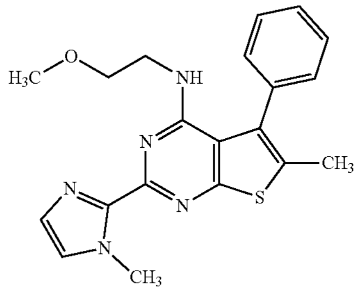 [SMILES: COCCNc1nc(-c2nccn2C)nc2sc(C)c(-c3ccccc3)c12] | A | B |
| 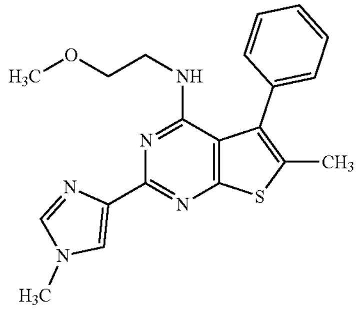 [SMILES: COCCNc1nc(-c2cn(C)cn2)nc2sc(C)c(-c3ccccc3)c12] | A | B |
| 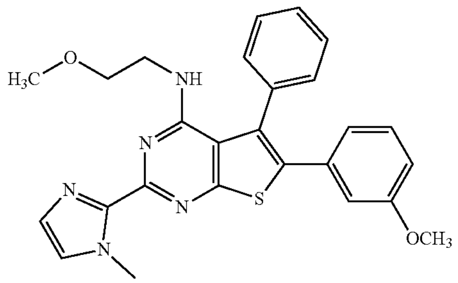 [SMILES: COCCNc1nc(-c2nccn2C)nc2sc(-c3cccc(OC)c3)c(-c3ccccc3)c12] | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 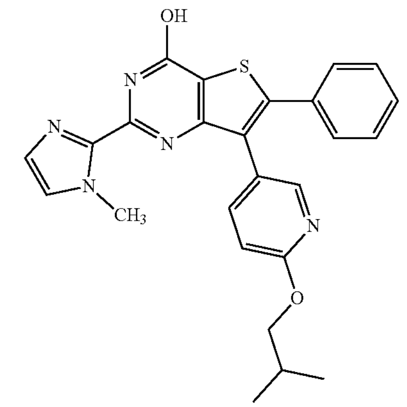 [SMILES: CC(C)COc1ccc(-c2c(-c3ccccc3)sc3c(O)nc(-c4nccn4C)nc23)cn1] | C | A |
| 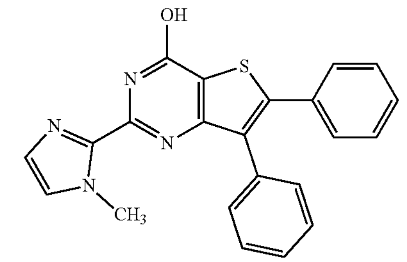 [SMILES: Cn1ccnc1-c1nc(O)c2sc(-c3ccccc3)c(-c3ccccc3)c2n1] | A | 0 |
| 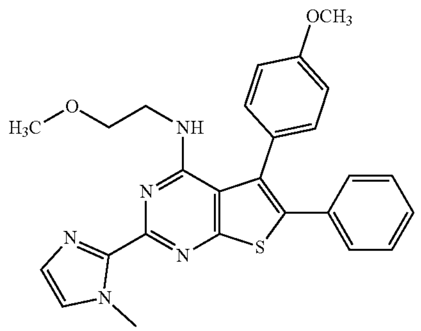 [SMILES: COCCNc1nc(-c2nccn2C)nc2sc(-c3ccccc3)c(-c3ccc(OC)cc3)c12] | D | C |
| 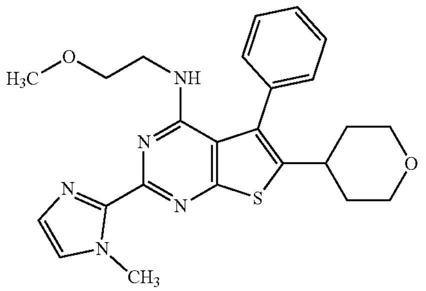 | D | D |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 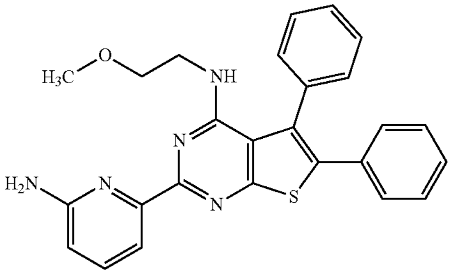 [SMILES: COCCNc1nc(-c2cccc(N)n2)nc2sc(-c3ccccc3)c(-c3ccccc3)c12] | B | B |
| 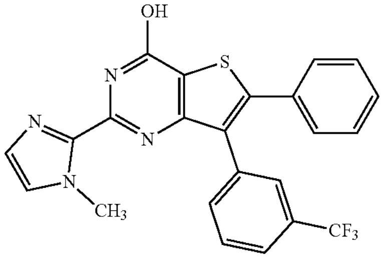 [SMILES: Cn1ccnc1-c1nc(O)c2sc(-c3ccccc3)c(-c3cccc(C(F)(F)F)c3)c2n1] | B | B |
| 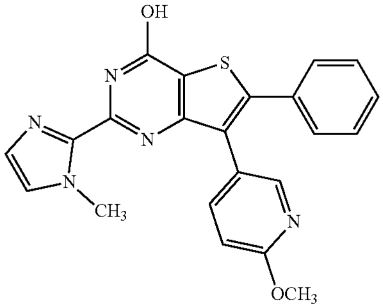 [SMILES: COc1ccc(-c2c(-c3ccccc3)sc3c(O)nc(-c4nccn4C)nc23)cn1] | B | B |
| 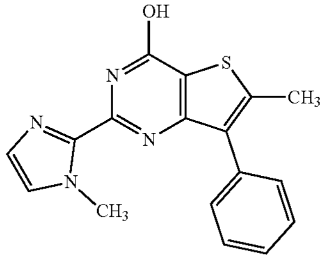 [SMILES: Cc1sc2c(O)nc(-c3nccn3C)nc2c1-c1ccccc1] | D | B |
| 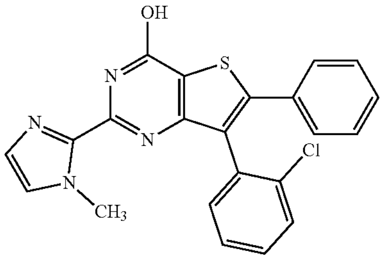 [SMILES: Cn1ccnc1-c1nc(O)c2sc(-c3ccccc3)c(-c3ccccc3Cl)c2n1] | D | C |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 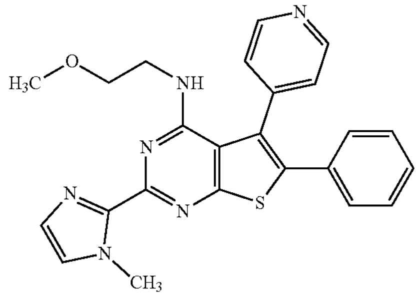 [SMILES: COCCNc1nc(-c2nccn2C)nc2sc(-c3ccccc3)c(-c3ccncc3)c12] | C | A |
| 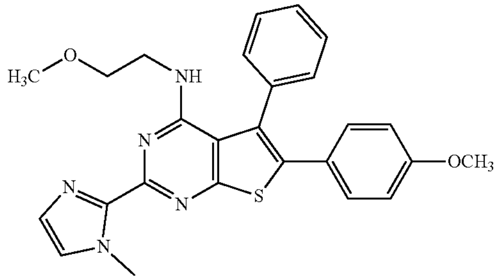 [SMILES: COCCNc1nc(-c2nccn2C)nc2sc(-c3ccc(OC)cc3)c(-c3ccccc3)c12] | D | C |
| 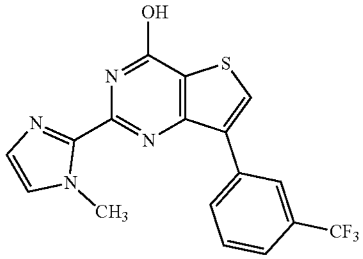 [SMILES: Cn1ccnc1-c1nc(O)c2scc(-c3cccc(C(F)(F)F)c3)c2n1] | D | C |
| 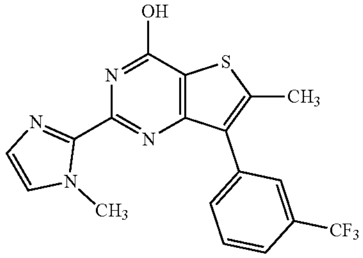 [SMILES: Cc1sc2c(O)nc(-c3nccn3C)nc2c1-c1cccc(C(F)(F)F)c1] | 0 | 0 |
| 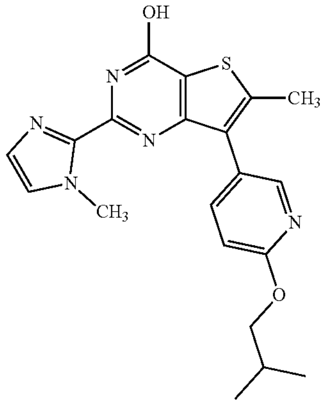 [SMILES: Cc1sc2c(O)nc(-c3nccn3C)nc2c1-c1ccc(OCC(C)C)nc1] | A | A |

TABLE 6-continued
IL-6 and TNFα % Inhibition at 30 μM in RAW 264.7 murine leukemia virus transformed macrophage cell lines
| Compound | IL-6 | TNF-α |
| --- | --- | --- |
| 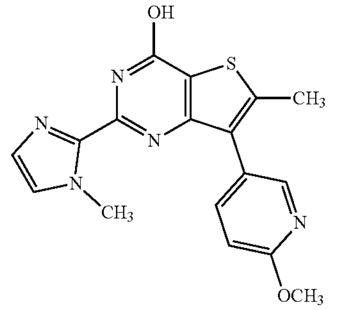 [SMILES: COc1ccc(-c2c(C)sc3c(O)nc(-c4nccn4C)nc23)cn1] | A | A |
| 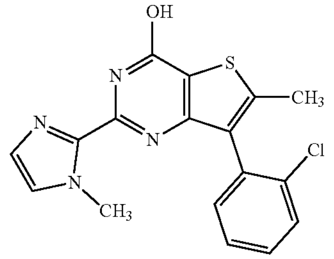 [SMILES: Cc1sc2c(O)nc(-c3nccn3C)nc2c1-c1ccccc1Cl] | B | A |
| 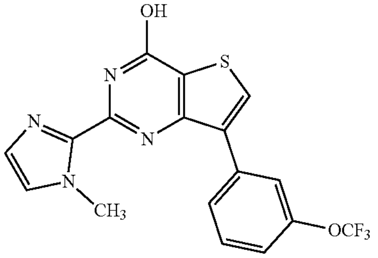 [SMILES: Cn1ccnc1-c1nc(O)c2scc(-c3cccc(OC(F)(F)F)c3)c2n1] | D | C |
| 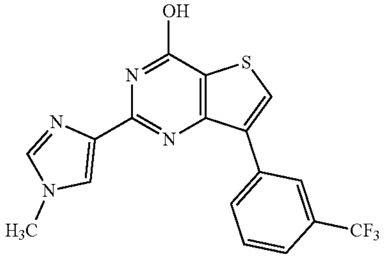 [SMILES: Cn1cnc(-c2nc(O)c3scc(-c4cccc(C(F)(F)F)c4)c3n2)c1] | 0 | 0 |
| 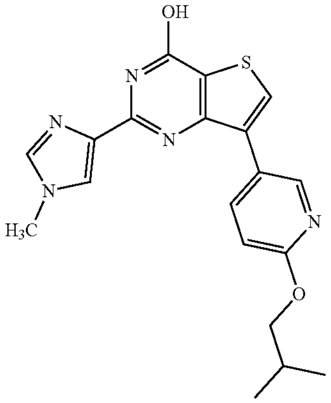 [SMILES: CC(C)COc1ccc(-c2csc3c(O)nc(-c4cn(C)cn4)nc23)cn1] | D | B |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 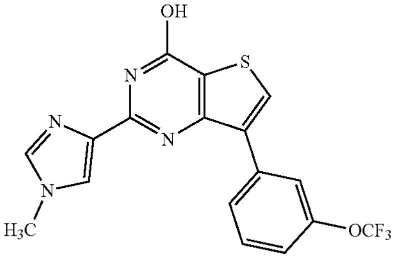 [SMILES: Cn1cnc(-c2nc(O)c3scc(-c4cccc(OC(F)(F)F)c4)c3n2)c1] | 0 | 0 |
| 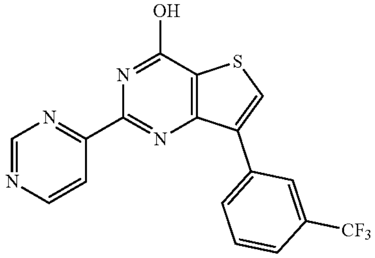 [SMILES: Oc1nc(-c2ccncn2)nc2c(-c3cccc(C(F)(F)F)c3)csc12] | B | 0 |
| 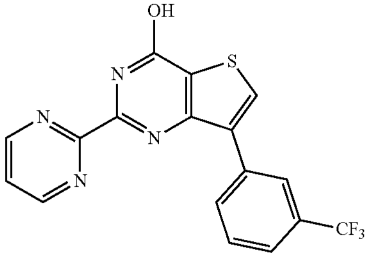 | A | B |
| 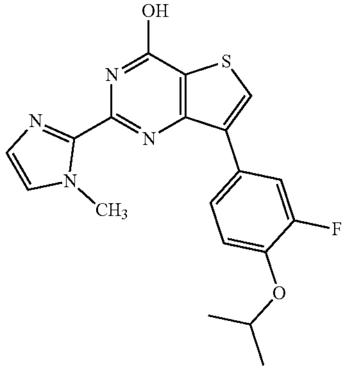 [SMILES: CC(C)Oc1ccc(-c2csc3c(O)nc(-c4nccn4C)nc23)cc1F] | A | 0 |
| 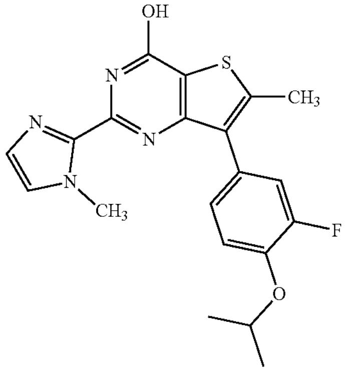 [SMILES: Cc1sc2c(O)nc(-c3nccn3C)nc2c1-c1ccc(OC(C)C)c(F)c1] | C | 0 |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 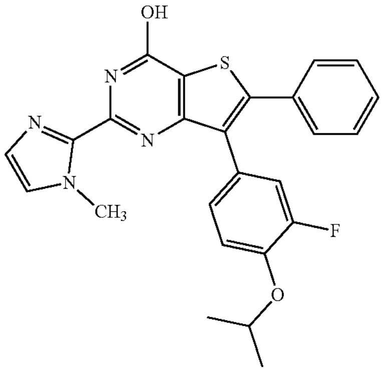 [SMILES: CC(C)Oc1ccc(-c2c(-c3ccccc3)sc3c(O)nc(-c4nccn4C)nc23)cc1F] | A | 0 |
| 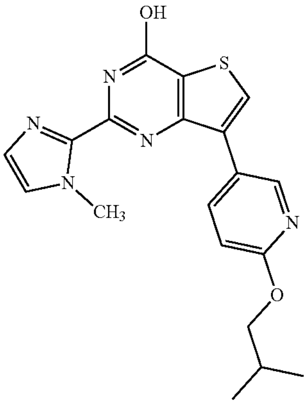 [SMILES: CC(C)COc1ccc(-c2csc3c(O)nc(-c4nccn4C)nc23)cn1] | D | D |
| 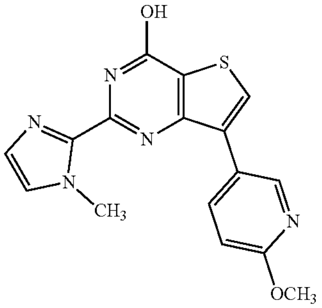 [SMILES: COc1ccc(-c2csc3c(O)nc(-c4nccn4C)nc23)cn1] | D | D |
| 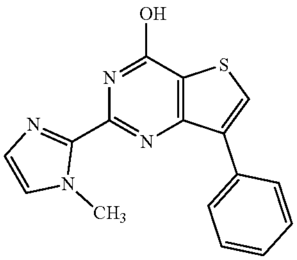 [SMILES: Cn1ccnc1-c1nc(O)c2scc(-c3ccccc3)c2n1] | D | C |

TABLE 6-continued
| IL-6 and TNFα % Inhibition at 30 μM in RAW 264.7 murine leukemia virus transformed macrophage cell lines | | |
|---|---|---|
| Compound | IL-6 | TNF-α |
| 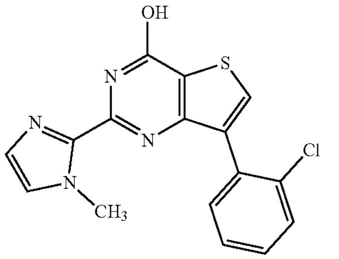 [SMILES: Cn1ccnc1-c1nc(O)c2scc(-c3ccccc3Cl)c2n1] | C | A |
| 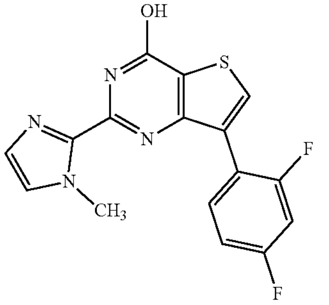 [SMILES: Cn1ccnc1-c1nc(O)c2scc(-c3ccc(F)cc3F)c2n1] | C | A |
| 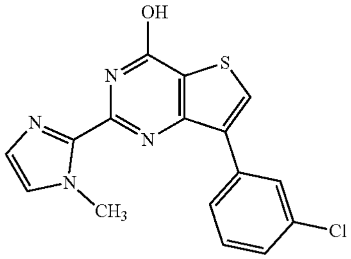 [SMILES: Cn1ccnc1-c1nc(O)c2scc(-c3cccc(Cl)c3)c2n1] | C | 0 |
| 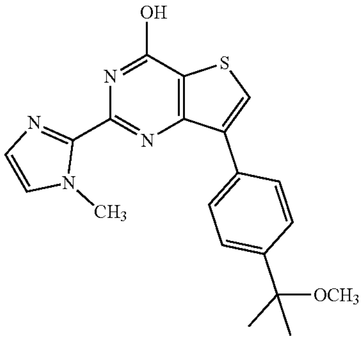 [SMILES: COC(C)(C)c1ccc(-c2csc3c(O)nc(-c4nccn4C)nc23)cc1] | B | 0 |
| 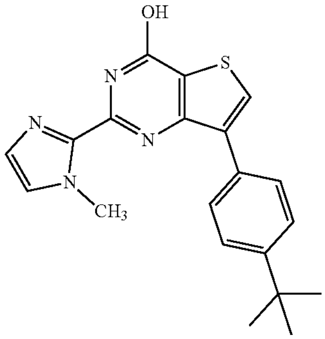 [SMILES: Cn1ccnc1-c1nc(O)c2scc(-c3ccc(C(C)(C)C)cc3)c2n1] | A | 0 |

TABLE 6-continued

| IL-6 and TNFα % Inhibition at 30 μM in RAW 264.7 murine leukemia virus transformed macrophage cell lines | | |
|---|---|---|
| Compound | IL-6 | TNF-α |
| 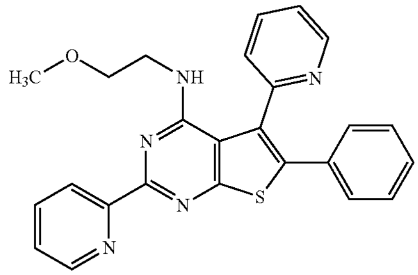 [SMILES: COCCNc1nc(-c2ccccn2)nc2sc(-c3ccccc3)c(-c3ccccn3)c12] | 0 | 0 |
| 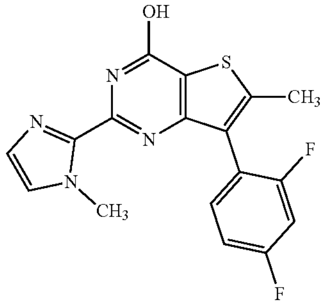 [SMILES: Cc1sc2c(O)nc(-c3nccn3C)nc2c1-c1ccc(F)cc1F] | C | 0 |
| 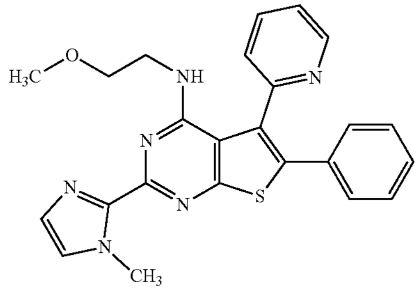 | D | D |

0 = 0% inhibition, A = 1-25% inhibition, B = 26-50% inhibition, C = 51-75% inhibition, D = 76-100% inhibition.

Example 5

Ras GTP Binding Domain Inhibition Assay

The following method was developed as specific assay for KRas G12D mutant protein.

Buffer-I:

50 mM Tris, pH 7.5

150 mM NaCl (optional)

1 mM MgCl2

1 mM DTT.

KRas G12D mutant protein was expressed as a His-tagged protein. Purified His-KRas G12D protein was diluted in buffer-I to a final concentration of 3-10 μg/ml.

200 μl of the diluted His-KRas G12D protein was added to a nickel coated 96 well plate and incubated overnight at 4° C.

The next day, wells were washed 3× in 200 μl of Buffer-I.

Then 200 μl of Buffer-I were added to each well in the presence of 1% DMSO.

Tested compounds were added to the protein-coated wells at a concentration of 20 μM, and incubated for 3 hours at room temperature. While performing $IC_{50}$ measurements a serial dilution of all tested concentrations was prepared.

Then 22 μl of Cy3-GTP or Cy5-GTP was added to each well. The labeled GTP was incubated for 45 min. at room temperature.

Following GTP incubation, wells were washed 3× in Buffer-I, and 200 μl of Buffer-I were added to each well.

Following washes, the amount of bound labeled-GTP was measured with an Eppendorf AF2200 plate reader.

By substituting KRas G12D mutant protein with KRas G12C mutant, KRas wild type, KRas Q61H mutant, KRas G12D/Q61H double mutant or KRas G12C/Q61H double mutant under the assay conditions described above, KRas G12C mutant KRas wild type, KRas Q61H mutant, KRas G12D/Q61H double mutant and KRas G12C/Q61H double mutant inhibition, respectively, were each determined.

Table 7 shows inhibition data for selected compounds tested in the screening assay described above.

TABLE 7
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 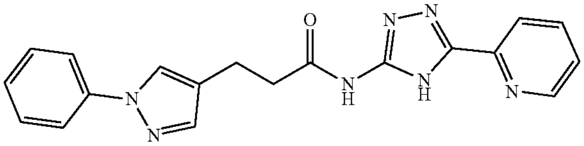 [SMILES: O=C(CCc1cnn(-c2ccccc2)c1)Nc1nnc(-c2ccccn2)[nH]1] | | | | C | | | |
| 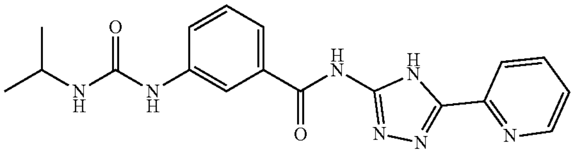 [SMILES: CC(C)NC(=O)Nc1cccc(C(=O)Nc2nnc(-c3ccccn3)[nH]2)c1] | | | | C | | | |
| 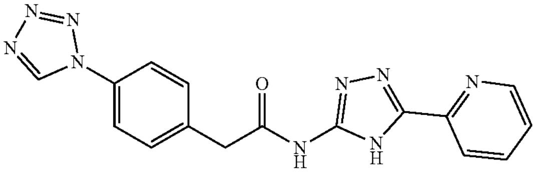 [SMILES: O=C(Cc1ccc(-n2cnnn2)cc1)Nc1nnc(-c2ccccn2)[nH]1] | | | | C | | | |
| 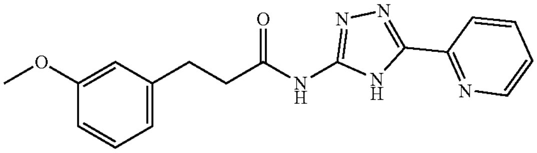 [SMILES: COc1cccc(CCC(=O)Nc2nnc(-c3ccccn3)[nH]2)c1] | | | | C | | | |
| 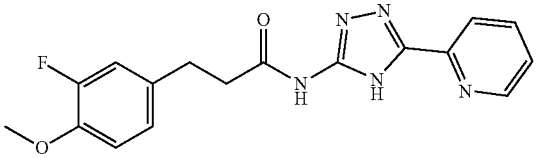 [SMILES: COc1ccc(CCC(=O)Nc2nnc(-c3ccccn3)[nH]2)cc1F] | | | | C | | | |
| 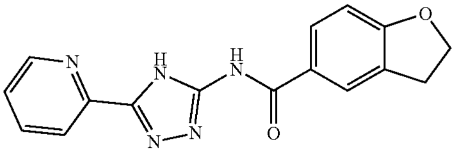 [SMILES: O=C(Nc1nnc(-c2ccccn2)[nH]1)c1ccc2c(c1)CCO2] | | | | C | | | |
| 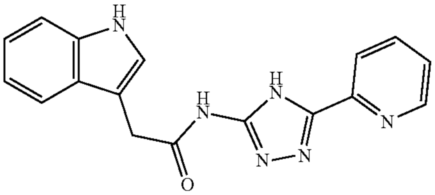 [SMILES: O=C(Cc1c[nH]c2ccccc12)Nc1nnc(-c2ccccn2)[nH]1] | | | | C | | | |
| 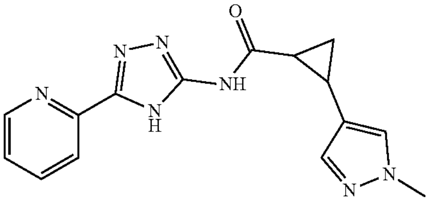 [SMILES: Cn1cc(C2CC2C(=O)Nc2nnc(-c3ccccn3)[nH]2)cn1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 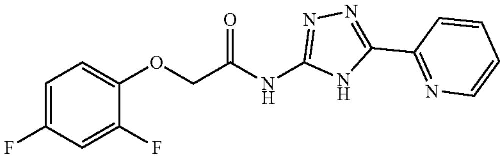 [SMILES: O=C(COc1ccc(F)cc1F)Nc1nnc(-c2ccccn2)[nH]1] | | | | C | | | |
| 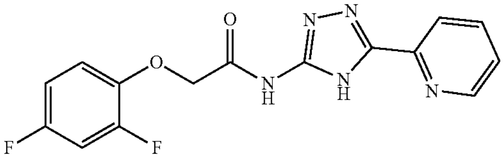 [SMILES: O=C(COc1ccc(F)cc1F)Nc1nnc(-c2ccccn2)[nH]1] | | | | C | | | |
| 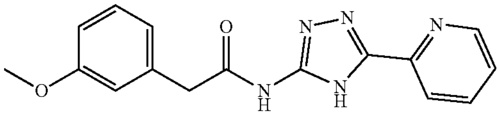 [SMILES: COc1cccc(CC(=O)Nc2nnc(-c3ccccn3)[nH]2)c1] | | | | C | | | |
| 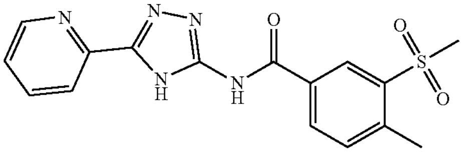 [SMILES: Cc1ccc(C(=O)Nc2nnc(-c3ccccn3)[nH]2)cc1S(C)(=O)=O] | | | | C | | | |
| 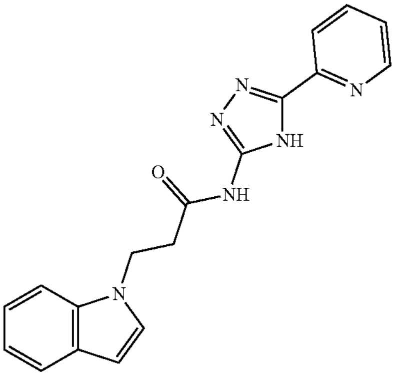 [SMILES: O=C(CCn1ccc2ccccc21)Nc1nnc(-c2ccccn2)[nH]1] | | | | C | | | |
| 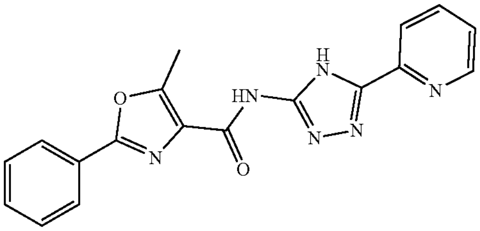 [SMILES: Cc1oc(-c2ccccc2)nc1C(=O)Nc1nnc(-c2ccccn2)[nH]1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 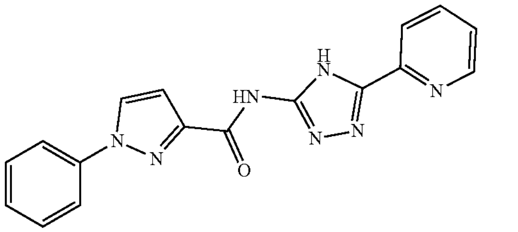 [SMILES: O=C(Nc1nnc(-c2ccccn2)[nH]1)c1ccn(-c2ccccc2)n1] | D | C | C | D | | | |
| 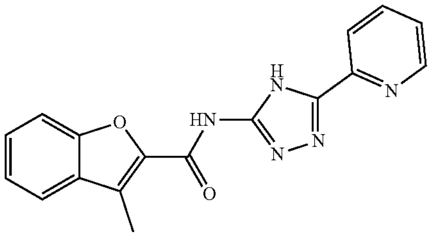 [SMILES: Cc1c(C(=O)Nc2nnc(-c3ccccn3)[nH]2)oc2ccccc12] | | | | C | | | |
| 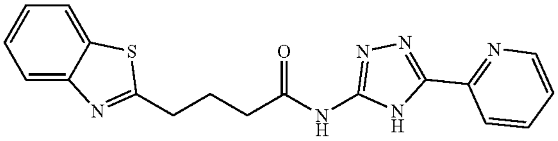 [SMILES: O=C(CCCc1nc2ccccc2s1)Nc1nnc(-c2ccccn2)[nH]1] | | | | C | | | |
| 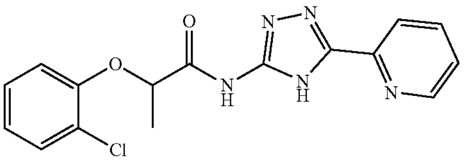 [SMILES: CC(Oc1ccccc1Cl)C(=O)Nc1nnc(-c2ccccn2)[nH]1] | | | | C | | | |
| 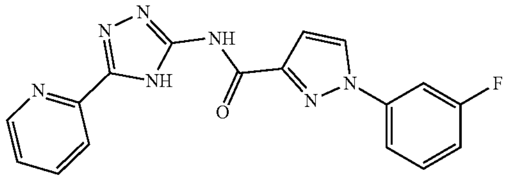 [SMILES: O=C(Nc1nnc(-c2ccccn2)[nH]1)c1ccn(-c2cccc(F)c2)n1] | | | | C | | | |
| 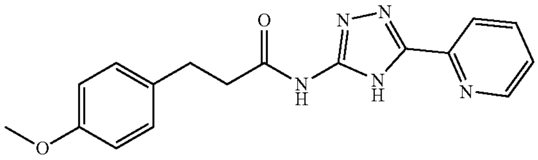 [SMILES: COc1ccc(CCC(=O)Nc2nnc(-c3ccccn3)[nH]2)cc1] | B | B | B | C | | | |
| 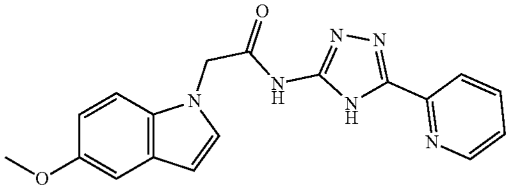 [SMILES: COc1ccc2c(ccn2CC(=O)Nc2nnc(-c3ccccn3)[nH]2)c1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 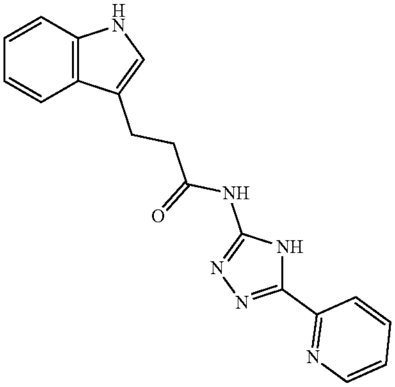 [SMILES: O=C(CCc1c[nH]c2ccccc12)Nc1nnc(-c2ccccn2)[nH]1] | | | | C | | | H |
| 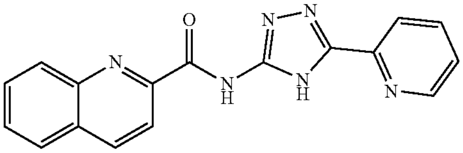 [SMILES: O=C(Nc1nnc(-c2ccccn2)[nH]1)c1ccc2ccccc2n1] | D | B | C | D | | | |
| 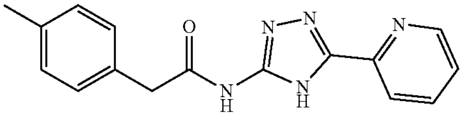 [SMILES: Cc1ccc(CC(=O)Nc2nnc(-c3ccccn3)[nH]2)cc1] | | | | C | | | |
| 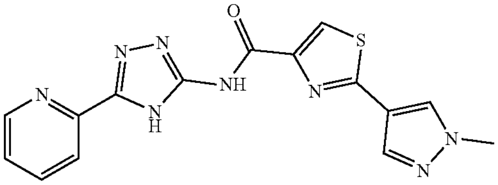 [SMILES: Cn1cc(-c2nc(C(=O)Nc3nnc(-c4ccccn4)[nH]3)cs2)cn1] | | | | D | | | |
| 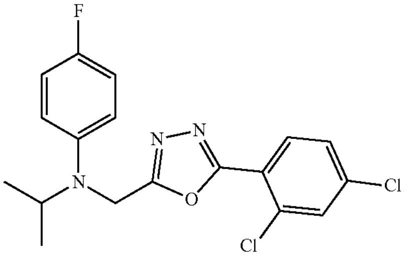 [SMILES: CC(C)N(Cc1nnc(-c2ccc(Cl)cc2Cl)o1)c1ccc(F)cc1] | | | | B | | | |
| 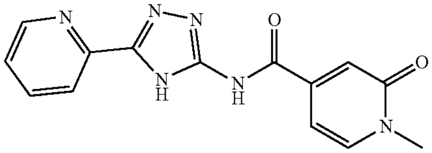 [SMILES: Cn1ccc(C(=O)Nc2nnc(-c3ccccn3)[nH]2)cc1=O] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 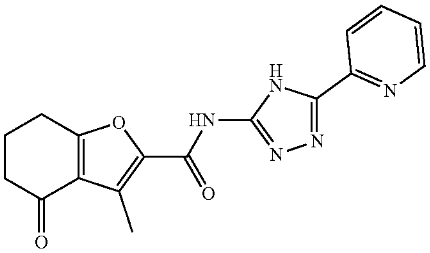 [SMILES: Cc1c(C(=O)Nc2nnc(-c3ccccn3)[nH]2)oc2c1C(=O)CCC2] | | | | C | | | |
| 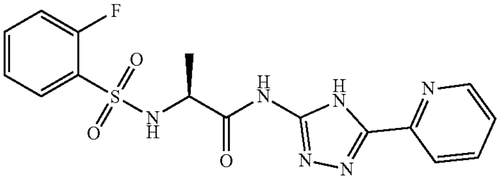 [SMILES: C[C@H](NS(=O)(=O)c1ccccc1F)C(=O)Nc1nnc(-c2ccccn2)[nH]1] | | | | C | | | |
| 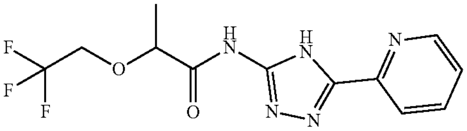 [SMILES: CC(OCC(F)(F)F)C(=O)Nc1nnc(-c2ccccn2)[nH]1] | | | | C | | | |
| 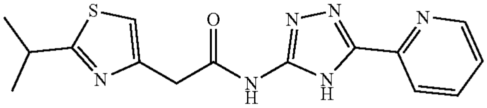 [SMILES: CC(C)c1nc(CC(=O)Nc2nnc(-c3ccccn3)[nH]2)cs1] | | | | C | | | |
| 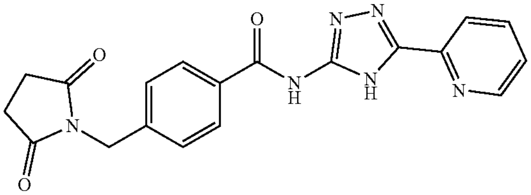 [SMILES: O=C(Nc1nnc(-c2ccccn2)[nH]1)c1ccc(CN2C(=O)CCC2=O)cc1] | | | | C | | | |
| 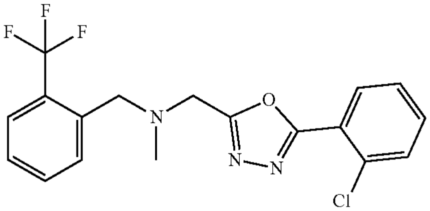 [SMILES: CN(Cc1nnc(-c2ccccc2Cl)o1)Cc1ccccc1C(F)(F)F] | B | A | A | C | | | |
| 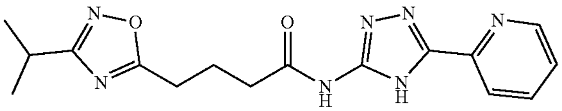 [SMILES: CC(C)c1noc(CCCC(=O)Nc2nnc(-c3ccccn3)[nH]2)n1] | | | | C | | | |
| 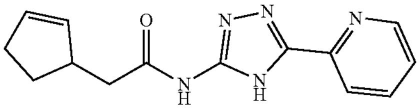 [SMILES: O=C(CC1C=CCC1)Nc1nnc(-c2ccccn2)[nH]1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 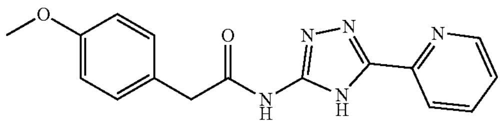 [SMILES: COc1ccc(CC(=O)Nc2nnc(-c3ccccn3)[nH]2)cc1] | | | | C | | | |
| 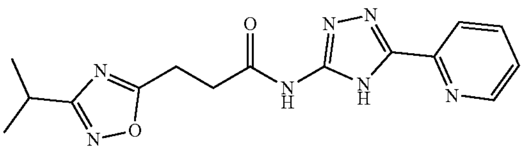 [SMILES: CC(C)c1noc(CCC(=O)Nc2nnc(-c3ccccn3)[nH]2)n1] | | | | C | | | |
| 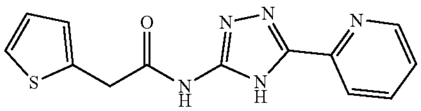 [SMILES: O=C(Cc1cccs1)Nc1nnc(-c2ccccn2)[nH]1] | | | | C | | | |
| 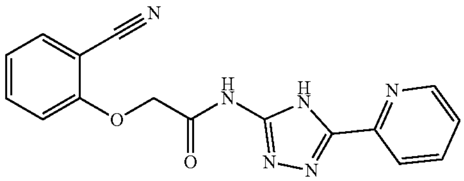 [SMILES: N#Cc1ccccc1OCC(=O)Nc1nnc(-c2ccccn2)[nH]1] | | | | C | | | |
| 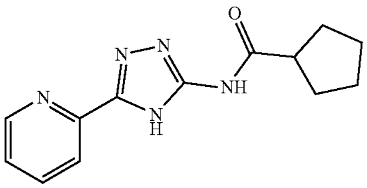 [SMILES: O=C(Nc1nnc(-c2ccccn2)[nH]1)C1CCCC1] | | | | C | | | |
| 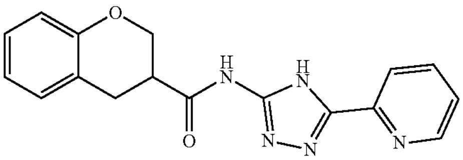 [SMILES: O=C(Nc1nnc(-c2ccccn2)[nH]1)C1COc2ccccc2C1] | | | | C | | | |
| 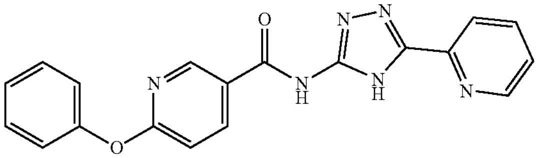 [SMILES: O=C(Nc1nnc(-c2ccccn2)[nH]1)c1ccc(Oc2ccccc2)nc1] | | | | C | | | |
| 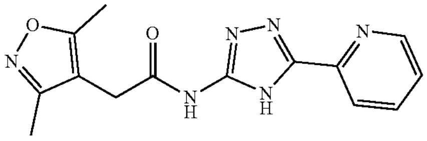 [SMILES: Cc1noc(C)c1CC(=O)Nc1nnc(-c2ccccn2)[nH]1] | | | | C | | | |
| 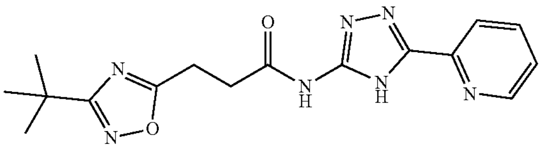 [SMILES: CC(C)(C)c1noc(CCC(=O)Nc2nnc(-c3ccccn3)[nH]2)n1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 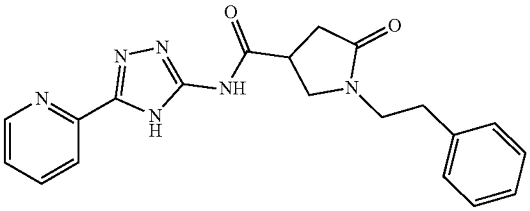 [SMILES: O=C(Nc1nnc(-c2ccccn2)[nH]1)C1CC(=O)N(CCc2ccccc2)C1] | | | | C | | | |
| 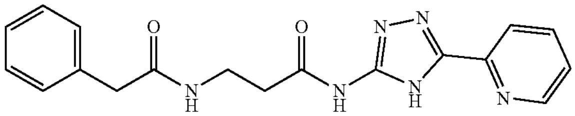 [SMILES: O=C(Cc1ccccc1)NCCC(=O)Nc1nnc(-c2ccccn2)[nH]1] | | | | C | | | |
| 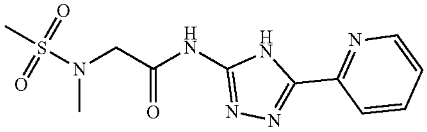 [SMILES: CN(CC(=O)Nc1nnc(-c2ccccn2)[nH]1)S(C)(=O)=O] | | | | C | | | |
| 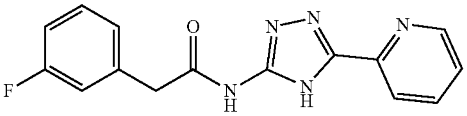 [SMILES: O=C(Cc1cccc(F)c1)Nc1nnc(-c2ccccn2)[nH]1] | | | | C | | | |
| 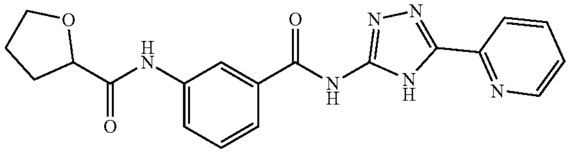 [SMILES: O=C(Nc1nnc(-c2ccccn2)[nH]1)c1cccc(NC(=O)C2CCCO2)c1] | | | | C | | | |
| 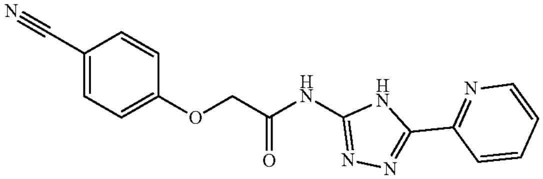 [SMILES: N#Cc1ccc(OCC(=O)Nc2nnc(-c3ccccn3)[nH]2)cc1] | | | | C | | | |
| 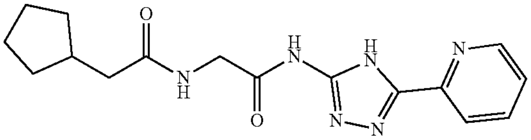 [SMILES: O=C(CC1CCCC1)NCC(=O)Nc1nnc(-c2ccccn2)[nH]1] | | | | C | | | |
| 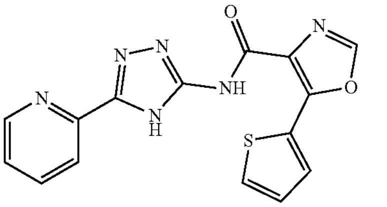 [SMILES: O=C(Nc1nnc(-c2ccccn2)[nH]1)c1ncoc1-c1cccs1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 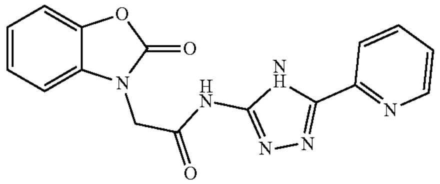 [SMILES: O=C(Cn1c(=O)oc2ccccc21)Nc1nnc(-c2ccccn2)[nH]1] | | | | C | | | |
| 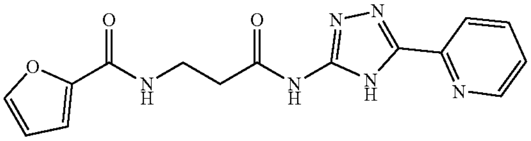 [SMILES: O=C(CCNC(=O)c1ccco1)Nc1nnc(-c2ccccn2)[nH]1] | | | | C | | | |
| 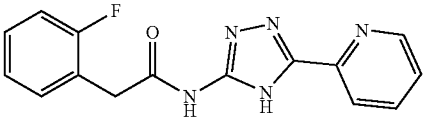 [SMILES: O=C(Cc1ccccc1F)Nc1nnc(-c2ccccn2)[nH]1] | | | | C | | | |
| 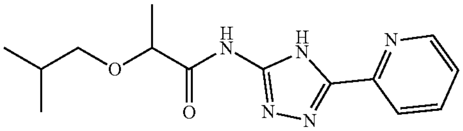 [SMILES: CC(C)COC(C)C(=O)Nc1nnc(-c2ccccn2)[nH]1] | | | | C | | | |
| 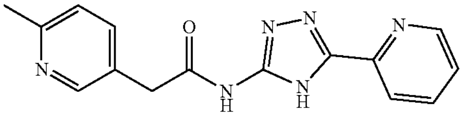 [SMILES: Cc1ccc(CC(=O)Nc2nnc(-c3ccccn3)[nH]2)cn1] | | | | C | | | |
| 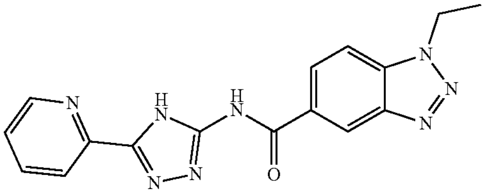 [SMILES: CCn1nnc2cc(C(=O)Nc3nnc(-c4ccccn4)[nH]3)ccc21] | | | | C | | | |
| 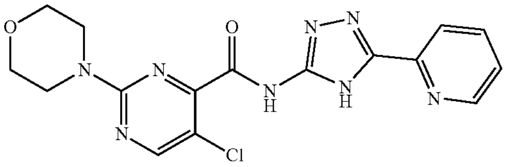 [SMILES: O=C(Nc1nnc(-c2ccccn2)[nH]1)c1nc(N2CCOCC2)ncc1Cl] | | | | C | | | |
| 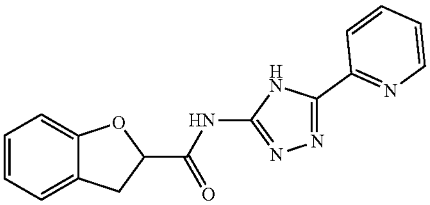 [SMILES: O=C(Nc1nnc(-c2ccccn2)[nH]1)C1Cc2ccccc2O1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 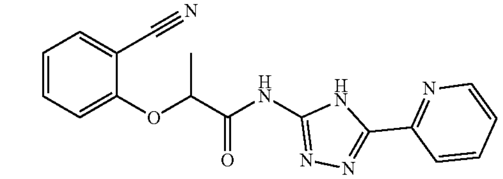 [SMILES: CC(Oc1ccccc1C#N)C(=O)Nc1nnc(-c2ccccn2)[nH]1] | | | | C | | | |
| 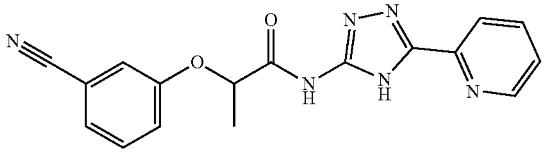 [SMILES: CC(Oc1cccc(C#N)c1)C(=O)Nc1nnc(-c2ccccn2)[nH]1] | | | | C | | | H |
| 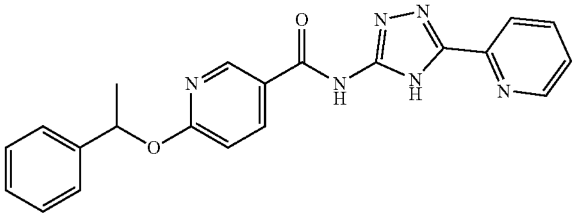 [SMILES: CC(Oc1ccc(C(=O)Nc2nnc(-c3ccccn3)[nH]2)cn1)c1ccccc1] | | | | C | | | |
| 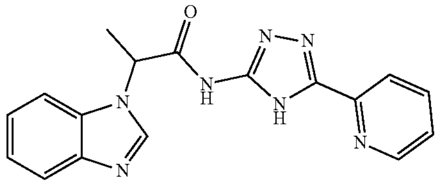 [SMILES: CC(C(=O)Nc1nnc(-c2ccccn2)[nH]1)n1cnc2ccccc21] | | | | C | | | |
| 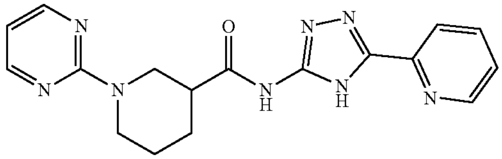 [SMILES: O=C(Nc1nnc(-c2ccccn2)[nH]1)C1CCCN(c2ncccn2)C1] | | | | C | | | |
| 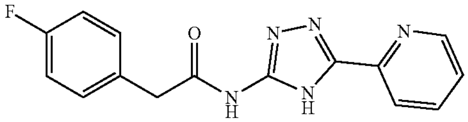 [SMILES: O=C(Cc1ccc(F)cc1)Nc1nnc(-c2ccccn2)[nH]1] | | | | C | | | |
| 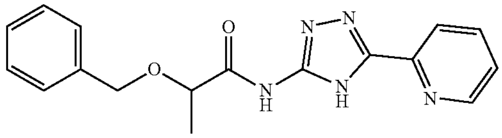 [SMILES: CC(OCc1ccccc1)C(=O)Nc1nnc(-c2ccccn2)[nH]1] | | | | C | | | |
| 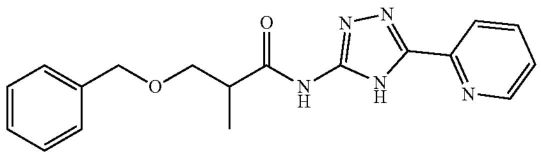 [SMILES: CC(COCc1ccccc1)C(=O)Nc1nnc(-c2ccccn2)[nH]1] | | | | C | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 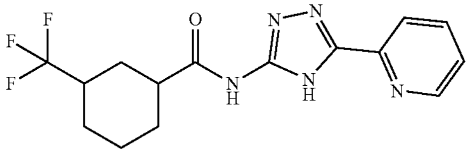 [SMILES: O=C(Nc1nnc(-c2ccccn2)[nH]1)C1CCCC(C(F)(F)F)C1] | | | | C | | | |
| 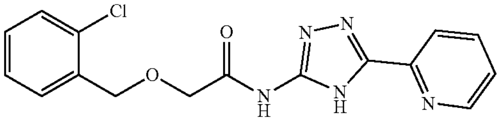 [SMILES: O=C(COCc1ccccc1Cl)Nc1nnc(-c2ccccn2)[nH]1] | | | | C | | | |
| 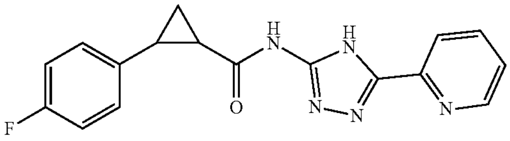 [SMILES: O=C(Nc1nnc(-c2ccccn2)[nH]1)C1CC1c1ccc(F)cc1] | | | | C | | | |
| 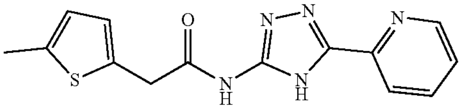 [SMILES: Cc1ccc(CC(=O)Nc2nnc(-c3ccccn3)[nH]2)s1] | | | | C | | | |
| 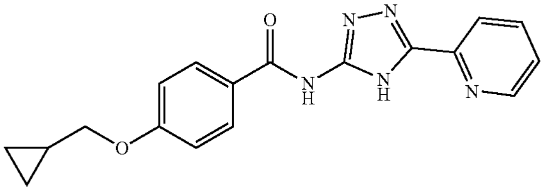 [SMILES: O=C(Nc1nnc(-c2ccccn2)[nH]1)c1ccc(OCC2CC2)cc1] | | | | C | | | |
| 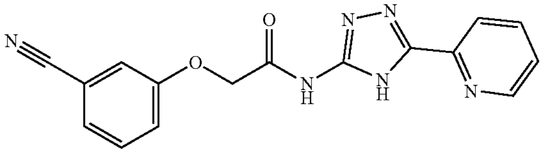 [SMILES: N#Cc1cccc(OCC(=O)Nc2nnc(-c3ccccn3)[nH]2)c1] | | | | C | | | |
| 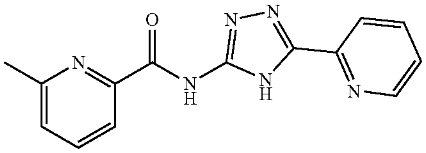 [SMILES: Cc1cccc(C(=O)Nc2nnc(-c3ccccn3)[nH]2)n1] | | | | C | | | |
| 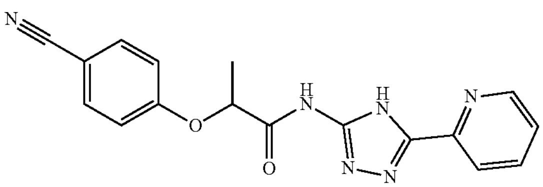 [SMILES: CC(Oc1ccc(C#N)cc1)C(=O)Nc1nnc(-c2ccccn2)[nH]1] | | | | C | | | |
| 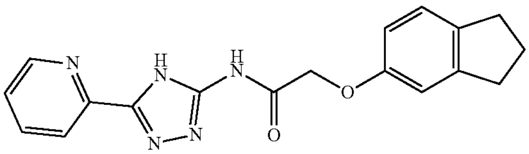 [SMILES: O=C(COc1ccc2c(c1)CCC2)Nc1nnc(-c2ccccn2)[nH]1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 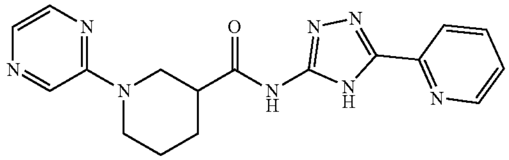 [SMILES: O=C(Nc1nnc(-c2ccccn2)[nH]1)C1CCCN(c2cnccn2)C1] | | | | C | | | |
| 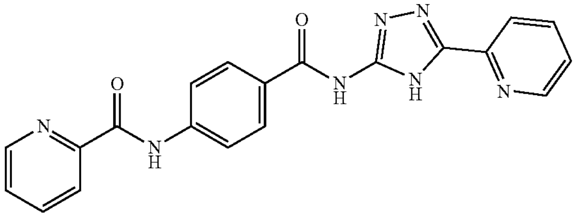 [SMILES: O=C(Nc1nnc(-c2ccccn2)[nH]1)c1ccc(NC(=O)c2ccccn2)cc1] | | | | C | | | |
| 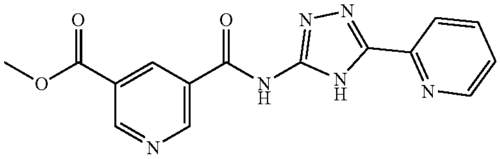 [SMILES: COC(=O)c1cncc(C(=O)Nc2nnc(-c3ccccn3)[nH]2)c1] | | | | C | | | |
| 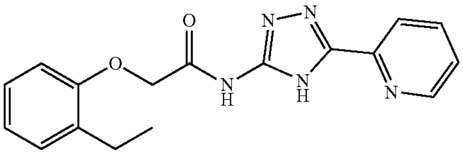 [SMILES: CCc1ccccc1OCC(=O)Nc1nnc(-c2ccccn2)[nH]1] | | | | C | | | |
| 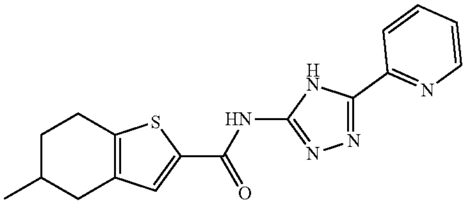 [SMILES: CC1CCc2sc(C(=O)Nc3nnc(-c4ccccn4)[nH]3)cc2C1] | | | | C | | | |
| 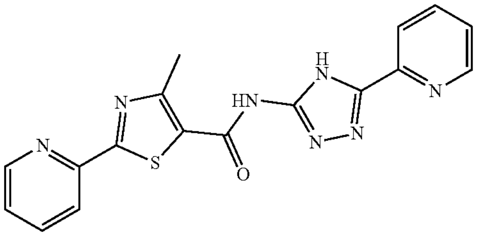 [SMILES: Cc1nc(-c2ccccn2)sc1C(=O)Nc1nnc(-c2ccccn2)[nH]1] | | | | C | | | |
| 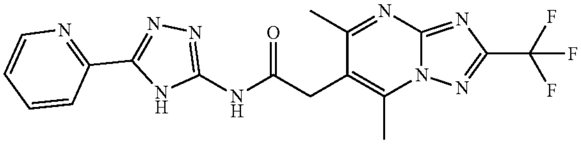 [SMILES: Cc1nc2nc(C(F)(F)F)nn2c(C)c1CC(=O)Nc1nnc(-c2ccccn2)[nH]1] | | | | C | | | |
| 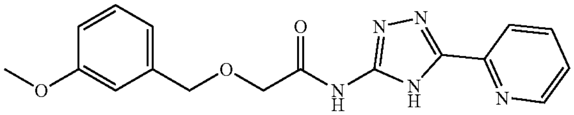 [SMILES: COc1cccc(COCC(=O)Nc2nnc(-c3ccccn3)[nH]2)c1] | | | | C | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 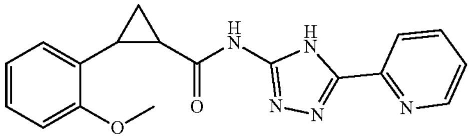 [SMILES: COc1ccccc1C1CC1C(=O)Nc1nnc(-c2ccccn2)[nH]1] | | | | C | | | |
| 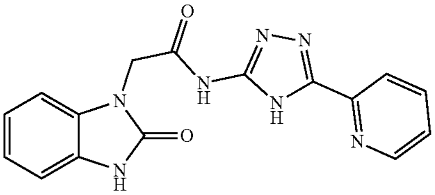 [SMILES: O=C(Cn1c(=O)[nH]c2ccccc21)Nc1nnc(-c2ccccn2)[nH]1] | | | | C | | | |
| 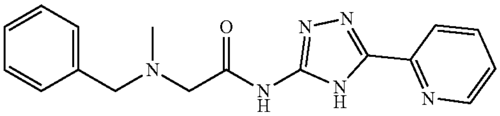 [SMILES: CN(CC(=O)Nc1nnc(-c2ccccn2)[nH]1)Cc1ccccc1] | | | | C | | | |
| 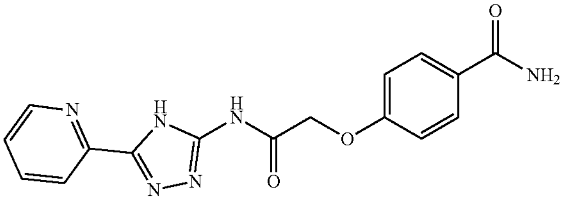 [SMILES: NC(=O)c1ccc(OCC(=O)Nc2nnc(-c3ccccn3)[nH]2)cc1] | | | | C | | | |
| 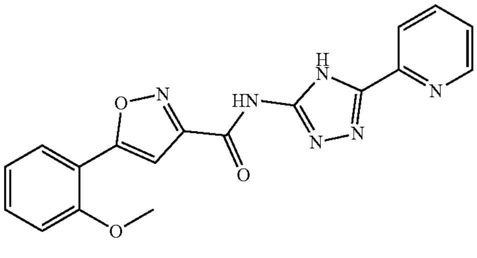 [SMILES: COc1ccccc1-c1cc(C(=O)Nc2nnc(-c3ccccn3)[nH]2)no1] | | | | C | | | |
| 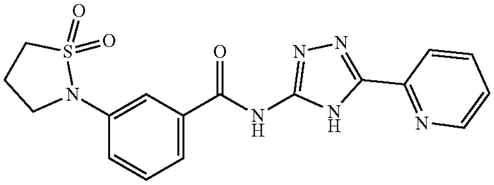 [SMILES: O=C(Nc1nnc(-c2ccccn2)[nH]1)c1cccc(N2CCCS2(=O)=O)c1] | | | | C | | | |
| 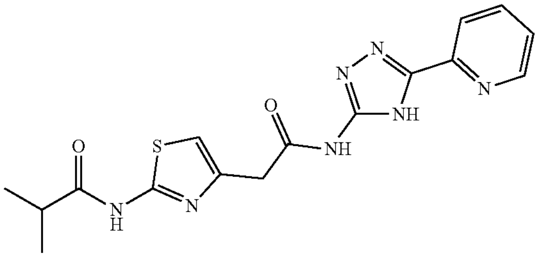 [SMILES: CC(C)C(=O)Nc1nc(CC(=O)Nc2nnc(-c3ccccn3)[nH]2)cs1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 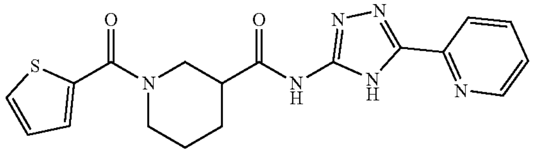 [SMILES: O=C(Nc1nnc(-c2ccccn2)[nH]1)C1CCCN(C(=O)c2cccs2)C1] | | | | C | | | |
| 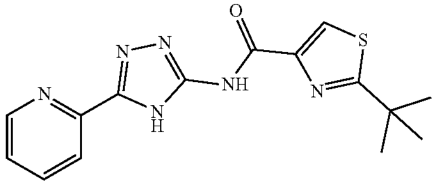 [SMILES: CC(C)(C)c1nc(C(=O)Nc2nnc(-c3ccccn3)[nH]2)cs1] | | | | C | | | |
| 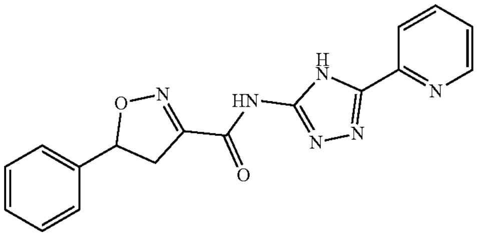 [SMILES: O=C(Nc1nnc(-c2ccccn2)[nH]1)C1=NOC(c2ccccc2)C1] | | | | C | | | |
| 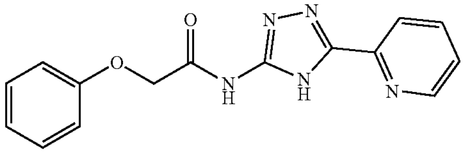 [SMILES: O=C(COc1ccccc1)Nc1nnc(-c2ccccn2)[nH]1] | | | | C | | | |
| 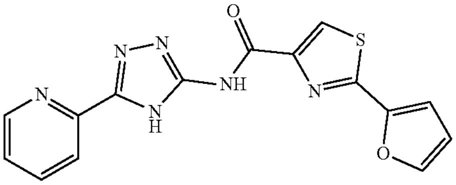 [SMILES: O=C(Nc1nnc(-c2ccccn2)[nH]1)c1csc(-c2ccco2)n1] | | | | C | | | |
| 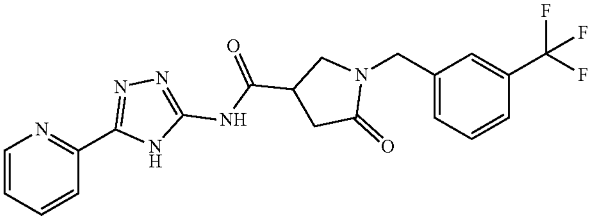 [SMILES: O=C(Nc1nnc(-c2ccccn2)[nH]1)C1CC(=O)N(Cc2cccc(C(F)(F)F)c2)C1] | C | A | B | C | | | |
| 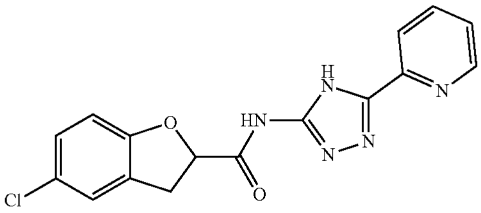 [SMILES: O=C(Nc1nnc(-c2ccccn2)[nH]1)C1Cc2cc(Cl)ccc2O1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 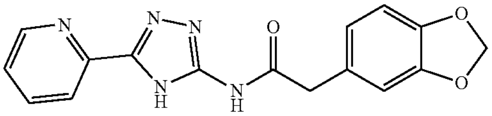 [SMILES: O=C(Cc1ccc2c(c1)OCO2)Nc1nnc(-c2ccccn2)[nH]1] | | | | C | | | |
| 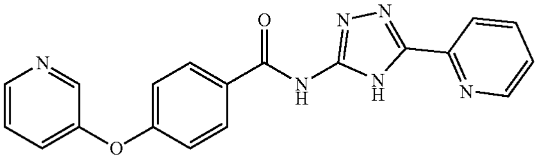 [SMILES: O=C(Nc1nnc(-c2ccccn2)[nH]1)c1ccc(Oc2cccnc2)cc1] | | | | C | | | |
| 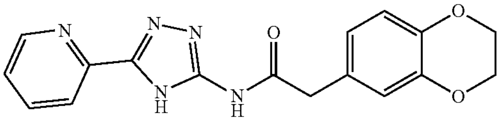 [SMILES: O=C(Cc1ccc2c(c1)OCCO2)Nc1nnc(-c2ccccn2)[nH]1] | | | | C | | | |
| 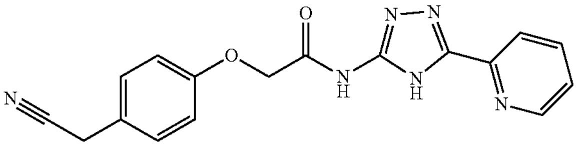 [SMILES: N#CCc1ccc(OCC(=O)Nc2nnc(-c3ccccn3)[nH]2)cc1] | | | | C | | | |
| 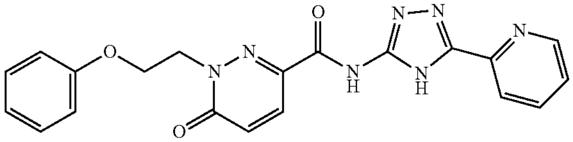 [SMILES: O=C(Nc1nnc(-c2ccccn2)[nH]1)c1ccc(=O)n(CCOc2ccccc2)n1] | | | | C | | | |
| 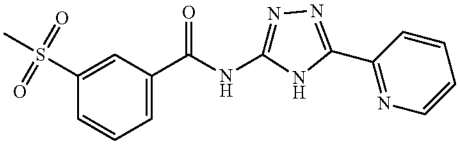 [SMILES: CS(=O)(=O)c1cccc(C(=O)Nc2nnc(-c3ccccn3)[nH]2)c1] | | | | C | | | |
| 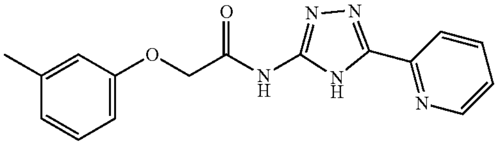 [SMILES: Cc1cccc(OCC(=O)Nc2nnc(-c3ccccn3)[nH]2)c1] | | | | C | | | G |
| 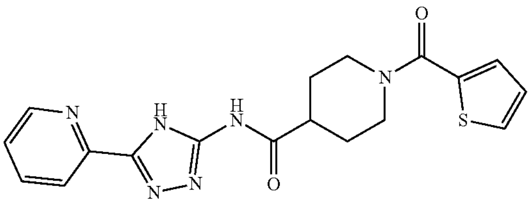 [SMILES: O=C(Nc1nnc(-c2ccccn2)[nH]1)C1CCN(C(=O)c2cccs2)CC1] | | | | C | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 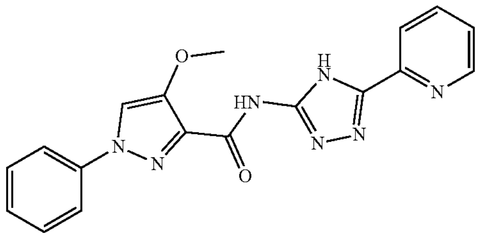 [SMILES: COc1cn(-c2ccccc2)nc1C(=O)Nc1nnc(-c2ccccn2)[nH]1] | | | | D | | | |
| 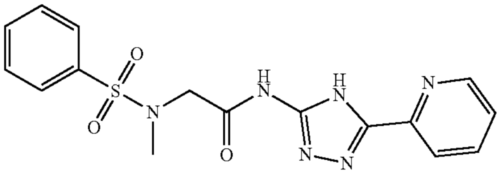 [SMILES: CN(CC(=O)Nc1nnc(-c2ccccn2)[nH]1)S(=O)(=O)c1ccccc1] | | | | D | | | |
| 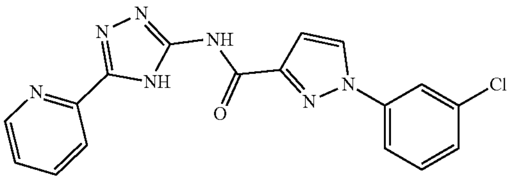 [SMILES: O=C(Nc1nnc(-c2ccccn2)[nH]1)c1ccn(-c2cccc(Cl)c2)n1] | D | A | B | D | | | |
| 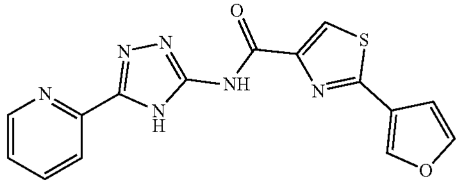 [SMILES: O=C(Nc1nnc(-c2ccccn2)[nH]1)c1csc(-c2ccoc2)n1] | | | | D | | | |
| 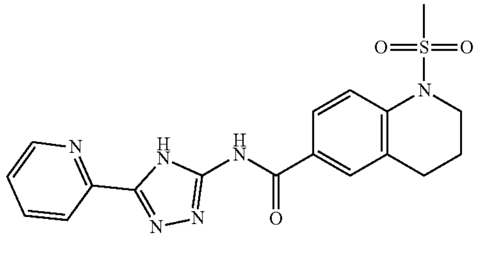 [SMILES: CS(=O)(=O)N1CCCc2cc(C(=O)Nc3nnc(-c4ccccn4)[nH]3)ccc21] | C | B | C | D | | | |
| 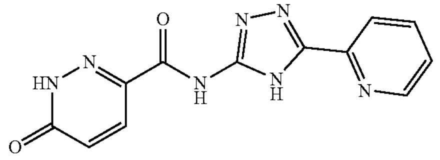 [SMILES: O=C(Nc1nnc(-c2ccccn2)[nH]1)c1ccc(=O)[nH]n1] | | | | C | | | |
| 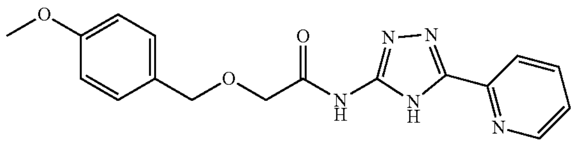 [SMILES: COc1ccc(COCC(=O)Nc2nnc(-c3ccccn3)[nH]2)cc1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 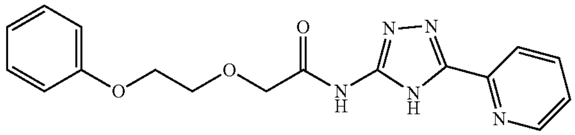 [SMILES: O=C(COCCOc1ccccc1)Nc1nnc(-c2ccccn2)[nH]1] | | | | D | | | |
| 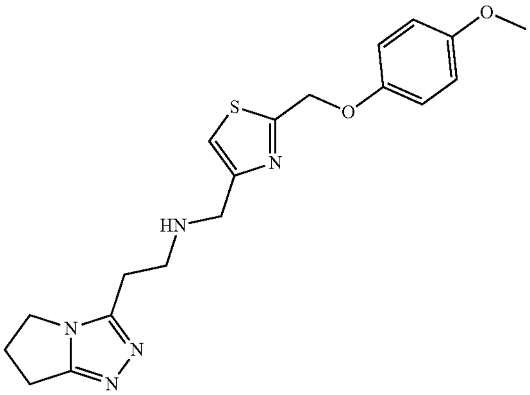 [SMILES: COc1ccc(OCc2nc(CNCCc3nnc4n3CCC4)cs2)cc1] | C | B | A | C | | | |
| 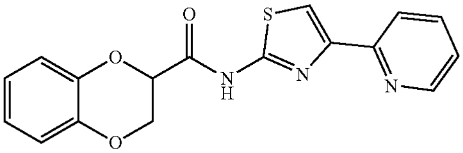 [SMILES: O=C(Nc1nc(-c2ccccn2)cs1)C1COc2ccccc2O1] | | | | C | | | |
| 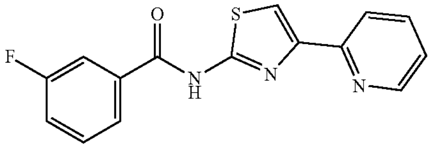 [SMILES: O=C(Nc1nc(-c2ccccn2)cs1)c1cccc(F)c1] | C | B | C | C | | | |
| 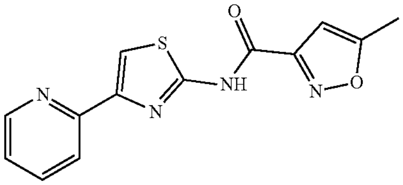 [SMILES: Cc1cc(C(=O)Nc2nc(-c3ccccn3)cs2)no1] | B | B | B | D | | | |
| 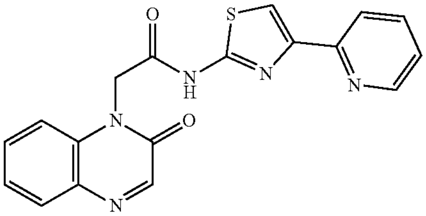 [SMILES: O=C(Cn1c(=O)cnc2ccccc21)Nc1nc(-c2ccccn2)cs1] | | | | C | | | |
| 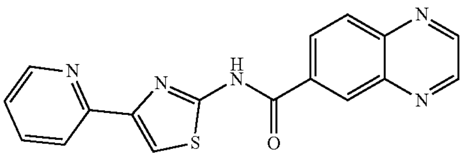 [SMILES: O=C(Nc1nc(-c2ccccn2)cs1)c1ccc2nccnc2c1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 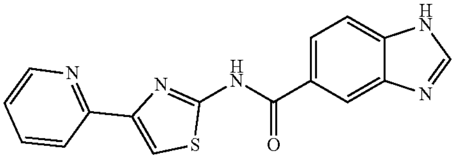 [SMILES: O=C(Nc1nc(-c2ccccn2)cs1)c1ccc2[nH]cnc2c1] | | | | C | | | |
| 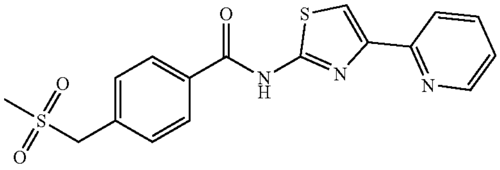 [SMILES: CS(=O)(=O)Cc1ccc(C(=O)Nc2nc(-c3ccccn3)cs2)cc1] | A | B | A | C | | | |
| 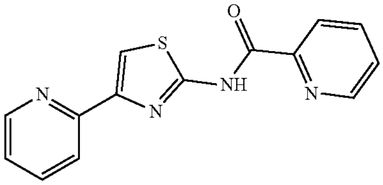 [SMILES: O=C(Nc1nc(-c2ccccn2)cs1)c1ccccn1] | C | C | C | D | | | |
| 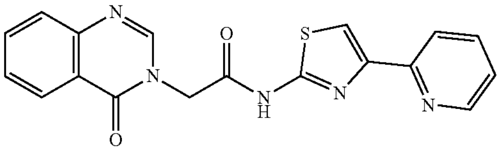 [SMILES: O=C(Cn1cnc2ccccc2c1=O)Nc1nc(-c2ccccn2)cs1] | | | | B | | | |
| 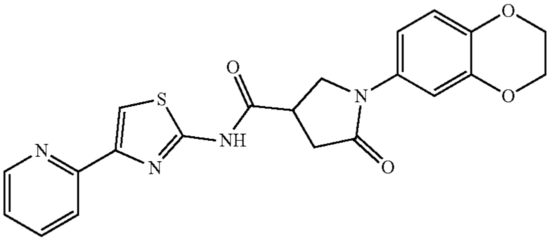 [SMILES: O=C(Nc1nc(-c2ccccn2)cs1)C1CC(=O)N(c2ccc3c(c2)OCCO3)C1] | | | | C | | | |
| 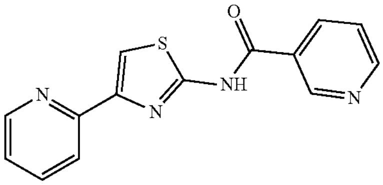 [SMILES: O=C(Nc1nc(-c2ccccn2)cs1)c1cccnc1] | C | C | B | C | | | |
| 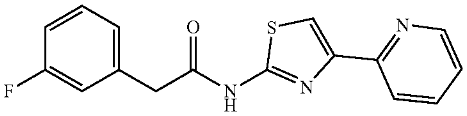 [SMILES: O=C(Cc1cccc(F)c1)Nc1nc(-c2ccccn2)cs1] | | | | B | | | |
| 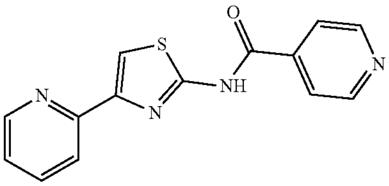 [SMILES: O=C(Nc1nc(-c2ccccn2)cs1)c1ccncc1] | C | C | C | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 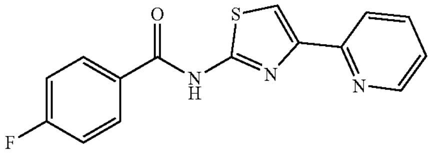 [SMILES: O=C(Nc1nc(-c2ccccn2)cs1)c1ccc(F)cc1] | | | | C | | | |
| 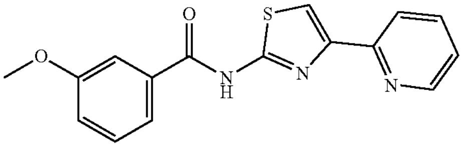 [SMILES: COc1cccc(C(=O)Nc2nc(-c3ccccn3)cs2)c1] | C | C | B | C | | | |
| 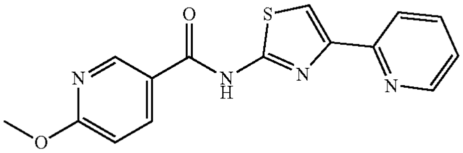 [SMILES: COc1ccc(C(=O)Nc2nc(-c3ccccn3)cs2)cn1] | D | C | C | C | | | |
| 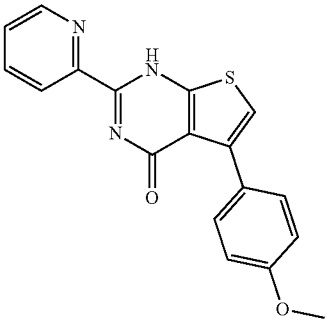 [SMILES: COc1ccc(-c2csc3[nH]c(-c4ccccn4)nc(=O)c23)cc1] | | | | C | | | |
| 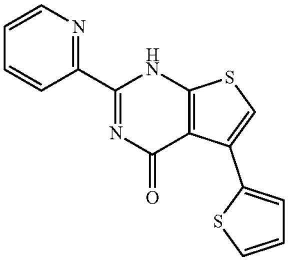 [SMILES: O=c1nc(-c2ccccn2)[nH]c2scc(-c3cccs3)c12] | | | | C | | | |
| 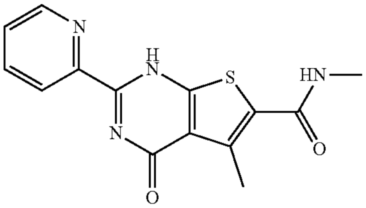 [SMILES: CNC(=O)c1sc2[nH]c(-c3ccccn3)nc(=O)c2c1C] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 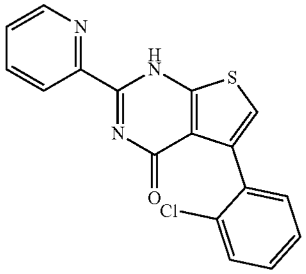 [SMILES: O=c1nc(-c2ccccn2)[nH]c2scc(-c3ccccc3Cl)c12] | C | B | B | C | | | |
| 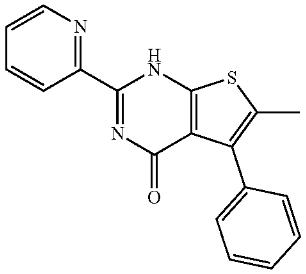 [SMILES: Cc1sc2[nH]c(-c3ccccn3)nc(=O)c2c1-c1ccccc1] | | | | C | | | |
| 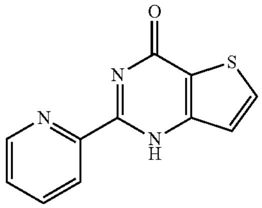 [SMILES: O=c1nc(-c2ccccn2)[nH]c2ccsc12] | | | | C | | | |
| 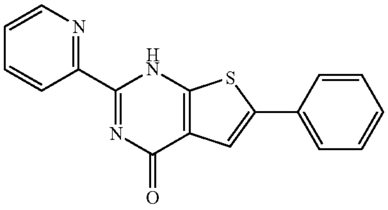 [SMILES: O=c1nc(-c2ccccn2)[nH]c2sc(-c3ccccc3)cc12] | | | | C | | | |
| 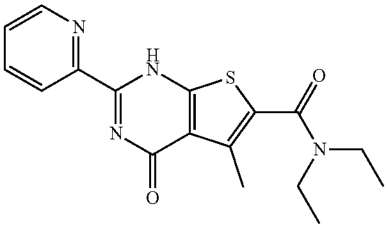 [SMILES: CCN(CC)C(=O)c1sc2[nH]c(-c3ccccn3)nc(=O)c2c1C] | | | | C | | | |
| 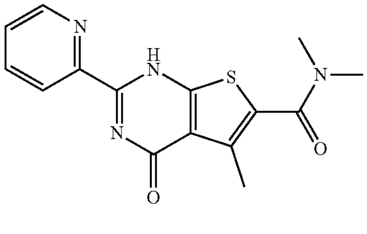 [SMILES: Cc1c(C(=O)N(C)C)sc2[nH]c(-c3ccccn3)nc(=O)c12] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 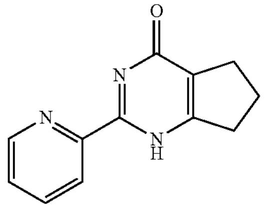 [SMILES: O=c1nc(-c2ccccn2)[nH]c2c1CCC2] | C | B | B | C | | | |
| 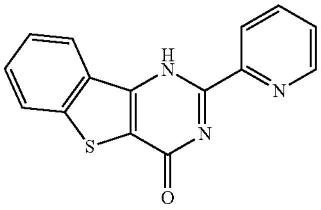 [SMILES: O=c1nc(-c2ccccn2)[nH]c2c1sc1ccccc12] | | | | C | | | F |
| 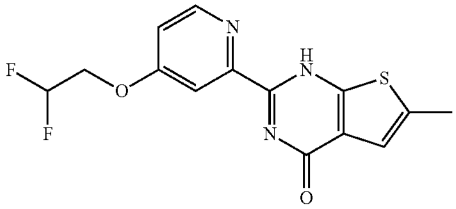 [SMILES: Cc1cc2c(=O)nc(-c3cc(OCC(F)F)ccn3)[nH]c2s1] | C | B | B | D | | | |
| 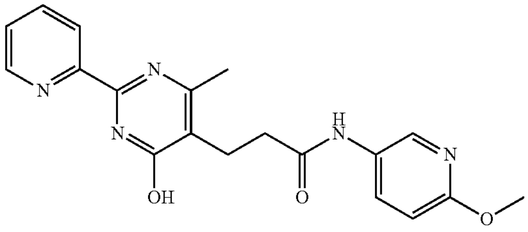 [SMILES: COc1ccc(NC(=O)CCc2c(C)nc(-c3ccccn3)nc2O)cn1] | | | | C | | | |
| 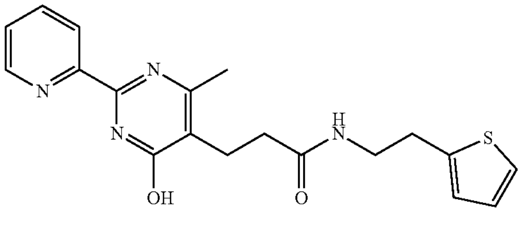 [SMILES: Cc1nc(-c2ccccn2)nc(O)c1CCC(=O)NCCc1cccs1] | | | | B | | | |
| 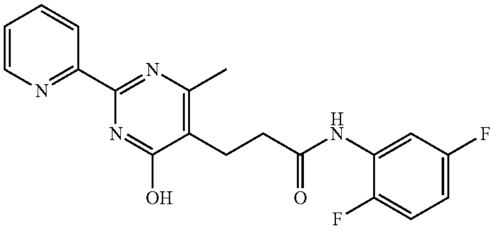 [SMILES: Cc1nc(-c2ccccn2)nc(O)c1CCC(=O)Nc1cc(F)ccc1F] | | | | C | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 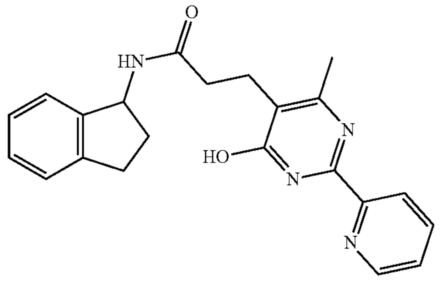 [SMILES: Cc1nc(-c2ccccn2)nc(O)c1CCC(=O)NC1CCc2ccccc21] | | | | B | | | |
| 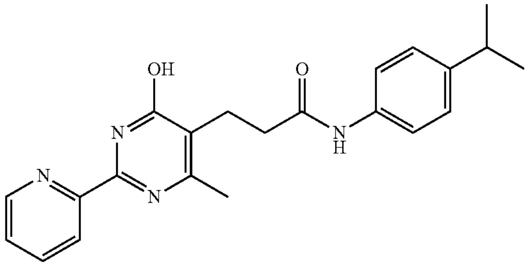 [SMILES: Cc1nc(-c2ccccn2)nc(O)c1CCC(=O)Nc1ccc(C(C)C)cc1] | | | | C | | | |
| 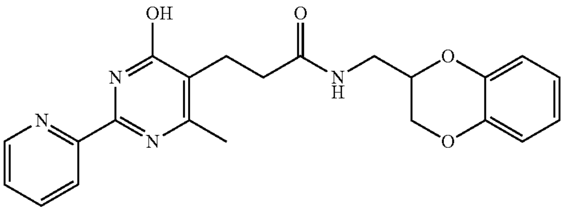 [SMILES: Cc1nc(-c2ccccn2)nc(O)c1CCC(=O)NCC1COc2ccccc2O1] | | | | B | | | |
| 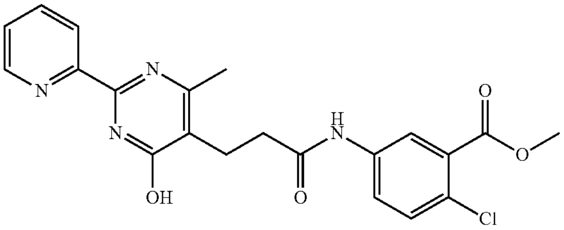 [SMILES: COC(=O)c1cc(NC(=O)CCc2c(C)nc(-c3ccccn3)nc2O)ccc1Cl] | | | | C | | | |
| 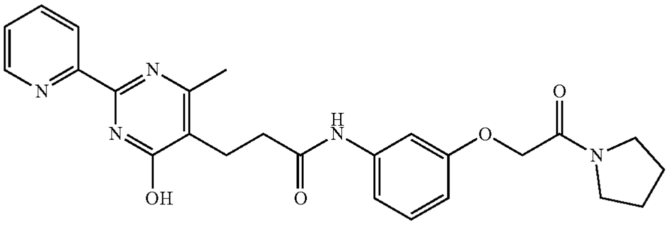 [SMILES: Cc1nc(-c2ccccn2)nc(O)c1CCC(=O)Nc1cccc(OCC(=O)N2CCCC2)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 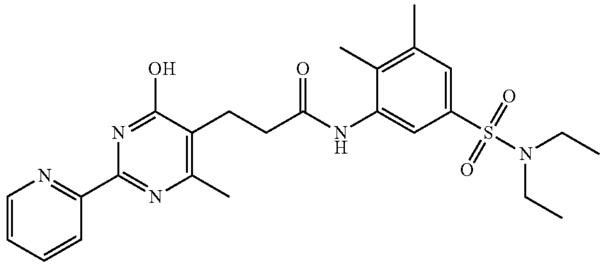 [SMILES: CCN(CC)S(=O)(=O)c1cc(C)c(C)c(NC(=O)CCc2c(C)nc(-c3ccccn3)nc2O)c1] | | | | C | | | |
| 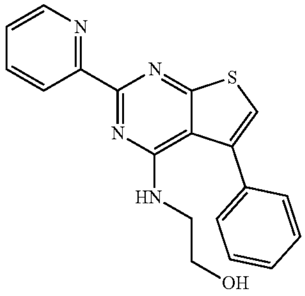 [SMILES: OCCNc1nc(-c2ccccn2)nc2scc(-c3ccccc3)c12] | C | A | A | B | | | |
| 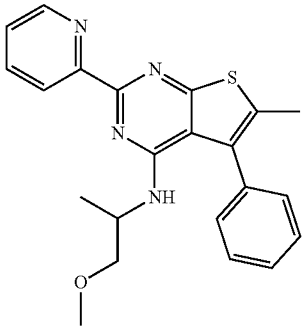 [SMILES: COCC(C)Nc1nc(-c2ccccn2)nc2sc(C)c(-c3ccccc3)c12] | C | B | B | C | | | |
| 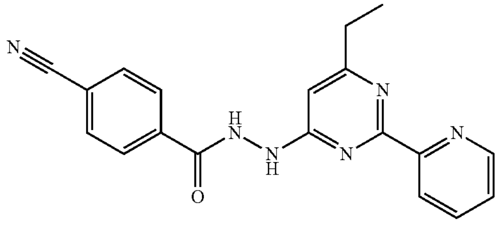 [SMILES: CCc1cc(NNC(=O)c2ccc(C#N)cc2)nc(-c2ccccn2)n1] | | | | C | | | |
| 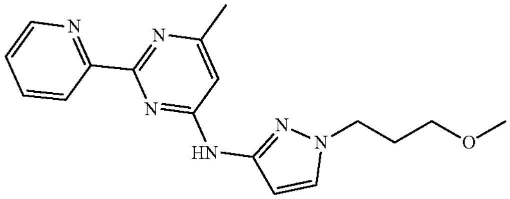 [SMILES: COCCCn1ccc(Nc2cc(C)nc(-c3ccccn3)n2)n1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 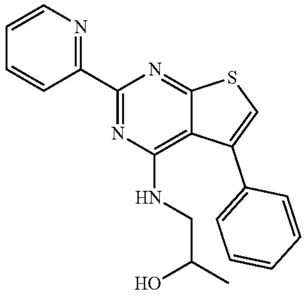 [SMILES: CC(O)CNc1nc(-c2ccccn2)nc2scc(-c3ccccc3)c12] | C | A | B | C | | | |
| 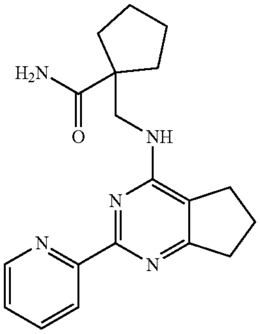 [SMILES: NC(=O)C1(CNc2nc(-c3ccccn3)nc3c2CCC3)CCCC1] | C | B | B | C | | | |
| 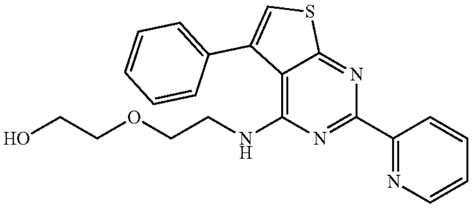 [SMILES: OCCOCCNc1nc(-c2ccccn2)nc2scc(-c3ccccc3)c12] | B | B | B | C | | | |
| 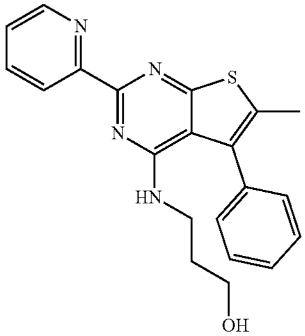 [SMILES: Cc1sc2nc(-c3ccccn3)nc(NCCCO)c2c1-c1ccccc1] | C | C | B | C | | | |
| 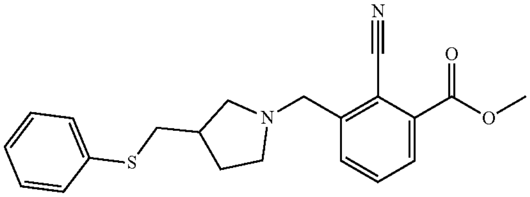 [SMILES: COC(=O)c1cccc(CN2CCC(CSc3ccccc3)C2)c1C#N] | A | B | A | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 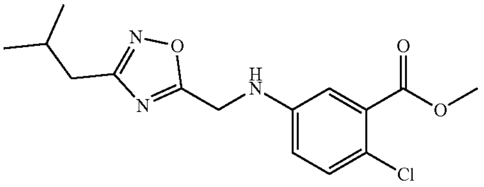 [SMILES: COC(=O)c1cc(NCc2nc(CC(C)C)no2)ccc1Cl] | C | B | A | C | | | |
| 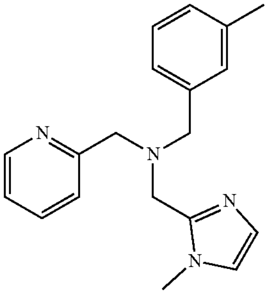 [SMILES: Cc1cccc(CN(Cc2ccccn2)Cc2nccn2C)c1] | C | B | B | C | | | |
| 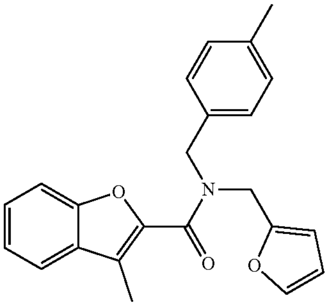 [SMILES: Cc1ccc(CN(Cc2ccco2)C(=O)c2oc3ccccc3c2C)cc1] | | | | C | | | |
| 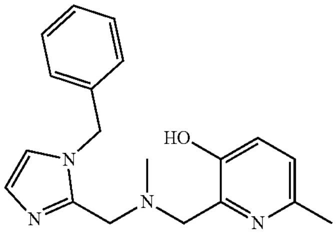 [SMILES: Cc1ccc(O)c(CN(C)Cc2nccn2Cc2ccccc2)n1] | | | | C | | | |
| 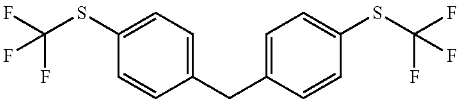 [SMILES: FC(F)(F)Sc1ccc(Cc2ccc(SC(F)(F)F)cc2)cc1] | | | | C | | | |
| 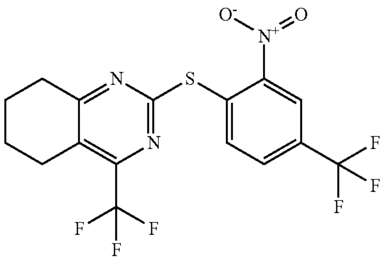 [SMILES: O=[N+]([O-])c1cc(C(F)(F)F)ccc1Sc1nc2c(c(C(F)(F)F)n1)CCCC2] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 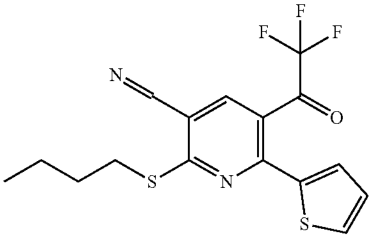 [SMILES: CCCCSc1nc(-c2cccs2)c(C(=O)C(F)(F)F)cc1C=N] | | | | C | | | |
| 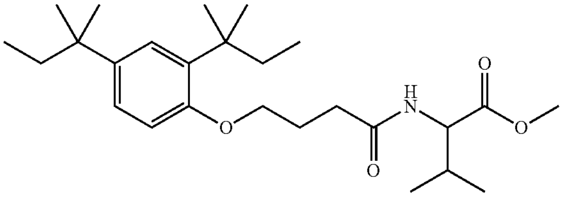 [SMILES: CCC(C)(C)c1ccc(OCCCC(=O)NC(C(=O)OC)C(C)C)c(C(C)(C)CC)c1] | | | | B | | | |
| 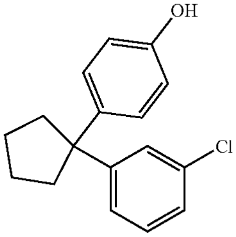 [SMILES: Oc1ccc(C2(c3cccc(Cl)c3)CCCC2)cc1] | | | | B | | | |
| 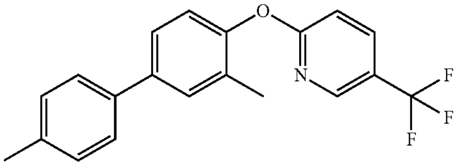 [SMILES: Cc1ccc(-c2ccc(Oc3ccc(C(F)(F)F)cn3)c(C)c2)cc1] | | | | C | | | |
| 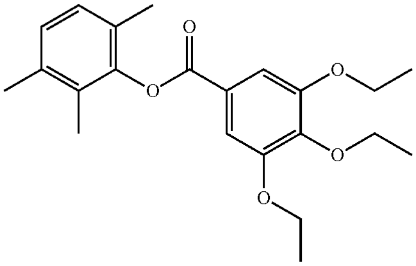 [SMILES: CCOc1cc(C(=O)Oc2c(C)ccc(C)c2C)cc(OCC)c1OCC] | | | | C | | | |
| 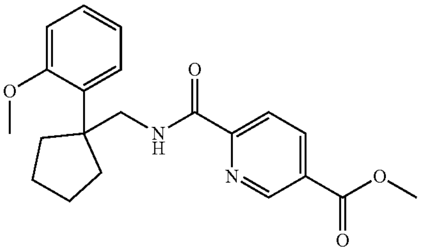 [SMILES: COC(=O)c1ccc(C(=O)NCC2(c3ccccc3OC)CCCC2)nc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 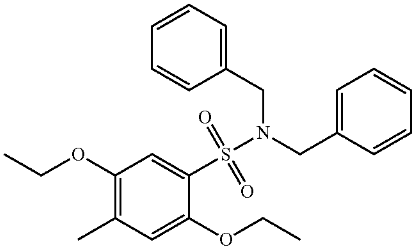 [SMILES: CCOc1cc(S(=O)(=O)N(Cc2ccccc2)Cc2ccccc2)c(OCC)cc1C] | | | | B | | | |
| 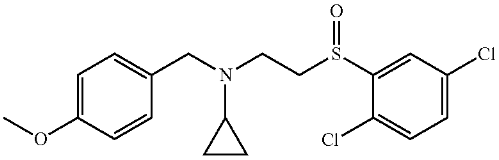 [SMILES: COc1ccc(CN(CCS(=O)c2cc(Cl)ccc2Cl)C2CC2)cc1] | | | | B | | | |
| 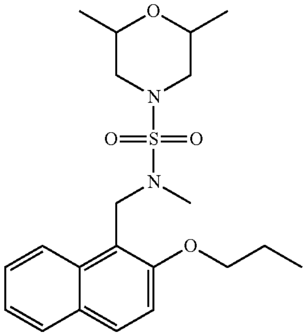 [SMILES: CCCOc1ccc2ccccc2c1CN(C)S(=O)(=O)N1CC(C)OC(C)C1] | | | | B | | | |
| 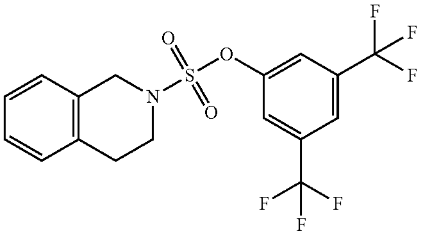 [SMILES: O=S(=O)(Oc1cc(C(F)(F)F)cc(C(F)(F)F)c1)N1CCc2ccccc2C1] | | | | C | | | |
| 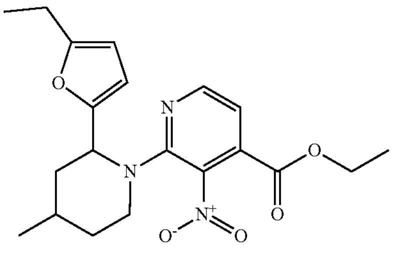 | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 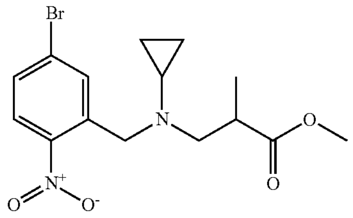 [SMILES: COC(=O)C(C)CN(Cc1cc(Br)ccc1[N+](=O)[O-])C1CC1] | | | | B | | | |
| 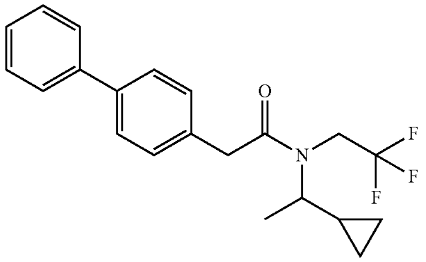 [SMILES: CC(C1CC1)N(CC(F)(F)F)C(=O)Cc1ccc(-c2ccccc2)cc1] | | | | C | | | |
| 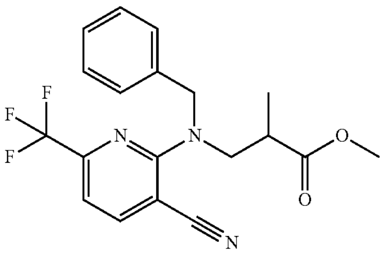 [SMILES: COC(=O)C(C)CN(Cc1ccccc1)c1nc(C(F)(F)F)ccc1C#N] | | | | B | | | |
| 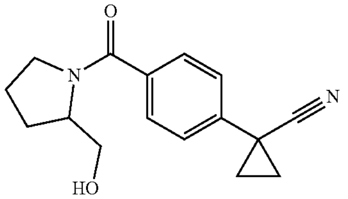 [SMILES: N#CC1(c2ccc(C(=O)N3CCCC3CO)cc2)CC1] | | | | D | | | |
| 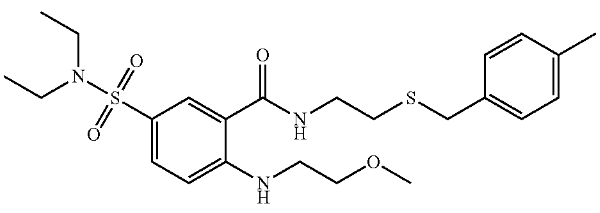 [SMILES: CCN(CC)S(=O)(=O)c1ccc(NCCOC)c(C(=O)NCCSCc2ccc(C)cc2)c1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 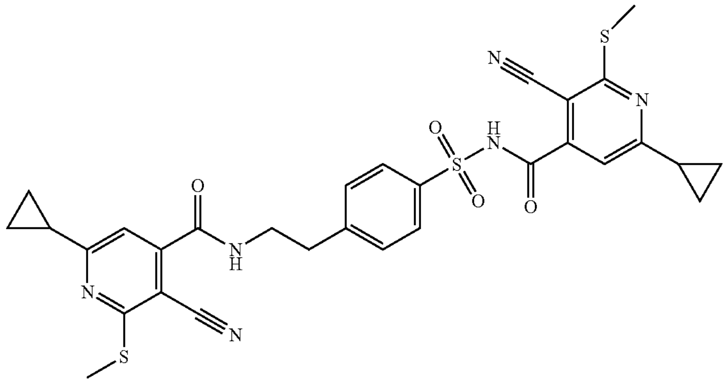 [SMILES: CSc1nc(C2CC2)cc(C(=O)NCCc2ccc(S(=O)(=O)NC(=O)c3cc(C4CC4)nc(SC)c3C#N)cc2)c1C#N] | | | | C | | | |
| 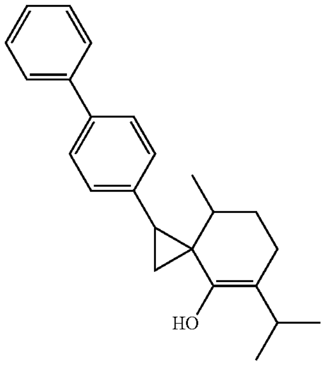 [SMILES: CC(C)C1=C(O)C2(CC2c2ccc(-c3ccccc3)cc2)C(C)CC1] | | | | B | | | |
| 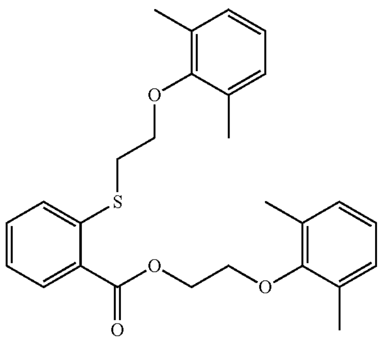 [SMILES: Cc1cccc(C)c1OCCOC(=O)c1ccccc1SCCOc1c(C)cccc1C] | | | | C | | | |
| 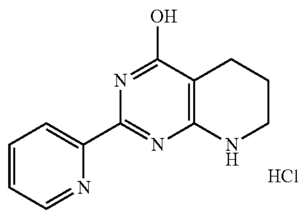 [SMILES: Oc1nc(-c2ccccn2)nc2c1CCCN2 ; Cl] HCl | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 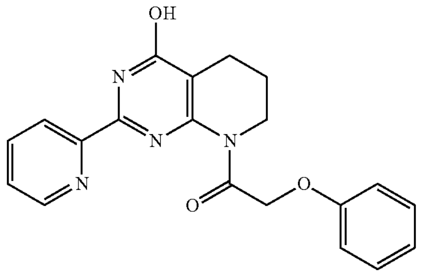 HCl | | | | D | | | |
| 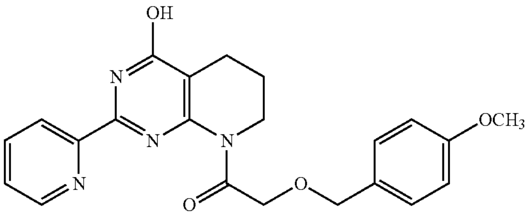 [SMILES: COc1ccc(COCC(=O)N2CCCc3c(O)nc(-c4ccccn4)nc32)cc1] | | | | D | | | H |
| 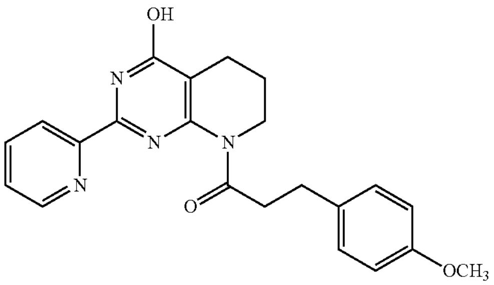 HCl | B | C | B | C | | | |
| 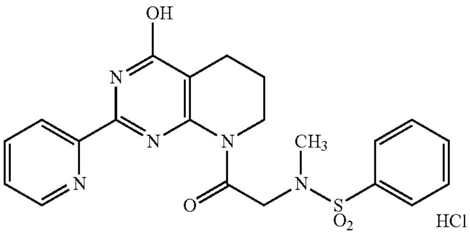 [SMILES: CN(CC(=O)N1CCCc2c(O)nc(-c3ccccn3)nc21)S(=O)(=O)c1ccccc1 ; Cl] HCl | | | | A | | | |
| 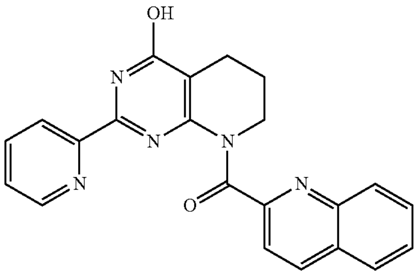 HCl | C | C | B | D | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 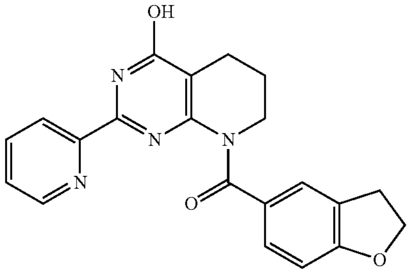 HCl | | | | A | | | |
| 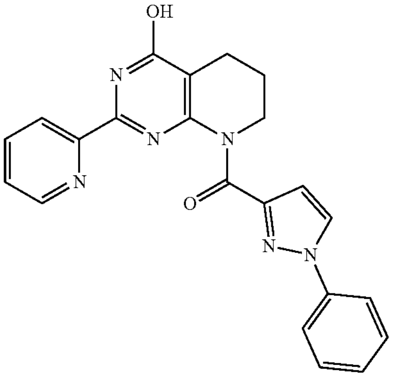 HCl | C | B | B | D | | | |
| 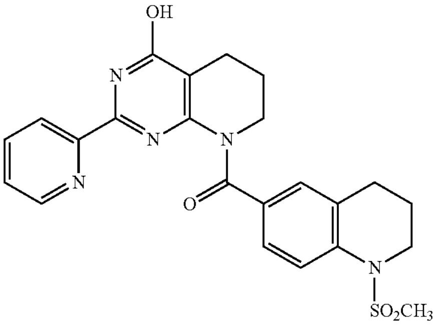 HCl | | | | B | | | |
| 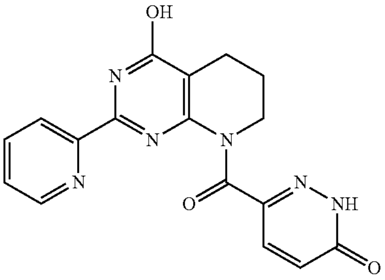 HCl | C | B | C | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 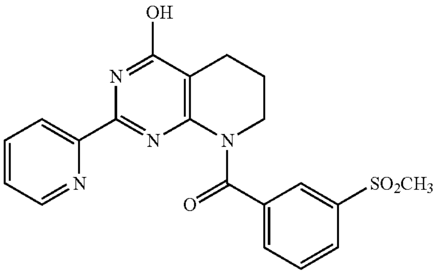 HCl | | | | C | | | G |
| 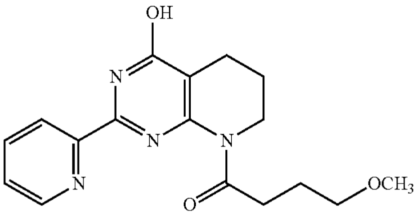 [SMILES: COCCCC(=O)N1CCCc2c(O)nc(-c3ccccn3)nc21] | | | | C | | | |
| 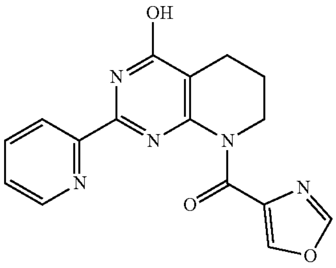 [SMILES: O=C(c1cocn1)N1CCCc2c(O)nc(-c3ccccn3)nc21] | | | | B | | | |
| 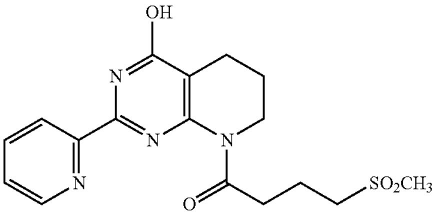 [SMILES: CS(=O)(=O)CCCC(=O)N1CCCc2c(O)nc(-c3ccccn3)nc21] | | | | C | | | |
| 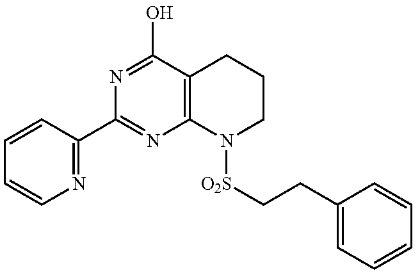 [SMILES: O=S(=O)(CCc1ccccc1)N1CCCc2c(O)nc(-c3ccccn3)nc21] | | | | 0 | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 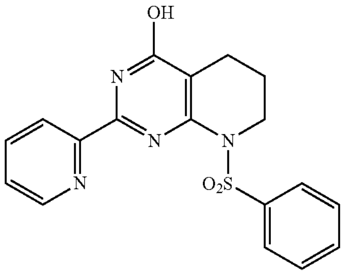 [SMILES: O=S(=O)(c1ccccc1)N1CCCc2c(O)nc(-c3ccccn3)nc21] | | | | A | | | |
| 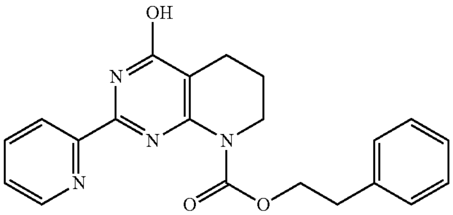 [SMILES: O=C(OCCc1ccccc1)N1CCCc2c(O)nc(-c3ccccn3)nc21] | C | B | C | D | | | |
| 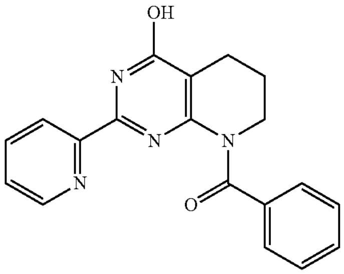 [SMILES: O=C(c1ccccc1)N1CCCc2c(O)nc(-c3ccccn3)nc21] | | | | B | | | |
| 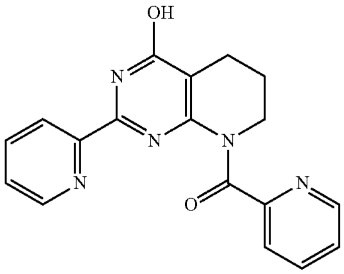 [SMILES: O=C(c1ccccn1)N1CCCc2c(O)nc(-c3ccccn3)nc21] | B | B | B | C | | | |
| 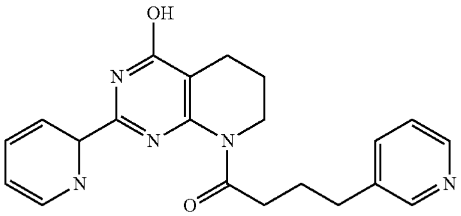 [SMILES: O=C(CCCc1cccnc1)N1CCCc2c(O)nc(C3C=CC=CN3)nc21] | C | C | B | C | | | |
| 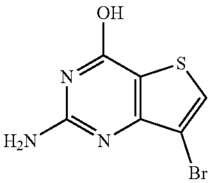 | | | | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 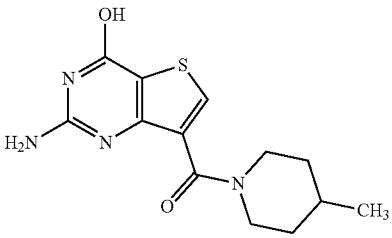 [SMILES: CC1CCN(C(=O)c2csc3c(O)nc(N)nc23)CC1] | | | | A | | | |
| 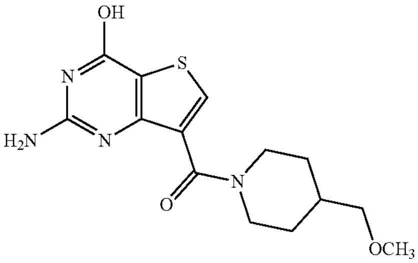 [SMILES: COCC1CCN(C(=O)c2csc3c(O)nc(N)nc23)CC1] | | | | A | | | |
| 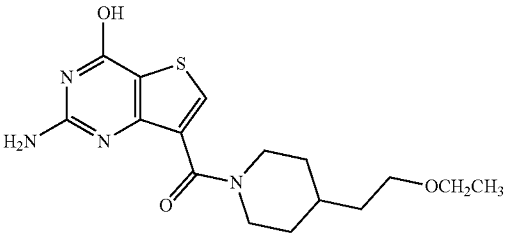 [SMILES: CCOCCC1CCN(C(=O)c2csc3c(O)nc(N)nc23)CC1] | | | | A | | | |
| 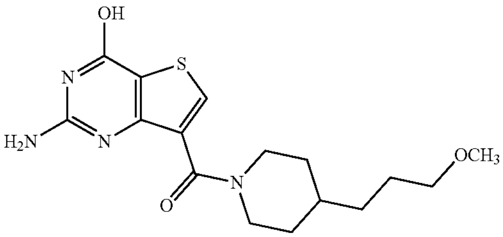 [SMILES: COCCCC1CCN(C(=O)c2csc3c(O)nc(N)nc23)CC1] | | | | B | | | |
| 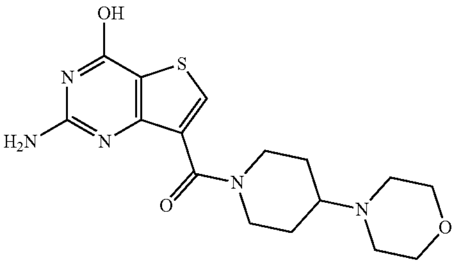 [SMILES: Nc1nc(O)c2scc(C(=O)N3CCC(N4CCOCC4)CC3)c2n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 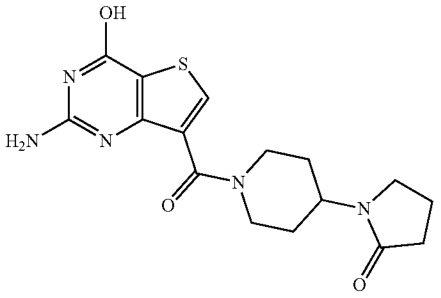 [SMILES: Nc1nc(O)c2scc(C(=O)N3CCC(N4CCCC4=O)CC3)c2n1] | | | | B | | | |
| 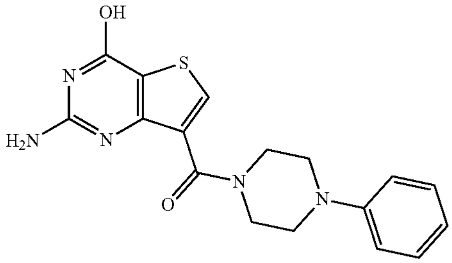 [SMILES: Nc1nc(O)c2scc(C(=O)N3CCN(c4ccccc4)CC3)c2n1] | | | | B | | | |
| 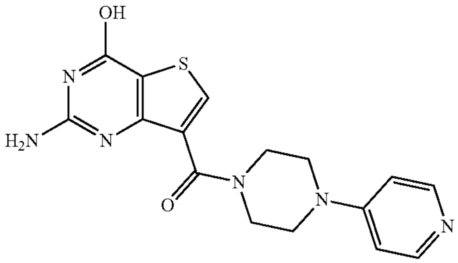 [SMILES: Nc1nc(O)c2scc(C(=O)N3CCN(c4ccncc4)CC3)c2n1] | | | | B | | | |
| 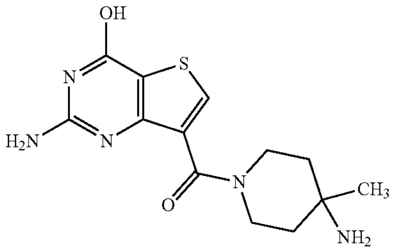 [SMILES: CC1(N)CCN(C(=O)c2csc3c(O)nc(N)nc23)CC1] | | | | A | | | |
| 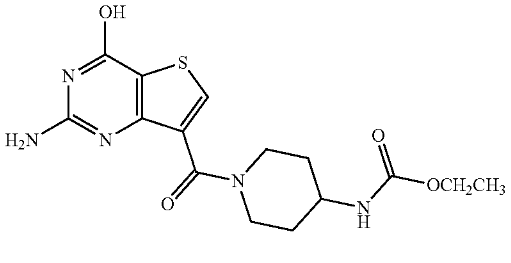 [SMILES: CCOC(=O)NC1CCN(C(=O)c2csc3c(O)nc(N)nc23)CC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 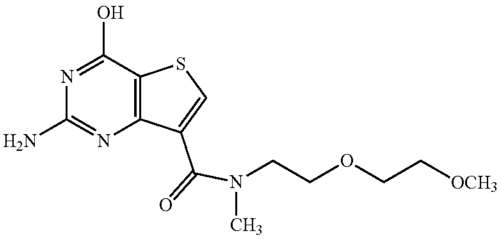 [SMILES: COCCOCCN(C)C(=O)c1csc2c(O)nc(N)nc12] | | | | A | | | |
| 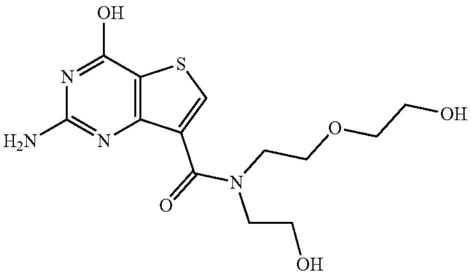 [SMILES: Nc1nc(O)c2scc(C(=O)N(CCO)CCOCCO)c2n1] | | | | A | | | |
| 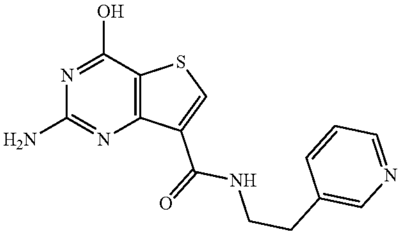 [SMILES: Nc1nc(O)c2scc(C(=O)NCCc3cccnc3)c2n1] | | | | A | | | |
| 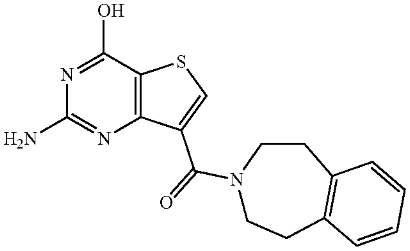 [SMILES: Nc1nc(O)c2scc(C(=O)N3CCc4ccccc4CC3)c2n1] | | | | A | | | |
| 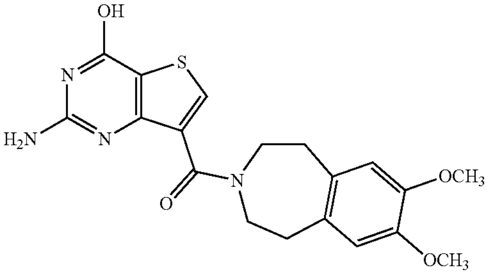 [SMILES: COc1cc2c(cc1OC)CCN(C(=O)c1csc3c(O)nc(N)nc13)CC2] | | | | B | | | |

TABLE 7-continued
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| % Inhibition at 20 μM of K-Ras mutant and wild-type protein | | | | | | | |
| 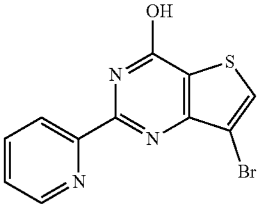 [SMILES: Oc1nc(-c2ccccn2)nc2c(Br)csc12] | B | B | B | C | | | |
| 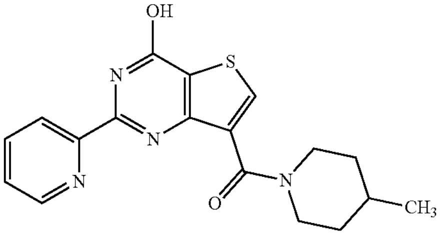 [SMILES: CC1CCN(C(=O)c2csc3c(O)nc(-c4ccccn4)nc23)CC1] | | | | C | | | |
| 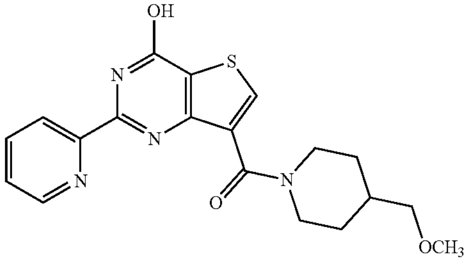 [SMILES: COCC1CCN(C(=O)c2csc3c(O)nc(-c4ccccn4)nc23)CC1] | | | | B | | | |
| 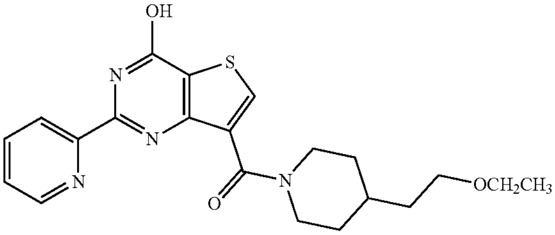 [SMILES: CCOCCC1CCN(C(=O)c2csc3c(O)nc(-c4ccccn4)nc23)CC1] | | | | C | | | |
| 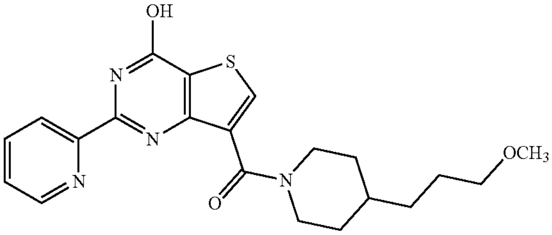 [SMILES: COCCCC1CCN(C(=O)c2csc3c(O)nc(-c4ccccn4)nc23)CC1] | | | | C | | | |
| 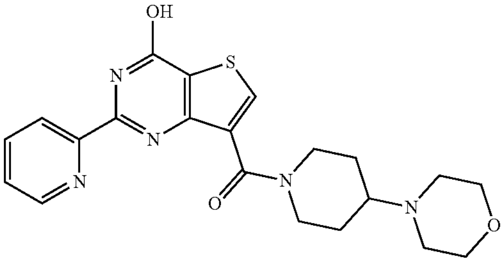 [SMILES: O=C(c1csc2c(O)nc(-c3ccccn3)nc12)N1CCC(N2CCOCC2)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 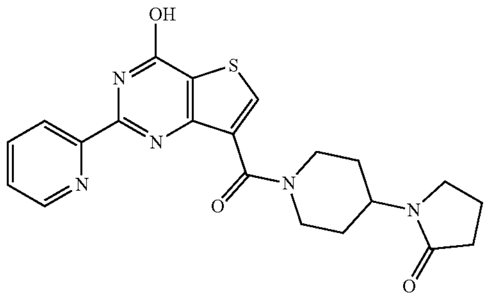 [SMILES: O=C(c1csc2c(O)nc(-c3ccccn3)nc12)N1CCC(N2CCCC2=O)CC1] | C | C | C | C | | | |
| 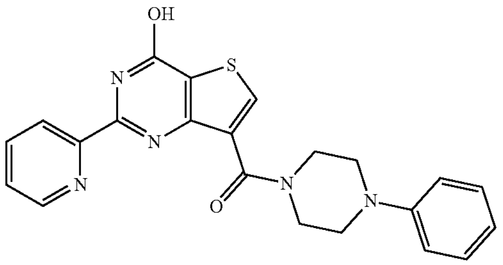 [SMILES: O=C(c1csc2c(O)nc(-c3ccccn3)nc12)N1CCN(c2ccccc2)CC1] | C | B | C | D | | | G |
| 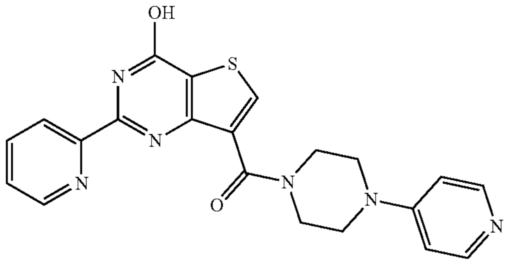 [SMILES: O=C(c1csc2c(O)nc(-c3ccccn3)nc12)N1CCN(c2ccncc2)CC1] | C | B | C | C | | | |
| 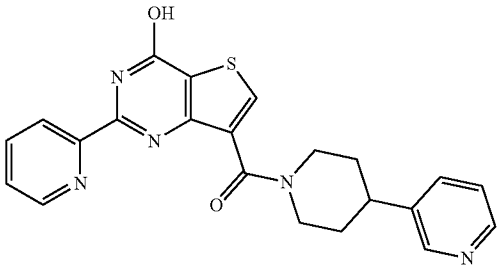 [SMILES: O=C(c1csc2c(O)nc(-c3ccccn3)nc12)N1CCC(c2cccnc2)CC1] | C | B | D | C | | | |
| 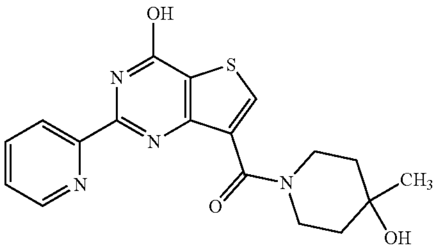 [SMILES: CC1(O)CCN(C(=O)c2csc3c(O)nc(-c4ccccn4)nc23)CC1] | C | B | C | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 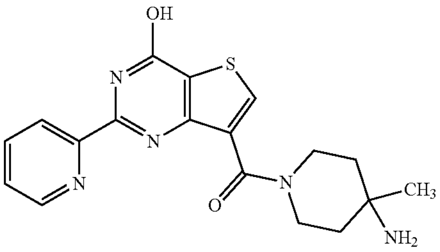 [SMILES: CC1(N)CCN(C(=O)c2csc3c(O)nc(-c4ccccn4)nc23)CC1] | C | D | B | D | | | |
| 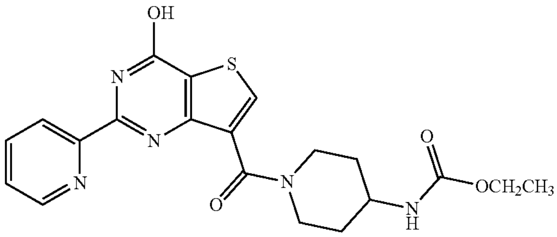 [SMILES: CCOC(=O)NC1CCN(C(=O)c2csc3c(O)nc(-c4ccccn4)nc23)CC1] | | | | C | | | |
| 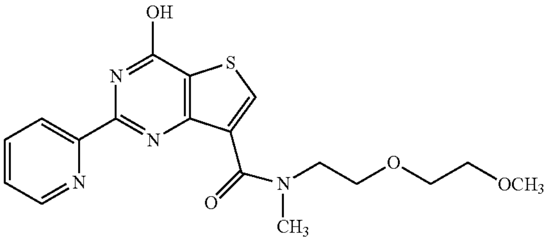 [SMILES: COCCOCCN(C)C(=O)c1csc2c(O)nc(-c3ccccn3)nc12] | | | | C | | | |
| 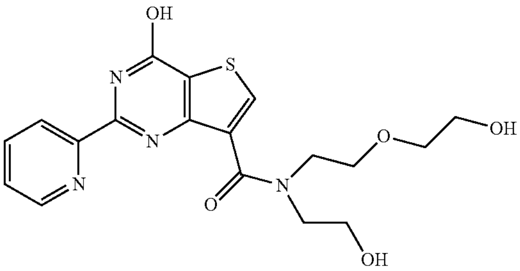 [SMILES: O=C(c1csc2c(O)nc(-c3ccccn3)nc12)N(CCO)CCOCCO] | C | C | B | D | | | |
| 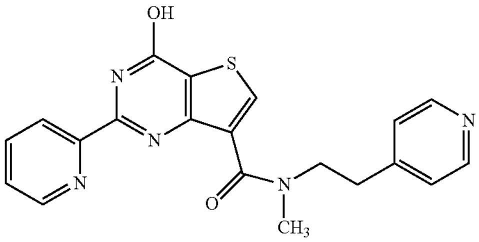 [SMILES: CN(CCc1ccncc1)C(=O)c1csc2c(O)nc(-c3ccccn3)nc12] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 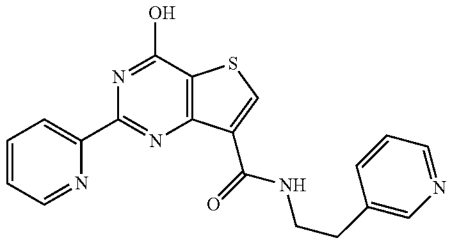 [SMILES: O=C(NCCc1cccnc1)c1csc2c(O)nc(-c3ccccn3)nc12] | C | B | D | C | | | |
| 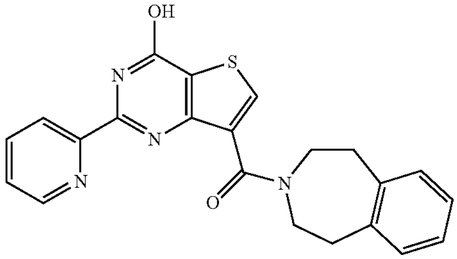 [SMILES: O=C(c1csc2c(O)nc(-c3ccccn3)nc12)N1CCc2ccccc2CC1] | | | | B | | | |
| 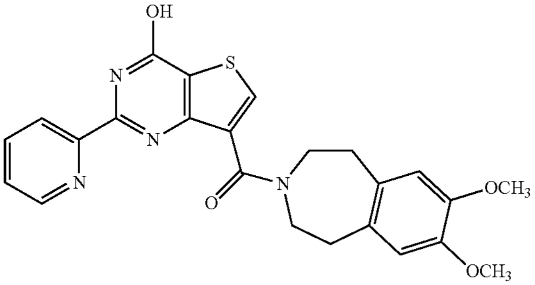 [SMILES: COc1cc2c(cc1OC)CCN(C(=O)c1csc3c(O)nc(-c4ccccn4)nc13)CC2] | | | | C | | | |
| 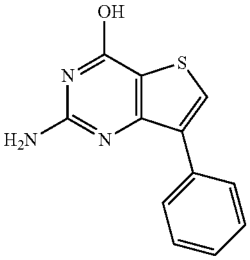 [SMILES: Nc1nc(O)c2scc(-c3ccccc3)c2n1] | | | | A | | | |
| 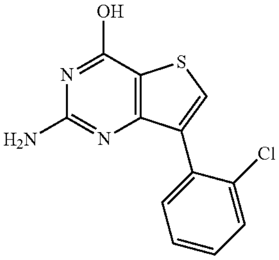 [SMILES: Nc1nc(O)c2scc(-c3ccccc3Cl)c2n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 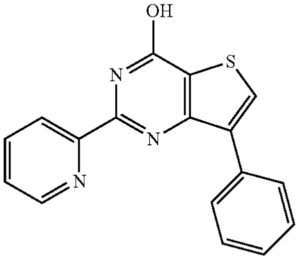 [SMILES: Oc1nc(-c2ccccn2)nc2c(-c3ccccc3)csc12] | | | | B | B | C | |
| 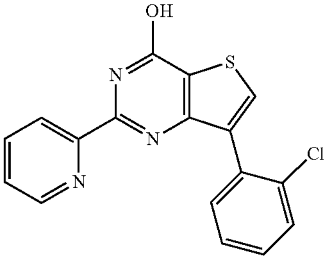 [SMILES: Oc1nc(-c2ccccn2)nc2c(-c3ccccc3Cl)csc12] | B | B | A | C | C | C | |
| 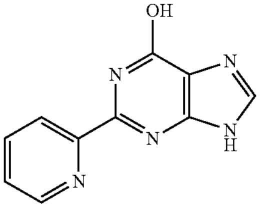 [SMILES: Oc1nc(-c2ccccn2)nc2[nH]cnc12] | | | | B | | | |
| 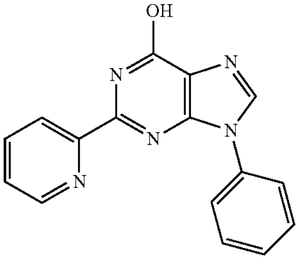 [SMILES: Oc1nc(-c2ccccn2)nc2c1ncn2-c1ccccc1] | C | B | C | C | | | |
| 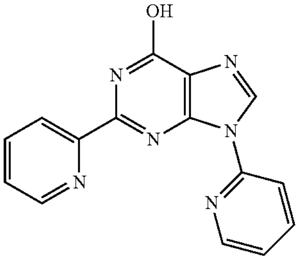 [SMILES: Oc1nc(-c2ccccn2)nc2c1ncn2-c1ccccn1] | | | | B | | | |
| 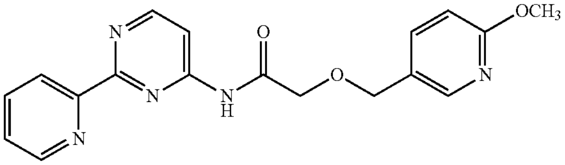 [SMILES: COc1ccc(COCC(=O)Nc2ccnc(-c3ccccn3)n2)cn1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 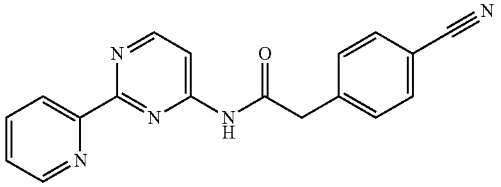 [SMILES: N#Cc1ccc(CC(=O)Nc2ccnc(-c3ccccn3)n2)cc1] | | | | B | | | |
| 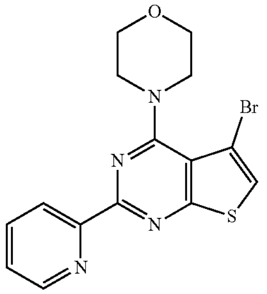 [SMILES: Brc1csc2nc(-c3ccccn3)nc(N3CCOCC3)c12] | | | | A | | | |
| 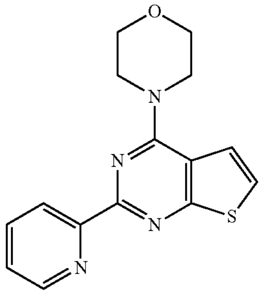 [SMILES: c1ccc(-c2nc(N3CCOCC3)c3ccsc3n2)nc1] | | | | C | | | |
| 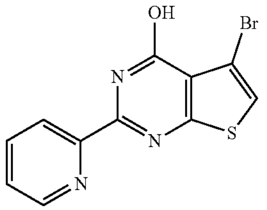 [SMILES: Oc1nc(-c2ccccn2)nc2scc(Br)c12] | C | B | C | C | C | D | |
| 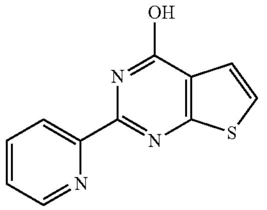 [SMILES: Oc1nc(-c2ccccn2)nc2sccc12] | B | B | B | C | C | C | F |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 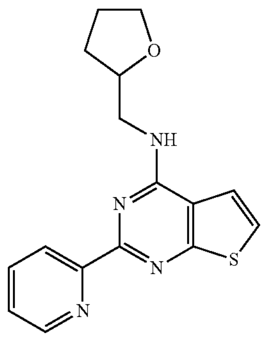 [SMILES: c1ccc(-c2nc(NCC3CCCO3)c3ccsc3n2)nc1] | C | C | B | B | | | |
| 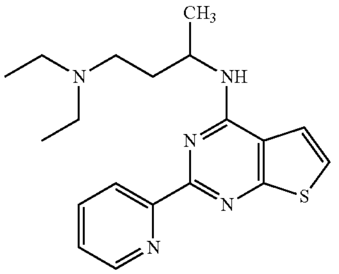 [SMILES: CCN(CC)CCC(C)Nc1nc(-c2ccccn2)nc2sccc12] | | | | B | | | |
| 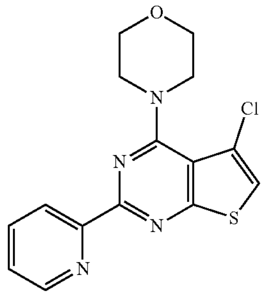 [SMILES: Clc1csc2nc(-c3ccccn3)nc(N3CCOCC3)c12] | | | | A | | | |
| 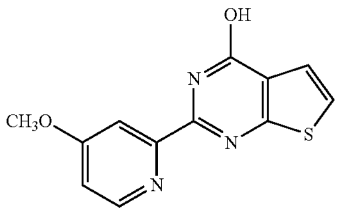 | C | C | B | C | C | C | G |
| 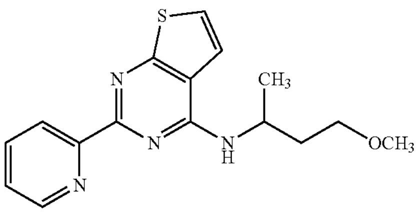 [SMILES: COCCC(C)Nc1nc(-c2ccccn2)nc2sccc12] | C | B | A | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 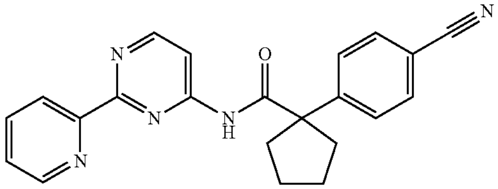 [SMILES: N#Cc1ccc(C2(C(=O)Nc3ccnc(-c4ccccn4)n3)CCCC2)cc1] | | | | B | | | |
| 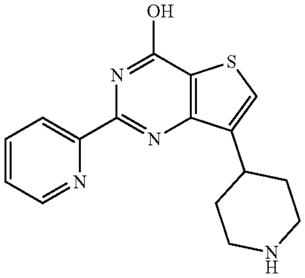 2 HCl | | | | C | | | |
| 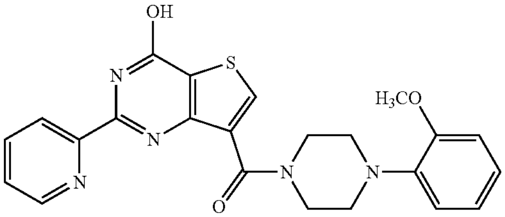 [SMILES: COc1ccccc1N1CCN(C(=O)c2csc3c(O)nc(-c4ccccn4)nc23)CC1] | | | | B | | | |
| 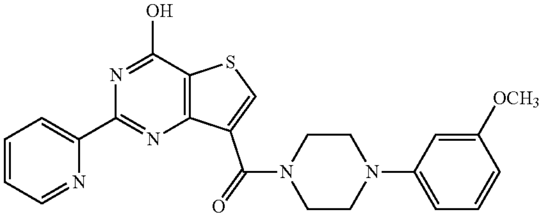 [SMILES: COc1cccc(N2CCN(C(=O)c3csc4c(O)nc(-c5ccccn5)nc34)CC2)c1] | | | | A | C | C | |
| 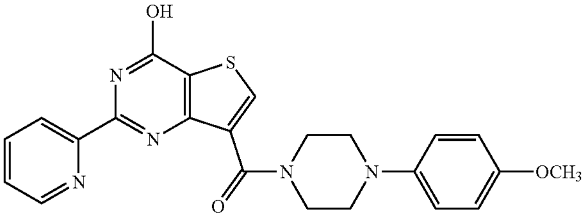 [SMILES: COc1ccc(N2CCN(C(=O)c3csc4c(O)nc(-c5ccccn5)nc34)CC2)cc1] | | | | B | | | |
| 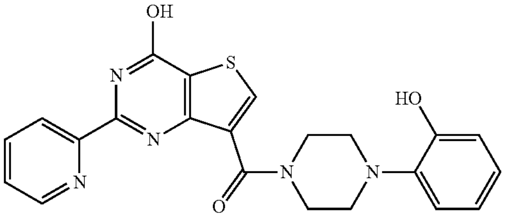 | B | B | A | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 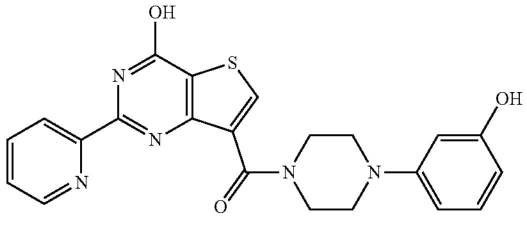 [SMILES: O=C(c1csc2c(O)nc(-c3ccccn3)nc12)N1CCN(c2cccc(O)c2)CC1] | | | | B | | | |
| 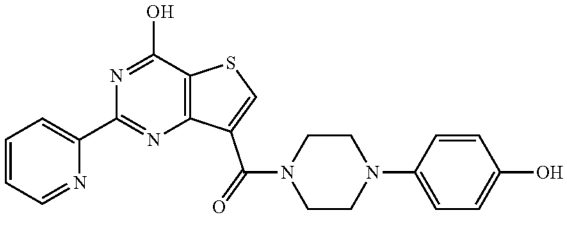 | | | | B | | | |
| 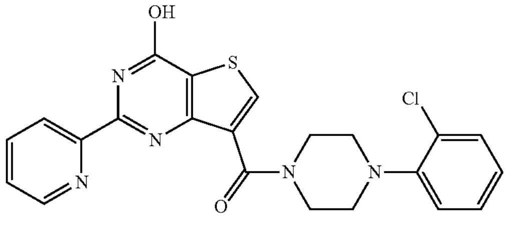 | | | | C | | | |
| 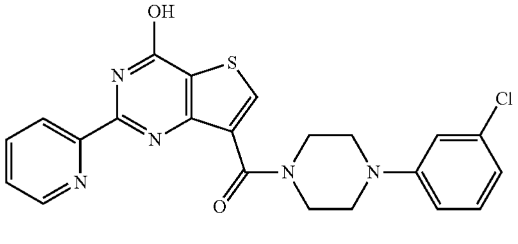 [SMILES: O=C(c1csc2c(O)nc(-c3ccccn3)nc12)N1CCN(c2cccc(Cl)c2)CC1] | | | | B | | | |
| 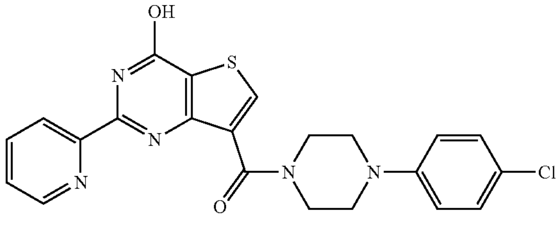 [SMILES: O=C(c1csc2c(O)nc(-c3ccccn3)nc12)N1CCN(c2ccc(Cl)cc2)CC1] | | | | B | | | |
| 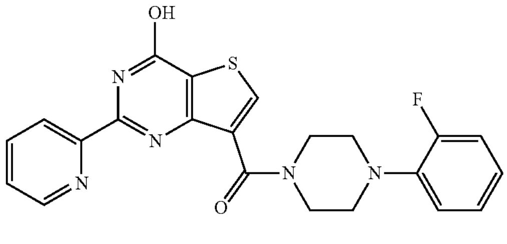 [SMILES: O=C(c1csc2c(O)nc(-c3ccccn3)nc12)N1CCN(c2ccccc2F)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 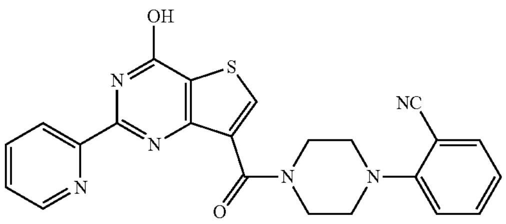 | | | | A | | | |
| 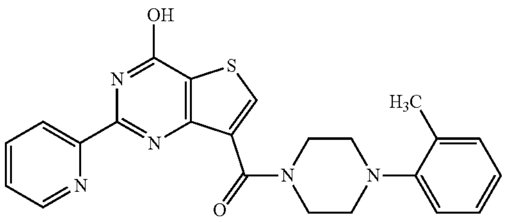 | | | | B | C | C | |
| 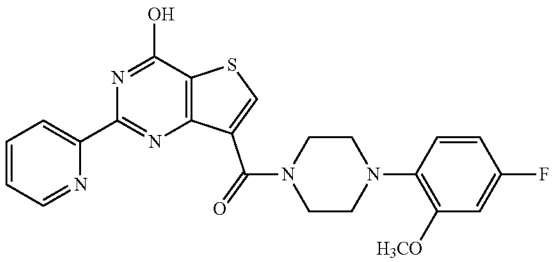 [SMILES: COc1cc(F)ccc1N1CCN(C(=O)c2csc3c(O)nc(-c4ccccn4)nc23)CC1] | | | | B | | | |
| 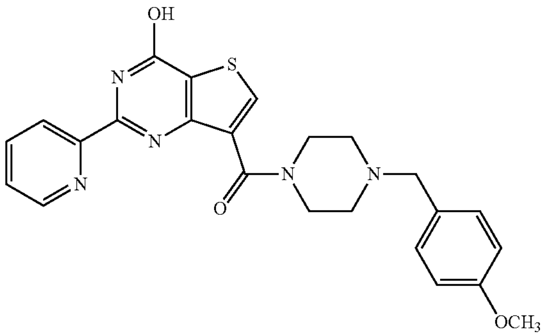 [SMILES: COc1ccc(CN2CCN(C(=O)c3csc4c(O)nc(-c5ccccn5)nc34)CC2)cc1] | | | | B | | | |
| 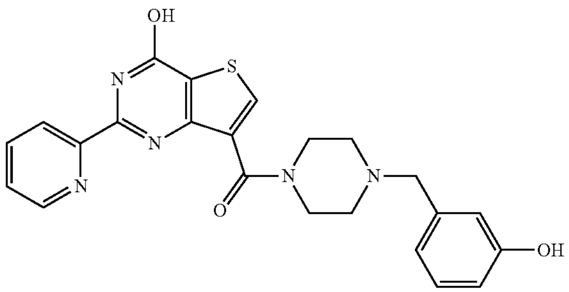 [SMILES: O=C(c1csc2c(O)nc(-c3ccccn3)nc12)N1CCN(Cc2cccc(O)c2)CC1] | | | | D | D | D | F |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 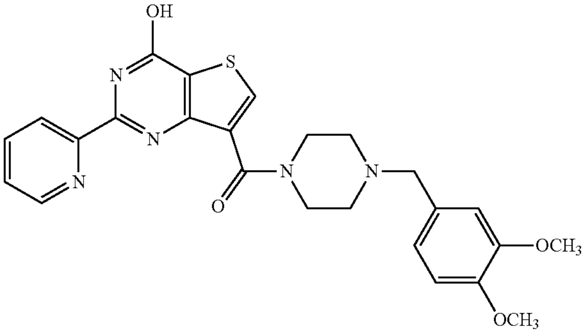 [SMILES: COc1ccc(CN2CCN(C(=O)c3csc4c(O)nc(-c5ccccn5)nc34)CC2)cc1OC] | | | | B | | | |
| 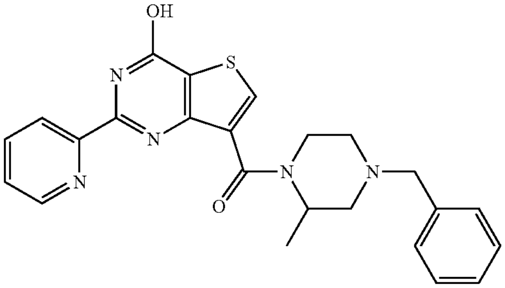 [SMILES: CC1CN(Cc2ccccc2)CCN1C(=O)c1csc2c(O)nc(-c3ccccn3)nc12] | | | | B | | | |
| 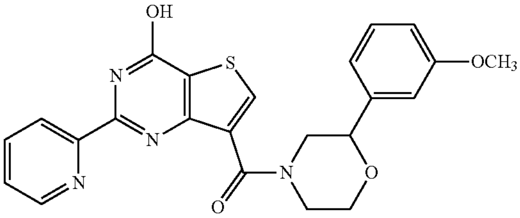 [SMILES: COc1cccc(C2CN(C(=O)c3csc4c(O)nc(-c5ccccn5)nc34)CCO2)c1] | | | | B | | | |
| 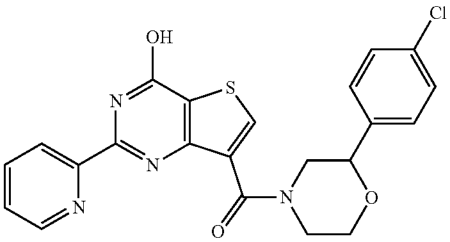 [SMILES: O=C(c1csc2c(O)nc(-c3ccccn3)nc12)N1CCOC(c2ccc(Cl)cc2)C1] | | | | B | | | |
| 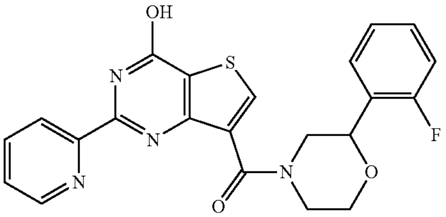 [SMILES: O=C(c1csc2c(O)nc(-c3ccccn3)nc12)N1CCOC(c2ccccc2F)C1] | C | B | D | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 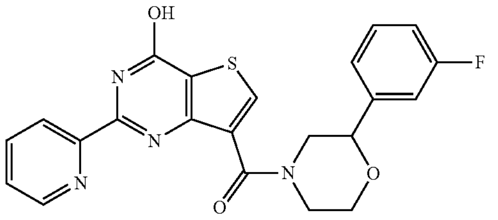 [SMILES: O=C(c1csc2c(O)nc(-c3ccccn3)nc12)N1CCOC(c2cccc(F)c2)C1] | | | | B | A | A | |
| 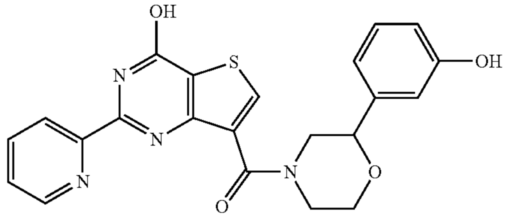 [SMILES: O=C(c1csc2c(O)nc(-c3ccccn3)nc12)N1CCOC(c2cccc(O)c2)C1] | | | | C | | | |
| 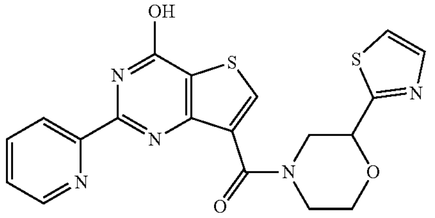 [SMILES: O=C(c1csc2c(O)nc(-c3ccccn3)nc12)N1CCOC(c2nccs2)C1] | | | | B | C | C | G |
| 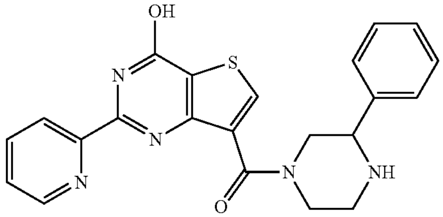 [SMILES: O=C(c1csc2c(O)nc(-c3ccccn3)nc12)N1CCNC(c2ccccc2)C1] | | | | B | | | |
| 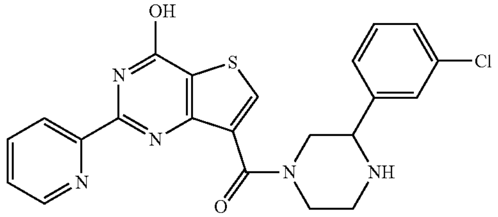 [SMILES: O=C(c1csc2c(O)nc(-c3ccccn3)nc12)N1CCNC(c2cccc(Cl)c2)C1] | | | | B | | | |
| 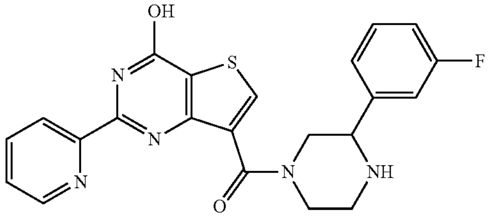 [SMILES: O=C(c1csc2c(O)nc(-c3ccccn3)nc12)N1CCNC(c2cccc(F)c2)C1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 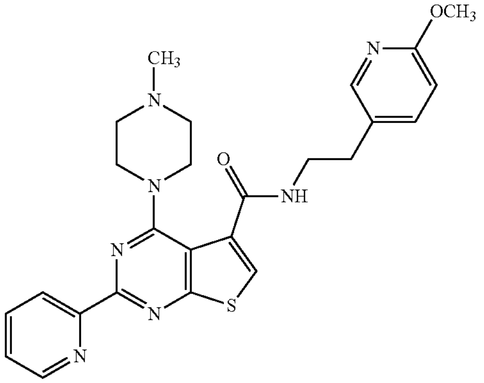 [SMILES: COc1ccc(CCNC(=O)c2csc3nc(-c4ccccn4)nc(N4CCN(C)CC4)c23)cn1] | B | B | B | B | | | |
| 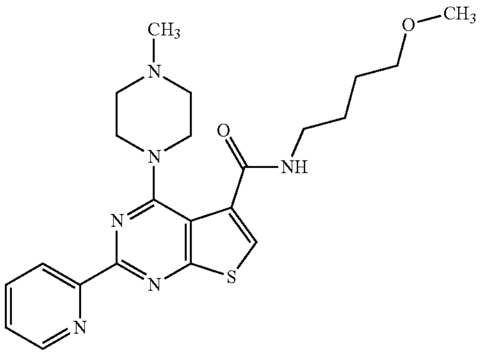 [SMILES: COCCCCNC(=O)c1csc2nc(-c3ccccn3)nc(N3CCN(C)CC3)c12] | B | B | A | B | | | |
| 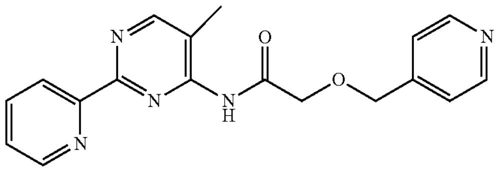 [SMILES: Cc1cnc(-c2ccccn2)nc1NC(=O)COCc1ccncc1] | C | C | C | C | | | |
| 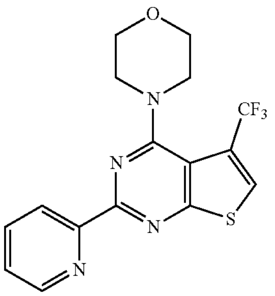 [SMILES: FC(F)(F)c1csc2nc(-c3ccccn3)nc(N3CCOCC3)c12] | | | | A | | | |
| 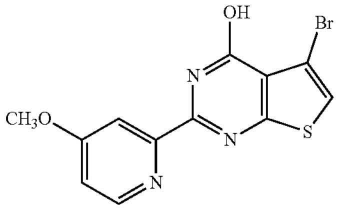 | | | | B | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 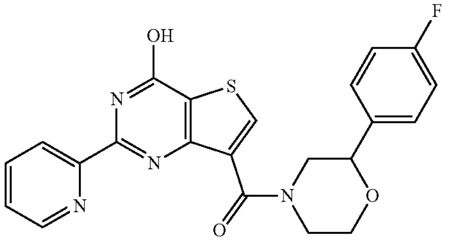 [SMILES: O=C(c1csc2c(O)nc(-c3ccccn3)nc12)N1CCOC(c2ccc(F)cc2)C1] | C | C | C | C | | | |
| 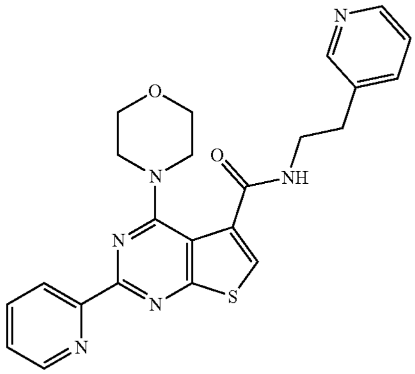 | | | | A | B | C | |
| 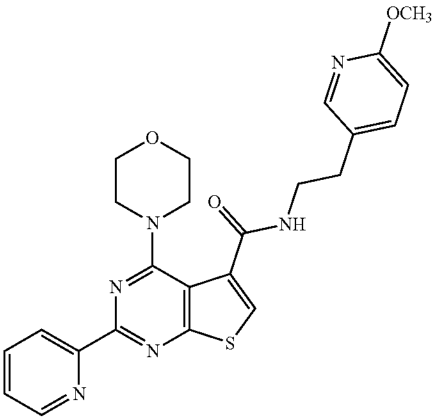 [SMILES: COc1ccc(CCNC(=O)c2csc3nc(-c4ccccn4)nc(N4CCOCC4)c23)cn1] | | | | B | B | C | |
| 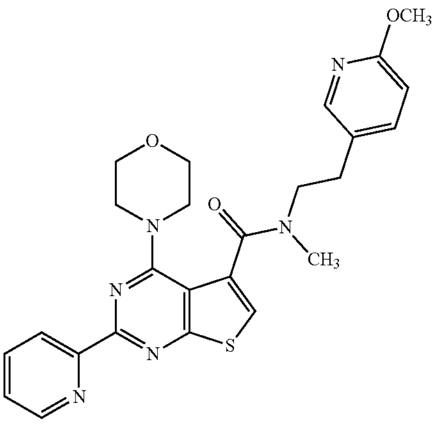 [SMILES: COc1ccc(CCN(C)C(=O)c2csc3nc(-c4ccccn4)nc(N4CCOCC4)c23)cn1] | | | | 0 | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 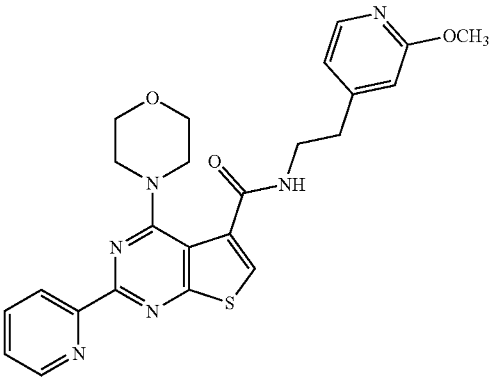 | | | | A | B | B | |
| 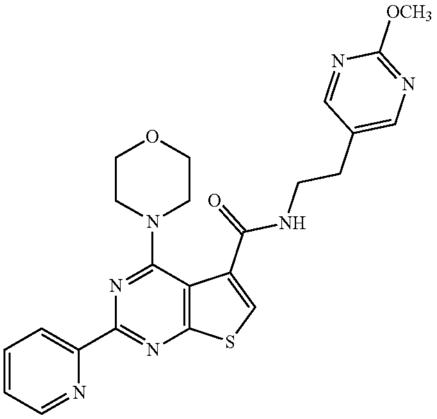 [SMILES: COc1ncc(CCNC(=O)c2csc3nc(-c4ccccn4)nc(N4CCOCC4)c23)cn1] | | | | A | B | B | |
| 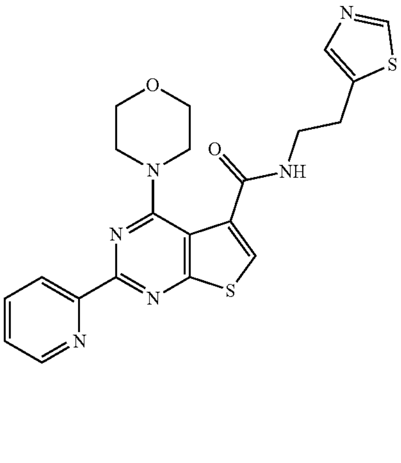 [SMILES: O=C(NCCc1cncs1)c1csc2nc(-c3ccccn3)nc(N3CCOCC3)c12] | | | | A | A | B | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 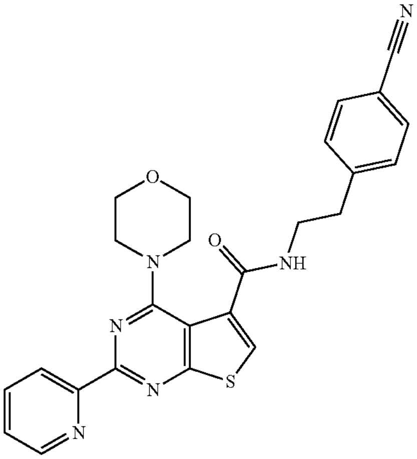 [SMILES: N#Cc1ccc(CCNC(=O)c2csc3nc(-c4ccccn4)nc(N4CCOCC4)c23)cc1] | | | | A | A | A | |
| 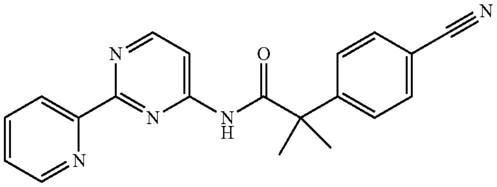 [SMILES: CC(C)(C(=O)Nc1ccnc(-c2ccccn2)n1)c1ccc(C#N)cc1] | | | | A | C | C | |
| 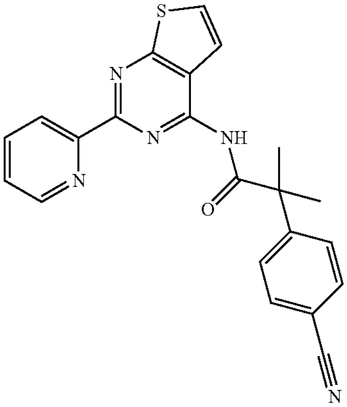 [SMILES: CC(C)(C(=O)Nc1nc(-c2ccccn2)nc2sccc12)c1ccc(C#N)cc1] | | | | 0 | A | A | |
| 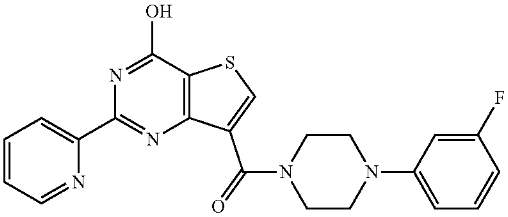 [SMILES: O=C(c1csc2c(O)nc(-c3ccccn3)nc12)N1CCN(c2cccc(F)c2)CC1] | | | | B | C | D | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 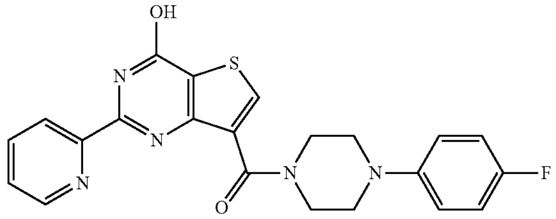 [SMILES: O=C(c1csc2c(O)nc(-c3ccccn3)nc12)N1CCN(c2ccc(F)cc2)CC1] | | | | 0 | B | B | |
| 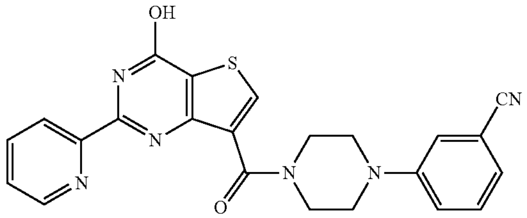 [SMILES: N#Cc1cccc(N2CCN(C(=O)c3csc4c(O)nc(-c5ccccn5)nc34)CC2)c1] | | | | A | B | B | |
| 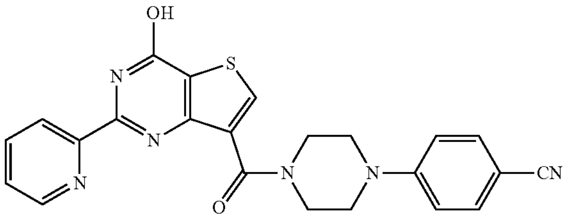 [SMILES: N#Cc1ccc(N2CCN(C(=O)c3csc4c(O)nc(-c5ccccn5)nc34)CC2)cc1] | | | | 0 | C | C | |
| 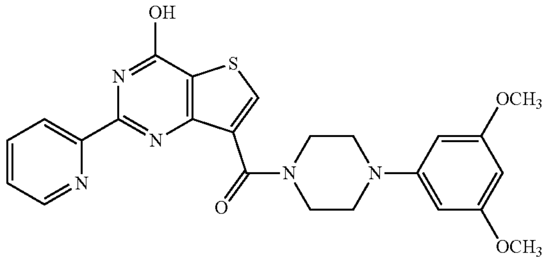 [SMILES: COc1cc(OC)cc(N2CCN(C(=O)c3csc4c(O)nc(-c5ccccn5)nc34)CC2)c1] | | | | 0 | A | A | |
| 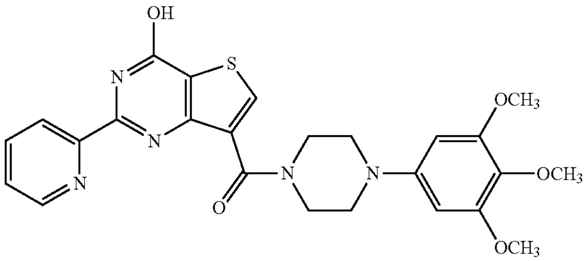 [SMILES: COc1cc(N2CCN(C(=O)c3csc4c(O)nc(-c5ccccn5)nc34)CC2)cc(OC)c1OC] | | | | 0 | A | B | |
| 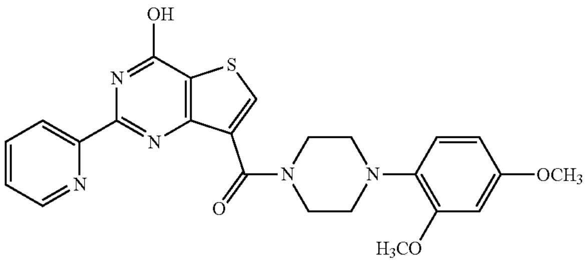 [SMILES: COc1ccc(N2CCN(C(=O)c3csc4c(O)nc(-c5ccccn5)nc34)CC2)c(OC)c1] | | | | B | C | C | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 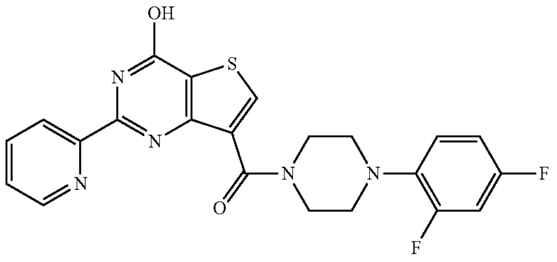 [SMILES: O=C(c1csc2c(O)nc(-c3ccccn3)nc12)N1CCN(c2ccc(F)cc2F)CC1] | | | | C | B | B | |
| 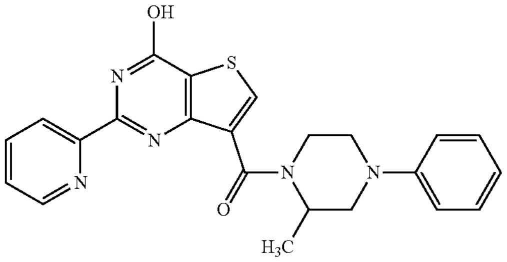 [SMILES: CC1CN(c2ccccc2)CCN1C(=O)c1csc2c(O)nc(-c3ccccn3)nc12] | D | C | B | C | D | D | G |
| 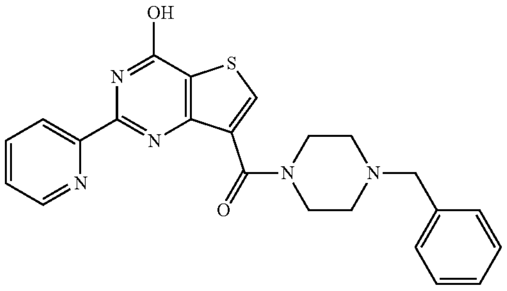 [SMILES: O=C(c1csc2c(O)nc(-c3ccccn3)nc12)N1CCN(Cc2ccccc2)CC1] | | | | B | C | D | |
| 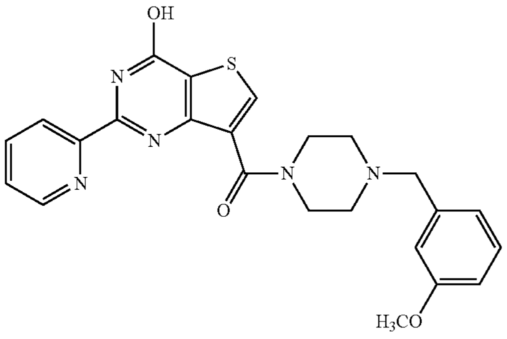 [SMILES: COc1cccc(CN2CCN(C(=O)c3csc4c(O)nc(-c5ccccn5)nc34)CC2)c1] | D | B | B | B | D | D | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 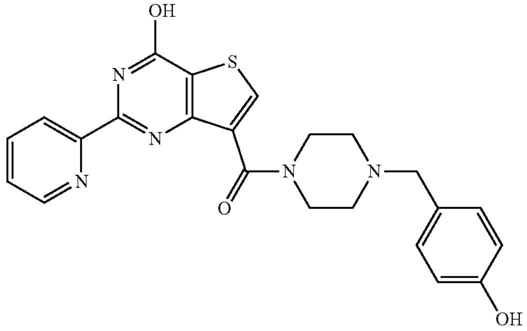 [SMILES: O=C(c1csc2c(O)nc(-c3ccccn3)nc12)N1CCN(Cc2ccc(O)cc2)CC1] | | | | A | B | B | |
| 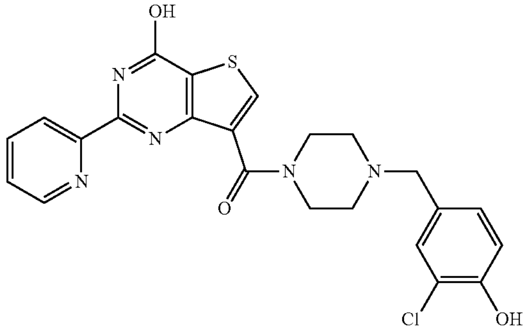 [SMILES: O=C(c1csc2c(O)nc(-c3ccccn3)nc12)N1CCN(Cc2ccc(O)c(Cl)c2)CC1] | | | | B | D | D | |
| 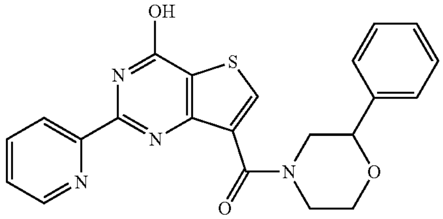 [SMILES: O=C(c1csc2c(O)nc(-c3ccccn3)nc12)N1CCOC(c2ccccc2)C1] | | | | A | B | C | |
| 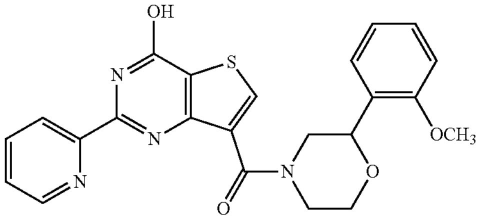 | | | | C | C | D | F |
| 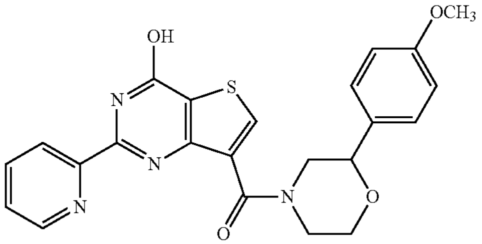 [SMILES: COc1ccc(C2CN(C(=O)c3csc4c(O)nc(-c5ccccn5)nc34)CCO2)cc1] | | | | B | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 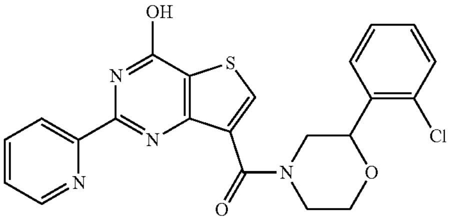 [SMILES: O=C(c1csc2c(O)nc(-c3ccccn3)nc12)N1CCOC(c2ccccc2Cl)C1] | B | B | C | C | D | D | G |
| 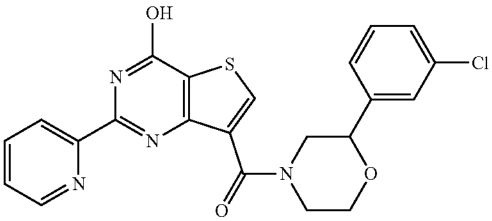 [SMILES: O=C(c1csc2c(O)nc(-c3ccccn3)nc12)N1CCOC(c2cccc(Cl)c2)C1] | | | | A | B | C | |
| 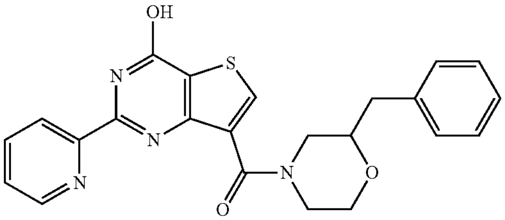 | | | | B | C | C | |
| 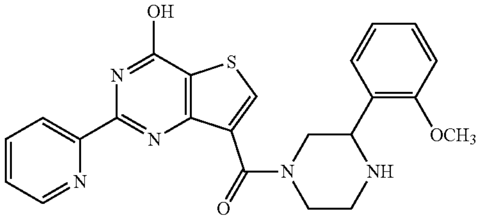 [SMILES: COc1ccccc1C1CN(C(=O)c2csc3c(O)nc(-c4ccccn4)nc23)CCN1] | | | | B | C | D | |
| 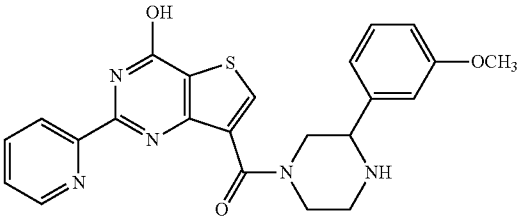 [SMILES: COc1cccc(C2CN(C(=O)c3csc4c(O)nc(-c5ccccn5)nc34)CCN2)c1] | C | B | B | B | C | D | F |
| 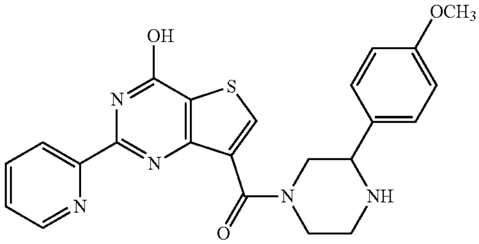 | | | | A | D | D | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 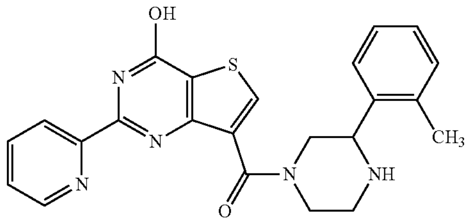 [SMILES: Cc1ccccc1C1CN(C(=O)c2csc3c(O)nc(-c4ccccn4)nc23)CCN1] | | | | B | C | D | |
| 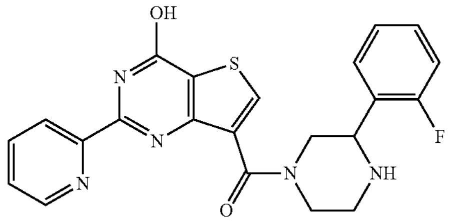 [SMILES: O=C(c1csc2c(O)nc(-c3ccccn3)nc12)N1CCNC(c2ccccc2F)C1] | | | | B | C | D | |
| 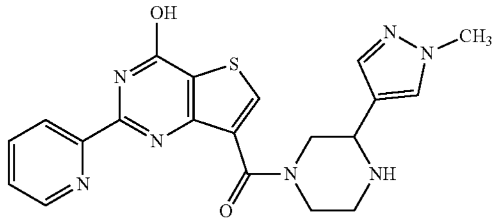 [SMILES: Cn1cc(C2CN(C(=O)c3csc4c(O)nc(-c5ccccn5)nc34)CCN2)cn1] | | | | A | C | C | |
| 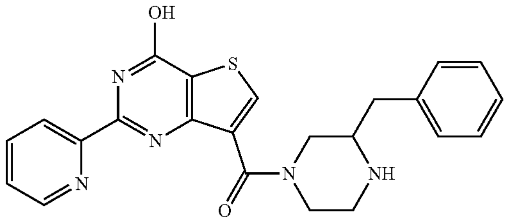 [SMILES: O=C(c1csc2c(O)nc(-c3ccccn3)nc12)N1CCNC(Cc2ccccc2)C1] | | | | B | C | C | |
| 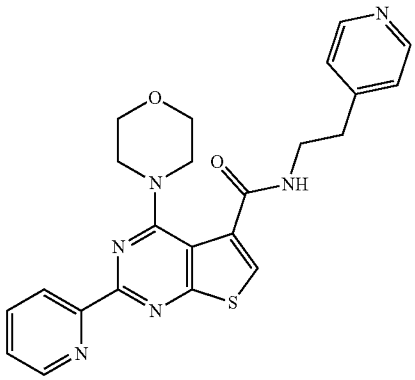 | | | | 0 | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 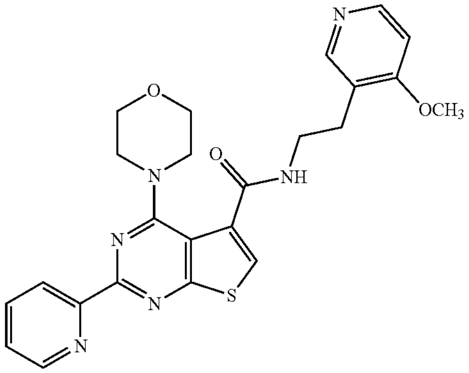 [SMILES: COc1ccncc1CCNC(=O)c1csc2nc(-c3ccccn3)nc(N3CCOCC3)c12] | | | | A | A | B | |
| 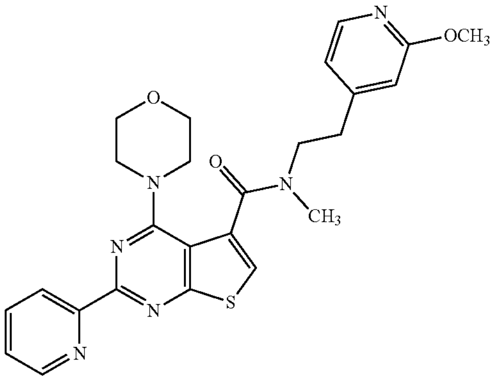 [SMILES: COc1cc(CCN(C)C(=O)c2csc3nc(-c4ccccn4)nc(N4CCOCC4)c23)ccn1] | | | | 0 | B | B | |
| 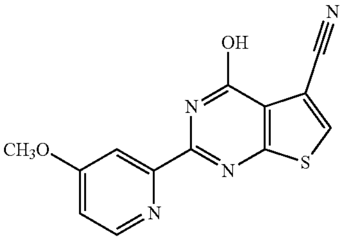 | | | | 0 | B | C | |
| 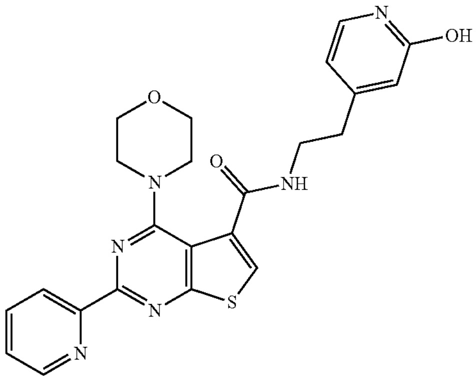 | | | | A | A | A | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 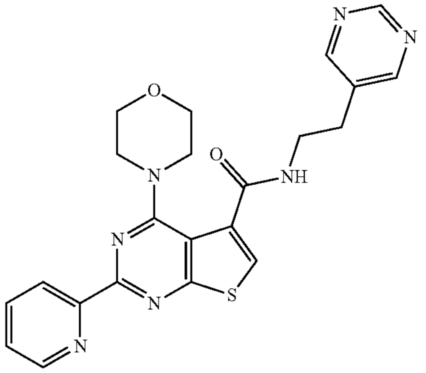 [SMILES: O=C(NCCc1cncnc1)c1csc2nc(-c3ccccn3)nc(N3CCOCC3)c12] | | | | A | B | B | |
| 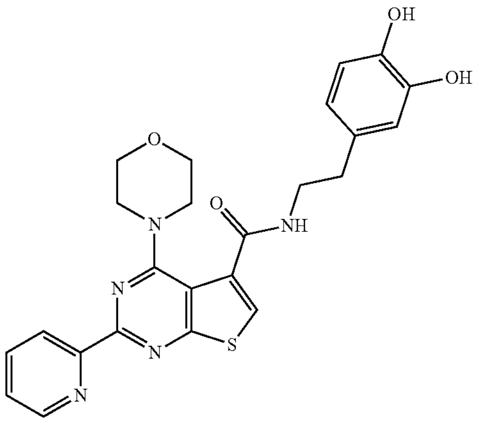 [SMILES: O=C(NCCc1ccc(O)c(O)c1)c1csc2nc(-c3ccccn3)nc(N3CCOCC3)c12] | | | | 0 | B | A | |
| 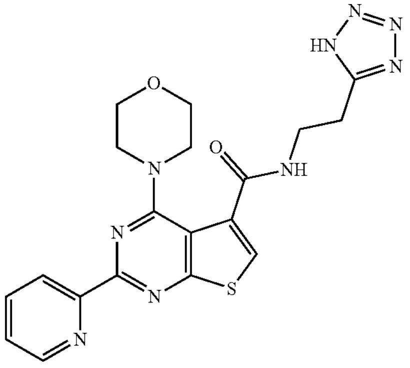 [SMILES: O=C(NCCc1nnn[nH]1)c1csc2nc(-c3ccccn3)nc(N3CCOCC3)c12] | | | | A | B | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 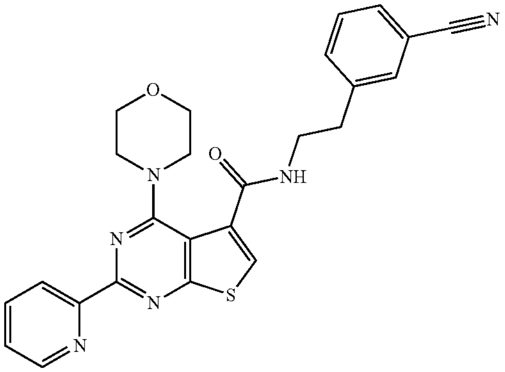 [SMILES: N#Cc1cccc(CCNC(=O)c2csc3nc(-c4ccccn4)nc(N4CCOCC4)c23)c1] | | | | A | B | B | |
| 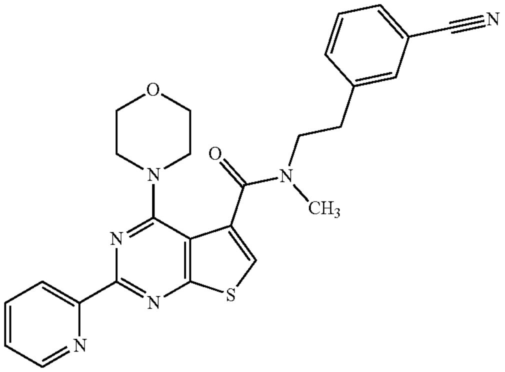 [SMILES: CN(CCc1cccc(C#N)c1)C(=O)c1csc2nc(-c3ccccn3)nc(N3CCOCC3)c12] | | | | A | C | C | |
| 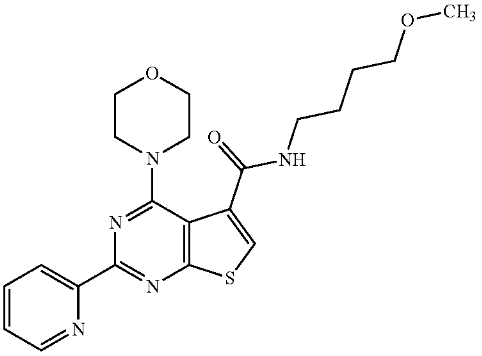 [SMILES: COCCCCNC(=O)c1csc2nc(-c3ccccn3)nc(N3CCOCC3)c12] | | | | A | A | B | |
| 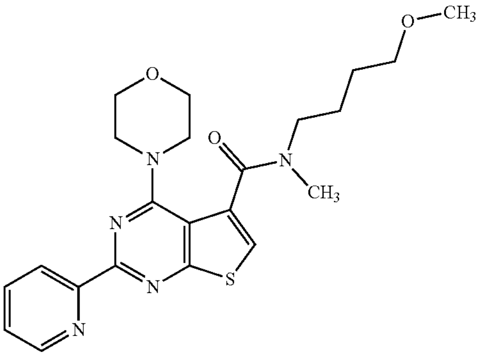 [SMILES: COCCCCN(C)C(=O)c1csc2nc(-c3ccccn3)nc(N3CCOCC3)c12] | | | | A | B | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 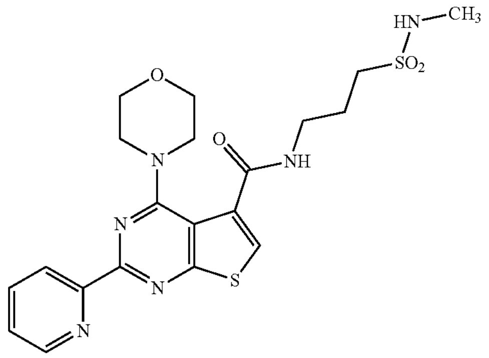 [SMILES: CNS(=O)(=O)CCCNC(=O)c1csc2nc(-c3ccccn3)nc(N3CCOCC3)c12] | | | | A | B | B | |
| 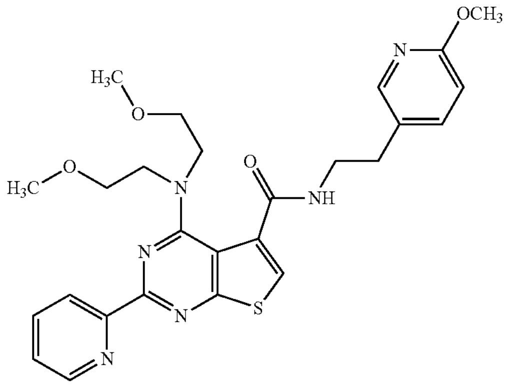 [SMILES: COCCN(CCOC)c1nc(-c2ccccn2)nc2scc(C(=O)NCCc3ccc(OC)nc3)c12] | | | | A | A | B | |
| 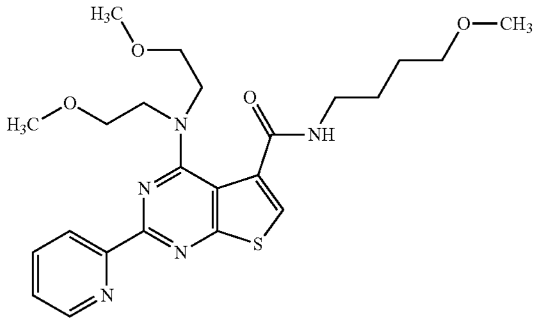 [SMILES: COCCCCNC(=O)c1csc2nc(-c3ccccn3)nc(N(CCOC)CCOC)c12] | | | | 0 | B | C | |
| 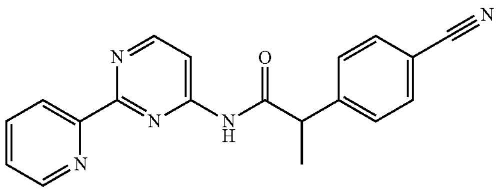 [SMILES: CC(C(=O)Nc1ccnc(-c2ccccn2)n1)c1ccc(C#N)cc1] | | | | A | C | C | |
| 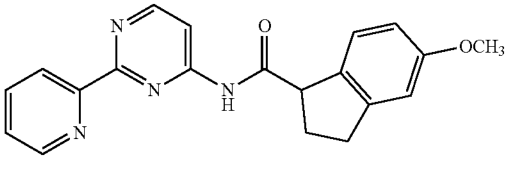 [SMILES: COc1ccc2c(c1)CCC2C(=O)Nc1ccnc(-c2ccccn2)n1] | | | | A | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 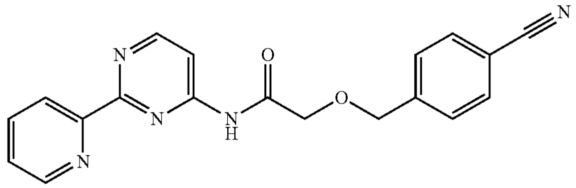 [SMILES: N#Cc1ccc(COCC(=O)Nc2ccnc(-c3ccccn3)n2)cc1] | | | | 0 | B | C | |
| 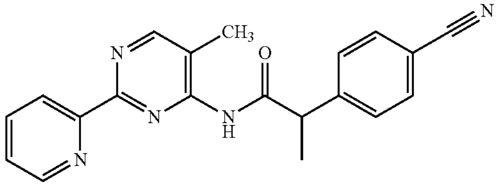 [SMILES: Cc1cnc(-c2ccccn2)nc1NC(=O)C(C)c1ccc(C#N)cc1] | | | | A | C | C | |
| 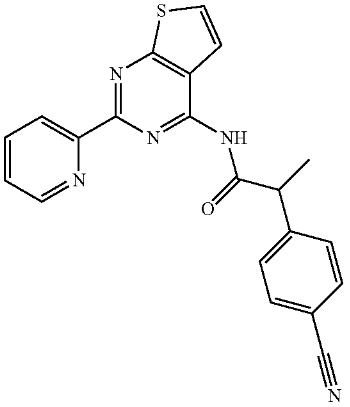 [SMILES: CC(C(=O)Nc1nc(-c2ccccn2)nc2sccc12)c1ccc(C#N)cc1] | | | | A | D | D | |
| 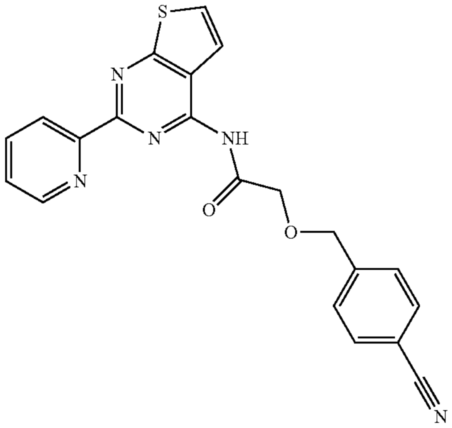 [SMILES: N#Cc1ccc(COCC(=O)Nc2nc(-c3ccccn3)nc3sccc23)cc1] | D | B | B | B | D | D | F |
| 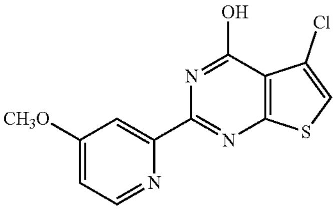 | C | B | C | C | D | D | F |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 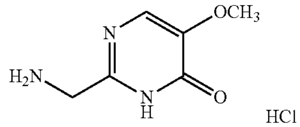 [SMILES: COc1cnc(CN)[nH]c1=O ; Cl] HCl | | | | B | A | B | |
| 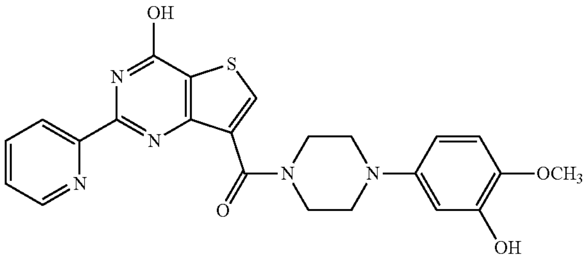 [SMILES: COc1ccc(N2CCN(C(=O)c3csc4c(O)nc(-c5ccccn5)nc34)CC2)cc1O] | | | | A | C | C | |
| 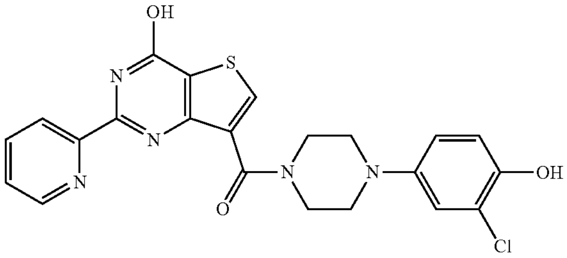 [SMILES: O=C(c1csc2c(O)nc(-c3ccccn3)nc12)N1CCN(c2ccc(O)c(Cl)c2)CC1] | | | | C | C | C | F |
| 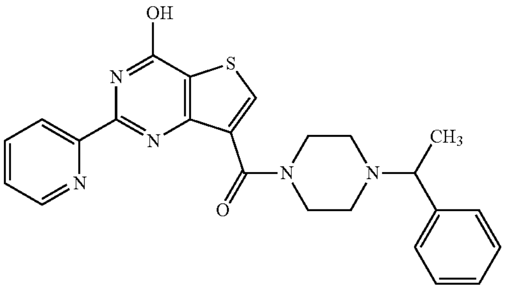 [SMILES: CC(c1ccccc1)N1CCN(C(=O)c2csc3c(O)nc(-c4ccccn4)nc23)CC1] | | | | C | C | D | F |
| 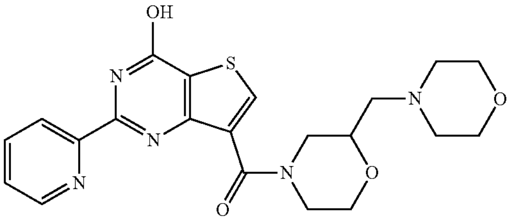 [SMILES: O=C(c1csc2c(O)nc(-c3ccccn3)nc12)N1CCOC(CN2CCOCC2)C1] | | | | A | B | C | |
| 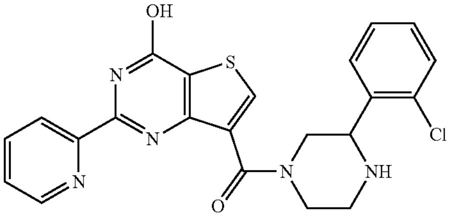 [SMILES: O=C(c1csc2c(O)nc(-c3ccccn3)nc12)N1CCNC(c2ccccc2Cl)C1] | | | | B | C | D | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 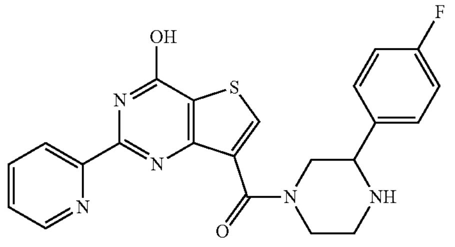 [SMILES: O=C(c1csc2c(O)nc(-c3ccccn3)nc12)N1CCNC(c2ccc(F)cc2)C1] | | | | A | D | D | |
| 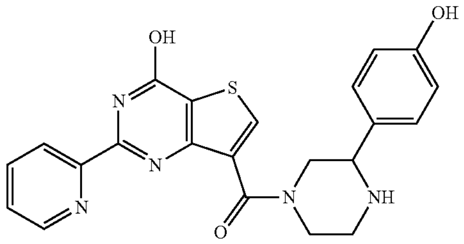 [SMILES: O=C(c1csc2c(O)nc(-c3ccccn3)nc12)N1CCNC(c2ccc(O)cc2)C1] | C | C | D | D | D | D | G |
| 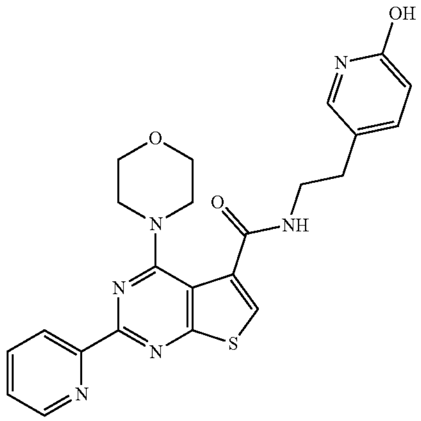 [SMILES: O=C(NCCc1ccc(O)nc1)c1csc2nc(-c3ccccn3)nc(N3CCOCC3)c12] | | | | A | | | |
| 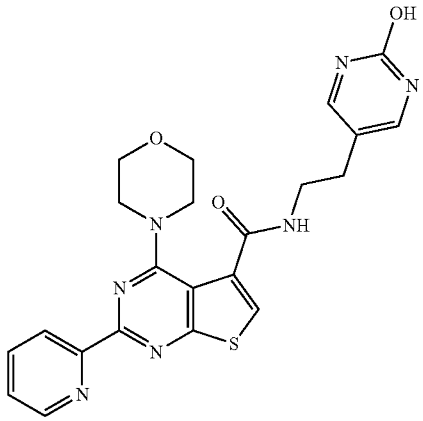 [SMILES: O=C(NCCc1cnc(O)nc1)c1csc2nc(-c3ccccn3)nc(N3CCOCC3)c12] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 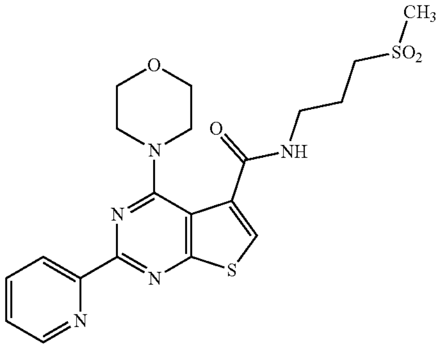 [SMILES: CS(=O)(=O)CCCNC(=O)c1csc2nc(-c3ccccn3)nc(N3CCOCC3)c12] | | | | A | | | |
| 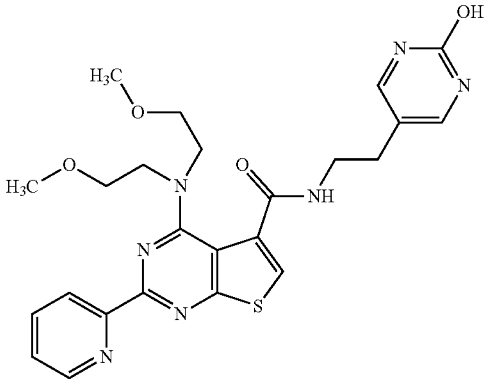 [SMILES: COCCN(CCOC)c1nc(-c2ccccn2)nc2scc(C(=O)NCCc3cnc(O)nc3)c12] | | | | A | | | |
| 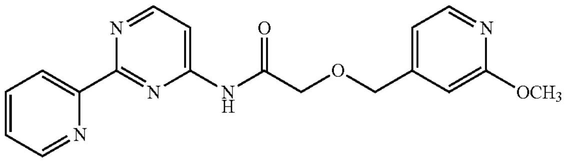 [SMILES: COc1cc(COCC(=O)Nc2ccnc(-c3ccccn3)n2)ccn1] | | | | B | | | |
| 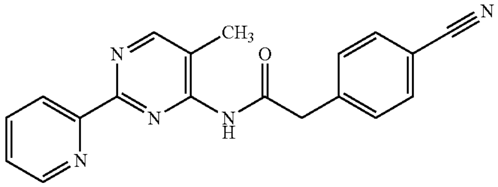 [SMILES: Cc1cnc(-c2ccccn2)nc1NC(=O)Cc1ccc(C#N)cc1] | | | | A | | | |
| 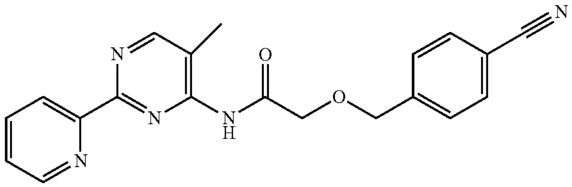 [SMILES: Cc1cnc(-c2ccccn2)nc1NC(=O)COCc1ccc(C#N)cc1] | | | | B | | | |
| 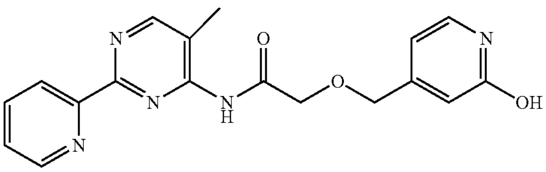 [SMILES: Cc1cnc(-c2ccccn2)nc1NC(=O)COCc1ccnc(O)c1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 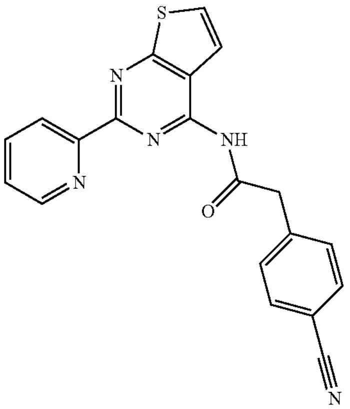 [SMILES: N#Cc1ccc(CC(=O)Nc2nc(-c3ccccn3)nc3sccc23)cc1] | | | | A | | | |
| 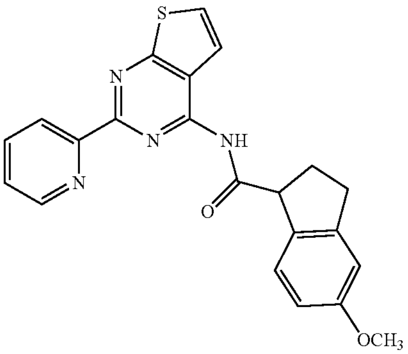 [SMILES: COc1ccc2c(c1)CCC2C(=O)Nc1nc(-c2ccccn2)nc2sccc12] | | | | A | | | |
| 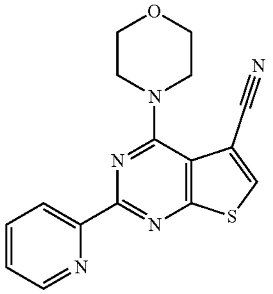 [SMILES: N#Cc1csc2nc(-c3ccccn3)nc(N3CCOCC3)c12] | | | | B | | | |
| 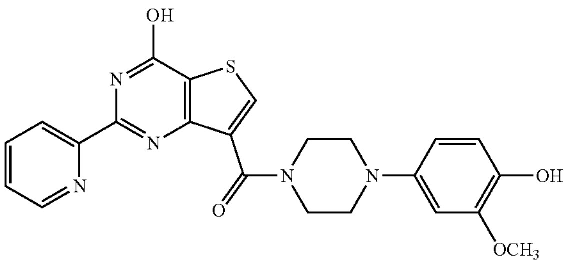 [SMILES: COc1cc(N2CCN(C(=O)c3csc4c(O)nc(-c5ccccn5)nc34)CC2)ccc1O] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 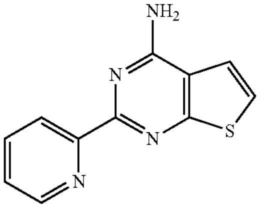 [SMILES: Nc1nc(-c2ccccn2)nc2sccc12] | | | | B | | | |
| 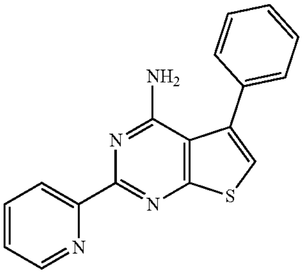 [SMILES: Nc1nc(-c2ccccn2)nc2scc(-c3ccccc3)c12] | | | | A | | | |
| 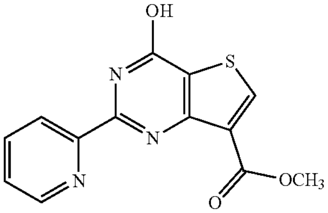 [SMILES: COC(=O)c1csc2c(O)nc(-c3ccccn3)nc12] | | | | A | | | |
| 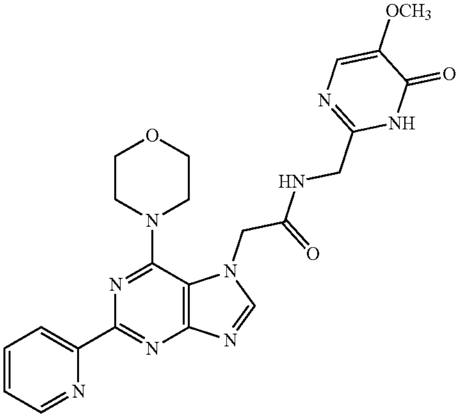 [SMILES: COc1cnc(CNC(=O)Cn2cnc3nc(-c4ccccn4)nc(N4CCOCC4)c32)[nH]c1=O] | | | | A | | | |
| 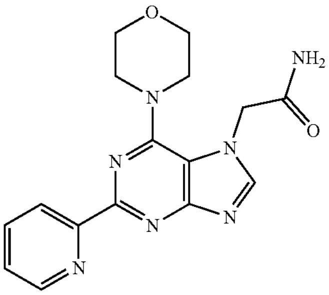 [SMILES: NC(=O)Cn1cnc2nc(-c3ccccn3)nc(N3CCOCC3)c21] | B | B | B | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 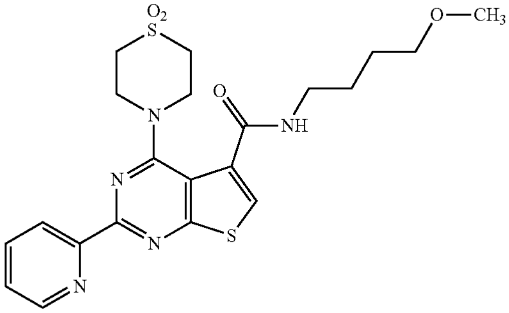 [SMILES: COCCCCNC(=O)c1csc2nc(-c3ccccn3)nc(N3CCS(=O)(=O)CC3)c12] | | | | A | A | A | |
| 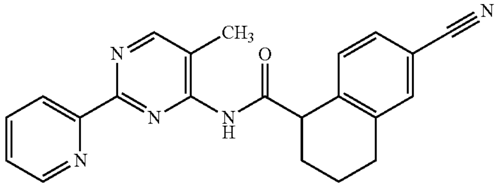 [SMILES: Cc1cnc(-c2ccccn2)nc1NC(=O)C1CCCc2cc(C#N)ccc21] | B | B | C | C | C | C | |
| 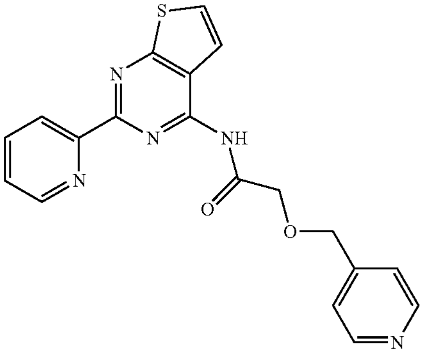 [SMILES: O=C(COCc1ccncc1)Nc1nc(-c2ccccn2)nc2sccc12] | C | C | B | C | C | C | |
| 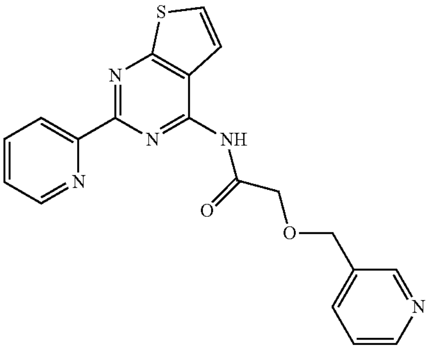 [SMILES: O=C(COCc1cccnc1)Nc1nc(-c2ccccn2)nc2sccc12] | C | C | C | C | D | D | |
| 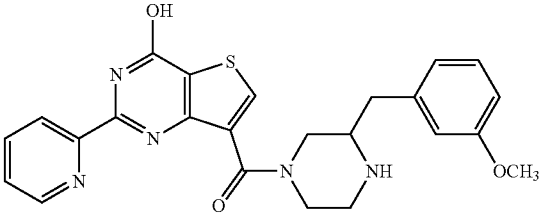 [SMILES: COc1cccc(CC2CN(C(=O)c3csc4c(O)nc(-c5ccccn5)nc34)CCN2)c1] | | | | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 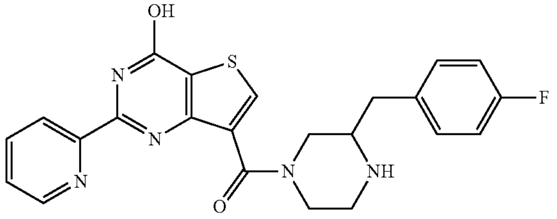 [SMILES: O=C(c1csc2c(O)nc(-c3ccccn3)nc12)N1CCNC(Cc2ccc(F)cc2)C1] | | | | C | C | C | |
| 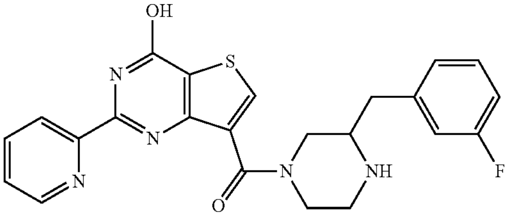 [SMILES: O=C(c1csc2c(O)nc(-c3ccccn3)nc12)N1CCNC(Cc2cccc(F)c2)C1] | | | | C | C | C | |
| 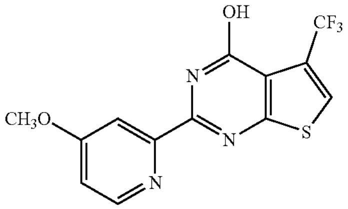 | | | | B | B | B | |
| 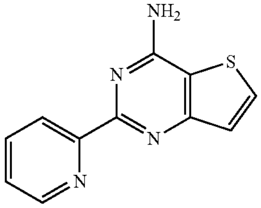 [SMILES: Nc1nc(-c2ccccn2)nc2ccsc12] | A | B | A | B | B | C | |
| 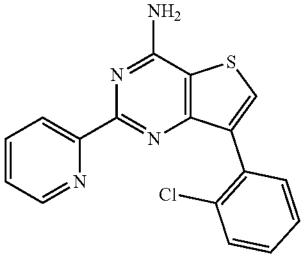 [SMILES: Nc1nc(-c2ccccn2)nc2c(-c3ccccc3Cl)csc12] | | | | A | A | A | |
| 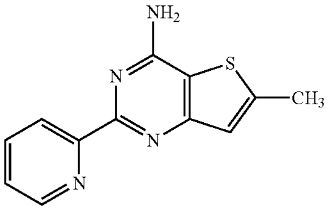 [SMILES: Cc1cc2nc(-c3ccccn3)nc(N)c2s1] | C | A | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 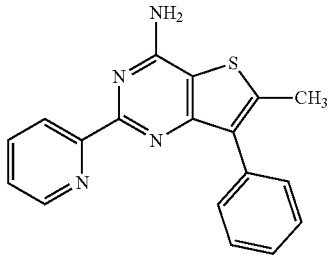 | | | | B | A | A | |
| 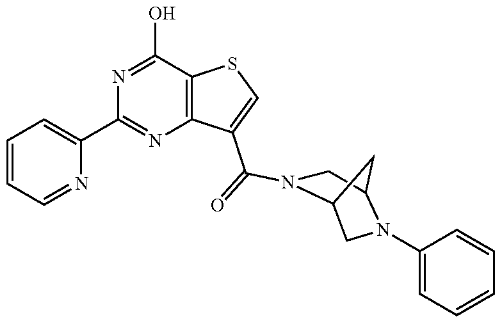 [SMILES: O=C(c1csc2c(O)nc(-c3ccccn3)nc12)N1CC2CC1CN2c1ccccc1] | C | B | B | D | D | D | |
| 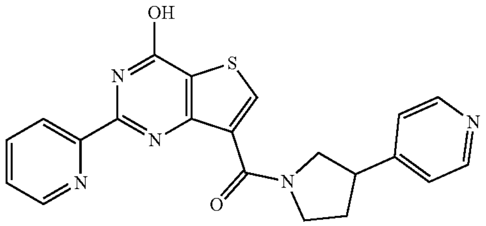 [SMILES: O=C(c1csc2c(O)nc(-c3ccccn3)nc12)N1CCC(c2ccncc2)C1] | C | C | C | C | C | C | |
| 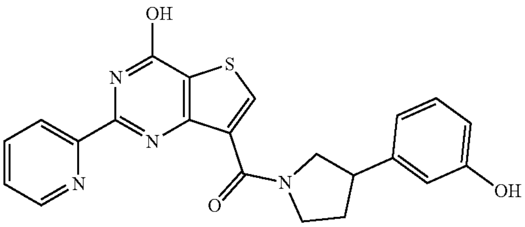 [SMILES: O=C(c1csc2c(O)nc(-c3ccccn3)nc12)N1CCC(c2cccc(O)c2)C1] | D | C | C | D | D | D | |
| 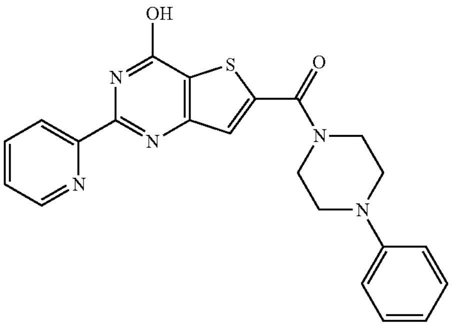 [SMILES: O=C(c1cc2nc(-c3ccccn3)nc(O)c2s1)N1CCN(c2ccccc2)CC1] | C | C | C | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 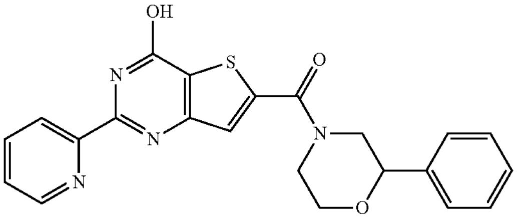 [SMILES: O=C(c1cc2nc(-c3ccccn3)nc(O)c2s1)N1CCOC(c2ccccc2)C1] | | | | C | C | D | |
| 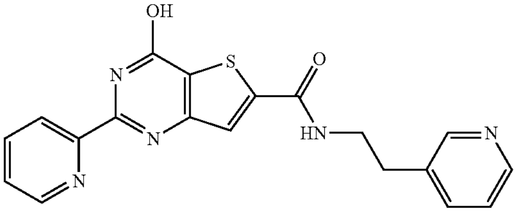 [SMILES: O=C(NCCc1cccnc1)c1cc2nc(-c3ccccn3)nc(O)c2s1] | | | | B | C | C | |
| 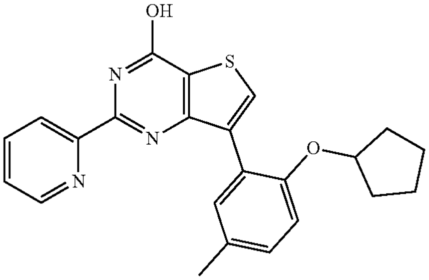 [SMILES: Cc1ccc(OC2CCCC2)c(-c2csc3c(O)nc(-c4ccccn4)nc23)c1] | | | | C | C | C | |
| 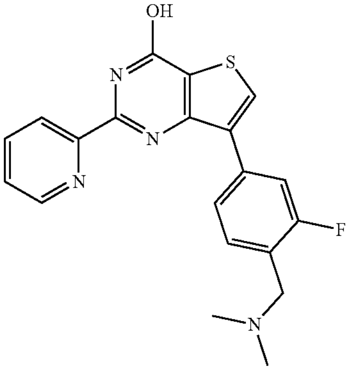 [SMILES: CN(C)Cc1ccc(-c2csc3c(O)nc(-c4ccccn4)nc23)cc1F] | D | B | C | D | D | D | |
| 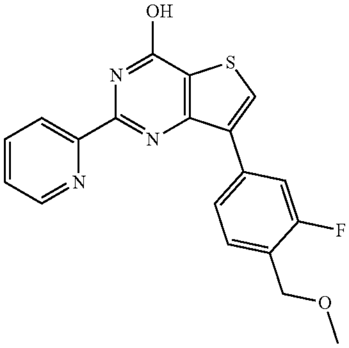 [SMILES: COCc1ccc(-c2csc3c(O)nc(-c4ccccn4)nc23)cc1F] | C | C | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 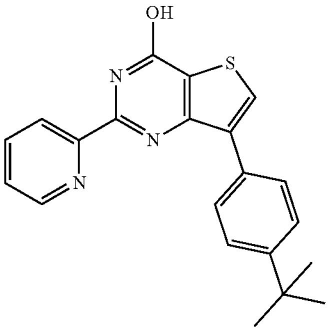 [SMILES: CC(C)(C)c1ccc(-c2csc3c(O)nc(-c4ccccn4)nc23)cc1] | | | | C | C | C | |
| 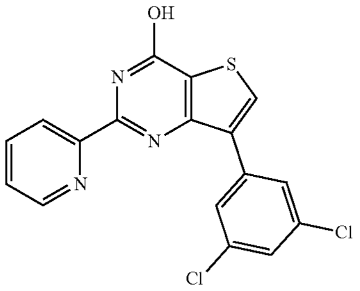 [SMILES: Oc1nc(-c2ccccn2)nc2c(-c3cc(Cl)cc(Cl)c3)csc12] | B | B | A | B | A | B | |
| 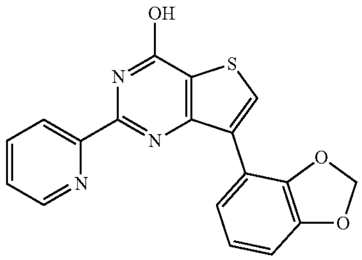 [SMILES: Oc1nc(-c2ccccn2)nc2c(-c3cccc4c3OCO4)csc12] | B | B | B | C | B | C | |
| 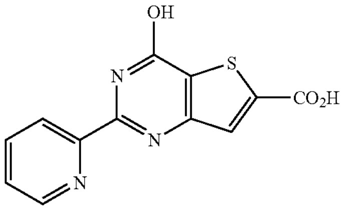 [SMILES: O=C(O)c1cc2nc(-c3ccccn3)nc(O)c2s1] | C | C | C | C | C | C | |
| 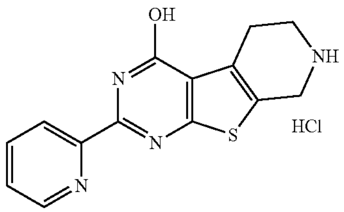 [SMILES: Oc1nc(-c2ccccn2)nc2sc3c(c12)CCNC3 ; Cl] | D | B | C | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 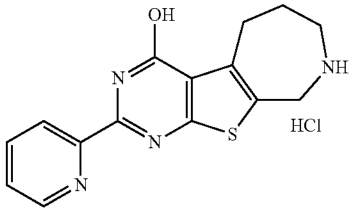 [SMILES: Oc1nc(-c2ccccn2)nc2sc3c(c12)CCCNC3 ; Cl] | C | C | B | B | B | B | |
| 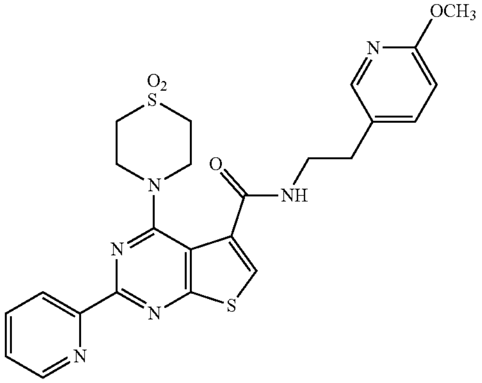 [SMILES: COc1ccc(CCNC(=O)c2csc3nc(-c4ccccn4)nc(N4CCS(=O)(=O)CC4)c23)cn1] | | | | B | B | B | |
| 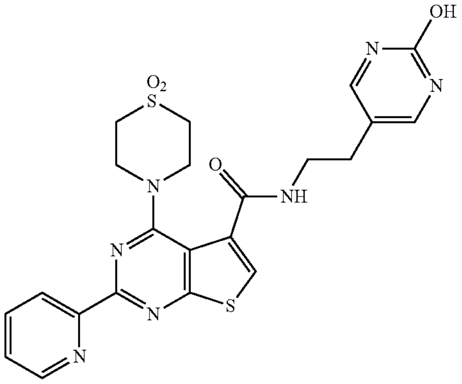 [SMILES: O=C(NCCc1cnc(O)nc1)c1csc2nc(-c3ccccn3)nc(N3CCS(=O)(=O)CC3)c12] | | | | B | A | B | |
| 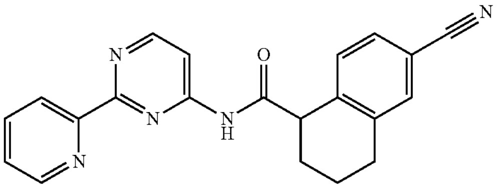 [SMILES: N#Cc1ccc2c(c1)CCCC2C(=O)Nc1ccnc(-c2ccccn2)n1] | | | | C | C | C | |
| 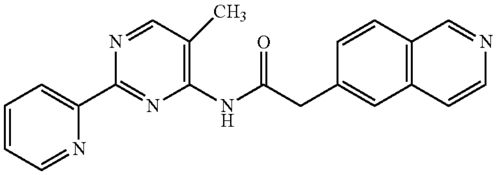 [SMILES: Cc1cnc(-c2ccccn2)nc1NC(=O)Cc1ccc2cnccc2c1] | C | B | C | C | C | C | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 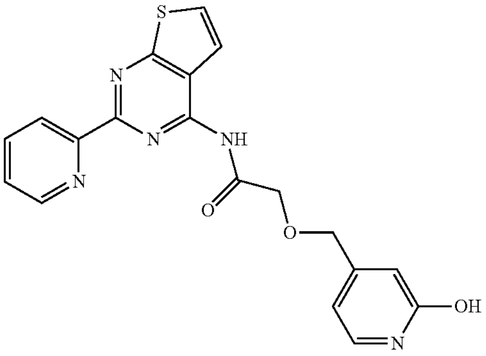 [SMILES: O=C(COCc1ccnc(O)c1)Nc1nc(-c2ccccn2)nc2sccc12] | B | B | B | C | C | C | |
| 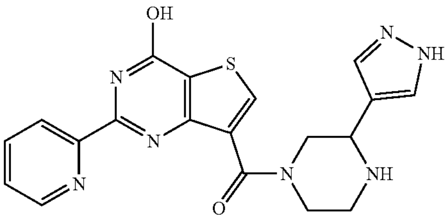 [SMILES: O=C(c1csc2c(O)nc(-c3ccccn3)nc12)N1CCNC(c2cn[nH]c2)C1] | B | B | B | C | C | D | |
| 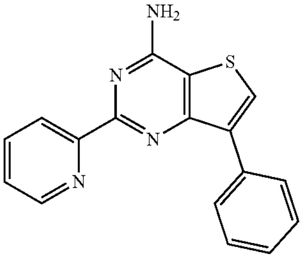 [SMILES: Nc1nc(-c2ccccn2)nc2c(-c3ccccc3)csc12] | B | A | B | B | C | B | |
| 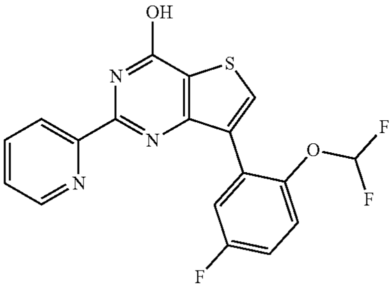 [SMILES: Oc1nc(-c2ccccn2)nc2c(-c3cc(F)ccc3OC(F)F)csc12] | C | B | A | B | B | C | |
| 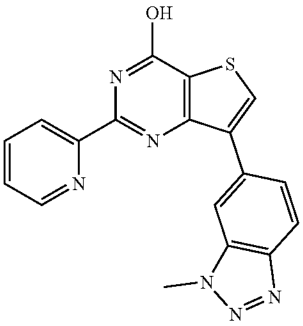 [SMILES: Cn1nnc2ccc(-c3csc4c(O)nc(-c5ccccn5)nc34)cc21] | C | A | D | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 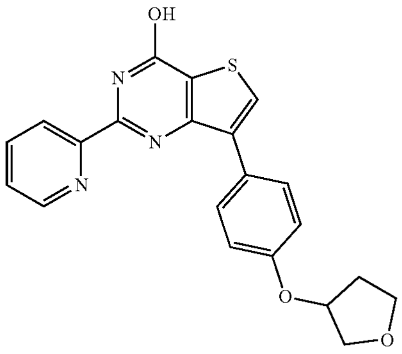 [SMILES: Oc1nc(-c2ccccn2)nc2c(-c3ccc(OC4CCOC4)cc3)csc12] | | | | B | A | B | |
| 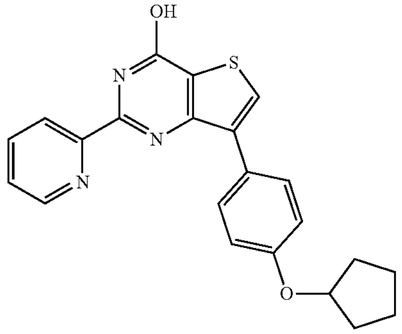 [SMILES: Oc1nc(-c2ccccn2)nc2c(-c3ccc(OC4CCCC4)cc3)csc12] | | | | B | B | B | |
| 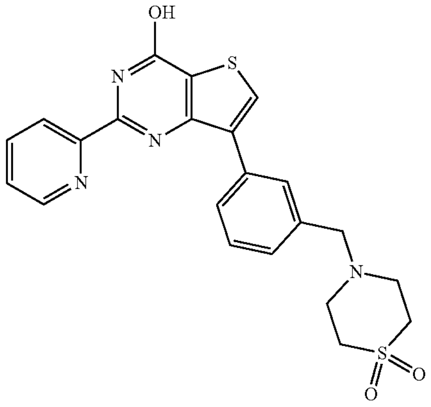 [SMILES: O=S1(=O)CCN(Cc2cccc(-c3csc4c(O)nc(-c5ccccn5)nc34)c2)CC1] | C | B | C | C | C | C | |
| 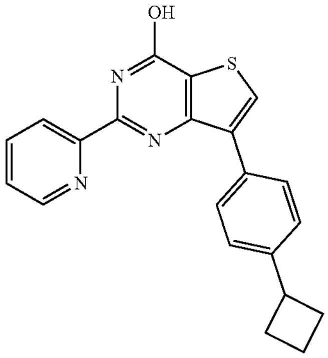 [SMILES: Oc1nc(-c2ccccn2)nc2c(-c3ccc(C4CCC4)cc3)csc12] | | | | C | C | C | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 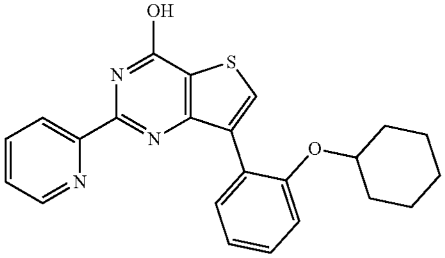 [SMILES: Oc1nc(-c2ccccn2)nc2c(-c3ccccc3OC3CCCCC3)csc12] | | | | C | C | C | |
| 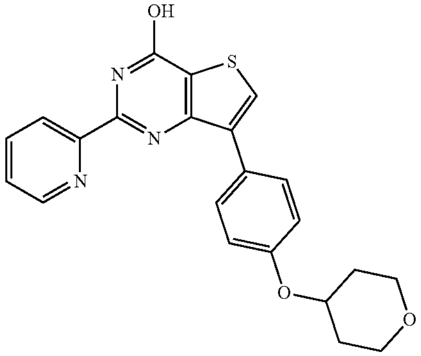 [SMILES: Oc1nc(-c2ccccn2)nc2c(-c3ccc(OC4CCOCC4)cc3)csc12] | | | | B | B | B | |
| 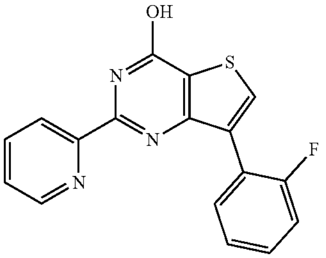 [SMILES: Oc1nc(-c2ccccn2)nc2c(-c3ccccc3F)csc12] | C | B | C | C | C | C | |
| 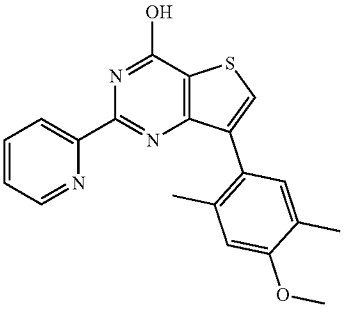 [SMILES: COc1cc(C)c(-c2csc3c(O)nc(-c4ccccn4)nc23)cc1C] | | | | B | A | A | |
| 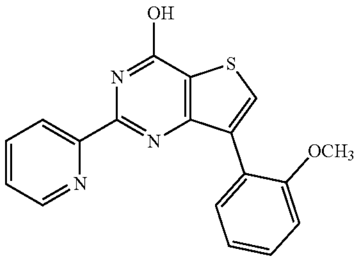 [SMILES: COc1ccccc1-c1csc2c(O)nc(-c3ccccn3)nc12] | C | B | B | B | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 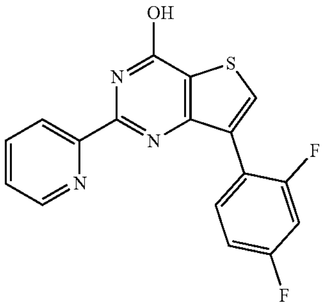 [SMILES: Oc1nc(-c2ccccn2)nc2c(-c3ccc(F)cc3F)csc12] | C | B | B | C | C | C | |
| 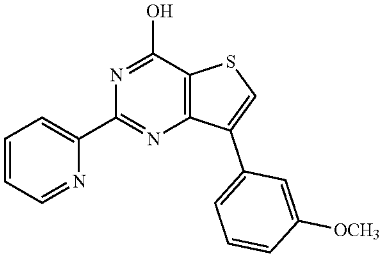 [SMILES: COc1cccc(-c2csc3c(O)nc(-c4ccccn4)nc23)c1] | D | B | C | B | A | A | |
| 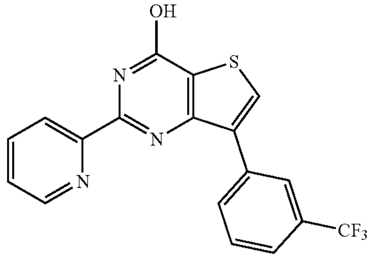 [SMILES: Oc1nc(-c2ccccn2)nc2c(-c3cccc(C(F)(F)F)c3)csc12] | C | B | B | B | B | C | |
| 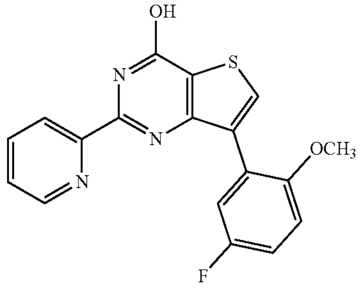 [SMILES: COc1ccc(F)cc1-c1csc2c(O)nc(-c3ccccn3)nc12] | C | B | B | C | B | B | |
| 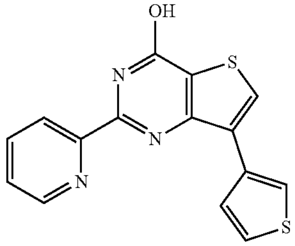 [SMILES: Oc1nc(-c2ccccn2)nc2c(-c3ccsc3)csc12] | C | C | A | B | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 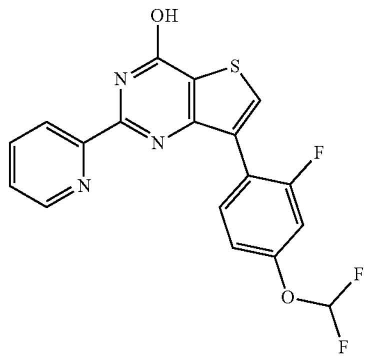 | C | B | C | C | C | C | |
| 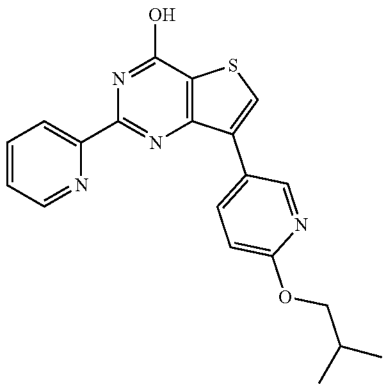 [SMILES: CC(C)COc1ccc(-c2csc3c(O)nc(-c4ccccn4)nc23)cn1] | C | C | C | C | C | C | |
| 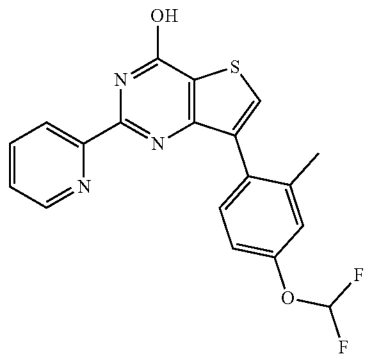 [SMILES: Cc1cc(OC(F)F)ccc1-c1csc2c(O)nc(-c3ccccn3)nc12] | | | | B | B | B | |
| 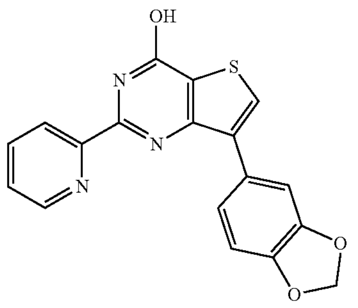 [SMILES: Oc1nc(-c2ccccn2)nc2c(-c3ccc4c(c3)OCO4)csc12] | C | B | C | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 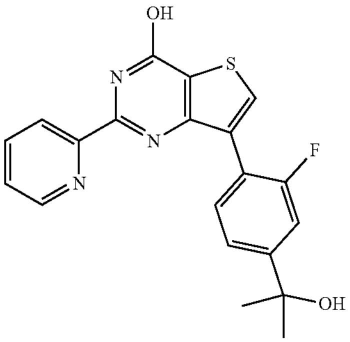 [SMILES: CC(C)(O)c1ccc(-c2csc3c(O)nc(-c4ccccn4)nc23)c(F)c1] | C | C | C | C | C | C | |
| 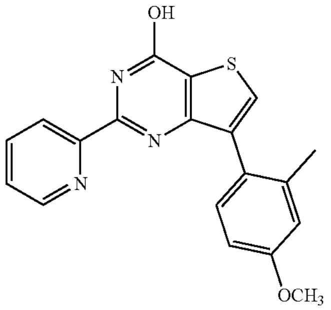 [SMILES: COc1ccc(-c2csc3c(O)nc(-c4ccccn4)nc23)c(C)c1] | C | C | B | C | C | C | |
| 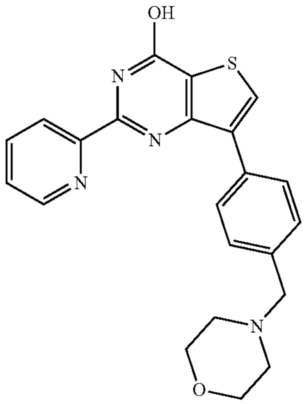 [SMILES: Oc1nc(-c2ccccn2)nc2c(-c3ccc(CN4CCOCC4)cc3)csc12] | | | | B | B | B | |
| 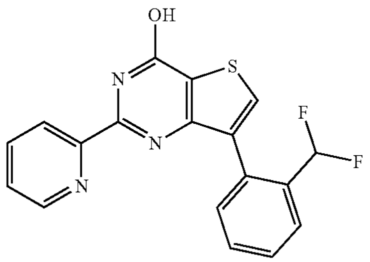 [SMILES: Oc1nc(-c2ccccn2)nc2c(-c3ccccc3C(F)F)csc12] | C | B | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 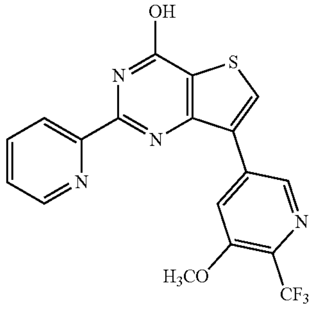 [SMILES: COc1cc(-c2csc3c(O)nc(-c4ccccn4)nc23)cnc1C(F)(F)F] | C | C | C | C | C | C | |
| 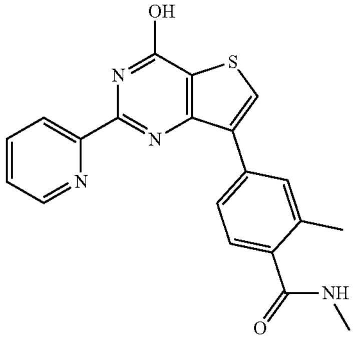 [SMILES: CNC(=O)c1ccc(-c2csc3c(O)nc(-c4ccccn4)nc23)cc1C] | B | B | B | B | B | B | |
| 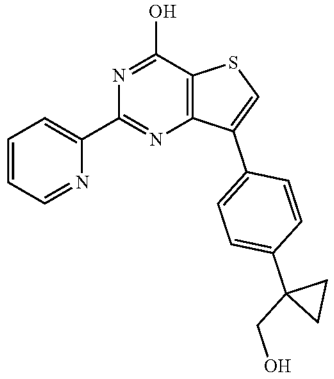 [SMILES: OCC1(c2ccc(-c3csc4c(O)nc(-c5ccccn5)nc34)cc2)CC1] | D | B | D | C | C | C | |
| 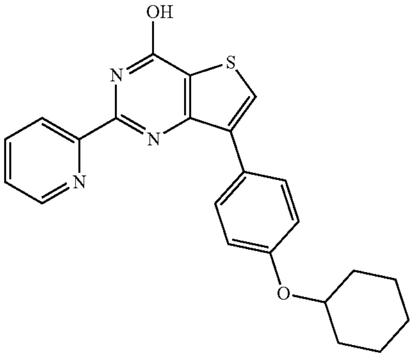 [SMILES: Oc1nc(-c2ccccn2)nc2c(-c3ccc(OC4CCCCC4)cc3)csc12] | | | | B | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 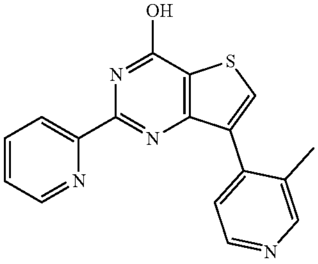 [SMILES: Cc1cnccc1-c1csc2c(O)nc(-c3ccccn3)nc12] | C | B | D | C | C | C | |
| 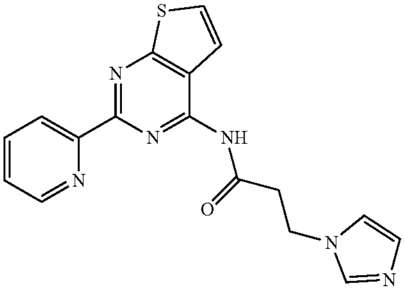 [SMILES: O=C(CCn1ccnc1)Nc1nc(-c2ccccn2)nc2sccc12] | D | B | C | C | C | D | |
| 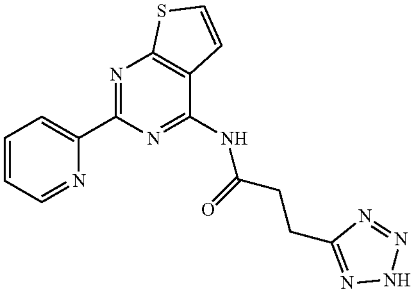 [SMILES: O=C(CCc1nn[nH]n1)Nc1nc(-c2ccccn2)nc2sccc12] | C | B | C | C | C | C | |
| 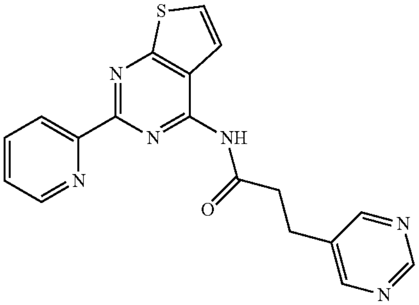 [SMILES: O=C(CCc1cncnc1)Nc1nc(-c2ccccn2)nc2sccc12] | C | B | C | C | D | C | |
| 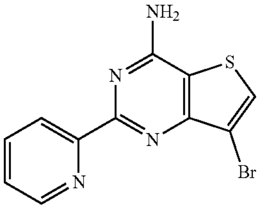 [SMILES: Nc1nc(-c2ccccn2)nc2c(Br)csc12] | | | | B | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 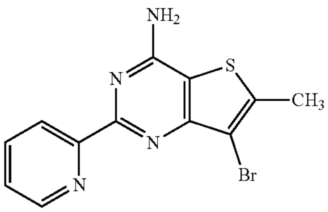 [SMILES: Cc1sc2c(N)nc(-c3ccccn3)nc2c1Br] | | | | B | B | A | |
| 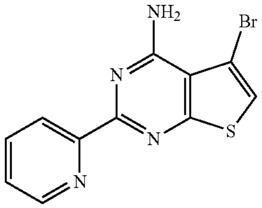 [SMILES: Nc1nc(-c2ccccn2)nc2scc(Br)c12] | | | | B | B | C | |
| 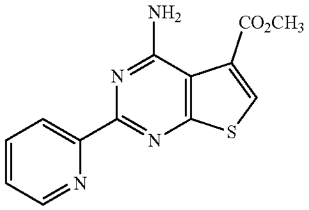 [SMILES: COC(=O)c1csc2nc(-c3ccccn3)nc(N)c12] | | | | B | B | B | |
| 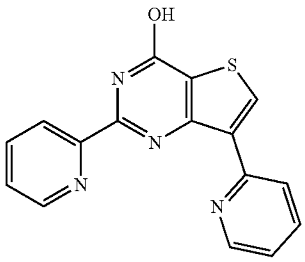 [SMILES: Oc1nc(-c2ccccn2)nc2c(-c3ccccn3)csc12] | B | B | C | A | C | B | |
| 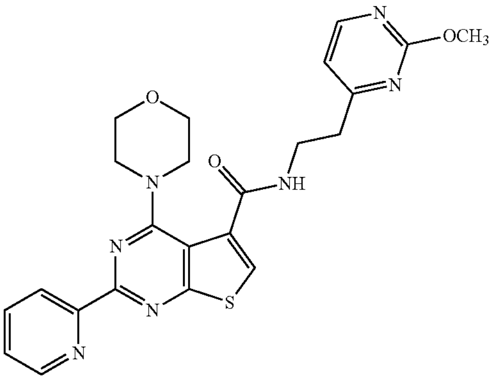 [SMILES: COc1nccc(CCNC(=O)c2csc3nc(-c4ccccn4)nc(N4CCOCC4)c23)n1] | | | | A | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 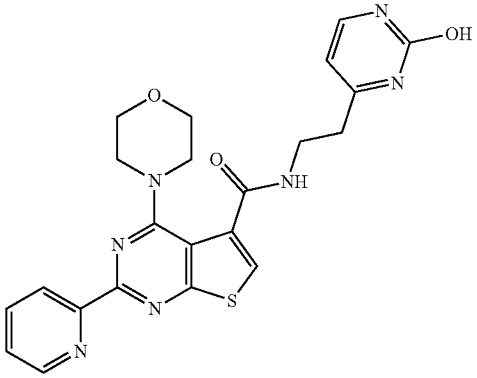 | | | | A | C | C | |
| 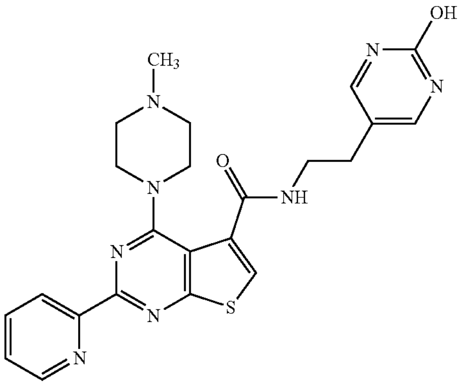 [SMILES: CN1CCN(c2nc(-c3ccccn3)nc3scc(C(=O)NCCc4cnc(O)nc4)c23)CC1] | C | A | A | B | C | C | E |
| 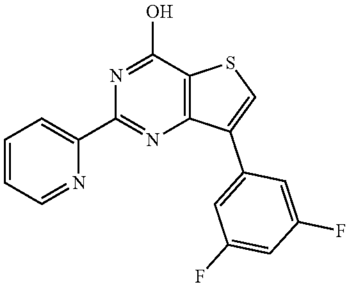 [SMILES: Oc1nc(-c2ccccn2)nc2c(-c3cc(F)cc(F)c3)csc12] | C | C | B | C | C | C | E |
| 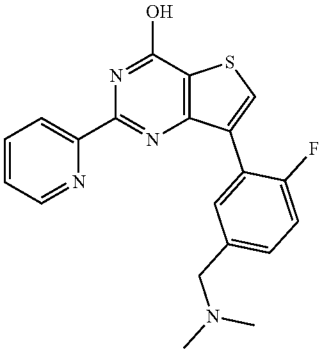 [SMILES: CN(C)Cc1ccc(F)c(-c2csc3c(O)nc(-c4ccccn4)nc23)c1] | C | B | C | B | C | C | F |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 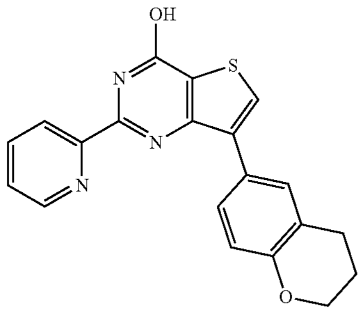 [SMILES: Oc1nc(-c2ccccn2)nc2c(-c3ccc4c(c3)CCCO4)csc12] | C | B | B | B | B | C | |
| 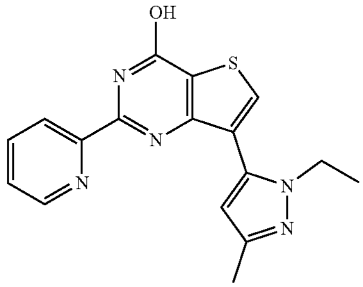 [SMILES: CCn1nc(C)cc1-c1csc2c(O)nc(-c3ccccn3)nc12] | | | | C | C | C | F |
| 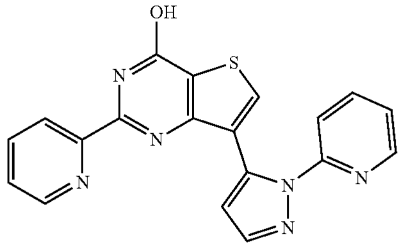 [SMILES: Oc1nc(-c2ccccn2)nc2c(-c3ccnn3-c3ccccn3)csc12] | | | | A | B | B | |
| 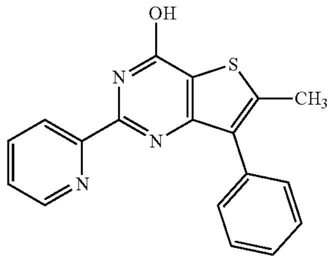 [SMILES: Cc1sc2c(O)nc(-c3ccccn3)nc2c1-c1ccccc1] | C | B | A | C | B | B | |
| 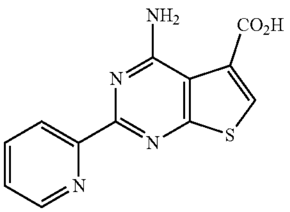 [SMILES: Nc1nc(-c2ccccn2)nc2scc(C(=O)O)c12] | | | | B | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 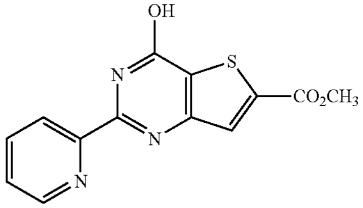 [SMILES: COC(=O)c1cc2nc(-c3ccccn3)nc(O)c2s1] | | | | C | C | C | E |
| 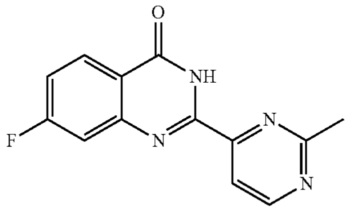 [SMILES: Cc1nccc(-c2nc3cc(F)ccc3c(=O)[nH]2)n1] | | | | D | | | |
| 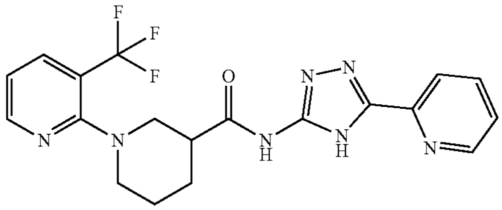 [SMILES: O=C(Nc1nnc(-c2ccccn2)[nH]1)C1CCCN(c2ncccc2C(F)(F)F)C1] | | | | C | | | |
| 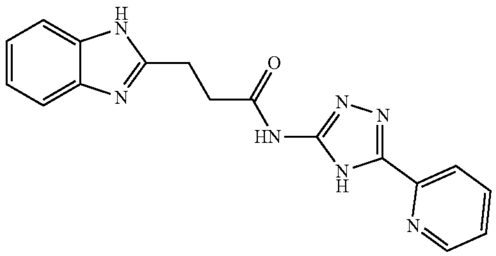 [SMILES: O=C(CCc1nc2ccccc2[nH]1)Nc1nnc(-c2ccccn2)[nH]1] | | | | C | | | |
| 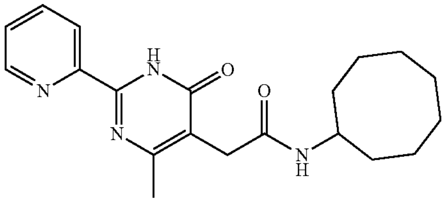 [SMILES: Cc1nc(-c2ccccn2)[nH]c(=O)c1CC(=O)NC1CCCCCCC1] | | | | C | | | |
| 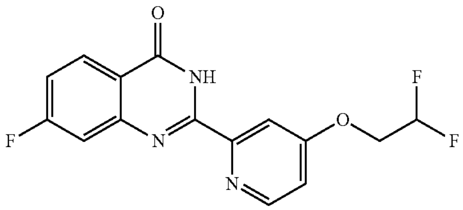 [SMILES: O=c1[nH]c(-c2cc(OCC(F)F)ccn2)nc2cc(F)ccc12] | | | | C | | | |
| 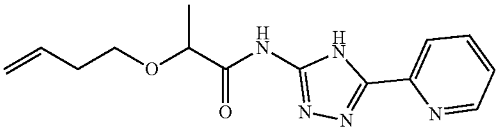 [SMILES: C=CCCOC(C)C(=O)Nc1nnc(-c2ccccn2)[nH]1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 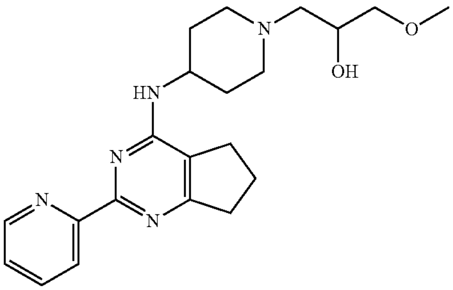 [SMILES: COCC(O)CN1CCC(Nc2nc(-c3ccccn3)nc3c2CCC3)CC1] | | | | B | | | |
| 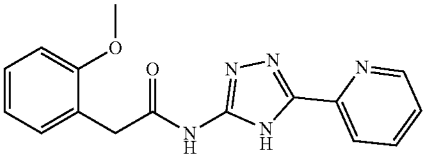 [SMILES: COc1ccccc1CC(=O)Nc1nnc(-c2ccccn2)[nH]1] | | | | B | | | |
| 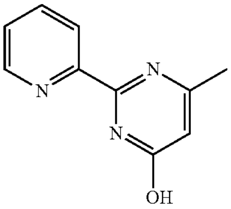 | | | | B | | | |
| 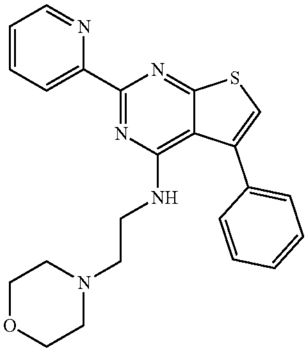 [SMILES: c1ccc(-c2csc3nc(-c4ccccn4)nc(NCCN4CCOCC4)c23)cc1] | | | | B | | | |
| 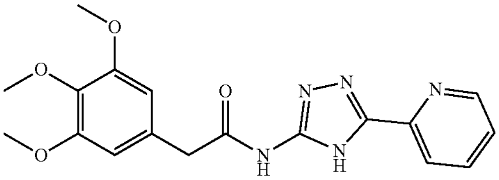 [SMILES: COc1cc(CC(=O)Nc2nnc(-c3ccccn3)[nH]2)cc(OC)c1OC] | | | | B | | | |
| 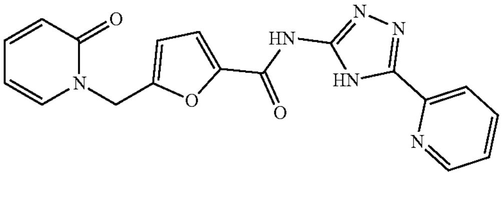 [SMILES: O=C(Nc1nnc(-c2ccccn2)[nH]1)c1ccc(Cn2ccccc2=O)o1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 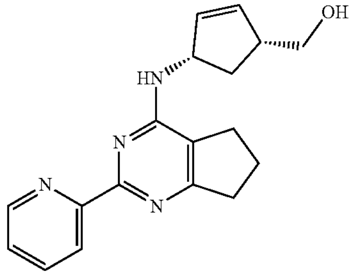 [SMILES: OC[C@H]1C=C[C@@H](Nc2nc(-c3ccccn3)nc3c2CCC3)C1] | | | | B | | | |
| 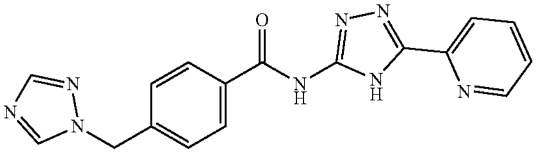 [SMILES: O=C(Nc1nnc(-c2ccccn2)[nH]1)c1ccc(Cn2cncn2)cc1] | | | | B | | | |
| 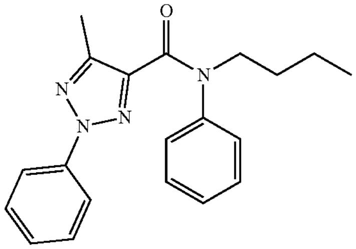 [SMILES: CCCCN(C(=O)c1nn(-c2ccccc2)nc1C)c1ccccc1] | | | | B | | | |
| 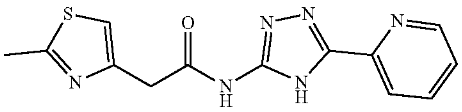 [SMILES: Cc1nc(CC(=O)Nc2nnc(-c3ccccn3)[nH]2)cs1] | | | | B | | | |
| 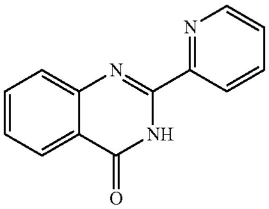 [SMILES: O=c1[nH]c(-c2ccccn2)nc2ccccc12] | | | | B | | | |
| 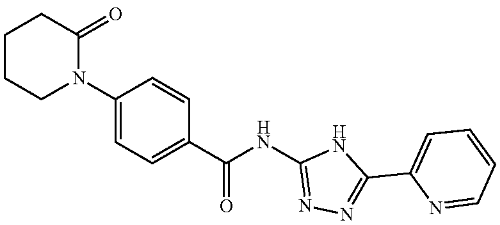 [SMILES: O=C(Nc1nnc(-c2ccccn2)[nH]1)c1ccc(N2CCCCC2=O)cc1] | | | | B | | | |
| 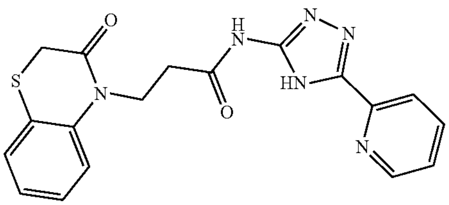 [SMILES: O=C(CCN1C(=O)CSc2ccccc21)Nc1nnc(-c2ccccn2)[nH]1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 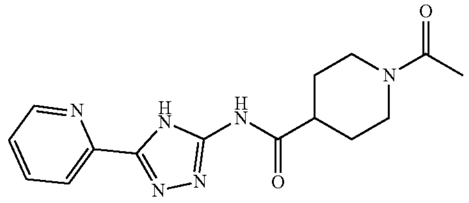 [SMILES: CC(=O)N1CCC(C(=O)Nc2nnc(-c3ccccn3)[nH]2)CC1] | | | | B | | | |
| 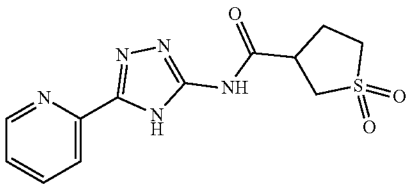 [SMILES: O=C(Nc1nnc(-c2ccccn2)[nH]1)C1CCS(=O)(=O)C1] | | | | B | | | |
| 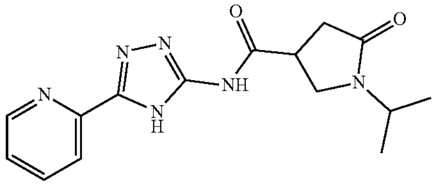 [SMILES: CC(C)N1CC(C(=O)Nc2nnc(-c3ccccn3)[nH]2)CC1=O] | | | | B | | | |
| 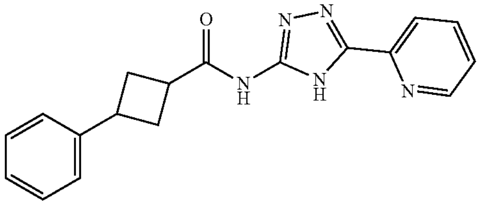 [SMILES: O=C(Nc1nnc(-c2ccccn2)[nH]1)C1CC(c2ccccc2)C1] | | | | B | | | |
| 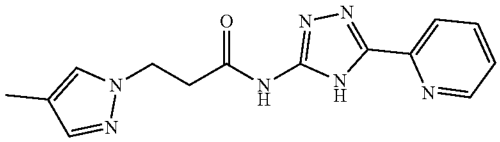 [SMILES: Cc1cnn(CCC(=O)Nc2nnc(-c3ccccn3)[nH]2)c1] | | | | B | | | |
| 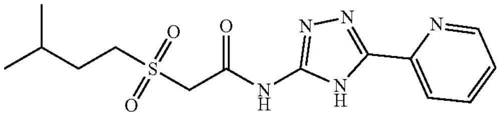 [SMILES: CC(C)CCS(=O)(=O)CC(=O)Nc1nnc(-c2ccccn2)[nH]1] | | | | B | | | |
| 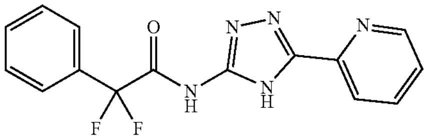 [SMILES: O=C(Nc1nnc(-c2ccccn2)[nH]1)C(F)(F)c1ccccc1] | | | | B | | | |
| 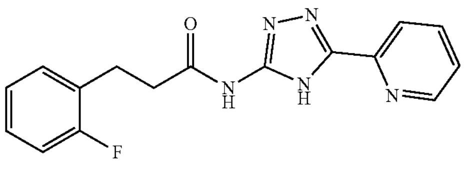 [SMILES: O=C(CCc1ccccc1F)Nc1nnc(-c2ccccn2)[nH]1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 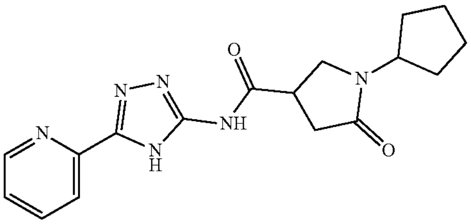 [SMILES: O=C(Nc1nnc(-c2ccccn2)[nH]1)C1CC(=O)N(C2CCCC2)C1] | | | | B | | | |
| 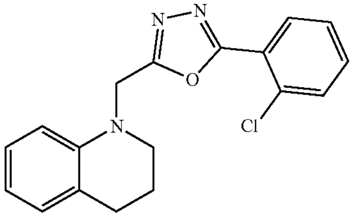 [SMILES: Clc1ccccc1-c1nnc(CN2CCCc3ccccc32)o1] | | | | B | | | |
| 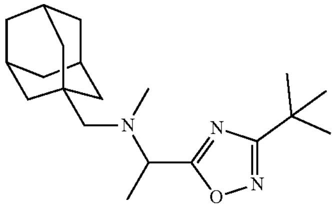 [SMILES: CC(c1nc(C(C)(C)C)no1)N(C)CC12CC3CC(CC(C3)C1)C2] | | | | B | | | |
| 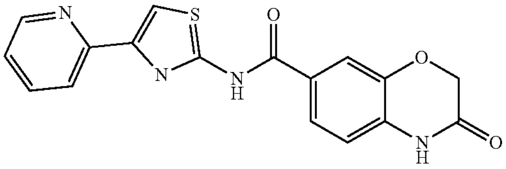 | | | | B | | | |
| 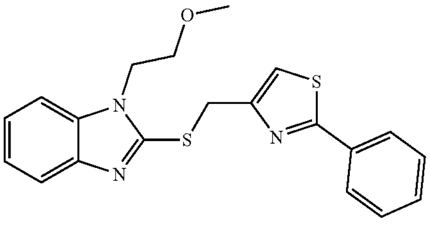 [SMILES: COCCn1c(SCc2csc(-c3ccccc3)n2)nc2ccccc21] | | | | B | | | |
| 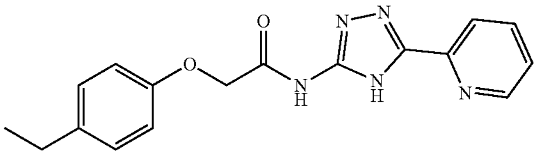 [SMILES: CCc1ccc(OCC(=O)Nc2nnc(-c3ccccn3)[nH]2)cc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 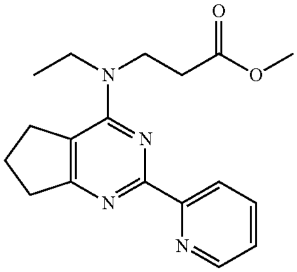 [SMILES: CCN(CCC(=O)OC)c1nc(-c2ccccn2)nc2c1CCC2] | | | | B | | | |
| 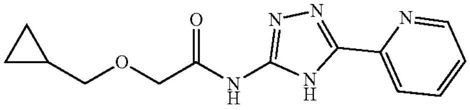 [SMILES: O=C(COCC1CC1)Nc1nnc(-c2ccccn2)[nH]1] | | | | B | | | |
| 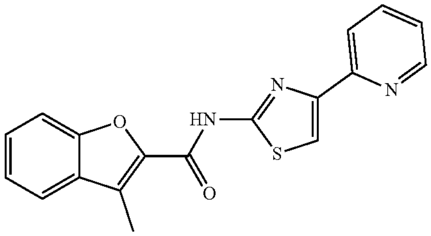 [SMILES: Cc1c(C(=O)Nc2nc(-c3ccccn3)cs2)oc2ccccc12] | | | | B | | | |
| 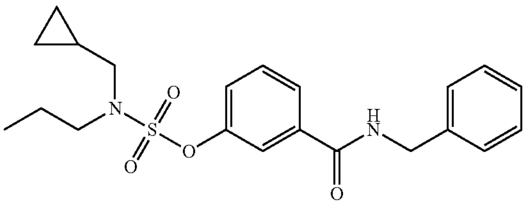 [SMILES: CCCN(CC1CC1)S(=O)(=O)Oc1cccc(C(=O)NCc2ccccc2)c1] | | | | B | | | |
| 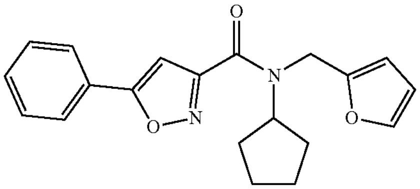 [SMILES: O=C(c1cc(-c2ccccc2)on1)N(Cc1ccco1)C1CCCC1] | | | | B | | | |
| 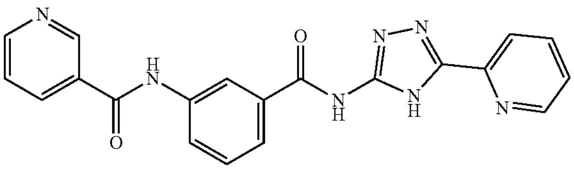 [SMILES: O=C(Nc1cccc(C(=O)Nc2nnc(-c3ccccn3)[nH]2)c1)c1cccnc1] | | | | B | | | |
| 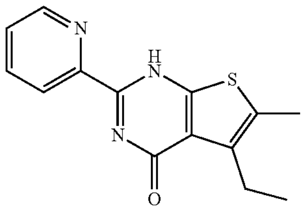 [SMILES: CCc1c(C)sc2[nH]c(-c3ccccn3)nc(=O)c12] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 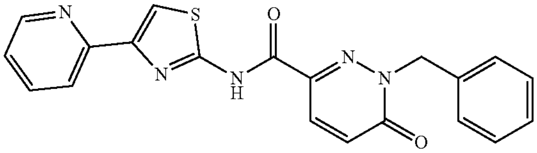 [SMILES: O=C(Nc1nc(-c2ccccn2)cs1)c1ccc(=O)n(Cc2ccccc2)n1] | | | | B | | | |
| 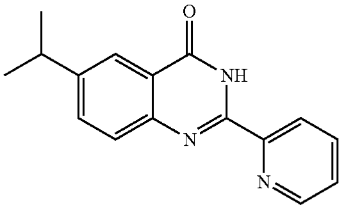 [SMILES: CC(C)c1ccc2nc(-c3ccccn3)[nH]c(=O)c2c1] | | | | B | | | |
| 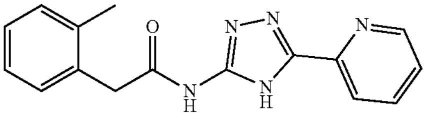 [SMILES: Cc1ccccc1CC(=O)Nc1nnc(-c2ccccn2)[nH]1] | | | | B | | | |
| 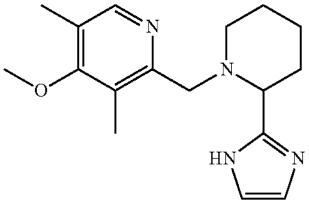 [SMILES: COc1c(C)cnc(CN2CCCCC2c2ncc[nH]2)c1C] | | | | B | | | |
| 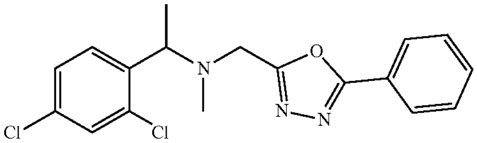 [SMILES: CC(c1ccc(Cl)cc1Cl)N(C)Cc1nnc(-c2ccccc2)o1] | | | | B | | | |
| 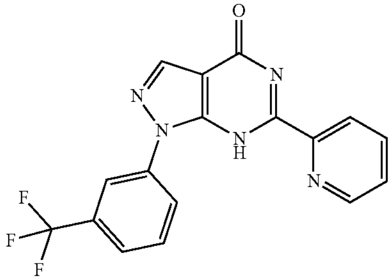 [SMILES: O=c1nc(-c2ccccn2)[nH]c2c1cnn2-c1cccc(C(F)(F)F)c1] | | | | B | | | |
| 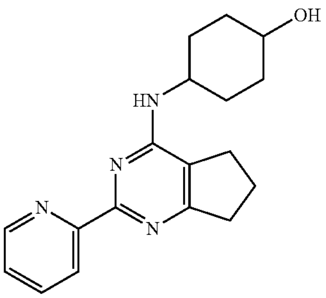 [SMILES: OC1CCC(Nc2nc(-c3ccccn3)nc3c2CCC3)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 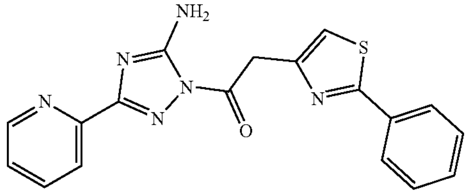 [SMILES: Nc1nc(-c2ccccn2)nn1C(=O)Cc1csc(-c2ccccc2)n1] | | | | B | | | |
| 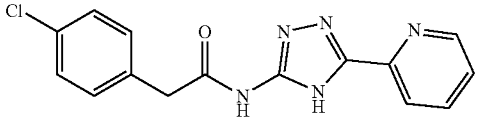 [SMILES: O=C(Cc1ccc(Cl)cc1)Nc1nnc(-c2ccccn2)[nH]1] | | | | B | | | |
| 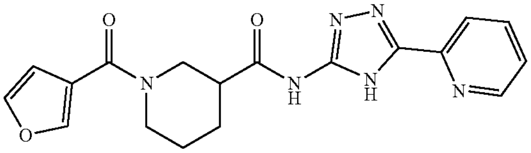 [SMILES: O=C(Nc1nnc(-c2ccccn2)[nH]1)C1CCCN(C(=O)c2ccoc2)C1] | | | | B | | | |
| 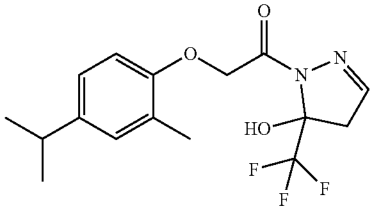 [SMILES: Cc1cc(C(C)C)ccc1OCC(=O)N1N=CCC1(O)C(F)(F)F] | | | | B | | | |
| 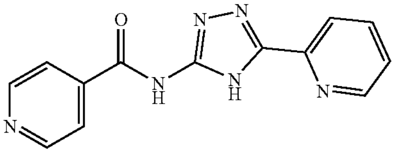 [SMILES: O=C(Nc1nnc(-c2ccccn2)[nH]1)c1ccncc1] | | | | B | | | |
| 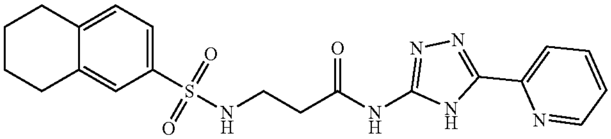 [SMILES: O=C(CCNS(=O)(=O)c1ccc2c(c1)CCCC2)Nc1nnc(-c2ccccn2)[nH]1] | | | | B | | | |
| 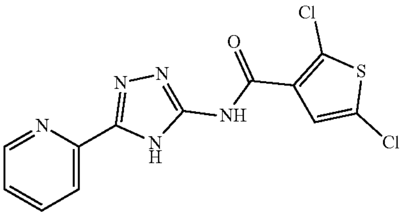 [SMILES: O=C(Nc1nnc(-c2ccccn2)[nH]1)c1cc(Cl)sc1Cl] | | | | B | | | |
| 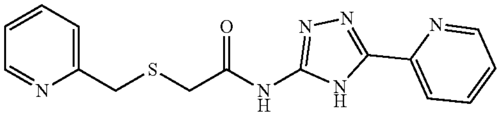 [SMILES: O=C(CSCc1ccccn1)Nc1nnc(-c2ccccn2)[nH]1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 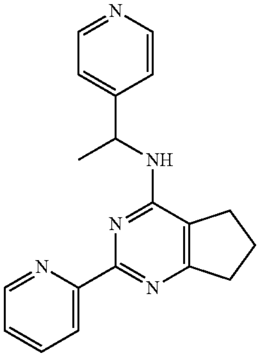 [SMILES: CC(Nc1nc(-c2ccccn2)nc2c1CCC2)c1ccncc1] | | | | B | | | |
| 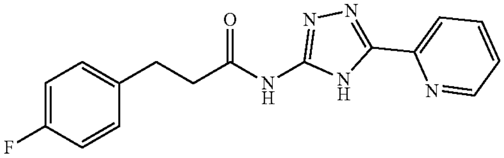 [SMILES: O=C(CCc1ccc(F)cc1)Nc1nnc(-c2ccccn2)[nH]1] | | | | B | | | |
| 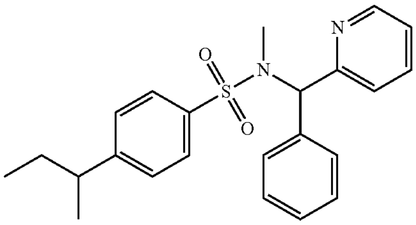 [SMILES: CCC(C)c1ccc(S(=O)(=O)N(C)C(c2ccccc2)c2ccccn2)cc1] | | | | B | | | |
| 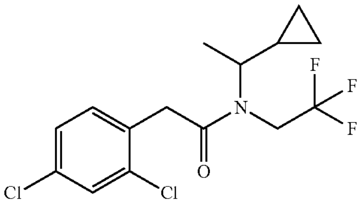 [SMILES: CC(C1CC1)N(CC(F)(F)F)C(=O)Cc1ccc(Cl)cc1Cl] | | | | B | | | |
| 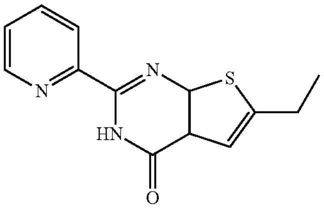 [SMILES: CCC1=CC2C(=O)NC(c3ccccn3)=NC2S1] | | | | B | | | |
| 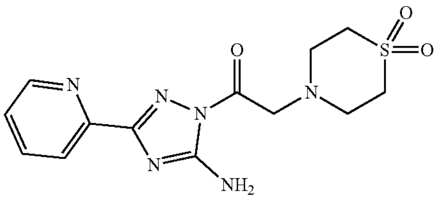 [SMILES: Nc1nc(-c2ccccn2)nn1C(=O)CN1CCS(=O)(=O)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 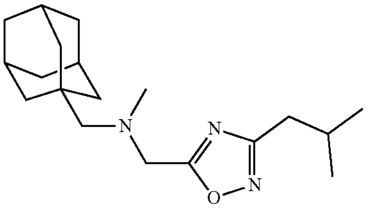 [SMILES: CC(C)Cc1noc(CN(C)CC23CC4CC(CC(C4)C2)C3)n1] | | | | B | | | |
| 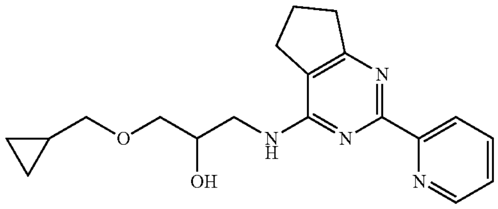 [SMILES: OC(CNc1nc(-c2ccccn2)nc2c1CCC2)COCC1CC1] | | | | B | | | |
| 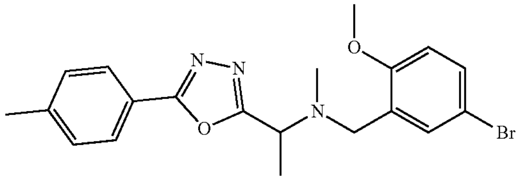 [SMILES: COc1ccc(Br)cc1CN(C)C(C)c1nnc(-c2ccc(C)cc2)o1] | | | | B | | | |
| 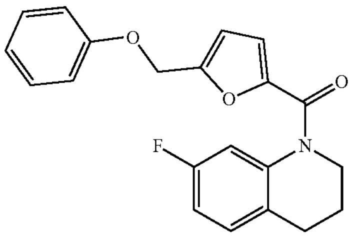 [SMILES: O=C(c1ccc(COc2ccccc2)o1)N1CCCc2ccc(F)cc21] | | | | B | | | |
| 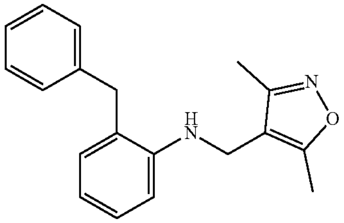 [SMILES: Cc1noc(C)c1CNc1ccccc1Cc1ccccc1] | | | | B | | | |
| 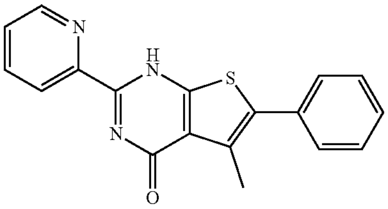 [SMILES: Cc1c(-c2ccccc2)sc2[nH]c(-c3ccccn3)nc(=O)c12] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 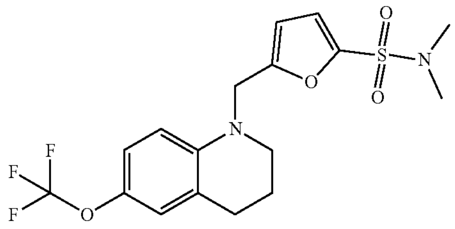 [SMILES: CN(C)S(=O)(=O)c1ccc(CN2CCCc3cc(OC(F)(F)F)ccc32)o1] | | | | B | | | |
| 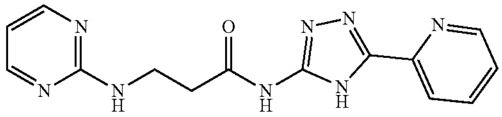 [SMILES: O=C(CCNc1ncccn1)Nc1nnc(-c2ccccn2)[nH]1] | | | | B | | | |
| 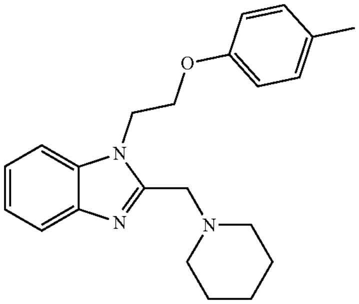 [SMILES: Cc1ccc(OCCn2c(CN3CCCCC3)nc3ccccc32)cc1] | | | | B | | | |
| 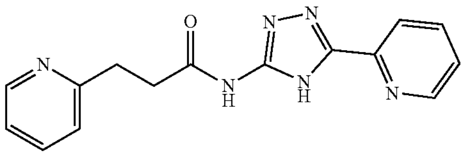 [SMILES: O=C(CCc1ccccn1)Nc1nnc(-c2ccccn2)[nH]1] | | | | B | | | |
| 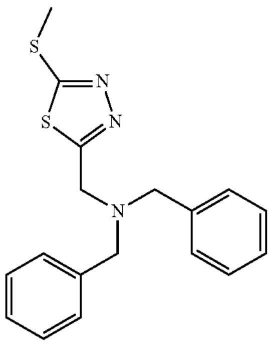 [SMILES: CSc1nnc(CN(Cc2ccccc2)Cc2ccccc2)s1] | | | | B | | | |
| 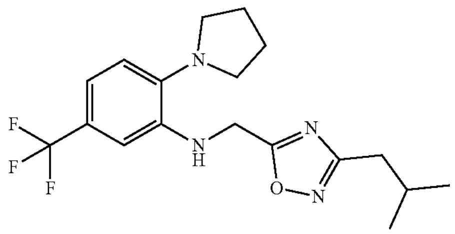 [SMILES: CC(C)Cc1noc(CNc2cc(C(F)(F)F)ccc2N2CCCC2)n1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 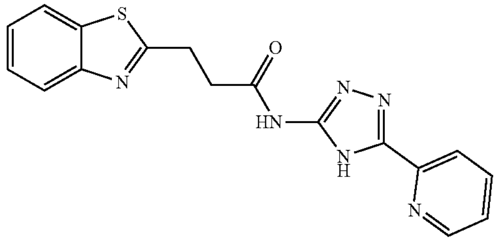 [SMILES: O=C(CCc1nc2ccccc2s1)Nc1nnc(-c2ccccn2)[nH]1] | | | | B | | | |
| 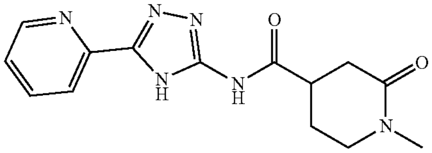 [SMILES: CN1CCC(C(=O)Nc2nnc(-c3ccccn3)[nH]2)CC1=O] | | | | B | | | |
| 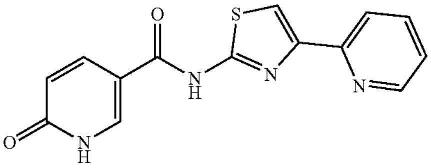 [SMILES: O=C(Nc1nc(-c2ccccn2)cs1)c1ccc(=O)[nH]c1] | | | | B | | | |
| 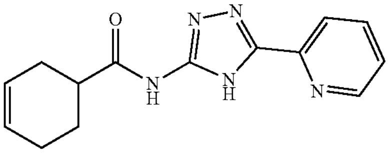 [SMILES: O=C(Nc1nnc(-c2ccccn2)[nH]1)C1CC=CCC1] | | | | B | | | |
| 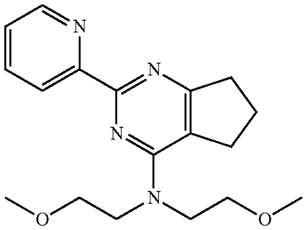 [SMILES: COCCN(CCOC)c1nc(-c2ccccn2)nc2c1CCC2] | | | | B | | | |
| 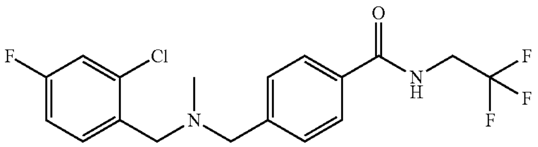 [SMILES: CN(Cc1ccc(C(=O)NCC(F)(F)F)cc1)Cc1ccc(F)cc1Cl] | | | | B | | | |
| 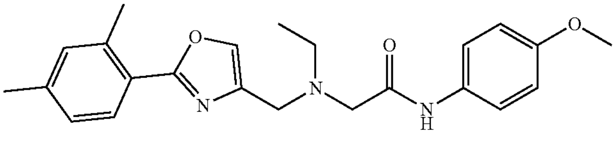 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 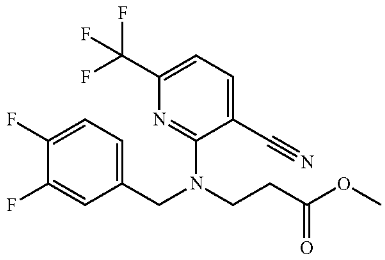 [SMILES: COC(=O)CCN(Cc1ccc(F)c(F)c1)c1nc(C(F)(F)F)ccc1C#N] | | | | B | | | |
| 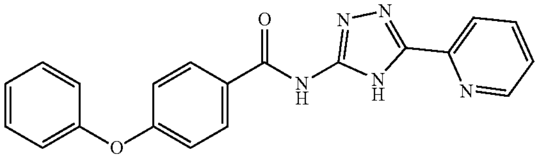 [SMILES: O=C(Nc1nnc(-c2ccccn2)[nH]1)c1ccc(Oc2ccccc2)cc1] | | | | B | | | |
| 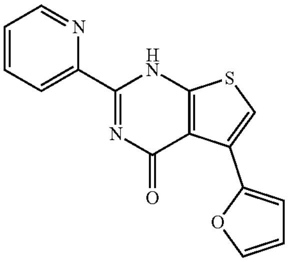 [SMILES: O=c1nc(-c2ccccn2)[nH]c2scc(-c3ccco3)c12] | | | | B | | | |
| 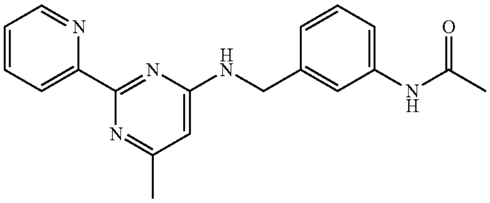 [SMILES: CC(=O)Nc1cccc(CNc2cc(C)nc(-c3ccccn3)n2)c1] | | | | B | | | |
| 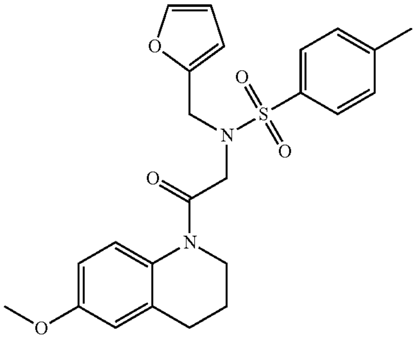 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 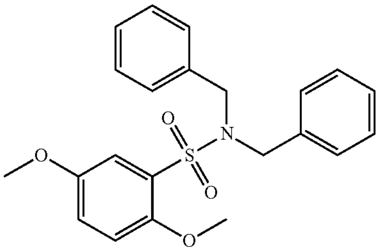 [SMILES: COc1ccc(OC)c(S(=O)(=O)N(Cc2ccccc2)Cc2ccccc2)c1] | | | | B | | | |
| 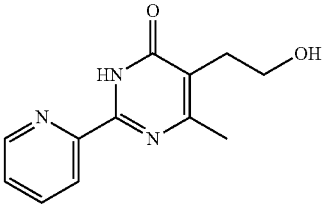 [SMILES: Cc1nc(-c2ccccn2)[nH]c(=O)c1CCO] | | | | B | | | |
| 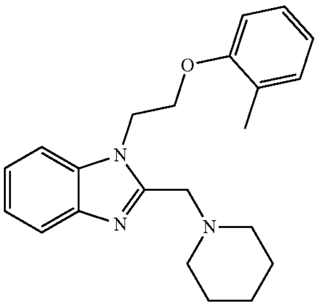 [SMILES: Cc1ccccc1OCCn1c(CN2CCCCC2)nc2ccccc21] | | | | B | | | |
| 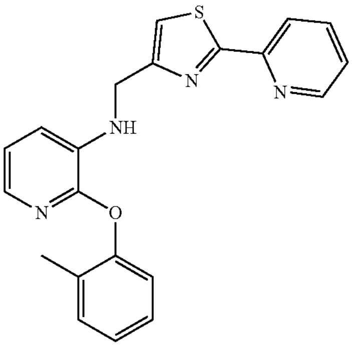 [SMILES: Cc1ccccc1Oc1ncccc1NCc1csc(-c2ccccn2)n1] | | | | B | | | |
| 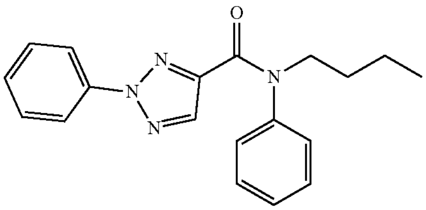 [SMILES: CCCCN(C(=O)c1cnn(-c2ccccc2)n1)c1ccccc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 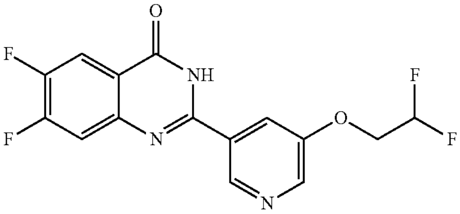 [SMILES: O=c1[nH]c(-c2cncc(OCC(F)F)c2)nc2cc(F)c(F)cc12] | | | | B | | | |
| 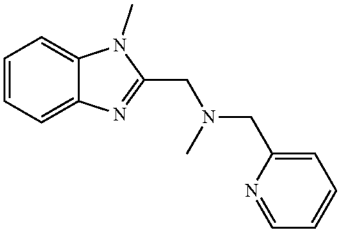 [SMILES: CN(Cc1ccccn1)Cc1nc2ccccc2n1C] | | | | B | | | |
| 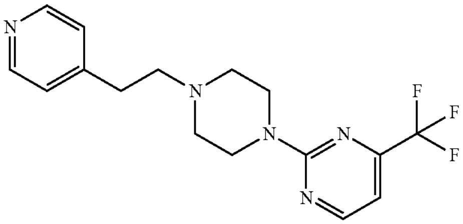 [SMILES: FC(F)(F)c1ccnc(N2CCN(CCc3ccncc3)CC2)n1] | | | | B | | | |
| 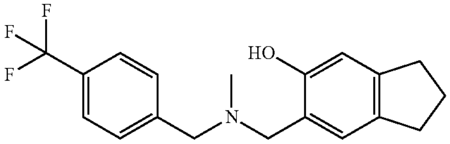 [SMILES: CN(Cc1ccc(C(F)(F)F)cc1)Cc1cc2c(cc1O)CCC2] | | | | B | | | |
| 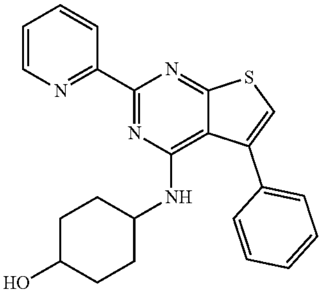 [SMILES: OC1CCC(Nc2nc(-c3ccccn3)nc3scc(-c4ccccc4)c23)CC1] | | | | B | | | |
| 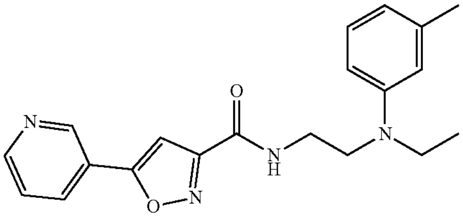 [SMILES: CCN(CCNC(=O)c1cc(-c2cccnc2)on1)c1cccc(C)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 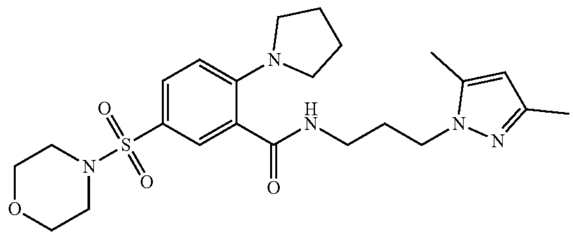 [SMILES: Cc1cc(C)n(CCCNC(=O)c2cc(S(=O)(=O)N3CCOCC3)ccc2N2CCCC2)n1] | | | | B | | | |
| 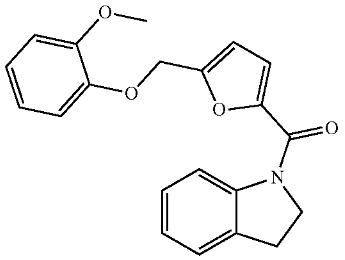 [SMILES: COc1ccccc1OCc1ccc(C(=O)N2CCc3ccccc32)o1] | | | | B | | | |
| 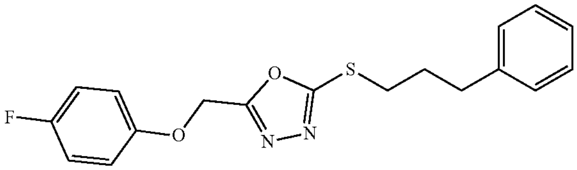 [SMILES: Fc1ccc(OCc2nnc(SCCCc3ccccc3)o2)cc1] | | | | B | | | |
| 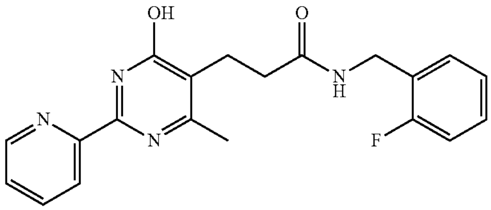 [SMILES: Cc1nc(-c2ccccn2)nc(O)c1CCC(=O)NCc1ccccc1F] | | | | B | | | |
| 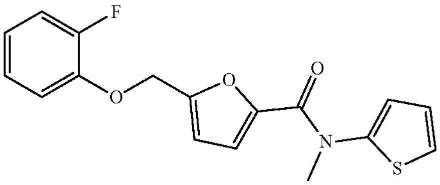 [SMILES: CN(C(=O)c1ccc(COc2ccccc2F)o1)c1cccs1] | | | | B | | | |
| 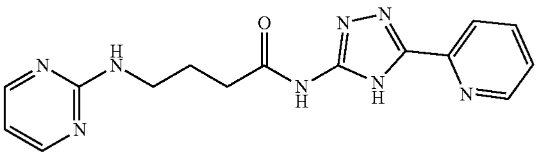 [SMILES: O=C(CCCNc1ncccn1)Nc1nnc(-c2ccccn2)[nH]1] | | | | B | | | |
| 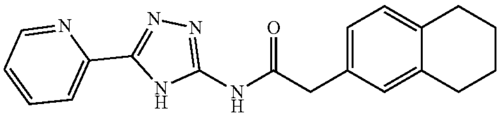 [SMILES: O=C(Cc1ccc2c(c1)CCCC2)Nc1nnc(-c2ccccn2)[nH]1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 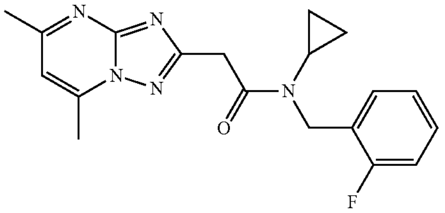 [SMILES: Cc1cc(C)n2nc(CC(=O)N(Cc3ccccc3F)C3CC3)nc2n1] | | | | B | | | |
| 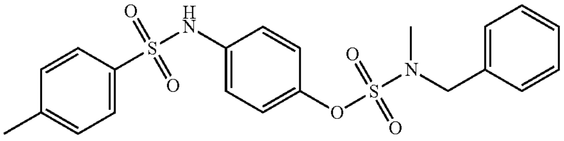 [SMILES: Cc1ccc(S(=O)(=O)Nc2ccc(OS(=O)(=O)N(C)Cc3ccccc3)cc2)cc1] | | | | B | | | |
| 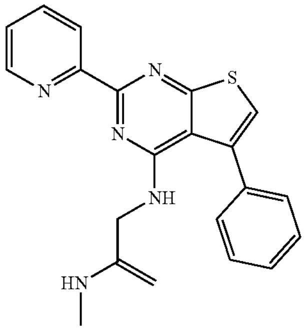 [SMILES: C=C(CNc1nc(-c2ccccn2)nc2scc(-c3ccccc3)c12)NC] | | | | B | | | |
| 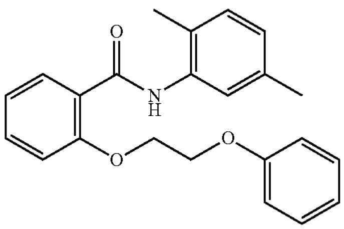 [SMILES: Cc1ccc(C)c(NC(=O)c2ccccc2OCCOc2ccccc2)c1] | | | | B | | | |
| 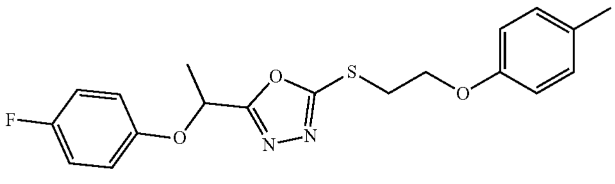 [SMILES: Cc1ccc(OCCSc2nnc(C(C)Oc3ccc(F)cc3)o2)cc1] | | | | B | | | |
| 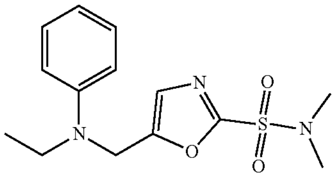 [SMILES: CCN(Cc1cnc(S(=O)(=O)N(C)C)o1)c1ccccc1] | | | | B | | | |
| 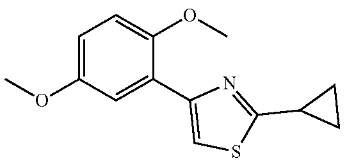 [SMILES: COc1ccc(OC)c(-c2csc(C3CC3)n2)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 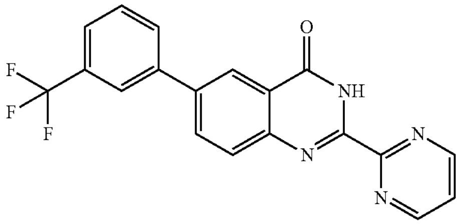 [SMILES: O=c1[nH]c(-c2ncccn2)nc2ccc(-c3cccc(C(F)(F)F)c3)cc12] | | | | B | | | |
| 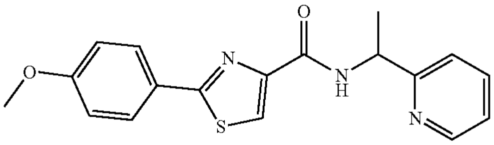 [SMILES: COc1ccc(-c2nc(C(=O)NC(C)c3ccccn3)cs2)cc1] | | | | B | | | |
| 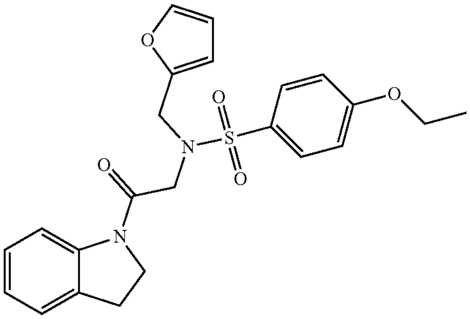 [SMILES: CCOc1ccc(S(=O)(=O)N(CC(=O)N2CCc3ccccc32)Cc2ccco2)cc1] | | | | B | | | |
| 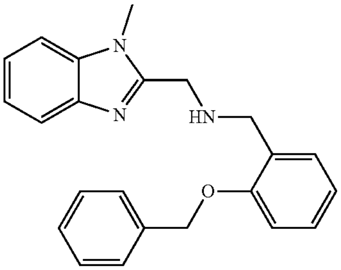 [SMILES: Cn1c(CNCc2ccccc2OCc2ccccc2)nc2ccccc21] | | | | B | | | |
| 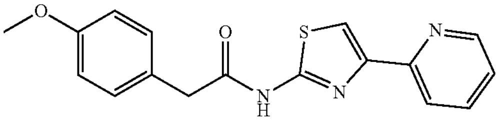 [SMILES: COc1ccc(CC(=O)Nc2nc(-c3ccccn3)cs2)cc1] | | | | B | | | |
| 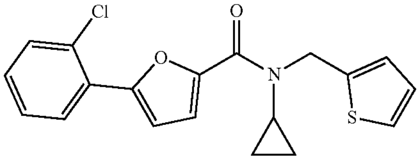 [SMILES: O=C(c1ccc(-c2ccccc2Cl)o1)N(Cc1cccs1)C1CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 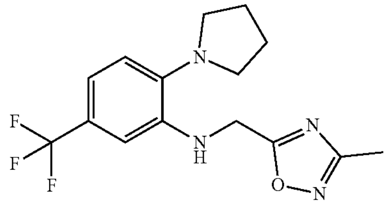 [SMILES: Cc1noc(CNc2cc(C(F)(F)F)ccc2N2CCCC2)n1] | | | | B | | | |
| 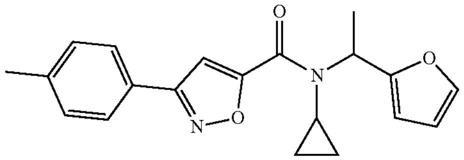 [SMILES: Cc1ccc(-c2cc(C(=O)N(C3CC3)C(C)c3ccco3)on2)cc1] | | | | B | | | |
| 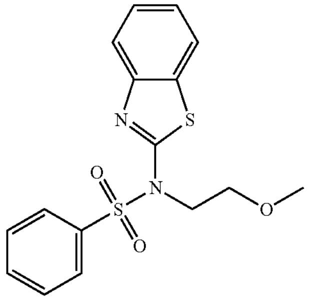 [SMILES: COCCN(c1nc2ccccc2s1)S(=O)(=O)c1ccccc1] | | | | B | | | |
| 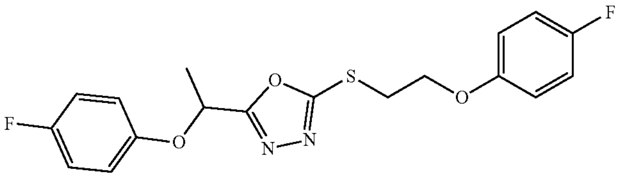 [SMILES: CC(Oc1ccc(F)cc1)c1nnc(SCCOc2ccc(F)cc2)o1] | | | | B | | | |
| 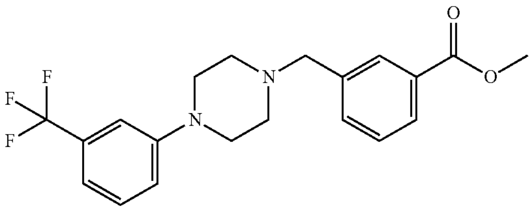 [SMILES: COC(=O)c1cccc(CN2CCN(c3cccc(C(F)(F)F)c3)CC2)c1] | | | | B | | | |
| 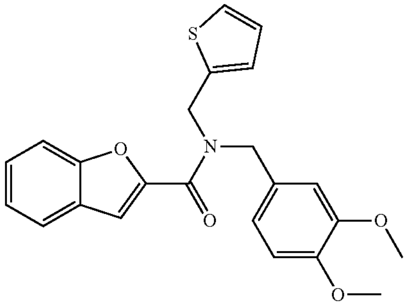 [SMILES: COc1ccc(CN(Cc2cccs2)C(=O)c2cc3ccccc3o2)cc1OC] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 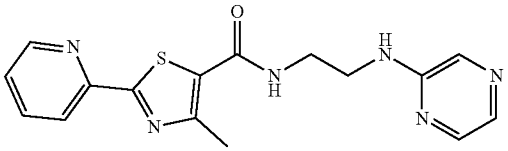 [SMILES: Cc1nc(-c2ccccn2)sc1C(=O)NCCNc1cnccn1] | | | | B | | | |
| 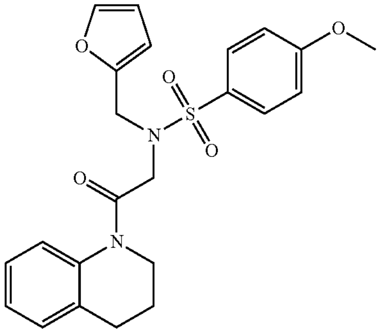 [SMILES: COc1ccc(S(=O)(=O)N(CC(=O)N2CCCc3ccccc32)Cc2ccco2)cc1] | | | | B | | | |
| 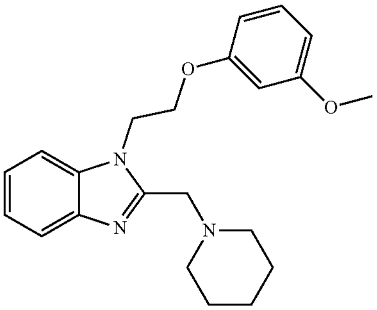 [SMILES: COc1cccc(OCCn2c(CN3CCCCC3)nc3ccccc32)c1] | | | | B | | | |
| 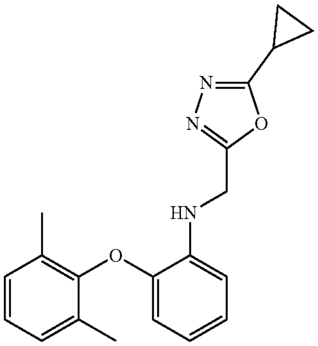 [SMILES: Cc1cccc(C)c1Oc1ccccc1NCc1nnc(C2CC2)o1] | | | | B | | | |
| 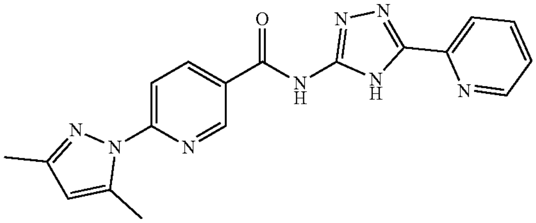 [SMILES: Cc1cc(C)n(-c2ccc(C(=O)Nc3nnc(-c4ccccn4)[nH]3)cn2)n1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 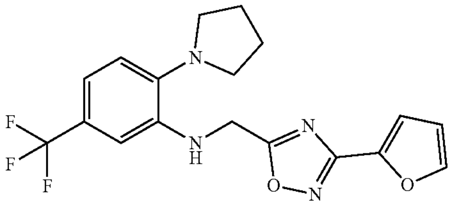 [SMILES: FC(F)(F)c1ccc(N2CCCC2)c(NCc2nc(-c3ccco3)no2)c1] | | | | B | | | |
| 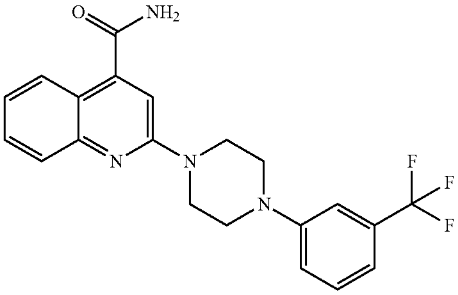 [SMILES: NC(=O)c1cc(N2CCN(c3cccc(C(F)(F)F)c3)CC2)nc2ccccc12] | | | | B | | | |
| 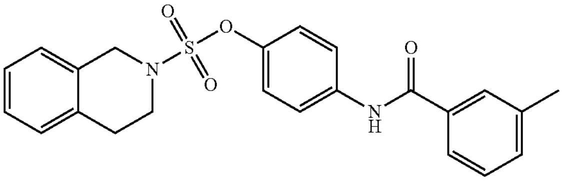 [SMILES: Cc1cccc(C(=O)Nc2ccc(OS(=O)(=O)N3CCc4ccccc4C3)cc2)c1] | | | | B | | | |
| 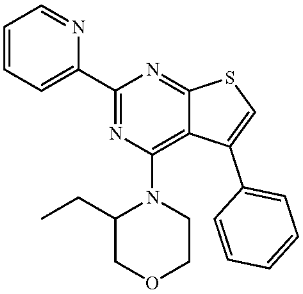 [SMILES: CCC1COCCN1c1nc(-c2ccccn2)nc2scc(-c3ccccc3)c12] | | | | B | | | |
| 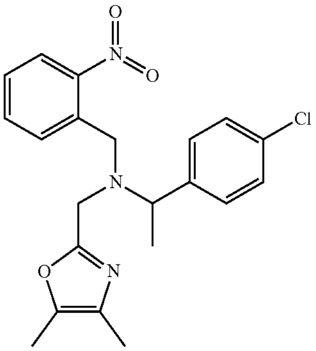 [SMILES: Cc1nc(CN(Cc2ccccc2[N+](=O)[O-])C(C)c2ccc(Cl)cc2)oc1C] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 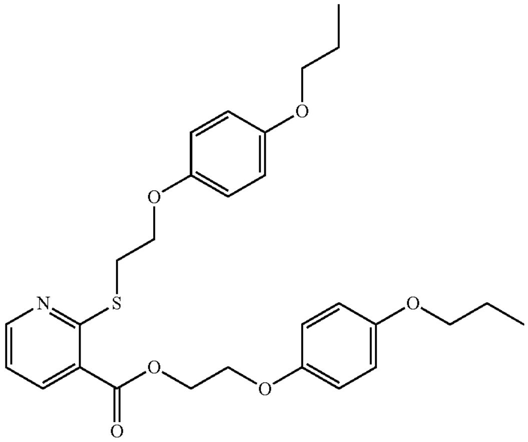 [SMILES: CCCOc1ccc(OCCOC(=O)c2cccnc2SCCOc2ccc(OCCC)cc2)cc1] | | | | B | | | |
| 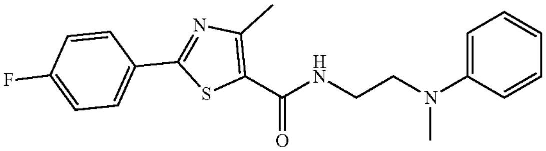 [SMILES: Cc1nc(-c2ccc(F)cc2)sc1C(=O)NCCN(C)c1ccccc1] | | | | B | | | |
| 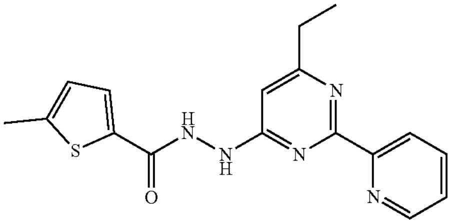 [SMILES: CCc1cc(NNC(=O)c2ccc(C)s2)nc(-c2ccccn2)n1] | | | | B | | | |
| 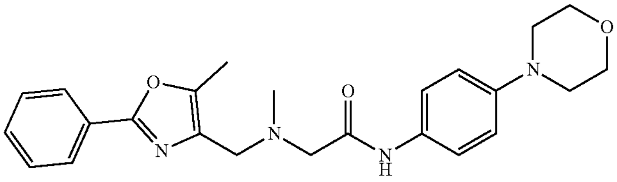 [SMILES: Cc1oc(-c2ccccc2)nc1CN(C)CC(=O)Nc1ccc(N2CCOCC2)cc1] | | | | B | | | |
| 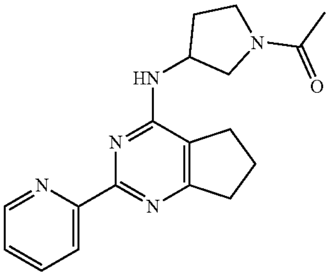 [SMILES: CC(=O)N1CCC(Nc2nc(-c3ccccn3)nc3c2CCC3)C1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 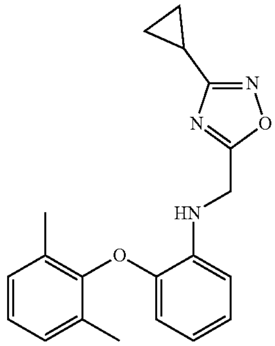 [SMILES: Cc1cccc(C)c1Oc1ccccc1NCc1nc(C2CC2)no1] | | | | B | | | |
| 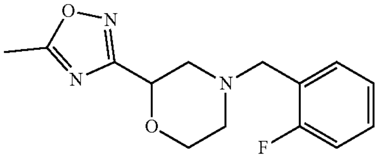 [SMILES: Cc1nc(C2CN(Cc3ccccc3F)CCO2)no1] | | | | B | | | |
| 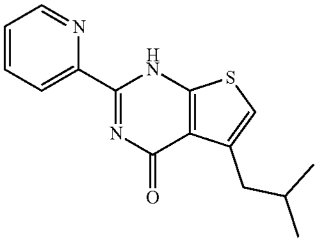 [SMILES: CC(C)Cc1csc2[nH]c(-c3ccccn3)nc(=O)c12] | | | | B | | | |
| 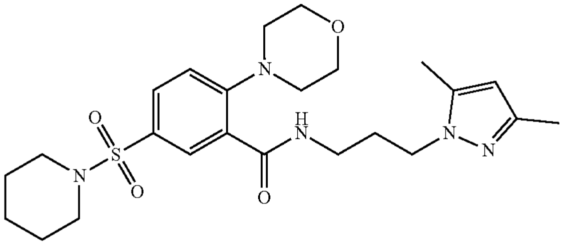 [SMILES: Cc1cc(C)n(CCCNC(=O)c2cc(S(=O)(=O)N3CCCCC3)ccc2N2CCOCC2)n1] | | | | B | | | |
| 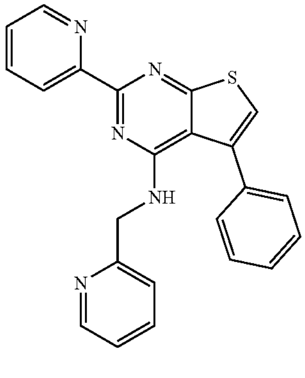 [SMILES: c1ccc(-c2csc3nc(-c4ccccn4)nc(NCc4ccccn4)c23)cc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 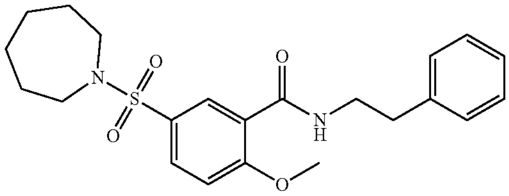 [SMILES: COc1ccc(S(=O)(=O)N2CCCCCC2)cc1C(=O)NCCc1ccccc1] | | | | B | | | |
| 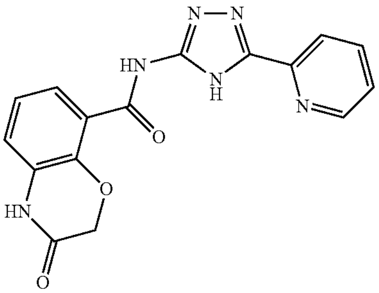 [SMILES: O=C1COc2c(cccc2C(=O)Nc2nnc(-c3ccccn3)[nH]2)N1] | | | | B | | | |
| 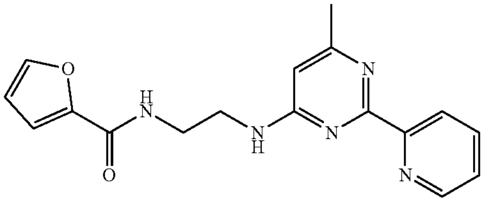 [SMILES: Cc1cc(NCCNC(=O)c2ccco2)nc(-c2ccccn2)n1] | | | | B | | | |
| 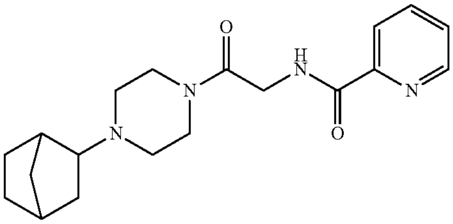 [SMILES: O=C(NCC(=O)N1CCN(C2CC3CCC2C3)CC1)c1ccccn1] | | | | B | | | |
| 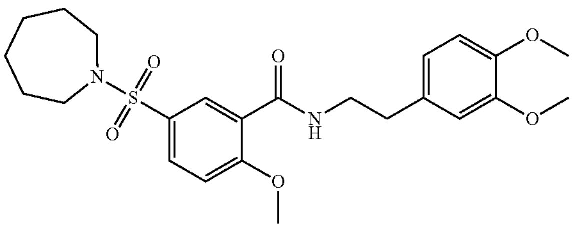 [SMILES: COc1ccc(CCNC(=O)c2cc(S(=O)(=O)N3CCCCCC3)ccc2OC)cc1OC] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 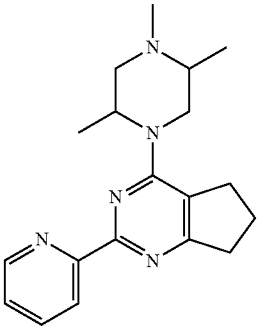 [SMILES: CC1CN(c2nc(-c3ccccn3)nc3c2CCC3)C(C)CN1C] | | | | B | | | |
| 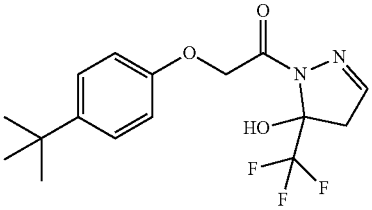 [SMILES: CC(C)(C)c1ccc(OCC(=O)N2N=CCC2(O)C(F)(F)F)cc1] | | | | B | | | |
| 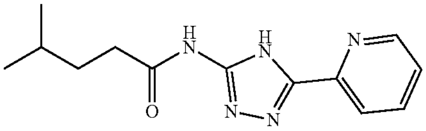 [SMILES: CC(C)CCC(=O)Nc1nnc(-c2ccccn2)[nH]1] | | | | B | | | |
| 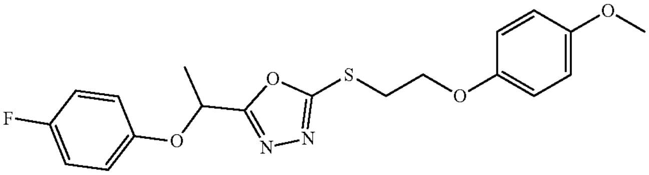 [SMILES: COc1ccc(OCCSc2nnc(C(C)Oc3ccc(F)cc3)o2)cc1] | | | | B | | | |
| 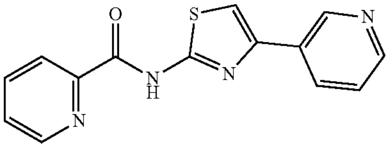 [SMILES: O=C(Nc1nc(-c2cccnc2)cs1)c1ccccn1] | | | | B | | | |
| 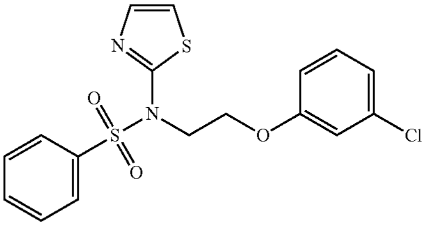 [SMILES: O=S(=O)(c1ccccc1)N(CCOc1cccc(Cl)c1)c1nccs1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 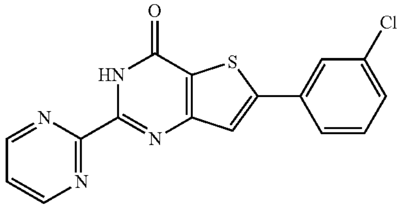 [SMILES: O=c1[nH]c(-c2ncccn2)nc2cc(-c3cccc(Cl)c3)sc12] | | | | B | | | |
| 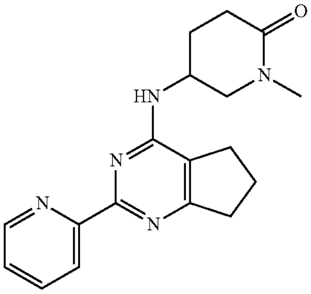 [SMILES: CN1CC(Nc2nc(-c3ccccn3)nc3c2CCC3)CCC1=O] | | | | B | | | |
| 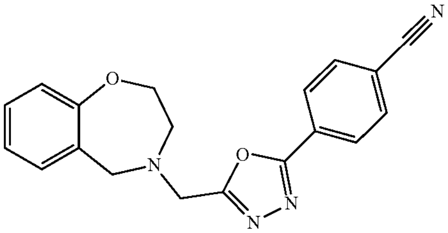 [SMILES: N#Cc1ccc(-c2nnc(CN3CCOc4ccccc4C3)o2)cc1] | | | | B | | | |
| 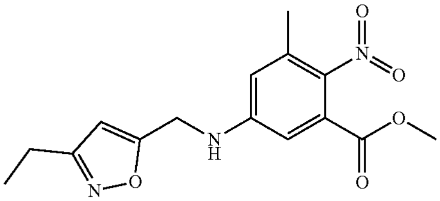 [SMILES: CCc1cc(CNc2cc(C)c([N+](=O)[O-])c(C(=O)OC)c2)on1] | | | | B | | | |
| 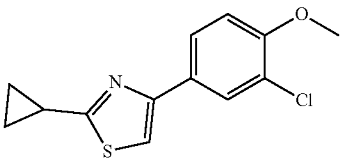 [SMILES: COc1ccc(-c2csc(C3CC3)n2)cc1Cl] | | | | B | | | |
| 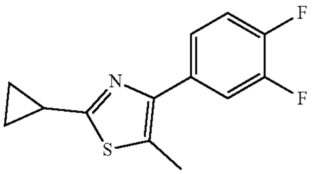 [SMILES: Cc1sc(C2CC2)nc1-c1ccc(F)c(F)c1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 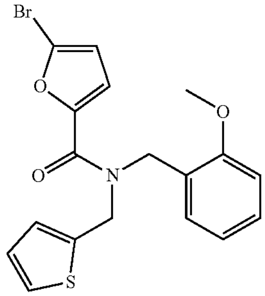 [SMILES: COc1ccccc1CN(Cc1cccs1)C(=O)c1ccc(Br)o1] | | | | B | | | |
| 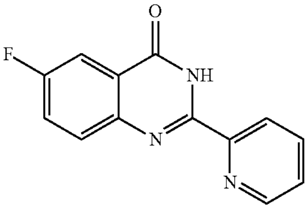 [SMILES: O=c1[nH]c(-c2ccccn2)nc2ccc(F)cc12] | | | | B | | | |
| 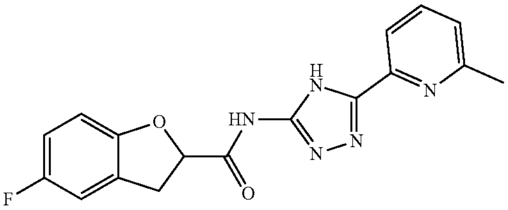 [SMILES: Cc1cccc(-c2nnc(NC(=O)C3Cc4cc(F)ccc4O3)[nH]2)n1] | | | | B | | | |
| 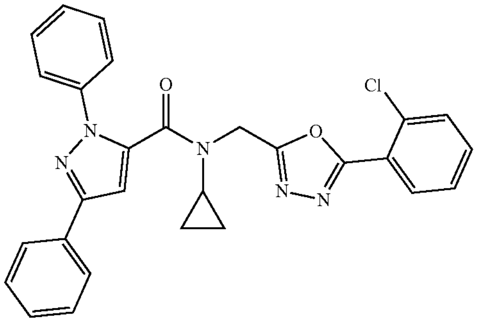 [SMILES: O=C(c1cc(-c2ccccc2)nn1-c1ccccc1)N(Cc1nnc(-c2ccccc2Cl)o1)C1CC1] | | | | B | | | |
| 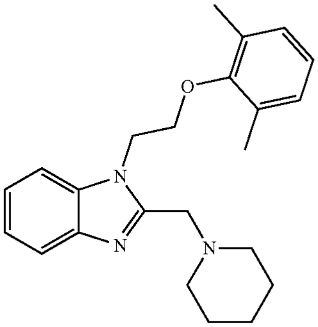 [SMILES: Cc1cccc(C)c1OCCn1c(CN2CCCCC2)nc2ccccc21] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 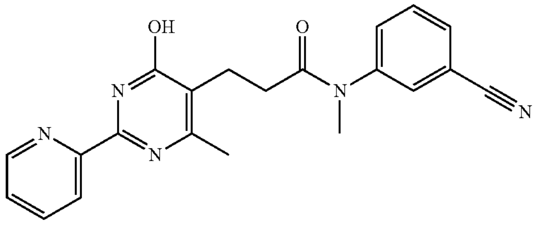 [SMILES: Cc1nc(-c2ccccn2)nc(O)c1CCC(=O)N(C)c1cccc(C#N)c1] | | | | B | | | |
| 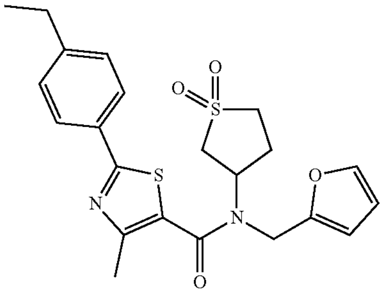 [SMILES: CCc1ccc(-c2nc(C)c(C(=O)N(Cc3ccco3)C3CCS(=O)(=O)C3)s2)cc1] | | | | B | | | |
| 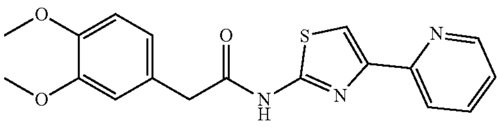 [SMILES: COc1ccc(CC(=O)Nc2nc(-c3ccccn3)cs2)cc1OC] | | | | B | | | |
| 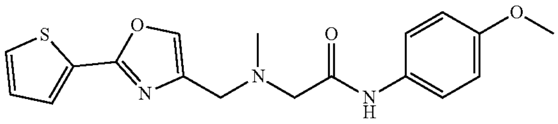 [SMILES: COc1ccc(NC(=O)CN(C)Cc2coc(-c3cccs3)n2)cc1] | | | | B | | | |
| 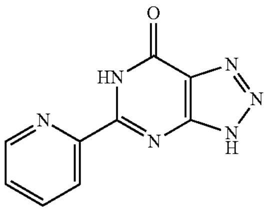 [SMILES: O=c1[nH]c(-c2ccccn2)nc2[nH]nnc12] | | | | B | | | |
| 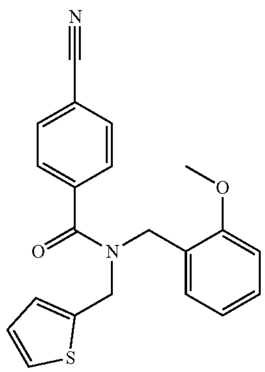 [SMILES: COc1ccccc1CN(Cc1cccs1)C(=O)c1ccc(C#N)cc1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 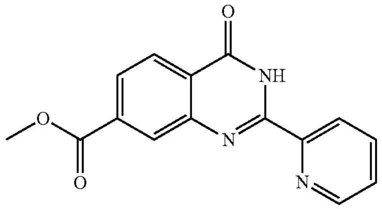 [SMILES: COC(=O)c1ccc2c(=O)[nH]c(-c3ccccn3)nc2c1] | | | | B | | | |
| 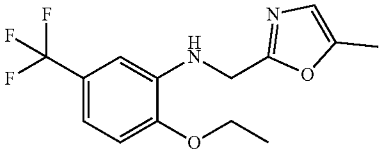 [SMILES: CCOc1ccc(C(F)(F)F)cc1NCc1ncc(C)o1] | | | | B | | | |
| 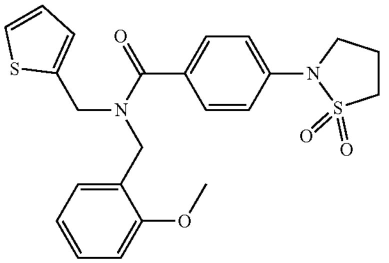 [SMILES: COc1ccccc1CN(Cc1cccs1)C(=O)c1ccc(N2CCCS2(=O)=O)cc1] | | | | B | | | |
| 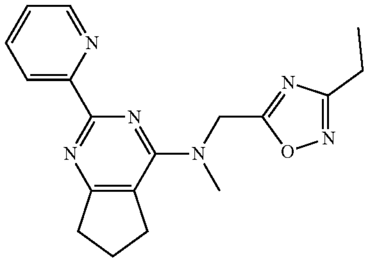 [SMILES: CCc1noc(CN(C)c2nc(-c3ccccn3)nc3c2CCC3)n1] | | | | B | | | |
| 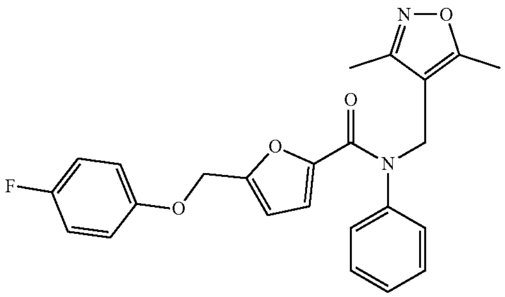 [SMILES: Cc1noc(C)c1CN(C(=O)c1ccc(COc2ccc(F)cc2)o1)c1ccccc1] | | | | B | | | |
| 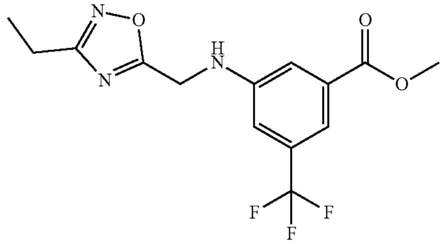 [SMILES: CCc1noc(CNc2cc(C(=O)OC)cc(C(F)(F)F)c2)n1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 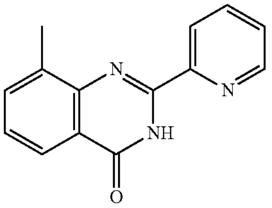 [SMILES: Cc1cccc2c(=O)[nH]c(-c3ccccn3)nc12] | | | | B | | | |
| 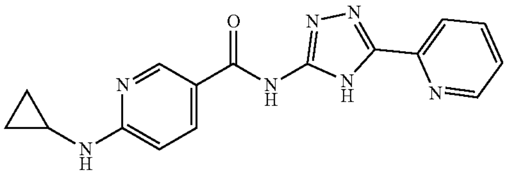 [SMILES: O=C(Nc1nnc(-c2ccccn2)[nH]1)c1ccc(NC2CC2)nc1] | | | | B | | | |
| 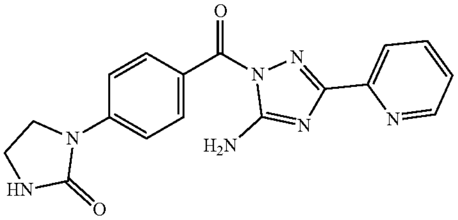 [SMILES: Nc1nc(-c2ccccn2)nn1C(=O)c1ccc(N2CCNC2=O)cc1] | | | | B | | | |
| 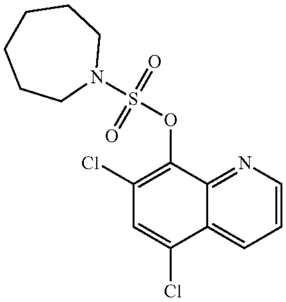 [SMILES: O=S(=O)(Oc1c(Cl)cc(Cl)c2cccnc12)N1CCCCCC1] | | | | B | | | |
| 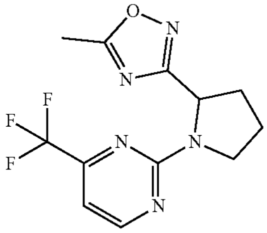 [SMILES: Cc1nc(C2CCCN2c2nccc(C(F)(F)F)n2)no1] | | | | B | | | |
| 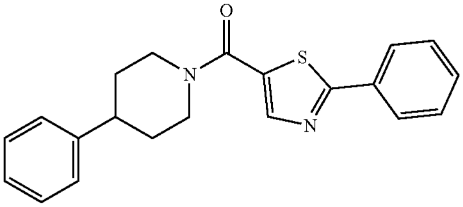 [SMILES: O=C(c1cnc(-c2ccccc2)s1)N1CCC(c2ccccc2)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 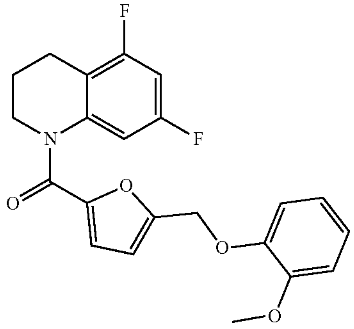 [SMILES: COc1ccccc1OCc1ccc(C(=O)N2CCCc3c(F)cc(F)cc32)o1] | | | | B | | | |
| 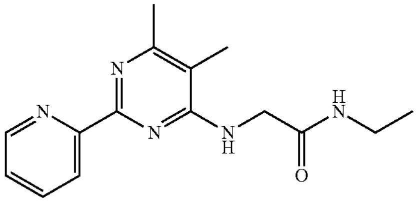 [SMILES: CCNC(=O)CNc1nc(-c2ccccn2)nc(C)c1C] | | | | B | | | |
| 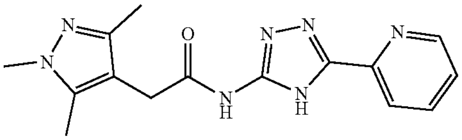 [SMILES: Cc1nn(C)c(C)c1CC(=O)Nc1nnc(-c2ccccn2)[nH]1] | | | | B | | | |
| 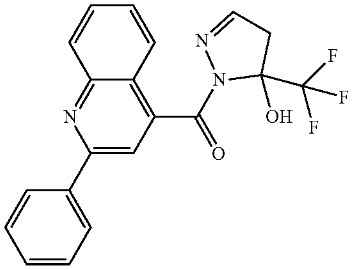 [SMILES: O=C(c1cc(-c2ccccc2)nc2ccccc12)N1N=CCC1(O)C(F)(F)F] | | | | B | | | |
| 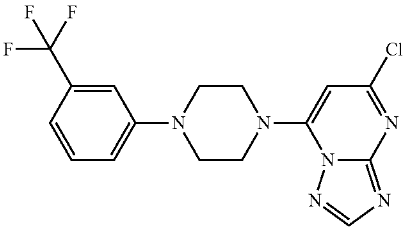 [SMILES: FC(F)(F)c1cccc(N2CCN(c3cc(Cl)nc4ncnn34)CC2)c1] | | | | B | | | |
| 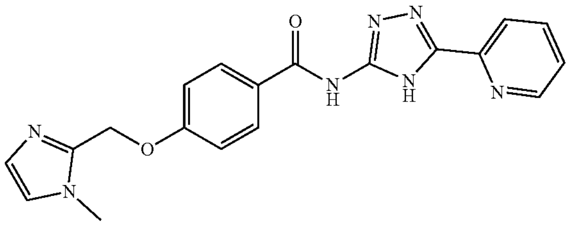 [SMILES: Cn1ccnc1COc1ccc(C(=O)Nc2nnc(-c3ccccn3)[nH]2)cc1] | | | | B | | | |

TABLE 7-continued
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H IC50 (μM) |
|---|---|---|---|---|---|---|---|
| % Inhibition at 20 μM of K-Ras mutant and wild-type protein | | | | | | | |
| 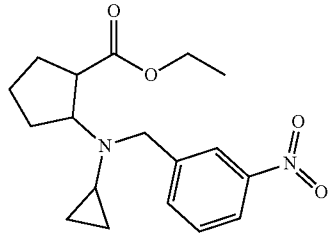 [SMILES: CCOC(=O)C1CCCC1N(Cc1cccc([N+](=O)[O-])c1)C1CC1] | | | | B | | | |
| 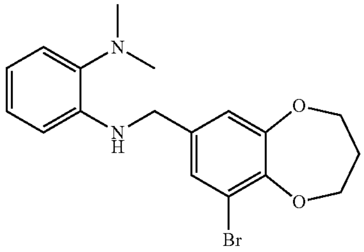 [SMILES: CN(C)c1ccccc1NCc1cc(Br)c2c(c1)OCCCO2] | | | | B | | | |
| 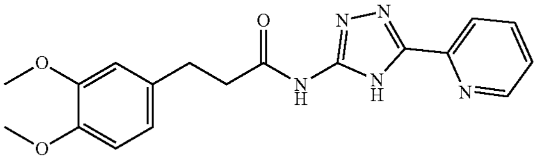 [SMILES: COc1ccc(CCC(=O)Nc2nnc(-c3ccccn3)[nH]2)cc1OC] | | | | B | | | |
| 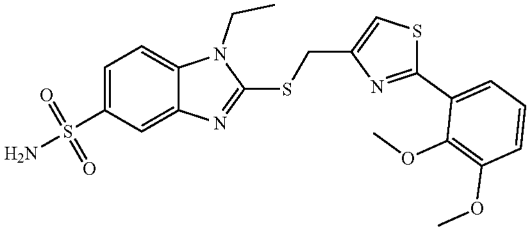 [SMILES: CCn1c(SCc2csc(-c3cccc(OC)c3OC)n2)nc2cc(S(N)(=O)=O)ccc21] | | | | B | | | |
| 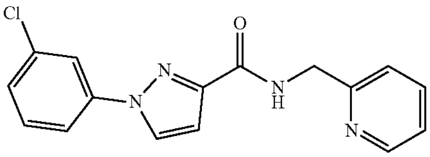 [SMILES: O=C(NCc1ccccn1)c1ccn(-c2cccc(Cl)c2)n1] | | | | B | | | |
| 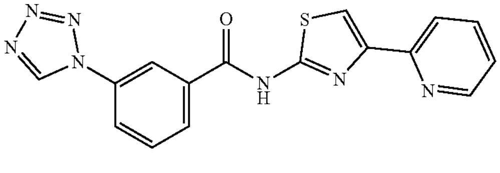 [SMILES: O=C(Nc1nc(-c2ccccn2)cs1)c1cccc(-n2cnnn2)c1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 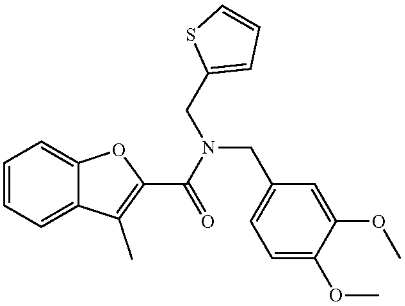 [SMILES: COc1ccc(CN(Cc2cccs2)C(=O)c2oc3ccccc3c2C)cc1OC] | | | | B | | | |
| 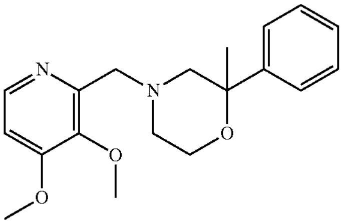 [SMILES: COc1ccnc(CN2CCOC(C)(c3ccccc3)C2)c1OC] | | | | B | | | |
| 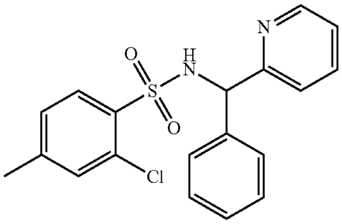 [SMILES: Cc1ccc(S(=O)(=O)NC(c2ccccc2)c2ccccn2)c(Cl)c1] | | | | B | | | |
| 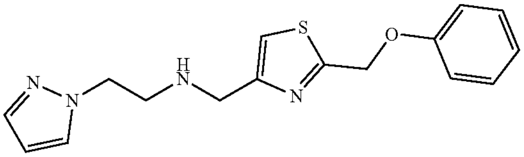 [SMILES: c1ccc(OCc2nc(CNCCn3cccn3)cs2)cc1] | | | | B | | | |
| 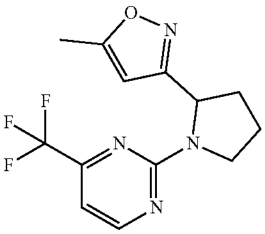 [SMILES: Cc1cc(C2CCCN2c2nccc(C(F)(F)F)n2)no1] | | | | B | | | |
| 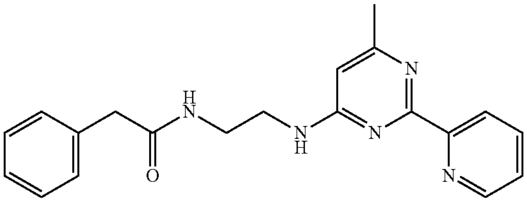 [SMILES: Cc1cc(NCCNC(=O)Cc2ccccc2)nc(-c2ccccn2)n1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 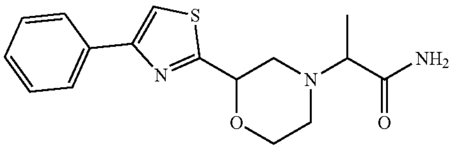 [SMILES: CC(C(N)=O)N1CCOC(c2nc(-c3ccccc3)cs2)C1] | | | | B | | | |
| 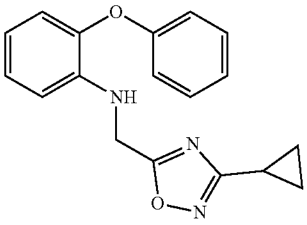 [SMILES: c1ccc(Oc2ccccc2NCc2nc(C3CC3)no2)cc1] | | | | B | | | |
| 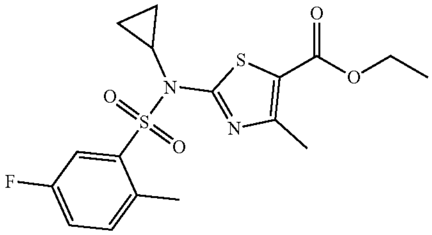 [SMILES: CCOC(=O)c1sc(N(C2CC2)S(=O)(=O)c2cc(F)ccc2C)nc1C] | | | | B | | | |
| 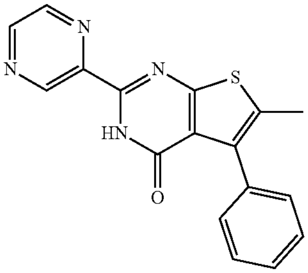 [SMILES: Cc1sc2nc(-c3cnccn3)[nH]c(=O)c2c1-c1ccccc1] | | | | B | | | |
| 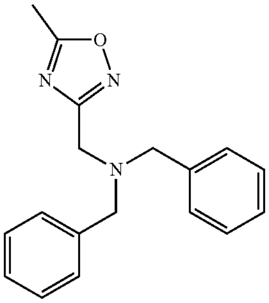 [SMILES: Cc1nc(CN(Cc2ccccc2)Cc2ccccc2)no1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 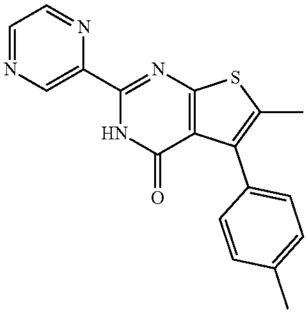 [SMILES: Cc1ccc(-c2c(C)sc3nc(-c4cnccn4)[nH]c(=O)c23)cc1] | | | | B | | | |
| 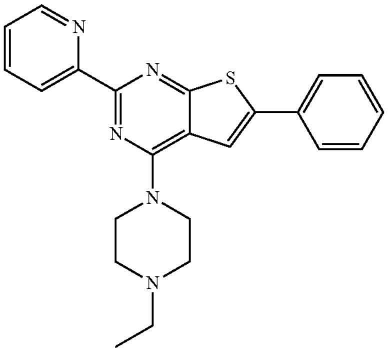 [SMILES: CCN1CCN(c2nc(-c3ccccn3)nc3sc(-c4ccccc4)cc23)CC1] | | | | B | | | |
| 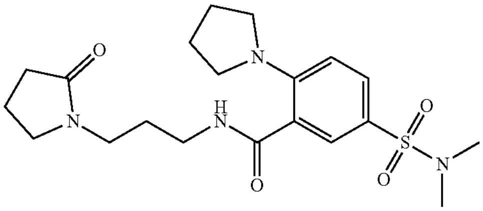 [SMILES: CN(C)S(=O)(=O)c1ccc(N2CCCC2)c(C(=O)NCCCN2CCCC2=O)c1] | | | | B | | | |
| 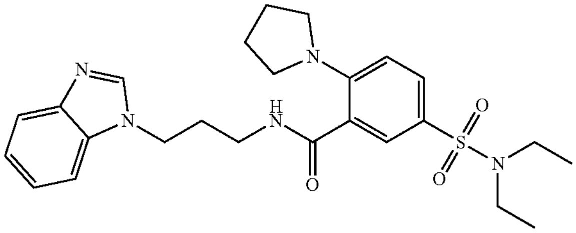 [SMILES: CCN(CC)S(=O)(=O)c1ccc(N2CCCC2)c(C(=O)NCCCn2cnc3ccccc32)c1] | | | | B | | | |
| 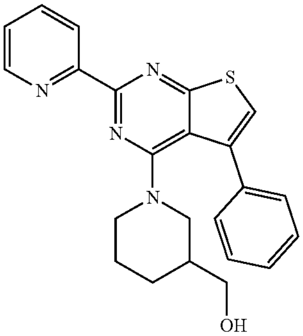 [SMILES: OCC1CCCN(c2nc(-c3ccccn3)nc3scc(-c4ccccc4)c23)C1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 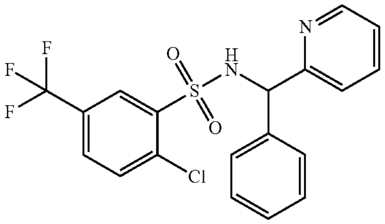 [SMILES: O=S(=O)(NC(c1ccccc1)c1ccccn1)c1cc(C(F)(F)F)ccc1Cl] | | | | B | | | |
| 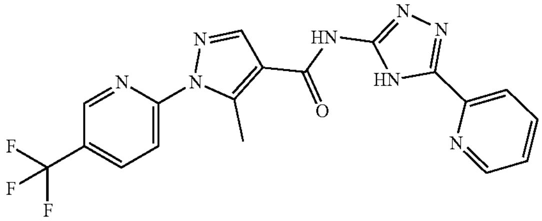 [SMILES: Cc1c(C(=O)Nc2nnc(-c3ccccn3)[nH]2)cnn1-c1ccc(C(F)(F)F)cn1] | | | | B | | | |
| 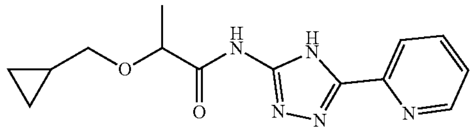 [SMILES: CC(OCC1CC1)C(=O)Nc1nnc(-c2ccccn2)[nH]1] | | | | B | | | |
| 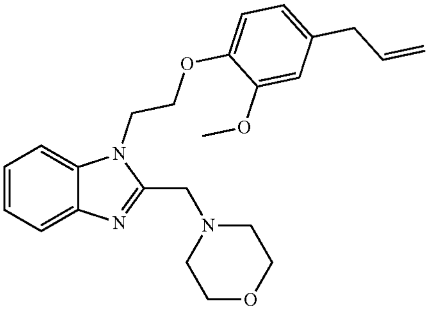 [SMILES: C=CCc1ccc(OCCn2c(CN3CCOCC3)nc3ccccc32)c(OC)c1] | | | | B | | | |
| 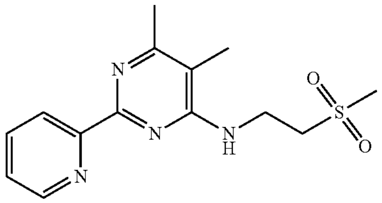 [SMILES: Cc1nc(-c2ccccn2)nc(NCCS(C)(=O)=O)c1C] | | | | B | | | |
| 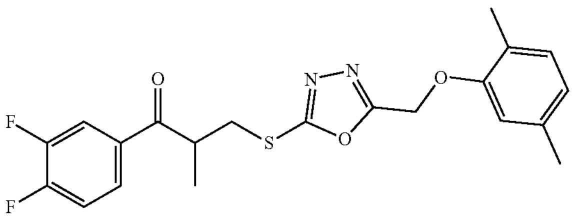 [SMILES: Cc1ccc(C)c(OCc2nnc(SCC(C)C(=O)c3ccc(F)c(F)c3)o2)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 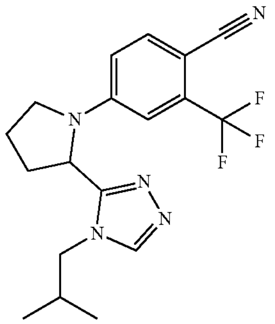 [SMILES: CC(C)Cn1cnnc1C1CCCN1c1ccc(C#N)c(C(F)(F)F)c1] | | | | B | | | |
| 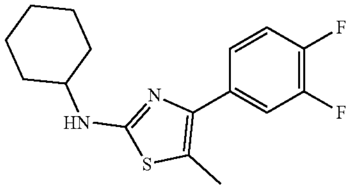 [SMILES: Cc1sc(NC2CCCCC2)nc1-c1ccc(F)c(F)c1] | | | | B | | | |
| 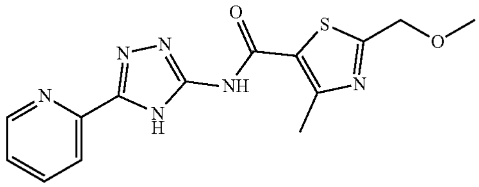 [SMILES: COCc1nc(C)c(C(=O)Nc2nnc(-c3ccccn3)[nH]2)s1] | | | | B | | | |
| 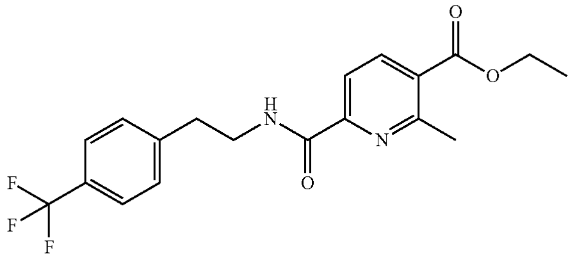 [SMILES: CCOC(=O)c1ccc(C(=O)NCCc2ccc(C(F)(F)F)cc2)nc1C] | | | | B | | | |
| 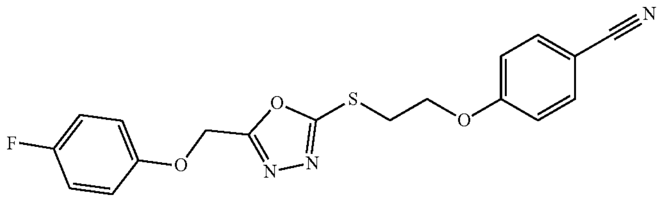 [SMILES: N#Cc1ccc(OCCSc2nnc(COc3ccc(F)cc3)o2)cc1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 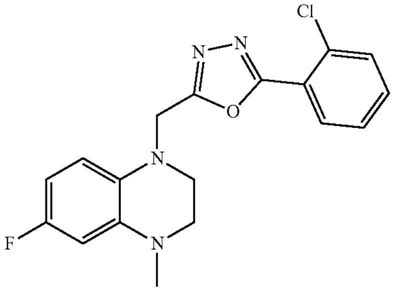 [SMILES: CN1CCN(Cc2nnc(-c3ccccc3Cl)o2)c2ccc(F)cc21] | | | | B | | | |
| 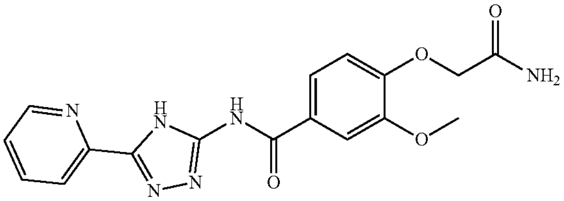 [SMILES: COc1cc(C(=O)Nc2nnc(-c3ccccn3)[nH]2)ccc1OCC(N)=O] | | | | B | | | |
| 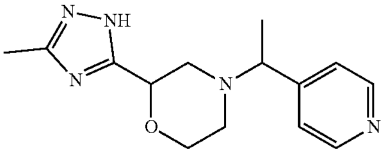 [SMILES: Cc1n[nH]c(C2CN(C(C)c3ccncc3)CCO2)n1] | | | | B | | | |
| 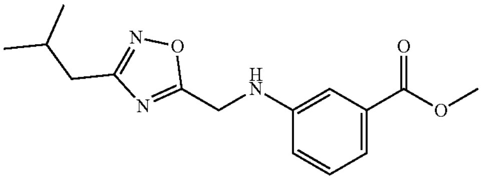 [SMILES: COC(=O)c1cccc(NCc2nc(CC(C)C)no2)c1] | | | | B | | | |
| 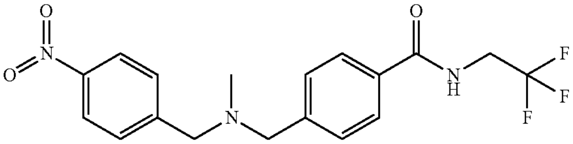 [SMILES: CN(Cc1ccc(C(=O)NCC(F)(F)F)cc1)Cc1ccc([N+](=O)[O-])cc1] | | | | B | | | |
| 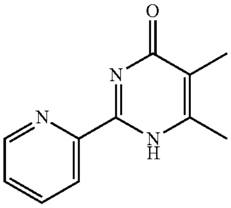 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 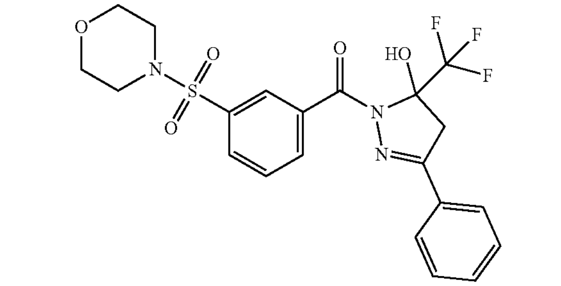 [SMILES: O=C(c1cccc(S(=O)(=O)N2CCOCC2)c1)N1N=C(c2ccccc2)CC1(O)C(F)(F)F] | | | | B | | | |
| 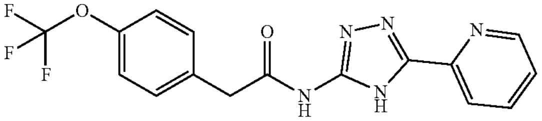 [SMILES: O=C(Cc1ccc(OC(F)(F)F)cc1)Nc1nnc(-c2ccccn2)[nH]1] | | | | B | | | |
| 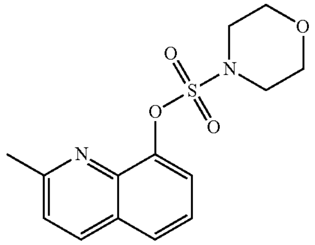 [SMILES: Cc1ccc2cccc(OS(=O)(=O)N3CCOCC3)c2n1] | | | | B | | | |
| 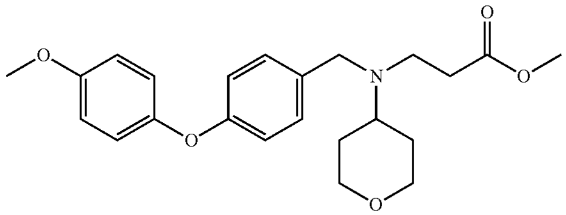 | | | | A | | | |
| 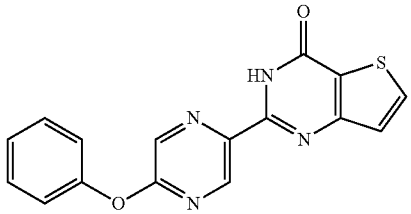 [SMILES: O=c1[nH]c(-c2cnc(Oc3ccccc3)cn2)nc2ccsc12] | | | | A | | | |
| 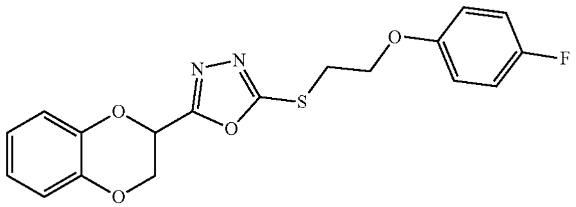 [SMILES: Fc1ccc(OCCSc2nnc(C3COc4ccccc4O3)o2)cc1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 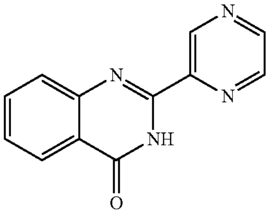 [SMILES: O=c1[nH]c(-c2cnccn2)nc2ccccc12] | | | | A | | | |
| 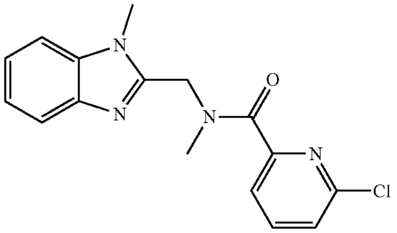 [SMILES: CN(Cc1nc2ccccc2n1C)C(=O)c1cccc(Cl)n1] | | | | A | | | |
| 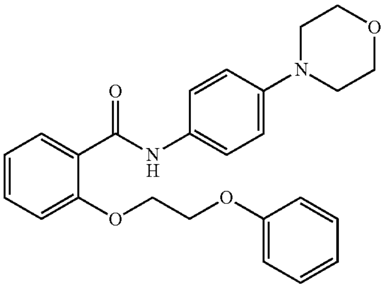 [SMILES: O=C(Nc1ccc(N2CCOCC2)cc1)c1ccccc1OCCOc1ccccc1] | | | | A | | | |
| 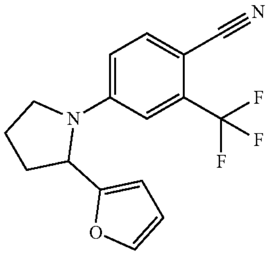 [SMILES: N#Cc1ccc(N2CCCC2c2ccco2)cc1C(F)(F)F] | | | | A | | | |
| 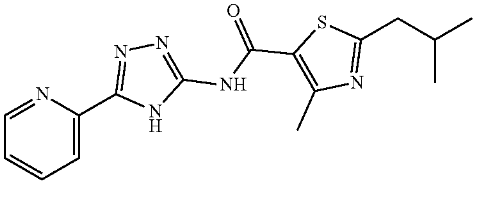 [SMILES: Cc1nc(CC(C)C)sc1C(=O)Nc1nnc(-c2ccccn2)[nH]1] | | | | A | | | |
| 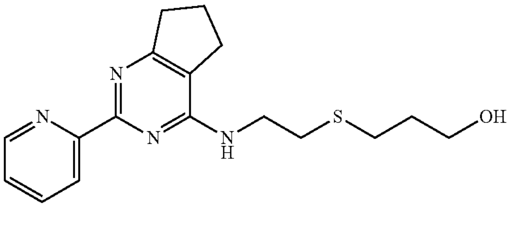 [SMILES: OCCCSCCNc1nc(-c2ccccn2)nc2c1CCC2] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 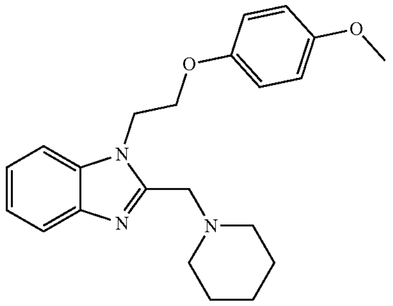 [SMILES: COc1ccc(OCCn2c(CN3CCCCC3)nc3ccccc32)cc1] | | | | A | | | |
| 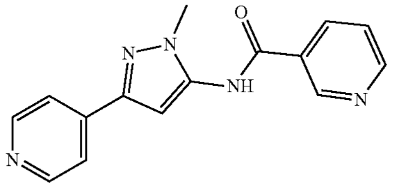 [SMILES: Cn1nc(-c2ccncc2)cc1NC(=O)c1cccnc1] | | | | A | | | |
| 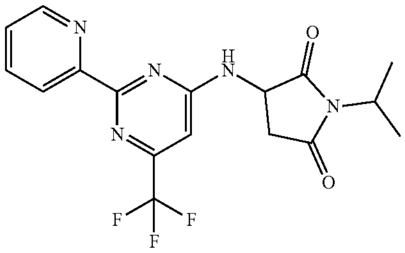 [SMILES: CC(C)N1C(=O)CC(Nc2cc(C(F)(F)F)nc(-c3ccccn3)n2)C1=O] | | | | A | | | |
| 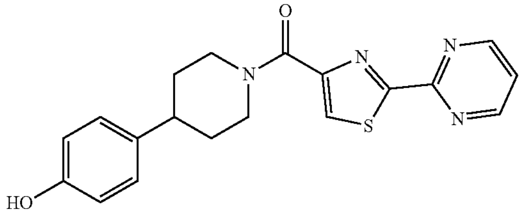 [SMILES: O=C(c1csc(-c2ncccn2)n1)N1CCC(c2ccc(O)cc2)CC1] | | | | A | | | |
| 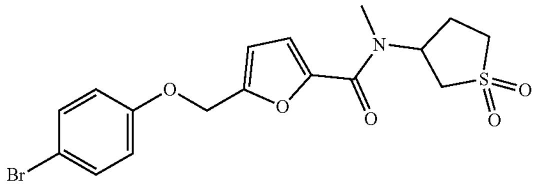 [SMILES: CN(C(=O)c1ccc(COc2ccc(Br)cc2)o1)C1CCS(=O)(=O)C1] | | | | A | | | |
| 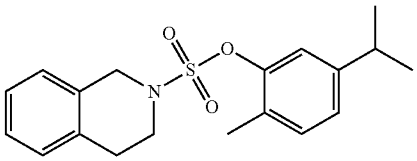 [SMILES: Cc1ccc(C(C)C)cc1OS(=O)(=O)N1CCc2ccccc2C1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 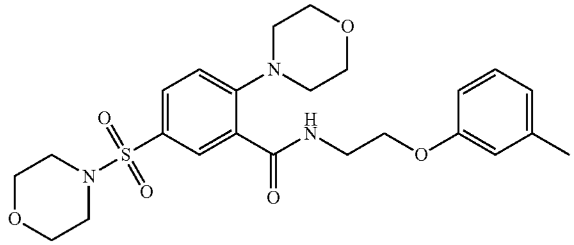 [SMILES: Cc1cccc(OCCNC(=O)c2cc(S(=O)(=O)N3CCOCC3)ccc2N2CCOCC2)c1] | | | | A | | | |
| 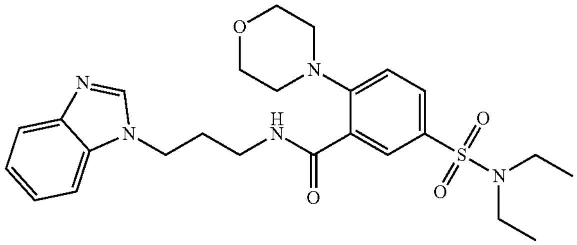 [SMILES: CCN(CC)S(=O)(=O)c1ccc(N2CCOCC2)c(C(=O)NCCCn2cnc3ccccc32)c1] | | | | A | | | |
| 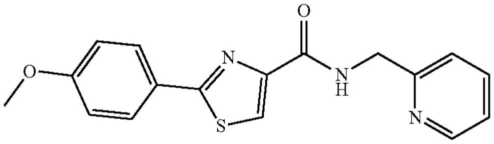 [SMILES: COc1ccc(-c2nc(C(=O)NCc3ccccn3)cs2)cc1] | | | | A | | | |
| 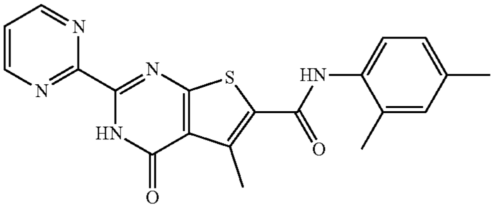 [SMILES: Cc1ccc(NC(=O)c2sc3nc(-c4ncccn4)[nH]c(=O)c3c2C)c(C)c1] | | | | A | | | |
| 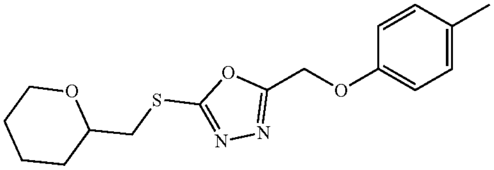 [SMILES: Cc1ccc(OCc2nnc(SCC3CCCCO3)o2)cc1] | | | | A | | | |
| 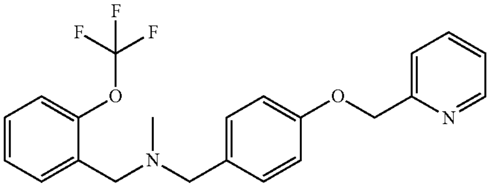 [SMILES: CN(Cc1ccc(OCc2ccccn2)cc1)Cc1ccccc1OC(F)(F)F] | | | | A | | | |
| 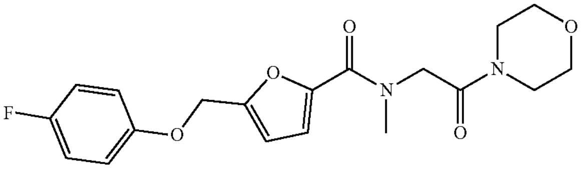 [SMILES: CN(CC(=O)N1CCOCC1)C(=O)c1ccc(COc2ccc(F)cc2)o1] | | | | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 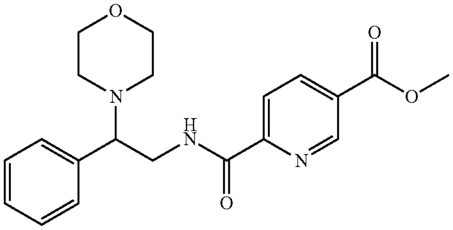 [SMILES: COC(=O)c1ccc(C(=O)NCC(c2ccccc2)N2CCOCC2)nc1] | | | | A | | | |
| 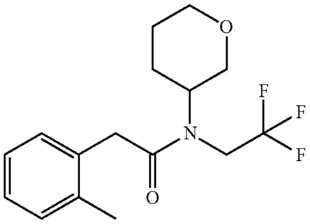 [SMILES: Cc1ccccc1CC(=O)N(CC(F)(F)F)C1CCCOC1] | | | | A | | | |
| 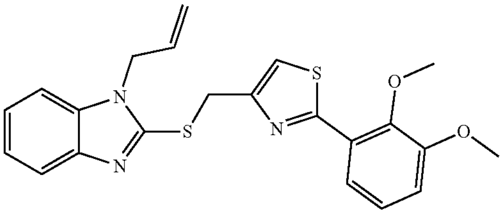 [SMILES: C=CCn1c(SCc2csc(-c3cccc(OC)c3OC)n2)nc2ccccc21] | | | | A | | | |
| 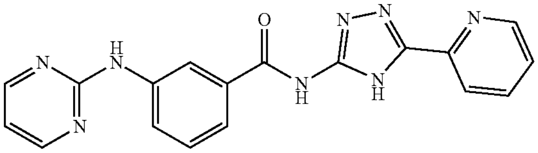 [SMILES: O=C(Nc1nnc(-c2ccccn2)[nH]1)c1cccc(Nc2ncccn2)c1] | | | | A | | | |
| 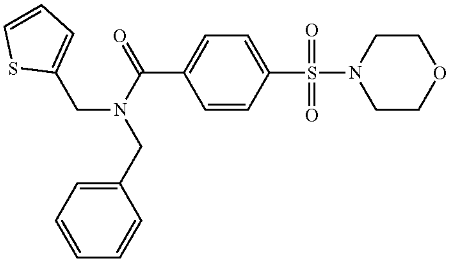 [SMILES: O=C(c1ccc(S(=O)(=O)N2CCOCC2)cc1)N(Cc1ccccc1)Cc1cccs1] | | | | A | | | |
| 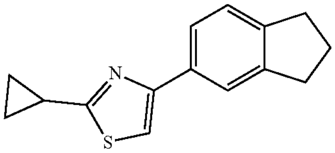 [SMILES: c1cc2c(cc1-c1csc(C3CC3)n1)CCC2] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 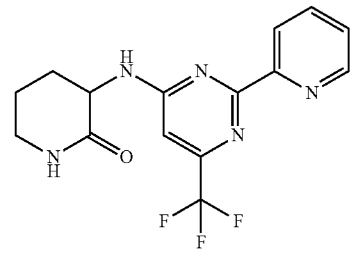 [SMILES: O=C1NCCCC1Nc1cc(C(F)(F)F)nc(-c2ccccn2)n1] | | | | A | | | |
| 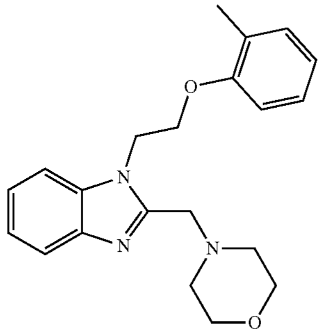 [SMILES: Cc1ccccc1OCCn1c(CN2CCOCC2)nc2ccccc21] | | | | A | | | |
| 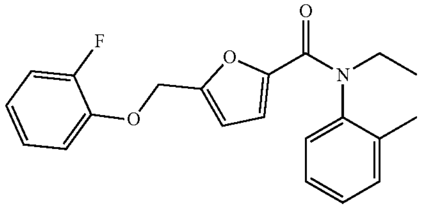 [SMILES: CCN(C(=O)c1ccc(COc2ccccc2F)o1)c1ccccc1C] | | | | A | | | |
| 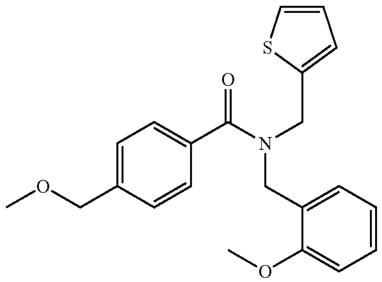 [SMILES: COCc1ccc(C(=O)N(Cc2cccs2)Cc2ccccc2OC)cc1] | | | | A | | | |
| 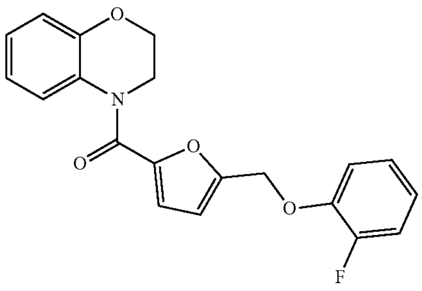 [SMILES: O=C(c1ccc(COc2ccccc2F)o1)N1CCOc2ccccc21] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 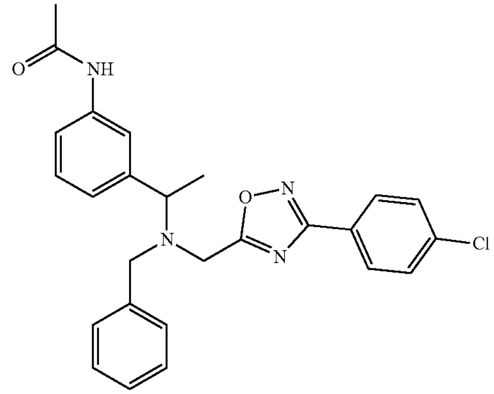 [SMILES: CC(=O)Nc1cccc(C(C)N(Cc2ccccc2)Cc2nc(-c3ccc(Cl)cc3)no2)c1] | | | | A | | | |
| 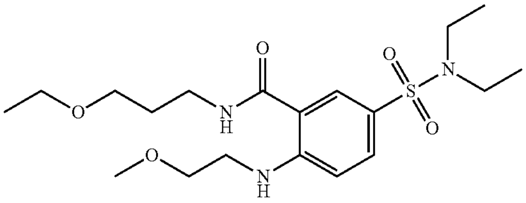 [SMILES: CCOCCCNC(=O)c1cc(S(=O)(=O)N(CC)CC)ccc1NCCOC] | | | | A | | | |
| 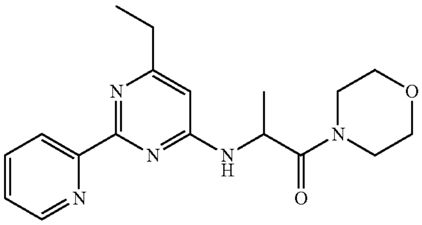 [SMILES: CCc1cc(NC(C)C(=O)N2CCOCC2)nc(-c2ccccn2)n1] | | | | A | | | |
| 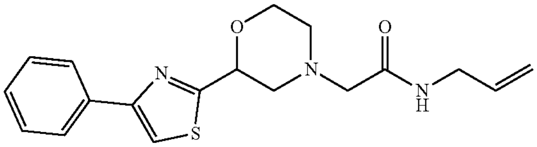 [SMILES: C=CCNC(=O)CN1CCOC(c2nc(-c3ccccc3)cs2)C1] | | | | A | | | |
| 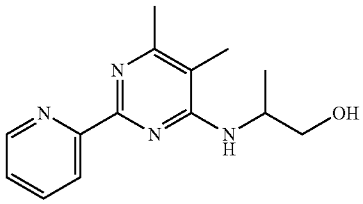 [SMILES: Cc1nc(-c2ccccn2)nc(NC(C)CO)c1C] | | | | A | | | |
| 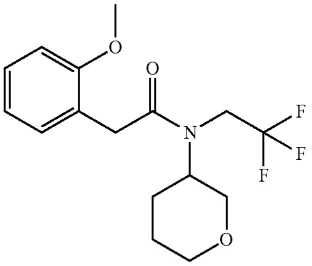 [SMILES: COc1ccccc1CC(=O)N(CC(F)(F)F)C1CCCOC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 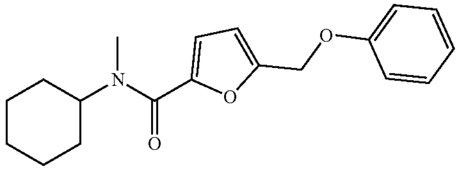 [SMILES: CN(C(=O)c1ccc(COc2ccccc2)o1)C1CCCCC1] | | | | A | | | |
| 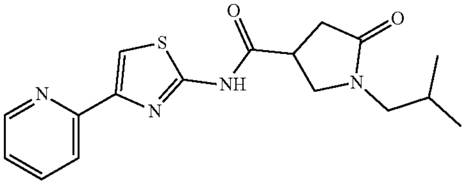 [SMILES: CC(C)CN1CC(C(=O)Nc2nc(-c3ccccn3)cs2)CC1=O] | | | | A | | | |
| 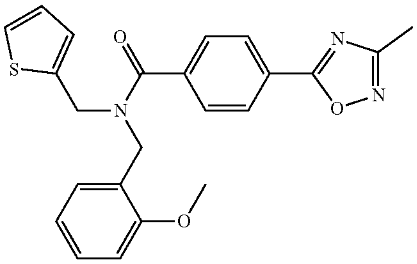 [SMILES: COc1ccccc1CN(Cc1cccs1)C(=O)c1ccc(-c2nc(C)no2)cc1] | | | | A | | | |
| 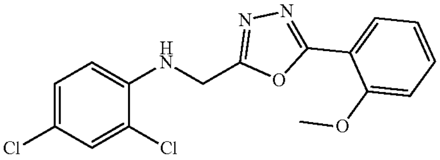 [SMILES: COc1ccccc1-c1nnc(CNc2ccc(Cl)cc2Cl)o1] | | | | A | | | |
| 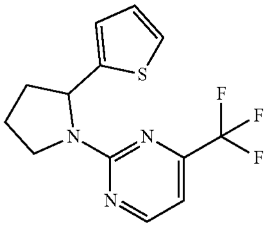 [SMILES: FC(F)(F)c1ccnc(N2CCCC2c2cccs2)n1] | | | | A | | | |
| 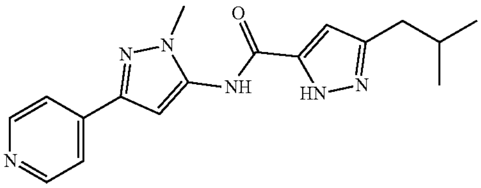 [SMILES: CC(C)Cc1cc(C(=O)Nc2cc(-c3ccncc3)nn2C)[nH]n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 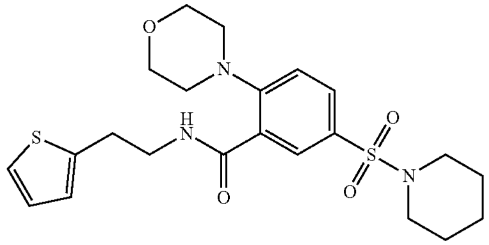 [SMILES: O=C(NCCc1cccs1)c1cc(S(=O)(=O)N2CCCCC2)ccc1N1CCOCC1] | | | | A | | | |
| 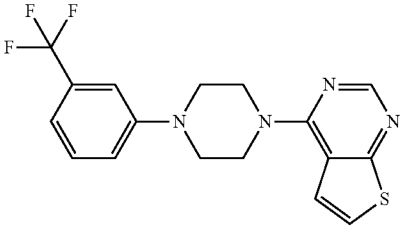 [SMILES: FC(F)(F)c1cccc(N2CCN(c3ncnc4sccc34)CC2)c1] | | | | A | | | |
| 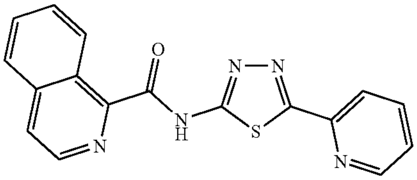 [SMILES: O=C(Nc1nnc(-c2ccccn2)s1)c1nccc2ccccc12] | | | | A | | | |
| 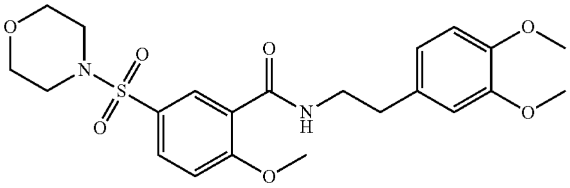 [SMILES: COc1ccc(CCNC(=O)c2cc(S(=O)(=O)N3CCOCC3)ccc2OC)cc1OC] | | | | A | | | |
| 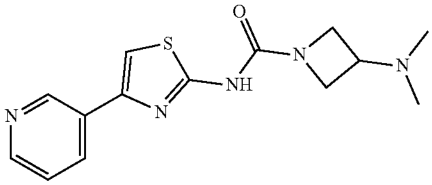 [SMILES: CN(C)C1CN(C(=O)Nc2nc(-c3cccnc3)cs2)C1] | | | | A | | | |
| 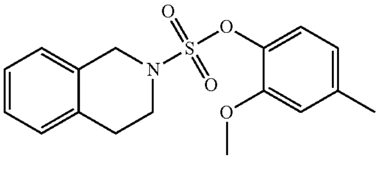 [SMILES: COc1cc(C)ccc1OS(=O)(=O)N1CCc2ccccc2C1] | | | | A | | | |
| 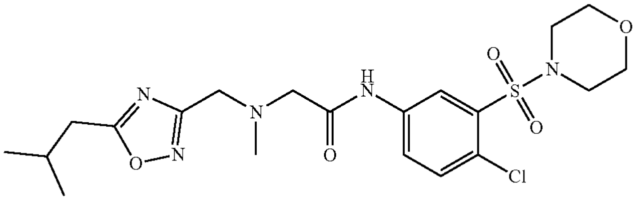 [SMILES: CC(C)Cc1nc(CN(C)CC(=O)Nc2ccc(Cl)c(S(=O)(=O)N3CCOCC3)c2)no1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 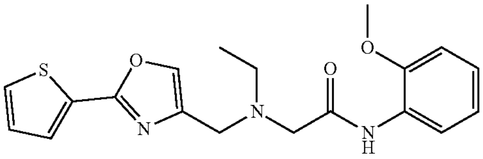 [SMILES: CCN(CC(=O)Nc1ccccc1OC)Cc1coc(-c2cccs2)n1] | | | | A | | | |
| 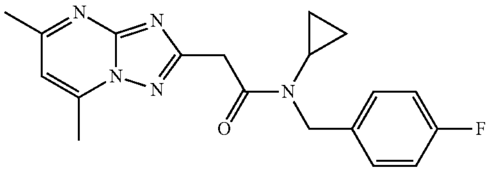 [SMILES: Cc1cc(C)n2nc(CC(=O)N(Cc3ccc(F)cc3)C3CC3)nc2n1] | | | | A | | | |
| 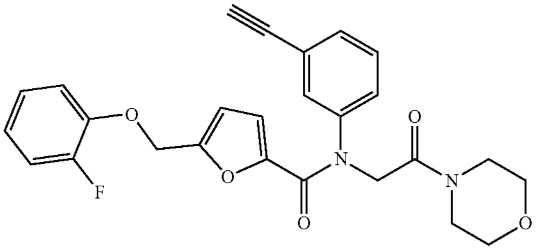 [SMILES: C#Cc1cccc(N(CC(=O)N2CCOCC2)C(=O)c2ccc(COc3ccccc3F)o2)c1] | | | | A | | | |
| 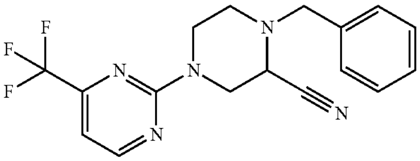 [SMILES: N#CC1CN(c2nccc(C(F)(F)F)n2)CCN1Cc1ccccc1] | | | | A | | | |
| 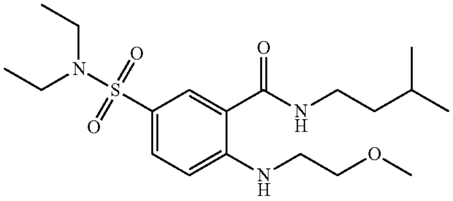 [SMILES: CCN(CC)S(=O)(=O)c1ccc(NCCOC)c(C(=O)NCCC(C)C)c1] | | | | A | | | |
| 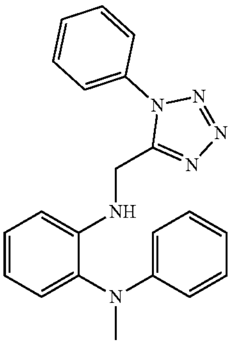 [SMILES: CN(c1ccccc1)c1ccccc1NCc1nnnn1-c1ccccc1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 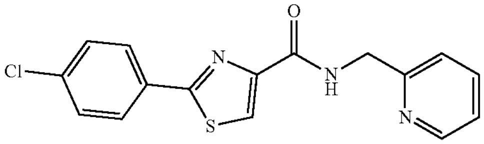 [SMILES: O=C(NCc1ccccn1)c1csc(-c2ccc(Cl)cc2)n1] | | | | A | | | |
| 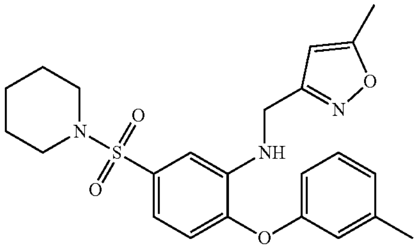 [SMILES: Cc1cccc(Oc2ccc(S(=O)(=O)N3CCCCC3)cc2NCc2cc(C)on2)c1] | | | | A | | | |
| 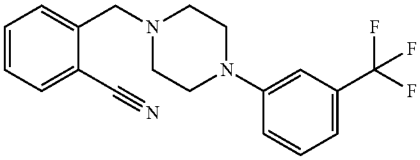 [SMILES: N#Cc1ccccc1CN1CCN(c2cccc(C(F)(F)F)c2)CC1] | | | | A | | | |
| 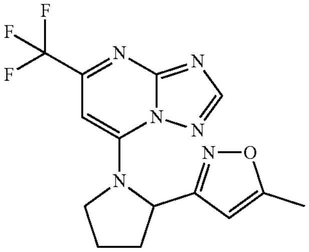 [SMILES: Cc1cc(C2CCCN2c2cc(C(F)(F)F)nc3ncnn23)no1] | | | | A | | | |
| 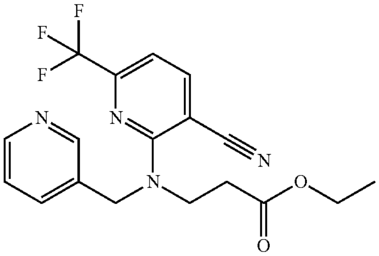 [SMILES: CCOC(=O)CCN(Cc1cccnc1)c1nc(C(F)(F)F)ccc1C#N] | | | | A | | | |
| 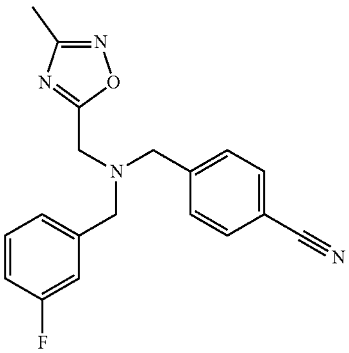 [SMILES: Cc1noc(CN(Cc2ccc(C#N)cc2)Cc2cccc(F)c2)n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 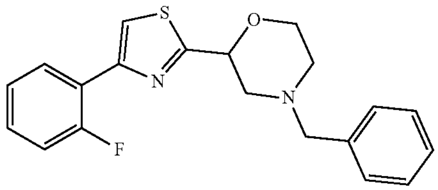 [SMILES: Fc1ccccc1-c1csc(C2CN(Cc3ccccc3)CCO2)n1] | | | | A | | | |
| 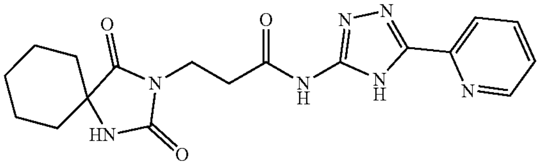 [SMILES: O=C(CCN1C(=O)NC2(CCCCC2)C1=O)Nc1nnc(-c2ccccn2)[nH]1] | | | | A | | | |
| 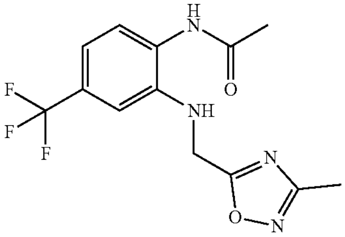 [SMILES: CC(=O)Nc1ccc(C(F)(F)F)cc1NCc1nc(C)no1] | | | | A | | | |
| 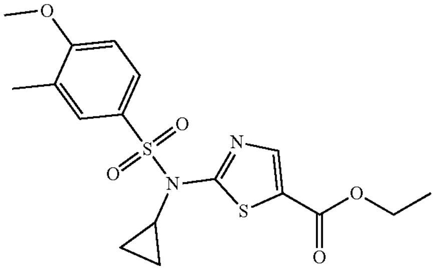 [SMILES: CCOC(=O)c1cnc(N(C2CC2)S(=O)(=O)c2ccc(OC)c(C)c2)s1] | | | | A | | | |
| 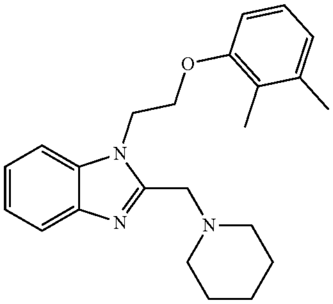 [SMILES: Cc1cccc(OCCn2c(CN3CCCCC3)nc3ccccc32)c1C] | | | | A | | | |
| 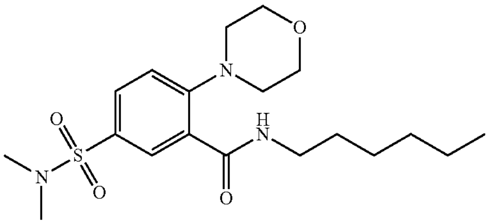 [SMILES: CCCCCCNC(=O)c1cc(S(=O)(=O)N(C)C)ccc1N1CCOCC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 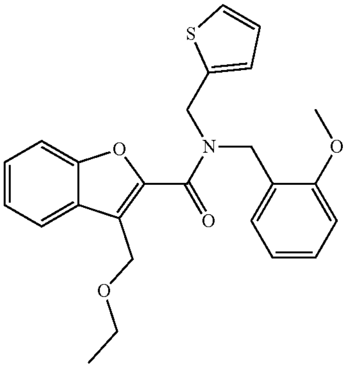 [SMILES: CCOCc1c(C(=O)N(Cc2cccs2)Cc2ccccc2OC)oc2ccccc12] | | | | A | | | |
| 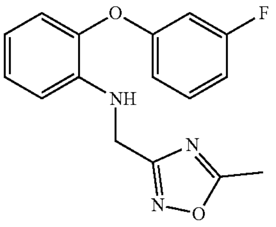 [SMILES: Cc1nc(CNc2ccccc2Oc2cccc(F)c2)no1] | | | | A | | | |
| 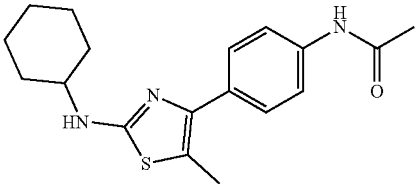 [SMILES: CC(=O)Nc1ccc(-c2nc(NC3CCCCC3)sc2C)cc1] | | | | A | | | |
| 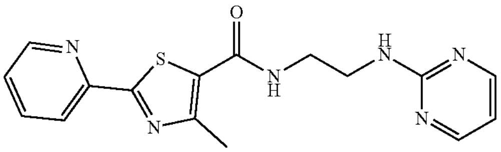 [SMILES: Cc1nc(-c2ccccn2)sc1C(=O)NCCNc1ncccn1] | | | | A | | | |
| 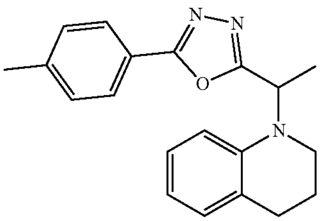 [SMILES: Cc1ccc(-c2nnc(C(C)N3CCCc4ccccc43)o2)cc1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 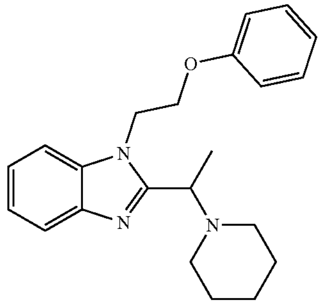 [SMILES: CC(c1nc2ccccc2n1CCOc1ccccc1)N1CCCCC1] | | | | A | | | |
| 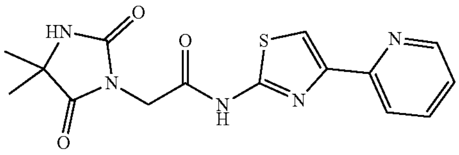 [SMILES: CC1(C)NC(=O)N(CC(=O)Nc2nc(-c3ccccn3)cs2)C1=O] | | | | A | | | |
| 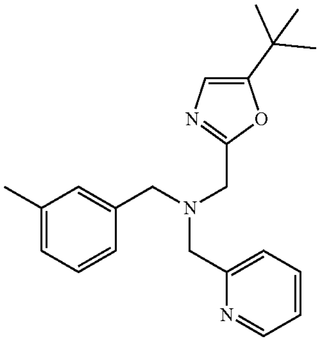 [SMILES: Cc1cccc(CN(Cc2ccccn2)Cc2ncc(C(C)(C)C)o2)c1] | | | | A | | | |
| 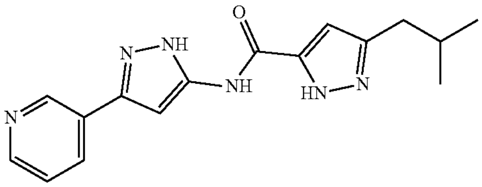 [SMILES: CC(C)Cc1cc(C(=O)Nc2cc(-c3cccnc3)n[nH]2)[nH]n1] | | | | A | | | |
| 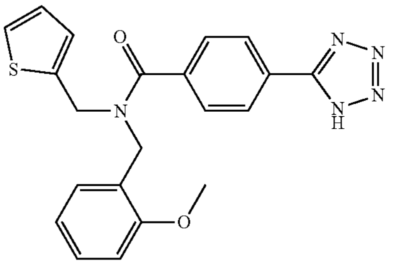 [SMILES: COc1ccccc1CN(Cc1cccs1)C(=O)c1ccc(-c2nnn[nH]2)cc1] | | | | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 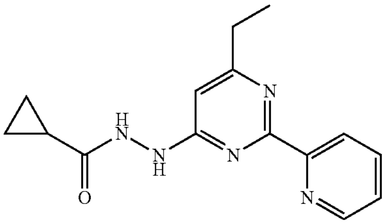 [SMILES: CCc1cc(NNC(=O)C2CC2)nc(-c2ccccn2)n1] | | | | A | | | |
| 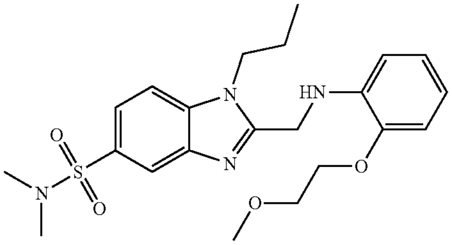 [SMILES: CCCn1c(CNc2ccccc2OCCOC)nc2cc(S(=O)(=O)N(C)C)ccc21] | | | | A | | | |
| 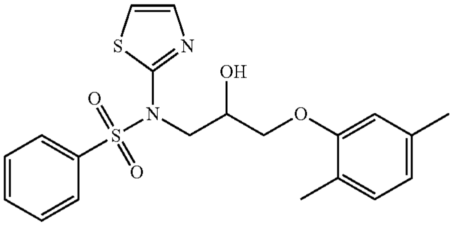 [SMILES: Cc1ccc(C)c(OCC(O)CN(c2nccs2)S(=O)(=O)c2ccccc2)c1] | | | | A | | | |
| 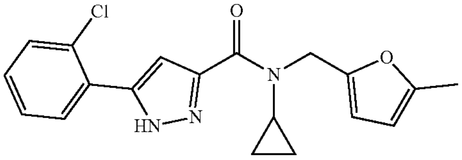 [SMILES: Cc1ccc(CN(C(=O)c2cc(-c3ccccc3Cl)[nH]n2)C2CC2)o1] | | | | A | | | |
| 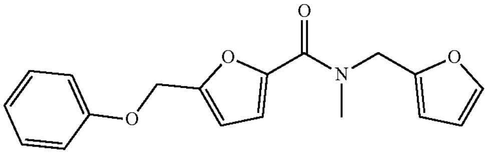 [SMILES: CN(Cc1ccco1)C(=O)c1ccc(COc2ccccc2)o1] | | | | A | | | |
| 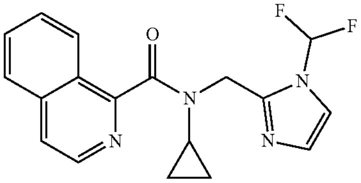 [SMILES: O=C(c1nccc2ccccc12)N(Cc1nccn1C(F)F)C1CC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 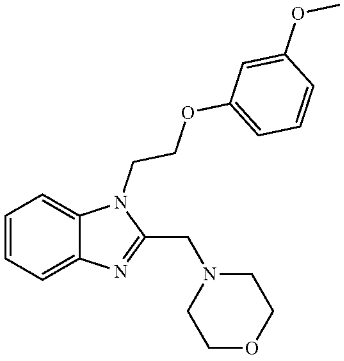 [SMILES: COc1cccc(OCCn2c(CN3CCOCC3)nc3ccccc32)c1] | | | | A | | | |
| 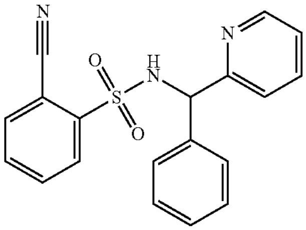 [SMILES: N#Cc1ccccc1S(=O)(=O)NC(c1ccccc1)c1ccccn1] | | | | A | | | |
| 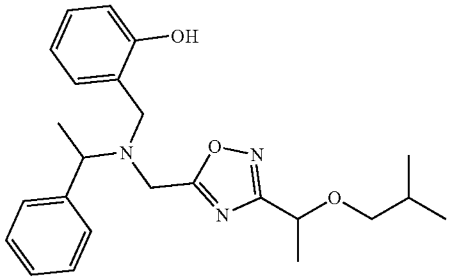 [SMILES: CC(C)COC(C)c1noc(CN(Cc2ccccc2O)C(C)c2ccccc2)n1] | | | | A | | | |
| 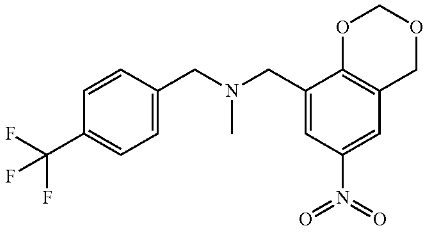 [SMILES: CN(Cc1ccc(C(F)(F)F)cc1)Cc1cc([N+](=O)[O-])cc2c1OCOC2] | | | | A | | | |
| 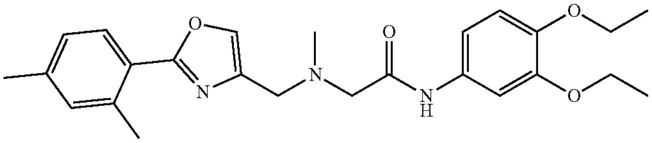 [SMILES: CCOc1ccc(NC(=O)CN(C)Cc2coc(-c3ccc(C)cc3C)n2)cc1OCC] | | | | A | | | |
| 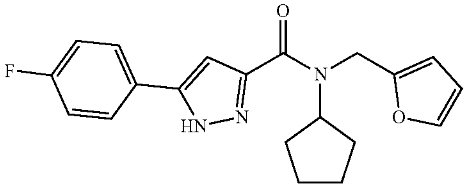 [SMILES: O=C(c1cc(-c2ccc(F)cc2)[nH]n1)N(Cc1ccco1)C1CCCC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 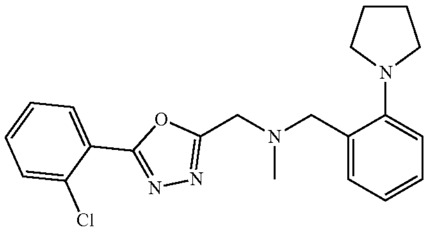 [SMILES: CN(Cc1nnc(-c2ccccc2Cl)o1)Cc1ccccc1N1CCCC1] | | | | A | | | |
| 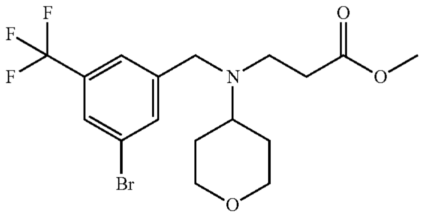 [SMILES: COC(=O)CCN(Cc1cc(Br)cc(C(F)(F)F)c1)C1CCOCC1] | | | | A | | | |
| 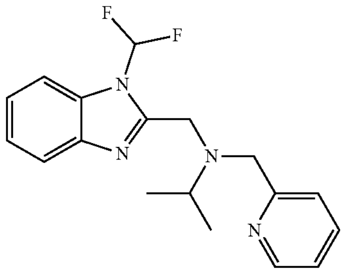 [SMILES: CC(C)N(Cc1ccccn1)Cc1nc2ccccc2n1C(F)F] | | | | A | | | |
| 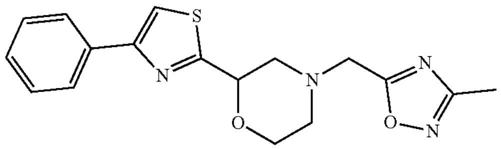 [SMILES: Cc1noc(CN2CCOC(c3nc(-c4ccccc4)cs3)C2)n1] | | | | A | | | |
| 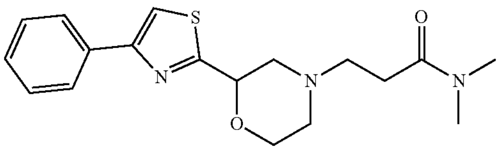 [SMILES: CN(C)C(=O)CCN1CCOC(c2nc(-c3ccccc3)cs2)C1] | | | | A | | | |
| 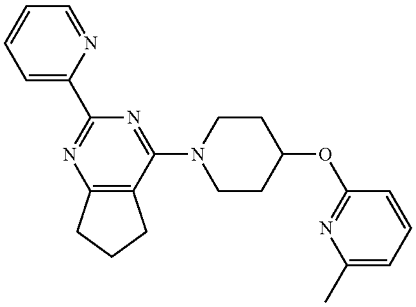 [SMILES: Cc1cccc(OC2CCN(c3nc(-c4ccccn4)nc4c3CCC4)CC2)n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 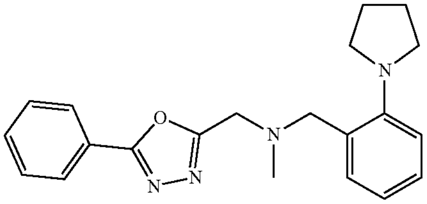 [SMILES: CN(Cc1nnc(-c2ccccc2)o1)Cc1ccccc1N1CCCC1] | | | | A | | | |
| 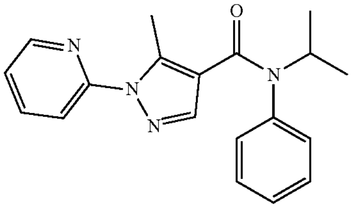 [SMILES: Cc1c(C(=O)N(c2ccccc2)C(C)C)cnn1-c1ccccn1] | | | | A | | | |
| 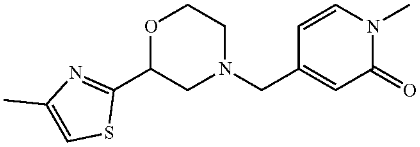 | | | | A | | | |
| 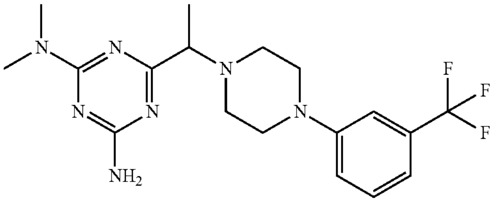 [SMILES: CC(c1nc(N)nc(N(C)C)n1)N1CCN(c2cccc(C(F)(F)F)c2)CC1] | | | | A | | | |
| 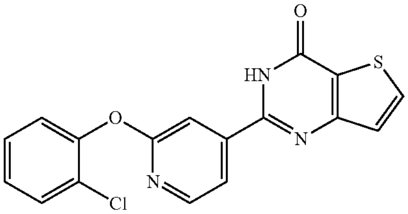 [SMILES: O=c1[nH]c(-c2ccnc(Oc3ccccc3Cl)c2)nc2ccsc12] | | | | A | | | |
| 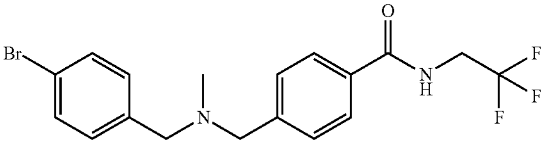 [SMILES: CN(Cc1ccc(Br)cc1)Cc1ccc(C(=O)NCC(F)(F)F)cc1] | | | | A | | | |
| 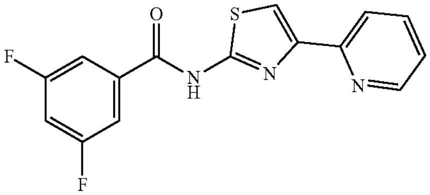 [SMILES: O=C(Nc1nc(-c2ccccn2)cs1)c1cc(F)cc(F)c1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 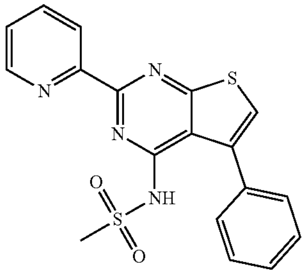 [SMILES: CS(=O)(=O)Nc1nc(-c2ccccn2)nc2scc(-c3ccccc3)c12] | | | | A | | | |
| 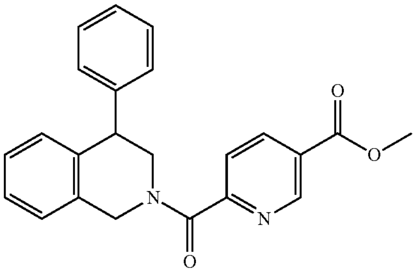 [SMILES: COC(=O)c1ccc(C(=O)N2Cc3ccccc3C(c3ccccc3)C2)nc1] | | | | A | | | |
| 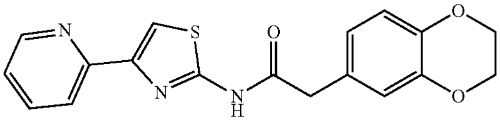 [SMILES: O=C(Cc1ccc2c(c1)OCCO2)Nc1nc(-c2ccccn2)cs1] | | | | A | | | |
| 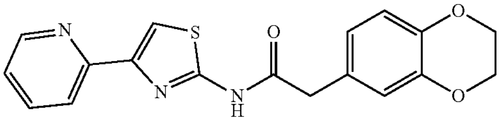 [SMILES: O=C(Cc1ccc2c(c1)OCCO2)Nc1nc(-c2ccccn2)cs1] | | | | A | | | |
| 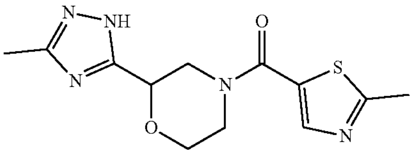 | | | | A | | | |
| 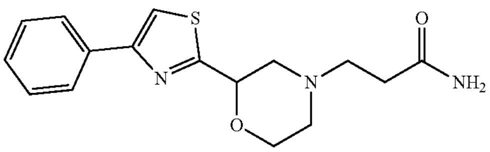 [SMILES: NC(=O)CCN1CCOC(c2nc(-c3ccccc3)cs2)C1] | | | | A | | | |
| 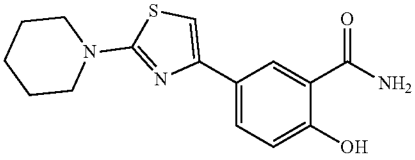 [SMILES: NC(=O)c1cc(-c2csc(N3CCCCC3)n2)ccc1O] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 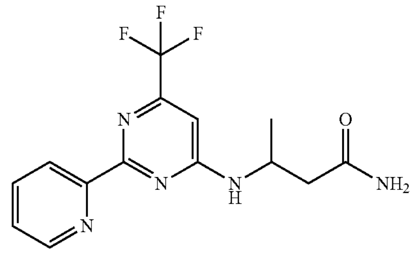 [SMILES: CC(CC(N)=O)Nc1cc(C(F)(F)F)nc(-c2ccccn2)n1] | | | | A | | | |
| 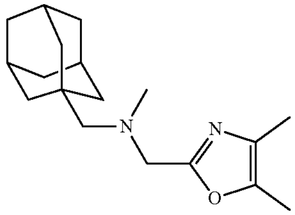 [SMILES: Cc1nc(CN(C)CC23CC4CC(CC(C4)C2)C3)oc1C] | | | | A | | | |
| 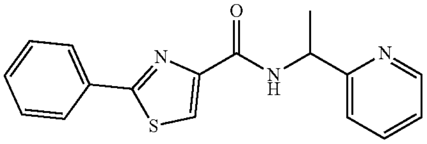 [SMILES: CC(NC(=O)c1csc(-c2ccccc2)n1)c1ccccn1] | | | | A | | | |
| 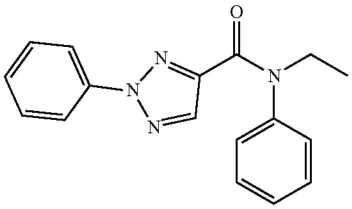 [SMILES: CCN(C(=O)c1cnn(-c2ccccc2)n1)c1ccccc1] | | | | A | | | |
| 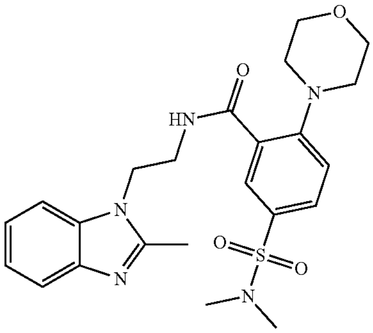 [SMILES: Cc1nc2ccccc2n1CCNC(=O)c1cc(S(=O)(=O)N(C)C)ccc1N1CCOCC1] | | | | A | | | |
| 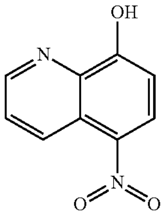 [SMILES: O=[N+]([O-])c1ccc(O)c2ncccc12] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 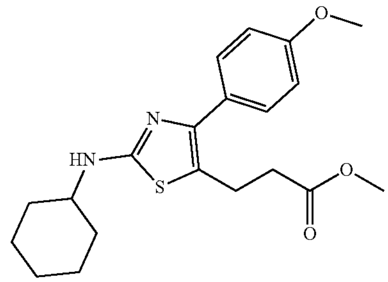 [SMILES: COC(=O)CCc1sc(NC2CCCCC2)nc1-c1ccc(OC)cc1] | | | | B | | | |
| 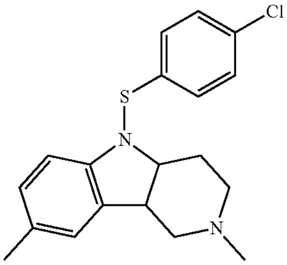 [SMILES: Cc1ccc2c(c1)C1CN(C)CCC1N2Sc1ccc(Cl)cc1] | | | | B | | | |
| 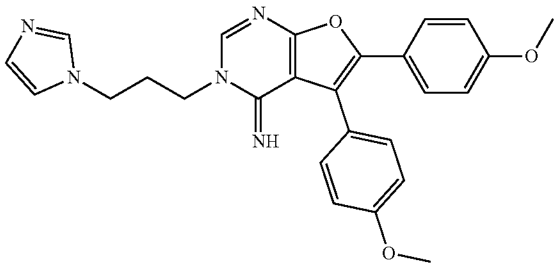 [SMILES: COc1ccc(-c2oc3ncn(CCCn4ccnc4)c(=N)c3c2-c2ccc(OC)cc2)cc1] | | | | B | | | |
| 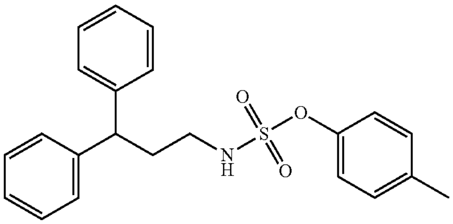 [SMILES: Cc1ccc(OS(=O)(=O)NCCC(c2ccccc2)c2ccccc2)cc1] | | | | A | | | |
| 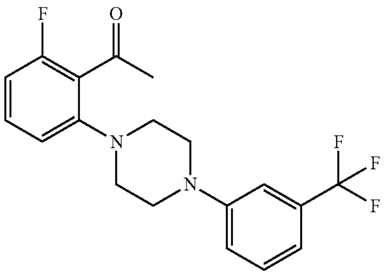 [SMILES: CC(=O)c1c(F)cccc1N1CCN(c2cccc(C(F)(F)F)c2)CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 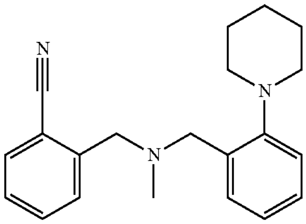 [SMILES: CN(Cc1ccccc1C#N)Cc1ccccc1N1CCCCC1] | | | | B | | | |
| 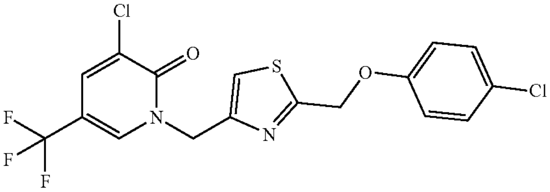 [SMILES: O=c1c(Cl)cc(C(F)(F)F)cn1Cc1csc(COc2ccc(Cl)cc2)n1] | | | | A | | | |
| 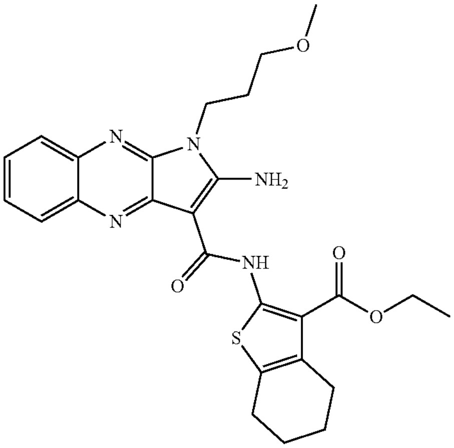 [SMILES: CCOC(=O)c1c(NC(=O)c2c(N)n(CCCOC)c3nc4ccccc4nc23)sc2c1CCCC2] | | | | A | | | |
| 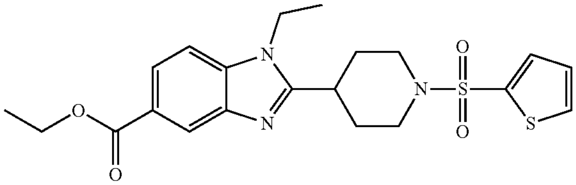 [SMILES: CCOC(=O)c1ccc2c(c1)nc(C1CCN(S(=O)(=O)c3cccs3)CC1)n2CC] | | | | B | | | |
| 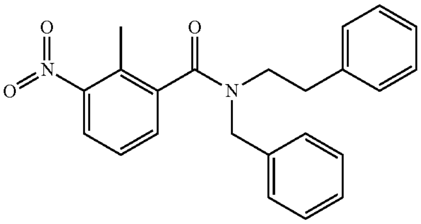 [SMILES: Cc1c(C(=O)N(CCc2ccccc2)Cc2ccccc2)cccc1[N+](=O)[O-]] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 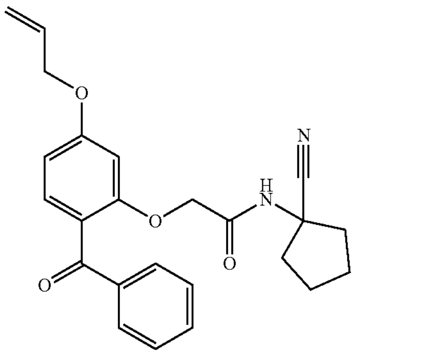 [SMILES: C=CCOc1ccc(C(=O)c2ccccc2)c(OCC(=O)NC2(C#N)CCCC2)c1] | | | | B | | | |
| 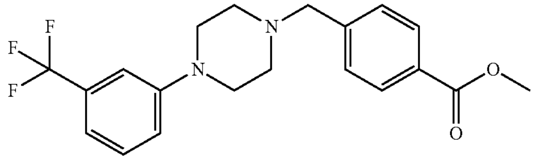 [SMILES: COC(=O)c1ccc(CN2CCN(c3cccc(C(F)(F)F)c3)CC2)cc1] | | | | B | | | |
| 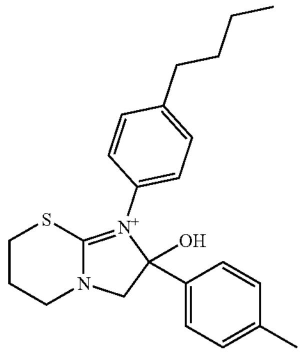 [SMILES: CCCCc1ccc([N+]2=C3SCCCN3CC2(O)c2ccc(C)cc2)cc1] | | | | B | | | |
| 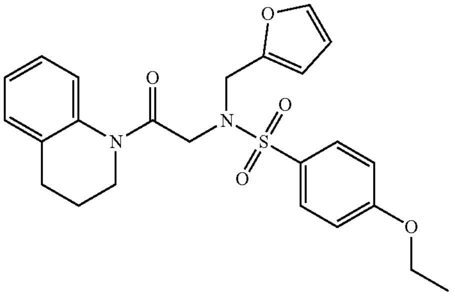 [SMILES: CCOc1ccc(S(=O)(=O)N(CC(=O)N2CCCc3ccccc32)Cc2ccco2)cc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 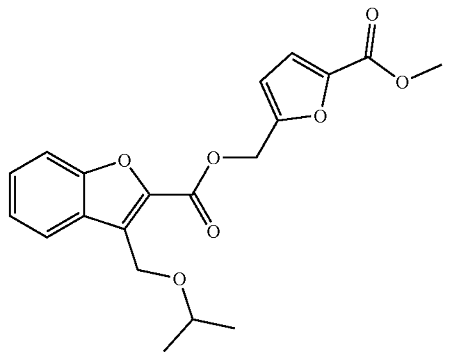 [SMILES: COC(=O)c1ccc(COC(=O)c2oc3ccccc3c2COC(C)C)o1] | | | | B | | | |
| 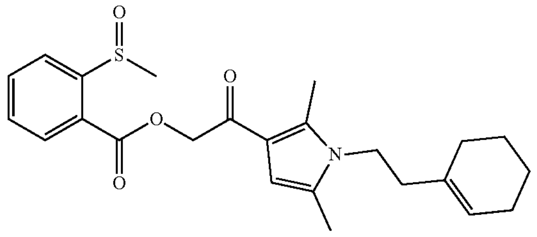 [SMILES: Cc1cc(C(=O)COC(=O)c2ccccc2S(C)=O)c(C)n1CCC1=CCCCC1] | | | | A | | | |
| 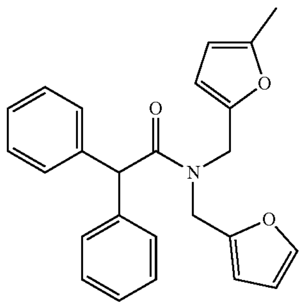 [SMILES: Cc1ccc(CN(Cc2ccco2)C(=O)C(c2ccccc2)c2ccccc2)o1] | | | | B | | | |
| 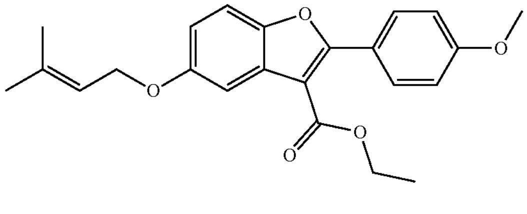 [SMILES: CCOC(=O)c1c(-c2ccc(OC)cc2)oc2ccc(OCC=C(C)C)cc12] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 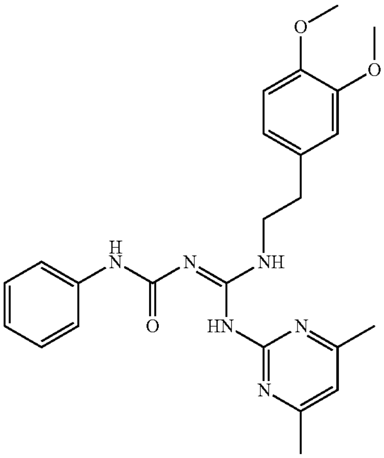 [SMILES: COc1ccc(CCN/C(=N/C(=O)Nc2ccccc2)Nc2nc(C)cc(C)n2)cc1OC] | | | | B | | | |
| 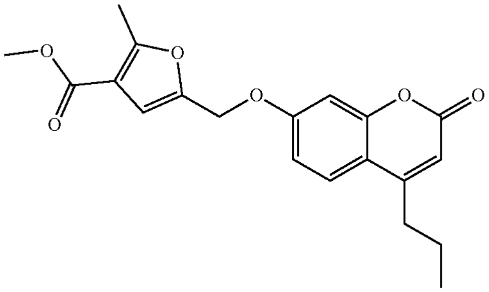 [SMILES: CCCc1cc(=O)oc2cc(OCc3cc(C(=O)OC)c(C)o3)ccc12] | | | | B | | | |
| 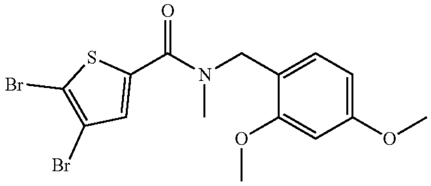 [SMILES: COc1ccc(CN(C)C(=O)c2cc(Br)c(Br)s2)c(OC)c1] | | | | B | | | |
| 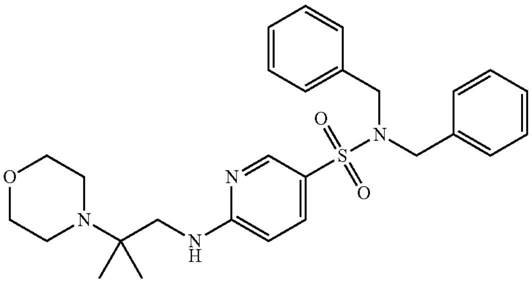 [SMILES: CC(C)(CNc1ccc(S(=O)(=O)N(Cc2ccccc2)Cc2ccccc2)cn1)N1CCOCC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 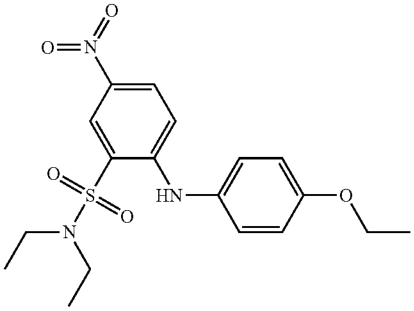 [SMILES: CCOc1ccc(Nc2ccc([N+](=O)[O-])cc2S(=O)(=O)N(CC)CC)cc1] | | | | B | | | |
| 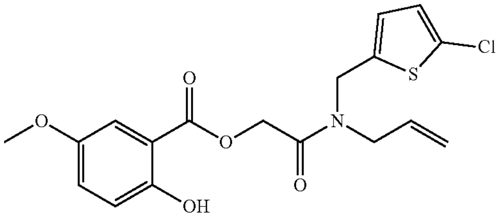 [SMILES: C=CCN(Cc1ccc(Cl)s1)C(=O)COC(=O)c1cc(OC)ccc1O] | | | | B | | | |
| 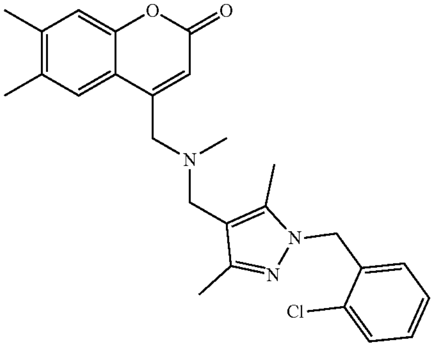 [SMILES: Cc1cc2oc(=O)cc(CN(C)Cc3c(C)nn(Cc4ccccc4Cl)c3C)c2cc1C] | | | | B | | | |
| 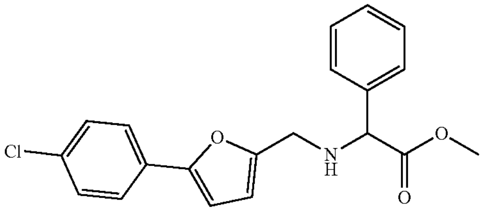 [SMILES: COC(=O)C(NCc1ccc(-c2ccc(Cl)cc2)o1)c1ccccc1] | | | | B | | | |
| 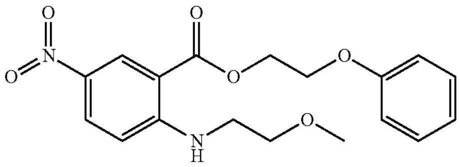 [SMILES: COCCNc1ccc([N+](=O)[O-])cc1C(=O)OCCOc1ccccc1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 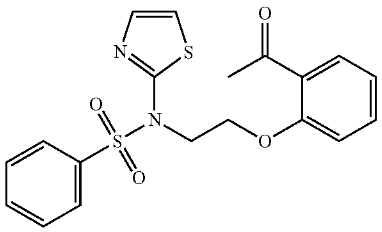 [SMILES: CC(=O)c1ccccc1OCCN(c1nccs1)S(=O)(=O)c1ccccc1] | | | | B | | | |
| 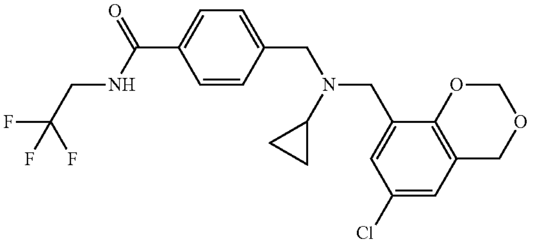 [SMILES: O=C(NCC(F)(F)F)c1ccc(CN(Cc2cc(Cl)cc3c2OCOC3)C2CC2)cc1] | | | | B | | | |
| 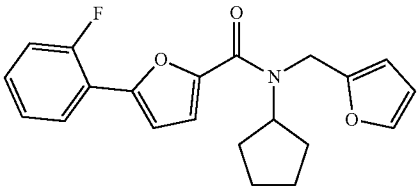 [SMILES: O=C(c1ccc(-c2ccccc2F)o1)N(Cc1ccco1)C1CCCC1] | | | | C | | | |
| 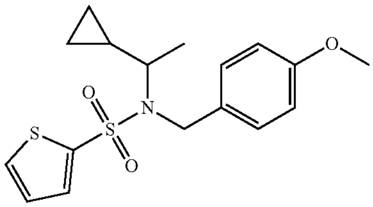 [SMILES: COc1ccc(CN(C(C)C2CC2)S(=O)(=O)c2cccs2)cc1] | | | | B | | | |
| 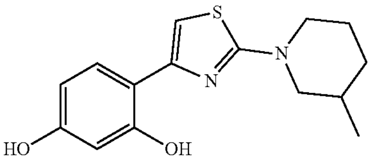 [SMILES: CC1CCCN(c2nc(-c3ccc(O)cc3O)cs2)C1] | | | | B | | | |
| 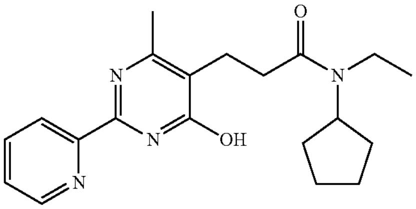 [SMILES: CCN(C(=O)CCc1c(C)nc(-c2ccccn2)nc1O)C1CCCC1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 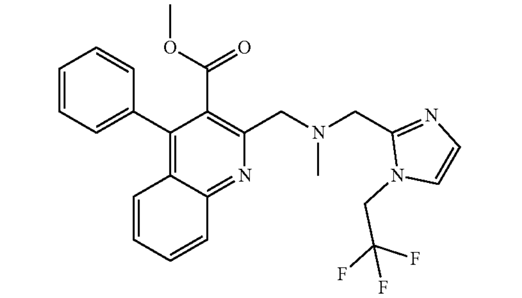 [SMILES: COC(=O)c1c(CN(C)Cc2nccn2CC(F)(F)F)nc2ccccc2c1-c1ccccc1] | | | | B | | | |
| 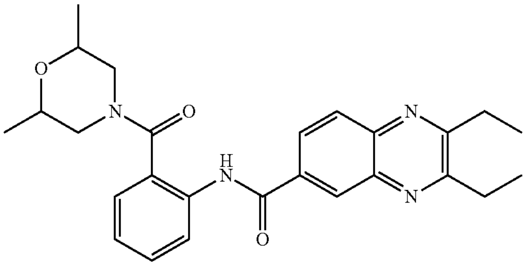 [SMILES: CCc1nc2ccc(C(=O)Nc3ccccc3C(=O)N3CC(C)OC(C)C3)cc2nc1CC] | | | | B | | | |
| 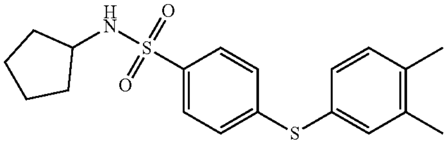 [SMILES: Cc1ccc(Sc2ccc(S(=O)(=O)NC3CCCC3)cc2)cc1C] | | | | A | | | |
| 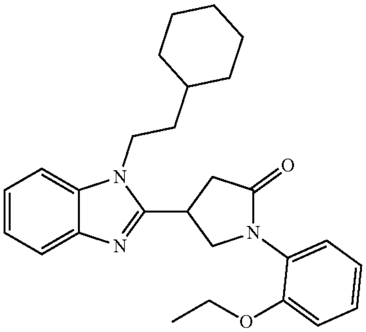 [SMILES: CCOc1ccccc1N1CC(c2nc3ccccc3n2CCC2CCCCC2)CC1=O] | | | | B | | | |
| 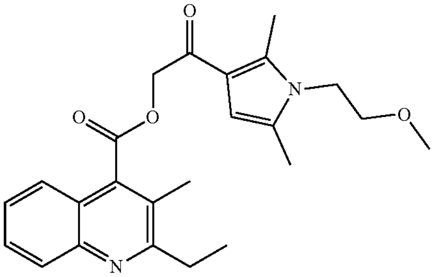 [SMILES: CCc1nc2ccccc2c(C(=O)OCC(=O)c2cc(C)n(CCOC)c2C)c1C] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 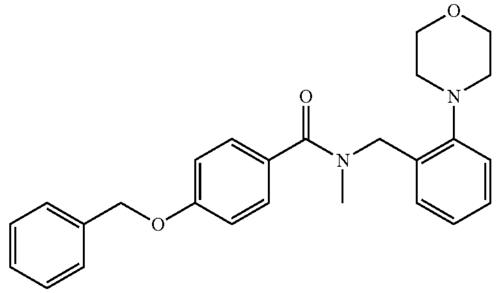 [SMILES: CN(Cc1ccccc1N1CCOCC1)C(=O)c1ccc(OCc2ccccc2)cc1] | | | | A | | | |
| 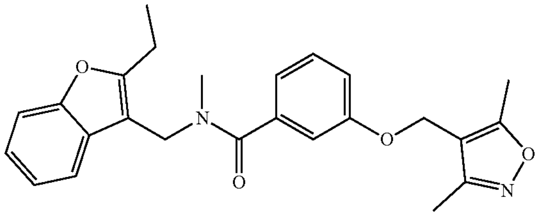 [SMILES: CCc1oc2ccccc2c1CN(C)C(=O)c1cccc(OCc2c(C)noc2C)c1] | | | | B | | | |
| 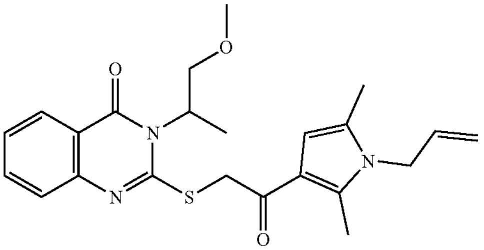 [SMILES: C=CCn1c(C)cc(C(=O)CSc2nc3ccccc3c(=O)n2C(C)COC)c1C] | | | | B | | | |
| 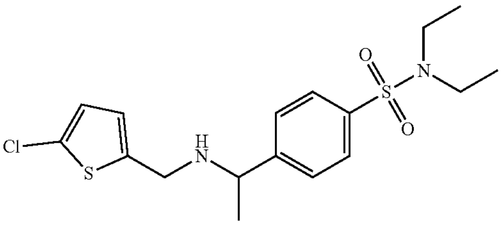 [SMILES: CCN(CC)S(=O)(=O)c1ccc(C(C)NCc2ccc(Cl)s2)cc1] | | | | B | | | |
| 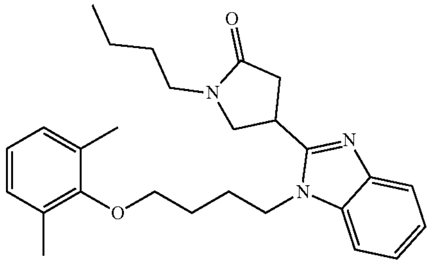 [SMILES: CCCCN1CC(c2nc3ccccc3n2CCCCOc2c(C)cccc2C)CC1=O] | | | | A | | | |
| 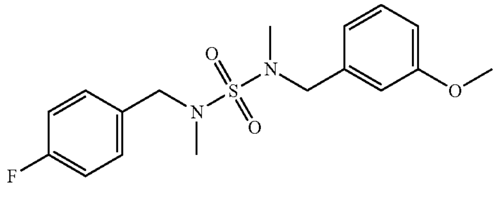 [SMILES: COc1cccc(CN(C)S(=O)(=O)N(C)Cc2ccc(F)cc2)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 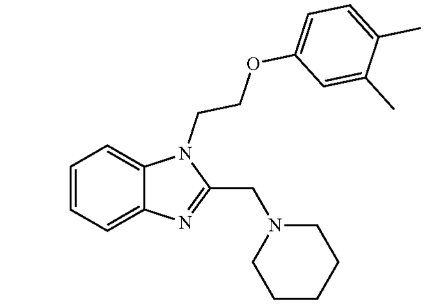 [SMILES: Cc1ccc(OCCn2c(CN3CCCCC3)nc3ccccc32)cc1C] | | | | B | | | |
| 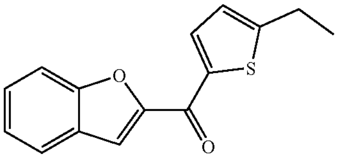 [SMILES: CCc1ccc(C(=O)c2cc3ccccc3o2)s1] | | | | B | | | |
| 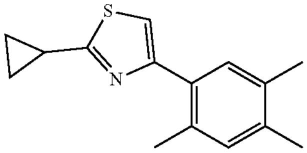 [SMILES: Cc1cc(C)c(-c2csc(C3CC3)n2)cc1C] | | | | B | | | |
| 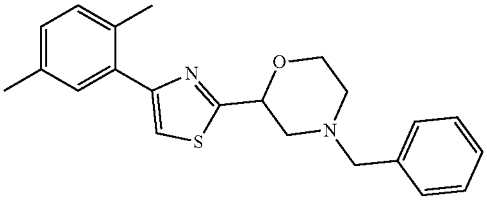 [SMILES: Cc1ccc(C)c(-c2csc(C3CN(Cc4ccccc4)CCO3)n2)c1] | | | | B | | | |
| 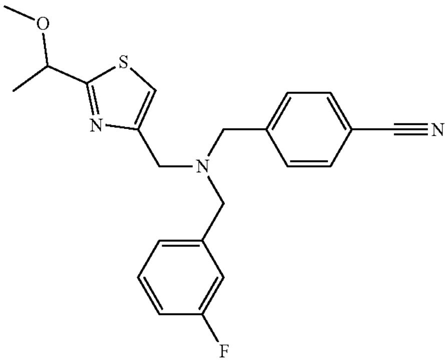 [SMILES: COC(C)c1nc(CN(Cc2ccc(C#N)cc2)Cc2cccc(F)c2)cs1] | | | | B | | | |
| 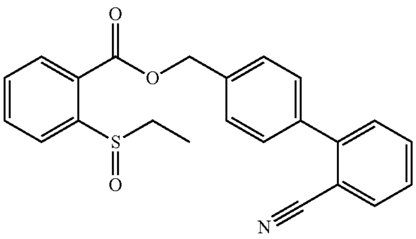 [SMILES: CCS(=O)c1ccccc1C(=O)OCc1ccc(-c2ccccc2C#N)cc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 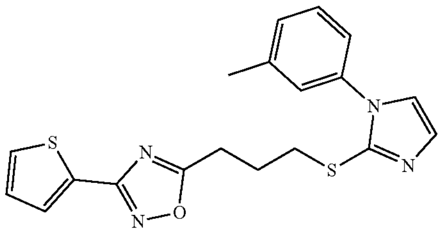 [SMILES: Cc1cccc(-n2ccnc2SCCCc2nc(-c3cccs3)no2)c1] | | | | B | | | |
| 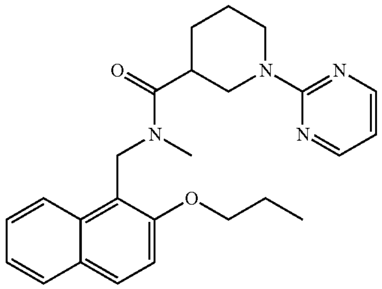 [SMILES: CCCOc1ccc2ccccc2c1CN(C)C(=O)C1CCCN(c2ncccn2)C1] | | | | B | | | |
| 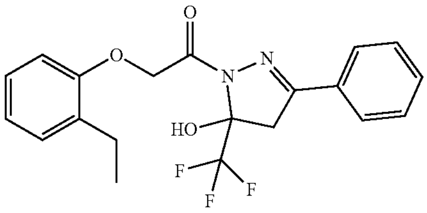 [SMILES: CCc1ccccc1OCC(=O)N1N=C(c2ccccc2)CC1(O)C(F)(F)F] | | | | B | | | |
| 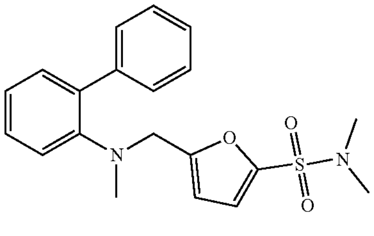 [SMILES: CN(Cc1ccc(S(=O)(=O)N(C)C)o1)c1ccccc1-c1ccccc1] | | | | A | | | |
| 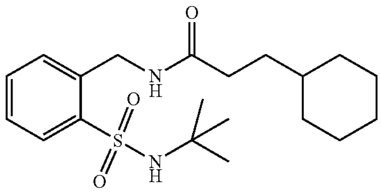 [SMILES: CC(C)(C)NS(=O)(=O)c1ccccc1CNC(=O)CCC1CCCCC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 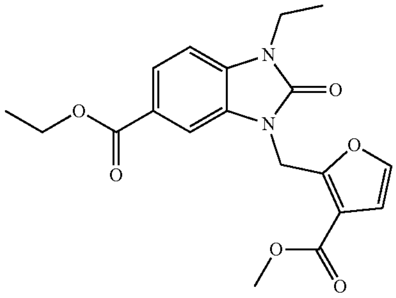 [SMILES: CCOC(=O)c1ccc2c(c1)n(Cc1occc1C(=O)OC)c(=O)n2CC] | | | | A | | | |
| 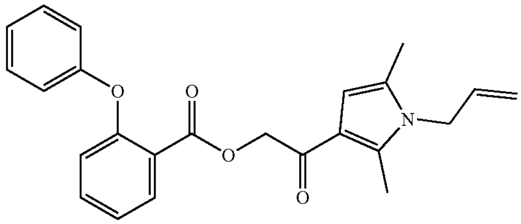 [SMILES: C=CCn1c(C)cc(C(=O)COC(=O)c2ccccc2Oc2ccccc2)c1C] | | | | C | | | |
| 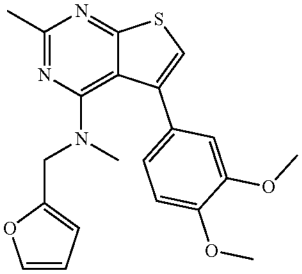 | | | | B | | | |
| 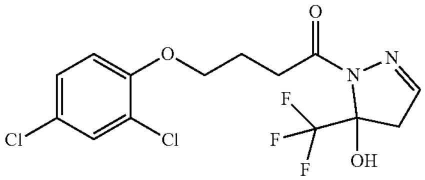 [SMILES: O=C(CCCOc1ccc(Cl)cc1Cl)N1N=CCC1(O)C(F)(F)F] | | | | B | | | |
| 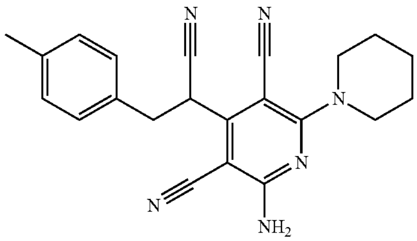 [SMILES: Cc1ccc(CC(C#N)c2c(C#N)c(N)nc(N3CCCCC3)c2C#N)cc1] | | | | A | | | |
| 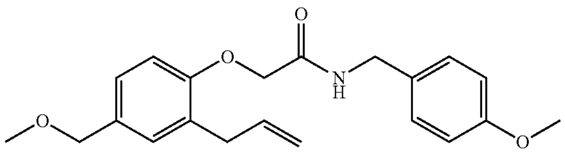 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 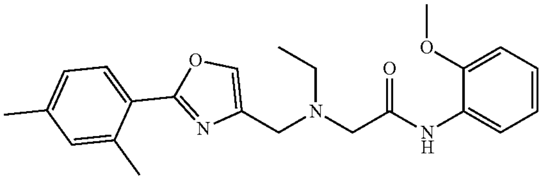 [SMILES: CCN(CC(=O)Nc1ccccc1OC)Cc1coc(-c2ccc(C)cc2C)n1] | | | | B | | | |
| 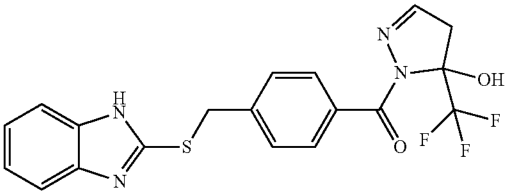 [SMILES: O=C(c1ccc(CSc2nc3ccccc3[nH]2)cc1)N1N=CCC1(O)C(F)(F)F] | | | | B | | | |
| 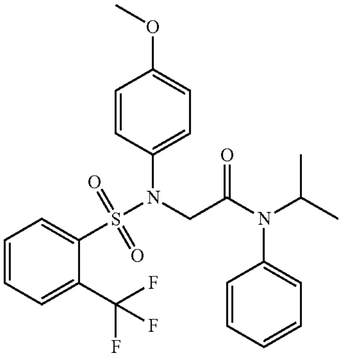 [SMILES: COc1ccc(N(CC(=O)N(c2ccccc2)C(C)C)S(=O)(=O)c2ccccc2C(F)(F)F)cc1] | | | | B | | | |
| 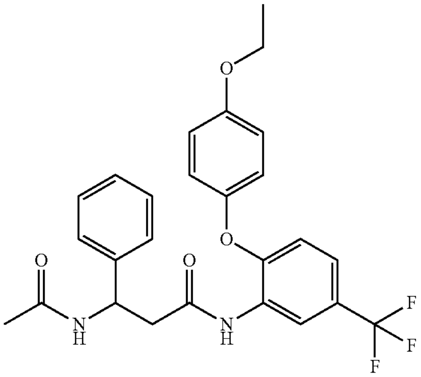 [SMILES: CCOc1ccc(Oc2ccc(C(F)(F)F)cc2NC(=O)CC(NC(C)=O)c2ccccc2)cc1] | | | | A | | | |
| 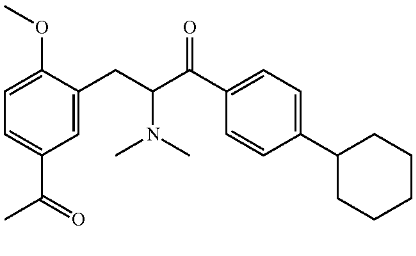 [SMILES: COc1ccc(C(C)=O)cc1CC(C(=O)c1ccc(C2CCCCC2)cc1)N(C)C] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 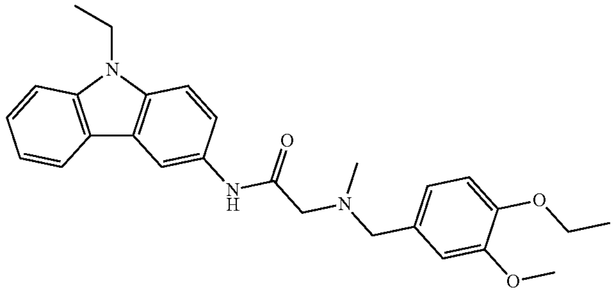 [SMILES: CCOc1ccc(CN(C)CC(=O)Nc2ccc3c(c2)c2ccccc2n3CC)cc1OC] | | | | B | | | |
| 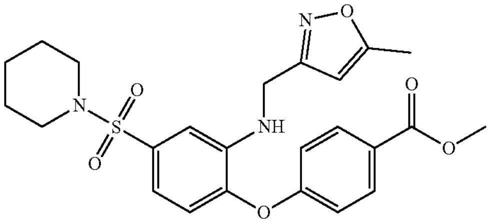 [SMILES: COC(=O)c1ccc(Oc2ccc(S(=O)(=O)N3CCCCC3)cc2NCc2cc(C)on2)cc1] | | | | B | | | |
| 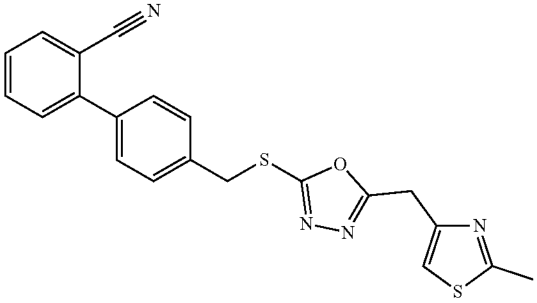 [SMILES: Cc1nc(Cc2nnc(SCc3ccc(-c4ccccc4C#N)cc3)o2)cs1] | | | | A | | | |
| 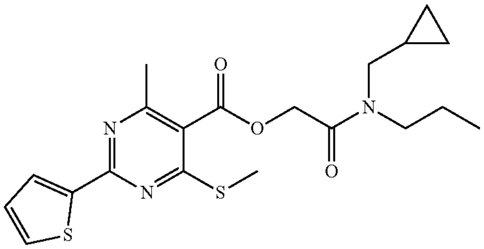 [SMILES: CCCN(CC1CC1)C(=O)COC(=O)c1c(C)nc(-c2cccs2)nc1SC] | | | | A | | | |
| 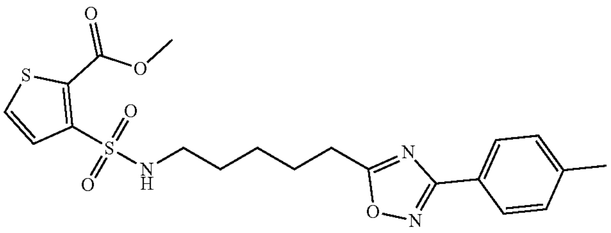 [SMILES: COC(=O)c1sccc1S(=O)(=O)NCCCCCc1nc(-c2ccc(C)cc2)no1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 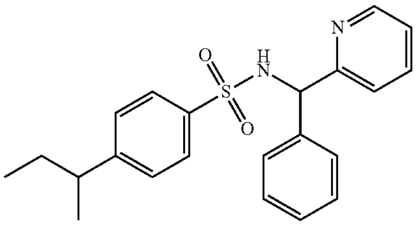 [SMILES: CCC(C)c1ccc(S(=O)(=O)NC(c2ccccc2)c2ccccn2)cc1] | | | | B | | | |
| 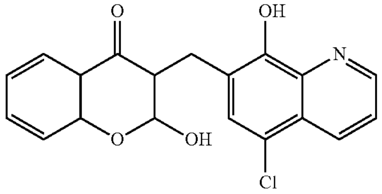 [SMILES: O=C1C2C=CC=CC2OC(O)C1Cc1cc(Cl)c2cccnc2c1O] | | | | B | | | |
| 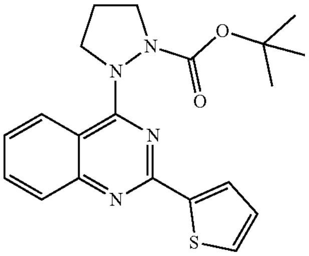 [SMILES: CC(C)(C)OC(=O)N1CCCN1c1nc(-c2cccs2)nc2ccccc12] | | | | B | | | |
| 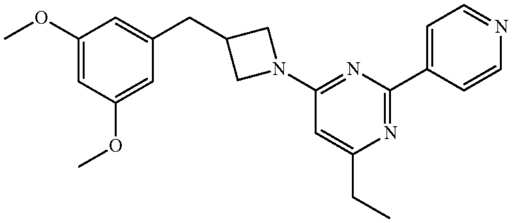 [SMILES: CCc1cc(N2CC(Cc3cc(OC)cc(OC)c3)C2)nc(-c2ccncc2)n1] | | | | A | | | |
| 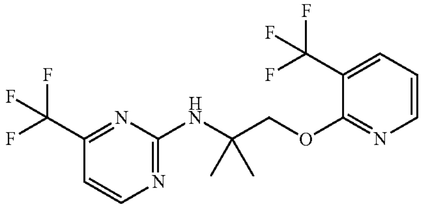 [SMILES: CC(C)(COc1ncccc1C(F)(F)F)Nc1nccc(C(F)(F)F)n1] | | | | B | | | |
| 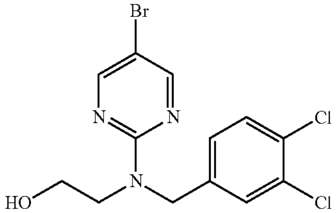 [SMILES: OCCN(Cc1ccc(Cl)c(Cl)c1)c1ncc(Br)cn1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 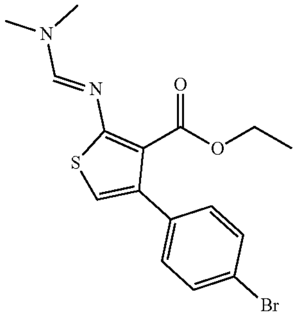 [SMILES: CCOC(=O)c1c(-c2ccc(Br)cc2)csc1/N=C/N(C)C] | | | | B | | | |
| 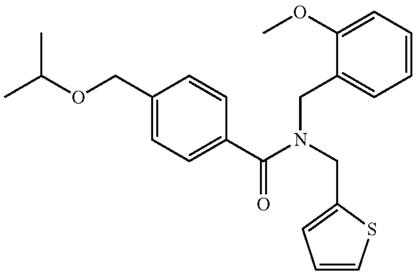 [SMILES: COc1ccccc1CN(Cc1cccs1)C(=O)c1ccc(COC(C)C)cc1] | | | | B | | | |
| 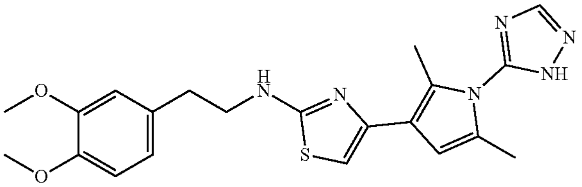 [SMILES: COc1ccc(CCNc2nc(-c3cc(C)n(-c4ncn[nH]4)c3C)cs2)cc1OC] | | | | B | | | |
| 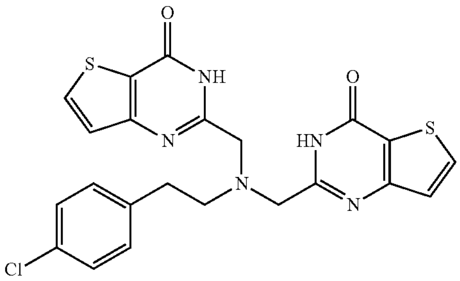 [SMILES: O=c1[nH]c(CN(CCc2ccc(Cl)cc2)Cc2nc3ccsc3c(=O)[nH]2)nc2ccsc12] | | | | B | | | |
| 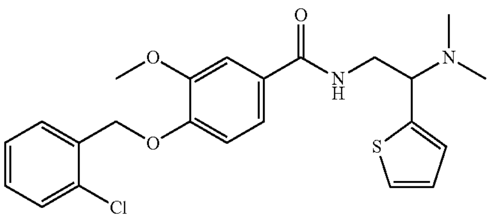 | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 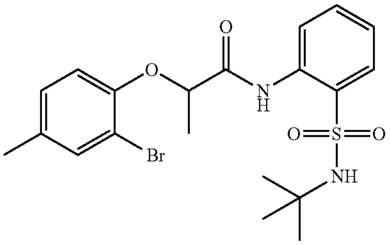 [SMILES: Cc1ccc(OC(C)C(=O)Nc2ccccc2S(=O)(=O)NC(C)(C)C)c(Br)c1] | | | | A | | | |
| 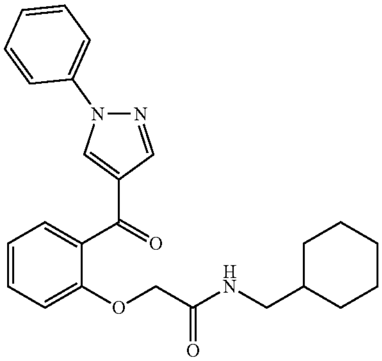 [SMILES: O=C(COc1ccccc1C(=O)c1cnn(-c2ccccc2)c1)NCC1CCCCC1] | | | | B | | | |
| 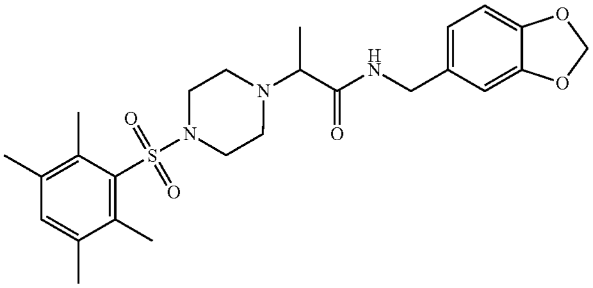 [SMILES: Cc1cc(C)c(C)c(S(=O)(=O)N2CCN(C(C)C(=O)NCc3ccc4c(c3)OCO4)CC2)c1C] | | | | A | | | |
| 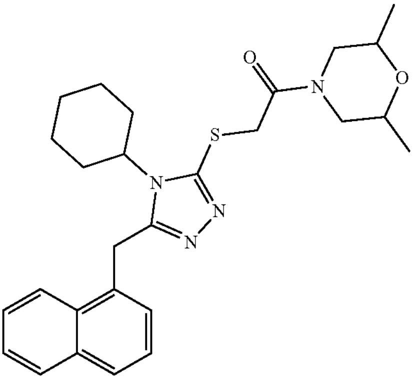 [SMILES: CC1CN(C(=O)CSc2nnc(Cc3cccc4ccccc34)n2C2CCCCC2)CC(C)O1] | | | | B | | | |
| 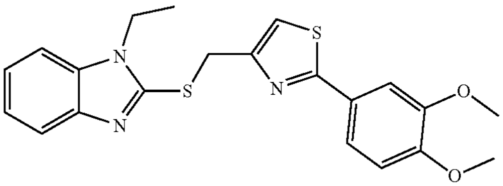 [SMILES: CCn1c(SCc2csc(-c3ccc(OC)c(OC)c3)n2)nc2ccccc21] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 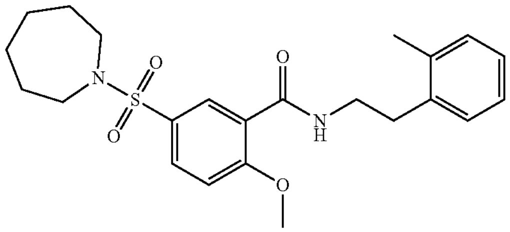 [SMILES: COc1ccc(S(=O)(=O)N2CCCCCC2)cc1C(=O)NCCc1ccccc1C] | | | | A | | | |
| 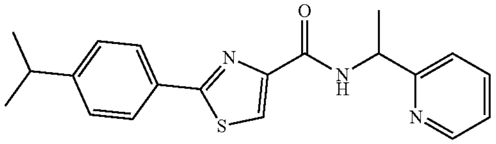 [SMILES: CC(C)c1ccc(-c2nc(C(=O)NC(C)c3ccccn3)cs2)cc1] | | | | B | | | |
| 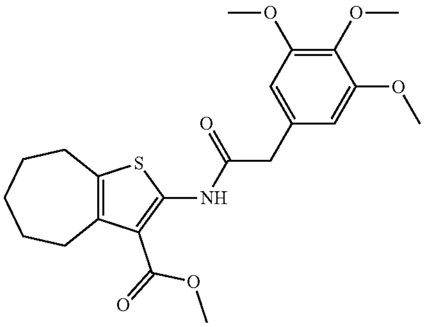 [SMILES: COC(=O)c1c(NC(=O)Cc2cc(OC)c(OC)c(OC)c2)sc2c1CCCCC2] | | | | B | | | |
| 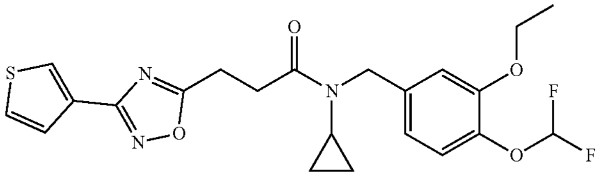 [SMILES: CCOc1cc(CN(C(=O)CCc2nc(-c3ccsc3)no2)C2CC2)ccc1OC(F)F] | | | | B | | | |
| 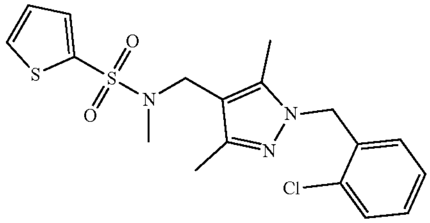 [SMILES: Cc1nn(Cc2ccccc2Cl)c(C)c1CN(C)S(=O)(=O)c1cccs1] | | | | A | | | |
| 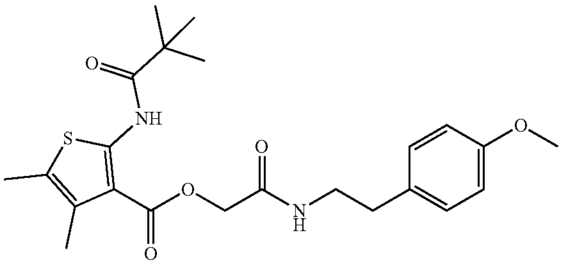 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 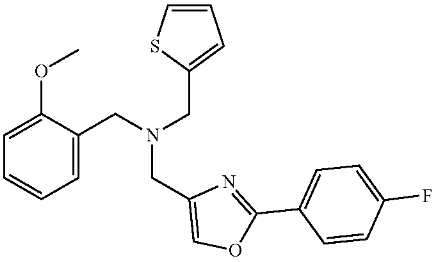 [SMILES: COc1ccccc1CN(Cc1coc(-c2ccc(F)cc2)n1)Cc1cccs1] | | | | A | | | |
| 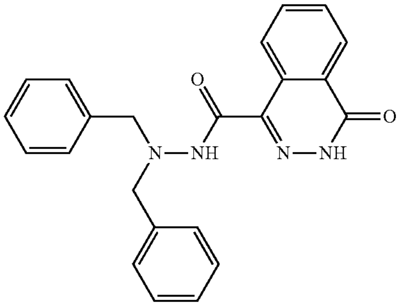 [SMILES: O=C(NN(Cc1ccccc1)Cc1ccccc1)c1n[nH]c(=O)c2ccccc12] | | | | B | | | |
| 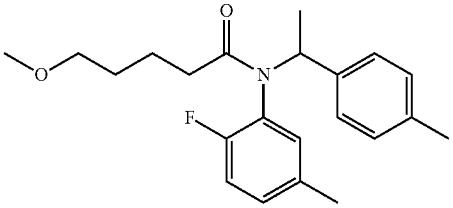 | | | | A | | | |
| 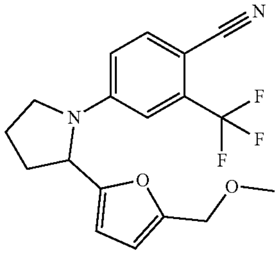 [SMILES: COCc1ccc(C2CCCN2c2ccc(C#N)c(C(F)(F)F)c2)o1] | | | | B | | | |
| 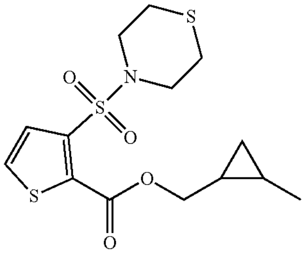 [SMILES: CC1CC1COC(=O)c1sccc1S(=O)(=O)N1CCSCC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 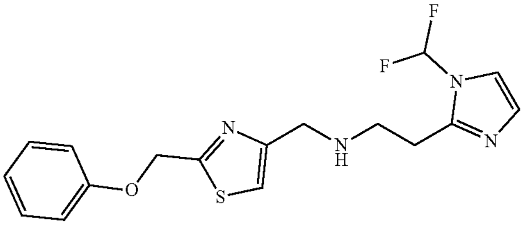 [SMILES: FC(F)n1ccnc1CCNCc1csc(COc2ccccc2)n1] | | | | C | | | |
| 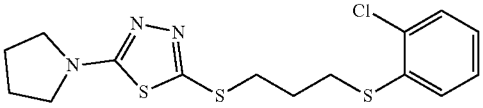 [SMILES: Clc1ccccc1SCCCSc1nnc(N2CCCC2)s1] | | | | B | | | |
| 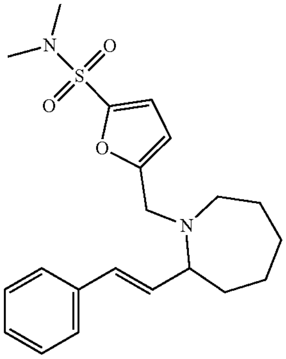 [SMILES: CN(C)S(=O)(=O)c1ccc(CN2CCCCCC2/C=C/c2ccccc2)o1] | | | | B | | | |
| 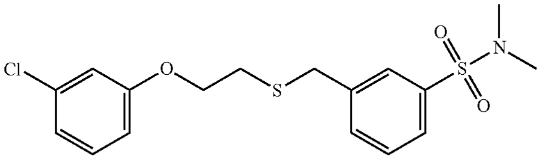 [SMILES: CN(C)S(=O)(=O)c1cccc(CSCCOc2cccc(Cl)c2)c1] | | | | B | | | |
| 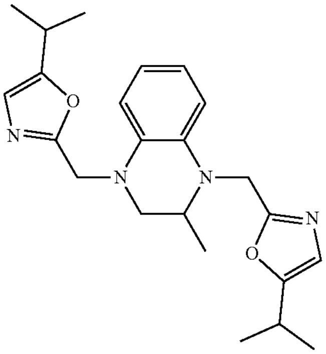 [SMILES: CC(C)c1cnc(CN2CC(C)N(Cc3ncc(C(C)C)o3)c3ccccc32)o1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 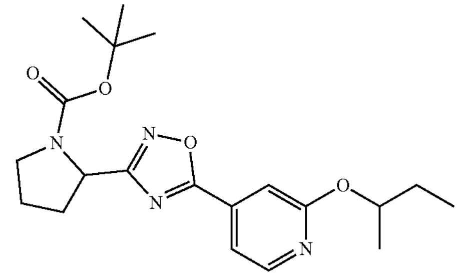 [SMILES: CCC(C)Oc1cc(-c2nc(C3CCCN3C(=O)OC(C)(C)C)no2)ccn1] | | | | B | | | |
| 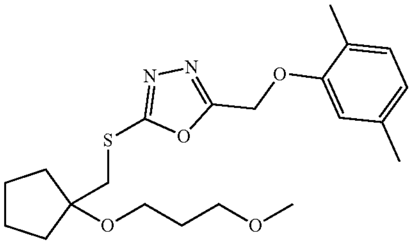 [SMILES: COCCCOC1(CSc2nnc(COc3cc(C)ccc3C)o2)CCCC1] | | | | B | | | |
| 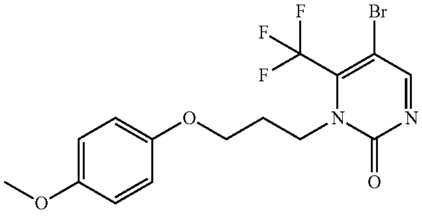 [SMILES: COc1ccc(OCCCn2c(C(F)(F)F)c(Br)cnc2=O)cc1] | | | | B | | | |
| 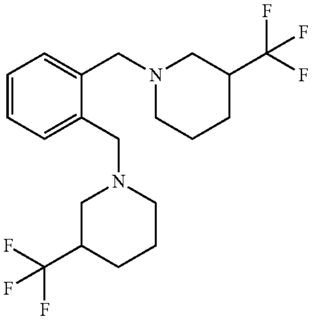 [SMILES: FC(F)(F)C1CCCN(Cc2ccccc2CN2CCCC(C(F)(F)F)C2)C1] | | | | B | | | |
| 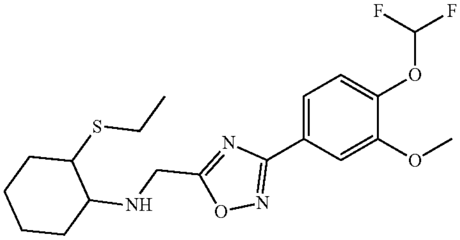 [SMILES: CCSC1CCCCC1NCc1nc(-c2ccc(OC(F)F)c(OC)c2)no1] | | | | B | | | |

TABLE 7-continued
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| % Inhibition at 20 μM of K-Ras mutant and wild-type protein | | | | | | | |
| 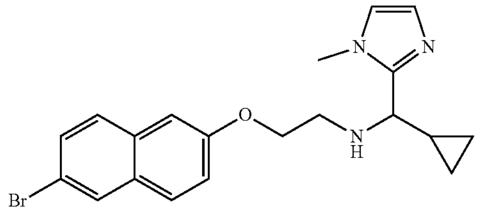 [SMILES: Cn1ccnc1C(NCCOc1ccc2cc(Br)ccc2c1)C1CC1] | | | | A | | | |
| 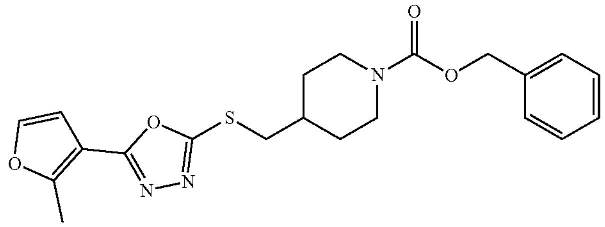 [SMILES: Cc1occc1-c1nnc(SCC2CCN(C(=O)OCc3ccccc3)CC2)o1] | | | | B | | | |
| 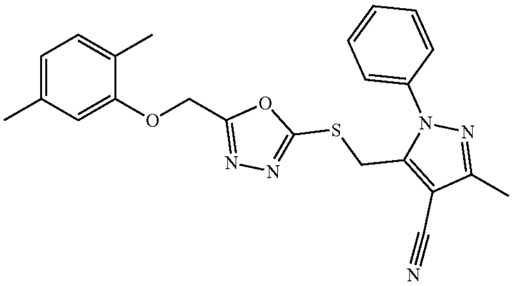 | | | | B | | | |
| 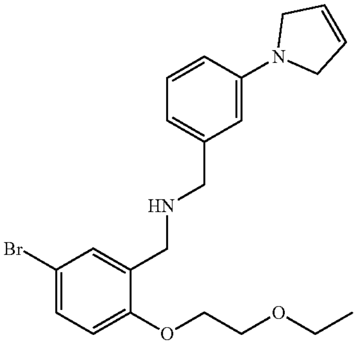 [SMILES: CCOCCOc1ccc(Br)cc1CNCc1cccc(N2CC=CC2)c1] | | | | B | | | |
| 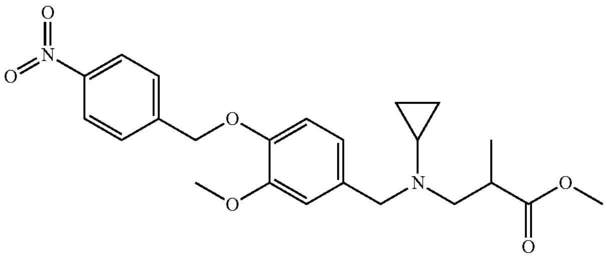 [SMILES: COC(=O)C(C)CN(Cc1ccc(OCc2ccc([N+](=O)[O-])cc2)c(OC)c1)C1CC1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 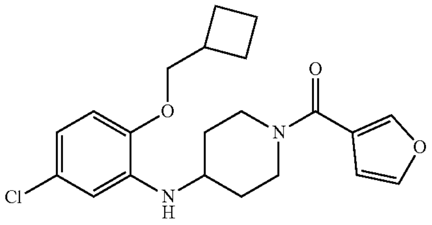 [SMILES: O=C(c1ccoc1)N1CCC(Nc2cc(Cl)ccc2OCC2CCC2)CC1] | | | | B | | | |
| 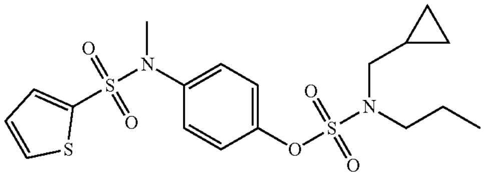 [SMILES: CCCN(CC1CC1)S(=O)(=O)Oc1ccc(N(C)S(=O)(=O)c2cccs2)cc1] | | | | B | | | |
| 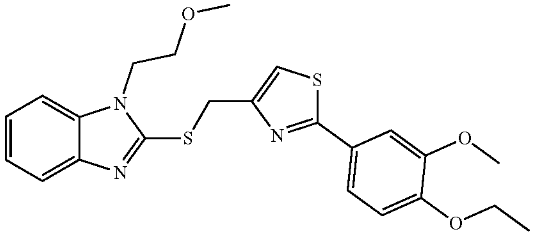 [SMILES: CCOc1ccc(-c2nc(CSc3nc4ccccc4n3CCOC)cs2)cc1OC] | | | | B | | | |
| 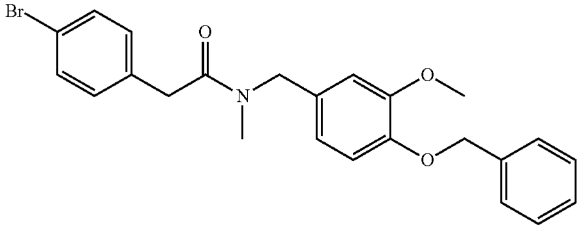 [SMILES: COc1cc(CN(C)C(=O)Cc2ccc(Br)cc2)ccc1OCc1ccccc1] | | | | A | | | |
| 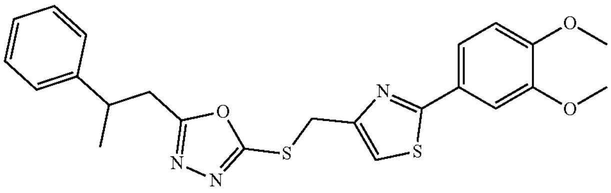 [SMILES: COc1ccc(-c2nc(CSc3nnc(CC(C)c4ccccc4)o3)cs2)cc1OC] | | | | B | | | |
| 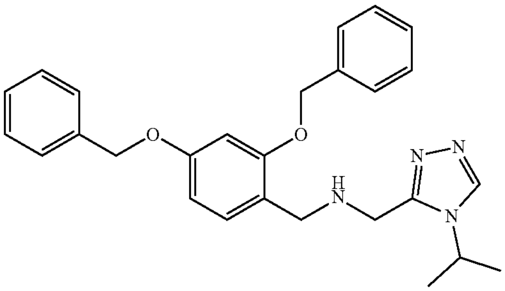 [SMILES: CC(C)n1cnnc1CNCc1ccc(OCc2ccccc2)cc1OCc1ccccc1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 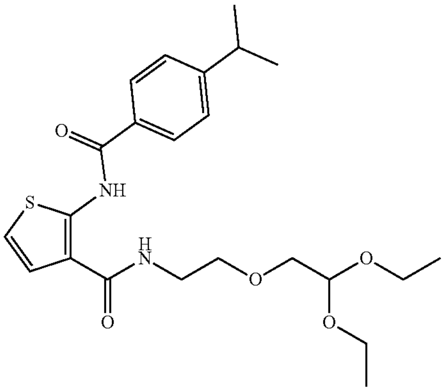 [SMILES: CCOC(COCCNC(=O)c1ccsc1NC(=O)c1ccc(C(C)C)cc1)OCC] | | | | A | | | |
| 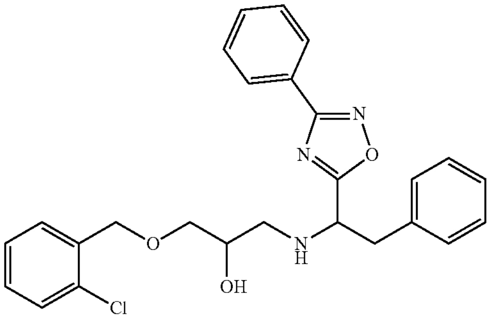 [SMILES: OC(CNC(Cc1ccccc1)c1nc(-c2ccccc2)no1)COCc1ccccc1Cl] | | | | B | | | |
| 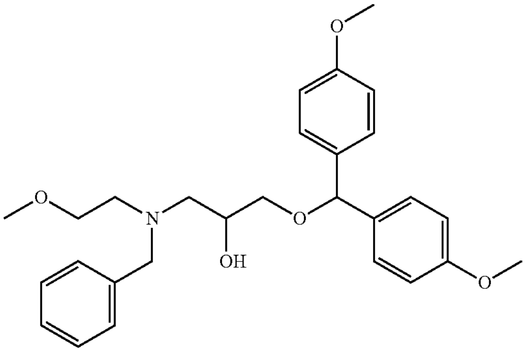 | | | | A | | | |
| 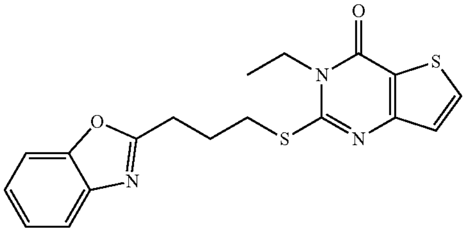 [SMILES: CCn1c(SCCCc2nc3ccccc3o2)nc2ccsc2c1=O] | | | | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 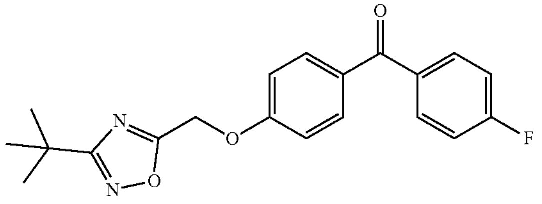 [SMILES: CC(C)(C)c1noc(COc2ccc(C(=O)c3ccc(F)cc3)cc2)n1] | | | | B | | | |
| 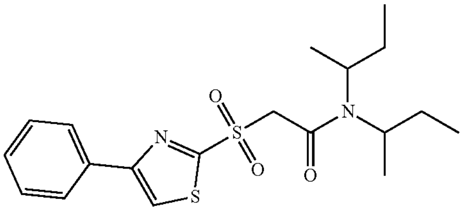 [SMILES: CCC(C)N(C(=O)CS(=O)(=O)c1nc(-c2ccccc2)cs1)C(C)CC] | | | | B | | | |
| 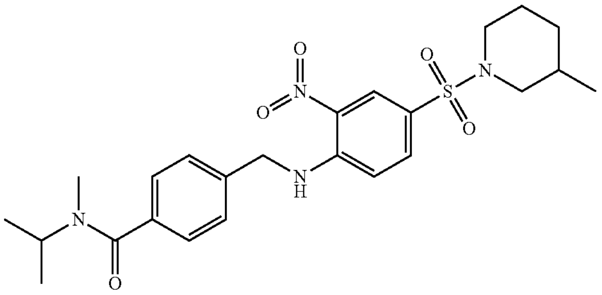 [SMILES: CC1CCCN(S(=O)(=O)c2ccc(NCc3ccc(C(=O)N(C)C(C)C)cc3)c([N+](=O)[O-])c2)C1] | | | | B | | | |
| 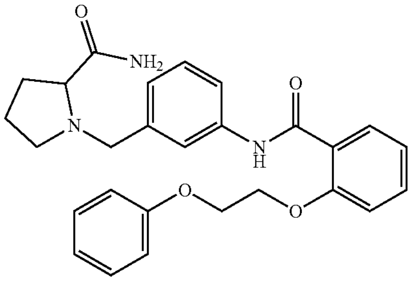 [SMILES: NC(=O)C1CCCN1Cc1cccc(NC(=O)c2ccccc2OCCOc2ccccc2)c1] | | | | B | | | |
| 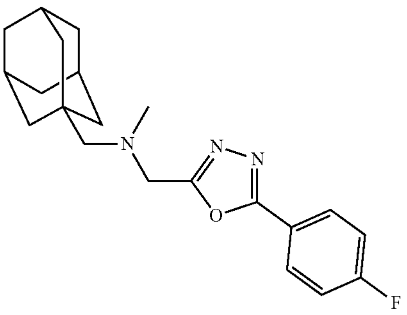 [SMILES: CN(Cc1nnc(-c2ccc(F)cc2)o1)CC12CC3CC(CC(C3)C1)C2] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 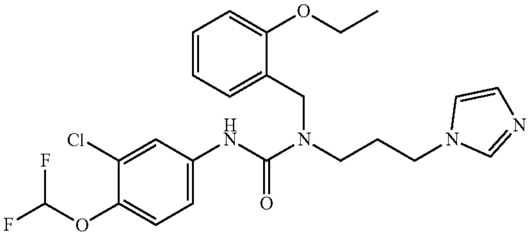 [SMILES: CCOc1ccccc1CN(CCCn1ccnc1)C(=O)Nc1ccc(OC(F)F)c(Cl)c1] | | | | B | | | |
| 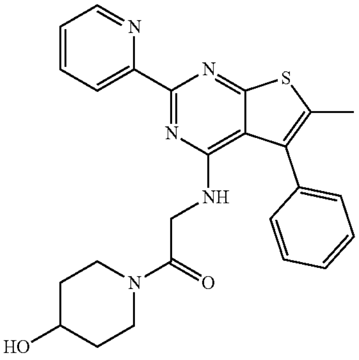 [SMILES: Cc1sc2nc(-c3ccccn3)nc(NCC(=O)N3CCC(O)CC3)c2c1-c1ccccc1] | | | | B | | | |
| 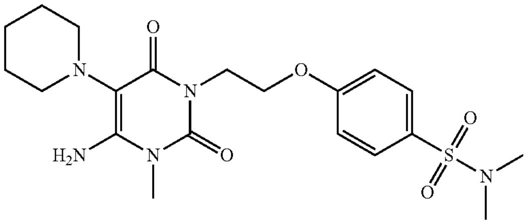 [SMILES: CN(C)S(=O)(=O)c1ccc(OCCn2c(=O)c(N3CCCCC3)c(N)n(C)c2=O)cc1] | | | | A | | | |
| 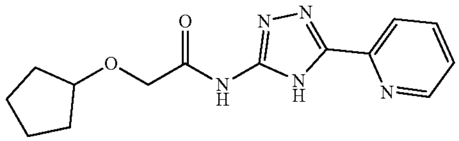 [SMILES: O=C(COC1CCCC1)Nc1nnc(-c2ccccn2)[nH]1] | | | | C | | | |
| 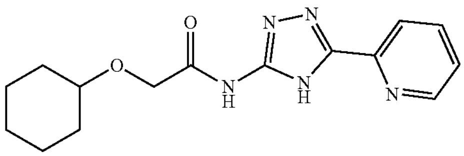 [SMILES: O=C(COC1CCCCC1)Nc1nnc(-c2ccccn2)[nH]1] | | | | C | | | |
| 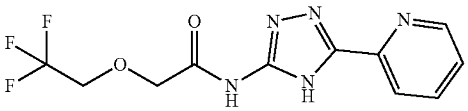 [SMILES: O=C(COCC(F)(F)F)Nc1nnc(-c2ccccn2)[nH]1] | | | | B | | | |
| 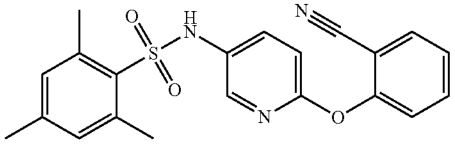 [SMILES: Cc1cc(C)c(S(=O)(=O)Nc2ccc(Oc3ccccc3C#N)nc2)c(C)c1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 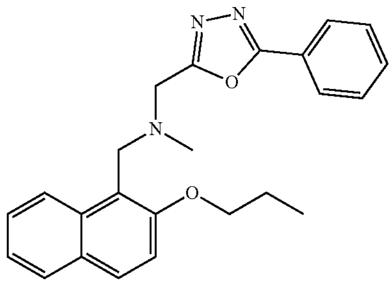 [SMILES: CCCOc1ccc2ccccc2c1CN(C)Cc1nnc(-c2ccccc2)o1] | | | | B | | | |
| 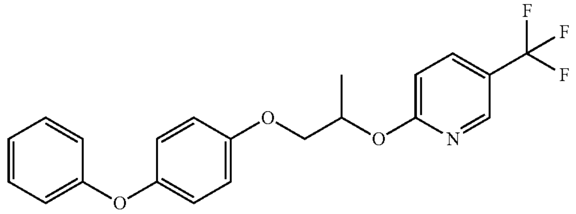 [SMILES: CC(COc1ccc(Oc2ccccc2)cc1)Oc1ccc(C(F)(F)F)cn1] | | | | C | | | |
| 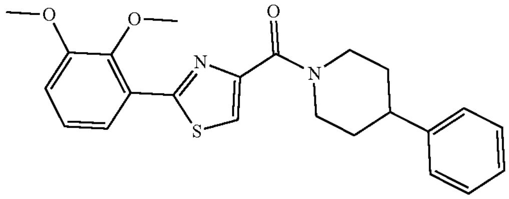 [SMILES: COc1cccc(-c2nc(C(=O)N3CCC(c4ccccc4)CC3)cs2)c1OC] | | | | B | | | |
| 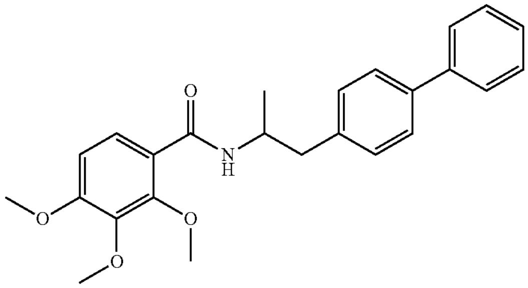 [SMILES: COc1ccc(C(=O)NC(C)Cc2ccc(-c3ccccc3)cc2)c(OC)c1OC] | | | | B | | | |
| 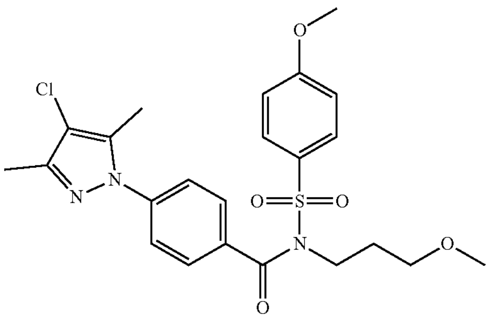 | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 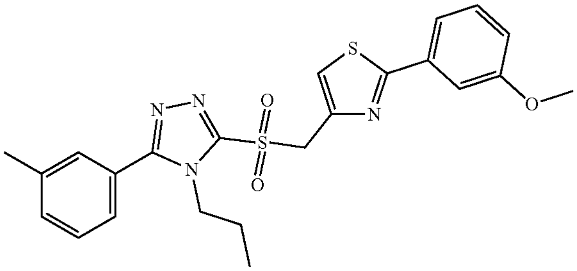 | | | | C | | | |
| 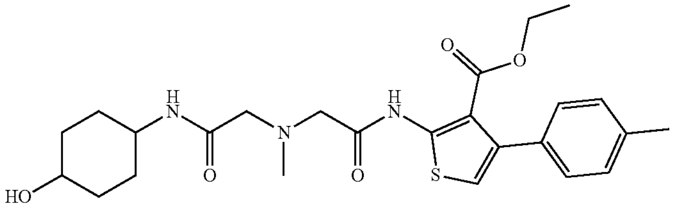 [SMILES: CCOC(=O)c1c(-c2ccc(C)cc2)csc1NC(=O)CN(C)CC(=O)NC1CCC(O)CC1] | | | | B | | | |
| 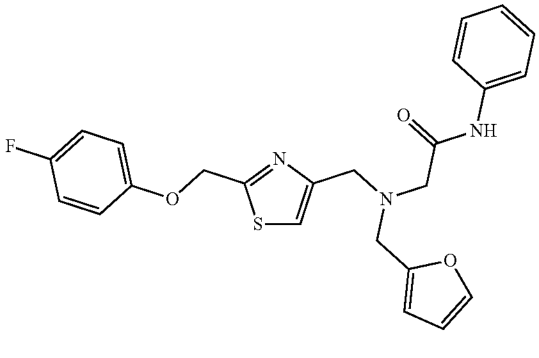 [SMILES: O=C(CN(Cc1csc(COc2ccc(F)cc2)n1)Cc1ccco1)Nc1ccccc1] | | | | B | | | |
| 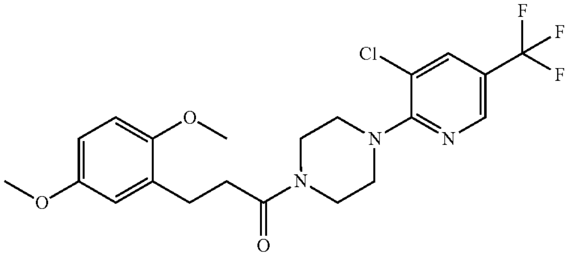 [SMILES: COc1ccc(OC)c(CCC(=O)N2CCN(c3ncc(C(F)(F)F)cc3Cl)CC2)c1] | | | | B | | | |
| 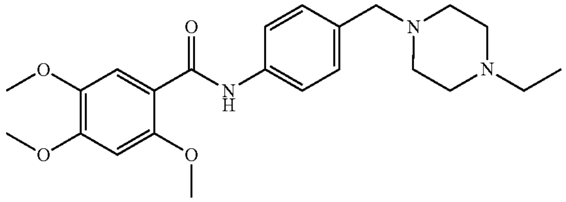 [SMILES: CCN1CCN(Cc2ccc(NC(=O)c3cc(OC)c(OC)cc3OC)cc2)CC1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 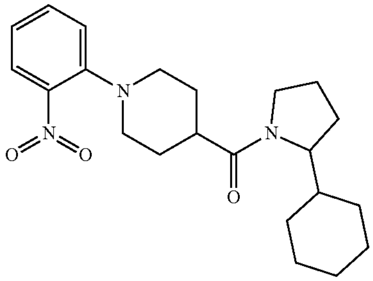 [SMILES: O=C(C1CCN(c2ccccc2[N+](=O)[O-])CC1)N1CCCC1C1CCCCC1] | | | | A | | | |
| 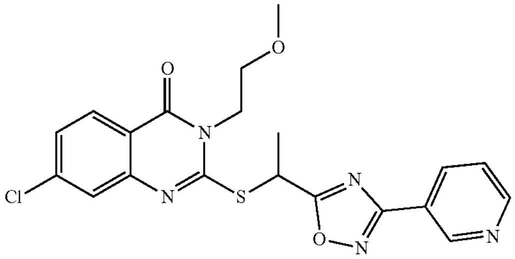 [SMILES: COCCn1c(SC(C)c2nc(-c3cccnc3)no2)nc2cc(Cl)ccc2c1=O] | | | | A | | | |
| 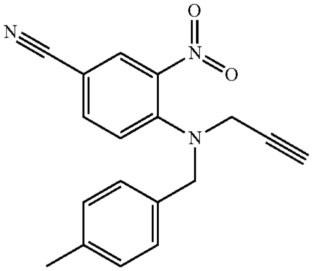 [SMILES: C#CCN(Cc1ccc(C)cc1)c1ccc(C#N)cc1[N+](=O)[O-]] | | | | A | | | |
| 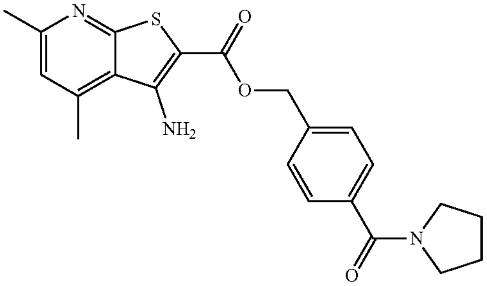 [SMILES: Cc1cc(C)c2c(N)c(C(=O)OCc3ccc(C(=O)N4CCCC4)cc3)sc2n1] | | | | A | | | |
| 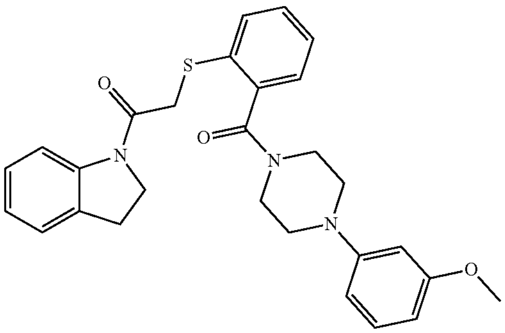 [SMILES: COc1cccc(N2CCN(C(=O)c3ccccc3SCC(=O)N3CCc4ccccc43)CC2)c1] | | | | A | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 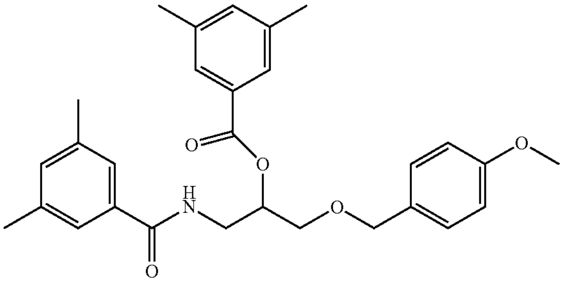 | | | | B | | | |
| 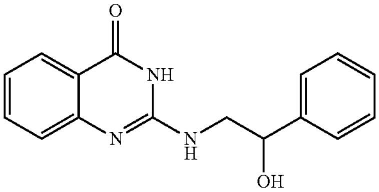 [SMILES: O=c1[nH]c(NCC(O)c2ccccc2)nc2ccccc12] | | | | A | | | |
| 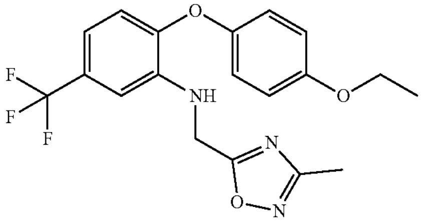 [SMILES: CCOc1ccc(Oc2ccc(C(F)(F)F)cc2NCc2nc(C)no2)cc1] | | | | C | | | |
| 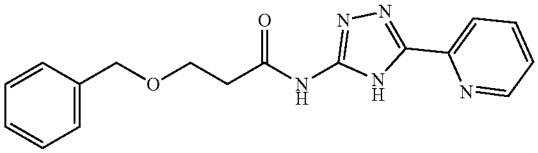 [SMILES: O=C(CCOCc1ccccc1)Nc1nnc(-c2ccccn2)[nH]1] | | | | C | | | |
| 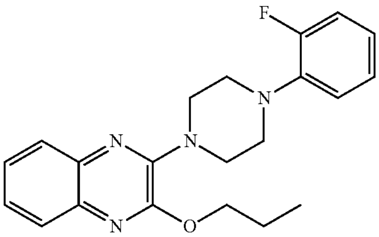 [SMILES: CCCOc1nc2ccccc2nc1N1CCN(c2ccccc2F)CC1] | | | | B | | | |
| 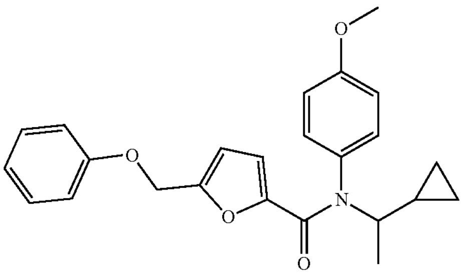 [SMILES: COc1ccc(N(C(=O)c2ccc(COc3ccccc3)o2)C(C)C2CC2)cc1] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 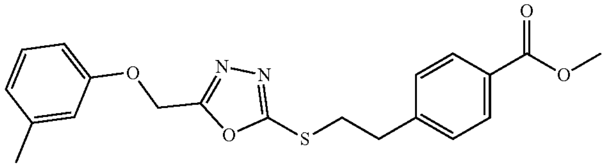 [SMILES: COC(=O)c1ccc(CCSc2nnc(COc3cccc(C)c3)o2)cc1] | | | | B | | | |
| 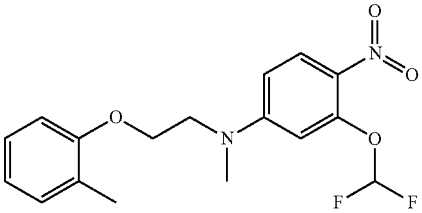 [SMILES: Cc1ccccc1OCCN(C)c1ccc([N+](=O)[O-])c(OC(F)F)c1] | | | | B | | | |
| 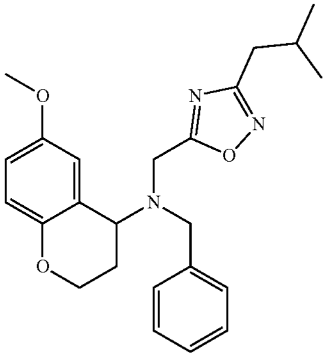 [SMILES: COc1ccc2c(c1)C(N(Cc1ccccc1)Cc1nc(CC(C)C)no1)CCO2] | | | | B | | | |
| 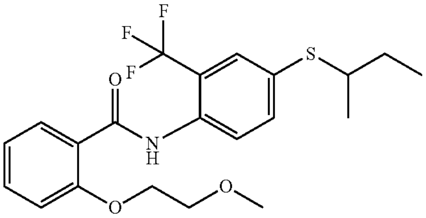 [SMILES: CCC(C)Sc1ccc(NC(=O)c2ccccc2OCCOC)c(C(F)(F)F)c1] | | | | B | | | |
| 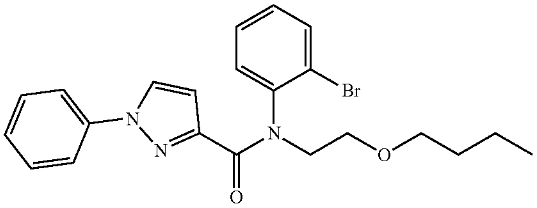 [SMILES: CCCCOCCN(C(=O)c1ccn(-c2ccccc2)n1)c1ccccc1Br] | | | | B | | | |
| 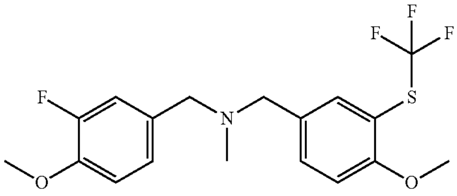 [SMILES: COc1ccc(CN(C)Cc2ccc(OC)c(SC(F)(F)F)c2)cc1F] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 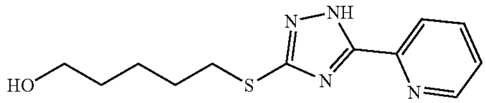 [SMILES: OCCCCCSc1n[nH]c(-c2ccccn2)n1] | | | | C | | | |
| 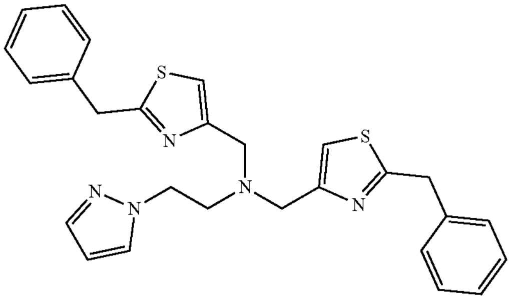 [SMILES: c1ccc(Cc2nc(CN(CCn3cccn3)Cc3csc(Cc4ccccc4)n3)cs2)cc1] | | | | A | | | |
| 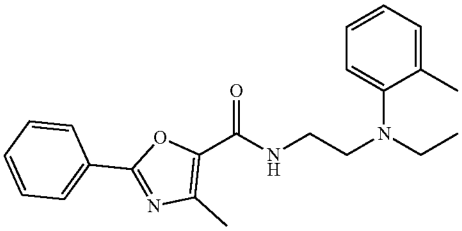 [SMILES: CCN(CCNC(=O)c1oc(-c2ccccc2)nc1C)c1ccccc1C] | | | | C | | | |
| 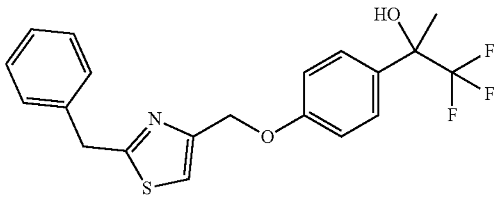 [SMILES: CC(O)(c1ccc(OCc2csc(Cc3ccccc3)n2)cc1)C(F)(F)F] | | | | B | | | |
| 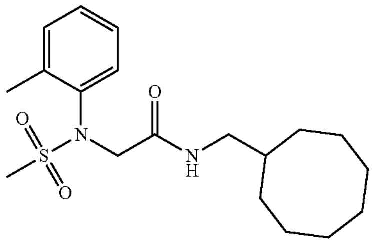 [SMILES: Cc1ccccc1N(CC(=O)NCC1CCCCCCC1)S(C)(=O)=O] | | | | A | | | |
| 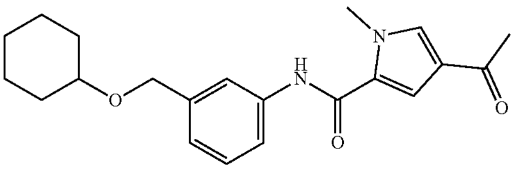 [SMILES: CC(=O)c1cc(C(=O)Nc2cccc(COC3CCCCC3)c2)n(C)c1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 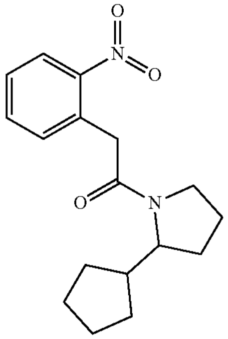 [SMILES: O=C(Cc1ccccc1[N+](=O)[O-])N1CCCC1C1CCCC1] | | | | A | | | |
| 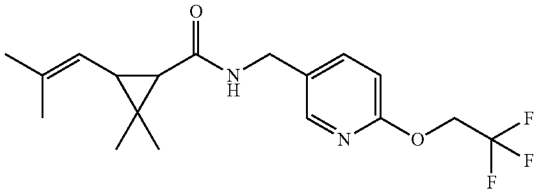 [SMILES: CC(C)=CC1C(C(=O)NCc2ccc(OCC(F)(F)F)nc2)C1(C)C] | | | | B | | | |
| 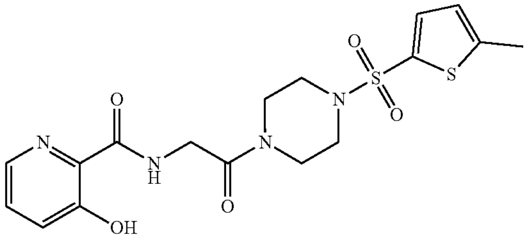 [SMILES: Cc1ccc(S(=O)(=O)N2CCN(C(=O)CNC(=O)c3ncccc3O)CC2)s1] | | | | B | | | |
| 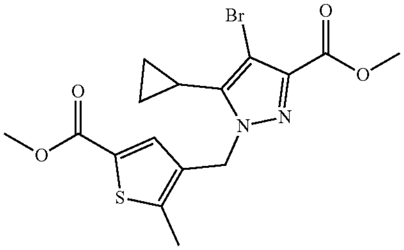 | | | | B | | | |
| 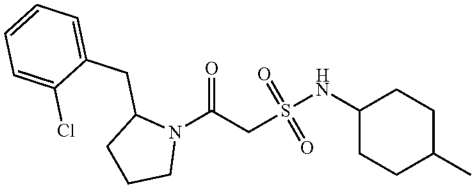 [SMILES: CC1CCC(NS(=O)(=O)CC(=O)N2CCCC2Cc2ccccc2Cl)CC1] | | | | B | | | |
| 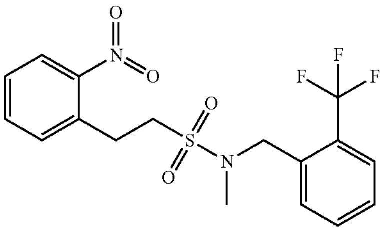 [SMILES: CN(Cc1ccccc1C(F)(F)F)S(=O)(=O)CCc1ccccc1[N+](=O)[O-]] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 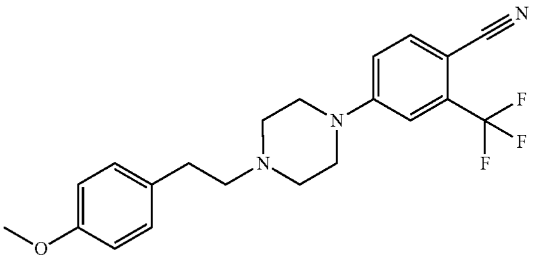 [SMILES: COc1ccc(CCN2CCN(c3ccc(C#N)c(C(F)(F)F)c3)CC2)cc1] | | | | B | | | |
| 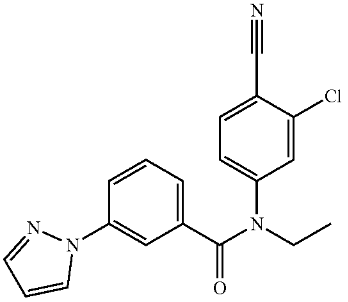 [SMILES: CCN(C(=O)c1cccc(-n2cccn2)c1)c1ccc(C#N)c(Cl)c1] | | | | A | | | |
| 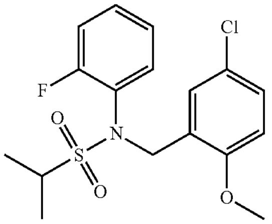 [SMILES: COc1ccc(Cl)cc1CN(c1ccccc1F)S(=O)(=O)C(C)C] | | | | B | | | |
| 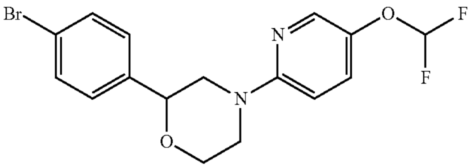 [SMILES: FC(F)Oc1ccc(N2CCOC(c3ccc(Br)cc3)C2)nc1] | | | | B | | | |
| 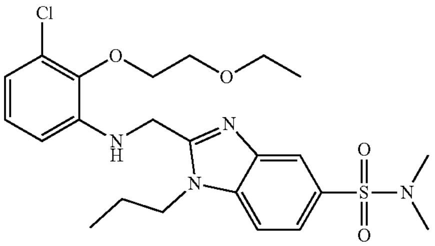 [SMILES: CCCn1c(CNc2cccc(Cl)c2OCCOCC)nc2cc(S(=O)(=O)N(C)C)ccc21] | | | | B | | | |
| 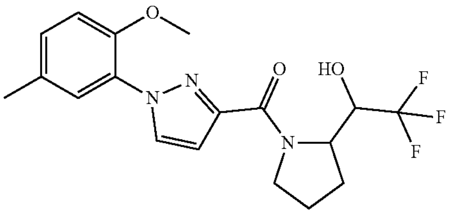 [SMILES: COc1ccc(C)cc1-n1ccc(C(=O)N2CCCC2C(O)C(F)(F)F)n1] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 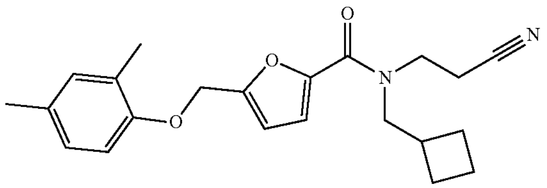 [SMILES: Cc1ccc(OCc2ccc(C(=O)N(CCC#N)CC3CCC3)o2)c(C)c1] | | | | C | | | |
| 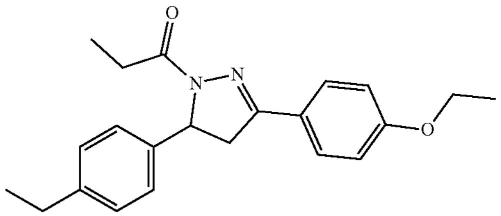 [SMILES: CCOc1ccc(C2=NN(C(=O)CC)C(c3ccc(CC)cc3)C2)cc1] | | | | B | | | |
| 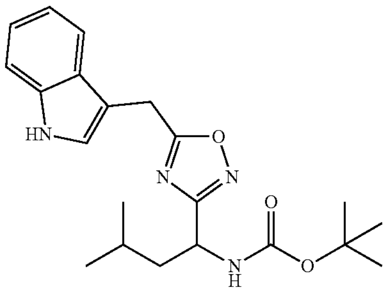 [SMILES: CC(C)CC(NC(=O)OC(C)(C)C)c1noc(Cc2c[nH]c3ccccc23)n1] | | | | A | | | |
| 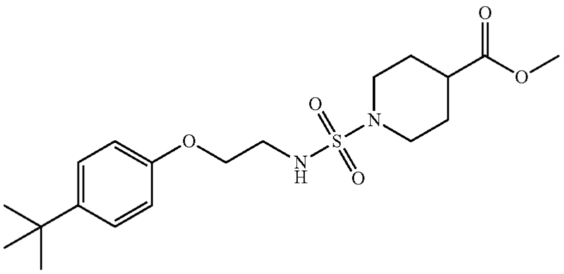 [SMILES: COC(=O)C1CCN(S(=O)(=O)NCCOc2ccc(C(C)(C)C)cc2)CC1] | | | | B | | | |
| 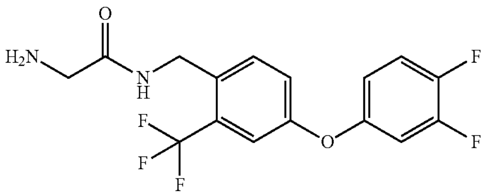 [SMILES: NCC(=O)NCc1ccc(Oc2ccc(F)c(F)c2)cc1C(F)(F)F] | | | | A | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 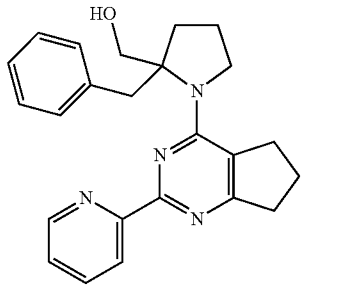 [SMILES: OCC1(Cc2ccccc2)CCCN1c1nc(-c2ccccn2)nc2c1CCC2] | | | | B | | | |
| 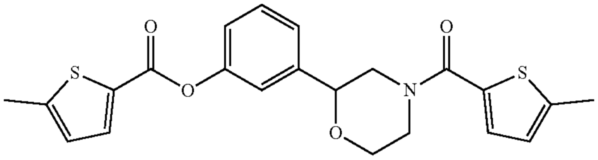 | | | | A | | | |
| 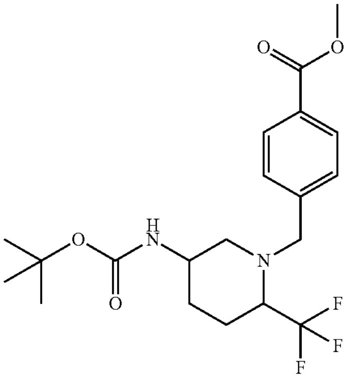 [SMILES: COC(=O)c1ccc(CN2CC(NC(=O)OC(C)(C)C)CCC2C(F)(F)F)cc1] | | | | B | | | |
| 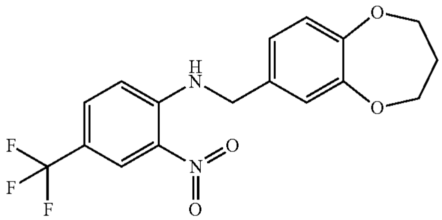 [SMILES: O=[N+]([O-])c1cc(C(F)(F)F)ccc1NCc1ccc2c(c1)OCCCO2] | | | | B | | | |
| 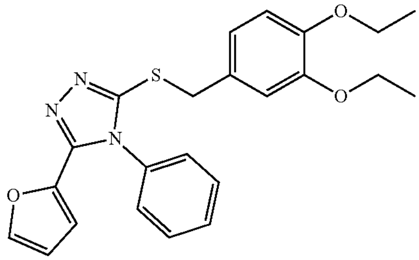 [SMILES: CCOc1ccc(CSc2nnc(-c3ccco3)n2-c2ccccc2)cc1OCC] | | | | B | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 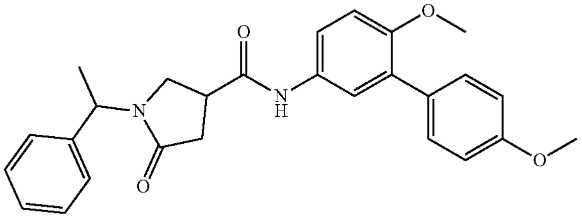 [SMILES: COc1ccc(-c2cc(NC(=O)C3CC(=O)N(C(C)c4ccccc4)C3)ccc2OC)cc1] | | | | A | | | |
| 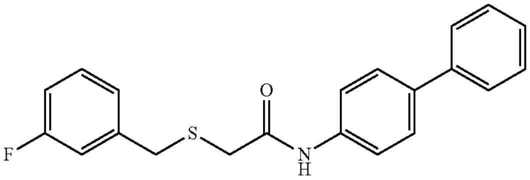 [SMILES: O=C(CSCc1cccc(F)c1)Nc1ccc(-c2ccccc2)cc1] | | | | B | | | |
| 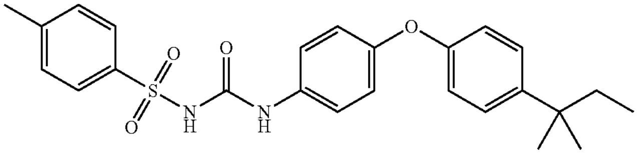 [SMILES: CCC(C)(C)c1ccc(Oc2ccc(NC(=O)NS(=O)(=O)c3ccc(C)cc3)cc2)cc1] | | | | C | | | |
| 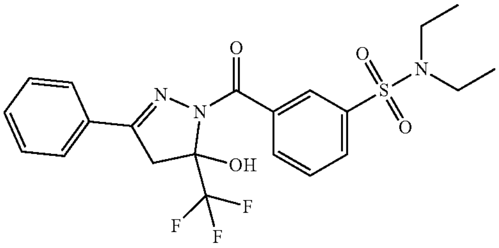 [SMILES: CCN(CC)S(=O)(=O)c1cccc(C(=O)N2N=C(c3ccccc3)CC2(O)C(F)(F)F)c1] | | | | B | | | |
| 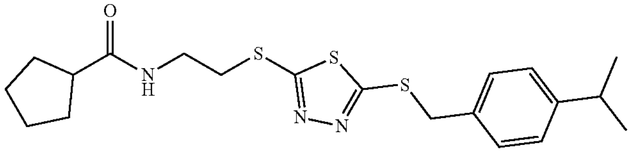 [SMILES: CC(C)c1ccc(CSc2nnc(SCCNC(=O)C3CCCC3)s2)cc1] | | | | C | | | |
| 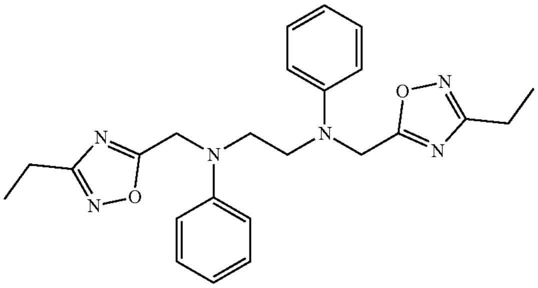 [SMILES: CCc1noc(CN(CCN(Cc2nc(CC)no2)c2ccccc2)c2ccccc2)n1] | | | | C | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 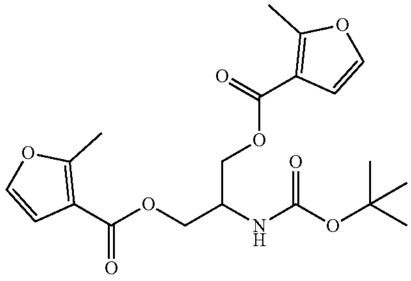 [SMILES: Cc1occc1C(=O)OCC(COC(=O)c1ccoc1C)NC(=O)OC(C)(C)C] | | | | B | | | |
| 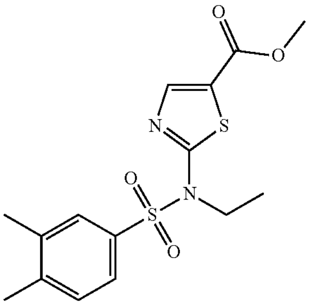 | | | | C | | | |
| 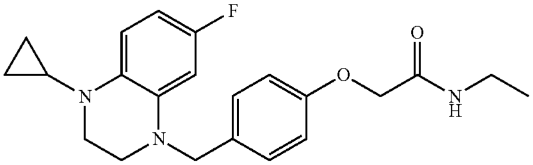 [SMILES: CCNC(=O)COc1ccc(CN2CCN(C3CC3)c3ccc(F)cc32)cc1] | | | | A | | | |
| 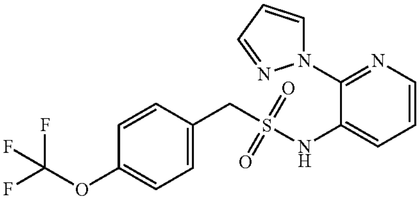 [SMILES: O=S(=O)(Cc1ccc(OC(F)(F)F)cc1)Nc1cccnc1-n1cccn1] | | | | B | | | |
| 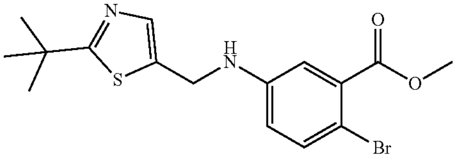 [SMILES: COC(=O)c1cc(NCc2cnc(C(C)(C)C)s2)ccc1Br] | | | | B | | | |
| 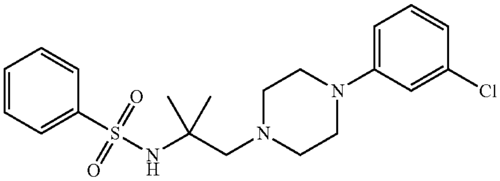 [SMILES: CC(C)(CN1CCN(c2cccc(Cl)c2)CC1)NS(=O)(=O)c1ccccc1] | | | | B | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 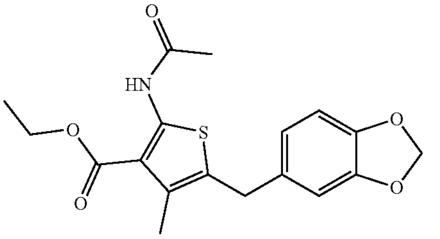 [SMILES: CCOC(=O)c1c(NC(C)=O)sc(Cc2ccc3c(c2)OCO3)c1C] | | | | B | | | |
| 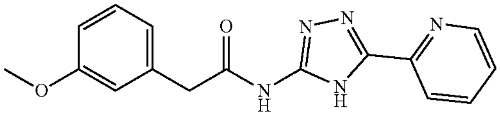 [SMILES: COc1cccc(CC(=O)Nc2nnc(-c3ccccn3)[nH]2)c1] | | | | C | | | |
| 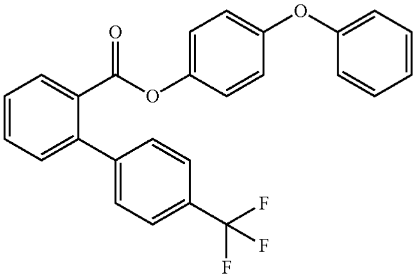 [SMILES: O=C(Oc1ccc(Oc2ccccc2)cc1)c1ccccc1-c1ccc(C(F)(F)F)cc1] | | | | B | | | |
| 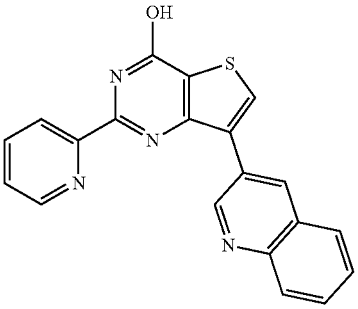 [SMILES: Oc1nc(-c2ccccn2)nc2c(-c3cnc4ccccc4c3)csc12] | | | | B | B | C | |
| 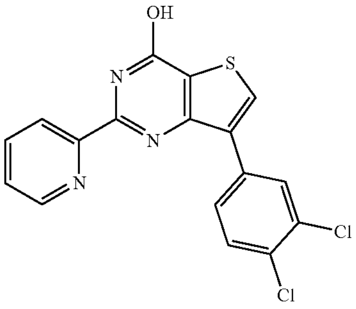 [SMILES: Oc1nc(-c2ccccn2)nc2c(-c3ccc(Cl)c(Cl)c3)csc12] | | | | B | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 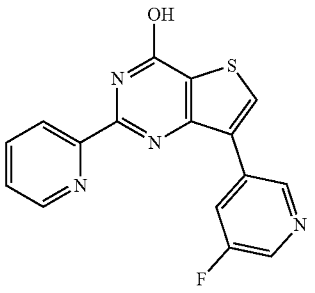 [SMILES: Oc1nc(-c2ccccn2)nc2c(-c3cncc(F)c3)csc12] | | | | A | A | A | |
| 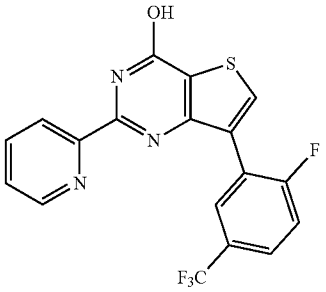 [SMILES: Oc1nc(-c2ccccn2)nc2c(-c3cc(C(F)(F)F)ccc3F)csc12] | | | | A | A | A | |
| 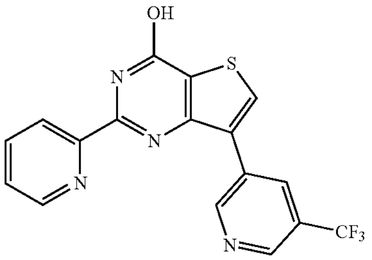 | | | | A | 0 | A | |
| 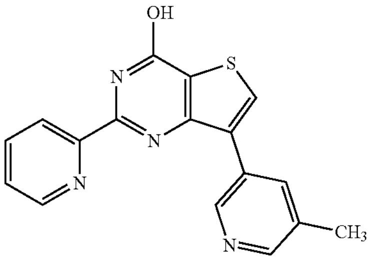 [SMILES: Cc1cncc(-c2csc3c(O)nc(-c4ccccn4)nc23)c1] | | | | B | B | B | |
| 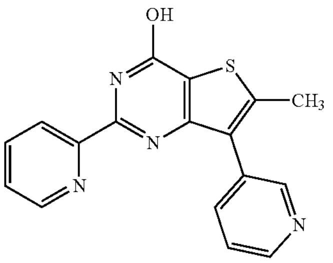 [SMILES: Cc1sc2c(O)nc(-c3ccccn3)nc2c1-c1cccnc1] | C | B | B | B | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 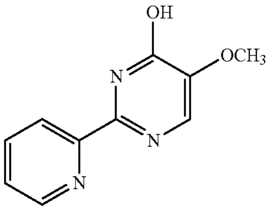 [SMILES: COc1cnc(-c2ccccn2)nc1O] | C | D | B | C | D | C | |
| 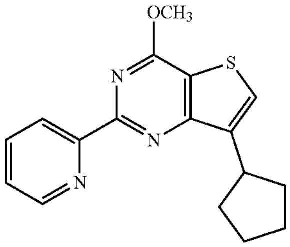 [SMILES: COc1nc(-c2ccccn2)nc2c(C3CCCC3)csc12] | B | B | B | C | C | D | |
| 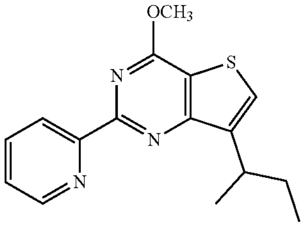 [SMILES: CCC(C)c1csc2c(OC)nc(-c3ccccn3)nc12] | B | B | B | C | C | C | |
| 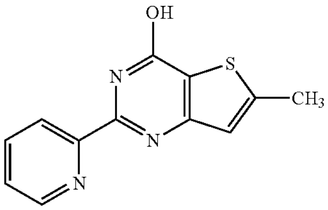 [SMILES: Cc1cc2nc(-c3ccccn3)nc(O)c2s1] | | | | C | C | C | |
| 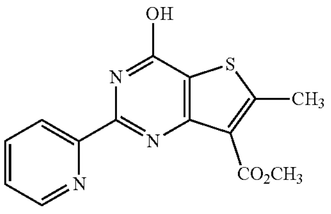 [SMILES: COC(=O)c1c(C)sc2c(O)nc(-c3ccccn3)nc12] | | | | C | C | C | |
| 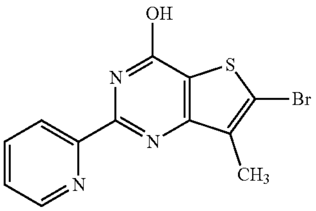 [SMILES: Cc1c(Br)sc2c(O)nc(-c3ccccn3)nc12] | | | | B | B | C | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 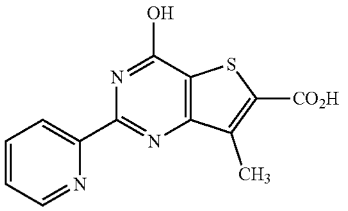 [SMILES: Cc1c(C(=O)O)sc2c(O)nc(-c3ccccn3)nc12] | B | A | A | C | C | C | |
| 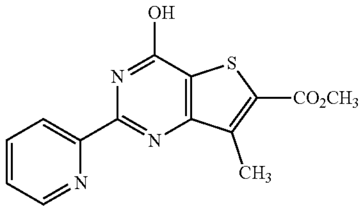 [SMILES: COC(=O)c1sc2c(O)nc(-c3ccccn3)nc2c1C] | | | | B | C | C | |
| 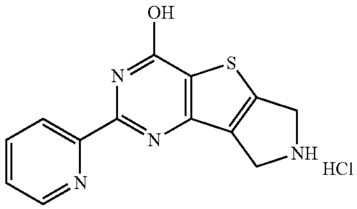 [SMILES: Oc1nc(-c2ccccn2)nc2c3c(sc12)CNC3 ; Cl] | | | | C | D | D | |
| 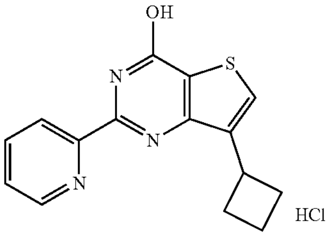 [SMILES: Oc1nc(-c2ccccn2)nc2c(C3CCC3)csc12 ; Cl] | C | B | B | C | C | C | |
| 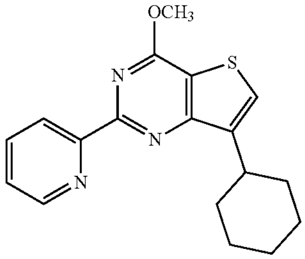 [SMILES: COc1nc(-c2ccccn2)nc2c(C3CCCCC3)csc12] | | | | A | 0 | A | |
| 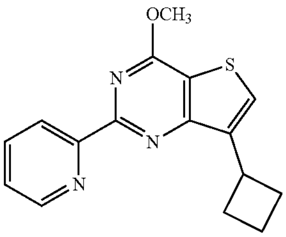 [SMILES: COc1nc(-c2ccccn2)nc2c(C3CCC3)csc12] | A | B | A | C | C | D | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 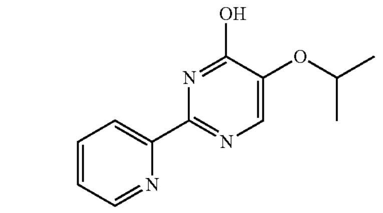 [SMILES: CC(C)Oc1cnc(-c2ccccn2)nc1O] | C | C | B | C | D | C | |
| 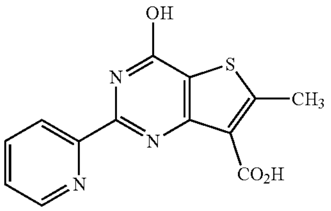 [SMILES: Cc1sc2c(O)nc(-c3ccccn3)nc2c1C(=O)O] | | | | B | B | B | |
| 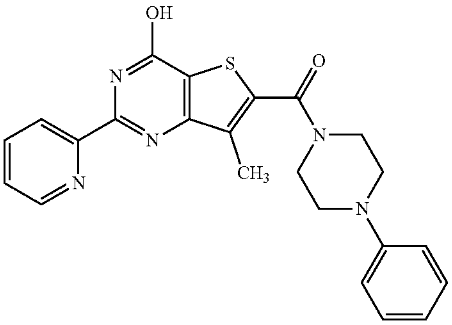 [SMILES: Cc1c(C(=O)N2CCN(c3ccccc3)CC2)sc2c(O)nc(-c3ccccn3)nc12] | | | | C | C | C | |
| 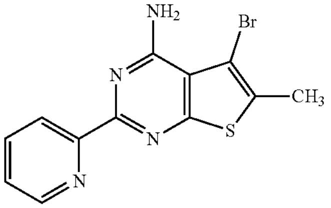 [SMILES: Cc1sc2nc(-c3ccccn3)nc(N)c2c1Br] | | | | B | B | B | |
| 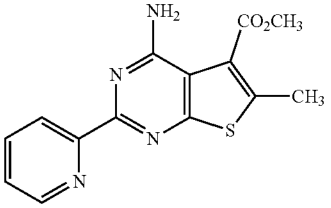 [SMILES: COC(=O)c1c(C)sc2nc(-c3ccccn3)nc(N)c12] | | | | C | B | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 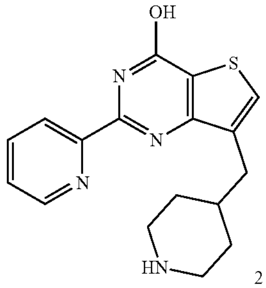 2 HCl | | | | C | C | C | |
| 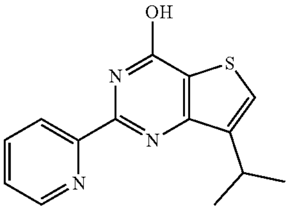 HCl | C | C | C | C | C | C | |
| 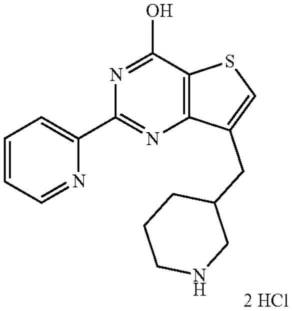 [SMILES: Oc1nc(-c2ccccn2)nc2c(CC3CCCNC3)csc12] 2 HCl | | | | B | C | C | |
| 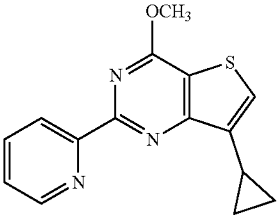 [SMILES: COc1nc(-c2ccccn2)nc2c(C3CC3)csc12] | | | | A | 0 | 0 | |
| 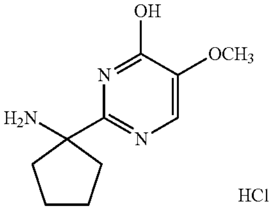 [SMILES: COc1cnc(C2(N)CCCC2)nc1O ; Cl] HCl | | | | A | A | 0 | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 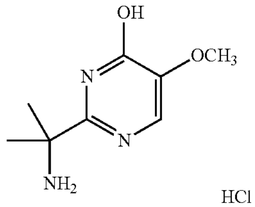 HCl | | | | A | A | 0 | |
| 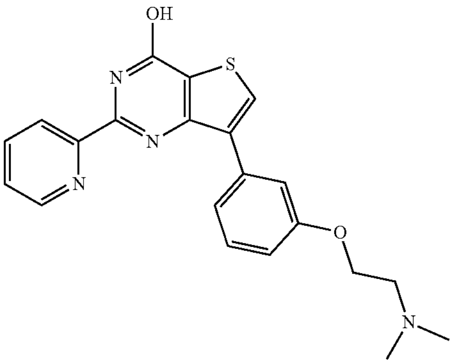 [SMILES: CN(C)CCOc1cccc(-c2csc3c(O)nc(-c4ccccn4)nc23)c1] | D | C | C | D | D | D | |
| 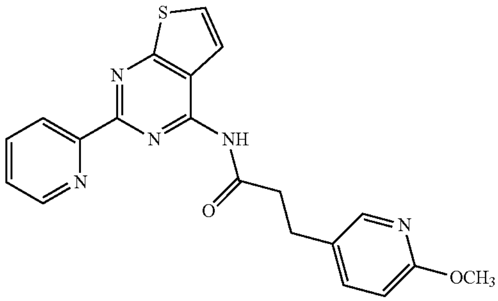 [SMILES: COc1ccc(CCC(=O)Nc2nc(-c3ccccn3)nc3sccc23)cn1] | C | B | B | C | C | D | |
| 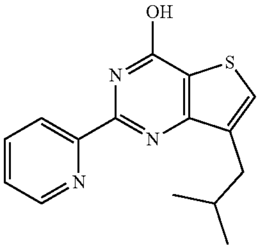 [SMILES: CC(C)Cc1csc2c(O)nc(-c3ccccn3)nc12] | C | B | B | C | C | D | |
| 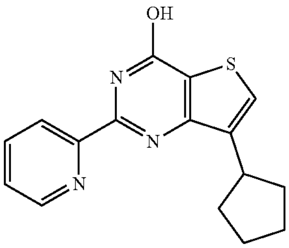 •HCl | C | B | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 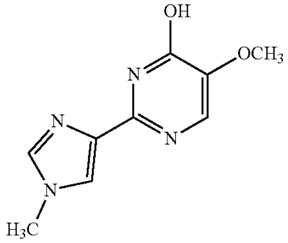 | C | C | B | C | C | D | |
| 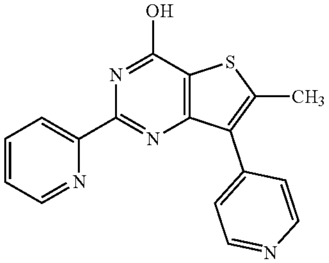 [SMILES: Cc1sc2c(O)nc(-c3ccccn3)nc2c1-c1ccncc1] | C | B | A | C | B | C | |
| 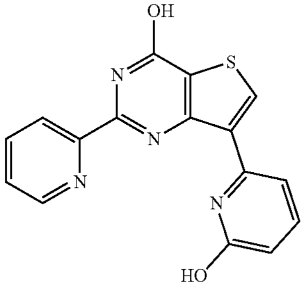 •HCl | B | B | C | C | C | D | |
| 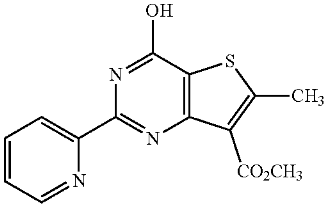 [SMILES: COC(=O)c1c(C)sc2c(O)nc(-c3ccccn3)nc12] | | | | C | C | D | |
| 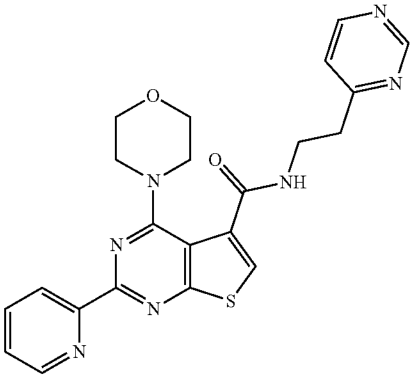 [SMILES: O=C(NCCc1ccncn1)c1csc2nc(-c3ccccn3)nc(N3CCOCC3)c12] | | | | B | B | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 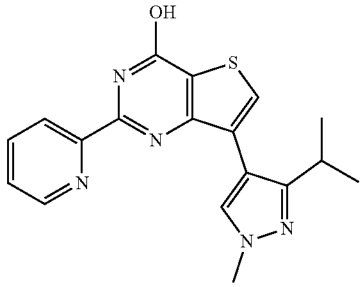 [SMILES: CC(C)c1nn(C)cc1-c1csc2c(O)nc(-c3ccccn3)nc12] | | | | C | C | C | |
| 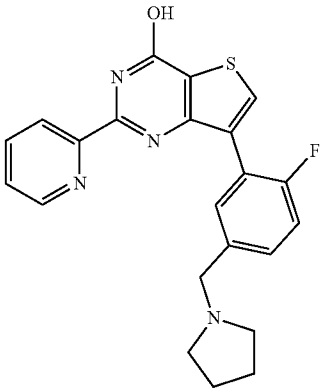 [SMILES: Oc1nc(-c2ccccn2)nc2c(-c3cc(CN4CCCC4)ccc3F)csc12] | D | C | B | C | C | D | |
| 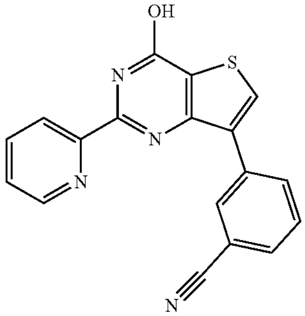 [SMILES: N#Cc1cccc(-c2csc3c(O)nc(-c4ccccn4)nc23)c1] | | | | A | A | B | |
| 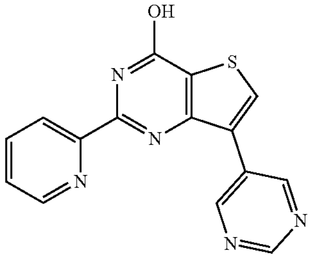 [SMILES: Oc1nc(-c2ccccn2)nc2c(-c3cncnc3)csc12] | | | | A | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 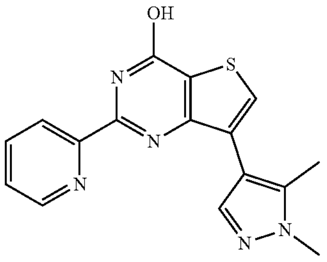 [SMILES: Cc1c(-c2csc3c(O)nc(-c4ccccn4)nc23)cnn1C] | | | | C | C | D | |
| 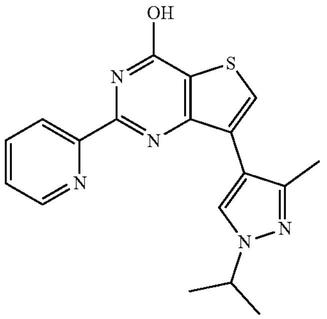 [SMILES: Cc1nn(C(C)C)cc1-c1csc2c(O)nc(-c3ccccn3)nc12] | C | B | B | C | C | C | |
| 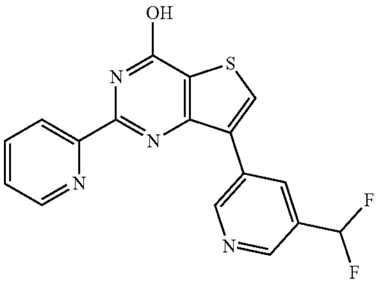 [SMILES: Oc1nc(-c2ccccn2)nc2c(-c3cncc(C(F)F)c3)csc12] | | | | A | A | A | |
| 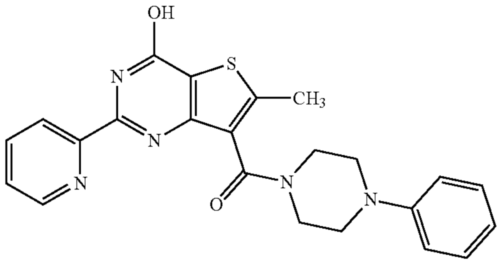 [SMILES: Cc1sc2c(O)nc(-c3ccccn3)nc2c1C(=O)N1CCN(c2ccccc2)CC1] | | | | B | C | C | |
| 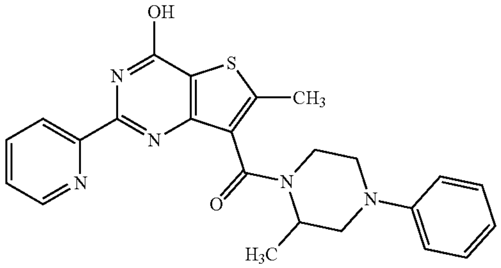 [SMILES: Cc1sc2c(O)nc(-c3ccccn3)nc2c1C(=O)N1CCN(c2ccccc2)CC1C] | C | C | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 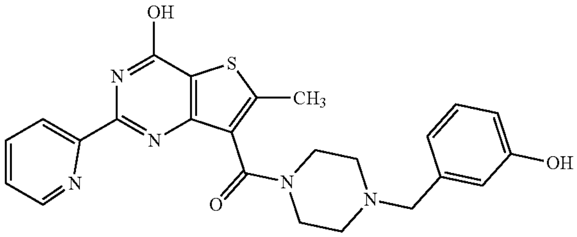 [SMILES: Cc1sc2c(O)nc(-c3ccccn3)nc2c1C(=O)N1CCN(Cc2cccc(O)c2)CC1] | B | A | A | C | C | C | |
| 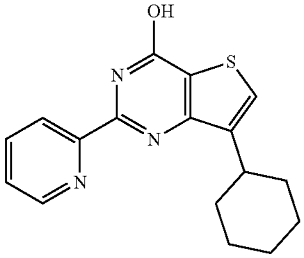 •HCl | | | | B | B | C | |
| 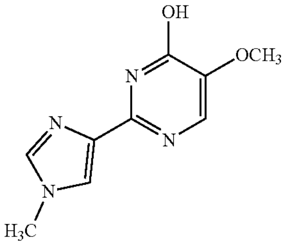 | C | C | B | C | C | D | |
| 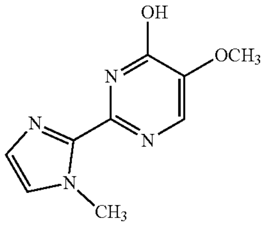 | D | C | C | D | D | D | |
| 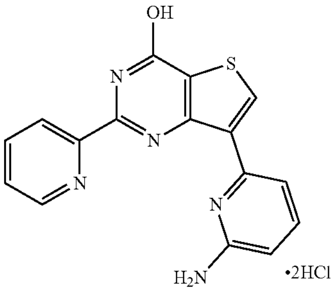 [SMILES: Nc1cccc(-c2csc3c(O)nc(-c4ccccn4)nc23)n1] •2HCl | C | B | C | C | C | D | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 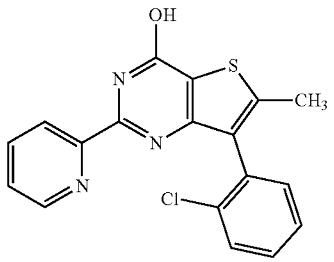 [SMILES: Cc1sc2c(O)nc(-c3ccccn3)nc2c1-c1ccccc1Cl] | C | A | A | C | C | D | |
| 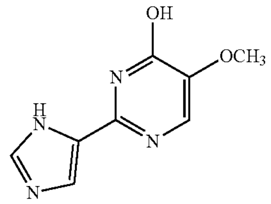 [SMILES: COc1cnc(-c2cnc[nH]2)nc1O] | C | C | C | C | C | C | |
| 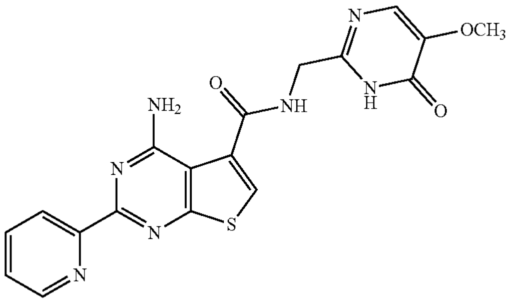 [SMILES: COc1cnc(CNC(=O)c2csc3nc(-c4ccccn4)nc(N)c23)[nH]c1=O] | | | | B | B | B | |
| 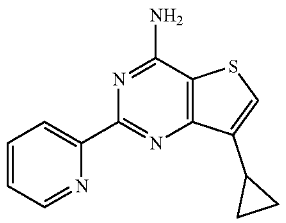 [SMILES: Nc1nc(-c2ccccn2)nc2c(C3CC3)csc12] | C | B | B | B | A | B | |
| 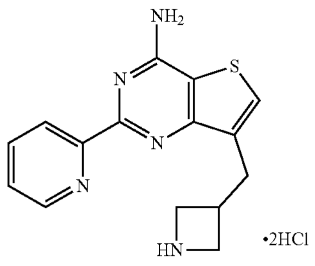 [SMILES: Nc1nc(-c2ccccn2)nc2c(CC3CNC3)csc12] | | | | B | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 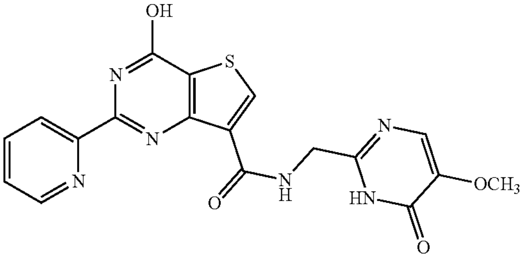 [SMILES: COc1cnc(CNC(=O)c2csc3c(O)nc(-c4ccccn4)nc23)[nH]c1=O] | | | | A | B | 0 | |
| 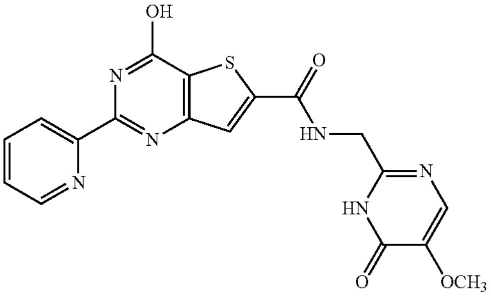 [SMILES: COc1cnc(CNC(=O)c2cc3nc(-c4ccccn4)nc(O)c3s2)[nH]c1=O] | | | | B | C | C | |
| 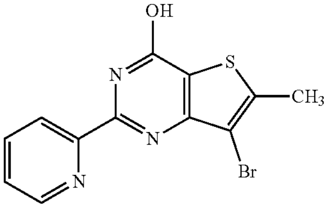 [SMILES: Cc1sc2c(O)nc(-c3ccccn3)nc2c1Br] | | | | B | B | A | |
| 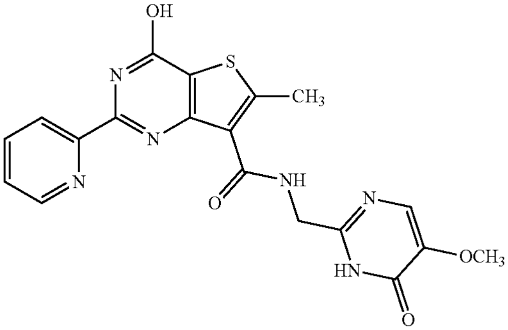 [SMILES: COc1cnc(CNC(=O)c2c(C)sc3c(O)nc(-c4ccccn4)nc23)[nH]c1=O] | | | | 0 | A | 0 | |
| 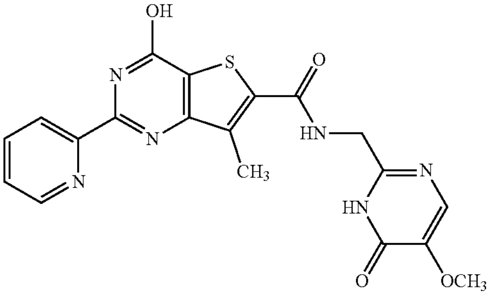 [SMILES: COc1cnc(CNC(=O)c2sc3c(O)nc(-c4ccccn4)nc3c2C)[nH]c1=O] | | | | A | B | 0 | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 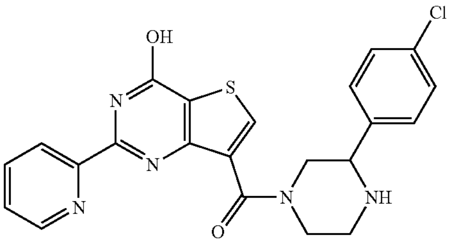 | | | | B | C | C | |
| 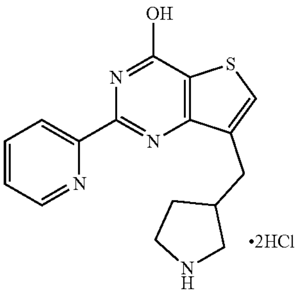 [SMILES: Oc1nc(-c2ccccn2)nc2c(CC3CCNC3)csc12] •2HCl | C | C | B | C | C | C | |
| 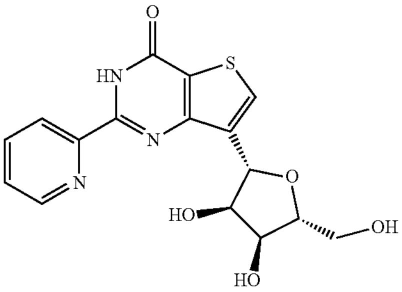 [SMILES: O=c1[nH]c(-c2ccccn2)nc2c([C@@H]3O[C@H](CO)[C@@H](O)[C@H]3O)csc12] | B | C | B | B | B | C | |
| 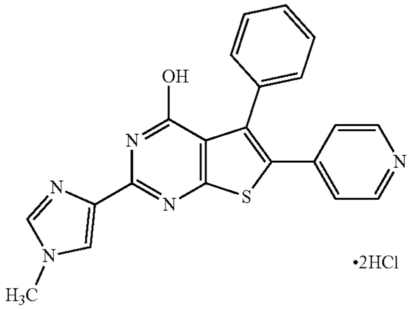 [SMILES: Cn1cnc(-c2nc(O)c3c(-c4ccccc4)c(-c4ccncc4)sc3n2)c1] •2HCl | | | | A | A | A | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 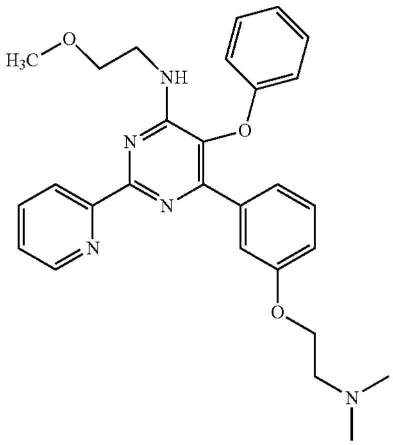 [SMILES: COCCNc1nc(-c2ccccn2)nc(-c2cccc(OCCN(C)C)c2)c1Oc1ccccc1] | | | | A | A | A | |
| 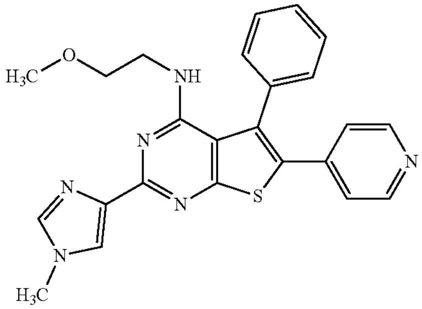 [SMILES: COCCNc1nc(-c2cn(C)cn2)nc2sc(-c3ccncc3)c(-c3ccccc3)c12] | C | C | C | D | C | D | |
| 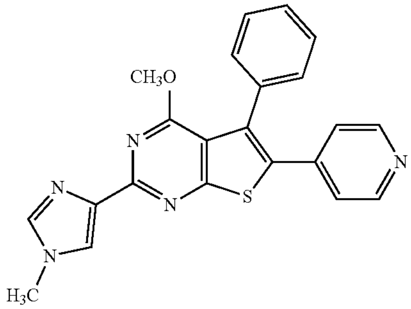 | B | B | A | B | A | B | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 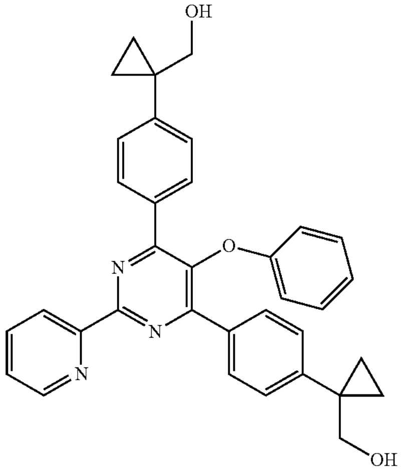 [SMILES: OCC1(c2ccc(-c3nc(-c4ccccn4)nc(-c4ccc(C5(CO)CC5)cc4)c3Oc3ccccc3)cc2)CC1] | | | | A | A | A | |
| 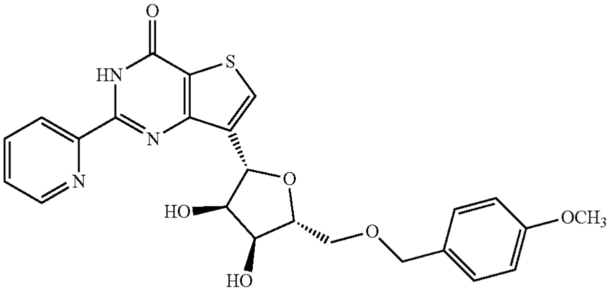 [SMILES: COc1ccc(COC[C@H]2O[C@@H](c3csc4c(=O)[nH]c(-c5ccccn5)nc34)[C@H](O)[C@@H]2O)cc1] | B | B | A | B | C | C | |
| 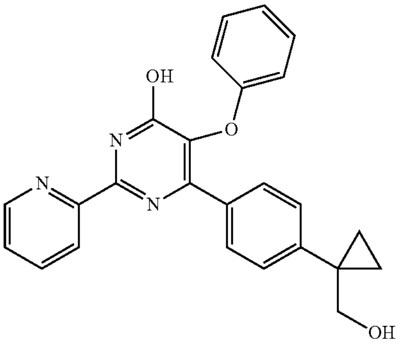 [SMILES: OCC1(c2ccc(-c3nc(-c4ccccn4)nc(O)c3Oc3ccccc3)cc2)CC1] | B | C | A | C | D | D | |
| 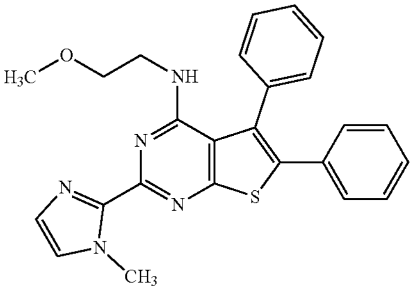 | D | C | A | C | C | C | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 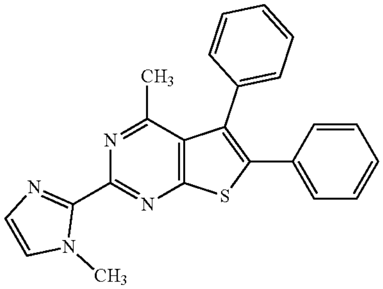 [SMILES: Cc1nc(-c2nccn2C)nc2sc(-c3ccccc3)c(-c3ccccc3)c12] | | | | A | A | A | |
| 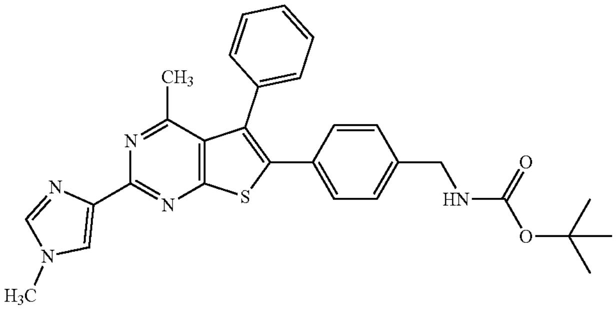 [SMILES: Cc1nc(-c2cn(C)cn2)nc2sc(-c3ccc(CNC(=O)OC(C)(C)C)cc3)c(-c3ccccc3)c12] | | | | A | A | A | |
| 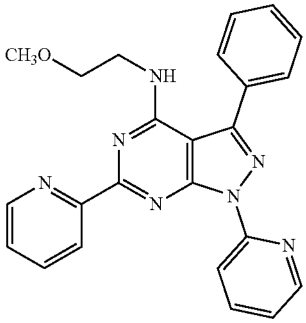 | C | C | C | C | D | C | |
| 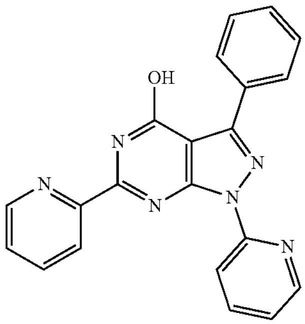 [SMILES: Oc1nc(-c2ccccn2)nc2c1c(-c1ccccc1)nn2-c1ccccn1] | C | C | B | C | C | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 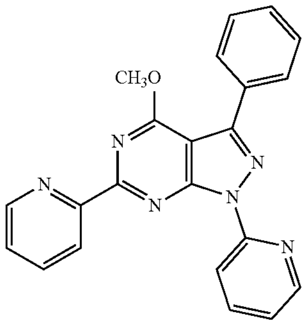 | C | C | B | C | B | C | |
| 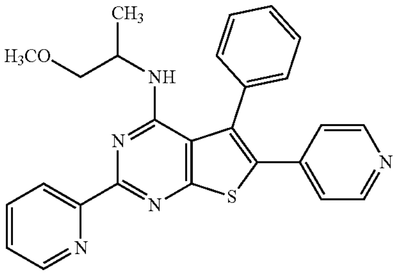 [SMILES: COCC(C)Nc1nc(-c2ccccn2)nc2sc(-c3ccncc3)c(-c3ccccc3)c12] | B | C | B | C | B | C | |
| 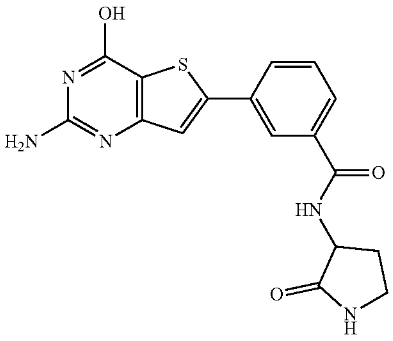 [SMILES: Nc1nc(O)c2sc(-c3cccc(C(=O)NC4CCNC4=O)c3)cc2n1] | | | | A | A | 0 | |
| 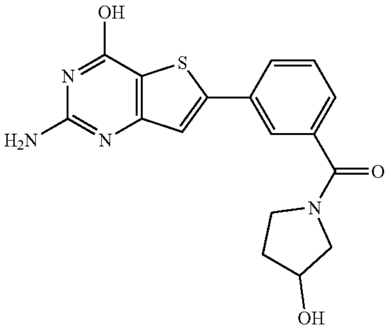 [SMILES: Nc1nc(O)c2sc(-c3cccc(C(=O)N4CCC(O)C4)c3)cc2n1] | | | | A | A | A | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 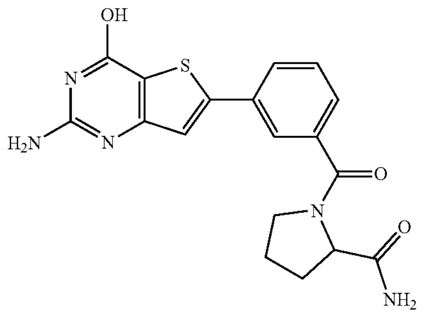 [SMILES: NC(=O)C1CCCN1C(=O)c1cccc(-c2cc3nc(N)nc(O)c3s2)c1] | | | | 0 | A | A | |
| 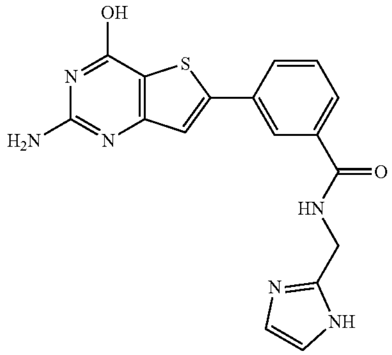 [SMILES: Nc1nc(O)c2sc(-c3cccc(C(=O)NCc4ncc[nH]4)c3)cc2n1] | | | | 0 | A | 0 | |
| 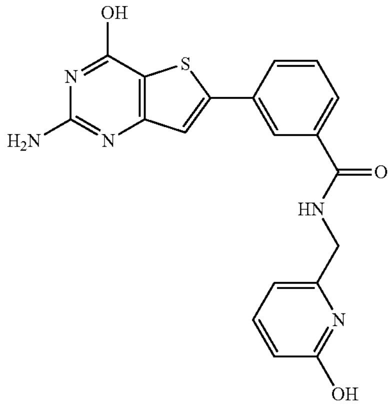 [SMILES: Nc1nc(O)c2sc(-c3cccc(C(=O)NCc4cccc(O)n4)c3)cc2n1] | | | | 0 | A | 0 | |
| 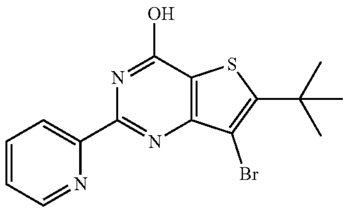 [SMILES: CC(C)(C)c1sc2c(O)nc(-c3ccccn3)nc2c1Br] | | | | B | B | C | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 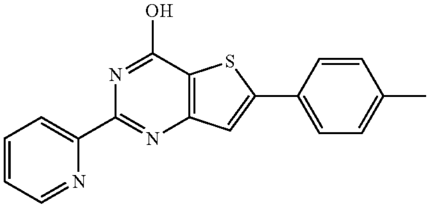 [SMILES: Cc1ccc(-c2cc3nc(-c4ccccn4)nc(O)c3s2)cc1] | | | | 0 | A | 0 | |
| 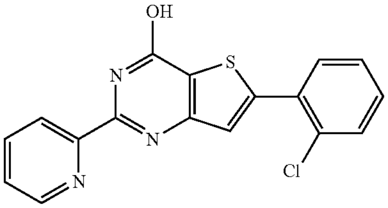 [SMILES: Oc1nc(-c2ccccn2)nc2cc(-c3ccccc3Cl)sc12] | | | | A | B | C | |
| 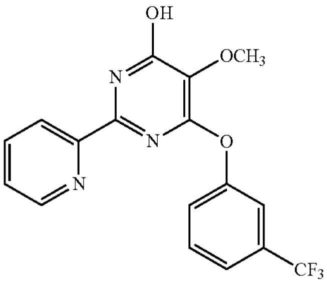 [SMILES: COc1c(O)nc(-c2ccccn2)nc1Oc1cccc(C(F)(F)F)c1] | D | B | B | C | D | C | |
| 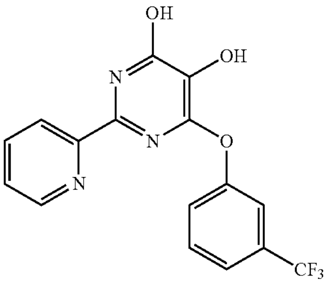 [SMILES: Oc1nc(-c2ccccn2)nc(Oc2cccc(C(F)(F)F)c2)c1O] | C | C | A | C | D | C | |
| 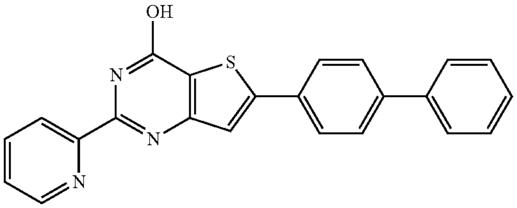 [SMILES: Oc1nc(-c2ccccn2)nc2cc(-c3ccc(-c4ccccc4)cc3)sc12] | | | | A | A | A | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 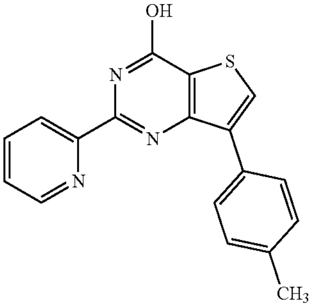 [SMILES: Cc1ccc(-c2csc3c(O)nc(-c4ccccn4)nc23)cc1] | | | | A | A | A | |
| 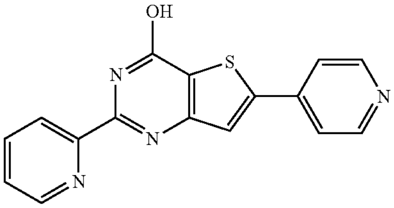 [SMILES: Oc1nc(-c2ccccn2)nc2cc(-c3ccncc3)sc12] | C | B | C | C | B | B | |
| 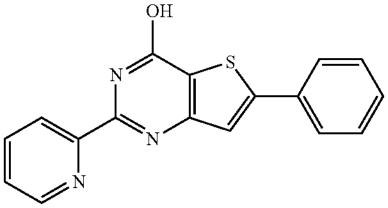 [SMILES: Oc1nc(-c2ccccn2)nc2cc(-c3ccccc3)sc12] | C | B | C | C | B | B | |
| 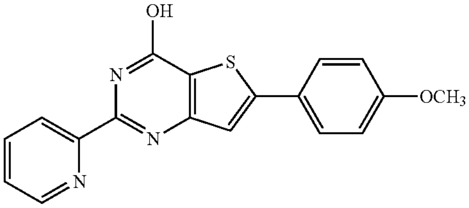 [SMILES: COc1ccc(-c2cc3nc(-c4ccccn4)nc(O)c3s2)cc1] | | | | A | A | A | |
| 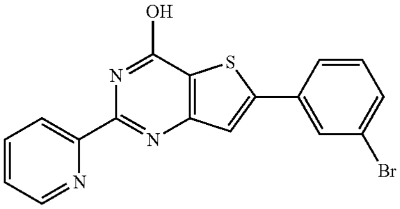 [SMILES: Oc1nc(-c2ccccn2)nc2cc(-c3cccc(Br)c3)sc12] | | | | B | A | B | |
| 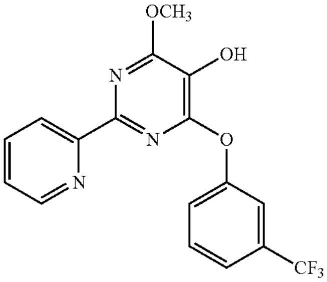 [SMILES: COc1nc(-c2ccccn2)nc(Oc2cccc(C(F)(F)F)c2)c1O] | C | B | A | | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 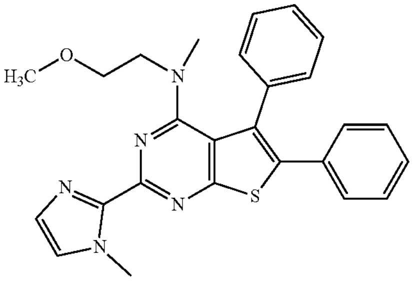 [SMILES: COCCN(C)c1nc(-c2nccn2C)nc2sc(-c3ccccc3)c(-c3ccccc3)c12] | C | B | C | | | | |
| 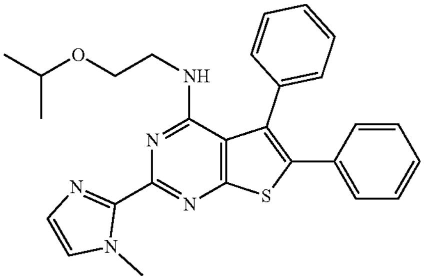 | C | C | C | | | | |
| 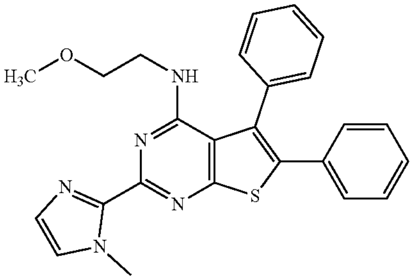 [SMILES: COCCNc1nc(-c2nccn2C)nc2sc(-c3ccccc3)c(-c3ccccc3)c12] | B | A | B | | | | |
| 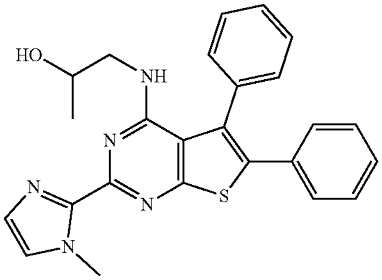 [SMILES: CC(O)CNc1nc(-c2nccn2C)nc2sc(-c3ccccc3)c(-c3ccccc3)c12] | A | A | A | | | | |
| 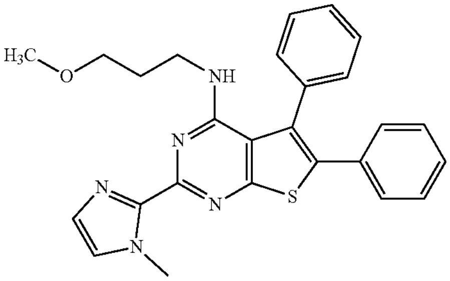 [SMILES: COCCCNc1nc(-c2nccn2C)nc2sc(-c3ccccc3)c(-c3ccccc3)c12] | C | C | C | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 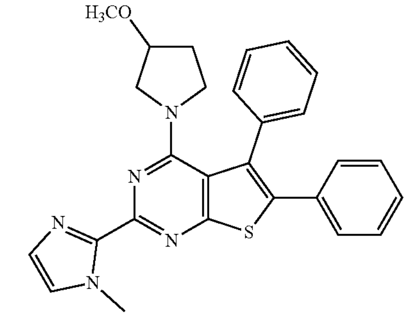 [SMILES: COC1CCN(c2nc(-c3nccn3C)nc3sc(-c4ccccc4)c(-c4ccccc4)c23)C1] | C | A | B | | | | |
| 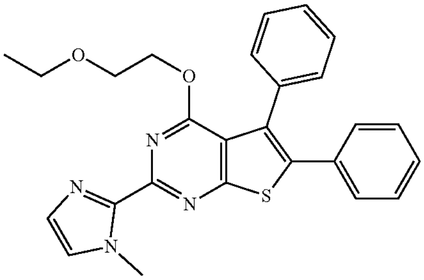 [SMILES: CCOCCOc1nc(-c2nccn2C)nc2sc(-c3ccccc3)c(-c3ccccc3)c12] | A | 0 | B | | | | |
| 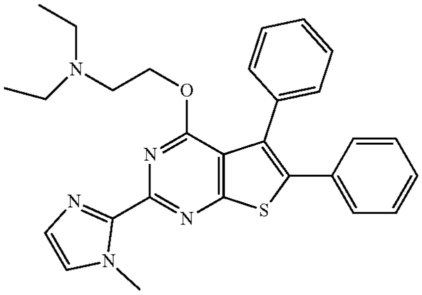 | B | B | C | | | | |
| 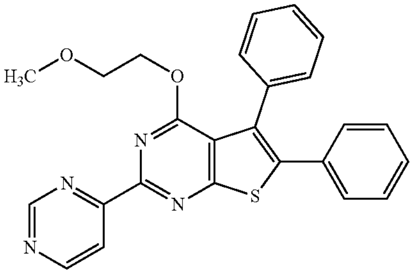 [SMILES: COCCOc1nc(-c2ccncn2)nc2sc(-c3ccccc3)c(-c3ccccc3)c12] | 0 | A | A | | | | |
| 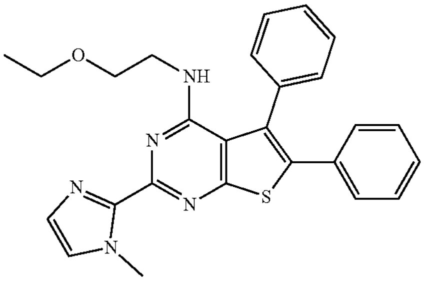 [SMILES: CCOCCNc1nc(-c2nccn2C)nc2sc(-c3ccccc3)c(-c3ccccc3)c12] | C | C | C | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 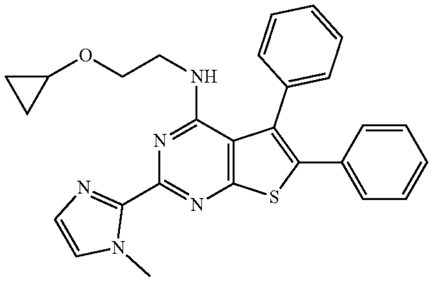 [SMILES: Cn1ccnc1-c1nc(NCCOC2CC2)c2c(-c3ccccc3)c(-c3ccccc3)sc2n1] | A | B | B | | | | |
| 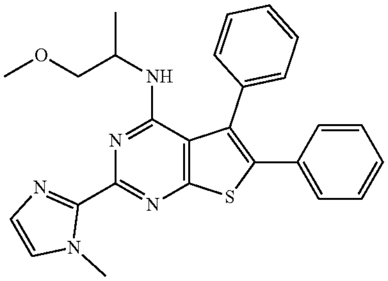 [SMILES: COCC(C)Nc1nc(-c2nccn2C)nc2sc(-c3ccccc3)c(-c3ccccc3)c12] | A | A | A | | | | |
| 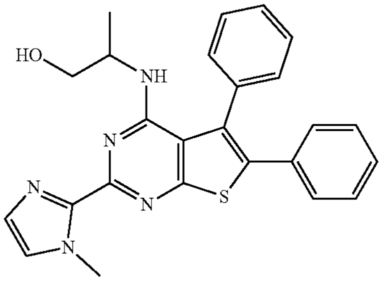 [SMILES: CC(CO)Nc1nc(-c2nccn2C)nc2sc(-c3ccccc3)c(-c3ccccc3)c12] | A | B | 0 | | | | |
| 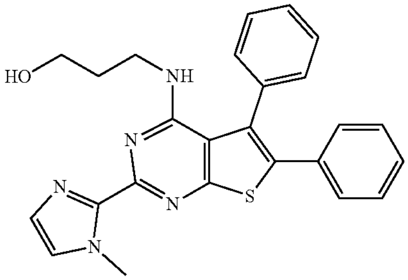 [SMILES: Cn1ccnc1-c1nc(NCCCO)c2c(-c3ccccc3)c(-c3ccccc3)sc2n1] | C | B | B | | | | |
| 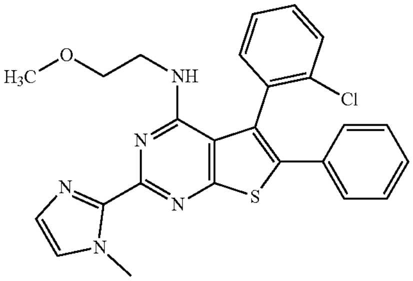 [SMILES: COCCNc1nc(-c2nccn2C)nc2sc(-c3ccccc3)c(-c3ccccc3Cl)c12] | B | B | A | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 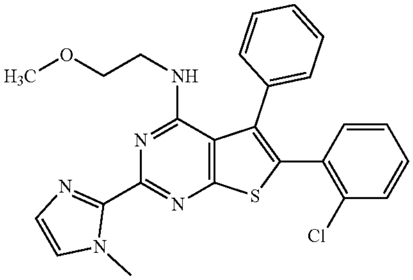 [SMILES: COCCNc1nc(-c2nccn2C)nc2sc(-c3ccccc3Cl)c(-c3ccccc3)c12] | A | A | A | | | | |
| 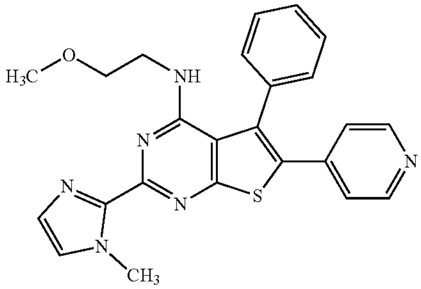 [SMILES: COCCNc1nc(-c2nccn2C)nc2sc(-c3ccncc3)c(-c3ccccc3)c12] | C | C | D | | | | |
| 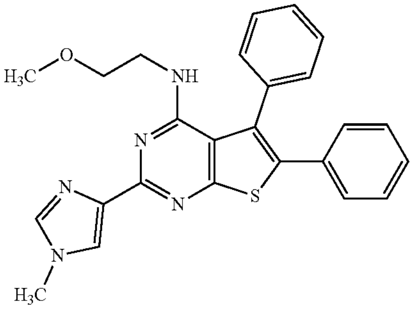 [SMILES: COCCNc1nc(-c2cn(C)cn2)nc2sc(-c3ccccc3)c(-c3ccccc3)c12] | B | B | C | | | | |
| 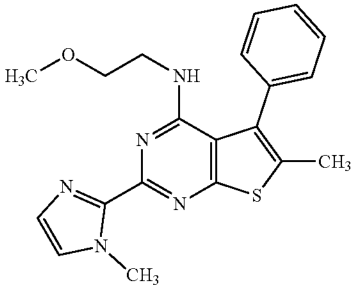 [SMILES: COCCNc1nc(-c2nccn2C)nc2sc(C)c(-c3ccccc3)c12] | C | C | C | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 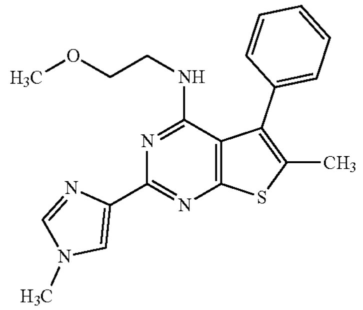 [SMILES: COCCNc1nc(-c2cn(C)cn2)nc2sc(C)c(-c3ccccc3)c12] | B | B | C | | | | |
| 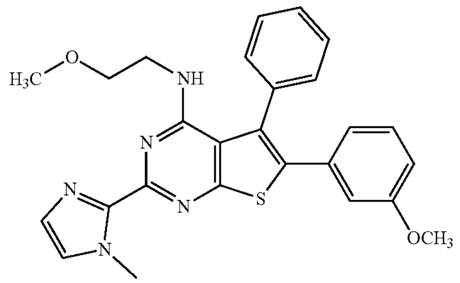 [SMILES: COCCNc1nc(-c2nccn2C)nc2sc(-c3cccc(OC)c3)c(-c3ccccc3)c12] | B | A | B | | | | |
| 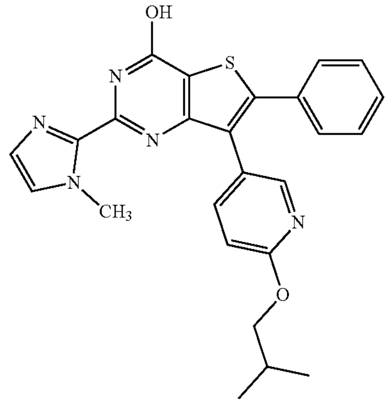 [SMILES: CC(C)COc1ccc(-c2c(-c3ccccc3)sc3c(O)nc(-c4nccn4C)nc23)cn1] | C | B | C | | | | |
| 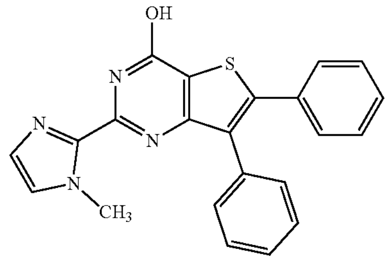 [SMILES: Cn1ccnc1-c1nc(O)c2sc(-c3ccccc3)c(-c3ccccc3)c2n1] | 0 | 0 | A | | | | |

TABLE 7-continued
| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 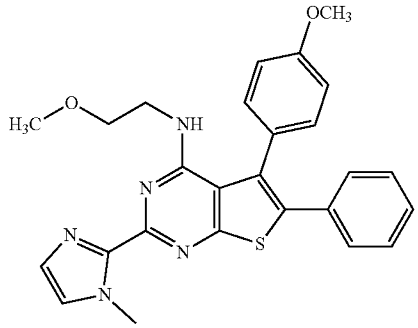 [SMILES: COCCNc1nc(-c2nccn2C)nc2sc(-c3ccccc3)c(-c3ccc(OC)cc3)c12] | B | B | B | | | | |
| 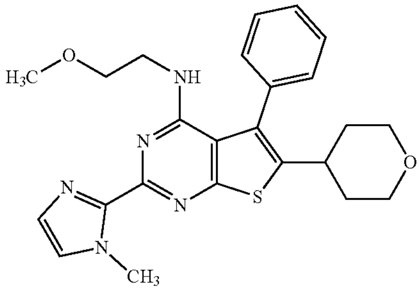 [SMILES: COCCNc1nc(-c2nccn2C)nc2sc(C3CCOCC3)c(-c3ccccc3)c12] | C | B | C | | | | |
| 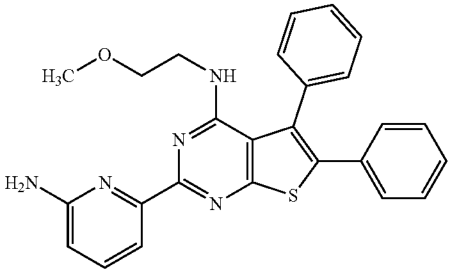 [SMILES: COCCNc1nc(-c2cccc(N)n2)nc2sc(-c3ccccc3)c(-c3ccccc3)c12] | 0 | A | 0 | | | | |
| 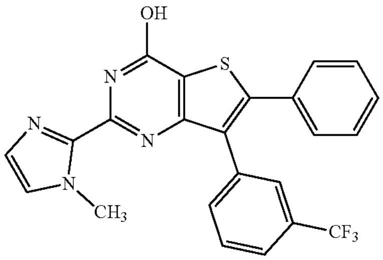 [SMILES: Cn1ccnc1-c1nc(O)c2sc(-c3ccccc3)c(-c3cccc(C(F)(F)F)c3)c2n1] | 0 | 0 | A | | | | |
| 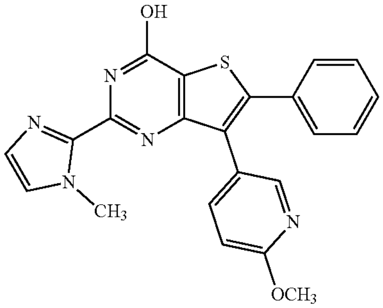 [SMILES: COc1ccc(-c2c(-c3ccccc3)sc3c(O)nc(-c4nccn4C)nc23)cn1] | A | A | A | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 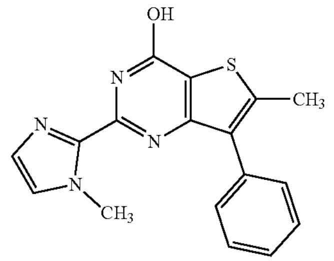 [SMILES: Cc1sc2c(O)nc(-c3nccn3C)nc2c1-c1ccccc1] | B | B | B | | | | |
| 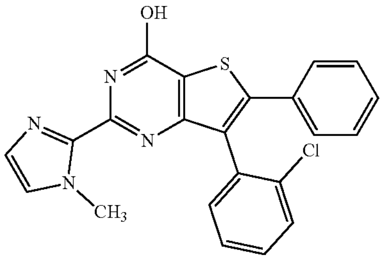 [SMILES: Cn1ccnc1-c1nc(O)c2sc(-c3ccccc3)c(-c3ccccc3Cl)c2n1] | C | C | B | | | | |
| 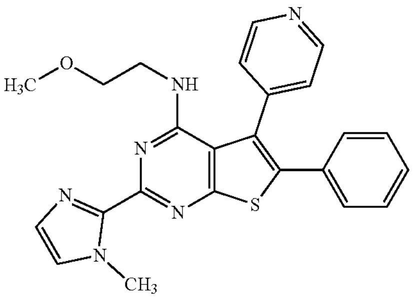 [SMILES: COCCNc1nc(-c2nccn2C)nc2sc(-c3ccccc3)c(-c3ccncc3)c12] | C | B | C | | | | |
| 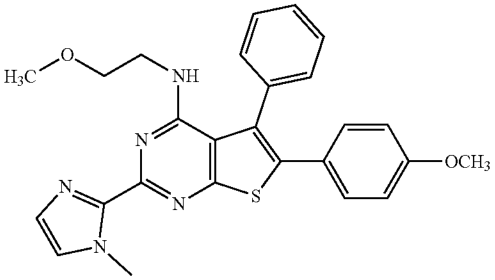 [SMILES: COCCNc1nc(-c2nccn2C)nc2sc(-c3ccc(OC)cc3)c(-c3ccccc3)c12] | B | A | A | | | | |
| 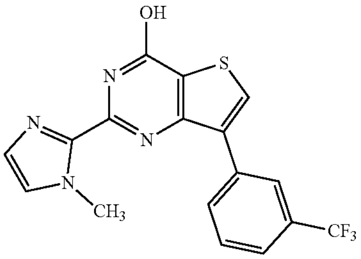 [SMILES: Cn1ccnc1-c1nc(O)c2scc(-c3cccc(C(F)(F)F)c3)c2n1] | B | A | B | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 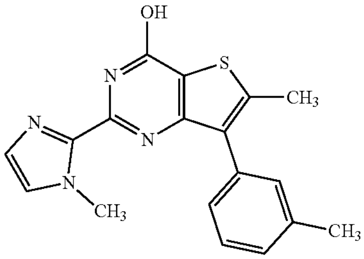 [SMILES: Cc1cccc(-c2c(C)sc3c(O)nc(-c4nccn4C)nc23)c1] | A | A | A | | | | |
| 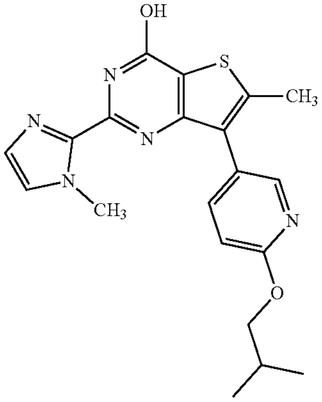 [SMILES: Cc1sc2c(O)nc(-c3nccn3C)nc2c1-c1ccc(OCC(C)C)nc1] | A | A | A | | | | |
| 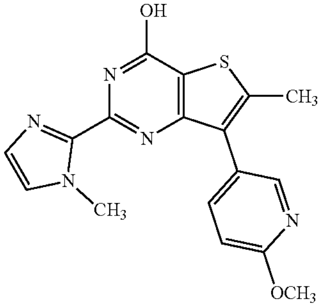 [SMILES: COc1ccc(-c2c(C)sc3c(O)nc(-c4nccn4C)nc23)cn1] | A | A | A | | | | |
| 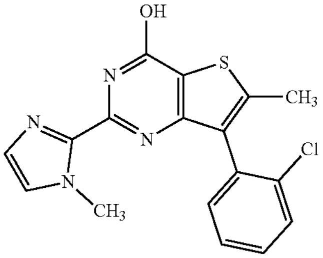 [SMILES: Cc1sc2c(O)nc(-c3nccn3C)nc2c1-c1ccccc1Cl] | B | A | B | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 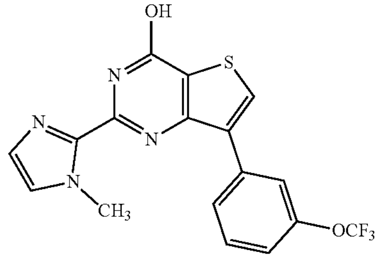 [SMILES: Cn1ccnc1-c1nc(O)c2scc(-c3cccc(OC(F)(F)F)c3)c2n1] | C | A | B | | | | |
| 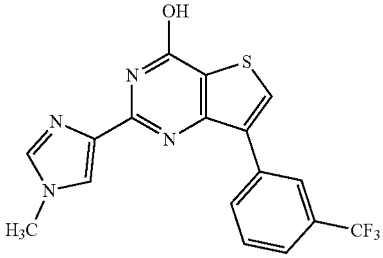 [SMILES: Cn1cnc(-c2nc(O)c3scc(-c4cccc(C(F)(F)F)c4)c3n2)c1] | B | B | C | | | | |
| 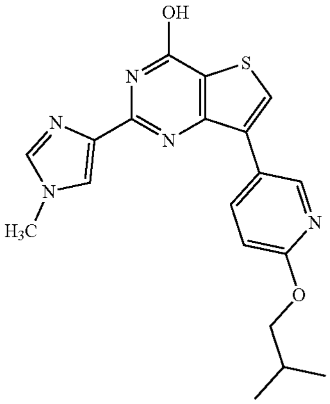 [SMILES: CC(C)COc1ccc(-c2csc3c(O)nc(-c4cn(C)cn4)nc23)cn1] | A | B | B | | | | |
| 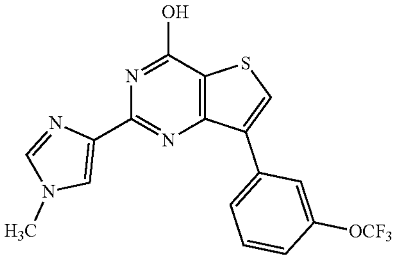 [SMILES: Cn1cnc(-c2nc(O)c3scc(-c4cccc(OC(F)(F)F)c4)c3n2)c1] | B | A | B | | | | |
| 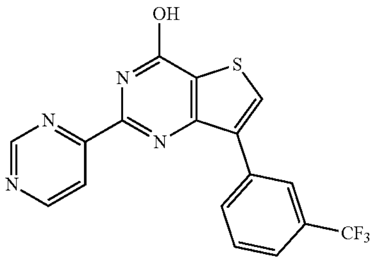 [SMILES: Oc1nc(-c2ccncn2)nc2c(-c3cccc(C(F)(F)F)c3)csc12] | A | B | B | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 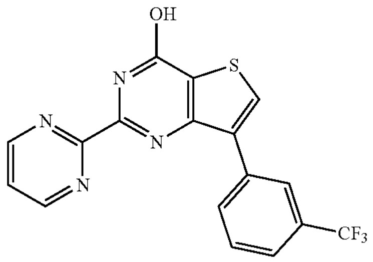 [SMILES: Oc1nc(-c2ncccn2)nc2c(-c3cccc(C(F)(F)F)c3)csc12] | B | B | C | | | | |
| 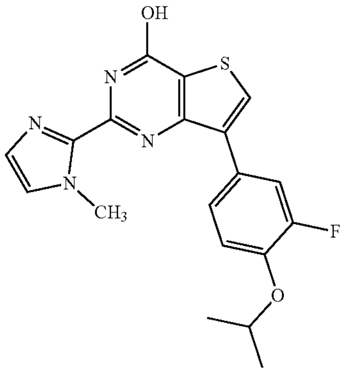 [SMILES: CC(C)Oc1ccc(-c2csc3c(O)nc(-c4nccn4C)nc23)cc1F] | B | B | B | | | | |
| 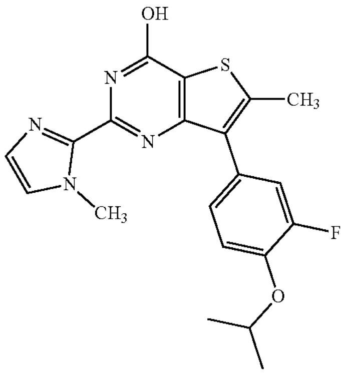 [SMILES: Cc1sc2c(O)nc(-c3nccn3C)nc2c1-c1ccc(OC(C)C)c(F)c1] | C | A | B | | | | |
| 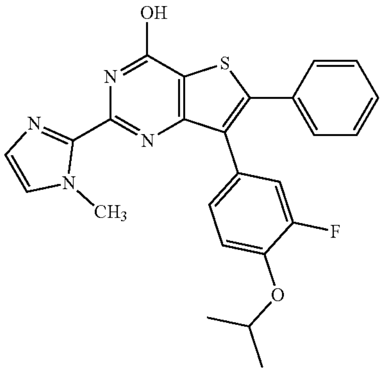 [SMILES: CC(C)Oc1ccc(-c2c(-c3ccccc3)sc3c(O)nc(-c4nccn4C)nc23)cc1F] | B | A | B | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 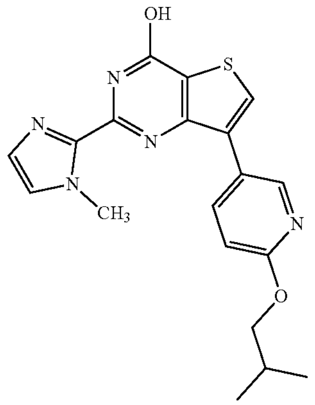 [SMILES: CC(C)COc1ccc(-c2csc3c(O)nc(-c4nccn4C)nc23)cn1] | D | B | B | | | | |
| 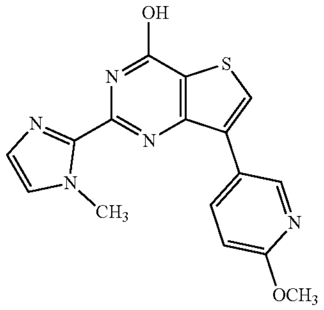 [SMILES: COc1ccc(-c2csc3c(O)nc(-c4nccn4C)nc23)cn1] | C | B | B | | | | |
| 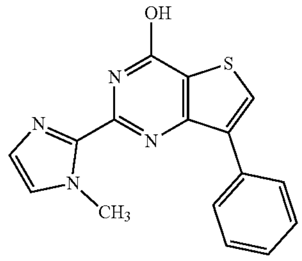 [SMILES: Cn1ccnc1-c1nc(O)c2scc(-c3ccccc3)c2n1] | C | B | B | | | | |
| 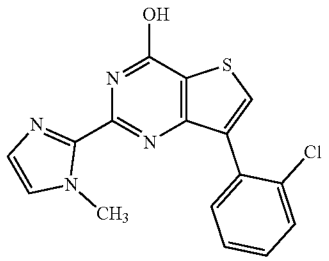 [SMILES: Cn1ccnc1-c1nc(O)c2scc(-c3ccccc3Cl)c2n1] | B | B | B | | | | |

TABLE 7-continued
% Inhibition at 20 μM of K-Ras mutant and wild-type protein
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
|---|---|---|---|---|---|---|---|
| 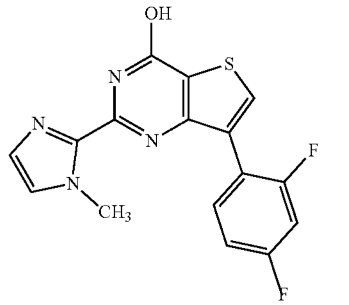 | B | A | A | | | | |
| 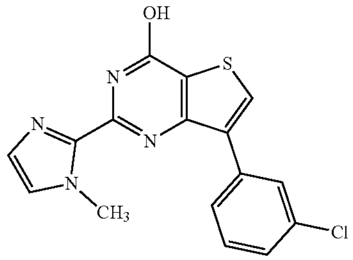 [SMILES: Cn1ccnc1-c1nc(O)c2scc(-c3cccc(Cl)c3)c2n1] | B | B | B | | | | |
| 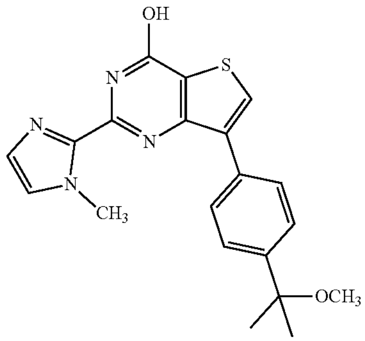 [SMILES: COC(C)(C)c1ccc(-c2csc3c(O)nc(-c4nccn4C)nc23)cc1] | B | 0 | B | | | | |
| 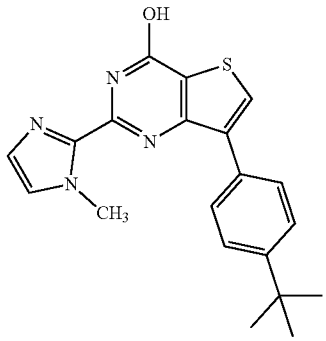 [SMILES: Cn1ccnc1-c1nc(O)c2scc(-c3ccc(C(C)(C)C)cc3)c2n1] | A | B | A | | | | |

TABLE 7-continued

| % Inhibition at 20 μM of K-Ras mutant and wild-type protein | | | | | | | |
|---|---|---|---|---|---|---|---|
| Structure | KRas G12D % Inh. | KRas G12C % Inh. | KRas wild type, % Inh. | KRas G12D Q61H % Inh. | KRas G12C Q61H % Inh. | KRas Q61H % Inh. | KRas G12D Q61H $IC_{50}$ (μM) |
| 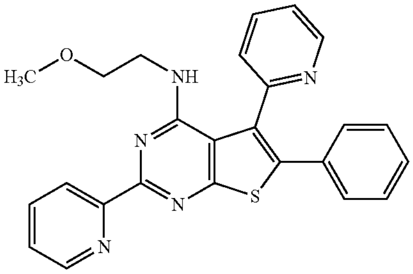 | A | A | 0 | | | | |
| 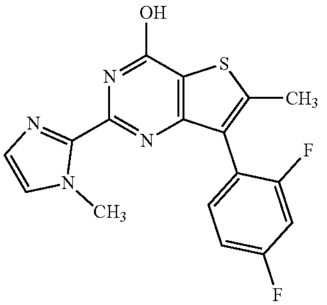 [SMILES: Cc1sc2c(O)nc(-c3nccn3C)nc2c1-c1ccc(F)cc1F] | A | A | A | | | | |
| 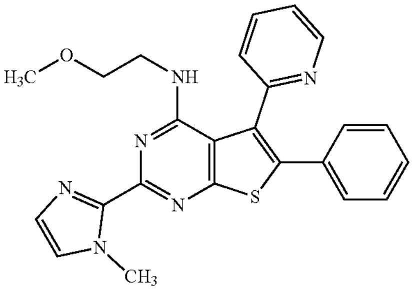 | B | B | C | | | | |

A = 1-25% inhibition, B = 25-50% inhibition, C = 51-75% inhibition, D = 76-100% inhibition. E = >30 μM $IC_{50}$, F = 11-30 μM $IC_{50}$, G = 5-10 μM $IC_{50}$, H = <5 μM $IC_{50}$.

Example 6

Rac and Rho Inhibition Assay

By substituting KRas G12D mutant protein with either Rac-1 or Rho-A under the assay conditions described in Example 5, Rac-1 and Rho-A inhibition, respectively, were each determined.

Table 8 shows inhibition data for selected compounds tested in the screening assays described above.

TABLE 8
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 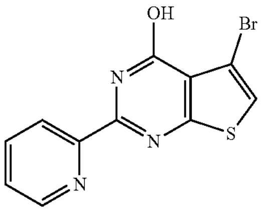 [SMILES: Oc1nc(-c2ccccn2)nc2scc(Br)c12] | C | C | D | D |
| 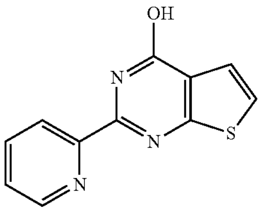 [SMILES: Oc1nc(-c2ccccn2)nc2sccc12] | B | C | D | D |
| 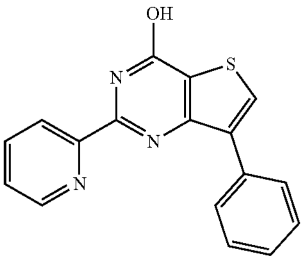 [SMILES: Oc1nc(-c2ccccn2)nc2c(-c3ccccc3)csc12] | | B | C | C |
| 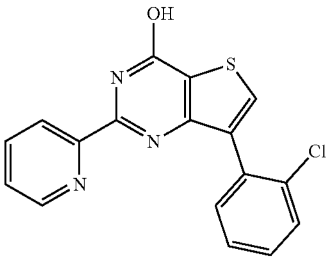 [SMILES: Oc1nc(-c2ccccn2)nc2c(-c3ccccc3Cl)csc12] | B | C | D | D |
| 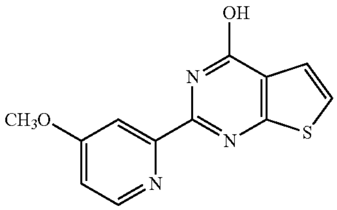 | C | C | D | C |
| 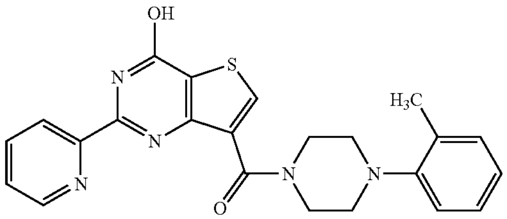 [SMILES: Cc1ccccc1N1CCN(C(=O)c2csc3c(O)nc(-c4ccccn4)nc23)CC1] | | B | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 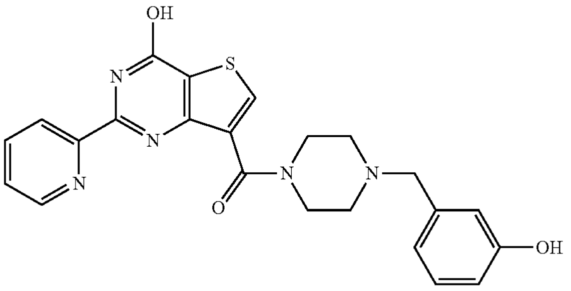 [SMILES: O=C(c1csc2c(O)nc(-c3ccccn3)nc12)N1CCN(Cc2cccc(O)c2)CC1] | | D | D | D |
| 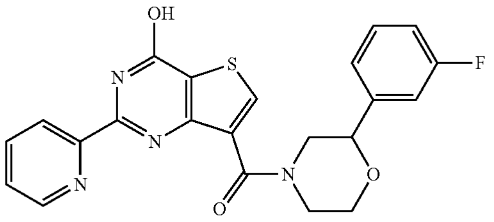 [SMILES: O=C(c1csc2c(O)nc(-c3ccccn3)nc12)N1CCOC(c2cccc(F)c2)C1] | | B | B | A |
| 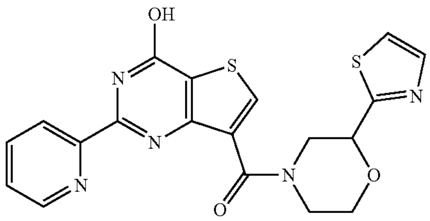 [SMILES: O=C(c1csc2c(O)nc(-c3ccccn3)nc12)N1CCOC(c2nccs2)C1] | | B | D | D |
| 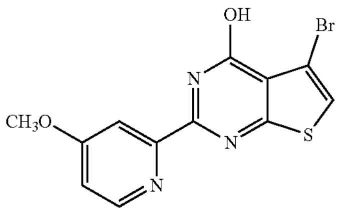 | | B | B | B |
| 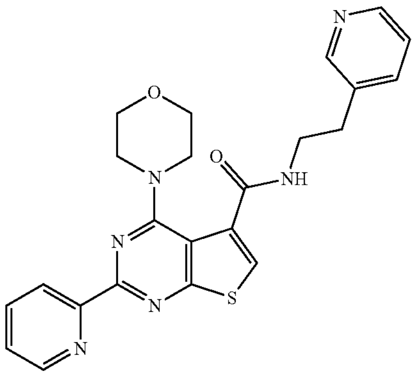 [SMILES: O=C(NCCc1cccnc1)c1csc2nc(-c3ccccn3)nc(N3CCOCC3)c12] | | A | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 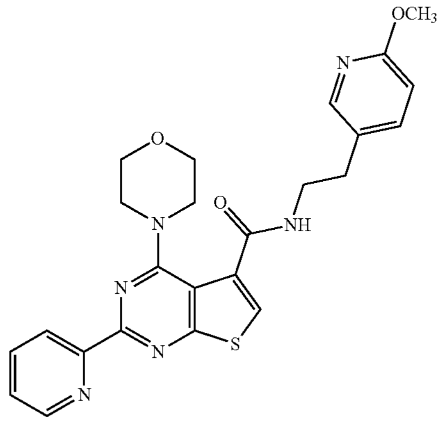 [SMILES: COc1ccc(CCNC(=O)c2csc3nc(-c4ccccn4)nc(N4CCOCC4)c23)cn1] | | B | C | C |
| 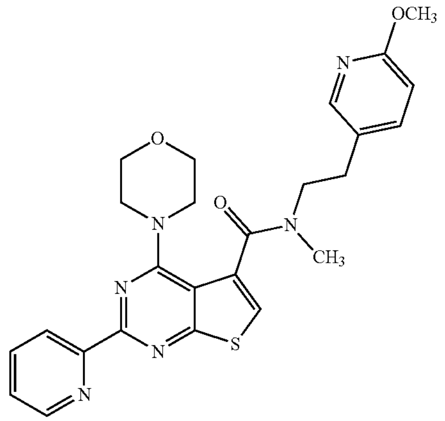 [SMILES: COc1ccc(CCN(C)C(=O)c2csc3nc(-c4ccccn4)nc(N4CCOCC4)c23)cn1] | | 0 | B | B |
| 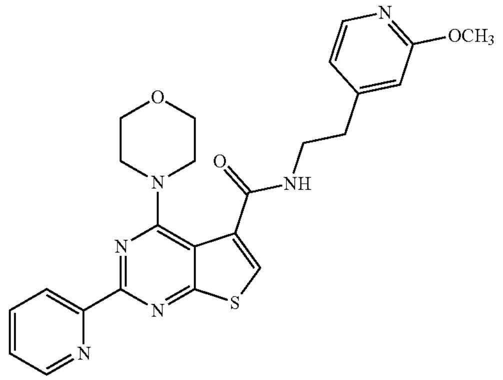 [SMILES: COc1cc(CCNC(=O)c2csc3nc(-c4ccccn4)nc(N4CCOCC4)c23)ccn1] | | A | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 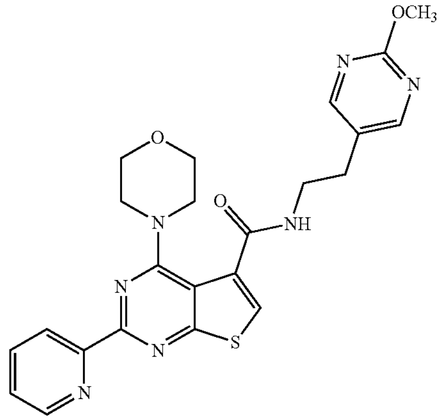 [SMILES: COc1ncc(CCNC(=O)c2csc3nc(-c4ccccn4)nc(N4CCOCC4)c23)cn1] | | A | C | C |
| 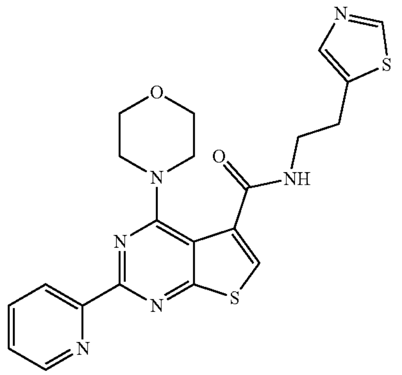 [SMILES: O=C(NCCc1cncs1)c1csc2nc(-c3ccccn3)nc(N3CCOCC3)c12] | | A | C | B |
| 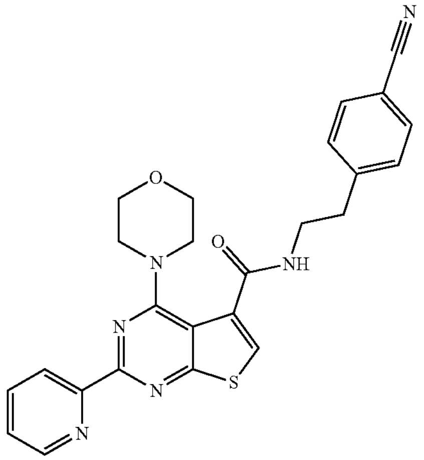 [SMILES: N#Cc1ccc(CCNC(=O)c2csc3nc(-c4ccccn4)nc(N4CCOCC4)c23)cc1] | | A | B | B |
| 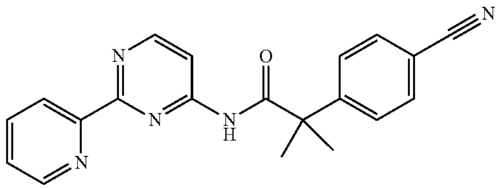 [SMILES: CC(C)(C(=O)Nc1ccnc(-c2ccccn2)n1)c1ccc(C#N)cc1] | | A | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 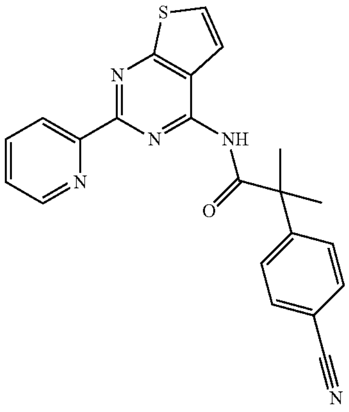 [SMILES: CC(C)(C(=O)Nc1nc(-c2ccccn2)nc2sccc12)c1ccc(C#N)cc1] | | 0 | D | C |
| 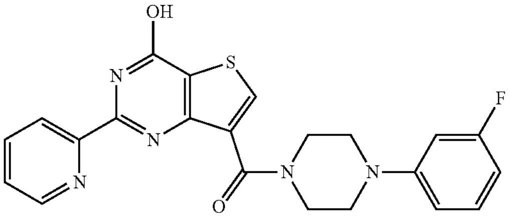 [SMILES: O=C(c1csc2c(O)nc(-c3ccccn3)nc12)N1CCN(c2cccc(F)c2)CC1] | | B | D | D |
| 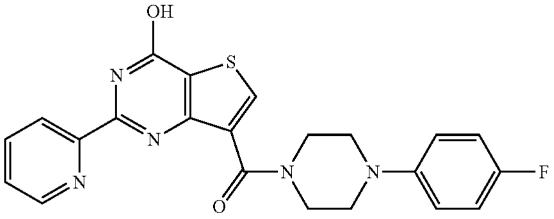 [SMILES: O=C(c1csc2c(O)nc(-c3ccccn3)nc12)N1CCN(c2ccc(F)cc2)CC1] | | 0 | C | C |
| 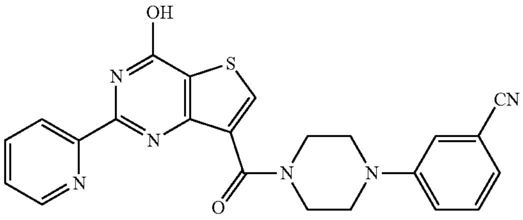 | | A | C | C |
| 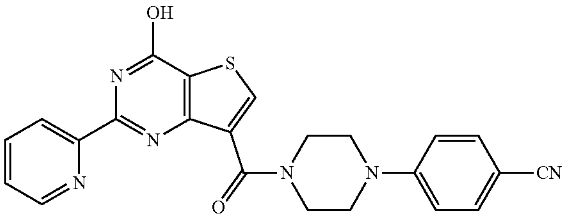 [SMILES: N#Cc1ccc(N2CCN(C(=O)c3csc4c(O)nc(-c5ccccn5)nc34)CC2)cc1] | | 0 | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 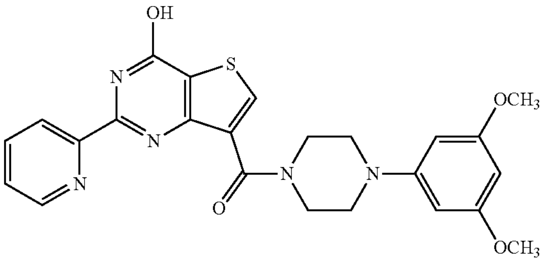 [SMILES: COc1cc(OC)cc(N2CCN(C(=O)c3csc4c(O)nc(-c5ccccn5)nc34)CC2)c1] | | 0 | B | B |
| 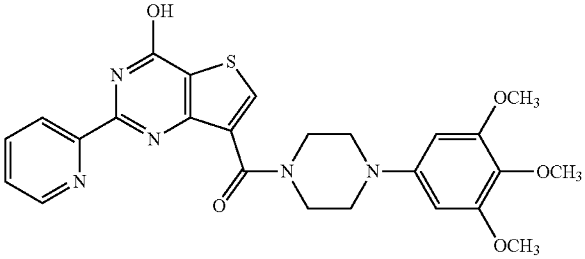 [SMILES: COc1cc(N2CCN(C(=O)c3csc4c(O)nc(-c5ccccn5)nc34)CC2)cc(OC)c1OC] | | 0 | A | B |
| 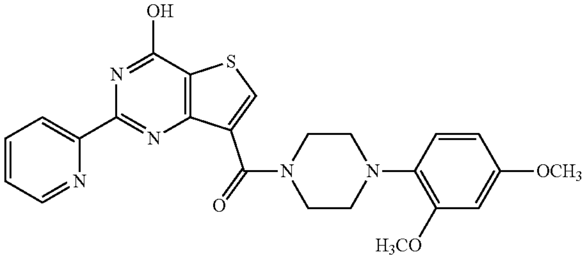 [SMILES: COc1ccc(N2CCN(C(=O)c3csc4c(O)nc(-c5ccccn5)nc34)CC2)c(OC)c1] | | B | D | C |
| 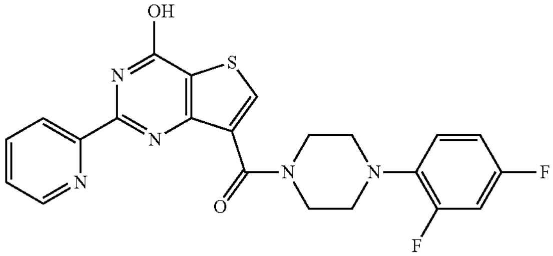 [SMILES: O=C(c1csc2c(O)nc(-c3ccccn3)nc12)N1CCN(c2ccc(F)cc2F)CC1] | | C | D | C |
| 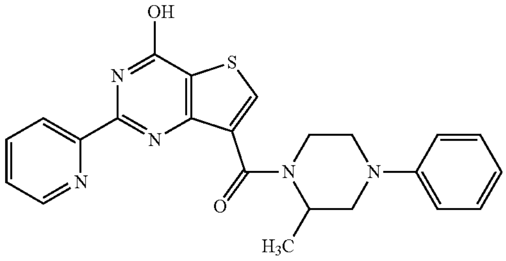 [SMILES: CC1CN(c2ccccc2)CCN1C(=O)c1csc2c(O)nc(-c3ccccn3)nc12] | D | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 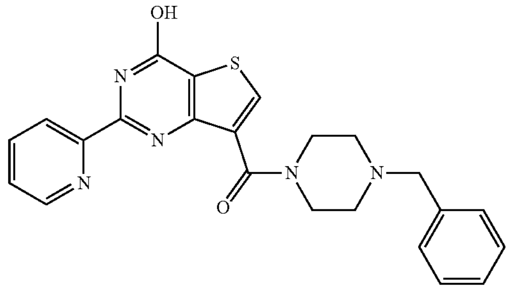 [SMILES: O=C(c1csc2c(O)nc(-c3ccccn3)nc12)N1CCN(Cc2ccccc2)CC1] | | B | C | D |
| 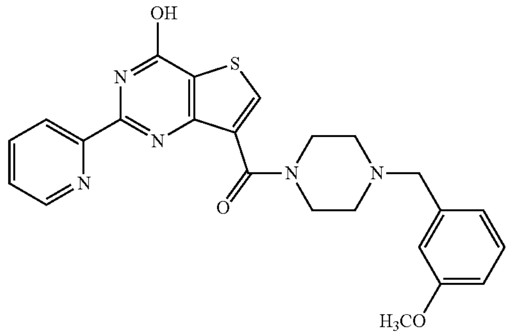 [SMILES: COc1cccc(CN2CCN(C(=O)c3csc4c(O)nc(-c5ccccn5)nc34)CC2)c1] | D | B | D | D |
| 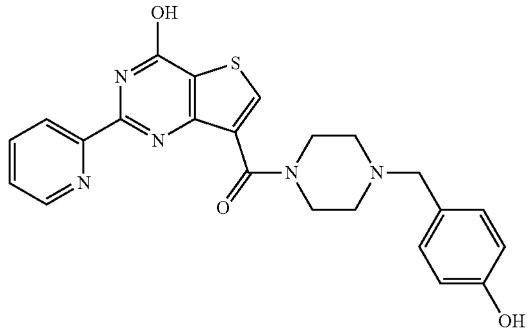 [SMILES: O=C(c1csc2c(O)nc(-c3ccccn3)nc12)N1CCN(Cc2ccc(O)cc2)CC1] | | A | C | B |
| 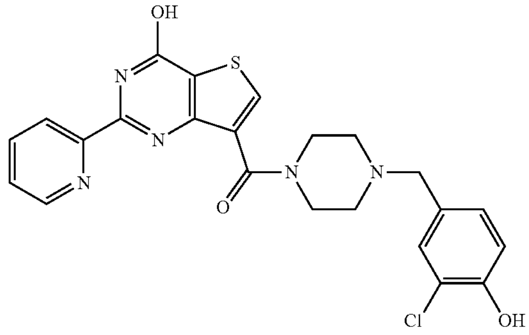 [SMILES: O=C(c1csc2c(O)nc(-c3ccccn3)nc12)N1CCN(Cc2ccc(O)c(Cl)c2)CC1] | | B | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 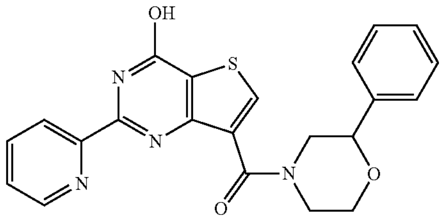 [SMILES: O=C(c1csc2c(O)nc(-c3ccccn3)nc12)N1CCOC(c2ccccc2)C1] | | A | B | C |
| 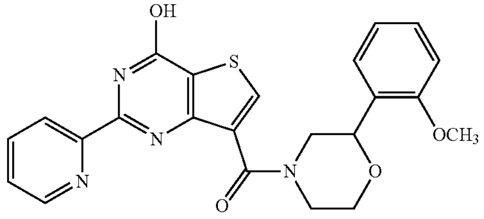 [SMILES: COc1ccccc1C1CN(C(=O)c2csc3c(O)nc(-c4ccccn4)nc23)CCO1] | | C | D | D |
| 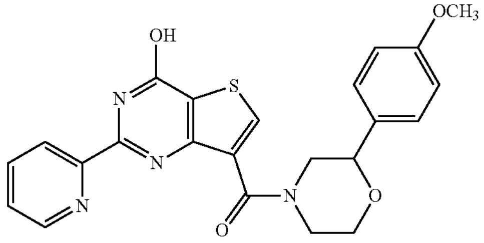 [SMILES: COc1ccc(C2CN(C(=O)c3csc4c(O)nc(-c5ccccn5)nc34)CCO2)cc1] | | B | B | B |
| 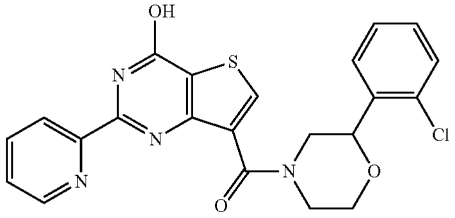 [SMILES: O=C(c1csc2c(O)nc(-c3ccccn3)nc12)N1CCOC(c2ccccc2Cl)C1] | B | C | C | D |
| 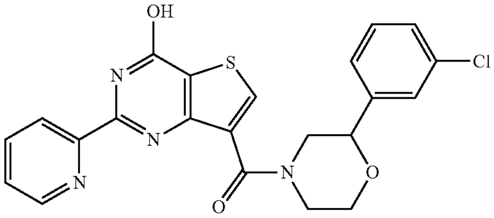 [SMILES: O=C(c1csc2c(O)nc(-c3ccccn3)nc12)N1CCOC(c2cccc(Cl)c2)C1] | | A | A | C |
| 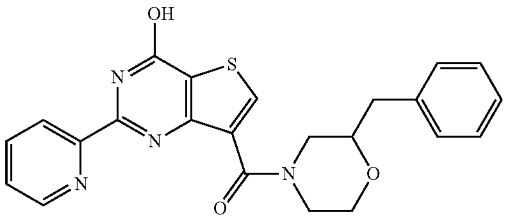 [SMILES: O=C(c1csc2c(O)nc(-c3ccccn3)nc12)N1CCOC(Cc2ccccc2)C1] | | B | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 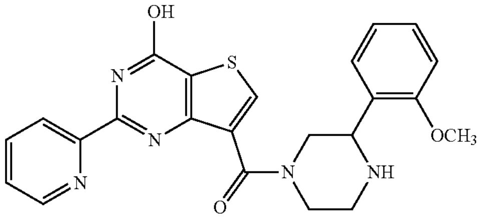 | | B | A | D |
| 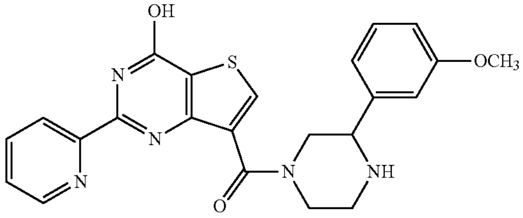 | C | B | D | D |
| 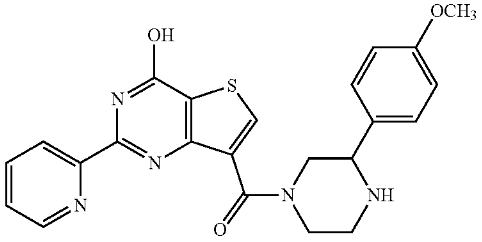 [SMILES: COc1ccc(C2CN(C(=O)c3csc4c(O)nc(-c5ccccn5)nc34)CCN2)cc1] | | A | D | D |
| 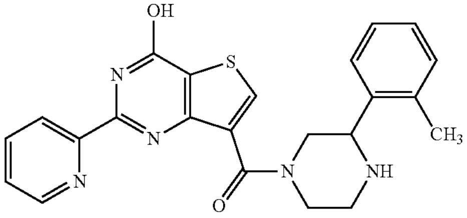 [SMILES: Cc1ccccc1C1CN(C(=O)c2csc3c(O)nc(-c4ccccn4)nc23)CCN1] | | B | D | D |
| 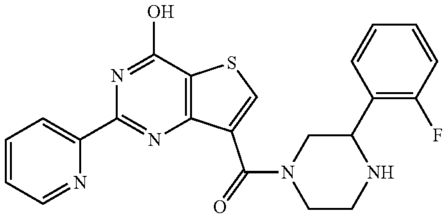 [SMILES: O=C(c1csc2c(O)nc(-c3ccccn3)nc12)N1CCNC(c2ccccc2F)C1] | | B | D | D |
| 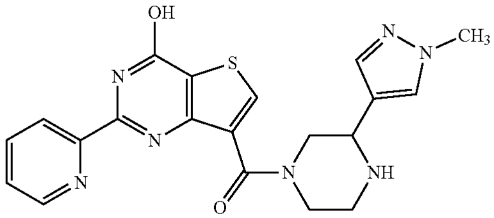 [SMILES: Cn1cc(C2CN(C(=O)c3csc4c(O)nc(-c5ccccn5)nc34)CCN2)cn1] | | A | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 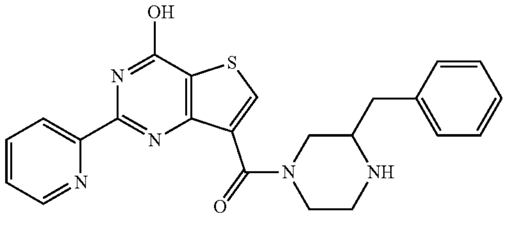 [SMILES: O=C(c1csc2c(O)nc(-c3ccccn3)nc12)N1CCNC(Cc2ccccc2)C1] | | B | D | D |
| 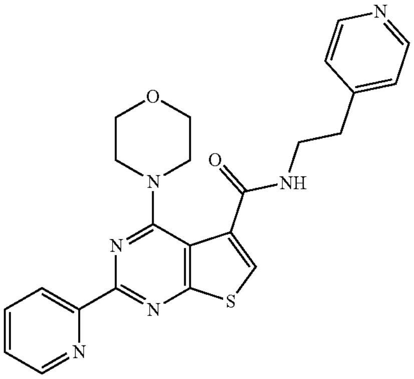 [SMILES: O=C(NCCc1ccncc1)c1csc2nc(-c3ccccn3)nc(N3CCOCC3)c12] | | 0 | D | C |
| 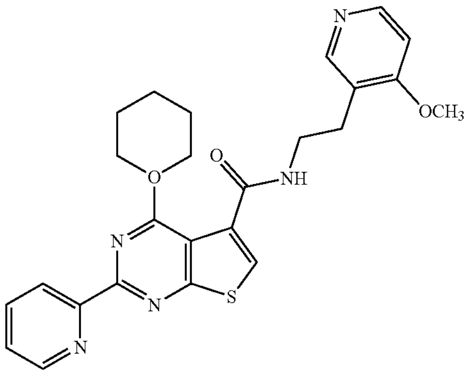 | | A | C | B |
| 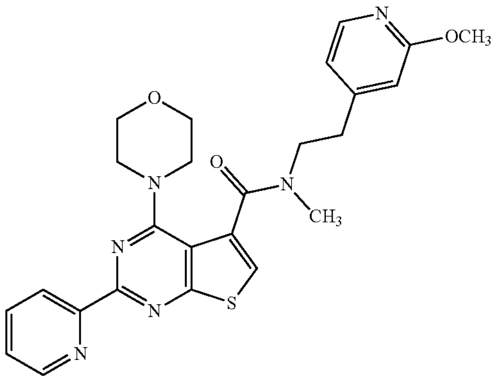 [SMILES: COc1cc(CCN(C)C(=O)c2csc3nc(-c4ccccn4)nc(N4CCOCC4)c23)ccn1] | | 0 | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 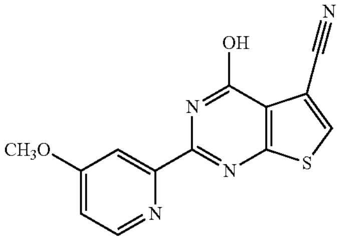 | | 0 | C | B |
| 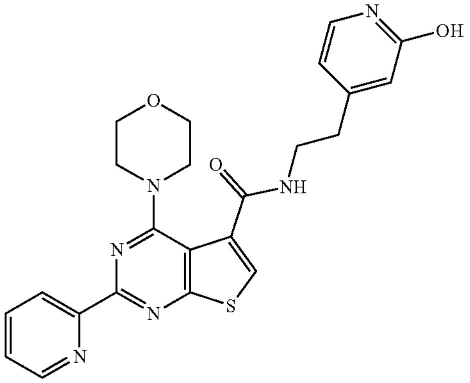 [SMILES: O=C(NCCc1ccnc(O)c1)c1csc2nc(-c3ccccn3)nc(N3CCOCC3)c12] | | A | B | B |
| 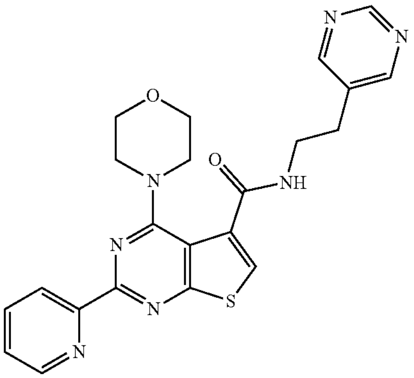 [SMILES: O=C(NCCc1cncnc1)c1csc2nc(-c3ccccn3)nc(N3CCOCC3)c12] | | A | C | C |
| 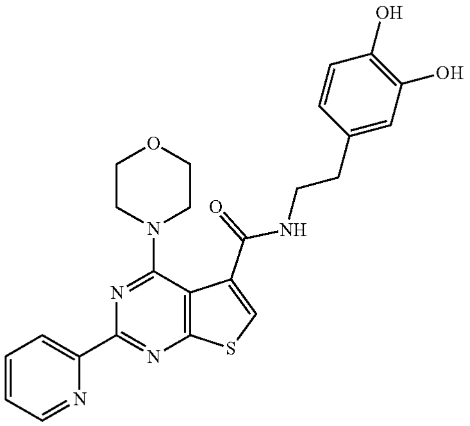 [SMILES: O=C(NCCc1ccc(O)c(O)c1)c1csc2nc(-c3ccccn3)nc(N3CCOCC3)c12] | | 0 | B | B |

TABLE 8-continued
% Inhibition at 20 µM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 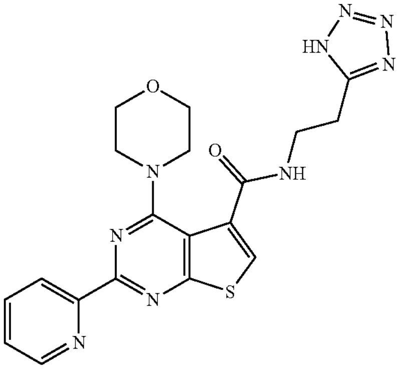 [SMILES: O=C(NCCc1nnn[nH]1)c1csc2nc(-c3ccccn3)nc(N3CCOCC3)c12] | | A | D | C |
| 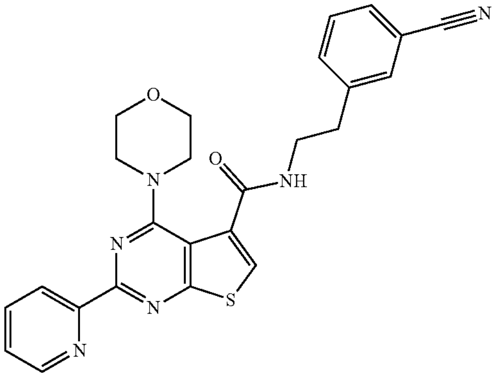 [SMILES: N#Cc1cccc(CCNC(=O)c2csc3nc(-c4ccccn4)nc(N4CCOCC4)c23)c1] | | A | C | C |
| 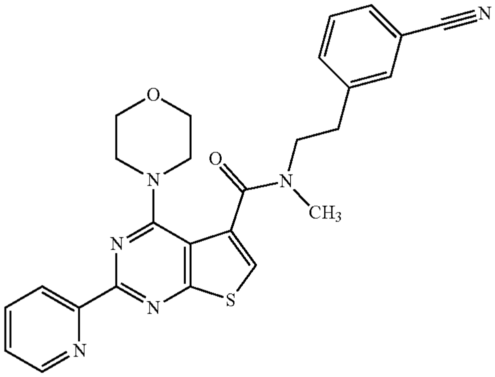 [SMILES: CN(CCc1cccc(C#N)c1)C(=O)c1csc2nc(-c3ccccn3)nc(N3CCOCC3)c12] | | A | D | C |
| 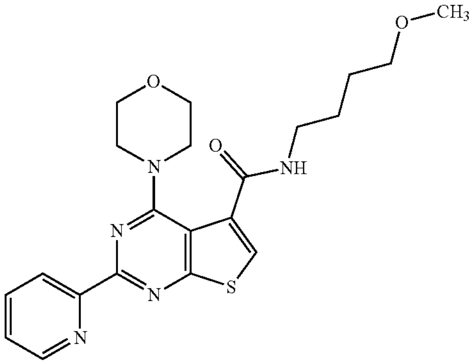 [SMILES: COCCCCNC(=O)c1csc2nc(-c3ccccn3)nc(N3CCOCC3)c12] | | A | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
| --- | --- | --- | --- | --- |
| 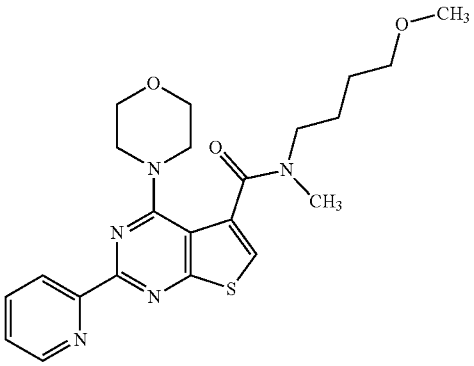 [SMILES: COCCCCN(C)C(=O)c1csc2nc(-c3ccccn3)nc(N3CCOCC3)c12] | | A | D | C |
| 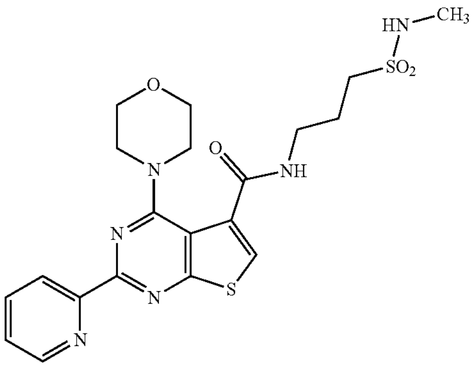 [SMILES: CNS(=O)(=O)CCCNC(=O)c1csc2nc(-c3ccccn3)nc(N3CCOCC3)c12] | | A | D | C |
| 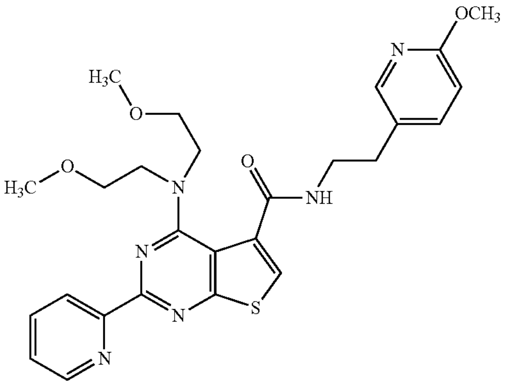 [SMILES: COCCN(CCOC)c1nc(-c2ccccn2)nc2scc(C(=O)NCCc3ccc(OC)nc3)c12] | | A | C | C |
| 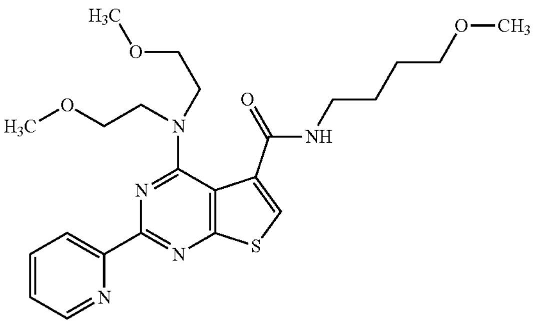 [SMILES: COCCCCNC(=O)c1csc2nc(-c3ccccn3)nc(N(CCOC)CCOC)c12] | | 0 | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 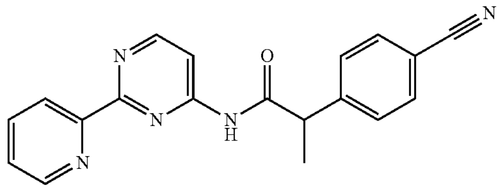 [SMILES: CC(C(=O)Nc1ccnc(-c2ccccn2)n1)c1ccc(C#N)cc1] | | A | D | C |
| 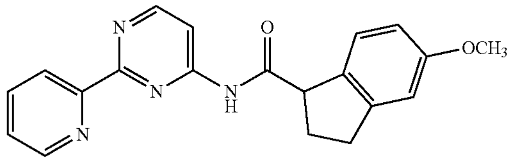 [SMILES: COc1ccc2c(c1)CCC2C(=O)Nc1ccnc(-c2ccccn2)n1] | | A | C | C |
| 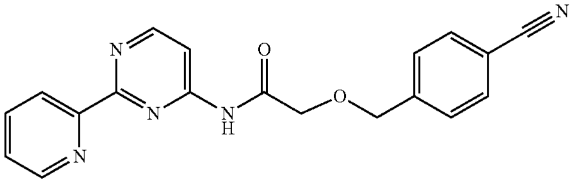 [SMILES: N#Cc1ccc(COCC(=O)Nc2ccnc(-c3ccccn3)n2)cc1] | | 0 | D | C |
| 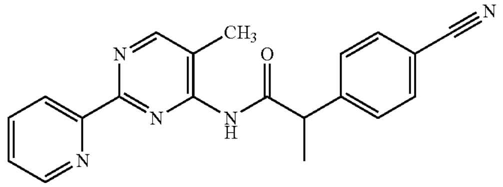 [SMILES: Cc1cnc(-c2ccccn2)nc1NC(=O)C(C)c1ccc(C#N)cc1] | | A | D | C |
| 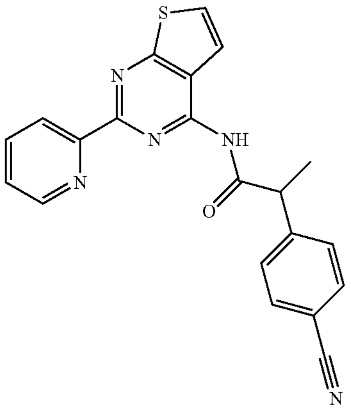 [SMILES: CC(C(=O)Nc1nc(-c2ccccn2)nc2sccc12)c1ccc(C#N)cc1] | | A | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 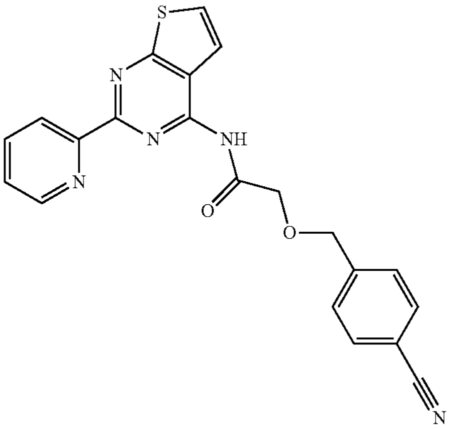 [SMILES: N#Cc1ccc(COCC(=O)Nc2nc(-c3ccccn3)nc3sccc23)cc1] | D | B | D | D |
| 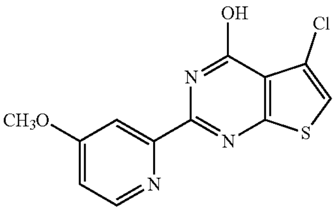 | C | C | D | D |
| 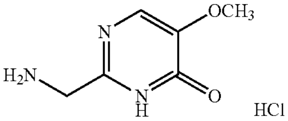 HCl | | B | B | B |
| 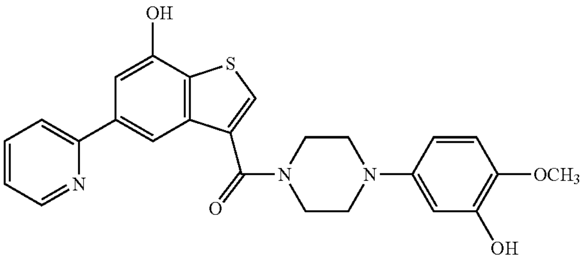 [SMILES: COc1ccc(N2CCN(C(=O)c3csc4c(O)cc(-c5ccccn5)cc34)CC2)cc1O] | | A | D | D |
| 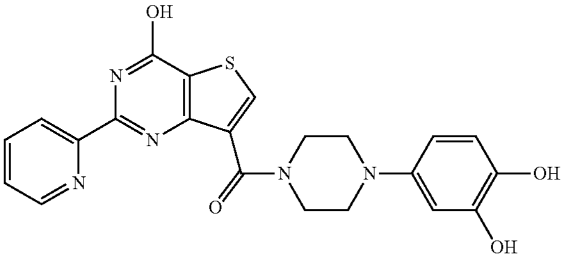 [SMILES: O=C(c1csc2c(O)nc(-c3ccccn3)nc12)N1CCN(c2ccc(O)c(O)c2)CC1] | | C | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 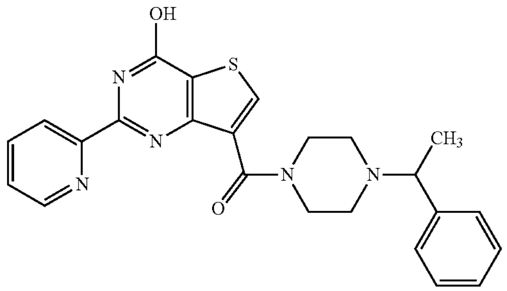 [SMILES: CC(c1ccccc1)N1CCN(C(=O)c2csc3c(O)nc(-c4ccccn4)nc23)CC1] | | C | D | D |
| 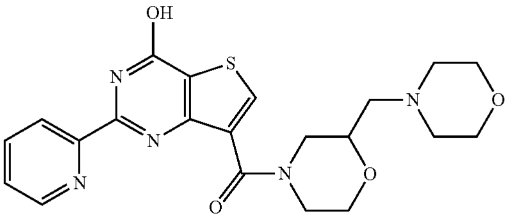 [SMILES: O=C(c1csc2c(O)nc(-c3ccccn3)nc12)N1CCOC(CN2CCOCC2)C1] | | A | D | C |
| 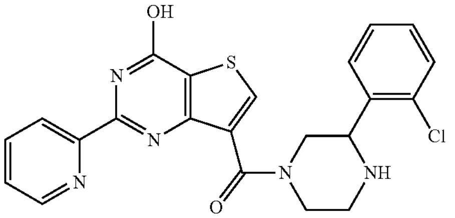 [SMILES: O=C(c1csc2c(O)nc(-c3ccccn3)nc12)N1CCNC(c2ccccc2Cl)C1] | | B | D | D |
| 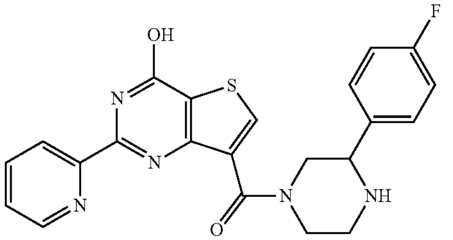 [SMILES: O=C(c1csc2c(O)nc(-c3ccccn3)nc12)N1CCNC(c2ccc(F)cc2)C1] | | A | D | D |
| 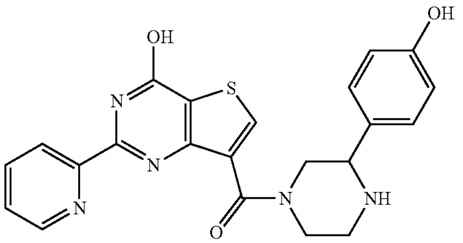 [SMILES: O=C(c1csc2c(O)nc(-c3ccccn3)nc12)N1CCNC(c2ccc(O)cc2)C1] | C | D | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 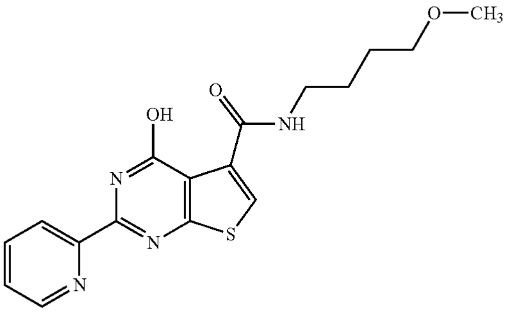 [SMILES: COCCCCNC(=O)c1csc2nc(-c3ccccn3)nc(O)c12] | | A | A | A |
| 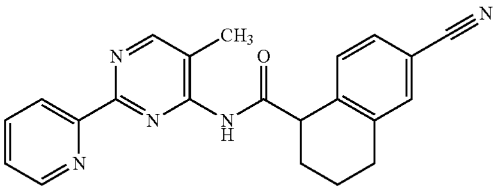 [SMILES: Cc1cnc(-c2ccccn2)nc1NC(=O)C1CCCc2cc(C#N)ccc21] | B | C | D | D |
| 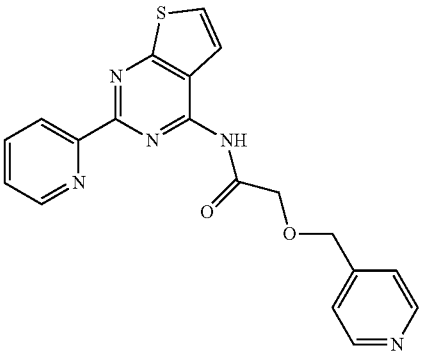 [SMILES: O=C(COCc1ccncc1)Nc1nc(-c2ccccn2)nc2sccc12] | C | C | D | D |
| 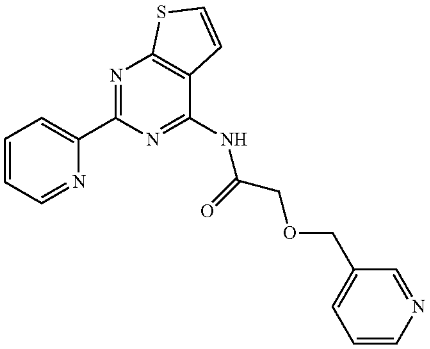 [SMILES: O=C(COCc1cccnc1)Nc1nc(-c2ccccn2)nc2sccc12] | C | C | D | D |
| 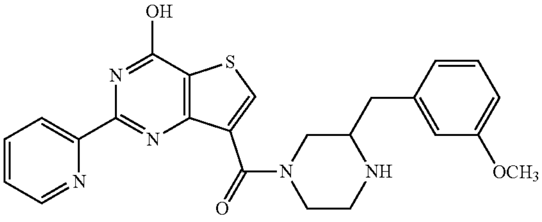 [SMILES: COc1cccc(CC2CN(C(=O)c3csc4c(O)nc(-c5ccccn5)nc34)CCN2)c1] | | C | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 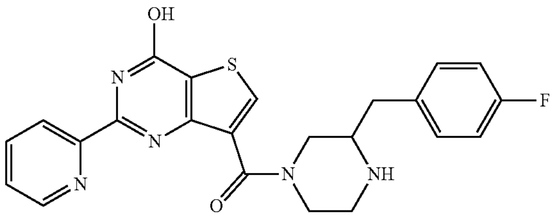 [SMILES: O=C(c1csc2c(O)nc(-c3ccccn3)nc12)N1CCNC(Cc2ccc(F)cc2)C1] | | C | D | D |
| 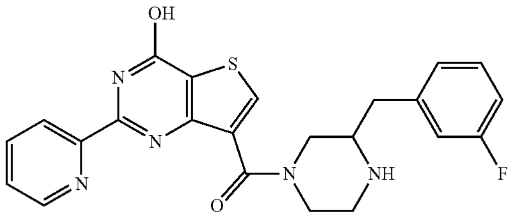 [SMILES: O=C(c1csc2c(O)nc(-c3ccccn3)nc12)N1CCNC(Cc2cccc(F)c2)C1] | | C | C | C |
| 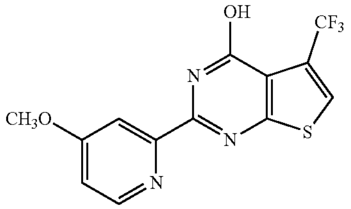 | | B | C | C |
| 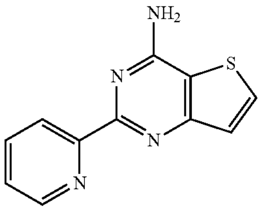 [SMILES: Nc1nc(-c2ccccn2)nc2ccsc12] | A | B | D | D |
| 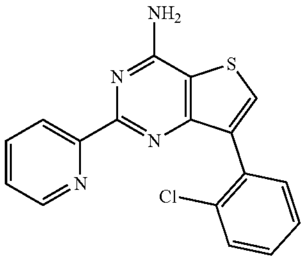 [SMILES: Nc1nc(-c2ccccn2)nc2c(-c3ccccc3Cl)csc12] | | A | B | B |
| 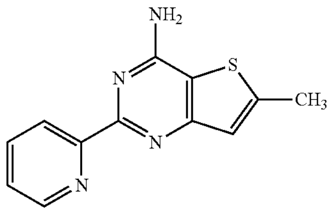 [SMILES: Cc1cc2nc(-c3ccccn3)nc(N)c2s1] | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
| --- | --- | --- | --- | --- |
| 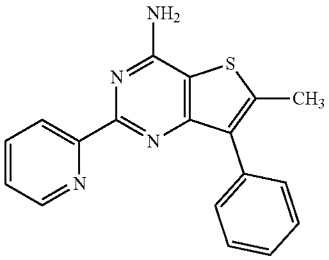 | | B | B | B |
| 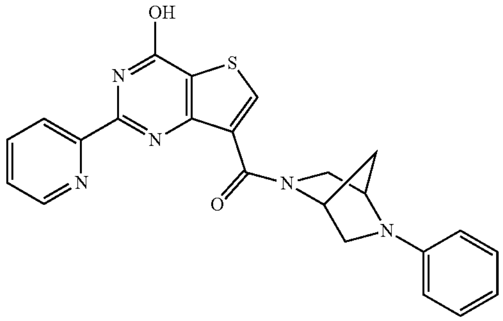 [SMILES: O=C(c1csc2c(O)nc(-c3ccccn3)nc12)N1CC2CC1CN2c1ccccc1] | C | D | D | D |
| 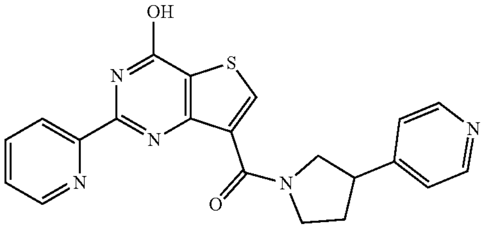 [SMILES: O=C(c1csc2c(O)nc(-c3ccccn3)nc12)N1CCC(c2ccncc2)C1] | C | C | C | D |
| 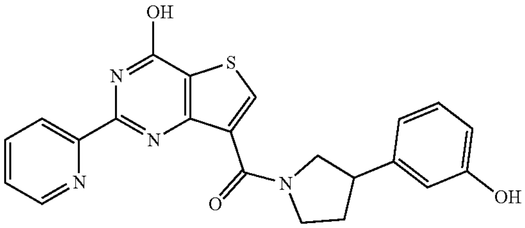 [SMILES: O=C(c1csc2c(O)nc(-c3ccccn3)nc12)N1CCC(c2cccc(O)c2)C1] | D | D | D | D |
| 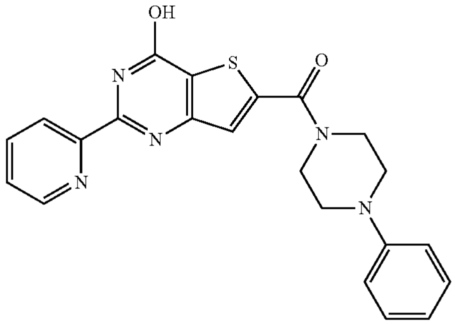 [SMILES: O=C(c1cc2nc(-c3ccccn3)nc(O)c2s1)N1CCN(c2ccccc2)CC1] | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 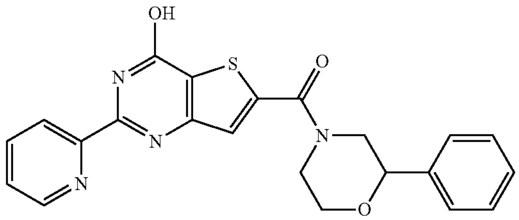 [SMILES: O=C(c1cc2nc(-c3ccccn3)nc(O)c2s1)N1CCOC(c2ccccc2)C1] | | C | D | D |
| 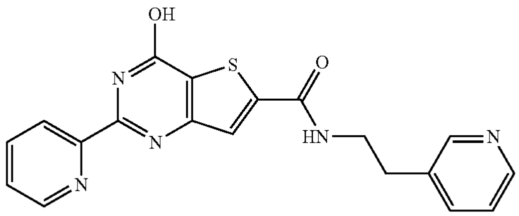 [SMILES: O=C(NCCc1cccnc1)c1cc2nc(-c3ccccn3)nc(O)c2s1] | | B | D | D |
| 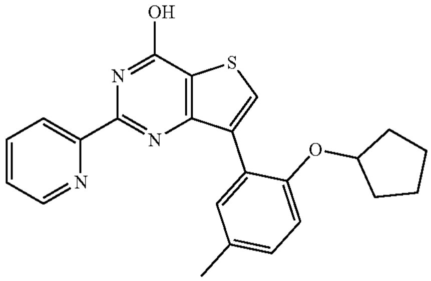 [SMILES: Cc1ccc(OC2CCCC2)c(-c2csc3c(O)nc(-c4ccccn4)nc23)c1] | | C | C | C |
| 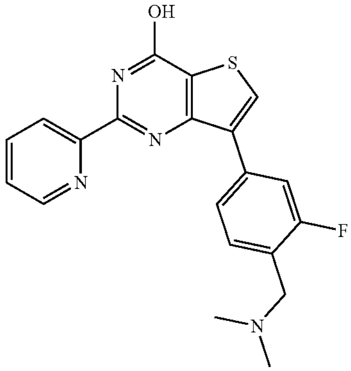 [SMILES: CN(C)Cc1ccc(-c2csc3c(O)nc(-c4ccccn4)nc23)cc1F] | D | D | D | D |
| 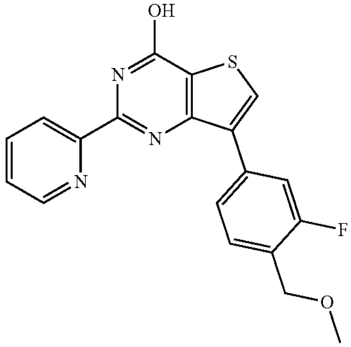 [SMILES: COCc1ccc(-c2csc3c(O)nc(-c4ccccn4)nc23)cc1F] | C | C | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 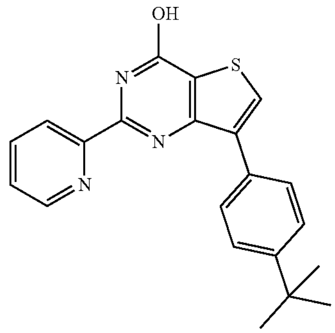 [SMILES: CC(C)(C)c1ccc(-c2csc3c(O)nc(-c4ccccn4)nc23)cc1] | | C | C | C |
| 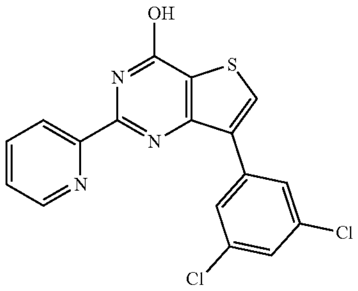 [SMILES: Oc1nc(-c2ccccn2)nc2c(-c3cc(Cl)cc(Cl)c3)csc12] | B | B | B | C |
| 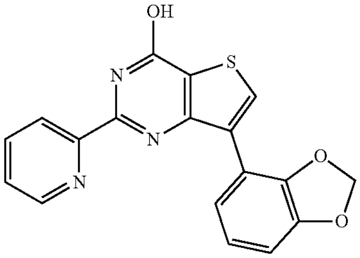 [SMILES: Oc1nc(-c2ccccn2)nc2c(-c3cccc4c3OCO4)csc12] | B | C | C | C |
| 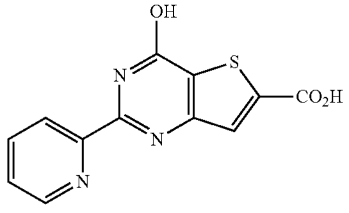 [SMILES: O=C(O)c1cc2nc(-c3ccccn3)nc(O)c2s1] | C | C | D | D |
| 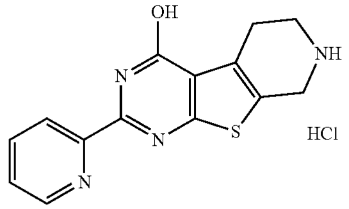 [SMILES: Oc1nc(-c2ccccn2)nc2sc3c(c12)CCNC3 ; Cl] HCl | D | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 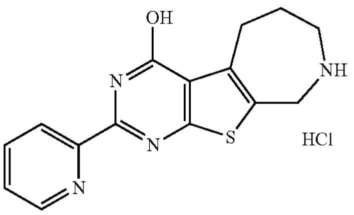 [SMILES: Oc1nc(-c2ccccn2)nc2sc3c(c12)CCCNC3 ; Cl] | C | B | D | C |
| 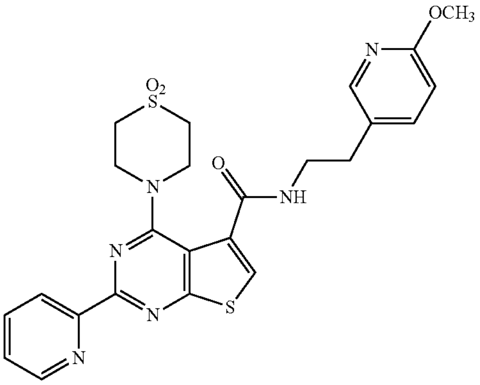 | | B | B | A |
| 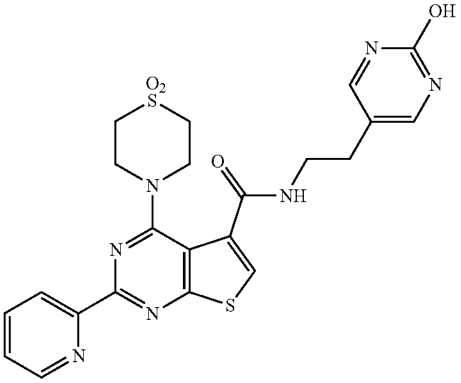 | | B | C | C |
| 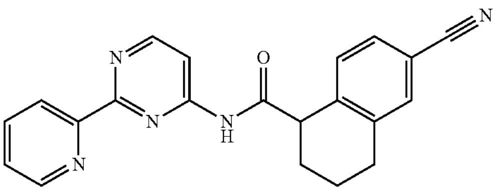 [SMILES: N#Cc1ccc2c(c1)CCCC2C(=O)Nc1ccnc(-c2ccccn2)n1] | | C | C | C |
| 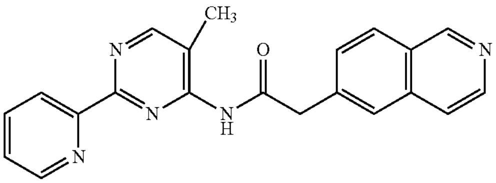 [SMILES: Cc1cnc(-c2ccccn2)nc1NC(=O)Cc1ccc2cnccc2c1] | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
| --- | --- | --- | --- | --- |
| 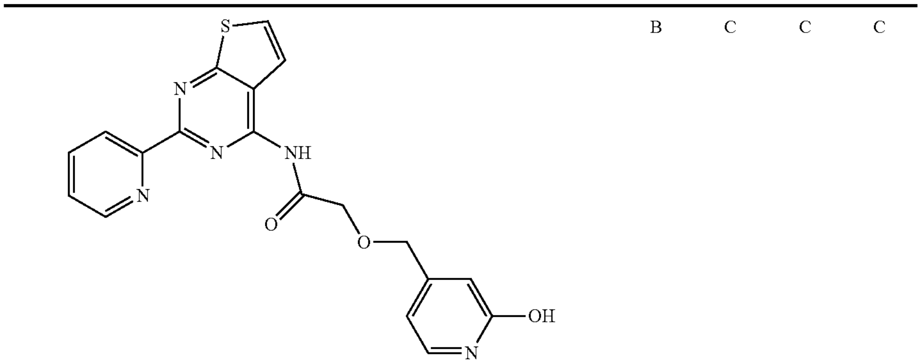 | B | C | C | C |
| 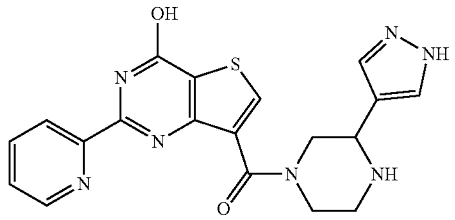 [SMILES: O=C(c1csc2c(O)nc(-c3ccccn3)nc12)N1CCNC(c2cn[nH]c2)C1] | B | C | D | D |
| 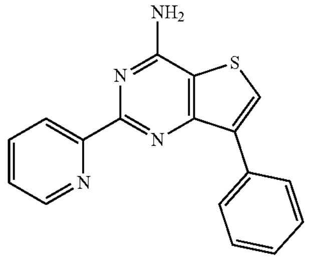 [SMILES: Nc1nc(-c2ccccn2)nc2c(-c3ccccc3)csc12] | B | B | C | C |
| 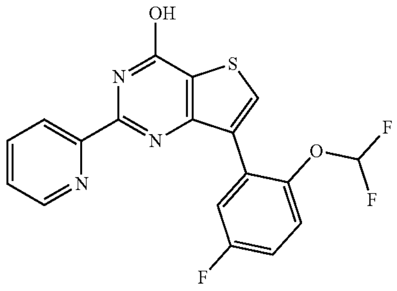 [SMILES: Oc1nc(-c2ccccn2)nc2c(-c3cc(F)ccc3OC(F)F)csc12] | C | B | C | B |
| 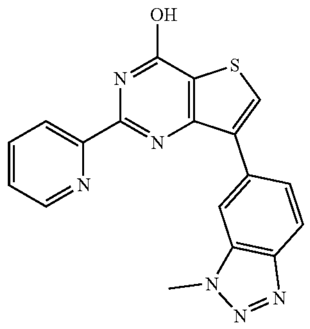 [SMILES: Cn1nnc2ccc(-c3csc4c(O)nc(-c5ccccn5)nc34)cc21] | C | C | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 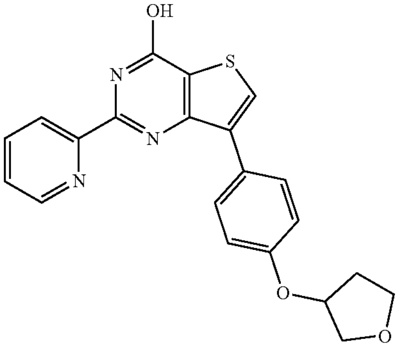 [SMILES: Oc1nc(-c2ccccn2)nc2c(-c3ccc(OC4CCOC4)cc3)csc12] | | B | C | D |
| 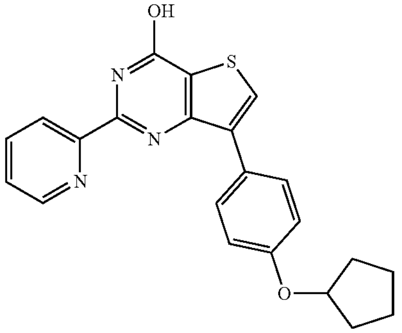 [SMILES: Oc1nc(-c2ccccn2)nc2c(-c3ccc(OC4CCCC4)cc3)csc12] | | B | B | B |
| 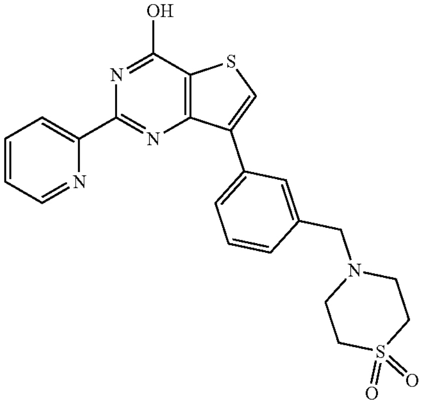 [SMILES: O=S1(=O)CCN(Cc2cccc(-c3csc4c(O)nc(-c5ccccn5)nc34)c2)CC1] | C | C | D | D |
| 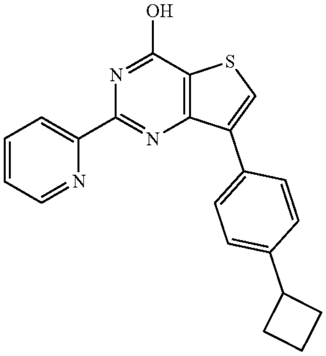 [SMILES: Oc1nc(-c2ccccn2)nc2c(-c3ccc(C4CCC4)cc3)csc12] | | C | C | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 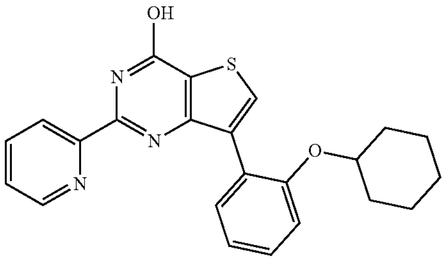 [SMILES: Oc1nc(-c2ccccn2)nc2c(-c3ccccc3OC3CCCCC3)csc12] | | C | C | C |
| 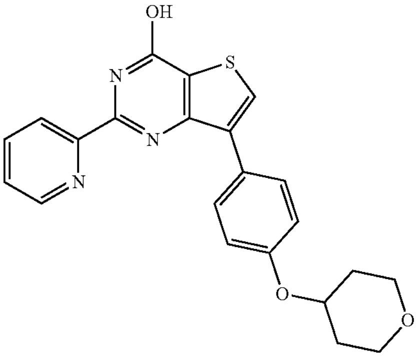 [SMILES: Oc1nc(-c2ccccn2)nc2c(-c3ccc(OC4CCOCC4)cc3)csc12] | | B | C | C |
| 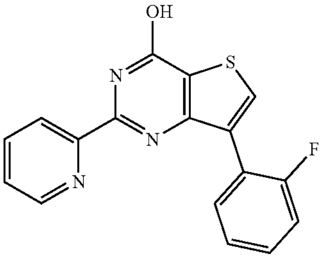 [SMILES: Oc1nc(-c2ccccn2)nc2c(-c3ccccc3F)csc12] | C | C | D | D |
| 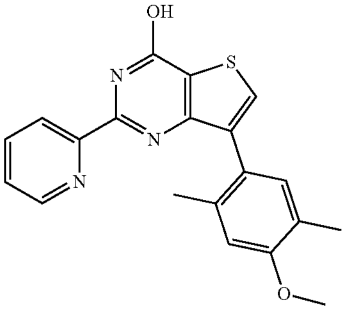 [SMILES: COc1cc(C)c(-c2csc3c(O)nc(-c4ccccn4)nc23)cc1C] | | B | C | B |
| 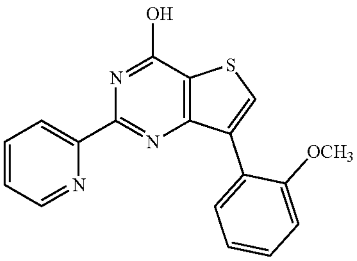 [SMILES: COc1ccccc1-c1csc2c(O)nc(-c3ccccn3)nc12] | C | B | D | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 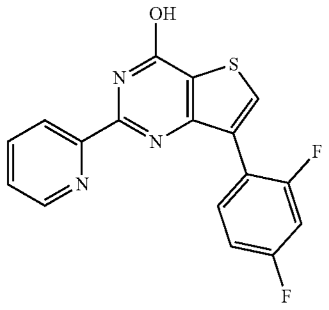 [SMILES: Oc1nc(-c2ccccn2)nc2c(-c3ccc(F)cc3F)csc12] | C | C | C | C |
| 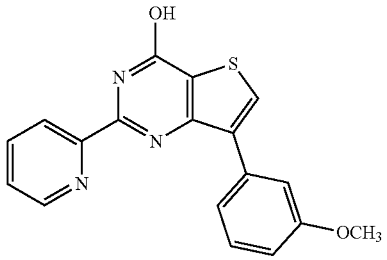 [SMILES: COc1cccc(-c2csc3c(O)nc(-c4ccccn4)nc23)c1] | D | B | C | C |
| 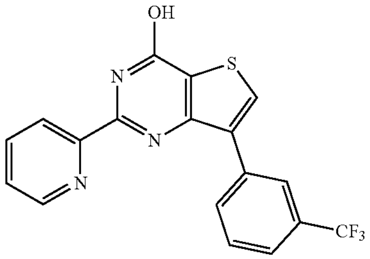 | C | B | C | B |
| 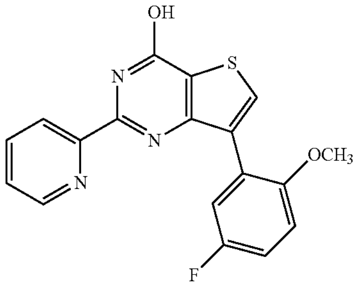 [SMILES: COc1ccc(F)cc1-c1csc2c(O)nc(-c3ccccn3)nc12] | C | C | C | C |
| 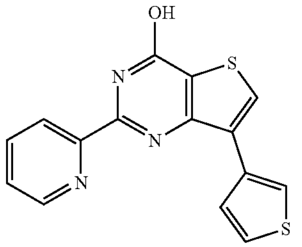 [SMILES: Oc1nc(-c2ccccn2)nc2c(-c3ccsc3)csc12] | C | B | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 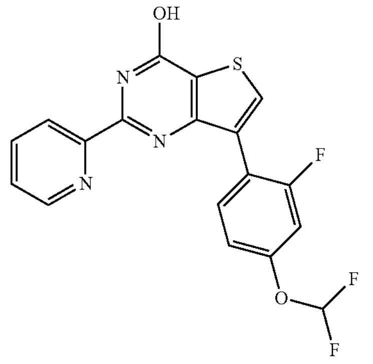 [SMILES: Oc1nc(-c2ccccn2)nc2c(-c3ccc(OC(F)F)cc3F)csc12] | C | C | D | D |
| 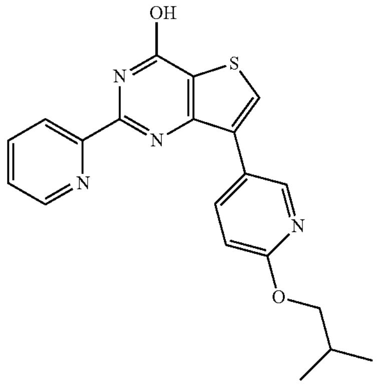 [SMILES: CC(C)COc1ccc(-c2csc3c(O)nc(-c4ccccn4)nc23)cn1] | C | C | D | C |
| 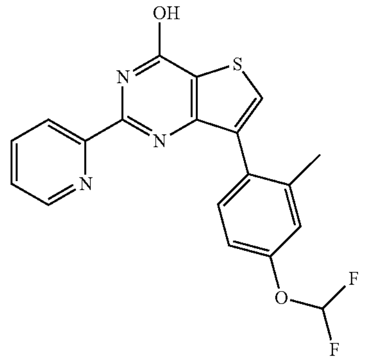 [SMILES: Cc1cc(OC(F)F)ccc1-c1csc2c(O)nc(-c3ccccn3)nc12] | | B | B | A |
| 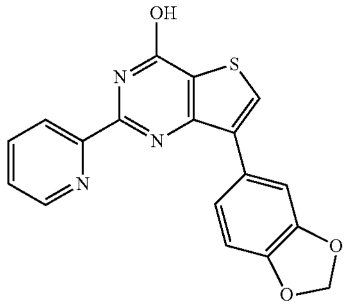 [SMILES: Oc1nc(-c2ccccn2)nc2c(-c3ccc4c(c3)OCO4)csc12] | C | C | D | C |

TABLE 8-continued
| % Inhibition at 20 µM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 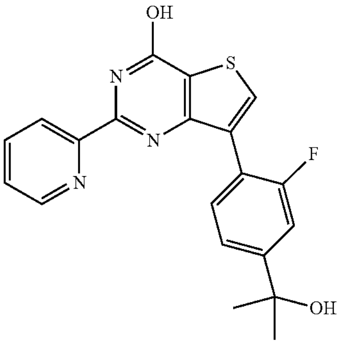 [SMILES: CC(C)(O)c1ccc(-c2csc3c(O)nc(-c4ccccn4)nc23)c(F)c1] | C | C | D | C |
| 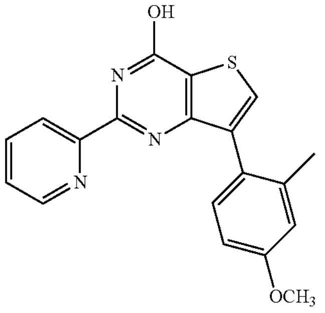 [SMILES: COc1ccc(-c2csc3c(O)nc(-c4ccccn4)nc23)c(C)c1] | C | C | D | D |
| 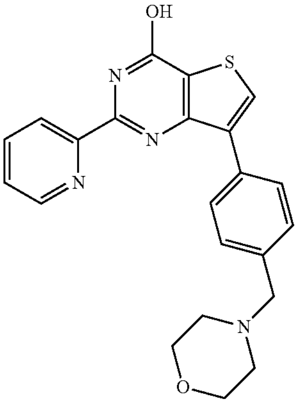 [SMILES: Oc1nc(-c2ccccn2)nc2c(-c3ccc(CN4CCOCC4)cc3)csc12] | | B | C | B |
| 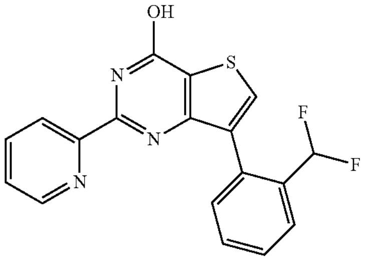 [SMILES: Oc1nc(-c2ccccn2)nc2c(-c3ccccc3C(F)F)csc12] | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 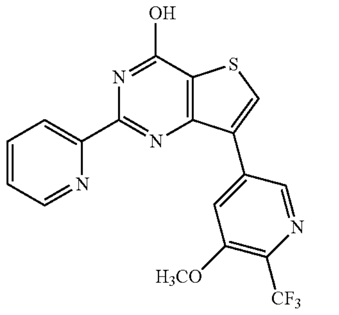 [SMILES: COc1cc(-c2csc3c(O)nc(-c4ccccn4)nc23)cnc1C(F)(F)F] | C | C | C | C |
| 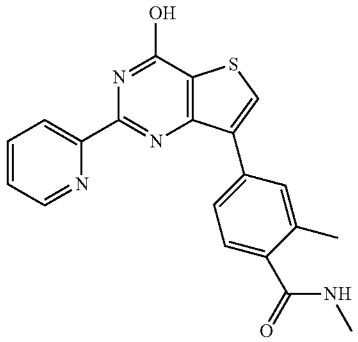 [SMILES: CNC(=O)c1ccc(-c2csc3c(O)nc(-c4ccccn4)nc23)cc1C] | B | B | C | C |
| 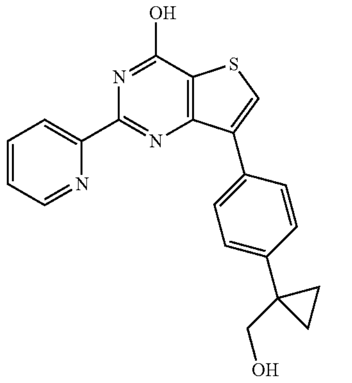 [SMILES: OCC1(c2ccc(-c3csc4c(O)nc(-c5ccccn5)nc34)cc2)CC1] | D | C | D | D |
| 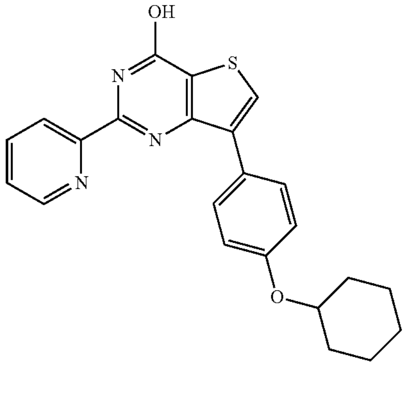 [SMILES: Oc1nc(-c2ccccn2)nc2c(-c3ccc(OC4CCCCC4)cc3)csc12] | | B | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 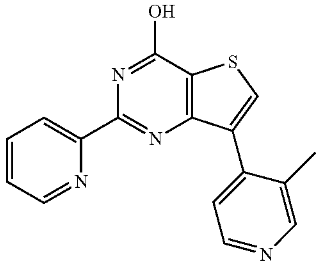 [SMILES: Cc1cnccc1-c1csc2c(O)nc(-c3ccccn3)nc12] | C | C | D | D |
| 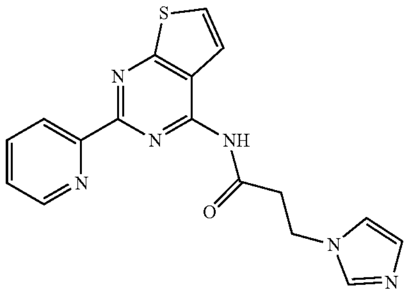 [SMILES: O=C(CCn1ccnc1)Nc1nc(-c2ccccn2)nc2sccc12] | D | C | D | D |
| 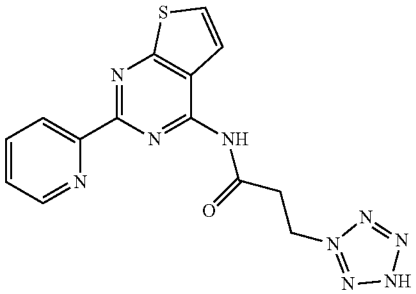 | C | C | D | D |
| 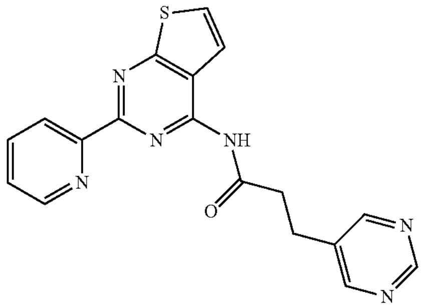 [SMILES: O=C(CCc1cncnc1)Nc1nc(-c2ccccn2)nc2sccc12] | C | C | D | D |
| 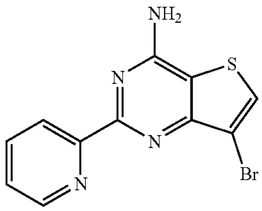 | | B | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 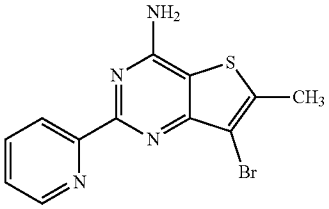 [SMILES: Cc1sc2c(N)nc(-c3ccccn3)nc2c1Br] | | B | B | B |
| 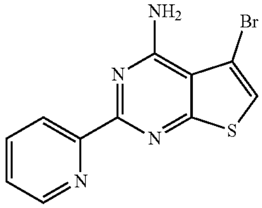 | | B | C | C |
| 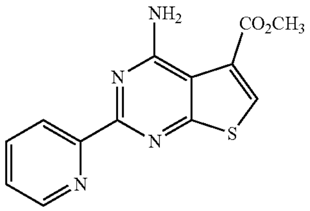 [SMILES: COC(=O)c1csc2nc(-c3ccccn3)nc(N)c12] | | B | C | C |
| 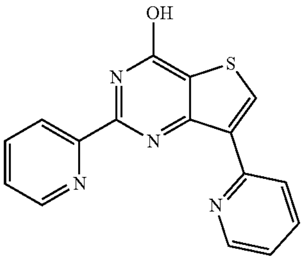 | B | A | C | C |
| 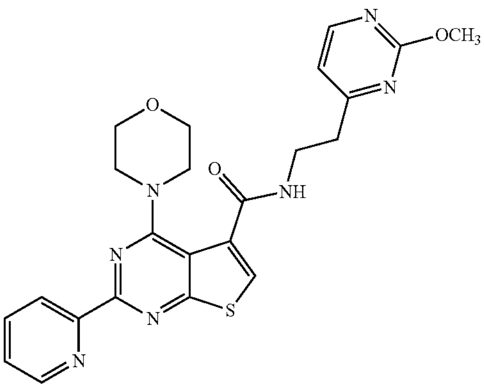 [SMILES: COc1nccc(CCNC(=O)c2csc3nc(-c4ccccn4)nc(N4CCOCC4)c23)n1] | | A | B | B |

TABLE 8-continued
| Structure | KRas G12D % Inh. | KRas G12D Q61H % Inh. | Rac-1 % Inh. | Rho-A % Inh. |
|---|---|---|---|---|
| % Inhibition at 20 μM of KRas G12D mutant, Rac-1 and Rho-A protein | | | | |
| 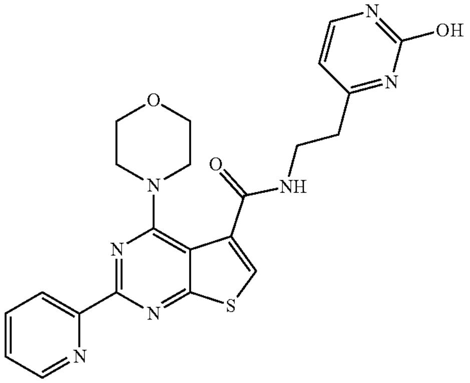 [SMILES: O=C(NCCc1ccnc(O)n1)c1csc2nc(-c3ccccn3)nc(N3CCOCC3)c12] | | A | C | C |
| 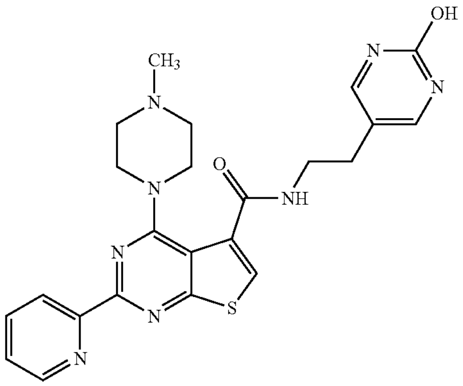 [SMILES: CN1CCN(c2nc(-c3ccccn3)nc3scc(C(=O)NCCc4cnc(O)nc4)c23)CC1] | C | B | C | C |
| 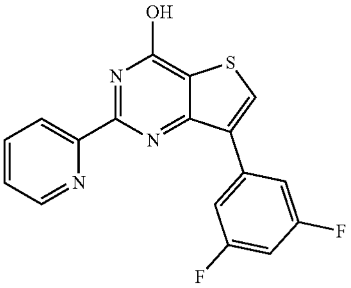 [SMILES: Oc1nc(-c2ccccn2)nc2c(-c3cc(F)cc(F)c3)csc12] | C | C | C | C |
| 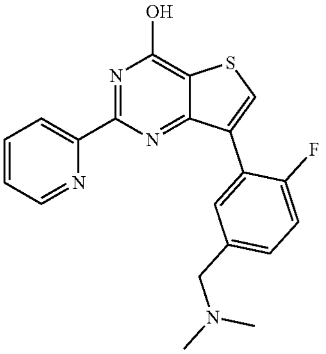 [SMILES: CN(C)Cc1ccc(F)c(-c2csc3c(O)nc(-c4ccccn4)nc23)c1] | C | B | C | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 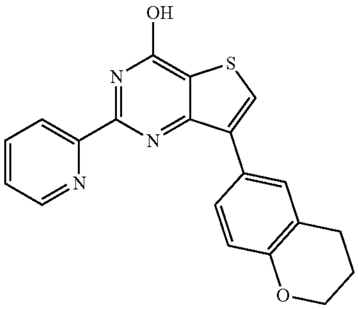 [SMILES: Oc1nc(-c2ccccn2)nc2c(-c3ccc4c(c3)CCCO4)csc12] | C | B | B | C |
| 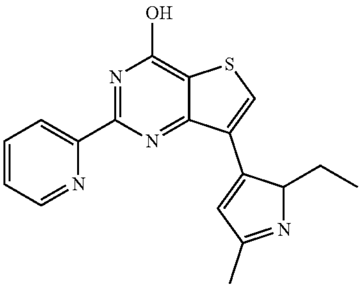 [SMILES: CCC1N=C(C)C=C1c1csc2c(O)nc(-c3ccccn3)nc12] | | C | C | D |
| 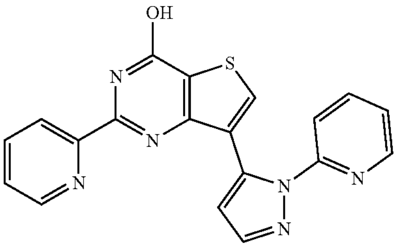 [SMILES: Oc1nc(-c2ccccn2)nc2c(-c3ccnn3-c3ccccn3)csc12] | | A | B | B |
| 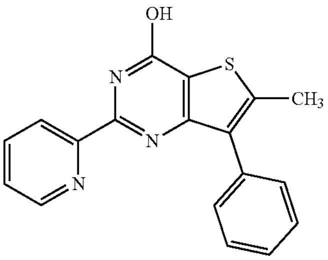 | C | C | C | C |
| 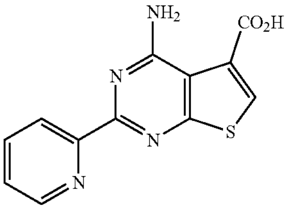 [SMILES: Nc1nc(-c2ccccn2)nc2scc(C(=O)O)c12] | | B | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 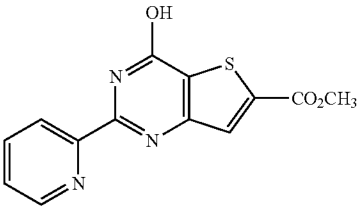 [SMILES: COC(=O)c1cc2nc(-c3ccccn3)nc(O)c2s1] | | C | C | D |
| 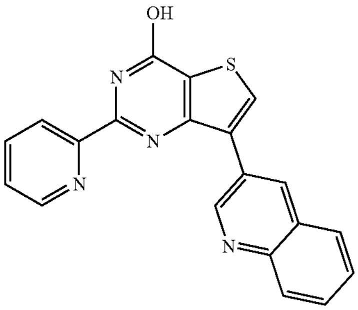 [SMILES: Oc1nc(-c2ccccn2)nc2c(-c3cnc4ccccc4c3)csc12] | | B | C | C |
| 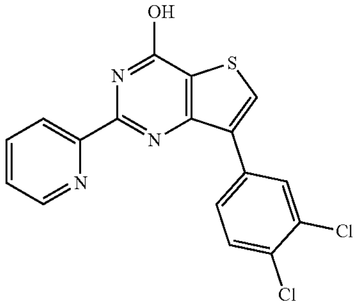 [SMILES: Oc1nc(-c2ccccn2)nc2c(-c3ccc(Cl)c(Cl)c3)csc12] | | B | B | C |
| 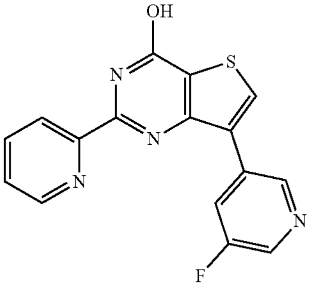 [SMILES: Oc1nc(-c2ccccn2)nc2c(-c3cncc(F)c3)csc12] | | A | A | A |
| 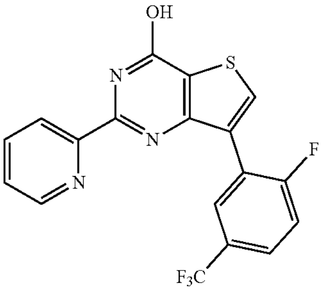 [SMILES: Oc1nc(-c2ccccn2)nc2c(-c3cc(C(F)(F)F)ccc3F)csc12] | | A | B | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 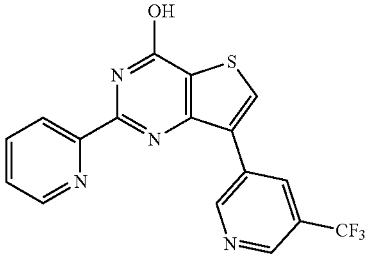 [SMILES: Oc1nc(-c2ccccn2)nc2c(-c3cncc(C(F)(F)F)c3)csc12] | | A | A | B |
| 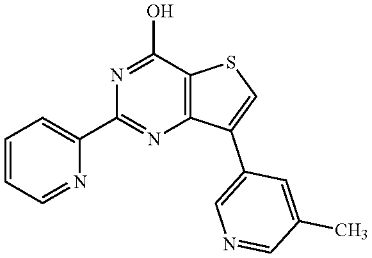 [SMILES: Cc1cncc(-c2csc3c(O)nc(-c4ccccn4)nc23)c1] | | B | C | B |
| 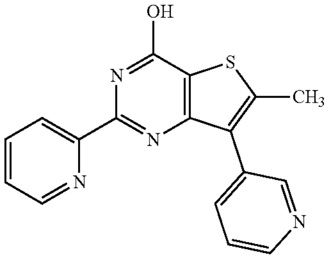 | C | B | C | B |
| 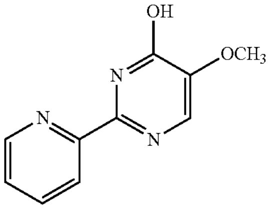 [SMILES: COc1cnc(-c2ccccn2)nc1O] | C | C | D | D |
| 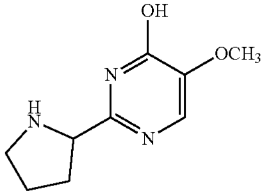 [SMILES: COc1cnc(C2CCCN2)nc1O] | | 0 | 0 | A |
| 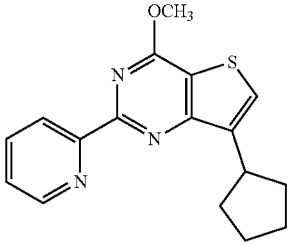 [SMILES: COc1nc(-c2ccccn2)nc2c(C3CCCC3)csc12] | B | C | D | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 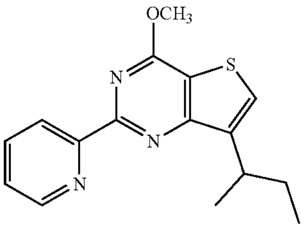 [SMILES: CCC(C)c1csc2c(OC)nc(-c3ccccn3)nc12] | B | C | D | C |
| 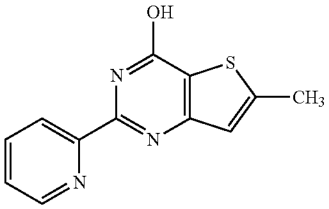 [SMILES: Cc1cc2nc(-c3ccccn3)nc(O)c2s1] | | C | D | D |
| 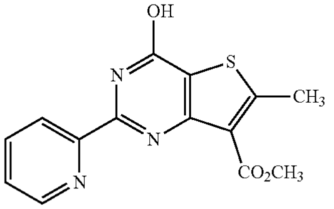 [SMILES: COC(=O)c1c(C)sc2c(O)nc(-c3ccccn3)nc12] | | C | D | D |
| 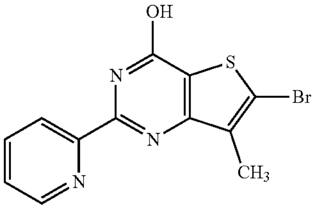 [SMILES: Cc1c(Br)sc2c(O)nc(-c3ccccn3)nc12] | | B | C | C |
| 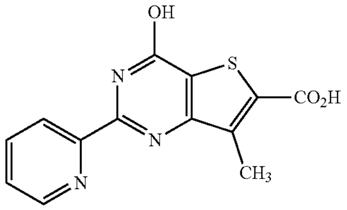 [SMILES: Cc1c(C(=O)O)sc2c(O)nc(-c3ccccn3)nc12] | B | C | D | C |
| 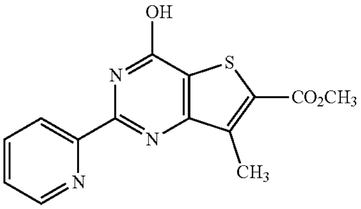 [SMILES: COC(=O)c1sc2c(O)nc(-c3ccccn3)nc2c1C] | | B | C | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 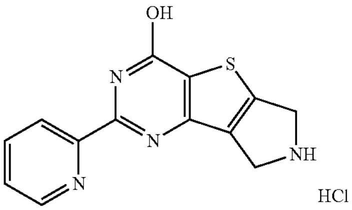 [SMILES: Oc1nc(-c2ccccn2)nc2c3c(sc12)CNC3 ; Cl] |  | C | D | D |
| 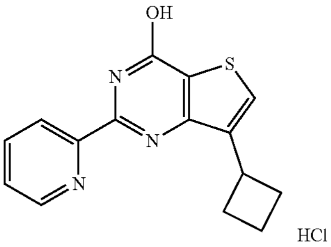 [SMILES: Oc1nc(-c2ccccn2)nc2c(C3CCC3)csc12 ; Cl] | C | C | D | D |
| 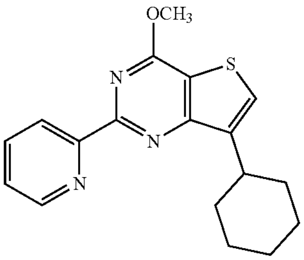 [SMILES: COc1nc(-c2ccccn2)nc2c(C3CCCCC3)csc12] |  | A | A | A |
| 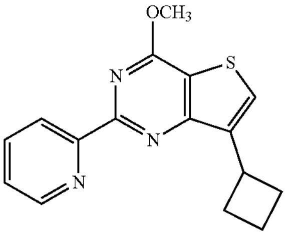 [SMILES: COc1nc(-c2ccccn2)nc2c(C3CCC3)csc12] |  | C | D | D |
| 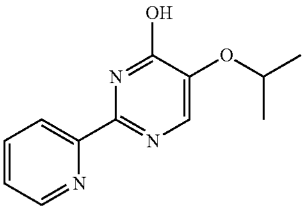 [SMILES: CC(C)Oc1cnc(-c2ccccn2)nc1O] | C | C | D | D |
| 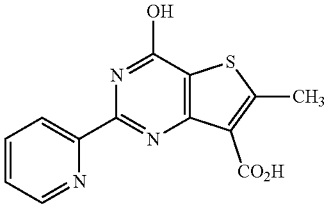 [SMILES: Cc1sc2c(O)nc(-c3ccccn3)nc2c1C(=O)O] |  | B | A | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 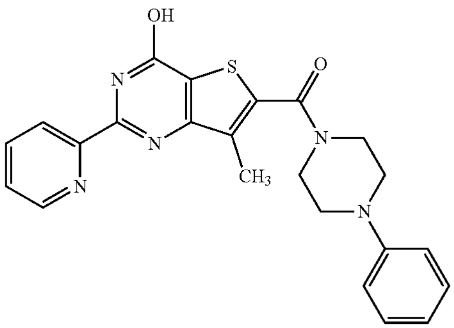 [SMILES: Cc1c(C(=O)N2CCN(c3ccccc3)CC2)sc2c(O)nc(-c3ccccn3)nc12] | | C | C | D |
| 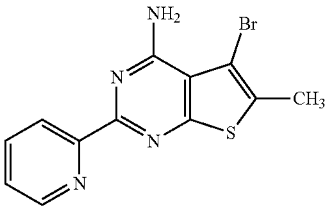 [SMILES: Cc1sc2nc(-c3ccccn3)nc(N)c2c1Br] | | B | B | C |
| 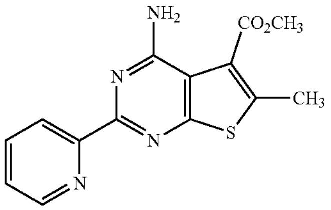 [SMILES: COC(=O)c1c(C)sc2nc(-c3ccccn3)nc(N)c12] | | C | B | C |
| 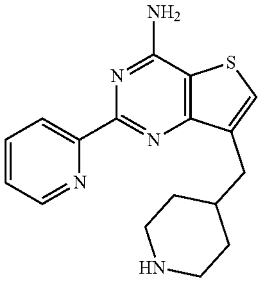 [SMILES: Nc1nc(-c2ccccn2)nc2c(CC3CCNCC3)csc12] | C | C | C | D |
| 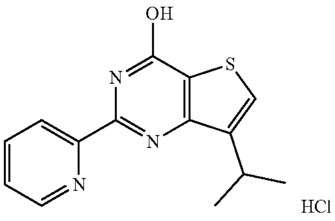 [SMILES: CC(C)c1csc2c(O)nc(-c3ccccn3)nc12 ; Cl] | C | C | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 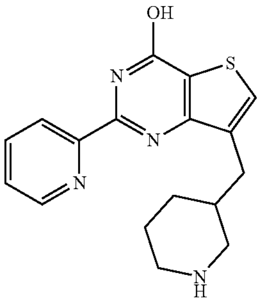 2 HCl | | B | C | D |
| 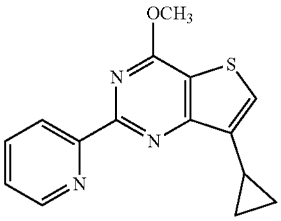 [SMILES: COc1nc(-c2ccccn2)nc2c(C3CC3)csc12] | | A | 0 | 0 |
| 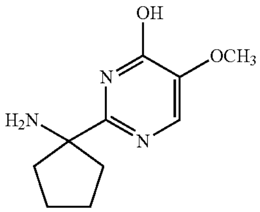 HCl | | A | A | A |
| 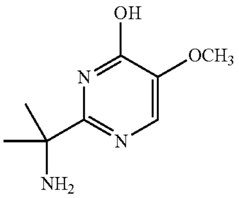 HCl | | A | A | 0 |
| 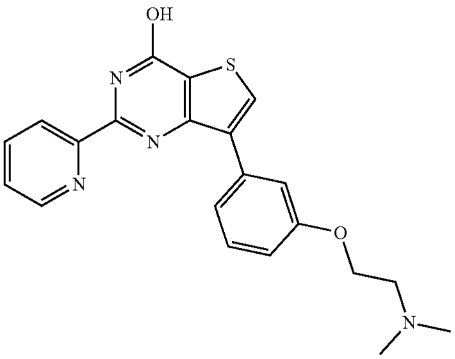 [SMILES: CN(C)CCOc1cccc(-c2csc3c(O)nc(-c4ccccn4)nc23)c1] | D | D | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 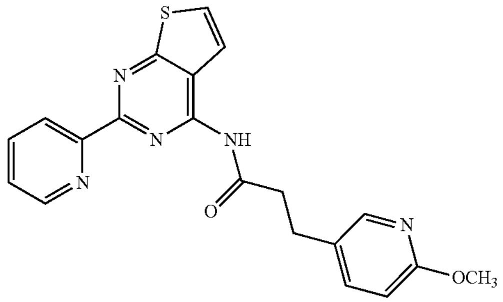 [SMILES: COc1ccc(CCC(=O)Nc2nc(-c3ccccn3)nc3sccc23)cn1] | C | C | D | D |
| 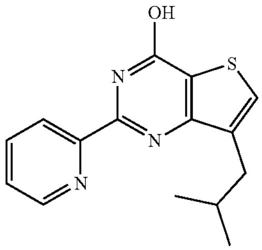 | C | C | D | D |
| 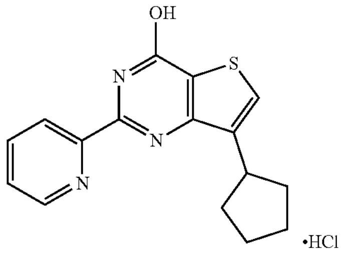 [SMILES: Oc1nc(-c2ccccn2)nc2c(C3CCCC3)csc12 ; Cl] | C | C | D | D |
| 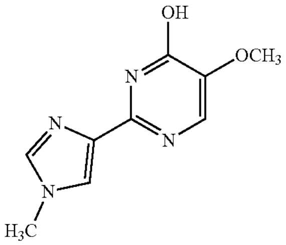 | C | C | D | D |
| 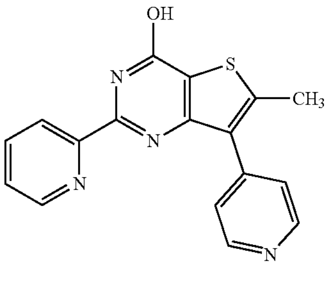 [SMILES: Cc1sc2c(O)nc(-c3ccccn3)nc2c1-c1ccncc1] | C | C | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 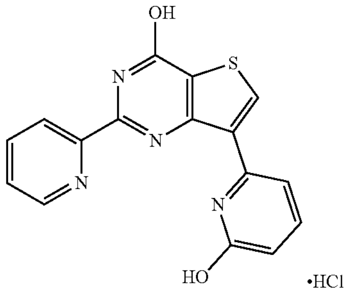 [SMILES: Oc1cccc(-c2csc3c(O)nc(-c4ccccn4)nc23)n1 ; Cl] | C | C | D | D |
| 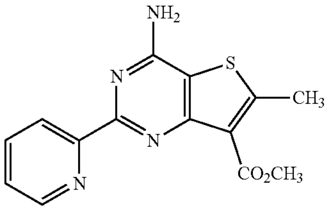 [SMILES: COC(=O)c1c(C)sc2c(N)nc(-c3ccccn3)nc12] | | C | D | D |
| 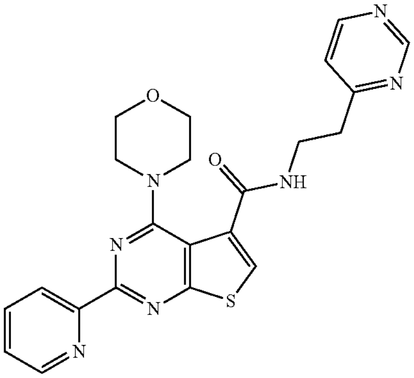 | | B | C | C |
| 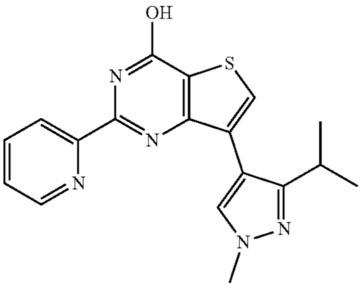 [SMILES: CC(C)c1nn(C)cc1-c1csc2c(O)nc(-c3ccccn3)nc12] | | C | C | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 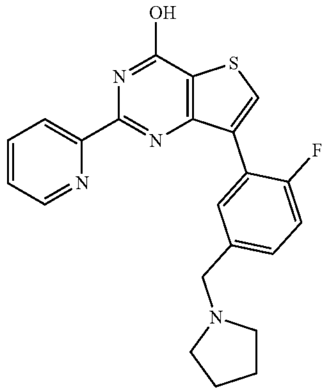 [SMILES: Oc1nc(-c2ccccn2)nc2c(-c3cc(CN4CCCC4)ccc3F)csc12] | D | C | D | D |
| 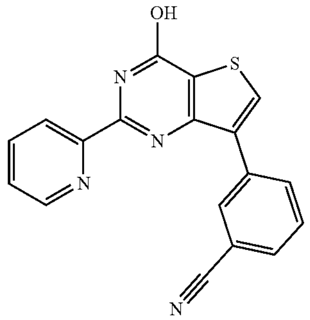 [SMILES: N#Cc1cccc(-c2csc3c(O)nc(-c4ccccn4)nc23)c1] | | A | A | A |
| 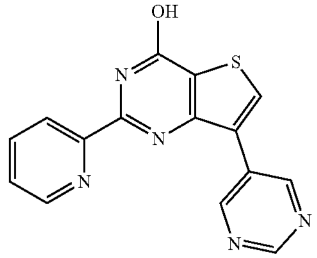 [SMILES: Oc1nc(-c2ccccn2)nc2c(-c3cncnc3)csc12] | | A | A | A |
| 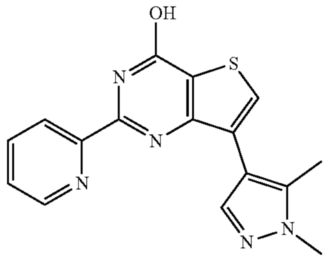 [SMILES: Cc1c(-c2csc3c(O)nc(-c4ccccn4)nc23)cnn1C] | | C | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 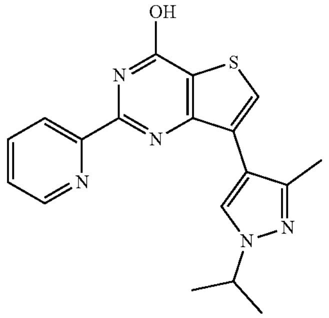 [SMILES: Cc1nn(C(C)C)cc1-c1csc2c(O)nc(-c3ccccn3)nc12] | C | C | D | D |
| 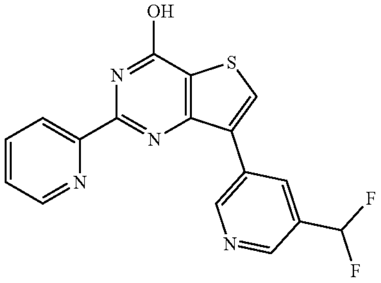 [SMILES: Oc1nc(-c2ccccn2)nc2c(-c3cncc(C(F)F)c3)csc12] | | A | A | 0 |
| 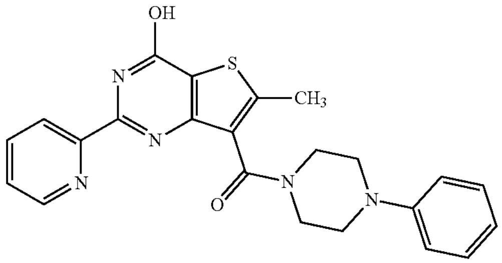 [SMILES: Cc1sc2c(O)nc(-c3ccccn3)nc2c1C(=O)N1CCN(c2ccccc2)CC1] | | B | D | D |
| 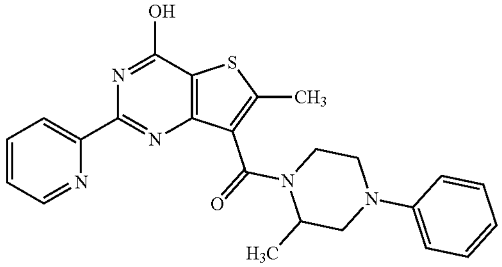 [SMILES: Cc1sc2c(O)nc(-c3ccccn3)nc2c1C(=O)N1CCN(c2ccccc2)CC1C] | C | C | C | C |
| 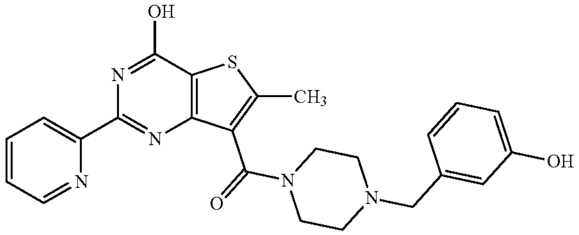 [SMILES: Cc1sc2c(O)nc(-c3ccccn3)nc2c1C(=O)N1CCN(Cc2cccc(O)c2)CC1] | B | C | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 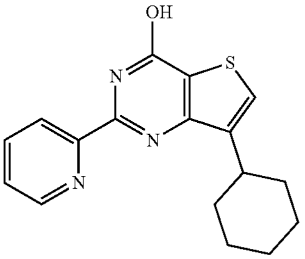 •HCl | | B | B | C |
| 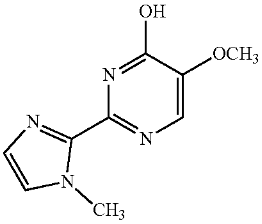 | D | D | D | D |
| 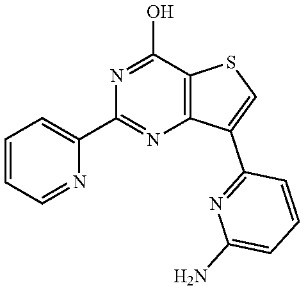 •2HCl | C | C | D | D |
| 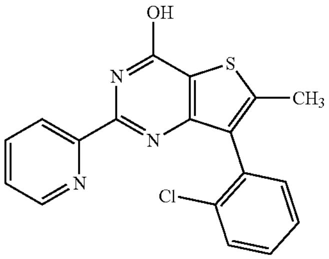 [SMILES: Cc1sc2c(O)nc(-c3ccccn3)nc2c1-c1ccccc1Cl] | C | C | D | D |
| 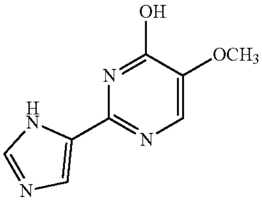 [SMILES: COc1cnc(-c2cnc[nH]2)nc1O] | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
| --- | --- | --- | --- | --- |
| 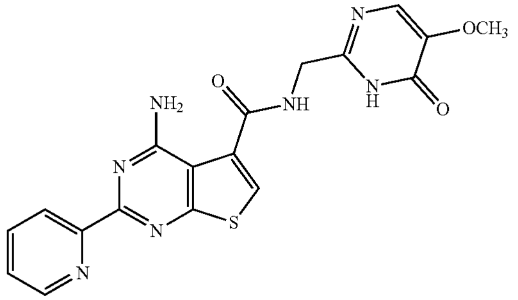 [SMILES: COc1cnc(CNC(=O)c2csc3nc(-c4ccccn4)nc(N)c23)[nH]c1=O] | | B | B | C |
| 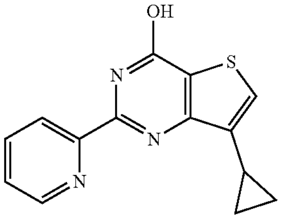 [SMILES: Oc1nc(-c2ccccn2)nc2c(C3CC3)csc12] | C | B | C | C |
| 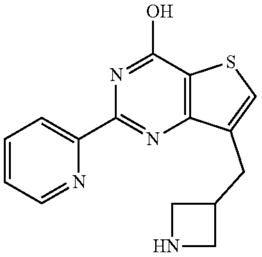 •2HCl | | B | D | D |
| 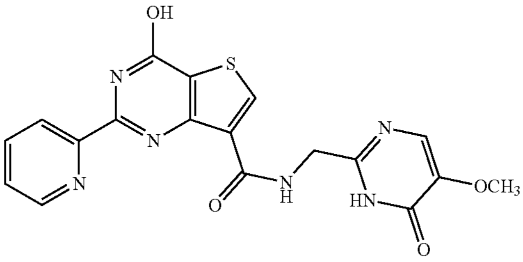 [SMILES: COc1cnc(CNC(=O)c2csc3c(O)nc(-c4ccccn4)nc23)[nH]c1=O] | | A | A | A |
| 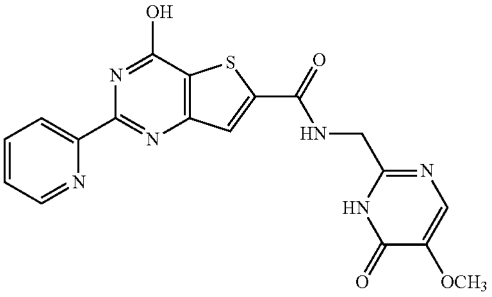 [SMILES: COc1cnc(CNC(=O)c2cc3nc(-c4ccccn4)nc(O)c3s2)[nH]c1=O] | | B | C | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 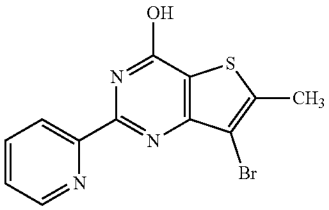 | | B | B | C |
| 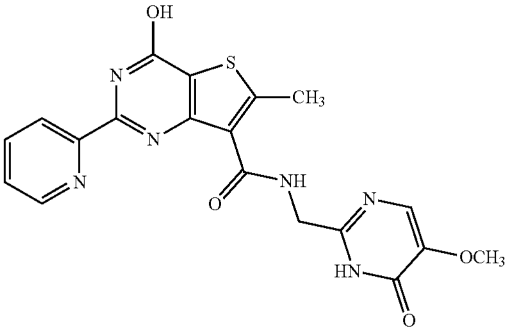 [SMILES: COc1cnc(CNC(=O)c2c(C)sc3c(O)nc(-c4ccccn4)nc23)[nH]c1=O] | | 0 | A | A |
| 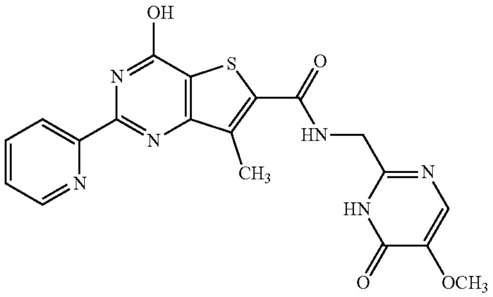 [SMILES: COc1cnc(CNC(=O)c2sc3c(O)nc(-c4ccccn4)nc3c2C)[nH]c1=O] | | A | 0 | A |
| 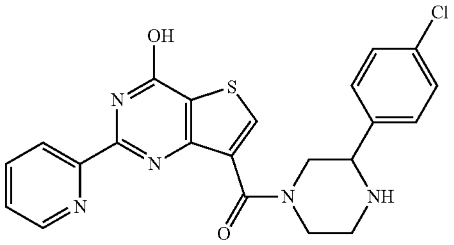 [SMILES: O=C(c1csc2c(O)nc(-c3ccccn3)nc12)N1CCNC(c2ccc(Cl)cc2)C1] | | B | D | D |
| 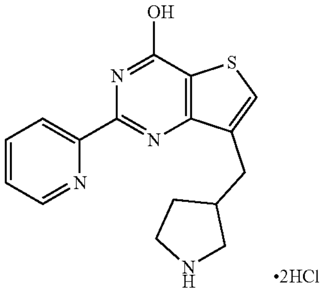 [SMILES: Oc1nc(-c2ccccn2)nc2c(CC3CCNC3)csc12] •2HCl | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 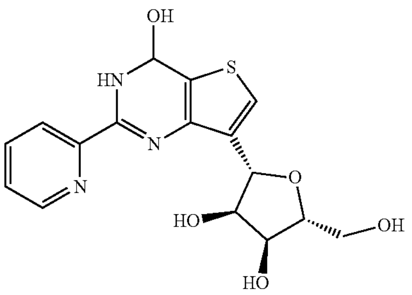 [SMILES: OC[C@H]1O[C@@H](c2csc3c2N=C(c2ccccn2)NC3O)[C@H](O)[C@@H]1O] | B | B | C | C |
| 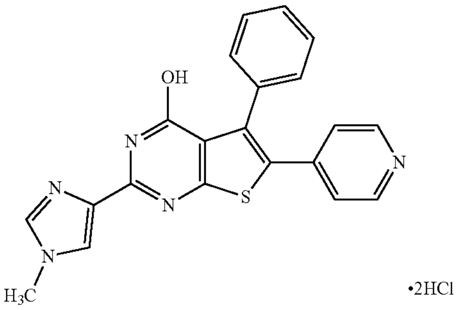 [SMILES: Cn1cnc(-c2nc(O)c3c(-c4ccccc4)c(-c4ccncc4)sc3n2)c1] •2HCl | | A | 0 | 0 |
| 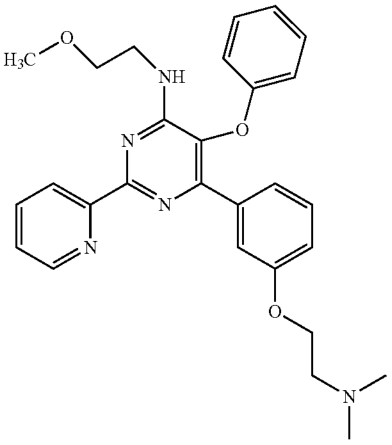 [SMILES: COCCNc1nc(-c2ccccn2)nc(-c2cccc(OCCN(C)C)c2)c1Oc1ccccc1] | | A | A | A |
| 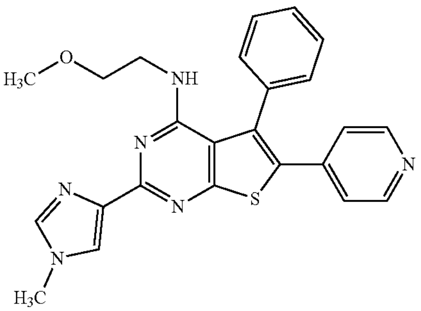 [SMILES: COCCNc1nc(-c2cn(C)cn2)nc2sc(-c3ccncc3)c(-c3ccccc3)c12] | C | D | D | D |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 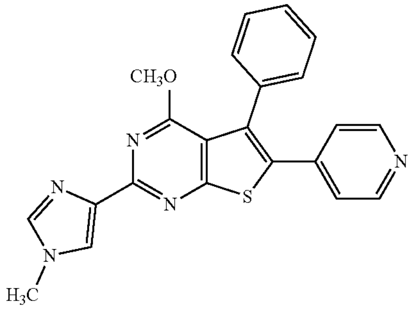 | B | B | B | C |
| 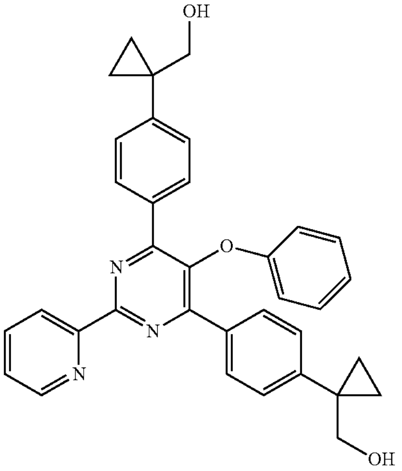 [SMILES: OCC1(c2ccc(-c3nc(-c4ccccn4)nc(-c4ccc(C5(CO)CC5)cc4)c3Oc3ccccc3)cc2)CC1] | | A | B | B |
| 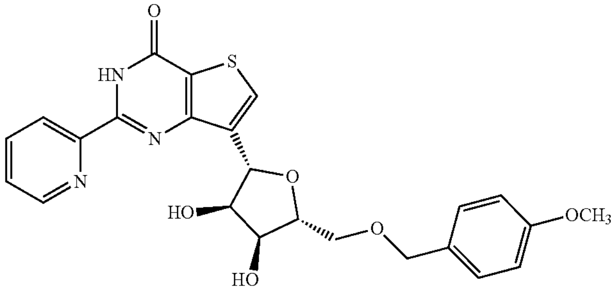 [SMILES: COc1ccc(COC[C@H]2O[C@@H](c3csc4c(=O)[nH]c(-c5ccccn5)nc34)[C@H](O)[C@@H]2O)cc1] | B | B | C | D |
| 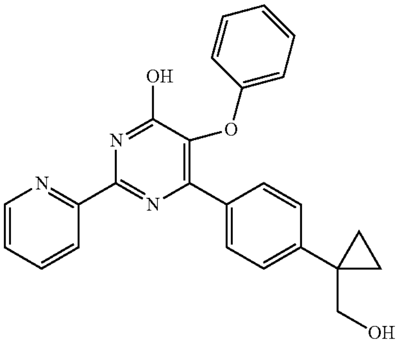 [SMILES: OCC1(c2ccc(-c3nc(-c4ccccn4)nc(O)c3Oc3ccccc3)cc2)CC1] | B | C | C | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 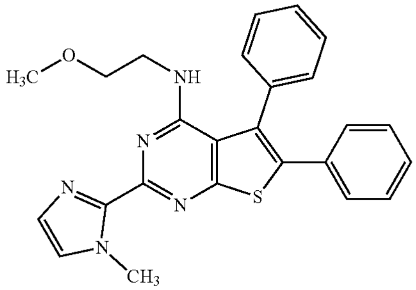 | D | C | D | C |
| 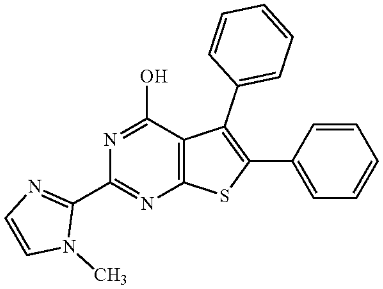 | | A | A | A |
| 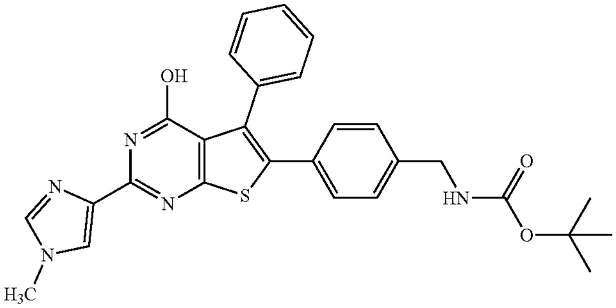 | | A | B | B |
| 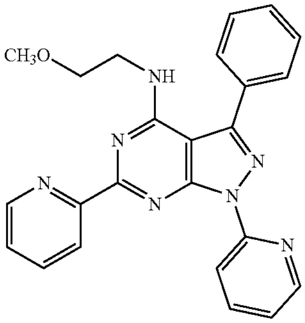 | C | C | D | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 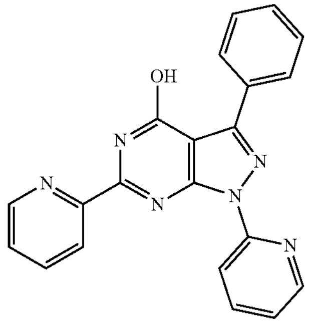 [SMILES: Oc1nc(-c2ccccn2)nc2c1c(-c1ccccc1)nn2-c1ccccn1] | C | C | C | C |
| 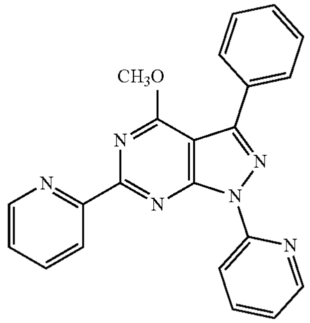 | C | C | D | D |
| 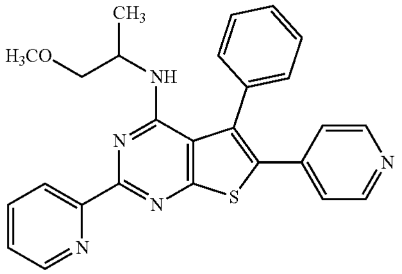 [SMILES: COCC(C)Nc1nc(-c2ccccn2)nc2sc(-c3ccncc3)c(-c3ccccc3)c12] | B | C | C | C |
| 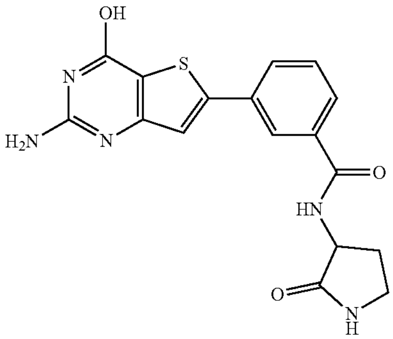 [SMILES: Nc1nc(O)c2sc(-c3cccc(C(=O)NC4CCNC4=O)c3)cc2n1] | | A | A | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 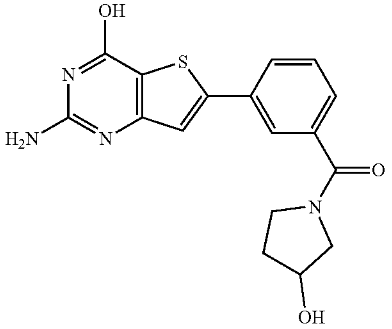 [SMILES: Nc1nc(O)c2sc(-c3cccc(C(=O)N4CCC(O)C4)c3)cc2n1] | | A | A | A |
| 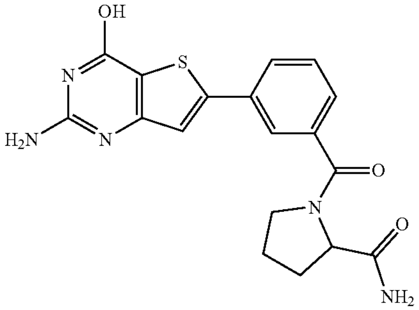 [SMILES: NC(=O)C1CCCN1C(=O)c1cccc(-c2cc3nc(N)nc(O)c3s2)c1] | | 0 | 0 | 0 |
| 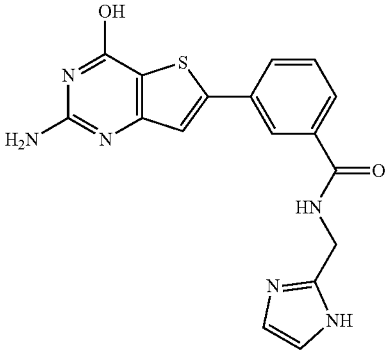 [SMILES: Nc1nc(O)c2sc(-c3cccc(C(=O)NCc4ncc[nH]4)c3)cc2n1] | | 0 | 0 | 0 |
| 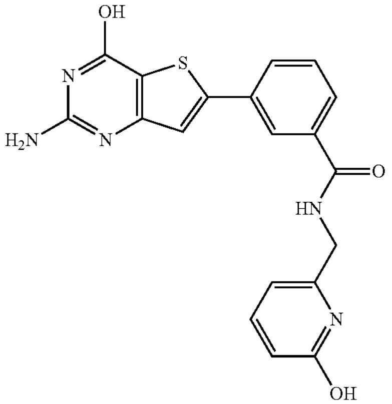 [SMILES: Nc1nc(O)c2sc(-c3cccc(C(=O)NCc4cccc(O)n4)c3)cc2n1] | | 0 | A | 0 |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 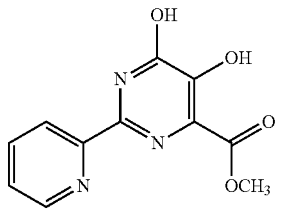 [SMILES: COC(=O)c1nc(-c2ccccn2)nc(O)c1O] | | C | D | D |
| 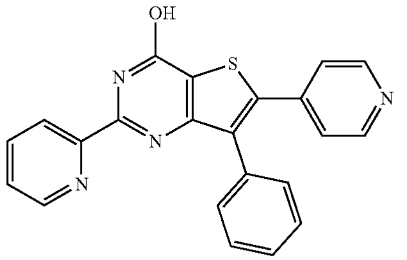 [SMILES: Oc1nc(-c2ccccn2)nc2c(-c3ccccc3)c(-c3ccncc3)sc12] | | 0 | D | C |
| 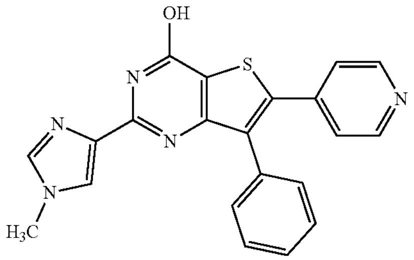 [SMILES: Cn1cnc(-c2nc(O)c3sc(-c4ccncc4)c(-c4ccccc4)c3n2)c1] | | 0 | A | B |
| 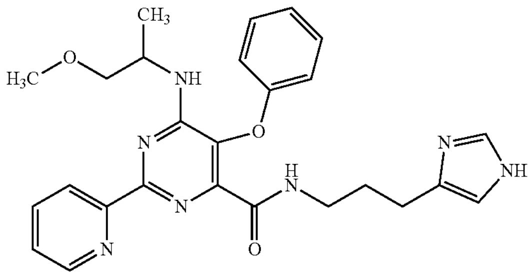 [SMILES: COCC(C)Nc1nc(-c2ccccn2)nc(C(=O)NCCCc2c[nH]cn2)c1Oc1ccccc1] | | A | B | B |
| 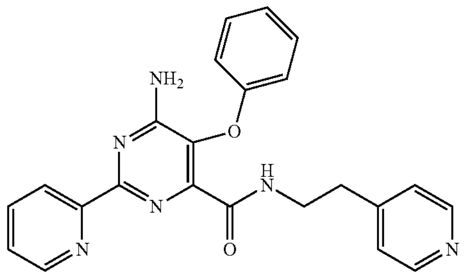 [SMILES: Nc1nc(-c2ccccn2)nc(C(=O)NCCc2ccncc2)c1Oc1ccccc1] | | B | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 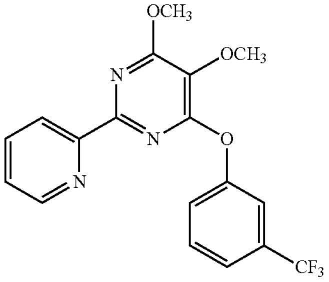 [SMILES: COc1nc(-c2ccccn2)nc(Oc2cccc(C(F)(F)F)c2)c1OC] | | A | A | 0 |
| 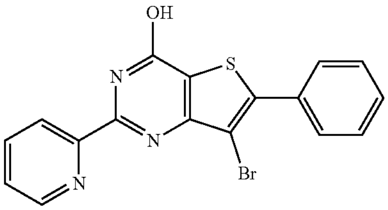 [SMILES: Oc1nc(-c2ccccn2)nc2c(Br)c(-c3ccccc3)sc12] | | 0 | B | A |
| 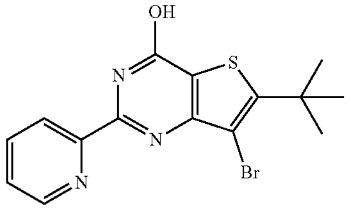 [SMILES: CC(C)(C)c1sc2c(O)nc(-c3ccccn3)nc2c1Br] | | B | B | B |
| 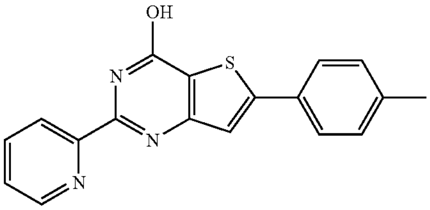 [SMILES: Cc1ccc(-c2cc3nc(-c4ccccn4)nc(O)c3s2)cc1] | | 0 | A | 0 |
| 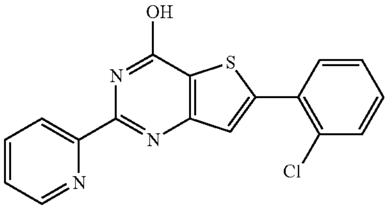 [SMILES: Oc1nc(-c2ccccn2)nc2cc(-c3ccccc3Cl)sc12] | | A | C | C |
| 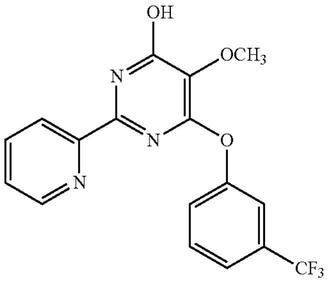 | D | C | C | D |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 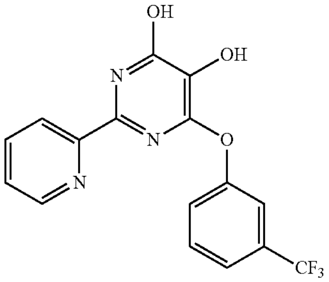 [SMILES: Oc1nc(-c2ccccn2)nc(Oc2cccc(C(F)(F)F)c2)c1O] | C | C | C | C |
| 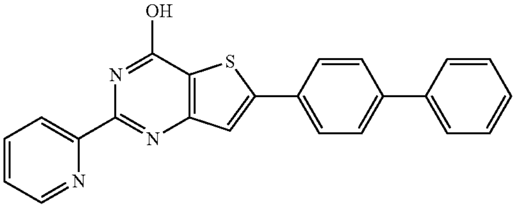 [SMILES: Oc1nc(-c2ccccn2)nc2cc(-c3ccc(-c4ccccc4)cc3)sc12] | | A | 0 | A |
| 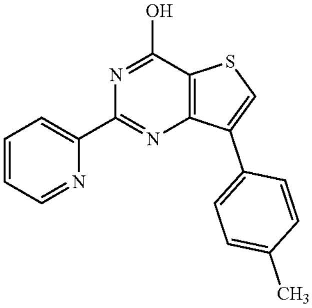 [SMILES: Cc1ccc(-c2csc3c(O)nc(-c4ccccn4)nc23)cc1] | | A | 0 | B |
| 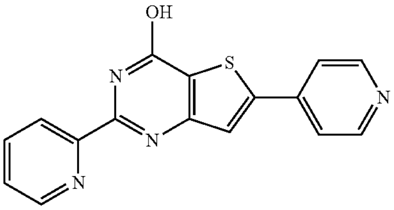 [SMILES: Oc1nc(-c2ccccn2)nc2cc(-c3ccncc3)sc12] | C | C | B | C |
| 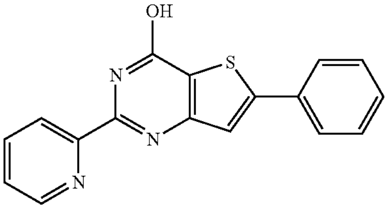 [SMILES: Oc1nc(-c2ccccn2)nc2cc(-c3ccccc3)sc12] | C | C | B | C |
| 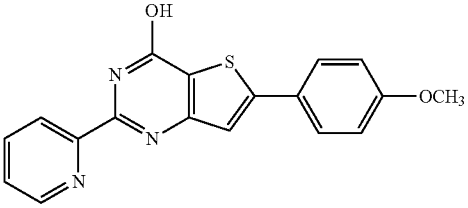 [SMILES: COc1ccc(-c2cc3nc(-c4ccccn4)nc(O)c3s2)cc1] | | A | 0 | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 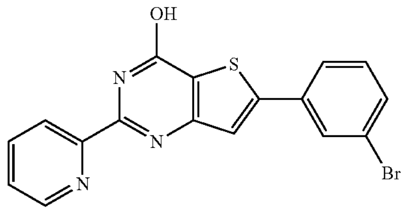 [SMILES: Oc1nc(-c2ccccn2)nc2cc(-c3cccc(Br)c3)sc12] | | B | A | B |
| 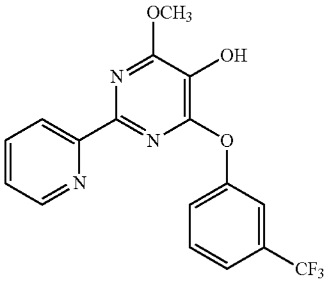 | C | | D | A |
| 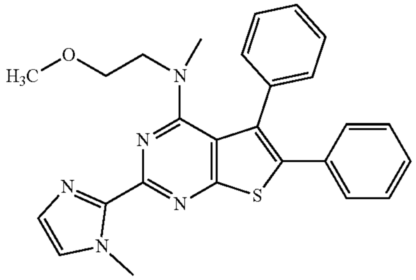 [SMILES: COCCN(C)c1nc(-c2nccn2C)nc2sc(-c3ccccc3)c(-c3ccccc3)c12] | C | | B | B |
| 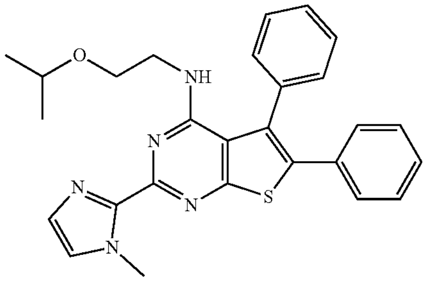 [SMILES: CC(C)OCCNc1nc(-c2nccn2C)nc2sc(-c3ccccc3)c(-c3ccccc3)c12] | C | | B | B |
| 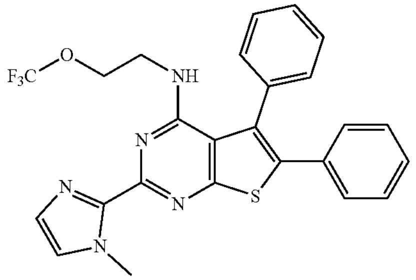 [SMILES: Cn1ccnc1-c1nc(NCCOC(F)(F)F)c2c(-c3ccccc3)c(-c3ccccc3)sc2n1] | B | | B | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 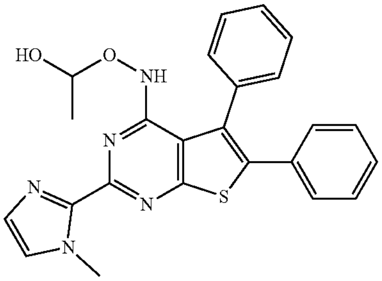 [SMILES: CC(O)ONc1nc(-c2nccn2C)nc2sc(-c3ccccc3)c(-c3ccccc3)c12] | A | | B | B |
| 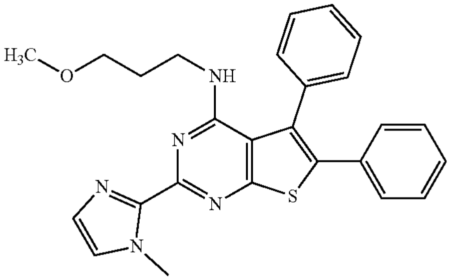 [SMILES: COCCCNc1nc(-c2nccn2C)nc2sc(-c3ccccc3)c(-c3ccccc3)c12] | C | | B | C |
| 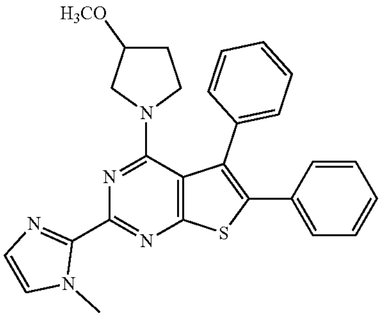 [SMILES: COC1CCN(c2nc(-c3nccn3C)nc3sc(-c4ccccc4)c(-c4ccccc4)c23)C1] | C | | B | 0 |
| 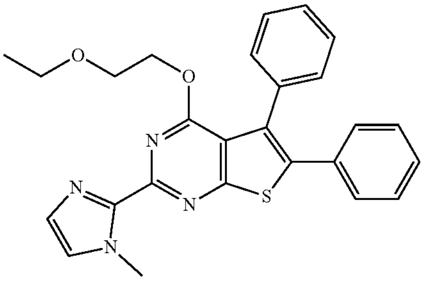 [SMILES: CCOCCOc1nc(-c2nccn2C)nc2sc(-c3ccccc3)c(-c3ccccc3)c12] | A | | A | B |
| 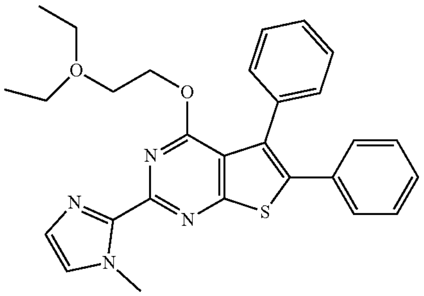 | B | | A | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 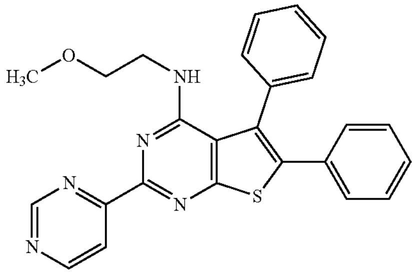 [SMILES: COCCNc1nc(-c2ccncn2)nc2sc(-c3ccccc3)c(-c3ccccc3)c12] | 0 | | A | A |
| 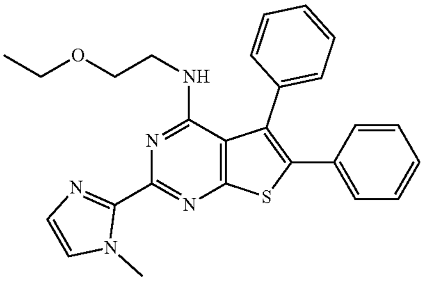 [SMILES: CCOCCNc1nc(-c2nccn2C)nc2sc(-c3ccccc3)c(-c3ccccc3)c12] | C | | C | C |
| 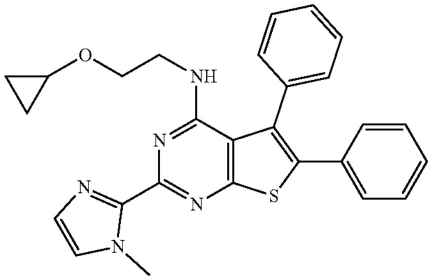 [SMILES: Cn1ccnc1-c1nc(NCCOC2CC2)c2c(-c3ccccc3)c(-c3ccccc3)sc2n1] | A | | B | A |
| 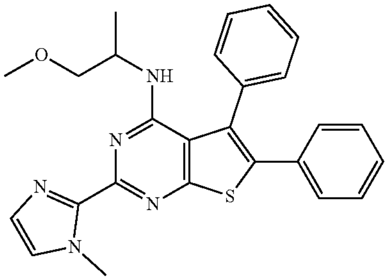 [SMILES: COCC(C)Nc1nc(-c2nccn2C)nc2sc(-c3ccccc3)c(-c3ccccc3)c12] | A | | A | A |
| 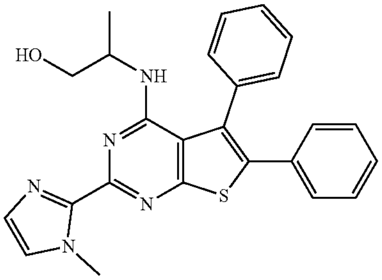 [SMILES: CC(CO)Nc1nc(-c2nccn2C)nc2sc(-c3ccccc3)c(-c3ccccc3)c12] | A | | A | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 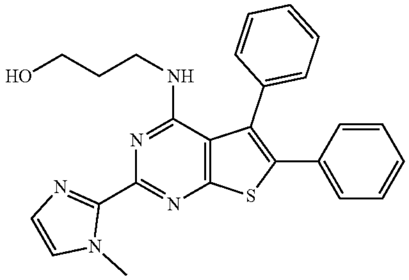 [SMILES: Cn1ccnc1-c1nc(NCCCO)c2c(-c3ccccc3)c(-c3ccccc3)sc2n1] | C | | C | C |
| 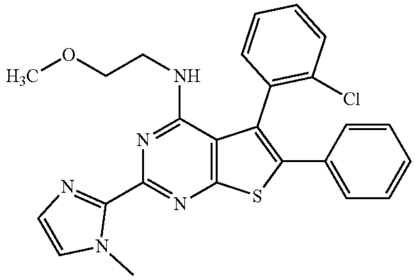 [SMILES: COCCNc1nc(-c2nccn2C)nc2sc(-c3ccccc3)c(-c3ccccc3Cl)c12] | B | | B | B |
| 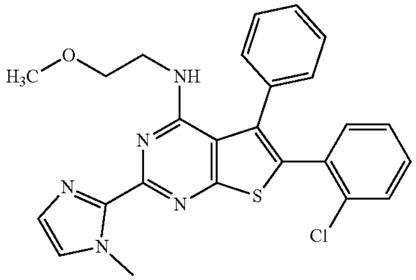 [SMILES: COCCNc1nc(-c2nccn2C)nc2sc(-c3ccccc3Cl)c(-c3ccccc3)c12] | A | | 0 | B |
| 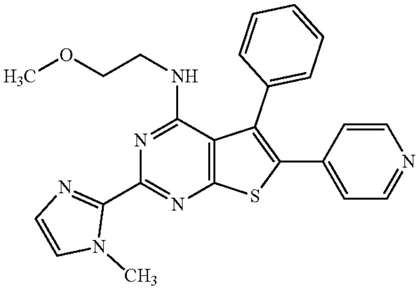 [SMILES: COCCNc1nc(-c2nccn2C)nc2sc(-c3ccncc3)c(-c3ccccc3)c12] | C | | C | C |
| 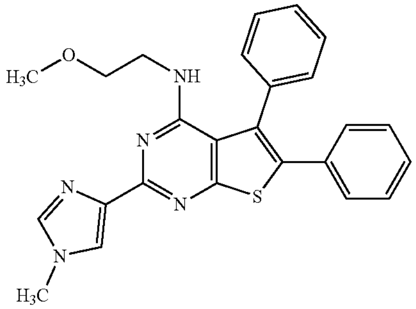 [SMILES: COCCNc1nc(-c2cn(C)cn2)nc2sc(-c3ccccc3)c(-c3ccccc3)c12] | B | | C | C |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 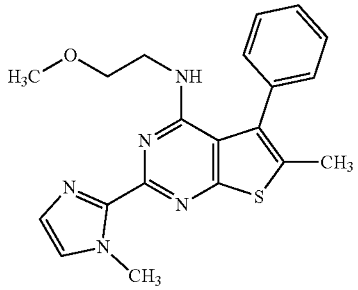 [SMILES: COCCNc1nc(-c2nccn2C)nc2sc(C)c(-c3ccccc3)c12] | C | | C | C |
| 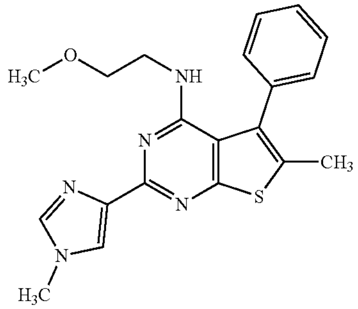 [SMILES: COCCNc1nc(-c2cn(C)cn2)nc2sc(C)c(-c3ccccc3)c12] | B | | C | C |
| 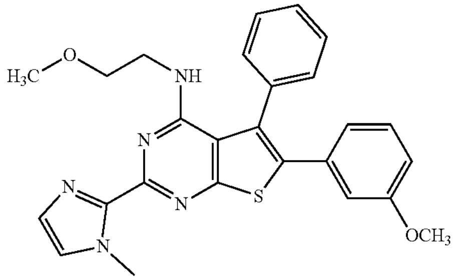 [SMILES: COCCNc1nc(-c2nccn2C)nc2sc(-c3cccc(OC)c3)c(-c3ccccc3)c12] | B | | A | C |
| 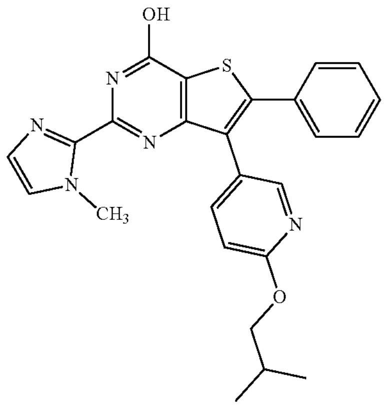 [SMILES: CC(C)COc1ccc(-c2c(-c3ccccc3)sc3c(O)nc(-c4nccn4C)nc23)cn1] | C | | C | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 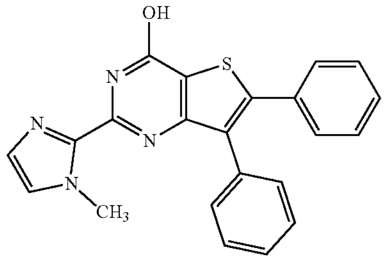 [SMILES: Cn1ccnc1-c1nc(O)c2sc(-c3ccccc3)c(-c3ccccc3)c2n1] | 0 | | 0 | A |
| 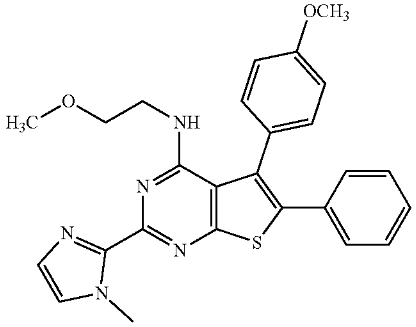 [SMILES: COCCNc1nc(-c2nccn2C)nc2sc(-c3ccccc3)c(-c3ccc(OC)cc3)c12] | B | | C | C |
| 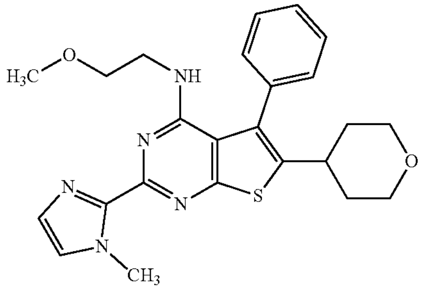 [SMILES: COCCNc1nc(-c2nccn2C)nc2sc(C3CCOCC3)c(-c3ccccc3)c12] | C | | D | C |
| 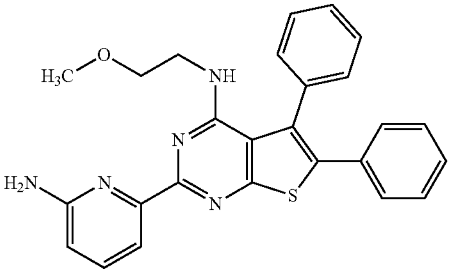 [SMILES: COCCNc1nc(-c2cccc(N)n2)nc2sc(-c3ccccc3)c(-c3ccccc3)c12] | 0 | | 0 | 0 |
| 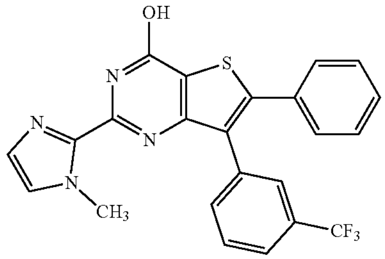 [SMILES: Cn1ccnc1-c1nc(O)c2sc(-c3ccccc3)c(-c3cccc(C(F)(F)F)c3)c2n1] | 0 | | A | 0 |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 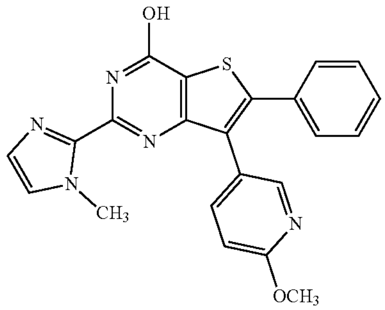 [SMILES: COc1ccc(-c2c(-c3ccccc3)sc3c(O)nc(-c4nccn4C)nc23)cn1] | A | | A | A |
| 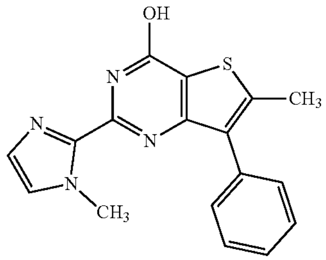 [SMILES: Cc1sc2c(O)nc(-c3nccn3C)nc2c1-c1ccccc1] | B | | B | C |
| 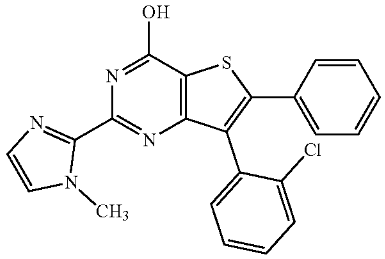 [SMILES: Cn1ccnc1-c1nc(O)c2sc(-c3ccccc3)c(-c3ccccc3Cl)c2n1] | C | | C | C |
| 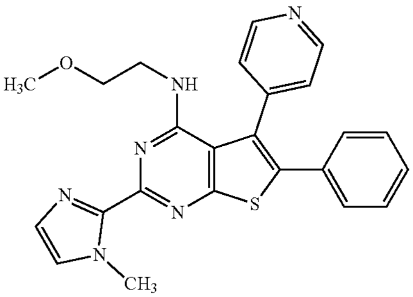 [SMILES: COCCNc1nc(-c2nccn2C)nc2sc(-c3ccccc3)c(-c3ccncc3)c12] | C | | D | D |
| 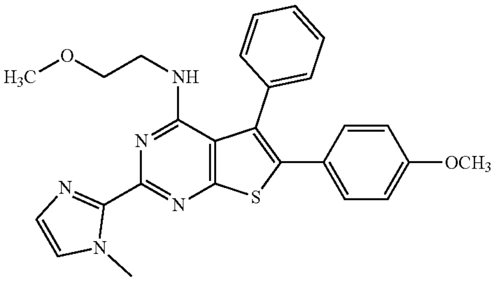 [SMILES: COCCNc1nc(-c2nccn2C)nc2sc(-c3ccc(OC)cc3)c(-c3ccccc3)c12] | B | | B | A |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 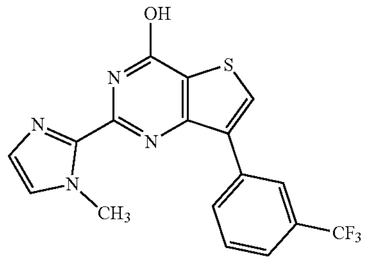 [SMILES: Cn1ccnc1-c1nc(O)c2scc(-c3cccc(C(F)(F)F)c3)c2n1] | B | | C | B |
| 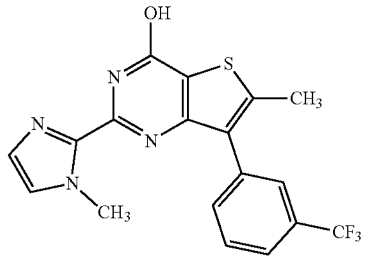 [SMILES: Cc1sc2c(O)nc(-c3nccn3C)nc2c1-c1cccc(C(F)(F)F)c1] | A | | B | 0 |
| 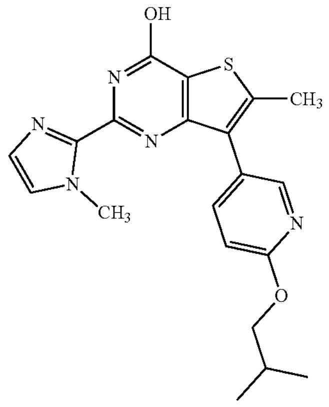 [SMILES: Cc1sc2c(O)nc(-c3nccn3C)nc2c1-c1ccc(OCC(C)C)nc1] | A | | B | A |
| 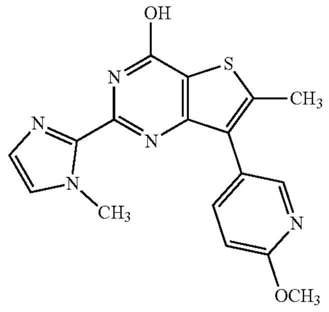 [SMILES: COc1ccc(-c2c(C)sc3c(O)nc(-c4nccn4C)nc23)cn1] | A | | A | 0 |

TABLE 8-continued
| % Inhibition at 20 μM of KRas G12D mutant, Rac-1 and Rho-A protein | | | | |
|---|---|---|---|---|
| Structure | KRas G12D % Inh. | KRas G12D Q61H % Inh. | Rac-1 % Inh. | Rho-A % Inh. |
| 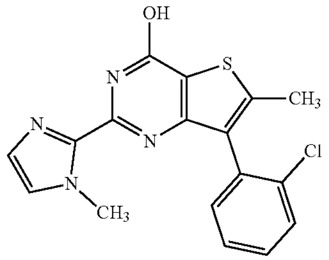 [SMILES: Cc1sc2c(O)nc(-c3nccn3C)nc2c1-c1ccccc1Cl] | B | | C | C |
| 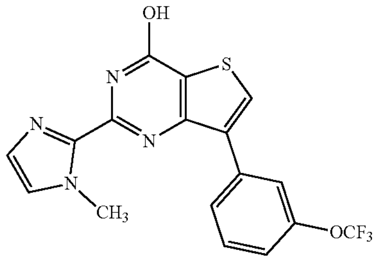 [SMILES: Cn1ccnc1-c1nc(O)c2scc(-c3cccc(OC(F)(F)F)c3)c2n1] | C | | C | B |
| 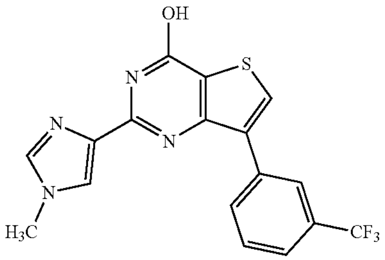 [SMILES: Cn1cnc(-c2nc(O)c3scc(-c4cccc(C(F)(F)F)c4)c3n2)c1] | B | | B | B |
| 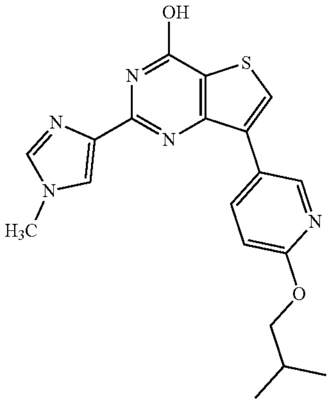 [SMILES: CC(C)COc1ccc(-c2csc3c(O)nc(-c4cn(C)cn4)nc23)cn1] | A | | B | B |
| 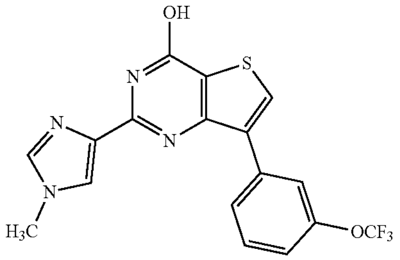 [SMILES: Cn1cnc(-c2nc(O)c3scc(-c4cccc(OC(F)(F)F)c4)c3n2)c1] | B | | B | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 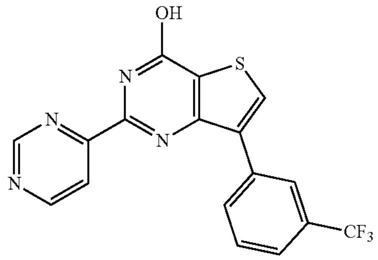 [SMILES: Oc1nc(-c2ccncn2)nc2c(-c3cccc(C(F)(F)F)c3)csc12] | A | | A | A |
| 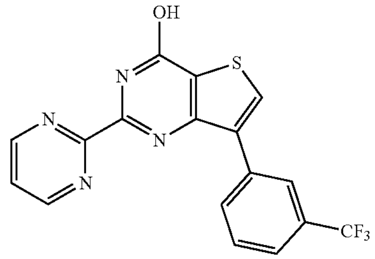 [SMILES: Oc1nc(-c2ncccn2)nc2c(-c3cccc(C(F)(F)F)c3)csc12] | B | | C | C |
| 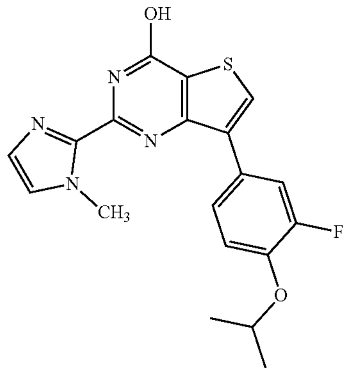 [SMILES: CC(C)Oc1ccc(-c2csc3c(O)nc(-c4nccn4C)nc23)cc1F] | B | | C | B |
| 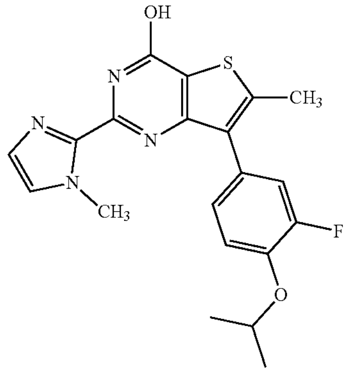 [SMILES: Cc1sc2c(O)nc(-c3nccn3C)nc2c1-c1ccc(OC(C)C)c(F)c1] | C | | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 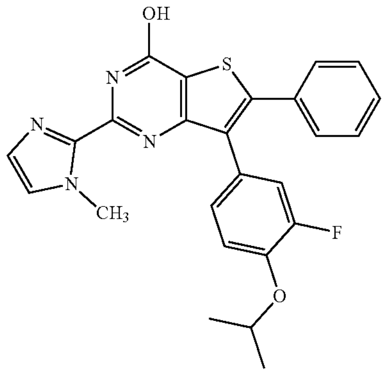 [SMILES: CC(C)Oc1ccc(-c2c(-c3ccccc3)sc3c(O)nc(-c4nccn4C)nc23)cc1F] | B | | C | B |
| 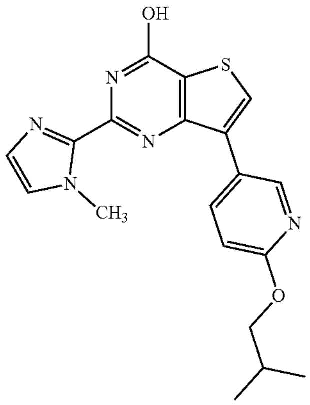 [SMILES: CC(C)COc1ccc(-c2csc3c(O)nc(-c4nccn4C)nc23)cn1] | D | | C | C |
| 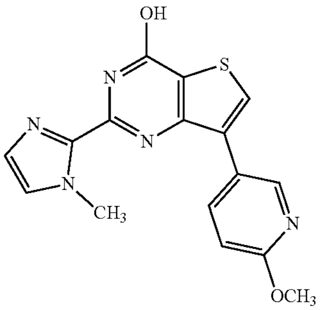 [SMILES: COc1ccc(-c2csc3c(O)nc(-c4nccn4C)nc23)cn1] | C | | C | C |
| 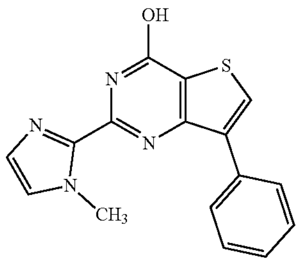 [SMILES: Cn1ccnc1-c1nc(O)c2scc(-c3ccccc3)c2n1] | C | | C | B |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 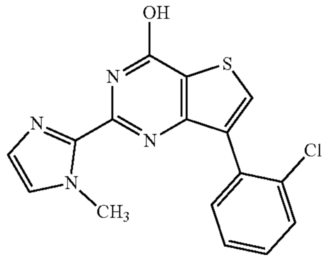 [SMILES: Cn1ccnc1-c1nc(O)c2scc(-c3ccccc3Cl)c2n1] | B | | C | C |
| 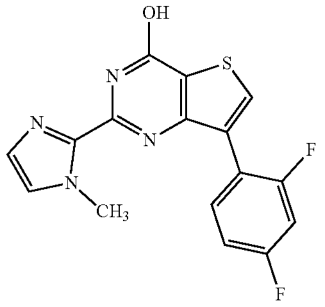 [SMILES: Cn1ccnc1-c1nc(O)c2scc(-c3ccc(F)cc3F)c2n1] | B | | C | B |
| 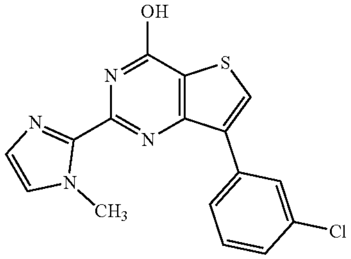 [SMILES: Cn1ccnc1-c1nc(O)c2scc(-c3cccc(Cl)c3)c2n1] | B | | C | C |
| 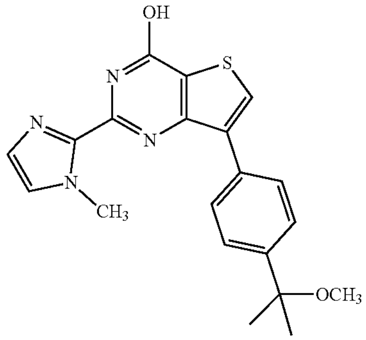 [SMILES: COC(C)(C)c1ccc(-c2csc3c(O)nc(-c4nccn4C)nc23)cc1] | B | | B | C |

TABLE 8-continued
% Inhibition at 20 μM of KRas G12D mutant, Rac-1 and Rho-A protein
| Structure | KRas G12D % Inh. | KRas G12D Q61H % Inh. | Rac-1 % Inh. | Rho-A % Inh. |
|---|---|---|---|---|
| 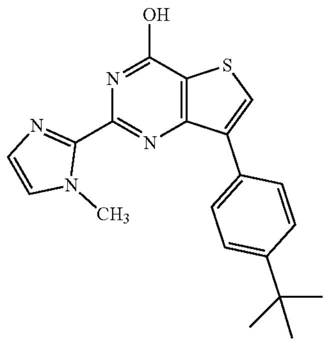 [SMILES: Cn1ccnc1-c1nc(O)c2scc(-c3ccc(C(C)(C)C)cc3)c2n1] | A | | B | B |
| 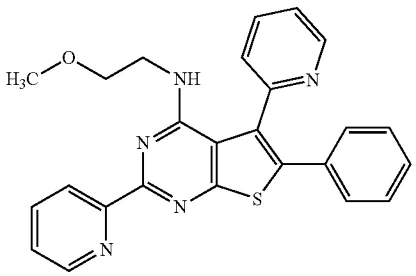 | A | | A | B |
| 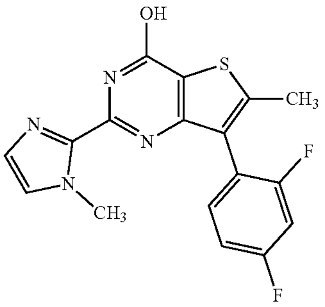 | A | | A | A |
| 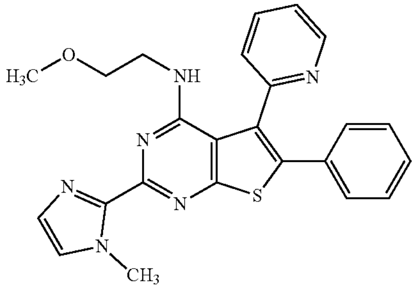 | B | | B | C |
A = 1-25% inhibition,
B = 25-50% inhibition,
C = 51-75% inhibition,
D = 76-100% inhibition

EXAMPLE 7

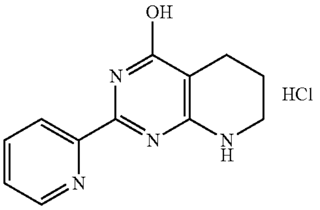

Compound 4 was prepared as described in Scheme 1. To a suspension of compound 4 (0.020 g, 0.088 mmol in dry acetonitrile (2 mL) a solution of 10% HCl in dry dioxane was added dropwise until pH 3. After standing for 0.5 h the solvents were removed in vacuum to obtain 0.023 g (0.088 mmol, 100%) of target compound.

EXAMPLE 8

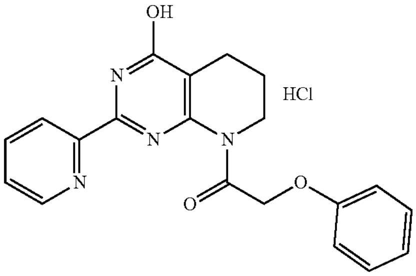

The target compound was prepared from compound 4 in Scheme 1, according to the procedure for amide synthesis described in Step D, Scheme 1.

EXAMPLE 9

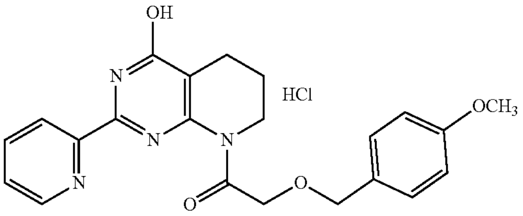

To a solution of compound 4 from Scheme 1 (0.150 g, 0.66 mmol) in acetonitrile, [(4-methoxybenzyl)oxy]acetic acid (0.129 g, 0.66 mmol), DIPEA (0.46 mL, 2.64 mmol), and DMAP (0.005 g, 0.04 mmol) were added. Then TBTU (0.847 g, 2.64 mmol) was added, the resulting mixture was refluxed for 8 hours, and evaporated under reduced pressure. The residue was purified by HPLC to yield the target amide.

EXAMPLE 10

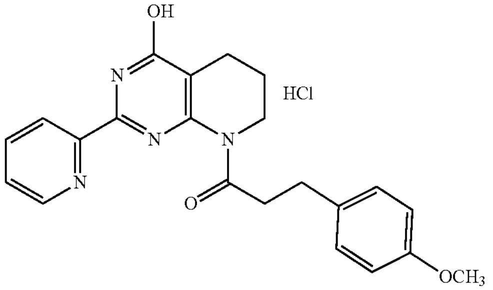

The target compound was prepared from compound 4 in Scheme 1, according to the procedure for amide synthesis described in Step D, Scheme 1.

EXAMPLE 11

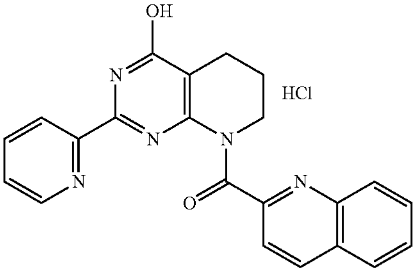

The target compound was prepared from compound 4 in Scheme 1, according to the general procedure for amide synthesis described in Step D, Scheme 1.

EXAMPLE 12

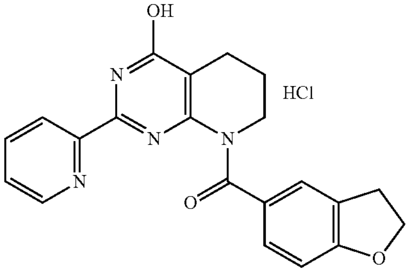

The target compound was prepared from compound 4 in Scheme 1, according to the general procedure for amide synthesis described in Step D, Scheme 1.

EXAMPLE 13

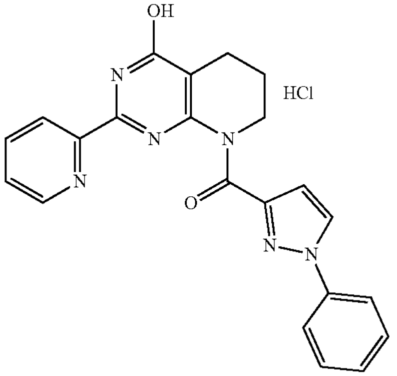

The target compound was prepared from compound 4 in Scheme 1, according to the general procedure for amide synthesis described in Step D, Scheme 1.

EXAMPLE 14

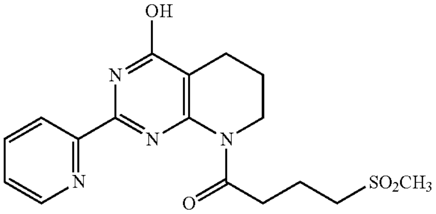

The target compound was prepared from compound 4 in Scheme 1, according to the general procedure for amide synthesis described in Step E, Scheme 1.

EXAMPLE 15

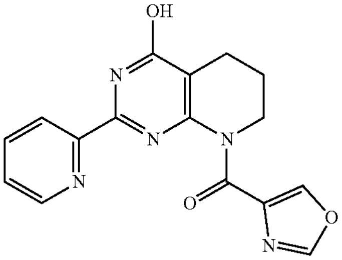

The target compound was prepared from compound 4 in Scheme 1, according to the general procedure for amide synthesis described in Step E, Scheme 1.

EXAMPLE 16

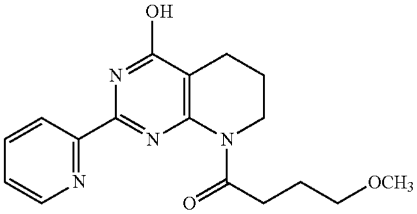

The target compound was prepared from compound 4 in Scheme 1, according to the general procedure for amide synthesis described in Step E, Scheme 1.

EXAMPLE 17

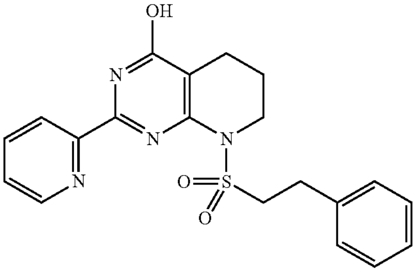

The target compound was prepared from compound 4 in Scheme 1, according to the general procedure for amide synthesis described in Step C, Scheme 1.

EXAMPLE 18

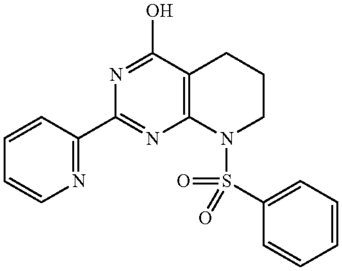

The target compound was prepared from compound 4 in Scheme 1, according to the general procedure for amide synthesis described in Step C, Scheme 1.

EXAMPLE 19

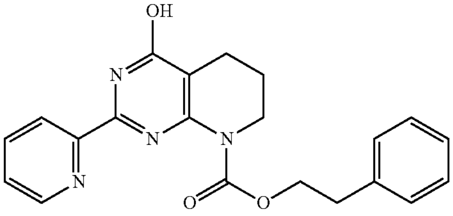

The target compound was prepared from compound 4 in Scheme 1, according to the general procedure described in Step E, Scheme 1.

EXAMPLE 20

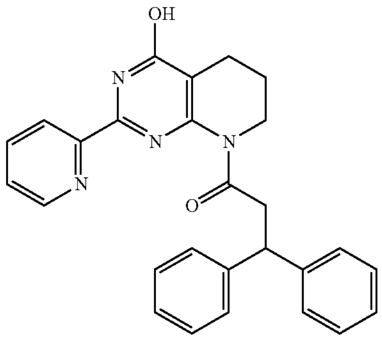

The target compound was prepared from compound 4 in Scheme 1, according to the general procedure for amide synthesis described in Step E, Scheme 1.

EXAMPLE 21

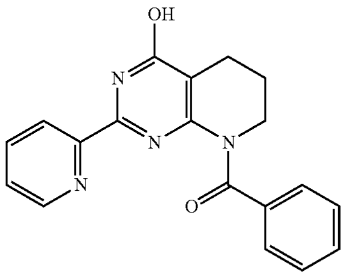

The target compound was prepared from compound 4 in Scheme 1, according to the general procedure for amide synthesis described in Step E, Scheme 1.

EXAMPLE 22

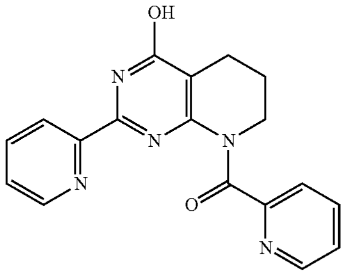

The target compound was prepared from compound 4 in Scheme 1, according to the general procedure for amide synthesis described in Step E, Scheme 1.

EXAMPLE 23

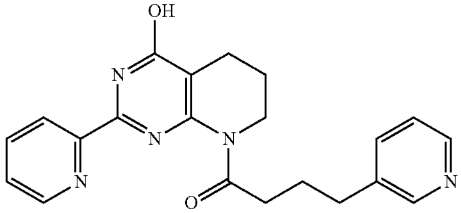

The target compound was prepared from compound 4 in Scheme 1, according to the general procedure for amide synthesis described in Step E, Scheme 1.

EXAMPLE 24

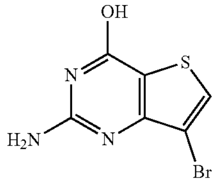

The target compound, compound 8 in Scheme 2, was prepared according to the procedure described in Scheme 2.

EXAMPLE 25

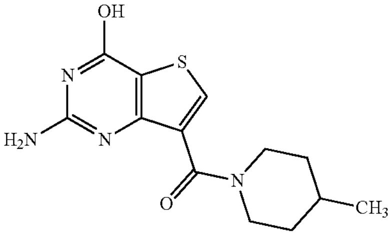

The target compound was prepared from compound 10 in Scheme 2, according to the general procedure for amide synthesis described in Step E, Scheme 2.

EXAMPLE 26

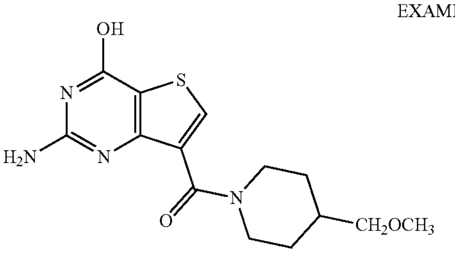

The target compound was prepared from compound 10 in Scheme 2, according to the general procedure for amide synthesis described in Step E, Scheme 2.

EXAMPLE 27

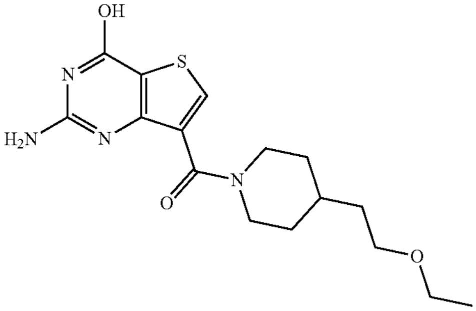

The target compound was prepared from compound 10 in Scheme 2, according to the general procedure for amide synthesis described in Step E, Scheme 2.

EXAMPLE 28

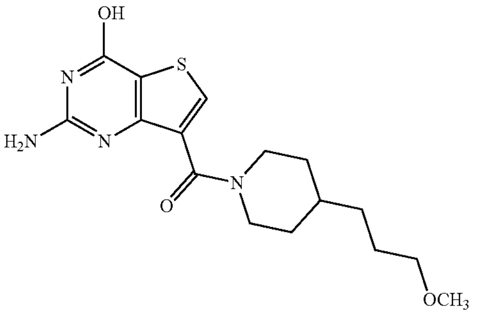

The target compound was prepared from compound 10 in Scheme 2, according to the general procedure for amide synthesis described in Step E, Scheme 2.

EXAMPLE 29

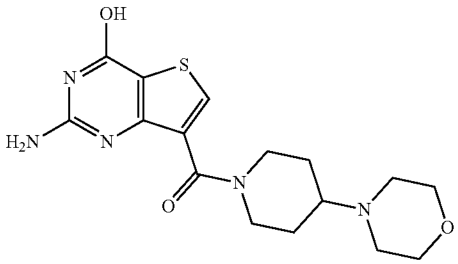

The target compound was prepared from compound 10 in Scheme 2, according to the general procedure for amide synthesis described in Step E, Scheme 2.

EXAMPLE 30

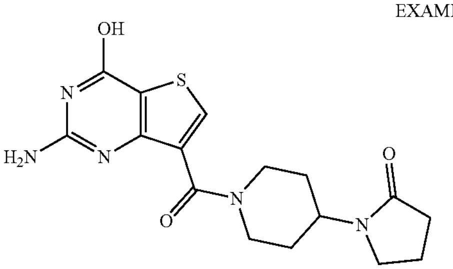

The target compound was prepared from compound 10 in Scheme 2, according to the general procedure for amide synthesis described in Step E, Scheme 2.

EXAMPLE 31

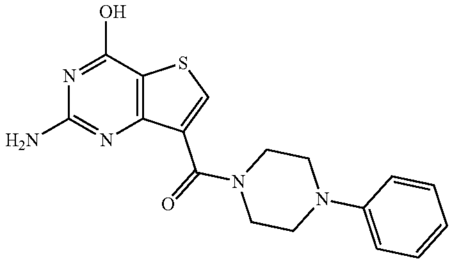

The target compound was prepared from compound 10 in Scheme 2, according to the general procedure for amide synthesis described in Step E, Scheme 2.

EXAMPLE 32

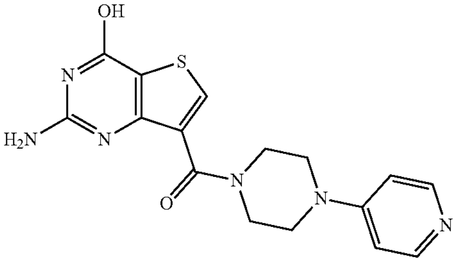

The target compound was prepared from compound 10 in Scheme 2, according to the general procedure for amide synthesis described in Step E, Scheme 2.

EXAMPLE 33

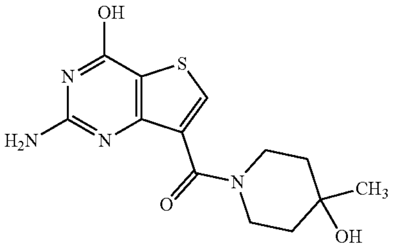

The target compound was prepared from compound 10 in Scheme 2, according to the general procedure for amide synthesis described in Step E, Scheme 2.

EXAMPLE 33

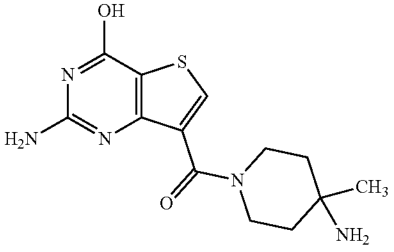

The target compound was prepared from compound 10 in Scheme 2, according to the general procedure for amide synthesis described in Step E, Scheme 2.

EXAMPLE 35

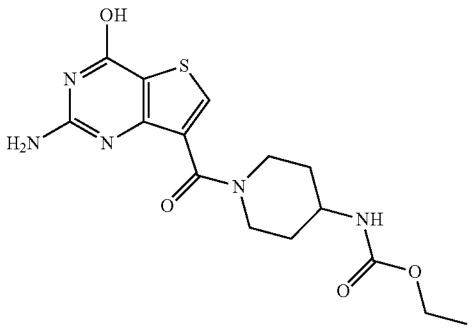

The target compound was prepared from compound 10 in Scheme 2, according to the general procedure for amide synthesis described in Step E, Scheme 2.

EXAMPLE 36

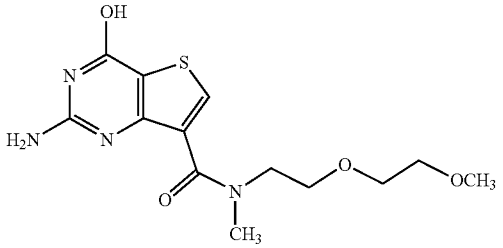

The target compound was prepared from compound 10 in Scheme 2, according to the general procedure for amide synthesis described in Step E, Scheme 2.

EXAMPLE 37

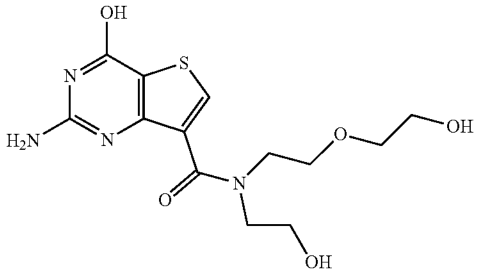

The target compound was prepared from compound 10 in Scheme 2, according to the general procedure for amide synthesis described in Step E, Scheme 2.

EXAMPLE 38

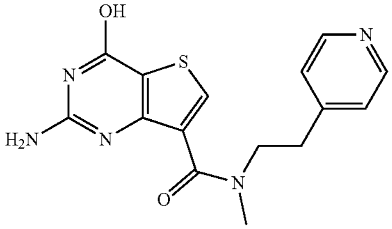

The target compound was prepared from compound 10 in Scheme 2, according to the general procedure for amide synthesis described in Step E, Scheme 2.

EXAMPLE 39

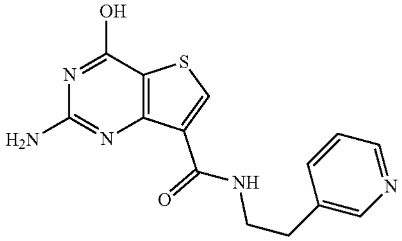

The target compound was prepared from compound 10 in Scheme 2, according to the general procedure for amide synthesis described in Step E, Scheme 2.

EXAMPLE 40

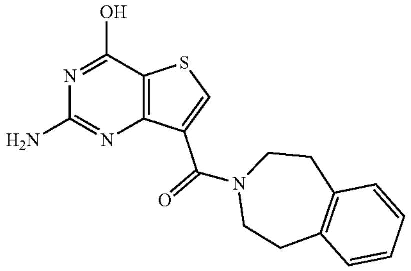

The target compound was prepared from compound 10 in Scheme 2, according to the general procedure for amide synthesis described in Step E, Scheme 2.

EXAMPLE 41

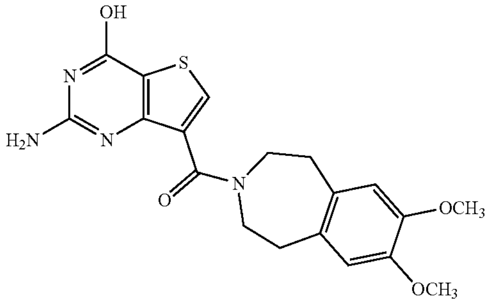

The target compound was prepared from compound 10 in Scheme 2, according to the general procedure for amide synthesis described in Step E, Scheme 2.

EXAMPLE 42

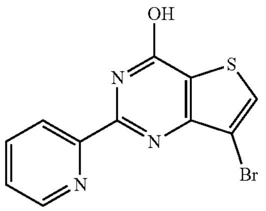

The target compound, compound 13 in Scheme 3, was prepared according to the procedure described in Scheme 3.

EXAMPLE 43

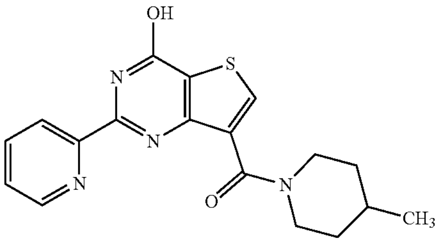

The target compound was prepared from compound 15 in Scheme 3, according to the general procedure for amide synthesis described in Step E, Scheme 3.

EXAMPLE 44

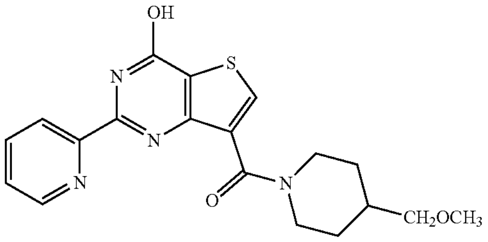

The target compound was prepared from compound 15 in Scheme 3, according to the general procedure for amide synthesis described in Step E, Scheme 3.

EXAMPLE 45

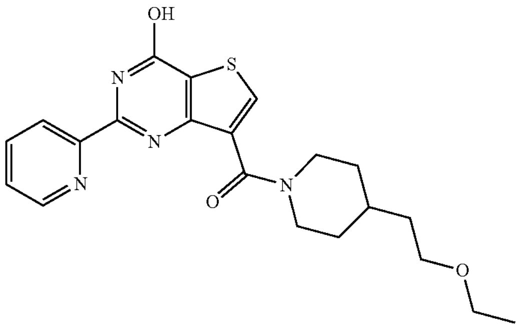

The target compound was prepared from compound 15 in Scheme 3, according to the general procedure for amide synthesis described in Step E, Scheme 3.

EXAMPLE 46

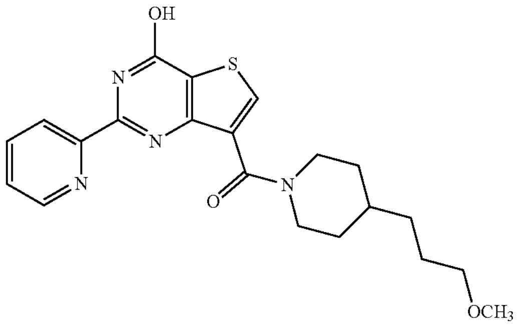

The target compound was prepared from compound 15 in Scheme 3, according to the general procedure for amide synthesis described in Step E, Scheme 3.

EXAMPLE 47

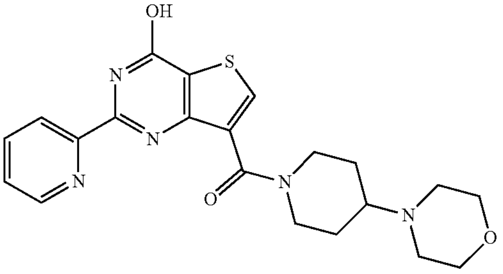

The target compound was prepared from compound 15 in Scheme 3, according to the general procedure for amide synthesis described in Step E, Scheme 3.

EXAMPLE 48

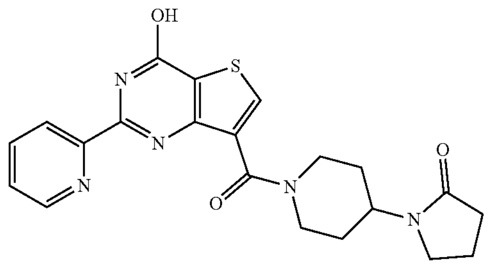

The target compound was prepared from compound 15 in Scheme 3, according to the general procedure for amide synthesis described in Step E, Scheme 3.

EXAMPLE 49

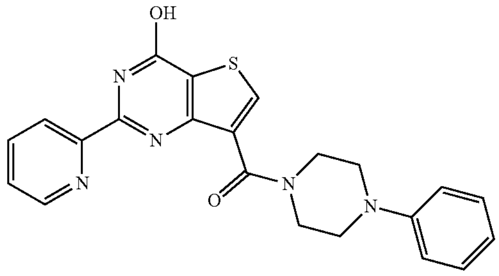

The target compound was prepared from compound 15 in Scheme 3, according to the general procedure for amide synthesis described in Step E, Scheme 3.

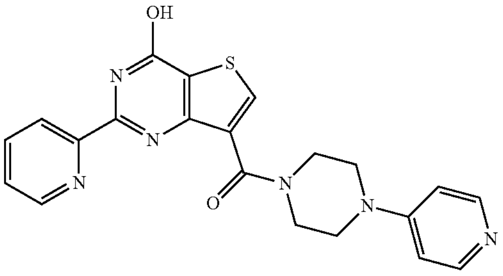

EXAMPLE 50

The target compound was prepared from compound 15 in Scheme 3, according to the general procedure for amide synthesis described in Step E, Scheme 3.

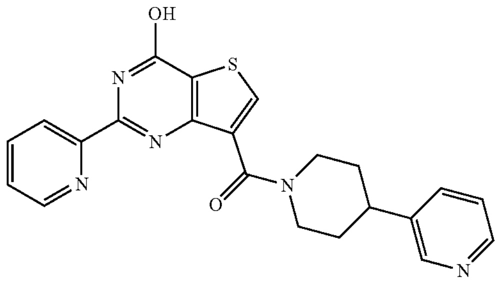

EXAMPLE 51

The target compound was prepared from compound 15 in Scheme 3, according to the general procedure for amide synthesis described in Step E, Scheme 3.

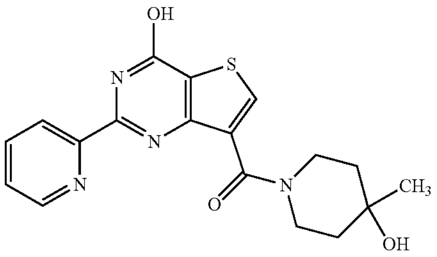

EXAMPLE 52

The target compound was prepared from compound 15 in Scheme 3, according to the general procedure for amide synthesis described in Step E, Scheme 3.

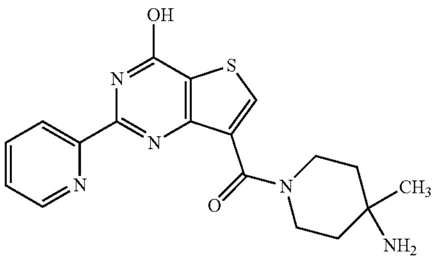

EXAMPLE 53

The target compound was prepared from compound 15 in Scheme 3, according to the general procedure for amide synthesis described in Step E, Scheme 3.

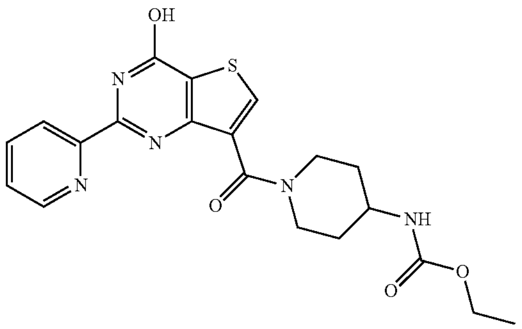

EXAMPLE 54

The target compound was prepared from compound 15 in Scheme 3, according to the general procedure for amide synthesis described in Step E, Scheme 3.

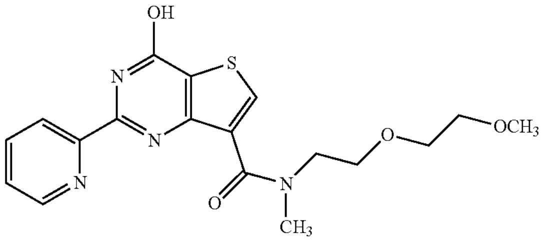

EXAMPLE 55

The target compound was prepared from compound 15 in Scheme 3, according to the general procedure for amide synthesis described in Step E, Scheme 3.

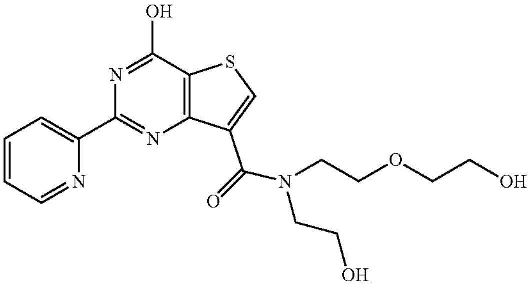

EXAMPLE 56

The target compound was prepared from compound 15 in Scheme 3, according to the general procedure for amide synthesis described in Step E, Scheme 3.

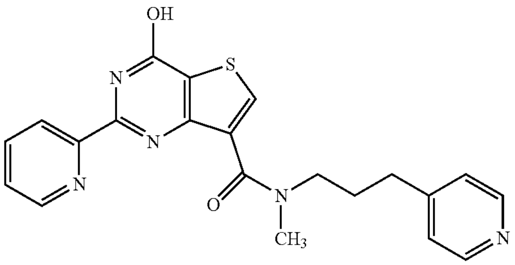

EXAMPLE 57

The target compound was prepared from compound 15 in Scheme 3, according to the general procedure for amide synthesis described in Step E, Scheme 3.

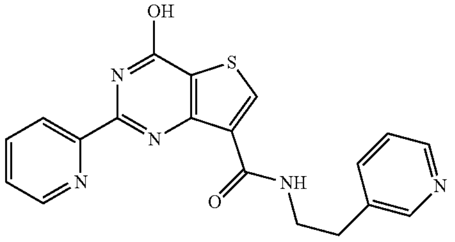

EXAMPLE 58

The target compound was prepared from compound 15 in Scheme 3, according to the general procedure for amide synthesis described in Step E, Scheme 3.

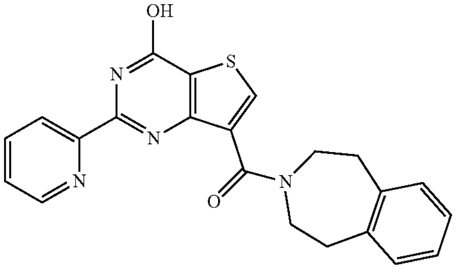

EXAMPLE 59

The target compound was prepared from compound 15 in Scheme 3, according to the general procedure for amide synthesis described in Step E, Scheme 3.

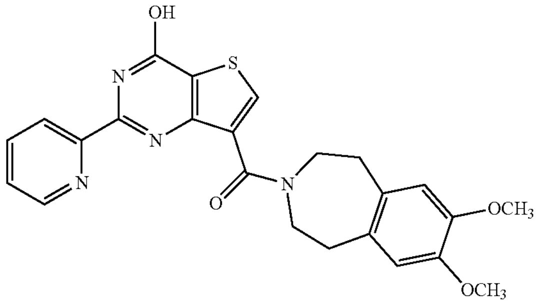

EXAMPLE 60

The target compound was prepared from compound 15 in Scheme 3, according to the general procedure for amide synthesis described in Step E, Scheme 3.

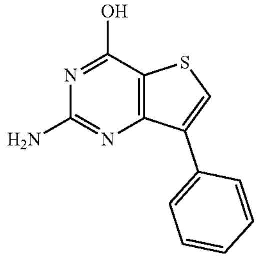

EXAMPLE 61

The target compound was prepared from compound 8 in Scheme 4, according to the procedure described in Scheme 4.

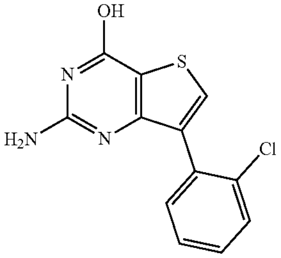

EXAMPLE 62

The target compound was prepared from compound 8 in Scheme 4, according to the procedure described in Scheme 4.

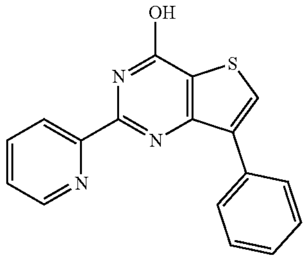

EXAMPLE 63

The target compound was prepared from compound 13 in Scheme 4, according to the procedure described in Scheme 4.

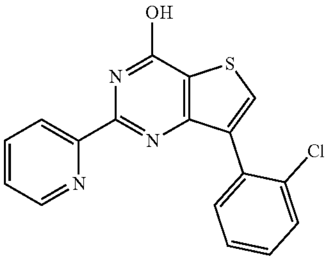

EXAMPLE 64

The target compound was prepared from compound 13 in Scheme 4, according to the procedure described in Scheme 4.

EXAMPLE 65

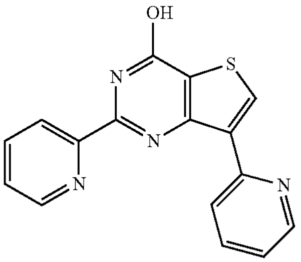

2 HCl

-continued

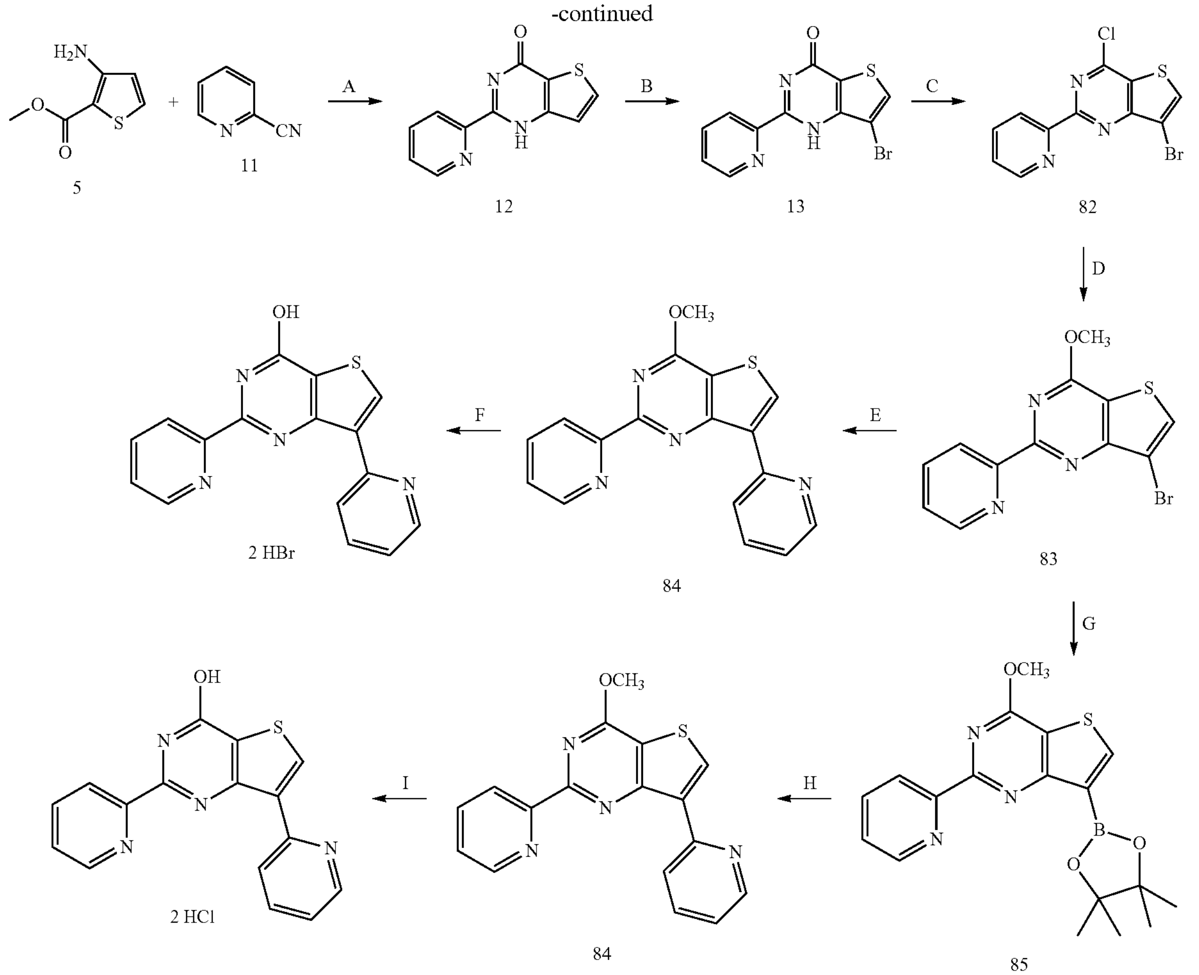

5 11 12 13 82 83 84 2 HBr 85 84 2 HCl

Step A: To a solution compound 5 of Scheme 2 (30 g, 0.19 mol) in 300 mL dioxane HCl was added compound 11 (23.85 g, 0.23 mol). The reaction mixture was stirred at rt overnight, diluted dioxane (300 mL), refluxed for 3h, cooled and evaporated. The resulting residue was washed by mixture EtOAc-iPrOH (1:2). The yield of 12 was 36 g (0.157 mol, 83%).

Step B: To a solution compound 12 (36 g, 0.157 mol) in 650 mL acetic acid, bromine (35 mL) was added at rt. The reaction mixture was refluxed 48h, cooled, evaporated, diluted with water. The resulting precipitate was filtered, washed with water and dried. The yield of 13 was 45 g (0.146 mol, 93%)

Step C: The compound 13 (40 g, 0.13 mol, 1 eq.) and phosphoryl chloride (300 mL) were heated at reflux for 24 h. The reaction mixture was then evaporated to dryness. The crude residue was dissolved in $CH_2Cl_2$ and washed carefully with ice-water and 5% $NaHCO_3$ solution. Organic layer was dried over $Na_2SO_4$ and evaporated to dryness giving sufficiently pure compound 82 as yellowish powder (40 g, yield 95%).

Step D: Sodium (2.8 g, 0.122 mol, 2 eq) was added in portions to methanol (400 mL). Once all the sodium metal had disappeared, 82 (20 g, 0.061 mol, 1 eq) was added and the mixture was stirred at ambient temperature overnight. The mixture was diluted with water and extracted with diethyl ether. The organic layer was washed with water, brine, dried ($Na_2SO_4$), filtered and the solvent was removed under reduced pressure to give 83 (15.86 g, yield 81%) as an orange solid, which was used in next step without purification.

Step E: Into a 500 mL flask were charged 83 (1 g, 3.10 mmol, 1 eq.), [1,1' bis(diphenylphosphino)-ferrocene]dichloropalladium(II)-dichloromethane complex (0.127 g, 0.15 mmol, 0.05 eq.), cuprous iodide (0.057 g, 0.30 mmol, 0.1 eq.), and THF (50 mL). The resulting mixture was degassed with alternating vacuum/nitrogen purges. The filtered 2-pyridylzinc bromide solution (9.30 mmol, prepared as described in *Org. Lett.,* 2015, 17, 3170-3173) was then added. The mixture was degassed one more time and then heated at reflux for 24 h. The reaction mixture was then cooled to 20° C. and treated with MTBE (methyl tert-butyl ether, 130 mL) and 1 N ammonium chloride (130 mL). The mixture was stirred at 20-30° C. for 30 min and then filtered. The lower aqueous layer was drawn off, and the remaining organic layer was treated with saturated aqueous $NH_4Cl$ (50 mL) and stirred for 30 min. After settling, the lower aqueous layer was removed and the organic layer was collected. The resulting organic solution was then filtered through a small pad of $SiO_2$. The $SiO_2$ pad was washed with MTBE (25 mL). The solvent was evaporated, and the residue was purified by HPLC to give the target compound (0.01 g, 0.031 mmol, 1% yield of 84).

Step F: A solution of 84 (0.01 g, 0.031 mmol) in HOAc (0.2 mL) and 48% aq.

HBr (0.2 mL) was warmed to 65° C. for 3 h, and then cooled to rt. The resulting solution was concentrated to dryness and the residue was suspended in EtOAc. The solid was filtered, washed with EtOAc (2 mL), dried to afford the target compound (0.101 g, 70% yield) as a dihydrobromide salt.

Step G: The compound 83 (1 g, 3.1 mmol, 1 eq.) was dissolved in THF and the solution was cooled to −78 *C, then 1.5 ml of nBuLi (1.2 eq.) was added dropwise and the resulting mixture was stirred for 20-30 minutes then, 0.823 ml (4.034 mmol, 1.3 eq.) of borolane was added and the reaction mixture was warmed up to rt. The reaction mixture was quenched with aq. sol. of $NH_4Cl$ and extracted with EA (3×30 ml), combined organics were dried over $Na_2SO_4$ and concentrated under vacuo to give compound 85 as a brown oil, which was used in next step without purification.

Step H: 0.3 g (1.56 mmol, 1 eq.) of 2-bromo-pyridine was mixed with compound 85 (1.66 mmol, 1.05 eq.) in dioxane with 0.992 g (7.18 mmol) of $K_2CO_3$ (25% aq. solution) and 0.02 mmol (0.026 g) of $Pd(dppf)Cl_2$ under Ar atmosphere for 12 h. Then the reaction was mixed with water, extracted with ethyl acetate (3×30 ml), the combined organics were dried over $Na_2SO_4$ and concentrated in vacuo to give the product as a brown oil. The target compound 84 was isolated using HPLC (ACN/H2O as a mobile phase), 0.155 g. Yield 31%

Step I: 0.05 g of compound 84 was stirred at 100° C. in conc. HCl for 2 day, and then the target compound was precipitated and isolated by filtration. Yield 42.4%.

EXAMPLE 66

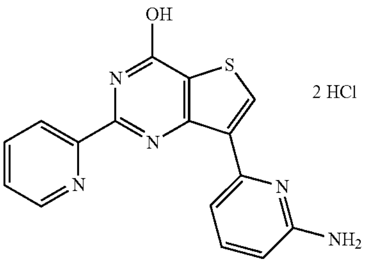

2 HCl

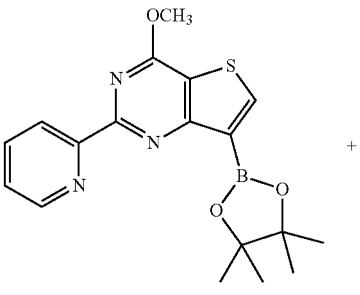

85

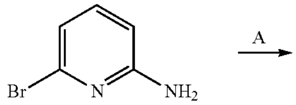

86

-continued

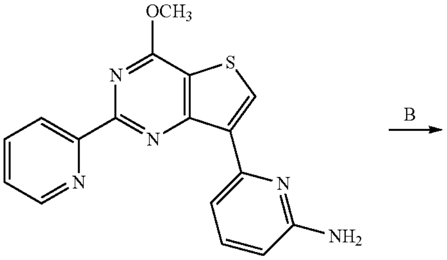

87

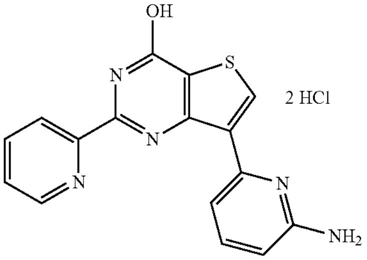

2 HCl

Step A: 0.27 g (1.56 mmol, 1 eq.) of 2-bromo-6-amino-pyridine 86 was mixed with compound 85, prepared in Step G, Example 65 (1.66 mmol, 1.05 eq.) in dioxane with 0.992 g (7.18 mmol) of $K_2CO_3$ (25% aq. solution) and 0.02 mmol (0.026 g) of $Pd(dppf)Cl_2$ under an argon atmosphere for 12 h. Then the reaction was mixed with water, extracted with ethyl acetate (3×30 ml), and the combined organics were dried over $Na_2SO_4$ and concentrated under vacuo to give compound 87 as a brown oil. Compound 87 was isolated using HPLC (ACN/$H_2O$ as a mobile phase), 0.158 g. Yield 30%

Step B: 0.158 g of compound 87 was stirred at 100 *C in conc. HCl for 2 days, then the target compound was precipitated and isolated by filtration. Yield 53.8%.

EXAMPLE 67

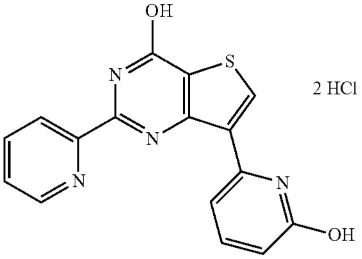

2 HCl

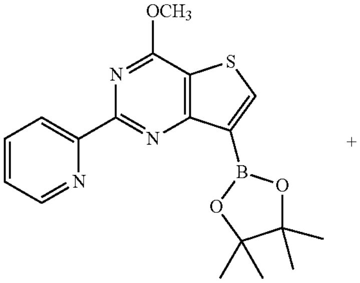

85

-continued

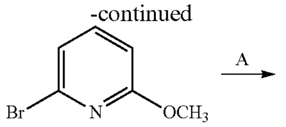

88

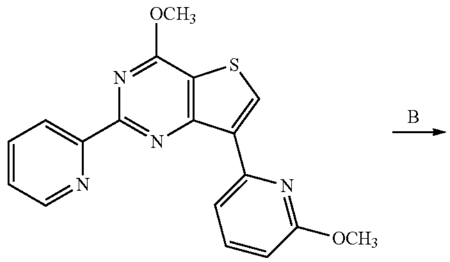

89

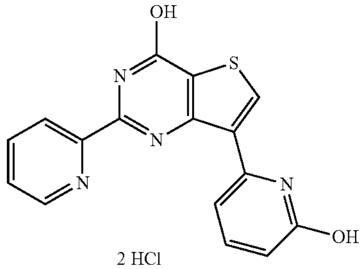

2 HCl

Step A: 0.3 g (1.56 mmol, 1 eq.) of 2-bromo-6-methoxypyridine 88 was mixed with compound 85 (1.66 mmol, 1.05 eq.) in dioxane with 0.992 g (7.18 mmol) of $K_2CO_3$ (25% aq. solution) and 0.02 mmol (0.026 g) of Pd(dppf)$Cl_2$ under an argon atmosphere for 12 h. Then the reaction was mixed with water, extracted with ethyl acetate (3x30 ml), and the combined organics were dried over $Na_2SO_4$ and concentrated in vacuo to give compound 89 as a brown oil. Compound 89 was isolated using HPLC (ACN/$H_2O$ as a mobile phase), 0.183 g. Yield 33%.

Step B: 0.05 g of compound 89 was stirred at 100 *C in conc. HCl for 2 days, and then the target compound was precipitated and isolated by filtration. Yield 38.4%.

EXAMPLE 68

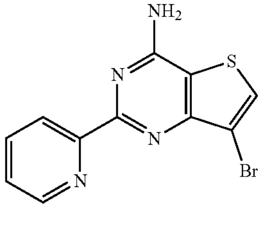

The target compound was prepared in Step D, Scheme 10 (compound 43).

EXAMPLE 69

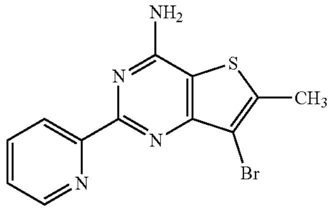

The target compound was prepared in Step D, Scheme 10 (compound 44).

EXAMPLE 70

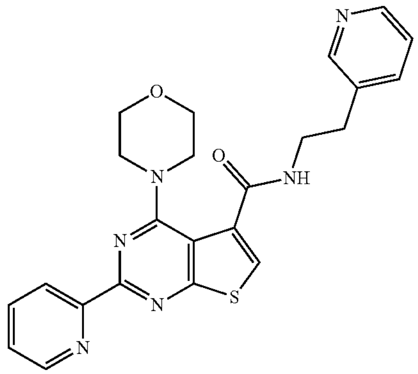

The target compound was prepared from compound 20 in Scheme 5, according to the general procedures described in Scheme 5 for Steps E, F and G, using morpholine as the amine in Step E, and the appropriate amine in Step G.

EXAMPLE 71

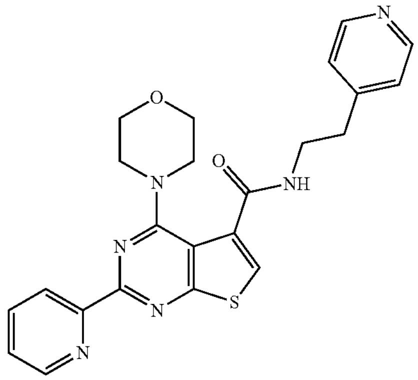

The target compound was prepared from compound 20 in Scheme 5, according to the general procedures described in Scheme 5 for Steps E, F and G, using morpholine as the amine in Step E, and the appropriate amine in Step G.

EXAMPLE 72

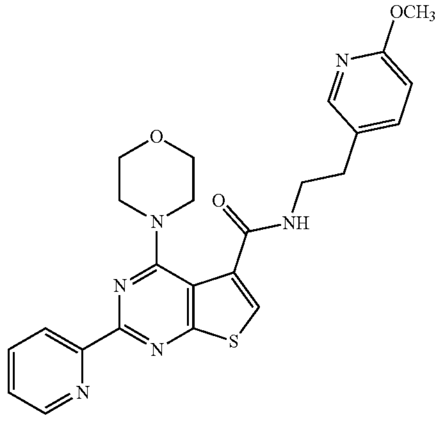

The target compound was prepared from compound 20 in Scheme 5, according to the general procedures described in Scheme 5 for Steps E, F and G, using morpholine as the amine in Step E, and the appropriate amine in Step G.

EXAMPLE 73

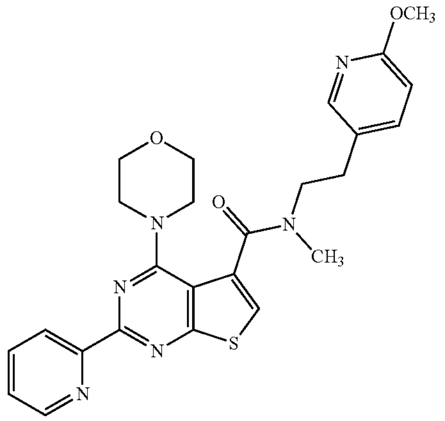

The target compound was prepared from compound 20 in Scheme 5, according to the general procedures described in Scheme 5 for Steps E, F and G, using morpholine as the amine in Step E, and the appropriate amine in Step G.

EXAMPLE 74

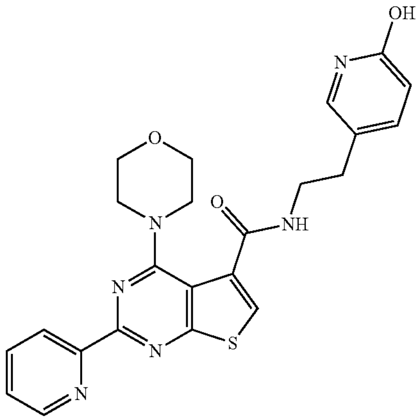

The target compound was prepared from compound 20 in Scheme 5, according to the general procedures described in Scheme 5 for Steps E, F and G, using morpholine as the amine in Step E, and the appropriate amine in Step G.

EXAMPLE 75

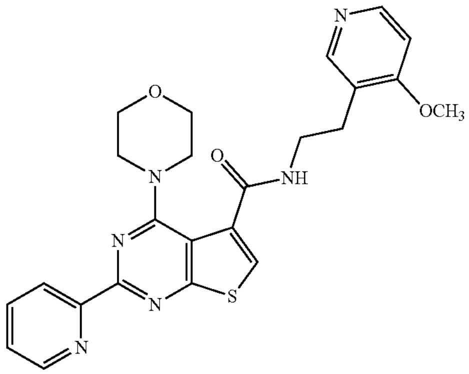

The target compound was prepared from compound 20 in Scheme 5, according to the general procedures described in Scheme 5 for Steps E, F and G, using morpholine as the amine in Step E, and the appropriate amine in Step G.

EXAMPLE 76

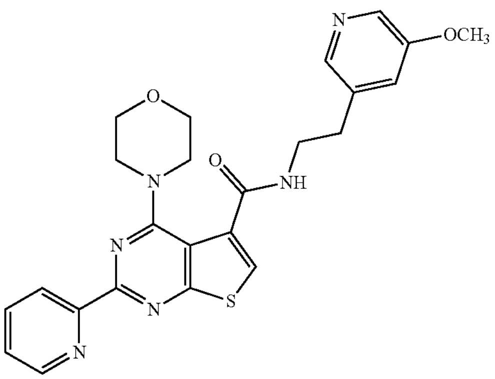

The target compound was prepared from compound 20 in Scheme 5, according to the general procedures described in Scheme 5 for Steps E, F and G, using morpholine as the amine in Step E, and the appropriate amine in Step G.

EXAMPLE 77

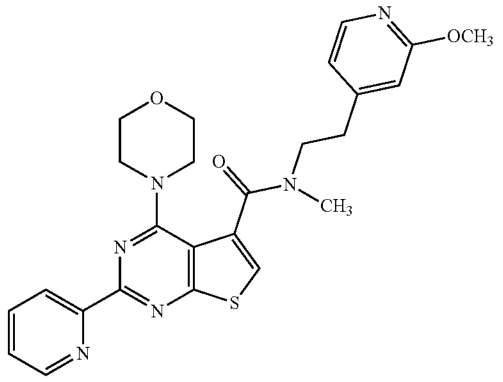

The target compound was prepared from compound 20 in Scheme 5, according to the general procedures described in Scheme 5 for Steps E, F and G, using morpholine as the amine in Step E, and the appropriate amine in Step G.

EXAMPLE 78

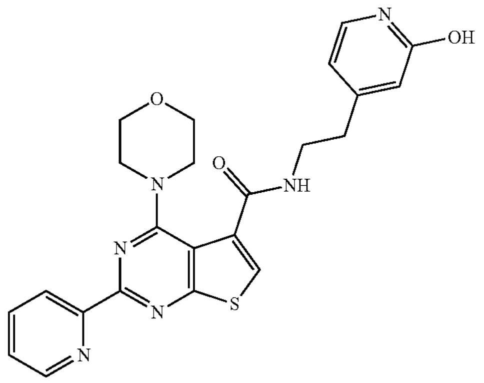

The target compound was prepared from compound 20 in Scheme 5, according to the general procedures described in Scheme 5 for Steps E, F and G, using morpholine as the amine in Step E, and the appropriate amine in Step G.

EXAMPLE 79

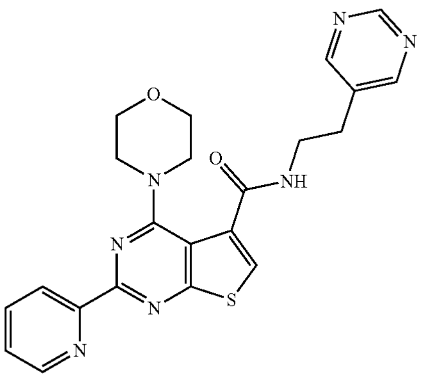

The target compound was prepared from compound 20 in Scheme 5, according to the general procedures described in Scheme 5 for Steps E, F and G, using morpholine as the amine in Step E, and the appropriate amine in Step G.

EXAMPLE 80

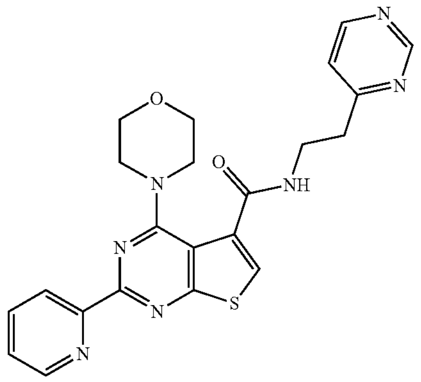

The target compound was prepared from compound 20 in Scheme 5, according to the general procedures described in Scheme 5 for Steps E, F and G, using morpholine as the amine in Step E, and the appropriate amine in Step G.

EXAMPLE 81

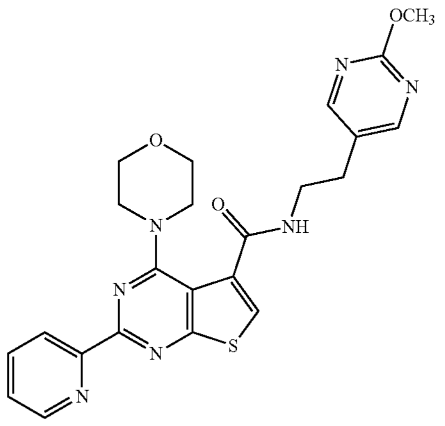

The target compound was prepared from compound 20 in Scheme 5, according to the general procedures described in Scheme 5 for Steps E, F and G, using morpholine as the amine in Step E, and the appropriate amine in Step G.

EXAMPLE 82

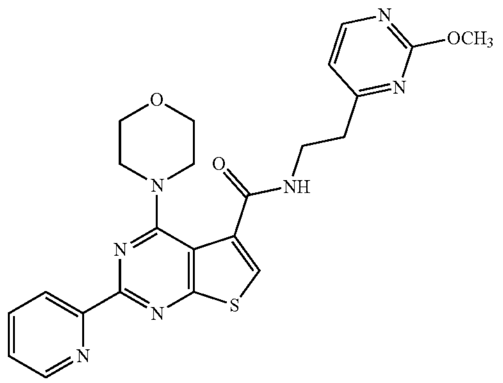

The target compound was prepared from compound 20 in Scheme 5, according to the general procedures described in Scheme 5 for Steps E, F and G, using morpholine as the amine in Step E, and the appropriate amine in Step G.

EXAMPLE 83

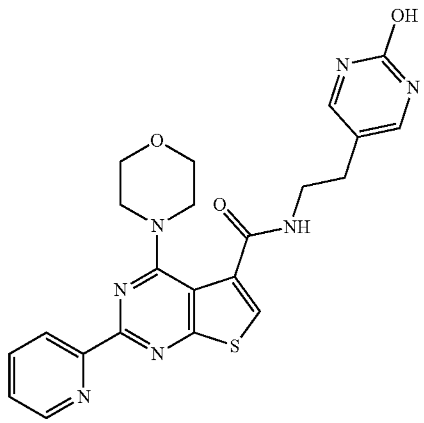

The target compound was prepared from compound 20 in Scheme 5, according to the general procedures described in Scheme 5 for Steps E, F and G, using morpholine as the amine in Step E, and the appropriate amine in Step G.

EXAMPLE 84

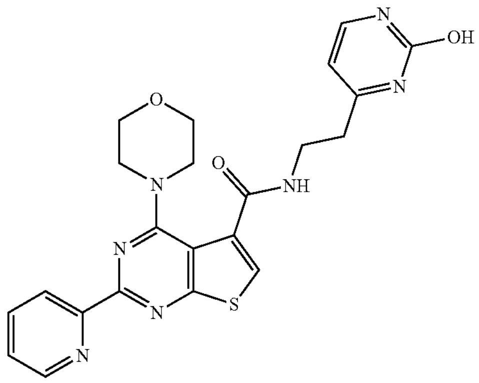

The target compound was prepared from compound 20 in Scheme 5, according to the general procedures described in Scheme 5 for Steps E, F and G, using morpholine as the amine in Step E, and the appropriate amine in Step G.

EXAMPLE 85

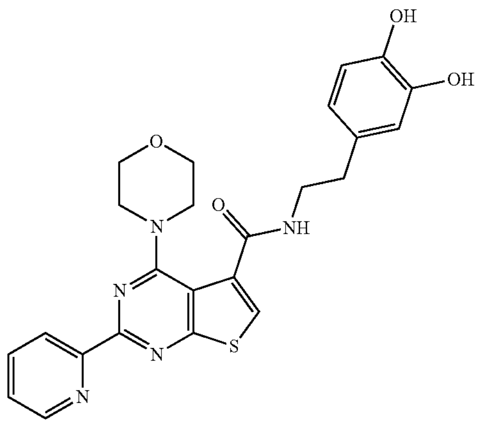

The target compound was prepared from compound 20 in Scheme 5, according to the general procedures described in Scheme 5 for Steps E, F and G, using morpholine as the amine in Step E, and the appropriate amine in Step G.

EXAMPLE 86

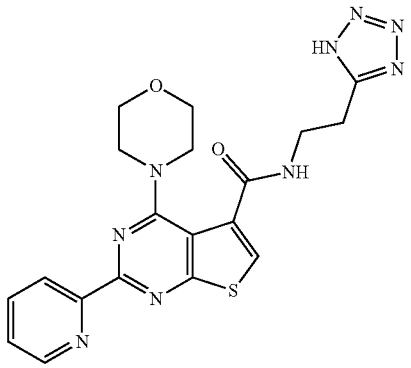

The target compound was prepared from compound 20 in Scheme 5, according to the general procedures described in Scheme 5 for Steps E, F and G, using morpholine as the amine in Step E, and the appropriate amine in Step G.

EXAMPLE 87

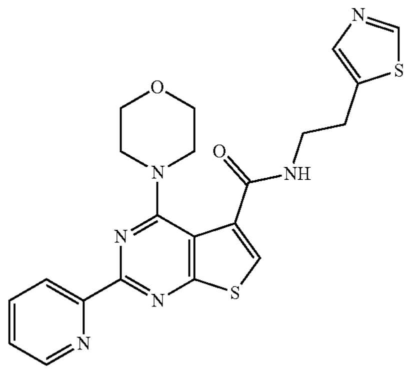

The target compound was prepared from compound 20 in Scheme 5, according to the general procedures described in Scheme 5 for Steps E, F and G, using morpholine as the amine in Step E, and the appropriate amine in Step G.

EXAMPLE 88

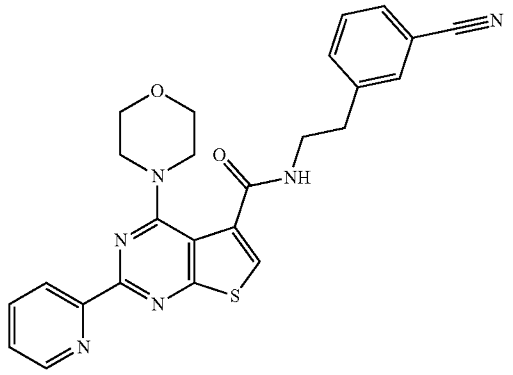

The target compound was prepared from compound 20 in Scheme 5, according to the general procedures described in Scheme 5 for Steps E, F and G, using morpholine as the amine in Step E, and the appropriate amine in Step G.

EXAMPLE 89

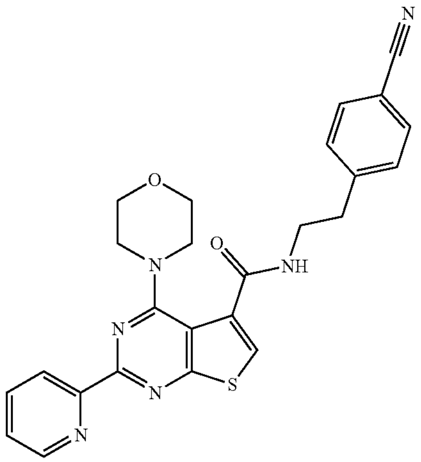

The target compound was prepared from compound 20 in Scheme 5, according to the general procedures described in Scheme 5 for Steps E, F and G, using morpholine as the amine in Step E, and the appropriate amine in Step G.

EXAMPLE 90

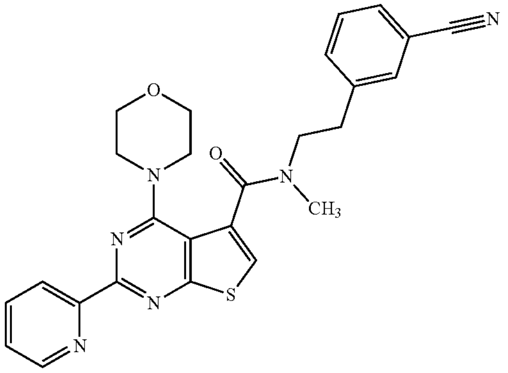

The target compound was prepared from compound 20 in Scheme 5, according to the general procedures described in Scheme 5 for Steps E, F and G, using morpholine as the amine in Step E, and the appropriate amine in Step G.

EXAMPLE 91

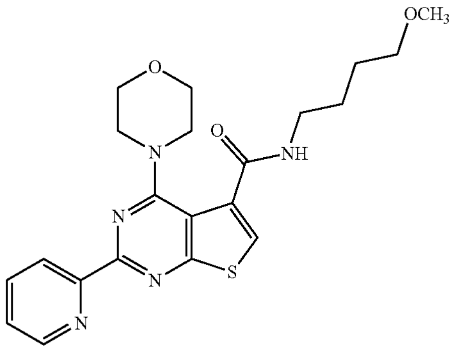

The target compound was prepared from compound 20 in Scheme 5, according to the general procedures described in Scheme 5 for Steps E, F and G, using morpholine as the amine in Step E, and the appropriate amine in Step G.

EXAMPLE 92

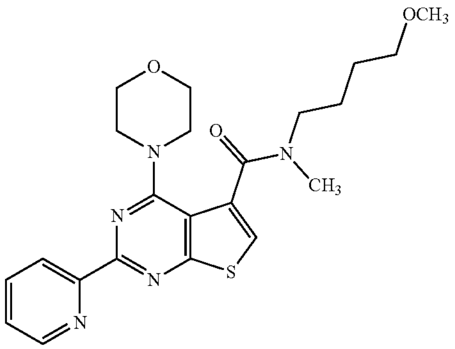

The target compound was prepared from compound 20 in Scheme 5, according to the general procedures described in Scheme 5 for Steps E, F and G, using morpholine as the amine in Step E, and the appropriate amine in Step G.

EXAMPLE 93

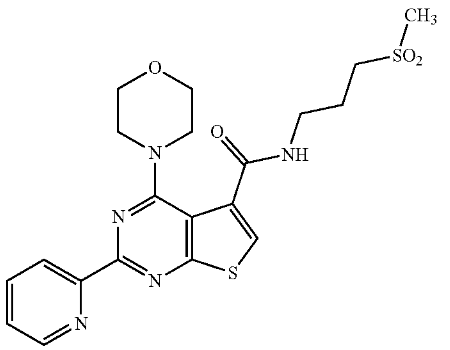

The target compound was prepared from compound 20 in Scheme 5, according to the general procedures described in Scheme 5 for Steps E, F and G, using morpholine as the amine in Step E, and the appropriate amine in Step G.

EXAMPLE 94

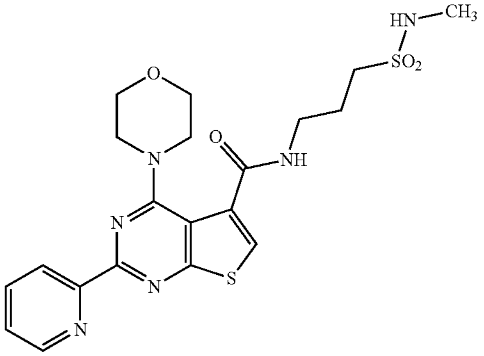

The target compound was prepared from compound 20 in Scheme 5, according to the general procedures described in Scheme 5 for Steps E, F and G, using morpholine as the amine in Step E, and the appropriate amine in Step G.

EXAMPLE 95

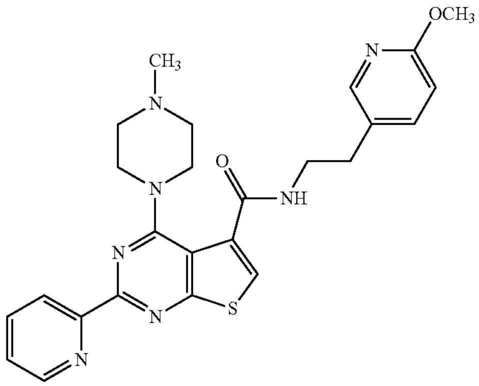

The target compound was prepared from compound 20 in Scheme 5, according to the general procedures described in Scheme 5 for Steps E, F and G, using N-methyl piperazine as the amine in Step E, and the appropriate amine in Step G.

EXAMPLE 96

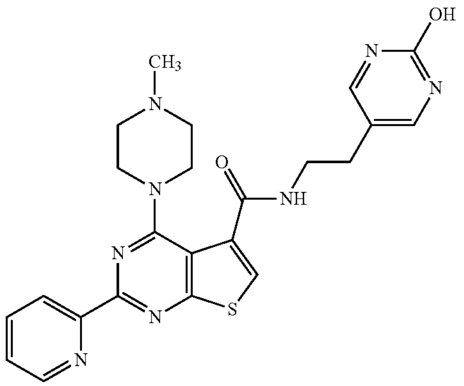

The target compound was prepared from compound 20 in Scheme 5, according to the general procedures described in Scheme 5 for Steps E, F and G, using N-methyl piperazine as the amine in Step E, and the appropriate amine in Step G.

EXAMPLE 97

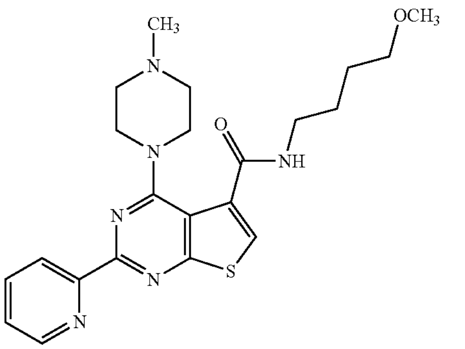

The target compound was prepared from compound 20 in Scheme 5, according to the general procedures described in Scheme 5 for Steps E, F and G, using N-methyl piperazine as the amine in Step E, and the appropriate amine in Step G.

EXAMPLE 98

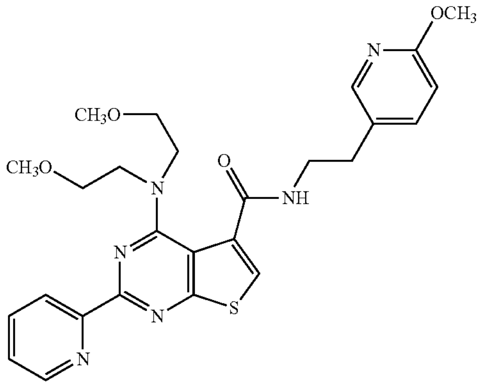

The target compound was prepared from compound 20 in Scheme 5, according to the general procedures described in Scheme 5 for Steps E, F and G, using bis(2-methoxyethyl) amine as the amine in Step E, and the appropriate amine in Step G.

EXAMPLE 99

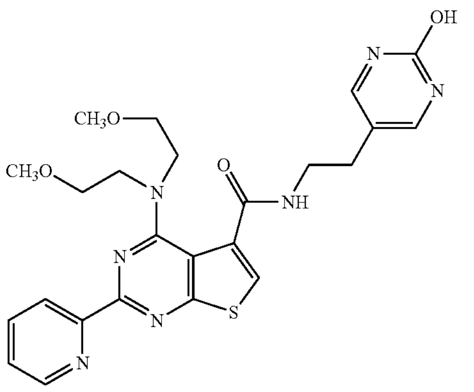

The target compound was prepared from compound 20 in Scheme 5, according to the general procedures described in Scheme 5 for Steps E, F and G, using bis(2-methoxyethyl) amine as the amine in Step E, and the appropriate amine in Step G.

EXAMPLE 100

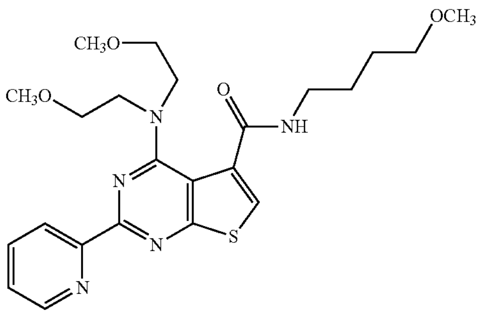

The target compound was prepared from compound 20 in Scheme 5, according to the general procedures described in Scheme 5 for Steps E, F and G and using bis(2-methoxyethyl)amine as the amine in Step E, and the appropriate amine in Step G.

EXAMPLE 101

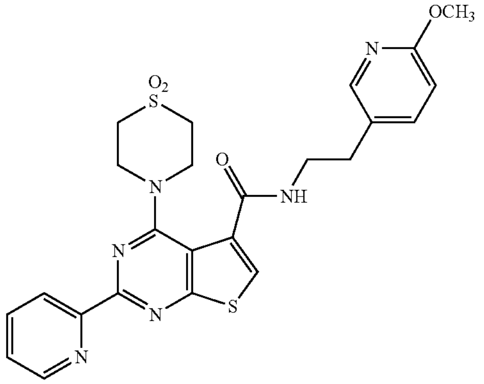

The target compound was prepared from compound 20 in Scheme 5, according to the general procedures described in Scheme 5 for Steps E, F and G, using thiomorpholine 1,1-dioxide as the amine in Step E, and the appropriate amine in Step G.

EXAMPLE 102

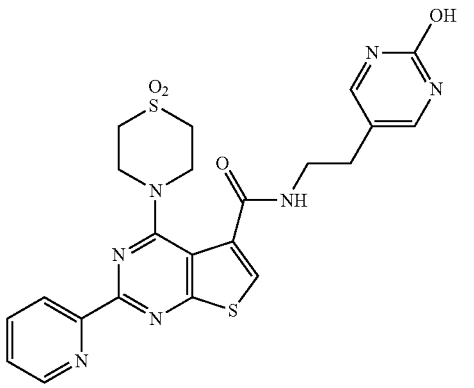

The target compound was prepared from compound 20 in Scheme 5, according to the general procedures described in Scheme 5 for Steps E, F and G and using thiomorpholine 1,1-dioxide as the amine in Step E, and the appropriate amine in Step G.

EXAMPLE 103

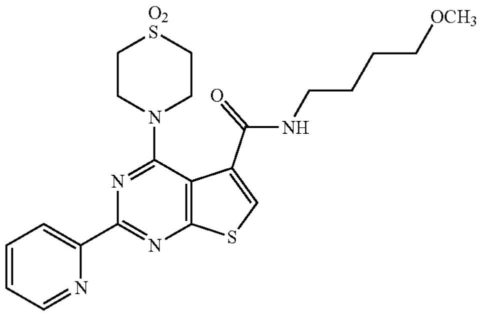

The target compound was prepared from compound 20 in Scheme 5, according to the general procedures described in Scheme 5 for Steps E, F and G and using thiomorpholine 1,1-dioxide as the amine in Step E, and the appropriate amine in Step G.

EXAMPLE 104

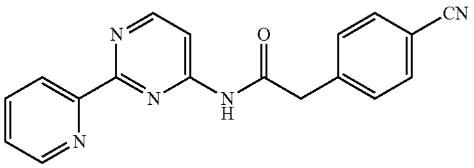

The target compound was prepared from compound 25 in Scheme 6, according to the procedure for amide synthesis described in Step B, Scheme 6.

EXAMPLE 105

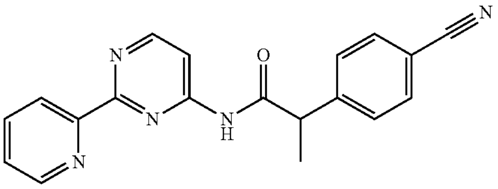

The target compound was prepared from compound 25 in Scheme 6, according to the procedure for amide synthesis described in Step B, Scheme 6.

EXAMPLE 106

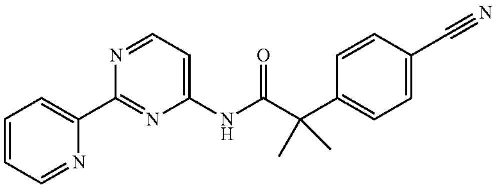

The target compound was prepared from compound 25 in Scheme 6, according to the procedure for amide synthesis described in Step B, Scheme 6.

EXAMPLE 107

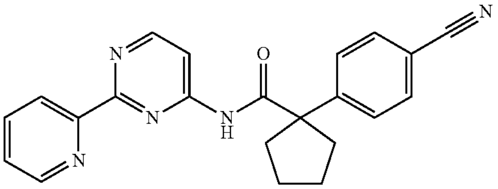

The target compound was prepared from compound 25 in Scheme 6, according to the procedure for amide synthesis described in Step B, Scheme 6.

EXAMPLE 108

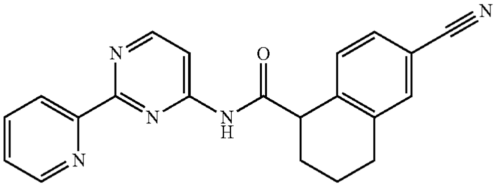

The target compound was prepared from compound 25 in Scheme 6, according to the procedure for amide synthesis described in Step B, Scheme 6.

EXAMPLE 109

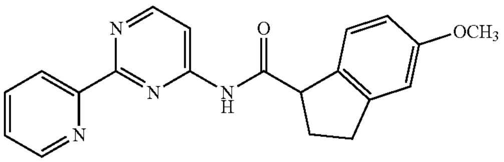

The target compound was prepared from compound 25 in Scheme 6, according to the procedure for amide synthesis described in Step B, Scheme 6.

EXAMPLE 110

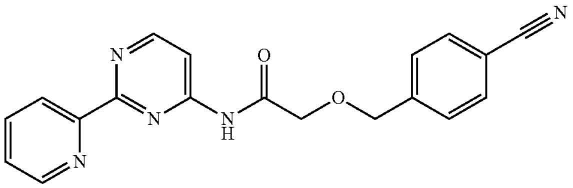

The target compound was prepared from compound 25 in Scheme 6, according to the procedure for amide synthesis described in Step B, Scheme 6.

EXAMPLE 111

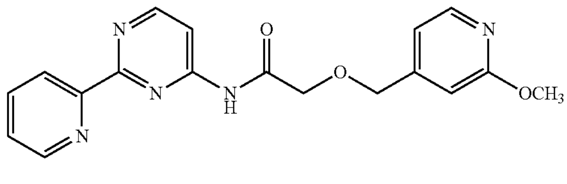

The target compound was prepared from compound 25 in Scheme 6, according to the procedure for amide synthesis described in Step B, Scheme 6.

EXAMPLE 112

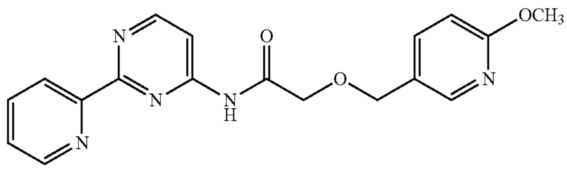

The target compound was prepared from compound 25 in Scheme 6, according to the procedure for amide synthesis described in Step B, Scheme 6.

EXAMPLE 113

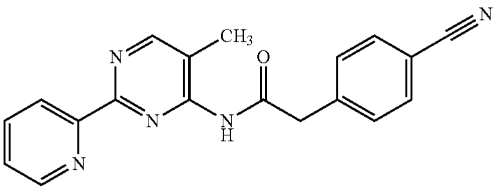

The target compound was prepared from compound 30 in Scheme 7, according to the procedure for amide synthesis described in Step E, Scheme 7.

EXAMPLE 114

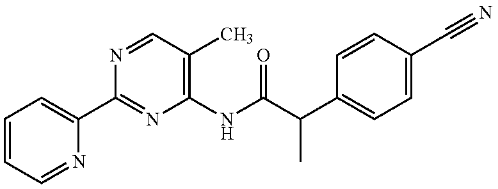

The target compound was prepared from compound 30 in Scheme 7, according to the procedure for amide synthesis described in Step E, Scheme 7.

EXAMPLE 115

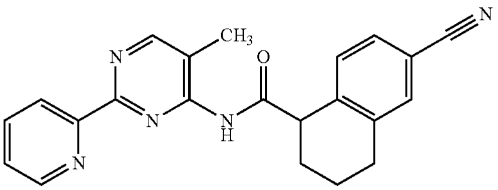

The target compound was prepared from compound 30 in Scheme 7, according to the procedure for amide synthesis described in Step E, Scheme 7.

EXAMPLE 116

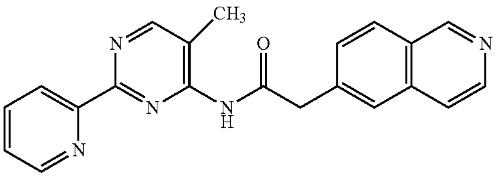

The target compound was prepared from compound 30 in Scheme 7, according to the procedure for amide synthesis described in Step E, Scheme 7.

EXAMPLE 117

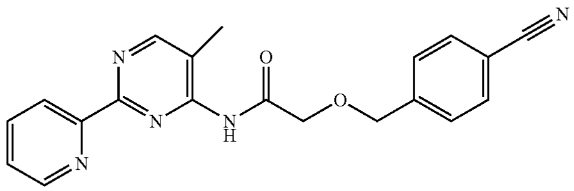

The target compound was prepared from compound 30 in Scheme 7, according to the procedure for amide synthesis described in Step E, Scheme 7.

EXAMPLE 118

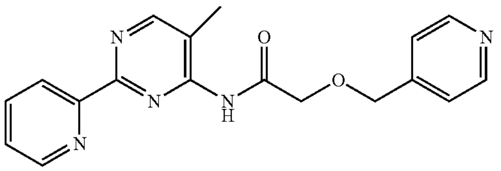

The target compound was prepared from compound 30 in Scheme 7, according to the procedure for amide synthesis described in Step E, Scheme 7.

EXAMPLE 119

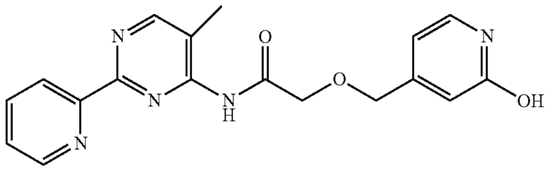

The target compound was prepared from compound 30 in Scheme 7, according to the procedure for amide synthesis described in Step E, Scheme 7.

EXAMPLE 120

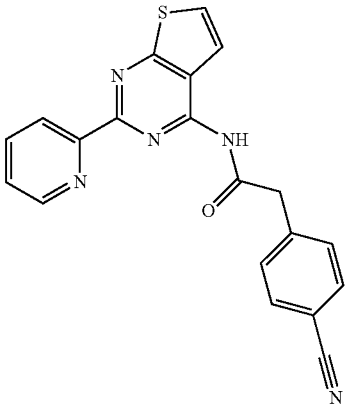

The target compound was prepared from compound 32 in Scheme 8, according to the procedure for amide synthesis described in Step C, Scheme 8.

EXAMPLE 121

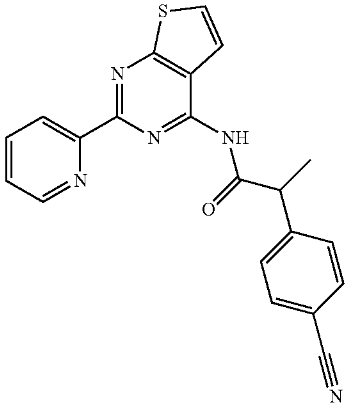

The target compound was prepared from compound 32 in Scheme 8, according to the procedure for amide synthesis described in Step C, Scheme 8.

EXAMPLE 122

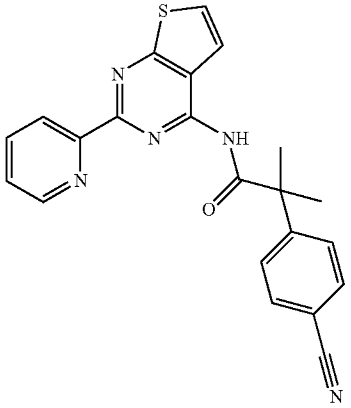

The target compound was prepared from compound 32 in Scheme 8, according to the procedure for amide synthesis described in Step C, Scheme 8.

EXAMPLE 123

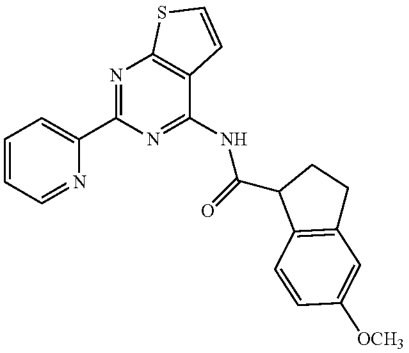

The target compound was prepared from compound 32 in Scheme 8, according to the procedure for amide synthesis described in Step C, Scheme 8.

EXAMPLE 124

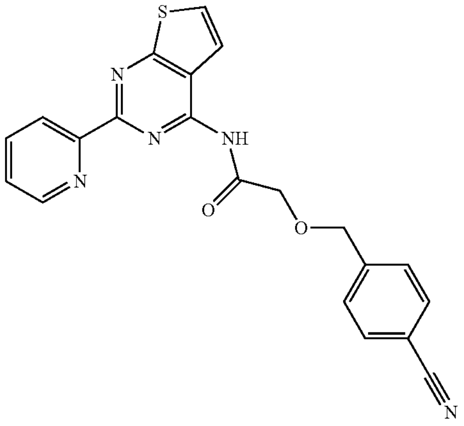

The target compound was prepared from compound 32 in Scheme 8, according to the procedure for amide synthesis described in Step C, Scheme 8.

EXAMPLE 125

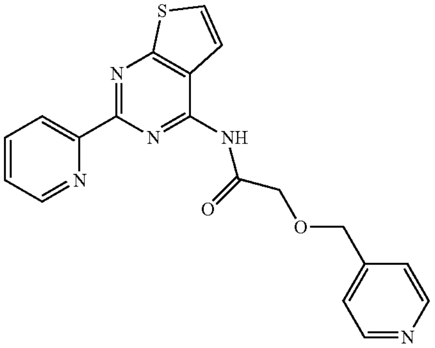

The target compound was prepared from compound 32 in Scheme 8, according to the procedure for amide synthesis described in Step C, Scheme 8.

EXAMPLE 126

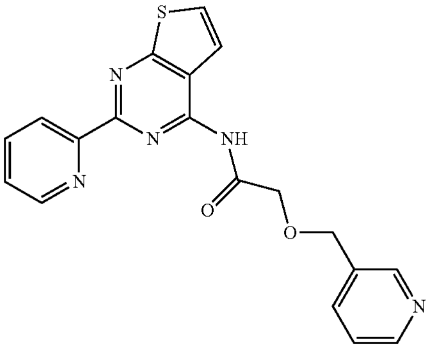

The target compound was prepared from compound 32 in Scheme 8, according to the procedure for amide synthesis described in Step C, Scheme 8.

EXAMPLE 127

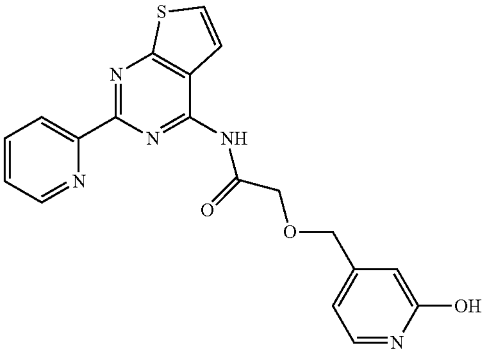

The target compound was prepared from compound 32 in Scheme 8, according to the procedure for amide synthesis described in Step C, Scheme 8.

EXAMPLE 128

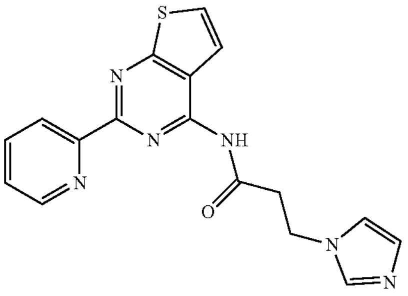

The target compound was prepared from compound 32 in Scheme 8, according to the procedure for amide synthesis described in Step C, Scheme 8.

EXAMPLE 129

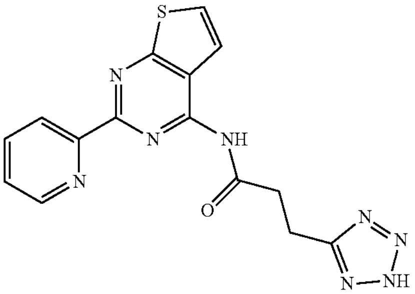

The target compound was prepared from compound 32 in Scheme 8, according to the procedure for amide synthesis described in Step C, Scheme 8.

EXAMPLE 130
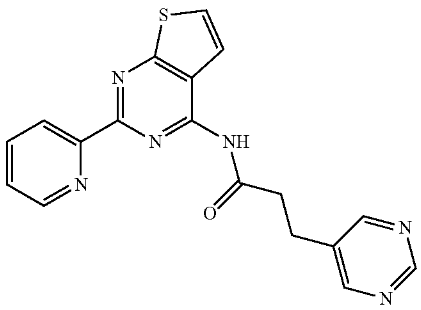
The target compound was prepared from compound 32 in Scheme 8, according to the procedure for amide synthesis described in Step C, Scheme 8.
EXAMPLE 131
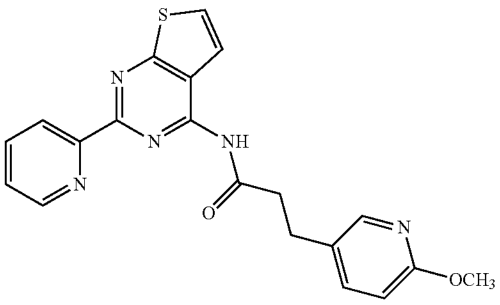
The target compound was prepared from compound 32 in Scheme 8, according to the procedure for amide synthesis described in Step C, Scheme 8.
EXAMPLE 132
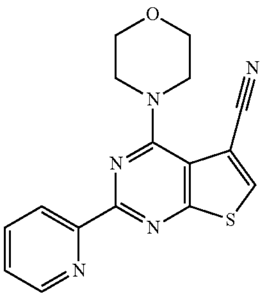
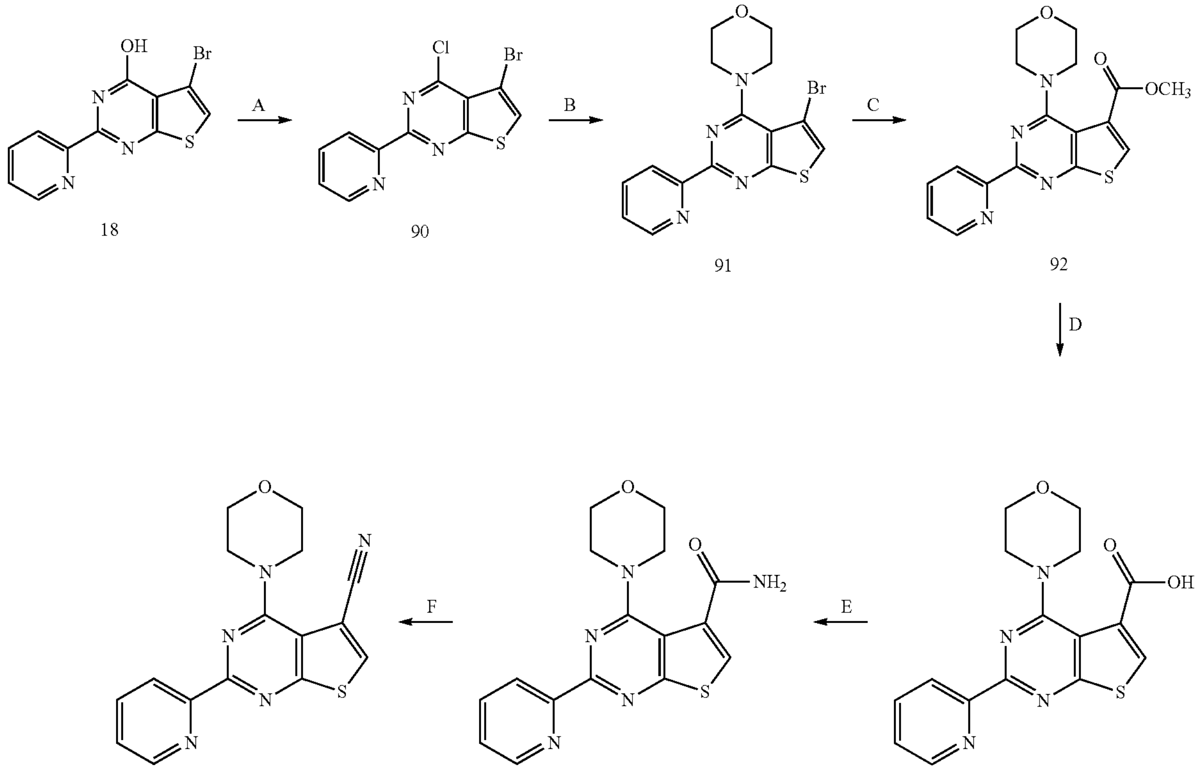
18 90 91 92 94 93

Step A: The compound 18, prepared as described in Scheme 5, (40 g, 0.13 mol, 1 eq.) and phosphoryl chloride (300 mL) were heated at reflux for 24 h. The reaction mixture was then evaporated to dryness. The crude residue was dissolved in $CH_2Cl_2$ and washed carefully with ice-water and 5% $NaHCO_3$ solution. The organic layer was dried over $Na_2SO_4$ and evaporated to dryness giving sufficiently pure compound 90 as yellowish powder (40 g, yield 95%).

Step B: To a stirred solution of 90 (10 g, 0.031 mol, 1 eq) in MeOH (100 mL), was added morpholine (8.1 g, 0.993 mol, 3 eq) and the reaction left to stir at reflux for 5 hours. The reaction mixture was diluted with water and extracted with $CHCl_3$. Organic layer was evaporated under reduced pressure to give crude product. The crude material was purified by column chromatography using $CHCl_3$:MeCN (1:4) as eluent to afford compound 91 (9.25 g, 0.024 mol, 80% yield).

Step C: The mixture of compound 91 (9 g, 0.023 mol) and 1,1'-Bis(diphenylphosphino)ferrocene]dichloropalladium (II) complex with dichloromethane CAS95464054 (2% mol) in methanol (200 ml) was stirred overnight under CO (10 bar) in autoclave. The reaction mixture was filtered and evaporated. The resulting residue was washed with water and dried. The yield of 92 was 6.55 g (0.0184 mol, 80% yield).

Step D: Compound 92 was added to a 1M solution of NaOH in methanol. The reaction mixture was heated at reflux overnight and evaporated. The solid residue was dissolved in water and acidified by 3N HCl to pH ~4-5. The precipitate being formed was filtered and washed with water and dried in vacuo to give 93.

Step E: To a solution of 93 (1 g, 2.93 mmol, 1 eq.) in DMF (10 mL) was added carbonyldiimidazole (CDI, CAS 530-62-1) (0.568 g, 3.51 mmol, 1.2 eq.). The resultant solution was stirred at room temperature for 1 h and mixed with aqueous ammonium (25%). The mixture was diluted with water and precipitate was filtered and air dried to give compound 94 as a white solid (0.9 g, 2.63 mmol, 90% yield).

Step F: Trifluoroacetic anhydride (0.46 g, 2.19 mmol, 1.5 eq.) was added via syringe to a stirring solution of compound 94 (0.5 g, 1.46 mmol, 1 eq.) and triethylamine (0.612 mL, 4.39 mmol, 3 eq.) in dichloromethane at 5° C. The cooling bath was removed, the resulting solution was warmed to room temperature and stirred for 16 hours. The mixture was concentrated in vacuo. Water was added to the residue and the product was extracted with dichloromethane (3×70 mL). The combined organic extracts were dried over sodium sulfate, filtered and concentrated to dryness. The product was purified by flash chromatography on silica to obtain the target compound as a light yellow solid (0.435 g, 1.348 mmol, 92% yield).

EXAMPLE 133

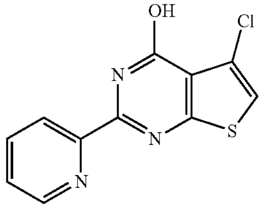

-continued

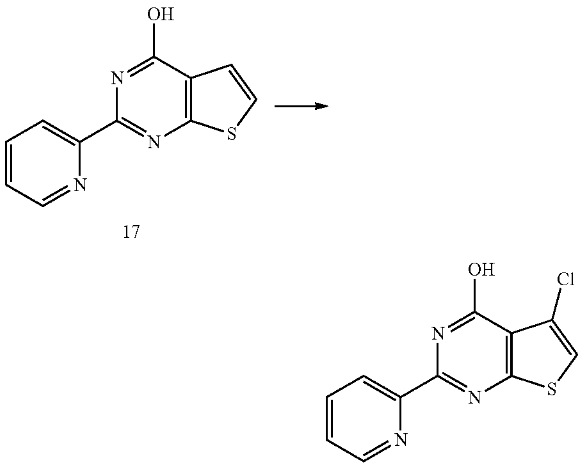

17

In a 1 L round bottom flask compound 17, prepared as described in Step A, Scheme 5 (10 g, 43.6 mmol), was taken up in acetic acid (500 mL) and NCS (6.95 g, 52.3 mmol, 1.2 eq.) was added. The reaction was heated at 60° C. for 6 hours. The reaction was then cooled to room temperature and quenched with water. The precipitate being formed was filtered and dried to give the target compound as a grey powder (9.3 g, 35.3 mmol, 81% yield).

EXAMPLE 134

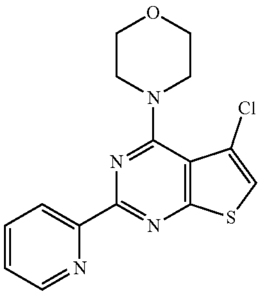

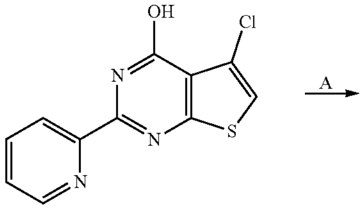

95
(Example 133)

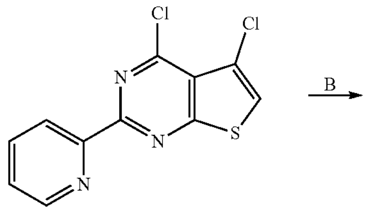

96

-continued

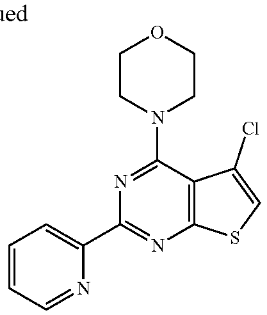

Step A: The compound 95 (Example 133) (20 g, 0.076 mol, 1 eq) and phosphoryl chloride (400 mL) were heated at reflux for 24 h. The reaction mixture was then evaporated to dryness. The crude residue was dissolved in $CH_2Cl_2$ and washed carefully with ice-water and 5% $NaHCO_3$ solution. Organic layer was dried over $Na_2SO_4$ and evaporated to dryness giving sufficiently pure compound 96 as yellowish powder (19.2 g, yield 90%).

Step C: To a stirred solution of 96 (1 g, 3.558 mol, 1 eq) in MeOH (30 mL), was added morpholine (0.93 g, 10.67 mmol, 3 eq) and the reaction left to stir at reflux for 5 hours. The reaction mixture was diluted with water and extracted with $CHCl_3$. The organic layer was evaporated under reduced pressure to give the crude product. The crude material was purified by column chromatography using $CHCl_3$:MeCN (1:4) as eluent to afford the target compound (0.896 g, 2.70 mmol, 76% yield).

EXAMPLE 135

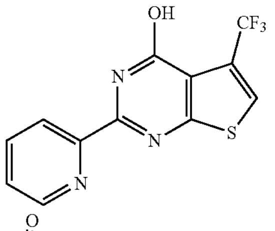

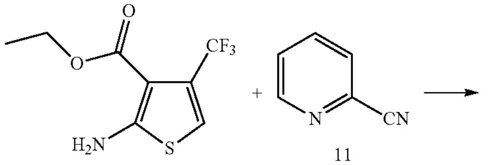

97 11

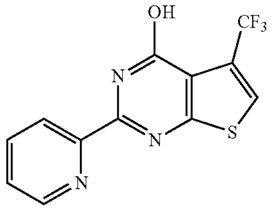

Step A: Compound 97 (10 g, 41.8 mmol, 1.0 eq) and pyridine-2-carbonitrile 11 (5.22 g, 50.16 mmol, 1.2 eq) were mixed in MeOH (150 mL). The mixture was cooled to 0° C., and sodium methoxide (6.77 g, 125.4 mmol, 3 eq) was added. The reaction mixture was stirred at reflux for 48 h, cooled to r.t, diluted with water, acidified by AcOH and extracted by EtOAc 3 times. The organic layer was evaporated under reduced pressure. Residue was purified by column chromatography to give the target compound as a light yellow solid (2.2 g, yield-17.7%).

EXAMPLE 136

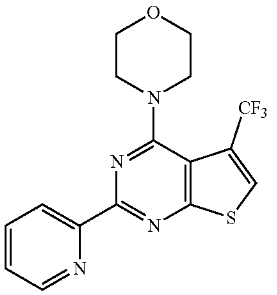

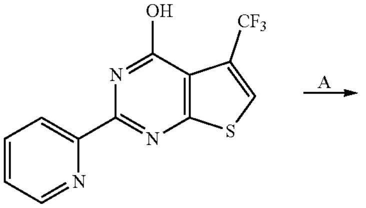

98
(Example 135)

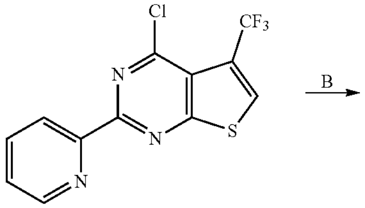

99

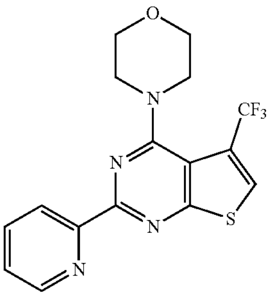

Step A: The compound 98 (Example 135) (2.0 g, 6.72 mmol, 1 eq.) and phosphoryl chloride (30 mL) were heated at reflux for 24 h. The reaction mixture was then evaporated to dryness. The crude residue was dissolved in $CH_2Cl_2$ and washed carefully with ice-water and 5% $NaHCO_3$ solution. Organic layer was dried over $Na_2SO_4$ and evaporated to dryness giving sufficiently pure compound 99 as grey powder (2.01 g, yield 95%).

Step B: To a stirred solution of compound 99 (1.5 g, 4.76 mmol) in MeOH, was added morpholine (1.24 g, 14.28 mmol, 3 eq.) and the reaction left to stir at reflux for 5 hours. The reaction mixture was diluted with water and extracted with $CHCl_3$. The organic layer was evaporated under reduced pressure to give crude product. The crude material was purified by column chromatography using $CHCl_3$: MeCN (10-30 percent) as eluent to afford the target compound as a white solid (1.25 g, yield 72%).

EXAMPLE 137

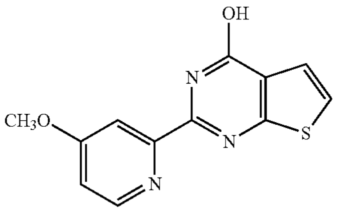

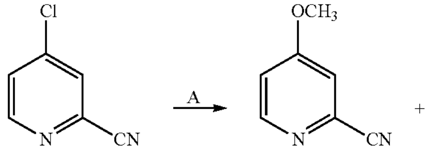

100 101

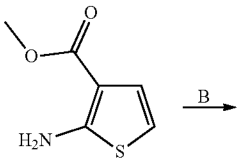

16

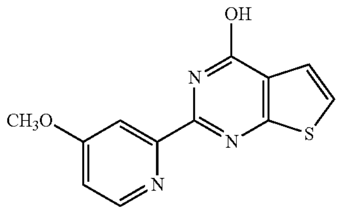

Steps A and B: Compound 100 (1,202 g, 8.68 mmol, 1.0 eq) was added to the cooled (0° C.) solution of sodium methoxide (0,516 g, 9.55 mmol, 1.1 eq) in methanol (20 mL). The reaction mixture was stirred at room temperature for 2h to give 101, then cooled to 0° C. Compound 16 (1,364 g, 8.68 mmol, 1.0 eq) and sodium methoxide (0,516 g, 9.55 mmol, 1.1 eq) were added to the resulting mixture at 0° C. The reaction mixture was stirred at reflux for 16-18h (monitored by TCL), cooled and concentrated in vacuo. The residue was diluted with water (30 mL), acidified by 5% HCl to pH=7 and extracted with $CH_2Cl_2$ (2×50 mL). The organic layer was washed with water, saturated sodium chloride, dried over $Na_2SO_4$, filtered and concentrated in vacuo. The solids were triturated with MTBE to give the target compound (1.1 g, 49% yield).

EXAMPLE 138

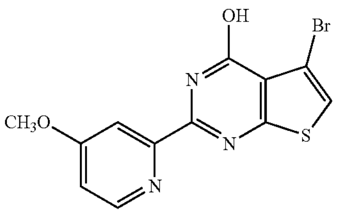

-continued

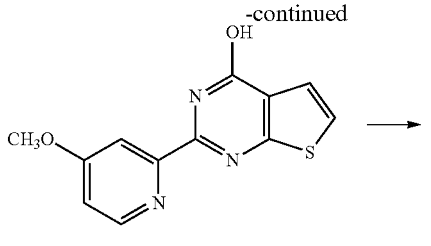

102
(Example 137)

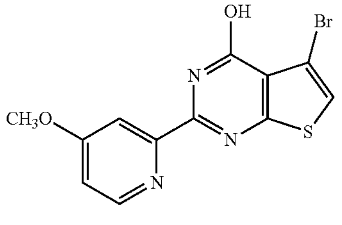

The compound 102 (Example 137) (1.38 g, 5.32 mmol) and NaOAc (0.873 g, 10.64 mmol) were dissolved in acetic acid (10 mL). To this mixture $Br_2$ (0.936 g, 5.86 mmol) was added. The resulting mixture was stirred at 80° C. for 16-18 h. Then the reaction mixture was cooled and evaporated to dryness. The residue was precipitated by water (50 mL), filtered, washed sequentially with isopropyl alcohol, hexanes and dried in vacuo to give 1.2 g of the target compound as a yellowish powder (67% yield).

EXAMPLE 139

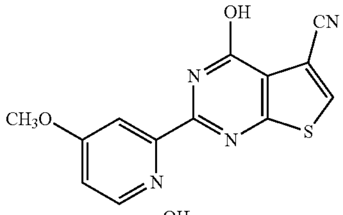

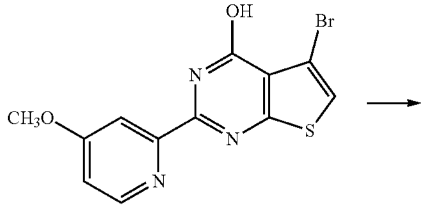

103
(Example 138)

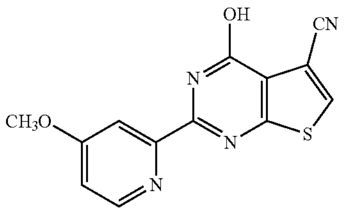

The mixture of 103 (Example 138) (0.3 g, 0.88 mmol) and CuCN (0.236 g, 2.64 mmol) was stirred at 150° C. for 3 h. The reaction mixture was cooled to room temperature, diluted with aqueous ammonia solution 25% (20 mL) and extracted with $CH_2Cl_2$ (2×50 mL). The organic layer was washed with water, dried over $Na_2SO_4$ and evaporated to dryness. The residue was purified by HPLC to give the target compound (11 mg, 67% yield).

EXAMPLE 140

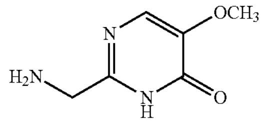

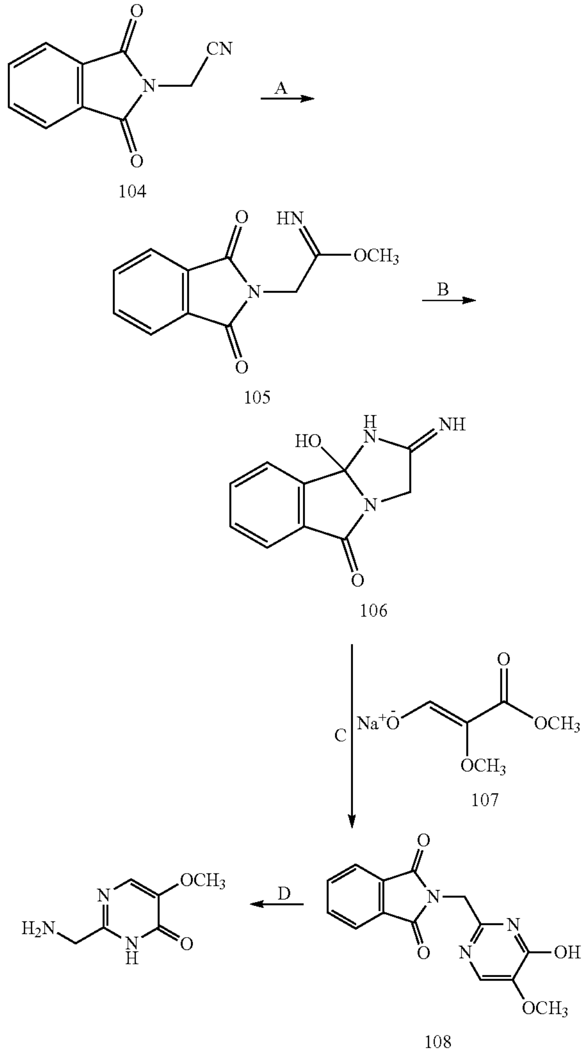

Step A: 1,3-Dioxo-1,3dihydro-isoindol-2-yl)-acetonitrile 104 (20 g, 106.8 mmol) was dissolved in 4N HCl in dioxane (200 mL). The mixture was stirred at room temperature, and MeOH (20 mL) was added. The solution turned cloudy shortly. The precipitate was collected and washed with ether to provide 18 g (66%) of 105.

Step B: A suspension of 105 (18 g, 70.7 mmol) in MeOH (270 mL) was added to a saturated $NH_3$/MeOH solution. The mixture was stirred at 0° C. and then was allowed to warm to room temperature. After all the volatiles were removed, the product 106 was used in the next step without further purification.

Step C: Compound 106 (16.95 g, 70.7 mmol) and the sodium salt of 3-hydroxy-2-methoxy-acrylic acid methyl ester 107 (13.07 g, 84.84 mmol) were mixed in MeOH (500 mL) and stirred at room temperature for 2 h, and then heated at reflux overnight. The crude mixture was filtered. After the filtrate was concentrated, the resulting residue was purified by column chromatography affording 1 g (5% yield) of 108.

Step D: Hydrazine (4 mL) was added to a suspension of 108 (0.5 g, 1.75 mmol) in EtOH (15 mL), and the mixture was stirred. The completion of reaction was monitored by TCL. The precipitate was filtered and the filtrate was purified by column chromatography to afford 10 mg (4% yield) of the target compound.

EXAMPLE 141

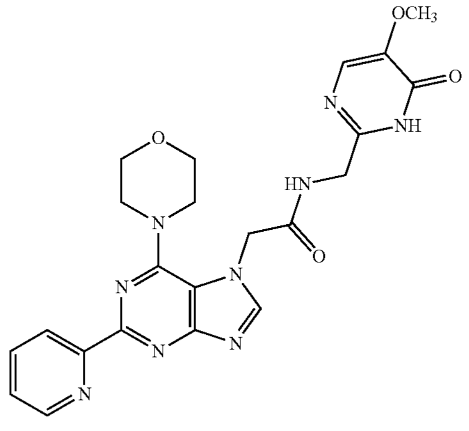

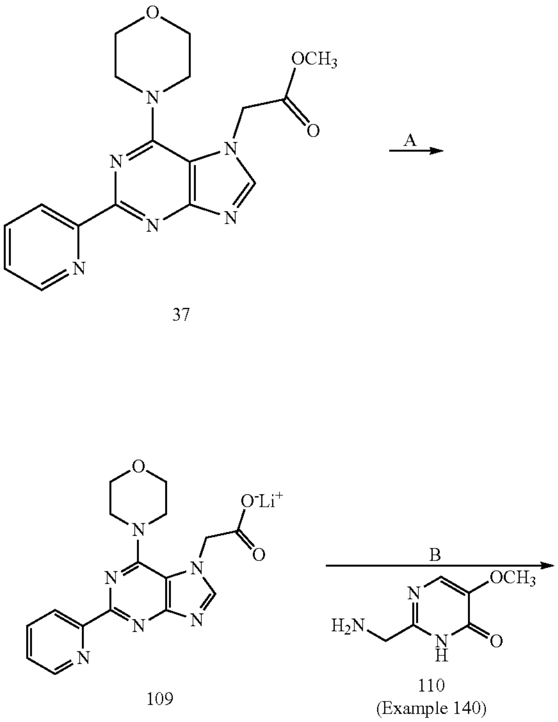

-continued

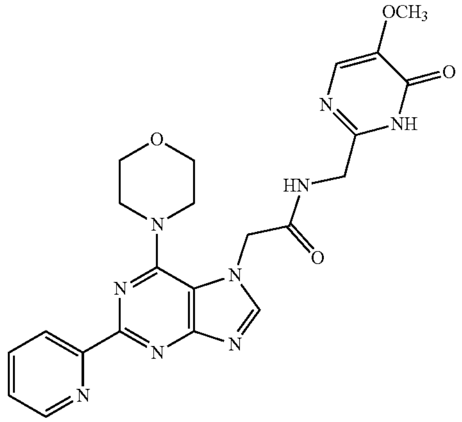

Step A: Lithium hydroxide (0.025 g, 0.6 mmol) was added to a solution of 37, prepared as described in Scheme 9 (0.14 g, 0.4 mmol) in THF/water (1:1, 20 mL). The reaction mixture was allowed to stir at room temperature overnight. The reaction mixture was concentrated and residue, compound 109, was directly used in the next step without further purification.

Step B: HATU (CAS [148893-10-1], 0.168 g, 0.44 mmol, 0.1 eq.), DIPEA and compound 110 (Example 140) were added sequentially to a solution of the lithium salt 109 (0.139 g, 0.4 mmol) in DMF (20 mL). The reaction mixture was allowed to stir at room temperature overnight. The reaction mixture was concentrated in vacuo. The residue was purified by HPLC affording the target compound (0.01 g, 5% yield).

EXAMPLE 142

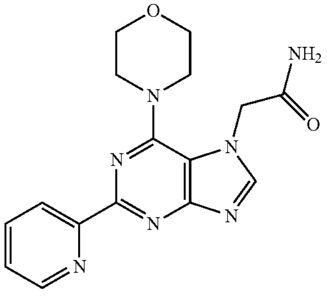

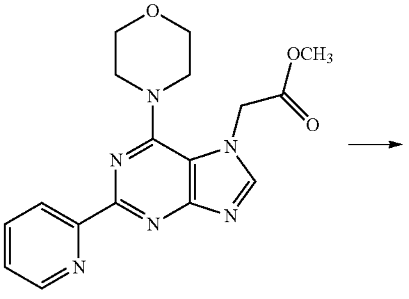

37

-continued

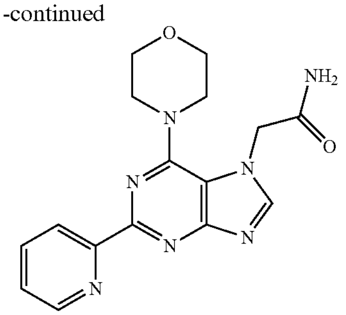

A suspension of 37, prepared as described in Step C, Scheme 9 (0.07 g, 0.2 mmol) in MeOH (5 mL) was added to a saturated $NH_3$/MeOH solution. The mixture was stirred 12h at room temperature. The precipitate was collected and washed with ether to provide 0.01 g (15% yield) of the target compound.

EXAMPLE 143

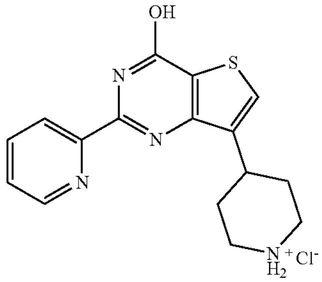

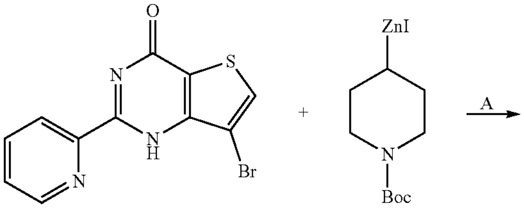

13 111

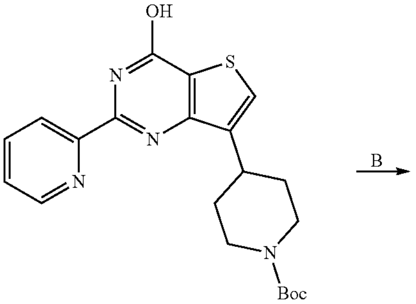

112

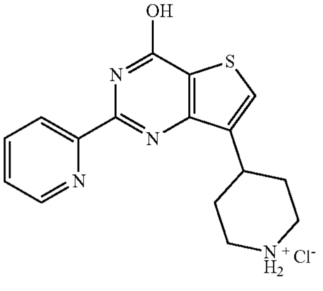

Step A: Into a 500 mL flask were charged 13 (1 g, 3.25 mmol, 1 eq.), [1,1' bis(diphenylphosphino)-ferrocene]dichloropalladium(II)-dichloromethane complex (0.132 g, 0.16 mmol, 0.05 eq.), cuprous iodide (0.061 g, 0.32 mmol, 0.1 eq.), and THF (50 mL). The resulting mixture was degassed with alternating vacuum/nitrogen purges. The filtered 4-piperidylzinc iodide solution 111 (9.75 mmol, prepared as described in *J. Org. Chem.* 2004, 69, 5120-5123) was then added. The mixture was degassed one more time and then heated at reflux for 24 h. The reaction mixture was then cooled to 20° C. and treated with MTBE (methyl tert-butyl ether, 130 mL) and 1 N ammonium chloride (130 mL). The mixture was stirred at 20-30° C. for 30 min and then filtered. The lower aqueous layer was drawn off, and the remaining organic layer was treated with saturated aqueous $NH_4Cl$ (50 mL) and stirred for 30 min. After settling, the lower aqueous layer was removed and the organic layer was collected. The resulting organic solution was then filtered through a small pad of $SiO_2$. The $SiO_2$ pad was washed with MTBE (25 mL). The solvent was evaporated, and the residue was purified by HPLC (0.202 g, 0.49 mmol, 15% yield of 112).

Step B: The mixture of 112 (0.1 g, 0.243 mmol) and 6N aqueous HCl (5 ml) was stirred at 50° C. for 5 h. The resulting solution was evaporated to dryness. The residue was triturated with dioxane and dried in vacuo to give the target compound. The yield was 80% (0.84 g, 0.242 mmol).

EXAMPLE 144

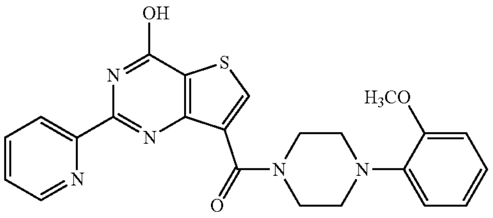

The target compound was prepared from compound 15 in Scheme 3, according to the general procedure for amide synthesis described in Step E, Scheme 3.

EXAMPLE 145

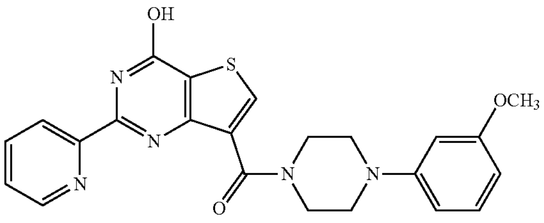

The target compound was prepared from compound 15 in Scheme 3, according to the general procedure for amide synthesis described in Step E, Scheme 3.

EXAMPLE 146

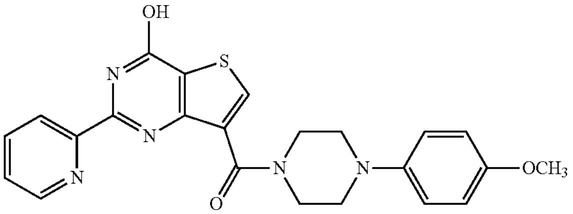

The target compound was prepared from compound 15 in Scheme 3, according to the general procedure for amide synthesis described in Step E, Scheme 3.

EXAMPLE 147

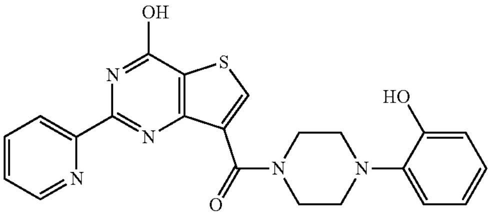

The target compound was prepared from compound 15 in Scheme 3, according to the general procedure for amide synthesis described in Step E, Scheme 3.

EXAMPLE 148

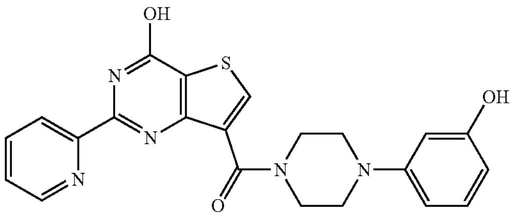

The target compound was prepared from compound 15 in Scheme 3, according to the general procedure for amide synthesis described in Step E, Scheme 3.

EXAMPLE 149

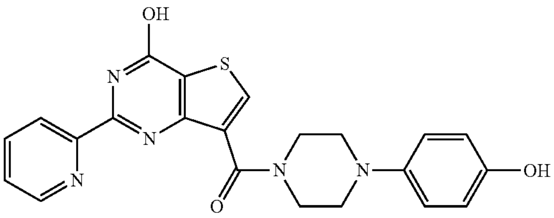

The target compound was prepared from compound 15 in Scheme 3, according to the general procedure for amide synthesis described in Step E, Scheme 3.

EXAMPLE 150

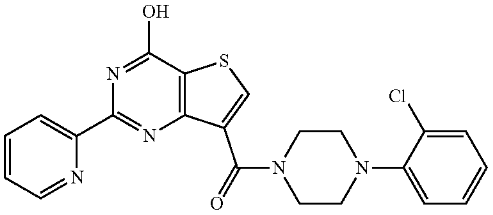

The target compound was prepared from compound 15 in Scheme 3, according to the general procedure for amide synthesis described in Step E, Scheme 3.

EXAMPLE 151

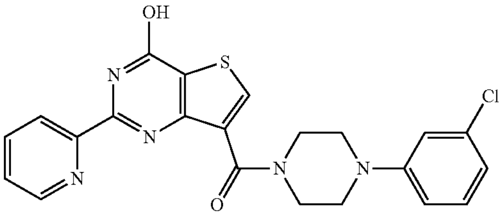

The target compound was prepared from compound 15 in Scheme 3, according to the general procedure for amide synthesis described in Step E, Scheme 3.

EXAMPLE 152

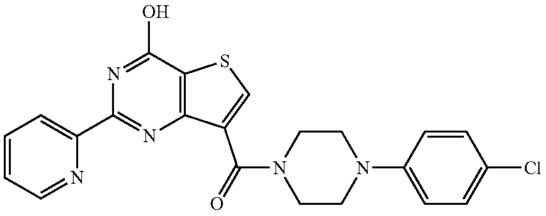

The target compound was prepared from compound 15 in Scheme 3, according to the general procedure for amide synthesis described in Step E, Scheme 3.

EXAMPLE 153

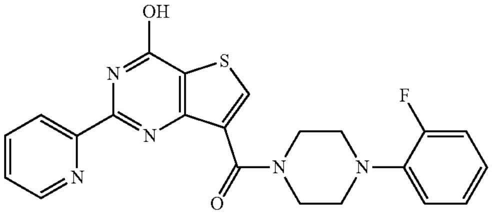

The target compound was prepared from compound 15 in Scheme 3, according to the general procedure for amide synthesis described in Step E, Scheme 3.

EXAMPLE 154

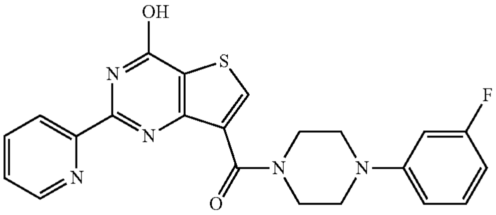

The target compound was prepared from compound 15 in Scheme 3, according to the general procedure for amide synthesis described in Step E, Scheme 3.

EXAMPLE 155

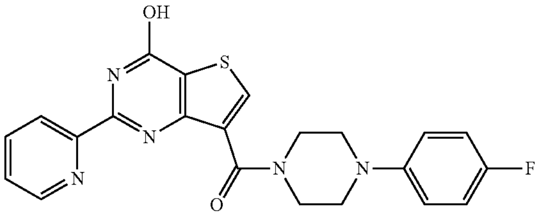

The target compound was prepared from compound 15 in Scheme 3, according to the general procedure for amide synthesis described in Step E, Scheme 3.

EXAMPLE 156

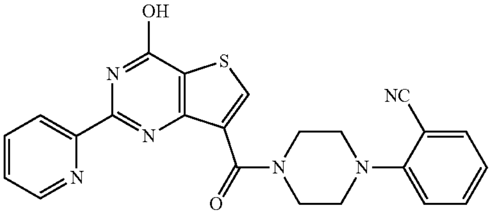

The target compound was prepared from compound 15 in Scheme 3, according to the general procedure for amide synthesis described in Step E, Scheme 3.

EXAMPLE 157

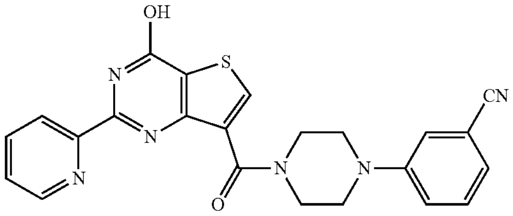

The target compound was prepared from compound 15 in Scheme 3, according to the general procedure for amide synthesis described in Step E, Scheme 3.

EXAMPLE 158

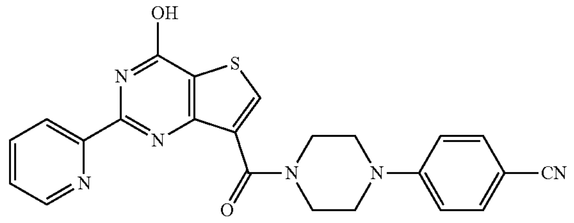

The target compound was prepared from compound 15 in Scheme 3, according to the general procedure for amide synthesis described in Step E, Scheme 3.

EXAMPLE 159

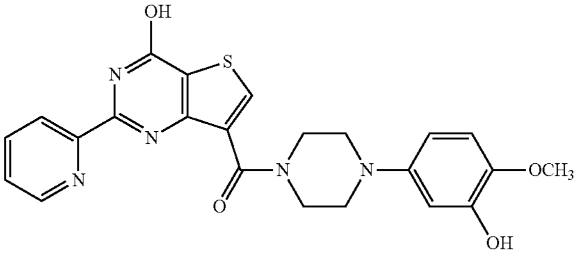

The target compound was prepared from compound 15 in Scheme 3, according to the general procedure for amide synthesis described in Step E, Scheme 3.

EXAMPLE 160

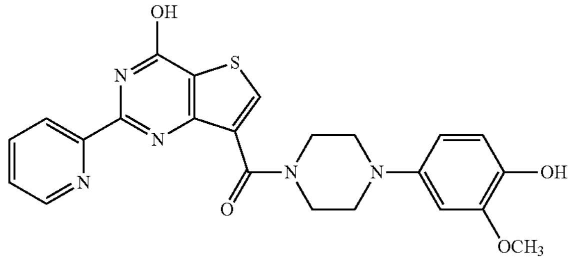

The target compound was prepared from compound 15 in Scheme 3, according to the general procedure for amide synthesis described in Step E, Scheme 3.

EXAMPLE 161

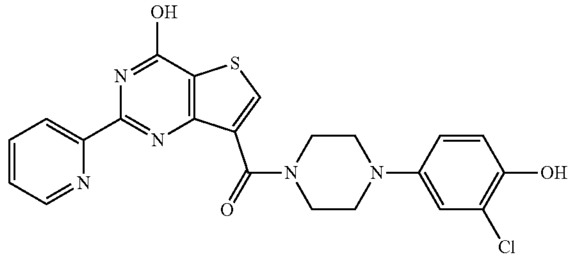

The target compound was prepared from compound 15 in Scheme 3, according to the general procedure for amide synthesis described in Step E, Scheme 3.

EXAMPLE 162

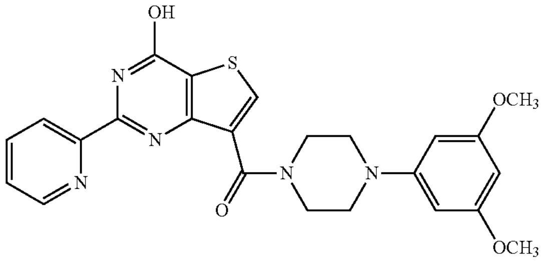

The target compound was prepared from compound 15 in Scheme 3, according to the general procedure for amide synthesis described in Step E, Scheme 3.

EXAMPLE 163

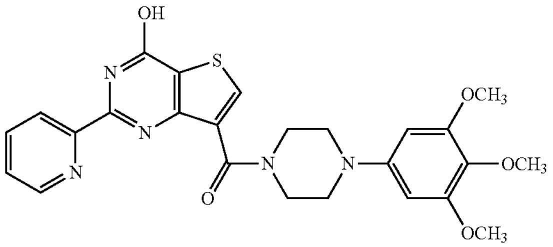

The target compound was prepared from compound 15 in Scheme 3, according to the general procedure for amide synthesis described in Step E, Scheme 3.

EXAMPLE 164

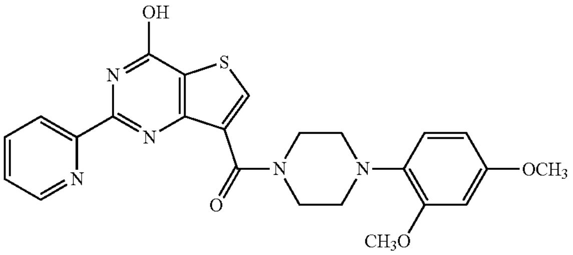

The target compound was prepared from compound 15 in Scheme 3, according to the general procedure for amide synthesis described in Step E, Scheme 3.

EXAMPLE 165

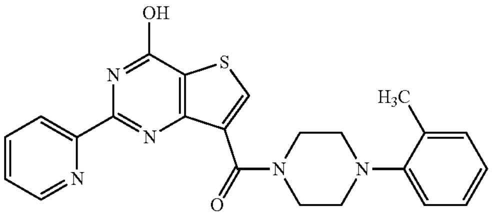

The target compound was prepared from compound 15 in Scheme 3, according to the general procedure for amide synthesis described in Step E, Scheme 3.

EXAMPLE 166

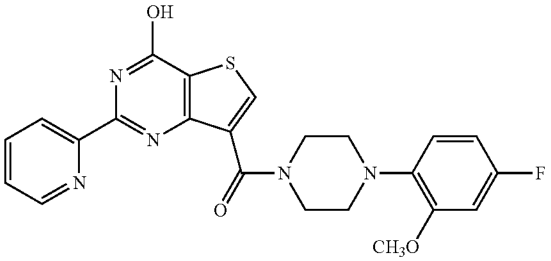

The target compound was prepared from compound 15 in Scheme 3, according to the general procedure for amide synthesis described in Step E, Scheme 3.

EXAMPLE 167

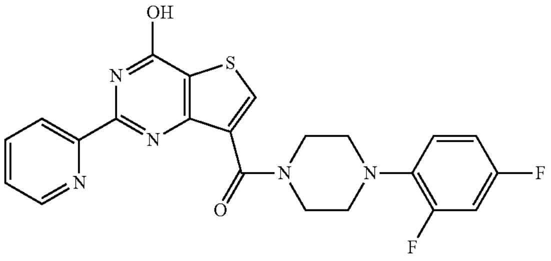

The target compound was prepared from compound 15 in Scheme 3, according to the general procedure for amide synthesis described in Step E, Scheme 3.

EXAMPLE 168

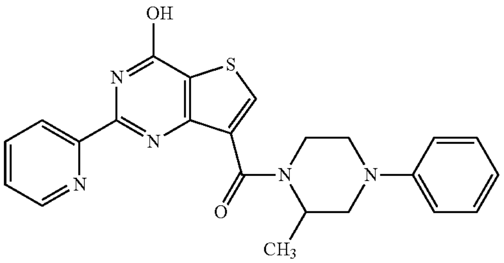

The target compound was prepared from compound 15 in Scheme 3, according to the general procedure for amide synthesis described in Step E, Scheme 3.

EXAMPLE 169

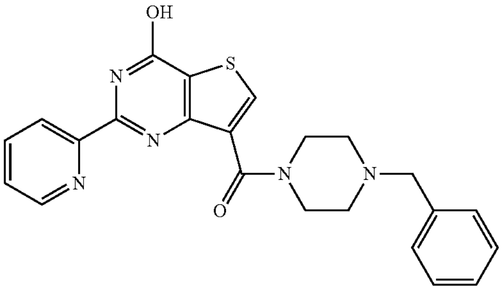

The target compound was prepared from compound 15 in Scheme 3, according to the general procedure for amide synthesis described in Step E, Scheme 3.

EXAMPLE 170

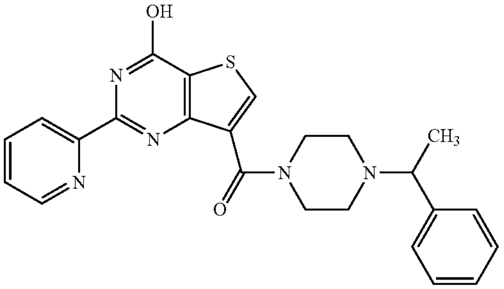

The target compound was prepared from compound 15 in Scheme 3, according to the general procedure for amide synthesis described in Step E, Scheme 3.

EXAMPLE 171

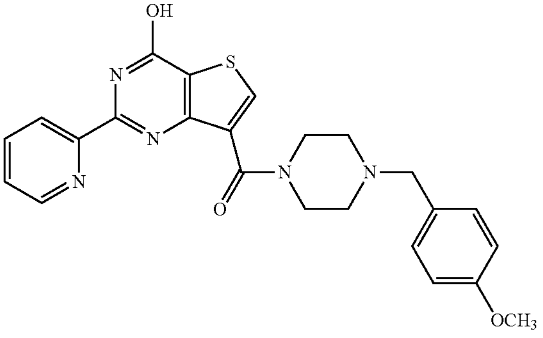

The target compound was prepared from compound 15 in Scheme 3, according to the general procedure for amide synthesis described in Step E, Scheme 3.

EXAMPLE 172

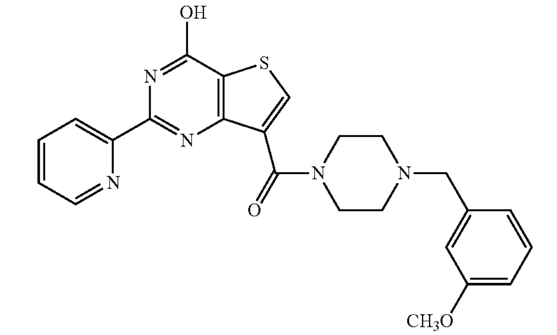

The target compound was prepared from compound 15 in Scheme 3, according to the general procedure for amide synthesis described in Step E, Scheme 3.

EXAMPLE 173

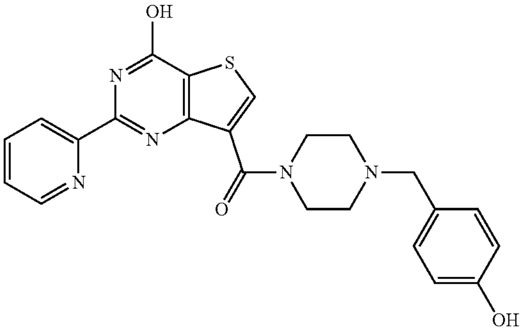

The target compound was prepared from compound 15 in Scheme 3, according to the general procedure for amide synthesis described in Step E, Scheme 3.

EXAMPLE 174

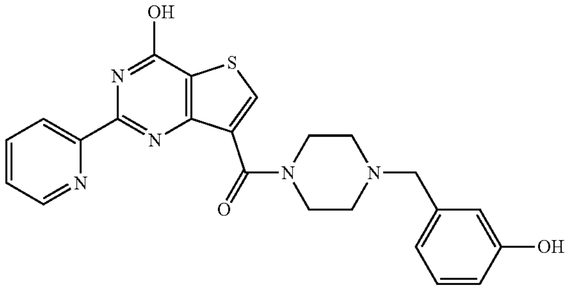

The target compound was prepared from compound 15 in Scheme 3, according to the general procedure for amide synthesis described in Step E, Scheme 3.

EXAMPLE 175

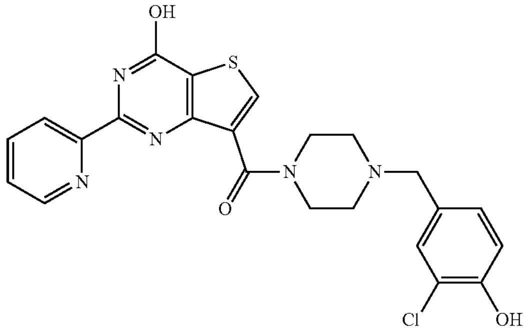

The target compound was prepared from compound 15 in Scheme 3, according to the general procedure for amide synthesis described in Step E, Scheme 3.

EXAMPLE 176

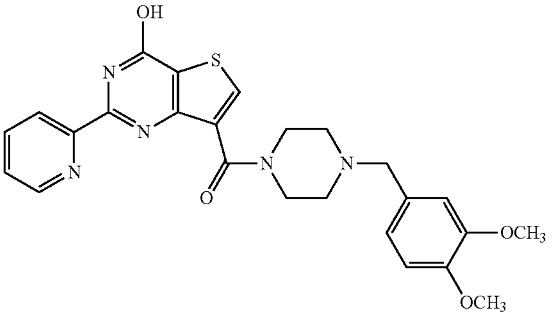

The target compound was prepared from compound 15 in Scheme 3, according to the general procedure for amide synthesis described in Step E, Scheme 3.

EXAMPLE 177

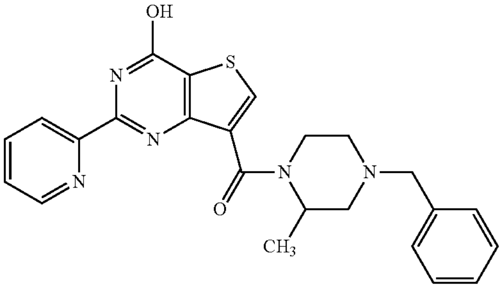

The target compound was prepared from compound 15 in Scheme 3, according to the general procedure for amide synthesis described in Step E, Scheme 3.

EXAMPLE 178

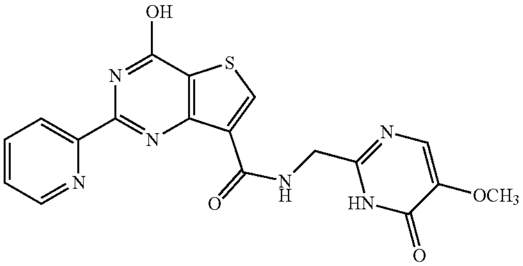

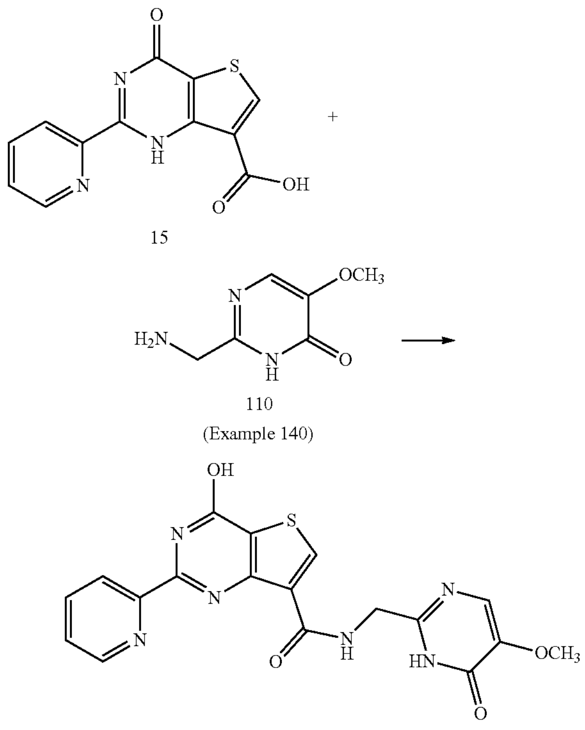

15

110

(Example 140)

The target compound was prepared from compound 15 in Scheme 3, according to the general procedure for amide synthesis described in Step E, Scheme 3, and using amine 110 (Example 140).

EXAMPLE 179

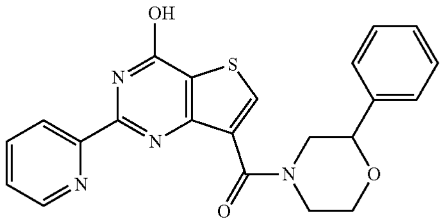

The target compound was prepared from compound 15 in Scheme 3, according to the general procedure for amide synthesis described in Step E, Scheme 3.

EXAMPLE 180

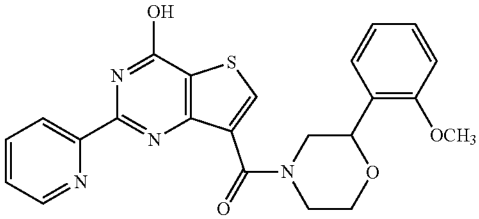

The target compound was prepared from compound 15 in Scheme 3, according to the general procedure for amide synthesis described in Step E, Scheme 3.

EXAMPLE 181

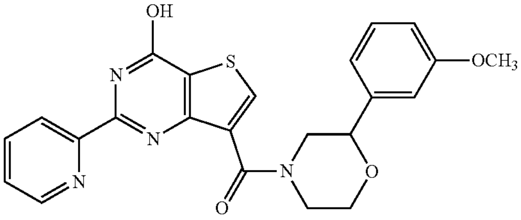

The target compound was prepared from compound 15 in Scheme 3, according to the general procedure for amide synthesis described in Step E, Scheme 3.

EXAMPLE 182

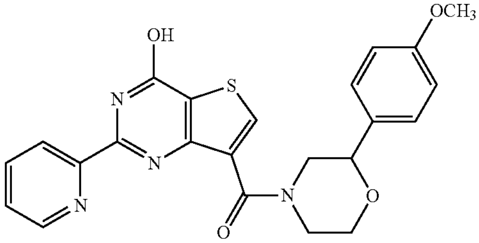

The target compound was prepared from compound 15 in Scheme 3, according to the general procedure for amide synthesis described in Step E, Scheme 3.

EXAMPLE 184

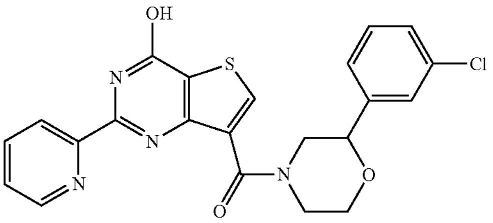

The target compound was prepared from compound 15 in Scheme 3, according to the general procedure for amide synthesis described in Step E, Scheme 3.

EXAMPLE 185

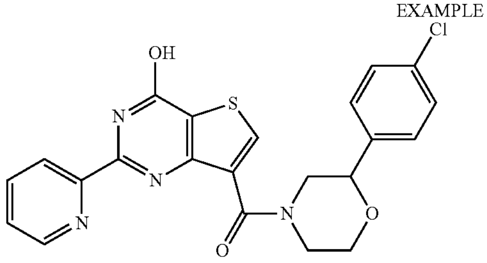

The target compound was prepared from compound 15 in Scheme 3, according to the general procedure for amide synthesis described in Step E, Scheme 3.

EXAMPLE 185

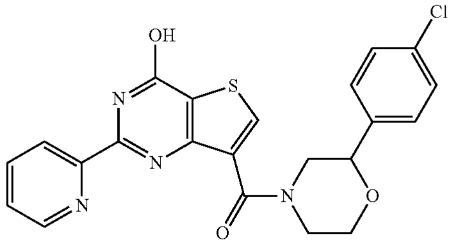

The target compound was prepared from compound 15 in Scheme 3, according to the general procedure for amide synthesis described in Step E, Scheme 3.

EXAMPLE 186

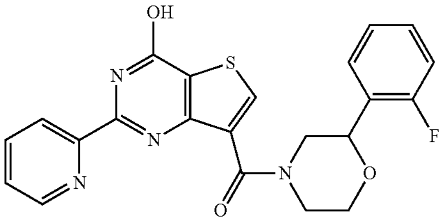

The target compound was prepared from compound 15 in Scheme 3, according to the general procedure for amide synthesis described in Step E, Scheme 3.

EXAMPLE 187

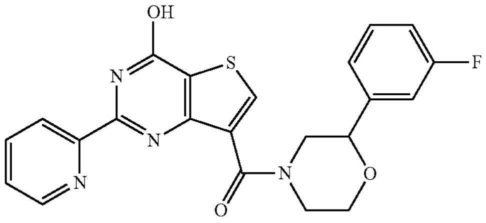

The target compound was prepared from compound 15 in Scheme 3, according to the general procedure for amide synthesis described in Step E, Scheme 3.

EXAMPLE 188

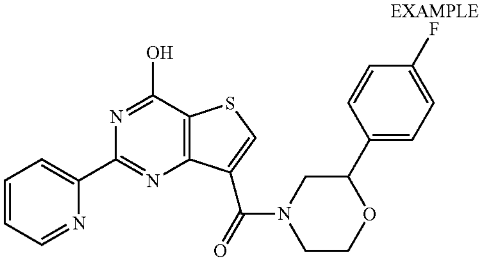

The target compound was prepared from compound 15 in Scheme 3, according to the general procedure for amide synthesis described in Step E, Scheme 3.

EXAMPLE 189

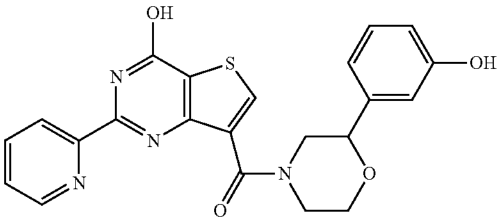

The target compound was prepared from compound 15 in Scheme 3, according to the general procedure for amide synthesis described in Step E, Scheme 3.

EXAMPLE 190

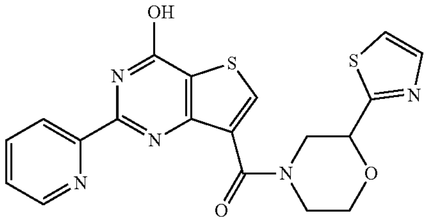

The target compound was prepared from compound 15 in Scheme 3, according to the general procedure for amide synthesis described in Step E, Scheme 3.

EXAMPLE 191

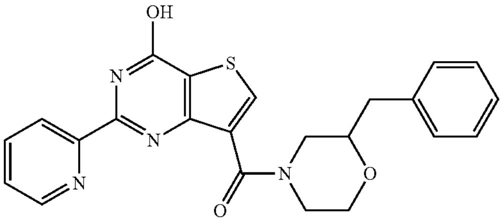

The target compound was prepared from compound 15 in Scheme 3, according to the general procedure for amide synthesis described in Step E, Scheme 3.

EXAMPLE 192

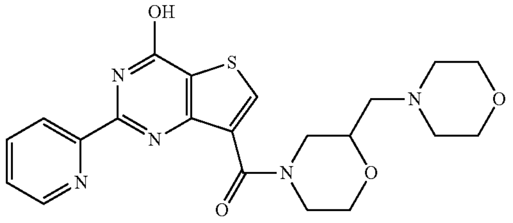

The target compound was prepared from compound 15 in Scheme 3, according to the general procedure for amide synthesis described in Step E, Scheme 3.

EXAMPLE 193

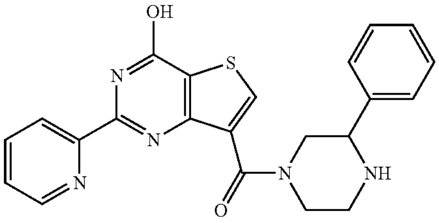

The target compound was prepared from compound 15 in Scheme 3, according to the general procedure for amide synthesis described in Step E, Scheme 3.

EXAMPLE 194

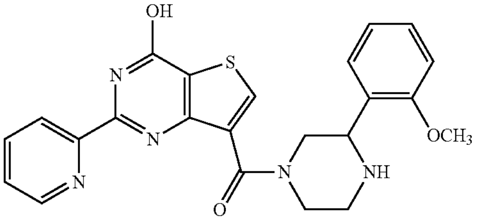

The target compound was prepared from compound 15 in Scheme 3, according to the general procedure for amide synthesis described in Step E, Scheme 3.

EXAMPLE 195

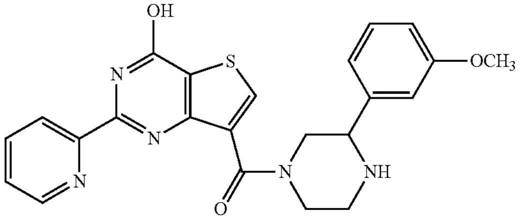

The target compound was prepared from compound 15 in Scheme 3, according to the general procedure for amide synthesis described in Step E, Scheme 3.

EXAMPLE 196

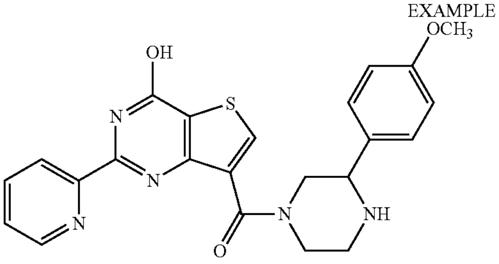

The target compound was prepared from compound 15 in Scheme 3, according to the general procedure for amide synthesis described in Step E, Scheme 3.

EXAMPLE 197

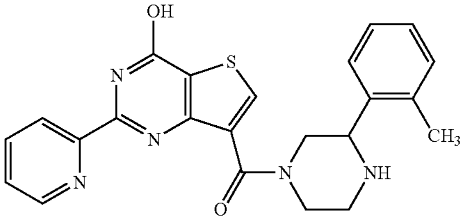

The target compound was prepared from compound 15 in Scheme 3, according to the general procedure for amide synthesis described in Step E, Scheme 3.

EXAMPLE 198

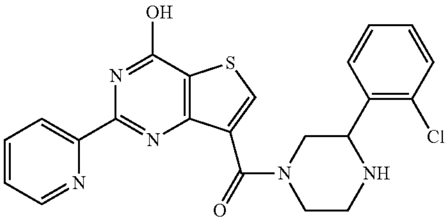

The target compound was prepared from compound 15 in Scheme 3, according to the general procedure for amide synthesis described in Step E, Scheme 3.

EXAMPLE 199

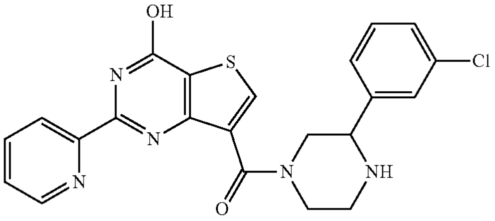

The target compound was prepared from compound 15 in Scheme 3, according to the general procedure for amide synthesis described in Step E, Scheme 3.

EXAMPLE 200

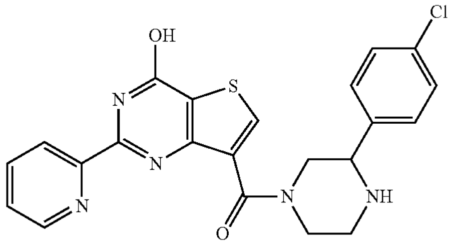

The target compound was prepared from compound 15 in Scheme 3, according to the general procedure for amide synthesis described in Step E, Scheme 3.

EXAMPLE 201

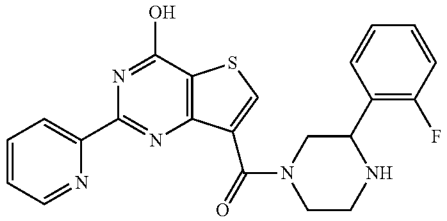

The target compound was prepared from compound 15 in Scheme 3, according to the general procedure for amide synthesis described in Step E, Scheme 3.

EXMAPLE 202

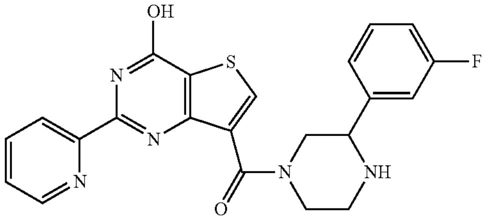

The target compound was prepared from compound 15 in Scheme 3, according to the general procedure for amide synthesis described in Step E, Scheme 3.

EXAMPLE 203

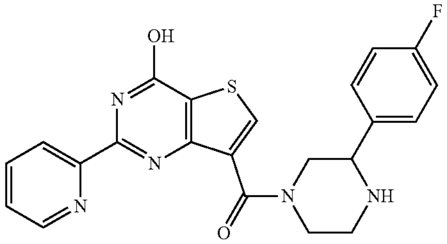

The target compound was prepared from compound 15 in Scheme 3, according to the general procedure for amide synthesis described in Step E, Scheme 3.

EXAMPLE 204

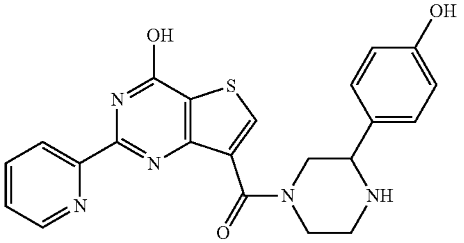

The target compound was prepared from compound 15 in Scheme 3, according to the general procedure for amide synthesis described in Step E, Scheme 3.

EXAMPLE 205

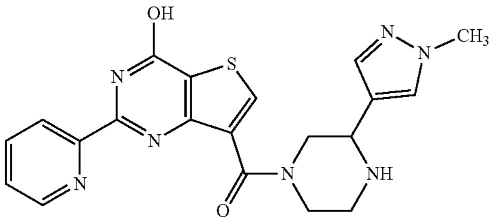

The target compound was prepared from compound 15 in Scheme 3, according to the general procedure for amide synthesis described in Step E, Scheme 3.

EXAMPLE 206

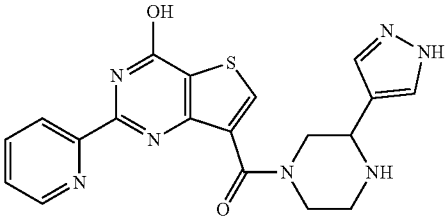

The target compound was prepared from compound 15 in Scheme 3, according to the general procedure for amide synthesis described in Step E, Scheme 3.

EXAMPLE 207

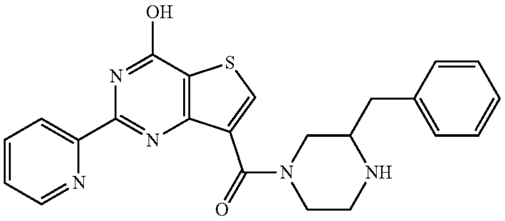

The target compound was prepared from compound 15 in Scheme 3, according to the general procedure for amide synthesis described in Step E, Scheme 3.

EXAMPLE 208

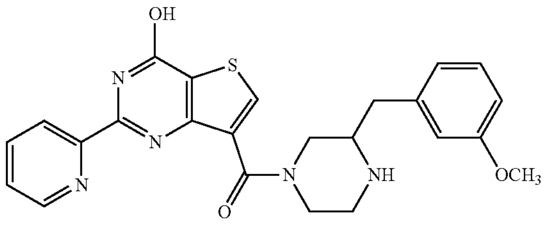

The target compound was prepared from compound 15 in Scheme 3, according to the general procedure for amide synthesis described in Step E, Scheme 3.

EXAMPLE 209

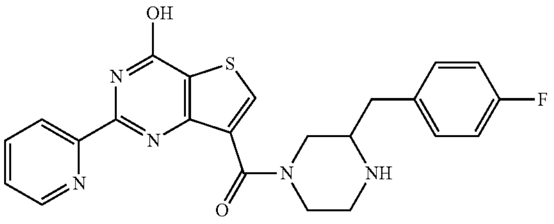

The target compound was prepared from compound 15 in Scheme 3, according to the general procedure for amide synthesis described in Step E, Scheme 3.

EXAMPLE 210

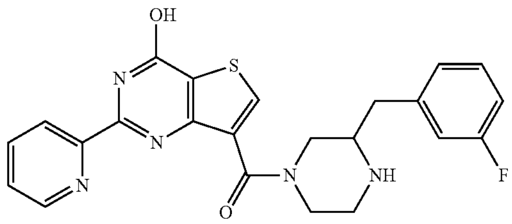

The target compound was prepared from compound 15 in Scheme 3, according to the general procedure for amide synthesis described in Step E, Scheme 3.

EXAMPLE 211

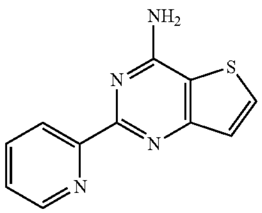

-continued

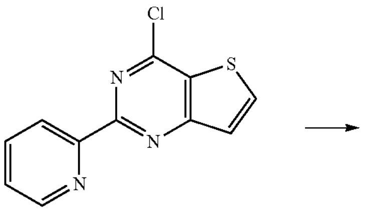

45

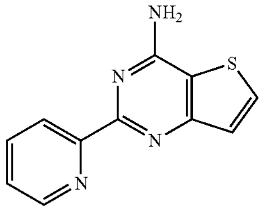

The target compound was prepared from compound 45, synthesized as described in Step E, Scheme 10, using a procedure analogous to Step B, Scheme 8 for the preparation of compound 32.

EXAMPLE 212

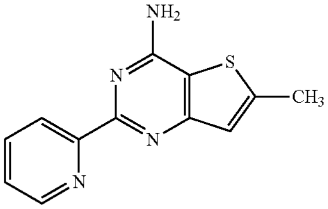

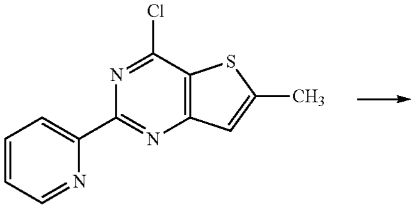

46

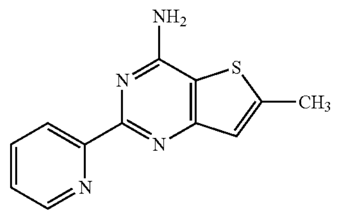

The target compound was prepared from compound 46, prepared as described in Step E, Scheme 10, using a procedure analogous to Step B, Scheme 8 for the preparation of compound 32.

EXAMPLE 213

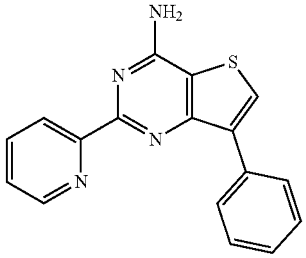

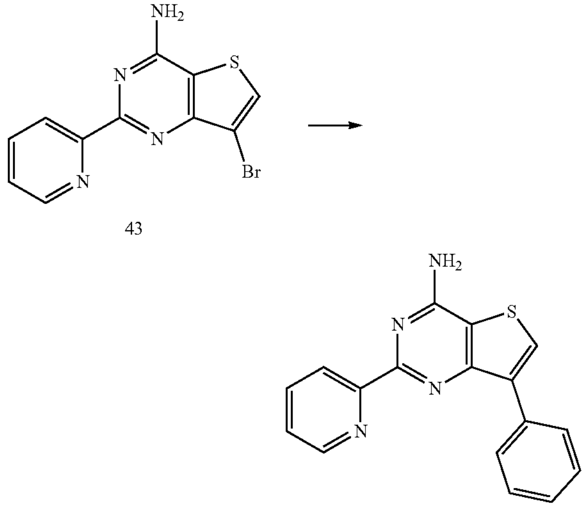

43

Reactions were conducted on a 100 mg scale. Compound 43, prepared as described in Scheme 10, Step D (1 eq.), aryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. The organic layer was evaporated and dried in vacuo. The residue was purified by HPLC to afford the title compounds (Yields: 30-40%).

EXAMPLE 214

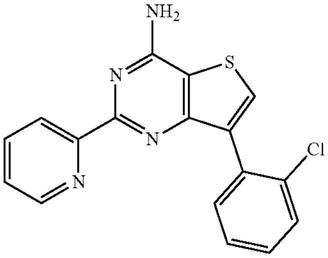

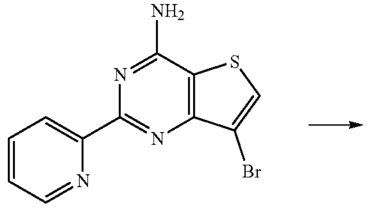

43

-continued

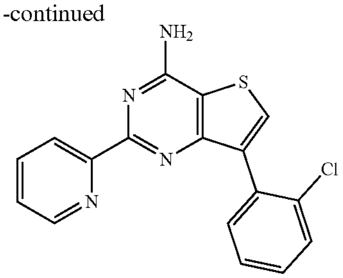

Reactions were conducted on a 100 mg scale. Compound 43, prepared as described in Scheme 10, Step D (1 eq.), aryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. The organic layer was evaporated and dried in vacuo. The residue was purified by HPLC to afford the title compounds (Yields: 30-40%).

EXAMPLE 215

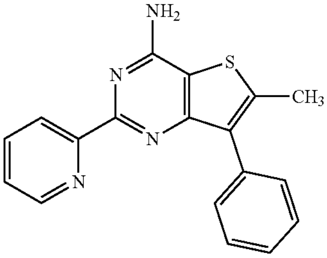

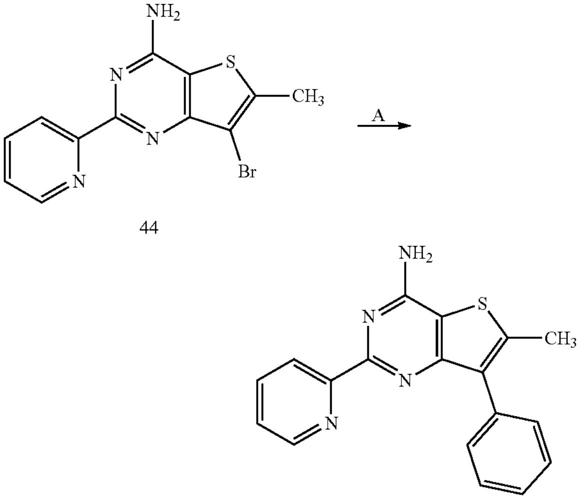

44

Reactions were conducted on a 100 mg scale. Compound 44, prepared as described in Scheme 10, Step D (1 eq.), aryl boronic acid (1.5 eq.), $K_2CO_3$ (3 eq.) and [1,1' bis(diphenylphosphino)-ferrocene]dichloropalladium(11)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. The organic layer was evaporated and dried in vacuo. The residue was purified by HPLC to afford the title compounds (Yields: 30-40%).

EXAMPLE 216

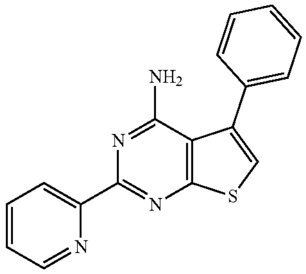

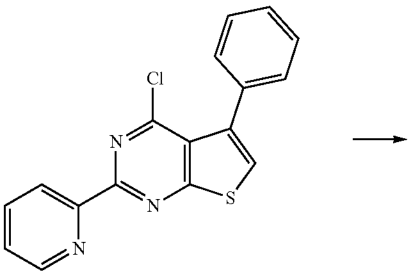

113

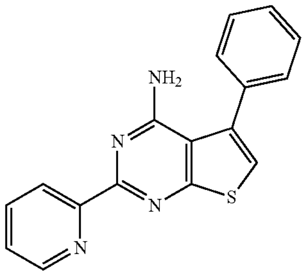

The target compound was prepared from compound 113, using a procedure analogous to Step B, Scheme 8 for the preparation of compound 32.

EXAMPLE 217

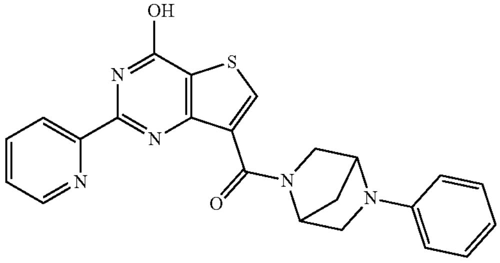

The target compound was prepared from compound 15 in Scheme 3, according to the general procedure for amide synthesis described in Step E, Scheme 3.

EXAMPLE 218

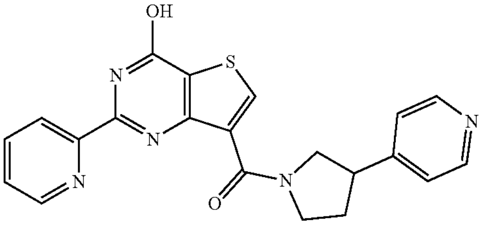

The target compound was prepared from compound 15 in Scheme 3, according to the general procedure for amide synthesis described in Step E, Scheme 3.

EXAMPLE 219

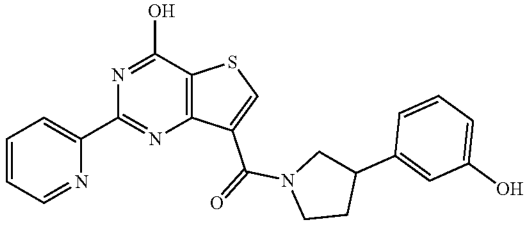

The target compound was prepared from compound 15 in Scheme 3, according to the general procedure for amide synthesis described in Step E, Scheme 3.

EXAMPLE 220

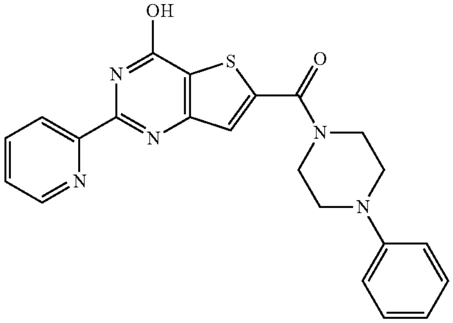

The target compound was prepared from compound 50 in Scheme 11, according to the general procedure for amide synthesis described in Step D, Scheme 11.

EXAMPLE 221

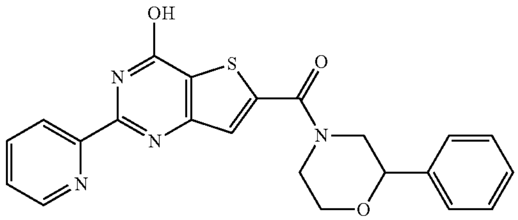

The target compound was prepared from compound 50 in Scheme 11, according to the general procedure for amide synthesis described in Step D, Scheme 11.

EXAMPLE 222

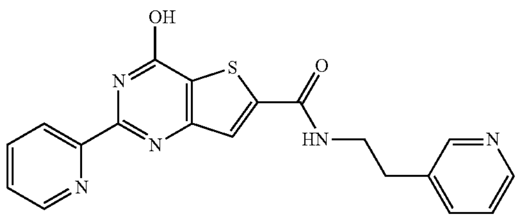

The target compound was prepared from compound 50 in Scheme 11, according to the general procedure for amide synthesis described in Step D, Scheme 11.

EXAMPLE 223

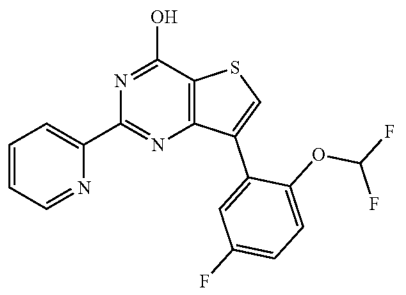

The target compound was prepared from compound 13 using the general procedure described in Scheme 12.

EXAMPLE 224

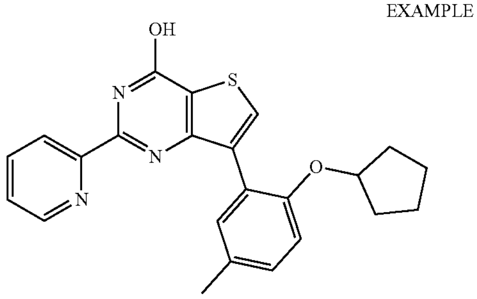

The target compound was prepared from compound 13 using the general procedure described in Scheme 12.

EXAMPLE 225

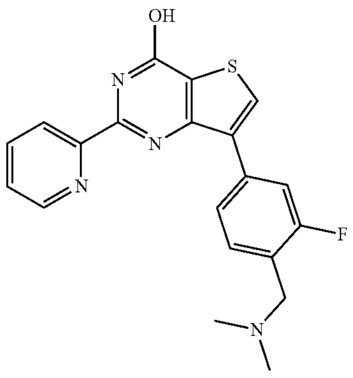

The target compound was prepared from compound 13 using the general procedure described in Scheme 12.

EXAMPLE 226

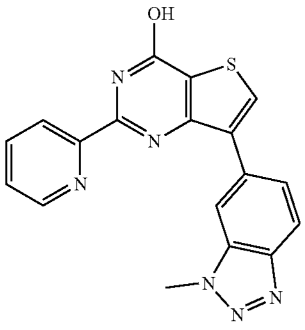

The target compound was prepared from compound 13 using the general procedure described in Scheme 12.

EXAMPLE 227

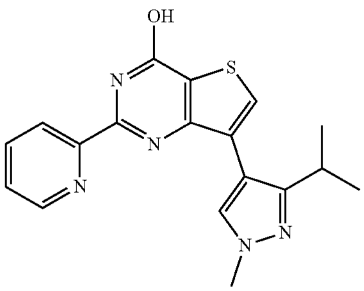

The target compound was prepared from compound 13 using the general procedure described in Scheme 12.

EXAMPLE 228

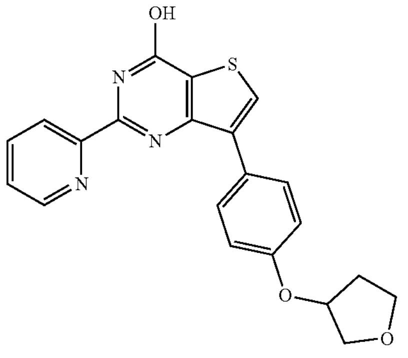

The target compound was prepared from compound 13 using the general procedure described in Scheme 12.

EXAMPLE 229

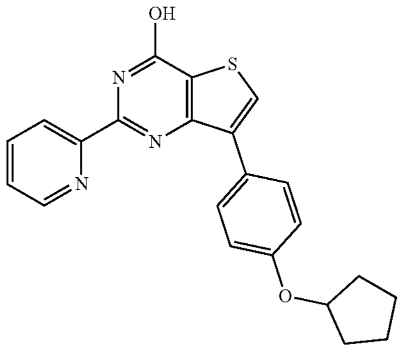

The target compound was prepared from compound 13 using the general procedure described in Scheme 12.

EXAMPLE 230

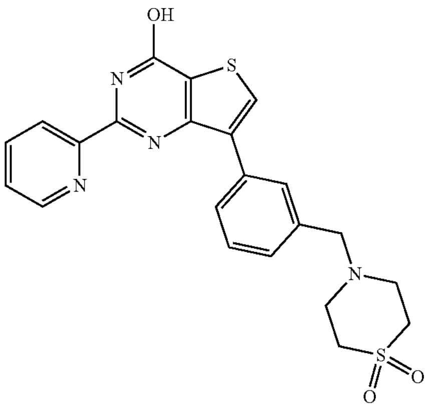

The target compound was prepared from compound 13 using the general procedure described in Scheme 12.

EXAMPLE 231

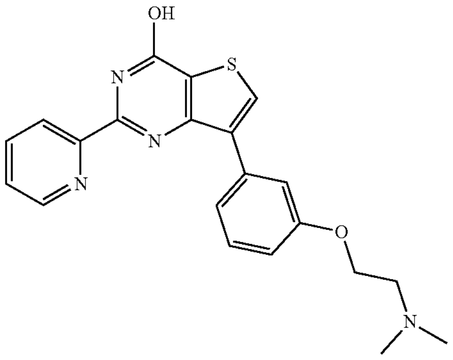

The target compound was prepared from compound 13 using the general procedure described in Scheme 12.

EXAMPLE 232

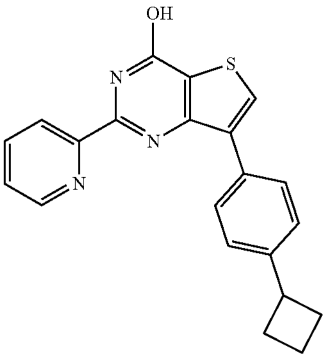

The target compound was prepared from compound 13 using the general procedure described in Scheme 12.

EXAMPLE 233

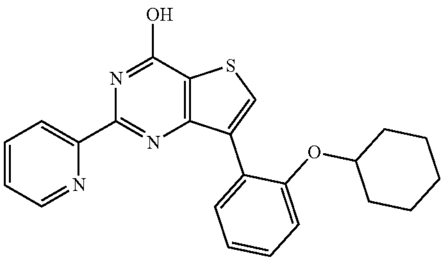

The target compound was prepared from compound 13 using the general procedure described in Scheme 12.

EXAMPLE 234

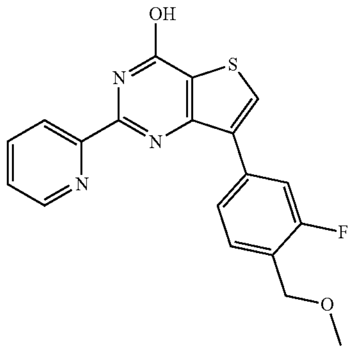

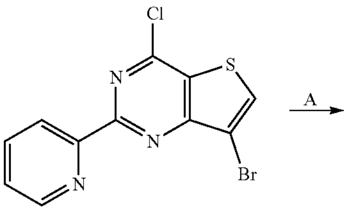

41

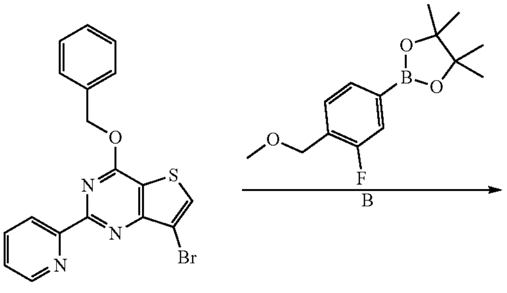

114

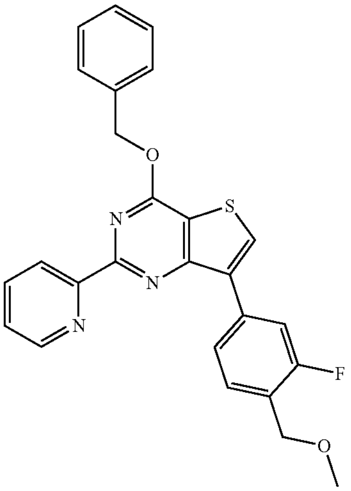

115

-continued

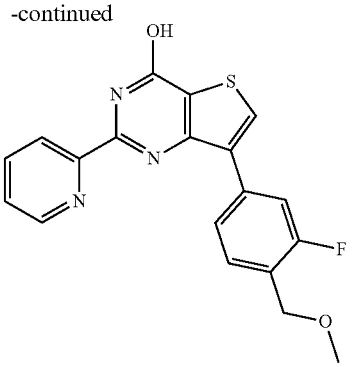

Step A: Sodium (2.8 g, 0.122 mol, 2 eq) was added in portions to benzyl alcohol solution (13.1 g, 0.122 mol 2 eq) if DMF (400 mL). Once all the sodium metal had disappeared, compound 41, prepared in Step C, Scheme 10 (20 g, 0.061 mol, 1 eq) was added and the mixture was stirred at ambient temperature overnight. The mixture was diluted with water and extracted with diethyl ether. The organic layer was washed with water, brine, dried ($Na_2SO_4$), filtered and the solvent was removed under reduced pressure to give the title compound 114 (19.6 g, yield 81%) as an orange solid, which was used in next step without purification.

Step B: A mixture of compound 114 (1 eq.), aryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with CH2Cl2, and washed with water. Organic layer was evaporated and dried in vacuo. The residue was purified by HPLC to afford the compound 115 in 50% yield.

Step C: Compound 115 and Pd/C (10%) in methanol (200 mL) was hydrogenated under 50 atm of hydrogen for 24 hr. Then, the mixture was filtered and the filtrate was evaporated to dryness to give the target compound in 90% yield (2 g scale).

EXAMPLE 235

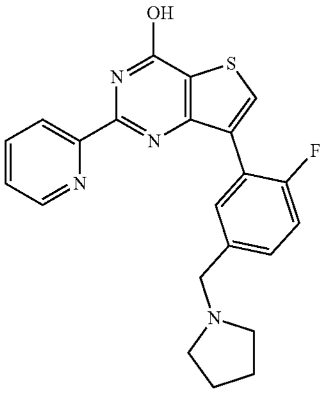

The target compound was prepared from compound 13 using the general procedure described in Scheme 12.

EXAMPLE 236

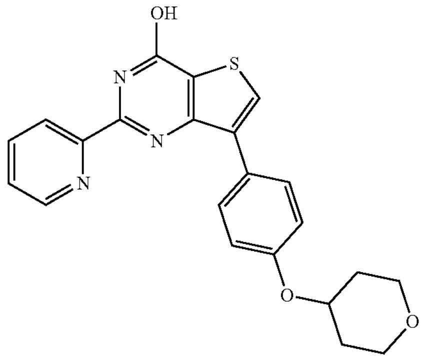

The target compound was prepared from compound 13 using the general procedure described in Scheme 12.

EXAMPLE 237

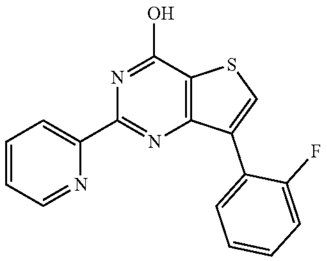

The target compound was prepared from compound 13 using the general procedure described in Scheme 12.

EXAMPLE 238

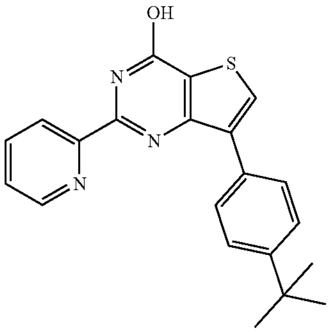

The target compound was prepared from compound 13 using the general procedure described in Scheme 12.

EXAMPLE 239

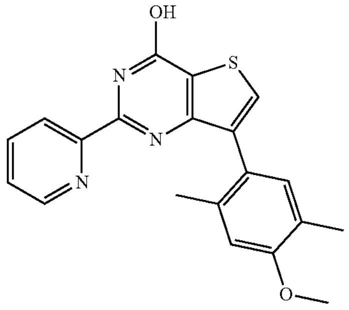

The target compound was prepared from compound 13 using the general procedure described in Scheme 12.

EXAMPLE 240

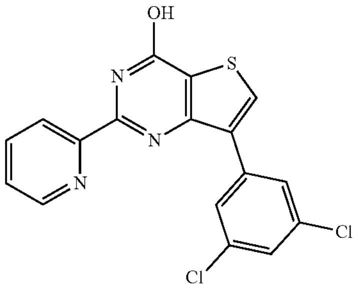

The target compound was prepared from compound 13 using the general procedure described in Scheme 12.

EXAMPLE 241

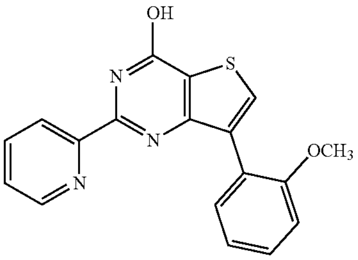

The target compound was prepared from compound 13 using the general procedure described in Scheme 12.

EXAMPLE 242

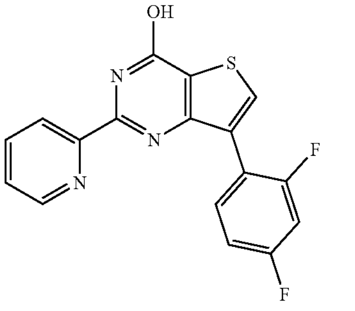

The target compound was prepared from compound 13 using the general procedure described in Scheme 12.

EXAMPLE 243

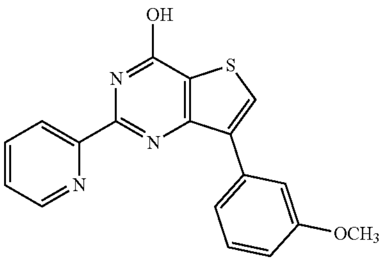

The target compound was prepared from compound 13 using the general procedure described in Scheme 12.

EXAMPLE 244

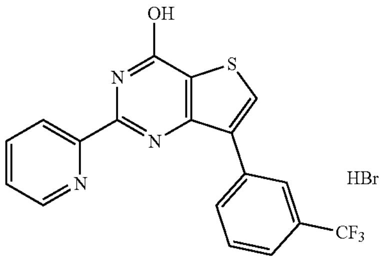

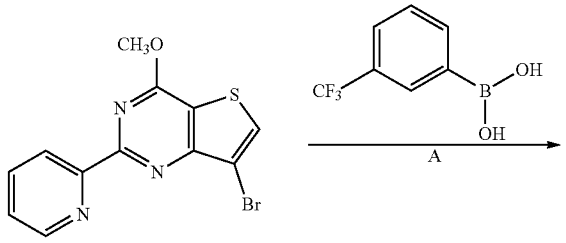

83

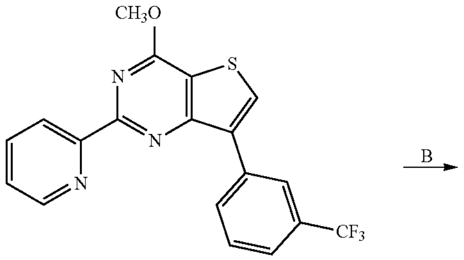

116

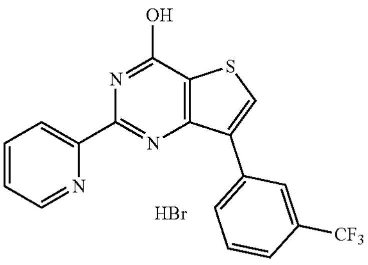

Step A: A mixture of compound 83 (prepared in Step D, Example 65) (5 g, 1 eq.), (3-(trifluoromethyl)phenyl)boronic acid (4.44 g, 1.5 eq.), $K_2CO_3$ (2.15 g, 3 eq.) and [1,1'-bis(diphenylphosphino)-ferrocene]dichloropalladium(II)-dichloromethane complex (0.623 g, 0.05 eq.) in a mixture of dioxane (300 ml) and $H_2O$ (300 ml) was stirred overnight under argon atmosphere at 95° C. After cooling down to room temperature, the mixture was diluted with $CH_2Cl_2$, and washed with water. Organic layer was evaporated and dried in vacuo. The residue was purified by HPLC to afford 116 (1.3 g, 22% yield).

Step B: The compound 116 (1.3 g) was heated in aqueous 58% HBr solution (100 mL) at 100° C. for 24 hr. Then, the mixture was evaporated to dryness and the product was precipitated with ethyl acetate to give the target compound as white solid (HBr, 1.4 g, 89%).

EXAMPLE 245

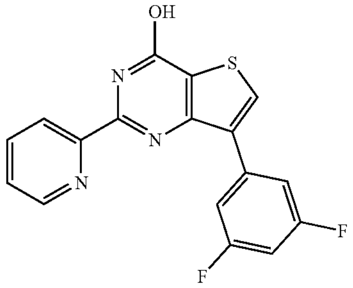

The target compound was prepared from compound 13 using the general procedure described in Scheme 12.

EXAMPLE 246

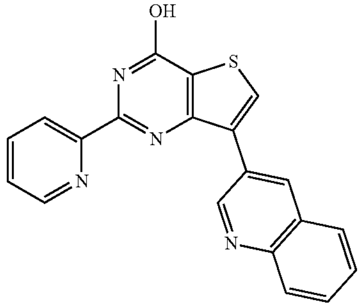

The target compound was prepared from compound 13 using the general procedure described in Scheme 12.

EXAMPLE 247

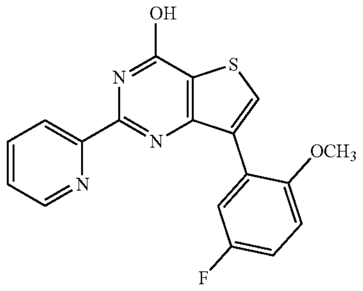

The target compound was prepared from compound 13 using the general procedure described in Scheme 12.

EXAMPLE 248

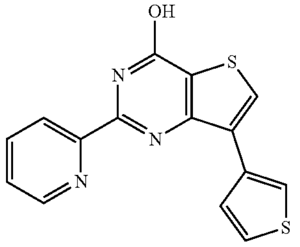

The target compound was prepared from compound 13 using the general procedure described in Scheme 12.

EXAMPLE 249

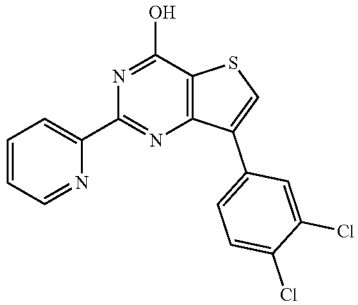

The target compound was prepared from compound 13 using the general procedure described in Scheme 12.

EXAMPLE 250

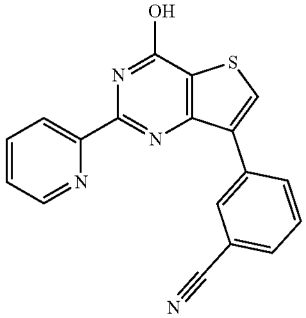

The target compound was prepared from compound 13 using the general procedure described in Scheme 12.

EXAMPLE 251

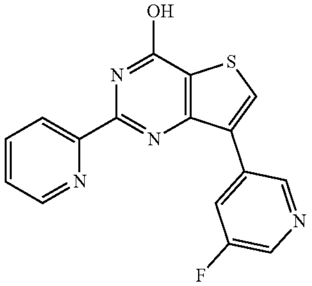

The target compound was prepared from compound 13 using the general procedure described in Scheme 12.

EXAMPLE 252

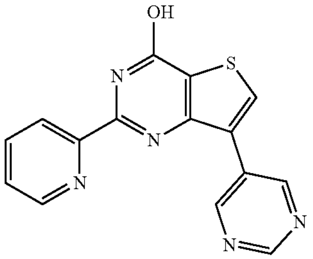

The target compound was prepared from compound 13 using the general procedure described in Scheme 12.

EXAMPLE 253

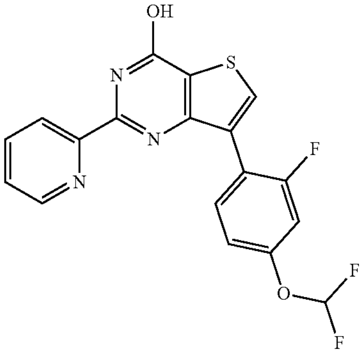

The target compound was prepared from compound 13 using the general procedure described in Scheme 12.

EXAMPLE 254

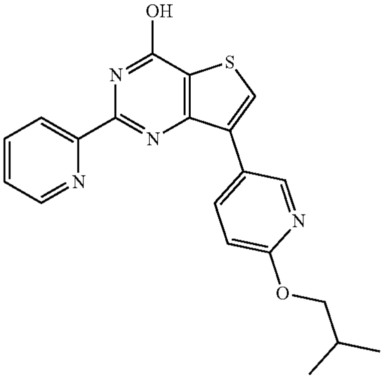

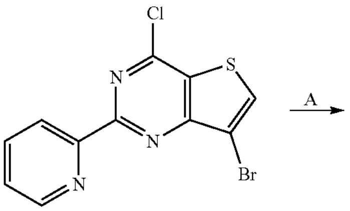

41

-continued

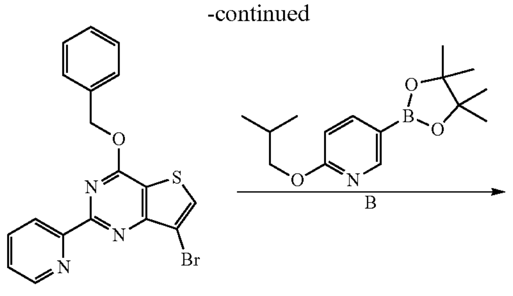

117

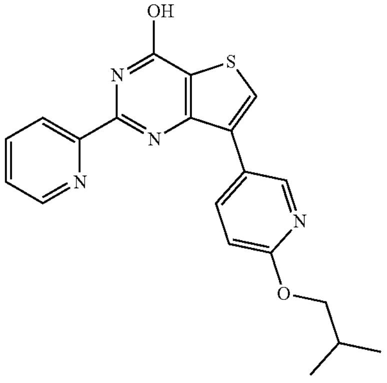

118

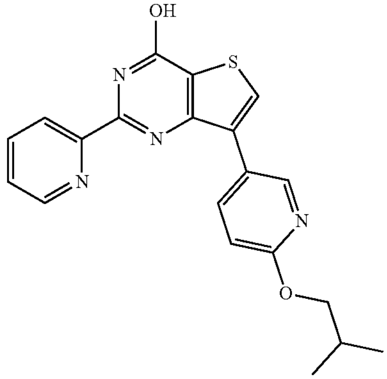

Step A: Sodium (2.8 g, 0.122 mol, 2 eq) was added in portions to benzyl alcohol solution (13.1 g, 0.122 mol 2 eq) if DMF (400 mL). Once all the sodium metal had disappeared, compound 41, prepared in Step C, Scheme 10 (20 g, 0.061 mol, 1 eq) was added and the mixture was stirred at ambient temperature overnight. The mixture was diluted with water and extracted with diethyl ether. The organic layer was washed with water, brine, dried ($Na_2SO_4$), filtered and the solvent was removed under reduced pressure to give the title compound 117 (19.6 g, yield 81%) as an orange solid, which was used in next step without purification.

Step B: A mixture of compound 117 (1 eq.), aryl boronic acid (1.5 eq.), $K_2CO_3$ (3 eq.) and [1,1' bis(diphenylphosphino)-ferrocene]dichloropalladium(II)-dichloromethane complex (0.05 eq.) in a mixture of dioxane (3 ml) and $H_2O$ (1 ml) was stirred overnight under argon atmosphere at 95° C. After cooling down to room temperature, the mixture was diluted with $CH_2Cl_2$, and washed with water. Organic layer was evaporated and dried in vacuo. The residue was purified by HPLC to afford the target compound in 50% yield.

Step C: Compound 118 and Pd/C (10%) in methanol (200 mL) was hydrogenated under 50 atm of hydrogen for 24 hr. Then, the mixture was filtered and the filtrate was evaporated to dryness to give the target compound in 90% yield (2 g scale).

EXAMPLE 255

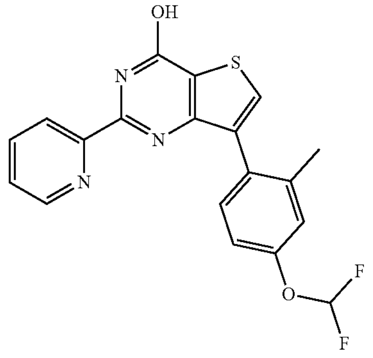

The target compound was prepared from compound 13 using the general procedure described in Scheme 12.

EXAMPLE 256

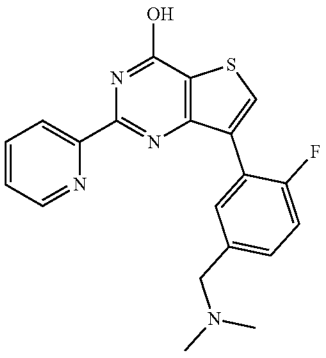

The target compound was prepared from compound 13 using the general procedure described in Scheme 12.

EXAMPLE 257

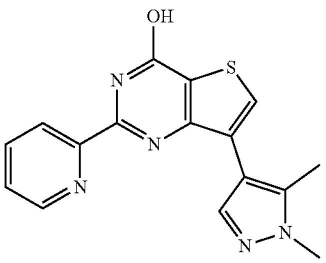

The target compound was prepared from compound 13 using the general procedure described in Scheme 12.

EXAMPLE 258

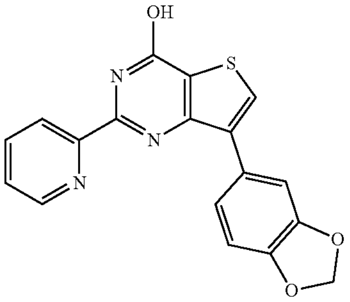

The target compound was prepared from compound 13 using the general procedure described in Scheme 12.

EXAMPLE 259

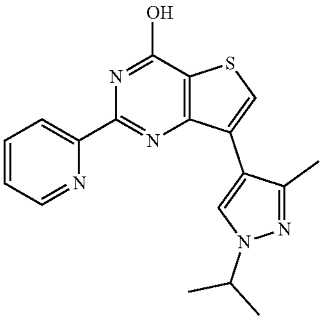

The target compound was prepared from compound 13 using the general procedure described in Scheme 12.

EXAMPLE 260

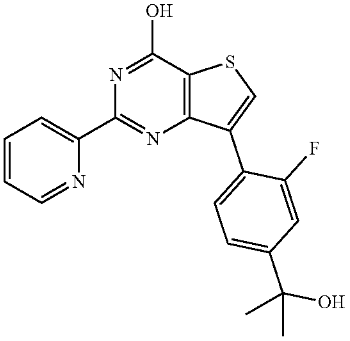

The target compound was prepared from compound 13 using the general procedure described in Scheme 12.

EXAMPLE 261

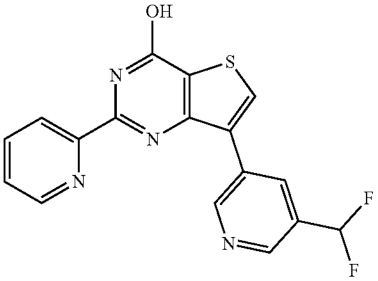

The target compound was prepared from compound 13 using the general procedure described in Scheme 12.

EXAMPLE 262

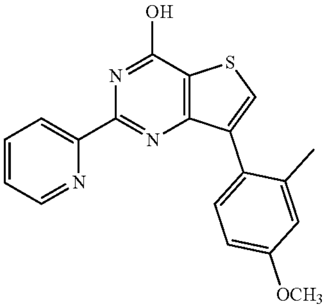

The target compound was prepared from compound 13 using the general procedure described in Scheme 12.

EXAMPLE 263

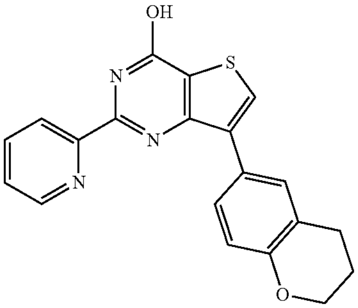

The target compound was prepared from compound 13 using the general procedure described in Scheme 12.

EXAMPLE 264

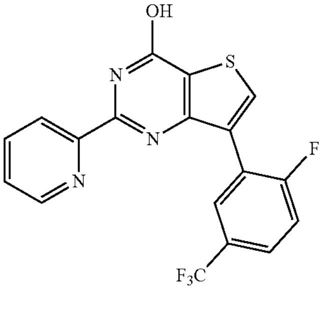

The target compound was prepared from compound 13 using the general procedure described in Scheme 12.

EXAMPLE 265

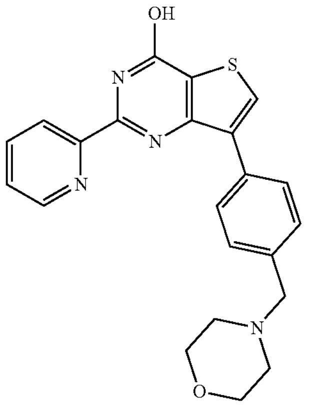

The target compound was prepared from compound 13 using the general procedure described in Scheme 12.

EXAMPLE 266

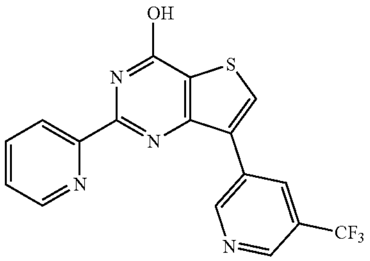

The target compound was prepared from compound 13 using the general procedure described in Scheme 12.

EXAMPLE 267

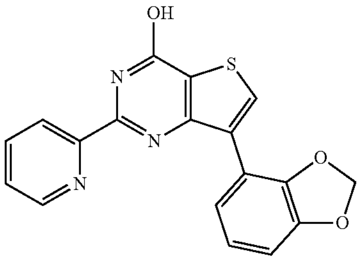

The target compound was prepared from compound 13 using the general procedure described in Scheme 12.

EXAMPLE 268

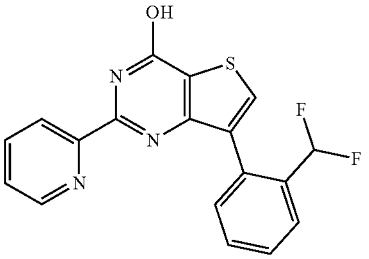

The target compound was prepared from compound 13 using the general procedure described in Scheme 12.

EXAMPLE 269

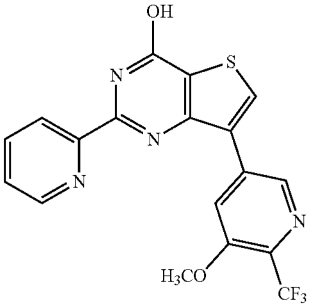

The target compound was prepared from compound 13 using the general procedure described in Scheme 12.

EXAMPLE 270

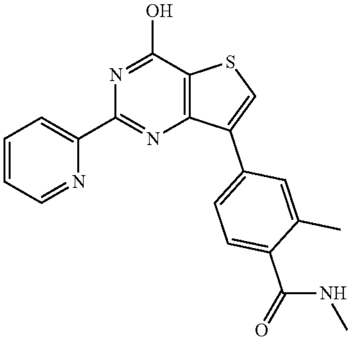

The target compound was prepared from compound 13 using the general procedure described in Scheme 12.

EXAMPLE 271

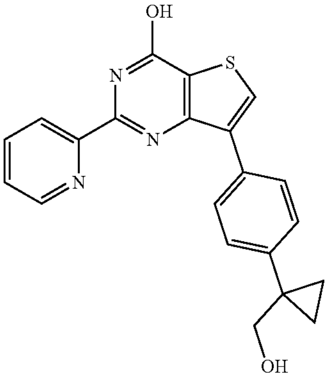

The target compound was prepared from compound 13 using the general procedure described in Scheme 12.

EXAMPLE 272

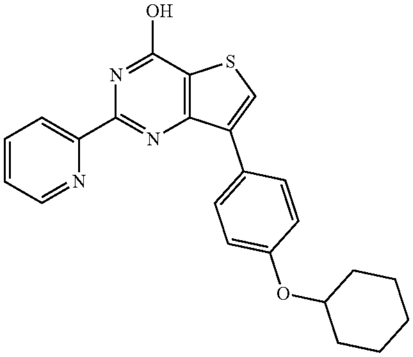

The target compound was prepared from compound 13 using the general procedure described in Scheme 12.

EXAMPLE 273

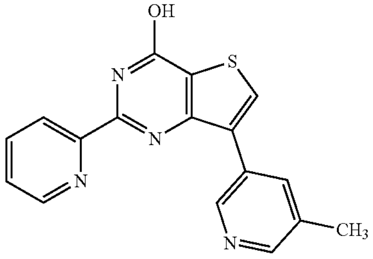

The target compound was prepared from compound 13 using the general procedure described in Scheme 12.

EXAMPLE 274

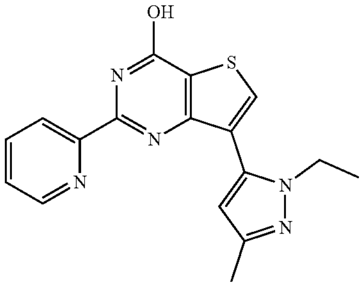

The target compound was prepared from compound 13 using the general procedure described in Scheme 12.

EXAMPLE 275

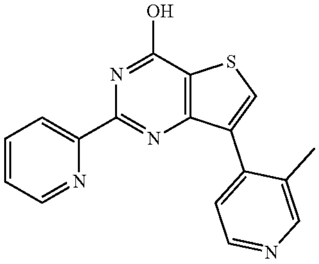

The target compound was prepared from compound 13 using the general procedure described in Scheme 12.

EXAMPLE 276

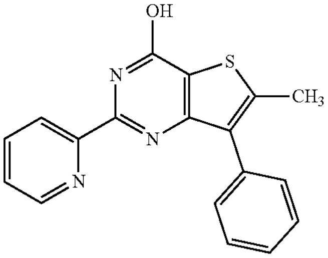

The target compound was prepared from compound 40, prepared in Step B, Scheme 10, using the general procedure described in Scheme 12.

EXAMPLE 277

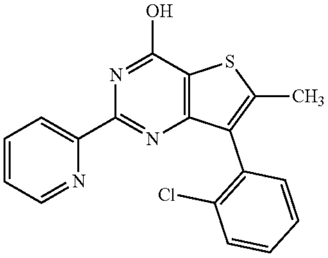

The target compound was prepared from compound 40, prepared in Step B, Scheme 10, using the general procedure described in Scheme 12.

EXAMPLE 278

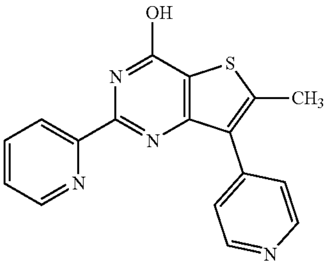

The target compound was prepared from compound 40, prepared in Step B, Scheme 10, using the general procedure described in Scheme 12.

EXAMPLE 279

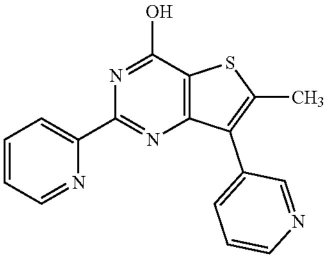

The target compound was prepared from compound 40, prepared in Step B, Scheme 10, using the general procedure described in Scheme 12.

EXAMPLE 280

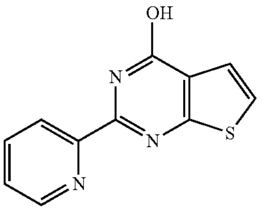

The target compound was prepared in Step A, Scheme 5 (compound 17).

EXAMPLE 281

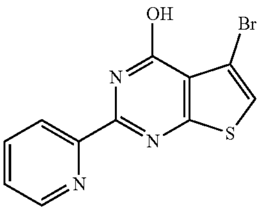

The target compound was prepared in Step B, Scheme 5 (compound 18).

EXAMPLE 282

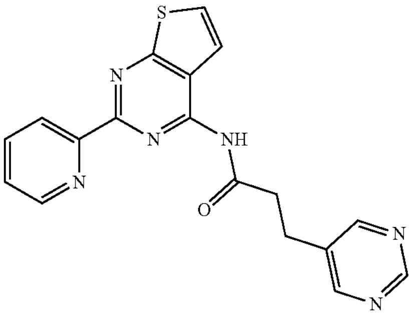

The target compound was prepared from compound 32 in Scheme 8, according to the procedure for amide synthesis described in Step C, Scheme 8.

EXAMPLE 283

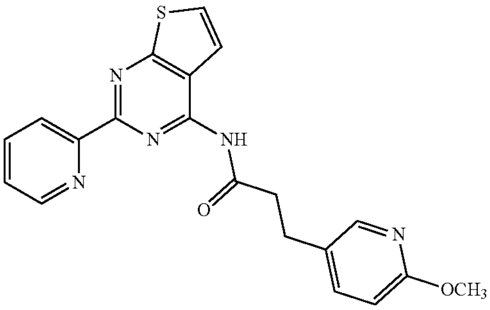

The target compound was prepared from compound 32 in Scheme 8, according to the procedure for amide synthesis described in Step C, Scheme 8.

EXAMPLE 284

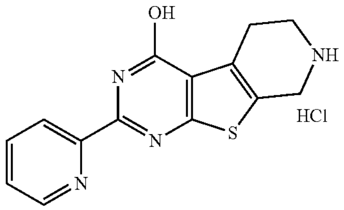

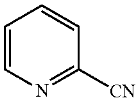

11

+

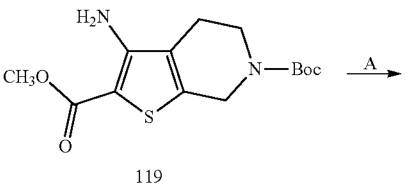

119

-continued

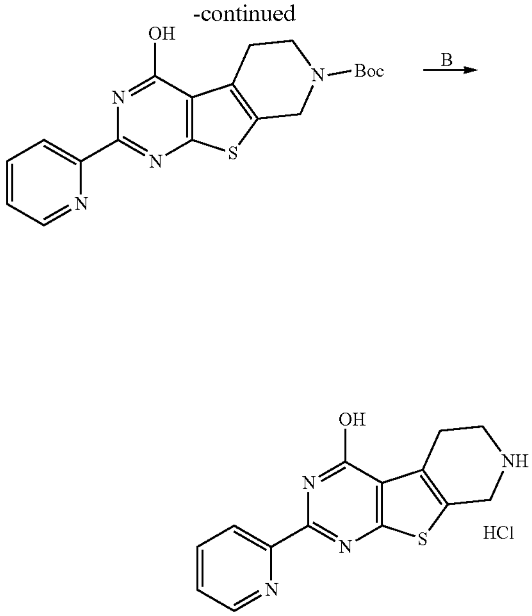

Step A: To a solution compound 114 (0.5 g, 1.6 mmol) in DMF (5 mL) was added KO-tBu (0.1 g, 0.89 mmol) and picolinonitrile 11 (0.2 g, 1.92 mmol). The reaction mixture was heated to 90° C. for 4 d and concentrated under reduced pressure. The resulting mixture was diluted with water and extracted with EtOAc. The organic layer was dried over $Na_2SO_4$ and evaporated. The crude product was chromatographed on a silics gel column to give compound 115. The yield was 18 mg (0.047 mmol, 3%).

Step B: Compound 115 (18 mg, 0.047 mmol) was dissolved in 5 mL 2M methanolic solution of HCl. The reaction mixture was stirred overnight and concentrated under reduced pressure. The resulting residue was washed with $Et_2O$ and dried. The yield of the target compound was 8 mg (0.025 mmol, 53%)

EXAMPLE 285

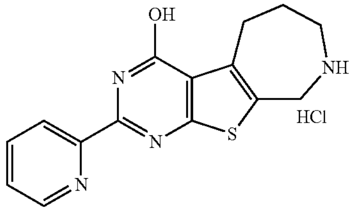

EXAMPLE 286

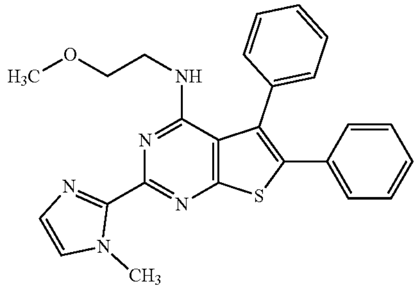

-continued

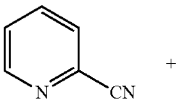

11

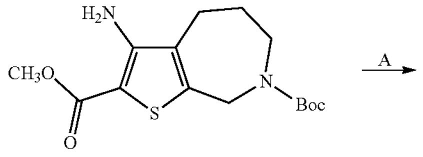

121

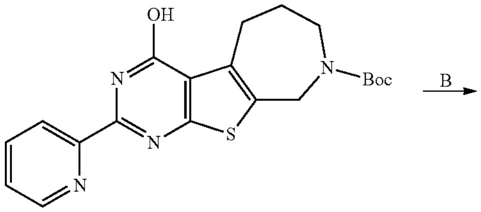

122

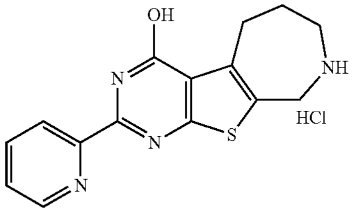

Step A: To a solution compound 116 (0.5 g, 1.5 mmol) in DMF (5 mL) was added KO-tBu (0.1 g, 0.89 mmol) and picolinonitrile (0.2 g, 1.92 mmol). The reaction mixture was heated to 90° C. for 4 d and concentrated under reduced pressure. The resulting mixture was diluted with water and extracted with EtOAc. The organic layer was dried over $Na_2SO_4$ and evaporated. The crude product was chromatographed on a silica gel column. The yield of compound 117 was 15 mg (0.038 mmol, 2.5%).

Step B: Compound 117 (15 mg, 0.038 mmol) was dissolved in 5 mL 2M methanolic solution of HCl. The reaction mixture was stirred overnight and concentrated under reduced pressure. The resulting residue was washed with $Et_2O$ and dried. The yield was 8 mg (0.024 mmol, 63%).

-continued

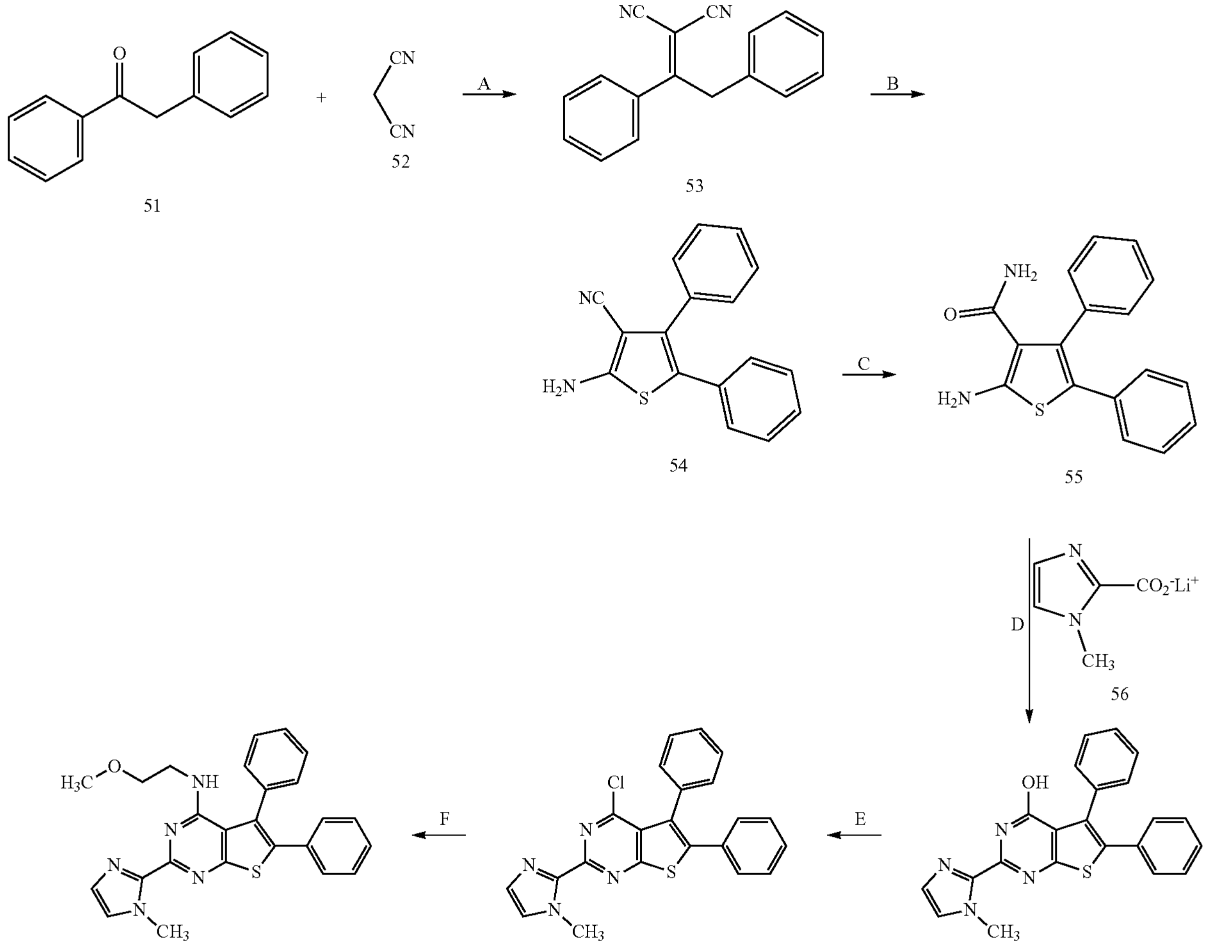

51 52 53 54 55 56 57 58

Step A: Hexamethyldisilazane (8.11 mL, 0.038 mol, 1.5 eq) was added dropwise to HOAc (7 mL). The resulting mixture was added to a suspension of malononitrile 52 (2.78 mL, 0.05 mol, 2.0 eq) and compound 51 (5 g, 0.025 mol, 5 g, 1.0 eq) in HOAc (5 mL). The reaction mixture was stirred with reflux overnight then, allowed to cool down to RT and diluted with toluene (30 mL) and water (20 mL). The organic layer was separated, washed with water (3*2 mL), dried over $Na_2SO_4$ and concentrated under reduced pressure affording compound 53 (4.75 g, 78% yield).

Step B: Sulphur (0.75, 0.023 mol, 1.2 eq) was added to a solution of compound 53 (4.75 g, 0.019 mol, 1.0 eq) in THF (20 mL). The resulting mixture was stirred at 50° C. for 30 min and then $NaHCO_3$ (1.64 g, 0.19 mol, 1.0 eq) was added. Then, the reaction mixture was stirred at 50° C. overnight and diluted with EtOAc. The organic phase was dried with $Na_2SO_4$ and evaporated in vacuo to obtain compound 54 (3.39 g, 63% yield).

Step C: The compound 54 (3.93 g, 0.012 mol, 1.0 eq) and 80% $H_2SO_4$ (10 mL) were stirred at RT for 18 h. After completion (monitored by LCMS), the reaction mixture was poured in ice and aqueous ammonia (5 mL) was added. The precipitate formed was filtered off, washed with water and air-dried to give compound 55. The yield was 2.35 g (65%).

Step D: Lithium 1-methyl-1H-imidazole-2-carboxylate 56 (1.32 g, 0.01 mol, 1.3 eq), triethylamine (1.67 g, 0.01 mol, 1.4 eq) and 1-methyl-1H-imidazole (1.64 g, 0.02 mol, 2.5 eq) were dissolved in $CH_2Cl_2$ (15 mL). The resulting mixture was cooled to 0° C. and methanesulfonyl chloride (1.1 g, 9.6 mmol, 1.2 eq) was added dropwise. Then, the resulting suspension was stirred for 30 min and compound 55 (2.35 g, 8.0 mmol, 1.0 eq) was added in one portion. The reaction mixture was stirred overnight and evaporated in vacuo. The residue was dissolved in DMSO and potassium tert-butoxide (1.79 g, 0.016 mol, 2.0 eq) was added. The resulting suspension was stirred overnight at 80° C. and HOAc (5 mL) was added. The resulting precipitate was filtered off, washed with water and dried to give compound 57. The yield was 2.34 g (76%).

Step E: The compound 57 (2.34 g, 6.1 mmol, 1.0 eq.) and phosphoryl chloride (7 mL) were stirred at 90° c. for 18 h. The reaction mixture was poured into ice and extracted with EtOAc. The organic layer was dried ($Na_2SO_4$), filtered and the solvent was removed under reduced pressure to give compound 58 (1.98 g, 81%).

Step F: To a solution of compound 58 (1.98 g, 4.94 mmol, 1.0 eq) in DMSO (3 mL) 2-methoxyethanamine (0.37 g, 4.94 mmol, 1.0 eq) and DIPEA (0.83 g, 6.42 mmol, 1.3 eq) were added. The resulting mixture was stirred overnight at 60° C. Then, the reaction suspension was poured into water and extracted with EtOAc. The solvent was evaporated and the residue was purified by HPLC to obtain the target compound (1.36 g, 63% yield).

EXAMPLE 287

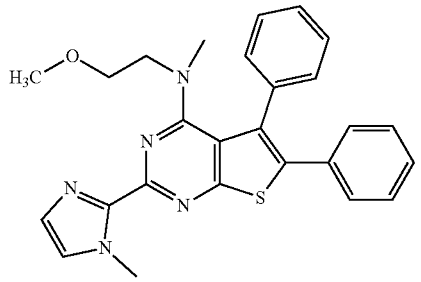

The target compound was prepared according to the procedure described in Scheme 13. The yields were: Step A 1.61 g, (80.5%); Step B 1.0 g (71.4%); Step C 342 mg (68%); Step D 155 mg (52%); Step E 136 mg (80%); Step F 48.3 mg (49%).

EXAMPLE 288

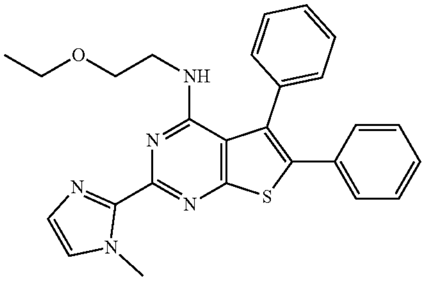

The target compound was prepared according to the procedure described in Scheme 13. The yields were: Step A 1.72 g (86%); Step B 1.02 g (73%); Step C 371 mg (74%); Step D 167 mg (56%); Step E 143 mg (84%); Step F 50.6 mg (51%).

EXAMPLE 289

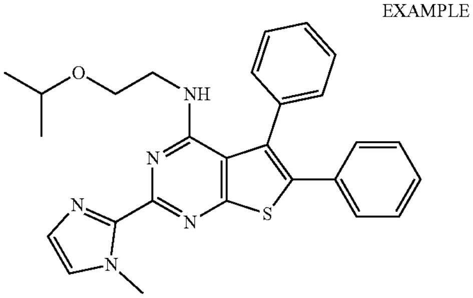

The target compound was prepared according to the procedure described in Scheme 13. The yields were: Step A 1.49 g (72.5%); Step B 0.81 g (57%); Step C 411 mg (82%); Step D 172 mg (57%); Step E 138 mg (81%); Step F 51.7 mg (52%).

EXAMPLE 290

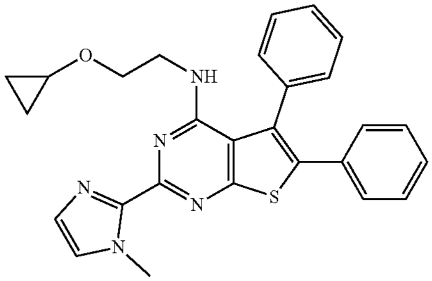

The target compound was prepared according to the procedure described in Scheme 13. The yields were: Step A 1.79 g (89.5%); Step B 1.10 g (80%); Step C 0.393 g (78%); Step D 169 mg (56%); Step E 142 mg (83%); Step F 18.3 mg (18%).

EXAMPLE 291

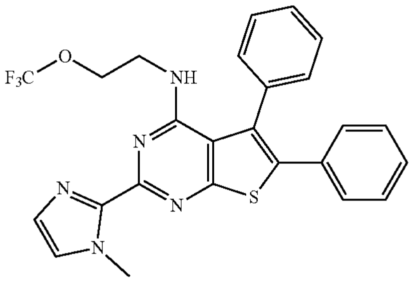

The target compound was prepared according to the procedure described in Scheme 13. The yields were: Step A 1.66 g (83%); Step B 1.06 g (76%); Step C 0.366 g (73%); Step D 176 mg (59%); Step E 152 mg (89%); Step F 11.1 mg (11%).

EXAMPLE 292

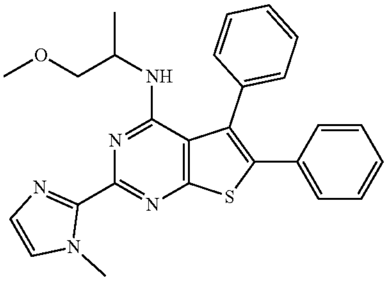

The target compound was prepared according to the procedure described in Scheme 13. The yields were: Step A 1.73 g (86.5%); Step B 0.97 g (69.3%); Step C 0.331 g (66%); Step D 181 mg (60%); Step E 146 mg (86%); Step F 48.3 mg (48%).

EXAMPLE 293

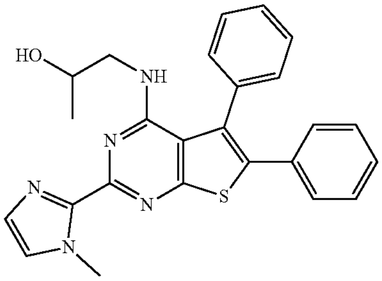

The target compound was prepared according to the procedure described in Scheme 13. The yields were: Step A 1.68 g (84%); Step B 1.11 g (79%); Step C 0.378 g (75%); Step D 159 mg (53%); Step E 151 mg (89%); Step F 46.1 mg (46%).

EXAMPLE 294

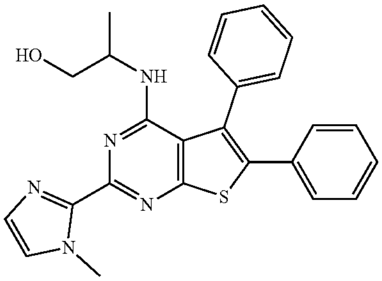

The target compound was prepared according to the procedure described in Scheme 13. The yields were: Step A 1.74 g (87%); Step B 1.07 g (76%); Step C 0.358 g (71%); Step D 179 mg (60%); Step E 149 mg (87%); Step F 11.2 mg (11%).

EXAMPLE 295

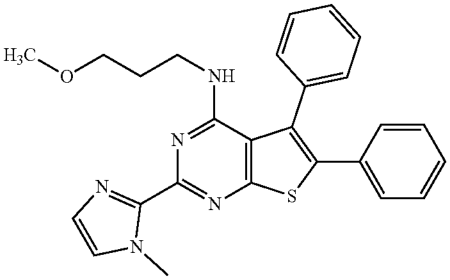

The target compound was prepared according to the procedure described in Scheme 13. The yields were: Step A 1.63 g (81.5%); Step B 0.89 g (63%); Step C 0.362 g (72%); Step D 177 mg (59%); Step E 137 mg (80%); Step F 52.9 mg (53%).

EXAMPLE 296

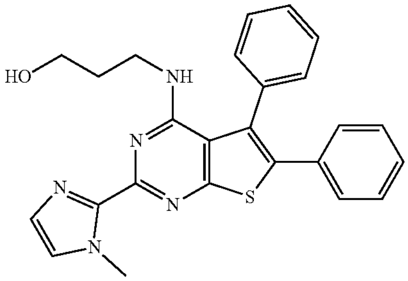

The target compound was prepared according to the procedure described in Scheme 13. The yields were: Step A 1.64 g (82%); Step B 1.01 g (72%); Step C 0.401 g (80%); Step D 164 mg (55%); Step E 131 mg (77%); Step F 51.0 mg (51%).

EXAMPLE 297

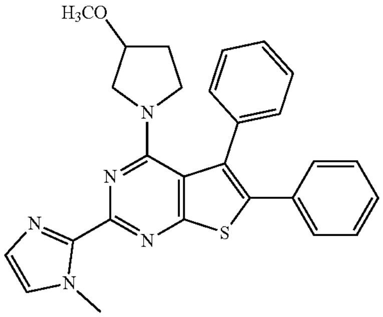

The target compound was prepared according to the procedure described in Scheme 13. The yields were: Step A 1.67 g (83.5%); Step B 0.98 g (70%); Step C 0.372 g (74%); Step D 185 mg (62%); Step E 147 mg (86%); Step F 58.6 mg (59%).

EXAMPLE 298

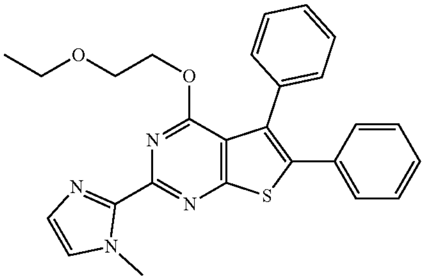

The target compound was prepared according to the procedure described in Scheme 13. The yields were: Step A 1.76 g (88%); Step B 1.04 g (74%); Step C 0.369 g (74%); Step D 163 mg (54%); Step E 150 mg (88%); Step F 24.4 mg (25%).

EXAMPLE 299

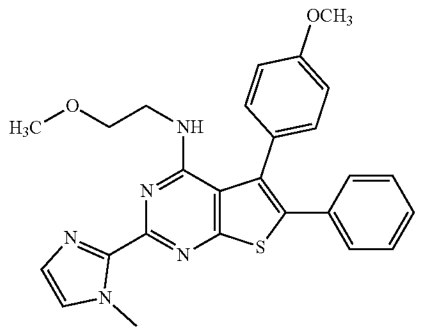

The target compound was prepared according to the procedure described in Scheme 14, using the conditions for Step C when R=4-methoxyphenyl. The yields were: Step A 1.66 g (83%); Step B 1.21 g (81%); Step C 0.305 g (61%); Step D 176 mg (59%); Step E 149 mg (83%); Step F 97 mg (97%).

EXAMPLE 300

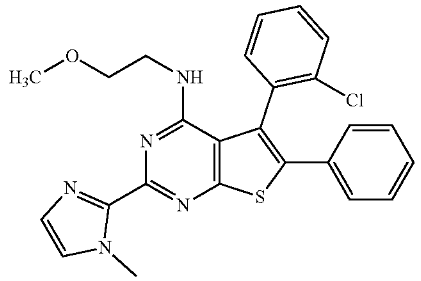

The target compound was prepared according to the procedure described in Scheme 14, using the conditions for Step C when R=2-chlorophenyl. The yields were: Step A 1.73 g (86.5%); Step B 1.14 g (76%); Step C 0.365 g (73%); Step D 183 mg (61%); Step E 159 mg (88%); Step F 57.2 mg (52%).

EXAMPLE 301

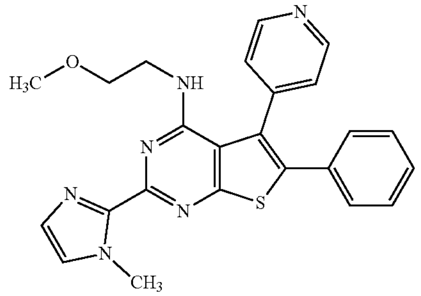

The target compound was prepared according to the procedure described in Scheme 14, using the conditions for Step C when R=4-pyridinyl. The yields were: Step A 1.68 g (84%); Step B 1.19 g (80%); Step C 0.35 g (70%); Step D 169 mg (56%); Step E 164 mg (91%); Step F 15 mg (15%).

EXAMPLE 302

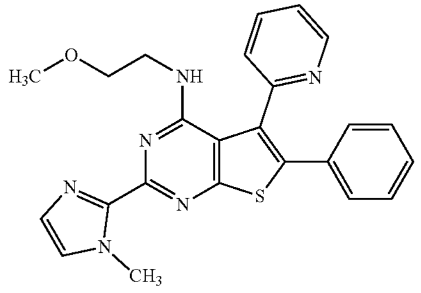

The target compound was prepared according to the procedure described in Scheme 14, using the conditions for Step C when R=2-pyridinyl. The yields were: Step A 1.59 g (79.5%); Step B 1.05 g (75%); Step C 0.37 g (74%); Step D 174 mg (58%); Step E 138 mg (77%); Step F 47.3 mg (47%).

EXAMPLE 303

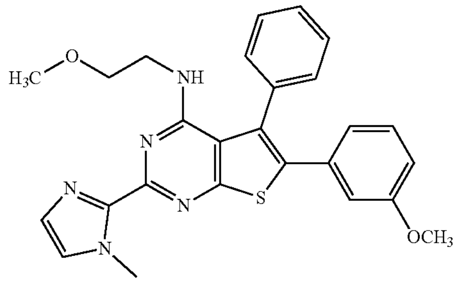

The target compound was prepared according to the procedure described in Scheme 15, using the conditions for Step C when R=3-methoxyphenyl. The yields were: Step A 1.65 g (82.5%); Step B 1.14 g (76%); Step C 0.365 g (73%); Step D 164 mg (55%); Step E 134 mg (78%); Step F 49.3 mg (50%).

EXAMPLE 304

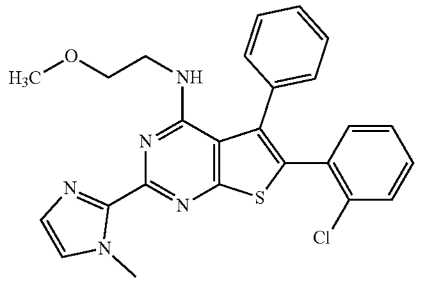

The target compound was prepared according to the procedure described in Scheme 15, using the conditions for Step C when R=2-chlorophenyl. The yields were: Step A 1.67 g (83.5%); Step B 1.07 g (71%); Step C 0.305 g (61%); Step D 179 mg (60%); Step E 147 mg (86%); Step F 56.5 mg (57%).

EXAMPLE 305

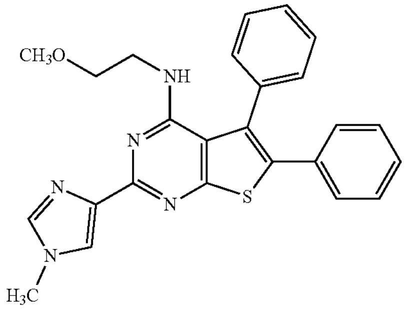

The target compound was prepared according to the procedure described in Scheme 16. The yields were: Step A 1.78 g (89%); 1.21 g (81%); Step C 0.389 g (78%); Step D 159 mg (53%); Step E 141 mg (88%); Step F 94.0 mg (94%).

EXAMPLE 306

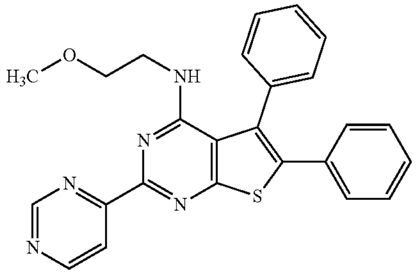

The target compound was prepared according to the procedure described in Scheme 16. The yields were: Step A 1.65 g (82.5%); Step B 1.26 g (84%); Step C 0.367 g (73%); Step D 173 mg (58%). Step E 134 mg (83%); Step F 57.3 mg (57%).

EXAMPLE 307

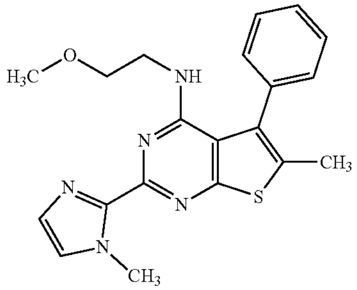

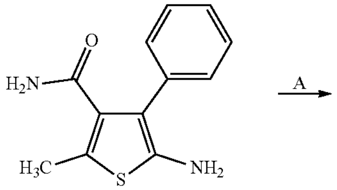

123

-continued

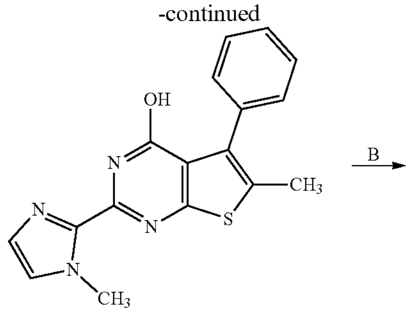

124

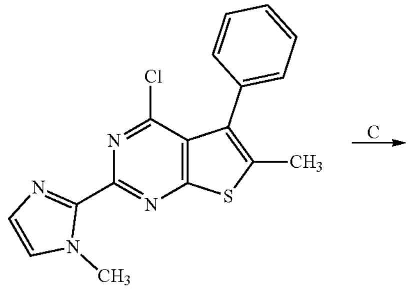

125

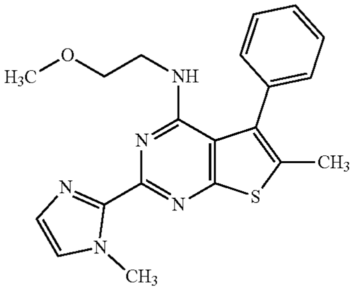

Step A: 2-Amino-5-methyl-4-phenylthiophene-3-carboxamide 123 (1.0 eq) was refluxed with 1-methylimidazole-2-carboxaldehyde (1.1 eq) in acetic (5 mL) acid for 24h. After completion of the reaction (confirmed by TLC), solution was cooled and diluted with water. The precipitate was filtered off and dried to give compound 124 (Yield—87%) as a brown solid. The scale was calculated on 700 mg theoretical yield of product. Yield: 595 mg (85%).

Step B: The compound 124 (1.0 eq) was added to phosphorous trichloride (3 mL) and the mixture was stirred with reflux for 12 h. Then the reaction mixture was poured into 25% ammonia solution in cold water (30 ml) and stirred for 1 h. The target compound was extracted with DCM (2*40 ml), dried ($Na_2SO_4$) and the solvent removed in vacuo to give crude product 125 as a brown solid. The reaction mixture was used in the next step without purification. The scale was calculated on a theoretical yield of 1 g of product. Yield: 0.66 g (65%).

Step C: To a solution of compound 125 (1.0 eq) in chloroform (10 mL) was added triethylamine (1.5 eq) and then 2-methoxyethylamine (1.0 eq). The reaction was stirred for an additional 24 hours at 60° C. After the completion of reaction (confirmed by TLC), the mixture was concentrated under reduced pressure, poured into $H_2O$ and extracted with EtOAc (2*40 ml), dried ($Na_2SO_4$), the solvent removed in vacuo to give crude product x as a brown solid. The crude product was purified using HPLC (gradient $H_2O/CH_3CN$ mixture) yielding 0.045 g of the target compound. The scale was calculated based on a theoretical yield of 0.45 g of final compound. Yield: 0.045 g (11.2%).

EXAMPLE 308

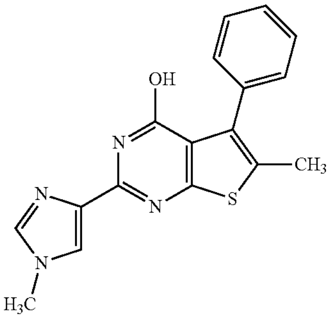

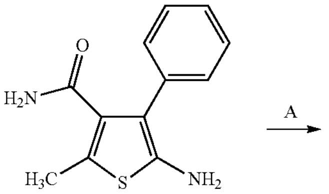

123

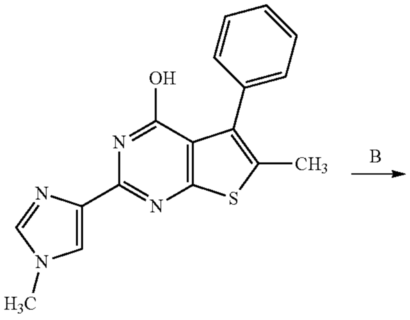

126

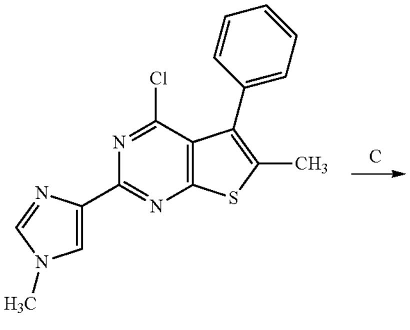

127

-continued

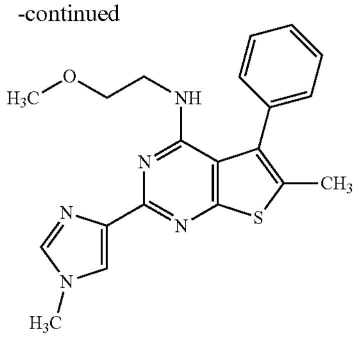

Step A: 2-Amino-5-methyl-4-phenylthiophene-3-carboxamide 123 (1.0 eq) was refluxed with 1-methylimidazole-4-carboxaldehyde (1.1 eq) in acetic (5 mL) acid for 24h. After completion of the reaction (confirmed by TLC), solution was cooled and diluted with water. The precipitate was filtered off and dried to give compound 126 (Yield—87%) as a brown solid. The scale was calculated on 700 mg theoretical yield of product. Yield: 609 mg (87%).

Step B: Compound 126 (1.0 eq) was added to phosphorous trichloride (3 mL) and the mixture was stirred with reflux for 12 h. Then the reaction mixture was poured into 25% ammonia solution in cold water (30 ml) and stirred for 1 h. The target compound was extracted with DCM (2*40 ml), dried ($Na_2SO_4$) and the solvent removed in vacuo to give crude product 127 as a brown solid. The reaction mixture was used in the next step without purification. The scale was calculated on a theoretical yield of 1 g of product. Yield: 0.47 g (47%).

Step C: To a solution of compound 127 (1.0 eq) in chloroform (10 mL) was added triethylamine (1.5 eq) and then 2-methoxyethylamine (1.0 eq). The reaction was stirred for an additional 24 hours at 60° C. After the completion of reaction (confirmed by TLC), the mixture was concentrated under reduced pressure, poured into H2O and extracted with EtOAc (2*40 ml), dried ($Na_2SO_4$), the solvent removed in vacuo to give crude product x as a brown solid. The crude product was purified using HPLC (gradient $H_2O/CH_3CN$ mixture) yielding 0.25 g of the target compound. The scale was calculated based on a theoretical yield of 0.45 g of final compound. Yield: 0.25 g (51.2%).

EXAMPLE 309

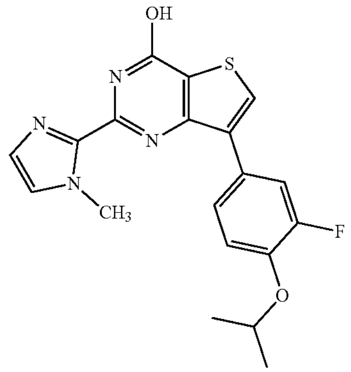

The target compound was prepared according to the procedure described in Scheme 17 for compound 76 using the appropriate reagents and starting materials. The yield after Step A was 0.82 g (82%). The yield after Step B was 0.23 g (46%). The yield of the target compound obtained from Step C was 152 mg (76%).

EXAMPLE 310

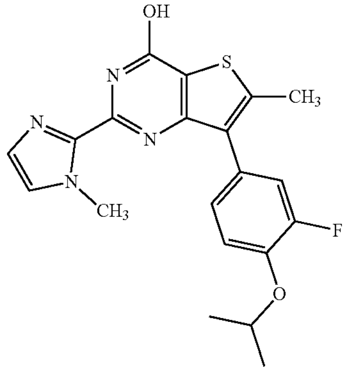

The target compound was prepared according to the procedure described in Scheme 17 for compound 76 using the appropriate reagents and starting materials. The yield after Step A was 0.63 g (63%). The yield after Step B was 0.25 g (50%). The yield of the target compound obtained from Step C was 31.5 mg (16%).

EXAMPLE 311

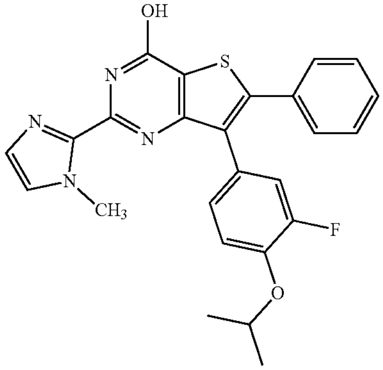

The target compound was prepared according to the procedure described in Scheme 17 for compound 76 using the appropriate reagents and starting materials. The yield after Step A was 0.77 g (57%). The yield after Step B was 0.33 g (66%). The yield of the target compound obtained from Step C was 31.3 mg (16%).

EXAMPLE 312

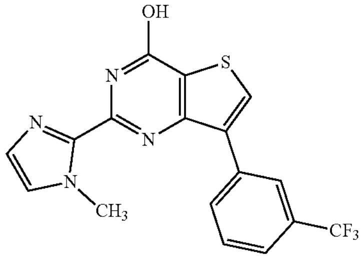

The target compound was prepared according to the procedure described in Scheme 17 for compound 76 using the appropriate reagents and starting materials. The yield after Step A was 0.86 g (87%). The yield after Step B was 0.27 g (54%). The yield of the target compound obtained from Step C was 137 mg (68.5%).

EXAMPLE 313

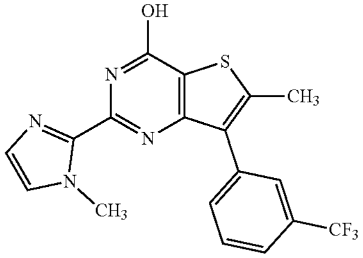

The target compound was prepared according to the procedure described in Scheme 17 for compound 76 using the appropriate reagents and starting materials. The yield after Step A was 0.91 g (91%). The yield after Step B was 0.34 g (68%). The yield of the target compound obtained from Step C was 36.5 mg (18%).

EXAMPLE 314

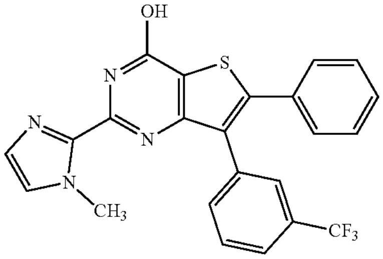

The target compound was prepared according to the procedure described in Scheme 17 for compound 76 using the appropriate reagents and starting materials. The yield after Step A was 0.76 g (76%). The yield after Step B was 0.28 g (56%). The yield of the target compound obtained from Step C was 99.8 mg (50%).

EXAMPLE 315

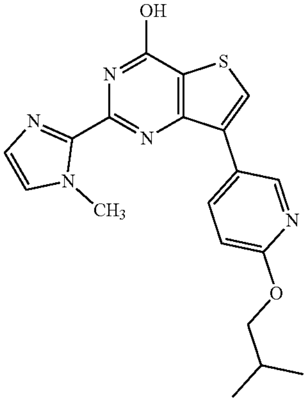

The target compound was prepared according to the procedure described in Scheme 17 for compound 76 using the appropriate reagents and starting materials. The yield after Step A was 0.86 g (86%). The yield after Step B was 0.31 g (62%). The yield of the target compound obtained from Step C was 93.6 mg (47%).

EXAMPLE 316

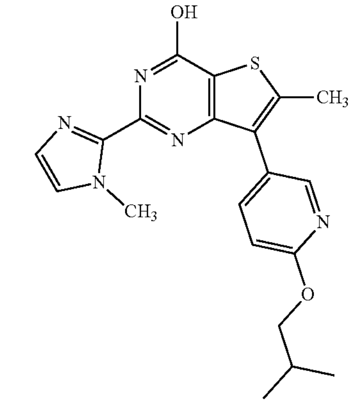

The target compound was prepared according to the procedure described in Scheme 17 for compound 76 using the appropriate reagents and starting materials. The yield after Step A was 0.93 g (93%). The yield after Step B was 0.23 g (46%). The yield of the target compound obtained from Step C was 96.8 mg (49%).

EXAMPLE 317

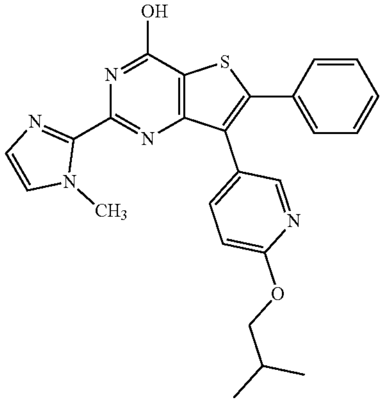

The target compound was prepared according to the procedure described in Scheme 17 for compound 76 using the appropriate reagents and starting materials. The yield after Step A was 0.84 g (84%). The yield after Step B was 0.33 g (66%). The yield of the target compound obtained from Step C was 55.1 mg (28%).

EXAMPLE 318

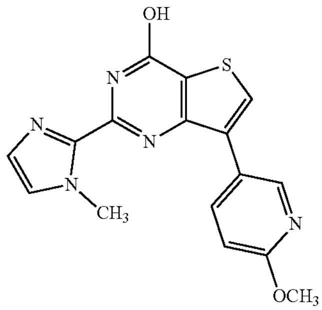

The target compound was prepared according to the procedure described in Scheme 17 for compound 76 using the appropriate reagents and starting materials. The yield after Step A was 0.79 g (79%). The yield after Step B was 0.34 g (68%). The yield of the target compound obtained from Step C was 20.5 mg (10%).

EXAMPLE 319

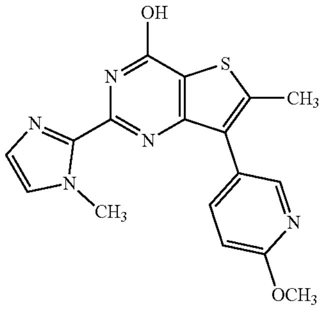

The target compound was prepared according to the procedure described in Scheme 17 for compound 76 using the appropriate reagents and starting materials. The yield after Step A was 0.84 g (84%). The yield after Step B was 0.29 g (58%). The yield of the target compound obtained from Step C was 57.5 mg (29%).

EXAMPLE 320

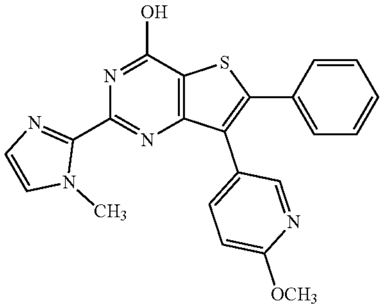

The target compound was prepared according to the procedure described in Scheme 17 for compound 76 using the appropriate reagents and starting materials. The yield after Step A was 0.92 g (92%). The yield after Step B was 0.31 g (62%). The yield of the target compound obtained from Step C was 112.6 mg (56%).

EXAMPLE 321

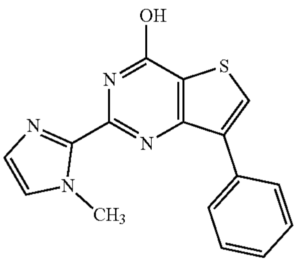

The target compound was prepared according to the procedure described in Scheme 17 for compound 76 using the appropriate reagents and starting materials. The yield after Step A was 0.88 g (88%). The yield after Step B was 0.29 g (58%). The yield of the target compound obtained from Step C was 142.7 mg (71%).

EXAMPLE 322

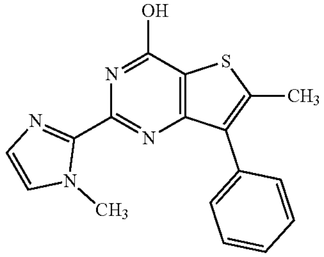

The target compound was prepared according to the procedure described in Scheme 17 for compound 76 using the appropriate reagents and starting materials. The yield after Step A was 0.94 g (94%). The yield after Step B was 0.30 g (60%). The yield of the target compound obtained from Step C was 112.2 mg (56%).

EXAMPLE 323

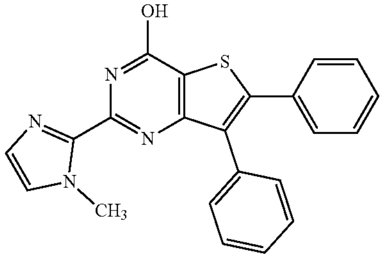

The target compound was prepared according to the procedure described in Scheme 17 for compound 76 using the appropriate reagents and starting materials. The yield after Step A was 0.69 g (69%). The yield after Step B was 0.26 g (52%). The yield of the target compound obtained from Step C was 15.2 mg (8%).

EXAMPLE 324

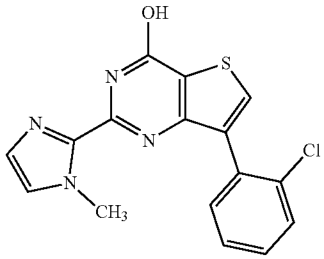

The target compound was prepared according to the procedure described in Scheme 17 for compound 76 using the appropriate reagents and starting materials. The yield after Step A was 0.90 g (90.5%). The yield after Step B was 0.35 g (70%). The yield of the target compound obtained from Step C was 71.1 mg (35.5%).

EXAMPLE 325

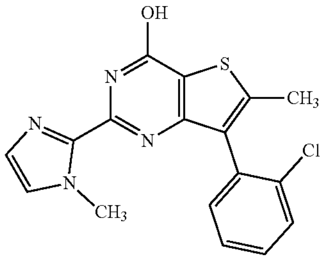

The target compound was prepared according to the procedure described in Scheme 17 for compound 76 using the appropriate reagents and starting materials. The yield after Step A was 0.93 g (93%). The yield after Step B was 0.27 g (54%). The yield of the target compound obtained from Step C was 77.2 mg (38%).

EXAMPLE 326

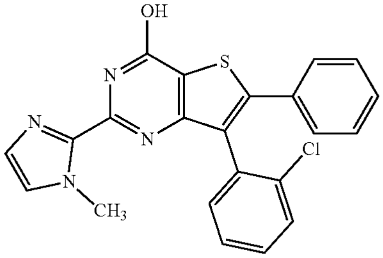

The target compound was prepared according to the procedure described in Scheme 17 for compound 76 using the appropriate reagents and starting materials. The yield after Step A was 0.89 g (89%). The yield after Step B was 0.32 g (64%). The yield of the target compound obtained from Step C was 19.8 mg (10%).

EXAMPLE 327

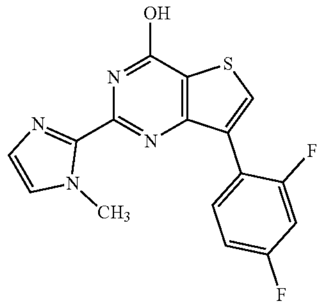

The target compound was prepared according to the procedure described in Scheme 17 for compound 76 using the appropriate reagents and starting materials. The yield after Step A was 0.79 g (79%). The yield after Step B was 0.29 g (58%). The yield of the target compound obtained from Step C was 174.8 mg (87%).

EXAMPLE 328

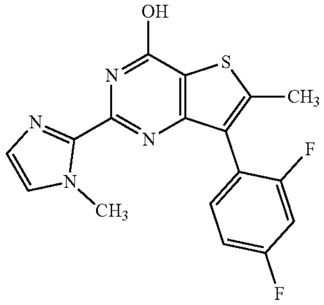 [SMILES: Cc1sc2c(O)nc(-c3nccn3C)nc2c1-c1ccc(F)cc1F]

The target compound was prepared according to the procedure described in Scheme 17 for compound 76 using the appropriate reagents and starting materials. The yield after Step A was 0.91 g (91%). The yield after Step B was 0.34 g (68%). The yield of the target compound obtained from Step C was 42.8 mg (21%).

EXAMPLE 329

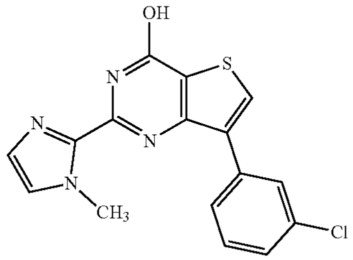

The target compound was prepared according to the procedure described in Scheme 17 for compound 76 using the appropriate reagents and starting materials. The yield after Step A was 0.88 g (88%). The yield after Step B was 0.27 g (54%). The yield of the target compound obtained from Step C was 82.7 mg (41%).

EXAMPLE 330

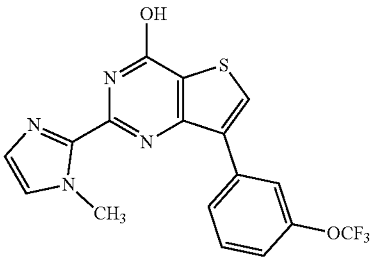

The target compound was prepared according to the procedure described in Scheme 17 for compound 76 using the appropriate reagents and starting materials. The yield after Step A was 0.94 g (94%). The yield after Step B was 0.24 g (48%). The yield of the target compound obtained from Step C was 180.5 mg (90%).

EXAMPLE 331

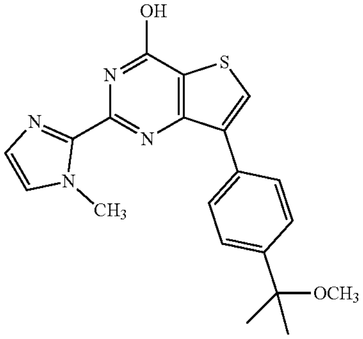

The target compound was prepared according to the procedure described in Scheme 17 for compound 76 using the appropriate reagents and starting materials. The yield after Step A was 0.87 g (87%). The yield after Step B was 0.30 g (60%). The yield of the target compound obtained from Step C was 116.8 mg (58%).

EXAMPLE 332

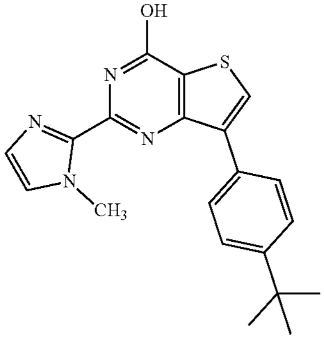

The target compound was prepared according to the procedure described in Scheme 17 for compound 76 using the appropriate reagents and starting materials. The yield after Step A was 0.85 g (85%). The yield after Step B was 0.27 g (54%). The yield of the target compound obtained from Step C was 31.5 mg (16%).

EXAMPLE 333

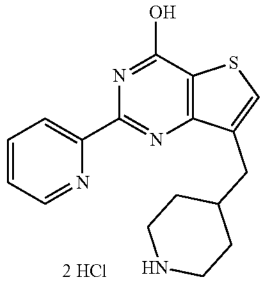

-continued

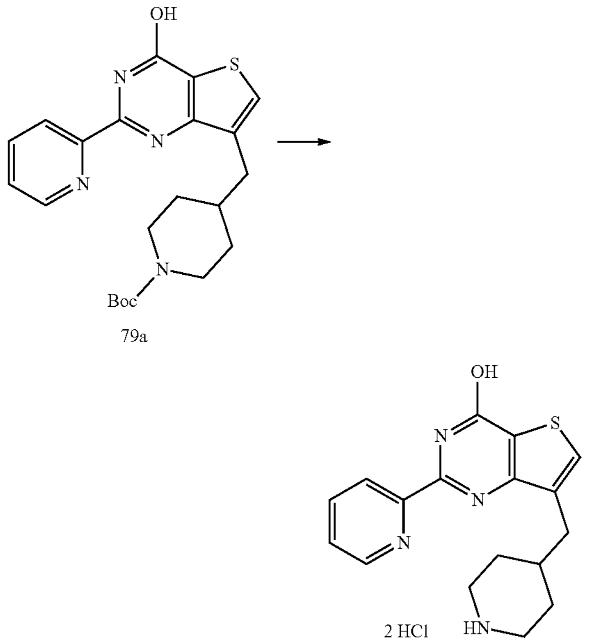

79a

Compound 79a was prepared according to the procedure described in Step A-B, Scheme 18 in 15% yield. The mixture of 79a (0.25 mmol) and 6N aqueous HCl (5 ml) was stirred at 50° C. for 5 h. The resulting solution was evaporated to dryness. The residue was triturated with dioxane and dried in vacuo to give pure target compound as the HCl salt in 90% yield.

EXAMPLE 334

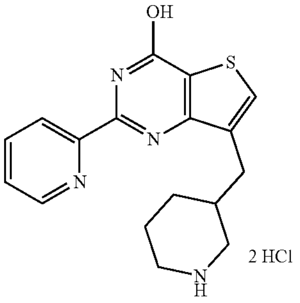

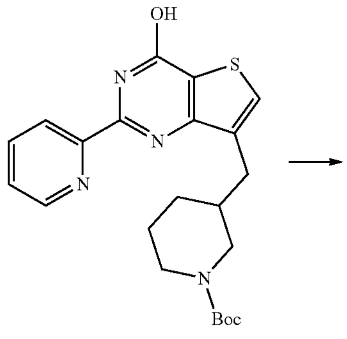

79b

-continued

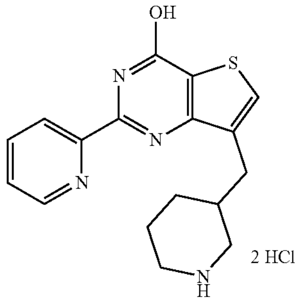

Compound 79b was prepared according to the procedure described in Step A-B, Scheme 18 in 17% yield. The mixture of 79b (0.25 mmol) and 6N aqueous HCl (5 ml) was stirred at 50° C. for 5 h. The resulting solution was evaporated to dryness. The residue was triturated with dioxane and dried in vacuo to give pure target compound as the HCl salt in 90% yield.

EXAMPLE 335

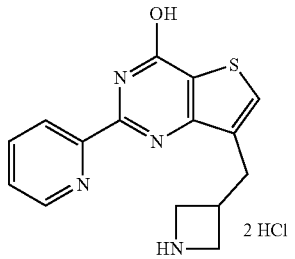

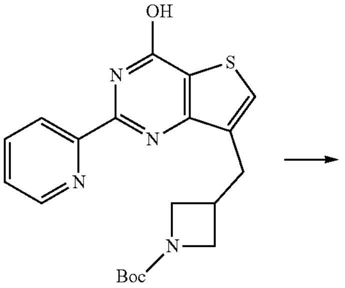

79c

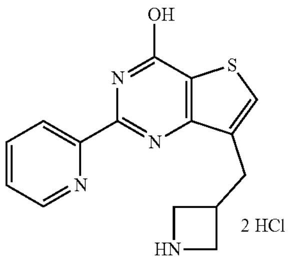

Compound 79c was prepared according to the procedure described in Step A-B, Scheme 18 in 19% yield. The mixture of 79c (0.25 mmol) and 6N aqueous HCl (5 ml) was stirred at 50° C. for 5 h. The resulting solution was evaporated to dryness. The residue was triturated with dioxane and dried in vacuo to give pure target compound as the HCl salt in 90% yield.

EXAMPLE 336

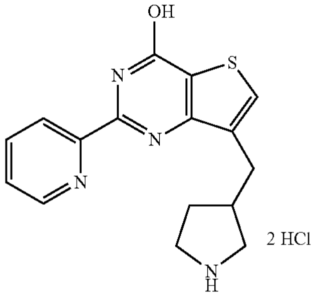

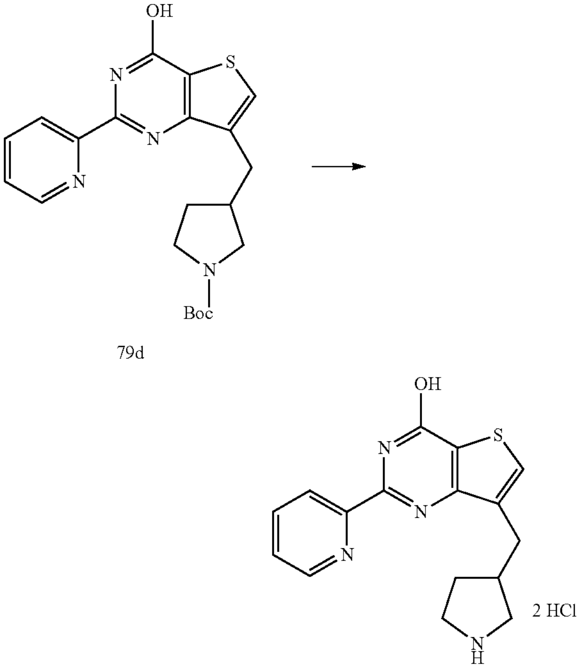

79d

Compound 79d was prepared according to the procedure described in Step A-B, Scheme 18 in 13% yield. The mixture of 79d (0.25 mmol) and 6N aqueous HCl (5 ml) was stirred at 50° C. for 5 h. The resulting solution was evaporated to dryness. The residue was triturated with dioxane and dried in vacuo to give pure target compound as the HCl salt in 90% yield.

EXAMPLE 337

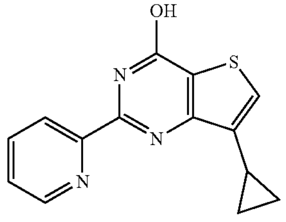

The target compound was prepared as described in Scheme 19, using the appropriate organozinc reagent (13% yield).

EXAMPLE 338

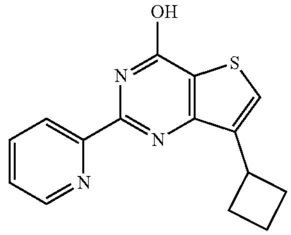

The target compound was prepared as described in Scheme 19, using the appropriate organozinc reagent (19% yield).

EXAMPLE 339

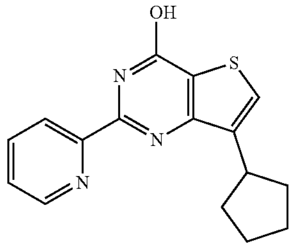

The target compound was prepared as described in Scheme 19, using the appropriate organozinc reagent (17% yield).

EXAMPLE 340

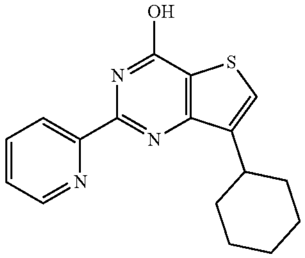

The target compound was prepared as described in Scheme 19, using the appropriate organozinc reagent (12% yield).

EXAMPLE 341

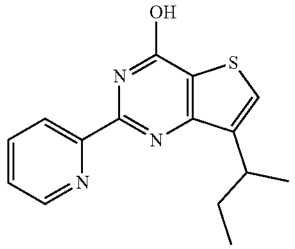

The target compound was prepared as described in Scheme 19, using the appropriate organozinc reagent (11% yield).

EXAMPLE 342

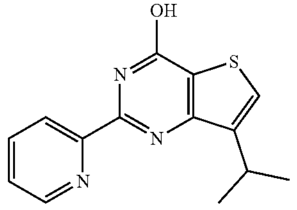

The target compound was prepared as described in Scheme 19, using the appropriate organozinc reagent (15% yield).

EXAMPLE 343

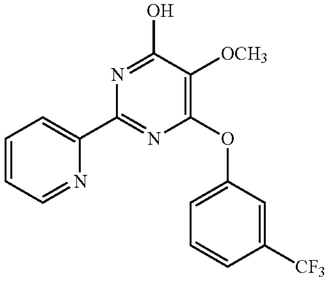

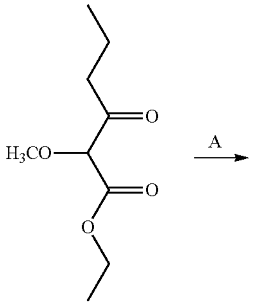

85

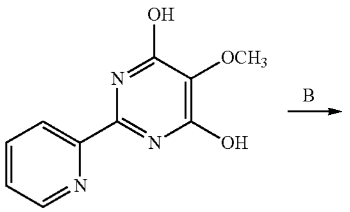

86

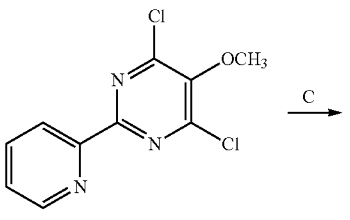

87

-continued

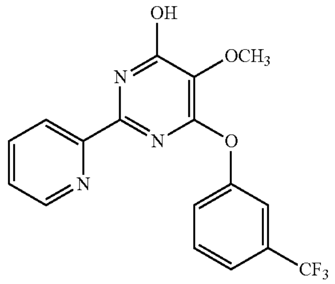

88

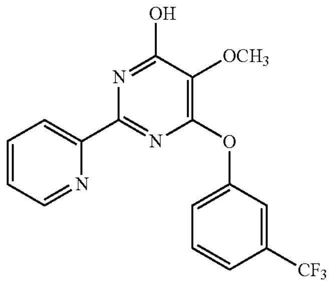

Step A: Sodium (2.27 g, 4 eq) was dissolved in MeOH (80 ml). To this solution, compound 85 (4 g, 1 eq) and amidine hydrochloride (3.88 g, 1 eq) was added. The resulting mixture was heated at 65° C. for 12 hours and evaporated in vacuo. The residue was taken up with cold water (10 ml), acidified with HCl conc. to pH=4 and allowed to stand in fridge for 2 hours. The precipitate was filtered, washed with water 10 ml and dried to obtain compound 86 (4.3 g).

Step B: To a suspension of compound 86 (4.3 g) in $POCl_3$ (35 ml), DMF (0.5 ml) was added. The reaction mixture was heated at 90° C. for 12 h and evaporated. The residue was quenched with ice-cold water (50 ml) and extracted with MTBE (3*50 ml). The organic extracts was washed with brine (2*50 ml), dried over $Na_2SO_4$ and evaporated in vacuo to obtain compound 87 (2.3 g).

Step C: To a solution of compound 87 (0.5 g, 1 eq) in DMF 5 ml was added phenol (0.32 g, 1 eq.) and $K_2CO_3$ (0.4 g, 1.5 eq). The resulting mixture was heated at 70° C. for 12 h, cooled, taken up with water (50 ml) and extracted with MTBE (3*30 ml). The organic extracts was washed with brine (2*30 ml), dried over $Na_2SO_4$ and evaporated in vacuo to obtain compound 88 (~0.6 g, 70% purity). This compound was used for the next step without purification.

Step D: To a solution of compound 88 (0.2 g, 1 eq) in THF (10 ml), a solution of NaOH (0.1 g, 5 eq) in water (2 ml) was added. The resulting mixture was stirred at 60° C. for 12h, acidified with HCl and evaporated. The residue was purified by HPLC to give the target compound.

EXAMPLE 344

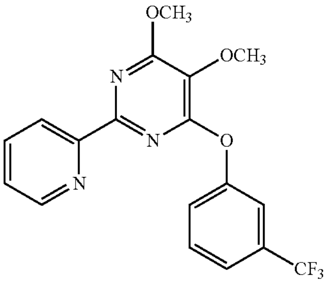

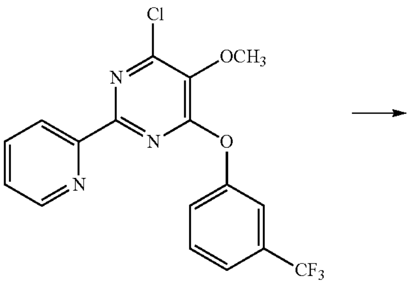

88

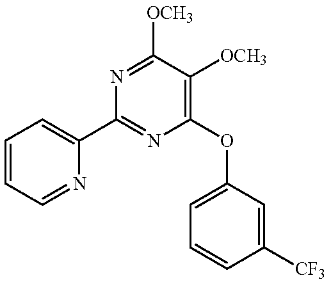

To a solution of compound 88, prepared as described in Step C, Example 343 (0.2 g, 1 eq) in dry MeOH (20 ml), t-BuOK (0.06 g, 1 eq) was added. The resulting mixture was stirred at 25° C. for 12h and evaporated. The residue was purified by HPLC to give the target compound.

EXAMPLE 345

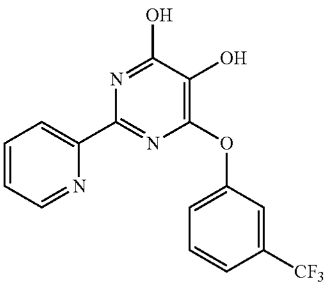

-continued

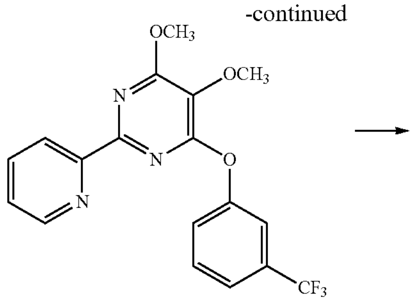

89
(Example 344)

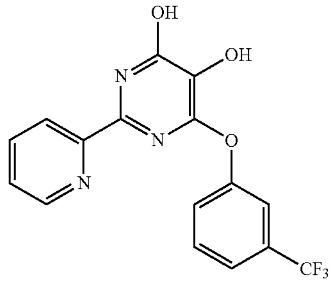

To a solution of compound 89 (Example 344), prepared as described in Example 338 (0.6 g, 1 eq) in DCM (40 ml), $BBr_3$ (1.2 g, 3 eq) was added. The resulting mixture was stirred at 25° C. for 12 h and evaporated in vacuo. The residue was quenched with water (10 ml) and extracted with DCM (3*30 ml). The organic extract was dried over $Na_2SO_4$ and evaporated under reduced pressure. The residue was purified by HPLC to give the target compound.

This disclosure is not to be limited in scope by the embodiments disclosed in the examples which are intended as single illustrations of individual aspects, and any methods which are functionally equivalent are within the scope of this disclosure. Indeed, various modifications in addition to those shown and described herein will become apparent to those skilled in the art from the foregoing description. Such modifications are intended to fall within the scope of the appended claims.

Various references such as patents, patent applications, and publications are cited herein, the disclosures of which are hereby incorporated by reference herein in their entireties.

What is claimed is:

1. A Ras inhibiting compound, wherein the Ras inhibiting compound:

a) has a structure that is calculated to have proximity of within 2.5 angstroms from and have a hydrogen bond interaction with one or more residues in the GTP binding site of a Ras protein, according to in silico molecular modeling software; and b) competitively inhibits binding of cellular GTP to the GTP binding site of the Ras protein as determined by a Ras protein GTP binding inhibition assay;

wherein the Ras protein GTP binding inhibition assay comprises:

i) contacting a test compound with the Ras protein;

ii) incubating a cyanine-labeled GTP with the test compound and the Ras protein; and iii) measuring the amount of the cyanine-labeled GTP bound to the Ras protein; and wherein the test compound is identified as a Ras inhibiting compound if the test compound competitively inhibits the binding of the cyanine-labeled GTP by more than 25% at a concentration of 20 μM as determined by the Ras protein GTP binding inhibition assay.

2. The Ras inhibiting compound of claim 1, wherein the competitive inhibition of the binding of cellular or cyanine-labeled GTP to the Ras protein by the Ras inhibiting compound results in inhibiting the activity or function of said Ras protein.

3. The Ras inhibiting compound of claim 1, wherein the Ras inhibiting compound has a binding affinity (Kd) to the Ras protein GTP binding site of less than 10 μM.

4. The Ras inhibiting compound of claim 2, wherein the Ras inhibiting compound inhibits the Ras activity and has an IC50 value of less than 10 μM.

5. The Ras inhibiting compound of claim 1, wherein the Ras inhibiting compound inhibits binding of the cyanine-labeled GTP with an IC50 value of less than 10 μM.

6. The Ras inhibiting compound of claim 1, wherein the cyanine-labeled GTP is a Cy3- or a Cy5-labeled GTP.

7. The Ras inhibiting compound of claim 1, wherein the Ras protein GTP binding inhibition assay is a cell-free assay.

8. The Ras inhibiting compound of claim 1, wherein the Ras protein is immobilized in the Ras protein GTP binding inhibition assay.

9. The Ras inhibiting compound of claim 1, wherein the Ras inhibiting compound has a molecular weight of less than 2000 Daltons.

10. The Ras inhibiting compound of claim 1, wherein the Ras inhibiting compound inhibits cellular proliferation.

11. The Ras inhibiting compound of claim 1, wherein the Ras protein is a Ras superfamily selected from DIRAS I; DIRAS2; DIRAS3; ERAS; GEM; HRAS; KRAS; MRAS; NKIRASI; NKIRAS2; NRAS; RALA; RALB; RAPIA; RAPIB; RAP2A; RAP2B; RAP2C; RASDI; RASD2; RASLIOA; RASLIOB; RASLI IA; RASLI IB; RASL12; REMI; REM2; RERG; RERGL; RRAD; RRAS; or RRAS2.

12. The Ras inhibiting compound of claim 1, wherein the Ras protein is wild-type HRAS, KRAS, or NRAS, or a mutant thereof.

13. The Ras inhibiting compound of claim 1, wherein the Ras protein is selected from the group consisting of KRas G12D mutant, KRas G12C mutant, KRas Q61H mutant, KRas G12D/Q61H double mutant, and KRas G12C/Q61H double mutant.

14. The Ras inhibiting compound of claim 1, wherein the competitive inhibition of the binding of cellular or cyanine-labeled GTP to the Ras protein by the Ras inhibiting compound induces an inactive conformation of said Ras protein.

15. The Ras inhibiting compound of claim 1, wherein the competitive inhibition of the binding of cellular or cyanine-labeled GTP to the Ras protein by the Ras inhibiting compound induces a GDP-bound conformation of said Ras protein.

16. The Ras inhibiting compound of claim 1, wherein the competitive inhibition of the binding of cellular or cyanine-labeled GTP to the Ras protein by the Ras inhibiting compound blocks a signal transduction pathway downstream of said Ras protein.

17. The Ras inhibiting compound of claim 16, wherein the signal transduction pathway downstream of said Ras protein is MAPK signaling pathway.

18. The Ras inhibiting compound of claim 1, wherein the Ras inhibiting compound inhibits activation of the MAPK signaling pathway.

19. The Ras inhibiting compound of claim 1, wherein the Ras inhibiting compound inhibits phosphorylation of MAPK in a cell-based assay.

20. The Ras inhibiting compound of claim 1, wherein the in silico molecular modeling software is Molecular Operating Environment software (MOE).

21. A Ras inhibiting compound, wherein the Ras inhibiting compound:

a) has a heterocyclic moiety selected from the group consisting of: an oxadiazolyl, a thiadiazolyl, a triazolyl, a 1,2,4-oxadiazolyl, a 1,2,4-thiadiazolyl, a 1,2,4-triazolyl, a 2-acylaminothiazolyl, a 2-(pyridine-2-yl)pyrimidinyl-4-amine, a 2-(pyridine-2-yl)pyrimidinyl-4-ol, a 2-(pyridine-2-yl)pyrimidine-4-(1H)-one, 2-(pyridin-2-yl)pyrimidin-4(3H)-one, a 2-(pyridin-2-yl)pyrimidin-4 (1H)-imine, a 2-(pyridin-2-yl)pyrimidin-4(3H)-imine, a 2-(pyridin-2-yl)pyrimidine-4-amine, a 2-(pyridin-2-yl)pyrimidine-4-ol, a 2-(pyridin-2-yl)pyrimidine-4-(1H)-one, a 2-(imidazol-2-yl)pyrimidin-4-ol, a 2-(imidazol-2-yl)pyrimidin-4(3H)-one, a 2-(imidazol-2-yl) pyrimidin-4(1H)-one, a 2-(imidazol-2-yl)pyrimidin-4-amine, a 2-(imidazol-2-yl)pyrimidin-4(3H)-imine, a 2-(imidazol-2-yl)pyrimidin-4(2H)-imine, a 2-(imidazol-4-yl)pyrimidin-4-ol, a 2-(imidazol-4-yl)pyrimidin-4(3H)-one, a 2-(imidazol-4-yl)pyrimidin-4(1H)-one, a 2-(imidazol-4-yl)pyrimidin-4-amine, a 2-(imidazol-4-yl)pyrimidin-4(3H)-imine, and a 2-(imidazol-4-yl)pyrimidin-4(1H)-imine, and is capable of interacting with one or more residues via hydrogen bond in a GTP binding site of a Ras protein, according to in silico molecular modeling software;

b) competitively inhibits binding of cellular GTP to the GTP binding site of the Ras protein as determined by a Ras protein GTP binding inhibition assay;

wherein the Ras protein GTP binding inhibition assay comprises:

i) contacting a test compound with the Ras protein;

ii) incubating a cyanine-labeled GTP with the test compound and the Ras protein; and iii) measuring the amount of the cyanine-labeled GTP bound to the Ras protein; and wherein the test compound is identified as a Ras inhibiting compound if the test compound competitively inhibits the binding of the cyanine-labeled GTP by more than 25% at a concentration of 20 μM as determined by the Ras protein GTP binding inhibition assay.

22. The Ras inhibiting compound of claim 21, wherein the Ras protein is a Ras superfamily selected from DIRAS I; DIRAS2; DIRAS3; ERAS; GEM; HRAS; KRAS; MRAS; NKIRASI; NKIRAS2; NRAS; RALA; RALB; RAPIA; RAPIB; RAP2A; RAP2B; RAP2C; RASDI; RASD2; RASLIOA; RASLIOB; RASLI IA; RASLI IB; RASL12; REMI; REM2; RERG; RERGL; RRAD; RRAS; or RRAS2.

23. The Ras inhibiting compound of claim 21, wherein the Ras protein is wild-type HRAS, KRAS, or NRAS, or a mutant thereof.

24. The Ras inhibiting compound of claim 21, wherein the competitive inhibition of the binding of cellular or cyanine-labeled GTP to the Ras protein by the Ras inhibiting compound results in inhibiting the activity or function of said Ras protein.

25. The Ras inhibiting compound of claim 21, wherein the Ras inhibiting compound has a binding affinity (Kd) to the Ras protein GTP binding domain of less than 10 μM.

26. The Ras inhibiting compound of claim 24, wherein the Ras inhibiting compound inhibits the Ras activity and has an IC50 value of less than 10 μM.

27. The Ras inhibiting compound of claim 21, wherein the Ras inhibiting compound inhibits binding of the cyanine-labeled GTP with an IC50 value of less than 10 μM.

28. The Ras inhibiting compound of claim 21, wherein the Ras inhibiting compound inhibits cellular proliferation.

29. The Ras inhibiting compound of claim 1, wherein the Ras inhibiting compound is predicted to competitively bind to the GTP binding site of the Ras protein, according to Molecular Operating Environment (MOE) software.

30. The Ras inhibiting compound of claim 1, wherein the Ras inhibiting compound is capable of interacting with one or more amino acid residues at a position of 11, 12, 13, 14, 15, 16, 17, 18, 28, 29, 30, 31, 32, 33, 34, 35, 36, 60, 61, 117, 119, 120, 145, 146, or 147, or with Mg202, in the Ras GTP binding domain.

31. The Ras inhibiting compound of claim 30, wherein the interacting of the Ras inhibiting compound with the one or more amino acid residues is predicted using Molecular Operating Environment (MOE) software.

32. The Ras inhibiting compound of claim 1, wherein the Ras inhibiting compound is capable of interacting with one or more amino acid residues selected from the group consisting of:

a) Gly13, Gly15, Lys16, Ser17, Ala18, Val29, Asp30, Asn116, Asp119, Leu120, Ser145, Ala146 and Lys147, in the KRas GTP binding domain;
b) Ala18, Asp30, Pro34, Lys117, Asp119, Leu120, Ala146 and Lys147, in the KRas GTP binding domain;
c) Asp12, Gly13, Ala18, Pro34, Asp119, Leu120, Lys147 and Mg202, in the KRas GTP binding domain;
d) Gly15, Ser17, Ala18, Phe28, Asp30, Tyr32, Asp119, Ala146 and Lys147, in the KRas GTP binding domain;
e) Gly13, Gly15, Ser17, Ala18, Tyr32, Asp33, Lys117, Lys147 and Mg202, in the KRas GTP binding domain;
f) Gly15, Phe28, Asn116, Asp119, Leu120, and Lys147, in the KRas GTP binding domain;
g) Asp12, Gly13, Ala18, Pro34 and Mg202, in the KRas GTP binding domain;
h) Gly15, Tyr32, Lys117, Asp119, Ala146 and Lys147, in the KRas GTP binding domain;
i) Gly13, Gly15, Ser17, Ala18, Asp30, Tyr32, Asp33 and Mg 202, in the KRas GTP binding domain;
j) Ala11, Gly12, Lys16, Ser17, Tyr32, Thr35, Lys36, Lys117, Asp119 and Mg 202, in the KRas GTP binding domain;
k) Gly12, Val14, Gly15, Lys16, Ser17, Phe28, Val29, Glu31, Thr35, Gly60, Lys117, Leu120 and Mg 202, in the KRas GTP binding domain; and
l) Ala11, Gly12, Gly15, Ser17, Ala18, Val29, Tyr32, Asp33, Thr35 and Mg 202, in the KRas GTP binding domain.

33. The Ras inhibiting compound of claim 1, wherein the Ras inhibiting compound is capable of interacting with one or more amino acid residues selected from the group consisting of:

a) Ala13, Gly15, Lys16, Thr17, Cys18, Lys116, Asp118, Leu119 and Mg 202, in the Rac-1 GTP binding domain;
b) Gly12, Ala13, Thr17, Ile33, Pro34, Val36, Ala59 and Mg 202, in the Rac-1 GTP binding domain; and
c) Ala13, Gly15, Lys16, Thr17, Cys18, Leu19, Phe28, Ile33, Thr115, Cys157, Ala159 and Mg 202, in the Rac-1 GTP binding domain.

34. The Ras inhibiting compound of claim 1, wherein the Ras inhibiting compound is capable of interacting with one or more amino acid residues selected from the group consisting of:

a) Cys16, Gly17, Lys18, Thr19, Phe30, Pro31, Val35, Lys118, Asp120 and Mg 202, in the Rho-A GTP binding domain;
b) Gly14, Ala15, Lys18, Thr19, Cys20, Pro31, Glu32, Tyr34, Val35, Pro36, Thr37 and Mg 202, in the Rho-A GTP binding domain; and
c) Gly17, Thr19, Phe30, Tyr34, Pro36, Thr37, Asp59, Lys118, Lys162 and Mg 202, in the Rho-A GTP binding domain.

35. The Ras inhibiting compound of claim 21, wherein the Ras inhibiting compound is predicted to competitively bind to the GTP binding site of the Ras protein, according to Molecular Operating Environment (MOE) software.

36. The Ras inhibiting compound of claim 21, wherein the Ras inhibiting compound is capable of interacting with one or more amino acid residues at a position of 11, 12, 13, 14, 15, 16, 17, 18, 28, 29, 30, 31, 32, 33, 34, 35, 36, 60, 61, 117, 119, 120, 145, 146, or 147, or with Mg202, in the Ras GTP binding domain.

37. The Ras inhibiting compound of claim 36, wherein the interacting of the Ras inhibiting compound with the one or more amino acid residues is predicted using Molecular Operating Environment (MOE) software.

38. The Ras inhibiting compound of claim 21, wherein the Ras inhibiting compound has a structure that is calculated to be proximate to within 2.5 angstroms of one or more residues in the GTP binding site of a Ras protein, according to in silico molecular modeling software.

39. The Ras inhibiting compound of claim 38, wherein the in silico molecular modeling software is Molecular Operating Environment (MOE) software.

* * * * *